US006693123B2

(12) United States Patent
Sebti et al.

(10) Patent No.: US 6,693,123 B2
(45) Date of Patent: Feb. 17, 2004

(54) INHIBITORS OF PROTEIN ISOPRENYL TRANSFERASES

(75) Inventors: Said M. Sebti, Tampa, FL (US); Andrew D. Hamilton, Guilford, CT (US); David J. Augeri, Kenosha, WI (US); Kenneth J. Barr, Chicago, IL (US); Greg B. Donner, Mundelein, IL (US); Stephen A. Fakhoury, Mundelein, IL (US); Stephen J. O'Connor, Wilmette, IL (US); Saul H. Rosenberg, Grayslake, IL (US); Wang Shen, Gurnee, IL (US); Bruce G. Szczepankiewicz, Lindenhurst, IL (US); Indrani W. Gunawardana, Libertyville, IL (US)

(73) Assignee: University of Pittsburgh, Pittsburgh, PA (US)

( * ) Notice: Subject to any disclaimer, the term of this patent is extended or adjusted under 35 U.S.C. 154(b) by 122 days.

(21) Appl. No.: 09/984,411

(22) Filed: Oct. 30, 2001

(65) Prior Publication Data

US 2002/0193596 A1 Dec. 19, 2002

Related U.S. Application Data

(63) Continuation of application No. 09/073,818, filed on May 7, 1998, now abandoned, which is a continuation-in-part of application No. 08/852,858, filed on May 7, 1997, now abandoned, which is a continuation-in-part of application No. 08/740,909, filed on Nov. 5, 1996, now abandoned
(60) Provisional application No. 60/007,247, filed on Nov. 6, 1995.

(51) Int. Cl.[7] .................... A61K 31/44; A61K 31/4965; C07D 419/00; C07D 213/06; C07D 257/00

(52) U.S. Cl. .................. 514/357; 514/352; 514/255.05; 514/256; 544/238; 544/333; 544/405; 546/264; 546/266; 548/252; 549/321

(58) Field of Search ................................ 514/352, 357, 514/255.05, 256; 544/238, 333, 405; 546/264, 266; 548/252; 549/321

(56) References Cited

U.S. PATENT DOCUMENTS 5,043,268 A 8/1991 Stock ......................... 436/578

(List continued on next page.)

FOREIGN PATENT DOCUMENTS

CA 2072033 6/1992

(List continued on next page.)

OTHER PUBLICATIONS

Hancock et al., "A Polybasic Domain or Palmitoylation is Required in Addition to the CAAX Motif to Localize P21ras to the Plasma Membrane," Cell, vol. 63, Oct. 5, 1990, pp. 133–139.

(List continued on next page.)

*Primary Examiner*—Alan L. Rotman
*Assistant Examiner*—Tamthom N. Truong
(74) *Attorney, Agent, or Firm*—Pillsbury Winthrop LLP

(57) ABSTRACT

Compounds having the formula

I

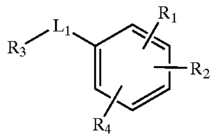

or a pharmaceutically acceptable salt thereof wherein $R_1$ is (a) hydrogen, (b) loweralkyl, (c) alkenyl, (d) alkoxy, (e) thioalkoxy, (f) halo, (g) haloalkyl, (h) aryl-$L_2$—, and (i) heterocyclic-$L_{2—; R}2$ is selected from (a)

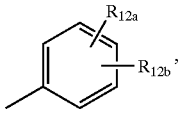

(b)

—C(O)NH—CH($R_{14}$)—C(O)$OR_{15}$, (c)

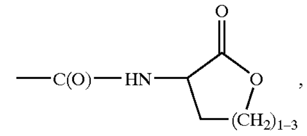

(d)

—C(O)NH—CH($R_{14}$)—C(O)$NHSO_2R_{16}$, (e) —C(O)NH—CH($R_{14}$)-tetrazolyl, (f) —C(O)NH-heterocyclic, and (g) —C(O)NH—CH($R_{14}$)—C(O)$NR_{17}R_{18}$; $R_3$ is heterocyclic, aryl, substituted or unsubstituted cycloalkyl; $R_4$ is hydrogen, lower alkyl, haloalkyl, halogen, aryl, arylakyl, heterocyclic, or (heterocyclic)alkyl; $L_1$ is absent or is selected from (a) —$L_4$—N($R_5$)—$L_5$—, (b) —$L_4$—O—$L_5$—, (c) —$L_4$—S(O)$_n$—$L_5$— (d) —$L_4$—$L_6$—C(W)—N($R_5$)—$L_5$—, (e) —$L_4$—$L_6$—S(O)$_m$—N($R_5$)—$L_5$—, (f) —$L_4$—N($R_5$)—C(W)—$L_7$—$L_5$—, (g) —$L_4$—N($R_5$)—S(O)$_p$—$L_7$—$L_5$—, (h) optionally substituted alkylene, (i) optionally substituted alkenylene, and (j) optionally substituted alkynylene are inhibitors of protein isoprenyl transferases. Also disclosed are protein isoprenyl transferase inhibiting compositions and a method of inhibiting protein isoprenyl transferases.

7 Claims, No Drawings

U.S. PATENT DOCUMENTS

| | | | | | |
|---|---|---|---|---|---|
| 5,141,851 | A | | 8/1992 | Brown et al. | 435/15 |
| 5,238,922 | A | | 8/1993 | Graham et al. | 514/18 |
| 5,534,537 | A | | 7/1996 | Ciccarone et al. | 514/397 |
| 5,578,629 | A | | 11/1996 | Ciccarone et al. | 514/397 |
| 5,631,280 | A | | 5/1997 | Ciccarone et al. | 514/416 |
| 6,022,884 | A | * | 2/2000 | Mantlo et al. | 514/352 |
| 6,184,237 | B1 | * | 2/2001 | Mantlo et al. | 514/335 |
| 6,384,080 | B1 | * | 5/2002 | Oku et al. | 514/604 |

FOREIGN PATENT DOCUMENTS

| | | | |
|---|---|---|---|
| EP | 0203587 | | 12/1986 |
| EP | 0456180 | | 11/1991 |
| EP | 0461869 | | 12/1991 |
| EP | 0512865 | | 11/1992 |
| EP | 0520823 | | 12/1992 |
| EP | 0528486 | | 2/1993 |
| EP | 0534546 | | 3/1993 |
| EP | 0535730 | | 4/1993 |
| WO | WO9116340 | | 10/1991 |
| WO | WO9218465 | | 10/1992 |
| WO | WO9409766 | | 5/1994 |
| WO | WO9525086 | | 9/1995 |
| WO | WO9630014 | | 10/1996 |
| WO | WO9630015 | | 10/1996 |
| WO | WO9706138 | | 2/1997 |
| WO | 97/17070 | * | 5/1997 |
| WO | WO9807692 | | 2/1998 |
| WO | WO9838162 | | 9/1998 |

OTHER PUBLICATIONS

Reiss et al, "Inhibition of Purified p21ras Farnesyl:Protein Transferase by Cys–AAX Tetrapeptides,"Cell, vol. 62, Jul. 13, 1990, pp. 81–88.

Willumsen et al., The p21 ras C–Terminus is required for transformation and membrane association, Nature, vol. 310, Aug. 16, 1984, pp. 583–586.

Kohl et al., Selective Inhibition of ras–Dependent Transformation by a Farnesyltransferase Inhibitor, Science, 260:1934–1937 (1993).

Nigam et al., Potent Inhibition of Human Tumor $p21^{ras}$ Farnesyltransferase etc., The Journal of Biological Chemistry, 1993, vol. 263, No. 28, pp. 20695–20698.

Gibbs, J.B., Ras C–Terminal Processing Enzymes–New Drug Targets, Cell, 65:1–4 (1991).

Gibbs et al., Farnesyltransferase Inhibitors: Ras Research Yields a Potential Cancer Therapuetic, Cell, 77:175–178.

Brown et al., Telrapeptide Inhibitors of Protein Farnesyltransferase: Amino–Terminal Substitution in Phenylalanine–Containing Tetrapeptides Restores Farnesylation, Proc. Natl. Acad. Sci. USA, 89:8313–8316 1992.

Graham et al., Pseudopeptide Inhibitors of Ras Farnesyl–Protein Transferase, J. Med. Chem., 37:725–732 (1994).

Garcia et al., Peptidomimetic Inhibitors of Ras Farnesylation and Function in Whole Cells, J. Biol. Chem., 268:18415–18418 (1993).

Qian et al., Design and Structural Requirements of Potent Peptidomimetic Inhibitors of P21ras Farnesyltransferase, J. Biol. Chem., 269:12410–12413 (1994).

Qian et al., Peptidomimetic Inhibitors of P21RAS farnesyltransferase: Hydrophobic Functionalization Leads to Disruption of P21RAS Membrane Association in Whole Cells, Bioorg. Med. Chem. Lett., 4:2579–2584 (1994).

Goldstein et al., Benzodiazepine Peptidomimetics: Potent Inhibitors of Ras Farnesylation in Animal Cells, Science, 260:1937–1942 (1993).

Vogt et al., A non–peptide Mimetic of Ras–CAAX: Selective Inhibition of Farnesyltransferase and Ras Processing, 1995) J. Biol. Chem 270:660–664.

Kohl et al., Protein Farnesyltransferase Inhibitors Block the Growth of RAS–Dependent Tmors in Nude Mice, (1994) Proc. Natl. Acad. Sci. USA 91:9141–9145.

Cox et al., The CAAX Peptidomimetic Compound B581 Specifically Blocks Farnesylated, but not Geranylgeranylated or Myristylated, Oncogenic Ras Signaling and Transformation, (1994) J. Biol. Chem. 269:19203–19206.

Lerner et al., Ras CAAX Peptidomimetic FTI–277 Selectively Blocks Oncogenic Ras Signaling by Inducting Cytoplasmic Accumulation of Inactive Ras–Raf Complexes (1995) J. Biol. Chem 270:26802–26806.

Sun et al., Ras CAAX Peptidomimetic FTI 276 Selectively Blocks Tumor Growth in Nude Mice of a Human Lung Carcinoma with K–Ras Mutation and p53 Deletion, (1995) Cancer Research 55, 4243–4247.

Augeri et al., Chemical Abstract 129:325737 (1998).

Sebti et al., Chemical Abstract 127:51002 (1997).

Omenn, Cancer Prevention, Cecil Textbook of Medicine, $20^{th}$ Ed., vol. 1, pp. 1008–10 (1996).

* cited by examiner

INHIBITORS OF PROTEIN ISOPRENYL TRANSFERASES

CROSS REFERENCE TO RELATED APPLICATIONS

This application is a continuation of U.S. Ser. No. 09/073,818, filed May 7, 1998 abandoned, which is a continuation-in-part of U.S. Ser. No. 08/852,858, filed May 7, 1997 abandoned, which is a continuation-in-part of U.S. Ser. No. 08/740909, filed Nov. 5, 1996 abandoned, which claims priority to U.S. Provisional Ser. No. 60/007,247, filed Nov. 6, 1995, the contents of which are incorporated herein by reference in their entirety.

TECHNICAL FIELD

The present invention relates to novel compounds which are useful in inhibiting protein isoprenyl transferases (for example, protein farnesyltransferase and protein geranylgeranyltransferase) and the farnesylation or geranylgeranylation of the oncogene protein Ras and other related small g-proteins, compositions containing such compounds and methods of using such compounds.

BACKGROUND OF THE INVENTION

Ras oncogenes are the most frequently identified activated oncogenes in human tumors. Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase, and thereby farnesylation of the Ras protein, blocks the ability of transformed cells to proliferate. Inhibition of protein geranylgeranyltransferase and, thereby, of geranylgeranylation of Ras proteins, also results in down regulation of Ras protein function.

Activation of Ras and other related small g-proteins that are farnesylated and/or geranylated also partially mediates smooth muscle cell proliferation (Circulation, I-3: 88 (1993), which is hereby incorporated herein by reference). Inhibition of protein isoprenyl transferases, and thereby farnesylation or geranylgeranylation of the Ras protein, also aids in the prevention of intimal hyperplasia associated with restenosis and atherosclerosis, a condition which compromises the success of angioplasty and surgical bypass for obstructive vascular lesions.

There is therefore a need for compounds which are inhibitors of protein farnesyltransferase and protein geranylgeranyltransferase.

SUMMARY OF THE INVENTION

In its principle embodiment, the invention provides a compound having the formula:

I

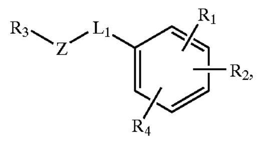

or a pharmaceutically acceptable salt thereof, wherein $R_1$ is selected from the group consisting of (1) hydrogen, (2) alkenyl, (3) alkynyl, (4) alkoxy, (5) haloalkyl, (6) halogen, (7) loweralkyl, (8) thioalkoxy, (9) aryl-$L_2$— wherein aryl is selected from the group consisting of (a) phenyl, (b) naphthyl, (c) dihydronaphthyl, (d) tetrahydronaphthyl, (e) indanyl, and (f) indenyl wherein (a)–(f) are unsubstituted or substituted with at least one of X, Y, or Z wherein X, Y, and Z are independently selected from the group consisting of alkenyl, alkynyl, alkoxy, aryl, aryloxy, carboxy, cyano, halogen, haloalkyl, hydroxy, hydroxyalkyl, loweralkyl, nitro, N-protected amino, and —NRR' wherein R and R' are independently selected from the group consisting of hydrogen and loweralkyl, oxo (=O), and thioalkoxy and $L_2$ is absent or is selected from the group consisting of $—CH_2—$, $—CH_2CH_2—$, $—CH(CH_3)—$,

—C(O)—, $S(O)_q$ wherein q is 0, 1 or 2, and

—N(R)—, and

(10) heterocycle-$L_2$— wherein $L_2$ is as defined above and the heterocycle is unsubstituted or substituted with 1, 2, 3 or 4 substituents independently selected from the group consisting of (a) loweralkyl, (b) hydroxy, (c) hydroxyalkyl, (d) halogen (e) cyano, (f) nitro, (g) oxo (=O), (h) —NRR', (i) N-protected amino, (j) alkoxy, (k) thioalkoxy, (l) haloalkyl, (m) carboxy, and (n) aryl;

$R_2$ is selected from the group consisting of (1)

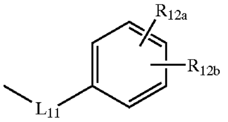

wherein $L_{11}$ is selected from the group consisting of
(a) a covalent bond,
(b) —C(W)N(R)— wherein R is defined previously and W is selected from the group consisting of O and S,
(c) —C(O)—,
(d) —N(R)C(W)—,
(e) —$CH_2$O—,
(f) —C(O)O—, and
(g) —$CH_2$N(R)—, $R_{12a}$ is selected from the group consisting of
(a) hydrogen,
(b) loweralkyl, and
(c) —C(O)$OR_{13}$ wherein $R_{13}$ is selected from the group consisting of
hydrogen and
a carboxy-protecting group, and $R_{12b}$ is selected from the group consisting of
(a) hydrogen and
(b) loweralkyl, with the proviso that $R_{12a}$ and $R_{12b}$ are not both hydrogen, (2) —$L_{11}$—C($R_{14}$)($R_v$)—C(O)$OR_{15}$ wherein $L_{11}$ is defined previously, $R_v$ is selected from the group consisting of
(a) hydrogen and
(b) loweralkyl, $R_{15}$ is selected from the group consisting of
(a) hydrogen,
(b) alkanoyloxyalkyl,
(c) loweralkyl, and
(b) a carboxy-protecting group, and $R_{14}$ is selected from the group consisting of
(a) alkoxyalkyl,
(b) alkoxyarylalkyl,
(c) alkoxycarbonylalkyl,
(d) alkylsulfinyalkyl,
(e) alkylsulfonylalkyl,
(f) alkynyl,
(g) aminoalkyl,
(h) aminocarbonylalkyl,
(i) aminothiocarbonylalkyl,
(j) aryl,
(k) arylalklyl,
(l) carboxyalkyl,
(m) cyanoalkyl,
(n) cycloalkyl,
(o) cycloalkylalkoxyalkyl,
(p) cycloalkylalkyl,
(q) (heterocyclic)alkyl,
(r) hydroxyalkyl,
(s) hydroxyarylalkyl,
(t) loweralkyl,
(u) sulfhydrylalkyl,
(v) thioalkoxyalkyl wherein the thioalkoxyalkyl is unsubstituted or substituted with 1, 2, 3, or 4 substituents selected from the group consisting of
halogen,
(w) thioalkoxyalkylamino, and
(x) thiocycloalkyloxyalkyl,

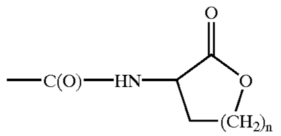

wherein n is 1–3, (4) —C(O)NH—CH($R_{14}$)—C(O)$NHSO_2R_{16}$ wherein $R_{14}$ is defined previously and $R_{16}$ is selected from the group consisting of
(a) loweralkyl,
(b) haloalkyl,
(c) aryl wherein the aryl is unsubstituted or substituted with 1, 2, 3, 4, or 5 substituents independently selected from the group consisting of
loweralkyl,
hydroxy,
hydroxyalkyl,
halogen,
cyano,
nitro,
oxo (=O),
—NRR'
N-protected amino,
alkoxy,
thioalkoxy,
haloalkyl,
carboxy, and
aryl, and
(d) heterocycle wherein the heterocycle is unsubstituted or substituted with substituents independently selected from the group consisting of
loweralkyl,
hydroxy,
hydroxyalkyl,
halogen,
cyano,
nitro,
oxo (=O),
—NRR',
N-protected amino,
alkoxy,
thioalkoxy,
haloalkyl,
carboxy, and
aryl;

(5) —C(O)NH—CH($R_{14}$)-tetrazolyl wherein the tetrazole ring is unsubstituted or substituted with loweralkyl or haloalkyl, (6) —$L_{11}$-heterocycle, (7) C(O)NH—CH($R_{14}$)—C(O)$NR_{17}R_{18}$ wherein $R_{14}$ is defined previously and $R_{17}$ and $R_{18}$ are independently selected from the group consisting of
(a) hydrogen,
(b) loweralkyl,
(c) arylalkyl,
(d) hydroxy, and
(e) dialkylaminoalkyl, (8) C(O)$OR_{15}$, and (9) C(O)NH—CH($R_{14}$)-heterocycle wherein $R_{14}$ is as previously defined and the heterocycle is unsubstituted or substituted with loweralkyl or haloalkyl;

$L_1$ is absent or is selected from the group consisting of

—$L_4$—N($R_5$)—$L_5$— wherein $L_4$ is absent or selected from the group consisting of
(a) $C_1$-to-$C_{10}$-alkylene and
(b) $C_2$-to-$C_{16}$-alkenylene,
wherein the alkylene and alkenylene groups are unsubstituted or substituted with 1, 2, 3 or 4 substituents independently selected from the group consisting of
alkenyl,
alkenyloxy,
alkenyloxyalkyl,
alkenyl[S(O)$_q$]alkyl,
alkoxy,
alkoxyalkyl wherein the alkoxyalkyl is unsubstituted or substituted with 1 or 2 hydroxyl substituents,
with the proviso that no two hydroxyls are attached to the same carbon,
alkoxycarbonyl wherein the alkoxycarbonyl is unsubstituted or substituted with 1, 2, or 3 substituents independently selected from the group consisting of
halogen and
cycloalkyl,
alkylsilyloxy,
alkyl[S(O)$_q$],
alkyl[S(O)$_q$]alkyl,
aryl wherein the aryl is unsubstituted or substituted with 1, 2, 3, 4, or 5 substituents independently selected from the group consisting of
alkoxy wherein the alkoxy is unsubstituted or substituted with substituents selected from the group consisting of cycloalkyl,
aryl,
arylalkyl,
aryloxy wherein the aryloxy is unsubstituted or substituted with 1, 2, 3, 4, or 5 substituents independently selected from the group consisting of,
halogen,
nitro, and
—NRR',
cycloalkyl,
halogen,
loweralkyl,
hydroxyl,
nitro,
—NRR', and
—$SO_2$NRR',
arylalkoxy wherein the arylalkoxy is unsubstituted or substituted with substituents selected from the group consisting of alkoxy,
arylalkyl,
arylalkyl[S(O)$_q$]alkyl,
aryl[S(O)$_q$],
aryl[S(O)$_q$]alkyl wherein the aryl[S(O)$_q$]alkyl is unsubstituted or substituted with 1, 2, 3, 4, or 5 substituents independently selected from alkoxy and loweralkyl,
arylalkoxyalkyl wherein the arylalkoxyalkyl is unsubstituted or substituted with substituents selected from the group consisting of
alkoxy, and
halogen,
aryloxy,
aryloxyalkyl wherein the aryloxyalkyl is unsubstituted or substituted with substituents selected from the group consisting of halogen,
carboxyl,
—C(O)N$R_C$$R_D$ wherein $R_C$ and $R_D$ are independently selected from the group consisting of
hydrogen,
loweralkyl, and
alkoxycarbonyl or
$R_C$ and $R_D$ together with the nitrogen to which they are attached form a ring selected from the group consisting of
morpholine,
piperidine,
pyrrolidine
thiomorpholine,
thiomorpholine sulfone, and
thiomorpholine sulfoxide,
wherein the ring formed by $R_C$ and $R_D$ together is unsubstituted or
substituted with 1 or 2 substituents independently selected from the group consisting of alkoxy and alkoxyalkyl,
cycloalkenyl wherein the cycloalkenyl is unsubstituted or substituted with 1 or 2 substituents selected from the group consisting of alkenyl,
cyclolalkoxy,
cycloalkoxycarbonyl,
cyclolalkoxyalkyl,
cyclolalkyl wherein the cycloalkyl is unsubstituted or substituted with 1, 2, 3, 4, or 5 substituents independently selected from the group consisting of aryl, loweralkyl, and alkanoyl,
cycloalkylalkoxy,
cycloalkylalkoxycarbonyl,
cycloalkylalkoxyalkyl,
cycloalkylalkyl,
cyclolalkyl[S(O)$_q$]alkyl,
cycloalkylalkyl[S(O)$_q$]alkyl,
fluorenyl,
heterocycle wherein the heterocycle is unsubstituted or substituted with 1, 2, 3, or 4 substituents independently selected from the group consisting of
alkoxy wherein the alkoxy is unsubstituted or substituted with 1 or 2 substituents independently selected from the group consisting of aryl and cycloalkyl,
alkoxyalkyl wherein the alkoxyalkyl is unsubstituted or substituted with 1 or 2 substituents independently selected from the group consisting of
aryl and
cycloalkyl,
alkoxycarbonyl wherein the alkoxycarbonyl is unsubstituted or substituted with 1 or 2 substituents independently selected from the group consisting of
aryl and
cycloalkyl,
aryl wherein the aryl is unsubstituted or substituted with 1, 2, 3, 4, or 5 substituents independently selected from the group consisting of
alkanoyl,
alkoxy,
carboxaldehyde,
haloalkyl,
halogen,
loweralkyl,
nitro,
—NRR', and thioalkoxy,
arylalkyl,
aryloxy,
cycloalkoxyalkyl,
cycloalkyl,
cycloalkylalkyl,
halogen,
heterocycle,
hydroxyl,
loweralkyl wherein the loweralkyl is unsubstituted or substituted with 1, 2, or 3 substituents independently selected from the group consisting of
heterocycle,
hydroxyl,
with the proviso that no two hydroxyls are attached to the same carbon, and
—$NR^{R3R3'}$ wherein $R^{R3}$ and $R^{R3'}$ are independently selected from the group consisting of
hydrogen
aryl,
loweralkyl,
aryl,
arylalkyl,
heterocycle,
(heterocyclic)alkyl,
cycloalkyl, and
cycloalkylalkyl, and
sulfhydryl,
(heterocyclic)alkoxy,
(heterocyclic)alkyl,
(heterocyclic)alkyl[$S(O)_q$]alkyl,
(heterocyclic)oxy,
(heterocyclic)alkoxyalkyl,
(heterocyclic)oxyalkyl,
heterocycle[$S(O)_q$]alkyl,
hydroxyl,
hydroxyalkyl,
imino,
N-protected amino,
═N—O-aryl, and
═N—OH,
═N—O-heterocycle wherein the heterocycle is unsubstituted or substituted with 1, 2, 3, or 4 substituents independently selected from the group consisting of
loweralkyl,
hydroxy,
hydroxyalkyl,
halogen,
cyano,
nitro,
oxo (═O),
—NRR'
N-protected amino,
alkoxy,
thioalkoxy,
haloalkyl,
carboxy, and
aryl,
═N—O-loweralkyl,
—$NR^{R3}R^{R3'}$,
—$NHNR_CR_D$,
—OG wherein G is a hydroxyl protecting group,
—O—NH—R,

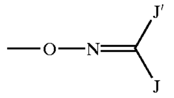

wherein J and J' are independently selected from the group consisting of
loweralkyl and
arylalkyl,
oxo,
oxyamino(alkyl)carbonylalkyl,
oxyamino(arylalkyl)carbonylalkyl,
oxyaminocarbonylalkyl,
—$SO_2$—A wherein A is selected from the group consisting of
loweralkyl,
aryl, and
heterocycle
wherein the loweralkyl, aryl, and heterocycle are unsubstituted or substituted with 1, 2, 3, 4, or 5 substituents independently selected from the group consisting of
alkoxy,
halogen,
haloalkyl,
loweralkyl, and
nitro,
sulfhydryl,
thioxo, and
thioalkoxy,
$L_5$ is absent or selected from the group consisting of
(a) $C_1$-to-$C_{10}$-alkylene and
(b) $C_2$-to-$C_{16}$-alkenylene
wherein (a) and (b) are unsubstituted or substituted as defined previously, and
$R_5$ is selected from the group consisting of
hydrogen,
alkanoyl wherein the alkanoyl is unsubstituted or substituted with substituents selected from the group consisting of aryl,
alkoxy,
alkoxyalkyl,
alkoxycarbonyl wherein the alkoxycarbonyl is unsubstituted or substituted with 1, 2 or 3 substituents independently selected from the group consisting of
aryl and
halogen,
alkylaminocarbonylalkyl wherein the alkylaminocarbonylalkyl is unsubstituted or substituted with 1 or 2 substituents independently selected from the group consisting of aryl,
(anthracenyl)alkyl,
aryl,
arylalkoxy,
arylalkyl wherein the arylalkyl is unsubstituted or substituted with 1, 2, 3, 4, or 5 substituents independently selected from the group consisting of
alkoxy,
aryl,
carboxyl,
cyano,
halogen,
haloalkoxy,
haloalkyl, nitro,
oxo, and
$—L_{11}—C(R_{14})(R_v)—C(O)OR_{15}$,
(aryl)oyl wherein the (aryl)oyl is unsubstituted or substituted with substituents selected from the group consisting of halogen,
aryloxycarbonyl,
carboxaldehyde,
—C(O)NRR',
cycloalkoxycarbonyl,
cycloalkylaminocarbonyl,
cycloalkylaminothiocarbonyl,
cyanoalkyl,
cyclolalkyl,
cycloalkylalkyl wherein the cycloalkylalkyl is unsubstituted or substituted with 1 or 2 hydroxyl substituents,
with the proviso that no two hydroxyls are attached to the same carbon,
(cyclolalkyl)oyl,
(9,10-dihydroanthracenyl)alkyl wherein the (9,10-dihydroanthracenyl)alkyl is unsubstituted or substituted with 1 or 2 oxo substituents,
haloalkyl,
heterocycle,
(heterocyclic)alkyl wherein the (heterocyclic)alkyl is unsubstituted or substituted with 1, 2, 3, 4, or 5 substituents selected from the group consisting of
loweralkyl,
(heterocyclic)oyl,
loweralkyl, wherein the loweralkyl is unsubstituted or substituted with substituents selected from the group consisting of —NRR',
$—SO_2—A$, and
thioalkoxyalkyl;

(2) $—L_4—O—L_5—$,
(3) $—L_4—S(O)_m—L_5—$ wherein $L_4$ and $L_5$ are defined previously and m is 0, 1, or 2,
(4) $—L_4—L_6—C(W)—N(R_{4'})—L_5—$ wherein $L_4$, W, and $L_5$ are defined previously, and $R_{4'}$ is selected from the group consisting of
(a) hydrogen,
(b) loweralkyl,
(c) aryl,
(d) arylalkyl,
(e) heterocycle,
(f) (heterocyclic)alkyl,
(g) cyclolakyl, and
(h) cycloalkylalkyl, and
$L_6$ is absent or is selected from the group consisting of
(a) —O—,
(b) —S—, and
(c) $—N(R_{4'})—$ wherein $R_{4'}$ is selected from the group consisting of
hydrogen,
loweralkyl,
aryl,
arylalkyl,
heterocycle,
(heterocyclic)alkyl,
cyclolakyl, and
cycloalkylalkyl,
(5) $—L_4—L_6—S(O)_m—N(R_7)—L_5—$,
(6) $—L_4—L_6—N(R_5)—S(O)_m—L_5—$,
(7) $—L_4—N(R_5)—C(W)—L_7—L_5—$ wherein $L_4$, $R_5$, W, and $L_5$ are defined previously and $L_7$ is absent or is selected from the group consisting of —O— and —S—,
(8) $C_1$–$C_{10}$-alkylene wherein the alkylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(9) $C_2$-to-$C_{10}$-alkenylene wherein the alkenylene group is unsubstituted or substituted with 1 or 2 substituents independently selected from the group consisting of
(a) aryl,
(b) arylalkyl,
(c) (aryl)oxyalkyl wherein the (aryl)oxyalkyl is unsubstituted or substituted with 1, 2, 3, 4, or 5 substituents selected from the group consisting of halogen,
(d) heterocycle,
(e) (hererocycle)alkyl,
(f) hydroxyalkyl,
(g) cyclolakyl,
(h) cycloalkylalkyl,
(i) alkylthioalkyl, and
(l) hydroxy,
(10) $C_2$-to-$C_{10}$-alkynylene wherein the alkynylene group is unsubstituted or substituted with 1 or 2 substituents independently selected from the group consisting of
(a) aryl,
(b) arylalkyl,
(c) heterocycle,
(d) (heterocyclic)alkyl,
(e) cyclolakyl,
(f) cycloalkylalkyl,
(g) alkylthioalkyl, and
(h) hydroxy,
(11) $—L_4$-heterocycle-$L_5—$,
(12) a covalent bond,
(13)

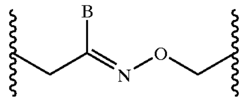

wherein B is selected from the group consisting of loweralkyl and arylalkyl, and
(14)

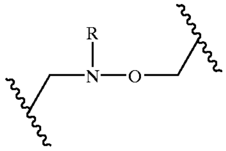
;

Z is selected from the group consisting of
(1) a covalent bond,
(2) —O—,
(3) $S(O)_q—$, and
(4) $—NR_z—$ wherein $R_z$ is selected from the group consisting of
(a) hydrogen,
(b) loweralkyl, (c) aryl,
(d) arylalkyl,
(e) heterocycle,
(f) (heterocyclic)alkyl,
(g) cyclolakyl, and
(h) cycloalkylalkyl;

$R_3$ is selected from the group consisting of
(1) pyridyl and
(2) imidazolyl
wherein the pyridyl or imidazolyl are unsubstituted or substituted with 1, 2, 3, 4, or 5 substituents independently selected from the group consisting of
(a) alkanoyl,
(b) alkoxy wherein the alkoxy is unsubstituted or substituted with 1, 2, 3, 4, or 5 substituents independently selected from the group consisting of
halogen,
aryl, and
cycloalkyl,
(c) alkoxyalkyl wherein the alkoxyalkyl is unsubstituted or substituted with 1 or 2, 3, 4 or 5 substituents independently selected from the group consisting of
aryl and
cycloalkyl,
(d) alkoxycarbonyl wherein the alkoxycarbonyl is unsubstituted or substituted with 1, 2, 3, 4, or 5 substituents independently selected from the group consisting of
aryl, and
cycloalkyl,
(e) alkylsilyloxyalkyl,
(f) arylalkyl,
(g) aryl wherein the aryl is unsubstituted or substituted with 1, 2, 3, 4, or 5 substituents independently selected from the group consisting of
alkanoyl,
alkoxy wherein the alkoxy is unsubstituted or substituted with 1 or 2 substituents selected from the group consisting of cycloalkyl,
carboxaldehyde,
haloalkyl,
halogen,
loweralkyl,
nitro,
—NRR', and
thioalkoxy,
(h) arylalkyl,
(i) aryloxy wherein the aryloxy is unsubstituted or substituted with 1, 2, 3, 4, or 5 substituents independently selected from the group consisting of,
halogen,
nitro, and
—NRR',
(j) (aryl)oyl,
(k) carboxaldehyde,
(l) carboxy,
(m) carboxyalkyl,
(n) —C(O)NRR" wherein R is defined previously and R" is selected from the group consisting of
hydrogen,
loweralkyl, and
carboxyalkyl,
(o) cyano,
(p) cyanoalkyl,
(q) cycloalkyl,
(r) cycloalkylalkyl,
(s) cycloalkoxyalkyl,
(t) halogen,
(u) haloalkyl wherein the haloalkyl is unsubstitute or substituted
with 1, 2, 3, 4, or 5 hydroxyl substituents, with the proviso that no two hydroxyls are attached to the same carbon,
(v) heterocycle,
(w) hydroxyl,
(x) hydroxyalkyl wherein the hydroxyalkyl is unsubstituted or substituted with substituents selected from the group consisting of aryl,
(y) loweralkyl wherein the loweralkyl is unsubstituted or substituted with substituents selected from the group consisting of
heterocycle,
hydroxyl,
with the proviso that no two hydroxyls are attached to the same carbon,
—$NR^{R3}R^{R3'}$, and
—P(O)(OR)(OR'),
(z) nitro,
(aa) —NRR',
(bb) oxo,
(cc) —$SO_2NR_{A'}R_{B'}$ wherein $R_{A'}$ and $R_{B'}$ are independently selected from the group consisting of
hydrogen,
(aryl)oyl,
loweralkyl, and
heterocycle wherein the heterocycle is unsubstituted or substituted with 1, 2, or 3 substituents independently selected from the group consisting of loweralkyl,
(dd) sulfhydryl, and
(ee) thioalkoxy;

$R_4$ is selected from the group consisting of
(1) hydrogen,
(2) loweralkyl,
(3) haloalkyl
(4) halogen,
(5) aryl,
(6) arylalkyl,
(7) heterocycle,
(8) (heterocyclic)alkyl,
(9) alkoxy, and
(10) —NRR'; or $L_1$, Z, and $R_3$ together are selected from the group consisting of
(1) aminoalkyl,
(1) haloalkyl,
(2) halogen,
(3) carboxaldehyde,
(4) (carboxaldehyde)alkyl, and
(5) hydroxyalkyl,
with the proviso that when $L_1$, Z, and $R_3$ together are (1)–(5), $R_1$ is other than hydrogen, or $L_1$, Z, $R_3$, and $R_4$ together are a pyrrolidinone ring wherein the pyrrolidinone ring is unsubstituted or substituted with heterocycle.

In a further aspect of the present invention are disclosed pharmaceutical compositions which comprise a compound of formula I in combination with a pharmaceutically acceptable carrier.

In yet another aspect of the present invention are disclosed pharmaceutical compositions which comprise a compound of formula I in combination with another chemotherapeutic agent and a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound of formula I.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal comprising administering to the patient a therapeutically effective amount of a compound of the invention alone or in combination with another chemotherapeutic agent.

In yet another aspect of the present invention is disclosed a method for treating or preventing intimal hyperplasia associated with restenosis and atherosclerosis in a mammal comprising administering to the mammal a therapeutically effective amount of a compound of claim 1.

The compounds of the invention can comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30, which is hereby incorporated herein by reference.

DETAILED DESCRIPTION

Definitions of Terms

As used herein the terms "Cys," "Glu," "Leu," "Lys," "Met," "nor-Leu," "nor-Val," "Phe," "Ser" and "Val" refer to cysteine, glutamine, leucine, lysine, methionine, norleucine, norvaline, phenylalanine, serine and valine in their L-, D- or DL forms. As used herein these amino acids are in their naturally occurring L-form.

As used herein, the term "carboxy protecting group" refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo (for example by enzymatic hydrolysis) to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields (as described in U.S. Pat. Nos. 3,840,556 and 3,719,667, the disclosures of which are hereby incorporated herein by reference). Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference.

Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy)ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, t-benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to $R_{29}C(O)$— wherein $R_{29}$ is a loweralkyl group. The alkanoyl groups of this invention can be optionally substituted.

The term "alkanoylaminoalkyl" as used herein refers to a loweralkyl radical to which is appended $R_{71}$—NH— wherein $R_{71}$ is an alkanoyl group. The alkanoylaminoalkyl groups of this invention can be optionally substituted.

The term "alkanoyloxy" as used herein refers to $R_{29}C(O)$—O— wherein $R_{29}$ is a loweralkyl group. The alkanoyloxy groups of this invention can be optionally substituted.

The term "alkanoyloxyalkyl" as used herein refers to a loweralkyl radical to which is appended an alkanoyloxy group. The alkanoyloxyalkyl groups of this invention can be optionally substituted.

The term "alkenyl" as used herein refers to a straight or branched chain hydrocarbon containing from 2 to 10 carbon atoms and also containing at least one carbon-carbon double bond. Examples of alkenyl include $—CH{=}CH_2$, $—CH_2CH{=}CH_2$, $—C(CH_3){=}CH_2$, $—CH_2CH{=}CHCH_3$, and the like. The alkenyl groups of this invention can be optionally substituted.

The term "alkenylene" as used herein refers to a divalent group derived from a straight or branched chain hydrocarbon containing from 2 to 20 carbon atoms and also containing at least one carbon-carbon double bond. Examples of alkenylene include $—CH{=}CH—$, $—CH_2CH{=}CH—$, $—C(CH_3){=}CH—$, $—CH_2CH{=}CHCH_2—$, and the like. The alkenylene groups of this invention can be optionally substituted.

The term "alkenyloxy" as used herein refers to an alkenyl group attached to the parent molecular group through an oxygen atom. The alkenyloxy groups of this invention can be optionally substituted.

The term "alkenyloxyalkyl" as used herein refers to a loweralkyl group to which is attached an alkenyloxy group. The alkenyloxyalkyl groups of this invention can be optionally substituted.

The term "alkoxy" as used herein refers to $R_{30}O$— wherein $R_{30}$ is loweralkyl as defined above. Representative examples of alkoxy groups include methoxy, ethoxy, t-butoxy and the like. The alkoxy groups of this invention can be optionally substituted.

The term "alkoxyalkyl" as used herein refers to a loweralkyl group to which is attached an alkoxy group. The alkoxyalkyl groups of this invention can be optionally substituted.

The term "alkoxyalkoxy" as used herein refers to $R_{31}O$—$R_{32}O$— wherein $R_{31}$ is loweralkyl as defined above and $R_{32}$ is an alkylene radical. Representative examples of alkoxyalkoxy groups include methoxymethoxy, ethoxymethoxy, t-butoxymethoxy and the like. The alkoxyalkoxy groups of this invention can be optionally substituted.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like. The alkoxyalkyl groups of this invention can be optionally substituted.

The term "alkoxyalkylcarbonyloxyalkyl" as used herein refers to a loweralkyl radical to which is appended $R_{66}$—C(O)—O— wherein $R_{66}$ is an alkoxyalkyl group.

The term "alkoxyarylalkyl" as used herein refers to a an arylalkyl group to which is attached an alkoxy group. The alkoxyarylalkyl groups of this invention can be optionally substituted.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like. The alkoxycarbonyl groups of this invention can be optionally substituted. The alkoxycarbonyl groups of this invention can be optionally substituted.

The term "alkoxycarbonylalkyl" as used herein refers to an alkoxylcarbonyl group as previously defined appended to a loweralkyl radical. Examples of alkoxycarbonylalkyl include methoxycarbonylmethyl, 2-ethoxycarbonylethyl and the like. The alkoxycarbonylalkyl groups of this invention can be optionally substituted.

The term "alkoxycarbonylaminoalkyl" as used herein refers to a loweralkyl radical to which is appended $R_{69}$—NH— wherein $R_{69}$ is an alkoxycarbonyl group. The alkoxycarbonylaminoalkyl groups of this invention can be optionally substituted.

The term "alkoxycarbonyloxyalkyl" as used herein refers to a loweralkyl radical to which is appended $R_{63}$—O— wherein $R_{63}$ is an alkoxycarbonyl group. The alkoxycarbonyloxyalkyl groups of this invention can be optionally substituted.

The term "alkylamino" as used herein refers to $R_{35}NH$— wherein $R_{35}$ is a loweralkyl group, for example, methylamino, ethylamino, butylamino, and the like. The alkylamino groups of this invention can be optionally substituted.

The term "alkylaminoalkyl" as used herein refers a loweralkyl radical to which is appended an alkylamino group.

The alkylaminoalkyl groups of this invention can be optionally substituted.

The term "alkylaminocarbonylaminoalkyl" as used herein refers to a loweralkyl radical to which is appended $R_{70}$—C(O)—NH— wherein $R_{70}$ is an alkylamino group. The alkylaminocarbonylaminoalkyl groups of this invention can be optionally substituted.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted.

The term "alkylsilyloxy" as used herein refers to a loweralkyl group to which is attached —OSi$R_{W'}R_{X'}R_{Y'}$ wherein $R_{W'}$, $R_{X'}$, and $R_{Y'}$ are selected from the group consisting of loweralkyl.

The term "alkylsulfinyl" as used herein refers to $R_{33}$S(O)— wherein $R_{33}$ is a loweralkyl group. The alkylsulfinyl groups of this invention can be optionally substituted.

The term "alkylsulfinylalkyl" as used herein refers to an alkyl group to which is attached a alkylsulfinyl group. The alkylsulfinylalkyl groups of this invention can be optionally substituted.

The term "alkylsulfonyl" as used herein refers to $R_{34}$S$(O)_2$— wherein $R_{34}$ is a loweralkyl group. The alkylsulfonyl groups of this invention can be optionally substituted.

The term "alkylsulfonylalkyl" as used herein refers to a loweralkyl radical to which is appended an alkylsulfonyl group. The alkylsulfonylalkyl groups of this invention can be optionally substituted.

The term alkylthioalkyl as used herein refers to a lower alkyl group as defined herein attached to the parent molecular moiety through a sulfur atom and an alkylene group. The alkylthioalkyl groups of this invention can be optionally substituted.

The term "alkynyl" as used herein refers to a straight or branched chain hydrocarbon containing from 2 to 10 carbon atoms and also containing at least one carbon-carbon triple bond. Examples of alkynyl include —C≡CH, —$CH_2$C≡CH, —$CH_2$C≡$CH_3$, and the like. The alkynyl groups of this invention can be optionally substituted.

The term "alkynylene" as used herein refers to a divalent group derived from a straight or branched chain hydrocarbon containing from 2 to 10 carbon atoms and also containing at least one carbon-carbon triple bond. Examples of alkynylene include —C≡C—, —$CH_2$C≡C—, —$CH_2$C≡C$CH_2$—, and the like. The alkynylene groups of this invention can be optionally substituted.

The term "amino" as used herein refers to —$NH_2$.

The term "aminocarbonyl" as used herein refers to an amino group attached to the parent molecular group through a carbonyl group. The aminocarbonyl groups of this invention can be optionally substituted.

The term "aminocarbonylalkyl" as used herein refers to an alkyl group to which is attached an aminocarbonyl group. The aminocarbonylalkyl groups of this invention can be optionally substituted.

The term "aminoalkyl" as used herein refers to a loweralkyl radical to which is appended an amino group. The aminoalkyl groups of this invention can be optionally substituted.

The term "aminothiocarbonyl" as used herein refers to an amino group attached to the parent molecular group through a thiocarbonylcarbonyl (C═S) group. The aminothiocarbonyl groups of this invention can be optionally substituted.

The term "aroyloxyalkyl" as used herein refers to a loweralkyl radical to which is appended an aroyloxy group (i.e., $R_{61}$—C(O)O— wherein $R_{61}$ is an aryl group). The aroyloxyalkyl groups of this invention can be optionally substituted.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, sulfhydryl, nitro, cyano, carboxaldehyde, carboxy, alkoxycarbonyl, haloalkyl-C(O)—NH—, haloalkenyl-C(O)—NH— and carboxamide. In addition, substituted aryl groups include tetrafluorophenyl and pentafluorophenyl.

The term "arylalkenyl" as used herein refers to an alkenyl radical to which is appended an aryl group. The arylalkenyl groups of this invention can be optionally substituted.

The term "arylalkenyloxycarbonyloxyalkyl" as used herein refers to a loweralkyl radical to which is appended $R_{68}$—O—C(O)—O— wherein $R_{68}$ is an arylalkenyl group. The arylalkenyloxycarbonyloxyalkyl groups of this invention can be optionally substituted.

The term "arylalkoxy" as used herein refers to an alkoxy group to which is attached an aryl group. The arylalkoxy groups of this invention can be optionally substituted.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like. The arylalkyl groups of this invention can be optionally substituted.

The term "arylalkylcarbonyloxyalkyl" as used herein refers to a loweralkyl radical to which is appended an arylalkylcarbonyloxy group (i.e., $R_{62}$C(O)O— wherein $R_{62}$ is an arylalkyl group). The arylalkylcarbonyloxyalkyl groups of this invention can be optionally substituted.

The term "aryloxy" as used herein refers to an aryl group attached to the parent molecular group through an oxygen atom. The aryloxy groups of this invention can be optionally substituted.

The term "aryloxycarbonyl" as used herein refers to an aryloxy group attached to the parent molecular group through a carbonyl group. The aryloxycarbonyl groups of this invention can be optionally substituted.

The term "aryloyl" as used herein refers to an aryl group attached to the parent molecular group through a carbonyl group. The aryloyl groups of this invention can be optionally substituted.

The term "arylalkyloxycarbonyloxyalkyl" as used herein refers to a loweralkyl radical to which is appended $R_{67}$—O—C(O)—O— wherein $R_{67}$ is an arylalkyl group. The arylalkyloxycarbonyloxyalkyl groups of this invention can be optionally substituted.

The term "aryloxyalkyl" as used herein refers to a loweralkyl radical to which is appended $R_{65}$—O— wherein $R_{65}$ is an aryl group. The aryloxyalkyl groups of this invention can be optionally substituted.

The term "arylalkoxy" as used herein refers to an alkoxy radical to which is appended $R_{65}$—O— wherein $R_{65}$ is an aryl group. The arylalkoxy groups of this invention can be optionally substituted.

The term "arylalkyloxyalkyl" as used herein refers to a loweralkyl radical to which is appended an arylalkoxy group. The arylalkyloxyalkyl groups of this invention can be optionally substituted.

The term "aryloxy" as used herein refers to $R_{65}$—O— wherein $R_{65}$ is an aryl group. The aryloxy groups of this invention can be optionally substituted. The aryloxy groups of this invention can be optionally substituted.

The term "(aryl)oyl" as used herein refers to an aryl group attached to the parent molecular group through a carbonyl group. The (aryl)oyl groups of this invention can be optionally substituted.

The term "aryloxythioalkoxyalkyl" as used herein refers to a loweralkyl radical to which is appended $R_{75}$—S— wherein $R_{75}$ is an aryloxyalkyl group. The aryloxythioalkoxyalkyl groups of this invention can be optionally substituted.

The term "aryloxycarbonyloxyalkyl" as used herein refers to a loweralkyl radical to which is appended $R_{65}$—O—C(O)—O— wherein $R_{65}$ is an aryl group. The aryloxycarbonyloxyalkyl groups of this invention can be optionally substituted.

The term "arylsulfonyl" as used herein refers to $R_{36}S(O)_2$— wherein $R_{36}$ is an aryl group. The arylsulfonyl groups of this invention can be optionally substituted.

The term "arylsulfonyloxy" as used herein refers to $R_{37}S(O)_2O$— wherein $R_{37}$ is an aryl group. The arylsulfonyloxy groups of this invention can be optionally substituted. The term "carboxy" as used herein refers to —COOH.

The term "carboxyalkyl" as used herein refers to a loweralkyl radical to which is appended a carboxy (—COOH) group. The carboxyalkyl groups of this invention can be optionally substituted.

The term "cyanoalkyl" as used herein used herein refers to a loweralkyl radical to which is appended a cyano (—CN) group. The cyanoalkyl groups of this invention can be optionally substituted.

The term "carboxaldehyde" as used herein used herein refers to —CHO.

The term "(carboxaldehyde)alkyl" as used herein used herein refers to a carboxaldehyde group attached to a loweralkyl group. The (carboxaldehyde)alkyl groups of this invention can be optionally substituted.

The terms "cycloalkanoyl" and "(cycloalkyl)oyl" refer to a cycloalkyl group attached to the parent molecular group through a carbonyl group. The cycloalkanoyl and (cycloalkyl)oyl groups of this invention can be optionally substituted.

The term "cycloalkanoylalkyl" as used herein refers to a loweralkyl radical to which is appended a cycloalkanoyl group (i.e., $R_{60}$—C(O)— wherein $R_{60}$ is a cycloalkyl group).

The cycloalkanoylalkyl groups of this invention can be optionally substituted.

The term "cycloalkylalkoxyalkyl" as used herein refers to an alkoxyalkyl group to which is attached a cycloalkyl group. The cycloalkylalkoxyalkyl groups of this invention can be optionally substituted.

The term "cycloalkenyl" as used herein refers to an alicyclic group comprising from 3 to 10 carbon atoms and containing a carbon-carbon double bond including, but not limited to, cyclopentenyl, cyclohexenyl and the like. The cycloalkenyl groups of this invention can be optionally substituted.

The term "cycloalkoxy" as used herein refers to a cycloalkyl group attached to the parent molecular group through an oxygen atom. The cycloalkoxy groups of this invention can be optionally substituted.

The term "cycloalkoxyalkyl" as used herein refers to a loweralkyl group to which is attached a cycloalkoxy group. The cycloalkoxyalkyl groups of this invention can be optionally substituted.

The term "cycloalkoxycarbonyl" as used herein refers to a cycloalkoxy group attached to the parent molecular group through a carbonyl group. The cycloalkoxycarbonyl groups of this invention can be optionally substituted.

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like. The cycloalkyl groups of this invention can be optionally substituted. The cycloalkyl groups of this invention can be optionally substituted.

The term "cycloalkylaminocarbonyl" as used herein refers to $NHR_{60'}C(O)$— wherein $R_{60'}$ is a cycloalkyl group. The cycloalkylaminocarbonyl groups of this invention can be optionally substituted.

The term "cycloalkylaminothiocarbonyl" as used herein refers to $NHR_{60'}C(S)$— wherein $R_{60'}$ is defined above. The cycloalkylaminothiocarbonyl groups of this invention can be optionally substituted.

The term "cycloalkylalkoxy" as used herein refers to an alkoxy radical to which is appended a cycloalkyl group. The cycloalkylalkoxy groups of this invention can be optionally substituted.

The term "cycloalkylalkoxyalkyl" as used herein refers to an alkyl radical to which is appended a cycloalkylalkoxy group. The cycloalkylalkoxyalkyl groups of this invention can be optionally substituted.

The term "cycloalkylalkoxycarbonyl" as used herein refers to a cycloalkylalkoxy radical attached to the parent molecular group through a carbonyl group. The cycloalkylalkoxycarbonyl groups of this invention can be optionally substituted.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl) ethyl, adamantylmethyl and the like. The cycloalkylalkyl groups of this invention can be optionally substituted.

The term "cycloalkyloxycarbonyloxyalkyl" as used herein refers to a loweralkyl radical to which is appended $R_{64}$—O—C(O)—O— wherein $R_{64}$ is a cycloalkyl group. The cycloalkyloxycarbonyloxyalkyl groups of this invention can be optionally substituted.

The term "dialkoxyalkyl" as used herein refers to a loweralkyl radical to which is appended two alkoxy groups. The dialkoxyalkyl groups of this invention can be optionally substituted.

The term "dialkylamino" as used herein refers to $R_{38}R_{39}N$— wherein $R_{38}$ and $R_{39}$ are independently selected from loweralkyl, for example dimethylamino, diethylamino, methyl propylamino, and the like. The dialkylamino groups of this invention can be optionally substituted.

The term "dialkylaminoalkyl" as used herein refers to a loweralkyl radical to which is appended a dialkylamino group. The dialkylaminoalkyl groups of this invention can be optionally substituted.

The term "dialkylaminocarbonylalkyl" as used herein refers to a loweralkyl radical to which is appended $R_{73}$—C(O)— wherein $R_{73}$ is a dialkylamino group. The dialkylaminocarbonylalkyl groups of this invention can be optionally substituted.

The term "dioxoalkyl" as used herein refers to a loweralkyl radical which is substituted with two oxo (=O) groups. The dioxoalkyl groups of this invention can be optionally substituted.

The term "dithioalkoxyalkyl" as used herein refers to a loweralkyl radical to which is appended two thioalkoxy groups. The dithioalkoxyalkyl groups of this invention can be optionally substituted.

The term "halogen" or "halo" as used herein refers to I, Br, Cl or F.

The term "haloalkenyl" as used herein refers to an alkenyl radical, as defined above, bearing at least one halogen substituent. The haloalkenyl groups of this invention can be optionally substituted.

The term "haloalkyl" as used herein refers to a lower alkyl radical, as defined above, bearing at least one halogen substituent, for example, chloromethyl, fluoroethyl or trifluoromethyl and the like. Haloalkyl can also include perfluoroalkyl wherein all hydrogens of a loweralkyl group are replaced with fluorides.

The term "heterocyclic ring" or "heterocyclic" or "heterocycle" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The term "heterocyclic" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring (for example, indolyl, quinolyl, isoquinolyl, tetrahydroquinolyl, benzofuryl or benzothienyl and the like). Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl and benzothienyl. Heterocyclics also include bridged bicyclic groups wherein a monocyclic heterocyclic group is bridged by an alkylene group, for example,

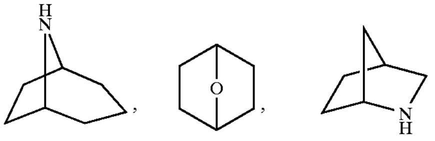

and the like.

Heterocyclics also include compounds of the formula

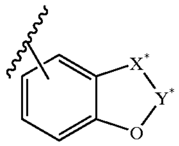

wherein X* is —$CH_2$—, —$CH_2O$— or —O— and Y* is —C(O)— or —(C(R")$_2$)$_v$— wherein R" is hydrogen or $C_1$–$C_4$-alkyl and v is 1, 2 or 3 such as 1,3-benzodioxolyl, 1,4-benzodioxanyl and the like.

Heterocyclics can be unsubstituted or substituted with one, two, three, four or five substituents independently selected from the group consisting of a) hydroxy, b) —SH, c) halo, d) oxo (=O), e) thioxo (=S), f) amino, g) —NHOH, h) alkylamino, i) dialkylamino, j) alkoxy, k) alkoxyalkoxy, l) haloalkyl, m) hydroxyalkyl, n) alkoxyalkyl, o) cycloalkyl which is unsubstituted or substituted with one, two, three or four loweralkyl groups, p) cycloalkenyl which is unsubstituted or substituted with one, two, three or four loweralkyl groups, q) alkenyl, r) alkynyl, s) aryl, t) arylalkyl, u) —COOH, v) —$SO_3H$, w) loweralkyl, x) alkoxycarbonyl, y) —C(O)$NH_2$, z) —C(S)$NH_2$, aa) —C(=N—OH)$NH_2$, bb) aryl-$L_{16}$—C(O)— wherein $L_{16}$ is an alkenylene radical, cc) —S—$L_{17}$—C(O)O$R_{40}$ wherein $L_{17}$ is an alkylene radical which is unsubstituted or substituted with one or two substituents independently selected from the group consisting of alkanoyl, oxo (=O) or methylamino (=CHN$R_{41}R_{42}$ wherein $R_{41}$ is hydrogen or loweralkyl and $R_{42}$ is loweralkyl) and $R_{40}$ is hydrogen or a carboxy-protecting group, dd) —S—$L_{18}$—C(O)N$R_{43}R_{44}$ wherein $L_{18}$ is an alkylene radical which is unsubstituted or substituted with one or two substituents independently selected from the group consisting of alkanoyl, oxo (=O) or methylamino (=CHN$R_{41}R_{42}$ wherein $R_{41}$ is hydrogen or loweralkyl and $R_{43}$ and $R_{44}$ are independently selected from the group consisting of hydrogen, loweralkyl and aryl, ee) —S—$L_{19}$—CN wherein $L_{19}$ is an alkylene radical, ff) —S—$L_{20}$—$R_{45}$ wherein $L_{20}$ is absent or is an alkylene radical or an alkenylene radical or an alkynylene radical wherein the alkylene, alkenylene or alkynylene radical is unsubstituted or substituted with oxo (=O) and $R_{45}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, gg) —O—$L_{21}$—$R_{46}$ wherein $L_{21}$ is absent or is an alkylene radical or an alkenylene radical or an alkynylene radical wherein the alkylene, alkenylene or alkynylene radical is unsubstituted or substituted with one or two substituents independently selected from the group consisting of alkanoyl, oxo (=O) or methylamino (=CHN$R_{41}R_{42}$ wherein $R_{41}$ is hydrogen or loweralkyl and $R_{46}$ is hydrogen, aryl, arylalkyl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, hh) —O—$S(O)_2$—$R_{47}$ wherein $R_{47}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ii) —$S(O)_2$—NH—$R_{48}$ wherein $R_{48}$ is aryl, arylalkyl, heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, jj) alkylsulfinyl, kk) alkylsulfonyl, ll) arylsulfonyl, mm) arylsulfonyloxy, nn) —C(=$NOR_{49}$)C(O)$OR_{50}$ wherein $R_{49}$ is hydrogen or loweralkyl and $R_{50}$ is hydrogen or a carboxy-protecting group, oo) alkoxycarbonylalkyl, pp) carboxyalkyl, qq) cyanoalkyl, rr) alkylaminoalkyl, ss) N-protected alkylaminoalkyl, tt) dialkylaminoalkyl, uu) dioxoalkyl, vv) loweralkyl-C(O)—, ww) loweralkyl-C(S)—, xx) aryl-C(O)—, yy) aryl-C(S)—, zz) loweralkyl-C(O)—O—, aaa) loweralkyl-S—C(S)— bbb) N-protected amino, ccc) aminoalkyl-C(O)—, ddd) N-protected aminoalkyl-C(O)— eee) aminoalkyl-C(S)—, fff) N-protected aminoalkyl-C(S)—, ggg) aminoalkyl, hhh) N-protected aminoalkyl, iii) formyl, jjj) cyano, kkk) nitro, lll) spiroalkyl, mmm) oxoalkyloxy, nnn) $R_{53}$—$L_{22}$—, wherein $L_{22}$ is alkenylene or alkynylene and $R_{53}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, ooo) aryl-NH—C(O)—, ppp) $R_{54}$—N=N— wherein $R_{54}$ is aryl or heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, qqq) =N—$R_{55}$ wherein $R_{55}$ is hydrogen, aryl, heterocyclic, —$S(O)_2$-aryl or —$S(O)_2$-heterocyclic wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, rrr) diarylalkyl-N=N—, sss) aryl-N($R_{56}$)— or arylalkyl-N($R_{56}$)— wherein $R_{56}$ is hydrogen or an N-protecting group, ttt) arylsulfonylalkyl, uuu) heterocyclicsulfonylalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, vvv) =C(CN)(C(O)$NH_2$), www) =C(CN)(C(O)O-loweralkyl), xxx) heterocyclic or heterocyclicalkyl wherein the heterocyclic is unsubstituted or substituted with one, two or three substituents independently selected from the group consisting of loweralkyl, hydroxy, hydroxyalkyl, halo, nitro, oxo (=O), amino, N-protected amino, alkoxy, thioalkoxy and haloalkyl, yyy) hydroxythioalkoxy, zzz) aryloxyalkyl, aaaa) aryloxyalkylthioalkoxy, bbbb) dialkoxyalkyl, cccc) dithioalkoxyalkyl, dddd) arylalkyl-NH—$L_{23}$— wherein L is an alkylene group, eeee) heterocyclicalkyl-NH—$L_{24}$— wherein $L_{24}$ is an alkylene group, ffff) aryl-$S(O)_2$—NH—$L_{25}$— wherein $L_{25}$ is an alkylene group, gggg) heterocyclic—$S(O)_2$—NH—$L_{26}$— wherein $L_{26}$ is an alkylene group, hhhh) aryl-C(O)—NH—$L_{27}$— wherein L is an alkylene group and iiii) heterocyclic—C(O)—NH—$L_{28}$— wherein $L_{28}$ is an alkylene group, jjjj) Ryy$(CH_2)_n$—X—Y—Z—$(CH_2)_m$ wherein Ryy is cycloalkyl, aryl and loweralkyl, n and m are independently 0–2, Z is O or absent, Y is absent, $CH_2$, CHOH or C(O), with the proviso that when X is O, Z is absent and with the proviso that when Z is O, X is absent and with the proviso that when Y is CHOH, X and Z are absent.

The term "(heterocyclic)alkoxy" as used herein refers to an alkoxy group to which is attached a heterocycle. The (heterocyclic)alkoxy groups of this invention can be optionally substituted.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like. The (heterocyclic)alkyl groups of this invention can be optionally substituted.

The term "(heterocyclic)oxy" as used herein refers to a heterocycle connected to the parent molecular group through an oxygen atom. The (heterocyclic)oxy groups of this invention can be optionally substituted.

The term "(heterocyclic)oxyalkyl" as used herein refers to a loweralkyl group to which is attached a (heterocyclic)oxy group. The (heterocyclic)oxyalkyl groups of this invention can be optionally substituted.

The term "(heterocyclic)alkoxyalkyl" as used herein refers to an alkoxyalkyl group to which is attached a heterocycle. The (heterocyclic)alkoxyalkyl groups of this invention can be optionally substituted.

The term "heterocycliccarbonyloxyalkyl" as used herein refers to a loweralkyl radical to which is appended $R_{72}$—C(O)—O— wherein $R_{72}$ is a heterocyclic group. The heterocycliccarbonyloxyalkyl groups of this invention can be optionally substituted.

The term "hydroxy" as used herein refers to —OH.

The term "hydroxyalkyl" as used herein refers to a loweralkyl radical to which is appended an hydroxy group. The hydroxyalkyl groups of this invention can be optionally substituted.

The term "hydroxyarylalkyl" as used herein refers to a arylalkyl group to which is appended a hydroxy group. The hydroxyarylalkyl groups of this invention can be optionally substituted.

The term "hydroxythioalkoxy" as used herein refers to $R_{51}$S— wherein $R_{51}$ is a hydroxyalkyl group. The hydroxythioalkoxy groups of this invention can be optionally substituted.

The term "loweralkyl" as used herein refers to branched or straight chain alkyl groups comprising one to ten carbon atoms, including methyl, ethyl, propyl, isopropyl, n-butyl, t-butyl, neopentyl and the like. The loweralkyl groups of this invention can be optionally substituted.

The term "N-protected alkylaminoalkyl" as used herein refers to an alkylaminoalkyl group wherein the nitrogen is N-protected. The N-protected alkylaminoalkyl groups of this invention can be optionally substituted.

The term "nitro" as used herein refers to —$NO_2$.

The term "oxo" as used herein refers to (=O).

The term "oxoalkyloxy" as used herein refers to an alkoxy radical wherein the loweralkyl moiety is substituted with an oxo (=O) group. The oxoalkyloxy groups of this invention can be optionally substituted.

The term oxyamino(alkyl)carbonylalkyl as used herein refers to.

The term oxyamino(arylalkyl)carbonylalkyl as used herein refers to.

The term oxyaminocarbonylalkyl as used herein refers to.

The term "spiroalkyl" as used herein refers to an alkylene diradical, both ends of which are bonded to the same carbon atom of the parent group to form a spirocyclic group. The spiroalkyl groups of this invention can be optionally substituted.

The term "sulfhydryl" as used herein refers to —SH.

The term "sulfhydrylalkyl" as used herein refers to a loweralkyl group to which is attached a sulfhydryl group. The sulfhydrylalkyl groups of this invention can be optionally substituted.

The term "thioalkoxy" as used herein refers to $R_{52}S$— wherein $R_{52}$ is loweralkyl. Examples of thioalkoxy include, but are not limited to, methylthio, ethylthio and the like. The thioalkoxy groups of this invention can be optionally substituted.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like. The thioalkoxyalkyl groups of this invention can be optionally substituted.

The term "thiocycloalkoxy" as used herein refers to a cycloalkyl group attached to the parent molecular group through a sulfur atom. The thiocycloalkoxy groups of this invention can be optionally substituted.

The term "thiocycloalkoxyalkyl" as used herein refers to a loweralkyl group to which is attached a thiocycloalkoxy group. The thiocycloalkoxyalkyl groups of this invention can be optionally substituted.

Preferred Embodiments

Preferred compounds of the invention are compounds of formula I wherein $R_1$ is unsubstituted or substituted phenyl and $R_2$ is —C(O)NH—CH($R_{14}$)—C(O)O$R_{15}$ or —C(O)NH—CH($R_{14}$)—C(O)NHSO$_2$$R_{16}$ wherein $L_2$, $R_{14}$ $R_{15}$ and $R_{16}$ are defined above.

More preferred compounds of the invention are compounds of formula I wherein $R_1$ is unsubstituted or substituted phenyl and $R_2$ is (a)

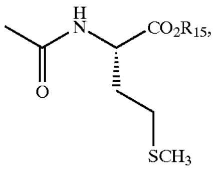

(b)

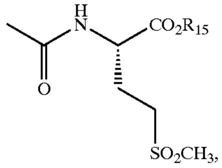

(c)

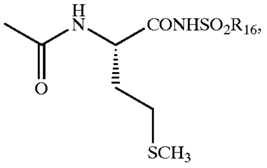

-continued (d)

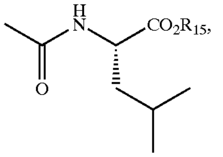

or (e)

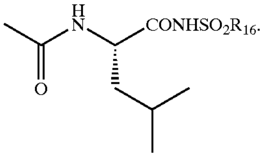

Still more preferred compounds have formula I wherein $R_3$ is selected from the group consisting of (a) pyridyl, (b) imidazolyl, and (c) furyl wherein the pyridyl, imidazolyl, or furyl group may be substituted with 1, 2 or 3 substituents selected from the group consisting of aryl, loweralkyl, halo, nitro, haloalkyl, hydroxy, hydroxyalkyl, amino, N-protected amino, alkoxy, and thioalkoxy.

Still more preferred compounds of the invention have the structure defined immediately above wherein $R_1$ is unsubstituted or substituted phenyl and $R_2$ is (a)

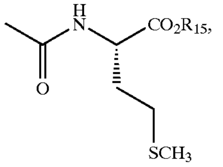

(b)

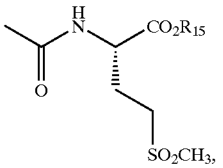

(c)

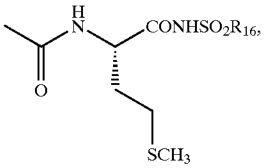

(d)

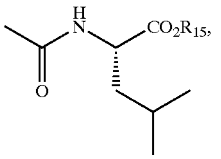

or (e)

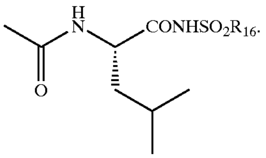

The most preferred compounds have the structure defined immediately above wherein $R_3$ is unsubstituted or substituted pyridyl or imidazolyl.

Protein Farnesyltransferase Inhibition

The ability of the compounds of the invention to inhibit protein farnesyltransferase or protein geranylgeranyltransferase can be measured according to the method of Moores, et al., J. Biol. Chem. 266: 14603 (1991) or the method of Vogt, et al., J. Biol. Chem. 270:660–664 (1995). In addition, procedures for determination of the inhibition of farnesylation of the oncogene protein Ras are described by Goldstein, et al., J. Biol. Chem., 266:15575–15578 (1991) and by Singh in U.S. Pat. No. 5,245,061.

In addition, in vitro inhibition of protein farnesyltransferase may be measured by the following procedure. Rat brain protein farnesyltransferase activity is measured using an Amersham Life Science commercial scintillation proximity assay kit and substituting a biotin-K Ras B fragment (biotin-Lys-Lys-Ser-Lys-Thr-Lys-Cys-Val-Ue-Met-$CO_2H$), 0.1 mM final concentration, for the biotin-lamin substrate provided by Amersham. The enzyme is purified according to Reiss, Y., et al., Cell, 62: 81–88 (1990), utilizing steps one through three. The specific activity of the enzyme is approximately 10 mmol substrate farnesylated/mg enzyme/hour. The percent inhibition of the farnesylation caused by the compounds of the invention (at $10\times10^{-6}$ M) compared to an uninhibited control sample is evaluated in the same Amersham test system.

The % inhibition of protein farnesyltransferase was determined for representative compounds of the invention. The results are summarized in Table 1.

TABLES 1–5

In Vitro Potencies of Representative Compounds

TABLE 1

10/23 Inhibition of farnesyltransferase

| Example | % inhibition at $1 \times 10^{-5}$ M |
|---|---|
| 200 | 93 |
| 350 | 53 |
| 351 | 82 |
| 352 | 52 |
| 353 | 62 |
| 354 | 47 |
| 355 | 43 |
| 356 | 58 |
| 357 | 56 |
| 358 | 45 |
| 359 | 36 |
| 360 | 88 |
| 361 | 97 |
| 362 | 83 |
| 363 | 96 |
| 364 | 69 |
| 365 | 97 |
| 366 | 83 |
| 367 | 81 |
| 368 | 71 |
| 369 | 87 |
| 370 | 86 |
| 371 | 66 |
| 372 | 69 |
| 373 | 76 |
| 374 | 61 |
| 375 | 68 |
| 376 | 80 |
| 377 | 71 |

TABLE 1-continued

10/23 Inhibition of farnesyltransferase

| Example | % inhibition at $1 \times 10^{-5}$ M |
|---|---|
| 378 | 54 |
| 380 | 45 |
| 381 | 79 |
| 382 | >50 |
| 383 | >50 |
| 387 | >50 |
| 388 | >50 |
| 390 | >50 |
| 639 | 44 |
| 659 | 55 |
| 663 | 43 |
| 664 | 75 |
| 669 | 52 |
| 670 | 78 |
| 672 | 48 |
| 674 | 40 |
| 676 | 76 |
| 678 | 73 |
| 680 | 58 |
| 683 | 57 |
| 684 | 48 |
| 685 | 55 |
| 686 | 48 |
| 687 | 78 |
| 688 | 71 |
| 689 | 73 |
| 690 | 61 |
| 692 | 74 |
| 699 | 74 |
| 700 | 68 |
| 701 | 64 |
| 702 | 79 |
| 704 | 67 |
| 705 | 72 |
| 706 | 53 |
| 707 | 66 |
| 708 | 76 |
| 709 | 55 |
| 710 | 45 |
| 711 | 46 |
| 712 | 69 |
| 713 | 40 |
| 714 | 56 |
| 715 | 67 |
| 717 | 75 |
| 718 | 40 |
| 750 | 44 |
| 752 | 58 |
| 753 | 55 |
| 754 | 40 |
| 755 | 44 |
| 756 | 47 |
| 757 | 58 |
| 758 | 46 |
| 759 | 49 |
| 952 | >50 |
| 955 | 50 |
| 974 | >50 |

TABLE 2

Inhibition of farnesyltransferase

| Example | % inhibition at $1 \times 10^{-6}$ M |
|---|---|
| 157 | 92 |
| 158 | 2 |
| 159 | 84 |
| 160 | 30 |
| 161 | 54 |
| 162 | 12 |

TABLE 2-continued

Inhibition of farnesyltransferase

| Example | % inhibition at 1 × $10^{-6}$ M |
|---|---|
| 163 | 18 |
| 164 | 92 |
| 165 | 74 |
| 166 | 97 |
| 167 | 98 |
| 168 | 92 |
| 183 | 98 |
| 184 | 36 |
| 185 | 93 |
| 186 | 86 |
| 187 | 68 |
| 188 | 40 |
| 189 | 88 |
| 190 | 4 |
| 191 | 28 |
| 192 | 95 |
| 193 | 4 |
| 196 | 43 |
| 197 | 1 |
| 201 | 63 |
| 202 | 31 |
| 203 | 76 |
| 204 | 98 |
| 205 | 98 |
| 206 | 67 |
| 207 | 98 |
| 208 | 98 |
| 209 | 74 |
| 210 | 5 |
| 211 | 98 |
| 212 | 12 |
| 213 | 98 |
| 214 | 97 |
| 215 | 82 |
| 216 | 67 |
| 217 | 99 |
| 218 | 89 |
| 219 | 56 |
| 220 | 92 |
| 221 | 55 |
| 222 | 41 |
| 223 | 63 |
| 224 | 41 |
| 225 | 93 |
| 226 | 23 |
| 227 | 94 |
| 228 | 39 |
| 231 | 50 |
| 233 | 65 |
| 234 | 4 |
| 235 | 95 |
| 237 | 98 |
| 238 | 22 |
| 239 | 97 |
| 240 | 98 |
| 241 | 41 |
| 242 | 99 |
| 243 | 23 |
| 244 | 21 |
| 245 | 50 |
| 248 | 79 |
| 249 | 77 |
| 250 | 96 |
| 252 | 98 |
| 253 | 99 |
| 254 | 96 |
| 255 | 98 |
| 256 | 98 |
| 257 | 98 |
| 258 | 98 |
| 259 | 98 |
| 260 | 98 |
| 261 | 98 |
| 262 | 98 |

TABLE 2-continued

Inhibition of farnesyltransferase

| Example | % inhibition at 1 × $10^{-6}$ M |
|---|---|
| 263 | 99 |
| 264 | 98 |
| 265 | 98 |
| 266 | 97 |
| 267 | 96 |
| 268 | 98 |
| 269 | 98 |
| 270 | 98 |
| 271 | 84 |
| 272 | 96 |
| 273 | 96 |
| 274 | 94 |
| 276 | 98 |
| 277 | 98 |
| 278 | 99 |
| 279 | 99 |
| 280 | 98 |
| 281 | 98 |
| 282 | 76 |
| 283 | 98 |
| 284 | 83 |
| 286 | 84 |
| 287 | 24 |
| 288 | 22 |
| 289 | 23 |
| 290 | 74 |
| 291 | 23 |
| 292 | 36 |
| 294 | 98 |
| 295 | 94 |
| 296 | 89 |
| 297 | 65 |
| 298 | 43 |
| 299 | 94 |
| 300 | 22 |
| 301 | 98 |
| 302 | 31 |
| 304 | 99 |
| 305 | 99 |
| 306 | 99 |
| 307 | 82 |
| 308 | 62 |
| 309 | 98 |
| 310 | 98 |
| 311 | 97 |
| 313 | 94 |
| 314 | 97 |
| 315 | 93 |
| 316 | 63 |
| 317 | 54 |
| 318 | 98 |
| 319 | 98 |
| 320 | 93 |
| 321 | 90 |
| 322 | 98 |
| 323 | 98 |
| 324 | 98 |
| 325 | 99 |
| 326 | 91 |
| 327 | 97 |
| 328 | 96 |
| 329 | 98 |
| 330 | 98 |
| 331 | 98 |
| 332 | 26 |
| 333 | 99 |
| 334 | 93 |
| 343 | 72 |
| 344 | 95 |
| 345 | 91 |
| 346 | 98 |
| 347 | 95 |
| 348 | 66 |
| 349 | 99 |

TABLE 2-continued

Inhibition of farnesyltransferase

| Example | % inhibition at 1 × $10^{-6}$ M |
|---|---|
| 379 | 21 |
| 541 | 37 |
| 542 | 67 |
| 544 | 35 |
| 545 | 88 |
| 546 | 97 |
| 547 | 91 |
| 550 | 96 |
| 728 | 78 |
| 552 | 88 |
| 553 | 92 |
| 554 | 96 |
| 555 | 85 |
| 556 | 99 |
| 557 | 93 |
| 560 | 91 |
| 561 | 91 |
| 564 | 98 |
| 565 | 94 |
| 566 | 98 |
| 568 | 93 |
| 569 | 91 |
| 572 | 91 |
| 575 | 70 |
| 576 | 88 |
| 577 | 94 |
| 582 | 99 |
| 583 | 98 |
| 587 | 97 |
| 595 | 97 |
| 607 | 96 |
| 610 | 94 |
| 613 | 97 |
| 617 | 99 |
| 620 | 98 |
| 626 | 61 |
| 627 | 85 |
| 632 | 43 |
| 633 | 32 |
| 636 | 72 |
| 641 | 34 |
| 642 | 48 |
| 644 | 54 |
| 386 | >50 |
| 399 | >50 |
| 403 | 99 |
| 404 | 98 |
| 405 | 98 |
| 406 | 95 |
| 407 | 98 |
| 435 | 96 |
| 451 | 85 |
| 452 | 96 |
| 453 | 90 |
| 456 | 81 |
| 457 | 92 |
| 460 | 88 |
| 463 | 91 |
| 465 | 92 |
| 466 | 93 |
| 467 | 97 |
| 468 | 96 |
| 469 | 92 |
| 470 | 95 |
| 471 | 94 |
| 472 | 97 |
| 473 | 96 |
| 474 | 92 |
| 475 | 21 |
| 476 | 91 |
| 477 | 98 |
| 478 | 98 |
| 479 | 95 |
| 480 | 87 |

TABLE 2-continued

Inhibition of farnesyltransferase

| Example | % inhibition at 1 × $10^{-6}$ M |
|---|---|
| 481 | 95 |
| 488 | 41 |
| 494 | 96 |
| 495 | 95 |
| 496 | 93 |
| 497 | 94 |
| 498 | 98 |
| 499 | 98 |
| 500 | 98 |
| 501 | 84 |
| 502 | 24 |
| 503 | 57 |
| 504 | 90 |
| 505 | 72 |
| 507 | 95 |
| 507 | 96 |
| 508 | 95 |
| 509 | 77 |
| 510 | 84 |
| 512 | 94 |
| 513 | 96 |
| 514 | 94 |
| 515 | 72 |
| 516 | 95 |
| 525 | 99 |
| 528 | 99 |
| 529 | 99 |
| 530 | 94 |
| 537 | 97 |
| 540 | 40 |
| 645 | 37 |
| 646 | 58 |
| 649 | 86 |
| 650 | 68 |
| 651 | 33 |
| 652 | 41 |
| 653 | 62 |
| 655 | 35 |
| 657 | 32 |
| 658 | 73 |
| 661 | 45 |
| 662 | 68 |
| 665 | 55 |
| 666 | 82 |
| 667 | 83 |
| 671 | 36 |
| 673 | 59 |
| 677 | 37 |
| 682 | 31 |
| 691 | 34 |
| 693 | 53 |
| 694 | 45 |
| 696 | 57 |
| 697 | 39 |
| 703 | 40 |
| 716 | 69 |
| 719 | 90 |
| 720 | 70 |
| 721 | 83 |
| 722 | 96 |
| 723 | 87 |
| 724 | 87 |
| 725 | 78 |
| 726 | 81 |
| 727 | 95 |
| 744 | 84 |
| 749 | 84 |
| 751 | 32 |
| 764 | 88 |
| 765 | 76 |
| 768 | 67 |
| 771 | 72 |
| 772 | 79 |
| 773 | 41 |

TABLE 2-continued

Inhibition of farnesyltransferase

| Example | % inhibition at 1 × $10^{-6}$ M |
|---|---|
| 774 | 48 |
| 775 | 32 |
| 776 | 36 |
| 777 | 83 |
| 782 | 96 |
| 786 | 34 |
| 787 | 70 |
| 788 | 44 |
| 789 | 86 |
| 790 | 88 |
| 791 | 53 |
| 792 | 88 |
| 793 | 94 |
| 794 | 92 |
| 796 | 35 |
| 797 | 35 |
| 806 | 72 |
| 807 | 90 |
| 808 | 88 |
| 809 | 78 |
| 810 | 89 |
| 812 | 94 |
| 813 | 95 |
| 816 | 87 |
| 824 | 90 |
| 831 | 92 |
| 832 | 80 |
| 834 | 55 |
| 835 | 96 |
| 844 | 92 |
| 846 | 85 |
| 850 | 90 |
| 862 | 95 |
| 866 | 62 |
| 867 | 71 |
| 868 | 89 |
| 872 | 74 |
| 878 | 95 |
| 879 | 95 |
| 886 | 35 |
| 889 | 95 |
| 902 | 85 |
| 903 | 78 |
| 908 | 88 |
| 910 | 42 |
| 911 | 65 |
| 918 | 97 |
| 923 | 78 |
| 924 | 77 |
| 925 | 87 |
| 926 | 69 |
| 936 | 69 |
| 937 | 95 |
| 962 | >50 |
| 964 | >50 |
| 979 | 26 |
| 982 | 64 |
| 987 | 93 |
| 988 | 92 |
| 989 | 88 |

TABLE 3

Inhibition of farnesyltransferase

| Example | % inhibition at 1 × $10^{-7}$ M |
|---|---|
| 434 | 93 |
| 436 | 89 |
| 437 | 89 |
| 438 | 90 |
| 439 | 80 |
| 440 | 92 |
| 441 | 91 |
| 442 | 88 |
| 443 | 97 |
| 444 | 95 |
| 445 | 94 |
| 446 | 91 |
| 447 | 91 |
| 448 | 92 |
| 449 | 91 |
| 450 | 96 |
| 455 | 83 |
| 458 | 87 |
| 459 | 92 |
| 461 | 93 |
| 462 | 91 |
| 464 | 86 |
| 482 | 96 |
| 483 | 95 |
| 484 | 97 |
| 485 | 96 |
| 486 | 97 |
| 487 | 81 |
| 489 | 86 |
| 490 | 70 |
| 491 | 94 |
| 492 | 95 |
| 493 | 51 |
| 511 | 82 |
| 519 | 89 |
| 520 | 97 |
| 521 | 94 |
| 522 | 93 |
| 523 | 97 |
| 524 | 99 |
| 526 | 96 |
| 527 | 97 |
| 531 | 74 |
| 532 | 88 |
| 533 | 91 |
| 534 | 84 |
| 535 | 89 |
| 536 | 79 |
| 539 | 89 |
| 548 | 86 |
| 549 | 98 |
| 551 | 93 |
| 558 | 87 |
| 559 | 96 |
| 562 | 95 |
| 563 | 95 |
| 570 | 92 |
| 571 | 88 |
| 573 | 72 |
| 574 | 81 |
| 578 | 90 |
| 579 | 92 |
| 580 | 90 |
| 581 | 96 |
| 584 | 96 |
| 585 | 96 |
| 589 | 91 |
| 590 | 95 |
| 592 | 93 |
| 593 | 86 |
| 594 | 95 |
| 597 | 75 |
| 600 | 93 |
| 601 | 92 |
| 602 | 97 |
| 604 | 86 |
| 609 | 95 |

TABLE 3-continued

Inhibition of farnesyltransferase

| Example | % inhibition at 1 × $10^{-7}$ M |
|---|---|
| 611 | 95 |
| 615 | 94 |
| 616 | 95 |
| 618 | 89 |
| 621 | 98 |
| 622 | 95 |
| 623 | 96 |
| 729 | 73 |
| 730 | 96 |
| 731 | 65 |
| 732 | 84 |
| 733 | 60 |
| 734 | 49 |
| 735 | 96 |
| 736 | 96 |
| 737 | 95 |
| 738 | 54 |
| 739 | 83 |
| 740 | 94 |
| 741 | 89 |
| 742 | 87 |
| 743 | 51 |
| 745 | 93 |
| 746 | 84 |
| 747 | 68 |
| 748 | 56 |
| 769 | 90 |
| 770 | 91 |
| 781 | 91 |
| 785 | 96 |
| 795 | 87 |
| 798 | 95 |
| 799 | 96 |
| 800 | 74 |
| 801 | 87 |
| 802 | 88 |
| 811 | 85 |
| 814 | 81 |
| 815 | 71 |
| 817 | 60 |
| 818 | 78 |
| 822 | 93 |
| 823 | 75 |
| 825 | 79 |
| 839 | 63 |
| 849 | 66 |
| 854 | 78 |
| 855 | 92 |
| 856 | 97 |
| 857 | 92 |
| 859 | 86 |
| 861 | 65 |
| 863 | 72 |
| 864 | 84 |
| 865 | 95 |
| 869 | 92 |
| 874 | 90 |
| 875 | 92 |
| 876 | 92 |
| 891 | 94 |
| 893 | 87 |
| 894 | 89 |
| 895 | 92 |
| 896 | 96 |
| 900 | 95 |
| 906 | 88 |
| 912 | 85 |
| 913 | 89 |
| 914 | 91 |
| 917 | 78 |
| 919 | 91 |
| 921 | 82 |
| 929 | 81 |
| 931 | 98 |

TABLE 3-continued

Inhibition of farnesyltransferase

| Example | % inhibition at 1 × $10^{-7}$ M |
|---|---|
| 933 | 91 |
| 935 | 72 |
| 940 | 92 |
| 941 | 90 |
| 945 | 80 |
| 947 | 79 |
| 948 | 75 |
| 949 | 57 |
| 950 | 71 |
| 951 | 71 |
| 959 | >50 |
| 983 | 66 |
| 984 | 86 |
| 990 | 84 |
| 993 | 90 |

TABLE 4

Inhibition of farnesyltransferase

| Example | % inhibition at 1 × $10^{-8}$ M |
|---|---|
| 384 | 91 |
| 397 | 50 |
| 398 | >50 |
| 400 | 98 |
| 401 | 66 |
| 408 | >95 |
| 409 | 84 |
| 410 | 94 |
| 517 | 92 |
| 518 | 90 |
| 567 | 69 |
| 586 | 90 |
| 588 | 68 |
| 591 | 82 |
| 599 | 86 |
| 603 | 94 |
| 605 | 68 |
| 606 | 93 |
| 608 | 91 |
| 612 | 96 |
| 614 | 92 |
| 619 | 95 |
| 760 | 95 |
| 762 | 84 |
| 763 | 92 |
| 766 | 95 |
| 767 | 97 |
| 779 | 70 |
| 780 | 71 |
| 803 | 95 |
| 804 | 95 |
| 805 | 96 |
| 819 | 76 |
| 820 | 66 |
| 821 | 75 |
| 826 | 92 |
| 827 | 77 |
| 828 | 87 |
| 829 | 92 |
| 833 | 78 |
| 836 | 95 |
| 837 | 91 |
| 838 | 92 |
| 840 | 73 |
| 841 | 93 |
| 842 | 88 |
| 843 | 96 |
| 845 | 85 |

TABLE 4-continued

Inhibition of farnesyltransferase

| Example | % inhibition at 1 × $10^{-8}$ M |
|---|---|
| 847 | 85 |
| 848 | 87 |
| 851 | 82 |
| 852 | 79 |
| 853 | 85 |
| 858 | 60 |
| 860 | 85 |
| 870 | 91 |
| 871 | 94 |
| 873 | 97 |
| 877 | 68 |
| 880 | 95 |
| 881 | 69 |
| 882 | 79 |
| 883 | 91 |
| 884 | 94 |
| 885 | 95 |
| 887 | 92 |
| 888 | 86 |
| 892 | 59 |
| 897 | 76 |
| 898 | 82 |
| 899 | 88 |
| 901 | 84 |
| 904 | 85 |
| 905 | 86 |
| 907 | 79 |
| 909 | 79 |
| 916 | 96 |
| 920 | 96 |
| 922 | 96 |
| 927 | 74 |
| 928 | 84 |
| 930 | 66 |
| 932 | 60 |
| 934 | 71 |
| 938 | 61 |
| 939 | 72 |
| 942 | 58 |
| 943 | 79 |
| 944 | 88 |
| 946 | 52 |
| 954 | >50 |
| 958 | >50 |
| 960 | >50 |
| 985 | 89 |
| 986 | 95 |
| 991 | 69 |
| 992 | 93 |
| 994 | 83 |
| 995 | 92 |
| 996 | 80 |

TABLE 5

Inhibition of geranylgeranyltransferase I.

| Example | Activity |
|---|---|
| 387 | >50% inhibition at 1 × $10^{-6}$ M |
| 388 | >50% inhibition at 1 × $10^{-7}$ M |
| 389 | >50% inhibition at 1 × $10^{-6}$ M |
| 390 | >50% inhibition at 1 × $10^{-5}$ M |
| 392 | >50% inhibition at 1 × $10^{-5}$ M |
| 399 | >50% inhibition at 1 × $10^{-6}$ M |
| 953 | >50% inhibition at 1 × $10^{-6}$ M |
| 955 | >50% inhibition at 1 × $10^{-7}$ M |
| 962 | >50% inhibition at 1 × $10^{-7}$ M |
| 964 | >50% inhibition at 1 × $10^{-6}$ M |
| 966 | >50% inhibition at 1 × $10^{-6}$ M |
| 967 | >50% inhibition at 1 × $10^{-6}$ M |

TABLE 5-continued

Inhibition of geranylgeranyltransferase I.

| Example | Activity |
|---|---|
| 969 | >50% inhibition at 1 × $10^{-5}$ M |
| 974 | >50% inhibition at 1 × $10^{-5}$ M |

TABLE 6

Inhibition of farnesyltransferase

| Example | % inhibition 10 μM | % inhibition 1 μM |
|---|---|---|
| 997 | | 91** |
| 998 | | 79** |
| 999 | | 90 |
| 1000 | | 82* |
| 1001 | | 92** |
| 1002 | | 82** |
| 1003 | | 92* |
| 1004 | | 92** |
| 1005 | | 95** |
| 1006 | | 95** |
| 1007 | | 85** |
| 1008 | | 95** |
| 1009 | | 86** |
| 1010 | | 90* |
| 1011 | | 92** |
| 1012 | | 88* |
| 1013 | | 80* |
| 1014 | | 91 |
| 1015 | | 59* |
| 1016 | | 92* |
| 1017 | | 51* |
| 1018 | | 97 |
| 1019 | | 70 |
| 1020 | | 39 |
| 1021 | | 93* |
| 1022 | | 91** |
| 1023 | | 89** |
| 1024 | | 89** |
| 1025 | | 91** |
| 1026 | | 74** |
| 1027 | | 81** |
| 1028 | | 92** |
| 1029 | | 82** |
| 1030 | | 92** |
| 1031 | | 90** |
| 1032 | | 93** |
| 1033 | | 76** |
| 1034 | | 77 |
| 1035 | | 76 |
| 1036 | | 79 |
| 1037 | | 88 |
| 1038 | | 57 |
| 1039 | | 89** |
| 1040 | | 90** |
| 1041 | | 48 |
| 1042 | | 88 |
| 1043 | | 90* |
| 1044 | | 76* |
| 1045 | | 86* |
| 1046 | | 93 |
| 1047 | | 95 |
| 1048 | | 78** |
| 1049 | | 93** |
| 1050 | | 62** |
| 1051 | | 79** |
| 1052 | | 91** |
| 1053 | | 60** |
| 1054 | | 89** |
| 1055 | | 85** |
| 1056 | | 75** |
| 1057 | | 82* |
| 1058 | | 89 |

TABLE 6-continued

Inhibition of farnesyltransferase

| Example | % inhibition 10 μM | % inhibition 1 μM |
|---|---|---|
| 1059 | | 92* |
| 1060 | | 42 |
| 1061 | | 88* |
| 1062 | | 93 |
| 1063 | | 92** |
| 1064 | | 95** |
| 1065 | | 78* |
| 1066 | | 73** |
| 1067 | | 93* |
| 1068 | | 79** |
| 1069 | | 74* |
| 1070 | | 93** |
| 1071 | | 95* |
| 1072 | | 82* |
| 1073 | | 93** |
| 1074 | | 82 |
| 1075 | | 90** |
| 1076 | | 69** |
| 1077 | | 93** |
| 1078 | | 86* |
| 1079 | | 90 |
| 1080 | | 87 |
| 1081 | | 61 |
| 1082 | | 84* |
| 1083 | | 88 |
| 1084 | | 76** |
| 1085 | | 93* |
| 1086 | | 87* |
| 1087 | | 76* |
| 1088 | | 73* |
| 1089 | | 86* |
| 1090 | | 81** |
| 1091 | | 87* |
| 1092 | | 74** |
| 1093 | | 95** |
| 1094 | | 96** |
| 1095 | | 76* |
| 1096 | | 86* |
| 1097 | | 80** |
| 1098 | | 60* |
| 1099 | | 87** |
| 1100 | | 82** |
| 1101 | | 86* |
| 1102 | | 84** |
| 1103 | | 92* |
| 1104 | | 89** |
| 1105 | | 91** |
| 1106 | | 67** |
| 1107 | | 88** |
| 1108 | | 95** |
| 1109 | | 74** |
| 1110 | | |
| 1111 | | 63** |
| 1112 | | 62 |
| 1113 | | 55 |
| 1114 | | 83** |
| 1115 | | 94* |
| 1116 | | 91** |
| 1117 | | 92* |
| 1118 | | 86* |
| 1119 | | 84** |
| 1120 | | 93 |
| 1121 | | 72* |
| 1122 | | 92** |
| 1123 | | 90* |
| 1124 | | 90* |
| 1125 | | 92* |
| 1126 | | 87 |
| 1127 | | 90* |
| 1128 | | 86* |
| 1129 | | 92** |
| 1130 | | 88** |
| 1131 | | 96** |
| 1132 | | 97* |

TABLE 6-continued

Inhibition of farnesyltransferase

| Example | % inhibition 10 μM | % inhibition 1 μM |
|---|---|---|
| 1133 | | 75* |
| 1134 | | 95** |
| 1135 | | 88* |
| 1136 | | 91 |
| 1137 | | 83** |
| 1138 | | 65* |
| 1139 | | 92* |
| 1140 | | 77** |
| 1141 | | 80* |
| 1142 | | 84** |
| 1143 | | 92* |
| 1144 | | 76* |
| 1145 | | 83* |
| 1146 | | 61** |
| 1147 | | 93* |
| 1148 | | 79** |
| 1149 | | 94* |
| 1150 | | 92* |
| 1151 | | 91* |
| 1152 | | 96* |
| 1153 | | 89* |
| 1154 | | 93* |
| 1155 | | 91* |
| 1156 | | 87 |
| 1157 | | 66** |
| 1158 | 75 | |
| 1159 | | 72* |
| 1160 | | 83* |
| 1161 | | 87* |
| 1162 | | 84* |
| 1163 | | 73** |
| 1164 | | 94 |
| 1165 | | 84* |
| 1166 | | 74** |
| 1167 | | 91* |
| 1168 | | 88* |
| 1169 | | 77 |
| 1170 | | 74* |
| 1171 | | 74** |
| 1172 | | 38* |
| 1173 | | 89** |
| 1174 | | 79** |
| 1175 | | 96 |
| 1176 | | 97* |
| 1177 | | 19 |
| 1178 | | 88** |
| 1179 | | 85* |
| 1180 | | 93* |
| 1181 | | 82* |
| 1182 | | 92** |
| 1183 | | 79** |
| 1184 | | 84** |
| 1185 | | 85** |
| 1186 | | 93** |
| 1187 | | 93** |
| 1188 | | 93** |
| 1189 | | 74** |
| 1190 | | 95** |
| 1191 | | 85** |
| 1192 | | 91* |
| 1193 | | 95** |
| 1194 | | 78** |
| 1195 | | 94* |
| 1196 | | 87* |
| 1197 | | 85* |
| 1198 | | 86* |
| 1199 | | 71 |
| 1200 | | 97* |
| 1201 | | 73* |
| 1202 | | 96** |
| 1203 | | 84* |
| 1204 | | 93* |
| 1205 | | 55** |
| 1206 | | 63** |

TABLE 6-continued

Inhibition of farnesyltransferase

| Example | % inhibition 10 μM | % inhibition 1 μM |
|---|---|---|
| 1207 | | 91* |
| 1208 | | 89* |
| 1209 | | 87* |
| 1210 | | 64** |
| 1211 | | 94 |
| 1212 | | 86* |
| 1213 | | 79** |
| 1214 | | 92** |
| 1215 | | 17 |
| 1216 | | 88** |
| 1217 | | 87* |
| 1218 | | 54** |
| 1219 | | 85** |
| 1220 | | |
| 1221 | | 82** |
| 1222 | | 89* |
| 1223 | | 91** |
| 1224 | | 88* |
| 1225 | | 92** |
| 1226 | | 69** |
| 1227 | | 91 |
| 1228 | | 88* |
| 1229 | | 66** |
| 1230 | | 77** |
| 1231 | | 93* |
| 1232 | | 68** |
| 1233 | | 77** |
| 1234 | | 71** |
| 1235 | | 86** |
| 1236 | | 83** |
| 1237 | | 89** |
| 1238 | | 91** |
| 1239 | | 85* |
| 1240 | | 64** |
| 1241 | | 74* |
| 1242 | | 75* |
| 1243 | | 95* |
| 1244 | | 84 |
| 1245 | | 92 |
| 1246 | | 82 |
| 1247 | | 95* |
| 1248 | | 88 |
| 1249 | | 89 |
| 1250 | | 79** |
| 1251 | | 91** |
| 1252 | | 84* |
| 1253 | | 76* |
| 1254 | | 67 |
| 1255 | | 82* |
| 1256 | | 95* |
| 1257 | | 93** |
| 1258 | | 97** |
| 1259 | | 89** |
| 1260 | | 90** |
| 1261 | | 94 |
| 1262 | | 95 |
| 1263 | | 85* |
| 1264 | | 83** |
| 1265 | | 90 |
| 1266 | | 85* |
| 1267 | | 96 |
| 1268 | | 95* |
| 1269 | | 84** |
| 1270 | | 91** |
| 1271 | | 78** |
| 1272 | | 73** |
| 1273 | | 94* |
| 1274 | | 89* |
| 1275 | | 86** |
| 1276 | | 88** |
| 1277 | | 90** |
| 1278 | | 68 |
| 1279 | | 87** |
| 1280 | | 78** |

TABLE 6-continued

Inhibition of farnesyltransferase

| Example | % inhibition 10 μM | % inhibition 1 μM |
|---|---|---|
| 1281 | | 81* |
| 1282 | | 69* |
| 1283 | | 74* |
| 1284 | | 86 |
| 1285 | | 94 |
| 1286 | | 85** |
| 1287 | | 95** |
| 1288 | | 69* |
| 1289 | | 93 |
| 1290 | | 80 |
| 1291 | | |
| 1292 | | |
| 1293 | | |
| 1294 | | |
| 1295 | | |
| 1296 | | |
| 1297 | | |
| 1298 | | 97** |
| 1299 | | 96** |
| 1300 | | 97* |
| 1301 | | 97* |
| 1302 | | 93** |
| 1303 | | 91** |
| 1304 | | 90** |
| 1305 | | 91** |
| 1306 | | 85** |
| 1307 | | 85** |
| 1308 | | 91** |
| 1309 | | 96* |
| 1310 | | 90** |
| 1311 | | 95** |
| 1312 | | 91** |
| 1313 | | 91** |
| 1314 | | 96* |
| 1315 | | 86* |
| 1316 | | 78* |
| 1317 | 99 | 96 |
| 1318 | | |
| 1319 | | 79** |
| 1320 | | 79 |
| 1321 | | |
| 1322 | | |
| 1323 | | |
| 1324 | | |
| 1325 | | |
| 1326 | | |
| 1327 | | |
| 1328 | | |
| 1329 | | |
| 1330 | | |
| 1331 | | |
| 1332 | | 92** |
| 1333 | | 95* |
| 1334 | | 72** |
| 1335 | | 90* |
| 1336 | | 74 |
| 1337 | | 83** |
| 1338 | | 65* |
| 1339 | | |
| 1340 | | 77* |
| 1341 | | 89 |
| 1342 | | |
| 1343 | | 88 |
| 1344 | | 93** |
| 1345 | | 94** |
| 1346 | | 94* |
| 1347 | | 81** |
| 1348 | | 78** |
| 1349 | | 92** |
| 1350 | | |
| 1351 | | |
| 1352 | | |
| 1353 | | |
| 1354 | | 38 |

TABLE 6-continued

Inhibition of farnesyltransferase

| Example | % inhibition 10 $\mu$M | % inhibition 1 $\mu$M |
|---|---|---|
| 1355 | | 46 |
| 1356 | | 80 |
| 1357 | | 78 |
| 1358 | | |
| 1359 | | |
| 1360 | | 98** |
| 1361 | | 96* |
| 1362 | | 83** |
| 1363 | | 88** |
| 1364 | | |
| 1365 | | |
| 1366 | | 79* |
| 1367 | | 93* |
| 1368 | | 92** |
| 1369 | | 94* |
| 1370 | | 86** |
| 1371 | | 94* |
| 1372 | | 95** |
| 1373 | | 95** |
| 1374 | | 93** |
| 1375 | | 80** |
| 1376 | | 86** |
| 1377 | | 95* |
| 1378 | | 68 |
| 1379 | | 41 |
| 1380 | | 87** |
| 1381 | | 65** |
| 1382 | | 86** |
| 1383 | | 88* |
| 1384 | | 69** |
| 1385 | | 93* |
| 1386 | | 88* |
| 1387 | | 82** |
| 1392 | | 93* |
| 1397 | | 87** |
| 1398 | | 81* |
| 1399 | | 94 |
| 1400 | | 95 |

*% inhibition at 0.1 $\mu$M
**% inhibition at 0.01 $\mu$M

Additional methods for the measurement of in vitro inhibition of protein prenylation (i.e., inhibition of farnesyltransferase or geranylgeranyltransferase) are described below.

Assays are performed using the glass fiber filter binding assay procedure with either rabbit reticulocyte lysate or Frase or GGTase I fractions isolated from bovine brains using a combination of hydrophobic and DEAE column chromatography procedures. Protein substrates are purchased from Panvera Corporation (H-ras for FTase, H-ras-CVLL for GGTase I). Tritium labeled prenyl lipid substrates (FPP or GGPP) are obtained from Amersham Life Science.

FTase $^3$H-Farnesyldiphosphate (final concentration 0.6 $\mu$M), H-Ras (final concentration 5.0 $\mu$M) and the test compound (various final concentrations from a stock solution in 50% DMSO/water; final concentration DMSO <2%) were mixed in buffer (50 mM HEPES (pH 7.5), 30 mM $MgCl_2$, 20 mM KCl, 10 $\mu$M $ZnCl_2$, 5 mM DTT, 0.01% Triton X-100) to give a final volume of 50 $\mu$L. The mixture was brought to 37° C., enzyme was added, and the reaction is incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial and 5 mL of scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

GGTase I $^3$H-geranylgeranyldiphosphate (final concentration 0.5 $\mu$M), H-Ras-CVLL (final concentration 5.0 $\mu$M) and the test compound (various final concentrations from a stock solution in 1:1 DMSO/water; final concentration DMSO <2%) were mixed in buffer (50 mM Tris-HCl (pH 7.2), 30 mM $MgCl_2$, 20 mM KCl, 10 $\mu$M $ZnCl_2$, 5 mM DTT, 0.01% Triton X-100) to give a final volume of 50 $\mu$L. The mixture was brought to 37° C., treated with enzyme, and incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial, and 5 mL scintillation fluid was added. The radioisotope retained on the glass fiber filter was counted to reflect the activity of the enzymes. The $IC_{50}$ value was calculated by measuring the activity of the enzyme over a suitable range of inhibitor concentrations.

Additionally, the ability of the compounds of the invention to inhibit prenylation in whole cells, inhibit anchorage-independent tumor cell growth and inhibit human tumor xenograft in mice could be demonstrated according to the methods described in PCT Patent Application No. WO95/25086, published Sep. 21, 1995, which is hereby incorporated herein by reference.

Pharmaceutical Compositions

The compounds of the present invention can be used in the form of pharmaceutically acceptable salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, parnoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I)–(XII) or separately by reacting the carboxylic acid function with a suitable base such as the hydroxide, carbonate or bicarbonate of a pharmaceutically acceptable metal cation or with ammonia or an organic primary, secondary or tertiary amine. Such pharmaceutically acceptable salts include, but are not limited to, cations based on the alkali and alkaline earth metals such as sodium, lithium, potassium, calcium, magnesium, aluminum salts and the like as well as nontoxic ammonium, quaternary ammonium, and amine cations including, but not limited to, ammonium, tetramethylammonium, tetraethylammonium, methylamine, dimethylamine, trimethylamine, triethylamine, ethylamine and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein isoprenyltransferases (i.e, protein farnesyltransferase and/or protein geranylgeranyltransferase) and the isoprenylation (i.e., farnesylation and/or geranylgeranylation) of Ras. These inhibitors of protein isoprenyltransferases are also useful for inhibiting or treating cancer in humans and other mammals. Examples of cancers which may be treated with the compounds of the invention include, but are not limited to, carcinomas such as lung, colorectal, bladder, breast, kidney, ovarian, liver, exocrine pancreatic, cervical, esophageal, stomach and small intestinal; sarcomas such as oesteroma, osteosarcoma, lepoma, liposarcoma, hemanioma and hemangiosarcoma; melanomas such as amelanotic and melanotic; mixed types of cancers such as carcinosarcoma, lymphoid tissue type, follicular reticulum, cell sarcoma and Hodgkins disease and leukemias, such as myeloid, acute lymphoblastic, chronic lymphocytic, acute myloblastic and chronic mylocytic.

The ability of the compounds of the invention to inhibit or treat cancer can be demonstrated according to the methods of Mazerska Z., Woynarowska B., Stefanska B., Borowski S., Drugs Exptl. Clin. Res. 13(6), 345–351 (1987) Bissery, M. C., Guenard F., Guerritte-Voegelein F., Lavelle F., Cancer Res. 51, 4845–4852 (1991) and Rygaard J., and Povlsen C., Acta Pathol. Microbiol. Scand. 77, 758 (1969), which are hereby incorporated herein by reference.

These inhibitors of protein isoprenyltransferases are also useful for treating or preventing restenosis in humans and other mammals. The ability of the compounds of the invention to treat or prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993), which are hereby incorporated herein by reference.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For treatment or prevention of restenosis, the total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, sublingually, by inhalation spray, rectally or topically in dosage unit formulations containing conventional nontoxic pharmaceutically acceptable carriers, adjuvants, and vehicles. Topical administration may also involve the use of transdermal administration such as transdermal patches or iontophoresis devices. The term parenteral as used herein includes subcutaneous injections, intravenous, intramuscular, intrastemal injection or infusion techniques.

Injectable preparations, for example sterile injectable aqueous or oleagenous suspensions, may be formulated according to the known art using suitable dispersing or wetting and suspending agents. The sterile injectable preparation may also be a sterile injectable solution or suspension in a nontoxic parenterally acceptable diluent or solvent (as in a solution in 1,3-propanediol, for example). Among the acceptable vehicles and solvents that may be employed are water, Ringer's solution and isotonic sodium chloride solution. Additionally, sterile, fixed oils are conventionally employed as a solvent or suspending medium. For this purpose, any bland fixed oil may be employed including synthetic mono- or diglycerides. Fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. These dosage forms may also comprise additional substances other than inert diluents such as lubricating agents like magnesium stearate. With capsules, tablets and pills, the dosage forms may also comprise buffering agents. Tablets and pills may also be prepared with enteric coatings.

Liquid dosage forms for oral administration may include pharmaceutically acceptable emulsions, solutions, suspensions, syrups and elixirs containing inert diluents commonly used in the art such as water. Such compositions may also comprise adjuvants such as wetting agents, emulsifying and suspending agents and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq., which is hereby incorporated herein by reference These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine and vinblastine) and etoposide (VP-16); hormones and hormone antagonists (tamoxifen and corticosteroids); and miscellaneous agents (cisplatin, taxol and brequinar).

The above compounds to be employed in combination with the isoprenyl protein transferase inhibitor of the invention will be used in therapeutic amounts as indicated in the Physicians' Desk Reference (PDR) 47th Edition (1993), which is incorporated herein by reference or by such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

Preparation of the Compounds of the Invention

In general, the compounds of the invention can be prepared by the processes illustrated in the following Schemes 1–16. In these general schemes compounds of the formula I are used to exemplify the methods, but the methods are intended to be applicable to all of the compounds of the invention.

SCHEME 1

A.

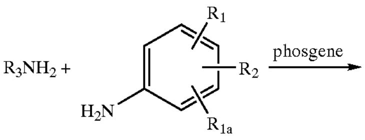

-continued

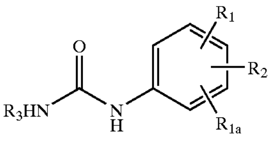

B.

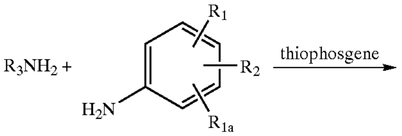

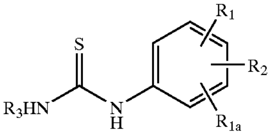

C.

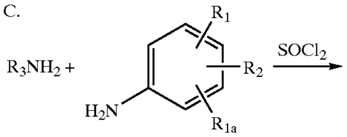

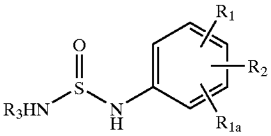

D.

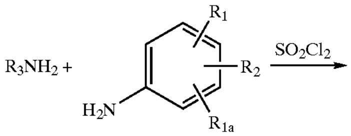

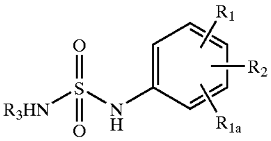

SCHEME 2

A.

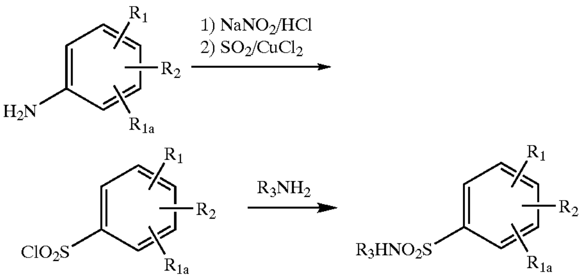

B.

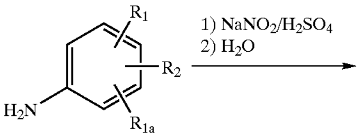

-continued
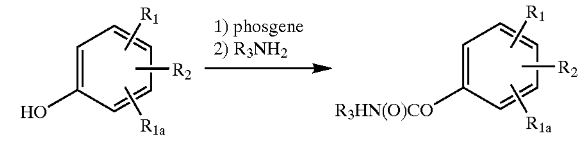
C.
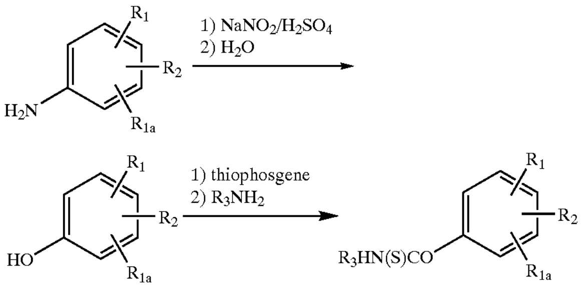
D.
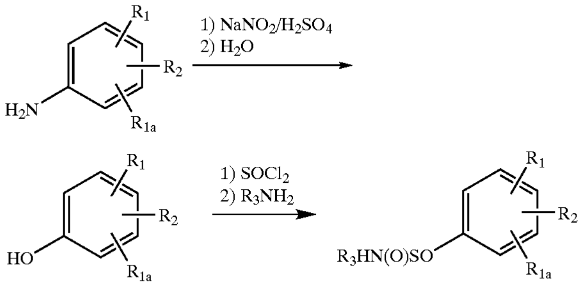
E.
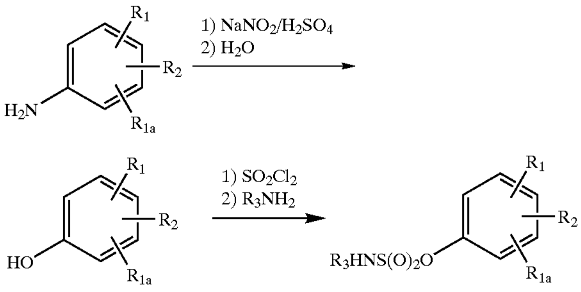
SCHEME 3
A.
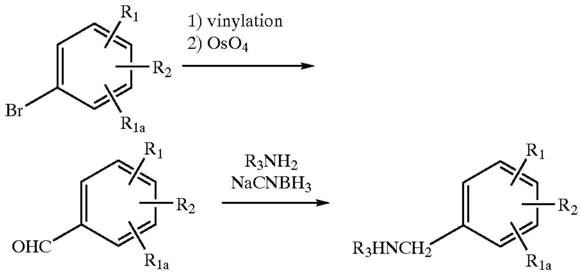
B.
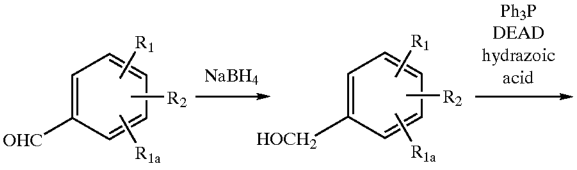
-continued
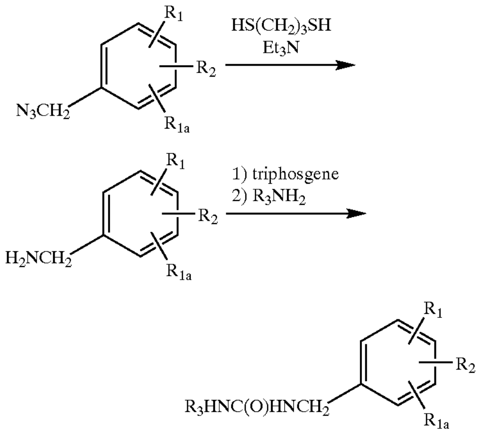
C.
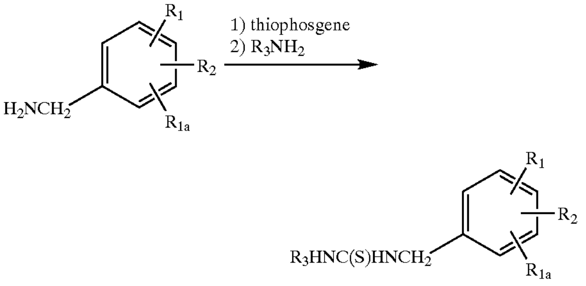
D.
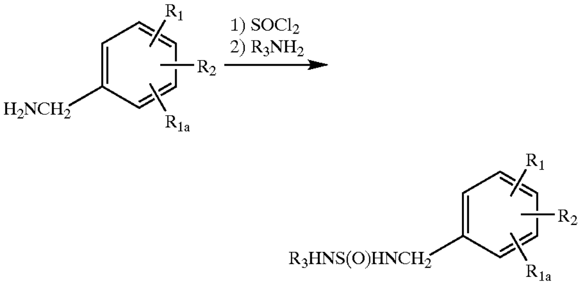
E.
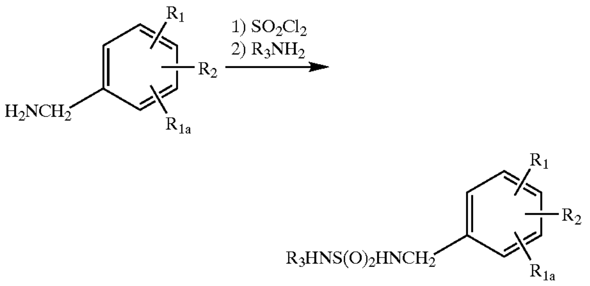
SCHEME 4
A.
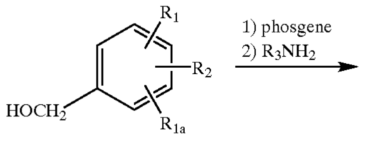

-continued
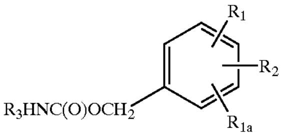
B.
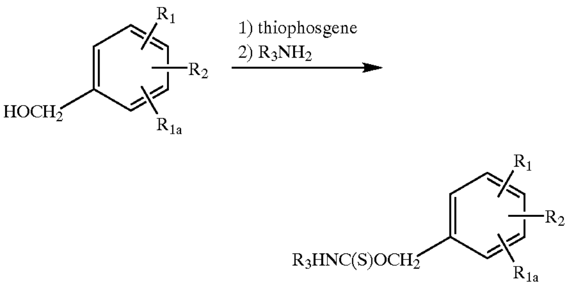
C.
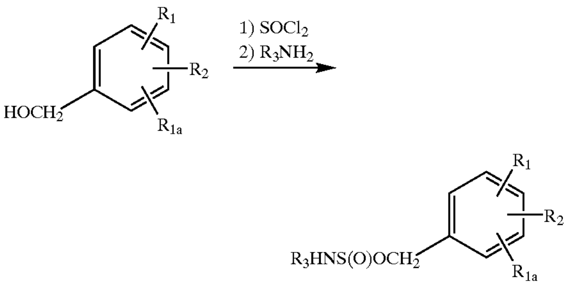
D.
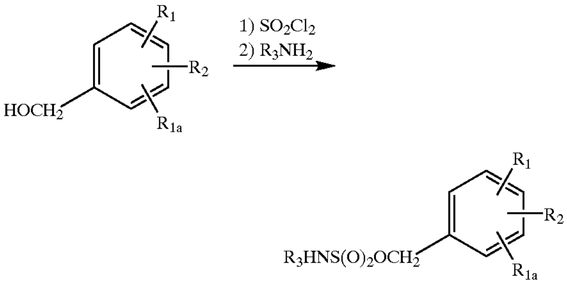
SCHEME 5
A.
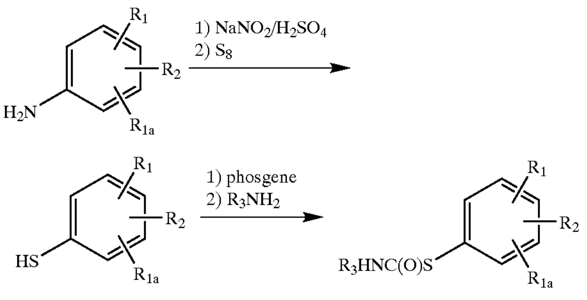
B.
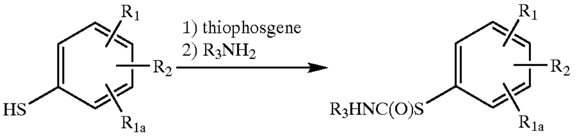
-continued
C.
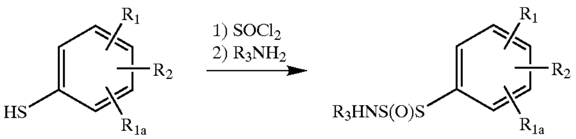
D.
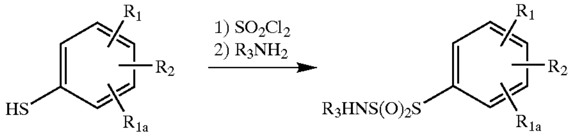
SCHEME 6
A.
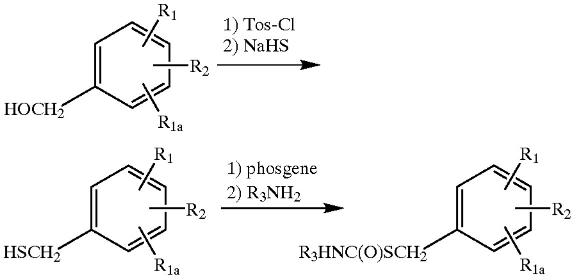
B.
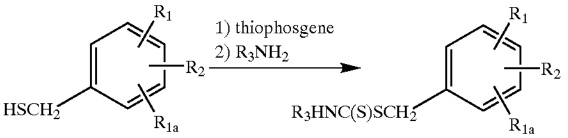
C.
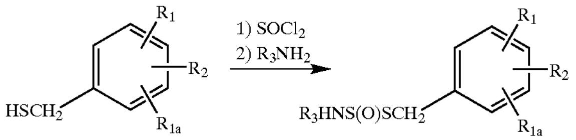
D.
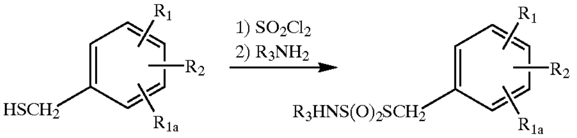
SCHEME 7
A.
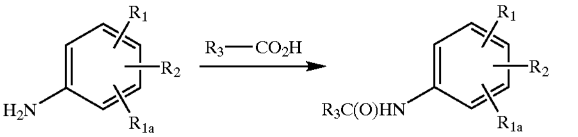
B.
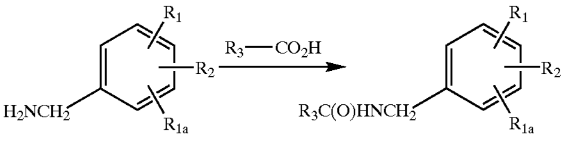

-continued
C.
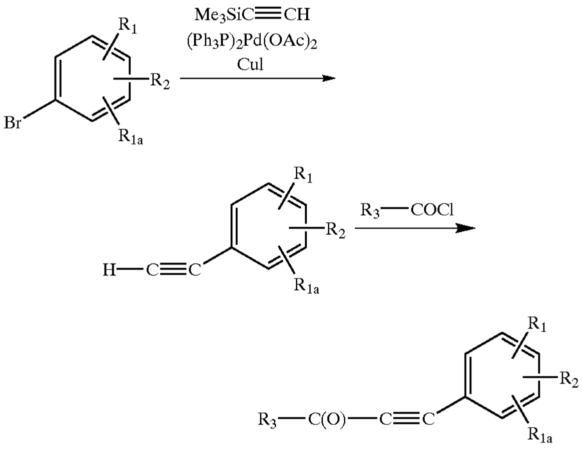
D.
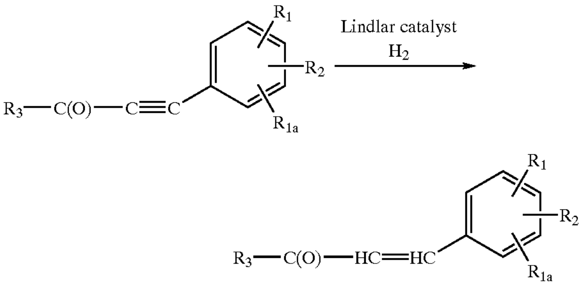
E.
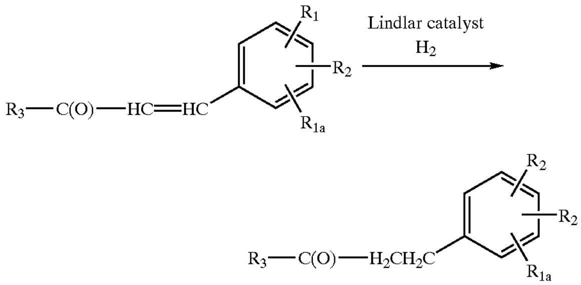
SCHEME 8
A.
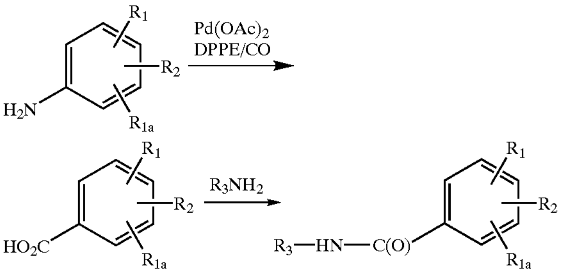
B.
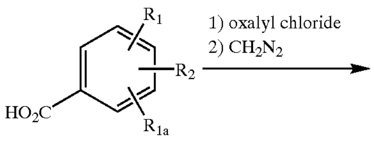
-continued
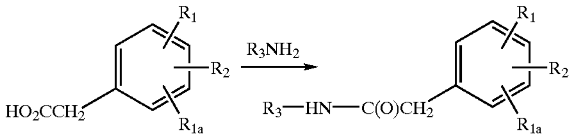
C.
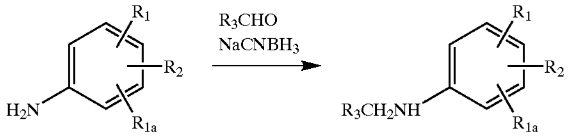
D.
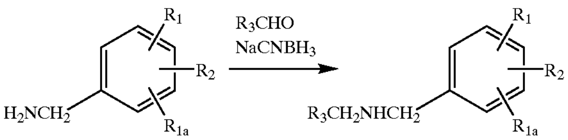
SCHEME 9
A.
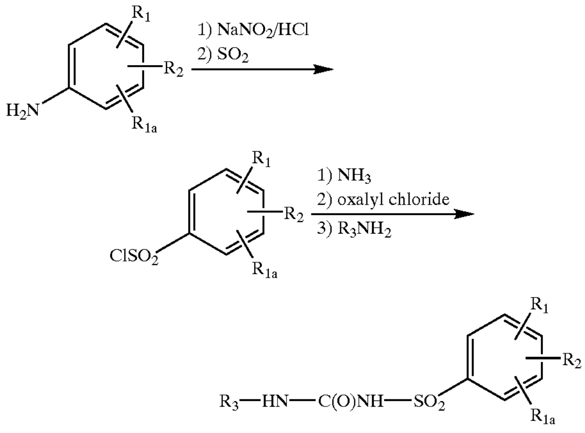
B.
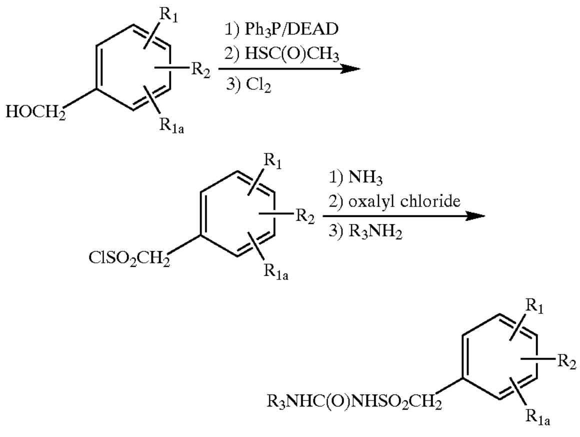
C.
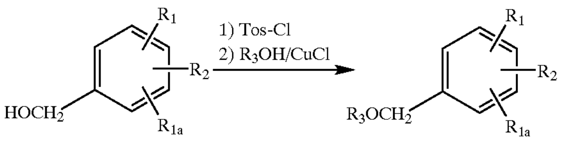

-continued
D.
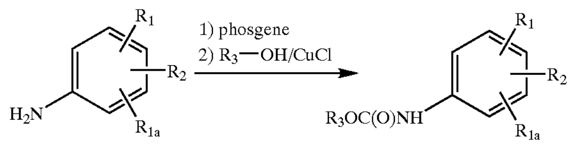
E.
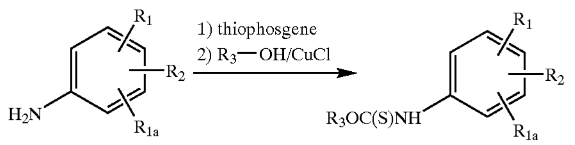
F.
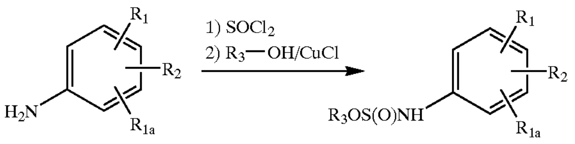
G.
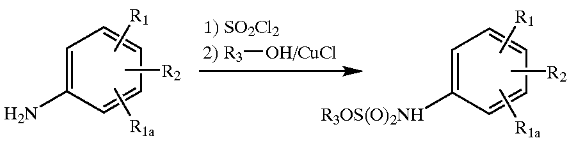
SCHEME 10
A.
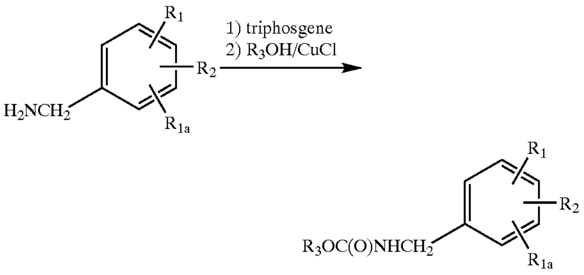
B.
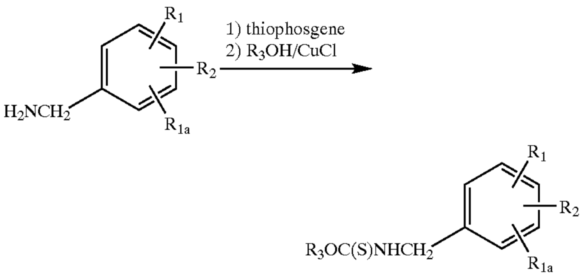
C.
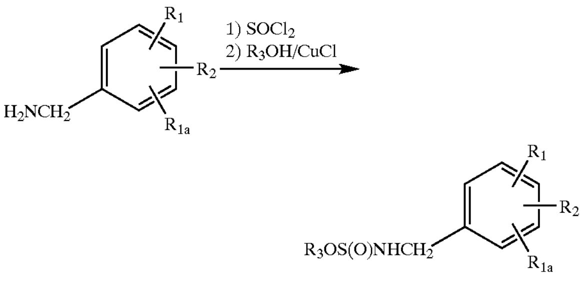
-continued
D.
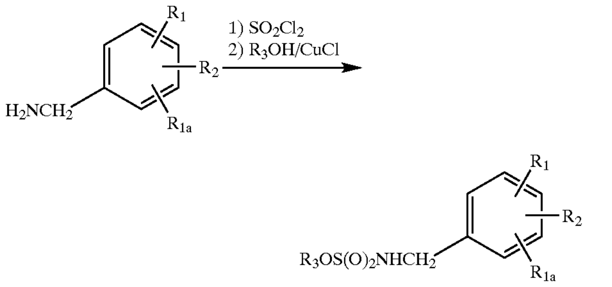
SCHEME 11
A.
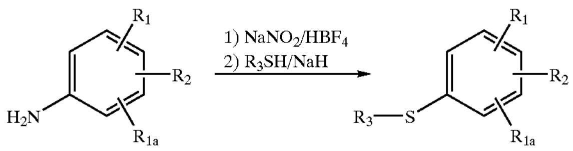
B.
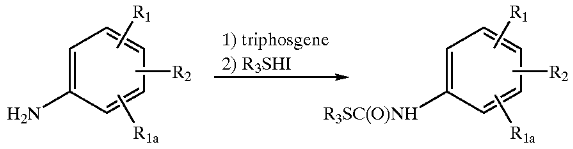
C.
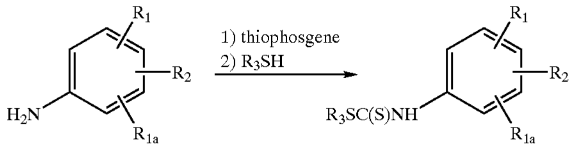
D.
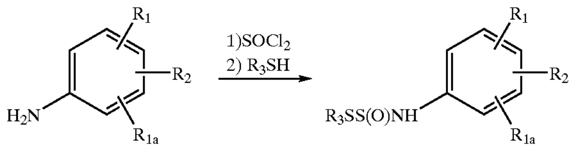
E.
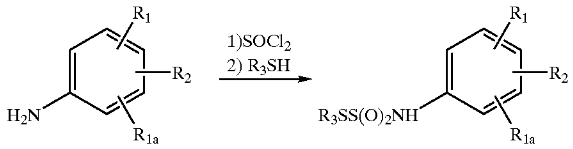
SCHEME 12
A.
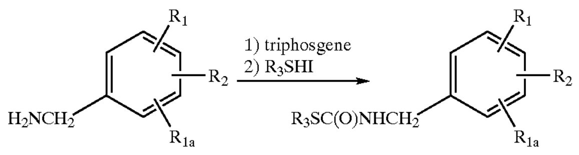

-continued
B.
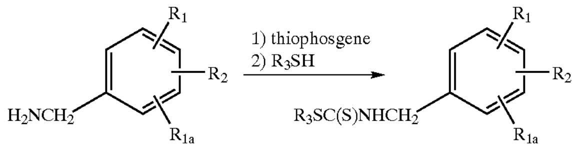
C.
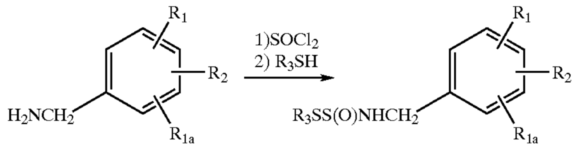
D.
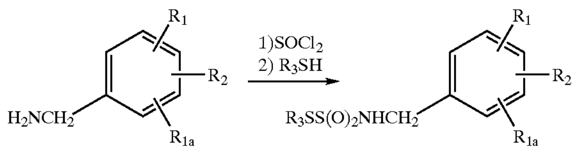
SCHEME 13
A.
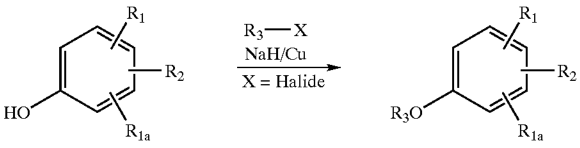
B.
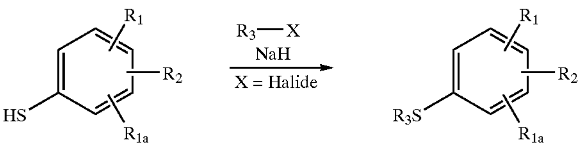
C.
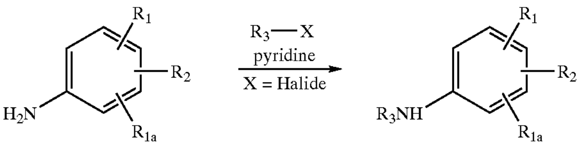
D.
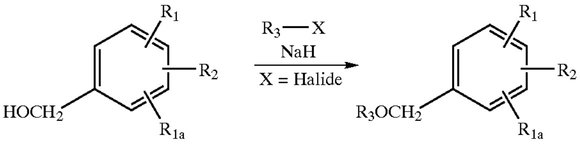
E.
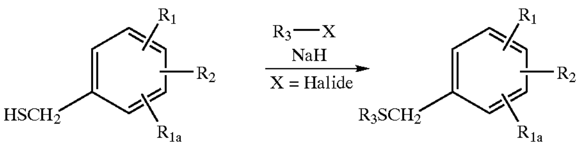
SCHEME 14
A.
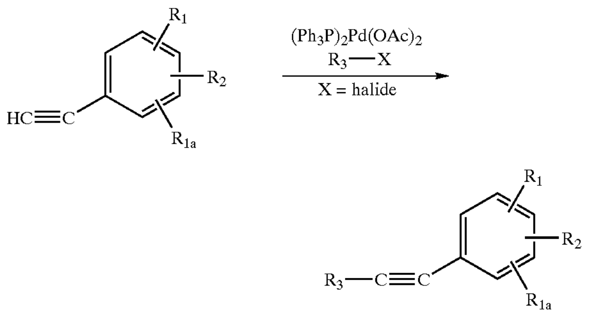
B.
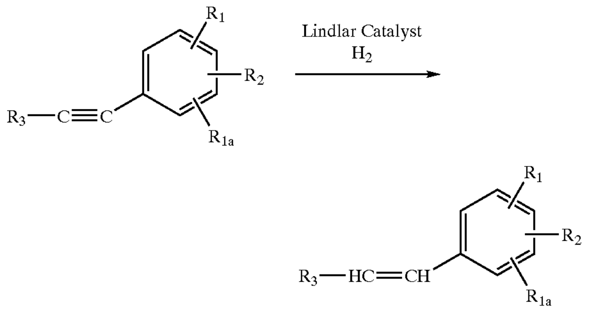
C.
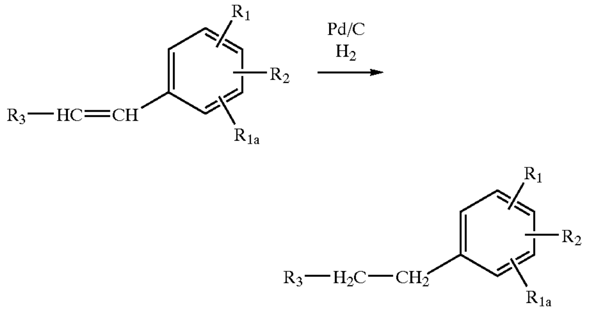
D.
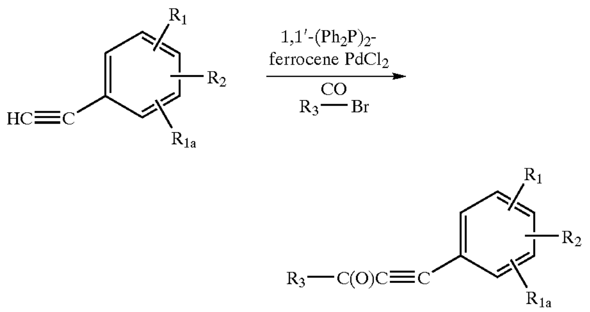
E.
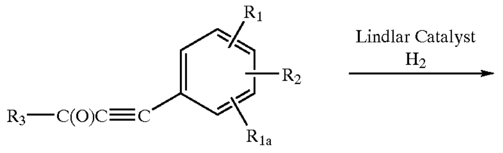

-continued

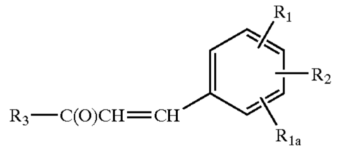

F.

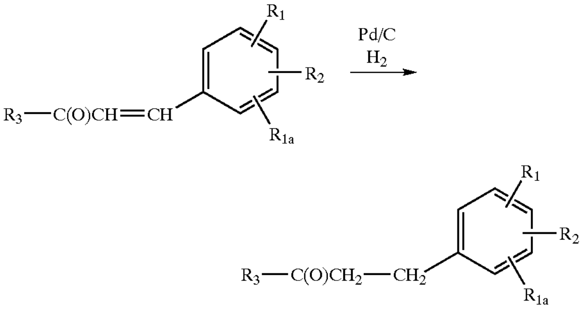

SCHEME 15

A.

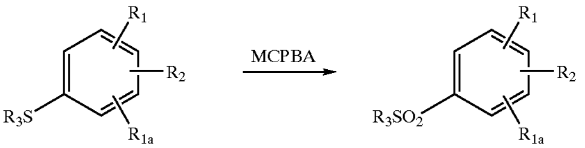

B.

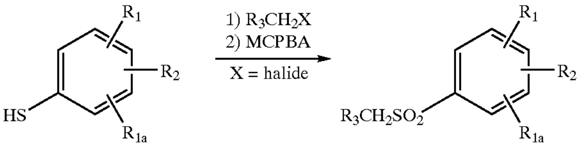

C.

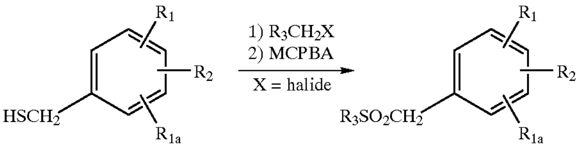

D.

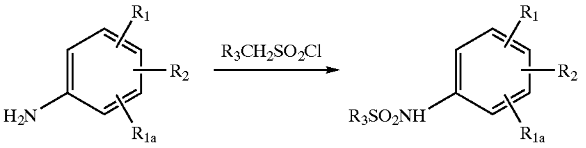

E.

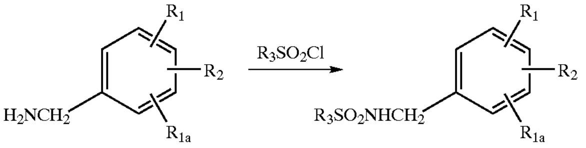

Scheme 16 illustrates an alternative method for preparing compounds wherein $R_2$ is —C(O)NH—CH($R_{14}$)—C(O)$OR_{15}$ or

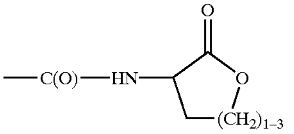

as defined above.

SCHEME 16

A.

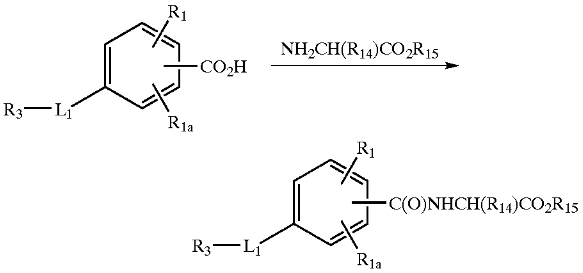

B.

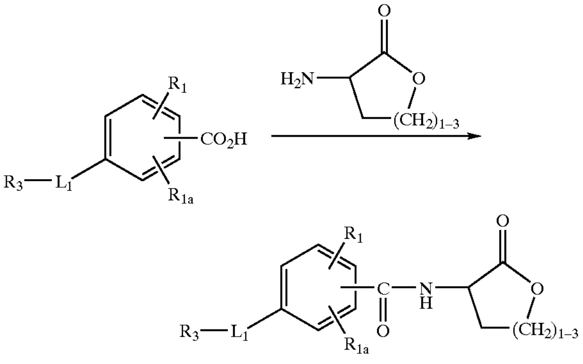

The foregoing may be better understood by reference to the following examples which are provided for illustration and not intended to limit the scope of the inventive concept.

In Tables 2–10, the abbreviation bz=benzoyl, bn=benzyl, Ph=phenyl, BOC=t-butyloxycarbonyl and TS=p-toluenesulfonyl.

Compound 1

(3-(Aminomethyl)benzoyl)-Met-$OCH_3$

Step A (3-(Chloromethyl)benzoyl-Met-$OCH_2$

To a solution of methionine methyl ester hydrochloride (2.0 g, 10 mmol) and 3-(chloromethyl)benzoyl chloride (2.08 g, 11.0 mmol) in methylene chloride (50 mL) was slowly added triethylamine (3.07 mL, 22.0 mmol) at ice bath temperature for 2 hours. The mixture was washed with 0.5 N HCl (50 mL×2), brine (50 mL×2) and water (50 mL×2) then dried over anhydrous $MgSO_4$ and concentrated under reduced pressure. The residue was purified by flash column chromatography (30% ethyl acetate in hexanes) to give the desired product (3.03 g) as a white solid: m.p. 82–83° C.; $^1H$ NMR ($CDCl_3$) δ 7.82 (1H, s), 7.74 (1H, d, J=7.7 Hz), 7.53 (1H, d, J=7.7 Hz), 7.42 (1H, t, J=7.7 Hz), 7.06 (1H, br d, J=7.6 Hz), 4.92 (1H, ddd, J=7.6, 7.1, 5.1 Hz), 4.59 (2H, s), 3.78 (3H, s), 2.58 (2H, t, J=7.1 Hz) 2.26 (1H, sm), 2.15 (1H, m), 2.10 (3H, s); $^{13}C$ NMR ($CDCl_3$) δ 172.59, 166.54, 138.13, 134.25, 131.95, 129.12, 127.42, 126.97, 52.72, 52.14, 45.55, 31.47, 30.12, 15.55.

Step B (3-(Azidomethyl)benzoyl-Met-$OCH_3$

A suspension of (3-(chloromethyl)benzoyl)-Met-$OCH_3$ (1.58 g, 5.0 mmol) and sodium azide (1.3 g, 20.0 mmol) in DMSO (40 mL) was stirred at 80° C. for 7 hours. The mixture was diluted with methylene chloride (100 mL), washed with brine (70 mL×2) and water (70 mL×2), and then dried over anhydrous $MgSO_4$. The solvent was evaporated under reduced pressure to give a yellow residue. Chromatography on silica gel (30% ethyl acetate in hexanes) to provide the desired product (1.45 g) as a colorless solid: m.p. 48–49° C.; $^1$H NMR ($CDCl_3$) δ 7.78 (2H, m), 7.49 (2H, m), 6.99 (1H, br d, J=7.4 Hz), 4.49 (1H, ddd, J=7.4, 7.1, 5.2 Hz), 4.42 (2H, s), 3.80 (3H, s), 2.60 (2H, t, J=7.4 Hz), 2.29 (1H, m), 2.17 (1H, m), 2.12 (3H, s); $^{13}$C NMR ($CDCl_3$) δ 177.50. 166.54, 135.97, 134.06, 131.18, 128.89, 126.84, 126.71, 54.09, 52.47, 51.95, 31.38, 30.00, 15.30.

Step C (3-(Aminomethyl)benzoyl)-Met-$OCH_3$

A suspension of (3-(azidomethyl)benzoyl)-Met-$OCH_3$ (1.29 g, 4.0 mmol) and 5% palladium on carbon (0.2 g) in methanol (40 mL) was stirred under a hydrogen atmosphere (1 atm) for two days at room temperature. The catalyst was removed by filtration through celite (1.5 g) and the solvent was evaporated in vacuo. The residue was washed with water (5 mL×2) and dried to give the desired product (1.12 g) as a colorless foam. $^1$H NMR ($CDCl_3$) δ 7.81 (1H, s), 7.68 (1H, d, J=7.4 Hz), 7.45 (1H, d, J=6.5 Hz), 7.36 (1H, t, J=7.4 Hz), 4.91 (1H, ddd, J=7.3, 7.1, 5.1 Hz), 3.90 (2H, s), 3.77 (3H, s), 3.21 (2H, br s), 2.59 (2H, t, J=7.4 Hz), 2.20 (1H, m), 2.12 (1H, m), 2.09 (3H, s).

Compound 2

(4-(Aminomethyl)benzoyl)-Met-$OCH_3$

The title compound is prepared according to the procedure used to prepare Compound 1 but replacing 3-(chloromethyl)benzoyl chloride with 4-(chloromethyl) benzoyl chloride.

Compound 3

(3-Aminobenzoyl)-Met-$OCH_3$

The title compound was prepared according to the procedure described in J. Biol. Chem. 269 12410–12413 (1994).

Compound 4

(4-Aminobenzoyl)-Met-$OCH_3$

Step A

N-BOC-4-Aminobenzoic Acid

4-Aminobenzoic acid (10 g, 72.9 mmol) was placed into a mixture of dioxane (145.8 mL) and 0.5 M NaOH (145.8 mL). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with 1N HCl to remove any unreacted starting material. The solution was dried over $Na_2SO_4$ and the solvent was removed in vacuo. The crude material was recrystallized from ethyl acetate/hexanes to provide the desired product (12.2 g): m.p. 189–190° C.; $^1$H NMR ($CD_3OD$) δ 1.52 (9H, s), 7.49 (2H, d, J=8.6 Hz), 7.91 (2H, d, J=8.6 Hz), 9.28 (1H, s), $^{13}$C NMR ($CD_3OD$) δ 28.59, 81.29, 118.54, 125.30, 131.81, 145.70, 155.00, 169.80; Anal. Calc. for $C_{12}H_{15}NO_4$, C: 60.76, H: 6.37, N: 5.90; Found, C: 60.52, H: 6.43, N: 5.83; HRMS Calc. for $C_{12}H_{15}NO_4$, 237.0961, Found, 237.1001.

Step B (N-BOC-4-Aminobenzoyl)-Met-$OCH_3$

Into a dried, nitrogen filled flask was placed N-BOC-4-aminobenzoic acid (8.77 g, 36.97 mmol) in dry methylene chloride (148 mL) along with methionine methyl ester hydrochloride (8.12 g, 40.66 mmol). This solution was cooled in an ice bath and triethylamine (6.7 mL), EDCI (7.80 g, 40.66 mmol) and hydroxybenzotriazole (HOBT, 5.50 g, 40.66 mmol) were added. The mixture was stirred overnight, diluted with more methylene chloride and was extracted three times each with 1 M HCl, 1M $NaHCO_3$ and water. The methylene chloride was dried over $MgSO_4$ and the solvent was removed in vacuo. The resulting solid was recrystallized from ethyl acetate/hexanes to yield the desired product (9.72 g): m.p. 184–185° C.; $^1$H NMR ($CDCl_3$) δ 1.53 (9H, s), 2.06–2.18 (4H, m), 2.23–2.33 (1H, m), 2.59 (2H, t, J=7.6 Hz), 3.80 (3H, s), 4.92 (1H, m), 7.45 (2H, d, J=8.7 Hz), 7.77 (2H, d, J=8.7 Hz); $^{13}$C NMR ($CDCl_3$) δ 15.59, 28.34, 30.15, 31.64, 52.10, 52.73, 81.20, 117.73, 127.8, 128.33, 141.88, 152.33, 166.50, 172.75; Anal. Calc. for $C_{18}H_{26}N_2O_5S$, C: 56.53, H: 6.85, N: 7.29; Found, C: 56.47, H: 6.86, N: 7.29; m/z (EI) 382 (M).

Step C (4-Aminobenzoyl)-Met-$OCH_3$ Hydrochloride

N-BOC-4-aminobenzoyl-Met-$OCH_3$ (3.53 g, 9.59 mmol) was placed into methylene chloride (30–35 mL) and to it was added 3M HCl/$EtO_2$ (38.4 mL). After standing, a white precipitate formed. After two hours the solution was decanted and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of the desired product was 2.87 g: m.p. 158–164° C.; $^1$H NMR ($CDCl_3$) δ 2.10 (3H, s), 2.12–2.29 (1H, m), 2.52–2.71 (1H, m), 2.59 (2H, t, J=7.6 Hz), 3.75 (3H, s), 4.79 (1H, m), 7.02 (2H, d, J=8.6 Hz), 7.55 (2H, d, J=8.6 Hz); $^{13}$C NMR ($CDCl_3$) δ 15.23, 31.43, 31.53, 52.91, 52.43, 124.35, 130.56, 135.31, 135.76, 168.95, 173.87; HRMS Calc. for $C_{13}H_{18}N_2O_3S$, 282.1038, Found 282.1009.

Compound 5

(4-Amino-3-methylbenzoyl)-Met-$OCH_3$

Step A

N-BOC-4-Amino-3-methylbenzoic Acid

4-Amino-3-methylbenzoic acid (5 g, 33.1 mmol) was reacted according to the same procedure as that used in the process for preparing N-BOC-4-aminobenzoic acid. The resulting orange-brown solid was recrystallized from ethyl acetate and hexanes to provide the desired product (4.99 g) as tan prismatic crystals: m.p. 180–182° C.; $^1H$ NMR ($CD_3OD$) δ 1.51 (9h, s), 2.27 (3H, s), 7.66 (1H, d, J=8.1 Hz), 7.79–7.82 (2H, m), 8.32 (1H, s); $^{13}C$ NMR ($CD_3OD$) δ 17.98, 28.62, 81.47, 123.12, 127.05, 129.14, 130.65, 132.99, 142.45, 155.33, 168.70; Anal. Calc. for $C_{13}H_{17}NO_4$, C: 62.15, H: 6.82, N: 5.58; Found C: 62.07, H: 6.86, N: 5.46; m/z (EI) 251; HRMS Calc. for $C_{13}H_{17}NO_4$, 251.1158; Found, 251.1153.

Step B (N-BOC-4-Amino-3-methylbenzoyl)-Met-$OCH_3$

N-BOC-4-amino-3-methylbenzoic acid (2.00 g, 7.96 mmol) was reacted with methionine methyl ester hydrochloride (1.75 g, 8.76 mmol), triethylamine (1.4 mL), EDCI (1.68 g, 8.76 mmol) and hydroxybenzotriazole (HOBT, 1.18 g, 8.76 mmol) in dry methylene chloride (31.8 mL) according to the procedure described for the preparation of N-BOC-4-aminobenzoyl)-Met-$OCH_3$. The resulting solid was recrystallized from ethyl acetate/hexanes to yield the desired product (2.61 g): m.p. 163–165° C.; $^1H$ NMR ($CDCl_3$) δ 1.54 (9H, s), 2.06–2.18 (4H, m), 2.23–2.34 (4H, m), 2.59 (2H, t, J=6.8 Hz), 3.80 (3H, s), 4.92 (1H, m), 6.45 (1H, s), 6.88 (1H, d, J=7.5 Hz), 7.63 (1H, d, J=8.6 Hz), 7.66 (1H, s), 8.05 (1H, d, J=8.6 Hz); $^{13}C$ NMR ($CDCl_3$) δ 15.47, 17.61, 28.22, 30.03, 31.55, 51.93, 52.57, 81.04, 118.73, 125.62, 127.66, 129.54, 139.89, 152.34, 166.58, 172.66.

Step C (4-Amino-3-methylbenzoyl)-Met-$OCH_3$ Hydrochloride

N-BOC-4-Amino-3-methylbenzoyl-Met-$OCH_3$ (0.99 g, 2.59 mmol) was dissolved in methylene chloride (15–20 mL) and precipitated with 3M HCl/$Et_2O$ (20.7 mL). A pale orange precipitate was obtained, washed with ether and dried overnight on the vacuum pump. The total yield of the desired product was 0.83 g: m.p. 157–159° C.; $^1H$ NMR ($CD_3OD$) δ 2.04 (3H, s), 2.11–2.25 (1H, m), 2.47 (3H, s), 2.52–2.68 (3H, m), 3.74 (3H, s), 4.75–4.80 (1H, m), 7.48 (1H, d, J=8.2 Hz), 7.81 (2H, d, J=8.2 Hz), 7.87 (1H, s); $^{13}C$ NMR ($CD_3OD$) δ 15.23, 17.28, 31.43, 31.51, 52.91, 53.37, 124.41, 127.85, 131.99, 133.63, 134.14, 135.65, 169.05, 173.84; Anal. Calc. for $C_{14}H_{21}N_2O_3S$, C: 50.52, H: 6.36, N: 8.42; Found C: 50.71, H: 6.40, N: 8.34.

Compound 6

(4-Amino-3-methoxybenzoyl)-Met-$OCH_3$

Step A

N-BOC-4-Amino-3-methoxybenzoic Acid

4-Amino-3-methoxybenzoic acid (1 g, 5.98 mmol) was reacted according to the same procedure as that used in the process for preparing N-BOC-4-aminobenzoic acid. The resulting solid was recrystallized from ethyl acetate and hexanes to provide the desired product (1.5 g) as tan crystals: m.p. 176–178° C.; $^1H$ NMR ($CD_3OD$) δ 1.52 (9H, s), 3.92 (3H, s), 7.56 (1H, s), 7.62 (1H, d, J=8.4 Hz), 7.96 (1H, s), 8.03 (1H, d, J=8.4 Hz); $^{13}C$ NMR ($CD_3OD$) δ 28.53, 56.35, 81.78, 112.01, 118.58, 124.20, 125.76, 133.84, 149.04, 154.20, 169.60; HRMS Calc. for $C_{13}H_{17}NO_5$, 267.1107; Found, 267.1103.

Step B (N-BOC-4-Amino-3-methoxybenzoyl)-Met-$OCH_3$

N-BOC-4-amino-3-methoxybenzoic acid (0.35 g, 1.31 mmol) was reacted with methionine methyl ester hydrochloride (0.9 g, 1.43 mmol) using EDCI according to the procedure described for the preparation of (N-BOC-4-aminobenzoyl)-Met-$OCH_3$. The resulting solid was recrystallized from ethyl acetate/hexanes to yield the desired product (0.36 g): m.p. 163–165° C.; $^1H$ NMR ($CDCl_3$) δ 1.53 (9H, s), 2.09–2.18 (4H, m), 2.23–2.35 (1H, m), 2.60 (2H, t, J=6.9 Hz), 3.80 (3H, s), 3.93 (3H, s), 4.92 (1H, br s), 6.93 (1H, d, J=7.6 Hz), 7.25 (1H, m), 7.31 (1H, d, J=10.2 Hz), 7.44 (1H, s), 8.15 (1H, d, J=8.5 Hz); $^{13}C$ NMR ($CDCl_3$) δ 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

Step C (4-Amino-3-methoxybenzoyl)-Met-$OCH_3$ Hydrochloride

N-BOC-4-Amino-3-methoxybenzoyl-Met-$OCH_3$ (0.71 g, 1.79 mmol) was dissolved in methylene chloride (4 mL) and precipitated with 3M HCl/$Et_2O$ (12 mL). A reddish precipitate was obtained, washed with ether and dried overnight on the vacuum pump. The total yield of the desired product was 0.55 g: m.p. 176–177° C.; $^1H$ NMR ($CD_3OD$) δ 2.08 (3H, s), 2.21 (2H, m), 2.61 (2H, m), 3.74 (3H, s), 4.02 (3H, s), 4.79 (1H, m), 7.50 (1H, d, J=8.2 Hz), 7.57 (1H, d, J=4.1 Hz), 7.67 (1H, s); $^{13}C$ NMR ($CD_3OD$) δ 15.26, 31.34, 31.42, 52.95, 53.38, 57.12, 112.29, 121.43, 124.57, 124.77, 136.15, 153.67, 168.79, 173.81.

Compound 7

(4-Amino-1-naphthoyl)-Met-$OCH_3$

Step A

4-Amino-1-naphthoic Acid

4-Amino-1-naphthalenecarbonitrile (1.5 g, 8.91 mmol) was suspended in a 50% KOH solution (18 mL). The heterogeneous solution was heated at reflux for 2–3 days. Once the solution became homogeneous and TLC showed no more starting material, the deep red solution was cooled and poured over 200 mL of water. The resulting solution was then filtered and the desired product was precipitated with concentrated HCl. The resulting red crystals were filtered and the filtrate was refiltered to give pink crystals. The first fraction of crystals was treated with activated carbon to remove some of the red color. A total of 1.51 g of the desired product was obtained: m.p. 169–171° C.; $^1H$ NMR ($CD_3OD$) δ 6.69 (1H, d, J=8.2 Hz), 7.38–7.43 (1H, m), 7.48–7.54 (1H, m), 8.03 (1H, d, J=8.5 Hz), 8.13 (1H, d, J=8.2 Hz), 9.09 (1H, d, J=8.5 Hz); $^{13}C$ NMR ($CD_3OD$) δ 107.39, 114.61, 122.99, 123.92, 125.21, 127.40, 128.48, 135.04, 151.35, 171.44; HRMS Calc. for $C_{11}H_7NO_2$, 187.0633; Found, 187.0642.

Step B

N-BOC-4-Amino-1-naphthoic Acid

4-Amino-1-naphthoic acid (0.86 g, 4.61 mmol) was dissolved in dioxane (9.2 mL). Di-t-butyl dicarbonate (1.11 g, 5.07 mmol) was added and the mixture was stirred overnight. The reaction mixture was worked up as described above for N-BOC-4-aminobenzoic acid to give 0.76 g of the desired product as a reddish pink solid: m.p. 194–195° C.; $^{1}$H NMR ($CD_3OD$) δ 1.56 (9H, s), 7.53–7.62 (2H, m), 7.79 (1H, d, J=8.1 Hz), 8.12 (1H, d, J=8.0 Hz), 8.22 (1H, d, J=8.18 Hz), 9.02 (1H, d, J=8.9 Hz); $^{13}$C NMR ($CD_3OD$) δ 26.68, 81.62, 119.06, 123.40, 124.57, 127.03, 127.37, 128.49, 128.77, 131.89, 133.76, 139.86, 155.95, 170.73; Anal. Calc. for $C_{17}H_{17}NO_4$, C: 66.90, H: 5.96, N: 4.88; Found C: 66.49, H: 6.08, N: 4.79; m/z (EI), 289; HRMS Calc. for $C_{16}H_{17}NO_4$, 287.1158; Found, 287.1151.

Step C (N-BOC-4-Amino-1-naphthoyl)-Met-$OCH_3$

N-BOC-4-Amino-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and triethylamine (0.27 mL) in methylene chloride (6.4 mL) were reacted as described above for N-BOC-4-aminobenzoyl-Met-$OCH_3$. After workup and recrystallization from ethyl acetate hexanes, the desired product (0.44 g) was obtained as pale pink crystals: m.p. 131–132° C.; $^{1}$H NMR ($CDCl_3$) δ 1.57 (9H, s), 2.11–2.21 (4H, m), 2.29–2.41 (1H, m), 2.65 (2H, t, J=7.1 Hz), 3.83 (3H, s), 4.99–5.06 (1H, m), 6.68 (1H, d, J=8.0 Hz), 7.02 (1H, s), 7.56–7.59 (2H, m), 7.69 (1H, d, J=7.9 Hz), 7.87–7.90 (1H, m), 8.02 (1H, d, J=7.9 Hz), 8.44–8.48 (1H, m); $^{13}$C NMR ($CDCl_3$) δ 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS Calc. for $C_{22}H_{28}N_2O_5S$, 432.1719; Found, 432.1702; m/z (FAB) 433 (M+1).

Step D (4-Amino-1-naphthoyl)-Met-$OCH_3$ Hydrochloride (N-BOC-4-Amino-1-naphtholyl)-Met-$OCH_3$ (0.57 g, 1.31 mmol) was deprotected with HCl/ether to yield the desired product (0.31 g) as a white solid: m.p. 178–181° C.; $^{1}$H NMR ($CD_3OD$) δ 2.08–2.16 (4H, m), 2.20–2.30 (1H, m), 2.57–2.75 (2H, m), 3.82 (3H, s), 4.87–4.91 (1H, m), 7.59 (1H, d, J=7.5 Hz), 7.67 (1H, d, J=7.5 Hz), 7.71–7.80 (2H, m), 8.03 (1H, dd, J=7.1, 2.0 Hz), 8.35 (1H, dd, J=6.8, 1.8 Hz); $^{13}$C NMR ($CD_3OD$) δ 15.23, 31.40, 53.01, 53.33, 119.90, 122.20, 126.15, 127.41, 127.77, 129.09, 129.31, 131.50, 132.33, 135.64, 171.77, 173.83; m/z (FAB), 369 (M+1).

Compound 8

(4-Amino-2-phenylbenzoyl)-Met-$OCH_3$

Step A

4-Nitro-2-phenyltoluene

2-Bromo-4-nitrotoluene (2.16 g, 10.00 mmol) and phenylboric acid (1.46 g, 12.00 mmol) were dissolved in anhydrous DMF (25 mL) under nitrogen. To this mixture was added $Pd(Ph_3P)_4$ (0.58 g, 5%). The mixture was heated at 100° C. overnight. The solution was poured onto 1N HCl and extracted with $Et_2O$. The crude product was chromatographed on silica gel using hexanes as eluent. After recrystallization from ethanol, the desired product (1.23 g) was obtained as pale orange needles: m.p. 69–71° C.; $^{1}$H NMR ($CDCl_3$) δ 2.36 (3H, s), 7.29–7.40 (2H, m), 7.41–7.49 (5H, m), 8.07–8.10 (2H, m); $^{13}$C NMR ($CDCl_3$) δ 20.68, 121.96, 124.51, 127.78, 128.41, 128.83, 131.06, 139.06, 139.44, 142.97, 143.48, 146.05; Anal. Calc. for $C_{13}H_{11}NO_2$, C: 73.26, H: 5.20, N: 6.57; Found, C: 73.10, H: 5.12, N: 6.50; m/z (EI) 213; HRMS Calc. for $C_{13}H_{11}NO_2$, 213.0790; Found, 213.0793.

Step B

4-Nitro-2-phenylbenzoic Acid

4-Nitro-2-phenyltoluene (0.5 g, 2.34 mmol) was dissolved in water (4.6 mL) and pyridine (2.3 mL). The mixture was heated to reflux and $KMnO_4$ (1.85 g, 11.7 mmol) was added. The reaction mixture was heated overnight and the solution was filtered and washed several times with boiling water. The aqueous solution was made acidic and the product was extracted into ethyl acetate. The ethyl acetate solution was dried over $Na_2SO_4$ and the solvent removed in vacuo to provide the desired product (0.37 g): m.p. 174–176° C., $^{1}$H NMR ($CD_3OD$) δ 7.38–7.48 (5H, m), 7.96 (1H, d, J=8.5 Hz), 8.21 (1H, d, J=2.3 Hz), 8.28 (1H, dd, J=8.48, 2.37 Hz); $^{13}$C NMR ($CD_3OD$) δ 122.95, 126.09, 129.27, 129.42, 129.49, 131.56, 139.26, 140.42, 144.41, 150.17, 170.52; m/z (EI) 243 (M).

Step C (4-Nitro-2-phenylbenzoyl)-Met-$OCH_3$

4-Nitro-2-phenylbenzoic acid (0.3 g, 1.23 mmol), methionine methyl ester hydrochloride salt (0.27 g, 1.35 mmol), EDCI (0.26 g, 1.35 mmol), HOBT (0.18 g, 1.35 mmol) and triethylamine (0.19 mL) in dry methylene chloride (4.9 mL) were reacted according the procedure described above for (N-BOC-4-aminobenzoyl)-Met-$OCH_3$. After recrystallization of the product from ethyl acetate hexanes, the desired product (0.41 g) was obtained: m.p. 98–101° C.; $^{1}$H NMR ($CDCl_3$) δ 1.62–1.73 (1H, m), 1.79–1.88 (1H, m), 1.91 (3H, s), 1.99 (2H, t, J=7.2 Hz), 3.59 (3H, s), 4.53 (1H, m), 6.45 (1H, d, J=7.8 Hz), 7.33–7.40 (5H, m), 7.67 (1H, d, J=8.3 Hz), 8.07–8.12 (2H, m); $^{13}$C NMR ($CDCl_3$) δ 14.92, 29.11, 30.67, 51.51, 52.29, 121.86, 124.74, 128.27, 128.60, 128.69, 129.52, 137.50, 140.56, 141.02, 148.09, 167.23, 171.23; m/z (FAB), 389 (M+1).

Step D (4-Amino-2-phenylbenzoyl)-Met-$OCH_3$ (4-Nitro-2-phenylbenzoyl)-Met-$OCH_3$ (0.35 g, 0.90 mmol) was dissolved in ethyl acetate (9.0 mL). To this mixture was added $SnCl_2.2H_2O$ (1.02 g, 4.5 mmol) and the reaction mixture was heated under nitrogen at reflux for one hour. The mixture was poured onto ice, the solution was made basic using $NaHCO_3$ and the product was extracted into ethyl acetate several times (7–8). The ethyl acetate solutions were combined, washed with brine and dried over $Na_2SO_4$. The solvent was removed in vacuo to the desired product (0.24 g) as a yellow solid: $^{1}$H NMR ($CDCl_3$) δ 1.58–1.70 (1H, m), 1.80–1.92 (1H, m), 1.98 (3H, s), 2.06 (2H, t, J=7.7 Hz), 3.62 (3H, s), 4.00 (2H, br s), 4.56–4.63 (1H, m), 5.84 (1H, d, J=7.7 Hz), 6.50 (1H, s), 6.61 (1H, d, J=8.4 Hz) 7.29–7.42 (5H, m), 7.58 (1H, d, J=8.3 Hz); $^{13}$C NMR ($CDCl_3$) δ 15.02, 29.25, 31.25, 51.57, 52.15, 113.27, 115.88, 123.52, 127.56, 128.37, 128.44, 130.92, 140.66, 141.44, 148.53, 168.58, 171.91.

Compound 9

(4-Amino-2-(2-thienyl)benzoyl)-Met-$OCH_3$

The title compound can be prepared according to the method used to prepare Compound 8, only substituting thiophene-2-boronic acid for phenyl boronic acid.

Compound 10

(4-Amino-2-(1-naphthyl)benzoyl)-Met-$OCH_3$

The title compound can be prepared according to the method used to prepare Compound 8, only substituting 1-naphthylboronic acid for phenylboronic acid.

Compound 11

4-Amino-3'-methylbiphenyl

The title compound was prepared by Suzuki coupling of 1-bromo-4-nitrobenzene and 1-bromo-3-methylbenzene.

Compound 12

4-Amino-4'-biphenyl Carboxylic Acid

Step A

4-Nitro-4'-methylbiphenyl

The title compound was prepared by Suzuki coupling of 1-bromo-4-nitrobenzene and 1-bromo-4-methylbenzene.

Step B

4-Nitro-4'-biphenyl Carboxylic Acid

The title compound was prepared by $KMnO_4$ oxidation of 4-nitro-4'-methylbiphenyl.

Step C

4-Amino-4'-biphenyl Carboxylic Acid

The title compound can be prepared by palladium catalyzed hydrogenation of 4-nitro-4'-biphenyl carboxylic acid.

Compound 13 4-Amino-3'-biphenyl Carboxylic Acid

Step A

4-Nitro-3'-methylbiphenyl

The title compound was prepared by Suzuki coupling of 1-bromo-4-nitrobenzene and 1-bromo-3-methylbenzene.

Step B

4-Nitro-3'-biphenyl Carboxylic Acid

The title compound was prepared by $KMnO_4$ oxidation of 4-nitro-3'-methylbiphenyl.

Step C

4-Amino-3'-biphenyl Carboxylic Acid

The title compound can be prepared by palladium catalyzed hydrogenation of 4-nitro-3'-biphenyl carboxylic acid.

Compound 14

4-Amino-2-methoxy-3'-biphenyl Carboxylic Acid

Step A

2-Methoxy-4-nitro-3'-methylbiphenyl

The title compound was prepared by reaction of 1-bromo-2-methoxy-4-nitrobenzene with 3-methylphenylboronic acid in the presence of palladium acetate.

Step B

2-Methoxy-4-nitro-3'-biphenyl Carboxylic Acid

The tide compound was prepared by $KMnO_4$ oxidation of 2-methoxy-4-nitro-3'-methylbiphenyl.

Step C

4-Amino-2-methoxy-3'-biphenyl Carboxylic Acid

The title compound can be prepared by palladium catalyzed hydrogenation of 2-methoxy-4-nitro-3'-biphenyl carboxylic acid.

Compound 15

4-Amino-2-isopropyloxy-3'-biphenyl Carboxylic Acid

The tide compound can be prepared by methods analogous to those used to prepare Compound 14.

Compound 16

4-Amino-2-phenyl-3'-biphenyl Carboxylic Acid

The title compound can be prepared by methods analogous to those used to prepare Compound 14.

Compound 17

(4-Amino-2-(3,5-dimethylphenylbenzoyl)-Met-$OCH_3$

Step A

2-Bromo-4-nitrobenzoic Acid

2-Bromo-4-nitrotoluene (5.0 g, 23.14 mmol) was dissolved in pyridine (23 mL) and water (46 mL). The heterogeneous mixture was heated to 60° C. and $KMnO_4$ (18.29 g, 115.7 mmol) was added carefully. The mixture was then heated under reflux overnight. The reaction mixture was filtered and washed with boiling water. The solution was then made acidic and extracted into ethyl acetate, dried over $Na_2SO_4$ and the solvent was removed in vacuo. The crude product was dissolved in aqueous NaOH and washed with hexanes. The aqueous phase was made acidic and the product was extracted into ethyl acetate. The ethyl acetate solutions were combined and dried over $Na_2SO_4$ and the solvent was removed in vacuo to provide the desired product (3.72 g): m.p. 158–160° C.; $^1$H NMR ($CD_3OD$) δ 7.81 (1H, d, J=8.5 Hz), 8.08 (1H, d, J=8.5 Hz), 8.30 (1H, s); $^{13}$C NMR ($CD_3OD$) δ 121.96, 122.75, 129.36, 132.24, 139.52, 149.54, 167.75; Anal. Calc. for $C_7H_4BrNO_4$.0.1 ethyl acetate, C: 34.88, H: 1.90, N: 5.50; Found, C: 34.68, H: 1.86, N: 5.82.

Step B 3,5-Dimethylphenylboronic Acid

Magnesium turnings (1.44 g, 59.43 mmol) were covered with dry THF (18.8 mL) in a dried, nitrogen filled flask fitted with an addition funnel and reflux condenser. To this was added 5-bromo-m-xylene (10 g, 54.03 mmol) in THF (15 mL) after initiation of the Grignard reaction. The addition was carried out over several minutes and the reaction mixture was heated at reflux for 1–2 hours until most of the magnesium had reacted. The reaction mixture was then cooled and transferred to an addition funnel fitted to an nitrogen filled flask containing triisopropyl borate (24.9 mL) at −70° C. The dropwise addition was carried out over several minutes and the mixture warmed to room temperature and stirred overnight. The grey solution was poured onto 2 M HCl and immediately turned yellow. The solution was extracted with $Et_2O$ and the $Et_2O$ fractions were combined, dried over $MgSO_4$ and the solvent was removed in vacuo to provide the desired product (2.41 g): m.p. 249–251° C.; $^1H$ NMR ($CDCl_3$) δ 2.44 (6H, s), 7.23 (1H, s), 7.84 (2H, s); $^{13}C$ NMR ($CD_3OD$) δ 21.36, 133.28, 134.39, 137.48.

Step C

4-Nitro-2-(3,5-dimethylphenyl)benzoic Acid

2-Bromo-4-nitrobenzoic acid (0.43 g, 2.03 mmol) and 3,5-dimethylphenyl boronic acid (0.334 g, 2.23 mmol) were dissolved in anhydrous DMF (25 mL) under nitrogen. To this mixture was added $Cs_2CO_3$ (1.66 g, 5.08 mmol) followed by $Pd(Ph_3P)_4$ (0.12 g, 5%). The mixture was heated at 100° C. overnight. The solution was poured onto 1N HCl and extracted with $Et_2O$. It was dried over $MgSO_4$ and the solvent was removed in vacuo. The crude product was chromatographed on silica gel using a 9:1 mixture of hexanes and ethyl acetate to provide the desired product (0.34 g): $^1H$ NMR ($CDCl_3$) δ 2.36 (6H, s), 6.99 (2H, s), 7.07 (1H, s), 8.03 (1H, d, J=9.0 Hz), 8.23–8.25 (2H, m); $^{13}C$ NMR ($CDCl_3$) δ 21.28, 121.68, 123.68, 125.74, 126.07, 130.22, 131.19, 131.31, 135.04, 138.21, 144.74, 170.75.

Step D (4-Nitro-2-(3,5-dimethylphenyl)benzoyl)-Met-$OCH_3$

4-Nitro-2-(3,5-dimethylphenyl)benzoic acid (0.15 g, 0.55 mmol), methionine methyl ester hydrochloride (0.11 g, 0.55 mmol), EDCI (0.11 g, 0.55 mmol), HOBT (0.07 g, 0.55 mmol) and triethylamine (0.08 mL) in dry methylene chloride (2.2 mL) were reacted and worked up according to the procedure for (N-BOC-4-aminobenzoyl)-Met-$OCH_3$ as described above. After recrystallization from ethyl acetate and hexanes, the desired product was obtained (0.13 g): m.p. 122–124° C.; $^1H$ NMR ($CDCl_3$) δ 1.2–1.84 (1H, m), 1.85–1.97 (1H, m), 2.01 (3H, s), 2.05 (3H, t, J=7.7 Hz), 2.38 (6H, s), 3.70 (3H, s), 4.67–4.74 (1H, m), 6.03 (1H, d, J=7.9 Hz), 7.05 (2H, s), 7.09 (1H, s), 7.84–7.87 (1H, m), 7.84–7.87 (1H, m), 8.23–8.26 (2H, m); $^{13}C$ NMR ($CDCl_3$) δ 15.20, 21.26, 29.22, 31.15, 51.79, 52.57, 122.07, 125.11, 126.27, 130.03, 130.53, 137.77, 138.82, 140.29, 141.56, 148.41, 167.14, 171.53.

Step E (4-Amino-2-(3,5-dimethylphenyl)benzoyl)-Met-$OCH_3$ (4-Nitro-2-(3,5-dimethylphenyl)benzoyl)-Met-$OCH_3$ (0.11 g, 0.26 mmol) was dissolved in ethyl acetate (3.0 mL). To this mixture was added $SnCl_2.2H_2O$ (0.3 g, 1.30 mmol) and the reaction was heated under nitrogen at reflux for 6 hours. The mixture was worked up as described above for (4-amino-2-phenylbenzoyl)-Met-$OCH_3$ to give the desired product (0.15 g): $^1H$ NMR ($CDCl_3$) δ 1.60–1.70 (1H, m), 1.80–1.90 (1H, m), 1.99 (3H, s), 2.05 (2H, t, J=7.6 Hz), 2.33 (6H, s), 3.64 (3H, s), 3.93 (2H, br s), 4.61–4.64 (1H, m), 5.82 (1H, d, J=7.7 Hz), 6.49 (1H, d, J=2.3 Hz), 6.62 (1H, dd, J=8.4, 2.4 Hz), 6.98 (2H, s), 7.00 (1H, s), 7.65 (1H, d, J=8.3 Hz); $^{13}C$ NMR ($CDCl_3$) δ 15.08, 21.17, 29.28, 31.49, 51.70, 52.18, 113.30, 115.94, 123.55, 126.36, 129.32, 131.23, 138.15, 140.72, 141.92, 148.40, 168.45, 172.01

Preparation 1

Anilines of the Formula B—$NH_2$

The anilines from Table 1, entries 10–126 (B—$NH_2$) are prepared using the procedures for Compounds 1–18 with the exception that methionine methyl ester is replaced by methioninesulfone methyl ester, (S-Me)cysteine methyl ester, serine methyl ester, (O-Me)serine methyl ester, (O-Me)homoserine methyl ester, homoserine lactone, isoleucine methyl ester, leucine methyl ester, norleucine methyl ester, norvaline methyl ester, cyclohexylalanine methyl ester, phenylalanine methyl ester, or glutamic acid dimethyl ester.

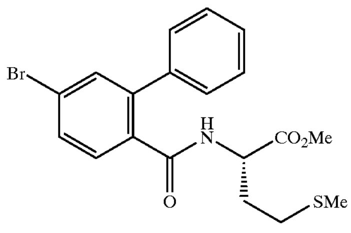

Preparation 2

4-Bromo-2-phenylbenzoyl Methionine Methyl Ester

Preparation 2A

4-Bromo-2-phenylbenzoic Acid Methyl Ester

A solution of methyl 4-amino-2-phenylbenzoic acid (1.0 equivalent) in dilute aqueous HBr is treated with $NaNO_2$ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

Preparation 2B

4-Bromo-2-phenylbenzoic Acid

To a solution of the resultant compound from Preparation 2A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

Preparation 2C

4-Bromo-2-phenylbenzoyl Methionine Methyl Ester

To a solution of the resultant compound from Preparation 2B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

Preparation 2D

4-Bromo-2-phenylbenzoyl Methionine Methyl Ester Alternate Procedure

A solution of 4-amino-2-phenylbenzoyl methionine methyl ester (1.0 equivalent) in dilute aqueous HBr is treated with $NaNO_2$ (1.1 equivalents) to form the diazonium salt. The reaction is treated with CuBr (1.1 equivalents) and heated. When judged complete by TLC analysis, the mixture is extracted into ethyl acetate which is dried and evaporated. The title arylbromide is purified by chromatography on silica gel.

Preparation 3

Arylbromide of the Formula B—Br

The anilines from Table 1 (B—$NH_2$) are reacted according to the procedures of Preparation 2 to provide the arylbromides listed in Table 2.

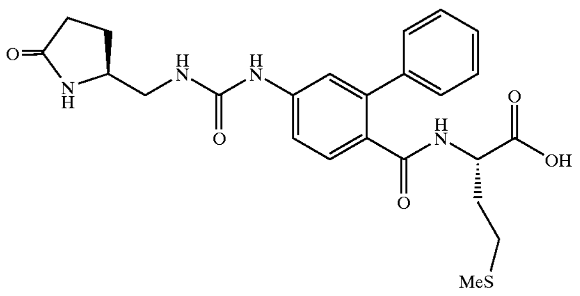

EXAMPLE 1

4-((S)-2-Pyrrolidone-5-aminomethylcarbonyl) amino-2-phenylbenzoyl Methionine

EXAMPLE 1A

Methyl 4-((S)-2-Pyrrolidone-5-aminomethylcarbonyl)amino-2-phenylbenzoate

To a solution of methyl 4-amino-2-phenylbenzoate hydrochloride (1.0 equivalent) in toluene is added triphosgene (0.33 equivalent) and the mixture is heated at reflux until judged complete by TLC analysis. The intermediate is reacted without further purification with (S)-5-aminomethyl-2-pyrrolidone (1.0 equivalent) and triethylamine (2.0 equivalents). When judged complete by TLC analysis, the reaction is taken up in ethyl acetate and washed with 1N HCl and brine, evaporated, and purified by chromatography on silica gel.

EXAMPLE 1B 4-((S)-2-Pyrrolidone-5-aminomethylcarbonyl) amino-2-phenylbenzoic Acid To a solution of the resultant compound from Example 1A (1.0 equivalent) in a 3:1 mixture of tetrahydrofuran (THF) and water is added an excess (1.5 equivalents) of LiOH. When hydrolysis is judged complete by TLC analysis, the solvent is evaporated and the remaining aqueous layer is acidified to pH=3 and extracted into ethyl acetate which is dried and evaporated prior to purification by chromatography on silica gel.

EXAMPLE 1C 4-((S)-2-Pyrrolidone-5-aminomethylcarbonylamino-2-phenylbenzoyl Methionine Methyl Ester To a solution of the resultant compound from Example 1B (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 1D 4-((S)-2-Pyrrolidone-5-aminomethylcarbonyl) amino-2-phenylbenzoyl Methionine Methyl Ester, Alternate Preparation To a solution of 4-amino-2-phenylbenzoyl methionine methyl ester (1.0 equivalent) in methylene chloride is added a solution of phosgene in toluene (1.0 equivalent) and triethylamine (2.0 equivalents). The intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 1E 4-((S)-2-Pyrrolidone-5-aminomethylcarbonyl) amino-2-phenylbenzoyl Methionine To a solution of the resultant compound from Example 1C in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

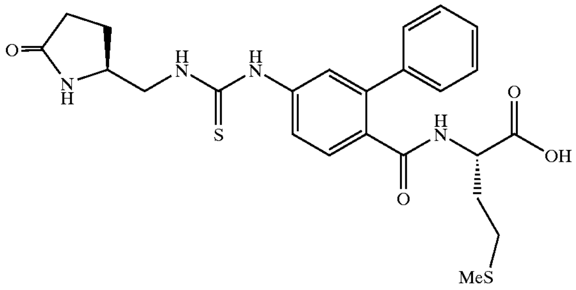

EXAMPLE 2

4-((S-2-Pyrrolidone-5-aminomethylthiocarbonyl) amino-2-phenylbenzoyl Methionine

The title compound is prepared as described in Example 1 with the exception that triphosgene (0.33 equivalent) is replaced by thiophosgene (1.0 equivalent).

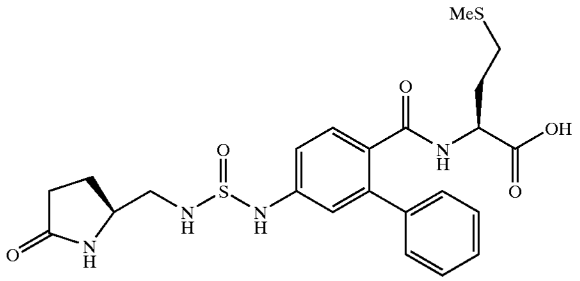

EXAMPLE 3

4-((S)-2'-Pyrrolidone-5-aminomethylsulfinyl)amino-2-phenylbenzoyl Methionine

EXAMPLE 3A 4-((S)-2-Pyrrolidone-5-aminomethylsulfinyl)amino-2-phenylbenzoyl Methionine Methyl Ester To a solution of 4-amino-2-phenylbenzoyl methionine methyl ester (1.0 equivalent) in methylene chloride is added thionyl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 3B 4-((S)-2-Pyrrolidone-5-aminomethylsulfinyl)amino-2-phenylbenzoyl Methionine To a solution of the resultant compound from Example 3A in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

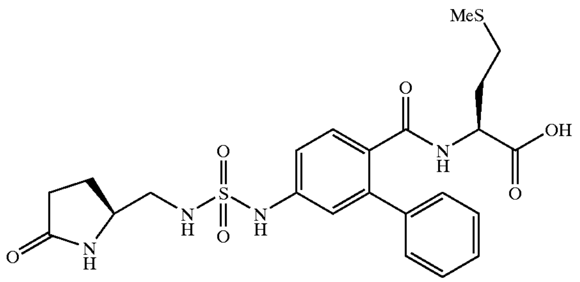

EXAMPLE 4

4-((S)-2-Pyrrolidone-5-aminomethylsulfonylamino)-2-phenylbenzoyl Methionine

EXAMPLE 4A 4-((S)-2-Pyrrolidone-5-aminomethylsulfonyl)amino-2-phenylbenzoyl Methionine Methyl Ester To a solution of 4-amino-2-phenylbenzoyl methionine methyl ester (1.0 equivalent) in methylene chloride is added sulfuryl chloride (1.0 equivalent) and triethylamine (2.0 equivalents). After the amine has fully reacted, (S)-5-aminomethyl-2-pyrrolidone (1.0 equivalent) is added. When the reaction is judged complete by TLC analysis, the product is isolated as described in Example 1A and purified by chromatography on silica gel.

EXAMPLE 4B 4-((S)-2-Pyrrolidone-5-aminomethylsulfonyl)amino-2-phenylbenzoyl Methionine Methyl Ester, Alternate Procedure A solution of 1 equivalent of 4-amino-2-phenylbenzoyl methionine methyl ester (1.0 equivalent) and sulfuryl chloride (1.0 equivalent) in acetonitrile with a catalytic amount of antimony(V)chloride is heated to reflux until judged complete by TLC analysis. The solution is then cooled, filtered, and all volatiles are removed under reduced pressure. The residue is taken up in dichloromethane and treated with triethylamine (1 equivalent and (S)-5-aminomethyl-2-pyrrolidone (1.0 equivalent). When the reaction is judged complete by TLC analysis, the product is isolated as described in Example 1A and purified by chromatography on silica gel.

EXAMPLE 4C 4-((S)-2-Pyrrolidone-5-aminomethylsulfonyl)amino-2-phenylbenzoyl Methionine Methyl Ester The resultant compound from Example 4A is hydrolyzed according to the procedure of Example 1B to give the title product.

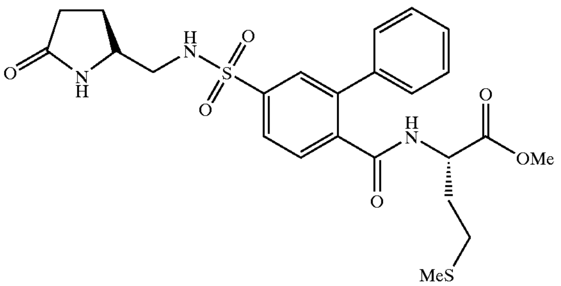

EXAMPLE 5

4-((S)-2-Pyrrolidone-5-methylaminosulfonyl)-2-phenylbenzoyl Methionine

EXAMPLE 5A

4-Chlorosulfonyl-2-phenylbenzoic Acid Methyl Ester

To a solution of methyl 4-amino-2-phenylbenzoate (1.0 equivalent) in concentrated HCl is added a solution of sodium nitrite (1.1 equivalents) until an excess of nitrous acid persists. The chlorodiazonium salt is poured into a solution of sulfur dioxide (10, equivalents), copper(II) chloride (0.5 equivalent) and KCl (1.1 equivalents) in dioxane. When TLC analysis indicated that the reaction is complete, the mixture is diluted with water and extracted into benzene which is dried and evaporated to give the title sulfonyl chloride

EXAMPLE 5B 4-((S)-2-Pyrrolidone-5-aminomethyl)sulfonyl-2-phenylbenzoic Acid Methyl Ester To a solution of the resultant compound from Example 5A (1.0 equivalent) in methylene chloride is added (S)-5- aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 5C 4-((S)-2-Pyrrolidone-5-aminomethylsulfonyl)-2-phenylbenzoic Acid

The resultant compound from Example 5B is hydrolyzed according to the procedure of Example 1B to give the title product.

EXAMPLE 5D 4-((S)-2-Pyrrolidone-5-aminomethyl)sulfonyl)-2-phenylbenzoyl Methionine Methyl Ester To a solution of the resultant compound from Example 5C (1.0 equivalent) in (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 5E 4-((S)-2-Pyrrolidone-5-aminomethylcarbonyl)amino-2-phenylbenzoyl Methionine Methyl Ester, Alternate Preparation To a solution of 4-amino-2-phenylbenzoyl methionine methyl ester (1.0 equivalent) in concentrated HCl is added a solution of sodium nitrite (1.1 equivalents) until an excess of nitrous acid persists at which time the chlorodiazonium salt will be treated with gaseous sulfur dioxide and copper (II) chloride to give the sulfonyl chloride (0.1 equivalent). This intermediate is reacted with (S)-5-aminomethyl-2-pyrrolidone (1.0 equivalent) and triethylamine (1.0 equivalent) according to the procedure of Example 5B to give the title compound.

EXAMPLE 5F 4-((S)-2-Pyrrolidone-5-aminomethylcarbonyl)amino-2-phenylbenzoyl methionine To a solution of the resultant compound from Example 5D (1.0 equivalent) in a 3:1 mixture of THF and water is added an excess of LiOH (1.5 equivalents). When hydrolysis is judged complete by TLC analysis, the solvent is evaporated and the remaining aqueous layer is acidified to pH=3 and extracted into ethyl acetate which is dried and evaporated prior to purification by chromatography on silica gel.

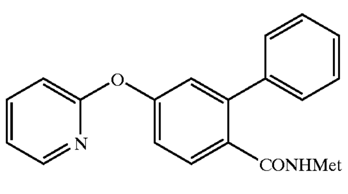

EXAMPLE 6

4-(2-Pyridyloxy)-2-phenylbenzoyl Methionine

EXAMPLE 6A

4-Hydroxy-2-phenylbenzoic Acid Methyl Ester

A solution of methyl 4-amino-2-phenylbenzoate (1.0 equivalent) in dilute aqueous $H_2SO_4$ is treated with $NaNO_2$ (1.1 equivalents) until an excess of nitrous acid persists to form the diazonium salt. This salt is then diluted further with water and heated. The mixture is extracted into ethyl acetate which is dried and evaporated. The title ester is purified by chromatography on silica gel.

EXAMPLE 6B 4-(2-Pyridyloxy)-2-phenylbenzoic Acid Methyl Ester

A solution of the resultant phenol from Example 6A (1.0 equivalent) is treated with 2-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6C 4-(2-Pyridyloxy)-2-phenylbenzoic Acid

A solution of the resultant ester from Example 6B (1.0 equivalent) in aqueous methanol is treated with NaOH (2.0 equivalents) and stirred until the reaction is deemed complete by TLC analysis. The mixture is acidified, diluted with water, and extracted into ethyl acetate which is dried and evaporated. Chromatography on silica gel provides the title product.

EXAMPLE 6D 4-(2-Pyridyloxy)-2-phenylbenzoyl Methionine Methyl Ester

The resultant product from Example 6C is coupled to methionine methyl ester according to the procedure of Example 1C to give the title compound.

EXAMPLE 6E 4-(2-Pyridyloxy)-2-phenylbenzoyl Methionine Methyl Ester, Alternate Procedure A solution of 4-amino-2-phenylbenzoyl methionine methyl ester (1.0 equivalent) in dilute aqueous $H_2SO_4$ is treated with $NaNO_2$ (1.1 equivalents) until an excess of nitrous acid persists to form the diazonium salt. This salt is then diluted further with water and heated to form the phenol which is purified by chromatography on silica gel. A solution of this phenol (1.0 equivalent) is treated with 3-bromopyridine (1.0 equivalent) in the presence of a NaH (1.0 equivalent), or $K_2CO_3$ (2.0 equivalents) and copper (1.0 equivalent) in DMF or pyridine. The product is isolated by removal of the solvent and chromatography on silica gel.

EXAMPLE 6F 4-(2-Pyridyloxy)-2-phenylbenzoyl Methionine

The resultant compound from Example 6E is hydrolyzed according to the procedure of Example 1B to give the title compound.

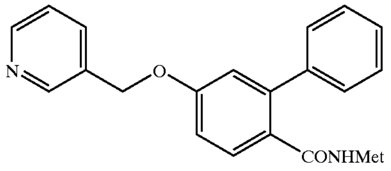

EXAMPLE 7

4-(3-Pyridylmethylenoxy)-2-phenylbenzoyl Methionine

The title compound is prepared as described in Example 6 with the exception that 2-bromopyridine is replaced by 3-chloromethylpyridine hydrochloride.

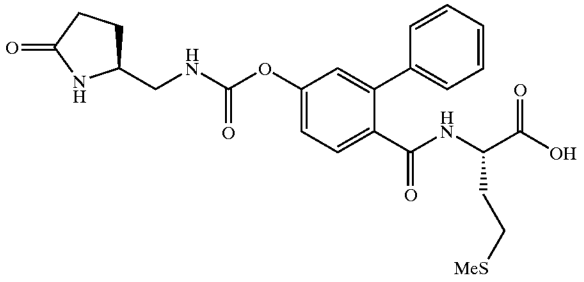

EXAMPLE 8

4-((S)-2-Pyrrolidone-5-aminomethyl)carbonyloxy-2-phenylbenzoyl Methionine

EXAMPLE 8A 4-((2-2-Pyrrolidone-5-aminomethyl)carbonyloxy-2-phenylbenzoyl Methionine Methyl Ester To a solution of 4-hydroxy-2-phenylbenzoyl methionine methyl ester (1.0 equivalent) from Example 6E in methylene chloride is added a solution of phosgene in toluene (1.0 equivalent) and p-dimethylaminopyridine (2.0 equivalents). When the reaction is judged complete by TLC analysis, the solvent is evaporated with toluene chasers. The chloroformate is reacted without further purification with (S)-5-aminomethyl-2-pyrrolidone (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 8B 4-((S)-2-Pyrrolidone-5-aminomethyl)carbonyloxy-2-phenylbenzoyl Methionine The resultant compound from Example 8A is hydrolyzed according to the procedure of Example 1B to give the title product.

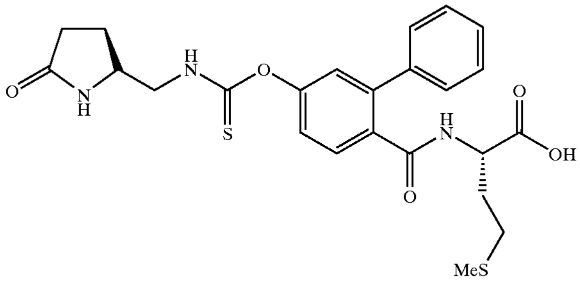

EXAMPLE 9

4-((S)-2-Pyrrolidone-5-aminomethyl) thiocarbonyloxy-2-phenylbenzoyl Methionine Methyl Ester The title compound is prepared as described in Example 8 with the exception that phosgene in toluene is replaced by thiophosgene.

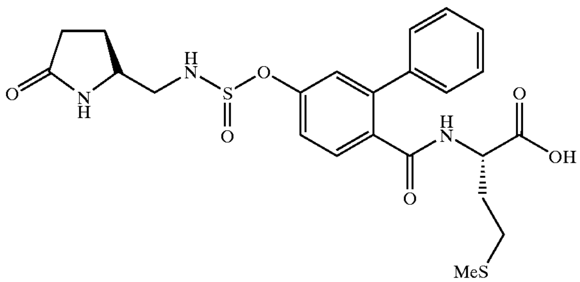

EXAMPLE 10

4-((S)-2-Pyrrolidone-5-aminomethyl)sulfinyloxy)-2-phenylbenzoyl Methionine

The title compound is prepared as described in Example 8 with the exception that phosgene in toluene is replaced by thionyl chloride.

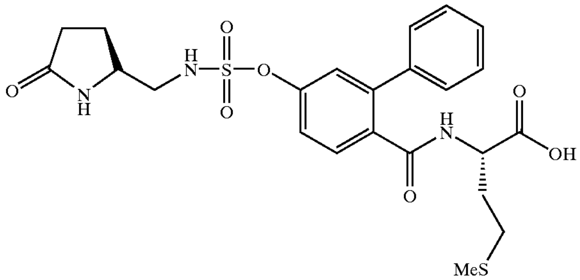

EXAMPLE 11

4-((S)-2-Pyrrolidone-5-aminomethyl)sulfonyloxy)-2-phenylbenzoyl Methionine

The title compound is prepared as described in Example 8 with the exception that phosgene in toluene is replaced by sulfuryl chloride.

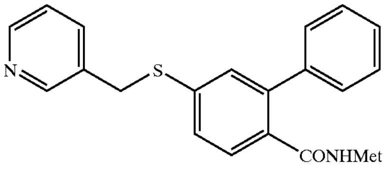

EXAMPLE 12

4-(3-Pyridylmethylenthio)-2-phenylbenzoyl Methionine

EXAMPLE 12A

4-Mercapto-2-phenylbenzoic Acid Methyl Ester

A solution of methyl 4-amino-2-phenylbenzoic acid (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel.

EXAMPLE 12B 4-(2-Pyridylmethylenthio)-2-phenylbenzoic Acid Methyl Ester

A solution of the resultant thiophenol (1.0 equivalent) from Example 12A is treated with 2-chloromethylpyridine hydrochloride (1.0 equivalent) in the presence of a NaH (2.0 equivalents), or $K_2CO_3$ (3.0 equivalent)s in DMF or pyridine. The product is isolated by removal of the solvent and chromatography on silica gel.

EXAMPLE 12C 4-(2-Pyridylthiomethylen)-2-phenylbenzoic Acid

The resultant compound from Example 12B is hydrolyzed according to the procedure of Example 6C to give the title acid.

EXAMPLE 12D 4-(2-Pyridylthiomethylen)-2-phenylbenzoyl Methionine Methyl Ester

The resultant product from Example 12C is coupled to methionine methyl ester according to the procedure of Example 1C to give the title compound.

EXAMPLE 12E 4-(2-Pyridylthiomethylen)-2-phenylbenzoyl Methionine Methyl Ester, Alternate Procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated to afford 2-phenyl-4-mercaptobenzoyl-methionine methyl ester. The thiophenol is purified by chromatography on silica gel. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12F 4-(2-Pyridylthiomethylen)-2-phenylbenzoyl Methionine Methyl Ester, Alternate Procedure 2

Methyl 4-amino-2-phenylbenzoate (100 mmol) is mixed in 50% sulfuric acid, and is cooled by a ice-water bath. To the above mixture with good stirring is added slowly a cold solution of sodium nitrite (110 mmol) in water, the reaction temperature is kept under 10° C. Powdered anhydrous sodium carbonate (100 mmol) is carefully added to the cold reaction mixture in small portions, until the reaction mixture reaches pH 7 to 8. Then, the reaction mixture is added in small portions to a solution of sodium p-methoxybenzylsulfide (prepared from reaction 110 mmol of p-methoxybenzylthiol with 55 mmol of 2.0 M NaOH aqueous solution). After completion of the addition, the reaction mixture is refluxed until judged complete by TLC analysis. The reaction mixture is then extracted with ether, and the organic extracts are washed sequentially with aqueous sodium carbonate solution, water and brine, dried with anhydrous magnesium sulfate, filtered, and concentrated in vacuo. The residue is then purified by column chromatography on silica gel. The product thus obtained is dissolved in methanol and water, followed by addition of lithium hydroxide (200 mmol), and the mixture is refluxed until hydrolysis is judged complete by TLC analysis. The reaction mixture is then acidified with 6 N HCl, and extracted into ethyl acetate. The organic extracts are washed with brine, dried with anhydrous sodium sulfate, and concentrated in vacuo. The crude product obtained is redissolved in methylene chloride, followed by addition of 1-(3-dimethylaminopropyl)-3-ethylcarbodiimide (1.1 equivalent) and 1-hydroxybenzotriazol (1.2 equivalent). The reaction is stirred until it is judged complete by TLC analysis, and then is diluted with ether. The mixture is washed with water, brine, dried over anhydrous magnesium sulfate, filtered, and concentrated in vacuo. The residue is then purified by column chromatography on silica gel. The resulting product is dissolved in trifluoroacetic acid and anisole (1.5 equivalent), and mercury diacetate (1.2 equivalent) is added. After TLC shows no starting material left, the reaction mixture is diluted with ether, washed with water, brine, dried over anhydrous magnesium sulfate, filtered, and concentrated in vacuo. The resulting crude material is purified,by column chromatography to afford 2-phenyl-4-mercaptobenzoyl-methionine methyl ester. A solution of this thiophenol (1.0 equivalent) is treated with 2-chloromethylpyridine hydrochloride (1.0 equivalent) in the presence of a NaH (2.0 equivalents), or $K_2CO_3$ (3.0 equivalents) in DMF or pyridine. The product is isolated by removal of the solvent and chromatography on silica gel.

EXAMPLE 12G 4-(3-Pyridylthiomethylen)-2-phenylbenzoyl Methionine

The resultant compound from Example 12D is hydrolyzed according to the procedure of Example 1B to give the tide product.

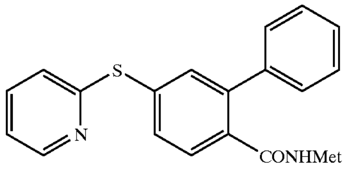

EXAMPLE 13

4-(2-Pyridylthio)-2-phenylbenzoyl Methionine

EXAMPLE 13A

4-Fluoro-2-phenylbenzoic Acid Methyl Ester

A solution of methyl 4-amino-2-phenylbenzoate (1.0 equivalent) in dilute aqueous $HBF_4$ is treated with $NaNO_2$ (1.1 equivalents) until an excess of nitrous acid persists. The mixture is extracted into ethyl acetate which is dried and evaporated. The title ester is purified by chromatography on silica gel.

EXAMPLE 13B

4-Fluoro-2-phenylbenzoic Acid

The resultant compound from Example 13A is hydrolyzed according to the procedure of Example 6C to give the tide acid.

EXAMPLE 13C

4-Fluoro-2-phenylbenzoyl Methionine Methyl Ester

The resultant product from Example 13B is coupled to methionine methyl ester according to the procedure of Example 1C to give the tide compound.

EXAMPLE 13D 4-(2-Pyridylthio)-2-phenylbenzoyl Methionine Methyl Ester

A mixture of the resultant fluorobenzoate from Example 13C (1.0 equivalent) and 2-mercaptopyridine (1.0 equivalent) is treated with $K_2CO_3$ (2.0 equivalents) or NaH (1.0 equivalent) in DMF or DMSO and is stirred until the reaction is judged complete by TLC analysis. The mixture is diluted with water and extracted into ethyl acetate which is dried and evaporated. Chromatography of the residue on silica gel affords the title compound.

EXAMPLE 13E 4-(2-Pyridylthio)-2-phenylbenzoyl Methionine Methyl Ester, Alternate Procedure 1

A solution of 4-amino-2-phenylbenzoyl methionine methyl ester (1.0 equivalent) in dilute aqueous $H_2SO_4$ is treated with $NaNO_2$ (1.1 equivalents) to form the diazonium salt. The reaction is treated with $S_8$ (10 equivalents) and heated. The mixture is extracted into ethyl acetate which is dried and evaporated. The title thiophenol is purified by chromatography on silica gel. A solution of this thiophenol (1.0 equivalent) is treated with 2-bromopyridine hydrobromide (1.0 equivalent) in the presence of a NaH (2.0 equivalent), or $K_2CO_3$ (3.0 equivalent)s in DMF or pyridine. The product is isolated by removal of the solvent and chromatography on silica gel.

EXAMPLE 13F 4-(2-Pyridylthio)-2-phenylbenzoyl Methionine Methyl Ester, Alternate Procedure 2

A solution of the resultant thiophenol from Example 12A (1.0 equivalent) is treated with 2-bromopyridine hydrobromide (1.0 equivalent) in the presence of a NaH (2.0 equivalents), or $K_2CO_3$ (3.0 equivalents) in DMF or pyridine. The product is isolated by removal of the solvent and chromatography on silica gel. The resultant ester is hydrolyzed according to the procedure of Example 6C and then is coupled to methionine methyl ester according to the procedure of Example 1C to give the title compound.

EXAMPLE 13G 4-(2-Pyridylthio)-2-phenylbenzoyl Methionine

The resultant compound from Example 13D is hydrolyzed according to the procedure of Example 1B to give the title product.

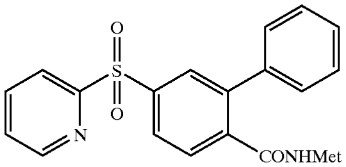

EXAMPLE 14

4-(2-Pyridylsulfonyl)-2-phenylbenzoyl Methionine

EXAMPLE 14A 4-(2-Pyridylsulfonyl)-2-phenylbenzoic Acid Methyl Ester

A solution of 4-(2-pyridylthio)-2-phenylbenzoic acid methyl ester (Example 13F) is carefully treated with two equivalents of meta-chloroperbenzoic acid in methylene chloride at low temperature and the reaction is then quenched with aqueous $Na_2SO_3$ when judged complete by TLC analysis. The layers are separated and the organic phase is extracted with aqueous $NaHCO_3$ to remove the m-chlorobenzoic acid. The product is isolated by removal of the solvent and is purified by chromatography on silica gel.

EXAMPLE 14B 4-(2-Pyridylsulfonyl)-2-phenylbenzoic Acid

The resultant compound from Example 14A is hydrolyzed according to the procedure of Example 6C to give the title acid.

EXAMPLE 14C 4-(2-Pyridylsulfonyl)-2-phenylbenzoyl Methionine Methyl Ester

The resultant product from Example 14B is coupled to methionine methyl ester according to the procedure of Example 1C to give the title compound.

EXAMPLE 14D 4-(2-Pyridylsulfonyl)-2-phenylbenzoyl Methionine

The resultant compound from Example 14C is hydrolyzed according to the procedure of Example 1B to give the title product.

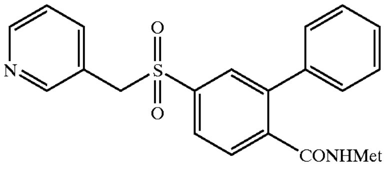

EXAMPLE 15

4-(3-Pyridylthiomethylen)-2-phenylbenzoyl Methionine

The title compound is prepared from the resultant product of Example 12B using the procedures from Example 14.

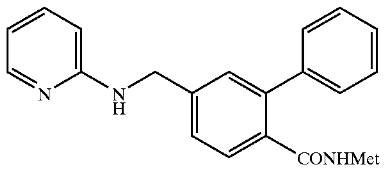

EXAMPLE 16

4-[(2-Aminopyridyl)methylene]-2-phenylbenzoyl Methionine

EXAMPLE 16A

2-Phenylterephthalic Acid Mono Methyl Ester

A solution of 4-bromo-2-phenylbenzoic acid methyl ester (1.0 equivalent), $Pd(OAc)_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 16B 4-(Hydroxymethyl)-2-phenylbenzoic Acid Methyl Ester

The resultant acid from Example 16A (1.0 equivalent) is treated with a slight excess of N-methylmorpholine (1.1 equivalent) and isobutylchloroformate (1.0 equivalent) in THF at 0° C. The mixture is then treated with $NaBH_4$ (1.0 equivalent) and aqueous $NaHCO_3$ and stirred at 0° C. until the reaction is judged complete by TLC analysis. The mixture is poured into dilute aqueous acid and extracted into ethyl acetate which is dried and evaporated. The product is purified by chromatography on silica gel.

EXAMPLE 16C 4-(Hydroxymethyl)-2-phenylbenzoic Acid

The resultant compound from Example 16B is hydrolyzed according to the procedure of Example 6C to give the title acid.

EXAMPLE 16D 4-(Hydroxymethyl)-2-phenylbenzoyl Methionine Methyl Ester

The resultant product from Example 16C is coupled to methionine methyl ester according to the procedure of Example 1C to give the title compound.

EXAMPLE 16E

4-Formyl-2-phenylbenzoyl Methionine Methyl Ester

A mixture of the resultant alcohol from Example 16D (1.0 equivalent), N-methylmorpholine-N-oxide (1.5 equivalents), molecular sieves, and a catalytic amount of TPAP is stirred in a $CH_2Cl_2$/acetonitrile mixture until the reaction is judged complete by TLC analysis. The mixture is diluted with ethyl ether and filtered through $SiO_2$. The product is purified by chromatography on silica gel.

EXAMPLE 16F 4-(Formyl)-2-phenylbenzoyl Methionine Methyl Ester, Alternate Procedure A mixture of (2-phenyl-4-bromobenzoyl) methionine methyl ester (100 mmol), 4,4,6-trimethyl-2-vinyl-1,3,2-dioxaborinane (100 mmol), tetrakis(triphenylphosphine) palladium(0) (3 mmol) in toluene and 2 M sodium carbonate in water (100 mL) is heated at 80° C. until the starting methyl ester disappears. The resulting mixture is extracted with ether, and washed with water, brine, dried over anhydrous magnesium sulfate, filtered, and concentrated in vacuo. The residue is then purified by column chromatography on silica gel. To a solution of the resulting vinyl compound in dioxane/water (4/1) is added osmium tetraoxide (0.03 equivalent), N-methylmorpholine N-oxide (3 equivalents), and the reaction is stirred at 25° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16G 4-(Hydroxymethyl)-2-phenylbenzoyl Methionine Methyl Ester, Alternate Procedure To a solution of the resultant compound from Example 16E in ethanol at 0° C. is added sodium borohydride (0.5 equivalent), and the reaction is stirred at 0° C. until TLC analysis shows the reaction to be complete. The reaction mixture is extracted with ether, which is washed with water and brine, dried over anhydrous magnesium sulfate, filtered, and concentrated in vacuo. The residue is then purified by column chromatography on silica gel to afford the title product.

EXAMPLE 16H

4-[(2-Aminopyridyl)methylene]-2-phenylbenzoyl Methionine Methyl Ester

A mixture of the resultant aldehyde from Example 16E (1.0 equivalent), 2-aminopyridine (1.0 equivalent) and $NaCNBH_3$ (1.5 equivalents) in methanol/acetic acid is stirred until the reaction is judged complete by TLC analysis. The mixture is poured into aqueous $NaHCO_3$ and extracted into ethyl acetate which is dried and evaporated. Chromatography of the residue on silica gel affords the title compound.

EXAMPLE 16I

4-[(2-Aminopyridyl)methylene]-2-phenylbenzoyl Methionine

The resultant compound from Example 16H is hydrolyzed according to the procedure of Example 1B to give the title product.

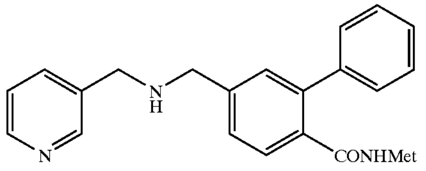

EXAMPLE 17

4-[(3-Aminomethylpyridyl)methylene]-2-phenylbenzoyl Methionine

Using the procedures of Examples 16F–G and replacing 2-aminopyridine with 3-aminomethylpyridine affords the title product.

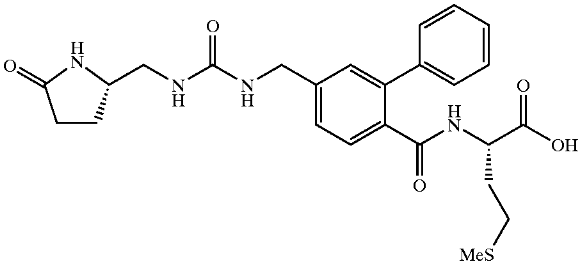

EXAMPLE 18

4-((S)-2-Pyrrolidone-5-aminomethylcarbonyl)aminomethyl-2-phenylbenzoyl Methionine

EXAMPLE 18A 4-(Azidomethyl)-2-phenylbenzoyl Methionine Methyl Ester

To triphenylphosphine (1.0 equivalent) in tetrahydrofuran (THF) at −78° C. is added diethyl azodicarboxylate (1.0 equivalent) in THF. To this mixture is added a solution of hydrazoic acid in benzene (2.0 equivalents) and then the resultant compound from Example 16D (1.0 equivalent). After one hour the mixture was warmed to room temperature, stirred until the reaction is judged complete by TLC analysis, evaporated and chromatographed on silica gel to afford the title product.

EXAMPLE 18B 4-(Aminomethyl)-2-phenylbenzoyl Methionine Methyl Ester

To the resultant compound from Example 18A in methanol is added triethylamine (3.0 equivalent) and propane 1,3-dithiol (3.0 equivalents). After the reaction is judged complete by TLC analysis, the mixture is filtered and evaporated. Chromatography of the residue on silica gel provides the title product.

EXAMPLE 18C 4-((S)-2-Pyrrolidone-5-aminomethylcarbonyl)aminomethyl-2-phenylbenzoyl Methionine Methyl Ester To a solution of the resultant compound from Example 18B (1.0 equivalent) in methylene chloride is added triphosgene (0.33 equivalent) and triethyl amine (2.0 equivalents). This intermediate is reacted without further purification with (S)-5-aminomethyl-2-pyrrolidone (1.0 equivalent) and triethylamine (1.0 equivalent). When judged complete by TLC analysis, the reaction is taken up in ethyl acetate and washed with 1N HCl and brine, evaporated, and purified by chromatography on silica gel.

EXAMPLE 18D 4-((S)-2-Pyrrolidone-5-aminomethylcarbonyl)aminomethyl-2-phenylbenzoyl Methionine The resultant compound from Example 18C is hydrolyzed according to the procedure of Example 1B to give the title product.

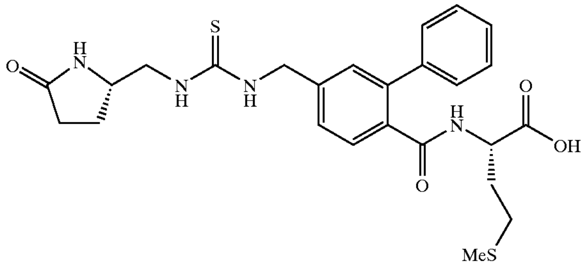

EXAMPLE 19

4-((S)-2-Pyrrolidone-5-aminomethylthiocarbonyl)aminomethyl-2-phenylbenzoyl Methionine The title compound is prepared as described in Example 18 with the exception that triphosgene (0.33 equivalent) is replaced by thiophosgene (1.0 equivalent).

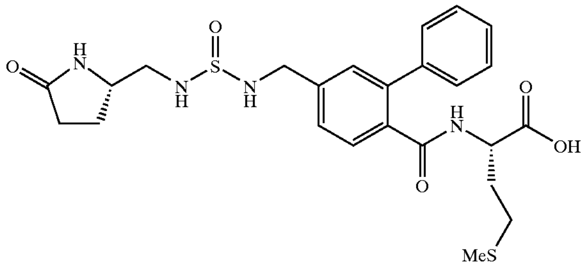

EXAMPLE 20

4-((S)-2-Pyrrolidone-5-aminomethylsulfinyl)aminomethyl-2-phenylbenzoyl Methionine The title compound is prepared as described in Example 18 with the exception that triphosgene (0.33 equivalent) is replaced by thionyl chloride (1.0 equivalent).

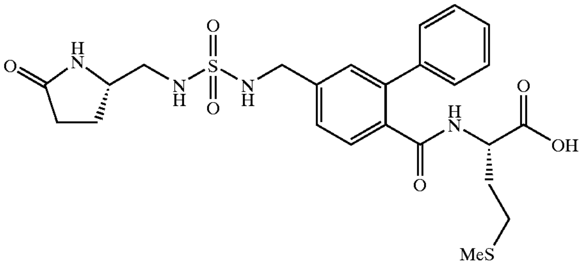

EXAMPLE 21

4-((S)-2-Pyrrolidone-5-aminomethylsulfonyl)aminomethyl-2-phenylbenzoyl Methionine Using the Procedure of Example 4 with the resultant compound from Example 18B affords the title product.

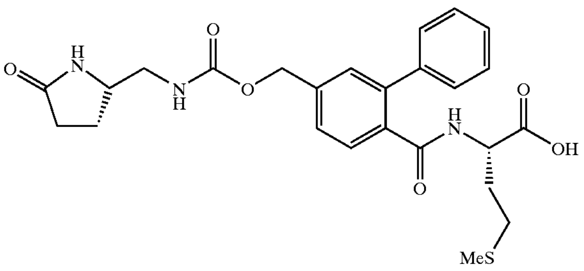

EXAMPLE 22

4-((S)-2-Pyrrolidone-5-aminomethylcarbonyloxymethylene)-2-phenylbenzoyl Methionine Using the procedure of Example 8 with the resultant compound from Example 16D provides the title product.

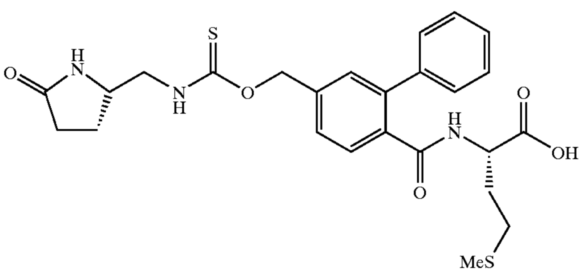

EXAMPLE 23

4-((S)-2-Pyrrolidone-5-aminomethyl)thiocarbonyloxymethylene)-2-phenylbenzoyl Methionine Using the procedure of Example 8 with the resultant compound from Example 16D and replacing triphosgene (0.33 equivalent) with thiophosgene (1.0 equivalent) provides the title product.

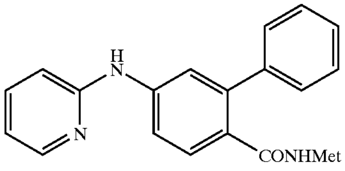

EXAMPLE 24

4-(2-Aminopyridyl)-2-phenylbenzoyl Methionine

EXAMPLE 24A 4-(2-Aminopyridyl)-2-phenylbenzoyl Methionine Methyl Ester

4-Amino-2-phenylbenzoyl methionine (1.0 equivalent) methyl ester and 2-bromopyridine hydrobromide (1.0 equivalent) in pyridine are heated until the reaction is judged complete by TLC analysis. The solvent is evaporated and the residue is taken up in ethyl acetate which is washed with water and brine, dried, and evaporated. Chromatography on silica gel affords the title product.

EXAMPLE 24B 4-(2-Aminopyridyl)-2-phenylbenzoyl Methionine

The resultant compound from Example 24A is hydrolyzed according to the procedure of Example 1B to give the title product.

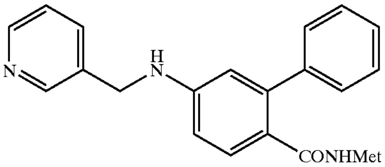

EXAMPLE 25

4-(3-Aminomethylpyridyl)-2-phenylbenzoyl Methionine

EXAMPLE 25A 4-(3-Aminomethylpyridyl)-2-phenylbenzoyl Methionine Methyl Ester A mixture of 3-pyridinecarboxaldehyde (1.0 equivalent), 4-amino-2-phenylbenzoyl methionine methyl ester (1.0 equivalent) and $NaCNBH_3$ (1.0 equivalent) in methanol/acetic acid is stirred until the reaction is judged complete by TLC analysis. The mixture is poured into aqueous $NaHCO_3$ and extracted into ethyl acetate which is dried and evaporated. Chromatography of the residue on silica gel affords the title compound.

EXAMPLE 25B 4-(3-Aminomethylpyridyl)-2-phenylbenzoyl Methionine

The resultant compound from Example 25A is hydrolyzed according to the procedure of Example 1B to give the title product.

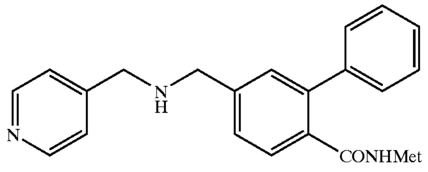

EXAMPLE 26

4-[(4-Aminomethylpyridyl)methylene]-2-phenylbenzoyl Methionine

Using the procedures of Examples 25 with the resultant amine from Example 18B and 3-pyridinecarboxaldehyde affords the title product.

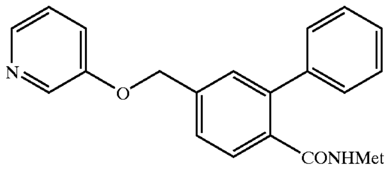

EXAMPLE 27

4-(3-Pyridyloxymethylene)-2-phenylbenzoyl Methionine

EXAMPLE 27A 4-(p-Toluenesulfonyloxy)-2-phenylbenzoyl Methionine Methyl Ester

The resultant compound from Example 16D (1.0 equivalent) and p-toluenesulfonyl chloride (1.0 equivalent) in pyridine are stirred until the reaction is judged complete by TLC analysis. The solvent is evaporated and the residue is taken up in ethyl acetate which is washed with water and brine, dried, and evaporated. Chromatography on silica gel affords the title product.

EXAMPLE 27B 4-(3-Pyridyloxymethylene)-2-phenylbenzoyl Methionine Methyl Ester 3-Hydroxypyridine (1.0 equivalent) is treated with sodium hydride (1.0 equivalent) in DMSO, then the resultant compound from Example 27A (1.0 equivalent) is added. When judged complete by TLC analysis, the reaction is diluted with water and ethyl acetate, the organic layer is dried and concentrated, and the crude title compound is purified by chromatography on silica gel.

EXAMPLE 27C 4-(3-Pyridyloxymethylene)-2-phenylbenzoyl Methionine

The resultant compound from Example 27B is hydrolyzed according to the procedure of Example 1B to give the title product.

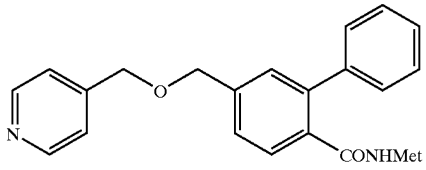

EXAMPLE 28

4-(3-Pyridylmethoxymethylene)-2-phenylbenzoyl Methionine

EXAMPLE 28A 4-(3-Pyridylmethoxymethylene)-2-phenylbenzoyl Methionine Methyl Ester Using the procedure of Example 27B but replacing 3-hydroxypyridine with 3-hydroxymethylpyridine affords the title compound.

EXAMPLE 28B 4-(3-Pyridylmethoxymethylene)-2-phenylbenzoyl Methionine Methyl Ester, Alternate Procedure The resultant compound from Example 16D (1.0 equivalent) is treated with sodium hydride (2.0 equivalents) in DMSO, then 3-chloromethylpyridine hydrochloride (1.0 equivalent) is added. When judged complete by TLC analysis, the reaction is diluted with water and ethyl acetate, the organic layer is dried and concentrated, and the crude title compound is purified by chromatography on silica gel.

EXAMPLE 28C 4-(3-Pyridylmethoxymethylene)-2-phenylbenzoyl Methionine Methyl Ester The resultant compound from Example 28A is hydrolyzed according to the procedure of Example 1B to give the title product.

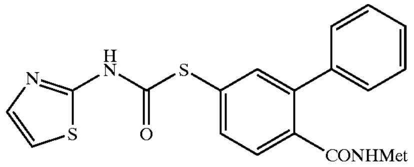

EXAMPLE 29

{2-Phenyl-4-[(thiazol-2-ylamino)carbonylthio]benzoyl}-methionine

EXAMPLE 29A

Thiazol-2-ylisocyanate

A solution of 2-aminothiazol (1.0 mmol), triphosgene (0.34 mmol) and triethylamine (1.0 mmol) in toluene (10 mL) is refluxed until TLC shows no starting amine left. The solvent is then removed in vacuo, and the resulting material is used without further purification.

EXAMPLE 29B

{2-Phenyl-4-[(thiazol-2-ylamino)carbonylthio]benzoyl}-metionine Methyl Ester

A solution of 2-phenyl-4-mercaptobenzoyl-methionine methyl ester from example 12E or 12F (1.0 mmol) and the isocyanate prepared in example 29A (1.0 mmol) in THF is refluxed until TLC shows no thiol left. The solvent is then evaporated in vacuo, and the residue is purified by column chromatography on silica gel to give the title compound.

EXAMPLE 29C

{2-Phenyl-4-[(thiazol-2-ylaminocarbonylthio] benzoyl}-metionine Methyl Ester, Alternate Procedure To a solution of 2-phenyl-4-mercaptobenzoyl-methionine methyl ester from example 12E or 12F (1 equivalent) in methylene chloride is added a solution of phosgene in toluene (1.0 equivalent) and pimethylaminopyridine (2.0 equivalents). When the reaction is judged complete by TLC analysis, the solvent is evaporated with toluene chasers. The thiochloroformate is reacted without further purification with 2-aminothiazol (1.0 equivalent) and triethylamine (1.0 equivalent) in dichloromethane. When judged complete by TLC analysis, the reaction is taken up in ethyl acetate and washed with 1N HCl and brine, evaporated, and purified by chromatography on silica gel.

EXAMPLE 29D

{2-Phenyl-4-[(thiazol-2-ylamino)carbonylthio] benzoyl}-methionine

The resultant compound from Example 29B is hydrolyzed according to the procedure of Example 1B to give the title product.

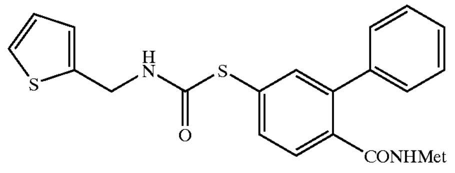

EXAMPLE 30

{2-Phenyl-4-[(thien-2-ylmethylamino)carbonylthio] benzoyl}-methionine

Using the procedure of Example 29 but replacing 2-aminothiazol with thien-2-ylmethylamine affords the title product.

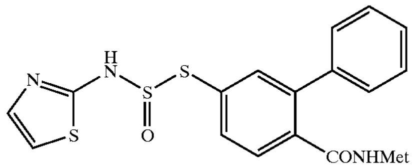

EXAMPLE 31

{2-Phenyl-4-[(thiazol-2-ylamino)thionylthio] benzoyl}-methionine

EXAMPLE 31A (N-Thionyl)thiazol-2-ylamine

A solution of 2-aminothiazol (1.0 mmol), in thionyl chloride is heated at reflux until the reaction is judged to be complete by TC analysis. Then, the excess thionylchloride is distilled out in vacuo. The resulting material is used without further purification.

EXAMPLE 31B

{2-Phenyl-4-[(thiazol-2-ylamino)thionylthio] benzoyl}-metionine Methyl Ester

Using the procedure of Example 29B but replacing the resultant product from Example 29A with the resultant product from Example 31A affords the title compound.

EXAMPLE 31C

{2-Phenyl-4-[(thiazol-2-ylamino)thionylthio] benzoyl}-metionine Methyl Ester, Alternate Procedure Using the procedure of Example 29C but replacing phosgene in toluene with thionyl chloride affords the title compound.

EXAMPLE 31D

{2-Phenyl-4-[(thiazol-2-ylamino)thionylthio] benzoyl}-methionine

The resultant compound from Example 31B is hydrolyzed according to the procedure of Example 1B to give the title product.

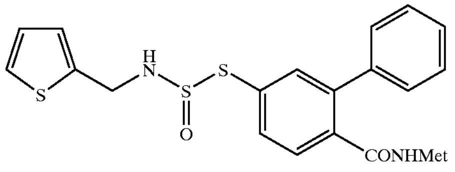

EXAMPLE 32

{2-Phenyl-4-[(thien-2-ylmethylamino)thionylthio] benzoyl}-methionine

Using the procedure of Example 31 but replacing 2-aminothiazol with thien-2-ylmethylamine affords the title product.

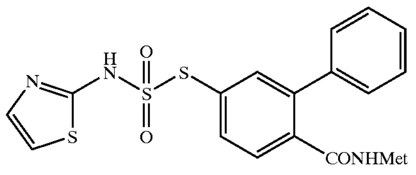

EXAMPLE 33

{2-Phenyl-4-[(thiazol-2-ylamino)sulfonylthio] benzoyl}-metionine Methyl Ester

Using the procedure of Example 31 but replacing thionyl chloride with sulfuryl chloride affords the title product.

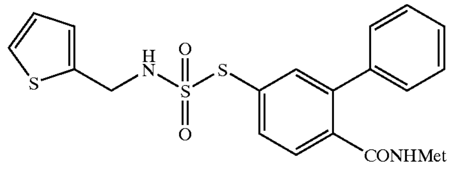

EXAMPLE 34

{2-Phenyl-4-[(thien-2-ylmethylamino)sulfonylthio] benzoyl }-methionine

Using the procedure of Example 31 but replacing 2-aminothiazol with thien-2-ylmethylamine and replacing thionyl chloride with sulfuryl chloride affords the title product.

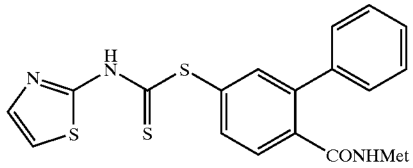

EXAMPLE 35

{2-Phenyl-4-[(thiazol-2-ylamin-6)thiocarbonylthio] benzoyl}-methionine

Using the procedure of Example 29 and replacing triphosgene (0.34 mmol) or a solution of phosgene in toluene (1.0 equivalent) with thiophosgene (1.0 mmol) affords the title product.

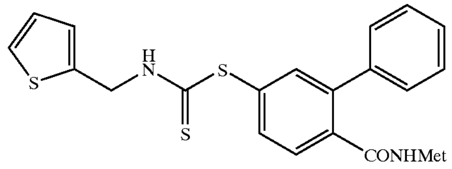

EXAMPLE 36

{2-Phenyl-4-[(thien-2-ylmethylamino) thiocarbonylthio]benzoyl}-methionine

Using the procedure of Example 29 and replacing triphosgene (0.34 mmol) or a solution of phosgene in toluene (1.0 equivalent) with thiophosgene (1.0 mmol) and replacing 2-aminothiazol with thien-2-ylmethylamine affords the title product.

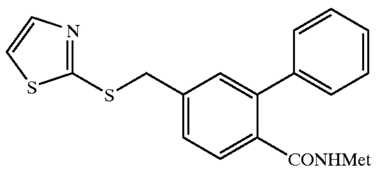

EXAMPLE 37

{2-Phenyl-4-[(thiazol-2-yl)thiomethyl]benzoyl}-methionine

EXAMPLE 37A

{2-Phenyl-4-[thiomethyl]benzoyl}-metionine Methyl Ester

The resultant product from Example 27A is dissolved DMF/water (2/1), and sodium hydrosulfide (5 equivalent) is added to the reaction mixture. The reaction is stirred until TLC analysis shows that the reaction is complete. Then, the reaction mixture is acidified with 3 N HCl to about pH 4, extracted with ether, and washed with water and brine, dried over anhydrous magnesium sulfate, filtered, and concentrated in vacuo. The residue is purified with column chromatography on silica gel to give the title compound.

EXAMPLE 37B

{2-Phenyl-4-[thiomethyl]benzoyl}-metionine Methyl Ester, Alternate Procedure

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16D (1.0 equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 37C

{2-Phenyl-4-[(thiazol-2-yl)thiomethyl]benzoyl}-metionine Methyl Ester

A mixture of the resultant thiol from Example 37A (1 mmol), 2-bromothiazole (1.5 mmol), and anhydrous potassium carbonate (5 mmol) in DMF is stirred at 100° C. until TLC analysis shows that the starting thiol disappeared. Then, the reaction mixture is diluted with water, extracted with ether, and washed with water and brine, dried over anhydrous magnesium sulfate, filtered, and concentrated in vacuo. The residue is purified by column chromatography on silica gel to give the title compound.

{2-Phenyl-4-[(thiazol-2-yl)thiomethyl]benzoyl}-methionine

The resultant compound from Example 37C is hydrolyzed according to the procedure of Example 1B to give the title product.

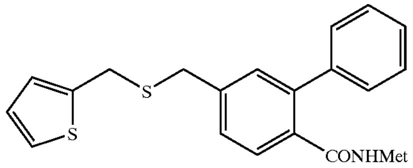

EXAMPLE 38

{2-Phenyl-4-[(thien-2-ylmethyl)thiomethyl] benzoyl}-methionine

Using the procedure of Example 37 and replacing 2-bromothiazole with 2-bromomethylthiophene affords the title product.

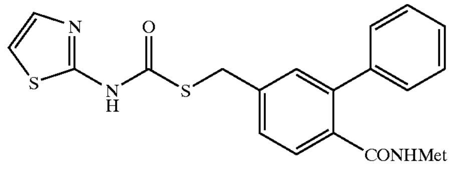

EXAMPLE 39

{2-Phenyl-4-[(thiazol-2-ylaminocarbonylthiomethyl] benzoal}-methionine

Using the procedure of Example 29 with the resultant product from Example 37A affords the title product.

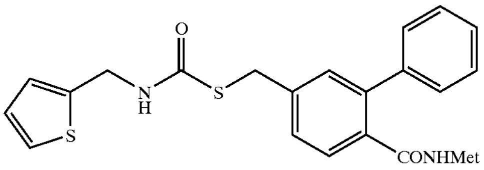

EXAMPLE 40

{2-Phenyl-4-[(thiazol-2-ylamino) carbonylthiomethyl]benzoyl}-methionine

Using the procedure of Example 29 with the resultant product from Example 37A and replacing 2-aminothiazol with thien-2-ylmethylamine affords the title product.

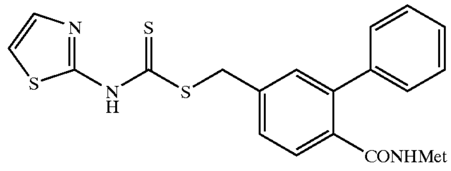

EXAMPLE 41

{2-Phenyl-4-[(thiazol-2-ylamino) thiocarbonylthiomethyl]benzoyl}-methionine

Using the procedure of Example 29 with the resultant product from Example 37A and replacing triphosgene (0.34 mmol) or a solution of phosgene in toluene (1.0 equivalent) with thiophosgene (1.0 mmol) affords the title product.

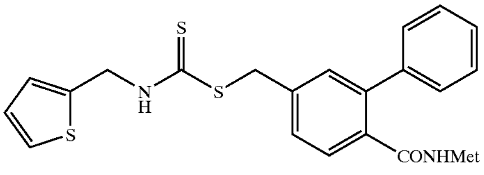

EXAMPLE 42

{2-Phenyl-4-[(thiazol-2-ylamino) thiocaronylthiomethyl]benzoyl}-methionine

Using the procedure of Example 29 with the resultant product from Example 37A, replacing triphosgene (0.34 mmol) or a solution of phosgene in toluene (1.0 equivalent) with thiophosgene (1.0 mmol), and replacing 2-aminothiazol with thien-2-ylmethylamine affords the title product.

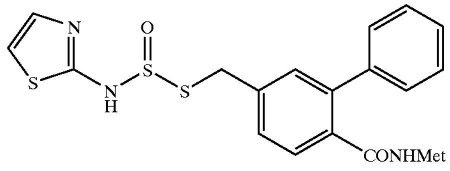

EXAMPLE 43

{2-Phenyl-[(thiazol-2-ylamino)thionylthiomethyl] benzoyl}-methionine

Using the procedure of Example 31 with the resultant product from Example 37A affords the title product.

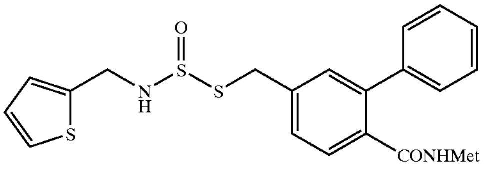

EXAMPLE 44

{2-Phenyl-4-[(thien-2-ylmethylamino) thionylthiomethyl]benzoyl}methionine

Using the procedure of Example 31 with the resultant product from Example 37A and replacing 2-aminothiazol with thien-2-ylmethylamine affords the title product.

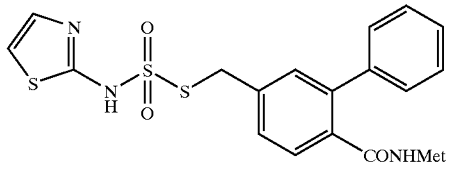

EXAMPLE 45

{2-Phenyl-4-[(thiazol-2-ylamino) sulfonylthiomethyl]benzoyl}-methionine

Using the procedure of Example 31 with the resultant product from Example 37A and replacing thionyl chloride with sulfuryl chloride affords the title product affords the title product.

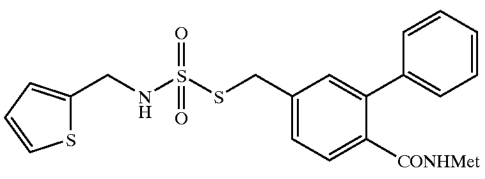

EXAMPLE 46

{2-Phenyl-4-[(thien-2-ylmethylamino) sulfonylthiomethyl]benzoyl}-methionine

Using the procedure of Example 31 with the resultant product from Example 37A, replacing thionyl chloride with sulfuryl chloride, and replacing 2-aminothiazol with thien-2-ylmethylamine affords the title product.

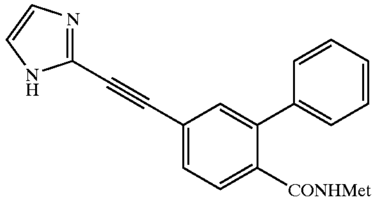

EXAMPLE 47

{4-[2-(Imidazol-2-yl)ethynyl]-2-phenylbenzoyl}methionine

EXAMPLE 47A (4-Ethynyl-2-phenylbenzoyl)metionine Methyl Ester

A mixture of (2-phenyl-4-bromobenzoyl)-methionine methyl ester (100 mmol), diethylamine (300 mmol), trimethylsilylacetylene (110 mmol), bis(triphenylphosphine) palladium diacetate (5 mmol) and copper(I) iodide (3 mmol) in toluene is heated at 60° C. until TLC analysis indicates the starting methyl ester has disappeared. The reaction mixture is concentrated in vacuo, redissolved in ether, filtered through silica gel, and concentrated. The residue is then dissolved in THF, and is treated with tetrabutylammonium fluoride (120 mmol). After TLC analysis indicates that no starting material is left, the reaction mixture is diluted with ether, washed with water and brine, dried over anhydrous magnesium sulfate, filtered, and concentrated in vacuo. The residue is then purified with column chromatography on silica gel to give the title product.

EXAMPLE 47B

{4-[2-(Imidazol-2-yl)ethynyl]-2-phenylbenzoyl}-metionine Methyl Ester

The resultant product from Example 47A (5 mmol) is mixed with 4-bromoimidazole (5 mmol), diethylamine (1 mL), bis(triphenylphosphine)palladium diacetate (0.1 mmol) and copper(I) iodide (0.1 mmol) in toluene. The mixture is stirred at 25° C. until TLC analysis indicates the reaction is complete. The reaction mixture is concentrated in vacuo, and the residue is purified with column chromatography on silica gel to give the title product.

EXAMPLE 47C

{4-[2-(Imidazol-2-yl)ethynyl]-2-phenylbenzoyl}-methionine

The resultant compound from Example 47B is hydrolyzed according to the procedure of Example 1B to give the title product.

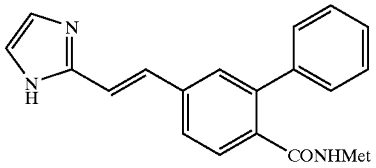

EXAMPLE 48

{4-[2-(Imidazol-4-yl)ethenyl]-2-phenylbenzoyl}-methionine

The resultant acetylene (3 mmol) from Example 47 is mixed with Lindlar catalyst (50 mg), 5 drops of quinoline in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

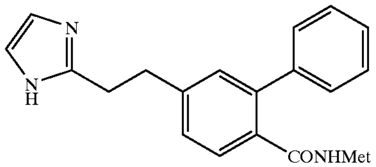

EXAMPLE 49

{4-[2-(Imidazol-4-yl)ethyl]-2-phenylbenzoyl}-methionine

The resultant olefin (1 mmol) from Example 48 is mixed with 5% palladium on carbon (100 mg) in ethyl acetate. The reaction mixture is attached to a hydrogenation apparatus, and then is detached from the apparatus after about 95% of the theoretical hydrogen has been absorbed. The reaction mixture is filtered and concentrated in vacuo. The crude product is purified with a column chromatography on silica gel to give the title compound.

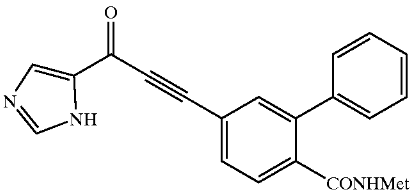

EXAMPLE 50

{4-[2-(Imidazol-4-ylcarbonyl)ethynyl]-2-phenylbenzoyl}-methionine

EXAMPLE 50A

{4-[2-(Imidazol-4-ylcarbonyl)ethynyl]-2-phenylbenzoyl}-metionine Methyl Ester

A stainless autoclave containing the resultant product from Example 47A (5 mmol), 4-bromoimidazole (5 mmol), 1,1'-bis(diphenylphosphine)-ferrocenepalladium dichloride (0.1 mmol), and triethylamine (10 mL) is flushed with nitrogen, and pressurized to 20 atm with carbon monoxide. The reaction mixture is stirred at 120° C. until judged complete by TLC analysis. After cooling, the triethylamine is evaporated in vacuo, and the residue is purified by column chromatography on silica gel to give the title compound.

EXAMPLE 50B

{4-[2-(Imidazol-4-ylcarbonyl)ethynyl]-2-phenylbenzoyl}-methionine

The resultant compound from Example 50A is hydrolyzed according to the procedure of Example 1B to give the title product.

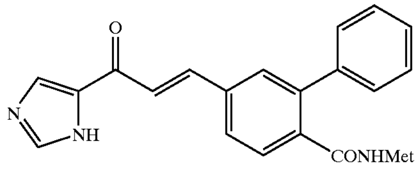

EXAMPLE 51

{4-[2-(Imidazol-4-ylcarbonyl)ethenyl]-2-phenylbenzoyl}-methionine

Using the procedure of Example 48 with the resultant compound from Example 50 affords the title product.

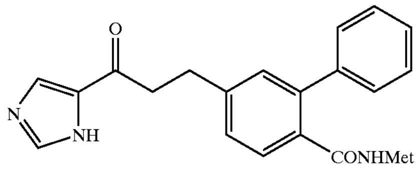

EXAMPLE 52

{4-[2-(Imidazol-4-ylcarbonyl)ethyl]-2-phenylbenzoyl}-methionine

Using the procedure of Example 49 with the resultant compound from Example 51 affords the title product.

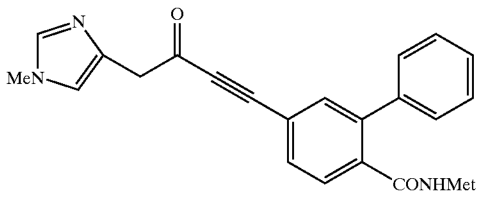

EXAMPLE 53

{4-[4-(1-Methylimidazol-4-yl)-3-keto-1-butynyl]-2-phenylbenzoyl}methionine

EXAMPLE 53A

{4-[4-(1-Methylimidazol-4-yl)-3-keto-1-butynyl]-2-phenylbenzoyl}-metionine Methyl Ester To a solution of 1-methyl-4-imidazoleacetic acid (5 mmol) in methylene chloride at 0° C. is added oxalyl chloride (6 mmol) and DMF (0.05 mmol). After 30 minute, the solvent is evaporated in vacuo. The residue is redissolved in dichloromethane, followed by the addition of the resultant acetylene from Example 47A (5 mmol), triethylamine (10 mmol), and copper(I) iodide (1 mmol). The reaction is stirred at 25° C. until TLC analysis indicates no starting material is left in with water and brine, dried over anhydrous magnesium sulfate, filtered, and concentrated in vacuo. The residue is then purified by column chromatography on silica gel to give the title compound.

EXAMPLE 53B

{4-[4-(1-Methylimidazol-4-yl)-3-keto-1-butynyl]-2-phenylbenzoyl}-methionine

The resultant compound from Example 53A is hydrolyzed according to the procedure of Example 1B to give the title product.

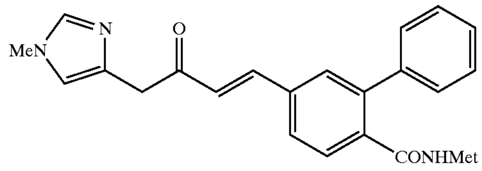

EXAMPLE 54

{4-[4-(1-Methylimidazol-4-yl)-3-keto-1-butenyl]-2-phenylbenzoyl}-methionine

Using the procedure of Example 48 with the resultant compound from Example 53 affords the title product.

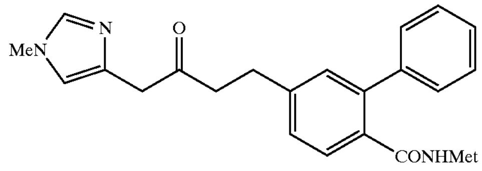

EXAMPLE 55

{4-[4-(1-Methylimidazol-4-yl)-3-keto-1-butyl]-2-phenylbenzoyl}-methionine

Using the procedure of Example 49 with the resultant compound from Example 53 affords the title product.

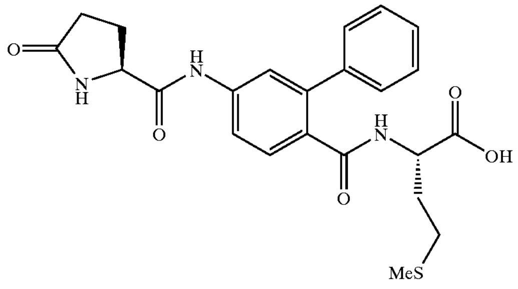

EXAMPLE 56

(S) Pyroglutamyl-(4-amino-2-phenyl)benzoyl Methionine

EXAMPLE 56A (S) Pyroglutamyl-(4-amino-2-phenyl)benzoyl Methionine Methyl Ester

To a solution of 4-amino-2-phenylbenzoyl methionine methyl ester (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 56B (S) Pyroglutamyl-(4-amino-2-phenyl)benzoyl Methionine

The resultant compound from Example 56A is hydrolyzed according to the procedure of Example 1B to give the title product.

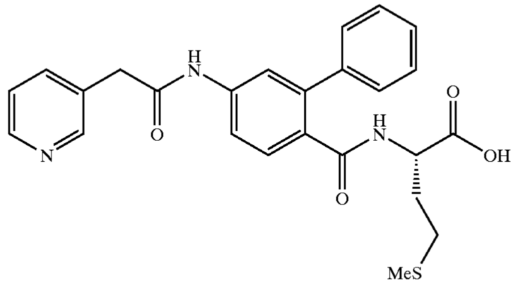

EXAMPLE 57

(S) Pyroglutamyl-(4-amino-2-phenyl)benzoyl Methionine

Using the procedure of Example 56 and replacing pyroglutamic acid with 3-pyridylacetic acid affords the title product.

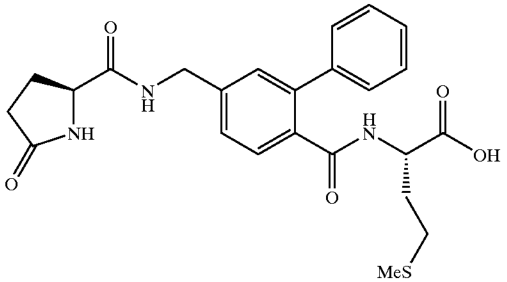

EXAMPLE 58

(S) Pyroglutamyl-(4-aminomethyl-2-phenyl)benzoyl Methionine

EXAMPLE 58A (S) Pyroglutamyl-(4-aminomethyl-2-phenyl)benzoyl Methionine Methyl Ester To a solution of the resultant amine from Example 18B (1.0 equivalent) in dimethylformamide (DMF) is added 3-hydroxy-1,2,3-benzotriazin-4(3H)-one (1.5 equivalents) followed by pyroglutamic acid (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 58B (S) Pyroglutamyl-(4-aminomethyl-2-phenyl)benzoyl Methionine

The resultant compound from Example 58A is hydrolyzed according to the procedure of Example 1B to give the title product.

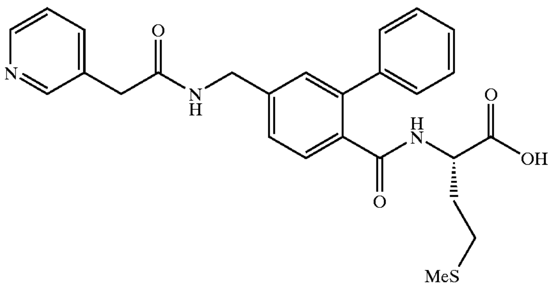

EXAMPLE 59

Naming Error (S) Pyroglutamyl-(4-aminomethyl-2-phenyl)benzoyl Methionine

Using the procedure of Example 58 and replacing pyroglutamic acid with 3-pyridylacetic acid affords the title product.

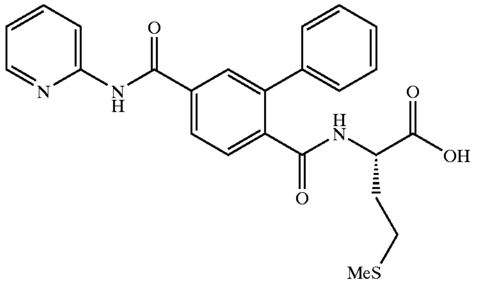

EXAMPLE 60

4-[(Pyridin-2-ylamino)carbonyl]-2-phenylbenzoyl Methionine

EXAMPLE 60A

4-Carboxy-2-phenylbenzoyl Methionine Methyl Ester

A solution of 4-bromo-2-phenylbenzoyl methionine methyl ester (1.0 equivalent), $Pd(OAc)_2$ (0.05 equivalent) and DPPE (1.0 equivalent) is heated in DMF to 65° C. under 4 atm. of carbon monoxide until TLC analysis indicates that the reaction is complete. The reaction mixture is poured into water and extracted with ethyl acetate which is dried and evaporated. The product is purified by chromatography on silica gel.

EXAMPLE 60B

4-[(Pyridin-2-ylamino)carbonyl]-2-phenylbenzoyl Methionine Methyl Ester

To a solution of the resultant acid from Example 60A (1.0 equivalent) in DMF is added 3-hydroxy-1,2,3-benzotriazin-4(3H)-one (1.5 equivalents) followed by 2-aminopyridine (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed by 1N HCl and saturated brine, and then is dried and evaporated. The crude reaction mixture is purified by column chromatography to afford the title product.

EXAMPLE 60C

4-[(Pyridin-2-ylamino)carbonyl]-2-phenylbenzoyl Methionine

The resultant compound from Example 60B is hydrolyzed according to the procedure of Example 1B to give the title product.

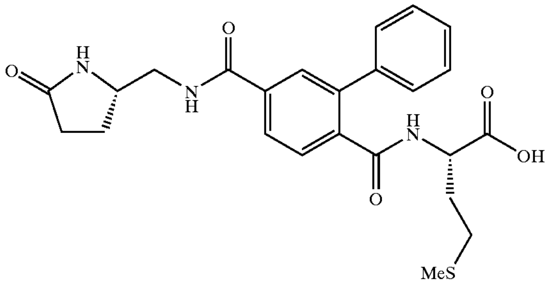

EXAMPLE 61

4-((S)-2-Pyrrolidone-5-aminomethyl)carbonyl)-2-phenylbenzoyl Methionine

Using the procedure of Example 60 and replacing 2-aminopyridine with (S)-5-aminomethyl-2-pyrrolidone affords the title product.

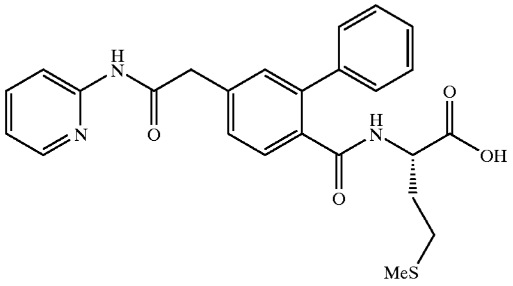

EXAMPLE 62

4-[(Pyridin-2-ylamino)carbonylmethyl]-2-phenylbenzoyl Methionine

EXAMPLE 62A

4-Diazocarbonyl-2-phenylbenzoyl Methionine Methyl Ester

The resultant acid from Example 60A (1 equivalent) in dichloromethane is treated with oxalyl chloride (1 equivalent) and DMF (0.05 equivalent). When gas evolution has ceased, the acid chloride solution is added to an ether solution of diazomethane. The reaction is stirred until judged complete by TLC analysis, and then is concentrated to give the crude title compound which is purified by chromatography on silica gel.

EXAMPLE 62B

4-Carboxymethyl-2-phenylbenzoyl Methionine Methyl Ester

The resultant compound from Example 62A (1 equivalent) in dioxane is added to a slurry of sodium thiosulfate (1.1 equivalents) and silver(I) oxide (0.5 equivalent) in water. The reaction is stirred until judged complete by TLC analysis, filtered, acidified, and extracted into ethyl acetate which is dried and evaporated. Chromatography of the residue on silica gel affords the title product.

EXAMPLE 62C

4-[(Pyridin-2-ylamino)carbonylmethyl]-2-phenylbenzoyl Methionine Methyl Ester

To a solution of the resultant acid from Example 62B (1.0 equivalent) in dimethylformamide (DMF) is added 3-hydroxy-1,2,3-benzotriazin-4(3H)-one (1.5 equivalents) followed by 2-aminopyridine (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 62D

4-[(Pyridin-2-ylamino)carbonylmethyl]-2-phenylbenzoyl Methionine

The resultant compound from Example 62C is hydrolyzed according to the procedure of Example 1B to give the title product.

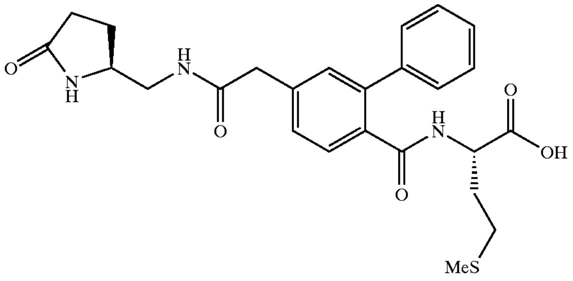

EXAMPLE 63

4-((S)-2-Pyrrolidone-5-aminomethyl) carbonylmethyl)-2-phenylbenzoyl Methionine

Using the procedure of Example 62 and replacing 2-aminopyridine with (S)-5-aminomethyl-2-pyrrolidone affords the title product.

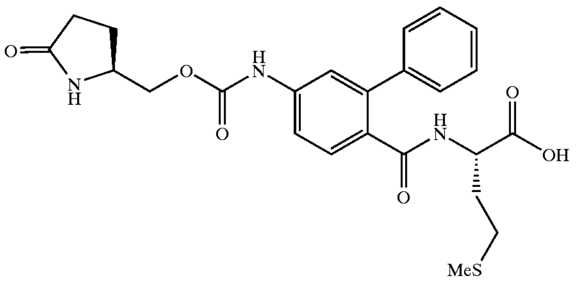

EXAMPLE 64

4-((S)-2-Pyrrolidone-5-methoxycarbonyl)amino-2-phenylbenzoyl Methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

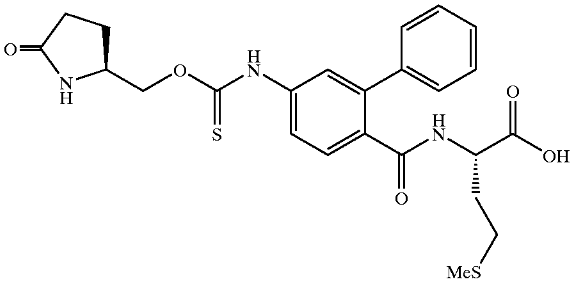

EXAMPLE 65

4-((S)-2-Pyrrolidone-5-methoxythiocarbonylamino-2-phenylbenzoyl Methionine

The title compound is prepared as described in Example 1 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

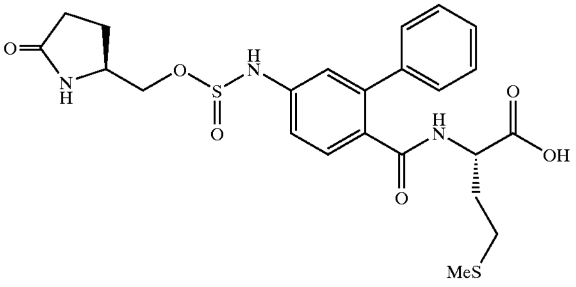

EXAMPLE 66

4-((S)-2-Pyrrolidone-5-methoxysulfinyl)amino-2-phenylbenzoyl Methionine

The title compound is prepared as described in Example 3 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

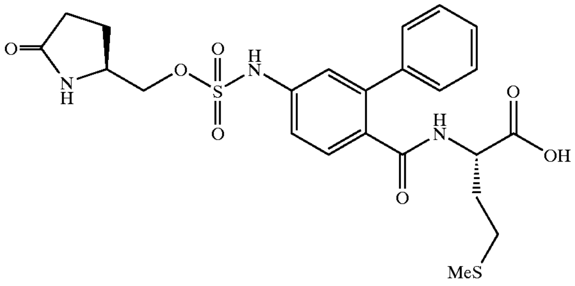

EXAMPLE 67

4-((S)-2-Pyrrolidone-5-methoxysulfonyl)amino-2-phenylbenzoyl Methionine

The title compound is prepared as described in Example 4 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

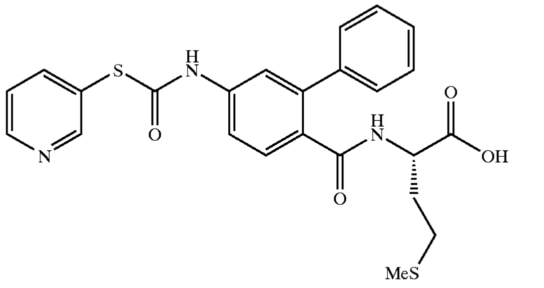

EXAMPLE 68

4-(Pyridin-3-ylmercaptocarbonyl)amino-2-phenylbenzoyl Methionine

The title compound is prepared as described in Example 1 with the exception that (S)-5-aminomethyl-2-pyrrolidone (1.0 equivalent) is replaced by 3-mercaptopyridine (1.0 equivalent).

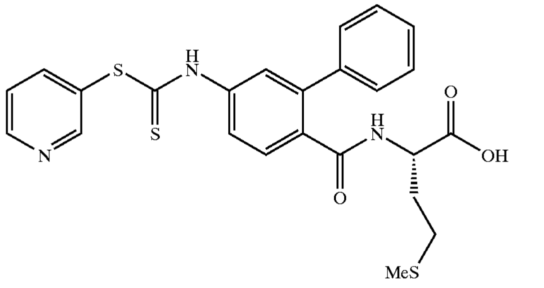

EXAMPLE 69

4-(Pyridin-3-ylmercaptothiocarbonyl)amino-2-phenylbenzoyl Methionine

The title compound is prepared as described in Example 1 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

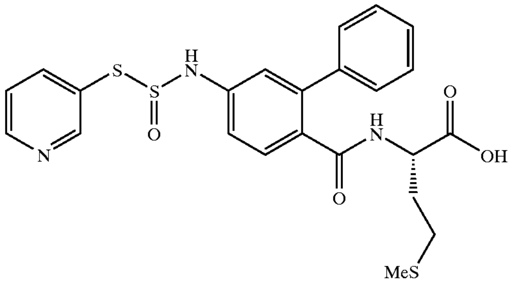

EXAMPLE 70

4-(Pyridin-3-ylmercaptosulfinyl)amino-2-phenylbenzoyl Methionine

The title compound is prepared as described in Example 3 with the exception that (S)-5-aminomethyl-2-pyrrolidone (1.0, equivalent) is replaced by 3-mercaptopyridine (1.0 equivalent).

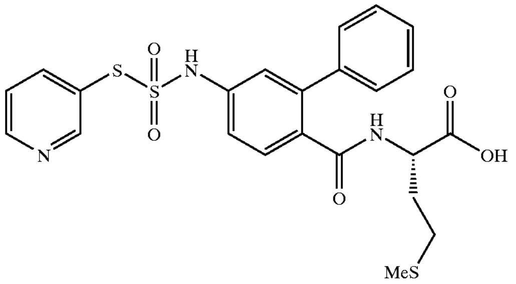

EXAMPLE 71

4-(Pyridin-3-ylmercaptosulfonyl)amino-2-phenylbenzoyl Methionine

The title compound is prepared as described in Example 4 with the exception that (S)-5-aminomethyl-2-pyrrolidone (1.0 equivalent) is replaced by 3-mercaptopyridine (1.0 equivalent).

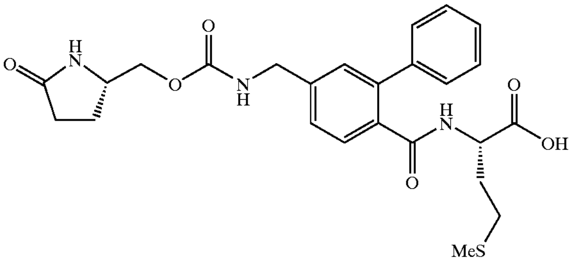

EXAMPLE 72

4-((S)-2-Pyrrolidone-5-methoxycarbonyl)aminomethyl-2-phenylbenzoyl Methionine

The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

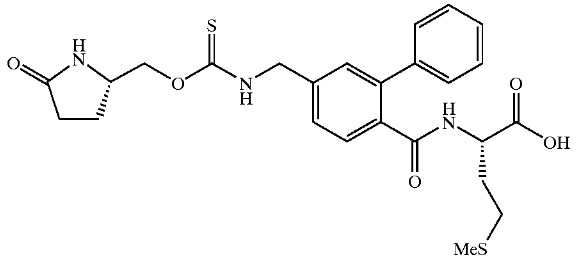

EXAMPLE 73

4-((S)-2-Pyrrolidone-5-methoxythiocarbonyl)aminomethyl-2-phenylbenzoyl Methionine The title compound is prepared as described in Example 18 with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent), and triphosgene (0.33 equivalent) is replaced by thiophosgene (1.0 equivalent).

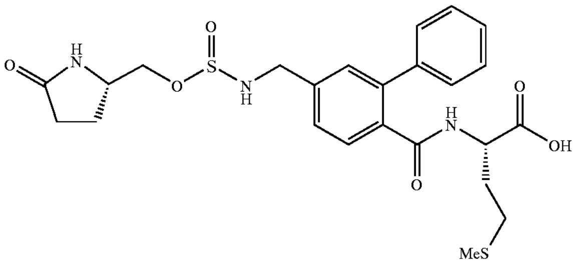

EXAMPLE 74

4-((S)-2-Pyrrolidone-5-methoxysulfinyl)aminomethyl-2-phenylbenzoyl Methionine

The tide compound is prepared as described in Example 3 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

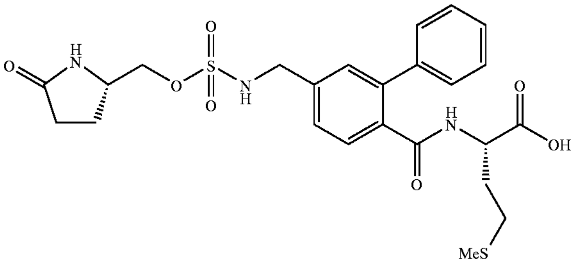

EXAMPLE 75

4-((S)-2-Pyrrolidone-5-methoxysulfonyl)aminomethyl-2-phenylbenzoyl Methionine

The title compound is prepared as described in Example 4 using the resultant amine from Example 18B with the exception that (S)-5-aminomethyl-2-pyrrolidone (1.0 equivalent) is replaced by (S)-5-hydroxymethyl-2-pyrrolidone (1.0 equivalent) and CuCl (0.1 equivalent).

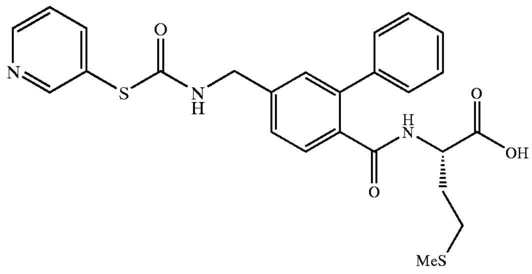

EXAMPLE 76

4-(Pyridin-3-ylmercaptocarbonyl)aminomethyl-2-phenylbenzoyl Methionine

The title compound is prepared as described in Example 18 with the exception that (S)-5-aminomethyl-2-pyrrolidone (1.0 equivalent) is replaced by 3-mercaptopyridine (1.0 equivalent).

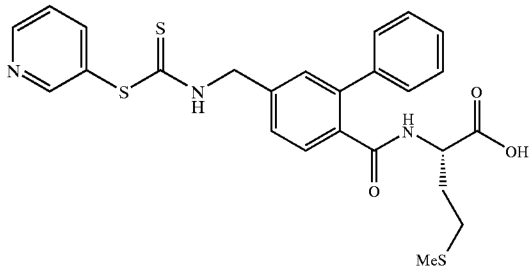

EXAMPLE 77

4-(Pyridin-3-ylmercaptocarbonyl)aminomethyl-2-phenylbenzoyl Methionine

The title compound is prepared as described in Example 18 with the exception that (S)-5-aminomethyl-2-pyrrolidone (1.0 equivalent) is replaced by 3-mercaptopyridine (1.0 equivalent), and triphosgene (0.33 equivalent) is replaced by thiophosgene (1.0 equivalent).

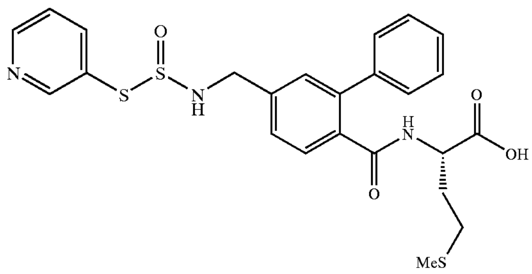

EXAMPLE 78

4-(Pyridin-3-ylmercaptosulfinyl)aminomethyl-2-phenylbenzoyl Methionine

The title compound is prepared as described in Example 3 using the resultant amine from Example 18B with the exception that (S)-5-aminomethyl-2-pyrrolidone (1.0 equivalent) is replaced by 3-mercaptopyridine (1.0 equivalent).

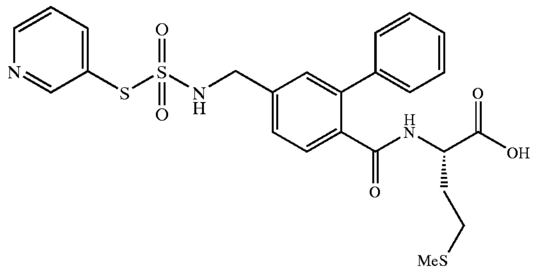

EXAMPLE 79

4-(Pyridin-3-ylmercaptosulfonyl)aminomethyl-2-phenylbenzoyl Methionine

The title compound is prepared as described in Example 4 using the resultant amine from Example 18B with the exception that (S)-5-aminomethyl-2-pyrrolidone (1.0 equivalent) is replaced by 3-mercaptopyridine (1.0 equivalent).

EXAMPLE 80

A—NH—CO—NH—B

The procedure of Example 1 is used with the exception that 4-amino-2-phenylbenzoyl methionine methyl ester is replaced by an aniline from Table 1 (B—$NH_2$) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 81

A—NH—CS—NH—B

The procedure of Example 1 is used with the exception that triphosgene (0.33 equivalent) is replaced by thiophosgene (1.0 equivalent), 4-amino-2-phenylbenzoyl methionine methyl ester is replaced by an aniline from Table 1 (B—$NH_2$) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 82

A—NH—SO—NH—B

The procedure of Example 3 is used with the exception that 4-amino-2-phenylbenzoyl methionine methyl ester is replaced by an aniline from Table 1 (B—$NH_2$) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 83

A—NH—$SO_2$—NH—B

The procedure of Example 4 is used with the exception that 4-amino-2-phenylbenzoyl methionine methyl ester is replaced by an aniline from Table 1 (B—$NH_2$) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 84

A—NH—$SO_2$—B

The procedure of Example 5 is used with the exception that 4-amino-2-phenylbenzoyl methionine methyl ester is replaced by an aniline from Table 1 (B—$NH_2$) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 85

A—NH—CO—O—B

The anilines from Table 1 (B—$NH_2$) are reacted according to the procedure of Example 6E. The resultant phenols are reacted according to the procedure of Example 8 with the exception that (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 86

A—NH—CS—O—B

The anilines from Table 1 (B—$NH_2$) are reacted according to the procedure of Example 6E. The resultant phenols are reacted according to the procedure of Example 8 with the exception that phosgene in toluene is replaced by thiophosgene and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 87

A—NH—SO—O—B

The anilines from Table 1 (B—$NH_2$) are reacted according to the procedure of Example 6E. The resultant phenols are reacted according to the procedure of Example 8 with the exception that phosgene in toluene is replaced by thionyl chloride and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, iso propyl, butyl, sec-butyl, isobutyl, isoamyl, hexyl, octyl, cyclohexyl or phenethyl esters.

EXAMPLE 88

A—NH—$SO_2$—O—B

The anilines from Table 1 (B—$NH_2$) are reacted according to the procedure of Example 6E. The resultant phenols are reacted according to the procedure of Example 8 with the exception that phosgene in toluene is replaced by sulfuryl chloride and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 89

A—NH—$CH_2$—B

The procedure of Example 16 is used with the exception that (2-phenyl-4-bromobenzoyl)methionine methyl ester is replaced by a bromide from Table 2 (B—Br) and 2-aminopyridine is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 90

A—NH—CO—NH—$CH_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 91

A—NH—CS—NH—$CH_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thiophosgene (1.0 equivalent) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 92

A—NH—SO—NH—$CH_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by thionyl chloride (1.0 equivalent) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety; in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 93

A—NH—$SO_2$—NH—$CH_2$—B

The bromides from Table 2 (B—Br) are reacted according to the procedures of Example 16F–G. The resultant alcohols are reacted according to the procedure of Example 18 with the exception that triphosgene (0.33 equivalent) is replaced by sulfuryl chloride (1.0 equivalent) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 94

A—NH—CO—O—$CH_2$—B

The bromides from Table 2 (B—Br) are reacted according to the procedures of Example 16F–G. The resultant alcohols are reacted according to the procedure of Example 8 with the exception that (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 95

A—NH—CS—O—$CH_2$—B

The bromides from Table 2 (B—Br) are reacted according to the procedures of Example 16F–G. The resultant alcohols are reacted according to the procedure of Example 8 with the exception that phosgene in toluene is replaced by thiophosgene and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 96

A—NH—CO—S—B

The anilines Table 1 (B—$NH_2$) are converted into the corresponding mercaptans according to the procedure of Example 12E. These mercaptans are reacted according to the procedure of Example 29 with the exception that 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 97

A—NH—CS—S—B

The anilines Table 1 (B—$NH_2$) are converted into the corresponding mercaptans according to the procedure of Example 12E. These mercaptans are reacted according to the procedure of Example 29 with the exception that phosgene in toluene is replaced by thiophosgene and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 98

A—NH—SO—S—B

The anilines Table 1 (B—$NH_2$) are converted into the corresponding mercaptans according to the procedure of Example 12E. These mercaptans are reacted according to the procedure of Example 29 with the exception that phosgene in toluene is replaced by thionyl chloride and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 99

A—NH—SO—S—B

The anilines Table 1 (B—$NH_2$) are converted into the corresponding mercaptans according to the procedure of Example 12E. These mercaptans are reacted according to the procedure of Example 29 with the exception that phosgene in toluene is replaced by sulfuryl chloride and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 100

A—NH—CO—S—$CH_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 101

A—NH—CS—S—$CH_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thiophosgene and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 102

A—NH—SO—S—$CH_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by thionyl chloride and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 103

A—NH—$SO_2$—S—$CH_2$—B

The bromides from Table 2 (B—Br) are reacted according to the procedures of Example 16F–G. The resultant alcohols are converted to the corresponding mercaptans according to the procedures of Examples 27A and 37A. These mercaptans are reacted according to the procedure of Example 29 with the exception that phosgene in toluene is replaced by sulfuryl chloride and 2-aminothiazol is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 104

A—CO—NH—B

The procedure of Example 56 is used with the exception that 4-amino-2-phenylbenzoyl methionine methyl ester is replaced by an aniline from Table 1 (B—$NH_2$) and pyroglutamic acid is replaced by an acid from Table 4 (A—$CO_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 105

A—CO—NH—$CH_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 58 with the exception that pyroglutamic acid is replaced by an acid from Table 4 (A—$CO_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 106

A—CO—C≡C—B

The bromides from Table 2 (B—Br) are reacted according to the procedure of Example 47A. The resultant acetylenes are reacted according to the procedure of Example 53 with the exception that 1-methyl-4-imidazoleacetic acid is replaced by an acid from Table 4 (A—$CO_2$H). For products derived from acids 164–238 and 262–269 from Table 4, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 107

A—CO—CH═CH—B

The products from Example 106 are reacted according to the procedure of Example 54.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 108

A—CO—$CH_2$—$CH_2$—B

The products from Example 107 are reacted according to the procedure of Example 55. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 109

A—NH—CO—B

The procedure of Example 60 is used with the exception that 4-bromo-2-phenylbenzoyl methionine methyl ester is replaced by a bromide from Table 2 (B—Br) and 2-aminopyridine is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 110

A—NH—CO—$CH_2$—B

The bromides from Table 2 (B—Br) are reacted according to the procedure of Example 60A. The resultant carbocyclic acids are reacted according to the procedure of Example 62 with the exception that 2-aminopyridine is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 111

A—CH—NH—B

The procedure of Example 25 is used with the exception that 4-amino-2-phenylbenzoyl methionine methyl ester is replaced by an amine from Table 1 (B—$NH_2$) and 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 112

A—$CH_2$—NH—$CH_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 25 with the exception that 3-pyridinecarboxaldehyde is replaced by an aldehyde from Table 5 (A—CHO). For products derived from aldehydes 360–432 and 433–440 from Table 5, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

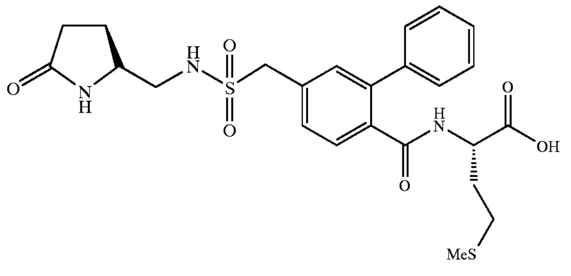

EXAMPLE 113

4-((S)-2-Pyrrolidone-5-aminomethyl)sulfonylmethyl)-2-phenylbenzoyl Methionine

EXAMPLE 113A

4-Thioacetoxymethyl-2-phenylbenzoic Acid Methyl Ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 16B (1.0 equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 113B

4-Chlorosulfonylmethylene-2-phenylbenzoic Acid Methyl Ester

The resultant compound from Example 113A in water is stirred vigorously while gaseous chlorine is bubbled through the mixture. When the reaction is judged to be done by TLC analysis, the reaction is extracted with dichloromethane which is dried and evaporated to afford the title product.

EXAMPLE 113C 4-((S)-2-Pyrrolidone-5-aminomethyl)sulfonylmethylene-2-phenylbenzoic Acid Methyl Ester To a solution of the resultant compound from Example 113B (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 113D 4-((S)-2-Pyrrolidone-5-aminomethyl)sulfonylmethylene-2-phenylbenzoic Acid The resultant compound from Example 113C is hydrolyzed according to the procedure of Example 1B to give the title product.

EXAMPLE 113E 4-((S)-2-Pyrrolidone-5-aminomethyl) sulfonylmethylene-2-phenylbenzoyl Methionine Methyl Ester To a solution of the resultant compound from Example 113D (1.0 equivalent) in dimethylformamide (DMF) is added 3-hydroxy-1,2,3-benzotriazin-4(3H)-one (1.5 equivalents) followed by methionine methyl ester (1.0 equivalent) and 1-(3-dimethylaminopropyl)-3-ethylcarbodiimide hydrochloride (1.5 equivalents). When judged complete by TLC analysis, the reaction is taken up in ethyl acetate which is washed with 1N HCl and saturated brine, and then is dried and evaporated. The crude reaction mixture is purified by column chromatography to afford the title product.

EXAMPLE 113F 4-((S)-2-Pyrrolidone-5-aminomethyl) sulfonylmethylene-2-phenylbenzoyl Methionine The resultant compound from Example 113E is hydrolyzed according to the procedure of Example 1B to give the title product.

EXAMPLE 114

A—NH—$SO_2$—$CH_2$—B

The procedure of Example i 13 is used with the exception that (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

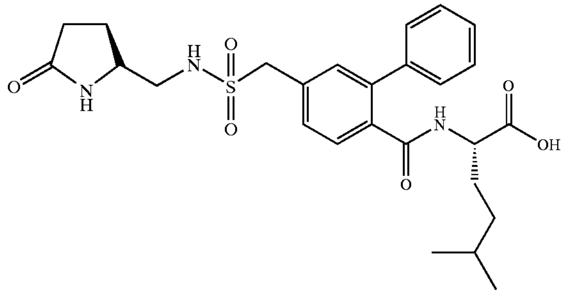

EXAMPLE 115

4-((S)-2-Pyrrolidone-5-aminomethyl) sulfonylmethyl)-2-phenylbenzoyl Leucine

EXAMPLE 115A 4-(Hydroxymethyl)-2-phenylbenzoyl Leucine Methyl Ester (2-phenyl-4-bromobenzoyl)-leucine methyl ester is reacted according to the procedures of Example 16F–G.

EXAMPLE 115B

4-Thioacetoxymethyl-2-phenylbenzoyl Leucine Methyl Ester

To triphenylphosphine (1.2 equivalents) in THF at −78° C. is added diethylazodicarboxylate (1.2 equivalents) in THF. After 10 min thiolacetic acid (1.3 equivalents) in THF is added followed by the resultant compound from Example 115A (1.0 equivalent) in THF. The reaction is stirred at −78° C. for 1 h and then at ambient temperature until it is judged to be complete by TLC analysis. The mixture is evaporated and the residue is taken up in methanol and is treated with $K_2CO_3$ (2 equivalents). When the reaction is judged to be complete by TLC analysis, the solvent is evaporated and the residue is chromatographed on silica gel to afford the title product.

EXAMPLE 115C

4-Chlorosulfonylmethylene-2-phenylbenzoyl Leucine Methyl Ester

The resultant compound from Example 115B in water is stirred vigorously while gaseous chlorine is bubbled through the mixture. When the reaction is judged to be done by TLC analysis, the reaction is extracted with dichloromethane which is dried and evaporated to afford the title product.

EXAMPLE 115D 4-((S)-2-Pyrrolidone-5-aminomethyl) sulfonylmethylene-2-phenylbenzoyl Leucine Methyl Ester To a solution of the resultant compound from Example 115C (1.0 equivalent) in methylene chloride is added (S)-5-aminomethyl-2-pyrrolidone (1.0 equivalent) and triethylamine (1.0 equivalent). When the reaction is judged complete by TLC analysis, the solvent is evaporated and the residue is purified by chromatography on silica gel.

EXAMPLE 115E 4-((S)-2-Pyrrolidone-5-aminomethyl) sulfonylmethylene-2-phenylbenzoyl Leucine The resultant compound from Example 115D is hydrolyzed according to the procedure of Example 1B to give the title product.

EXAMPLE 116

A—NH—$SO_2$—$CH_2$

The procedure of Example 115 is used with the exception that (2-phenyl-4-bromobenzoyl)-leucine methyl ester is replaced by a bromide from Table 2, entries 28–132 (B—Br) and (S)-5-aminomethyl-2-pyrrolidone is replaced by an amine from Table 3 (A—$NH_2$). For products derived from amines 146–206 from Table 3, the final LiOH hydrolysis step also hydrolyzes the ester on the fragment of the final compound that is derived from amines 146–206.

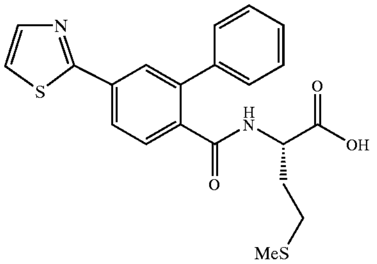

EXAMPLE 117

4-(2-Thiazolyl)-2-phenylbenzoyl Methionine

EXAMPLE 117A

2-Thiazole Boronic Acid

A solution of thiazole (1.0 equivalent) is lithiated with a slight excess of n-butyl lithium in THF (1.05 equivalents)

and then treated with trimethyl borate (1.05 equivalents). The reaction mixture is quenched by the addition of aqueous HCl and the resulting boronate ester is cleaved by the addition of excess aqueous NaOH. After acidification and extraction into ethyl acetate the crude boronic acid is used without further purification.

EXAMPLE 117B 4-(2-Thiazolyl)-2-phenylbenzoyl Methionine Methyl Ester

A mixture of 4-bromo-2-phenylbenzoic acid methyl ester (1.0 equivalent), 2-thiazole boronic acid (1.0 equivalent) and catalytic $Pd(PPh_3)_4$ is heated in a two phase system of toluene and aqueous $Na_2CO_3$. After cooling, the resulting biaryl compound is isolated by evaporation of the organic phase and is purified by chromatography on silica gel.

EXAMPLE 117C 4-(2-Thiazolyl)-2-phenylbenzoyl Methionine

The resultant compound from Example 117C is hydrolyzed according to the procedure of Example 1B to give the title product.

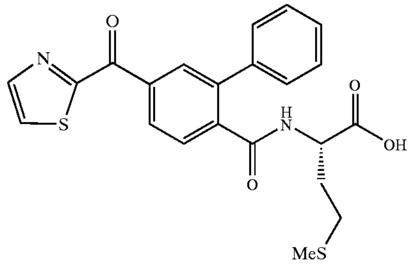

EXAMPLE 118

4-(2-Thiazolylcarbonyl)-2-phenylbenzoyl Methionine

EXAMPLE 118A 4-(2-Thiazolylcarbonyl)-2-phenylbenzoyl Methionine Methyl Ester

A mixture of 4-bromo-2-phenylbenzoic acid methyl ester (1.0 equivalent), 2-thiazole boronic acid from Example 117A (1.0 equivalent) and catalytic $Pd(PPh_3)_4$ is heated in a two phase system of toluene and aqueous $Na_2CO_3$ previously purged with a large excess of carbon monoxide. The resulting diaryl ketone is isolated by evaporation of the organic phase and is purified by chromatography on silica gel.

EXAMPLE 118B 4-(2-Thiazolylcarbonyl)-2-phenylbenzoyl Methionine

The resultant compound from Example 118A is hydrolyzed according to the procedure of Example 1B to give the title product.

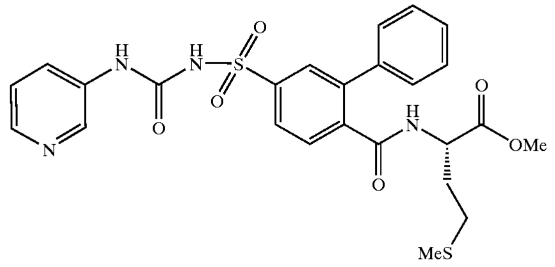

EXAMPLE 119

4-[(3-Aminopyridyl)carbonylaminosulfonyl]-2-phenylbenzoyl Methionine

EXAMPLE 119A

4-Aminosulfonyl-2-phenylbenzoyl Methionine Methyl Ester

To a solution of 4-chlorosulfonyl-2-phenylbenzoyl methionine methyl ester from Example 5E in dichloromethane is added aqueous ammonia and the mixture is stirred until the reaction is judged complete by TLC analysis. The organic phase is separated, dried and evaporated and the product is purified by chromatography on silica gel.

EXAMPLE 119B

4-Isocyanatosulfonyl-2-phenylbenzoyl Methionine Methyl Ester

A mixture of the resultant sulfonamide from Example 119A in chlorobenzene is treated with oxalyl chloride according to the procedure of Franz et al. (*J. Org. Chem*, 1964, 29, 2592) to give the title compound.

EXAMPLE 119C

4-[(A-Aminopyridyl)carbonylaminosulfonyl]-2-phenylbenzoyl Methionine Methyl Ester A mixture of the resultant isocyanate from Example 119B (1 equivalent) in dichloromethane is treated with 3-aminopyridine (1 equivalent) and stirred until the reaction is judged complete by tic analysis. The solvent is evaporated and the product is purified by chromatography on silica gel.

EXAMPLE 119D

4-[(A-Aminopyridyl)carbonylaminosulfonyl]-2-phenylbenzoyl Methionine

The resultant compound from Example 119C is hydrolyzed according to the procedure of Example 1B to give the title product.

EXAMPLE 120

$$A—NH—CO—NH—SO_2—B$$

The anilines from Table 1 ($B—NH_2$) are reacted according to the procedures of Example 5E to afford the corresponding sulfonyl chlorides. These are reacted according to the procedure of Example 119 with the exception that 3-aminopyridine is replaced by an amine from Table 3 ($A—NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 121

A—NH—CO—NH—$SO_2$—$CH_2$—B

The bromides from Table 2, entries 28–132 (B—Br) are reacted according to the procedures of Example 115A–C to afford the corresponding sulfonyl chlorides. These are reacted according to the procedure of Example 119 with the exception that 3-aminopyridine is replaced by an amine from Table 3 (A—$NH_2$). For products derived from amines 146–206 from Table 3, the final LiOH hydrolysis step also hydrolyzes the ester on the fragment of the final compound that is derived from amines 146–206.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 122

A—O—$CH_2$—B

The bromides from Table 2 (B—Br) are reacted according to the procedures of Example 16F–G. The resultant alcohols are reacted according to the procedure of Example 27 with the exception that 3-hydroxypyridine is replaced by an alcohol from Table 6 (A—OH). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 123

A—O—CO—NH—B

The procedure of Example 1 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl, or phenethyl esters.

EXAMPLE 124

A—O—CS—NH—B

The procedure of Example 1 is used with the exception that 4-amino-2-phenylbenzoyl methionine methyl ester is replaced by an aniline from Table 1 (B—$NH_2$), (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 125

A—O—SO—NH—B

The procedure of Example 3 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 126

A—O—$SO_2$—NH—B

The procedure of Example 4 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 127

A—O—CO—NH—$CH_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal estermoiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 128

A—O—CS—NH—$CH_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone (1.0 equivalent) is replaced by an alcohol from Table 6 (A—OH, 1.0 equivalent) and CuCl (0.1 equivalent), and triphosgene (0.33 equivalent) is replaced by thiophosgene (1.0 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 129

A—O—SO—NH—$CH_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 130

A—O—SO—NH—$CH_2$—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone (1.0 equivalent) is replaced by an alcohol from Table 6 (A—OH, 1.0 equivalent) and CuCl (0.1 equivalent). For products derived from alcohols 280–359 and 408–431 from Table 6, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 131

A—S—B

The anilines from Table 1 (B—$NH_2$) are reacted according to the procedures of Example 13A. The resultant fluorides are reacted according to the procedure of Example 13 with the exception that 2-mercaptopyridine is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 132

A—S—CO—NH—B

The procedure of Example 1 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 133

A—S—CS—NH—B

The procedure of Example 1 is used with the exception that 4-amino-2-phenylbenzoyl methionine methyl ester is replaced by an aniline from Table 1 (B—$NR_2$), (S)-5-aminomethyl-2-pyrrolidone (1.0 equivalent) is replaced by a mercaptan from Table 7 (A—SH), and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 134

A—S—SO—NH—B

The procedure of Example 3 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 135

A—S—$SO_2$—NH—B

The procedure of Example 4 is used with the exception that 4-amino-2-phenylbenzoyl methionine methyl ester is replaced by an aniline from Table 1 (B—$NH_2$) and (S)-5-aminomethyl-2-pyrrolidone (1.0 equivalent) is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 136

A—S—CO—NH—$CH_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 137

A—S—CS—NH—$CH_2$—B

The bromides from Table 2 (B—Br) are reacted according to the procedures of Example 16F–G. The resultant alcohols are reacted according to the procedure of Example 18 with the exception that (S)-5-aminomethyl-2-pyrrolidone is replaced by a mercaptan from Table 7 (A—SH) and triphosgene (0.33 equivalent) is replaced by thiophosgene (1.0 equivalent). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 138

A—S—SO—NH—$CH_2$—B

The bromides from Table 2 (B—Br) are reacted according to the procedures of Example 16F–G and 18A–B. The resultant amines are reacted according to the procedure of Example 3 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 139

A—S—$SO_2$—NH—$CH_2$—B

The bromides from Table 2 (B—Br) are reacted according to the procedures of Example 16F–G and 18A–B. The resultant amines are reacted according to the procedure of Example 4 with the exception that (S)-5-aminomethyl-2-pyrrolidone is replaced by a mercaptan from Table 7 (A—SH). For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 140

A—O—B

The procedure of Example 6 is used with the exception that 4-amino-2-phenylbenzoyl methionine methyl ester is replaced by an aniline from Table 1 (B—$NH_2$) and 3-bromopyridine is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 141

A—S—B

The procedure of Example 12 is used with the exception that 4-amino-2-phenylbenzoyl methionine methyl ester is replaced by an aniline from Table 1 (B—$NH_2$) and 2-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 142

A—NH—B

The procedure of Example 24 is used with the exception that 4-amino-2-phenylbenzoyl methionine methyl ester is replaced by an aniline from Table 1 (B—$NH_2$) and 2-bromopyridine hydrobromide is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 143

A—O—$CH_2$—B

The bromides from Table 2 (B—Br) are reacted according to the procedures of Example 16F–G. The resultant alcohols are reacted according to the procedure of Example 28 with the exception that 3-chloromethylpyridine hydrochloride is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 144

A—S—$CH_2$—B

The bromides from Table 2 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 145

A—C≡C—B

The procedure of Example 47 is used with the exception that (2-phenyl-4-bromobenzoyl)-methionine methyl ester is replaced by a bromide from Table 2 (B—Br) and 4-bromoimidazole is replaced by a halide from Table 8 (A—Cl, A—Br, or A—I). For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 146

A—CH═CH—B

The products from Example 145 are reacted according to the procedure of Example 48. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 147

A—$CH_2$—$CH_2$—B

The products from Example 146 are reacted according to the procedure of Example 49. This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 148

A—CO—C≡C—B

The bromides from Table 2 (B—Br) are reacted according to the procedure of Example 47A. The resultant acetylenes are reacted according to the procedure of Example 50 with the exception that 4-bromoimidazole is replaced by a halide from Table 8 (A—Cl, A—Br, or A—I). For products derived from halides 202–230 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 149

A—CO—CH═CH—B

The products from Example 148 are reacted according to the procedure of Example 48.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 150

A—CO—$CH_2$—$CH_2$—B

The products from Example 149 are reacted according to the procedure of Example 49.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

EXAMPLE 151

A—$SO_2$—B

The anilines from Table 1, entries 28–132 (B—$NH_2$), are reacted according to the procedures of Example 13A. The resultant fluorides are reacted according to the procedure of Example 13 with the exception that 2-mercaptopyridine is replaced by a mercaptan from Table 7 (A—SH). The resultant sulfides are oxidized according to the procedure of Example 14A. For products derived from mercaptans 301–394 from Table 7, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 152

A—$CH_2SO_2$—B

The procedure of Example 12 is used with the exception that 4-amino-2-phenylbenzoyl methionine methyl ester is replaced by an aniline from Table 1, entries 28–132 (B—$NH_2$) and 2-chloromethylpyridine hydrochloride is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 153

A—$SO_2$—$CH_2$—B

The bromides from Table 2, entries 28–132 (B—Br) are reacted according to the procedures of Example 16F–G. The resultant alcohols are reacted according to the procedure of Example 37 with the exception that 2-bromothiazole is replaced by a halide from Table 8 (A—Cl, A—Br, or A—I). The resultant sulfides are oxidized according to the procedure of Example 14A. For products derived from halides 202–239 from Table 8, the LiOH hydrolysis step is followed by removal of the tert-butyloxycarbonyl (Boc) amine protecting group by stirring the resultant compound from the LiOH hydrolysis step in a 1:1 mixture of dichloromethane and trifluoroacetic acid until TLC analysis indicates that the reaction is complete. The solvent is evaporated and the residue is purified by chromatography on silica gel.

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

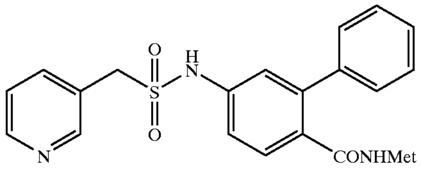

EXAMPLE 154

{4-[(3-Sulfonylmethylpyridyl)amino]-2-phenylbenzoyl}methionine

EXAMPLE 154A

{4-[(3-Sulfonylmethylpyridyl)amino]-2-phenylbenzoyl}methionine Methyl Ester

A mixture of 3-chlorosulfonylmethylpyridine hydrochloride (1.0 equivalent) and (4-amino-2-phenylbenzoyl) methionine methyl ester (1.0 equivalent) in dichloromethane is treated with triethylamine (2.2 equivalents). When judged complete by TLC analysis, the reaction is diluted with ethyl acetate, and then is washed with pH 4 water, saturated $NaHCO_3$, and brine. The mixture is dried and concentrated to give the crude title compound which is purified by chromatography on silica gel.

EXAMPLE 154B

{4-[(3-Sulfonylmethylpyridyl)amino]-2-phenylbenzoyl}methionine

The resultant compound from Example 154A is hydrolyzed according to the procedure of Example 1B to give the title product.

EXAMPLE 155

A—$CH_2SO_2$—NH—B

The procedure of Example 154 is used with the exception that 4-amino-2-phenylbenzoyl methionine methyl ester is replaced by an aniline from Table 1 (B—$NH_2$) and 3-chlorosulfonylmethylpyridine hydrochloride is replaced by a sulfonyl chloride from Table 9 (A—$SO_2Cl$).

This example also encompasses compounds comprising a C-terminal ester moiety, in which case the final LiOH step is eliminated and the amino acid methyl esters used to prepare the anilines in Table 1 are replaced by the corresponding ethyl, propyl, isopropyl, butyl, sec-butyl, isobutyl, isoamyl, hexyl, octyl, cyclohexyl or phenethyl esters.

EXAMPLE 156

A—$SO_2$—NH—$CH_2$—B

The bromides from Table 2 (B—Br) are reacted according to the procedures of Example 16F–G. The resultant alcohols are converted to the corresponding amines according to the procedures of Examples 18A–B. These amines are reacted according to the procedure of Example 154 with the exception that -chlorosulfonylmethylpyridine hydrochloride is replaced by a sulfonyl chloride from Table 9 (A—$SO_2Cl$).

This example also encompasses compounds comprising a C-terminal ester moiety, in which case the final LiOH step is eliminated and the amino acid methyl esters used to prepare the bromides in Table 2 are replaced by the corresponding ethyl, propyl, isopropyl, butyl, sec-butyl, isobutyl, isoamyl, hexyl, octyl, cyclohexyl or phenethyl esters.

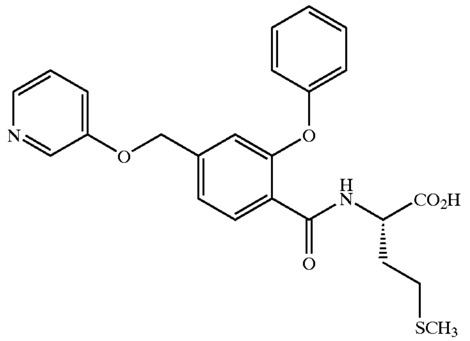

EXAMPLE 157

[4-(3-Pyridyloxymethylene)-2-phenoxybenzoyl] methionine

EXAMPLE 157A

Dimethylphenoxyterephthalate

To a solution of phenol (10.8 g) in anisole (40 mL) and DMF (90 mL) was added potassium tert-butoxide (12.1 g).

The mixture was heated for 40 minutes while continuously passing a nitrogen stream through the reaction flask (~20 mL of solvent distilled over). The mixture was cooled to ambient temperature and dimethyl nitroterephthalate (23.9 g) was added. The resulting black mixture was stirred for 1 hour at ambient temperature and two hours at 100–105° C. The reaction mixture was poured into ice containing 2 mL of concentrated HCl. The mixture was extracted with ether. The ether layer was washed with water (3×) and saturated aqueous $NaHCO_3$ (2×). The organic phase was dried over $MgSO_4$, filtered, and concentrated in vacuo to give 24.1 g of an oil. Chromatography on silica gel (10% ethyl acetate-hexanes) gave dimethy phenoxyterephthalate (15.9 g).

EXAMPLE 157B

4-Carbomethoxy-3-phenoxybenzoic Acid

To a mixture of dimethyl phenoxyterephthalate (10.4 g) in water. (50 mL) was added 50% aqueous NaOH (2.32 g) and water (4 mL) and the reaction mixture was stirred overnight at ambient temperature. The reaction mixture was concentrated in vacuo and the residue was partitioned between water and ether. The aqueous phase was acidified (a solid formed) and extracted with dichloromethane. The organic phase was dried over $Na_2SO_4$, filtered, and concentrated in vacuo to give 4-carbomethoxy-3-phenoxybenzoic acid (6.6 g) as a 68:32 mixture of hydrolysis isomers.

EXAMPLE 157C

4-Hydroxymethyl-2-phenoxybenzoic Acid Methyl Ester

To a 0° C. solution in THF (9 mL) of 4-carbomethoxy-3-phenoxybenzoic acid (5.88 g), prepared as in Example 157B, was added borane-THF (1.0 M, 30 mL). The reaction mixture was stirred for 1 hour at 0° C. and 1.5 hours at ambient temperature. The reaction mixture was cooled in an ice bath and water (20 mL) was added slowly, followed by slow addition of 1:1 conc. HCl-water. The mixture was stirred for 10 minutes at ambient temperature and then toluene was added. The layers were separated and the aqueous phase was extracted with toluene. The combined organic layers were washed with saturated aqueous $KHCO_3$, dried over $Na_2SO_4$, filtered, and concentrated in vacuo to give 5.32 g of colorless oil. Chromatography on silica gel (30% ethyl acetate-hexanes) gave 4-hydroxymethyl-2-phenoxybenzoic acid methyl ester (4.77 g).

EXAMPLE 157D

4-Bromomethyl-2-phenoxybenzoic Acid Methyl Ester

To a solution in DMF (10 mL) of 4-hydroxymethyl-2-phenoxybenzoic acid methyl ester (2.82 g), prepared as in Example 157C, was added LiBr (1.04 g) and PBr3 (3.65 g) and the reaction mixture was stirred for 20 minutes at ambient temperature. The reaction mixture was poured into water and extracted with toluene. The organic phase was washed twice with water, dried over $Na_2SO_4$, filtered, and concentrated in vacuo to give 4-bromomethyl-2-phenoxybenzoic acid methyl ester (3.37 g).

EXAMPLE 157E 4-(3-Pyridyloxymethyl)-2-phenoxybenzoic Acid Methyl Ester

To a solution in toluene (25 mL) of 4-bromomethyl-2-phenoxybenzoic acid methyl ester (3.37 g), prepared as in Example 157E, was added 18-crown-6 (0.52 g) and the potassium 3-pyridyloxide (2.20 g). The reaction mixture was heated at 70° C. for 1 hour during which time a black, insoluble tar formed. The reaction mixture was cooled to ambient temperature and diluted with toluene. The toluene was decanted from the tar and the tar was dissolved in 1:1 THF-water (20 mL). The aqueous THF was added to the toluene and the mixture was washed twice with brine, dried over $Na_2SO_4$, filtered, and concentrated in vacuo to give a black oil. Chromatography on silica gel (1:1 ethyl acetate-hexanes) gave 4-(3-pyridyloxymethyl)-2-phenoxybenzoic acid methyl ester (2.47 g).

EXAMPLE 157F 4-(3-Pyridyloxymethylene)-2-phenoxybenzoic Acid

To a solution in methanol (15 mL) of 4-(3-pyridyloxymethylene)-2-phenoxybenzoic acid methyl ester (2.46 g), prepared as in Example 157E, was added a solution of 5% aqeuous KOH (2.00 g) in water (3 mL). The reaction mixture was heated at reflux for 1.5 hours. The reaction mixture was concentrated in vacuo and the residue was dissolved in water. The aqueous phase was acidified with acetic acid with cooling and stirring. The resulting solid was filtered, washed with water, and dissolved in THF. The THF solution was dried over $Na_2SO_4$, filtered, and concentrated in vacuo to give 4-(3-pyridyloxymethyl)-2-phenoxybenzoic acid (2.17 g).

EXAMPLE 157G

[4-(3-pyridyloxymethyl)-2-phenoxybenzoyl] methionine Methyl Ester

To a solution in DMF (3 mL) of 4-(3-pyridyloxymethylene)-2-phenoxybenzoic acid (321 mg), prepared as in Example 157F, was added 3-hydroxy-1,2,3-benzotriazin-4(3H)-one (345 mg, 1.5 mmol) followed by methionine methyl ester hydrochloride (300 mg, 1.5 mmol), ethyl dimethylaminopropyl carbodiimide hydrochloride (288 mg, 1.5 mmol), and triethylamine (280 mg). The reaction mixture was stirred for 15 hours at ambient temperature. The reaction mixture was diluted with water and extracted with toluene. The toluene solution was washed with, dried over $Na_2SO_4$, filtered, and concentrated in vacuo. Chromatography on silica gel (75% ethyl acetate-hexanes) gave [4-(3-pyridyloxymethyl)-2-phenoxybenzoyl] methionine methyl ester (425 mg, 98%).

EXAMPLE 157H

[4-(3-Pyridyloxymethyl)-2-phenoxybenzoyl] methionine

To a solution in 5:1 methanol-$H_2O$ (3.5 mL) of [4-(3-pyridyloxymethyl)-2-phenoxybenzoyl]methionine methyl ester (440 mg), prepared as in Example 157G, was added a solution of 50% NaOH (354 mg) in water (0.8 mL) and the reaction mixture was heated at 60° C. for 15 minutes. The reaction mixture was concentrated in vacuo and the residue was taken up in $H_2O$ (3, mL). The aqueous solution was acidified with concentrated HCl (415 mg) and 2 drops of ethyl acetate were added. The resulting solid was filtered and dried in a vacuum oven at 60° C. for 3 hours to give [4-(3-pyridyloxymethyl)-2-phenoxybenzoyl]methionine (373 mg). mp 195° C.; $^1H$ NMR (300 MHz, DMSO-$d_6$) δ 1.90 (m, 4H), 2.37 (m, 2H), 4.44 (m, 1H), 5.20 (s, 2H), 7.01 (s, 2H), 7.04 (s, 1H), 7.16 (t, 1H, J=7.4 Hz), 3.66 (m, 5H), 7.70 (d, 1H, J=9.0 Hz), 8.17 (dd, 1H, J=4.4, 1.5 Hz), 8.30 (d, 1H, J=3 Hz). Anal calcd for $C_{24}H_{24}N_2O_5S$: C, 63.70; H, 5.35; N, 6:59. Found: C, 63.46; H, 5.11; N, 6.08.

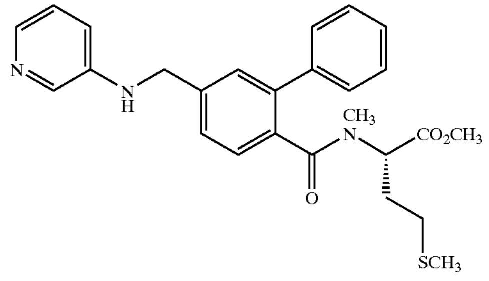

EXAMPLE 158

[4-(3-Pyridylaminomethylene)-2-phenylbenzoyl]-N-methylmetionine Methyl Ester

EXAMPLE 158A

Dimethyl 2-Phenylterephthalate

A mixture of dimethyl 2-iodoterephthalate (22.8 g, 71.4 mmol) and tetrakis(triphenylphosphine)palladium(0) (4.14 g, 3.38 mmol) in toluene (120 mL) was stirred for 10 minutes. Aqueous sodium carbonate (2 M, 160 mL) and a solution in methanol (40 mL) of phenylboronic acid (10.4 g, 85.3 mmol) were then added and the reaction mixture was stirred at reflux for 15 hours. The reaction mixture was cooled to ambient temperature and extracted with ether. The organic phase was washed with water (2×) and brine, dried, and concentrated in vacuo to give dimethyl 2-phenylterephthalate as a dark brown oil (18.4 g) which was used without further purification.

EXAMPLE 158B

2-Phenylmonomethylterephthalate

To a solution in 1:1 THF-methanol of the 2-phenylterephthalate prepared in Example 158A (18.4 g) was added a solution of KOH (4.56 g, 71.5 mmol) in water (30 mL). The reaction mixture was stirred overnight at ambient temperature and then was diluted in water and the methanol was evaporated in vacuo. The residue was filtered through a pad of Celite with a water rinse. The filtrate was extracted twice with ethyl acetate and the aqueous phase was cooled in an ice-water bath and concentrated HCl (10 mL) was added. The resulting suspension was stirred for 30 minutes and then was filtered. The solid was recrystallized from 25% aqueous ethanol to give 2-phenylmonomethylterephthalate (10.4 g). The mother liquor was concentrated and the residue was purified by chromatography on silica gel (97:2:1, then 96:3:1 chloroform-methanol-acetic acid) to give and additional 1.74 g of the desired compound.

EXAMPLE 158C

4-Hydroxymethyl-2-phenylbenzoic Acid Methyl Ester

To a 0° C. solution in THF (40 mL) of 2-phenylmonomethylterephthalate (10.5 g, 41 mmol) was added borane-THF (1.0 M, 82 mL, 82 mmol) such that the reaction temperature remained below 6° C. The reaction mixture was stirred for 0.5 hours, then the cold bath was removed and stirring was continued for 2 hours. The reaction mixture was again cooled to 0° C. and aqueous HCl (3 M, 100 mL) was added slowly. The cold bath was removed and the reaction mixture was stirred for 1 hour. The THF was evaporated and the residue was extracted with ethyl acetate (3×). The combined organic extracts were washed with 1M aqueous NaOH (2×), water (2×) and brine, dried, filtered, and concentrated in vacuo to give 4-hydroxymethyl-2-phenylbenzoic acid methyl ester (9.75 g).

EXAMPLE 158D

4-Hydroxymethyl-2-phenylbenzoic Acid

The desired compound was prepared by saponification of 4-hydroxymethyl-2-phenylbenzoic acid methyl ester, prepared as in Example 158C using the procedure of Example 158B.

EXAMPLE 158E

4-Carboxyaldehyde-2-phenylbenzoic Acid

To a mechanically-stirred solution of 4-hydroxymethyl-2-phenylbenzoic acid (2.28 g, 10 mmol), prepared as in Example 158D, in dichloromethane (50 mL) was added $MnO_2$ and the reaction mixture was stirred overnight at ambient temperature. The reaction mixture was filtered and partitioned between ethyl acetate and aqueous 3N HCl, and the mixture was stirred vigorously for 0.5 hours. The mixture was filtered through Celite with ethyl acetate rinsings. The combined organic layers were dried, filtered and concentrated. Chromatography on silica gel gave 4-carboxaldehyde-2-phenylbenzoic acid (1.65 g).

EXAMPLE 158F (4-Carboxaldehyde-2-phenylbenzoyl)-N-methylmetionine Methyl Ester

To a solution in dichloromethane (5 mL) of 4-carboxyaldehyde-2-phenylbenzoic acid (310 mg, 1.37 mmol), prepared as in Example 158E, was added oxalyl chloride (125 μL, 1.44 mmol) and DMF (5 μL) and the reaction mixture was stirred until bubbling ceased. The reaction mixture was stirred for a further 15 minutes and then was cooled to about 5° C. and a solution in dichloromethane (5.5 mL) and toluene (2.5 mL) of N-methylmethionine methyl ester hydrochloride (310 mg, 1.45 mmol) and 4-methylmorpholine (475 μL, 4.32 mmol) was added. The reaction mixture was stirred cold for 15 minutes and then the cold bath was removed and stirring was continued at ambient temperature for 1.5 hours. The reaction mixture was diluted with ethyl acetate and washed with aqueous 2N HCl (3×), saturated aqueous sodium bicarbonate (3×) and brine, dried over sodium sulfate, filtered, and concentrated in vacuo to give a white solid chromatography on silica gel (35% ethyl acetate-hexane) gave (4-carboxaldehyde-2-phenylbenzoyl)-N-methylmethionine methyl ester (317 mg, 60%).

EXAMPLE 158G

[4-(3-Pyridylaminomethyl)-2-phenylbenzoyl]-N-methylmethionine Methyl Ester

To a solution in methanol (3 mL) of (4-carboxyaldehyde-2-phenylbenzoyl)-N-methylmethionine methyl ester (310 mg, 0.80 mmol), prepared as in Example 158F, was added 3-aminopyridine (118 mg, 1.25 mmol) and acetic acid (0.90 mL). The reaction mixture was stirred for 30–40 minutes at ambient temperature and sodium cyanoborohydride (152 mg, 2.45 mmol) was added and stirring was continued for 2 hours. The reaction mixture was partitioned between ethyl acetate and aqueous 2N NaOH. The aqueous phase was extracted with ethyl acetate. The combined organic extracts were washed with 2N NaOH, twice with water, twice with brine, dried over $Na_2SO_4$, filtered, and concentrated in vacuo. Chromatography on silica gel (ethyl acetate) gave [4-(3-Pyridylaminomethyl)-2-phenylbenzoyl]-N-methylmethionine methyl ester (270 mg, 73%) as a white foam. $^1H$ NMR (300 MHz, $D_3COD$) δ 7.93 (d, 1H), 7.74 (dd, 1H), 7.50 (d, 1H), 7.40 (m, 7H), 7.11 (ddd, 1H), 7.02 (ddd, 1H), 5.22 and 4.58 (both m, total 1H), 4.45 (s, 2H), 3.70 and 3.65 (both br s, total 3H), 2.65 and 2.45 (both br s, total 3H), 2.22 and 2.06 (both m, total 2H), 2.00 (br s, 3H), 1.77 (m, 2H); MS (DCI-$NH_3$) m/e 464 $(M+H)^+$. Anal calcd for $C_{26}H_{29}N_3O_3S$: C, 67.36; H, 6.31; N, 9.06. Found: C, 67.11; H, 6.23; N, 8.84.

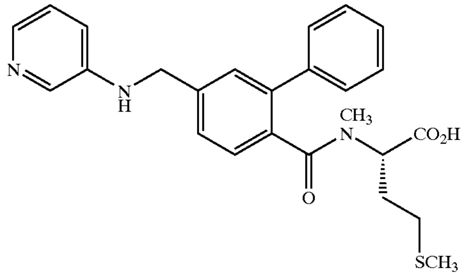

EXAMPLE 159

[4-(3-Pyridylaminomethyl)-2-phenylbenzoyl]-N-methylmethionine

To a 0° C. solution in THF (3.0 mL) of [4-(3-Pyridylaminomethylene)-2-phenylbenzoyl-]N-methylmethionine methyl ester (135 mg, 0.29 mmol), prepared as in Example 158, was added a solution of lithium hydroxide hydrate (20 mg, 0.49 mmol) in water (1 mL). Methanol (1 mL) and water (0.5 mL) were then added to obtain a clear solution. The reaction mixture was stirred for 1.5 hours and then the cold bath was removed and stirring was continued for 2.5 hours. The reaction mixture was partitioned between water which was taken to pH 4 with HCl and ethyl acetate. The aqueous phase was extracted three times with chloroform. The combined organic layers were dried over $Na_2SO_4$, filtered, and concentrated in vacuo. The residue was dissolved in acetonitrile-methanol. The solution was diluted with water, frozen, and lyophilized to give [4-(3-pyridylaminomethyl)-2-phenylbenzoyl]-N-methylmethionine (120 mg) as a white powder. $^1H$ NMR (300 MHz, $D_3COD$) δ 7.93 (d, 1H), 7.78 (dd, 1H), 7.50 (d, 1H), 7.38 (m, 7H), 7.20 (m, 1H), 7.12 (m, 1H), 5.20 and 4.55 (both m, total 1H), 4.45 (s, 2H), 2.70 and 2.45 (both br s, total 3H), 2.24 and 2.10 (both m, total 2H), 2.00 (br s, 3H), 1.80 and 1.68 (both m, 2H); MS (DCI-$NH_3$) m/e 450 $(M+H)^+$. Anal calcd for $C_{25}H_{27}N_3O_3S.0.65$ HCl: C, 63.45; H, 5.89; N, 8.88. Found: C, 63.51; H, 5.54; N, 8.53.

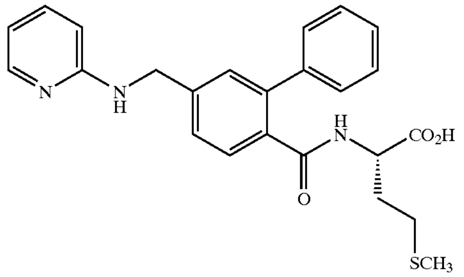

EXAMPLE 160

[4-(2-Pyridylaminomethyl)-2-phenylbenzoyl]methionine

EXAMPLE 160A (4-Hydroxymethyl-2-phenylbenzoyl)methionine Methyl Ester

To a solution in 1:3 DMF-dichloromethane (100 mL) of 4-hydroxymethyl-2-phenylbenzoic acid (5.2 g, 23 mmol), prepared as in Example 158D, at 5–10° C. was added 1-(3-dimethylaminopropyl)-3-ethylcarbodiimide hydrochloride (4.8 g, 25 mmol), 3-hydroxy-1,2,3-benzotriazin-4(3H)-one (4.1 g, 25 mmol), methionine methyl ester hydrochloride (5.0 g, 25 mmol) and 4-methylmorpholine (2.8 mL, 25 mmol). The reaction was warmed slowly to ambient temperature and stirred overnight. The reaction mixture was diluted with ethyl acetate and washed with aqueous 1M $H_3PO_4$. The organic phase was washed with brine, dried over $Na_2SO_4$, filtered, and concentrated in vacuo. Chromatography on silica gel (65% ethyl acetate-hexanes) gave [4-hydroxymethyl-2-phenylbenzoyl]methionine methyl ester (5.15 g, 60%).

EXAMPLE 160B (4-Carboxyaldehyde-2-phenylbenzoyl)methionine Methyl Ester

A solution of DMSO (1.95 g, 27 mmol) in dichloromethane (100 mL) was cooled to −78° C. and oxalyl chloride (1.8 mL, 20 mmol) was added dropwise. After 15 minutes, a solution in dichloromethane (35 mL) of [4-hydroxymethyl-2-phenylbenzoyl]methionine methyl ester (5.1 g, 13.7 mmol), prepared as in Example 160A, was added dropwise and the reaction mixture was stirred for one hour at −78° C. Triethylamine (7.6 mL, 55 mmol) was then added and the reaction mixture was warmed to ambient temperature. The reaction mixture was diluted with ethyl ether, washed twice with brine, dried over $Na_2SO_4$, filtered, and concentrated in vacuo to give an orange gum. The gum was dissolved in hot ethyl acetate (50 mL) and hexanes (10–20 mL) were added. The cloudy suspension was cooled in the refrigerator and the supernatant was decanted from a small amount of insoluble material. The supernatant was concentrated in vacuo and the residue was left under high vacuum for three days to give (4-carboxyaldehyde-2-phenylbenzoyl)methionine methyl ester (4.9 g) as a light-orange solid.

EXAMPLE 160C

[4-(2-Pyridylaminomethyl)-2-phenylbenzoyl]methionine Methyl Ester

A suspension in toluene (17 mL) of [4-carboxyaldehyde-2-phenylbenzoyl]methylmethionine methyl ester (800 mg, 2.15 mmol), prepared as in Example 160B, 2-aminopyridine (253 mg, 2.69 mmol) and p-toluenesulfonic acid hydrate (22 mg, 0.11 mmol) were heated under reflux overnight using a Dean-Stark trap containing 10 mL of toluene. The reaction mixture was concentrated in vacuo. The residue was taken up in isopropanol (20 mL) and p-toluenesulfonic acid hydrate was added to get to pH 4. Sodium cyanoborohydride (625 mg, 10 mmol) was added along with absolute ethanol (20 mL) to obtain a clear solution. The pH was then adjusted to pH 4 using p-toluenesulfonic acid hydrate and the reaction mixture was stirred for 2 hours while the pH was periodically readjusted to about 4. The reaction mixture was then partitioned between ethyl acetate and aqueous 2N sodium hydroxide. The organic phase was washed with aqueous 2N sodium hydroxide, twice with brine, dried over $Na_2SO_4$, filtered, and concentrated in vacuo. Chromatography on silica gel (55:45 chloroformethyl acetate) gave [4-(2-Pyridylaminomethyl)-2-phenylbenzoyl]methionine methyl ester (125 mg).

EXAMPLE 160D

[4-(2-Pyridylaminomethyl)-2-phenyl]benzoyl Methionine

The [4-(2-Pyridylaminomethyl)-2-phenylbenzoyl] methionine methyl ester was then hydrolyzed using lithium hydroxide hydrate according to the method of Example 159, except using methanol instead of THF. $^1$H NMR (300 MHz, DMSO-$d_6$) d 8.54 (d, 1H), 7.97 (d, 1H), 7.86 (m, 1H), 7.50–7.30 (envelope, 7H), 7.04 (d, 1H), 6.83 (m, 1H), 4.70 (d, 2H), 4.30 (m, 1H), 2.24 (m, 2H), 2.00 (s, 3H), 1.85 (m, 2H); MS (DCI-$NH_3$) m/e 436 $(M+H)^+$, 434 $(M-H)^-$. Anal calcd for $C_{24}H_{25}N_3O_3S$.1.4HCl: C, 59.24; H, 5.47; N, 8.64. Found: C, 59.36; H, 5.24; N, 8.42.

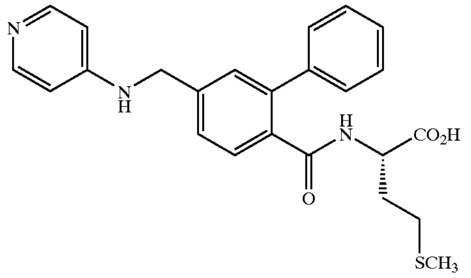

EXAMPLE 161

[4-(4-Pyridylaminomethyl)-2-phenylbenzoyl] methionine

The desired compound was prepared according to the method of Examples 160C and D, except substituting 4-aminopyridine for 2-aminopyridine. $^1$H NMR (300 MHz, DMSO-d6) d 8.47 (d, 1H), 8.05 (d, 2H), 7.94 (t, 1H), 7.37 (m, 8H), 6.63 (d, 2H), 4.50 (d, 2H), 4.27 (m, 1H), 2.24 (m, 2H), 2.00 (s, 3H), 1.85 (m, 2H); MS (DCI-$NH_3$) m/e 436 $(M+H)^+$, 434 $(M-H)^-$. Anal calcd for $C_{24}H_{25}N_3O_3S$.HCl: C, 61.07; H, 5.55; N, 8.90. Found: C, 61.38; H, 5.66; N, 9.01.

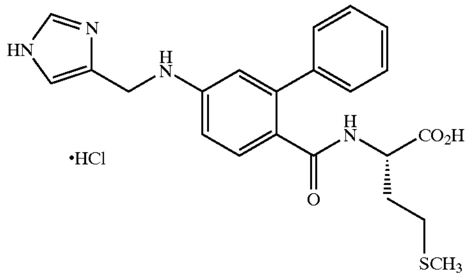

EXAMPLE 167

[4-(1H-Imidazol-4-ylmethyl)amino-2-phenylbenzoyl]methionine Hydrochloride

EXAMPLE 167A

4-Hydroxymethyl-1H-1-triphenylmethylimidazole

To a mixture in DMF (25 mL) of 4-hydroxymethylimidazole hydrochloride (10.0 g, 74 mmol) and triethylamine (25 mL, 180 mmol) was added a solution of triphenylmethyl chloride (22 g, 79 mmol) in DMF (75 mL) and the thick reaction mixture was spun overnight on the rotary evaporator. The solid was filtered off, washed with DMF and water, and dried overnight over Drierite® to give 4-hydroxymethyl-1H-1-triphenylmethylimidazole (23 g).

EXAMPLE 167B 1H-1-Triphenylmethylimidazole-4-carboxaldehyde

A mechanically-stirred slurry in dioxane (400 mL) of 4-hydroxymethyl-1H-1-triphenylmethylimidazole (9.6 g, 28 mmol), prepared as in Example 167A, was heated to 77° C. to dissolve the solid. The reaction mixture was cooled to ambient temperature and $MnO_2$ (20.5 g, 236 mmol) was added all at once. The black slurry was warmed to 85° C. and stirred for 5.5 hours. The reaction mixture was filtered through Celite and the filtrate was concentrated in vacuo to give a crystalline solid. Recrystallization from dichloromethane-hexanes to give 1H-1-triphenylmethylimidazole-4-carboxyaldehyde (5.1 g).

EXAMPLE 167C

[4-(1H-trimethylphenylimidazol-4-ylmethyl)amino-2-phenylbenzoyl]methionine Methyl Ester 1H-1-triphenylmethylimidazole-4-carboxyaldehyde was reductively animated with 4-amino-2-phenylbenzoyl methionine methyl ester (compound 8) according to the procedure of Example 158B.

EXAMPLE 167D

[4-(1H-Imidazol-4-ylmethyl)amino-2-phenylbenzoyl]methionine Methyl Ester

To a solution in dichloromethane (5 mL) of [4-(1H-trimethylphenylimidazol-4-ylmethyl)amino-2-phenylbenzoyl]methionine (365 mg, 0.54 mmol), prepared as in Example 167C, was added triethylsilane (0.41 mL, 2.57 mmol). The reaction mixture was cooled to 0° C. and trifluoroacetic acid (5 mL) was added dropwise. The reaction mixture was stirred for 1.5 hours at 0° C. and then was concentrated in vacuo and azeotroped with toluene. The residue was partitioned between water and ethyl acetate. The aqueous phase was extracted with ethyl acetate. The initial ethyl acetate extract was diltued with hexane and extracted with water. The second ethyl acetate extract was concentrated in vacuo and the residue was combined with the two aqueous phases. The aqueous solution was frozen and lyophylized to give [4-(1H-imidazol-4-ylmethyl)amino-2-phenylbenzoyl]methionine methyl ester (260 mg).

EXAMPLE 167E

[4-(1H-imidazol-4-ylmethyl)amino-2-phenylbenzoyl]methionine Hydrochloride

The desired compound was prepared by saponification of [4-(1H-imidazol-4-ylmethyl)amino-2-phenylbenzoyl] methionine methyl ester, prepared as in Example 167D according to the procedure of Example 165. $^{1}H$ NMR (300 MHz, DMSO-$d_6$) δ 9.01 (d, 1H), 8.02 (d, 1H), 7.55 (d, 1H), 7.31 (m, 5H), 7.27 (d, 1H), 6.66 (dd, 1H), 6.60 (d, 1H), 6.59 (br s, 1H), 4.42 (s, 2H), 4.23 (m, 1H), 2.24 (m, 2H), 2.00 (s, 3H), 1.85 (m, 2H); MS (APCI) m/e 425 $(M+H)^+$, 423 $(M-H)^-$. Anal calcd for $C_{22}H_{24}N_4O_3S.2HCl.0.5H_2O$: C, 52.18; H, 5.37; N, 11.06. Found: C, 52.36; H, 5.18; N, 10.57.

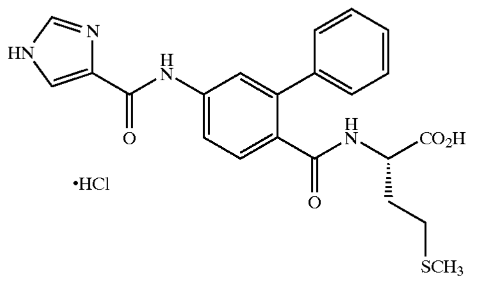

EXAMPLE 168

[4-(1H-Imidazol-4-ylcarbonyl)amino-2-phenylbenzoyl]methionine Hydrochloride

EXAMPLE 168A 1H-1-Triphenylmethylimidazole-4-carboxylic Acid

To a slurry of 1H-1-triphenylmethylimidazole-4-carboxaldehyde (1.0 g, 3.0 mmol), prepared as in Example 167B, tert-butyl alcohol (60 mL), 2-methyl-2-butene (15 mL, 140 mmol) was added $KH_2PO_4$ (2.82 g, 21 mmol) and 80% sodium chlorite (3.1 g in 25 mL $H_2O$, 27 mmol). The reaction mixture was stirred for 1.5 hours using a mechanical stirrer. The pH was adjusted to 3–3.5 and the white solid was filtered off and rinsed with water. The solid was dried under high vacuum over $P_2O_5$ for two days to give 1H-1-triphenylmethylimidazole-4-carboxylic acid (956 mg, 91%).

EXAMPLE 168B

[4-(1H-1-Triphenylmethylimidazol-4-ylcarbonyl) amino-2-phenylbenzoyl]methionine Methyl Ester The desired compound was prepared by coupling of 1H-1-triphenylmethylimidazole-4-carboxylic acid, prepared as in Example 168A, with 4-amino-2-phenylbenzoyl methionine methyl ester (compound 8) according to the method of Example 163D.

EXAMPLE 168C

[4-(1H-Imidazol-4-ylcarbonyl)amino-2-phenylbenzoyl]methionine Hydrochloride

The desired compound was prepared according to the method of Examples 167D and E, except substituting [4-

(1H-1-triphenylmethylimidazol-4-ylcarbonyl)amino-2-phenylbenzoyl]methionine methyl ester, prepared as in Example 168B for [4-(1H-trimethylphenylimidazol-4-ylmethyl)amino-2-phenylbenzoyl]methionine. $^{1}H$ NMR (300 MHz, DMSO-$d_6$) d 10.43 (s, 1H), 8.50 (s, 1H), 8.47 (d, 1H), 8.17 (s, 1H), 7.86 (m, 2H), 7.40 (m, 6H), 4.30 (m, 1H), 2.24 (m, 2H), 2.00 (s, 3H), 1.85 (m, 2H); MS (DCI-$NH_3$) m/e 439 $(M+H)^+$. Anal calcd for $C_{22}H_{22}N_4O_4S.HCl.H_2O$: C, 53.60; H, 5.11; N, 11.36. Found: C, 53.58; H, 5.00; N, 11.01.

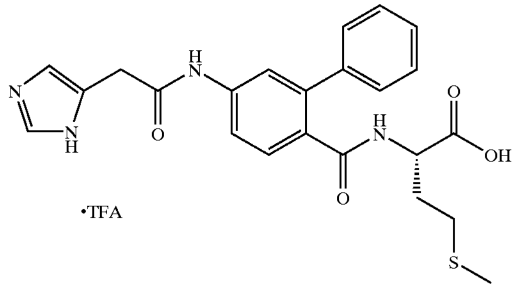

EXAMPLE 174

[4-(1H-Imidazole-4-ylacetamido)-2-phenylbenzoyl] methionine Trifluoroacetate

EXAMPLE 174A

N-(4-Toluenesulfonylimidazole-4-yl-acetic Acid

To a solution of 4-imidazole acetic acid hydrochloride (1 g, 6.15 mmol) in 6.2 mL of 1 N NaOH and 18 mL of water was added 4-toluenesulfonyl chloride (1.29 g, 6.77 mmol) and the mixture was stirred at ambient temperature. The pH of the mixture was maintained at 8.5 by addition of 1 N NaOH. After 3 hours, a total volume of 12 mL of 1 N NaOH was added and a clear solution was obtained. This solution was extracted with ether and the aqueous solution was acidified to pH 1 with 3 N HCl. The mixture was cooled in an ice bath and N-(4-Toluenesulfonyl)imidazole-4-yl-acetic acid was isolated by filtration (white crystals, 1.10 g, 63% yield). m.p. 105–106° C. (decomp); $^{1}H$ NMR ($CDCl_3$) δ 10.0 (br, 1H), 8.04 (s, 1H), 7.82 (d, J=8.2 Hz, 2H), 7.37 (d, J=8.2 Hz, 2H), 7.28 (s, 1H), 3.65 (s, 2H), 2.45 (s, 3H). $^{13}C$ NMR ($CD_3OD$) δ 173.6, 148.1, 138.9, 138.0, 136.1, 131.6, 128.7, 117.0, 34.0, 21.6.

EXAMPLE 174B

N-(4-Toluenesulfonyl)imidazole-4-yl-acetic Acid N-Methyl-O-methylcarboxamide

To a suspension of N-(4-toluenesulfonyl)imidazole-4-yl-acetic acid (911 mg, 3.25 mmol) and N-methyl-O-methylbydroxylamine hydrochloride (317 mg, 3.25 mmol) in 30 mL of methylene chloride was added triethylamine (0.5 mL, 3.62 mmol) and ethyl dimethylaminopropyl carbodiimide hydrochloride (623 mg, 3.25 mmol). The mixture was stirred at ambient temperature for 7 hours and then worked up. The crude product was purified by flash column chromatography (5% methanol-ethyl acetate) to give N-(4-Toluenesulfonyl)imidazole-4-yl-acetic acid N-methyl-O-methylcarboxamide (1.0 g, yield 90%); $^{1}H$ NMR ($CDCl_3$) δ 7.91 (s, 1H), 7.77 (d, 8.4 Hz, 2H), 7.31 (d, 8.4 Hz, 2H), 7.30 (s, 1H), 3.70 (s, 2H), 3.64 (s, 3H), 3.16 (s, 3H), 2.38 (s, 3H); $^{13}C$ NMR ($CDCl_3$) δ 170.4, 145.8, 137.9, 135.5, 134.4, 130.0, 126.9, 114.9, 60.9, 31.7, 31.3, 21.2.

EXAMPLE 174C

{4-[1-(4-Toluenesulfonyl)imidazole-4-yl) acetamido]-2-phenylbenzoyl}methionine Methyl Ester To a suspension of N-(4-toluenesulfonyl)imidazole-4-yl-acetic acid N-methyl-O-methylcarboxamide (100 mg, 0.357 mmol), prepared as in Example 174B was added diisopropylethylamine (125 μL) and tetramethylfluoroformamidinium hexafluorophosphate (94 mg, 0.357 mmol, prepared as described in J. Am. Chem. Soc. 1995, 117, 5401–5402). The mixture was stirred for 5 minutes and then 4-amino-2-phenylbenzoyl methionine methyl ester hydrochloride (compound 8, 140 mg, 0.355 mmol) and diisopropylethylamine (65 μL) was added. After 5 hours, the reaction was worked up. The crude product was recrystallized from methylene chloride and hexane to give {4-[1-(4-toluenesulfonyl)imidazole-4-ylacetamido]-2-phenylbenzoyl}methionine methyl ester (92 mg, yield 41%); m.p. 202–203° C.; $^1$H NMR ($CDCl_3$) δ 9.27 (s, 1H, amide), 8.04 (s, 1H, imidazole), 7.85 (d, J=8.2 Hz, 2H, tolyl), 7.70 (d, J=8.5 Hz, 1H), 7.61 (d, J=8.5 Hz, 1H), 7.49 (s, 1H), 7.45 (m, 5H), 7.36 (d, J=8.2 Hz, 2H, tosyl), 7.19 (s, 1H, imidazole), 5.83 (d, J=7.6 Hz, 1H, amide), 4.62 (ddd, J=7.1 Hz, 1H, Met α H), 3.65 (s, 3H, $OCH_3$), 3.62 (s, 2H, acetyl), 2.44 (s, 3H, tosyl), 2.07 (t, J=7.5 Hz, 2H, $CH_2S$), 2.00 (s, 3H, $SCH_3$), 1.84–1.93 (m, 1H, Met $CH_2$), 1.64–1.76 (s, 1H, Met $CH_2$); $^{13}$C NMR ($CDCl_3$) δ 172.4, 169.2, 168.2, 146.6, 140.4, 140.2, 138.7, 134.3, 131.1, 130.7, 129.0, 128.4, 128.2, 127.4, 127.3, 120.3, 117.3, 115.5, 52.1, 51.3, 36.1, 30.0, 29.6, 21.2, 14.5.

EXAMPLE 174D

[4-(1H-Imidazole-4-ylacetamido)-2-phenylbenzoyl] methionine Trifluoroacetate

{4-[1-(4-toluenesulfonyl)imidazole-4-ylacetamido]-2-phenylbenzoyl}methionine methyl ester (33 mg, 0.053 mmol), prepared as in Example 174C was dissolved in a mixture of THF (4 mL) and 0.5 N NaOH (0.6 mL). The mixture was stirred at 0° C. for 2 hours and then evaporated. The residue was acidified with 1 N HCl and the aqueous solution was lyophilized to give a solid mixture. This mixture was purified by preparative HPLC (C18, acetonitrile-water) to give 4-(1H-imidazole-4-yl)acetamido-2-phenylbenzoyl]methionine as a trifluoroacetate salt (17.6 mg, 55% yield); $^1$H NMR ($CD_3OD$) δ 8.85 (s, 1H, imidazole), 7.67 (s, 1H, imidazole), 7.64 (d, J=8.1 Hz, 1H, aminophenyl), 7.52 (d, J=8.1 Hz, 1H, aminophenyl), 7.46 (s, 1H, aminophenyl), 7.33–7.40 (m, 5H, phenyl), 4.48 (dd, J=4.0, 5.5 Hz, 1H, Met α H), 3.96 (s, 2H, acetyl), 2.15–2.22 (m, 1H), 2.01–2.11 (m, 1H), 2.00 (s, 3H), 1.85–1.99 (m, 1H), 1.76–1.81 (m, 1H).

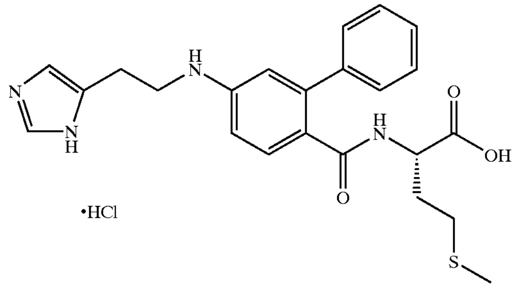

EXAMPLE 175

[4-(1H-Imidazole-4-ylethylamino)-2-phenylbenzoyl] methionine Hydrochloride

EXAMPLE 175A

{4-[1-(4-Toluenesulfonyl)imidazole-4-ylethylamino]-2-phenylbenzoyl}methionine Methyl Ester N-(4-toluenesulfonyl)imidazole-4-yl-acetic acid N-methyl-O-methylcarboxamide (1.86 g, 5.77 mmol), prepared as in Example 174B, was dissolved in 15 mL of THF and 15 mL of ether. This solution was cooled to −78° C. and $LiAlH_4$ (215 mg, 5.81 mmol) was added. The mixture was stirred for 20 minutes and then worked up with 1 N HCl. The mixture was extracted with ether. The ether solution was washed with concentrated sodium bicarbonate and dried. After evaporating solvents, a crude solid was obtained (1.61 g). $^1$H NMR showed it contained 28% aldehyde, 20% unreacted carboxamide and 50% of destosylated side product. This mixture was dissolved in 20 mL of methanol and 1 mL of acetic acid. 4-Amino-2-phenylbenzoyl methionine methyl ester hydrochloride (compound 8, 640 mg, 1.62 mmol) was added to the above solution and the reaction was stirred at ambient temperature. After 15 minutes, sodium cyanoborohydride (152 mg, 2.42 mmol) was added. The mixture was stirred for 15 hours and then evaporated. The residue was extracted with concentrated sodium bicarbonate and methylene chloride. The methylene chloride solution was dried and evaporated. The residue was purified by flash column chromatography (ethyl acetate-hexane 4:1) to give {4-[1-(4-toluenesulfonyl)imidazole-4-ylethylamino]-2-phenylbenzoyl}methionine methyl ester as a fluffy solid (500 mg, 51%); $[\alpha]^{25}_D$=+0.60 (c=1.10, $CDCl_3$); $^1$H NMR ($CDCl_3$) δ 7.95 (s, 1H, imidazole), 7.79 (d, J=8.0 Hz, 2H, tosyl), 7.68 (d, J=8.5 Hz, 1H, aminophenyl), 7.37–7.45 (m, 5H), 7.33 (d, J=8.0 Hz, 2H, tosyl), 7.05 (s, 1H, imidazole), 6.57 (d, J=8.5 Hz, 1H, aminophenyl), 6.41 (s, 1H, aminophenyl), 5.66 (d, J=7.6 Hz, 1H, amide), 4.61 (ddd, J=5.2, 7.2 and 7.6 Hz, 1H, Met α H), 4.46 (t, J=5.6 Hz, 1H, amine), 3.67 (s, 3H, $OCH_3$), 3.43 (q, J=6.3 Hz, 2H, ethylene), 2.82 (t, J=6.4 Hz, 2H, ethylene), 2.43 (s, 3H), 2.08 (t, J=7.7 Hz, 2H, $CH_2S$), 2.00 (s, 3H, $SCH_3$), 1.82–1.90 (m, 1H), 1.58–1.70 (m, 1H); $^{13}$C NMR ($CDCl_3$) δ 171. 168.3, 149.4, 146.1, 142.3, 141.5, 141.0, 136.1, 134.5, 131.0, 130.2, 128.5, 128.3, 127.5, 127.1, 122.3, 113.7, 113.6, 111.0, 52.0, 51.5, 42.2, 31.5, 29.3, 27.2, 21.5, 15.0.

EXAMPLE 175B

[4-(1H-Imidazole-4-ylethylamino)-2-phenylbenzoyl] methionine Hydrochloride

{4-[1-(4-toluenesulfonyl)imidazole-4-ylethylamino]-2-phenylbenzoyl}methionine methyl ester (303 mg, 0.50 mmol), prepared as in Example 175A, was dissolved in a mixture of THF (4 mL) and 0.5 N NaOH (4.0 mL). The mixture was stirred at 0° C. for 2 hours and then evaporated. After acidification with 1 N HCl, the aqueous solution was lyophilized. The crude solid was purified by reverse phase preparative HPLC to give a trifluoroacetate salt (140 mg, 51%). This trifluoroacetate salt was dissolved in 1 N HCl and the aqueous solution was lyophilized to give [4-(1H-imidazole-4-ylethylamino)-2-phenylbenzoyl]methionine hydrochloride; $[\alpha]^{25}_{D}$=−25.5 (c=1.1, $H_2O$); $^1H$ NMR ($CD_3OD$) δ 8.79 (s, 1H, imidazole), 7.48 (d, J=8.4 Hz, 1H), 7.32–7.39 (m, 6H), 6.84 (d, J=8.4 Hz, 1H), 6.77 (s, 1H), 4.45 (dd, J=4.1 and 5.1 Hz, 1H, Met α H), 3.58 (t, J=7.0 Hz, 2H), 3.08 (t, J=7.0 Hz, 2H), 2.16–2.24 (m, 1H), 2.05–2.14 (m, 1H), 2.00 (s, 3H), 1.92–1.98 (m, 1H), 1.72–1.85 (m, 1H); $^{13}C$ NMR ($CD_3OD$) δ 174.8, 172.4, 145.1, 143.5, 141.3, 134.9, 131.8, 131.3, 130.9, 129.7, 129.6, 129.0, 119.7, 118.1, 116.6, 53.0, 46.5, 31.6, 31.0, 24.2, 15.0.

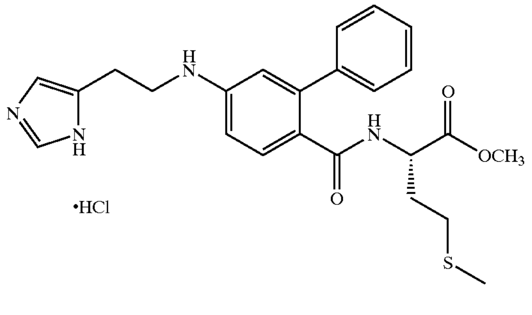

EXAMPLE 176

[4-(1H-Imidazole-4-ylethylamino)-2-phenylbenzoyl] methionine Methyl Ester Hydrochloride {4-[1-(4-toluenesulfonyl)imidazole-4-ylethylamino-]2-phenylbenzoyl}methionine methyl ester (90.2 mg, 0.1488 mmol), prepared as in Example 175A, was dissolved in 5 mL of THF. To this solution was added 3-hydroxy-1,2,3-benzotriazin-4(3H)-one (80.4 mg, 0.5956 mmol) and the mixture was stirred at ambient temperature. After 2 hours, TLC showed the disappearance of starting material. The solution was evaporated and the residue was extracted with ethyl acetate and 1 N HCl. The aqueous solution was neutralized with 1 N NaOH to pH 8.5 and then extracted with ethyl acetate. After evaporating solvents, the residue was dissolved in 1 N HCl and the solution was lyophilized to give [4-(1H-imidazole-4-ylethylamino)-2-phenylbenzoyl]methionine methyl ester hydrochloride (62.6 mg, yield 80%); $[\alpha]^{25}_{D}$=−34.0 (c=1.50, $H_2O$); $^1H$ NMR ($CD_3OD$) δ 8.82 (s, 1H, imidazole), 7.53 (d, 1H, J=8.4 Hz, aminophenyl), 7.35–7.46 (m, 6H, imidazole and phenyl), 7.07 (d, 1H, J=8.4 Hz, aminophenyl), 7.01 (s, 1H, aminophenyl), 4.50 (dd, J=4.0 Hz, 1H, Met α H), 3.70 (s, 3H, $OCH_3$), 3.65 (t, J=7.1 Hz, 2H, ethylene), 3.15 (t, J=7.1 Hz, 2H, ethylene), 2.14–2.23 (m, 1H), 2.04–2.12 (m, 1H), 1.99 (s, 3H, $SCH_3$), 1.89–1.96 (m, 1H), 1.73–1.82 (m, 1H); $^{13}C$ NMR ($CD_3OD$) δ 173.6, 172.2, 143.7, 143.3, 140.9, 135.2, 132.8, 131.4, 131.3, 129.8, 129.7, 129.1, 121.2, 118.2, 118.1, 53.0, 52.8, 47.6, 31.3, 30.8, 23.8, 15.0.

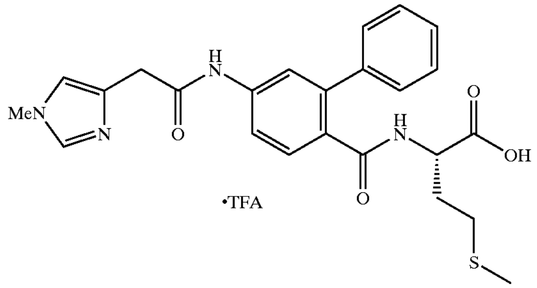

EXAMPLE 177

[4-(1-Methylimidazole-4-ylacetamido)-2-phenylbenzoyl]methionine Trifluoroacetate

EXAMPLE 177A

[4-(1-Methylimidazole-4-ylacetamido)-2-phenylbenzoyl]methionine Methyl Ester 4-Amino-2-phenylbenzoyl methionine methyl ester hydrochloride (compound 8, 111.8 mg, 0.2833 mmol) and N-methylimidazole-4-yl-acetic acid hydrochloride (50 mg, 0.2832 mmol) were suspended in 10 mL of methylene chloride. To this solution was added diisopropylethylamine (197 μL, 4.0 eq) and O-benzotriazol-1-yl-N,N,N',N'-tetramethyluroniumhexafluorophosphate (107.4 mg, 0.2833 mmol). After stirring at ambient temperature for 2 days, the reaction was worked up by washing with dilute HCl (PH=3.0) and concentrated sodium bicarbonate. After evaporating solvents, the residue was purified by flash column chromatography ($CH_2Cl_2$-Methanol, 10:1) to give [4-(1-Methylimidazole-4-ylacetamido)-2-phenylbenzoyl]methionine methyl ester (106 mg, 78%); m.p. 69–70° C.; $^1H$ NMR ($CDCl_3$) δ 9.89 (s, 1H, amide), 7.67 (d, J=8.4 Hz, 1H), 7.60 (d, J=8.4 Hz, 1H), 7.55 (s, 1H), 7.46 (s, 1H, imidazole), 7.34–7.42 (m, 5H), 6.81 (s, 1H, imidazole), 5.90 (d, J=7.7 Hz, 1H, amide), 4.63 (ddd, J=5.1, 7.3 and 7.7 Hz, 1H, Met α H), 3.72 (s, 3H, $OCH_3$), 3.64 (s, 5H, N-methyl and imidazole acetyl), 2.10 (t, J=7.6 Hz, 2H), 1.98 (s, 3H), 1.83–1.94 (m, 1H), 1.66–1.75 (m, 1H); $^{13}C$ NMR ($CDCl_3$) δ 171.7, 169.0, 168.9, 140.3, 140.1, 139.8, 137.3, 135.3, 129.6, 129.3, 128.5, 128.3, 127.5, 120.6, 118.5, 118.0, 52.1, 51.6, 36.3, 33.3, 30.8, 29.4, 15.0; LRMS (EI) for $C_{25}H_{28}O_4N_4S$ 480 ($M^+$, 20), 406 (100), 318 (50); HRMS (EI) calcd 480.1813, obsd 480.1829.

EXAMPLE 177B

[4-(1-Methylimidazole-4-ylacetamido)-2-phenylbenzoyl]methionine Trifluoroacetate 4-[1-Methylimidazole-4-ylacetamido-2-phenylbenzoyl] methionine methyl ester (70 mg, 0.1458 mmol), prepared as in Example 177A, was dissolved in a mixture of THF (2.0 mL) and 0.5 N LiOH (0.5 mL). The mixture was stirred at 0° C. for 1 hour. After evaporating solvents, the residue was acidified with 1 N HCl. The aqueous solution was lyophilized and the crude solid was purified by reverse phase preparative HPLC to give [4-(1-Methylimidazole-4-ylacetamido)-2-phenylbenzoyl]methionine as a TFA salt (50 mg, 60%). $^1H$ NMR ($CD_3OD$) δ 8.83 (s, 1H, imidazole), 7.66 (s, 1H, imidazole), 7.64 (d, J=8.5 Hz, 1H), 7.52 (d, J=8.5 Hz, 1H), 7.48 (s, 1H), 7.32–7.43 (m, 5H), 4.48 (dd, J=4.1 and 9.5 Hz, 1H, Met α H), 3.92 (s, 5H, N-methyl and imidazole acetyl), 2.13–2.22 (m, 1H), 2.00–2.10 (m, 1H), 2.00 (s, 3H), 1.94–2.00 (m, 1H), 1.72–1.84 (m, 1H); $^{13}C$ NMR ($CD_3OD$) δ 174.9, 172.8, 168.2, 142.4, 141.4, 141.2, 136.7, 132.7, 130.0, 129.7, 129.5, 129.4, 128.8, 122.8, 122.2, 119.2, 53.0, 36.1, 33.0, 31.5, 31.0, 15.0.

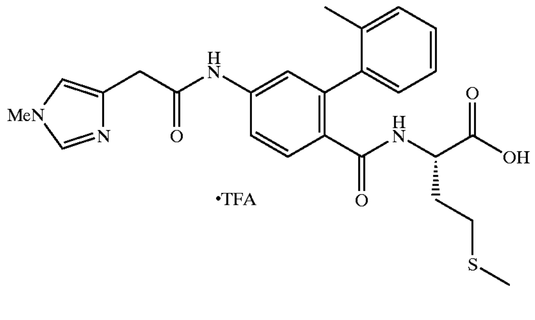

EXAMPLE 178

[4-(1H-1-Methylimidazole-4-ylacetamido)-2-(2-methylphenyl)benzoyl]methionine Trifluoroacetate

EXAMPLE 178A

4-Nitro-2-(2-methylphenyl)benzoic Acid Methyl Ester

The coupling of 4-nitro-2-bromobenzoic acid methyl ester with 2-methylphenylboronic acid in DMF at 100° C. in the presence of $Pd(PPh_3)_4$ (1.5% eq) and $Na_3PO_4$ (2.5 eq) gave 4-nitro-2-(2-methylphenyl)benzoic acid methyl ester as a colorless oil (43% yield after column chromatography purification 6:1=hexane/ethyl acetate). $^1H$ NMR ($CDCl_3$) δ 8.26 (d, J=8.6 Hz, 1H), 8.13 (s, 1H), 8.08 (d, J=8.6 Hz, 1H), 7.21–7.34 (m, 3H), 7.06 (d, J=7.5 hz, 1H), 3.65 (s, 3H), 2.09 (s, 3H); $^{13}C$ NMR ($CDCl_3$) δ 165.8 148.5, 143.5, 138.5, 135.9, 134.6, 130.5, 129.3, 127.9, 127.7, 125.1, 121.5, 51.8, 19.3 (expect 12 aromatic C, observed 11); LRMS (EI) 271; HRMS (EI) calcd for $C_{15}H_{13}NO_4$ 271.0844, obsd 271.0852.

EXAMPLE 178B

4-Nitro-2-(2-methylphenyl)benzoic Acid

4-Nitro-2-(2-methylphenyl)benzoic acid methyl ester, prepared as in Example 178A, was saponified using aqueous NaOH—$CH_3OH$ to give 4-nitro-2-(2-methylphenyl)benzoic acid; HRMS calcd for $C_{14}H_{11}NO_4$ 257.0688, obsd 257.0699.

EXAMPLE 178C

[4-Nitro-2-(2-methylphenylbenzoyl]methionine Methyl Ester Hydrochloride

4-Nitro-2-(2-methylphenyl)benzoic acid (2.31 g, 9 mmol), prepared as in Example 178B, was coupled with L-methionine methyl ester (1.0 eq) in the presence of ethyl dimethylaminopropyl carbodiimide hydrochloride (EDCI, 1.0 eq) and 3-hydroxy-1,2,3-benzotriazin-4(3H)-one (HOBT, 1.0 eq) to give [4-nitro-2-(2-methylphenyl)benzoyl] methionine methyl ester as a pale yellow oil (3.54 g, 98% yield); $^1H$ NMR showed diastereomers due to restricted carbon-carbon bond rotation; $^1H$ NMR ($CDCl_3$) δ 8.26–8.30 (d, J=8.5 Hz, 1H), 8.10 (s, 1H), 8.03–8.09 (m, 1H), 7.27–7.42 (m, 3.5H), 7.18 (d, J=7.4 Hz, 0.5H), 6.03 (br, 1H, amide), 4.59–4.67 (m, 1H), 3.67 (s, 3H), 2.23 (s, 1.5H, $PhCH_3$), 2.06 (s, 1.5H, $PhCH_3$), 1.98–2.03 (m, 5H), 1.81–1.93 (m, 1H), 1.59–1.69 (m, 1H).

EXAMPLE 178D

[4-Amino-2-(2-methylphenylbenzoyl]methionine Methyl Ester Hydrochloride

[4-Nitro-2-(2-methylphenyl)benzoyl]methionine methyl ester was reduced to a corresponding amine by stannous chloride in ethyl acetate at 78° C. The free amine was treated with methylene chloride and 3 N HCl in ether to give [4-amino-2-(2-methylphenyl)benzoyl]methionine methyl ester hydrochloride (85% yield); $[\alpha]^{25}_D$=−28.3 (c=1.0, methanol); $^1H$ NMR ($CD_3OD$) δ 7.74 (d, J=8.2 Hz, 1H), 7.47 (d, J=8.2 Hz, 1H), 7.23–7.30 (m, 5H), 4.47 (m, 1H), 3.69 (s, 3H), 2.06–2.18 (m, 4H), 1.99 (s, 3H), 1.97 (m, 2H), 1.74 (m, 1H); $^{13}C$ NMR ($CD_3OD$) δ 173.3, 170.8, 143.3, 139.7, 138.1, 137.2, 133.5, 131.49 130.8, 130.6, 129.6, 128.8, 126.2, 123.1, 66.9, 52.9, 31.5, 30.8, 20.4, 15.1.

EXAMPLE 178E

[4-(1H-1-Methylimidazole-4-ylacetamido)-2-(2-methylphenyl)benzoyl]methionine Methyl Ester The desired compound was prepared by coupling of 4-amino-2-(2-methylphenyl)benzoyl methionine methyl ester hydrochloride, prepared as in Example 178D, with N-methylimidazole-4-yl-acetic acid according to the method of Example 178C (yield 58%, purified by column chromatography (10:1 $CH_2Cl_2$—$CH_3OH$); m.p 69–70° C.; $[\alpha]^{25}_D$=+17.5 (c=4.4, $CHCl_3$); $^1H$ NMR ($CDCl_3$) δ 9.91 (s, 1H), 7.90–7.99 (m, 1H), 7.65 (m, 1H), 7.45 (s, 1H), 7.40 (d, J=6.2 Hz, 1H), 7.26–7.31 (m, 3H), 7.15–7.20 (m, 1H), 6.79 (s, 1H), 5.86 (d, J=7.1 Hz, 1H amide), 4.56–4.64 (m, 1H), 3.67 (s, 4H), 3.64 (s, 4H), 2.17 (s, 1.5H, $PhCH_3$), 1.93–2.05 (m, 6.5H), 1.80–1.89 (m, 1H), 1.51–1.61 (m, 1H); $^{13}C$ NMR ($CDCl_3$) δ 171.7, 171.6, 168.7, 167.1, 166.7, 140.5, 140.4, 140.1, 139.8, 137.5, 136.0, 135.5, 130.5, 130.3, 128.9, 128.7, 128.5, 128.1, 128.0, 126.0, 125.9, 120.5, 118.2, 118.1, 52.1, 51.5, 51.4, 36.4, 33.2, 31.3, 29.1, 19.7, 15.0 (diastereomers shown in NMR data are due to restricted carbon-carbon bond rotation); HRMS calcd for $C_{26}H_{30}O_4N_4S$ 494.1988, obsd 494.1986.

EXAMPLE 178F

[4-(1H-1-Methylimidazole-4-ylacetamido)-2-(2-methylphenyl)benzoyl]methionine Trifluoroacetate

[4-(1H-1-Methylimidazole-4-ylacetamido)-2-(2-methylphenyl)benzoyl]methionine methyl ester (72 mg, 0.1472 mmol) was saponified using 0.5 N LiOH (0.58 mL, 0.29 mmol) in 2.0 mL of THF as described in Example 177B. The acid was purified by reverse phase preparative HPLC to give [4-(1-methylimidazole-4-ylacetamido)-2-(2-methylphenyl)benzoyl]methionine trifluoroacetate (70 mg, 87% yield); $^1H$ NMR showed a complex due to diastereomers caused by restricted bond rotation; $^1H$ NMR ($CD_3OD$) δ 8.81 (s, 1H), 7.68 (m, 2H), 7.46–7.49 (m, 2H), 7.25 (m, 4H), 4.43 (m, 1H), 3.91 (m, 5H), 2.08–2.17 (m, 4H), 1.94–1.99 (m, 5H), 1.69 (m, 1H).

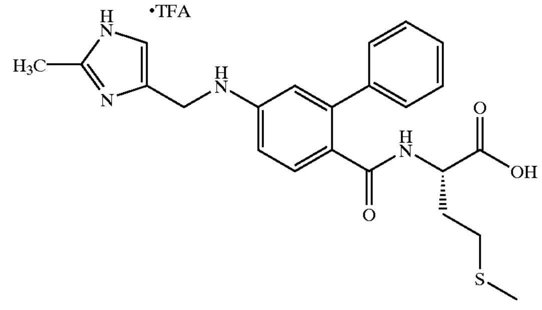

EXAMPLE 180

[4-(1-H-2-Methylimidazole-4-ylmethylamino)-2-phenylbenzoyl]methionine Trifluoroacetate

EXAMPLE 180A

4-Hydroxymethyl-2-methylimidazole 1,3-Dihydroxyacetone (6.2 g, 50 mmol) and ethyl acetimidate hydrochloride (4.5 g, 50 mmol) were added to an autoclave to which 50 mL of liquid ammonia was added. The apparatus was sealed and heated (68–70° C.) with stirring for 4 hours. After cooling the reaction mixture was extracted with hot acetonitrile which upon cooling formed a precipitate which was collected to give 4-hydroxymethyl-2-methylimidazole (2.3 g, 41%); $^1$H NMR (300 MHz, $CDCl_3$) δ 6.75 (s, 1H), 4.50 (s, 2H), 2.35 (s, 3H); $^{13}$C NMR (75 MHz, $CDCl_3$) δ 143.48, 135.98, 116.25, 55.59, 12.95.

EXAMPLE 180B

4-Hydroxymethyl-2-methyl-1-p-toluenesulfonylimidazole

4-Hydroxymethyl-2-methylimidazole (0.7 g, 6.25 mmol), prepared as in Example 180A, and p-toluenesulfonylchloride (1.2 g, 6.25 mmol) were suspended in 5 mL of distilled water and 3 mL of THF. Sodium hydroxide (1N) was added to maintain a pH of 9 over a period of 3 hours. The reaction mixture was extracted with ethyl acetate (3×50 mL). The extracts were combined, dried over magnesium sulfate, concentrated and crystallized from ethyl acetate, collected by vacuum filtration and dried to give 4-hydroxymethyl-2-methyl-1-p-toluenesulfonylimidazole (0.5 g, 35%) as a white solid; m.p. 140–143°; $^1$H NMR (300 MHz, $CDCl_3$) δ 7.78 (d, 8.25 2H), 7.36 (d, J=8.25 Hz, 2H), 7.33 (s, 1H), 4.49 (s, 2H), 2.50 (s, 3H), 2.45 (s, 3H); $^{13}$C NMR (75 MHz, $CDCl_3$) δ 146.38, 140.96, 134.85, 130.51, 127.57, 116.05, 57.37, 21.84, 15.02; MS m/e calc'd: 266.0725, found: 266.0714.

EXAMPLE 180C (2-Methyl-1-p-toluenesulfonylimidazole-4-yl)-carboxaldehyde

4-Hydroxymethyl-2-methyl-1-p-toluenesulfonylimidazole (0.75 g, 2.8 mmol), prepared as in Example 180B, was dissolved into 10 mL of methylene chloride and manganese(IV)oxide (2.0 g, 23 mmol) added over an 8 hour period. The reaction mixture was stirred at room temperature for an additional 16 hours. The reaction mixture was filtered through a celite plug and concentrated to leave a slightly yellow oil. The residue was crystallized from ethyl acetate, collected and dried to give (2-methyl-1-p-toluenesulfonylimidazole-4-yl)carboxaldehyde (0.44 g, 59%) as a white solid; mp 106–109° C.; $^1$H NMR (300 MHz, $CDCl_3$) δ 9.82 (s, 1H), 8.09 (s, 1H), 7.84 (d, J=7.53, 2H), 7.42 (d, J=7.44, 2H), 2.56 (s, 3H), 2.48 (s, 3H); $^{13}$C NMR (75 MHz, $CDCl_3$) δ 184.95, 147.32, 139.63, 133.81, 130.83, 127.94, 125.35, 21.93, 15.18.

EXAMPLE 180D

[4-(1H-2-Methyl-1-p-toluenesulfonylimidazole-4-ylmethylamino)-2-phenylbenzoyl]methionine Methyl Ester (2-Methyl-1-p-toluenesulfonylimidazole-4-yl) carboxaldehyde (0.10 g, 0.38 mmol), prepared as in Example 180C, and 4-amino-2-phenylbenzoyl-methionine methyl ester hydrochloride (0.037 g, 0.09 mmol) were dissolved in 10 mL of 95% methanol and 5% acetic acid and stirred for 15 minutes. Sodium cyanoborohydride (0.048 g, 0.76 mmol) was then added and the reaction was stirred for 0.5 hour. Additional (2-Methyl-1-p-toluenesulfonylimidazol-4-yl)carboxaldehyde (0.10 g, 0.038 mmol) and sodium cyanoborohydride (0.048 g, 0.076 mmol) were then added, followed by 4-amino-2-phenylbenzoyl methionine methyl ester hydrochloride (compound 8, 0.037 g, 1.7 mmol). Additional carboxaldehyde (0.24 g, 0.91 mmol) and 4-amino-2-phenylbenzylmethionine methyl ester hydrochloride (0.180 g, 0.46 mmol) were then added and the reaction was stirred at room temperature for 0.5 hour. The reaction mixture was concentrated and the residue taken up in ethyl acetate and washed with a saturated solution of sodium bicarbonate. The organic phase was dried over magnesium sulfate and concentrated. The residue was purified by flash chromatography (4:1 ethyl acetate/hexanes) to give [4-(1H-2-methyl-1-p-toluenesulfonylimidazol-4-ylmethylamino)-2-phenylbenzoyl]methionine methyl ester (0.185 g, 47%) as a white foam; $^1$H NMR (300 MHz, $CDCl_3$) δ 7.73 (d, J=8.28 Hz, 2H), 7.67 (d, J=8.52 Hz, 2H), 7.42–7.27 (m, 7H), 6.62 (dd, J=7.23, 2.25 Hz, 1H), 6.49 (d, J=2.25 Hz, 1H), 5.71 (d, J=7.59 Hz, 1H), 4.66–4.59 (m, 1H, α CH Met.), 4.55 (t, J=5.46 Hz, 1H), 4.22 (d, J=5.34 Hz, 2H), 3.65 (s, 3H), 2.62 (s, 3H), 2.50 (s, 3H), 2.10 (t, J=7.65 Hz, 2H), 2.01 (s, 3H), 1.94–1.78 (m, 1H), 1.72–1.60 (m, 1H); $^{13}$C NMR (75 MHz, $CDCl_3$) δ 172.26, 168.67, 149.40, 146.34, 141.62, 141.30, 138.38, 134.99, 131.44, 130.58, 128.95, 128.83, 128.02, 127.50, 123.54, 116.28, 114.45, 111.67, 52.51, 52.01, 41.45, 31.68, 29.71, 21.91, 15.49, 15.35.

EXAMPLE 180E

[4-(1-H-2-Methylimidazol-4-ylmethyamino)-2-phenylbenzoyl]methionine Trifluoroacetate

[4-(1H-2-methyl-1-p-toluenesulfonylimidazol-4-ylmethylamino)-2-phenylbenzoyl]methionine methyl ester (0.1 g, 0.165 mmol), prepared as in Example 180D, was dissolved in 2 mL of THF and cooled to 0° C. Lithium hydroxide (2 mL, 0.5M) was slowly added and the reaction mixture was stirred for 6 hours. Aqueous HCl (3 mL, 0.5M) was added and excess THF removed under vacuum. The aqueous layer was lyophilized and the resulting solid was purified by reverse phase preparative HPLC (Waters 25×10 cm, C-18 column, 220 nm UV detector, flow rate 15 mL/min, linear gradient from 5% acetonitrile and 95% water, containing 0.1% TFA to 60% acetonitrile in 40 minutes) to give [4-(1-H-2-methylimidazol-4- ylmethyamino)-2-phenylbenzoyl]methionine trifluoroacetate as a white solid (0.03 g, 52%); $^1$H NMR (300 MHz, $CDCl_3$) δ 14.12 (br, s, 1H), 13.92 (br, s, 1H), 12.55 (br s 1H), 8.06 (d, J=7.8 Hz, 1H), 7.39 (s, 1H), 7.28–7.22 (m, 7H), 6.62 (d, J=8.7 Hz, 1H), 6.56 (s, 1H), 4.32 (s, 2H), 4.23–4.16 (m , 1H, α CH Met.), 2.49 (s, 3H), 2.29–2.12 (m, 2H), 1.96 (s, 3H), 1.84–1.73 (m, 2H).

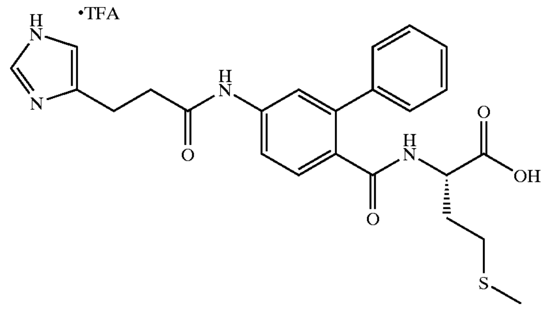

EXAMPLE 181

[4-((1-H-imidazol-4-yl)-3-propylcarbonylamino)-2-phenylbenzoyl]methionine Trifluoroacetate

EXAMPLE 181A trans-Urocanic Acid-methyl Ester

Urocanic acid (0.6 g, 4.3 mmol) was suspended in methanol and HCl gas bubbled through so refluxing commenced for 1 hour After cooling the precipitate was collected by vacuum filtration, washed with hexanes and dried to give trans-urocanic acid-methyl ester (0.74 g, 91%) as a white solid. m.p. 239–242° C.; $^1$H NMR (300 MHz, $CDCl_3$) δ 9.26 (s, 1H), 8.07 (s, 1H), 7.59 (d, J=16.3 Hz, 1H), 6.89 (d, J=16.2 Hz, 1H), 3.74 (s, 3H).

EXAMPLE 181B 3-(1-H-Imidazol-4-yl)propanoic Acid Methyl Ester

Trans-urocanic acid-methyl ester (0.6 g, 3.2 mmol) was dissolved in methanol (20 mL), and hydrogenated at room temperature using 10% Palladium on carbon (0.04 g) under a hydrogen atmosphere (40 psi) for 5.5 hours. The reaction mixture was filtered through a celite plug and concentrated. The residue was crystallized from ethyl ether, collected and dried to give 3-(1-H-imidazol-4-yl)propanoic acid methyl ester (0.56 g, 93%) as a white solid; m.p. 105–108° C.; $^1$H NMR (300 MHz, $CDCl_3$) δ 8.99 (s, 1H), 7.40 (s, 1H), 3.58 (s, 3H); MS m/e calc: 154.0742, found: 154.0750.

EXAMPLE 181C 3-(1-H-1-Triphenylmethylimidazol-4-yl)propanoic Acid Methyl Ester

To a solution of 3-(1-H-imidazol-4-yl)propanoic acid methyl ester (0.5 g, 2.6 mmol), prepared as in Example 181B, and triphenylmethylchloride (0.73 g, 2.6 mmol) in 10 mL of methylene chloride was added triethylamine (0.58 g, 5.2 mmol). The reaction mixture was stirred at room temperature for 3 hours. The organics were washed with distilled water, dried using magnesium sulfate and concentrated under vacuum. The residue was crystallized from ether and hexanes, collected by vacuum filtration and dried to give 3-(1H-1-triphenylmethylimidazol-4-yl)propanoic acid methyl ester (0.81 g, 79%) as a white solid; m.p. 140–141° C.; $^1$H NMR (300 MHz, $CDCl_3$) δ 7.39–7.30 (m, 10H), 7.15–7.77 (m, 6H), 6.55 (s, 1H), 3.62 (s, 3H), 2.87 (t, J=7.32 Hz, 2H), 2.66 (t, J=7.74 Hz, 2H).

EXAMPLE 181D 3-(1H-1-Triphenylmethylimidazol-4-yl)propanoic Acid

To a 0° C. solution of 3-(1H-1-triphenylmethylimidazol-4-yl)propanoic acid methyl ester (0.6 g, 1.5 mmol), prepared as in Example 181C, was slowly added lithium hydroxide (6 mL, 0.5M) and the reaction mixture was stirred for 2 hours. The THF was removed under vacuum and the aqueous layer was acidified using HCl (6 mL, 0.5M). A white precipitate which formed was collected by vacuum filtration and dried to give 3-(1H-1-triphenylmethylimidazol-4-yl)propanoic acid (0.53 g, 93%) as a white solid; m.p. 182–186° C.; $^1$H NMR (300 MHz, DMSO-$d_6$) δ 7.40–7.38 (m, 9H), 7.26 (s, 1H), 7.09–7.07 (m, 6H), 6.64 (s, 1H), 2.67 (t, J=6.66 Hz, 2H), 2.49 (t, J=6.78 Hz, 2H).

EXAMPLE 181E

[4-((1H-1-Triphenylmethylimidazol-4-yl)-3-propylcarbonylamino)-2-phenylbenzoyl]methionine Methyl Ester To a 0° C. solution of 3-(1H-1-triphenylmethylimidazol-4-yl)propanoic acid (0.5 g, 1.3 mmol), prepared as in Example 181 D, ethyl dimethylaminopropyl carbodiimide hydrochloride (0.27 g, 1.4 mmol), 3-hydroxy-1,2,3-benzotriazin-4(3H)-one (HOBT, 0.18 g, 1.3 mmol), and 4-amino-2-phenylbenzoyl-methionine methyl ester hydrochloride (0.52 g, 1.3 mmol) in 10 mL, of methylene chloride, was added triethylamine (0.13 g, 1.3 mmol) and the reaction mixture was stirred for 16 hours at room temperature under a nitrogen atmosphere. The reaction mixture was washed first with distilled water followed by 0.5N HCl. The organics were dried using magnesium sulfate and concentrated. The residue was purified by flash chromatography (19:1 chloroform/hexanes) to give [((1H-triphenylmethylimidazol-4-yl)-3-propylcarbonylamino)-2-phenylbenzoyl]methionine methyl ester (0.38 g, 40%) as a white foam; $^1$H NMR (300 MHz, $CDCl_3$) δ 9.96 (s, 1H), 7.70 (d, 1H), 7.69–7.56 (m, 2H), 7.56–7.23 (m, 17H), 7.08–7.05 (m, 4H), 6.62 (s, 1H), 5.8 (d, J=7.68 Hz, 1H), 5.85 (d, J=7.68 Hz, 1H), 4.64 (dd, J=7.26, 6.23 Hz, 1H), 3.65 (s, 3H), 2.95–2.91 (m, 2H), 2.81–2.77 (m, 2H).

EXAMPLE 181F

[4-(1H-Imidazol-4-yl)-3-propylcarbonylamino-2-phenylbenzoyl]methionine Trifluoroacetate To a 0° C. solution of [4-(1H-1-triphenylmethylimidazol-4-yl)-3-propylcarbonylamino-2-phenylbenzoyl]methionine methyl ester (0.16 g, 0.23 mmol), prepared as in Example 181E, in 4.4 mL of THF was slowly added lithium hydroxide (4.4 mL, 0.5M) and the reaction mixture was stirred for 2 hours. The pH was adjusted using 0.5 M HCl and the mixture was extracted with ethyl acetate (3x50 mL). The extracts were combined, dried over magnesium sulfate and concentrated to an oil. The oil was taken up in methylene chloride (4 mL) to which trifluoroacetic acid (8 mL) was added which produced a deep yellow color. Immediately after the addition of TFA, triethylsilane was added dropwise until the reaction mixture was nearly colorless. The reaction was stirred for 2 hours at ambient temperature and concentrated to give a solid which was washed with diethyl ether. The solid was collected by vacuum filtration, washed with additional diethyl ether and dried to yield [4-(1H-imidazol-4-yl)-3-propylcarbonylamino-2-phenylbenzoyl]methionine trifluoroacetate (0.073 g, 36%). $^1H$ NMR (300 MHz, $CD_3OD$) δ 8.72 (s, 1H), 7.64 (br s, 2H), 7.35–7.50 (m, 8H), 4.50 (br s, 2H), 2.80 (br s, 2H), 2.19 (br s, 2H), 2.00 (s, 3H), 1.82 (br s, 2H). MS m/e 467 $(M+H)^+$.

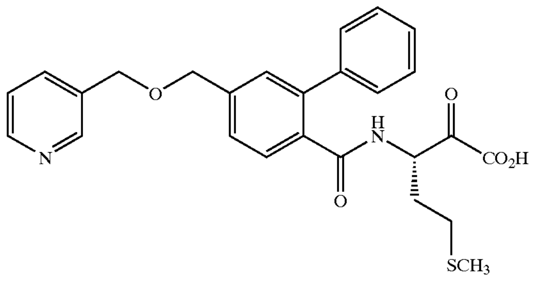

EXAMPLE 183

[4-(3-Pyridylmethyloxymethyl)-2-phenylbenzoyl]methionine Hydrochloride

EXAMPLE 183A

[4-(3-Pyridylmethyloxymethyl)-2-phenylbenzoic Acid Methyl Ester

To a solution in DMF of 3-pyridinemethanol (0.59 mL) was added sodium hydride (60% in mineral oil, 0.19 g), and the mixture was stirred until gas evolution ceased. A solution of 2-phenyl-4-bromomethylbenzoic acid methyl ester (0.98 g) in DMF was then added and the reaction mixture was stirred until the bromide was consumed. The reaction mixture was partitioned between ethyl acetate and water. The organic phase was washed with brine, dried, and concentrated. The residue was purified by chromatography on silica gel (1:1 ethyl acetate-hexanes) to give [4-(3-pyridylmethyloxymethyl)-2-phenylbenzoic acid methyl ester (0.58 g).

EXAMPLE 183B 4-(3-Pyridylmethyloxymethyl)-2-phenylbenzoic Acid

To a solution in methanol (5 mL) of [4-(3-pyridylmethyloxymethyl)-2-phenylbenzoic acid methyl ester (0.58 g), prepared as in Example 183A, was added saturated aqueous lithium hydroxide and the reaction mixture was stirred overnight at ambient temperature. The reaction mixture was warmed to 60° C. and stirred for 4 hours. The reaction mixture was concentrated in vacuo and the residue was taken up in water. The aqueous phase was taken to pH 5 with aqueous 3N HCl and extracted with chloroform. The organic phase was concentrated in vacuo to give 4-(3-pyridylmethyloxymethyl)-2-phenylbenzoic acid (0.52 g).

EXAMPLE 183C

[4-(3-Pyridylmethyloxymethyl)-2-phenylbenzoyl]methionine Methyl Ester

The desired compound was prepared by coupling of 4-(3-pyridylmethyloxymethyl)-2-phenylbenzoic acid with methionine methyl ester hydrochloride as described in Example 163D.

EXAMPLE 183D

[4-(3-Pyridylmethyloxymethyl)-2-phenylbenzoyl]methionine

The desired compound was prepared by saponification of [4-(3-pyridylmethyloxymethyl)-2-phenylbenzoyl]methionine methyl ester, prepared as in Example 183C using the procedure of Example 183B; $^1H$ NMR ($CDCl_3$, 300 MHz) δ 1.66–2.17 (4H, m), 2.02 (3H, s), 4.62 (1H, m), 4.76 (2H, s), 4.78 (2H, s), 6.31 (1H, d, J=6.3 Hz), 7.23–7.44 (7H, m), 7.71 (1H, d, J=7.8 Hz), 7.86 (1H, m), 8.34 (1H, m), 8.65 (1H, m), 8.72 (1H, m); MS (DCI/$NH_3$) m/e 451 $(M+H)^+$. Anal calcd for $C_{25}H_26N_2O_4S$.1.45HCl: C, 59.65; H, 5.50; N, 5.56. Found: C, 59.80; H, 5.11; N, 5.26.

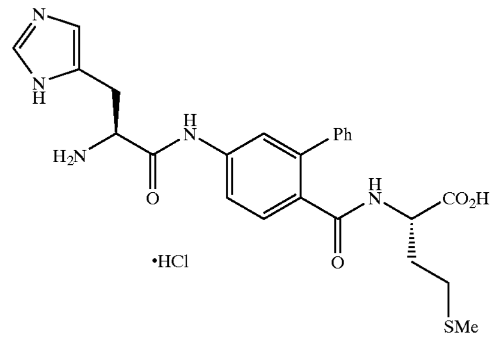

EXAMPLE 184

[4-(L-Histidyl)-2-phenylbenzoyl]methionine Hydrochloride

EXAMPLE 184A

[4-(bis-tert-Butoxycarbonyl-L-histidyl)-2-phenylbenzoyl]methionine Methyl Ester

Bis-tert-butoxycarbonyl-L-His (1.78 g, 5.00 mmol) was added to a solution of [4-amino-2-phenylbenzoyl]methionine methyl ester (compound 8, 1.79 g, 5.00 mmol), 3-hydroxy-1,2,3-benzotriazin-4(3H)-one (HOOBT, 2.50 g, 15.0 mmol), 1-(3-dimethylaminopropyl)-3-ethylcarbodiimide (EDC, 2.93 g, 15.0 mmol), and N-methylmorpholine (NMM) in DMF (25 mL). The reaction mixture was stirred at ambient temperature for 17 hours and then was concentrated under reduced pressure (50° C., 0.1 mm Hg) to provide an amber oil. The oil was dissolved in ethyl acetate (25 mL) and the solution was extracted with saturated aqueous $NaHCO_3$ (3×10 mL), followed by brine (10 mL). The combined aqueous layers were back-extracted with ethyl acetate (10 mL), and the combined organic portions were dried ($MgSO_4$) and then concentrated under reduced pressure to provide a yellow solid. Flash column chromatography (90:8:2 to 70:28:2 hexane-Ethyl acetate-$Et_3N$) afforded 1.32 g (38%) of [4-(bis-tert-butoxycarbonyl-L-histidyl)-2-phenylbenzoyl methionine methyl ester; $^1H$ NMR ($CDCl_3$) δ 1.41 (s, 9H), 1.58 (s, 9H), 1.61–1.78 (m, 1H), 1.83–1.95 (m, 1H), 1.98 (s, 3H), 2.04–2.13 (comp, 2H), 2.99 (dd, 1H), 3.18 (dd, 1H), 3.63 (s, 3H), 4.50–4.92 (comp, 2H), 5.84 (d, 1H), 6.32 (d, 1H), 7.21 (s, 1H), 7.30–7.42 (comp, 5H), 7.45 (m, 1H), 7.68 (d, 1H), 8.02 (s, 1H), 9.63 (br, 1H). LRMS (CI): 696 $(M+1)^+$.

EXAMPLE 184B

[4-(L-Histidyl)-2-phenylbenzoyl]methionine Methyl Ester Hydrochloride

[4-(bis-tert-butoxycarbonyl-L-histidyl)-2-phenylbenzoyl methionine methyl ester (0.992 g, 1.42 mmol), prepared as in Example 184A, was dissolved in 4 M HCl/dioxane (15 mL), upon which gas evolution was observed. The clear amber solution was stirred for 6 hours, during which time a white precipitate formed. The mixture was treated with ethyl ether and the precipitate was isolated by filtration to provide 0.779 g (100%) of [4-(L-histidyl)-2-phenylbenzoyl methionine methyl ester (believed to be the mono-hydrochloride salt); $^1$H NMR ($CD_3OD$) δ 1.72–1.87 (m, 1H), 1.95–2.03 (comp, 4H), 2.08–2.28 (comp, 2H), 3.38–3.60 (comp, 2H), 3.67 (s, 3H), 4.45–4.57 (comp, 2H), 7.30–7.46 (comp, 6H), 7.53 (d, 1H), 7.69 (d, 1H), 7.77 (app s, 1H), 8.90 (s, 1H). LRMS (CI): 496 $(M+1)^+$.

EXAMPLE 184C

[4-(L-Histidyl)-2-phenylbenzoyl]methionine Hydrochloride

To a solution of [4-(L-histidyl)-2-phenylbenzoyl methionine methyl ester hydrochloride (98.9 mg, 0.200 mmol), prepared as in Example 184B, in THF/$H_2O$ (4:1, 20 mL) was added LiOH.$H_2O$ (68.5 mg, 1.60 mmol). The solution was stirred for 6 hours and then was treated with 1 M aqueous HCl (20 mL). The mixture was lyopholized to provide a white solid. Recrystallization from methanol afforded [4-(L-histidyl)-2-phenylbenzoyl]methionine hydrochloride (31 mg, 32%) as a white solid. $^1$H NMR ($D_2O$) δ 1.68–1.82 (m, 1H), 1.88–1.99 (comp, 2H), 2.02 (s, 3H), 2.00–2.12 (m, 1H), 3.28–3.32 (m, 2H), 3.49 (d, 2H), 4.28–4.34 (m, 1H), 4.44 (t, 1H), 7.36–7.53 (comp, 8H), 7.57 (m, 1H), 8.67 (m, 1H); LRMS (CI): 482 $(M+1)^+$, 701.

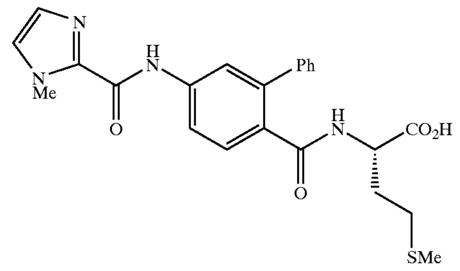

EXAMPLE 186

[4-(1H-1-Methylimidazol-2-ylcarboxyamino)-2-phenylbenzoyl]methionine

EXAMPLE 186A

[1-Ethoxy-2-(1-methyl-1H-imidazol-2-yl)ethenyl] carbonic Acid Ethyl Ester

Triethylamine (10.2 g, 100.0 mmol) was added to a solution of 1,2-dimethylimidazole (2.45 g, 25.0 mmol) in acetonitrile (25 mL) at 0° C. Ethyl chloroformate (6.15 g, 55.0 mmol) was added dropwise (1 drop/sec) and the reaction mixture was slowly warmed to ambient temperature. After 4 hours, the reaction mixture was concentrated under reduced pressure, and the residue was treated with 1:1 sat'd aqueous $NaHCO_3/H_2O$ (25 mL). The mixture was extracted with dichloromethane (4×25 mL), and the organic extracts were rinsed with brine (25 mL), dried over $MgSO_4$, filtered, and concentrated under reduced pressure to provide an amber oil. Flash column chromatography (ethyl acetate:$CH_2Cl_2$:Methanol:$HCO_2H$; 40:40:18:2 to 30:30:38:2) afforded 3.13 g (13%) of a 3:1 mixture of formic acid and the desired compound. $^1$H NMR ($CDCl_3$) δ 1.2–1.6 (br, 6H), 3.7–3.9 (br, 3H), 4.2–4.6 (br, 4H), 7.1 (br, 1H), 7.3 (br, 1H), 8.2 (br), 10.8 (br). LRMS (CI): 241 $(M+1)^+$, 169 $(54318\text{–}148C+1)^+$.

EXAMPLE 186B (1H-1-Methylimidazol-2-yl)acetic Acid

The formic acid contaminated material prepared in Example 186A (3.13 g, ca 3.50 mmol) from above was dissolved in 3 M aqueous HBr (30 mL). The solution was heated to reflux for 30 hours, after which lyopholization afforded 0.783 g (ca 100%) of (1H-1-methylimidazol-2-yl) acetic acid. $^1$H NMR ($CD_3OD$) δ 3.40 (s, 3H), 5.38 (s, 3H), 7.32–7.36 (comp, 2H), 7.41–7.46 (comp, 3H), 7.76–7.78 (m, 1H), 7.78–7.80 (m, 1H), 7.87 (d, J=8.8 Hz, 1H). LRMS (CI): 304 $(M+18)^+$, 287 $(M+1)^+$.

EXAMPLE 186C

[4-(1H-Methylimidazol-2-ylcarboxyamino)-2-phenylbenzoyl]methionine Methyl Ester

Triethylamine (1.23 g, 12.0 mmol) was added dropwise to a solution of [4-amino-2-phenylbenzoyl]methionine, methyl ester hydrochloride (Compound 8, 1.00 g, 2.03 mmol), (1H-1-methylimidazol-2-yl)acetic acid (0.783 g, 3.54 mmol), prepared as in Example 186B, 3-hydroxy-1,2,3-benzotriazin-4(3H)-one (1.06 g, 6.37 mmol), and 1-(3-dimethylaminopropyl)-3-ethylcarbodiimide (1.25 g, 6.37 mmol) in DMF (35 mL). The reaction mixture was stirred at ambient temperature for 16 hours and then concentrated under reduced pressure (50° C., 0.1 mm Hg) to provide an amber oil. Flash column chromatography (ethyl acetate:$CH_2Cl_2$:Methanol:$HCO_2H$ 30:30:38:2), followed by a second chromatography (ethyl acetate:$HCO_2H$ 92:2) afforded 0.891 g (52%) of a ca 1:1 mixture of triethylamine hydrochloride and the desired compound. $^1$H NMR ($CDCl_3$) δ 1.05–1.35 (t, 9H of TEA.HCl), 1.80–1.92 (m, 1H), 1.94–2.08 (comp, 4H), 2.12–2.22 (m, 1H), 2.22–2.37 (m, 1H), 3.10–3.24 (comp, 6 H of TEA.HCl+?), 3.72 (s, 2H), 3.91 (s, 3H), 4.50–4.61 (m, 1H), 7.33–7.45 (comp, 7H), 7.46 (d, 1H), 7.64–7.70 (comp, 2H). Note $^1$H spectrum poorly resolved such that assignments uncertain. LRMS (CI): 481 $(M+1)^+$.

EXAMPLE 186D

[4-(1H-1-Methylimidazol-2-ylcarboxyamino)-2-phenylbenzoyl]methionine

Lithium hydroxide hydrate (1.71 g, 40.0 mmol) was added to a solution of the triethylamine hydrochloride contaminated methyl ester prepared in Example 186C (0.891 g, 1.00 mmol) in THF/$H_2O$ (4:1, 50 mL). The solution was stirred for 5 hours and then extracted with pentane (40 mL then 20 mL). The mixture was carefully acidified by the addition of 3 M aqueous HCl and then lyopholized. Flash column chromatography (ethyl acetate:$CH_2Cl_2$:Methanol:$HCO_2H$ (30:30:39:1)) followed by filtration of the concentrate through celite with methanol rinses afforded 0.080 g (ca 9%) of a 4:1 mixture of $HCO_2H$ and [4-(1H-1-methylimidazol-2-ylcarboxyamino)-2-phenylbenzoyl]methionine. $^1$H NMR ($CD_3OD$): δ 1.2–1.5 (small amount unidentified impurity), 1.8–1.9 (br m, 1H), 1.9–2.1 (br, comp 5H), 2.1–2.3 (br m, 1H), 3.6–4.0 (br m, 2H), 4.0 (s, 3H), 4.4–4.5 (br, m, 1H), 7.3–7.5 (br comp, 6H), 7.5–7.6 (br comp, 2H), 7.6–7.8 (br m, 2H). LRMS (CI): 467 $(M+1)^+$.

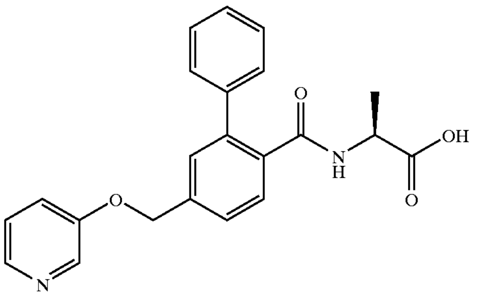

EXAMPLE 187

[4-(3-Pyridyloxymethyl)-2-phenylbenzoyl]alanine

EXAMPLE 187A

4-Chloromethyl-2-phenylbenzoic Acid Methyl Ester

To a solution of 10.5 g (43.3 mmol) of methyl 4-hydroxymethyl-2-phenylbenzoate in 50 mL of N,N-dimethylformamide was added 4.5 mL (62 mmol) of thionyl chloride, and 2.0 g (47 mmol) of lithium chloride. The reaction was complete upon dissolution of the lithium chloride. The solution was poured into 350 mL of water, then extracted with diethyl ether (3×100 mL). The combined diethyl ether layers were back extracted with water (2×100 mL), saturated aqueous sodium bicarbonate solution (1×100 mL), and brine (1×100 mL), dried over magnesium sulfate, filtered, and concentrated in vacuo to 11.1 g (98%) of 4-chloromethyl-2-phenylbenzoic acid methyl ester as a pale yellow oil.

EXAMPLE 187B 4-(3-Pyridyloxymethyl)-2-phenylbenzoic Acid Methyl Ester

To a solution of 11.1 g (42.3 mmol) of 4-chloromethyl-2-phenylbenzoic acid methyl ester, prepared as in Example 187A, in 150 mL of toluene was added 1.7 g (6.4 mmol) of 18-Crown-6, and 8.40 g (63.1 mmol) of 3-hydroxypyridine, potassium salt. The reaction was stirred at ambient temperature for 20 minutes, then heated to reflux under $N_2$. After 3 hours, the mixture was poured into 100 mL of water. The layers were separated, then the aqueous layer was extracted with ethyl acetate (3×100 mL). The combined organic layers were back extracted with 2M aqueous NaOH (2×30 mL), brine (1×100 mL), dried over magnesium sulfate, filtered, and concentrated to an oil which slowly crystallized. The product was recrystallized from 50 mL of 2-propanol to give 6.78 g of a tan solid. The supernatant was concentrated and purified via silica gel chromatography (50:50 hexanes:ethyl acetate) to give another 2.18 g of product, for a total yield of 8.96 g (66%). $^1$H NMR (300 MHz, d6-DMSO) δ 3.60 (s, 3H), 5.33 (s, 2H), 7.28–7.54 (m, 8H), 7.57 (dd, J=1.5, 9.0 Hz, 1H), 7.78 (d, J=9 Hz, 1H), 8.18 (dd, J=1.0, 5.5 Hz, 1H), 8.38 (d, J=3.0 Hz, 1H).

EXAMPLE 187C 4-(3-Pyridyloxymethyl)-2-phenylbenzoic Acid

To 2.60 g (8.14 mmol) of 4-(3-pyridyloxymethyl)-2-phenylbenzoic acid methyl ester, prepared as in Example 187B, was added 15 mL of methanol, and a solution of 0.79 g (12 mmol) of 85% KOH in 3 mL of water. The mixture was stirred at reflux for 3 hours, then concentrated in vacuo. The residue was taken up in 5 mL of water and treated with 12 mL of 1M aqueous HCl. The precipitated product was filtered and washed with a small amount of water. The combined washings and filtrate were adjusted to pH 4 with 1M HCl, and additional precipitate was collected, then washed with water. The combined precipitates were dried in vacuo to give 4-(3-pyridyloxymethyl)-2-phenylbenzoic acid (2.48 g, 99%) as an off-white powder. $^1$H NMR (300 MHz, d6-DMSO) δ 5.31 (s, 2H), 7.31–7.56 (m, 9H), 7.76 (d, J=7.5 Hz, 1H), 8.19 (dd, J=1.0, 6.0 Hz, 1H), 8.39 (d, J=3.0 Hz, 1H), 12.8 (br s, 1H).

EXAMPLE 187D

[4-(3-Pyridyloxymethyl)-2-phenylbenzoyl]alanine Methyl Ester

To a solution of 100 mg (0.33 mmol) of 4-(3-pyridyloxymethyl)-2-phenylbenzoic acid, L-alanine methyl ester hydrochloride (1.5 mmol), 69 mg (0.36 mmol) of 1-(3-dimethylaminopropyl)-3-ethylcarbodiimide hydrochloride, and 59 mg (0.36 mmol) of 3-hydroxy1,2,3-benzotriazin-4(3H)-one in 1 mL of N,N-dimethylformamide was added 5 drops of triethylamine. The mixture was stirred at ambient temperature for 24 hours, then poured into 10 mL of 0.6M aqueous sodium bicarbonate and extracted with ethyl acetate (3×5 mL). The combined ethyl acetate layers were back extracted with water (2×5 mL), then brine (1×5 mL), dried over magnesium sulfate, filtered, and concentrated in vacuo. The product was purified via chromatography over silica gel, eluting with an appropriate mixture of hexanes and ethyl acetate.

EXAMPLE 187E

[4-(3-Pyridyloxymethyl)-2-phenylbenzoyl]alanine

To approximately 0.3 mmol of [4-(3-pyridyloxymethyl)-2-phenylbenzoyl]alanine methyl ester, prepared as in Example 187D, was added 1 mL of 1.39M NaOH in 5:1 methanol: water. The mixture was heated to reflux for 20 minutes, then 1 mL of water, 1.4 mL of 1M aqueous HCl, and 5 mL of ethyl acetate were added sequentially. The biphasic mixture was stirred, then separated, and the aqueous layer was extracted with additional ethyl acetate (2×5 mL). The combined ethyl acetate layers were dried over magnesium sulfate, filtered, and concentrated to give 4-(3-pyridyloxymethyl)-2-phenylbenzoyl-L-alanine as a foam. $^1$H NMR (300 MHz, d6-DMSO) δ 1.11 (d, J=7.1 Hz, 3H), 4.14 (quintet, J=7.3 Hz, 1H), 5.21 (s, 2H), 7.22–7.45 (m, 1H), 8.10 (d, J=4.1 Hz, 1H), 8.29 (d, J=1.7 Hz, 1H), 8.46 (d, J=7.5 Hz, 1H), 12.42 (br s, 1H); MS (DCI) m/e 377 $(M+H)^+$, 394 $(M+NH)^+$. Anal calcd for $C_{22}H_{20}N_2O_4$.0.15HCl: C, 69.19; H, 5.32; N, 7.34. Found: C, 69.22; H, 5.01; N, 7.07.

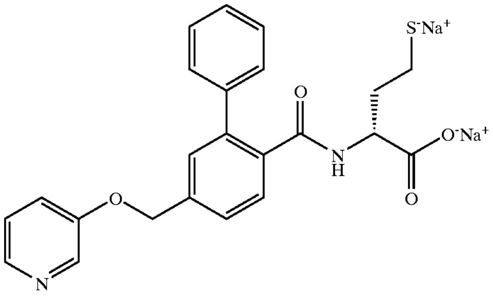

EXAMPLE 188

[4-(3-Pyridyloxymethyl)-2-phenylbenzoyl]cysteine Disodium Salt

EXAMPLE 188A

[4-(3-Pyridyloxymethyl)-2-phenylbenzoyl] homocysteine Thiolactone

The desired compound was prepared according to the method of Example 187D, except substituting DL homocysteine thiolactone hydrochloride for L-alanine methyl ester hydrochloride.

EXAMPLE 188B

[4-(3-Pyridyloxymethyl)-2-phenylbenzoyl]cysteine Disodium Salt

To 51 mg (0.13 mmol) of [4-(3-pyridyloxymethyl)-2-phenylbenzoyl]homocysteine thiolactone, prepared as in Example 188A, was added 1 mL of 0.25 M NaOH in 9:1 methanol:water. The mixture was heated at reflux for 1 hour, then concentrated in vacuo to a white solid. $^1$H NMR (300 MHz, d6-DMSO) δ 1.68–1.95 (m, 2H), 2.05–2.42 (m, 2H), 3.80–3.95 (m, 1H), 5.27 (s, 2H), 7.28–7.49 (m, 1H), 8.18 (dd, J=1.2, 4.6 Hz, 1H), 8.38 (d, J=2.7 Hz, 1H); MS (DCI) m/e 405 (—$H_2O$). Anal calcd for $C_{23}H_{20}N_2O_4SNa_2$.1.35$H_2O$: C, 56.29; H, 4.66; N; 5.71. Found: C, 56.33; H, 4.84; N, 5.55.

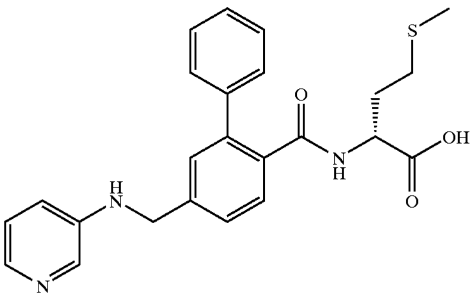

EXAMPLE 189

[4-(3-Pyridylaminomethyl)-2-phenylbenzoyl] methionine

EXAMPLE 189A

[4-(3-Pyridylaminomethyl)-2-phenylbenzoic Acid Methyl Ester

To a solution of 1.72 g (7.16 mmol) of 4-methoxycarbonyl-3-phenylbenzaldehyde in 21 mL of methanol was added 7 mL of glacial acetic acid, the 875 mg (9.31 mmol) of 3-aminopyridine. The solution was stirred at ambient temperature for 1 hour, then cooled with an ice bath. Next, 750 mg (11.9 mmol) of sodium cyanoborohydride was added in small portions, keeping the ensuing bubbling under control. After 30 minutes, the ice bath was removed, and the reaction was stirred for 18 hours at ambient temperature. The reaction was concentrated in vacuo, then the residue was taken up in 75 mL of water and extracted with ethyl acetate (2x35 mL). The combined ethyl acetate layers were back extracted with saturated aqueous sodium bicarbonate solution (2x35 mL), then brine (1x35 mL), dried over magnesium sulfate, filtered, and concentrated to an oil. Purification via silica gel chromatography(ethyl acetate) provided 4-(3-pyridylamionomethyl)-2-phenylbenzoic acid methyl ester (2.10 g, 92%) as a colorless oil.

EXAMPLE 189B

[4-(3-Pyridylaminomethyl)-2-phenylbenzoyl] methionine

The desired compound was prepared according to the method of Example 187, steps C, D and E, except substituting 4-(3-pyridylamionomethyl)-2-phenylbenzoic acid methyl ester, prepared as in Example 189A, for [4-(3-pyridyloxymethyl)-2-phenylbenzoylalanine methyl ester, and substituting D-methionine methyl ester hydrochloride for L-alanine methyl ester hydrochloride. $^1$H NMR (300 MHz, d6-DMSO) δ 1.75–1.91 (m, 2H), 1.98 (s, 3H), 2.16–2.27 (m, 2H), 4.27 (m, 1H), 4.39 (d, J=6.4 Hz, 2H), 6.62 (t, J=6.4 Hz, 1H), 7.40 (ddd, J=1.4, 2.7, 8.5 Hz, 1H), 7.03 (dd, J=4.6, 8.3 Hz, 1H), 7.30–7.41 (m, 8H), 7.40 (d, J=4.1 Hz, 1H), 7.97 (d, J=2.7 Hz, 1H), 8.50 (d, J=7.8 Hz, 1H), 12.65 (br s, 1H); MS (DCI) m/e 436 $(M+H)^+$. Anal calcd for $C_{24}H_{25}N_3O_3S$.0.9O$H_2O$: C, 63.81; H, 5.98; N, 9.30. Found: C, 63.82; H, 5.61; N, 9.16.

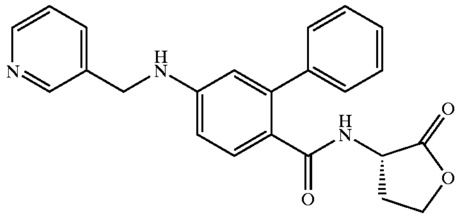

EXAMPLE 190

[4-(3-Pyridylmethylamino)-2-phenylbenzoyl] homoserine Lactone

EXAMPLE 190A

4-Amino-2-phenylbenzoic Acid Hydrochloride

4-Nitro-2-phenylbenzoic acid (10.5 g, 43.2 mmol) and tin(II) chloride dihydrate (34.1 g, 0.15 mol) were combined and refluxed in 250 mL ethyl acetate for 1 hour. An equal volume of water was added followed by solid $NaHCO_3$ to pH 8. The mixture was extracted with ethyl acetate. The combined ethyl acetate extracts were washed with brine and concentrated to a thick oil. The oil was diluted with ether and excess anhydrous HCl was added. The resulting precipitate was collected and dried to provide 4-Amino-2-phenylbenzoic acid hydrochloride (3.2 g). MS m/e 214 $(M+H)^+$. $^1$H NMR (d6-DMSO, 300 MHz) δ 6.65 (d, J=3 Hz, 1H), 6.79 (m, 1H), 7.20–7.72 (m, 6H).

EXAMPLE 190B 4-(3-Pyridylmethylamino)-2-phenylbenzoic Acid Acetic Acid Salt

3-Pyridinecarboxaldehyde (1.2 mL, 12.8 mmol) and 4-amino-2-phenylbenzoic acid hydrochloride (3.2 g, 12.8 mmol), prepared in Example 190A, were dissolved in 100 mL 1% acetic acid in methanol. After stirring for 10 minutes, $NaBH_3CN$ was added, and stirring was continued for 18 hours. The reaction was evaporated to dryness under reduced pressure and partitioned between ethyl acetate and water. The aqueous phase was extracted with ethyl acetate. The organic extracts were combined, washed with brine, and dried over $Na_2SO_4$ to give 4-(3-Pyridylmethylamino)-2-phenylbenzoic acid acetic acid salt (4.35 g, 90%) of the title compound. MS m/e 305 $(M+H)^+$. $^1H$ NMR ($d_6$-DMSO, 300 MHz) δ 4.41 (s, 2H), 6.45 (d, J=3 Hz, 1H), 6.60 (m, 1H), 7.15–7.90 (m, 10H), 8.48 (m, 1H), 8.60 (m, 1H).

EXAMPLE 190C 4-(3-Pyridylmethylamino)-2-phenylbenzoyl] homoserine Lactone 4-(3-Pyridylmethylamino)-2-phenylbenzoic acid acetic acid salt (0.20.g, 0.55 mmol), prepared as in Example 190B, and L-homoserine lactone (0.19 g, 1.37 mmol), 1-(3-dimethylaminopropyl)-3-ethylcarbodiimide hydrochloride (0.27 g, 1.43 mmol), and 3-hydroxyl1,2,3-benzotriazin-4 (3H)-one (0.25 g, 1.65 mmol) were combined in 10 mL DMF. Triethylamine (1.65 mmol) was added, and the reaction was stirred overnight at room temperature. The reaction mixture was diluted with HCl (1 M, 10 mL) and extracted with ethyl acetate. Solid $NaHCO_3$ was added to pH 8. The aqueous was extracted with ethyl acetate. The combined extracts were washed with brine and dried over $Na_2SO_4$. Flash chromatography (2% Methanol in ethyl acetate to 4% Methanol in ethyl acetate) provided [4-(3-pyridylmethylamino)-2-phenylbenzoyl]homoserine lactone (140 mg). MS m/e 436 $(M+H)^+$. $^1H$ NMR ($CDCl_3$, 300 MHz) δ 1.73 (m, 2H), 2.65 (m, 2H), 4.1–4.5 (m, 2H), 5.52 (m, 1H), 6.51 (d, J=3 Hz, 1H), 6.65 (m, 1H), 7.25–7.44 (m, 8H), 7.49 (m, 2H), 8.56 (m, 1H), 8.63 (d, J=3 Hz, 1H).

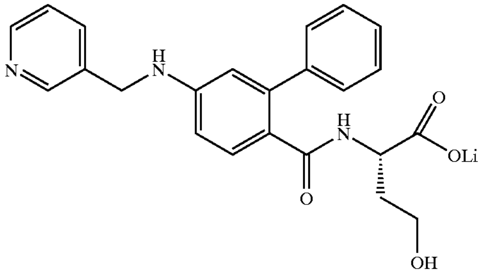

EXAMPLE 191

Lithium 4-(3-Pyridylmethylamino)-2-phenylbenzoyl-L-homoserinate

[4-(3-Pyridylmethylamino)-2-phenylbenzoyl]homoserine lactone (55 mg, 0.14 mmol), prepared as in Example 190, was dissolved in 1 mL of methanol and treated with aqueous 1.0 M LiOH (0.15 mmol). After 18 hours at ambient temperature, the mixture was evaporated to provide the title compound in quantitative yield. $^1H$ NMR ($d_6$-DMSO, 300 MHz) δ 1.43 (m, 1H), 1.60 (m, 1H), 3.59 (m, 1H), 4.1 (m, 1H), 4.38 (m, 2H), 6.33 (m, 1H), 6.6 (m, 2H), 6.83 (m, 1H), 7.22–7.38 (m, 8H), 7.74 (m, 2H), 8.45 (m, 1H), 8.59 (d, J=3 Hz, 1H).

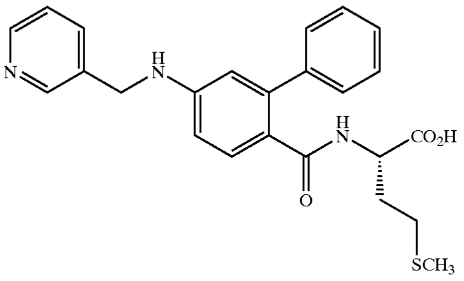

EXAMPLE 192

[4-(3-Pyridylmethylamino)-2-phenylbenzoyl] methionine

EXAMPLE 192A (4-Nitro-2-phenylbenzoyl)methionine Methyl Ester

4-Nitro-2-phenylbenzoic acid (50.0 g, 205 mmol) and 3-hydroxyl1,2,3-benzotriazin-4(3H)-one (36.89 g, 226 mmol) were dissolved in 500 mL DMF. 1-(3-dimethylaminopropyl)-3-ethylcarbodiimide hydrochloride (47.3 g, 247 mmol) and methionine methyl ester hydrochloride (53.37 g, 267 mmol) were added followed by triethylamine (31.5 mL, 226 mmol). Additional triethylamine was added to raise the pH to 6~7. After 1 hour at ambient temperature, the reaction mixture was concentrated to 200 mL, diluted with 500 mL ethyl acetate, washed with 1 M HCl, 5% $NaHCO_3$, and brine, and dried over $Na_2SO_4$ to provide (4-nitro-2-phenylbenzoyl)methionine methyl ester which was used directly without further purification. MS m/e 389 $(M+H)^+$. $^1H$ NMR ($CDCl_3$, 300 MHz) δ 1.78 (m, 2H), 2.01 (s, 3H), 2.60 (m, 2H), 3.69 (s, 3H), 4.69 (m, 1H), 6.02 (d, J=8 Hz, 1H), 7.48,(m, 5H), 7.85 (m, 1H), 8.27 (m, 2H).

EXAMPLE 192B (4-Amino-2-phenylbenzoyl)methionine Methyl Ester Hydrochloride

Tin(II) dichloride dihydrate (157 g, 696 mmol) was added to a solution of (4-nitro-2-phenylbenzoyl)methionine methyl ester (67.9 g, 175 mmol) in 500 mL ethyl acetate and the reaction mixture was heated at reflux for 1 hour. The reaction mixture was cooled to ambient temperature and stirring was continuted for 18 hours. The reaction mixture was concentrated to 200 mL, and 500 mL $H_2O$ was added. Solid $NaHCO_3$ was added to pH 8 before extracting with ethyl acetate. The ethyl acetate extract were washed with 5% $NaHCO_3$ and brine, dried over $Na_2SO_4$, and concentrated. The residue was dissolved in ether with a minimum of ethyl acetate added to keep the material in solution and treated with anhydrous HCl. The solid was collected and washed with ether to provide (4-amino-2-phenylbenzoyl)methionine methyl ester hydrochloride in 83% yield. MS m/e 359 $(M+H)^+$. $^1H$ NMR ($d_6$-DMSO, 300 MHz) δ 1.83 (m, 2H), 1.99 (s, 3H), 2.23 (m, 2H), 3.63 (s, 3H), 4.33 (m, 1H), 7.03 (m, 2H), 7.35 (m, 6H), 7.48 (d, J=8 Hz, 1H).

EXAMPLE 192C

[4-(3-Pyridylmethylamino)-2-phenylbenzoyl] methionine Methyl Ester (4-Amino-2-phenylbenzoyl)methionine methyl ester hydrochloride (5.0 g, 12.7 mmol), prepared as in Example 192B, and 3-pyridinecarboxaldehyde (1.25 mL, 13.3 mmol) were dissolved in 100 mL 1% acetic acid in methanol. After 10 minutes, sodium cyanoborohydride (0.95 g, 15.9 mmol) was added. After stirring at room temperature 18 hours, the reaction mixture was evaporated and partitioned between 5% $NaHCO_3$ and ethyl acetate. The organic layer was washed with 5% $NaHCO_3$ and brine, dried over $Na_2SO_4$, and evaporated to provide [4-(3-pyridylmethylamino)-2-phenylbenzoyl]methionine methyl ester which was used without further purification. MS m/e 450 $(M+H)^+$. $^1H$ NMR ($CDCl_3$, 300 MHz) δ 1.65 (m, 2H), 1.87 (m, 2H), 2.00 (s, 3H), 3.63 (s, 4H), 4.42 (s, 2H), 4.61 (m, 1H), 5.69 (d, J=7 Hz, 1H), 6.50 (d, J=3 Hz, 1H), 6.63 (m, 1H), 7.45 (m, 6H), 7.68 (m, 2H), 8.55 (m, 1H), 8.62 (d, J=3 Hz, 1H).

EXAMPLE 192D

[4-(3-Pridylmethylamino-2-phenylbenzoyl]methionine

Excess LiOH (3 M) was added to a solution in methanol of [4-(3-pyridylmethylamino)-2-phenylbenzoyl]methionine methyl ester (5.69 g, 12.7 mmol), prepared as in Example 192C and the reaction mixture was stirred at ambient temperature for 72 hours. The reaction mixture was concentrated and partitioned between ether and water. The aqueous layer was washed with ether, acidified to pH 4~5 with HCl, and extracted with ethyl acetate. The combined ethyl acetate extracts were washed with brine and dried over $Na_2SO_4$ to give the title compound in 98% yield. MS m/e 436 $(M+H)^+$. $^1H$ NMR ($d_6$-DMSO, 300 MHz) δ 1.91 (m, 2H), 1.99 (s, 3H), 2.22 (m, 2H), 3.36 (bs, 1H), 4.11 (m, 1H), 4.40 (s, 2H), 6.57 (m, 2H), 6.75 (bs, 1H), 7.3 (m, 6H), 7.79 (m, 1H), 7.99 (m, 1H), 8.46 (m, 1H), 8.30 (d, J=3 Hz, 1H), 12.48 (bs, 1H).

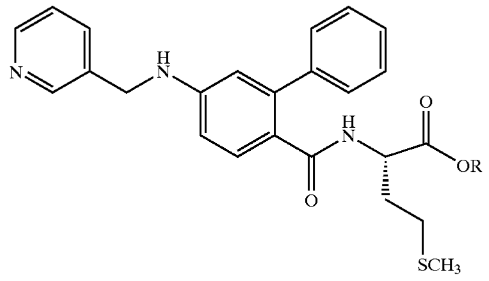

EXAMPLES 193–195

EXAMPLE 193

[4-(3-Pyridylmethylamino)-2-phenylbenzoyl]methionine Isoamyl Ester

[4-(3-pyridylmethylamino)-2-phenylbenzoyl]methionine (200 mg, 0.46 mmol), prepared as in Example 192, carbonyldiimidazole (74 mg, 0.46 mmol), and isoamyl alcohol (40 mg, 0.46 mmol) were combined in 10 mL THF. After 2 hours at room temperature, sodium ethoxide (2.68 M in ethanol, 0.02 mmol) was added. After an additional 18 hours, the mixture was evaporated to dryness, partitioned between ethyl acetate and water, washed with water and brine, dried over $Na_2SO_4$, and chromatographed (Ethyl acetate) to give [4-(3-pyridylmethylamino)-2-phenylbenzoyl-L-methionine isoamyl ester (90 mg). MS m/e 506 $(M+H)^+$. $^1H$ NMR ($CDCl_3$, 300 MHz) δ 0.90 (d, J=7 Hz, 6H), 1.48 (m, 2H), 1.64 (m, 4H), 1.88 (m, 1H), 2.01 (s, 3H), 2.11 (t, J=7 Hz, 2H), 4.08 (m, 2H), 4.42 (s, 2H), 4.60 (m, 1H), 5.87 (d, J=8 Hz, 1H), 6.51 (d, J=3 Hz, 1H), 6.63 (m, 1H), 7.28–7.44 (m, 5H), 7.68 (m, 2H), 8.55 (m, 1H), 8.63 (s, 1H).

EXAMPLE 194

[4-(3-Pyridylmethylamino)-2-phenylbenzoyl]methionine 1-Adamantylethyl Ester

The desired compound was prepared according to the method of Example 193, except substituting 2-adamantaneethanol for isoamyl alcohol. MS m/e 598 $(M+H)^+$. $^1H$ NMR ($CDCl_3$, 300 MHz) δ 1.6 (m, 17H), 1.94 (m, 2H), 2.01 (s, 3H), 2.10 (m, 2H), 4.09 (m, 2H), 4.40 (m, 2H), 4.59 (m, 1H), 5.72 (d, J=7 Hz, 1H), 6.51 (d, J=3 Hz, 1H), 6.63 (m, 1H), 7.3 (m, 8H), 7.68 (m, 1H), 8.60 (m, 2H).

EXAMPLE 195

[4-(3-Pyridylmethylamino)-2-phenylbenzoyl]methionine Octyl Ester

The desired compound was prepared according to the method of Example 193, except substituting octanol for isoamyl alcohol. MS m/e 548 $(M+H)^+$. $^1H$ NMR ($CDCl_3$, 300 MHz) δ 0.88 (t, J=7 Hz, 3H), 1.28 (m, 10H), 1.6 (m, 2H), 2.01 (s, 3H), 2.10 (m, 2H), 4.02 (m, 2H), 4.4 (m, 2H), 4.61 (m, 1H), 5.71 (d, J=7 Hz, 1H), 6.50 (d, J=3 Hz, 1H), 6.63 (m, 1H), 7.39 (m, 9H), 7.68 (m, 2H), 8.55 (m, 1H), 8.63 (m, 1H).

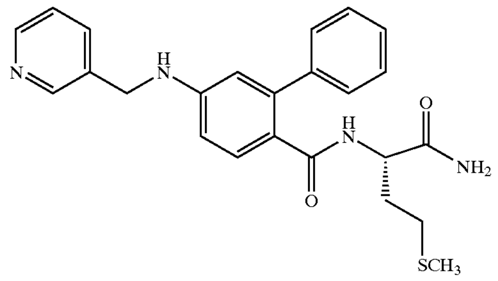

EXAMPLE 196

[4-(3-Pyridylmethylamino)-2-phenylbenzoyl]methionineamide

[4-(3-pyridylmethylamino)-2-phenylbenzoyl]methionine methyl ester (80 mg, 0.18 mmol), prepared as in Example 192C, was dissolved in methanol (5 mL), cooled to 0° C., and the solution was saturated with anhydrous ammonia. The reaction was sealed for 72 hours at ambient temperature. Evaporation to dryness afforded [4-(3-pyridylmethylamino)-2-phenylbenzoyl]methionineamide (78 mg). MS m/e 435 $(M+H)^+$. $^1H$ NMR ($CDCl_3$, 300 MHz) δ 1.59 (m, 2H), 1.83 (m, 2H), 2.02 (s, 3H), 4.43 (s, 2H), 4.51 (m, 1H), 5.16 (s, 1H), 5.64 (m, 1H), 6.14 (m, 1H), 6.50 (d, J=3 Hz, 1H), 6.63 (m, 1H), 7.38 (m, 7H), 7.66 (m, 2H), 8.55 (m, 1H), 8.62 (m, 1H).

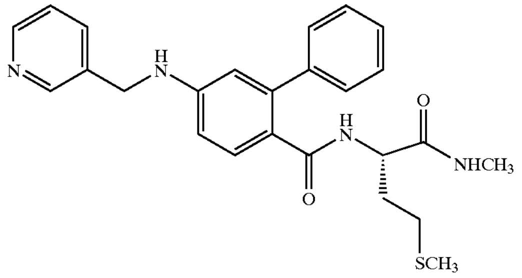

EXAMPLE 197

[4-(3-Pyridylmethylamino)-2-phenylbenzoyl]methioninemethylamide

[4-(3-pyridylmethylamino)-2-phenylbenzoyl]methionine methyl ester (370 mg, 0.82 mmol), prepared as in Example 192C, was dissolved in THF (5 mL) and saturated with anhydrous methylamine. The reaction was sealed and heated at 75° C. for 24 hours. The reaction mixture was evaporated to dryness and chromatographed (5% methanol-ethyl acetate) to give [4-(3-pyridylmethylamino)-2-phenylbenzoyl]methioninemethylamide (111 mg). MS m/e 449 $(M+H)^+$. $^1H$ NMR ($CDCl_3$, 300 MHz) δ 1.80 (m, 2H), 2.02 (s, 3H), 2.12 (m, 2H), 2.70 (d, J=5 Hz, 3H), 4.45 (m, 3H), 5.65 (d, J=8 Hz, 1H), 6.10 (m, 1H), 6.50 (d, J=3 Hz, 1H), 6.63 (m, 1H), 7.38 (m, 7H), 7.66 (m, 2H), 8.59 (m, 2H).

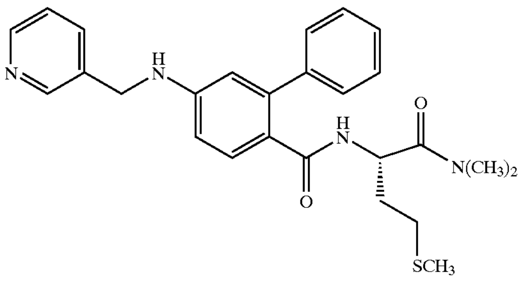

EXAMPLE 198

[4-(3-Pyridylmethylamino)-2-phenylbenzoyl]methioninedimethylamide

[4-(3-pyridylmethylamino)-2-phenylbenzoyl]methionine methyl ester (340 mg, 0.76 mmol), prepared as in Example 192C, was dissolved in THF (5 mL) and saturated with anhydrous dimethylamine. The reaction was sealed and heated at 60° C. for 72 hours. The reaction mixture was evaporated to dryness and chromatographed (5% methanol-ethyl acetate) to give [4-(3-pyridylmethylamino)-2-phenylbenzoyl]methioninedimethylamide (40 mg). MS m/e 463 $(M+H)^+$. $^1H$ NMR ($CDCl_3$, 300 MHz) δ 1.71 (m, 2H), 2.05 (s, 3H), 2.21 (m, 2H), 2.87 (s, 3H), 3.06 (s, 3H), 4.11 (m, 1H), 4.43 (s, 2H), 5.02 (m, 1H), 6.01 (d, J=8 Hz, 1H), 6.50 (d, J=3 Hz, 1H), 6.61 (m, 1H), 7.38 (m, 7H), 7.59 (d, J=9 Hz, 1H), 7.72 (d, J=9 Hz, 1H), 8.63 (bs, 1H).

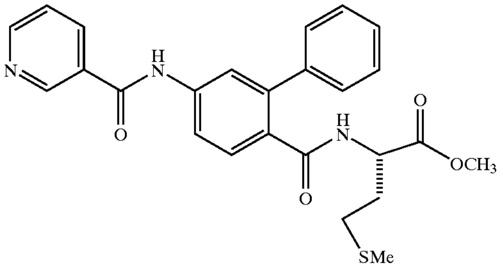

EXAMPLE 199

[4-(3-Pyridylcarbonylamino)-2-phenylbenzoyl]methionine Methyl Ester

Nicotinic acid (345 mg, 2.8 mmol) was suspended in 10 mL of dichloromethane and oxalyl chloride (2.8 mL of a 2.0 M soln in methylene chloride) was added by syringe followed by one drop of DMF. The reaction mixture was stirred at 25° C. for 2 hours and then was evaporated and azeotroped with toluene. The resulting acid chloride was then dissolved in dichloromethane and a solution of (4-amino-2-phenylbenzoyl)methionine methyl ester (669 mg, 1.87 mmol), prepared as in Example 192B, in 5 mL of dichloromethane was added followed by 4 mL of saturated aqeuous $NaHCO_3$ and the reaction was stirred at 25° C. for 3 hours. The layers were separated and the organic layer was dried over $Na_2SO_4$, filtered and evaporated to give 830 mg (96%) of [4-(3-pyridylcarbonylamino)-2-phenylbenzoyl]methionine methyl ester as an oil. $^1H$ NMR (300 mHz, $CDCl_3$) δ 9.2 (d, 1H), 8.76 (d, 1H), 8.42 (bs, 1H), 8.2 (dt, 1H), 7.72–7.65 (m, 2H), 7.6 (dd, 1H), 7.45–7.35 (m, 5H), 6.02 (bd, 1H), 4.65 (dq, 1H), 3.68 (s, 3H), 2.20 (t, 2H), 2.01 (s, 3H), 1.98–1.88 (m, 1H), 1.80–1.78 (m, 1H). CIMS 464 $(M+H)^+$.

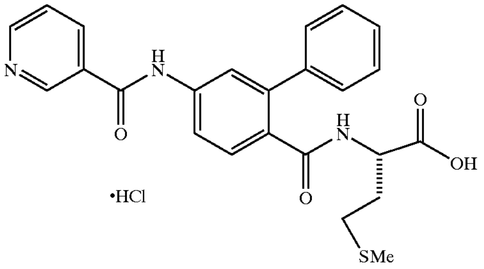

EXAMPLE 200

[4-(3-Pyridylcarbonylamino)-2-phenylbenzoyl]methionine Hydrochloride

[4-(3-pyridylcarbonylamino)-2-phenylbenzoyl]methionine methyl ester (830 mg, 1.79 mmol), prepared as in Example 199, was dissolved in 8 mL THF and cooled to 0° C. LiOH monohydrate (226 mg, 5.38 mmol) was added followed by 2 mL of $H_2O$. The reaction was complete in 2 hours. The solvents were evaporated and the residue was acidified to pH=3 with 1N HCl. The resulting precipitate was taken up in ethyl acetate and the solution was washed with water, dried over $Na_2SO_4$ and evaporated. The residue was crystallized from hot ethanol to give 281 mg (32%) of [4-(3-pyridylcarbonylamino)-2-phenylbenzoyl methionine hydrochloride as a white crystalline solid. $^1H$ NMR (300 mHz, $CD_3OD$) δ 9.4 (d, 1H), 9.1 (d, 1H), 9.0 (d, 1H), 8.2 (dd, 1H), 7.85–7.80 (m, 2H), 7.58 (dd, 1H), 7.45–7.32 (m, 5H), 4.52–4.45 (m, 1H), 2.20–2.02 (m, 2H), 2.00 (s, 3H), 1.90–1.80 (m, 2H), 1.15 (t, 1H). CIMS 450 $(M+H)^+$.

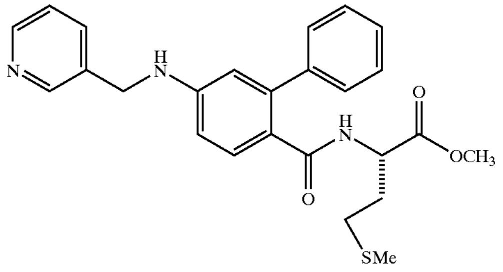

EXAMPLE 201

[4-(3-Pyridylmethylamino)-2-phenylbenzoyl] methionine Methyl Ester (4-Amino-2-phenylbenzoyl)methionine methyl ester (1.15 g, 3.21 mmol), prepared as in Example 192B, and 3-pyridine carboxaldehyde (361 mg, 3.37 mmol) were combined in 15 mL methanol and sodium cyanoborohydride (302 mg, 4.81 mmol) was added followed by crushed molecular sieves. The reaction was adjusted to pH=6 with acetic acid and stirred at 25° C. for 3 hours. The reaction was concentrated and transferred directly to a column of silica gel and purified by flash chromatography (5%methanol-ethyl acetate) to give [4(3-pyridylmethylamino)-2-phenylbenzoyl]methionine methyl ester (1.38 g, 95%) as an oil that solidified after standing. $^1H$ NMR (300 mHz, $CDCl_3$) δ 8.6 (d, 1H), 8.52 (dd, 1H), 7.72–7.65 (m, 2H), 7.45–7.30 (m, 6H), 6.62 (dd, 1H), 6.48 (d, 1H), 5.72 (bd, 1H), 4.64 (dq, 1H), 4.42 (bs, 2H), 3.64 (s, 3H), 2.25–2.05 (m, 3H), 2.00 (s, 3H), 1.95–1.80 (m, 1H), 1.72–1.60 (m, 1H); CIMS $MH^+$ 450.

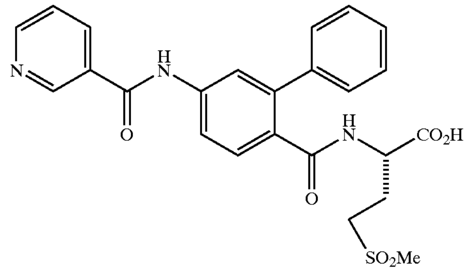

EXAMPLE 203

[4-(3-Pyridylcarbonylamino)-2-phenylbenzoyl]-2-amino-4-(methylsulfonyl)butanoic Acid

EXAMPLE 203A

[4-(3-Pyridylcarbonylamino)-2-phenylbenzoyl-2-amino-4-(methylsulfonyl)butanoic Acid Methyl Ester

[4-Amino-2-phenylbenzoyl-L-methionine methyl ester (46 mg, 0.0.092 mmol), prepared as in Example 201, was protected as the HCl pyridinium salt and was dissolved in 5 mL of $CH_2Cl_2$, cooled to −78° C. and treated with a solution of m-chloroperbenzoic acid (44 mg, 0. 184 mmol) in 2 mL of $CH_2Cl_2$ and warmed to 0° C. After 0.5 hours, the reaction was quenched with dimethyl sulfide and evaporated. Purification by flash chromatography (5% methanol-ethyl acetate) gave [4-(3-pyridylcarbonylamino)-2-phenylbenzoyl]-2-amino-4-(methylsulfonyl)butanoic acid methyl ester (43 mg, 88%) as a white solid.

EXAMPLE 203B

[4-(3-Pyridylcarbonylamino)-2-phenylbenzoyl]-2-amino-4-(methylsulfonyl)butanoic Acid The [4-(3-pyridylcarbonylamino)-2-phenylbenzoyl]-2-amino-4-(methylsulfonyl)butanoic acid methyl ester prepared in Example 203A (43 mg, 0.081 mmol) was dissolved in 3 mL of THF and a solution of LiOH monohydrate was in 1 mL of $H_2O$ was added. The reaction mixture was stirred at 25° C. for 1 hour and then was evaporated. Formic acid (1 mL) was added to acidify to pH=3. The reaction was then evaporated once again and 1 mL of $H_2O$ was added along with 5 mL of ethyl acetate to dissolve the mixture. The ethyl acetate layer was dried over $Na_2SO_4$, filtered and evaporated and the residue was lyophilized from acetonitrile/$H_2O$ to give [4-(3-pyridylcarbonylamino)-2-phenylbenzoyl]-2-amino-4-(methylsulfonyl)butanoic acid (36 mg, 88%) as a white solid. $^1H$ NMR (300 mHz, $CD_3OD$) δ 9.12 (d, 1H), 8.70 (d, 1H), 8.42 (dt, 1H), 7.85–7.80 (m, 2H), 7.65–7.40 (m, 8H), 4.50 (m, 1H), 2.90 (s, 3H), 2.88–2.80 (m, 1H), 2.70–2.58 (m, 1H), 2.35–2.20 (m, 1H), 2.10–1.95 (m, 1H). HRMS calcd $C_{24}H_{23}N_3SO_6$ $MH^+$ 482.1386, found 482.1373.

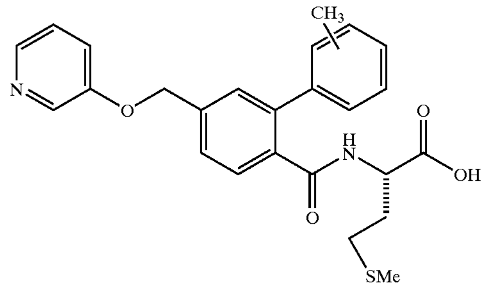

EXAMPLES 204–206

EXAMPLE 204

[4-(3-Pyridyloxymethyl)-2-(2-methylphenyl)benzoyl Methionine Methyl Ester

EXAMPLE 204A 2-(Trifluoromethanesulfonyloxy)-4-methylbenzoic Acid Methyl Ester

To a −10° C. solution of 4-methylsalicylic acid methyl ester (22.46 g, 0.135 mol) in 100 mL of pyridine was added triflic anhydride (45.8 g, 0.162 mol) dropwise by addition funnel while keeping the temperature below 0° C. the reaction mixture was then warmed to ambient temperature and after 12 hours was poured over a mixture of 100 mL conc. HCl/300 g ice in a large erylenmeyer flask. After the ice melted, the mixture was transferred to a separatory funnel and the aqueous layer was extracted with ethyl acetate (3×100 mL). The ethyl acetate layers were combined and washed with 1N HCl, then sat'd aqueous $NaHCO_3$, then brine and then filtered and evaporated to give 35.66 g (88%)

of 2-(trifluoromethanesulfonyloxy)-4-methylbenzoic acid methyl ester as a yellow oil.

EXAMPLE 204B 2-(Trifluoromethanesulfonyloxy)-4-bromomethylbenzoic Acid Methyl Ester To a stirred solution of 2-(trifluoromethanesulfonyloxy)-4-methylbenzoic acid methyl ester (19.6 g, 65.8 mmol), prepared as in Example 204A, in 250 mL $CCl_4$ was added N-bromosuccinimide (12.29 g, 69.1 mmol) followed by 2,2'-azobisisobutyronitrile (108 mg, 0.658 mmol) and the reaction was heated to reflux. After 16 hours, the reaction was evaporated and the residue was purified by flash chromatography over silica gel (10% ethyl acetate-hexanes) to give 19.9 g (80%) of 2-(trifluoromethanesulfonyloxy)-4-bromomethylbenzoic acid methyl ester as a yellow oil.

EXAMPLE 204C 4-(3-Pyridyloxymethyl)-2-(trifluoromethanesulfonyloxy)benzoic Acid Methyl Ester A solution of 2-(trifluoromethanesulfonyloxy)-4-bromomethylbenzoic acid methyl ester (2.97 g, 7.87 mmol), prepared as in Example 204B, in 20 mL of $CH_2Cl_2$ was combined with a solution of the potassium alkoxide of 3-OH pyridine (1.57 g, 11.8 mmol) in 20 mL of $H_2O$. Tetrabutylammonium bromide (3.80 g, 11.8 mmol) was added and the reaction was stirred vigorously at 25° C. for 1.5 hours. The reaction was poured into a separatory funnel and the layers were separated. The aqueous layer was washed with $CH_2Cl_2$ (2×50 mL) and the $CH_2Cl_2$ layer was washed twice with water. The organic layers were combined and dried over $Na_2SO_4$, filtered and evaporated to an oil and purifed by flash chromatography over silica gel to give 4-(3-pyridyloxymethyl)-2-(trifluoromethanesulfonyloxy)benzoic acid methyl ester (861 mg, 28%) as a light brown oil.

EXAMPLE 204D 4-(3-Pyridyloxymethyl)-2-(2-methylphenyl)benzoic Acid Methyl Ester

To a solution of 4-(3-pyridyloxymethyl)-2-(trifluoromethanesulfonyloxy)benzoic acid methyl ester (216 mg, 0.55 mmol), prepared as in Example 203C, in 4 mL of DMF at 25° C. was added $PdCl_2(PPh_3)_2$ (38 mg, 0.055 mmol, 10 mol %) followed by 2-tolyl boronic acid (113 mg, 0.83 mmol) and $Cs_2CO_3$ (270 mg, 0.83 mmol) and the reaction was heated to 80° C. for 12 hours. The reaction was then cooled to ambient temperature, taken up in 50 mL ethyl acetate, and washed with $H_2O$ (5×10 mL). The organic phase was dried over $Na_2SO_4$, filtered and evaporated to an oil. Purification by radial chromatography using a gradient of 25% ethyl acetate-hexanes to 75% ethyl acetate-hexanes gave 4-(3-pyridyloxymethyl)-2-(2-methylphenyl)benzoic acid methyl ester (178 mg, 97%) as an oil.

EXAMPLE 204E 4-(3-Pyridyloxymethyl)-2-(2-methylphenyl)benzoic Acid

The 4-(3-pyridyloxymethyl)-2-(2-methylphenyl)benzoic acid methyl ester prepared in Example 204D (160 mg, 0.48 mmol) was dissolved in 5 mL of methanol and 1 mL of saturated aqueous LiOH was added. The reaction was heated to reflux for 1 hour. The reaction was then evaporated and 1 mL of formic acid was added to acidify the crude product 1 to pH=3. The reaction was evaporated again to remove formic acid and 5 mL of ethyl acetate and 1 mL of $H_2O$ were added to completely solubilize the reaction mixture. The aqueous layer was extracted with ethyl acetate (3×5 mL) and all the ethyl acetate layers were combined and dried over $Na_2SO_4$, filtered and evaporated to give 4-(3-pyridyloxymethyl)-2-(2-methylphenyl)benzoic acid (131 mg, 86%) as an oil.

EXAMPLE 204F

[4-(3-Pyridyloxymethyl)-2-(2-methylphenylbenzoyl] methionine Methyl Ester

The 4-(3-pyridyloxymethyl)-2-(2-methylphenyl)benzoic acid prepared in Example 204E (153 mg, 0.48 mmol) was dissolved in 2 mL of DMF and 3-hydroxy1,2,3-benzotriazin-4(3H)-one (39 mg, 0.24 mmol) was added followed by methionine methyl ester HCl (48 mg, 0.24 mmol), (3-dimethylaminopropyl)-3-ethylcarbodiimide hydrochloride (46 mg, 0.24 mmol) and triethylamine (0.03 mL, 0.32 mmol) and the reaction mixture was stirred for 16 hours at 25° C. The reaction mixture was taken up in ethyl acetate and washed three times with water and three times with brine. The ethyl acetate layer was dried over $Na_2SO_4$, filtered and evaporated to an oil. Purification by radial chromatography (2–8%methanol-chloroform gradient with 0.25% $NH_40H$) gave 4-(3-pyridyloxymethyl)-2-(2-methylphenyl)benzoyl]methionine methyl ester (72 mg, 32%) as an oil.

EXAMPLE 204G

[4-(3-Pyridyloxymethyl)-2-(2-methylphenyl) benzoyl]methionine

The [4-(3-pyridyloxymethyl)-2-(2-methylphenyl) benzoyl]methionine methyl ester prepared in Example 204F (72 mg, 0.15 mmol) was dissolved in 3 mL of THF and 1 mL of saturated aqueous LiOH was added. The reaction mixture was stirred at room temperature for 1 hour. The reaction was thoroughly evaporated and formic acid was added until pH=3 was obtained at which time the reaction was evaporated to dryness and 10 mL of ethyl acetate was added followed by a minimum quantity of $H_2O$ (1 mL) to completely solubilize the free acid and the water soluble salts, respectively. The layers were separated and the aqueous layer was extracted with ethyl acetate (3×5 mL). The ethyl acetate layers were combined, dried over $Na_2SO_4$, filtered and evaporated to give 58 mg (84%) of [4-(3-pyridyloxymethyl)-2-(2-methylphenyl)benzoyl]methionine as an amorphous solid. $^1H$ NMR (300 mHz, $CD_3OD$) δ 8.30 (d, 1H), 8.15 (dd, 1H), 7.68 (bd, 1H), 7.58–7.48 (m, 2H), 7.40–7.30 (m, 2H), 7.26–7.16 (m, 4H), 5.25 (s, 2H), 4.50–4.40 (m, 1H), 2.20–2.02 (m, 5H), 2.00 (s, 3H), 2.00–1.90 (m, 1H), 1.80–1.68 (m, 1H) CIMS $MH^+$ 451.

EXAMPLE 205

[4-(3-Pyridyloxymethyl)-2-(3-methylphenyl) benzoyl]methionine

The desired compound was prepared according to the method of Example 204, except substituting 3-methylphenyl boronic acid for 2-methylphenyl boronic acid. $^1H$ NMR (300 mHz, $CD_3OD$) δ 8.30 (d, 1H), 8.15 (d, 1H), 7.68–7.48 (m, 6H), 7.40–7.16 (m, 4H), 5.25 (s, 2H), 4.50–4.40 (m, 1H), 2.40 (s, 3H), 2.18–1.75 (m, 7H); CIMS $MH^+$ 451.

EXAMPLE 206

[4-(3-Pyridyloxymethyl)-2-(4-methylphenylbenzoyl] methionine

The desired compound was prepared according to the method of Example 204, except substituting 4-methylphenyl boronic acid for 2-methylphenyl boronic acid. $^1$H NMR (300 mHz, $CD_3OD$) δ 8.30 (d, 1H), 8.15 (d, 1H), 7.58–7.44 (m, 4H), 7.40–7.28 (m, 3H), 7.24–7.10 (m, 3H), 5.25 (s, 2H), 4.42 (dd, 1H), 2.10–1.90 (m, 6H), 1.84–170 (m, 1H). CIMS MH$^+$ 451.

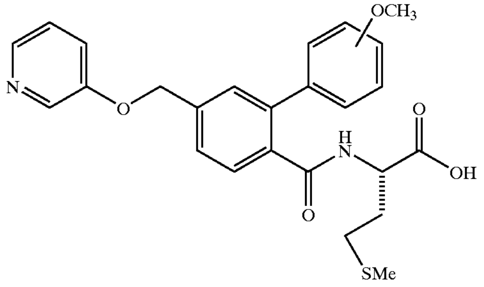

EXAMPLES 207–209

EXAMPLE 207

[4-(3-Pyridyloxymethyl)-2-(2-methoxyphenyl) benzoyl]methionine

The desired compound was prepared according to the method of Example 204, except substituting 2-methoxyphenyl boronic acid for 2-methylphenyl boronic acid. $^1$H NMR (300 mHz, $CD_3OD$) δ 8.30 (d, 1H), 8.15 (d, 1H), 7.68 (bd, 1H), 7.54–7.50 (m, 2H), 7.38–7.32 (m, 3H), 7.22 (dd, 1H), 7.04–6.98 (m, 2H), 5.25 (s, 2H), 4.42 (dd, 1H), 3.74 (s, 3H), 2.16–2.08 (m, 2H), 2.00 (s, 3H), 1.98–1.86 (m, 1H), 1.78–164 (m, 1H). CIMS MH$^+$ 467.

EXAMPLE 208

[4-(3-Pyridyloxymethyl)-2-(3-methoxyphenylbenzoyl]methionine

The desired compound was prepared according to the method of Example 204, except substituting 3-methoxyphenyl boronic acid for 2-methylphenyl boronic acid. $^1$H NMR (300 mHz, $CD_3OD$) δ 8.34 (s, 1H), 8.15 (d, 1H), 7.60–7.54 (m, 4H), 7.38–7.24 (m, 3H), 7.02–6.90 (m, 3H), 5.25 (s, 2H), 4.44 (dd, 1H), 3.82 (s, 3H), 2.18–190 (m, 6H), 1.92–1.82 (m, 1H); CIMS MH$^+$ 467.

EXAMPLE 209

[4-(3-Pyridyloxymethyl)-2-(4-methoxyphenyl) benzoyl]methionine

The desired compound was prepared according to the method of Example 204, except substituting 4-methoxyphenyl boronic acid for 2-methylphenyl boronic acid. $^1$H NMR (300 mHz, $CD_3OD$) δ 8.34 (s, 1H), 8.15 (bs, 1H), 7.72–7.42 (m, 6H), 7.40–7.35 (m, 2H), 6.96–6.90 (m, 2H), 5.25 (s, 2H), 4.44 (dd, 1H), 3.84 (s, 3H), 2.20–190 (m, 6H), 1.88–1.76 (m, 1H); CIMS MH$^+$ 467.

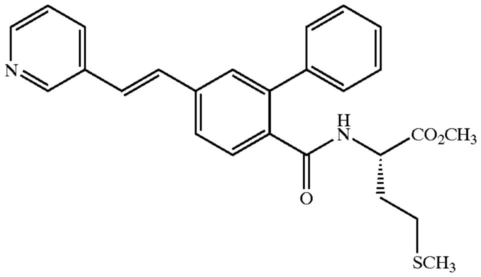

EXAMPLE 210

{4-[2-(Pyrid-3-yl)ethenyl]-2-phenylbenzoyl}methionine Methyl Ester

EXAMPLE 210A

2-Phenyl-4-nitrobenzoic Acid Methyl Ester

A mixture of methyl 2-chloro-4-nitrobenzoate (44.2 g, 205 mmol), phenylboronic acid (27.5 g, 226 mmol), sodium carbonate (2.0 M in water, 123 mL, 246 mmol), and bis (triphenylphosphine)palladium(II) chloride (2.8 g, 4 mmol) in dioxane (300 mL) was degassed by nitrogen, and heated at 90–95° C. for 20 hours. The reaction mixture was diluted with ether (500 mL) and ethyl actate (500 mL), washed with water (2 times, 200 mL each) and brine, dried over anhydrous magnesium sulfate, filtered, and concentrated in vacuo. The residue was recrystalized from hexane-ethyl acetate (1/1) to give 2-phenyl-4-nitrobenzoic acid methyl ester as a white solid (43.3 g). The mother liquid from the recrystalization was concentrated in vacuo, and the residue was purified by column chromataography (80:15:5 hexane-chloroform-ethyl acetate) to yield an additional 5.2 g of the desired compound (total yield 48.5 g, 92%). $^1$H NMR (300 MHz, $CDCl_3$) δ 8.25 (d, 1H), 8.24 (dd, 1H), 7.94 (dd, 1H), 7.44 (m, 3H), 7.35 (m, 2H), 3.67 (s, 3H).

EXAMPLE 210B

2-Phenyl-4-aminobenzoic Acid Methyl Ester

A mixture of the 2-phenyl-4-nitrobenzoic acid methyl ester prepared in Example 210A (48.4 g, 188 mmol), palladium (10%) on carbon (2.1 g), and ammonium formate (59.4 g, 941 mmol) in methanol (500 mL) was refluxed for 3 hours. The solvent was removed in vacuo, and the residue was desolved in a miminum amount of hot methanol (about 30 mL). To this solution was added chloroform and ether (1/1 ratio, 400 mL), and the mixture was filtered through a plug of silica gel (80 g) and rinsed with chloroform. The filtrate was concentrated in vacuo to give pure 2-phenyl-4-aminobenzoic acid methyl ester (42.4 g, 99%). $^1$H NMR (300 MHz, $CDCl_3$) δ 7.80 (d, 1H), 7.40–7.25 (m, 5H), 6.65 (dd, 1H), 6.57 (d, 1H), 3.60 (s 3H).

EXAMPLE 210C

4-Iodo-2-phenylbenzoic Acid Methyl Ester

To a 0° C. suspension of the 2-phenyl-4-aminobenzoic acid methyl ester prepared in Example 210B (4.54 g, 20 mmol) in 6.0 N HCl (20 mL) and acetone (10 mL) was added dropwise a solution of sodium nitrite (1.66 g, 24 mmol) in a minimum amount of water. After 30 minutes, potassium iodide (6.64 g, 40 mmol) in a minimum amount of water was added dropwise to the reaction mixture. The internal temperature of the reaction mixture was maintained under 5° C. for both additions. The reaction mixture was then stirred at ambient temperature for one hour. The reaction mixture was diluted with ether (200 mL), washed with water, sodium bisulfite (10% aqueous solution), water and brine, dried over anhydrous magnesium sulfate, filtered, and concentrated in vacuo. The residue was purified by column chromatography (8% ethyl acetate-hexane) to give 4-iodo-2-phenylbenzoic acid methyl ester (3.98 g, 59%). $^1$H NMR (300 MHz, $CDCl_3$) δ 7.77 (m, 2H), 7.55 (d, 1H), 7.38 (m, 3H), 7.27 (m, 2H), 3.63 (s, 3H). Ms (CI+): 356 $(M+NH_4)^+$.

EXAMPLE 210D (4-Iodo-2-phenylbenzoyl)methionine Methyl Ester

A mixture of the 4-iodo-2-phenylbenzoic acid methyl ester prepared in Example 21° C. (2.77 g, 8.20 mmol) in aqueous saturated lithium hydroxide (3 mL) and methanol (10 mL) was heated at 60° C. for 12 hours. The mixture was then acidified with concentrated HCl to pH about 2, and extracted twice with ethyl acetate (50 mL each). The combine extracts was washed with brine, dried over anhydrous magnesium sulfate, filtered, and concentrated in vacuo. The residue was suspended in dichloromethane (10 mL), and oxalyl chloride (2.0 M in dichloromethane, 6.2 mL)was added, followed by a small drop of DMF. The mixture was stirred at room temperature for 1 hour, and then was concentrated in vacuo, followed by further drying under high vacuum for 10 minutes. To the residue was added dichloromethane (20 mL), L-methionine methyl ester hydrochloride (1.64 g, 8.05 mmol) and triethylamine (3.4 mL, 24.6 mmol). The reaction mixture was stirred at room temperature for 12 hours. The mixture was diluted with ether (50 mL), filtered through silica gel (30 g), and concentrated in vacuo. The crude product was purified by column chromatography (40:40:20 hexane-chloroform-ether) to give (4-iodo-2-phenylbenzoyl)methionine methyl ester (3.46 g, 90%). $^1$H NMR (300 MHz, $CDCl_3$) δ 7.76 (m, 2H), 7.42 (m, 6H), 5.88 (br d, 1H), 4.65 (m, 1H), 3.68 (s, 3H), 2.05 (m, 2H), 2.00 (s, 3H), 1.90 (m, 1H), 1.73 (m, 1H).

EXAMPLE 210E

3-Vinylpyridine

To a slurry of methyltriphenylphosphine chloride (18.0 g, 50.5 mmol) in THF (20 mL) was added slowly sodium bis(trimethylsilyl)amide (1.0 M solution in THF, 50 mL). After the mixture was stirred at room temperature for 30 minutes, the reaction was cooled to 0° C., and 3-pyridinecarboxaldehyde (4.72 mL, 50.0 mmol) was added slowly to the mixture. After 30 minutes, the reaction mixture was diluted with ether (100 mL) and filtered through silica gel (100 g), rinsed with ether, and concentrated in vacuo. The resulting liquid was diluted with 1:1 hexane-ether (50 mL), and was again filtered through silica gel (50 g), rinsed with 70:30 ether-hexane and concentrated in vacuo to give3-vinylpyridine (4.31 g, 82%). $^1$H NMR (300 MHz, $CDCl_3$) δ 8.63 (d, 1H), 8.50 (dd, 1H), 7.74 (m, 1H), 7.26 (m, 1H), 6.71 (dd, 1H), 5.83 (d, 1H), 5.39 (d, 1H).

EXAMPLE 210F

{4-[2-(Pyrid-3-yl)ethenyl]-2-phenylbenzoyl}methionine Methyl Ester

A mixture of the (4-iodo-2-phenylbenzoyl)methionine methyl ester prepared in Example 210D (655 mg, 1.40 mmol), the vinylpyridine prepared in Example 210E (221 mg, 1.5 mmol), triethylamine (0.29 mL, 2.10 mmol), [1,1'-bis(diphenylphosphino)ferrocene]palladium(II) chloride, complexed to dichloromethane (1:1) (114 mg, 0.14 mmol) in DMF (2 mL) was degassed with nitrogen, and heated at 100° C. for 14 hours. The reaction mixture was diluted with ether (100 mL), washed with water and brine, dried over anhydrous magnesium sulfate, filtered, and concentrated in vacuo. The residue was purified by column chromatography (ethyl acetate) to give {4-[2-(pyrid-3-yl)ethenyl]-2-phenylbenzoyl}methionine methyl ester (366 mg, 56%). $^1$H NMR (300 MHz, $CDCl_3$) δ 8.75 (d, 1H), 8.51 (dd, 1H), 7.85 (dt, 1H), 7.76 (d, 1H), 7.59 (dd, 1H), 7.48 (dd, 1H), 7.44 (m, 5H), 7.31 (dd, 1H), 7.22 (d, 1H), 7.16 (d, 1H), 5.94 (br d, 1H), 4.69 (m, 1H), 3.68 (s, 3H), 2.08 (m, 2H), 2.02 (s, 3H), 1.93 (m, 1H), 1.76 (m, 1H). MS ($APCI^+$) m/e 447 $(M+H)^+$.

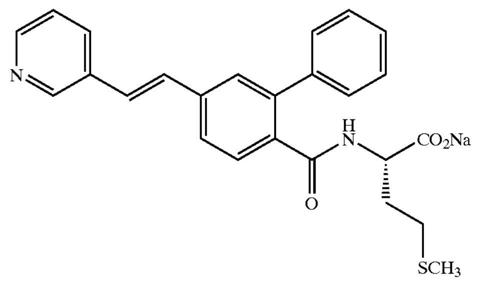

EXAMPLE 211

{4-[2-(Pyrid-3-yl)ethenyl]-2-phenylbenzoyl}methionine Sodium Salt

To a solution of the {4-[2-(pyrid-3-yl)ethenyl]-2-phenylbenzoyl}methionine methyl ester prepared in Example 210 (136 mg, 0.304 mmol) in methanol (2 mL) was added a solution of sodium hydroxide (0.979 N, 0.334 mL). After 14 hours, the solvent was evaporated in vacuo to give {4-[2-(pyrid-3-yl)ethenyl]-2-phenylbenzoyl}methionine sodium salt (141 mg, 100%). $^1$H NMR (300 MHz, DMSO-$d_6$) δ 8.90 (d, 1H), 8.46 (dd, 1H), 8.07 (dt, 1H), 7.64 (m, 2H), 7.50–7.35 (m, 10H), 3.78 (m, 1H), 2.10 (m, 2H), 1.98 (s, 3H), 1.76 (m, 2H). MS ($APCI^+$) m/e 433 $(M+H)^+$.

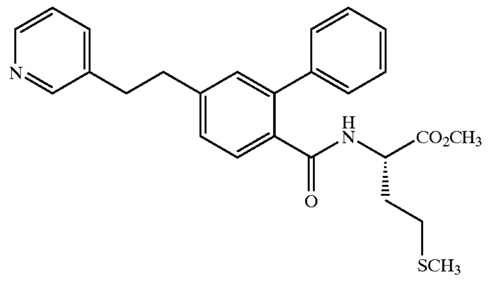

EXAMPLE 212

{4-[2-(Pyrid-3-yl)ethyl]-2-phenylbenzoyl}methionine Methyl Ester

A mixture of the {4-[2-(pyrid-3-yl)ethenyl]-2-phenylbenzoyl}methionine methyl ester prepared in Example 210 (160 mg, 0.36 mmol) and palladium (10%) on carbon (460 mg, 0.43 mmol of palladium) in methanol was flushed with hydrogen, and stirred under a positive hydrogen pressure for 8 hours. The mixture was then filtered through Celite, rinsed with ethyl acetate, and concentrated in vacuo. The residue was purified by column chromatography (ethyl acetate) give {4-[2-(pyrid-3-yl)ethyl]-2-phenylbenzoyl}methionine methyl ester (115 mg, 71%). $^1H$ NMR (300 MHz, $CDCl_3$) δ 8.45 (m, 2H), 7.64 (d, 1H), 7.40 (m, 7H), 7.22 (dd, 2H), 7.10 (d, 1H), 5.87 (br d, 1H), 4.68 (m, 1H), 3.67 (s, 3H), 2.99 (m, 4H), 2.08 (m, 2H), 2.02 (s, 3H), 1.93 (m, 1H), 1.76 (m, 1H). MS ($APCI^+$) m/e 449 $(M+H)^+$.

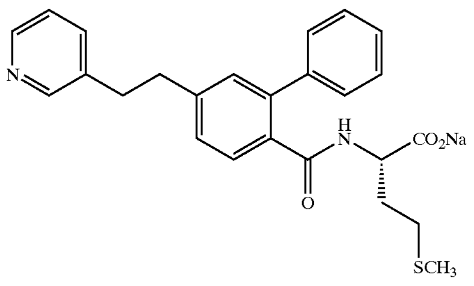

EXAMPLE 213

{4-[2-(Pyrid-3-yl)ethyl]-2-phenylbenzoyl}methionine Sodium Salt

The desired compound was prepared by saponification of {4-[2-(pyrid-3-yl)ethyl]-2-phenylbenzoyl}methionine methyl ester, prepared as in Example 212 according to the procedure of Example 211. $^1H$ NMR (300 MHz, DMSO-$d_6$) δ 8.45 (d, 1H), 8.40 (dd, 1H), 7.69 (dt, 1H), 7.40–7.20 (m, 9H), 7.07 (br d, 1H), 3.76 (m, 1H), 2.97 (s, 4H), 2.10 (m, 2H), 1.96 (s, 3H), 1.76 (m, 2H). MS ($APCI^+$) m/e 435 $(M+H)^+$as the acid form.

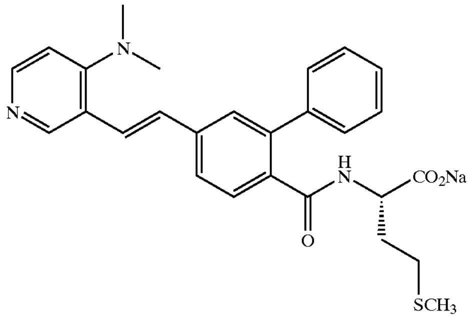

EXAMPLE 214

{4-[2-(4-Dimethylaminopyrid-3-yl)ethenyl]-2-phenylbenzoyl}methionine Sodium Salt

EXAMPLE 214A

3-Bromo-4-dimethylaminopyridine

To a mixture of 4-dimethylaminopyridine (5.00 g, 41 mmol), potassium carbonate (50 g in 50 mL of water), tetrabutylammonium hydrogensulfate (1.4 g, 4.1 mmol) and dichloromethane (100 mL) was added a solution of bromine (4.2 mL, 82 mmol) in dichloromethane (30 mL) via an addition funnel over 30 minutes. After 3 hours, the reaction mixture was diluted with ether (100 mL), washed with water and brine, dried over anhydrous sodium sulfate, filtered, and concentrated in vacuo. The residue was then purified by column chromatography (ethyl acetate) to give 3-bromo-4-dimethylaminopyridine (4.89 g, 59%). $^1H$ NMR (300 MHz, $CDCl_3$) δ 8.51 (s, 1H), 8.27 (d, 1H), 6.79 (d, 1H), 2.97 (s, 6H).

EXAMPLE 214B

3-Vinyl-4-dimethylaminopyridine

A mixture of the 3-bromo-4-dimethylaminopyridine prepared in Example 214A (1.29 g, 6.39 mmol) vinyltributyltin (2.23 g, 7.02 mmol), bis(triphenylphosphine)palladium(II) chloride (224 mg, 0.32 mmol) in toluene (10 mL) was heated at 100° C. for 12 hours. To the stirring reaction mixture at room temperature was added ether (30 mL), water (0.2 mL) and 1,8-diazabicyclo[5.4.0]undec-7-ene (0.5 mL). The resulting mixture was filtered through silica gel (15 g), rinsed with ethyl acetate, and concentrated in vacua. The residue was purified by column chromatography (50% ethyl acetate-hexanes, then ethyl acetate) to give 3-vinyl-4-dimethylaminopyridine (1.11 g, contaminated with about 10 mol % of tributyltin. derivatives). $^1H$ NMR (300 MHz, $CDCl_3$) δ 8.39 (s, 1H), 8.26 (d, 1H), 6.77 (dd, 1H), 6.70 (d, 1H), 5.65 (dd, 1H), 5.29 (dd, 1H), 2.87 (s, 6H).

EXAMPLE 214C

{4-[2-(4-Dimethylaminopyrid-3-yl)ethenyl]-2-phenylbenzoyl}methionine Methyl Ester The desired compound was prepared according to the method of Example 210, except substituting 3-vinyl-4-dimethylaminopyridine, prepared as in Example 214B, for 3-vinylpyridine. $^1H$ NMR (300 MHz, $CDCl_3$) δ 8.52 (br s, 1H), 8.30 (br d, 1H), 7.76 (d, 1H), 7.59 (dd, 1H), 7.47 (m, 6H), 7.22 (d, 1H), 7.03 (d, 1H), 6.78 (br d, 1H), 5.95 (br d, 1H), 4.69 (m, 1H), 3.67 (s, 3H), 2.92 (s, 6H), 2.10 (m, 2H), 2.02 (s, 3H), 1.93 (m, 1H), 1.76 (m, 1H). MS ($CI^+$) m/e 490 $(M+H)^+$.

EXAMPLE 214D

{4-[2-(4-Dimethylaminopyrid-3-yl)ethenyl]-2-phenylbenzoyl}methionine Sodium Salt The desired compound was prepared by saponification of {4-[2-(4-dimethylaminopyrid-3-yl)ethenyl]-2-phenylbenzoyl}methionine methyl ester, prepared as in Example 214C, according to the method of Example 211. $^1H$ NMR (300 MHz, DMSO-$d_6$) δ 8.42 (s 1H), 8.11 (d, 1H), 7.58 (d, 1H), 7.47–7.07 (m, 10H), 6.79 (d, 1H), 3.76 (m, 1H), 2.97 (s, 6H), 2.02 (m, 2H), 1.88 (s, 3H), 1.68 (m, 2H). MS ($APCI^+$) m/e 476 $(M+H)^+$as the acid form.

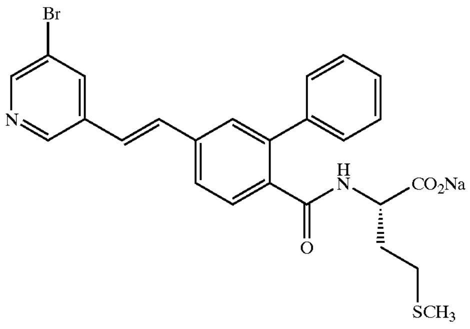

EXAMPLE 215

{4-[2-(5-Bromopyrid-3-yl)ethenyl]-2-phenylbenzoyl}methionine Sodium Salt

EXAMPLE 215A

3-Vinyl-5-bromopyridine

The desired compound was prepared according to the method of Example 214B, except substituting 3,5-dibromopyridine for 3-bromo-4-dimethylaminopyridine. $^1$H NMR (300 MHz, DMSO-$d_6$) δ 8.56 (d, 1H), 8.53 (d, 1H), 7.87 (t, 1H), 6.64 (dd, 1H), 5.85 (d, 1H), 5.44 (d, 1H).

EXAMPLE 215B

{4-[2-(5-Bromopyrid-3-yl)ethenyl]-2-phenylbenzoyl}methionine Sodium Salt

The desired compound was prepared according to the method of Examples 214C and D, except substituting 3-vinyl-5-bromopyridine, prepared as in Example 215A, for 3-vinyl-4-dimethylaminopyridine. $^1$H NMR (300 MHz, $CDCl_3$) δ 8.79 (d, 1H), 8.59 (d, 1H), 8.39 (br s, 1H), 7.66–7.34 (m, 11H), 3.78 (m, 1H), 2.13 (m, 2H), 1.98 (s, 3H), 1.77 (m, 2H). MS (APCI+) m/e ($^{79}$Br) 511 $(M+H)^+$as the acid form.

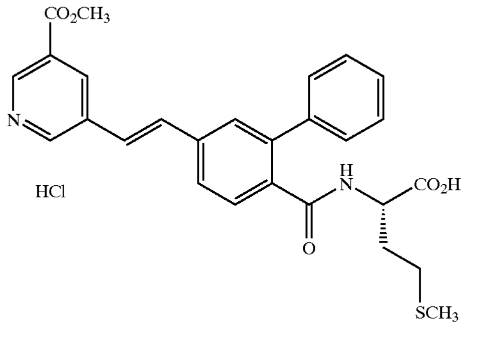

EXAMPLE 216

{4-[2-(5-Carboxymethylpyrid-3-yl)ethenyl]-2-phenylbenzoyl}methionine Hydrochloride

EXAMPLE 216A

3-Vinyl-5-carboxymethylpyridine

The desired compound was prepared according to the method of Example 214B, except substituting methyl 3-bromonicotinate for 3-bromo-4-dimethylaminopyridine. $^1$H NMR (300 MHz, DMSO-$d_6$) δ 9.09 (d, 1H), 8.78 (d, 1H), 8.34 (t, 1H), 6.76 (dd, 1H), 5.93 (d, 1H), 5.49 (d, 1H), 3.97 (s, 3H).

EXAMPLE 216B

{4-2-(5-Caboxymethylpyrid-3-yl)ethenyl]-2-phenylbenzoyl}methionine Methyl Ester

The desired compound was prepared according to the method of Example 210F, except substituting 3-vinyl-5-carboxymethylpyridine, prepared as in Example 216A, for 3-vinylpyridine. $^1$H NMR (300 MHz, $CDCl_3$) δ 9.11 (d, 1H), 8.87 (d, 1H), 8.45 (t, 1H), 7.78 (d, 1H), 7.59 (dd, 1H), 7.51 (d, 1H), 7.47 (m, 5H), 7.30 (d, 1H), 7.20 (d, 1H), 5.91 (br d, 1H), 4.68 (m, 1H), 3.97 (s, 3H), 3.67 (s, 3H), 2.08 (m, 2H), 2.02 (s, 3H), 1.94 (m, 1H), 1.76 (m, 1H). MS ($CI^+$) m/e 505 $(M+H)^+$.

EXAMPLE 216C

{4-[2-(5-Carboxymethylpyrid-3-yl)ethenyl]-2-phenylbenzoyl}methionine Hydrochloride To a solution of the {4-[2-(5-carboxymethylpyrid-3-yl)ethenyl]-2-phenylbenzoyl}methionine methyl ester prepared in Example 216B (90.4 mg, 0.179 mmol) in methanol (2 mL) was added a solution of sodidum hydroxide (0.979 N, 0.098 mL). After 14 hours, additional sodium hydroxide (0.979 N, 0.036 mL) was added to the reaction mixture. After 5 hours, tlc indicated that no starting material remained. The reaction was then quenched with hodrogen chloride (1.0 M in ether, 1 mL), and the solvent was evaporated in vacuo to give the title compound (105 mg, 100%) as a mixture of nicotinic acid methyl ester and nicotinic acid (ratio, 1:2). $^1$H NMR (300 MHz, DMSO-$d_6$) δ 9.07, 9.04 (2 d's, 1H), 8.98 (d, 1H), 8.67, 8.57 (m's, 2H), 7.80–7.30 (m, 1H), 4.11 (m, 1H), 3.95 (s, from the methyl ester), 2.20 (m, 2H), 2.00 (s, 3H), 1.94 (m, 2H). MS ($APCI^+$) m/e 491 $(M+H)^+$for the diacid, 505 $(M+H)^+$for nicotinic acid methyl ester.

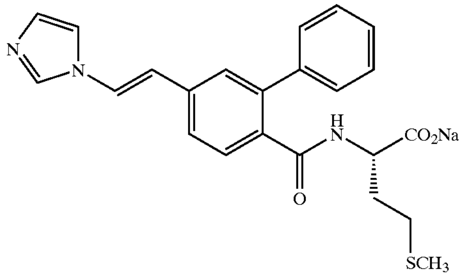

EXAMPLE 217

{4-[2-(1-H-Imidazole-1-yl)ethenyl]-2-phenylbenzoyl}methionine Sodium Salt

The desired compound was prepared according to the method of Examples 210 and 211, except substituting 1-vinylimidazole for 3-vinylpyridine. $^1$H NMR (300 MHz, DMSO-$d_6$) δ 8.02 (m, 2H), 7.71 (s, 1H), 7.53–7.30 (m, 8H), 7.15 (m, 2H), 7.07 (d, 1H), 3.73 (m, 1H), 2.10 (m, 2H), 1.97 (s, 3H), 1.77 (m, 2H). MS ($APCI^+$) m/e 444 $(M+Na)^+$as the acid form.

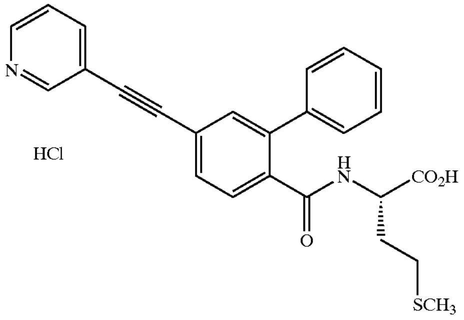

EXAMPLE 218

{4-[(Pyrid-3-yl)ethynyl]-2-phenylbenzoyl}methionine Hydrochloride

EXAMPLE 218A

{4-[(Pyrid-3-yl)ethynyl]-2-phenylbenzoyl}methionine Methyl Ester

A mixture of (4-iodo-2-phenylbenzoyl)methionine methyl ester, prepared as in Example 210D, (469 mg, 1.0 mmol), [1,1'-bis(diphenylphosphino)ferrocene]palladium (II) chloride, complexed to dichloromethane (1:1) (82 mg, 0.10 mmol), and ethynyltributyltin (315 mg, 1.0 mmol) in DMF (5 mL) was heated at 80° C. for 6 hours at which point thin layer chromatography indicated no starting iodide left. 3-Bromopyridine (0.114 mL, 1.2 mmol) and triethylamine (0.42 mL, 3.0 mmol) were added and the reaction mixture was heated at 100° C. for 14 hours. The reaction mixture was diluted with ether (50 mL) and ethyl acetate (50 mL), washed with water and brine, dried over anhydrous magnesium sulfate, and filtered. To the filtrate was added 3 drops of water, followed by 1,8-diazabicyclo[5.4.0]undec-7-ene (0.2 mL) with swirling. The resulting milky mixture was filtered through silica gel (15 g), rinsed with ethyl acetate, and concentrated in vacuo. The residue was then purified by column chromatography (50% ethyl acetate-hexane, then ethyl acetate) to give {4-[(pyrid-3-yl)ethynyl]-2-phenylbenzoyl}methionine methyl ester (109 mg, 24%). $^1$H NMR (300 MHz, $CDCl_3$) δ 8.79 (s, 1H), 8.58 (dd, 1H), 7.82 (dt, 1H), 7.74 (d, 1H), 7.59 (dd, 1H), 7.57 (s, 1H), 7.45 (m, 5H), 7.31 (dd, 1H), 5.93 (br d, 1H), 4.69 (m, 1H), 3.68 (s, 3H), 2.08 (m, 2H), 2.02 (s, 3H), 1.93 (m, 1H), 1.76 (m, 1H). MS ($CI^+$) m/e 445 $(M+H)^+$.

EXAMPLE 218B

{4-[(Pyrid-3-yl)ethynyl]-2-phenylbenzoyl}methionine Hydrochloride

To a solution of the {4-[(pyrid-3-yl)ethynyl]-2-phenylbenzoyl}methionine methyl ester prepared in Example 217A (48 mg, 0.108 mmol) in methanol (2 mL) was added aqueous sodidum hydroxide (0.979 N, 0.120 mL). After 14 hours, the reaction was quenched with hydrochloric acid (3.0 N, 0.1 mL), and the solvent was evaporated in vacuo to give {4-[(pyrid-3-yl)ethynyl]-2-phenylbenzoyl}methionine hydrochloride (61 mg, 100%). $^1$H NMR (300 MHz, DMSO-$d_6$) δ 8.95 (d, 1H), 8.89 (d, 1H), 8.84 (dd, 1H), 8.11 (dt, 1H), 7.68 (dd, 1H), 7.63 (d, 1H), 7.57 (dd, 1H), 7.51 (d, 1H), 7.46 (m, 2H), 7.38 (m, 2H), 4.31 (m, 1H), 2.24 (m, 2H), 2.00 (s, 3H), 1.86 (m, 2H). MS ($APCI^+$) m/e 431 $(M+H)^+$as the acid form.

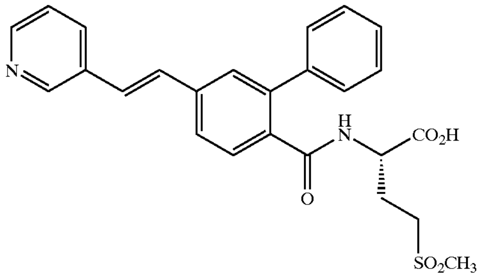

EXAMPLE 220

N-{4-[2-(Pyrid-3-yl)ethenyl]-2-phenylbenzoyl]-2-amino-4-(methylsulfonyl)butanoic Acid

EXAMPLE 220A

N-{4-[2-(Pyrid-3-yl)ethenyl]-2-phenylbenzoyl]-2-amino-4-(methylsulfonyl)butanoic Acid Methyl Ester To a solution of {4-[2-(pyrid-3-yl)ethenyl]-2-phenylbenzoyl}methionine methyl ester (521 mg, 1.17 mmol), prepared as in Example 210, 4-methylmorpholine N-oxide (551 mg, 4.68 mmol), methylsulfonamide (222 mg, 2.34 mmol) and quinuclidine (13 mg, 0.12 mmol) in tert-butanol (5 mL) and water (5 mL) was added a solution of osmium tetraoxide (2.5 wt % in tert-butanol, 0.73 mL, 0.058 mmol) and the mixture was stirred at 45° C. for 18 hours. The reaction mixture was diluted with ethyl acetate (100 mL), washed with water and brine, dried over anhydrous sodium sulfate, filtered, and concentrated in vacuo. The residue was purified by column chromatography (ethyl acetate, then 5% methanol-ethyl acetate) to give compound la (71 mg, 15%) as the first fraction, and compound 12a (285 mg, 56%, a 1:1 mixture of diastereomers) as the second fraction. For compound 11a: $^1$H NMR (300 MHz, $CDCl_3$): δ 8.74 (s, 1H), 8.53 (d, 1H), 7.87 (dt, 1H), 7.73 (d, 1H), 7.60 (dd, 1H), 7.48 (m, 6H), 7.32 (dd, 1H), 7.19 (s, 2H), 6.02 (br d, 1H), 4.68 (m, 1H), 3.70 (s, 1H), 2.95 (s, 3H), 2.77 (m, 1H), 2.65 (m, 1H), 2.27 (m, 1H), 1.99 (m, 1H). MS ($CI^+$) m/e 479 $(M+H)^+$.

For Compound 12a

EXAMPLE 220B

N-{4-[2-(Pyrid-3-yl)ethenyl]-2-phenylbenzoyl]-2-amino-4-(methylsulfonyl)butanoic Acid The desired compound was prepared by saponification of the product of Example 220A using the procedure of Example 211. $^1$H NMR (300 MHz, DMSO-$d_6$) δ 8.80 (d, 1H), 8.45 (dd, 1H), 8.07 (dt, 1H), 7.65 (m, 2H), 7.54 (d, 1H), 7.43 (m, 8H), 7.25 (br d, 1H), 3.88 (m, 1H), 2.89 (s, 3H), 2.78 (m, 2H), 1.96 (m, 2H). MS (FAB+) m/e 487 $(M+Na)^+$as the acid form.

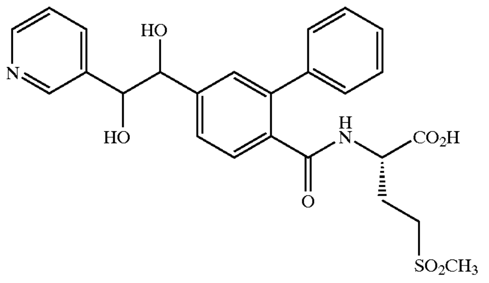

EXAMPLE 221

N-{4-[2-(Pyrid-3-yl)-1,2-dihydroxyethyl]-2-phenylbenzoyl]-2-amino-4-(methylsulfonyl)butanoic Acid

EXAMPLE 221A

N-{4-[2-(Pyrid-3-yl)-1,2-dihydroxyethyl]-2-phenylbenzoyl]-2-amino-4-(methylsulfonyl)butanoic Acid Methyl Ester The desired product was a side product in Example 220A. $^1H$ NMR (300 MHz, $CDCl_3$) δ 8.47 (2 d's, 1H), 8.19, 8.15 (2 s's, 1H), 7.61 (2 dt's, 1H), 7.57 (d, 1H), 7.40 (m, 2H), 7.23 (m, 5H), 7.00 (dd, 1H), 6.25 (2 d's, 1H), 4.76 (m, 2H), 4.63 (m, 1H), 3.70, 3.68 (2 s's, 3H), 2.92, 2.93 (2 s's, 3H), 2.80–2.52 (m, 2H), 2.24 (m, 1H), 1.97 (m, 1H). MS ($CI^+$) m/e 513 $(M+H)^+$.

EXAMPLE 221B

N-{4-[2-(Pyrid-3-yl)-1,2-dihydroxyethyl]-2-phenylbenzoyl]-2-amino-4-(methylsulfonyl)butanoic Acid The desired compound was prepared by saponification of the product of Example 221A using the procedure of Example 211. $^1H$ NMR (300 MHz, DMSO-$d_6$) δ 8.36 (m, 2H), 7.58, 7.55 (2 d's, 1H), 7.39–7.19 (m, 9H), 7.06 (s, 1H), 4.75, 4.74 (2 s's, 2H), 3.75 (m, 1H), 2.87 (s, 3H), 2.77 (m, 2H), 1.95 (m, 1H). MS ($APCI^+$) m/e 499 (M+H+) as the acid form.

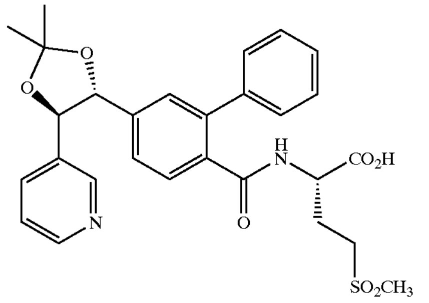

EXAMPLE 222

N-{4-[2,2-Dimethyl-4-(3-pyridyl)-1,3-dioxolan-5-yl-]-2-phenylbenzoyl}-2-amino-4-methanesulfonylbutanoic Acid

EXAMPLE 222A

N-{4-[2,2-Dimethyl-4-(3-pyridyl)-1,3-dioxolan-5-yl]-2-phenylbenzoyl}-2-amino-4-methanesulfonylbutanoic Acid A solution of N-{4-[2-(pyrid-3-yl)-1,2-dihydroxyethyl]-2-phenylbenzoyl]-2-amino-4-(methylsulfonyl)butanoic acid methyl ester (79 mg, 0.154 mmol), prepared as in Example 221A, toluenesulfonic acid (20 mg) in 2,2-dimethoxypropane (0.5 mL) and DMF (1 mL) was stirred at 50° C. for 6 hours. The reaction mixture was diluted with ether (100 mL), washed with saturated aqueous sodium bicarbonate, water and brine, dried over anhydrous magnesium sulfate, filtered, and concentrated in vacuo. The residue was purified by column chromatography (ethyl acetate) to give N-{4-[4-(pyrid-3-yl)-3,3-dimethylcyclohexyl]-2-phenylbenzoyl]-2-amino-4-(methylsulfonyl)butanoic acid methyl ester (71 mg, 84%). $^1H$ NMR (300 MHz, $CDCl_3$) δ 8.61 (br s, 1H), 8.50 (d, 1H), 7.66 (m, 2H), 7.45–7.35 (m, 6H), 7.24 (m, 2H), 6.0 (2 d'd, 1H), 4.78 (m, 2H), 4.67 (m, 1H), 3.70 (s, 3H), 3.69 (s, 3H), 2.96 (s, 3H), 2.80–2.60 (m, 2H), 2.28 (m, 1H), 1.99 (m, 1H). MS ($CI^+$) m/e 553 $(M+H)^+$.

EXAMPLE 222B

N-{4-[4-(Pyrid-3-yl)-3,3-dimethylcyclohexyl]-2-phenylbenzoyl]-2-amino-4-(methylsulfonyl)butanoic Acid The desired compound was prepared by saponification of the product of Example 222A using the procedure of Example 211. $^1H$ NMR (300 MHz, DMSO-$d_6$) δ 8.55 (dt, 1H), 8.48 (d, 1H), 7.76, 7.73 (2 q's, 1H), 7.47–7.07 (m, 10H), 4.90 (m, 2H), 3.90 (m, 1H), 3.16 (s, 6H), 2.73 (m, 1H), 2.28 (m, 1H), 1.94 (m, 2H). MS ($APCI^+$) m/e 561 $(M+Na)^+$.

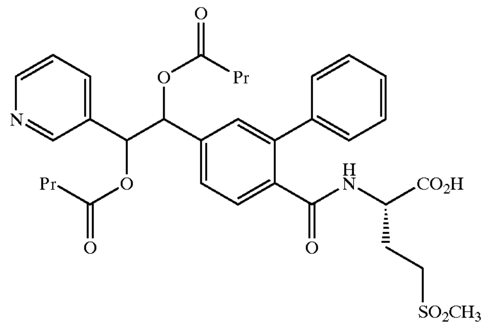

EXAMPLE 223

N-{4-[2-(Pyrid-3-yl)-1,2-propionoylethyl]-2-phenylbenzoyl]-2-amino-4-(methylsulfonyl)butanoic Acid

EXAMPLE 223A

N-{4-[2-(Pyrid-3-yl)-1,2-propionoylethyl]-2-phenylbenzoyl]-2-amino-4-(methylsulfonyl)butanoic Acid Methyl Ester To a solution of N-{4-[2-(pyrid-3-yl)-1,2-dihydroxyethyl]-2-phenylbenzoyl]-2-amino-4-(methylsulfonyl)butanoic acid methyl ester (71 mg, 0.134 mmol), prepared as in Example 221 A and 4-dimethylaminopyridine (3 mg) in dichloromethane (3 mL) was added propionic anhydride (0.066 mL, 0.402 mmol) and the reaction was stirred for 4 hours. The reaction mixture was diluted with ether (50 mL), washed with water and brine, dried over anhydrous magnesium sulfate, filtered, and concentrated in vacuo. The residue was purified by column chromatography (ethyl acetate) to give N-{4-[2-(pyrid-3-yl)-1,2-propionoylethyl]-2-phenylbenzoyl]-2-amino-4-(methylsulfonyl)butanoic acid methyl ester (79 mg, 90%).

$^1H$ NMR (300 MHz, $CDCl_3$) δ 8.52 (br s, 1H), 8.39 (br s, 1H), 7.60 (d, 1H), 7.55 (m, 1H), 7.41 (m, 3H), 7.26 (m, 4H), 7.07 (dd, 1H), 6.12 (m, 3H), 4.62 (m, 1H), 3.681, 3.684 (2 s's, 3H), 2.840, 2.843 (2 s's, 3H), 2.78–2.57 (m, 2H), 2.34 (m, 4H), 2.25 (m, 1H), 1.97 (m, 1H), 1.63 (m, 4H), 0.92 (m, 6H). MS ($CI^+$) m/e 653 $(M+H)^+$.

EXAMPLE 223B

N-{4-[2-(Pyrid-3-yl)-1,2-propionoylethyl]-2-phenylbenzoyl]-2-amino-4-(methylsulfonyl)butanoic Acid To a solution of the N-{4-[2-(pyrid-3-yl)-1,2-propionoylethyl]-2-phenylbenzoyl]-2-amino-4-(methylsulfonyl)butanoic acid methyl ester prepared in Example 223A (71 mg, 0.109 mmol) in anhydrous ether (2 mL) and THF (2 mL) was added solid potassium trimethylsilanolate (41 mg, 0.327 mmol). After 1 hour, hydrogen chloride (4.0 N in 1,4-dioxane, 0.1 mL) was added to the reaction mixture and the solvent was evaporated in vacuo to give N-{4-[2-(pyrid-3-yl)-1,2-propionoylethyl]-2-phenylbenzoyl]-2-amino-4-(methylsulfonyl)butanoic acid (82 mg, 100%). $^1H$ NMR (300 MHz, DMSO-$d_6$) δ 8.77–8.60 (m, 3H), 8.28 (br d, 1H), 7.88 (br s, 1H), 7.43–7.22 (m, 8H), 5.05 (d, 1H), 4.91 (d, 1H), 4.30 (m, 1H), 2.94 (s, 3H), 2.92–2.70 (m, 2H), 2.40–2.10 (m, 5H), 1.98 (m, 1H), 1.47 (m, 4H), 1.90–1.72 (m, 6H). MS ($FAB^-$) m/e 637 $(M-H)^-$ (only major peak above molecular weight 500).

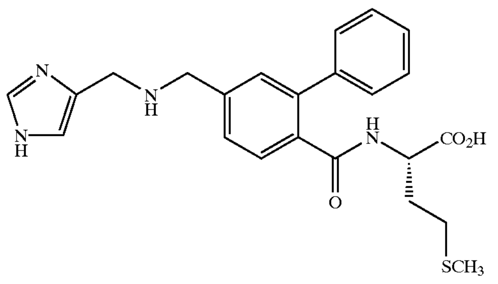

EXAMPLE 225

[4-(1H-Imidazol-4-ylmethylaminomethyl)-2-phenylbenzoyl]methionine

EXAMPLE 225A

4-Azidomethyl-1H-1-triphenylmethylimidazole

To a −10° C. solution in toluene (3 mL) of triphenylphosphine (787 mg, 3.0 mmol) was added a solution of diethylazodicarboxylate (0.47 mL, 3.0 mmol) in toluene (3 mL) dropwise over 10 minutes. A slurry of 4-hydroxymethyl-1H-1-triphenylmethylimidazole (684 mg, 2.0 mmol), prepared as in Example 167A, in dichloromethane (10 mL) was added and the reaction mixture was stirred for 30 minutes. A 1 M solution of $HN_3$ in toluene (10 mL, 10 mmol) was added, the cold bath was removed, and the reaction mixture was stirred for 1 hour. The reaction mixture was diluted with ethyl acetate and extracted with aqueous 1N sodium hydroxide, water and brine, dried over sodium sulfate, filtered, and concentrated in vacuo. Chromatography on silica gel (50% ethyl acetate-chloroform) gave 4-azidomethyl-1H-1-triphenylmethylimidazole (626 mg, 86%).

EXAMPLE 225B

[4-(1H-1-Triphenylmethylimidazol-4-ylmethylaminomethyl)-2-phenylbenzoyl]methionine Methyl Ester To a solution in THF (3 mL) of 4-azidomethyl-1H-1-triphenylmethylimidazole (220 mg, 0.60 mmol), prepared as in Example 225A, and (4-carboxyaldehyde-2-phenylbenzoyl)methionine methyl ester (186 mg, 0.50 mmol), prepared as in Example 160B, was added triphenylphosphine (157 mg, 0.60 mmol) and the reaction mixture was stirred for 1 hour and at 65° C. for 3 hours. The reaction mixture was cooled to ambient temperature and 2-propanol (2 mL) and sodium cyanoborohydride (94 mg, 1.5 mmol) were added. The reaction mixture was stirred for 0.5 hours and then was poured into aqueous 2N sodium hydroxide. The mixture was extracted twice with ethyl acetate. The combined organic extracts were washed with water, saturated aqueous sodium bicarbonate and brine, dried over sodium sulfate, filtered, and concentrated in vacuo. Chromatography on silica gel (50% methanol-chloroform) followed by another chromatography (ethyl acetate) gave [4-(1H-1-triphenylmethylimidazol-4-ylmethylaminomethyl)-2-phenylbenzoyl]methionine methyl ester (231 mg, 66%).

EXAMPLE 225C

[4-(1H-Imidazol-4-ylmethylaminomethyl)-2-phenylbenzoyl]methionine

The desired compound was prepared by saponification of the methyl ester and deprotection of the imidazole using the procedures of Examples 167E and 167D respectively. $^1H$ NMR (300 MHz, $D_2O$) δ 8.72 (s, 1H), 7.40–7.67 (m, 9H), 4.51 (s, 2H), 4.43 (s, 2H), 4.38 (m, 1H), 2.03 (s, 3H), 1.90–2.09 (m, 3H), 1.79 (m, 1H). MS (CI $NH_3$) m/e 439 $(M+H)^+$, 359, 227. Anal calcd for $C_{23}H_{26}N_4O_3S$+2.4 trifluoroacetic acid: C, 46.89, H, 4.02, N, 7.87. Found: C, 46.79; H, 4.16, N, 7.87.

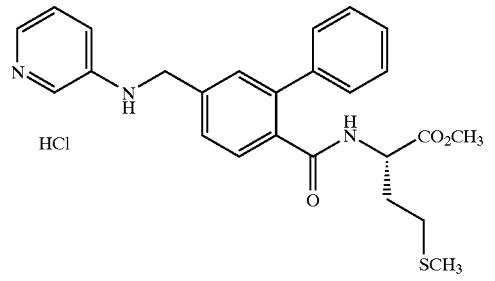

EXAMPLE 226

[4-(Pyrid-3-ylaminomethyl)-2-phenylbenzoyl]methionine Methyl Ester Hydrochloride

EXAMPLE 226A

[4-(Pyrid-3-ylaminomethyl)-2-phenylbenzoyl]methionine Methyl Ester

To a solution of (4-carboxyaldehyde-2-phenylbenzoyl)methionine methyl ester (2.5 g, 6.7 mmol), prepared as in Example 160B, in methanol (15 mL) was added 3-aminopyridine (941 mg, 10 mmol) and acetic acid (5 mL). The reaction mixture was stirred for 1 hour and sodium cyanoborohydride (0.85 g, 13.5 mmol) was added. The reaction mixture was stirred for 2 hours and additional sodium cyanoborohydride (0.42 g, 6.7 mmol) was added. Stirring was continued for an additional 2 hours and then the reaction mixture was poured into aqueous 1N sodium hydroxide. The mixture was extracted with ethyl acetate (3×). The combined organic extracts were washed with saturated aqueous sodium bicarbonate (2×), water (3×) and brine, dried over sodium sulfate, filtered, and concentrated in vacuo. Successive chromatographiss on silica gel (ethyl acetate) gave [4-(pyrid-3-ylaminomethyl)-2-phenylbenzoyl] methionine methyl ester (2.2 g, 73%).

EXAMPLE 226B

[4-(Pyrid-3-ylaminomethyl)-2-phenylbenzoyl] methionine Methyl Ester hydrochloride To a solution in ethyl acetate (20 mL) of [4-(pyrid-3-ylaminomethyl)-2-phenylbenzoyl]methionine methyl ester (2.96 g, 6.58 mmol), prepared as in Example 226A, was added HCl (1.0 M in ethyl acetate, 20 mL, 20 mmol) dropwise. The reaction mixture was stirred for 10 minutes and then was concentrated and the residue was azeotroped with toluene. Water (50 mL) was added and the milky mixture was concentrated and lyophilized to give [4-(pyrid-3-ylaminomethyl)-2-phenylbenzoyl]methionine methyl ester hydrochloride (3.04 g, 95%). $^1$H NMR (300 MHz, DMSO $d_6$) δ 8.66 (d, 1H), 8.11 (s, 1H), 8.02 (t, 1H), 7.84 (bt, 1H), 7.71 (m, 2H), 7.44 (m, 3H), 7.26 (m, 5H), 4.53 (bd, 2H), 4.36 (ddd, 1H), 3.64 (s, 3H), 2.23 (m, 2H), 1.98 (s, 3H), 3.85 (m, 2H). MS (CI $NH_3$) m/e 450 $(M+H)^+$, 374, 319, 287. Anal calcd for $C_{25}H_{28}ClN_3O_3S$+0.58 $H_2O$): C, 60.48; H, 5.92; N, 8.46; Cl, 7.29. Found: C, 60.49; H, 5.58; N, 8.40; Cl 7.84.

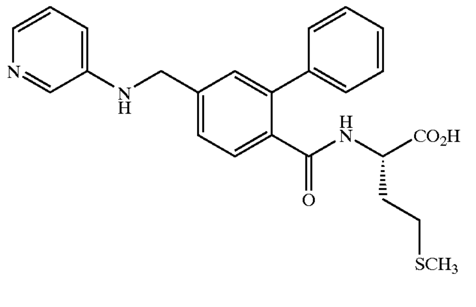

EXAMPLE 227

[4-(Pyrid-3-ylaminomethyl)-2-phenylbenzoyl] methionine

To a solution of [4-(pyrid-3-ylaminomethyl)-2-phenylbenzoyl]methionine methyl ester hydrochloride (72 mg, 0.16 mmol) in THF (3 mL) was added a solution of lithium hydroxide hydrate (13 mg, 0.32 mmol) in water (1 mL) and the reaction mixture was stirred for 30 minutes. The THF was evaporated in vacuo and the residue was taken up in aqueous 3N HCl. The solution was concentrated and the residue was purified by preparative HPLC (70% acetonitrile-0.1% aqueous trifluoroacetic acid) to give [4-(pyrid-3-ylaminomethyl)-2-phenylbenzoyl]methionine (39 mg, 50%). $^1$H NMR (300 MHz., DMSO-$d_6$) δ 8.48 (d, 1H), 8.17 (m, 1H), 7.97 (m, 1H), 7.56 (m, 2H), 7.29–7.44 (m, 7H), 4.51 (bd, 2H), 4.48 (ddd, 1H), 2.24 (m, 2H), 1.99 (s, 3H), 1.85 (m, 2H). MS (CI $NH_3$) m/e 436 $(M+H)^+$, 418, 319, 287, 194, 165. Anal calcd for $C_{24}H_{25}N_3O_3S$ (+1.26 TFA): C, 55.00; H, 4.57; N, 7.25. Found: C, 54.97; H, 4.58; N, 7.33.

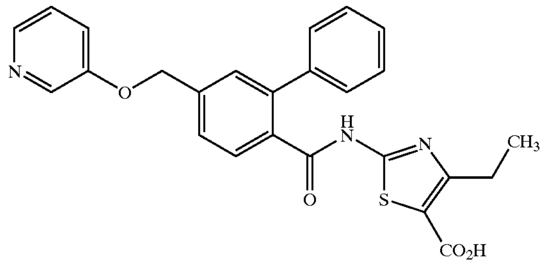

EXAMPLE 228

2-[4-(Pyrid-3-yloxymethyl)-2-phenylbenzoyl]-4-ethylthiazole-5-carboxylic Acid

EXAMPLE 228A

4-Methyl-2-phenylbenzoic Acid Methyl Ester

The desired compound was prepared according to the method of Example 157A, except substituting 4-methyl-2-hydroxybenzoic acid methyl ester for 2-iodoterephthalate.

EXAMPLE 228B

4-Bromomethyl-2-phenylbenzoic Acid Methyl Ester

A mixture of 4-methyl-2-phenylbenzoic acid methyl ester (2.26 g, 10 mmol), prepared as in Example 227B, N-bromosuccinimide (1.87 g, 10.5 mmol) and 2,2'-azobisisobutyronitrile (25 mg) in carbon tetrachloride (40 mL) was stirred at reflux for 7 hours. The reaction mixture was poured into ethyl acetate and extracted with water (2×), aqueous sodium hydrogen sulfite and brine, dried, filtered, and concentrated in vacuo. Chromatography on silica gel (10% ethyl acetate-hexane) gave 4-bromomethyl-2-phenylbenzoic acid methyl ester (2.57 g, 84%).

EXAMPLE 228C 4-(3-Pyridyloxymethyl)-2-phenylbenzoic Acid Methyl Ester

To a mechanically-stirred 0° C. solution of 3-hydroxypyridine (4.4 g, 46 mmol) in DME (20 mL) was added potassium hexamethyldisilazide (0.5 M in toluene, 88.5 mL, 44 mmol) and the mixture was stirred for 15 minutes. 18-Crown-6 (1.46 g, 5.5 mmol) and a solution of 4-bromomethyl-2-phenylbenzoic acid methyl ester (6.8 g, 22 mmol) in toluene (25 mL) was added and the reaction mixture was vigorously stirred overnight. The reaction mixture was poured into 200 mL of water and the layers were separated. The aqueous phase was extracted with 2 portions of ethyl acetate and the combined organic phases were extracted with water and brine, dried ($MgSO_4$), filtered and concentrated. The resulting oil was purified by flash chromatography (65% ethyl acetate-hexane) to give 4-(3-pyridyloxymethyl)-2-phenylbenzoic acid methyl ester (3.4 g).

EXAMPLE 228D 4-(3-Pyridyloxymethyl)-2-phenylbenzoic Acid

To a solution of 4-(3-pyridyloxymethyl)-2-phenylbenzoic acid methyl ester (3.4 g, 10.6 mmol), prepared as in Example 228C, in methanol (30 mL) was added aqueous 4N sodium hydroxide and the reaction mixture was heated at reflux for 6 hours. The methanol was distilled of in vacuo and the residue was taken up in water. The aqueous solution was taken to pH 4 with HCl and the resulting precipitate was filtered off and dried to give 4-(3-pyridyloxymethyl)-2-phenylbenzoic acid (3.2 g).

EXAMPLE 228E

2-[4-(Pyrid-3-yloxymethyl)-2-phenylbenzoyl]-4-ethylthiazole-5-carboxylic Acid Ethyl Ester To a −12° C. solution in DMF (2 mL) of 2-amino-4-ethylthiazole-5-carboxylic acid methyl ester (80 mg, 0.40 mmol), prepared as described in J. Chem. Soc. Perkin 1, 1982, 154, was added lithium hexamethyldisilazide (1.0 M in THF, 0.76 mL, 0.76 mmol) and the resulting yellow solution was stirred for 30 minutes. In a separate flask 4-(3-pyridyloxymethyl)-2-phenylbenzoic acid (101 mg, 0.33 mmol), prepared as in Example 228D and carbonyldiimidazole (60 mg, 0.37 mmol) were dissolved in THF and stirred for 1 hour. The resulting imidazolide solution was then added to the thiazole solution at −10° C. and the mixture was stirred for 30 minutes. The cold bath was then removed and stirring was continued for 30 minutes. The reaction mixture was quenched with saturated aqueous ammonium chloride and poured into water. The mixture was extracted twice with dichloromethane. The combine organic extracts were dried, filtered and concentrated. The solid residue was recrystallized from ethyl acetate-methanol to give 2-[4-(pyrid-3-yloxymethyl)-2-phenylbenzoyl]4-ethylthiazole-5-carboxylic acid ethyl ester (75 mg).

EXAMPLE 228 F

2-[4-(Pyrid-3-yloxymethyl)-2-phenylbenzoyl]-4-ethylthiazole-5-carboxylic Acid

To a solution in 1:1 THF-water (3 mL) of 2-[4-(pyrid-3-yloxymethyl)-2-phenylbenzoyl]4-ethylthiazole-5-carboxylic acid ethyl ester (72 mg, 0.15 mmol), prepared as in Example 228E, was added aqueous 4N NaOH (0.12 mL, 0.48 mmol) and the reaction mixture was heated at reflux for 5 hours. The reaction mixture was cooled to ambient temperature and the THF was evaporated. The residue was diluted with water and taken to pH 3.5 with HCl. The mixture was extracted with 20% isopropanol-chloroform (3×). The combined organic extracts were dried, filtered and concentrated in vacuo to give 2-[4-(pyrid-3-yloxymethyl)-2-phenylbenzoyl]-4-ethylthiazole-5-carboxylic (52 mg, 75%) as a white solid. $^1$H NMR (300 MHz., DMSO-$d_6$) δ 12.87 (bs, 1H), 12.81 (bs, 1H), 8.40 (d, 1H), 8.18 (d, 1H), 7.66 (d, 1H), 7.57 (m, 2H), 7.49 (ddd, 1H), 7.29–7.43 (m, 5H), 5.32 (s, 2H), 2.95 (q, 2H), 1.14 (t, 3H). MS (CI $NH_3$) m/e 460 $(M+H)^+$, 306. Anal calcd for $C_{25}H_{21}N_3O_4S$: C, 65.35; H, 4.61; N, 9.14. Found: C, 65.23; H, 4.52; N, 8.82.

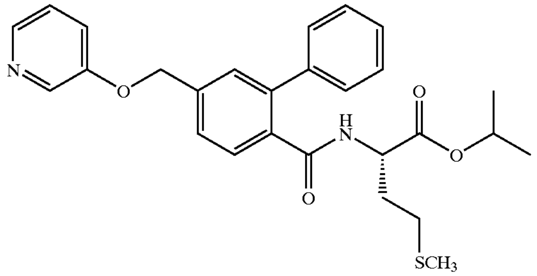

EXAMPLE 229

[4-(3-Pyridyloxymethyl)-2-phenylbenzoyl] methionine Isopropyl Ester

EXAMPLE 229A

N-tert-Butoxycarbonymethionine Isopropyl Ester

To a solution of N-tert-butoxycarbonylmethionine (2.49 g, 10 mmol) in DMF (50 mL) was added 3-hydroxy-1,2,3-benzotriazin-4(3H)-one (1.74 mg, 11 mmol), 4-dimethylaminopyridine (244 mg, 2.0 mmol),ethyl dimethylaminopropyl carbodiimide hydrochloride (2.11 g, 11 mmol) and isopropanol (2.3 mL, 30 mmol) and the reaction mixture was stirred for 27 hours. The reaction mixture was poured into water and extracted three times with ethyl acetate. The combined organic extracts were washed with aqueous sodium hydroxide (2×), aqueous HCl (2×), water (2×) and brine, dried, filtered, and concentrated in vacuo. Chromatography on silica gel (20% ethyl acetate-hexanes) gave N-tert-butoxycarbonymethionine isopropyl ester (1.26 g, 43%).

EXAMPLE 229B

Methionine Isopropyl Ester Hydrochloride

To a solution of N-tert-butoxycarbonymethionine isopropyl ester (291 mg, 1.0 mmol), prepared as in Example 229A, in dioxane (1 mL) was added 4N HCl-dioxane (4 mL) and the mixture was stirred for 3 hours. The reaction mixture was concentrated in vacuo to give methionine isopropyl ester hydrochloride (240 mg) which was used without further purification.

EXAMPLE 229C

[4-(3-Pyridyloxymethyl)-2-phenylbenzoyl] methionine Isopropyl Ester

The desired compound was prepared by coupling of 4-(3-pyridyloxymethyl)-2-phenylbenzoic acid, prepared as in Example 228D with methionine isopropyl ester hydrochloride, prepared as in Example 229B using the procedure of Example 186C. $^1$H NMR (300 MHz, $CD_3OD$) δ 8.70 (d, 1H), 8.46 (d, 1H), 8.31 (ddd, 1H), 8.01 (dd, 1H), 7.58 (m, 3H), 7.33–7.47 (m, 5H), 5.45 (s, 2H), 5.00 (heptet, 1H), 4.44 (m, 1H), 2.00–2.24 (m, 2H), 2.01 (s, 3H), 1.96 (m, 1H), 1.77 (m, 1H), 1.24 (d, 3H), 1.22 (d, 3H). MS (CI $NH_3$) m/e 479 $(M+H)^+$, 451, 419, 320, 288, 192. Anal calcd for $C_{27}H_{31}ClN_2O_4S$ (+0.60 H2O): C, 61.67; H, 6.17; N, 5.33. Found: C, 61.67; H, 6.17; N, 5.33.

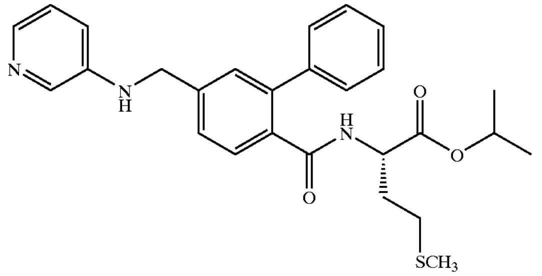

EXAMPLE 230

[4-(3-Pyridylaminomethyl)-2-phenylbenzoyl] methionine Isopropyl Ester

EXAMPLE 230A (4-Hydroxymethyl-2-phenylbenzoyl)methionine Isopropyl Ester

The desired compound was prepared according to the method of Example 229C, except substituting 4-hydroxymethylbenzoic acid, prepared as in Example 158D, for 4-(3-pyridyloxymethyl)-2-phenylbenzoic acid.

EXAMPLE 230B (4-Carboxaldehyde-2-phenylbenzoyl)methionine Isopropyl Ester

The desired compound was prepared by oxidation of the product of Example 230 using the procedure of Example 160B.

EXAMPLE 230C

[4-(3-Pyridylaminomethyl)-2-phenylbenzoyl] methionine Isopropyl Ester

The desired compound was prepared by reductive animation of the product of Example 230B with 3-aminopyridine according to the method of Example 226A. $^1$H NMR (300 MHz, $CD_3OD$) δ 7.97 (m, 1H), 7.86 (dd, 1H), 7.43–7.52 (m, 5H), 7.31–7.42 (m, 5H), 4.98 (heptet, 1H), 4.52 (s, 2H), 4.43 (m, 1H), 2.12 (m, 1H), 2.03 (m, 1H), 1.99 (s, 3H), 1.01 (m, 1H), 1.75 (m, 1H), 1.15 (d, 3H), 1.13 (d, 3H). MS (CI $NH_3$) m/e 478 $(M+H)^+$, 319, 287. Anal calcd for $C_{27}H_{32}ClN_3O_3S$ (+0.58 $H_2O$): C, 61.83; H, 6.37; N, 8.01. Found: C, 61.82; H, 6.04; N, 7.74.

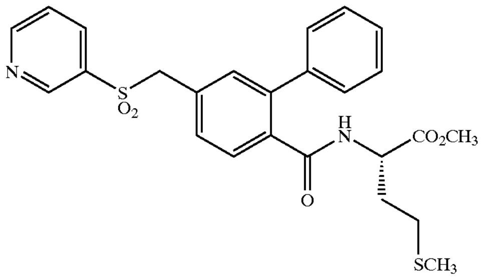

EXAMPLE 232

[4-(3-Pyridylsulfonylmethyl)-2-phenylbenzoyl] methionine Methyl Ester

EXAMPLE 232A

3-Dimethylthiocarbamoylpyridine

To a solution in DMF (50 mL) of 3-hydroxypyridine (4.76 g, 50 mmol) was added 1,1-diazabicyclo[2.2.2]octane (6.80 g, 150 mmol) and dimethylthiocarbamoyl chloride (18.5 g, 150 mmol) and the reaction mixture was stirred for 0.5 hours at ambient temperature and 18 hours at 55° C. The reaction mixture was cooled to ambient temperature and poured into ether. The ethereal solution was washed with aqueous 2N sodium hydroxide (2×), water (2×) and brine, dried, filtered and concentrated in vacuo. Chromatography on silica gel (1:1 ethyl acetate-hexane) gave 3-dimethylthiocarbamoylpyridine (5.46 g).

EXAMPLE 232B

3-Dimethylaminocarbonylthiopyridine

The desired compound was prepared by heating the 3-dimethylthiocarbamoylpyridine prepared in Example 232A at 250° C. for 1.25 hours followed by cooling and chromatography on silica gel (55%, then 75% ethyl acetate-hexane).

EXAMPLE 232C

3-Thiopyridine Sodium Salt

To a solution of 3-dimethylaminocarbonylthiopyridine (1.23 g, 6.7 mmol), prepared as in Example 232B, in methanol (10 mL) was added aqueous 2N sodium hydroxide and the reaction mixture was stirred at reflux for 2 hours. The reaction mixture was cooled to ambient temperature and evaporated to dryness to give 3-thiopyridine sodium salt as a brown solid which was used without further purification.

EXAMPLE 232D 4-(3-Pyridylthiomethyl)-2-phenylbenzoic Acid Methyl Ester

To a −10° C. suspension in DME (10 mL) of the 3-thiopyridine sodium salt prepared in Example 232C (450 mg, 3.25 mmol) was added catalytic 18-crown-6 and a solution of 3-bromomethyl-2-phenylbenzoic acid (916 mg, 8.3 mmol), prepared as in Example 228B, in DME (5 mL) over 5 minutes. The cold bath was allowed to warm to ambient temperature and the reaction mixture was stirred for 24 hours. The reaction mixture was poured into water and extracted with ethyl acetate (3×). The combined organic extracts were washed with brine, dried, filtered and concentrated. Chromatography on silica gel (40% ethyl acetate-hexane) gave 4-(3-pyridylthiomethyl)-2-phenylbenzoic acid methyl ester (611 mg, 60%).

EXAMPLE 232E 4-(3-Pyridylsulfonylmethyl)-2-phenylbenzoic Acid Methyl Ester

To a 0° C. solution of trifluoroacetic anhydride (2.5 mL, 17.9 mmol) in dichloromethane (10 mL) was added aqueous 30% hydrogen peroxide (0.56 mL, 5.4 mmol) and a solution of 4-(3-pyridylthiomethyl)-2-phenylbenzoic acid methyl ester (600 mg, 17.4 mmol), prepared as in Example 232D, in dichloromethane (5 mL). The reaction mixture was stirred for 1 hour, then the cold bath was removed and stirring was continued for 0.5 hour. The reaction mixture was partitioned between ether and aqueous 2N sodium hydroxide and the aqueous phase was extracted with ether. The combined ethereal layers were washed with aqueous 2N sodium bisulfite, water and brine, dried, filtered and concentrated in vacuo to give 4-(3-pyridylsulfonylmethyl)-2-phenylbenzoic acid methyl ester (620 mg) which was used without further purification.

EXAMPLE 232F

[4-(3-Pyridylsulfonylmethyl)-2-phenylbenzoyl] methionine Methyl Ester

The desired compound was prepared from 4-(3-pyridylsulfonylmethyl)-2-phenylbenzoic acid methyl ester by saponification of the methyl ester using the procedure of Example 228D, and coupling with methionine methyl ester according to the procedure of Example 186C. mp 152–154° C. $^1H$ NMR (300 MHz, $CDCl_3$) δ 8.95 (d, 1H), 8.87 (dd, 1H), 7.94 (ddd, 1H), 7.66 (d, 1H), 7.43 (m, 4H), 7.30 (m, 2H), 7.21 (dd, 1H), 7.10 (d, 1H), 5.91 (bd, 1H), 4.66 (ddd, 1H), 4.42 (s, 2H), 3.68 (s, 3H), 2.08 (t, 2H), 2.02 (s, 3H), 1.93 (m, 1H), 1.75 (m, 1H). MS (CI $NH_3$) m/e 516 $(M+NH_4)^+$, 499 $(M+H)^+$. Anal calc' for $C_{25}H_{26}N_2O_5S_2$: C, 60.22; H, 5.25; N, 5.62. Found: C, 60.28; H, 4.94; N, 5.56.

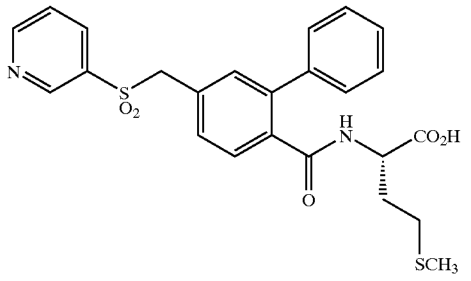

EXAMPLE 233

[4-(3-Pyridylsulfonylmethyl)-2-phenylbenzoyl] methionine

The desired compound was prepared by saponification of [4-(3-pyridylsulfonylmethyl)-2-phenylbenzoyl]methionine methyl ester, prepared as in Example 232, according to the method of Example 159. $^1H$ NMR (300 MHz., DMSO $d_6$) δ 12.68 (bs, 1H), 8.92 (m, 2H), 8.59 (bd, 1H), 8.18 (ddd, 1H), 7.68 (m, 1H), 7.32 (m, 7H), 7.18 (d, 1H), 4.94 (s, 1H), 4.29 (ddd, 1H), 2.22 (m, 2H), 1.99 (s, 3H), 1.85 (m, 2H). MS (CI $NH_3$) m/e 502 $(M+NH_4)^+$, (485 $M+H)^+$. Anal calcd for $C_{24}H_{24}N_2O_5S_2$ (+4.50 H2O): C, 58.51; H 5.09; N, 5.69. Found: C, 58.51; H, 4.82; N, 5.69.

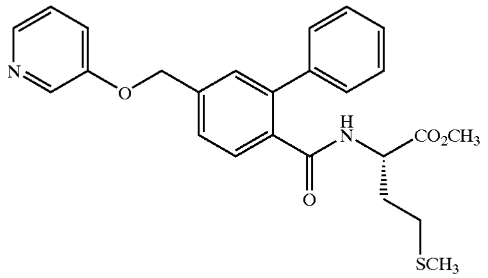

EXAMPLE 234

[4-(3-Pyridyloxymethyl)-2-phenylbenzoyl] methionine Methyl Ester

EXAMPLE 234A

4-Methyl-2-phenylbenzoic Acid

To a solution of 4-methyl-2-phenylbenzoic acid methyl ester (1.83 g, 8.09 mmol), prepared as in Example 227A, in methanol (16 mL) was added aqueous 4N sodium hydroxide (5 mL) and the reaction mixture was stirred for 60 hours, after which additional aqueous 4N sodium hydroxide (5 mL) was added and the mixture was heated at reflux for 5 hours. The reaction mixture was cooled to ambient temperature and the methanol was evaporated in vacuo. The aqueous residue was acidified with 4N sulfuric acid and extracted with ethyl acetate (3×). The combined organic extracts were dried, filtered, and concentrated in vacuo to give 4-methyl-2-phenylbenzoic acid (1.67 g) as a white solid.

EXAMPLE 234B

4-Bromomethyl-2-phenylbenzoic Acid

A mixture of 4-methyl-2-phenylbenzoic acid (1.66 g, 7.82 mmol), prepared as in Example 227B, N-bromosuccinimide (1.40 g, 8.21 mmol) and 2,2'-azobisisobutyronitrile (25 mg) in carbon tetrachloride (30 mL) was stirred at reflux for 1 hour. The reaction mixture was poured into ethyl acetate and extracted with water (3×) and brine, dried, filtered, and concentrated in vacuo to give 4-bromomethyl-2-phenylbenzoic acid (2.26 g).

EXAMPLE 234C (4-Bromomethyl-2-phenylbenzoyl)methionine Methyl Ester

To a solution in dichloromethane (25 mL) of 4-bromomethyl-2-phenylbenzoic acid (2.16 g, 7.42 mmol), prepared as in Example 234B, was added oxalyl chloride (0.84 mL, 965 mmol) and 2 drops on DMF and the reaction mixture was stirred for 2 hours. The reaction mixture was concentrated in vacuo and azeotroped with toluene. The residue was dissolved in dichloromethane (15 mL) and then was added to a solution in dichloromethane (15 mL) of methionine methyl ester hydrochloride (1.78 g, 8.90 mmol) and diisopropylethylamine (3.10 g, 17.81 mmol) (prepared at −10° C.) dropwise. The reaction mixture was stirred for 30 minutes and then was poured into ether and extracted with water, aqueous 3N HCl (2×) and brine, dried, filtered and concentrated in vacuo. Chromatography on silica gel (5% ethyl acetate-chloroforn) to give (4-bromomethyl-2-phenylbenzoyl)methionine methyl ester (2.42 g, 75%).

EXAMPLE 234D

[4-(3-Pyridyloxymethyl)-2-phenylbenzoyl] methionine Methyl Ester

To a 0° C. suspension in DMF (2 mL) of sodium hydride (90% in mineral oil, 38 mg, 0.95 mmol) was added a solution of 3-hydroxypyridine (95 mg, 1.0 mmol) in DMF (2 mL) dropwise and the mixture was stirred for 0.5 hours. A solution of (4-bromomethyl-2-phenylbenzoyl)methionine methyl ester (218 mg, 0.5 mmol) in DMF (1 mL) was added and the reaction mixture was stirred for 18 hours. The reaction mixture was poured into aqueous 2N sodium hydroxide and the mixture was extracted with ethyl acetate (3×). The combined organic extracts were dried, filtered and concentrated in vacuo. Chromatography on silica gel (60% ethyl acetate-hexanes, then ethyl acetate) gave [4-(3-pyridyloxymethyl)-2-phenylbenzoyl]methionine methyl ester (58 mg). $^1H$ NMR (300 MHz, DMSO-$d_6$) δ 12.66 (bs, 1H), 8.58 (d, 1H), 8.38 (d, 1H), 8.17 (dd, 1H), 7.30–7.56 (m, 10H), 5.29 (s, 2H), 4.29 (ddd, 1H), 2.23 (m, 2H), 1.98 (s, 3H), 1.84 (m, 2H). MS (CI $NH_3$) m/e 454 $(M+NH_4)^+$, 437

$(M+H)^+$. Anal calcd for $C_{24}H_{24}N_2O_4S$ (+0.41 $H_2O$): C, 64.94; H, 5.64; N, 6.31. Found: C, 64.94; H, 5.35; N,S 6.14.

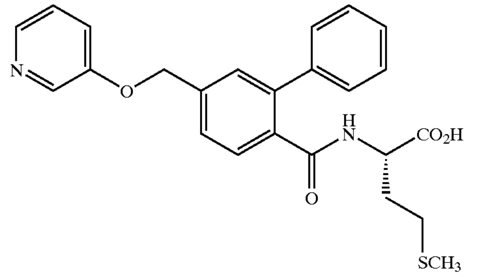

EXAMPLE 235

[4-(3-Pyridyloxymethyl)-2-phenylbenzoyl] methionine

The desired compound was prepared by saponification of [4-(3-pyridyloxymethyl)-2-phenylbenzoyl]methionine methyl ester, prepared as in Example 234, according to the procedure of Example 159. $^1H$ NMR (300 MHz., $CDCl_3$) δ 8.41 (dd, 1H), 8.26 (dd, 1H), 7.74 (d, 1H), 7.47 (dd, 1H), 7.43 (m, 6H), 7.14 (m, 2H), 5.92 (bd, 1H), 5.18 (s, 2H), 4.67 (ddd, 1H), 3.67 (s, 3H), 2.08 (t, 2H), 2.01 (s, 3H), 1.92 (m, 1H), 1.73 (m, 1H). MS (CI $NH_3$) m/e 451 $(M+H)^+$, 320, 288. Anal calcd for $C_{25}H_{26}N_2O_4S$: C, 66.65; H, 5.82; N, 6.22. Found: C, 66.53; H, 5.71; N, 6.16.

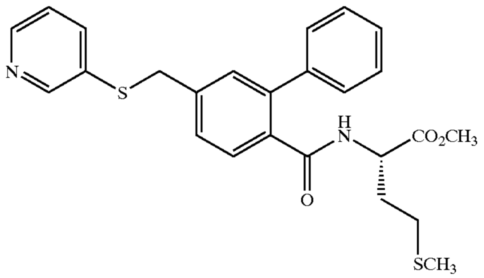

EXAMPLE 236

[4-(3-Pyridylthiomethyl)-2-phenylbenzoyl] methionine Methyl Ester

The desired compound was prepared by reaction of (4-bromomethyl-2-phenylbenzoyl)methionine methyl ester, prepared as in Example 234C, with 3-thiopyridine sodium salt, prepared as in Example 232C, according to the method of Example 234D. $^1H$ NMR (300 MHz, $CDCl_3$) δ 8.56 (m, 1H), 8.45, (dd, 1H), 7.66 (d, 1H), 7.38 (ddd, 1H), 7.30–7.47 (m, 6H), 7.21 (m, 2H), 5.87 (bd, 1H), 4.65 (ddd, 1H), 4.14 (s, 2H), 3.67 (s, 3H), 2.06 (m, 2H), 2.01 (s, 3H), 1.92 (m, 1H), 1.74 (m, 1H). MS (CI $NH_3$) m/e 467 $(M+H)^+$, 304. Anal calcd for $C_{25}H_{26}N_2O_3S_2$: C, 64.35; H, 5.62; N, 6.00. Found: C, 64.21; H, 5.61; N, 6.00.

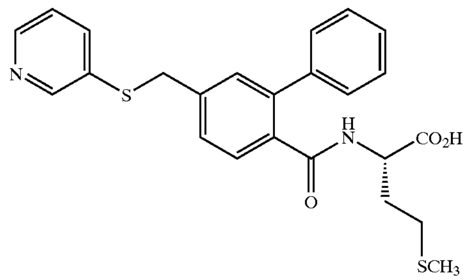

EXAMPLE 237

[4-(3-Pyridylthiomethyl)-2-phenylbenzoyl] methionine

The desired compound was prepared by saponification of [4-(3-pyridylthiomethyl)-2-phenylbenzoyl]methionine methyl ester, prepared as in Example 236 using the procedure of Example 159. $^1H$ nmr (300 MHz., DMSO-$d_6$): δ 8.54, m, 1H; 8.39, dd, 1H; 7.83, m, 2H; 7.29–7.47, m, 8H; 4.39, s, 2H; 4.24, m, 1H; 2.25, m, 2H; 1.98, s, 3H; 1.85, m, 2H. MS (CI $NH_3$): 453 ($MH^+$); 304, 194. EA: calc'd for $C_{24}H_{24}N_2O_3S_2$: C, 63.69; H, 5.34; N, 6.19; found C, 63.35; H, 5.20; N, 6.02.

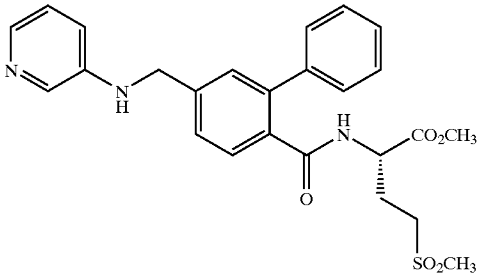

EXAMPLE 238

N-[4-(3-Pyridylaminomethyl)-2-phenylbenzoyl]-2-amino-4-(methylsulfonyl)butanoic Acid Methyl Ester

EXAMPLE 238A 2-amino-4-(methylsulfonyl)butanoic Acid Methyl Ester

To a 0° C. suspension of 2-amino-4-(methylsulfonyl) butanoic acid (5.05 g, 27.9 mmol) in methanol (50 mL) was added thionyl chloride (3.0 mL, 41.8 mmol). The cold bath was allowed to warm to ambient temperature and the reaction mixture was stirred for 48 hours. The reaction mixture was dilted with water and taken to pH 6 with solid potassium carbonate. The aqueous mixture was extracted with dichloromethane (3×). The combined organic extracts were dried, filtered and concentrated in vacuo to give the methyl ester (1.14 g).

EXAMPLE 238B (4-Carboxaldehyde-2-phenylbenzoyl)-2-amino-4-(methylsulfonyl)butanoic Acid Methyl Ester The desired compound was prepared by coupling of 2-amino-4-(methylsulfonyl)butanoic acid, prepared as in Example 238A, and 4-carboxaldehyde-2-phenylbenzoic acid, prepared as in Example 158E, according to the method of Example 186C, except that no triethylamine was required.

EXAMPLE 238C

N-[4-(3-Pyridylaminomethyl)-2-phenylbenzoyl]-2-amino-4-(methylsulfonyl)butanoic Acid Methyl Ester The desired compound was prepared by reductive animation of the product of Example 238B with 3-aminopyridine according to the method of Example 158G. $^1H$ NMR (300 MHz., $CDCl_3$) δ 8.09 (m, 1H), 8.00 (bd, 1H), 7.68 (d, 1H), 7.34–7.44 (m, 7H), 7.07 (dd, 1H), 6.88 (ddt, 1H), 5.99 (bd, 1H), 4.68 (ddd, 1H), 4.45 (bd, 2H), 4.24 (bs, 1H), 3.68 (s, 3H), 2.83 (s, 3H), 2.57–2.85 (m, 2H), 2.27 (m, 1H), 1.98 (m, 1H). MS (CI $NH_3^-$) m/e 482 $(M+H)^+$. Anal calcd for $C_{25}H_{27}N_3O_5S$: C, 62.36; H, 5.65; N, 8.73. Found: C, 61.88; H, 5.69; N, 8.60.

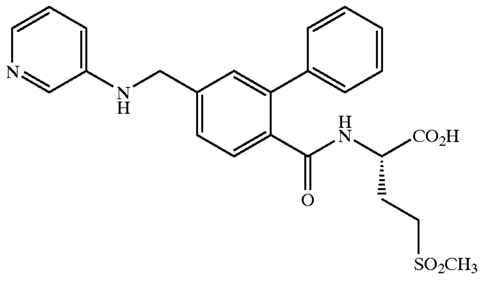

EXAMPLE 239

N-[4-(3-Pyridylaminomethyl)-2-phenylbenzoyl]-2-amino-4-(methylsulfonyl)butanoic Acid The desired compound was prepared by saponification of the product of Example 238C according to the procedure of Example 159. $^1H$ NMR (300 MHz., $D_2O$) δ 7.95 (m, 1H), 7.92 (m, 1H), 7.40–7.64 (m, 10H), 4.58 (s, 2H), 4.22 (ddd, 1H), 3.01 (s, 3H), 2.71 (m, 1H), 2.48 (m, 1H), 2.17 (m, 1H), 1.93 (m, 1H). MS FAB(+) m/e 468 $(M+H)^+$. FAB(−): 466 $(M-H)^-$.

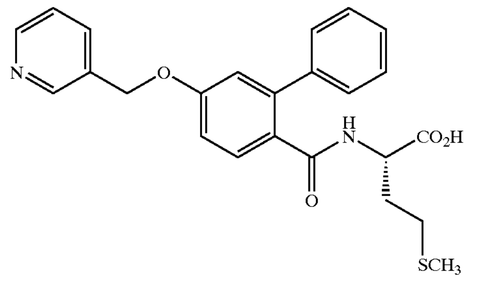

EXAMPLE 240

[4-(3-Pyridylmethyloxy)-2-phenylbenzoyl-]methionine

EXAMPLE 240A 2,4-Dihydroxybenzoic Acid Methyl Ester

To a solution in methanol (50 mL) of 2,4-dihydroxybenzoic acid (1.54 g, 10 mmol) was added sulfuric acid (0.5 mL) and trimethyl orthoformate (1.6 mL, 15 mmol) and the reaction mixture was stirred at reflux for 36 hours. The reaction mixture was cooled to ambient temperature and diluted with water. The methanol was evaporated in vacuo. The residue was diluted with water and extracted with ether (3×). The combined ether extracts were washed with saturated aqueous sodium bicarbonate (2×) and brine, dried, filtered and concentrated in vacuo to give 2,4-dihydroxybenzoic acid methyl ester (1.34 g) as a white solid.

EXAMPLE 240B 4-(3-Pyridylmethyoxy)-2-hydroxybenzoic Acid Methyl Ester

A mixture in acetone (40 mL) and water (10 mL) of 2,4-dihydroxybenzoic acid methyl ester (1.19 g, 7.08 mmol), prepared as in Example 240A, 3-chloromethylpyridine hydrochloride (2.32 g, 14.2 mmol) and potassium carbonate (2.44 g, 21.2 mmol) was stirred at reflux for 24 hours, then acetone (10 mL) and piperidine (1 g) were added and reflux was continued for 12 hours. The reaction mixture was cooled to ambient temperature, poured into water, and extracted with ethyl acetate (3×). The combined organic extracts were washed with aqueous sodium hydroxide and water, dried, filtered and concentrated in vacuo. The residue was recrystallized from aqueous ethanol to give 4-(3-pyridylmethyloxy)-2-hydroxybenzoic acid methyl ester (0.57 g, 31%).

EXAMPLE 240C 4-(3-Pyridylmethyloxy)-2-trifluoromethanesulfonyloxybenzoic Acid Methyl Ester To a −10° C. solution in pyridine (3 mL) of 4-(3-pyridylmethyloxy)-2-hydroxybenzoic acid methyl ester (0.56 g, 2.16 mmol), prepared as in Example 240B, was added triflic anhydride (0.73 mL, 4.32 mmol). The cold bath was allowed to warm to ambient temperature and the reaction mixture was stirred for 96 hours. The reaction mixture was poured into water, made basic with aqueous 2N sodium hydroxide and extracted with ethyl acetate. The combined organic extracts were washed with water (2×) and brine, dried, filtered and concentrated. Purification by chromatography on silica gel (60% ethyl acetate-hexanes) gave 4-(3-pyridylmethyloxy)-2-trifluoromethanesulfonyloxybenzoic acid methyl ester (519 mg, 61%).

EXAMPLE 240D 4-(3-Pyridylmethyloxy)-2-phenylbenzoic Acid Methyl Ester

The desired compound was prepared according to the method of Example 158A, except substituting 4-(3-pyridylmethyloxy)-2-trifluoromethanesulfonyloxybenzoic acid methyl ester, prepared as in Example 240C for 2-iodoterephthalate.

EXAMPLE 240E 4-(3-Pyridylmethyloxy)-2-phenylbenzoic Acid

The desired compound was prepared by saponification of the product of Example 240D using the procedure of Example 234A.

EXAMPLE 240F

[4-(3-Pyridylmethyloxy)-2-phenylbenzoyl]methionine Methyl Ester

The desired compound was prepared by according to the procedure used in step C of the preparation of compound 8, except substituting 4-(3-pyridylmethyloxy)-2-phenylbenzoic acid, prepared as in Example 240E, for 4-nitro-2-phenylbenzoic acid.

EXAMPLE 240G

[4-(3-Pyridylmethyloxy)-2-phenylbenzoyl]methionine

The desired compound was prepared by saponification of the compound of Example 240F using the procedure of Example 159. $^1$H NMR (300 MHz, DMSO-$d_6$) δ 8.69 (bs, 1H), 8.55 (bd, 1H), 8.39 (d, 1H), 7.88 (dt, 1H), 7.40 (m, 6H), 7.07 (dd, 1H), 7.03 (d, 1H), 5.17 (s, 2H), 4.28 (ddd, 1H), 2.25 (m, 2H), 2.00 (s, 3H), 1.84 (m, 2H). MS (CI, $NH_3$) m/e 454 $(M+NH_4)^+$, 437 $(M+H)^+$, 419, 320, 288. Anal calcd for $C_{24}H_{24}N_2O_4S$ (+0.23 $H_2O$): C, 65.42; H, 5.59; N, 5.99. Found: C, 65.41; H, 5.42; N, 5.99.

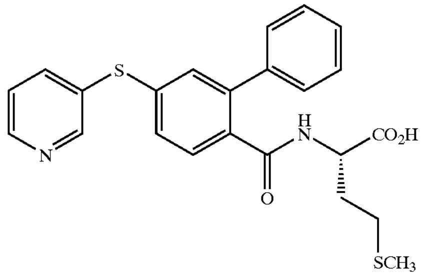

EXAMPLE 241

[4-(3-Pyridylthio-2-phenylbenzoyl]methionine

EXAMPLE 241A

3-Pyridylthio-2-phenylbenzoic acid tert-Butyl Ester

To a mixture in DMF (2 mL) of 4-nitro-2-phenylbenzoic acid tert-butyl ester (403 mg, 1.35 mmol), prepared by esterification of 4-nitro-2-phenylbenzoic acid (compound 8, step B), and 3-thiopyridine sodium salt (224 mg, 1.68 mmol), prepared as in 232C, was stirred at 100° C. for 60 hours. The reaction mixture was cooled to ambient temperature and diluted with saturated aqueous sodium bicarbonate. The mixture was extracted with ether (3×). The combined ether extracts were dried over magnesium sulfate, filtered, and concentrated in vacuo to give a brown oil. Chromatography on silica gel (10% ethyl acetate-hexanes) gave 3-pyridylthio-2-phenylbenzoic acid tert-butyl ester as a colorless oil (248 mg, 51%).

EXAMPLE 241B

3-Pyridylthio-2-phenylbenzoic Acid

To a 0° C. solution in dichloromethane (1 mL) of 3-pyridylthio-2-phenylbenzoic acid tert-butyl ester (245 mg, 0.67 mmol), prepared as in Example 241 A, and triethylsilane (390 mg, 3.4 mmol) was added trifluoroacetic acid (1.53 g, 13.4 mmol) and the reaction mixture was warmed to ambient temperature and stirred for 18 hours. The reaction mixture was concentrated and azeotroped with toluene (3×) to give 3-pyridylthio-2-phenylbenzoic acid (209 mg) as a translucent film which was used without further purification.

EXAMPLE 241C

[4-(3-Pyridyl)thio-2-phenylbenzoyl]methionine

The desired compound was prepared according to the method of Examples 240F and G, except substituting 3-pyridylthio-2-phenylbenzoic acid for 4-(3-pyridyloxymethyl)-2-phenylbenzoic acid. $^1$H NMR (300 MHz, DMSO-$d_6$) d 1.60 (m, 1H), 1.85 (m, 1H), 2.00 (s, 3H), 2.10 (m, 2H), 4.50 (m, 1H), 5.85 (m, 1H), 7.25–7.40 (m, 8H), 7.60–7.80 (m, 2H), 8.45 (dd, 1H), 8.65 (dd, 1H). MS (CI, $NH_3$) m/e 407 $(M+H)^+$.

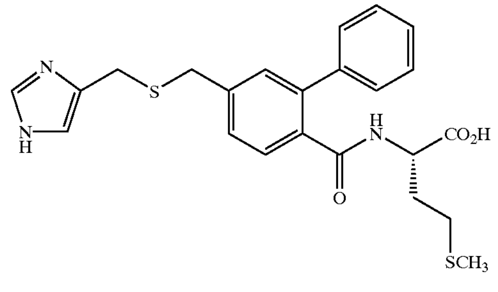

EXAMPLE 242

[4-(1H-Imidazol-4-ylmethylthiomethyl)-2-phenylbenzoyl]methionine

EXAMPLE 242A 1H-1-Triphenylmethylimidazol-4-ylmethylthiolacetic Acid

The desired compound was prepared according to the method of Example 225A, except substituting thiolacetic acid for $HN_3$.

EXAMPLE 242B 1H-1-Triphenylmethylimidazol-4-ylmethylthiol Sodium Salt

A mixture of 1H-1-triphenylmethylimidazol-4-ylmethylthiolacetic acid (1.80 g, 4.5 mmol), prepared as in Example 242A, and sodium hydroxide (204 mg, 5.0 mmol) in 3:1 methanol-water was stirred for 18 hours at ambient temperature. The resulting tan solid was filtered and dried to give 1H-1-triphenylmethylimidazol-3-ylmethylthiol sodium salt which was used without further purification.

EXAMPLE 242C 4-(1H-1-Triphenylmethylimadazol-4-ylmethyl)-2-phenylbenzoic Acid Methyl Ester A solution in DME of 1H-1-triphenylmethylimidazol-4-ylmethylthiol sodium salt (946 mg, 2.5 mmol), prepared as in Example 242B, and 4-bromomethyl-2-phenylbenzoic acid methyl ester (305 mg, 1.0 mmol) was stirred at 50° C. for 18 hours. The reaction mixture was concentrated and the residue purified by chromatography on silica gel (1:1 ethyl acetate-hexanes) to give 4-(1H-1-triphenylmethylimadazol-4-ylmethyl)-2-phenylbenzoic acid methyl ester.

EXAMPLE 242D 4-(1H-1-Triphenylmethylimadazol-4-ylmethyl)-2-phenylbenzoic Acid

A mixture of 4-(1H-1-triphenylmethylimadazol-3-ylmethyl)-2-phenylbenzoic acid methyl ester (200 mg, 0.34 mmol) and sodium hydroxide (69 mg, 1.7 mmol) in 3:1 methanol-water (0.18 mL) was stirred at reflux for 8 hours.

The reaction mixture was concentrated and the residue taken up in water. The aqueous solution was taken to pH 5 and extracted. The organic extracts were dried over magnesium sulfate, filtered and concentrated in vacuo to give 4-(1H-1-triphenylmethylimadazol-4-ylmethyl)-2-phenylbenzoic acid (160 mg) as a solid.

EXAMPLE 242E

[4-(1H-1-Triphenylmethylimdazol-4-ylmethylthiomethyl)-2-phenylbenzoyl]methionine Methyl Ester The desired compound was prepared by according to the procedure used in step C of the preparation of compound 8, except substituting 4-(1H-1-triphenylmethylimadazol-3-ylmethyl)-2-phenylbenzoic acid, prepared as in Example 242C, for 4-nitro-2-phenylbenzoic acid.

EXAMPLE 242E

[4-(1H-1-Triphenylmethylimidazol-4-ylmethylthiomethyl)-2-phenylbenzoyl Methionine The desired compound was prepared by saponification of [4-(1H-imidazol-4-ylmethylthiomethyl)-2-phenylbenzoyl] methionine methyl ester, prepared as in Example 242E, using the procedure of Example 165.

EXAMPLE 242F

[4-(1H-imidazol-4-ylmethylthiomethyl)-2-phenylbenzoyl]methionine

The desired compound was prepared by deprotection of the compound of Example 242E using the procedure of Example 167D. $^{1}$H NMR (300 MHz, DMSO-$d_6$) δ 1.85 (m, 1H), 2.00 (s, 3H), 2.20–2.40 (m, 2H), 3.80 (s, 2H), 3.85 (s, 2H), 4.30 (m, 1H), 7.40 (m, 8H), 7.50 (s, 2H), 8.50 (d, 1H), 8.90 (s, 1H), 13.0 (br s, 1H). MS (CI, $NH_3$) m/e 456 $(M+H)^+$.

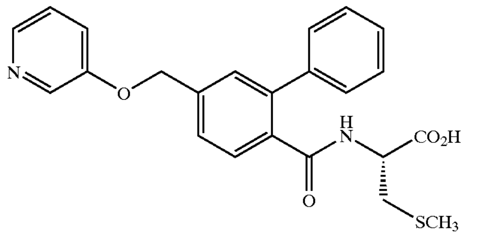

EXAMPLE 243

[4-(3-Pyridyloxymethyl)-2-phenylbenzoyl]cysteine

EXAMPLE 243A

Cysteine Methyl Ester Hydrochloride

To a 0° C. slurry in methanol of L-cysteine (1.23 g, 9.1 mmol) was added thionyl chloride (0.75 mL, 10.3 mmol). The cold bath was removed and the reaction mixture was stirred for 15 minutes and then overnight at 45° C. The reaction mixture was cooled to ambient temperature and concentrated to a white solid. The white solid was azeotroped with methanol to give cysteine methyl ester hydrochloride.

EXAMPLE 243B

[4-(3-Pyridyloxymethyl)-2-phenylbenzoyl]cysteine Methyl Ester

The desired compound was prepared by coupling of cysteine methyl ester hydrochloride and 4-(3-pyridylmethyloxy)-2-phenylbenzoic acid, prepared as in Example 238D using the procedure of Example 184A.

EXAMPLE 243C

[4-(3-Pyridyloxymethyl)-2-phenylbenzoyl]cysteine

The desired compound was prepared by saponification of [4-(3-pyridyloxymethyl)-2-phenylbenzoyl]cysteine methyl ester, prepared as in Example 242E, using the procedure of Example 165. $^{1}$H NMR (300 MHz, DMSO-$d_6$) d 8.77 (d, 1H), 0.58 (d, 1H), 8.35 (d, 1H), 7.85 (dd, 1H), 7.63 (dd, 1H), 7.52 (m, 5H), 7.36 (m, 3H), 5.38 (s, 2H), 4.44 (m, 1H), 3.90 (dd, 1H), 3.72 (dd, 1H), 2.05 (s 3H). MS (DCI-$NH_3$) m/e 423 $(M+H)^+$, 440 $(M+NH_4)^+$.

EXAMPLE 244

N-[4-(3-Pyridyloxymethyl)-2-phenylbenzoyl] norleucine

The desired compound was prepared according to the method of Example 243, except substituting norleucine methyl ester hydrochloride for cysteine methyl ester hydrochloride. $^{1}$H NMR (300 MHz, DMSO-$d_6$) δ 8.60 (d, 1H), 8.53 (d, 1H), 8.37 (d, 1H), 7.90 (dd, 1H), 7.70 (dd, 1H), 7.52 (d, 1H), 7.51 (s, 1H), 7.42 (m, 3H), 7.38 (m, 3H), 5.38 (s, 2H), 4.16 (m, 1H), 1.60 (m, 2H), 1.20 (m, 2H), 1.10 (m, 2H), 0.82 (t, 3H). MS (DCI-$NH_3$) m/e 419 $(M+H)^+$, 436 $(M+NH_4)^+$.

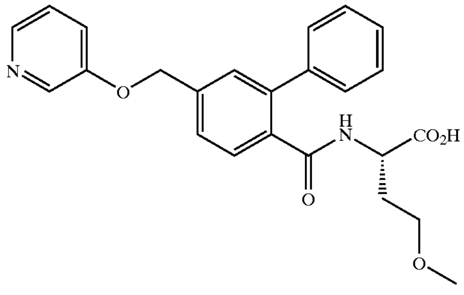

EXAMPLE 245

N-[4-(3-Pyridyloxymethyl)-2-phenylbenzoyl]-2-amino-3-methoxybuiyric Acid

The desired compound was prepared according to the method of Example 243, except substituting L-2-amino-3-methoxybutyric acid methyl ester hydrochloride for cysteine methyl ester hydrochloride. $^{1}$H NMR (300 MHz, DMSO-$d_6$) δ 8.57 (d, 1H), 8.42 (d, 1H), 8.22 (d, 1H), 7.60 (dd, 1H), 7.50 (m, 2H), 7.40 (m, 7H), 5.33 (s, 2H), 4.24 (m, 1H), 3.17 (s, 3H), 3.15 (m, 2H), 1.93 (m, 1H), 1.77 (m, 1H). MS (APCI) m/e 421 $(M+H)^+$, 419 $(M-H)^-$. Anal calcd for $C_{24}H_{24}N_2O_5 \cdot 0.5\ H_2O$: C, 67.12; H, 5.87; N, 6.52. Found: C, 67.38; H, 5.57; N, 6.72.

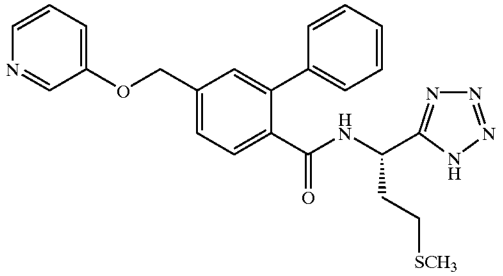

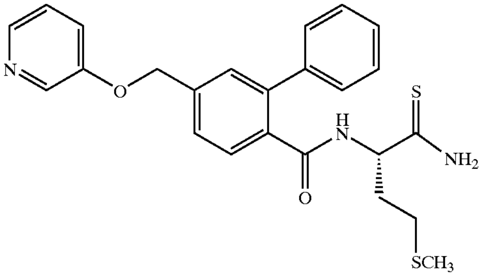

EXAMPLE 246

N-[3-(Methylthio)-1-(1H-tetrazol-5-yl)propyl]-4-(3-pyridyloxymethyl)-2-phenylbenzamide

EXAMPLE 246A

5-[-1-(N-tert-Butoxycarbonylamino-3-thiomethylpropyl-1H-1-(2-cyanoethyl)tetrazole To a solution in THF (40 mL) of 1-(N-tertbutoxycarbonyl) amino-4-thiomethylbutyric acid N-(2-cyanoethyl)amide (1.2 g, 4.0 mmol) was added triphenyphosphine (2.1 g, 8.0 mmol), diethylazodicarboxylate (1.35 mL, 8.5 mmol) and trimethylsilylazide (1.05 mL, 7.9 mmol) and the reaction mixture was stirred overnight at ambient temperature. The reaction mixture was concentrated in vacuo and the residue was purified by chromatography on silica gel (7.5% ether-dichloromethane) to give the desired compound as a soft, off-white powder.

EXAMPLE 246B

5-[-1-Amino-3-thiomethylpropyl]-1H-1-(2-cyanoethyl)tetrazole Hydrochloride

The compound of Example 246A (370 mg) and thiophenol (0.20 mL) were dissolved in 1M HCl in ethyl acetate (10 mL) and the reaction mixture was stirred for 2 hours at ambient temperature. The reaction mixture was concentrated and the residue was partitioned between ether and water. The aqueous phase was washed twice with ether and then was frozen and lyophilized to give the desired compound (233 mg) as a tan glass.

EXAMPLE 246C

N-[3-(Methylthio)-1-(1H-tetrazol-5-yl)propyl]-4-(3-pyridyloxymethyl)-2-phenylbenzamide The desired compound was prepared according to the method of Example 243, except substituting 5-[-1-amino-3-thiomethylpropyl]-1H-1-(2-cyanoethyl)tetrazole hydrochloride, prepared as in Example 246B, for cysteine methyl ester hydrochloride. $^1$H NMR (300 MHz, DMSO-$d_6$) δ 8.96 (d, 1H), 8.37 (d, 4H), 8.17 (dd, 1H), 7.50 (m, 4H), 7.30 (m, 6H), 5.19 (s, 2H), 5.18 (m, 1H), 2.28 (m, 2H), 2.06 (m, 2H), 2.00 (s, 3H). MS (DCI-$NH_3$) m/e 461 $(M+H)^+$. Anal calcd for $C_{24}H_{24}N_6O_2S.0.5H_2O$: C, 61.39; H, 5.37; N, 17.90. Found: C, 61.24; H, 5.26; N, 17.80.

EXAMPLE 247

[4-(3-Pyridyloxymethyl)-2-phenylbenzoyl] methionine Thioamide

EXAMPLE 247A

N-tert-Butoxycarbonylmethionine Thioamide

To a 0° C. solution in THF (160 mL) of N-tert-butoxycarbonylmethionine (4.0.g, 16 mmol) was added N-methylmorpholine (1.84 mL, 16.2 mmol) and isobutyl chloroformate (2.1 mL, 16.2 mmol) and the reaction mixture was stirred for 20 minutes at 0° C. Concentrated $NH_4OH$ (7 mL) was added and stirring was continued at 0° C. for 2 hours. The reaction mixture was concentrated in vacuo and the residue was partitioned between ethyl acetate and aqueous 1M $H_3PO_4$. The organic phase was washed twice with saturated aqueous sodium bicarbonate (2×) and brine, dried, filtered and concentrated to give N-tert-butoxycarbonylmethionine amide (3.43 g) as a white solid.

EXAMPLE 247B

N-tert-Butoxycarbonylmethionine Thioamide

To a solution in THF (200 mL) of N-tert-butoxycarbonylmethionine amide (3.4 g, 14 mmol), prepared as in Example 247A, was added Lawesson's reagent (8.3 g, 20 mmol) and THF (50 mL) and the reaction mixture was stirred 2 days at ambient temperature. The reaction mixture was concentrated in vacuo to give an off-white solid (12.2 g). Chromatography on silica gel (33% ethyl acetate-hexanes) to give N-tert-butoxycarbonylmethionine thioamide (1.1 g) as a colorless glass.

EXAMPLE 247C

[4-(3-Pyridyloxymethyl)-2-phenylbenzoyl] methionine Amide

N-tert-butoxycarbonylmethionine thioamide (140 mg, 0.53 mmol), prepared as in Example 247B, was dissolved in 4N HCl-dioxane (5 mL) and the mixture was stirred for 1 hour. The reaction mixture was concentrated in vacuo to give methionine thioamide which was coupled with 4-(3-pyridylmethyloxy)-2-phenylbenzoic acid, prepared as in Example 238D using the procedure of Example 184A. $^1$H NMR ($CDCl_3$) δ 8.40 (dd, 1H), 8.25 (dd, 1H), 8.00 (br s, 1H), 7.70 (d, 1H), 7.42 (m, 6H), 7.33 (br s, 1H), 7.25 (m, 3H), 6.49 (d, 2H), 5.20 (s, 2H), 4.95 (m, 1H), 2.30 (m, 2H), 2.06 (s, 3H), 1.90 (m, 2H). MS (DCI-$NH_3$) m/e 452 $(M+H)^+$.

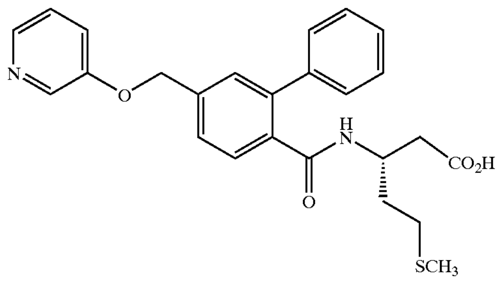

EXAMPLE 248

N-[4-(3-Pyridyloxymethyl)-2-phenylbenzoyl]-2-amino-5-thiomethylpentanoic Acid

EXAMPLE 248A

N-tert-Butoxycarbonylmethionine Diazo Ketone

To a 0° C. solution in THF (40 mL) of N-tert-butoxycarbonylmethionine (2.0 g, 8.0 mmol) was added N-methylmorpholine (0.93 mL, 8.5 mmol) and isobutyl chloroformate (1.05 mL, 8.1 mmol). The reaction mixture was stirred for 20 minutes at 0° C. and then was filtered through a plug of Celite. To the filtrate was added $TMSCHN_2$ (2.0 M in hexane, 8.0 mL, 16 mmol) and acetonitrile (17 mL). The reaction mixture was stirred for 2.5 hours at 0° C., then additional $TMSCHN_2$ solution (5–10 mL) was added, the cold bath was removed and stirring was continued overnight. The reaction mixture was concentrated in vacuo and the residue was partitioned between ethyl acetate and saturated aqueous sodium bicarbonate. The organic phase was washed with saturated aqueous sodium bicarbonate and brine, dried over sodium sulfate, filtered and concentrated. Chromatography on silica gel (33% ethyl acetate-hexane) gave the desired compound (465 mg) as a thick orange oil.

EXAMPLE 248B

N-tert-Butoxycarbonyl-2-amino-5-thiomethylpentanoic Acid Methyl Ester

To absolution in methanol (20 mL) of N-tert-butoxycarbonylmethionine diazo ketone (460 mg, 1.68 mmol), prepared as in Example 248A, was added a solution of silver benzoate (104 mg, 0.45 mmol) in triethylamine (2 mL) and the reaction mixture was stirred for 2.5 hours. The reaction mixture was concentrated in vacuo and the residue was purified by chromatography on silica gel (20% ethyl acetate-hexane) to give N-tert-butoxycarbonyl-2-amino-5-thiomethylpentanoic acid methyl ester (405 mg) as a thick oil.

EXAMPLE 248C

N-[4-(3-Pyridyloxymethyl)-2-phenylbenzoyl]-2-amino-5-thiomethylpentanoic Acid Methyl Ester The desired compound was prepared according to the method of Example 247C, except substituting N-tert-butoxycarbonyl-2-amino-5-thiomethylpentanoic acid methyl ester, prepared as in Example 248B, for N-tert-butoxycarbonylmethionine thioamide.

EXAMPLE 248D

N-[4-(3-Pyridyloxymethyl)-2-phenylbenzoyl]2-amino-5-thiomethylpentanoic Acid

The desired compound was prepared by saponification of the compound of Example 248C using the method of Example 165. $^1$H NMR (300 MHz, DMSO-$d_6$) δ 8.56 (d, 1H), 8.36 (d, 1H), 8.20 (d, 1H), 7.75 (dd, 1H), 7.57 (m, 3H), 7.44 (m, 6H), 5.19 (s, 2H), 2.38 (m, 2H), 2.25 (m, 2H), 2.05 (s, 3H), 1.68 (m, 2H). MS (APCI) m/e 451 $(M+H)^+$. Anal calcd for $C_{25}H_{26}N_2O_4S.1.25H_2O$: C, 63.47; H, 6.07; N, 5.92. Found: C, 63.21; H, 5.82; N, 5.68.

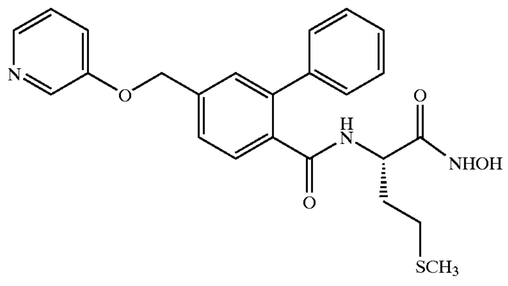

EXAMPLE 249

[4-(3-Pyridyloxymethyl)-2-phenylbenzoyl]methionine Hydroxamic Acid

A slurry in methanol of [4-(3-pyridyloxymethyl)-2-phenylbenzoyl]methionine methyl ester (143 mg, 0.32 mmol), prepared as in Example 234, hydroxylamine hydrochloride (26 mg, 0.37 mmol) and potassium carbonate (106 mg, 0.77 mmol) was stirred at ambient temperature for 4 hours, then a solution of potassium hydroxide in methanol (0.33 mL) was added and stirring was continued overnight at ambient temperature. The reaction mixture was filtered and the filtrate was diluted with water and taken to pH 4. The aqueous phase was extracted with 3:1 chloroform-isopropanol. The organic extract was washed with brine, dried over sodium sulfate, filtered, and concentrated in vacuo. Purification by prep HPLC gave [4-(3-pyridyloxymethyl)-2-phenylbenzoyl]methionine hydroxamic acid (92 mg). $^1$H NMR (300 MHz, DMSO-$d_6$) δ 10.58 (br s, 1H), 8.58 (d, 1H), 8.40 (d, 1H), 8.33 (d, 1H), 7.80 (dd, 1H), 7.60 (dd, 1H), 7.50 (m, 3H), 7.36 (m, 5H), 5.35 (s, 2H), 4.20 (m, 1H), 2.12 (m, 2H), 1.98 (s, 3H), 1.70 (m, 2H). MS (APCI) m/e 452 $(M+H)^+$.

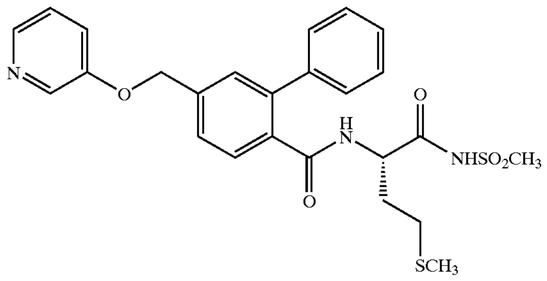

EXAMPLE 250

[4-(3-Pyridyloxymethyl)-2-phenylbenzoyl]methionine Methylsulfonimide

A solution in THF (5 mL) of [4-(3-pyridyloxymethyl)-2-phenylbenzoyl]methionine (143 mg, 0.32 mmol), prepared as in Example 235, and carbonyldiimidazole (136 mg, 0.84 mmol) was stirred overnight at 45–50° C. A 1.6 mL aliquot of the reaction mixture was removed and to it was added methanesulfonamide (78 mg, 0.82 mmol) and DBU (0.12 mL, 0.80 mmol) and the mixture was stirred overnight at ambient temperature. The reaction mixture was partitioned between ethty acetate and pH 4 water. The organic phase was washed with water and brine, dried over sodium sulfate, filtered and concentrated in vacuo. Chromatographyl on silica gel (98.5:1.5:0.5 chloroform-methanol-acetic acid) gave [4-(3-pyridyloxymethyl)-2-phenylbenzoyl]methionine methylsulfonyl amide. (31 mg after azeotroping and lyophilization). $^{1}$H NMR (300 MHz, DMSO-$d_6$) δ 8.62 (d, 1H), 8.39 (d, 1H), 8.18 (d, 1H), 7.50 (m, 4H), 7.36 (m, 6H), 5.28 (s, 2H), 4.27 (m, 1H), 3.21 (s, 3H), 2.20 (t, 2H), 2.02 (s, 3H), 1.81 (m, 2H). MS (APCI) m/e 514 $(M+H)^+$. Anal calcd for $C_{25}H_{27}N_3O_3S_2$.1.25$H_2O$: C, 56.01; H, 5.55; N, 7.84. Found: C, 55.72; H, 5.08; N, 8.18.

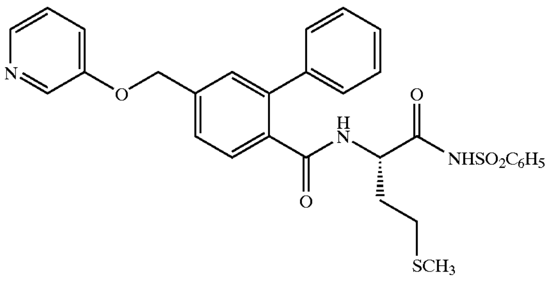

EXAMPLE 251

[4-(3-Pyridyloxymethyl)-2-phenylbenzoyl]methionine Phenylsulfonimide

The desired compound was prepared by addition of phenylsulfonamide and DBU to a second 1.6 mL aliquot of the reaction mixture used in Example 250. $^{1}$H NMR (DMSO-$d_6$) δ 8.49 (d, 1H), 8.38 (d, 1H), 8.18 (d, 1H), 7.91 (d, 2H), 7.73 (m, 1H), 7.63 (m, 2H), 7.46 (m, 3H), 7.41 (d, 1H), 7.32 (m, 6H), 5.27 (s, 2H), 4.25 (m, 1H), 2.09 (t, 2H), 1.97 (s, 3H), 1.70 (m, 2H). MS (ESI) m/e 576 $(M+H)^+$.

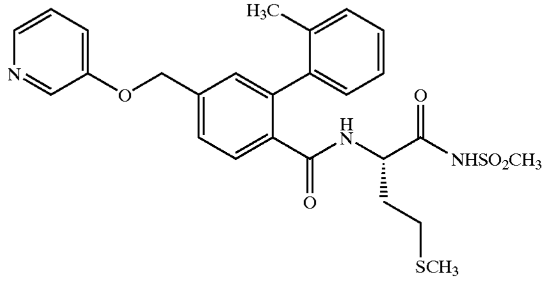

EXAMPLE 252

[4-(3-Pyridyloxymethyl)-2-(2-methylphenyl)benzoyl]methionine Methylsulfonimide

EXAMPLE 252A

N-tert-Butoxycarbonylmethionine Methylsulfonimide

The desired compound was prepared according to the method of Example 250, except substituting N-tert-butoxycarbonymethionine for [4-(3-pyridyloxymethyl)-2-phenylbenzoyl]methionine methyl ester.

EXAMPLE 252

[4-(3-Pyridyloxymethyl)-2-(2-methylphenyl)benzoyl]methionine Methylsulfonimide

The desired compound was prepared according to the method of Example 247C, except substituting N-tert-butoxycarbonylmethionine methylsulfonyl amide, prepared as in Example 252A and 4-(3-pyridylmethyloxy)-2-(2-methylphenyl)benzoic acid, prepared as in Example 204E for N-tert-butoxycarbonylmethionine thioamide and 4-(3-pyridylmethyloxy)-2-phenylbenzoic acid respectively. $^{1}$H NMR (300 MHz, DMSO-$d_6$) δ 8.38 (d, 1H), 8.30 (br s, 1H), 8.18 (d, 1H), 7.57 (m, 2H), 7.45 (ddd, 1H), 7.35 (dd, 1H), 7.30 (br s, 1H), 7.20 (m, 4H), 5.27 (s, 2H), 4.20 (m, 1H), 3.17 (s, 3H), 2.18–1.98 (envelope, 8H), 1.77 (m, 2H). MS (APCI) m/e 528 $(M+H)^+$. Anal calcd for $C_{26}H_{29}N_3O_5S_2$.0.25$H_2O$: C, 58.68; H, 5.59; N, 7.90. Found: C, 58.62; H, 5.46; N, 7.84.

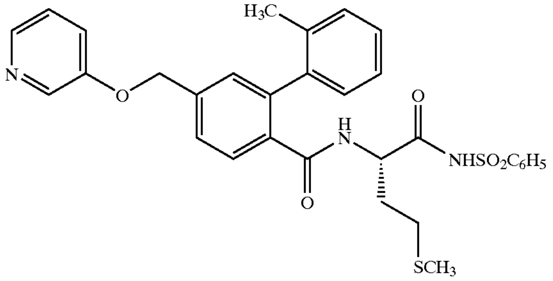

EXAMPLE 253

[4-(3-Pyridyloxymethyl)-2-(2-methylphenyl)benzoyl]methionine Phenylsulfonimide

The desired compound was prepared according to the method of Example 252, except substituting benzenesulfonamide for methylsulfonamide. $^{1}$H NMR (300 MHz, DMSO-$d_6$) δ 8.38 (d, 1H), 8.18 (br s, 1H), 8.18 (d, 1H), 7.86 (m, 2H), 7.73 (m, 1H), 7.62 (m, 2H), 7.50 (m, 2H), 7.45 (ddd, 1H), 7.35 (dd, 1H), 7.30–7.00 (envelope, 6H), 5.27 (s, 2H), 4.17 (m, 1H), 1.98 (m, 8H), 1.60 (m, 2H). MS (APCI) 590 $(M+H)^+$. Anal calcd for $C_{31}H_{31}N_3O_5S_2$.0.5$H_2O$: C, 62.19; H, 5.39; N, 7.02. Found: C, 62.31; H, 5.03; N, 6.83.

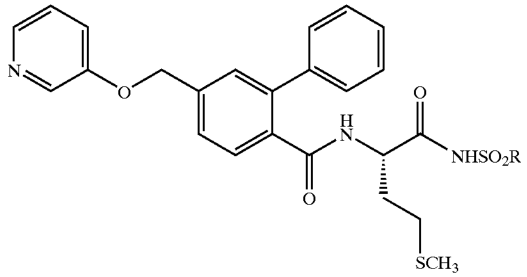

EXAMPLES 254–271

Examples 254–271 were prepared by stirring a solution in dichloromethane of [4-(3-pyridyloxymethyl)-2-phenylbenzoyl]methionine methyl ester, prepared as in Example 234, or [4-(3-pyridyloxymethyl)-2-phenylbenzoyl]methionine, prepared as in Example 235, with $H_2NSO_2R_2$, (2.6 equiv.), ethyl dimethylaminopropyl carbodiimide hydrochloride (1.1 equiv.) and 4-dimethylaminopyridine (0.5 equiv.). Non-commercial sulfonamides were prepared by reaction of sulfonyl chloride $R_2SO_2Cl$ and concentrated $NH_4OH$ in THF.

| Example | R | Physical Data $^1$H NMR (300 MHz, DMSO-d6) MS (APCI) m/e |
|---|---|---|
| 254 | isopropyl | $^1$H NMR δ 8.67 (d, 1H), 8.38 (d, 1H), 8.19 (d, 1H), 7.50 (m, 4H), 7.35 (m, 5H), 5.30 (s, 2H), 4.26 (m, 1H), 3.60 (m, 1H), 2.22 (m, 2H), 2.02 (s, 3H), 1.81 (m, 2H), 1.28 (d, 3H), 1.20 (d, 3H). MS 542 $(M + H)^+$. |
| 255 | 3-tolyl | $^1$H NMR δ 8.55 (d, 1H), 8.38 (d, 1H), 8.18 (dd, 1H), 7.72 (m, 2H), 7.50 (m, 5H), 7.40 (d, 1H), 7.15 (m, 3H), 7.27 (m, 3H), 5.29 (s, 2H), 4.26 (m, 1H), 2.40 (s, 3H), 2.08 (m, 2H), 1.95 (s, 3H), 1.68 (m, 2H). MS 590 (M + H)+. |
| 256 | 4-fluorophenyl | $^1$H NMR δ 8.57 (d, 1H), 8.38 (d, 1H), 8.18 (d, 1H), 7.98 (m, 2H), 7.55–7.25 (envelope, 12H), 5.29 (s, 2H), 4.23 (m, 1H), 2.11 (m, 2H), 1.96 (s, 3H), 1.70 (m, 2H). MS (APCI) m/e 594 $(M + H)^+$. |
| 257 | 4-chlorophenyl | $^1$H NMR δ 8.60 (d, 1H), 8.40 (d, 1H), 8.20 (d, 1H), 7.98 (m, 2H), 7.93 (d, 2H), 7.72 (d, 2H), 7.50 (m, 3H), 7.42, 7.34, 7.27 (all m, total 7H), 5.30 (s, 2H), 4.23 (m, 1H), 2.13 (m, 2H), 1.96 (s, 3H), 1.70 (m, 2H). MS 610, 612 $(M + H)^+$. |
| 258 | 4-bromophenyl | $^1$H NMR δ 8.60 (d, 1H), 8.40 (d, 1H), 8.20 (d, 1H), 7.85 (m, 4H), 7.50 (m, 3H), 7.42, 7.34, 7.27 (all m, total 7H), 5.30 (s, 2H), 4.23 (m, 1H), 2.13 (m, 2H), 1.96 (s, 3H), 1.70 (m, 2H). 654, 656 $(M + H)^+$. |
| 259 | 3-thienyl | $^1$H NMR δ 8.58 (d, 1H), 8.39 (d, 1H), 8.19 (d, 1H), 8.06 (dd, 1H), 7.78 (dd, 1H), 7.50 (m, 3H), 7.43 (d, 1H), 7.35 (m, 6H), 7.22 (dd, 1H), 5.30 (s, 2H), 4.23 (m, 1H), 2.10 (m, 2H), 1.96 (s, 3H), 1.70 (m, 2H). MS 582 $(M + H)^+$. |
| 260 | 4-trifluoro-methylphenyl | $^1$H NMR 5 8.55 (br d, 1H), 8.38 (d, 1H), 8.18 (d, 1H), 8.10 (d, 2H), 8.01 (d, 2H), 7.72 (d, 2H), 7.50 (m, 3H), 7.40 (d, 1H), 7.35 (m, 3H), 7.25 (m, 3H), 5.30 (s; 2H), 4.23 (m, 1H), 2.15 (m, 2H), 1.96 (s, 3H), 1.75 (m, 2H). MS 644 $(M + H)^+$. |
| 261 | 4-ethylphenyl | $^1$H NMR δ 8.38 (d, 1H), 8.17 (dd, 1H), 7.78 (m, 2H), 7.50–7.25 (envelope, 13 H), 5.28 (s, 2H), 4.22 (m, 1H), 2.70 (m, 2H), 2.07 (m, 2H), 1.95 (s, 3H), 1.70 (m, 2H), 1.20 (m, 3H). MS 604 $(M + H)^+$. |
| 262 | 4-tert-butylphenyl | $^1$H NMR δ 8.53 (br d, 1H), 8.38 (d, 1H), 8.18 (d, 1H), 7.83 (d, 2H), 7.63 (d, 2H), 7.48 (m, 3H), 7.41 (d, 1H), 7.35 (m, 3H), 7.30 (m, 3H), 5.29 (s, 2H), 4.24 (m, 1H), 2.08 (m, 2H), 1.95 (s, 3H), 1.70 (m, 2H), 1.53 (s, 9H). MS 632 $(M + H)^+$. |
| 263 | 4-methoxyphenyl | $^1$H NMR δ 8.53 (br d, 1H), 8.38 (d, 1H), 8.18 (d, 1H), 7.83 (d, 2H), 7.50 (m, 3H), 7.42 (d, 1H), 7.35 (m, 3H), 7.30 (m, 3H), 7.15 (d, 2H), 5.29 (s, 2H), 4.23 (m, 1H), 3.85 (s, 3H), 2.08 (m, 2H), 1.96 (s, 3H), 1.67 (m, 2H). MS 606 $(M + H)^+$. |
| 264 | 4-tolyl | $^1$H NMR δ 8.52 (br d, 1H), 8.38 (d, 1H), 8.18 (d, 1H), 7.80 (d, 2H), 7.45 (m, 6H), 7.30 (m, 6H), 5.27 (s, 2H), 4.25 (m, 1H), 2.40 (s, 3H), 2.08 (t, 2H), 1.97 (s, 3H), 1.70 (m, 2H). MS 590 $(M + H)^+$. |
| 265 | trifluoromethyl | $^1$H NMR δ 8.69 (d, 1H), 8.42 (d, 1H), 8.06 (dd, 1H), 7.95 (d, 1H), 7.80 (dd, 1H), 7.52 (m, 3H), 7.44 (m, 2H), 7.36 (m, 3H), 5.40 (s, 2H), 4.20 (m, 1H), 2.19 (m, 2H), 1.98 (s, 3H), 1.85, 1.75 (m, m, total 2H). |
| 266 | benzyl | $^1$H NMR δ 8.62 (br d, 1H), 8.50 (d, 1H), 8.27 (br d, 1H), 7.72 (dd, 1H), 7.53 (m, 4H), 7.38 (m, 5H), 5.35 (s, 2H), 4.30 (m, 1H), 3.30 (m, 2H), 2.23 (m, 2H), 2.01 (s, 3H), 1.82 (m, 2H).. MS 590 $(M + H)^+$. |
| 267 | ethyl | $^1$H NMR δ 8.62 (br d, 1H), 8.50 (d, 1H), 8.27 (br d, 1H), 7.72 (dd, 1H), 7.53 (m, 4H), 7.38 (m, 5H), 5.35 (s, 2H), 4.30 (m, 1H), 3.30 (m, 2H), 2.23 (m, 2H), 2.01 (s, 3H), 1.82 (m, 2H). MS 528 $(M + H)^+$. |
| 268 | 1-naphthyl | $^1$H NMR δ 8.57 (d, 1H), 8.43 (br s, 1H), 8.40 (d, 1H), 8.33 (d, 2H), 8.24 (br d, 1H), 8.15 (d, 1H), 7.70 (m, 4H), 7.46 (m, 3H), 7.36 (d, 1H), 7.27 (m, 5H), 5.28 (s, 2H), 4.25 (m, 1H), 1.90 (m, 2H), 1.82 (s, 3H), 1.57 (m, 1H), 1.40 (m, 1H). MS 626 $(M + H)^+$. |
| 269 | 2-naphthyl | $^1$H NMR δ 8.62 (s, 1H), 8.54 (br d, 1H), 8.36 (d, 1H), 8.23 (d, 1H), 8.16 (m, 2H), 8.09 (d, 1H), 7.85 (dd, 1H), 7.74 (m, 2H), 7.44 (m, 3H), 7.33 (m, 4H), 7.15 (m, 3H), 5.26 (s, 2H), 4.27 (m, 1H), 2.10 (m, 2H), 1.93 (s, 3H), 1.70 (m, 2H). MS MS 626 $(M + H)^+$. |
| 270 | 4-nitrophenyl | $^1$H NMR δ 8.57 (d, 1H), 8.41 (m, 3H), 8.20 (dd, 1H), 8.16 (d, 2H), 7.50 (m, 3H), 7.41 (d, 1H), 7.34 (m, 3H), 7.26 (m, 3H), 5.28 (s, 2H), 4.24 (m, 1H), 2.16 |

-continued

| Example | R | Physical Data $^1H$ NMR (300 MHz, DMSO-d6) MS (APCI) m/e |
|---|---|---|
| | | (m, 2H), 1.97 (s, 3H), 1.72 (m, 2H). MS 621 $(M + H)^+$. |
| 271 | 2-tolyl | $^1H$ NMR δ 8.55 (d, 1H), 8.51 (br s, 1H), 8.29 (br d, 1H), 7.96 (dd, 1H), 7.73 (br dd, 1H), 7.60 (m, 1H), 7.50 (m, 3H), 7.41 (m, 3H), 7.32 (m, 2H), 7.26 (m, 3H), 5.33 (s, 2H), 4.30 (m, 1H), 2.58 (s, 3H), 2.10 (m, 2H), 1.97 (s, 3H), 1.70 (m, 2H). MS 590 $(M + H)^+$. |

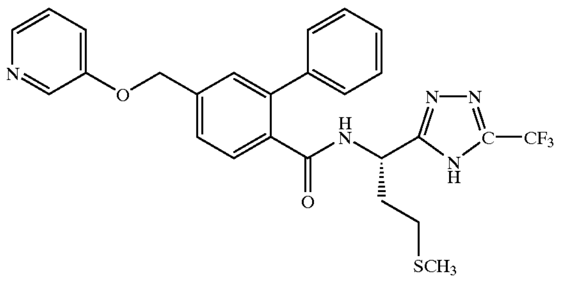

EXAMPLE 272

N-[3-(Methylthio)-1-(2-trifluoromethyl-1H-1,3,4-triazol-5-yl)propyl]-4-(3-pyridyloxymethyl)-2-phenylbenzamide

EXAMPLE 272A 1-(N-tert-Butoxycarbony)-3-thiomethylpropyl-1-amidazone Hydroidide

To a solution in acetone (4 mL) of N-tert-butoxycarbonylmethionine amide (940 mg, 3.56 mmol), prepared as in Example 247A, was added iodomethane (0.265 mL, 4.26 mmol). The reaction mixture was stirred for 2.5 hours, additional iodomethane (0.5 mL, 8.0 mmol) was added and stirring was continued for 2 hours. The reaction mixture was diluted with ether and filtered, and the filtrated was concentrated in vacuo to give a yellow solid. The solid was taken up in methanol (3 mL) and cooled to 0° C. and a solution of hydrazine (0.115 mL, 3.67 mmol) in methanol (3 mL) was added dropwise over about 5 minutes. The reaction mixture was stirred for 4 hours. The reaction mixture was diluted with ether and the cloudy solution was left standing in the refrigerator overnight. The supernatant was decanted from a pink oil which separated off and the oil was dried under high vacuum to give 1-(N-tert-butoxycarbony)-3-thiomethylpropyl-1-amidazone hydroidide (850 mg) as a pink glass.

EXAMPLE 272B

2-[1-(N-tert-Butoxycarbonylamino)-2-thiomethylpropyl]-5-trifluoromethyl-(1H-1,3,4) triazole To a 0° C. slurry of 1-(N-tert-butoxycarbony)-3-thiomethylpropyl-1-amidazone hydroidide (780 mg, 2.0 mmol), prepared as in Example 246A, in toluene (20 mL) was added pyridine (0.54 mL, 6.7 mmol) and trifluoroacetic anhydride (0.26 mL, 1.8 mmol) and the reaction mixture was stirred and warmed to ambient temperature over 4.5 hours during which a substantial amount of solid formed. THF (30 mL) was added to form a solution and the reaction mixture was stirred for 2.5 days. The reaction mixture was diluted with ethyl acetate and washed with aqueous 1 M $H_3PO_4$ and brine, dried over sodium sulfate, filtered and concentrated in vacuo. Chromatography on silica gel (25% ethyl acetate-hexane) gave the desired compound (76 mg).

EXAMPLE 272C

2-[1-amino-2-thiomethylpropyl]-5-trifluoromethyl-(1H-1,3,4)triazole Hydrochloride The desired compound was prepared by treatment of the product of Example 247B with 4N HCl-dioxane using the procedure of Example 247C.

EXAMPLE 272D

N-[3-(Methylthio)-1-(2-trifluoromethyl-1H-1,3,4-triazol-5-yl)propyl]-4-(3-pyridyloxymethyl)-2-phenylbenzamide The desired compound was prepared by coupling of 2-[1-amino-2-thiomethylpropyl]-5-trifluoromethyl-(1H-1,3,4)triazole hydrochloride, prepared as in Example 251C and 4-(3-pyridylmethyloxy)-2-phenylbenzoic acid, prepared as in Example 238D using the method of Example 184A. $^1H$ NMR (300 MHz, DMSO-$d_6$) δ 8.66 (br d, 1H), 8.38 (d, 1H), 8.18 (d, 1H), 7.61 (d, 1H), 7.53 (dd, 1H), 7.45 (ddd, 1H), 7.35 (dd, 1H), 7.28 (br s, 1H), 7.20–7.00 (envelope, 4H), 5.27 (s, 2H), 5.06 (m, 1H), 2.20 (m, 2H), 2.00 (m, 8H). MS (ESI) m/e 542 $(M+H)^+$. Anal calcd for $C_{27}H_{26}F_3N_5O_2.0.5H_2O$: C, 58.90; H, 4.94; N, 12.72. Found: C, 58.85; H, 4.56; N, 12.84.

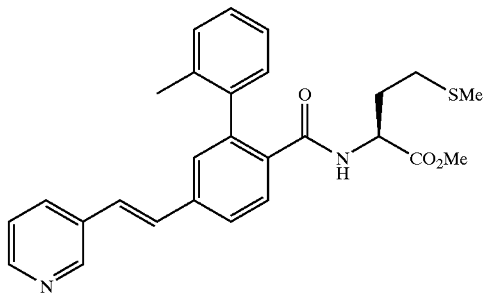

EXAMPLE 275

{4-[2-(Pyrid-3-yl)ethenyl]-2-(2-methylphenyl)benzoyl}methionine Methyl Ester

The desired compound was prepared according to the method of Example 210, except substituting 2-methylphenylboronic acid for phenylboronic acid. $^1H$ NMR (300 MHz, $CDCl_3$) δ 8.74 (d, 1H), 8.52 (d, 1H), 8.01 (dd, 1H), 7.88 (dd, 1H), 7.62 (dd, 1H), 7.40–7.28 (m, 6H), 7.19, 7.18 (2 d's, 2H), 5.95 (d, 1H), 4.65 (m, 1H), 3.67 (s, 3H), 2.23, 2.11 (2 s's, 3H), 2.10–2.00 (m, 2H), 2.03 (s, 3H), 1.89 (m, 1H), 1.61 (m, 1H). MS ($CI^+$) m/e 484 $(M+H)^+$.

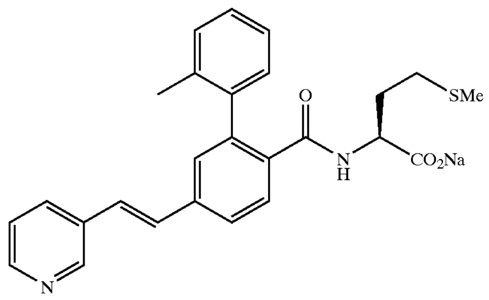

EXAMPLE 276

{4-[2-(Pyrid-3-yl)ethenyl]-2-(2-methylphenyl) benzoyl}methionine Sodium Salt

To a solution of {4-[2-(pyrid-3-yl)ethenyl]-2-(2-methylphenyl)benzoyl}methionine methyl ester, prepared as in Example 274, (3.285 g, 7.13 mmol) in methanol (10 mL) was added a solution of sodium hydroxide (0.979 N, 7.35 mL). After 15 hours, the solvent was evaporated in vacuo to give the title compound (3.35 g, 100%). $^1H$ NMR (300 MHz, DMSO-$d_6$) δ 8.79 (d, 1H), 8.46 (dd, 1H), 8.05 (dt, 1H), 7.70–7.53 (m, 3H), 7.48–7.37 (m, 4H), 7.27–7.18 (m, 3H), 6.97 (m, 1H), 3.50 (m, 1H), 2.21, 2.03 (2 s's, 3H), 2.00–1.92 (m, 2H), 1.93 (s, 3H), 1.70 (m, 1H), 1.58 (m, 1H). MS (APCI) m/e 445 $(M-H)^-$ as the acid form.

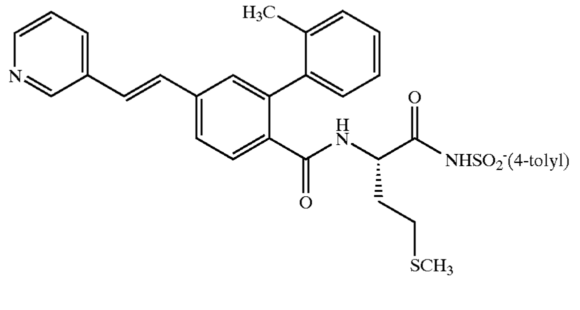

EXAMPLE 277

{4-[2-(Pyrid-3-yl)ethenyl]-2-(2-methylphenyl) benzoyl}methionine 4-Tolylsulfonamide The desired compound was prepared according to the method of Example 262, except substituting {4-[2-(pyrid-3-yl)ethenyl]-2-(2-methylphenyl)benzoyl}methionine, prepared as in Example 276, for [4-(3-pyridyloxymethyl)-2-phenylbenzoyl]methionine. $^1H$ NMR (500 MHz, DMSO-$d_6$) δ 8.50 (d, 1H), 8.13 (d, 1H), 8.07 (br s, 1H), 7.78 (d, 2H), 7.68 (d, 1H), 7.62 (m, 1H), 7.57–7.40 (envelope 7H), 7.24–7.04 (envelope, 4H), 4.19 (m, 1H), 2.41 (s, 3H), 2.17–1.95 (envelope, 5H), 1.94 (s, 3H), 1.64 (m, 2H). MS (APCI) m/e 600 $(M+H)^+$, 617 $(M+NH4)^+$. Anal calcd for $C_{33}H_{33}N_3O_4S_2.0.6\ H_2O$: C, 64.92; H, 5.65; N, 6.88. Found: C, 64.95, H, 5.62; N, 6.19.

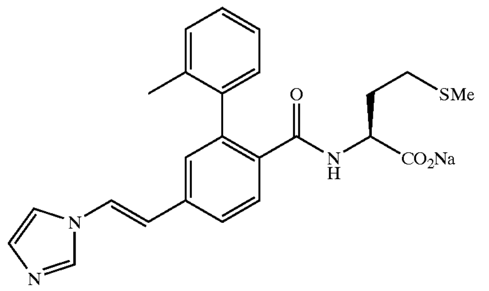

EXAMPLE 278

{4-[2-(1H-1-Imidazolyl)ethenyl]-2-(2-methylphenyl) benzoyl}methionine Sodium Salt

EXAMPLE 278A

{4-[2-(1H-1-Imidazolyl)ethenyl]-2-(2-methylphenyl) benzoyl}methionine Methyl Ester The desired compound was prepared according to the method of Example 274, except substituting 1-vinylimidizole for 3-vinylpyridine.

EXAMPLE 278B

{4-[2-(1H-1-Imidazolylethenyl]-2-(2-methylphenyl) benzoyl}methionine Sodium Salt The desired compound was prepared by saponification of the compound of Example 277A according to the method of Example 276. $^1H$ NMR (300 MHz, DMSO-$d_6$): δ 8.00 (d, 1H), 7.95 (d, 1H), 7.69 (s, 1H), 7.61–7.51 (m, 2H), 7.37–6.92 (m, 8H), 2.20, 2.00 (2 s's, 3H), 2.00–1.92 (m, 2H), 1.93 (s, 3H), 1.70 (m, 1H), 1.58 (m, 1H). MS (APCI) m/e 434 $(M-H)^-$ as the acid form.

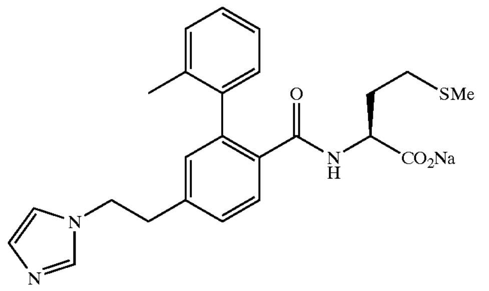

EXAMPLE 279

{4-[2-(1H-1-Imidazolyl)ethyl]-2-(2-methylphenyl) benzoyl}methionine Sodium Salt

EXAMPLE 279A

{4-[2-(1H-1-Imidazolyl)ethyl]-2-(2-methylphenyl) benzoyl}methionine Methyl Ester A mixture of the product of Example 278A (171 mg, 0.38 mmol) and palladium (10%) on carbon (489 mg, 0.46 mmol of palladium) in methanol was flushed with hydrogen, and stirred under a hydrogen balloon for 5 hours. The mixture was then filtered through Celite, rinsed, with ethyl acetate, and concentrated in vacuo. The residue was purified by column chromatography (5% methanol-ethyl acetate) to give the title compound (97 mg, 56%).

EXAMPLE 279B

{4-[2-(1H-1-Imidazolyl)ethyl]-2-(2-methylphenyl) benzoyl}methionine Sodium Salt

The desired compound was prepared by saponification of the product of Example 279A using the procedure of Example 276. $^1H$ NMR (300 MHz, DMSO-$d_6$) δ 7.62 (s, 1H), 7.51 (s, 1H), 7.44 (d, 1H), 7.36–7.14 (m, 5H), 6.98–6.82 (m, 3H). MS (APCI-) m/e 436 $(M-H)^-$ as the acid form.

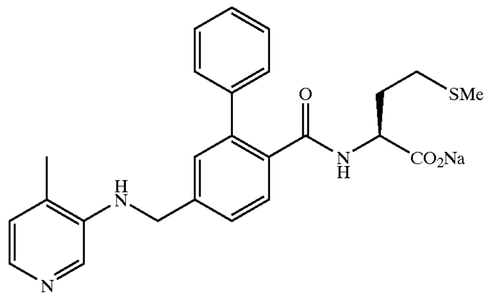

EXAMPLE 280

4-(4-Methylpyrid-3-ylaminomethyl)-2-phenylbenzoyl]methionine Sodium Salt

EXAMPLE 280A

4-Methyl-3-aminopyridine

A mixture of 4-methyl-3-nitropyridine (414.4 mg, 3 mmol) and palladium (10%) on carbon (100 mg) in methanol (5 mL) was flushed with hydrogen, and stirred under a hydrogen balloon for 5 hours. The mixture was then filtered through Celite, rinsed with methanol, and concentrated in vacuo. The residue was used without further purification.

EXAMPLE 280B 4-(4-Methylpyrid-3-ylaminomethyl)-2-phenylbenzoic Acid Methyl Ester A mixture of 4-methyl-3-aminopyridine (3.0 mmol), prepared as in Example 280A, 4-carboxaldehyde-2-phenylbenzoic acid methyl ester (480 mg, 2 mmol), prepared as in Example 160B, molecular sieves (size 4 Å, 1 g) and p-toluenesulfonic acid (10 mg) in toluene (3 mL) were stirred at 80° C. for 6 hours. After the reaction was cooled to room temperature, THF (2 mL), sodium borohydride (200 mg, 6 mmol), and ethanol (2 mL) was added to the reaction mixture sequentially. After 15 hours at room temperature, the reaction mixture was filtered through Celite and rinsed with ethyl acetate (80 mL). The organic phase was washed with saturated aqueous ammonium chloride, water and brine, dried over anhydrous sodium sulfate, filtered and concentrated in vacuo. The residue was then purified by column chromatography (ethyl ether) to give the title compound (454 mg, 66%).

EXAMPLE 280C

[4-(4-Methylpyrid-3-ylaminomethyl)-2-phenylbenzoyl]methionine Methyl Ester

A solution of the product of Example 280B (446 mg, 1.3 mmol) and aqueous saturated lithium hydroxide (3 mL) in methanol (5 mL) was heated at 60° C. for 15 hours. The reaction mixture was then neutralized with hydrogen chloride (4 N in dioxane, 5 mL). The reaction mixture was concentrated in vacuo to dryness. To the residue was added sequentially L-methionine methyl ester hydrochloride (311 mg, 1.56 mmol), 3-hydroxy 1,2,3-benzotriazin-4(3H)-one (318 mg, 1.95 mmol), 1-(3-dimethylaminopropyl)-3-ethylcarbodimide (374 mg, 1.95 mmol), THF (10 mL) and pyridine (1 mL). After 15 hours, the reaction mixture was diluted with ethyl acetate, washed with water and brine, dried over anhydrous magnesium sulfate, filtered and concentrated in vacuo. The residue was then purified by column chromatography (ethyl acetate) to give the title compound.

EXAMPLE 280D

[4-(4-Methylpyrid-3-ylaminomethyl)-2-phenylbenzoyl]methionine Sodium Salt

The desired compound was prepared by saponification of the product of Example 280C using the procedure of Example 276. $^1H$ NMR (300 MHz, DMSO-$d_6$) δ 7.72 (s, 1H), 7.70 (d, 1H) 7.41–7.36 (m, 7H), 7.15 (d, 1H), 6.96 (d, 1H), 5.93 (br t, 1H), 4.49 (d, 2H), 3.78 (m, 1H), 2.17 (s, 3H), 2.16–2.02 (m, 2H), 1.95 (s, 3H), 1.85–1.08 (m, 2H). MS $(APCI^+)$ m/e 450 $(M+H)^+$.

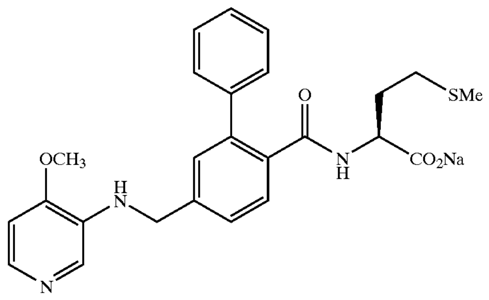

EXAMPLE 281

[4-(4-Methoxypyrid-3-ylaminomethyl)-2-phenylbenzoyl]methionine Sodium Salt

The desired compound was prepared according to the method of Example 280, except substituting 4-methoxy-3-nitropyridine for 4-methyl-3-nitropyridine. $^1H$ NMR (300 MHz, DMSO-$d_6$) δ 7.75 (d, 1H), 7.66 (s, 1H), 7.40–7.30 (m, 7H), 7.13 (d, 1H), 6.83 (d, 1H), 5.77 (t, 1H), 4.42 (d, 1H), 3.86 (s, 3H), 3.73 (m, 1H), 2.10 (m, 2H), 1.95 (s, 3H), 1.75 (m, 2H). MS $(APCI^+)$ m/e 466 $(M+H)^+$.

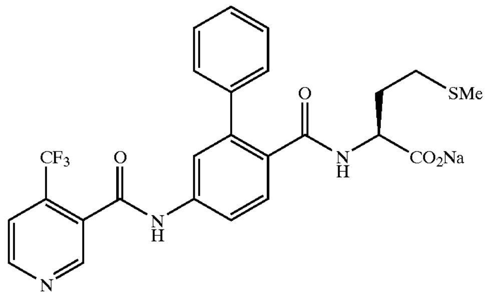

EXAMPLE 282

[4-(4-Trifluoromethylpyrid-3-ylcarbonylamino)-2-phenylbenzoyl]methionine Sodium Salt

EXAMPLE 282A

[4-(4-Trifluoromethylpyrid-3-ylcarboxyamino)-2-phenylbenzoyl]methionine Methyl Ester A mixture of 4-trifluoromethylnicotinic acid (100 mg, 0.523 mmol), (4-amino-2-phenylbenzoyl)methionine methyl ester hydrochloride (206 mg, 0.52 mmol), prepared as in Example 192B, 3-hydroxy1,2,3-benzotriazin-4(3H)-one (120 mg, 0.628 mmol), 1-(3-dimethylaminopropyl)-3-ethylcarbodiimide (125 mg, 0.628 mmol) in THF (5 mL) was stirred 15 hours. The reaction mixture was diluted with ethyl acetate, washed with water and brine, dried over anhydrous magnesium sulfate, filtered and concentrated in vacuo. The residue was purified by column chromatography (50% ethyl acetate-hexane) to give the title compound (157 mg, 57%).

EXAMPLE 282B

[4-(4-Trifluoromethylpyrid-3-ylcarbonylamino)-2-phenylbenzoyl]methionine Sodium Salt The desired compound was prepared by saponification of the product of Example 282A using the procedure of Example 276. $^1$H NMR (300 MHz, DMSO-$d_6$) δ 10.99 (br s, 1H), 9.03 (s, 1H), 8.97 (d, 1H), 7.89 (d, 1H), 7.72 (d, 1H), 7.68 (dd, 1H), 7.48 (d, 1H), 7.41–32 (m, 5H), 7.12 (d, 1H), 3.77 (m, 1H), 2.10 (m, 2H), 2.01 (s, 3H), 1.75 (m, 2H). MS (APCI$^+$) m/e 518 (M+H)$^+$.

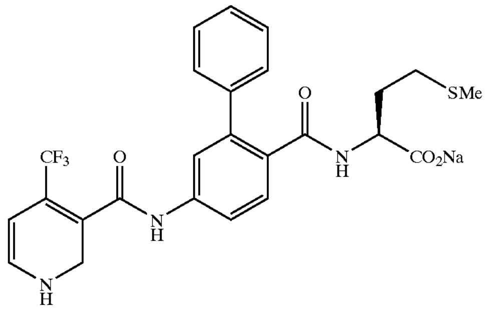

EXAMPLE 283

[4-(1H-4-Trifluoromethyl-1,2-dihydropyrid-3-ylcarbonylamino)-2-phenylbenzoyl]methionine Sodium Salt

EXAMPLE 283A (4-Nitro-2-phenylbenzoyl)methionine 2-Trimethylsilylethyl Ester A mixture of (4-nitro-2-phenylbenzoyl)methionine methyl ester (7.69 g, 30 mmol), prepared as in Example 192A and aqueous saturated lithium hydroxide (20 mL) in methanol (50 mL) was refluxed for 6 hours. The reaction mixture was carefully acidified with concentrated hydrochloric acid (10 mL), and extracted with ethyl acetate (4×). The combine extracts were washed with brine, dried over anhydrous magnesium sulfate, filtered and concentrated in vacuo. The residue was dissolved in dichloromethane (50 mL) and THF (10 mL) and 2-trimethylsilylethanol (3.72 g, 31.5 mmol), 1,3-diisopropylcarbodiimide (5.17 mL, 33 mmol) and 4-dimethylaminopyridine (30 mg) were added sequentially. After 4 hours, aqueous hydrochloric acid (0.1 N, 0.5 mL) was added and the reaction mixture was stirred for another 2 hours. The reaction mixture was then filtered through silica gel (40 g), and the filtrate was concentrated in vacuo. The residue was purified by column chromatography (5% ethyl ether-hexane) to give the title compound (8.90 g, 87%).

EXAMPLE 283B (4-Amino-2-phenylbenzoyl)methionine 2-Trimethylsilylethyl Ester A mixture of the product of Example 283A (8.85 g, 25.8 mmol), ammonium formate (4.88 g, 77.4 mmol) and palladium (10%) on carbon (1 g) in methanol was refluxed for 5 hours. The mixture was then filtered through Celite and rinsed with ethyl acetate. The filtrate was diluted with ethyl acetate, washed with water and brine, dried over anhydrous sodium sulfate, filtered and concentrated in vacuo to give the title compound which was used without further purification.

EXAMPLE 283C 4-(4-Trifluoromethylpyrid-3-ylcarbonylamino)-2-phenylbenzoic Acid 2-Trimethylsilylethyl Ester A mixture of 4-trifluoromethylnicotinic acid (472 mg, 2.46 mmol), the product of Example 283B (771 mg, 2.46 mmol), 3-hydroxy1,2,3-benzotriazin-4(3H)-one (481 mg, 2.95 mmol), 1-(3-dimethylaminopropyl)-3-ethylcarbodiimide (566 mg, 2.95 mmol) in DMF (8 mL) was stirred room temperature for 15 hours. The reaction mixture was diluted with ethyl acetate (100 mL), washed with water and brine, dried over anhydrous magnesium sulfate, filtered and concentrated in vacuo. The residue was purified by column chromatography (30% ethyl acetate-hexane) to give the title compound (1.04 g, 87%).

EXAMPLE 283D 4-(1H-4-Trifluoromethyl-1,2-dihydropyrid-3-ylcarbonylamino)-2-phenylbenzoic Acid 2-Trimethylsilylethyl Ester A solution of the product of Example 283C (1.02 g, 2.09 mmol), tetrabutylammonium borohydride (539 mg, 2.1 mmol) in 1,2-dichloroethane (10 mL) was heated at 80° C. for 6 hours. The reaction mixture was diluted with ethyl acetate, washed with saturated sodium bicarbonate, water and brine, dried over anhydrous magnesium sulfate, filtered and concentrated in vacuo. The residue was purified by column chromatography (30% ethyl acetate-hexane) to give the title compound (247 mg, 24%).

EXAMPLE 283E

[4-(1H-4-Trifluoromethyl-1,2-dihydropyrid-3-ylcarbonylamino)-2-phenylbenzoyl]methionine Methyl Ester A solution of the product of Example 283D (227 mg, 0.48 mmol) and tetrabutylammonium fluoride (261 mg, 1.0 mmol) in dioxane was heated at 80° C. for 90 min. The solvent was, then evaporated, and the residue was further dried under high vacuum (2 mmHg) for 1 hour. To the residue was added L-methionine methyl ester hydrochloride (115 mg, 0.58 mmol), 3-hydroxy-1,2,3-benzotriazin-4(3H)-one (163 mg, 1.0 mmol), 1-(3-dimethylaminopropyl)-3-ethylcarbodiimide (192 mg, 1.0 mmol), DMF (5 mL) and triethylamine (0.3 mL). After 15 hours, the reaction mixture was diluted with ethyl acetate, washed with water and brine, dried over anhydrous magnesium sulfate, filtered and concentrated in vacuo. The residue was purified by column chromatography (50% ethyl acetate-hexanes) to give the title compound (179 mg, 69%).

EXAMPLE 283F

[4-(1H-4-Trifluoromethyl-1,2-dihydropyrid-3-ylcarbonylamino)-2-phenylbenzoyl]methionine Sodium Salt The desired compound was prepared by saponification of the product of Example 283E using the procedure of Example 276. $^1H$ NMR (300 MHz, DMSO-$d_6$) δ 9.67 (s, 1H), 8.87 (br s, 1H), 7.68 (m, 2H), 7.54 (s, 1H), 7.41–7.30 (m, 6H), 7.03 (dd, 1H), 6.51 (d, 1H), 4.67 (t, 1H), 4.48 (m, 1H), 3.78 (m, 1H), 2.14 (m, 2H), 1.96 (s, 3H), 1.77 (m, 2H). MS ($APCI^+$) m/e 520 $(M+H)^+$.

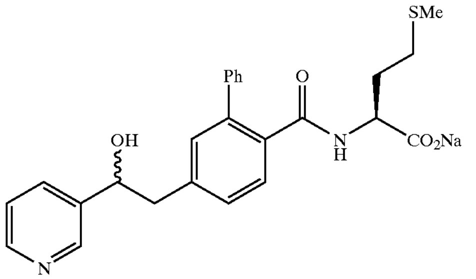

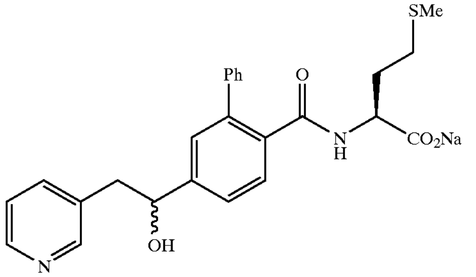

EXAMPLE 284

{4-[2-(3-Pyridy)-2-hydroxyethyl]-2-phenylbenzoyl]methionine Sodium Salt and {4-[2-(3-Pyridy)-1-hydroxyethyl]-2-phenylbenzoyl}methionine Sodium Salt

EXAMPLE 284A

4-[2-(3-Pyridyl)ethenyl]-2-phenylbenzoic Acid Methyl Ester

A mixture of the 4-iodo-2-phenylbenzoic acid methyl ester (6.11 g, 18.1 mmol), prepared as in Example 210C, 3-vinylpyridine (2.85 g, 27.1 mmol), prepared as in Example 210E, [1,1'-bis(diphenylphosphino)ferrocene]palladium(II) chloride, complexed to dichloromethane (1:1) (444 mg, 0.543 mmol) and triethylamine (5.05 g, 36.2 mmol), in 1-methyl-2-pyrrolidinone (30 mL) was degassed with nitrogen and heated at 80° C. for 18 hours. The reaction mixture was diluted with ether, filtered through silica gel, and rinsed with ethyl acetate. The filtrate was washed with water and brine, dried over anhydrous magnesium sulfate, filtered and concentrated in vacuo. The residue was purified by column chromatography (30% ethyl acetate-hexane) to give the title compound (4.82 g, 84%).

EXAMPLE 284B

4-[2-(3-Pryidyl)-1,2-dihydroxyethyl]-2-phenylbenzoic Acid Methyl Ester

To a solution of the product of Example 284A (575 mg, 1.83 mmol), 4-methylmorpholine N-oxide (642 mg, 5.48 mmol), methylsulfonamide (174 mg, 1.83 mmol) and quinuclidine (203 mg, 1.83 mmol) in tert-butanol (5 mL) and water (5 mL) was added a solution of osmium tetraoxide (2.5 wt % in tert-butanol, 1.2 mL, 0.091 mmol). The mixture was then stirred at 70° C. for 5 hours. The reaction mixture was diluted with ethyl acetate, washed with water and brine, dried over anhydrous sodium sulfate, filtered, and concentrated in vacuo. The residue was purified by column chromatography (ethyl acetate and 2% methanol-ethyl acetate) to give the title compound (323 mg, 51%).

EXAMPLE 284C

4-[2-(3-Pryidyl)-1,2-dihydroxyethyl Thio Ketal]-2-phenylbenzoic Acid Methyl Ester A solution of the product of Example 284B (250 mg, 0.716 mmol) and 1,1'-thiocarbonyldiimidazole (171 mg, 0.86 mmol) in THF (5 mL) was stirred at 50° C. for 5 hours. The reaction mixture was diluted with ether, washed with saturated aqueous ammonium chloride, water and brine, dried over anhydrous magnesium sulfate, filtered and concentrated in vacuo. The residue was purified by column chromatography (50% ethyl acetate-hexane) to give the title compound (227 mg, 81%).

EXAMPLE 284D

4-[2-(3-Pryidyl)-1-hydroxyethyl]-2-phenylbenzoic Acid Methyl Ester and 4-[2-(3-Pryidyl)-2-hydroxyethyl]-2-phenylbenzoic Acid Methyl Ester A solution of the product of Example 284C (220 mg, 0.562 mmol), tributyltin hydride (0.30 mL, 1.1 mmol) and azobisisobutyronitrile (AIBN, 10 mg) in toluene was heated at 110° C. for 2 hours. The reaction mixture was diluted with ether, washed with 10% aqueous sodium hydroxide, water and brine, dried over anhydrous magnesium sulfate, filtered and concentrated in vacuo. The residue was purified by column chromatography (20%, then 50% ethyl acetate-hexane, then ethyl acetate) to give the bis-deoxy compound as the first fraction (53 mg, 30%), and the desired product as the second fraction (117 mg, 63%, a mixture of two regioisomers).

EXAMPLE 284E

{4-[2-(3-Pyridy)-2-hydroxyethyl]-2-phenylbenzoyl}methionine Sodium Salt and {4-[2-(3-Pyridy)-1-hydroxyethyl]-2-phenylbenzoyl}methionine Sodium Salt The desired compounds were prepared from the product of Example 284D according to the method of Examples 280C and D. $^1H$ NMR (300 MHz, DMSO-$d_6$) δ 8.61–8.37 (m, 2H), 7.79–7.60 (m, 1H), 6.02–7.00 (m, 10H), 3.88 (m, 1H), 3.77 (m, 1H), 2.95 (m, 2H), 2.15–2.02 (m, 2H), 2.00, 1.99, 1.96, 1.95 (4 s's, 3H), 1.90–1.70 (m, 2H). MS ($APCI^+$) m/e 451 $(M+H)^+$.

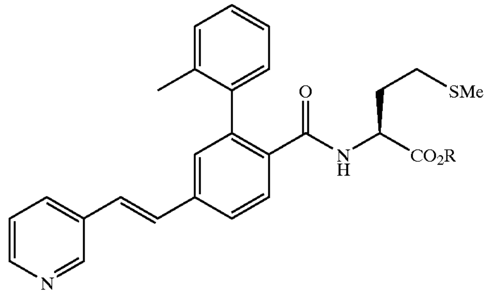

EXAMPLES 292–296

EXAMPLE 292

{4-[2-(Pyrid-3-yl)ethenyl]-2-(2-methylphenyl) benzyl}methionine Butyl Ester

{4-[2-(pyrid-3-yl)ethenyl]-2-(2-methylphenyl) benzoyl}methionine (138 mg, 0.30 mmol) was heated at 100° C. for 2 hours in n-butanol (5 mL) with 1 drop of $H_2SO_4$. The reaction was evaporated to dryness, partitioned between ethyl acetate and 5% $NaHCO_3$, washed with water and brine, and dried over $Na_2SO_4$ to provide the title compound in 86% yield. $^1H$ NMR ($CDCl_3$, 300 MHz) δ 0.92 (t, 3H), 1.35 (m, 2H), 1.60 (m, 2H), 1.86 (m, 1H), 2.1 (m, 9H), 4.08 (m, 2H), 4.62 (m, 1H), 5.97 (d, 1H), 7.18–8.04 (m, 1H), 8.53 (s, 1H), 8.77 (s, 1H). MS m/e 503 $(M+H)^+$.

EXAMPLE 293

N-(4-(3-Pyridylethylenyl)-2-(2-tolyl)benzoyl)-L-methionine Octadecyl Ester

{4-[2-(pyrid-3-yl)ethenyl]-2-(2-methylphenyl) benzoyl}methionine (50 mg, 0.11 mmol), 1-octadecanol (30 mg, 0.11 mmol), and carbonyldiimidazole (18 mg, 0.11 mmol) were combined and dissolved in THF (2 mL) and heated to reflux for 18 hours. The mixture was diluted with ethyl acetate and washed with 5% $NaHCO_3$ and brine and dried over $Na_2SO_4$. Flash chromatography (50% ethyl acetate-hexane, provided the title compound (35.4 mg). MS m/e 699 $(M+H)^+$.

EXAMPLE 294

{4-[2-(Pyrid-3-yl)ethenyl]-2-(2-methylphenyl) benzoyl}methionine Dimethylaminoethyl Ester The desired compound was prepared according to the method of Example 292, except substituting N,N-dimethylethanolamine for n-butanol. $^1H$ NMR ($CDCl_3$, 300 MHz) δ 1.62 (m, 1H), 1.87 (m, 1H), 2.1 (m, 12H), 2.40 (m, 4H), 2.72 (m, 1H), 4.28 (m, 1H), 4.59 (m, 1H), 6.05 (m, 1H), 7.18–8.03 (m, 1H), 8.52 (m, 1H), 8.75 (m, 1H). MS m/e 518 $(M+H)^+$.

EXAMPLE 295

{4-[2-(Pyrid-3-yl)ethenyl]-2-(2-methylphenylbenzoyl}methionine Acetyloxymethyl Ester {4-[2-(pyrid-3-yl)ethenyl]-2-(2-methylphenyl) benzoyl}methionine (75 mg, 0.17 mmol), bromomethyl acetate (26 mg, 0.17 mmol), and potassium iodide (9 mg, 0.06 mmol) were dissolved in DMF (2 mL), treated with sodium hydride (60% suspension in mineral oil, 6.7 mg, 0.17 mmol), and heated at 100° C. for 8 hours. The mixture was diluted with ethyl acetate, washed with 5% $NaHCO_3$ and brine and dried over sodium sulfate. Chromatography on silica gel (50% ethyl acetate-hexane) afforded the title compound. $^1H$ NMR ($CDCl_3$, 300 MHz) δ 1.60 (m, 1H), 1.89 (m, 1H), 2.0–2.2 (m, 1H), 4.64 (m, 1H), 5.72 (m, 2H), 5.91 (m, 1H), 7.15–7.64 (m, 9H), 8.02 (m, 2H), 8.57 (m, 1H), 8.79 (m, 1H). MS m/e 519 $(M+H)^+$.

EXAMPLE 296

{4-[2-(Pyrid-3-yl)ethenyl]-2-(2-methylphenylbenzoyl}methionine Pivaloyloxymethyl Ester The desired compound was prepared according to the method of Example 295, except substituting chloromethyl pivalate for bromomethyl acetate. $^1H$ NMR ($CDCl_3$, 300 MHz) δ 1.19 (s, 9H), 1.59 (m, 1H), 1.84 (m, 1H), 2.1 (m, 8H), 4.63 (m, 1H), 5.72 (m, 2H), 5.88 (m, 1H), 7.15–7.41 (m, 8H), 7.62 (m, 1H), 8.0 (m, 2H), 8.54 (m, 1H), 8.77 (m, 1H). MS m/e 561 $(M+H)^+$.

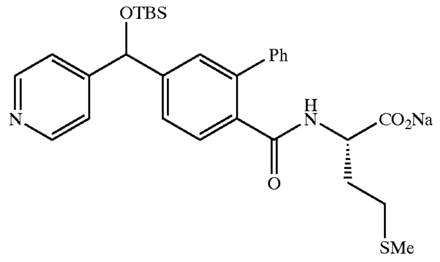

EXAMPLE 297

[4-(4-Pyridyl-t-butyldimethylsilyloxymethyl)-2-phenylbenzoyl]methionine Sodium Salt

EXAMPLE 297A 4-(4-Pyridylhydroxymethyl)-2-phenylbenzoic Acid Methyl Ester

A solution of 4-bromopyridine (0.32 g, 2.0 mmol) in ether (10 mL) was cooled to −78° C. and treated with butyllithium. After 10 minutes, 4-carboxaldehyde-2-phenylbenzoic acid methyl ester (0.53 g, 2.2 mmol), prepared as in Example 160B, in ether (5 mL) was added. Stirring was continued for 15 minutes before allowing the reaction to warm to ambient temperature over 2 hours. The reaction mixture was evaporated to dryness. The residue was dissolved in ethyl acetate and washed with water and brine, dried and concentrated. Chromatography on silica gel (ethyl acetate) gave the title compound (769 mg).

EXAMPLE 297B 4-(4-Pyridyl-t-butyldimethylsilyloxymethyl)-2-phenylbenzoic Acid Methyl Ester 4-(4-Pyridylhydroxymethyl)-2-phenylbenzoic acid methyl ester (769 mg, 2.41 mmol), prepared as in Example 297A, diisopropylethylamine (0.84 mL, 4.8 mmol), and t-butyldimethylsilyl triflate (1.1 mL, 4.8 mmol) were dissolved in methylene chloride (50 mL) and stirred for 18 hours. TLC indicated the presence of the alcohol so additional base (1 mL) and triflate (0.5 mL) were added. After 15 minutes, all starting alcohol was consumed. The reaction mixture was washed with water, 5% $NaHCO_3$, and brine, dried over $Na_2SO_4$, and concentrated. Chromatography on silica gel (20% ethyl acetate-hexane) provided the desired compound in a 93% yield.

EXAMPLE 297C 4-(4-Pyridyl-t-butyldimethylsilyloxymethyl)-2-phenylbenzoic Acid 4-(4-Pyridyl-t-butyldimethylsilyloxymethyl)-2-phenylbenzoic acid methyl ester (0.97 g, 2.24 mmol), prepared as in Example 297B, was dissolved in methanol. Saturated aqueous LiOH (1 mL) was added, and the solution was reluxed overnight. The reaction was evaporated to dryness and partitioned between ethyl acetate and water. The organic layer was dried over $Na_2SO_4$ to provide the title compound in 27% yield.

EXAMPLE 297D

[4-(4-Pyridyl-t-butyldimethylsilyloxymethyl)-2-phenylbenzoyl)methionine Methyl Ester The desired compound was prepared by coupling of the product of Example 297C and methionine methyl ester hydrochloride according to the method of Example 290B.

EXAMPLE 297E

[4-(4-Pyridyl-t-buiyldimethylsilyloxymethyl)-2-phenylbenzoyl]methionine Sodium Salt

[4-(4-pyridyl-t-butyldimethylsilyloxymethyl)-2-phenylbenzoyl)methionine methyl ester (25.0 mg, 44 μmol), prepared as in Example 297D, was dissolved in methanol (5 mL) and stirred with NaOH (1.0 M, 44 μmol) at 55° C. for 72 hours. The reaction was evaporated to dryness and lyophilized from water to provide the title compound (19.4). $^1H$ NMR ($d_6$-DMSO, 300 MHz) δ 0.03 (s, 6H), 0.91 (s, 9H), 1.75 (m, 1H), 1.96 (m, 3H), 2.09 (m, 1H), 2.5 (m, 2H), 3.75 (m, 1H), 6.02 (s, 1H), 7.2–7.5 (m, 10H), 8.50 (m, 2H). MS m/e 551 $(M+H)^+$.

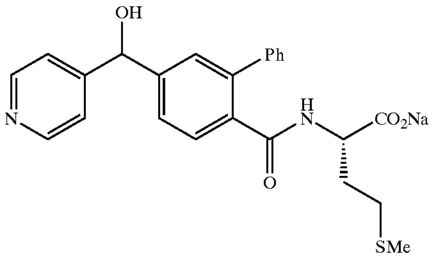

EXAMPLE 298

[4-(4-Pyridylhydroxymethyl)-2-phenylbenzoyl] methionine Sodium Salt

The desired compound was prepared from 4-(4-Pyridylhydroxymethyl)-2-phenylbenzoic acid methyl ester, prepared as in Example 297A according to the method of Examples 297C, D, and E. $^1H$ NMR ($CDCl_3$, 300 MHz) δ 1.78 (m, 1H), 1.96 (m, 3H), 2.09 (m, 3H), 3.73 (m, 1H), 5.80 (s, 1H), 7.13 (m, 1H), 7.2–7.5 (m, 10H), 8.48 (m, 2H). MS m/e 437 $(M+H)^+$.

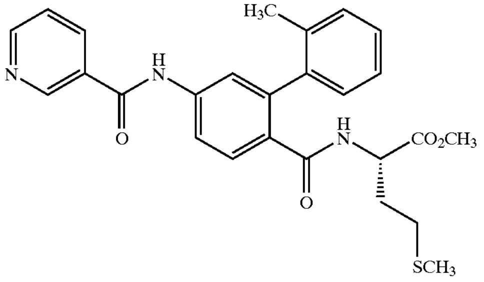

EXAMPLE 300

[4-(3-Pyridylcarbonylamino)-2-(2-methylphenyl) benzoyl]methionine Methyl Ester

To a stirred solution of the [4-amino-2-(2-methylphenyl) benzoyl]methionine methyl ester (85 mg, 0.23 mmol) in $CH_2Cl_2$ (5 mL) was added nicotinic acid chloride hydrochloride (81 mg, 0.46 mmol) and saturated $NaHCO_3$ (2 mL). The reaction was stirred at ambient temperature for 2 hours. The reaction was diluted with $CH_2Cl_2$ (10 mL), the layers were separated and the organic layer washed with saturated aqueous $NaHCO_3$ (5 mL), dried ($MgSO_4$) and concentrated in vacuo. Flash chromatography ($CH_2Cl_2$-methanol 50:1) and crystallization from ethyl acetate gave the desired compound (87 mg, 80%) as a white powder. $^1H$ NMR (300 MHz, $CDCl_3$) δ 9.10 (dd, 1H, J=2.4, 1.0 Hz), 8.80 (dd, 1H, J=4.7, 1.7 Hz), 8.21 (ddd, 1H, J=7.8, 2.4, 1.7 Hz), 8.09–8.00 (m, 2H), 7.71–7.66 (m, 1H), 7.64–7.61 (m, 1H), 7.46 (ddd, 1H, J=7.8, 4.7, 1.0 Hz), 7.35–7.20 (m, 4H), 5.92 (bd, J=7.5 Hz), 4.67–4.57 (m, 1H), 3.66 (s, 3H), 2.23–2.01 (4 s and m, 8H), 2.00 (m, 1H), 1.65–1.52 (m, 1H). MS m/z 478 $(M+1)^+$.

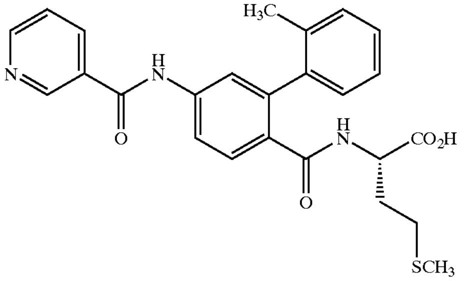

EXAMPLE 301

[4-(3-Pyridylcarbonylamino)-2-(2-methylphenyl) benzoyl]methionine

To a stirred solution of the product of Example 300 (140 mg, 0.29 mmol) in THF (6 mL) was added a solution of $LiOH.H_2O$ (37 mg, 88 mmol) in $H_2O$ (1 mL) and the resulting solution stirred for 2 hours at ambient temperature. The reaction was concentrated in vacuo and 1 N HCl was added to the residue. The resulting precipitate was filtered and washed with $H_2O$. Lyopholization gave the title compound (87 mg, 59%) as a white powder. $^1H$ NMR (300 MHz, DMSO-$d_6$, 90° C.) δ 9.12 (d, 1H, J=2.4 Hz), 8.74 (dd, 1H, J=4.9, 1.9 Hz), 8.31 (dt, 1H, J=7.9, 1.8 Hz), 7.84 (dd, 1H, J=7.9, 1.8 Hz), 7.63 (s, 1H), 7.61 (d, 1H, J=2.4 Hz), 7.54 (dd, 1H, J=7.9, 4.9 Hz), 7.45 (d, 1H, J=7.9 Hz), 7.23–7.21 (m, 2H), 7.19–7.15 (m, 2H), 4.30–4.26 (m, 1H), 2.28–2.22 (m, 1H), 2.20–2.14 (m, 1H), 2.11 (s, 3H), 1.98 (s, 3H), 1.88–1.81 (m, 1H), 1.75–1.68 (m, 1H), MS m/z 464 $(M+1)^+$, 446. Anal calcd for $C_{25}H_{25}N_3O_4S.HCl.0.5\ H_2O$ (509.01): C, 58.99; H, 5.35; N, 8.26. Found: C, 59.38; H, 5.49; N, 7.89.

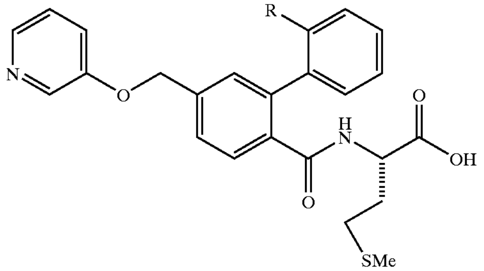

EXAMPLES 304–306

EXAMPLE 304

[4-(3-Pyridyloxymethyl)-2-(2-trifluoromethylphenyl)benzoyl]methionine

EXAMPLE 304A

4-Hydroxyethyl-2-aminobenzoic Acid Methyl Ester

To a solution of dimethylaminoterphthalate (3.07 g, 14.7 mmol) in 30 mL of a 2:1 mixture of THF: $Et_2O$ at −78° C. was added neat DIBAL (6.27 g, 44.1 mmol, 3.0 eq.) and the reaction was warmed to 0° C. over 4 hours. The reaction was quenched with 5 mL of methanol followed by 5 mL of saturated aqueous sodium tartrate. The mixture was stirred overnight and then was taken up in ethyl acetate. The layers were separated and the ethyl acetate layer was washed with saturated aqueous $NaHCO_3$and brine and then dried over $Na_2SO_4$, filtered and evaporated to an oil. Purification by chromatography on silica gel (50% ethyl acetate-hexane) gave the desired compound (1.03 g, 39%) of 1b as a colorless oil.

EXAMPLE 304B

4-Hydroxymethyl-2-aminobenzoic Acid Methyl Ester

To a stirred solution of the product of Example 304A (152 mg, 0.84 mmol) in acetone (20 mL) and 3N $H_2SO_4$ (20 mL) at −15° C. was added a solution of $NaNO_2$ (1.34 g, 19.4 mmol) in $H_2O$ (10 mL) dropwise by addition funnel. After the addition was complete, urea (210 mg, 3.52 mmol) was added followed by a solution of KI (5.11 g, 30.8 mmol) in $H_2O$ (5 mL), the ice bath was removed, and the reaction warmed to ambient temperature. After 2 hours, the reaction was quenched with saturated aqueous $NaHSO_3$ and the acetone was evaporated. The aqueous layer was extracted with ethyl acetate (3×). The combined ethyl acetate layers were dried over $Na_2SO_4$, filtered and evaporated to an oil. Purification by chromatography on silica gel (25% ethyl acetate-hexane) gave the iodide (4.31 g, 84%) as a light yellow oil.

EXAMPLE 304C

4-(3-Pyridyloxymethyl)-2-iodobenzoic Acid Methyl Ester

To a solution of the iodide prepared in Example 304B (6.01 g, 20.6 mmol) in DMF (30 mL) was added $SOCl_2$ and LiCl and the reaction was stirred at 25° C. for 5 minutes. The reaction mixture was taken up in ethyl acetate, washed with $H_2O$ (3×) and brine (4×), dried over $Na_2SO_4$, filtered and evaporated to an oil. The benzyl chloride (6.39 g, 20.6 mmol) was dissolved in toluene and 18-crown-6 (8.17 g, 30.9 mmol) was added followed by the potassium salt of 3-pyridinol and the reaction was heated to reflux. The reaction was complete in 2 hours. The reaction mixture was cooled to ambient temperature and washed with $H_2O$ (3×), dried over $Na_2SO_4$, filtered and evaporated to an oil. Purification by chromatography on silica gel (gradient of 50% ethyl acetate-hexanes to 75% ethyl acetate-hexanes) gave the desired pyridyl ether (3.01 g, 40%).

EXAMPLE 304D

4-(3-Pyridyloxymethyl)-2-(2-trifluoromethylphenyl) benzoic Acid Methyl Ester To a solution of the pyridyl ether prepared in Example 304C (365 mg, 0.96 mmol) in DMF (4 mL) at 25° C. was added $PdCl_2(PPh_3)_2$ (67 mg, 0.096 mmol, 10 mol %) followed by 2-trifluoromethyl boronic acid (366 mg, 1.93 mmol) and $Cs_2CO_3$ (629 mg, 1.93 mmol) and the reaction was heated at 80° C. for 12 hours. The reaction was then cooled and taken up in ethyl acetate. The organic phase was washed with $H_2O$ (5×), dried over $Na_2SO_4$, filtered and evaporated to an oil. Purification by radial chromatography (gradient of 25% ethyl acetate-hexanes to 75% ethyl acetate-hexanes) gave the desired compound (261 mg, 70%) as an oil.

EXAMPLE 304E

4-(3-Pyridyloxymethyl)-2-(2-trifluoromethylphenyl) benzoic Acid

The product of Example 304D (241 mg, 0.62 mmol) was dissolved in methanol (5 mL) and saturated aqueous LiOH (1 mL) was added. The reaction was heated at reflux for 1 hour. The reaction mixture was then evaporated and fomlic acid (1 mL) was added to acidify the crude product to pH3. The reaction was evaporated again to remove formic acid and ethyl acetate (5 mL) and $H_2O$ (1 mL) were added to completely solubilize the reaction mixture. The aqueous layer was extracted with ethyl acetate (3×) and the ethyl acetate layers were combined and dried over $Na_2SO_4$, filtered and evaporated to give the acid (231 mg, 100%).

EXAMPLE 304F

[4-(3-Pyridyloxymethyl)-2-(2-trifluoromethylphenyl)benzoyl]methionine Methyl Ester The of Example 304E (231 mg, 0.62 mmol) was dissolved in DMF (4 mL) and HOOBT (152 mg, 0.93 mmol) was added followed by methionine methyl ester HCl (185 mg, 0.93 mmol), EDCI (179 mg, 0.93 mmol) and $Et_3N$ (0.18 mL, 1.24 mmol). The reaction was stirred for 12 hours at 25° C. and then was taken up in ethyl acetate and washed with $H_2O$ (3×) and brine (3×). The ethyl acetate layer was dried over $Na_2SO_4$, filtered and evaporated to an oil. Purification by radial chromatography (25% ethyl acetate-hexanes to 50% ethyl acetate-hexanes to 5% methanol-ethyl acetate) gave the desired compound (291 mg, 91%) as an oil.

EXAMPLE 304G

[4-(3-Pyridyloxymethyl)-2-(2-trifluoromethylphenyl)benzoyl]methionine

The product of Example 304F (291 mg, 0.56 mmol) was dissolved in THF(4 mL) and saturated aqueous LiOH (1 mL). Water (1 mL) was added and the reaction mixture was stirred at room temperature for 1 hour. The reaction mixture was thoroughly evaporated and formic acid was added to pH3 The reaction was evaporated to dryness and ethyl acetate (10 mL) was added followed by a minimum quantity of $H_2O$ (~1 mL) to completely solubilize the free acid and the water soluble salts, respectively. The layers were separated and the aqueous layer was extracted with ethyl acetate (3×). The ethyl acetate layers were combined and dried over $Na_2SO_4$, filtered, and evaporated and then lyophilized to give the title compound (242 mg, 86%) as an amorphous white solid. $^1$H NMR (300 MHz, $CD_3OD$) δ 8.30 (bs, 1H), 8.14 (m, 1H), 7.76–7.33 (m, 9H), 5.28 (s, 2H), 4.87–4.40 (m, 1H), 2.40–2.06 (m, 2H), 2.04–1.94 (m, 4H contains methionine SMe), 1.92–1.80 (m, 1H). MS (CI) 505 $(M+H)^+$ 505. Anal calcd for $C_{25}H_{23}O_4N_2SF_3$: $0.65H_2O$ solvate: C, 58.17; H, 4.74; N, 5.43. Found: C, 58.17; H, 4.80; N, 5.31. HRMS FAB Calcd m/z $MH^+$ for $C_{25}H_{23}O_4N_2SF_3$ 505.1409, found 505.1408.

EXAMPLE 305

[4-(3-Pyridyloxymethyl)-2-(2-chlorophenyl)benzoyl] methionine Methyl Ester

The desired compound was prepared according to the method of Example 304, except substituting 2-ethylphenylboronic acid for 2-trifluoromethylphenylboronic acid. $^1$H NMR (300 MHz, $CD_3OD$) δ 8.30 (bs, 1H), 8.14 (d, J=4.4 Hz, 1H), 7.71–7.17 (m, 9H), 5.29 (s, 2H), 4.87–4.43 (m, 1H), 2.54–2.37 (m 2H), 2.24–1.84 (m, 7H, contains SMe), 1.90–1.82 (m, 1H), 1.04 and 0.97 (rotameric triplets, J=7.3 Hz, 3H). MS (CI) 465 $(M+H)^+$. Anal calcd for $C_{26}H_{28}O_4N_2S$: $0.22H_2O$ solvate: C, 66.65; H, 6.12; N, 5.98. Found: C, 66.64; H, 6.22; N, 5.85. HRMS FAB Calcd m/z $MH^+$ for $C_{26}H_{28}O_4N_2S$ 465.1848, found 465.1865.

EXAMPLE 306

[4-(3-Pyridyloxymethyl)-2-(2-ethylphenyl)benzoyl] methionine Methyl Ester

The desired compound was prepared according to the method of Example 304, except substituting 2-chlorophenylboronic acid for 2-trifluoromethylphenylboronic acid. $^1$H NMR (500 MHz, $CD_3OD$) δ 8.31 (bs, 1H), 8.14 (d, J=4.4 Hz, 1H), 7.70–7.34 (m, 9H), 5.29 (s, 2H), 4.48–4.45 (m, 1H), 2.30–2.22 (m, 1H), 2.20–2.15 (m, 1H), 2.05–1.95 (m, 4H, contains SMe), 1.86–1.76 (m, 1H). MS (CI) 471 $(M+H)^+$. Anal calcd for $C_{24}H_{23}O_4N_2SCl$: C, 61.21; H, 4.92; N, 5.95. Found: C, 61.31; H, 5.20; N, 5.61. HRMS FAB Calcd m/z $MH^+$ for $C_{24}H_{23}O_4N_2SCl$ 471.1145, found 471.1165.

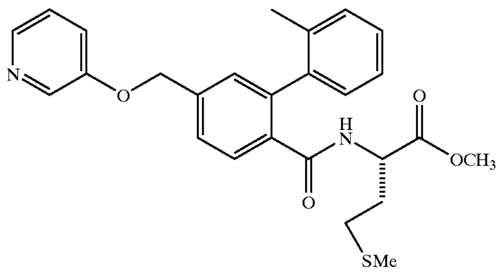

EXAMPLE 307

[4-(3-Pyridyloxymethyl)-2-(2-methylphenyl) benzoyl]methionine Methyl Ester

The desired compound was prepared by saponification of 4-(3-pyridyloxymethyl)-2-(2-methylphenyl)benzoic acid methyl ester, prepared as in Example 204D, followed by coupling with methionine methyl ester hydrochloride and saponification as described in Examples 304E–G. $^1$H NMR (300 MHz, $CDCl_3$) δ 8.40 (bs, 1H), 8.25 (dd, J=4.1, 1.9 Hz, 1H), 7.99 (dd, J=22.8, 8.1 Hz, 1H), 7.53–7.50 (m, 1H), 7.36–7.21 (m, 7H), 5.91 (bd, J=7.7 Hz, 1H (NH)), 5.18 (s, 2H), 4.70–4.58 (m, 1H), 3.66 (s, 3H, OMe), 2.18–2.00 (m, 5H), 1.95–1.82 (m, 1H), 1.65–1.55 (m, 4H, contains SMe). MS (CI) 465 $(M+H)^+$. Anal calcd for $C_{26}H_{28}O_4N_2S$: $0.30H_2O$ solvate: C, 66.45; H, 6.13; N, 5.96. Found: C, 66.45; H, 6.15; N, 5.97. HRMS FAB Calcd m/z $MH^+$ for $C_{26}H_{28}O_4N_2S$ 465.1848, found 465.1869.

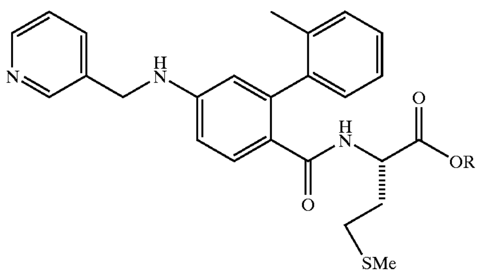

EXAMPLE 308

[4-(3-Pyridylmethylamino)-2-(2-methylphenyl) benzoyl]methionine Methyl Ester

EXAMPLE 308A

4-Nitro-2-(2-methylphenyl)benzoic Acid

To a solution in 4:1 THF-water (20 mL) was added saturated aqueous LiOH (4 mL) and the reaction was stirred at reflux for 2 hours. The THF was evaporated and the residue was acidified with 2 mL of formic acid, stripped and partitioned between ethyl acetate and $H_2O$. The ethyl acetate layer was dried over $Na_2SO_4$, filtered and evaporated to give the acid as an oil which solidified upon standing.

EXAMPLE 308B

[4-Nitro-2-(2-methylphenyl)benzoyl]methionine Methyl Ester

The product of Example 308A (604 mg, 2.35 mmol) and HOOBT (574 mg, 3.52 mmol) were dissolved in DMF (10 mL) and methionine methyl ester HCl (679 mg, 3.52 mmol) and EDCI (676 mg, 3.52 mmol) were added followed by $Et_3N$ (476 mg, 0.65 mL, 4.7 mmol). The reaction was stirred for 12 hours and then was taken up in ethyl acetate and washed successively with brine (3×) and water (3×). The ethyl acetate layer was dried over $Na_2SO_4$, filtered and evaporated. Purification by chromatography on silica gel (5% methanol-ethyl acetate) gave the desired compound (940 mg, 98%).

EXAMPLE 308C

[4-Amino-2-(2-methylphenyl)benzoyl]methionine Methyl Ester

To a solution of the product of Example 308B (940 mg, 2.33 mmol) in ethyl acetate (50 mL) was added $SnCl_2.2H_2O$ (1.85 g, 8.18 mmol) and the reaction was heated at reflux for 1 hour. The reaction mixture was cooled and basified to pH8 gradually with solid $NaHCO_3$, stirred overnight, and extracted with ethyl acetate. The ethyl acetate extract was concentrated and the residue was purified by chromatography on silica gel (5% methanol-ethyl acetate) to give the aniline (450 mg, 52%) as an oil.

EXAMPLE 308D

[4-(3-Pyridylmethylamino)-2-(2-methylphenyl) benzoyl]methionine Methyl Ester

The aniline prepared in Example 308C (180 mg, 0.48 mmol) and 3-pyridine carboxaldehyde (55 mg, 0.51 mmol) were combined in methanol (4 mL) and sodium cyanoborohydride (48 mg, 0.77 mmol) was added followed by 100 mg of crushed molecular sieves. The reaction was adjusted to pH6 with acetic acid and stirred at 25° C. for 3 hours. The reaction was concentrated and transferred directly to a column of silica gel and purified by flash chromatography (5% methanol-ethyl acetate) to give the tide compound (182 mg, 82%) as an oil that solidified after standing. $^1$H NMR (300 MHz, $CD_3OD$) δ 8.54 (d, J=2.4 Hz, 1H), 8.40 (dd, J=5.1, 1.3 Hz, 1H), 7.84 (bd, J=8.4 Hz, 1H), 7.65–7.55 (m, 1H), 7.40 (dd, J=7.8, 4.7 Hz, 1H), 7.30–7.10 (m, 4H), 6.66 (dd, J=8.8, 2.3 Hz, 1H), 6.37 (d, J=2.3 Hz, 1H), 4.45 (s, 2H), 3.64 (s, 3H), 2.10–1.98 (m, 8H), 1.90–1.78 (m, 1H), 1.65–1.55 (m, 1H). MS (CI) 464 $(M+H)^+$. HRMS FAB Calcd m/z $MH^+$ for $C_{26}H_{29}O_3N_3S$ 464.2008, found 464.2023.

EXAMPLE 309

[4-(3-Pyridylmethylamino)-2-(2-methylphenyl) benzoyl]methionine

The desired compound was prepared by saponification of the product of Example 308 according to the method of Example 304G. $^1$H NMR (300 MHz, $CD_3OD$) δ 8.81 (bs, 1H), 8.76 (bd, J=11.8 Hz, 1H), 8.64–8.61 (m, 1H), 8.07 (dd, J=8.5, 6.1 Hz, 1H), 7.65–7.58 (m, 1H), 7.28–7.18 (m, 4H), 6.70 (dd, J=8.5, 2.4 Hz, 1H), 6.40 (d, J=2.3 Hz, 1H), 4.68 (s, 2H), 4.44–4.38 (m, 1H), 2.14–1.99 (m, 8H), 1.90–1.80 (m, 1H), 1.65–1.55 (m, 1H). MS (CI) 450 $(M+H)^+$. Anal calcd for $C_{25}H_{28}O_3N_3SCl$: 1.10$H_2O$ and 0.80 HCl solvate: C, 56.12; H, 5.84; N, 7.85. Found: C, 56.11; H, 5.85; N, 8.03. HRMS FAB Calcd m/z $MH^+$ for $C_{25}H_{27}O_3N_3S$ 450.1851, found 450.1864.

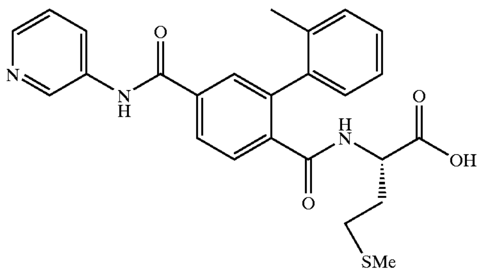

EXAMPLE 310

[4-(3-Pyridylaminocarbonyl)-2-(2-methylphenyl) benzoyl]methionine

The desired compound was prepared by saponification of [4-(3-pyridylaminocarbonyl)-2-(2-methylphenyl)benzoyl] methionine according to the method of Example 304G. $^1$H NMR (300 MHz, $CD_3OD$) 8.90 (bs, 1H), 8.32–8.25 (m, 2H), 8.11–8.05 (m, 1H), 7.85 (bs, 1H), 7.78 (d, J=8.1 Hz, 1H), 7.45 (dd, J=8.5, 4.8 Hz, 1H), 7.28–7.18 (m, 5H), 4.50–4.40 (m, 1H), 2.20–1.65 (m, 10H). MS (CI) 464 $(M+H)^+$.

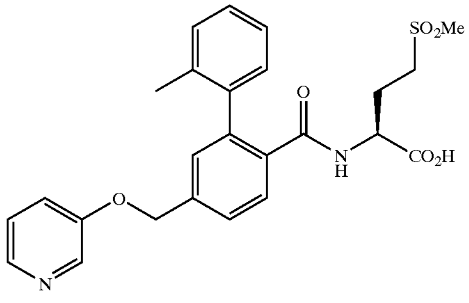

EXAMPLE 311

N-[4-(3-Pyridyloxymethyl)-2-(2-methylphenyl) benzoyl]-2-amino-4-(methylsulfonyl)butanoic Acid The desired compound was prepared according to the method of Example 204F, except substituting methionine sulfone methyl ester hydrochloride for methionine methyl ester hydrochloride. $^1$H NMR (300 MHz, DMSO-$d_6$) δ 8.40 (1H, d, J=7 Hz), 8.37 (1H, d, J=7 Hz), 7.57 (2H, bs), 7.47 (1H, dd, J=8, 3 Hz), 7.33 (1H, dd, J=7, 5 Hz), 7.30 (1H, s), 7.21 (2H, bs), 7.16 (2H, m), 5.25 (2H, s), 4.21 (1H, bs), 2.92 (3H, s), 2.83 (1H, m), 2.70 (4H, m), 2.05 (3H, bs), 1.90 (2H, m). MS (DCI, $NH_3$) m/e 483 $(M+H)^+$. Anal calcd for $C_{25}H_{28}N_2O_7S.1H_2O$: C, 59.99; H, 5.64; N, 5.60. Found C, 59.93; H, 5.60; N, 5.45.

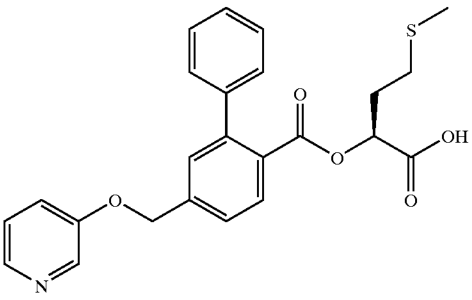

EXAMPLE 312

2-[4-(3-Pyridyloxy)-2-phenylbenzoyloxy]-4-thiomethylbutyric Acid

EXAMPLE 312A

2-[4-(3-Pyridyloxy)-2-phenylbenzoyloxy]-4-thiomethylbutyric Acid Methyl Ester

To a mixture of 4-(3-pyridyloxymethyl)-2-phenylbenzoic acid (305 mg, 1.00 mmol) and 2-(methanesulfonyloxy)-4-(thiomethyl)butyric acid methyl ester (231 mg, 1.10 mmol) was added 6 mL of toluene and 180 μL of N,N-diethylisopropylamine. The mixture was stirred at reflux for 21 hours, then was cooled to 25° C. and poured into aqueous 1.2M $NaHCO_3$. The layers were shaken and separated and the aqueous layer was extracted with ethyl acetate (2×). The combined organic layers were extracted with brine, dried over magnesium sulfate, filtered, and concentrated to an oil. Purification by silica gel chromatography (50% hexanes-ethyl acetate) gave the desired compound (212 mg, 47%) as a colorless oil.

EXAMPLE 312B

2-[4-(3-Pyridyloxy)-2-phenylbenzoyloxy]-4-thiomethylbutyric Acid

To a solution of the product of Example 312A (50 mg, 0.11 mmol) of in tetrahydrofuran (1 mL) was added aqueous 2M LiOH (0.2 mL). The mixture was stirred at 25° C. for 24 hours, then concentrated in vacuo. The residue was taken up in water, and extracted with ethyl acetate (3×). The aqueous layer was acidified to pH 3 and extracted again with ethyl acetate (3×). The second set of ethyl acetate layers was dried over magnesium sulfate and concentrated in vacuo to a white foam. $^1$H NMR (300 MHz, DMSO) δ 1.81 (m, 2H), 1.98 (s, 3H), 2.07 (m, 2H), 4.95 (dd, J=4.0, 8.5 Hz, 1H), 5.33 (s, 2H), 7.36 (m, 3H), 7.40 (m, 3H), 7.48 (ddd, J=1.1, 2.9, 8.5 Hz, 1H), 7.52 (d, J=1.5 Hz, 1H), 7.60 (dd, J=1.5, 8.1 Hz, 1H), 7.86 (d, J=8.1 Hz, 1H), 8.19 (d, J=1H), 8.39 (d, J=2.2 Hz, 1H). MS (DCI) m/e 438 $(M+H)^+$. Anal calcd for $C_{24}H_{23}NO_5S.0.65H_2O$: C, 64.17; H, 5.45; N, 3.12. Found: C, 64.19; H, 5.53; N, 2.74.

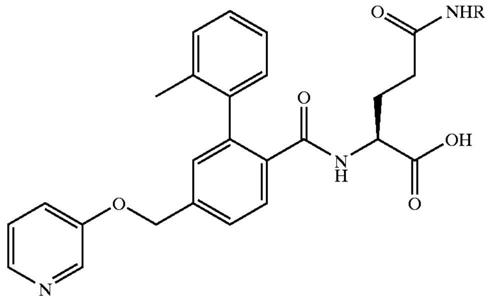

EXAMPLES 313–315

EXAMPLE 313

(S)-2-N-[4-(3-Pyridyloxymethyl)-2-(2-methyl)phenylbenzoyl]amino-4-(aminocarbonyl)butanoic Acid

EXAMPLE 313A (S)-2-N-[4-(3-Pyridyloxymethyl)-2-(2-methylphenyl)benzoyl]amino-4-(aminocarbbnyl)butanoic Acid tert-Butyl Ester The desired compound was prepared by coupling of 4-(3-pyridyloxymethyl)-2-(2-methylphenyl)benzoic acid with glutamine tert-butyl ester hydrochloride according to the method of Example 187D.

EXAMPLE 313B (S)-2-N-[4-(3-Pyridyloxymethyl)-2-(2-methyl)phenylbenzoyl]amino-4-(aminocarbonyl)butanoic Acid Trifluoroacetic Acid Salt The desired compound was prepared by stirring the product of Example 315A in 1:1 trifluoroacetic acid-4N HCl-dioxane for an amount of time sufficient to consume the starting ester, followed by concentration in vacuo. $^1$H NMR (300 MHz, DMSO) δ 1.70 (m, 1H), 1.85 (m, 1H), 1.97 (t, J=7.5 Hz, 2H), 2.05 (s, 3H), 2.08 (s, shoulder to 2.05), 4.11 (m, 1H), 5.34 (s, 2H), 6.77 (bs, 1H), 7.13 (m, 3H), 7.20 (m, 2H), 7.31 (s, 1H), 7.61 (m, 3H), 7.79 (d, J=8.5 Hz, 1H), 8.30 (d, J=7.7 Hz, 1H), 8.32 (d, J=5.1 Hz, 1H), 8.54 (d, J=2.9 Hz, 1H). MS (DCI) m/e 430 $(MH^+-H_2O)$; Anal calcd for $C_{25}H_{25}N_3O_5$.2.45 TFA: C, 49.41; H, 7 3.81; N, 5.78. Found: C, 49.39; H, 4.01; N, 5.85.

EXAMPLE 314

(S)-2-N-[4-(3-Pyridyloxymethyl)-2-(2-methylphenyl)benzoyl]amino-4-(N-methylaminocarbonyl)butanoic Acid The desired compound was prepared according to the method of Example 313, except substituting 2-amino-4-(N-methylaminocarbonyl)butanoic acid tert-butyl ester for glutamine tert-butyl ester. $^1$H NMR (300 MHz, $CD_3OD$) δ 1.78 (m, 1H), 1.96 (m, 3H), 2.11 (bs, 1.5H), 2.14 (bs, 1.5H), 2.68 (s, 3H), 4.30 (dd, J=3.9, 9.0 Hz, 1H), 5.44 (s, 2H), 7.20 (bs, 2H), 7.24 (m, 1H), 7.40 (bs, 1H), 7.60 (dd, J=1.7, 7.9 Hz, 1H), 7.72 (m, 1H), 8.00 (dd, J=5.5, 8.8 Hz, 1H), 8.30 (ddd, J=1.1, 2.9 Hz, 8.8H), 8.47 (d, J=5.5 Hz, 1H), 8.69 (d, J=2.6 Hz, 1H). MS (FAB) m/e 462 $(M+H)^+$. Anal calcd for $C_{26}H_{27}N_3O_5$.3.60 TFA: C, 45.69; H, 3.79; N, 5.02. Found: C, 45.73; H, 3.54; N, 4.82.

EXAMPLE 315

(S)-2-N-[4-(3-Pyridyloxymethyl)-2-(2-methylphenyl)benzoyl]amino-4-(N-ethylaminocarbonyl)butanoic Acid The desired compound was prepared according to the method of Example 313, except substituting 2-amino-4-(N-ethylaminocarbonyl)butanoic acid tert-butyl ester for glutamine tert-butyl ester. $^1$H NMR (300 MHz, DMSO) δ 0.99 (t, J=7.4 Hz, 3H), 1.72 (m, 1H), 1.86 (m, 1H), 1.96 (t, J=7.2 Hz, 2H), 2.05 (bs, 3H), 2.08 (s (shoulder to 2.05)), 3.04 (m, 2H), 4.07 (m, 1H), 5.37 (s, 2H), 7.12 (m, 2H), 7.20 (m, 2H), 7.32 (bs, 1H), 7.54 (dd, J=1.5, 8.1 Hz, 1H), 7.60 (d, J=8.1 Hz, 1H), 7.65 (bs, 1H), 7.71 (dd, J=5.1, 8.8 Hz, 1H), 7.93 (dd, J=2.2, 8.5 Hz, 1H), 8.31 (d, J=7.7 Hz, 1H), 8.39 (d, J=4.5 Hz, 1H), 8.62 (d, J=2.6 Hz, 1H). MS (DCI) m/e 476 $(M+H)^+$. Anal calcd for $C_{27}H_{29}N_3O_5$.3.05 TFA.1.2$H_2O$: C, 47.05; H, 4.11; N, 4.97. Found: C, 7.00; H, 4.00; N, 5.28.

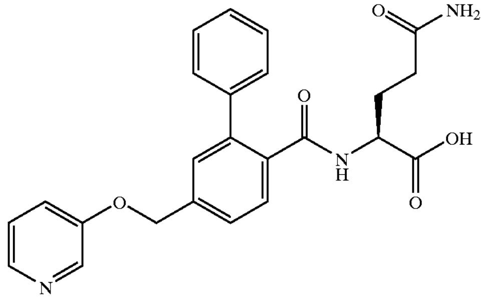

EXAMPLE 316

(S)-2-N-[4-(3-Pyridyloxymethyl)-2-phenylbenzoyl]amino-4-(aminocarbonyl)butanoic Acid The desired compound was prepared according to the method of Example 215, except substituting 4-(3-pyridyloxymethyl)-2-phenylbenzoic acid for 4-(3-pyridyloxymethyl)-2-(2-methylphenyl)benzoic acid. $^1$H NMR (300 MHz, DMSO) δ 1.79 (m, 1H), 1.95 (m, 1H), 2.09 (m, 2H), 4.18 (m, 1H), 5.42 (s, 2H), 6.80 (bs, 1H), 7.25 (m, 2H), 7.35 (m, 3H), 7.45 (m, 2H), 7.55 (m, 3H), 7.86 (dd, J=5.2, 8.5 Hz, 1H), 8.10 (d, J=7.7 Hz, 1H), 8.46 (d, J=4.4 Hz, 1H), 8.69 (d, J=8.1 Hz, 1H), 8.71 (bs, 1H); MS (DCI) m/e 434 ($MH^+$); Anal calcd for $C_{24}H_{23}N_3O_5$.2.40HCl: C, 55.33. H, 4.91. N, 8.07. Found: C, 55.32; H, 5.06; N, 8.21.

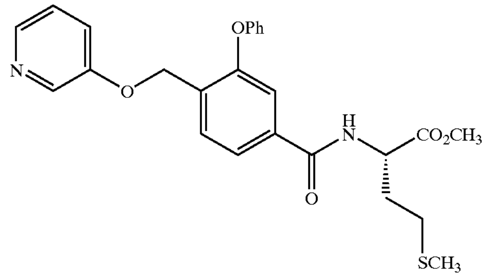

EXAMPLE 317

[4-(3-Pyridyloxymethyl)-3-phenoxybenzoyl] methionine

The desired compound was prepared according to the method of Examples 157C–H, except substituting 4-carbonylmethoxy-2-phenoxybenzoic acid for 4-carbonylmethoxy-3-phenoxybenzoic acid. $^1$H NMR (300 MHz, DMSO-$d_6$) δ 2.03 (s, 3H), 2.0–2.3 (m, 2H), 2.5–2.6 (m, 2H), 4.4–4.5 (m, 1H), 5.25 (s, 2H), 7.03 (d, J=8 Hz, 2H), 7.17 (t, J=8 Hz, 1H), 7.33–7.55 (m, 5H), 7.7–7.8 (m, 2H), 8.20 (d, J=4 Hz, 1H), 8.35 (d, J=3 Hz, 1H), 8.71 and 8.83 (d, J=8 Hz, 1H).

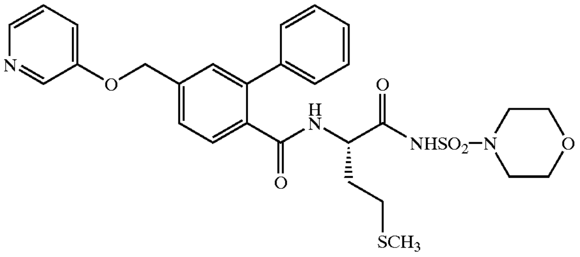

EXAMPLE 318

[4-(3-Pyridyloxymethyl)-2-phenylbenzoyl] methionine 1-Morpholinylsulfonimide

The desired compound was prepared according to the method of Example 254 using 1-morpholine sulfonamide (prepared as described by *Chem. Ber.* 1972, 105 (9), 2791). $^1$H NMR (300 MHz, DMSO-$d_6$) δ 1.73–1.9 (m, 2H), 2.03 (s, 3H), 2.15–2.28 (m, 2H), 3.15–3.25 (m, 4H), 3.58–3.65 (m, 4H), 4.20–4.29 (m, 1H), 5.30 (s, 2H), 7.30–7.57 (m, 10H), 8.18 (d, J=4 Hz, 1H), 8.39 (d, J=3 Hz, 1H), 8.61 (d, J=8 Hz, 1H).

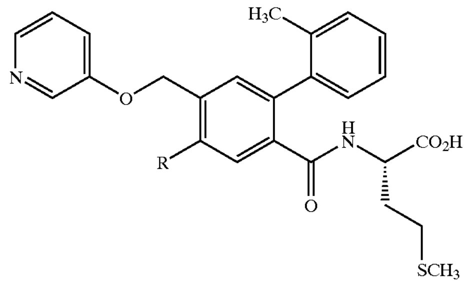

EXAMPLES 319 AND 320

EXAMPLE 319

[4-(3-Pyridyloxymethyl)-2-(2-methylphenyl)-5-butylbenzoyl]methionine

EXAMPLE 319A

2-Amino-5-bromoterephthalate Dimethyl Ester

To a −12° C. suspension in dichloromethane of 2-aminoterephthalate (10.46 g, 50 mmol) and pyridine (8.1 mL, 100 mmol) was added as solution of bromine (2.6 mL, 52.5 mmol) in dichloromethane (25 mL) over 0.5 hours and the reaction mixture was warmed slowly to ambient temperature and stirred overnight. Aqueous workup followed by recrystallization from 95% ethanol gave the desired compound (11 g, 77%).

EXAMPLE 319B 2-(2-Methylphenyl)-5-aminoterephthalate Dimethyl Ester

A solution of palladium acetate (260 mg, 1.16 mmol) and triphenylphosphine (1.21 g, 4.63 mmol) was stirred for 10 minutes at ambient temperature and then the product of Example 319A (11.1 g, 38.6 mmol), 2-methylphenylboronic acid (5.77 g, 42.4 mmol), ethanol (18 mL) and aqueous 2M sodium carbonate (157 mL) were added. The reaction mixture was warmed to reflux and stirred for 18 hours. The reaction mixture was cooled to ambient temperature and diluted with ether. The aqueous phase was extracted with ether. The combined organic layers were washed with water, dried, filtered and concentrated in vacuo to give an orange oil. Chromatography on silica gel (25% ethyl acetate-hexanes) gave the desired compound (9.6 g, 83%) as a yellow solid.

EXAMPLE 319C 2-(2-Methylphenyl)-5-iodoterephthalate Dimethyl Ester

A mixture of the product of Example 319B (7.00 g, 23.4 mmol) and aqueous 3M HCl (50 mL) in acetone (500 mL) was cooled to 0° C. and a solution of $NaNO_2$ (1.78 g, 25.7 mmol) in water (20 mL) was added dropwise. The reaction mixture was stirred for 1 hour and then urea (0.53 g, 8.88 mmol) and a solution of KI (6.79 g, 40.9 mmol) in water (20 mL) was added at a rate such that the reaction temperature remained below 0° C. The reaction mixture was stirred for 0.5 hours, then the cold bath was removed and stirring was continued for 2 hours. The reaction mixture was diluted with water (400 mL) and NaHSO3 was added until the brown color disappeared. The reaction mixture was filtered and the solid was recrystallized from 20:1 aqueous ethanol to give the desired compound (6.46 g, 67%). mp 105–109° C.

EXAMPLE 319D 2-(2-Methylphenyl)-5-iodoterephthalate 1-Methyl Ester

The desired compound was prepared by reaction of a solution of the product of Example 319C in THF with aqueous LiOH at 0° C. according to the method of Example 159.

EXAMPLE 319E 2-(2-Methylphenyl)-4-hydroxymethyl-5-iodobenzoic Acid Methyl Ester

The desired compound was prepared by reduction of the product of Example 319D using the procedure of Example 157C.

EXAMPLE 319F 2-(2-Methylphenyl)-4-bromomethyl-5-iodobenzoic Acid Methyl Ester

To a −10° C. solution in dichloromethane of the product of Example 319E (830 mg, 2.17 mmol) and carbon tetrabromide (864 mg, 2.60 mmol) was added triphenylphosphine (626 mg, 2.39 mmol) and the reaction mixture was warmed to 0° C. over 1 hour. The cold bath was then removed and stirring was continued for 2 hours. The reaction mixture was concentrated in vacuo and purified by chromatography on silica gel (5% ethyl acetate-hexanes) to give the desired compound (1.1 g) which also contained some triphenylphosphine.

EXAMPLE 319G 4-(3-Pyridyloxymethyl)-2-(2-methylphenyl)-5-iodobenzoic Acid Methyl Ester To a solution in dichloromethane (10 mL) of benzyltriethylammonium bromide (1.18 g, 4.34 mmol) was added 3-hydroxypyridine potassium salt (586 mg, 4.34 mmol) and the mixture was stirred for 15 minutes. A solution of the product of Example 319F (960 mg, 2.17 mmol) in dichloromethane (4 mL) was added and the reaction mixture was stirred overnight. The reaction mixture was washed with water, dried, filtered and concentrated in vacuo. Chromatography on silica gel (35% ethy acetate-hexanes) gave the desired compound (480 mg, 49%).

EXAMPLE 319H 4-(3-Pyridyloxymethyl)-2-(2-methylphenyl)-5-butylbenzoic Acid Methyl Ester To a solution of tributylborane (0.10 mL, 0.41 mmol) in degassed DMF was added a solution of the product of Example 319G (150 mg, 0.33 mmol) in DMF (1 mL) followed by bis(diphenylphosphinoferrocenyl)palladium(II) chloride (8 mg, 0.01 mmol) and potassium phosphate (212 mg, 1.0 mmol) and the reaction mixture was stirred at 65° C. for 3 hours. The reaction mixture was cooled to ambient temperature and poured into water. The aqueous phase was extracted with ethy acetate (2×). The combined organic layers were washed with water and brine, dried, and filtered through a plug of silica gel (ethyl acetate) to give the desired compound (162 mg) which was used without further purification.

EXAMPLE 319I 4-(3-Pyridyloxymethyl)-2-(2-methylphenyl)-5-butylbenzoic Acid

The desired product was prepared by saponification of the methyl ester in the product of Example 319H using the method of Example 234A.

EXAMPLE 319J

[4-(3-Pyridyloxymethyl)-2-(2-methylphenyl)-5-butylbenzoyl]methione Methyl Ester

The desired compound was prepared by coupling to the product of Example 319I with methionine methyl ester hydrochloride using the procedure used in step C of the preparation of compound 8.

EXAMPLE 319K

[4-(3-Pyridyloxymethyl)-2-(2-methylphenyl)-5-butylbenzoyl]methione

The desired compound was prepared by saponification of the product of Example 319J using the method of Example 159. $^1H$ NMR (300 MHz, DMSO-$d_6$) δ 8.36 (d, 1H), 8.18 (dd, 1H), 8.09 (bd, 1H), 7.48 (m, 1H), 7.37 (s, 1H), 7.32 (dd, 1H), 7.27 (s, 1H), 7.19 (m, 2H), 7.11 (m, 2H), 5.28 (s, 2H), 4.21 (m, 1H), 2.74 (dd, 2H), 1.98–2.20 (m, 5H), 1.96 (s, 3H), 1.37–1.90 (m, 6H), 0.92 (t, 3H). MS (CI, $NH_3$) m/e 507, 489. Anal calcd for $C_{29}H_{34}N_2O_4S.0.50H_2O$: C, 67.55; H, 6.84; N, 5.43. Found: C, 67.55; H, 6.69; N, 5.33.

EXAMPLE 320

[4-(3-Pyridyloxymethyl)-2-(2-methylphenyl)-5-isobutylbenzoyl]methionine

To a −78° C. solution in ether (1 mL) of tert-butyllithium (1.7 M in ether, 0.75 mL, 1.28 mmol) was added a solution of iodoisobutane (0.74 mL, 0.64 mmol) in ether (1 mL) and the mixture was stirred for 30 minutes. 9-methoxy-9-borabicyclo[3.3.1]nonane (1.0 M in ether, 0.66 mL, 0.66 mmol) was added and the reaction mixture was warmed to 30° C. and stirred for 30 minutes. A solution of the product of Example 319G (218 mg, 0.53 mmol) in DMF (4 mL) was then added, followed by bis(diphenylphosphinoferrocenyl) palladium(II) chloride (13 mg, 0.016 mmol) and potassium phosphate (338 mg, 1.59 mmol). The reaction mixture was stirred at 65° C. under a stream of nitrogen for 2 hours. Workup as described in Example 319H, followed by saponification, coupling and saponification as described in Example 319I–J gave the title compound. $^1H$ NMR (300 MHz, DMSO-$d_6$) δ 8.35 (d, 1H), 8.18 (dd, 1H), 8.06 (bd, 1H), 7.49 (dq, 1H), 7.35 (s, 1H), 7.33 (dd, 1H), 7.27 (s, 1H), 7.18 (m, 2H), 7.03 (m, 2H), 5.25 (s, 1H), 4.22 (m, 1H), 2.63 (bd, 2H), 2.12 (heptet, 1H), 2.03 (m, 4H), 1.96 (s, 3H), 1.64–1.90 (m, 3H), 0.96 (d, 6H). MS (CI, $NH_3$) m/e 507, 489, 221, 204. Anal calcd for $C_{29}H_{34}N_2O_4S.0.50H_2O$: C, 67.90; H, 6.82; N, 5.46. Found: C, 67.91; H, 6.68; N, 5.40.

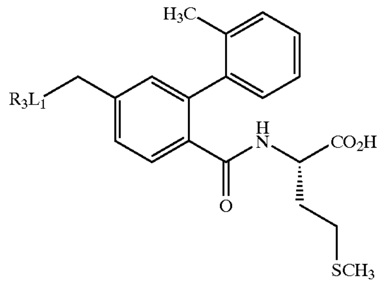

EXAMPLE 324

[4-(3-Pyridylthiomethyl)-2-(2-methylphenyl)benzoyl Methionine

To a solution in DMF (2 mL) of 4-chloromethyl-2-(2-methylphenyl)benzoic acid methyl ester (275 mg, 1.0 mmol) was added 3-pyridinethiol potassium salt (224 mg, 1.5 mmol). The reaction mixture was stirred for 30 minutes and then was poured into water. The mixture was extracted with ethyl acetate (3×). The combined organic extracts were washed with water and brine, dried, filtered and concentrated in vacuo. Chromatography on silica gel (40% ethyl acetate-hexanes) gave 4-(3-pyridylthiomethyl)-2-(2-methylphenyl)benzoic acid methyl ester which was converted to the title compound by saponification of the methyl ester, coupling with methionine methyl ester hydrochloride, and saponification as described in Examples 319I–J. $^1$H NMR (300 MHz, DMSO-$d_6$) δ 12.53 (bs, 1H), 8.49 (d, 1H), 8.38 (dd, 1H), 8.11 (d, 1H), 7.79 (dt, 1H), 7.43 (s, 2H), 7.31 (dd, 1H), 7.19 (m, 2H), 7.11 (m, 2H), 7.05 (m, 1H), 4.36 (s, 2H), 4.20 (m, 1H), 1.92–2.23 (m, 8H), 1.66–1.90 (m, 2H). MS (CI, $NH_3$) m/e 467, 449. Anal calcd for $C_{25}H_{26}N_2O_3S_2$: C, 64.35; H, 5.62; N, 6.00. Found: C, 64.00; H, 5.62; N, 5.89.

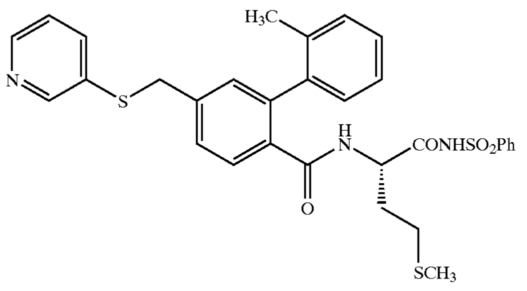

EXAMPLE 325

[4-(3-Pyridylthiomethyl)-2-(2-methylphenyl)benzoyl Methionine Phenylsulfonimide The desired compound was prepared by coupling of 4-(3-pyridylthiomethyl)-2-(2-methylphenyl)benzoic acid with methionine phenylsulfonimide hydrochloride using the procedure used in step C of the preparation of compound 8. $^1$H NMR (300 MHz, $CDCl_3$) δ 8.50 (m, 2H), 8.02 (m, 2H), 7.93 (t, 1H), 7.62 (m, 2H), 7.51 (m, 2H), 7.17–7.42 (m, 5H), 7.09 (m, 2H), 5.71 (d, 1H), 4.40 (m, 1H), 4.13 (s, 2H), 1.86–2.13 (m, 8H), 1.71 (m, 1H), 1.25 (m, 1H). MS (CI, $NH_3$) m/e 606, 225. Anal calcd for $C_{31}H_{31}N_3O_4S_3$ 1.53 TFA: C, 52.43; H, 4.20; N, 5.39. Found: C, 52.42; H, 4.14; N, 5.43.

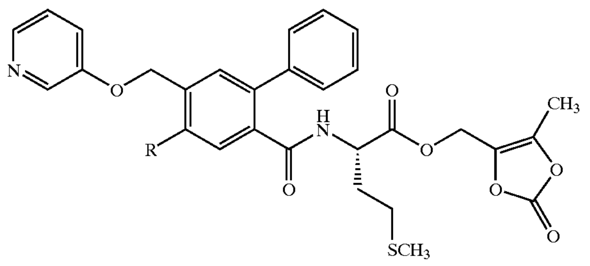

EXAMPLE 326

[4-(3-Pyridyloxymethyl)-2-phenylbenzoyl] methionine O-Dimethylvinylene Carbonate Ester

EXAMPLE 326A

1-Bromomethyl-2-methylvinylene Carbonate

A mixture of dimethylvinylene carbonate (11.4 g, 100 mmol), N-bromosuccinmide (17.8 g, 100 mmol) and 2,2'-azobisisobutyronitrile (250 mg) in carbon tetrachloride (400 mL) was stirred at reflux for 4 hours. Aqueous workup followed by vacuum distillation (110–112° C., 3.5 mm Hg) gave the desired compound (9.26 g, 48%).

EXAMPLE 326B

[4-(3-Pyridyloxymethyl)-2-phenylbenzoyl] methionine O-Dimethylvinylene Carbonate Ester To a solution in DMF (1 mL) of [4-(3-pyridyloxymethyl)-2-phenylbenzoyl]methionine. (132 mg, 0.30 mmol) was added cesium carbonate (55 mg, 0.17 mmol). After stirring for 15 minutes, a solution of the product of Example 326A (64 mg, 0.33 mmol) in DMF (0.2 mL) and the reaction mixture was stirred for 2 hours. The reaction mixture was poured into water and extracted with ethyl acetate (3×). The combined organic layers were washed with water and brine, dried, filtered and concentrate. Chromatography on silica gel (80% ethyl acetate-hexanes) gave the title compound (128 mg, 78%). $^1$H NMR (300 MHz, $CDCl_3$) δ 8.41 (bs, 1H), 8.18 (bs, 1H), 7.75 (d, 1H), 7.50 (dd, 1H), 7.44 (m, 5H), 7.30 (m, 2H), 5.89 (d, 1H), 5.20 (s, 2H), 4.83 (s, 2H), 4.64 (ddd, 1H), 2.07 (s, 3H), 1.86 (m, 9H), 1.73 (m, 1H). MS (CI, $NH_3$) m/e 549, 226.

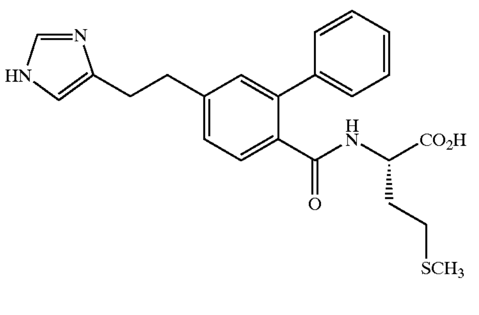

EXAMPLE 329

{4-[2-(1H-Imidazol-4-yl)ethyl]-2-phenylbenzoyl}methionine

EXAMPLE 329A

Diethyl (2-Phenyl-4-carboxymethylbenzyl) phosphonate

A slurry in THF of diethylphosphite (1.75 g, 12.7 mmol) and sodium hydride 60% in mineral oil, 305 mg, 12.7 mmol)

was stirred for 1.5 hours and then 4-chloromethyl-2-phenylbenzoic acid methyl ester was added and the reaction mixture was stirred for 18 hours at ambient temperature and 18 hours at reflux. The reaction mixture was concentrated in vacuo and the residue was partitioned between ethyl acetate and brine. The organic phase was dried over magnesium sulfate, filtered and concentrated in vacuo to give a yellow oil. Chromatography on silica gel (1:1 ethyl acetate-hexanes) gave the desired compound (3.19 g, 77%) as a colorless oil.

EXAMPLE 329B

4-[2-(1H-1-Triphenylmethylimidazol-3-yl)ethenyl]-2-phenylbenzoic Acid Methyl Ester To a 0° C. slurry in THF (2 mL) of sodium hydride (60% in mineral oil, 61.3 mg, 1.5 mmol) was added a solution of the product of Example 329B (402 mg, 1.5 mmol) in THF (3 mL) and the mixture was stirred for 2 hours. A solution of 1H-1-triphenylmethylimidazole-4-carboxaldehyde (761 mg, 2.35 mmol) in THF (2 mL) was added and the reaction mixture was heated at reflux for 8 hours. The reaction mixture was cooled to ambient temperature and concentrated in vacuo. The residue was partitioned between ethyl acetate and brine. The organic phase was dried over magnesium sulfate, filtered and concentrated in vacuo to give a yellow oil. Chromatography on silica gel (1:1 ethyl acetate-hexanes) gave the desired compound (740 mg, 90%) as a white solid.

EXAMPLE 329C

4-[2-(1H-1-Triphenylmethylimidazol-3-yl)ethyl]-2-phenylbenzoic Acid Methyl Ester The desired compound was prepared by catalytic (10% Pd/C) hydrogenation of the product of Example 329B.

EXAMPLE 329D

{4-[2-(1H-1-Triphenylmethylimidazol-4-yl)ethyl]-2-phenylbenzoyl}methionine

The desired compound was prepared by saponification of the product of Example 329C using aqueous lithium hydroxide and methanol at reflux, followed by coupling to the acid with methionine ethyl ester hydrochloride using the procedure of step c in the preparation of compound 8, and saponification of the ethyl ester using aqueous lithium hydroxide in aqueous THF.

EXAMPLE 329E

{4-[2-(1H-Imidazol-4-yl)ethyl]-2-phenylbenzoyl}methionine

A mixture of the product of Example 329D (15 mg, 0.02 mmol), trifluoroacetic acid (26 mg, 0.23 mmol) and triethylsilane (27 mg, 0.23 mmol) in dichloromethane (1 mL) was stirred for 18 hours. The reaction mixture was concentrated in vacuo and the residue was partitioned between water and 1:1 ethyl acetate-hexanes. The aqueous phase was freeze-dried to give the title compound as the trifluoroacetate salt. $^1$H NMR (300 MHz, DMSO-$d_6$) δ 1.9 (m, 3H), 2.0 (s, 3H), 2.3 (m, 2H), 4.1 (m, 1H), 4.2–4.4 (m, 4H), 7.3–7.5 (m, 8H), 7.7 (br d, 1H), 8.5 (d, 1H), 9.0 (s, 1H), 12 (br s, 1H). MS (DCI, $NH_3$) m/e 424 $(M+H)^+$.

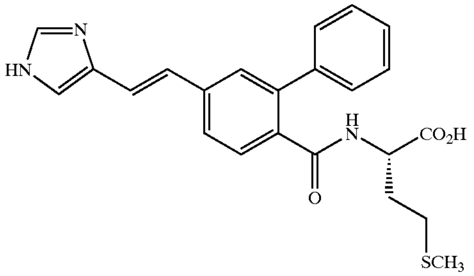

EXAMPLE 330

{4-[2-(1H-Imidazol-4-yl)ethyl]-2-phenylbenzoyl}methionine

The desired compound was prepared according to the method of Examples 329A, B, D and E. $^1$H NMR (300 MHz, DMSO-$d_6$) δ 1.9 (m, 3H), 2.0 (s, 3H), 2.3 (m, 2H), 4.6 (m, 1H), 5.8 (d, 1H), 6.1 (d, 1H), 7.3–7.5 (m, 8H), 7.7 (br d, 1H), 8.5 (d, 1H), 9.0 (s, 1H), 12 (br s, 1H). MS (DCI, $NH_3$) m/e 390 $(M+H)^+$.

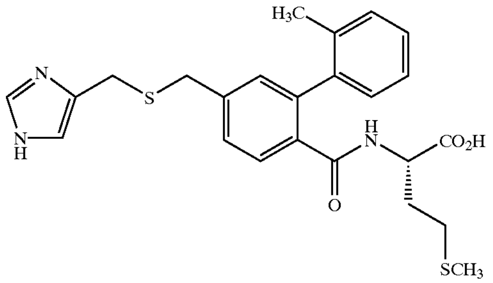

EXAMPLE 331

[4-(1H-Imidazol-4-ylmethylthiomethyl)-2-(2-methylphenyl)benzoyl]methionine

EXAMPLE 331A

4-Hydroxymethyl-2-(2-methylphenyl)benzoic Acid Methyl Ester

The desired compound was prepared according to the method of Example 158, except substituting 2-methylphenylboronic acid for phenyl boronic acid in Example 158A.

EXAMPLE 331B

4-Bromomethyl-2-(2-methylphenyl)benzoic Acid Methyl Ester

To a stirred solution of 4-hydroxymethyl-2-(2-methylphenyl)benzoic acid methyl ester prepared in Example 331A (10.85 g, 42.2 mmol) in dry DMF (40 mL) at 0° C. was added successively lithium bromide (4.00 g, 46.6 mmol, 1.1 eq) and phosphorus tribromide (4.18 mL, 44.5 mmol, 1.05 eq) at a rate such that the temperature did not exceed 5° C. On completion of the addition the mixture was warmed to ambient temperature, and quenched by the addition of ice. The resultant solution was partitioned between water and ether; the ethereal solution was dried ($Na_2SO_4$), filtered and the solvent removed under reduced pressure to afford the title compound (13 g, 96%) as a colorless oil.

EXAMPLE 331C

[4-(1H-Imidazol-4-ylmethylthiomethyl)-2-(2-methylphenyl)benzoyl]methionine

The desired compound was prepared according to the method of Example 242, except substituting 4-bromomethyl-2-(2-methylphenyl)benzoic acid methyl ester, prepared as in Example 331B, for 4-bromomethyl-2-phenylbenzoic acid methyl ester. $^1H$ NMR (300 MHz, DMSO-$d_6$) δ 1.8 (m, 3H), 2.0 (s, 3H), 2.5 (m, 2H), 3.8 (s, 2H), 3.9 (s, 2H), 4.3 (m, 1H), 7.3 (m, 8H), 7.5 (br d, 1H), 8.5 (d, 1H), 8.9 (br s, 1H), 2 (br s, 1H). MS (DCI, $NH_3$) m/e 456 $(M+H)^+$.

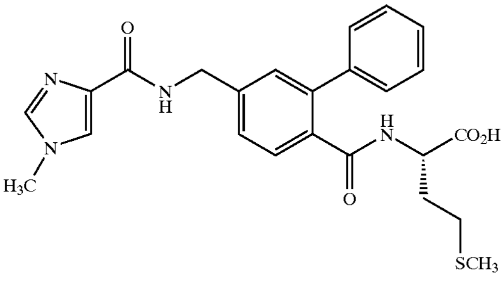

EXAMPLE 332

[4-(1H-1-Methylimidazol-4-ylcarbonylaminomethyl)-2-phenylbenzoyl]methionine

EXAMPLE 332A

4-Azidomethyl-2-phenylbenzoic Acid Methyl Ester

A mixture of 4-bromomethyl-2-phenylbenzoic acid methyl ester (1.5 g, 4.9 mmol), sodium azide (1.28 g, 19.7 mmol) and tetrabutylammonium iodide (1.3 g, 4.9 mmol) in DMF (16 mL) was heated at 75° C. for 18 hours. The reaction mixture was diluted with water and extracted twice with ethyl acetate. The combined organic extracts were dried over magnesium sulfate, filtered and concentrated in vacuo. Chromatography on silica gel (15% ethyl acetate-hexanes) to give the desired azide as a colorless oil (1.01 g).

EXAMPLE 332B

[4-Azidomethyl-2-phenylbenzoyl]methionine Methyl Ester

The desired compound was prepared by saponification of the product of Example 332A using sodium hydroxide in refluxing aqueous methanol, followed by coupling of the resulting acid with methionine methyl ester hydrochloride using the procedure of step C in the preparation of compound 8.

EXAMPLE 332C

[4-Aminomethyl-2-phenylbenzoyl]methionine Methyl Ester

A solution of the product of Example 332B (1.00 g, 2.5 mmol) and triphenylphosphine (0.98 g, 3.75 mmol) in THF (10 mL) was heated at reflux for 4 hours. The reaction mixture was cooled to ambient temperature, water (0.45 mL) was added, and the reaction mixture was stirred for 18 hours. The reaction mixture was concentrated in vacuo and the residue was partitioned between water and ethyl acetate. The organic phase was washed with brine, dried over sodium sulfate, filtered and concentrated in vacuo. Chromatography on silica gel (25% ethyl acetate-hexane, then 1% ammonia-ethyl acetate) gave the desired compound as a colorless oil (900 mg, 97%).

EXAMPLE 332D

[4-(1H-1-Methylimidazol-4-ylcarbonylaminomethyl)-2-phenylbenzoyl]methionine

The desired compound was prepared by coupling of the product of Example 332C with 1H-1-methylimidazole-4-carboxylic acid using the procedure used in step C of the preparation of compound 8, followed by saponification of the methyl ester using sodium hydroxide in aqueous THF. $^1H$ NMR (300 MHz, DMSO-$d_6$) δ 1.8 (m, 3H), 2.1 (s, 3H), 2.5 (m, 2H), 3.6 (m, 1H), 3.8 (m, 3H), 4.8 (m, 1H), 4.9 (d, 2H), 7.3 (m, 8H), 7.4 (d, 1H), 8.3 (d, 1H), 12.0 (br s, 1H). MS (DCI, $NH_3$) m/e 467 $(M+H)^+$.

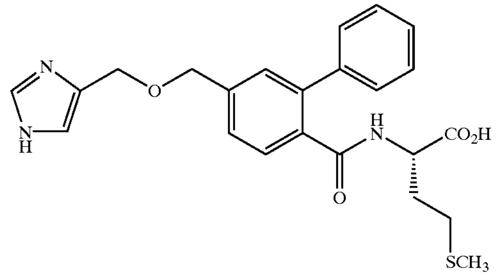

EXAMPLE 333

[4-(1H-Imidazol-4-yl-methyloxymethyl)-2-phenylbenzoyl]methionine

The desired compound was prepared according to the method of Examples 242C–F, except substituting 1H-1-triphenylmethylimidazol-4-ylmethanol sodium salt for 1H-1-triphenylmethylimidazol-4-ylmethylthiol sodium salt, and 4-chloromethyl-2-phenylbenzoic acid methyl ester for 4-bromomethyl-2-phenylbenzoic acid methyl ester. $^1H$ NMR (300 MHz, DMSO-$d_6$) δ 1.6 (m, 3H), 2.1 (s, 3H), 2.4 (m, 2H), 3.6 (s, 2H), 3.7 (s, 2H), 4.3 (m, 1H), 7.2 (m, 8H), 7.5 (br d, 1H), 8.5 (d, 1H), 8.9 (br s, 1H), 12 (br s, 1H). MS (DCI, $NH_3$) m/e 440 $(M+H)^+$.

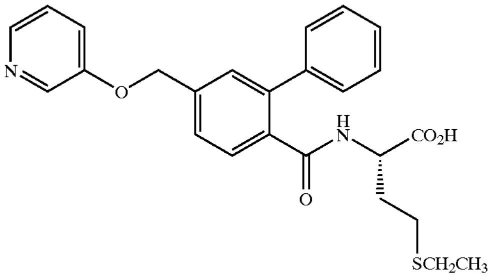

EXAMPLE 334

2-N-[4-(3-Pyridyloxy)-2-phenylbenzoyl]ethionine

The desired compound was prepared according to the method of Example 235, except substituting ethionine methyl ester hydrochloride for methionine methyl ester hydrochloride.

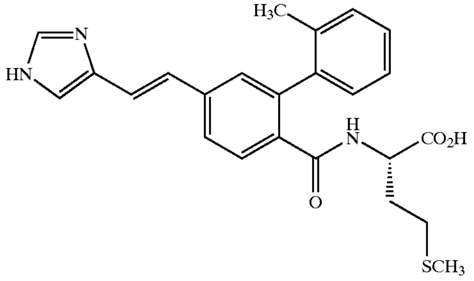

EXAMPLE 335

{4-[2-(1H-Imidazol-4-yl)ethenyl]-2-(2-methylphenyl)benzoyl Methionine

The desired compound was prepared according to the method of Example 330, except substituting 4-chloromethyl-2-(2-methylphenyl)benzoic acid methyl ester for 4-chloromethyl-2-phenylbenzoic acid methyl ester. $^1H$ NMR (300 MHz, DMSO-$d_6$) δ 1.90 (s, 3H), 2.10–2.20 (m, 8H), 4.20 (m, 2H), 7.10–7.40 (m, 7H), 7.50 (m, 2H), 7.70 (d, 1H), 8.20 (brd, 1H), 8.80 (d, 1H). MS (DCI-$NH_3$) 436 $(M+H)^+$.

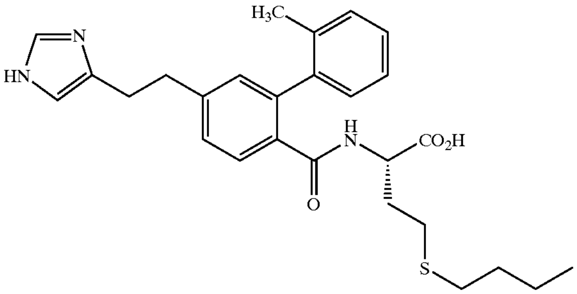

EXAMPLE 336

2-N-{4-[2-(1H-Imidazol-4-yl)ethyl]-2-(2-methylphenyl)benzoyl}amino-4-(thiobutyl)butanoic Acid

EXAMPLE 336A

2-N-tert-Butoxycarbonylamino-4-hydroxybutanoic Acid Benzyl Ester

To a 0° C. solution in THF (103 mL) of N-tert-butoxycarbonylaspartic acid 1-benzyl ester (10.0 g, 30.9 mmol) was added borane-THF (1 M in THF, 61.8 m]L, 61.8 mmol) over 10 minutes. The cold bath was then removed and the reaction mixture was stirred for 3 hours. The reaction mixture was cooled to 0° C. and quenched with brine. The layers were separated and the aqueous phase was extracted with ethyl acetate. The combined organic layers were washed with brine, dried over magnesium sulfate, filtered, and concentrated in vacuo. Chromatography on silica gel (15% ethyl acetate-hexanes) gave the desired compound as a colorless oil (4.11 g, 43%).

EXAMPLE 336B

2-N-tert-Butoxycarbonylamino-4-methanesulfonyloxybutanoic Acid Benzyl Ester

To a 0° C. solution in dichloromethane (151 mL) of the product of Example 334B (14.68 g, 45.4 mmol) was added triethylamine (9.19 g, 90.8 mmol) and methanesulfonyl chloride (5.72 g, 50 mmol) and the reaction mixture was stirred for 2 hours. The reaction mixture was concentrated in vacuo and the residue was partitioned between ethyl acetate and brine. The organic phase was dried over magnesium sulfate, filtered and concentrated in vacuo. Chromatography on silica gel (25% ethyl acetate-hexanes) gave the desired compound (15.99 g, 91%).

EXAMPLE 336C

2-N-tert-Butoxycarbonylamino-4-(thiobutyl)butanoic Acid Benzyl Ester

To a suspension in THF (6 mL) of sodium hydride (60% in mineral oil, 568 mg, 14.2 mmol) was added butanethiol (1.23 g, 14.2 mmol) and the mixture was stirred for 0.5 hours. A solution of the product of Example 336B (1.83 g, 4.73 mmol) in THF (15.7 mL) was added and the reaction mixture was stirred for 3 hours. The reaction mixture was cooled to 0° C., quenched with water and extracted with ethyl acetate. The organic phase was dried over magnesium sulfate, filtered and concentrated in vacuo. Chromatography on silica gel (5% ethyl acetate-hexanes) gave the desired compound 1.74 g, 97%).

EXAMPLE 336D

2-Amino-4-(thiobutyl)butanoic Acid Methyl Ester Hydrochloride

To a solution in methanol (5 mL) of the product of Example 336B (1.00 g, 2.62 mmol) was added aqueous 1M lithium hydroxide (13.1 mL) and the reaction mixture was stirred for 4 hours. The methanol was evaporated and the aqueous residue was extracted with ethyl acetate. The organic extract was discarded and the aqueous phase was adjusted to pH 2 with aqueous 1N HCl and extracted with ethyl acetate. The ethyl acetate extract was dried over magnesium sulfate, filtered and concentrated in vacuo to give a colorless oil. The oil was dissolved in methanol (25 mL) and thionyl chloride (1.56 g, 13.1 mmol) was added. The reaction mixture was stirred at reflux for 4 hours, cooled to ambient temperature and concentrated to a colorless oil which was used without further purification.

EXAMPLE 336E

2-N-{4-[2-(1H-Imidazol-4-yl)ethyl]-2-(2-methylphenyl)benzoyl}amino-4-(thiobuty)butanoic Acid The desired compound was prepared from the product of Example 336D and 4-[2-(1H-imidazol-4-yl)ethyl]-2-(2- methylphenyl)benzoic acid methyl ester according to the method of Example 329D and E. $^1H$ NMR (300 MHz, DMSO-$d_6$) δ 1.2 (m, 4H), 1.4–1.6 (m, 5H), 1.8–2.1 (m, 5H), 3.2 (s, 3H), 3.5 (br s, 1H), 4.3 (m, 4H), 7.0–7.4 (m, 7H), 8.2 (brd, 1H), 8.9 (d, 1H), 12 (br s, 2H). MS (DCI-$NH_3$) 480 $(M+H)^+$.

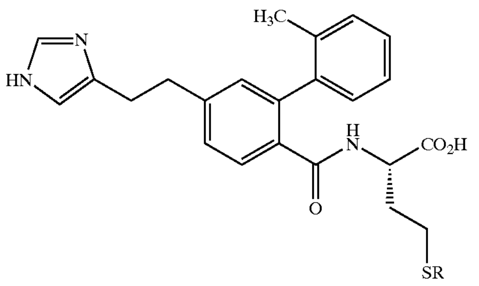

EXAMPLES 337–342

The compounds of Examples 337–341 were prepared according to the method of Example 336, except substituting the desired thiol for butanethiol.

| Example | R | Physical Data $^1H$ NMR (300 MHz, DMSO-d6) MS (DCI—$NH_3$) m/e |
|---|---|---|
| 337 | propyl | $^1H$ NMR δ 1.1 (m, 3H), 1.3–1.6 (m, 4H), 1.8–2.1 (m, 5H), 3.3 (s, 3H), 3.4 (br s, 1H), 4.3 (m, 4H), 7.0–7.4 (m, 7H), 8.2 (brd, 1H), 8.9 (d, 1H), 12 (br s, 1H). MS 466 $(M + H)^+$. |
| 338 | methyl | $^1H$ NMR δ 1.6 (m, 4H), 1.9 (s, 4H), 2.2–2.4 (m, 1H), 3.0 (s, 3H), 4.2 (br m, 4H), 7.0–7.5 (m, 7H), 8.1 (brd, 1H), 8.9 (d, 1H), 12.0 (br s, 2H). MS 438 $(M + H)^+$. |
| 339 | pentyl | $^1H$ NMR δ 1.3 (m, 5H), 1.4–1.6 (m, 6H), 1.8–2.2 (m, 5H), 3.1 (s, 3H), 3.5 (br s, 1H), 4.2 (m, 4H), 7.0–7.4 (m, 7H), 8.2 (brd, 1H), 8.9 (d, 1H), 12.0 (br s, 2H). MS 494 $(M + H)^+$. |
| 340 | iso-propyl | $^1H$ NMR δ 1.1 (d, 6H), 1.8 (m, 3H), 2.2–2.4 (m, 2H), 2.8 (septet, 1H), 3.0 (s, 3H), 3.4 (br s, 1H), 4.2 (m, 4H), 7.0–7.2 (m, 7H), 8.2 (brd, 1H), 8.9 (d, 1H), 12.0 (br s, 2H). MS 466 $(M + H)^+$. |
| 341 | cyclo-pentyl | $^1H$ NMR δ 1.1 (m, 9H), 1.8 (m, 3H), 2.0–2.3 (m, 2H), 3.0 (s, 3H), 3.4 (br s, 1H), 4.1 (m, 4H), 7.0–7.3 (m, 7H), 8.2 (brd, 1H), 8.9 (d, 1H), 12 (br s, 2H). MS 492 $(M + H)^+$. |
| 342 | cyclo-hexyl | $^1H$ NMR δ 1.1 (m, 11H), 1.7 (m, 3H), 1.9–2.4 (m, 2H), 3.1 (s, 3H), 3.2 (br s, 1H), 4.1 (m, 4H), 7.0–7.4 (m, 7H), 8.2 (brd, 1H), 8.8 (d, 1H), 12 (br s, 2H). MS 506 $(M + H)^+$. |

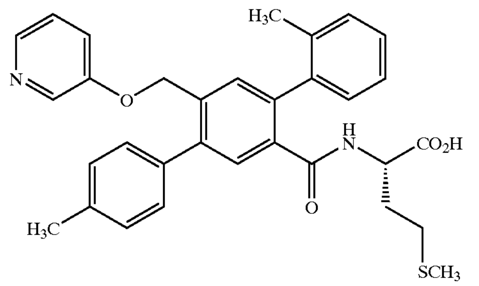

EXAMPLE 343

[4-(3-Pyridyloxymethyl)-5-(4-methylphenyl)-2-(2-methylphenyl)benzoyl Methionine

EXAMPLE 343A

[4-(3-Pyridyloxymethyl)-5-(4-methylphenyl)-2-(2-methylphenyl)benzoyl Methionine Methyl Ester To a solution of tetrakis(triphenylphosphine)palladium(0) (2 mg) in toluene (1 mL) was added a solution of 4-(3-pyridyloxymethyl)-5-iodo-2-(2-methylphenyl)benzoic acid methyl ester (100 mg, 0.22 mmol), prepared as in Example 219G, in toluene (3 mL). The mixture was stirred for 10 minutes, then a solution of 4-methylphenylboronic acid (33 mg, 0.24 mmol) in ethanol (2 mL) and aqueous 2M sodium carbonate were added. The reaction mixture was stirred overnight at reflux and additional catalyst (20 mg), boronic acid (20 mg) and base (0.5 mL) were added and reflux was continued for 4 hours. The reaction mixture was cooled to ambient temperature, diluted with ether, washed with water and brine, dried over sodium carbonate, filtered and concentrated in vacuo. Chromatography on silica gel (30% ethyl acetate-hexanes) gave the desired compound (98 mg).

EXAMPLE 343B

[4-(3-Pyridyloxymethyl)-5-(4-methylphenyl)-2-(2-methylphenyl)benzoyl Methionine

The desired compound was prepared by saponification of the compound of Example 343A, followed by coupling with methionine methyl ester hydrochloride and saponification of the methyl ester as described above. $^1H$ NMR (300 MHz, $CDCl_3$) δ 8.31 (1H, d, J=9 Hz), 8.19 (1H, d, J=3 Hz), 7.90 (1H, d, J=4 Hz), 7.42 (1H, s), 7.40–7.20 (10H, m), 6.07 (1H, d, J=9 Hz), 5.08 (2H, m), 4.62 (1H, m), 2.40 (3H, s), 2.25–2.10 (5H, 2.02 (3H, s), 2.00–1.55 (2H, m). MS (DCI, $NH_3$) m/e 541 $(M+H)^+$. Anal calcd for $C_{32}H_{32}N_2O_4S.0.50H_2O$: C, 69.92; H, 6.05; N, 5.10. Found: C, 69.94; H, 6.20; N, 4.90.

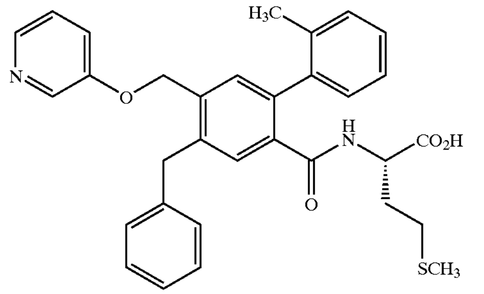

EXAMPLE 344

[4-(3-Pyridyloxymethyl)-5-phenylmethyl-2-(2-methylphenyl)benzoyl Methionine

EXAMPLE 344A

[4-(3-Pyridyloxymethyl)-5-phenylmethyl-2-(2-methylphenylabenzoyl Methionine Methyl Ester To a solution in DMF (2 mL) of bis (diphenylphosphinoferrocenyl)palladium(II) chloride (30 mg) and cesium chloride (213 mg, 0.654 mmol) was added a solution of 4-(3-pyridyloxymethyl)-5-iodo-2-(2-methylphenyl)benzoic acid methyl ester (100 mg, 0.22 mmol), prepared as in Example 219G, and 9-benzyl-9-borabicyclo[3.3.1]nonane (0.5 M in THF, 1.31 mL, 10.6 mmol) and the reaction mixture was stirred at 70° C. for 3 hours. The reaction mixture was cooled to ambient temperature and partitioned between water and ethyl acetate. The organic phase was washed with water and brine, dried over sodium carbonate, filtered and concentrated in vacuo. Chromatography on silica gel (30% ethyl acetate-hexanes) gave the desired compound.

EXAMPLE 344B

[4-(3-Pyridyloxymethyl)-5-methylphenyl-2-(2-methylphenyl)benzoyl Methionine

The desired compound was prepared by saponification of the compound of Example 343A, followed by coupling with methionine methyl ester hydrochloride and saponification of the methyl ester as described above. $^1$H NMR (300 MHz, $CDCl_3$) δ 8.27 (1H, d, J=3 Hz), 8.19 (1H, dd, J=6, 2 Hz), 7.88 (1H, s), 7.40–7.00 (12H, m), 6.00 (1H, d, J=9 Hz), 5.08 (1H, d, J=12 Hz), 5.01 (1H, d, J=12 Hz), 4.62 (1H, m), 4.15 (2H, s), 2.20–2.05 (5H, m), 2.02 (3H, s), 1.92 (1H, m) 1.60 (1H, m). MS (DCI, $NH_3$) m/e 541 $(M+H)^+$. Anal calcd for $C_{32}H_{32}N_2O_4S.0.25H_2O$: C, 70.50; H, 6.01; N, 5.14. Found: C, 70.23; H, 5.84; N, 4.94.

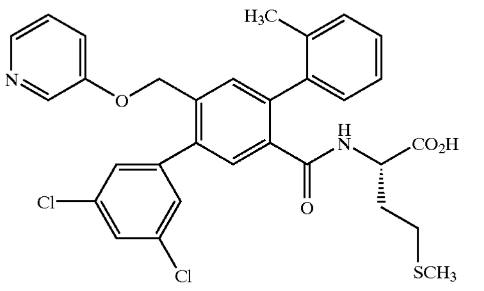

EXAMPLE 345

[4-(3-Pyridyloxymethyl)-5-(3,5-dichlorolphenyl)-2-(2-methylphenyl)benzoyl Methionine The desired compound was prepared according to the method of Example 343, except substituting 3,5-dichlorophenylboronic acid for 4-methylphenylboronic acid. $^1$H NMR (300 MHz, $CDCl_3$) δ 8.37 (1H, d, J=9 Hz), 8.21 (1H, d, J=3 Hz), 7.85 (1H, d, J=4 Hz), 7.44 (1H, s), 7.40–7.20 (9H, m), 6.08 (1H, d, J=9 Hz), 5.03 (2H, s), 4.62 (1H, m), 2.25–2.05 (5H, m), 2.02 (3H, s), 1.95 (1H, m) 1.64 (1H, m). MS (DCI, $NH_3$) m/e 595 $(M+H)^+$. Anal calcd for $C_{31}H_{28}Cl_2N_2O_4S.0.20H_2O$: C, 62.15; H, 4.78; N, 4.68. Found: C, 61.86; H, 4.38; N, 4.38.

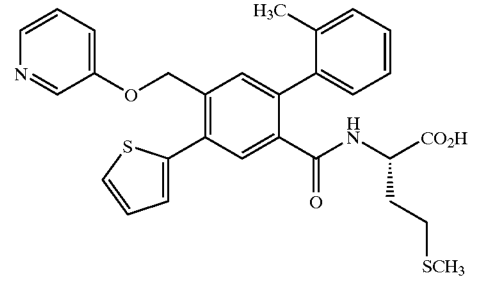

EXAMPLE 346

[4-(3-Pyridyloxymethyl)-5-(2-thienyl)-2-(2-methylphenyl)benzoyl Methionine

The desired compound was prepared according to the method of Example 343, except substituting 2-thienylboronic acid for 4-methylphenylboronicacid. $^1$H NMR (300 MHz, $CDCl_3$) δ 8.38 (1H, d, J=3 Hz), 8.20 (1H, dd, J=3, 1 Hz), 8.03 (1H, s), 7.43 (1H, s), 7.39 (1H, dd, J=6, 2 Hz), 7.38–7.20 (6H, m), 7.15 (1H, dd, J=3,1 Hz), 7.08 (1H, m), 6.07 (1H, d, J=9 Hz), 5.10 (2H, m), 4.61 (1H, m), 2.20–2.05 (5H, m), 2.02 (3H, s), 1.93 (1H, m) 1.62 (1H, m). MS (DCI, $NH_3$) m/e 533 $(M+H)^+$. Anal calcd for $C_{29}H_{28}N_2O_4S_2$ $0.25H_2O$: C, 64.84; H, 5.35; N, 4.21. Found: C, 64.55; H, 4.83; N, 4.85.

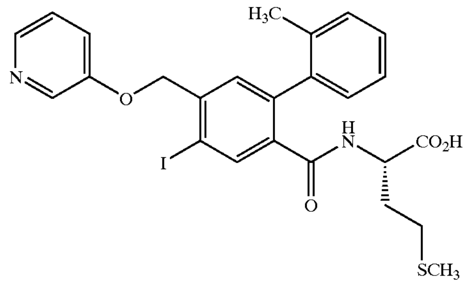

EXAMPLE 347

[4-(3-Pyridyloxymethyl)-5-iodo-2-(2-methylphenyl) benzoyl Methionine

The desired compound was prepared by saponification of 4-(3-pyridyloxymethyl)-5-iodo-2-(2-methylphenyl)benzoic acid methyl ester, prepared as in Example 219G, followed by coupling with methionine methyl ester hydrochloride and saponification of the methyl ester as described above. $^1$H NMR (300 MHz, DMSO-$d_6$) δ 12.68 (1H, bs), 8.45 (1H, d, J=9 Hz), 8.37 (1H, d, J=3 Hz), 8.20 (1H, d, J=4 Hz), 7.93 (1H, s), 7.48 (1H, m), 7.37 (2H, m), 7.30–7.00 (4H, m), 5.20 (2H, s), 4.22 (1H, m), 2.30–2.00 (5H, m), 1.96 (3H, s), 1.80 (2H, m). MS m/e (DCI, $NH_3$) m/e 577 $(M+H)^+$. Anal calcd for $C_{25}H_{25}IN_2O_4S$: C, 51.85; H, 4.40; N, 4.84. Found: C, 51.91; H, 4.47; N, 4.69.

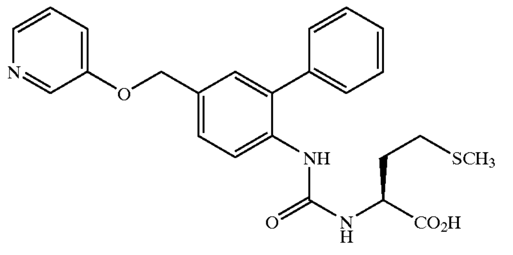

EXAMPLE 348

[4-(3-Pyridyloxymethyl)-2-(phenyl) phenylaminocarbonyl]methionine

To a solution in toluene of 4-(3-pyridyloxymethyl)-2-phenylbenzoic acid (126 mg) was added diphenylphosphoryl azide (0.11 mL) and triethylamine (0.075 mL) and the reaction mixture was heated at 100° C. for 20 minutes. A solution in dichloromethane of methionine methyl ester (prepared by addition of triethylamine to the dichloromethane solution) was added and the reaction mixture was stirred at 100° C. for 1 hour and then overnight at ambient temperature. The precipitated product was isolated by filtration and rinsed with ethyl acetate. The filtrate was concentrated and purified by chromatography on silica gel (80% ethyl acetate-hexanes) to give the methyl ester (100 mg). Saponification of the methyl ester using saturated aqueous lithium hydroxide in methanol gave the title compound. $^1H$ NMR (DMSO, 300 MHz) δ 1.77 (1H, td, J=7.5, 14.7 Hz), 1.95 (1H, tdd, J=5.7, 7.5, 14.7 Hz), 2.04 (3H, s), 2.45 (2H, t, J=7.5 Hz), 4.22 (1H, td, J=5.7, 7.5 Hz), 5.14 (2H, s), 6.98 (1H, d, J=8.1 Hz), 7.25 (1H, d, J=2.1 Hz), 7.29–7.53 (8H, m), 7.60 (1H, s), 7.92 (1H, d, J=8.7 Hz), 8.16 (1H, dd, J=0.9, 5.1 Hz), 8.35 (1H, d, J=2.7 Hz). MS (FAB/APCI) m/e 452 $(M+H)^+$, 450 $(M-H)^-$, 486 $(M-Cl)^-$. Anal calcd for $C_{24}H_{25}N_3O_4S.0.30H_2O$: C, 63.08; H, 5.65; N, 9.20. Found: C, 63.11; H, 5.42; N, 8.67.

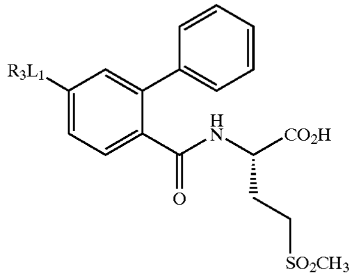

EXAMPLES 350–357

All reactions were performed either in a Manual solid phase synthesis flask using a 120° rotary shaker or on an Advanced ChemTech Model 396 Multiple Peptide Synthesizer (Advanced ChemTech Inc.; Louisville, Ky.) at ambient temperature.

After the reactions were performed the finished compounds were cleaved from the resin. Usually, 80–90 mg of the dried resin containing the desired amide; urea; or secondary amine was treated with a 1.50 mL solution of 95/5 (v:v) trifluoroacetic acid/water for 1.5 h at ambient temperature. The spent resin was removed by filtration and the resulting cleavage solution evaporated in-vacuo. In most cases, 5–20 mg of crude compound was obtained. Compounds obtained had the desired MW as determined by electrospray mass spectroscopy and had an HPLC purity of 40–90%, or were further purified by partition chromatography to afford compounds of 40–60% HPLC purity. Two types of gradients were used for the reverse phase HPLC. For the amides. and ureas a gradient starting with 100% water-0.1% Trifluoroacetic acid and finishing with 100% acetonitrile-0.1% Trifluoracetic acid during a 30 minute period was used. For the secondary amines a gradient beginning with 100% water-5 mmol ammonium acetate and finishing with 80% acetonitrile-water-5 mmol ammonium acetate during 25 minutes was used.

80 mg of resin (substitution 0.40 mmol/g) containing [4-amino-2-phenylbenzoyl]methionine-Wang-polystyrene resin was shaken for 3 min. with 1.0 mL. of N-methylpyrrolidone (NMP). The solvent was drained and the resin was treated 2×(3 min) with 1 mL. NMP. To the now swollen resin were then added 0.20 mL NMP; 0.20 mL of a 1.92 M diisopropylethylamine (DIEA)/NMP solution (15 eq.); 1.00 mL of a 0.180 mM/NMP solution of the desired carboxylic acid (5 eq.); and finally 0.20 mL of a 0.90 M Bromo-tris-pyrrolidino-phosphonium hexafluorophosphate (PyBrop; 5 equiv.)1/NMP solution. The reaction slurry was then mixed for 6 h and drained. The resin was then washed with NMP (3×; 1.0 mL; 3 min. ea); isopropanol (IPA; 5×; 1.0 mL; 3 min. ea.); NMP (3×; 1.0 mL; 3 min. ea.); methanol (MEOH; 2×; 1.0 ml; 3 min. ea.); and finally diethyl ether (2×; 1.0 mL; 3 min. ea.). The resin was then dried and subjected to cleavage conditions described above.

| Example | $R_3L_1$ | MS $(M + H)^{\pm}$ |
|---|---|---|
| 350 | 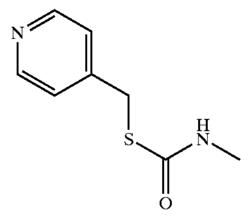 | 496 |
| 351 | 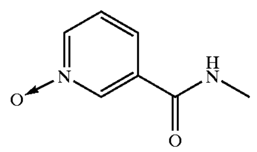 | 466 |
| 352 | 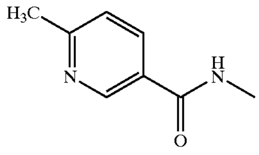 | 464 |
| 353 | 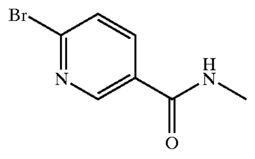 | 528 |

-continued

| Example | $R_3L_1$ | MS (M + H)$^{\pm}$ |
|---|---|---|
| 357 | 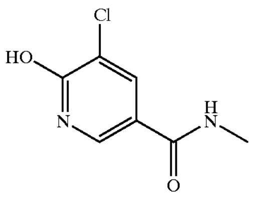 | 502 |

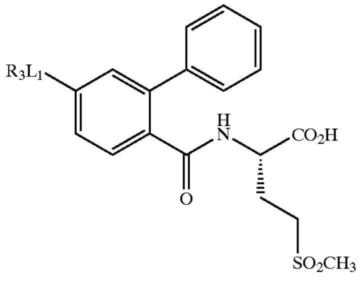

EXAMPLES 358–359

90 mg of resin (substitution 0.39 mmol/g.) containing [4-amino-2-phenylbenzoyl]methionine-Wang-polystyrene resin was shaken with 1.0 mL. dimethylformamide (DMF) for 3 min. The solvent was drained and the resin was then washed with DMF (3×; 1.0 mL; 3 min. ea.); tetrahydrofuran (THF; 4×; 1.0 mL; 3 min. ea.); THF/dichloromethane (DCM) 1:1 (v:v) (4×; 1.0 mL; 3 min. ea.). The resin was then treated with 0.20 mL of DCM/THF (1:1) and a 1.0 mL solution of 0.50 M. p-Nitrophenylchloroformate/0.50 M DIEA in a 1:1 solvent mixture of DCM/THF. The resin suspension was then shaken for 15 min. and to the suspension was then added 0.020 mL of neat DIEA. After shaking for an additional 15 min.; the solvents were drained away and the resin was then washed with DCM/THF (1:1) (4×; 1.0 mL; 3 min. ea.) The resin was then treated with 0.20 mL of DMF and 1.0 mL of a DMF solution containing 0.50 M of the desired primary or secondary amine and 0.50 M of DIEA. The suspension was shaken for 30 min. The solvent was drained off and the resin was then washed with DMF (4×; 1.0 mL; 3 min. ea); THF (4×; 1.0 mL; 3 min. ea.); DCM[1HF (4×; 1.0 mL; 3 min. ea); diethyl ether (4×; 1.0 mL; 3 min. ea.). The resin was then dried and subjected to cleavage from the resin as described above.

| Example | $R_3L_1$ | MS (M + H)$^+$ |
|---|---|---|
| 359 | 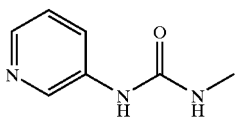 | 465 |

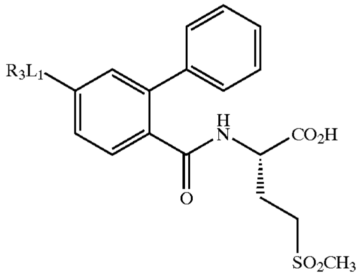

EXAMPLES 363, 367, 368 AND 376

Typically 80 mg of resin (substitution of 0.40 mmol/g) containing 4-formyl-2-phenylbenzamide-L-Methionine-Wang-polystyrene resin was swollen with 1.0 mL of dimethyl acetamide (DMA) for 3 min. The solvent was drained and the resin was then washed with additional DMA (2×; 1.0 mL; 3 min. ea.). The resin was then suspended in 0.20 mL of DMA and to the suspension was then added a 1.0 mL solution containing 0.48 mM of the desired primary amine (10 eq.) in a 3:1 (v:v) solution of DMA/acetic acid. The resin was shaken for 2 h and was then treated with 0.25 mL of a 2.4 mM solution of sodium cyanoborohydride (10 eq.) in DMA. The resin-slurry was shaken for an additional 2 h. The solvents were drained and the resin was then washed with DMA (6×; 1.0 mL; 3 min. ea.); DMF (6×; 1.0 mL; 3 min. ea.); IPA (6×; 1.0 mL; 3 min. ea.); DMF (6×; 1.0 mL; 3 min. ea.); MEOH (6×; 1.0 mL; 3 min. ea.); diethyl ether (6×; 1.0 mL; 3 min. ea.). The resin was dried and then subjected to cleavage as described above.

| Example | $R_3L_1$ | MS (M + H)$^{\pm}$ |
|---|---|---|
| 363 | 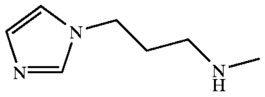 | 468 |
| 367 | 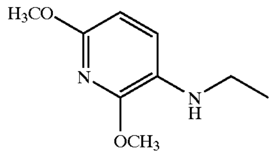 | 497 |

-continued

| Example | $R_3L_1$ | MS $(M + H)^{+}$ |
|---|---|---|
| 368 | 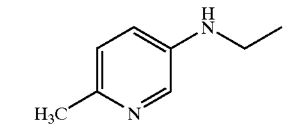 | 451 |
| 376 | 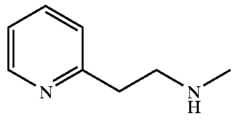 | 465 |

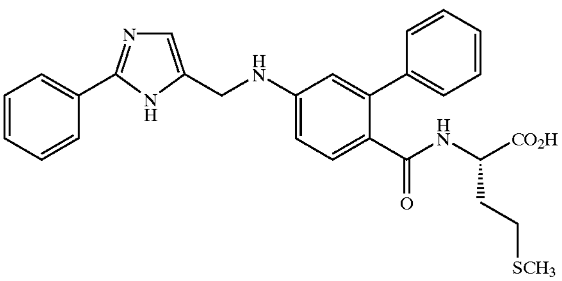

EXAMPLE 382

4-[N-(1-H-2-Phenylimidazole-4-yl)methylamino-2-phenylbenzoyl]-methionine

EXAMPLE 382A

4-[N-(1-H-2-Phenylimidazole-4-yl)methylene (amino-2-phenylbenzoyl)]-methionine-methylester 1-p-toluenesulfonylimidazole-4-carboxaldehyde (0.05 g, 0.3 mmol) and N-(4-amino-2-phenylbenzoyl)-methionine methyl ester hydrochloride (0.057 g, 0.08 mmol) were dissolve in 10 mLs of 95% methanol and 5% acetic acid and stirred for 10 mins. before adding 2 equivalents of sodium cyanoborohydride (0.034 g, 0.54 mmol) The reaction was stirred for ½ h and an additional amount of carboxaldehyde (0.10 g, 0.58 mmol), 2 equivalents sodium cyanoborohydride (0.073 g, 1.2 mmol) and amine hydrochloride salt (0.172 g, 0.44 mmol) were added. The reaction was stirred at room temperature for 1 Hr. The reaction mixture was concentrated and the residue taken up in ethyl acetate and washed with a saturated solution of sodium bicarbonate. The organic phase was dried over magnesium sulfate and concentrated The residue was purified twice by flash chromatography (19:1 chloroform/methanol) to give the desired compound as a white foam (0.22 g, 74%). $^1H$ NMR (300 MHz, $CDCl_3$) δ 7.64 (d, J=6.78 Hz, 2H), 7.43 (d, J=8.43 Hz, 1H), 7.24–7.32 (m, 8H), 6.83 (s, 1H), 6.46 (d, J=8.43 Hz, 1H), 6.39 (d, J=1.7 Hz, 1H), 5.91 (d, J=7.59 Hz, 1H), 4.74 (s, J=broad Hz, 1H), 4.59 (dd, J=7.5, 5.76 Hz, 1H), 4.22 (s, 2H), 3.59 (s, 3H), 2.08 (t, J=6.93 Hz, 2H), 1.97 (s, 3H), 1.80–1.89 (m, 1H), 1.58–1.73 (m, 1H).

EXAMPLE 382B

4-[N-(1-H-2-Phenylimidazole-4-yl)methylene (amino-2-phenylbenzoyl)]-methionine

The compound of Example 382A (0.1 g, 0.19 mmol) was dissolved into 2 mL. of THF and cooled to 0° C. Lithium hydroxide (2 mLs, 0.5M) was slowly added to the reaction mixture and stirred for 3 Hrs. The pH was adjusted using 0.5 M HCl and a white precipitate was collected by vacuum filtration and purified twice by reverse phase preparative HPLC (Waters 25×10 cm, C-18 column, 220 nm UV detector, flow rate 15 mLs/min, linear gradient from 5% acetonitrile and 95% water containing 0.1% TFA to 60% acetonitrile in 40 minutes). Fractions containing pure compound were combined and lyophilized to yield the title compound (0.021 g, 18%) as a TFA salt: $^1H$ NMR (300 MHz, methanol-$d_4$) δ 8.04 (d, J=7.8 Hz, 1H), 7.79 (dd, J=7.3 Hz, 2H), 7.60–7.62 (m, 4H), 7.27–7.30 (m, 6H), 6.69 (dd, J=8.4 Hz, 1H), 6.63 (d, J=2.1, 1H) 4.42 (s, 2H), 4.19–4.26 (m, 1H), 2.14–2.32 (m, 2H), 1.98 (s, 3H), 1.75–1.87 (m, 2H).

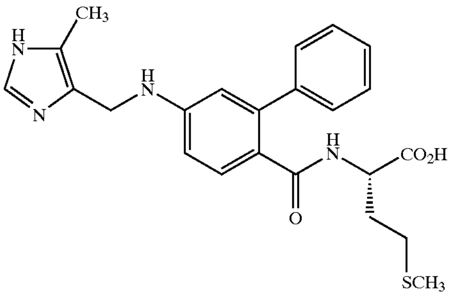

EXAMPLE 383

4-[N-(5-Methyl-1-H-imidazole-4-yl)-methylene-(amino-2-phenylbenzol)]methionine

EXAMPLE 383A

4-[N-(5-Methyl-1-p-toluenesulfonylimidazole-4-yl)-methylene-(amino-2-phenylbenzoyl)]methionine Methyl Ester 1-p-toluenesulfonylimidazole-4-carboxaldehyde (0.2 g, 0.76 mmol) and N-(4-amino-2-phenylbenzoyl)-methionine methyl ester hydrochloride (0.224 g, 0.57 mmol) were dissolve in 5 mL of 95% methanol and 5% acetic acid and stirred for 15 min before adding 2 equivalents of sodium cyanoborohydride (0.095 g, 1.5 mmol) The reaction was stirred for ½ h and the addition of reagents added twice more without the addition of sodium cyanoborohydride the second time. The reaction was concentrated and the residue purified twice by flash chromatography first using (19:1 chloroform/methanol) followed by 4:1 chloroform/acetonitrile to give the desired compound (0.74 g, 74%) as a white solid. $^1$H NMR (300 MHz, $CDCl_3$) δ 8.09 (s, 1H), 7.76 (d, J=8.37 Hz, 2H), 7.64 (d, J=8.52 Hz, 2H), 7.43–7.24 (m, 8H), 6.60 (dd, J=8.43, 2.16 Hz, 1H), 6.46 (d, J=2.16 Hz, 1H), 5.79 (d, J=7.68 Hz, 1H), 4.61 (dd, J=6.2, 6.21 Hz, 1H), 4.10 (s, 2H), 3.63 (s, 3H), 2.44 (s, 3H), 2.25 (s, 3H), 2.09 (t, J=7.38 Hz, 2H), 193–1.83 (m, 1H), 1.71–1.59 (m, 1H); $^{13}$C NMR (75 MHz, $CDCl_3$) δ 172.2, 168.7, 149.5, 146.5, 141.7, 141.3, 137.4, 136.9, 134.8, 131.3, 130.6, 128.9, 128.7, 127.9, 127.7, 124.0, 114.3, 111.8, 52.5, 51.9, 40.2, 31.8, 29.6, 21.9, 15.4, 9.5.

EXAMPLE 383B

4-[N-(5-Methyl-1-H-imidazole-4-yl)methylene-(amino-2-phenylbenzoyl)]methionine

The above protected sulfonamide prepared in Example 383A (0.5 g, 0.8 mmol) was dissolved into 8 mL. of THF and cooled to 0° C. Lithium hydroxide (8 mL, 0.5M) was slowly added to the reaction mixture and stirred for 4 h. Excess THF was removed under vacuum and the pH was adjusted with HCl and the aqueous phase extracted with ethyl acetate. The organic layer was washed with a saturated solution of sodium bicarbonate, dried over magnesium sulfate and concentrated to an oil. The residue was purified by reverse phase preparative HPLC (Waters 25×10 cm, C-18 column, 220 nm UV detector, flow rate 15 mLs/min, linear gradient from 5% acetonitrile and 95% water containing 0.1% TFA to 60% acetonitrile in 40 minutes). Fractions containing pure compound were combined and lyophilized to yield the titled compound as a TFA salt. $^1$H NMR (300 MHz, methanol-$d_4$) δ 8.68 (s, 1H), 7.42 (d, J=8.34 Hz, 1H), 7.27–7.36 (m, 6H), 6.65 (dd, J=8.46, 1.7 Hz, 1H), 6.58 (d, J=2.3 Hz, 1H), 4.41–4.46 (m, 3H), 2.35 (s, 3H), 2.03–2.23 (m, 2H), 2.00 (s, 3H), 1.74–1.99 (m, 2H).

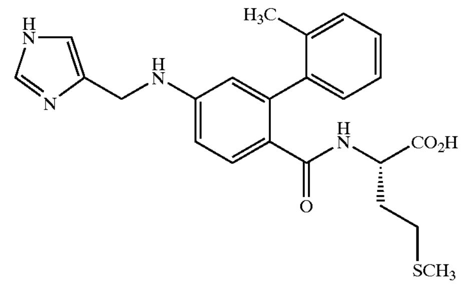

EXAMPLE 384

4-[N-(1-H-Imidazole-4-yl)methylamino-2-(2-methylphenylbenzoyl)]methionine

EXAMPLE 384A

4-[N-(1-Triphenylmethylimidazole-4-yl)methylamino-2-(2-methylphenyl)]methoinine

1-Triphenylmethylimidazole-4-carboxaldehyde (0.3 g, 0.7 mmol) and N-(4-amino-2-(2-methylphenylbenzoyl) methionine methyl ester hydrochloride (0.25 g, 0.7 mmol) were dissolve in 10 mLs of 95% methanol and 5% acetic acid and stirred for 30 mins. before adding 1 equivalent of sodium cyanoborohydride (0.044 g, 0.7 mmol) The reaction was stirred for 3 hours while additional aldehyde was added until all of the amine hydrochloride had disappeared. The reaction mixture was concentrated and the residue taken up in ethyl acetate and washed with a saturated solution of sodium bicarbonate. The organic phase was dried over magnesium sulfate and concentrated The residue was purified by flash chromatography (1:1ethyl acetate/hexanes) to give the desired compound as a white foam (0.36 g, 74%). $^1$H NMR (300 MHz, $CDCl_3$) δ 7.45 (s, 1H), 7.25–7.35 (m, 13H), 7.09–7.13 (m, 6H), 6.74 (s, 1H), 6.65 (dd, J=9.3, 1.5 Hz, 1H), 6.34 (d, J=2.5 Hz, 1H), 5.69 (t, J=7.35 Hz, 1H), 4.56–4.61 (m, 1H), 4.27 (d, J=4.8 Hz, 2H), 3.64 (s, 3H), 2.00–2.15 (m, 8H), 1.79–1.86 (m, 1H), 1.48–1.56 (m, 1H); $^{13}$C NMR (75 MHz, $CDCl_3$) δ 172.4, 167.6, 167.2, 150.3, 142.4, 141.4, 141.2, 139.1, 138.2, 136.6, 132.3, 132.0, 130.8, 130.6, 129.9, 129.2, 128.9, 128.3, 126.5, 126.4, 121.9, 121.4, 119.3, 114.2, 112.0, 75.6, 52.4, 51.7, 41.8, 32.0, 29.6, 20.1, 15.4.

EXAMPLE 384B

4-[N-(1-H-Imidazole-4-yl)methylamino-2-(2-methylphenylbenzoyl)]methionine

The compound of Example 384A (0.15 g, 0.22 mmol) was dissolved into 3.5 mLs. of THF and cooled to 0° C. Lithium hydroxide (18.1 mg dissolved in 3.5 mLs. of water) was slowly added to the reaction mixture and stirred for 1Hr. The pH was adjusted using 1 N HCl and placed under vacuum to remove excess THF. The residue was taken up in ethyl acetate and dried over magnesium chloride and excess solvent removed under vacuum. The residue was taken up in 4 mls. of methylene chloride and 8 mls. of trifluoroacetic acid and the reaction mixture was immediately quenched with triethylsilane until colorless. The reaction was stirred for an addition 2 h and concentrated to an oil. The residue was dissolved in methylene chloride and 3 N HCl was added. The solids were vacuum filtered and dried under vacuum to give the title compound (0.050 g, 50%) as a HCl salt. $^1$H NMR (300 MHz, CD30D) δ 8.65 (s, 1H), 7.58–7.66 (m, 1H), 7.49 (s, 1H), 7.11–7.25 (m, 4H), 6.80 (dd, J=8.6, 2.4 Hz, 1H), 6.50 (d, J=1.9 Hz, 1H), 4.53 (s, 2H), 4.39–4.40 (m, 1H), 2.04–2.12 (m, 5H), 1.98 (s, 3H), 1.81–1.90 (m, 1H), 1.46–1.64 (m, 1H).

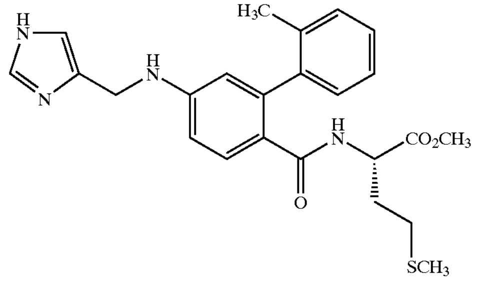

4-[N-(1-H-Imidazole-4-yl)methylene(amino-2-(2-methylphenylbenzoyl))]-methionine Methyl Ester The compound of Example 384A (0.135g, 0.22 mmol) was dissolved into 4 mls. of methylene chloride and 8 mL of trifluoroacetic acid and the reaction mixture was immediately quenched with triethylsilane until colorless. The reaction was stirred for an addition 2 h and concentrated to an oil. The residue was taken up in methylene chloride and 3 N HCl was added The solids were vacuum filtered collected and dried under vacuum to give the title compound (0.050 g, 50%) as a HCl salt $^1$H NMR (300 MHz, CD30D) δ 8.84 (s, 1H), 7.57–7.65 (m, 1H), 7.47 (s, 1H), 7.11–7.26 (m, 4H), 6.73 (d, J=8.64 Hz, 1H), 6.43 (s, 1H), 4.50 (s, 2H), 4.39–4.46 (m, 1H), 3.64 (s, 3H), 2.04–2.12 (m, 5H), 1.98 (s, 3H), 1.84–1.94 (m, 1H), 1.57–41.62 (m, 1H).

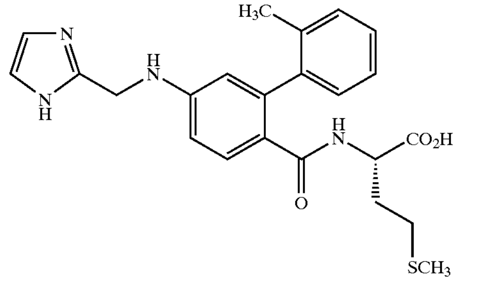

EXAMPLE 386

4-[N-(1-H-Imidazole-2-yl)methylamino-2-(2-methylphenyl)benzoyl]methionine

EXAMPLE 386A

4-[N-(1-Triphenylmethylimidazole-2-yl)methylamino-2-(2-methylphenyl)benzoyl]methionine 1-Triphenylmethylimidazole-2-carboxaldehyde (0.5 g, 1.5 mmol) and N-(4-amino-2-(2-methylphenylbenzoyl) methionine methyl ester hydrochloride (0.25 g, 0.7 mmol) were dissolve in 30 mLs of 95% methanol and 5% acetic acid and stirred for 30 min. before adding 1 equivalent of sodium cyanoborohydride (0.09 g, 1.5 mmol). The reaction was stirred over a period of 3 hours while additional aldehyde was added until all of the amine hydrochloride had disappeared. The reaction mixture was concentrated and the residue taken up in ethyl acetate and washed with a saturated solution of sodium bicarbonate. The organic phase was dried over magnesium sulfate and concentrated The residue was purified by flash chromatography (19:1 chloroform/methanol) to give the desired compound as a white foam (0.55 g, 55%). $^1$H NMR (300 MHz, $CDCl_3$) δ 7.53 (d, J=8.5 Hz, 1H), 7.23–7.43 (m, 15H), 7.13–7.16 (m, 6H), 7.03 (d, J=1.4 Hz, 1H), 6.87 (d, J=1.1 Hz, 1H), 6.2 (dd, J=8.5, 2.2 Hz, 1H), 6.10 (d, J=2.2 Hz, 1H), 5.61 (d, J=7.7 Hz, 1H), 5.05 (br.s, 1H), 4.59 (dd, J=9.9, 4.7 Hz, 1H), 3.63 (s, 3H), 3.33 (br.s, 2H), 2.05 (t, J=7.7 Hz, 2H), 2.00 (s, 3H), 1.80–1.91 (m, 2H), 1.24–1.29 (m, 2H).

EXAMPLE 386B

4-[N-(1-H-imidazole-2-yl)methylamino-2-(2-methylphenyl)benzoyl]methionine

The product of Example 386A (0.45 g, 0.66 mmol) was dissolved into 3.5 mLs. of THF and cooled to 0° C. Lithium hydroxide (18.1 mg dissolved in 3.5 mLs. of water) was slowly added to the reaction mixture and stirred for 2 Hr. The pH was adjusted using 1 N HCl and placed under vacuum to remove excess THF. The residue was taken up in ethyl acetate and dried over magnesium chloride and excess solvent removed under vacuum. The residue was taken up in 4 mls. of methylene chloride and 8 mls. of trifluoroacetic acid and the reaction mixture was immediately quenched with triethylsilane until colorless. The reaction was stirred for an addition 2 hrs and concentrated to an oil. The residue was purified by reverse phase preparative HPLC (Waters 25×10 cm, C-18 column, 220 nm UV detector, flow rate 15 mLs/min, linear gradient from 5% acetonitrile and 95% water containing 0.1% TFA to 60% acetonitrile in 40 minutes). Fractions containing pure compound were combined and lyophilized to yield the title compound as a TFA salt. $^1$H NMR (300 MHz, DMSO-$d_6$) δ 8.11 (d, 1H), 7.60 (s, 1H), 7.3–7.4 (m, 6H), 6.82 (br.s, 1H), 6.55–6.60 (m, 2H), 4.69 (s, 2H), 4.20–4.30 (m, 1H), 2.10–2.30 (m, 2H), 2.07 (s, 3H), 1.75–1.86 (m, 2H).

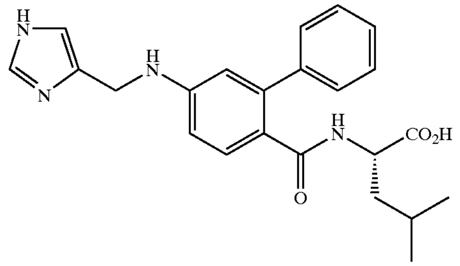

EXAMPLE 387

4-[N-(1H-Imidazol-4-yl)methylamino-2-phenylbenzoyl]leucine

EXAMPLE 387

4-[N-(1-Trityl-imidazol-4-yl)methylene(amino-2-phenylbenzoyl]leucine Methylester To a solution of 2-phenyl-4-amino-benzoyl leucinemethyl ester hydrochloride (0.25 g, 0.74 mmol) in methanol was added tritylimidazole-4-carboxaldehyde (0.25 g, 0.74 mmoles) followed by 1 mL of glacial acetic acid and the reaction stirred for 30 min. This was followed by the addition of $NaCNBH_3$ (0.046 g, 0.74 mmoles) and the reaction was stirred at room temperature for 2 h. The solvent was evaporated and the residue dissolved in ethyl acetate (3 mL), and chromatographed on a silica gel column (1.05"× 23") to afford a white solid. (0.30 g, 61%). $^1$H NMR (300 MHz, $CDCl_3$) 0.79 (dd, 6H), 1.10–1.35 (m, 3H), 3.64 (s, 3H), 4.28 (d, 2H), 4.51 (m, 1H), 4,66 (br s, 1H), 5.45 (d, 1H), 6.49 (s, 1H), 6.64 (dd, 1H), 6.74 (s, 1H), 7.12 (m, 6H), 7.09–7.27 (m, 15H), 7.48 (s, 1H), 7.69 (d, 1H).

EXAMPLE 387B

4-[N-(1-Trityl-imidazol-4-yl)methylamino-2-phenylbenzoyl]leucine

The compound of Example 387A (0.30 g, 0.45 mmoles) was dissolved in 15 mL of THF/$H_2O$ (3:2) and LiOH (0.035 g, 0.91 mmoles) was added. The reaction was stirred at room temperature for 2 h. The THF was evaporated and the residue dissolved in 15 mL water, and 1N HCl added to lower the pH to 2. The compound is then extracted with ethyl acetate (3×25 mL), dried and the solvents evaporated to afford the free carboxylic acid as a white solid. (0.25 g, 84%).

EXAMPLE 387C

4-[N-(1H-Imidazol-4-yl)methylamino-2-phenylbenzoyl]leucine

The compound of Example 387B (0.25 g, 0.38 mmol) was dissolved in 10 mL dichloromethane and 3 mL trifluoroacetic acid followed by the addition of 1.5 mL of triethylsilane and the reaction stirred at room temperature for 2 hours. The solvents were evaporated and ether added followed by the addition of 6 N HCl in ether to precipitate the desired compound (0.12 g, 77%) which was collected by rapid filtration. $^1$H NMR (300 MHz, DMSO-$d_6$) 0.76 (dd, 6H), 1.38 (m, 2H), 1.55 (m, 1H), 4.19 (m, 1H), 4.42 (d, 2H), 6.63 (s, 1H), 6.73 (d, 1H), 7.31–7.36 (m, 6H), 7.63 (s, 1H), 8.23 (d, 1H), 9.09 (s, 1H).

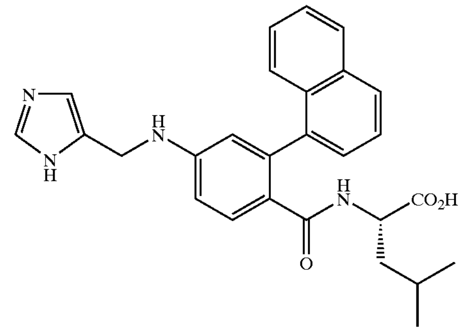

EXAMPLE 388

4-[N-(1H-Imidazol-4-yl)methylamino-2-(1-naphthyl)benzoyl]leucine

EXAMPLE 388A

4-[N-(1-Trityl-imidazol-4-yl)methylamino-2-(1-naphthyl)benzoyl]leucine Methyl Ester To a solution of 2-(1-naphthyl)-4-amino-benzoyl leucinemethyl ester hydrochloride (0.59 g, 1.5 mmoles) in methanol was added tritylimidazole-4-carboxaldehyde (0.61 g, 1.80 mmoles) followed by 1 mL of glacial acetic acid and the reaction stirred for 30 min. This was followed by the addition of $NaCNBH_3$ (0.34 g, 5.4 mmoles) and the reaction was stirred at room temperature for 2 hours. The solvent was evaporated and the residue dissolved in ethyl acetate (3 mL), and chromatographed on a silica gel column (1.05"x23") to afford a white solid. (0.72 g, 67%). $^1$H NMR (300 MHz, $CDCl_3$) 0.13 (m, 0.8H), 0.44 (m, 5.2H), 0.57 (m, 2H), 0.93 (m, 1H), 3.40 (s, 1H), 3.57 (s, 2H), 4.24 (m, 1H), 5.37–5.47 (dd, 1H), 6.49 (s, 1H), 7.08 (m, 2H), 7.09–7.11 (m, 6H), 7.30–7.32 (m, 11H), 7.49–7.57 (m, 5H), 7.80 (m, 2H), 8.08 (d, 1H).

EXAMPLE 388B

4-[N-(1-Trityl-imidazol-4-yl)methylamino-2-(1-naphthyl)benzoyl]leucine

The compound of Example 388A (0.24 g, 0.34 mmoles) was dissolved in 10 mL of THF/$H_2O$ (2:1) and LiOH (0.029 g, 0.68 mmoles) was added. The reaction was stirred at room temperature for 2 h. The THF was evaporated and the residue dissolved in 15 mL water, and 1N HCl added to lower the pH to 2. The compound is then extracted with ethyl acetate (3x25 mL), dried and the solvents evaporated to afford the free carboxylic acid as a white solid. (0.20 g, 84%).

EXAMPLE 388C

4-[N-(1H-imidazol-4-yl)methylamino-2-(1-naphthyl) benzoyl]leucine

The product of Example 388B (0.20 g, 0.29 mmoles) was dissolved in 10 mL dichloromethane and 3 mL trifluoroacetic acid followed by the addition of 1.5 mL of triethylsilane and the reaction stirred at room temperature for 2 hours. The solvents were evaporated and ether added followed by the addition of 6 N HCl in ether to precipitate the desired compound (0.096 g, 74%) which was collected by rapid filtration. $^1$H NMR (300 MHz, DMSO-$d_6$) 0.37 (m, 3H), 0.65 (m, 3H), 1.08 (m, 2H), 1.25 (m, 1H), 3.89 (m, 1H), 4.37 (d, 2H), 6.53 (s, 1H), 6.79 (m, 1H), 7.01 (m, 1H), 7.42–7.62 (m, 8H), 7.86–7.94 (m, 2H), 8.86 (s, 1H).

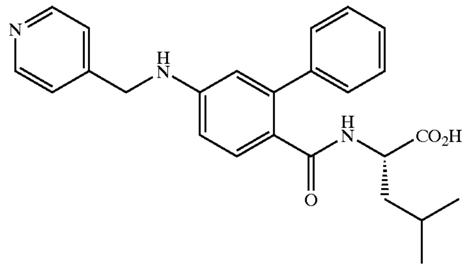

EXAMPLE 389

5-[N-(4-Pyridinyl)methylamino-2-phenylbenzoyl] leucine

EXAMPLE 389A

5-[N-(4-Pyridinyl)methylamino-2-phenylbenzoyl] leucine Methyl Ester

To a solution of 2-phenyl-5-amino-benzoyl leucinemethylester hydrochloride (0.50 g, 1.47 mmoles) in methanol was added pyridine-4-carboxaldehyde (0.164 g, 1.53 mmoles). This was followed by the addition of 1–2 mL of glacial acetic acid, and $NaCNBH_3$ (0.16 g, 2.56 mmoles) and the reaction was stirred at room temperature for 30 min. The solvents were evaporated and the residue dissolved in 25 mL ethyl acetate and washed with saturated $NaHCO_3$ (30 mL), concentrated to 3 mL and chromatographed on a silica gel column (1.05"x23") using ethyl acetate:hexanes (4:1) to afford the desired compound as a yellowish solid. (0.40 g, 63%). $^1$H NMR (300 MHz, $CDCl_3$) 0.76 (m, 6H), 1.10–1.17 (m, 2H), 1.27–1.32 (m, 1H), 3.62 (s, 3H), 4.43–4.53 (overlapping m & s, 3H), 5.60 (d, 1H), 6.61–6.65 (dd, 1H), 6.97 (d, 1H), 7.13 (d, 1H), 7.25–7.35 (m, 8H) 8.55 (m, 2H).

EXAMPLE 389B

5-[N-(4-Pyridinyl)methylamino-2-phenylbenzoyl] leucine

The product of Example 389A (0.22 g, 0.51 mmoles) was dissolved in 10 mL THF/$H_2O$ (2:1), cooled to 0° C. and LiOH (0.04 g, 1.02 mmoles) added. The reaction was stirred at 0° C. for 1 h, followed by stirring at room temperature for 2 hours. The solvents were evaporated and the residue passed through a bed of silica gel and eluted with $CH_2Cl_2$:$CH_3OH$ (9:1) to afford the title compound (0.19 g, 90%) as a white solid. $^1$H NMR (300 MHz, DMSO-$d_6$) 0.79 (t, 6H), 1.19 (m, 2H), 1.42 (m, 1H), 4.06 (m, 1H), 4.36 (d, 2H), 6.53 (dd, 1H), 6.81 (m, 2H), 7.04 (d, 1H), 7.17–7.31 (m, 6H), 7.59 (d, 1H), 8.46 (d, 2H).

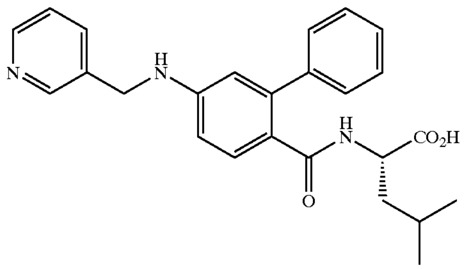

EXAMPLE 390

5-[N-(3-Pyridinyl)methylamino-2-phenylbenzoyl]leucine

The desired compound was prepared according to the method of Example 389, except substituting pyridine-3-carboxaldehyde for pyridine-4-carboxaldehyde. $^1H$ NMR (300 MHz, DMSO-$d_6$) 0.79 (d, 6H), 1.23 (m, 1H), 1.34 (m, 1H), 1.54 (m, 1H), 3.84 (m, 1H), 4.33 (d, 2H), 6.63 (d, 1H), 6.75 (s, 2H), 7.05 (m, 2H), 7.18–7.35 (m, 6H), 7.76 (d, 1H), 8.43 (, 1H), 8.59 (s, 1H).

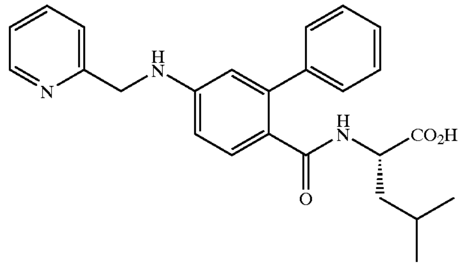

EXAMPLE 391

5-[N-(2-Pyridinyl)methylamino-2-phenylbenzoyl]leucine

The desired compound was prepared according to the method of Example 389, except substituting pyridine-3-carboxaldehyde for pyridine-4-carboxaldehyde. $^1H$ NMR (300 MHz, DMSO-$d_6$) 0.79 (dd, 6H), 1.27 (m, 2H), 1.50 (m, 1H), 3.89 (m, 1H), 4.38 (d, 2H), 6.60 (m, 1H), 6.69 (s, 1H), 7.03 (d, 1H), 7.17–7.36 (m, 7H), 7.38 (d, 1H), 7.73 (t, 1H), 8.51 (d, 1H).

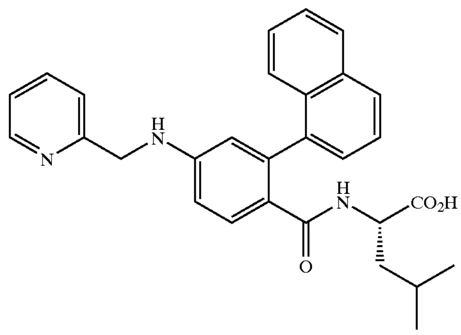

EXAMPLE 392

4-[N-(2-Pyridinyl)methylamino-2-(1-naphthyl)benzoyl]leucine

EXAMPLE 392A

4-[N-(2-Pyridinyl)methylamino-2-(1-naphthyl)benzoyl]leucine Methyl Ester

To a solution of 2-(1-naphthyl)-4-amino-benzoyl leucinemethylester hydrochloride (0.20 g, 0.51 mmoles) in 15 mL methanol was added pyridine-2-carboxaldehyde (0.06 g, 0.51 mmoles). This was followed by the addition of 1–2 mL of glacial acetic acid, and $NaCNBH_3$ (0.05 g, 0.77 mmoles) and the reaction was stirred at room temperature for 30 min. The solvents were evaporated and the residue dissolved in 25 mL ethyl acetate and washed with saturated $NaHCO_3$ (30 mL), concentrated to 3 mL and chromatographed on a silica gel column (1.05"x23") using ethyl acetate:hexanes (4:1) to afford the desired compound (0.15 g, 61%) as a yellowish solid. $^1H$ NMR (300 MHz, $CDCl_3$) 0.13 (m, 0.8H), 0.48 (m, 5.2H), 0.57–0.64 (m, 2H), 0.96–1.1 (m, 1H), 3.4 (s, 1H), 3.61 (s, 2H), 4.21 (m, 1H), 4.50 (m, 2H), 5.40 (m, 1H), 5.48 (br t, 1H), 6.57 (d, 1H), 6.82 (dd, 1H), 7.23–7.52 (m, 7H), 7.85 (m, 1H), 7.92–8.04 (m, 3H), 8.57 (d, 1H).

EXAMPLE 392B

4-[N-(2-Pyridinyl)methylamino-2-(1-naphthyl)benzoyl]leucine

The compound of Example 397A (0.15 g, 0.31 mmoles) was dissolved in 10 mL THF/$H_2O$ (2:1), cooled to 0° C. and LiOH (0.03 g, 0.62 mmoles) added. The reaction was stirred at 0° C. for 1 h, followed by stirring at room temperature for 2 hours. The solvents were evaporated and the residue passed through a bed of silica gel and eluted with $CHCl_3$:$CH_3OH$ (9:1) to afford the title compound (0.13 g, 86%) as a white solid. $^1H$ NMR (300 MHz, DMSO-$d_6$) 0.45 (m, 7H), 0.81 (m, 1H), 1.08 (m, 1H), 3.77 (m, 1H), 4.39 (s, 2H), 6.22 (d, 1H), 6.50 (m, 1H), 6.72 (d, 1H), 7.15 (br s, 1H), 7.18–7.51 (m, 8H), 7.81 (m, 1H), 7.88 (m, 2H), 8.48 (m, 1H).

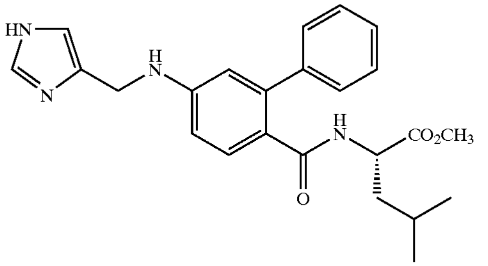

EXAMPLE 393

4-[N-(1H-Imidazol-4-yl)methylamino-2-phenylbenzoyl]leucine Methyl Ester

The compound of Example 387A (0.45 g, 0.68 mmoles) was dissolved in 10 mL dichloromethane and 3 mL TFA added, followed by the addition of 1.5 mL triethylsilane. The colorless solution was stirred at room temperature for 2 hours, following which the solvent was evaporated, the residue dissolved in ethyl acetate and washed with saturated $NaHCO_3$ (25 mL). The organic layer was dried and evaporated to afford the title compound (0.24 g, 84%) as a white solid. $^{1}H$ NMR (300 MHz, DMSO-$d_6$) 0.76 (d, 3H), 0.81 (d, 3H), 1.38 (m, 2H), 1.52 (m, 1H), 3.60 (s, 3H), 4.19 (m, 1H), 4.42 (d, 2H), 6.61 (s, 1H), 6.67 (dd, 1H), 7.22–7.35 (m, 6H), 7.55 (s, 1H), 8.18 (d, 1H), 9.04 (s, 1H).

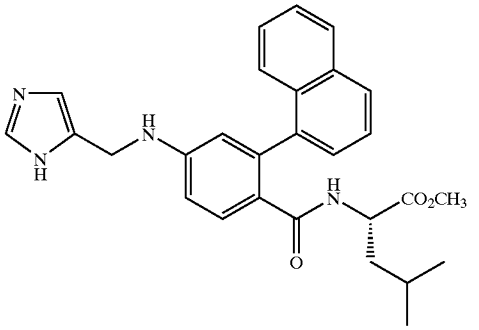

EXAMPLE 394

4-[N-(1H-Imidazol-4-yl)methylamino-2-(1-naphthyl)benzoyl]leucine

The desired compound was prepared from the compound of Example 388A using the method of Example 393. $^{1}H$ NMR (300 MHz, DMSO-$d_6$) 0.38–0.74 (m, 6H), 0.91 (m, 2H), 1.11 (m, 1H), 3.46 (s, 3H), 3.94 (m, 1H), 4.41 (d, 2H), 6.55 (s, 1H), 6.79 (m, 1H), 7.34–7.57 (m, 8H), 7.83–7.94 (m, 3H), 9.05 (s, 1H).

EXAMPLES 397 AND 399

The following compounds were prepared using the materials and methods described above.

| Example | |
|---|---|
| 397 | 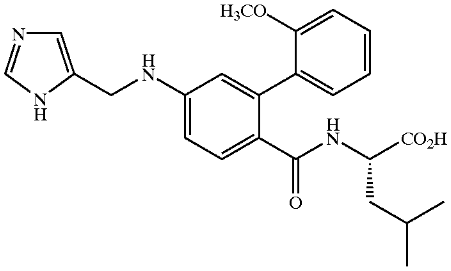 |
| 399 | 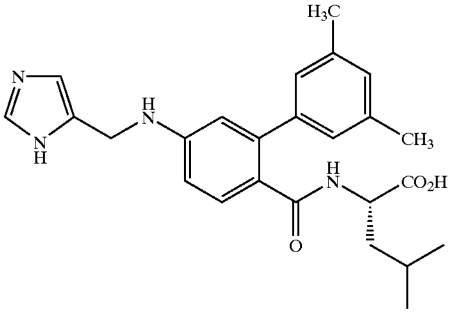 |

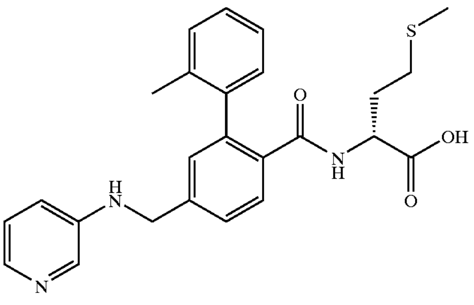

EXAMPLE 400

[4-(3-Pyridylaminomethyl)-2-(2-methylphenyl)benzoyl]methionine

The desired compound was prepared according to the method of Example 189, except substituting [4-(3-pyridylaminomethyl)-2-(2-methylphenyl)phenylbenzoyl]methionine for [4-(3-pyridylaminomethyl)-2-phenylbenzoyl]methionine. $^{1}H$ (300 MHz, DMSO $d_6$): δ 8.08, (d, 1H), 7.96, (d, 1H), 7.73, (d, 1H) 7.44, (m, 2H) 7.19, (m, 3H) 7.11, (m, 2H) 7.03, (dd, 1H) 6.89, (m, 1H) 6.56, (t, 1H) 4.39, (d, 2H) 4.20, (ddd, 1H) 1.96–2.22, (m, 5H) 1.95, (s, 3H) 1.63–1.90, (m, 2H) MS (DCI, $NH_3$): 450 $(MH)^+$, 100%. anal. calc for $C_{25}H_{27}N_3O_3S.0.62H_2O$: C, 65.17; H, 6.18; N, 9.12. Found: C, 65.18; H, 5.85; N, 9.04.

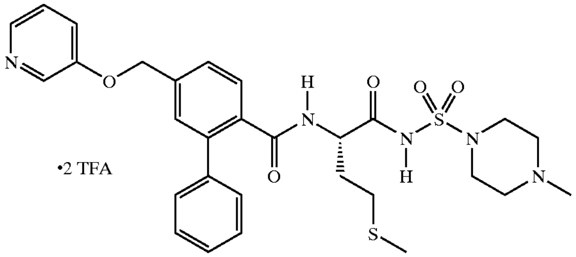

•2 TFA

EXAMPLE 401

[4-(3-Pyridyloxymethyl)-2-phenylbenzoyl]methionine 4-Methylpiperazinesulfonimide The desired compound was prepared according to the method of Example 250, except substituting 4-methylpiperazinesulfonamide for methylsulfonamide. $^{1}H$ (DMSO-$d_6$) δ 8.72 (d, 1H), 8.43 (d, 1H), 8.22 (dd, 1H), 7.60, 7.53, 7.47, 7.40 (all m, total 10H), 5.35 (s, 2H), 4.17 (m, 1H), 3.80, 3.40, 3.20 (all very broad peaks, total 8H), 2.75 (s, 3H), 2.20 (m, 2H), 2.02 (s, 3H), 1.80 (m, 2H). MS (ESI) 598 $(M+H)^+$. Anal calcd for $C_{29}H_{35}N_5O_5S_2.2.35$ TFA: C, 46.76; H, 4.35; N, 8.09. Found: C, 46.78; H, 4.20; N, 8.17.

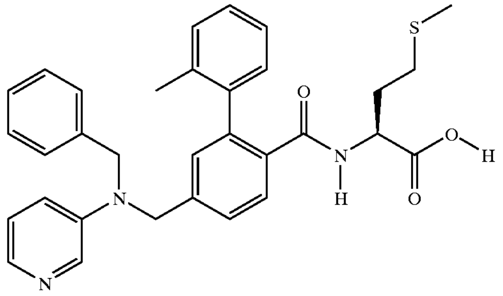

EXAMPLE 407

[4-(N-Benzyl-N-3-pyridylaminomethyl)-2-(2-methylphenyl)benzoyl]methionine

EXAMPLE 407A

Methyl [4-(N-Benzyl-N-3-pyridylaminomethyl)-2-(2-methylphenyl)benzoate

To a stirred solution of 1.6 M n-butyllithium in hexanes (49.8 mL, 79.7 mmol, 1.95 eq) in dry THF (50 mL) at −30° C. was added a solution of N-benzyl-3-aminopyridine (15.0 g, 81.7 mmol, 2 eq) in THF (20 mL). After 20 minutes a solution of methyl 4-bromomethyl-2-(2-methylphenyl) benzoate (13 g, 40.88 mmol) in THF (30 mL) was added and the temperature was raised to −10° C. After 2 hours the reaction was quenched by the addition of water. The solvent was evaporated in vacuo and the residue partitioned into ether. The ethereal solution was dried ($Na_2SO_4$), concentrated in vacuo, and the residue purified by flash chromatography on silica gel (50% ethyl acetate-hexanes) to yield the title compound (13.51 g, 78%).

EXAMPLE 407B

[4-(N-Benzyl-N-3-pyridylaminomethyl)-2-(2-methylphenyl)benzoic Acid

To a stirred solution of the product of Example 407A (13.51 g, 32 mmol) in methanol (100 mL) was added 4 N aqueous sodium hydroxide (32 mL, 128 mmol, 4 eq). The mixture was boiled under reflux for 3 hours, after which time the solvent was removed in vacuo, and the residue diluted with water (300 mL). The mixture was carefully acidified to pH 3.5 with 1 N hydrochloric acid, and the resultant precipitate (12.34 g, 94%) was collected by filtration.

EXAMPLE 407C

[4-(N-Benzyl-N-3-pyridylaminomethyl)-2-(2-methylphenyl)benzoyl]methionine Methyl Ester To a stirred solution of product of Example 407B (12.34 g, 29 mmol) in DMF (80 mL) was added successively methionine methyl ester hydrochloride (7.53 g, 37.7 mmol, 1.3 eq), HOOBt (5.21 g, 31.9 mmol, 1.1 eq), EDCI (6.11 g, 31.9 mmol, 1.1 eq) and 4-methylmorpholine (5.1 mL, 46.4 mmol, 1.6 eq). The mixture was stirred overnight, then poured into water and extracted with ethyl acetate. The organic solution was washed successively with water, sodium carbonate and sodium chloride, dried ($Na_2SO_4$), concentrated in vacuo, and the residue purified by flash chromatography on silica gel eluting with 70% ethyl acetate—hexanes changing to 100% ethyl acetate to yield the title compound (15.51 g, 96%).

EXAMPLE 407D

[4-(N-Benzyl-N-3-pyridylaminomethyl)-2-(2-methylphenyl)benzoyl]methionine

To a stirred solution of the ester resulting from example 407C (15.51 g, 28 mmol) on methanol (120 mL) at 0° C. was added 1 N aqueous lithium hydroxide (56 mL, 56 mmol, 2 eq). The cooling bath was removed and the mixture was stirred for 2 hours. The solvent was removed in vacuo and the residue diluted with water (400 mL). The solution was carefully acidified to pH 4, and the resultant precipitate collected by filtration to afford the title compound (14.08 g, 100%). $^1H$ NMR (300 MHz, DMSO $d_6$) δ 8.18 (d, 1H), 8.03 (bs, 1H), 7.82 (bs, 1H), 7.48 (d, 1H), 7.30 (m, 6H), 7.19 (m, 2H), 7.10 (m, 4H), 4.84 (s, 2H), 4.79 (s, 2H), 1.96–2.23 (m, 5H), 1.96 (s, 3H), 1.63–1.89 (m, 2H). MS m/e 540 $(M+H)^+$, 522. Anal calcd for $C_{32}H_{33}N_3O_3S$ ($+1.18H_2O$): C, 68.51; N, 7.31. Found: C, 68.52; H, 6.35; N, 7.49.

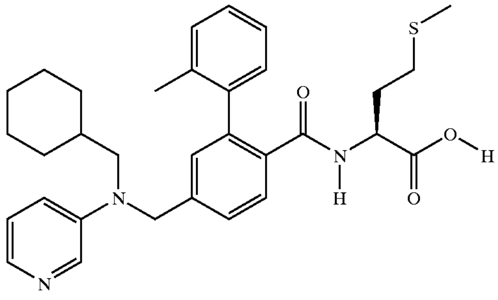

EXAMPLE 408

4-(N-Cyclohexylmethyl-N-3-pyridylaminomethyl)-2-(2-methylphenyl)benzoyl]methionine The desired compound was prepared in accordance with Example 407 except substituting N-cyclohexylmethyl-3-aminopyridine for N-benzyl-3-aminopyridine in Example 407A. $^1H$ NMR (300 MHz, DMSO $d_6$) δ 8.18 (d, 1H), 8.02 (d, 1H), 7.79 (d, 1H), 7.44 (d, 1H), 7.25 (d, 1H), 7.03–7.19 (m, 6H), 6.97 (s, 1H), 4.71 (s, 2H), 4.1.9 (ddd, 1H), 2.14 (m, 1H), 1.96–2.10 (m, 4H), 1.95 (s, 3H), 1.57–1.89 (m, 8H), 1.17 (m, 3H), 1.01 (m, 2H). MS (ESI+) m/e 546. (ESI−) m/e 544. Anal calcd for $C_{32}H_{39}N_3O_3S$ ($+0.99\ H_2O$): C, 68.21; H, 7.18; N, 7.46. Found: C, 68.20; H, 7.33; N, 7.46.

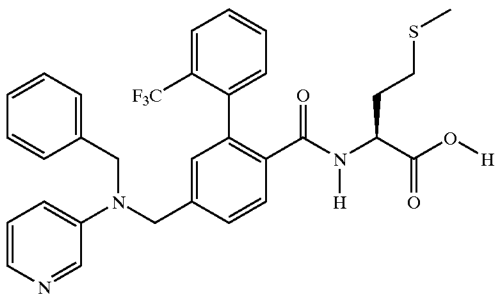

EXAMPLE 409

[4-(N-Benzyl-N-3-pyridylaminomethyl)-2-(2-trifluoromethylphenyl)benzoyl]methionine The desired compound was prepared in accordance with Example 407 except substituting methyl 4-bromomethyl-2-

(2-trifluromethylphenyl)benzoate for methyl 4-bromomethyl-2-(2-methylphenyl)benzoate in Example 407A. $^{1}$H NMR (300 MHz, DMSO $d_6$) δ 8.28 (dd, 1H), 8.03 (d, 1H), 7.83 (d, 1H), 7.71 (m, 1H), 7.57 (m, 3H), 7.42 (d, 1H), 7.30 (m, 6H), 7.09 (m, 3H), 4.84 (s, 2H), 4.78 (s, 2H), 4.23 (ddd, 1H), 2.33 (m, 2H), 1.98 (s, 3H), 1.90 (m, 2H). MS (CI, $NH_3$) m/e 594 $(M+H)^+$, 576. Anal calcd for $C_{32}H_{30}F_3N_3O_3S$ (+1.42 $H_2O$): C, 62.07; H, 5.35; N, 6.79. Found: C, 62.07; H, 5.35; N, 6.68.

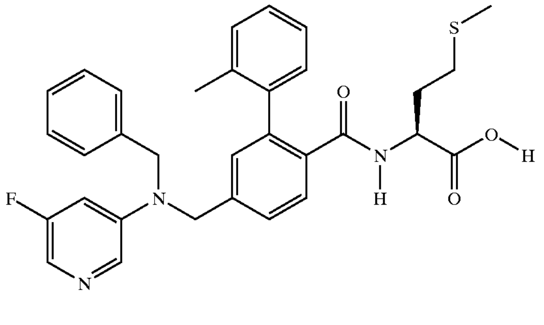

EXAMPLE 410

[4-(N-Benzyl-N-3-(5-fluorolpyridyl)aminomethyl)-2-(2-methylphenyl)benzoyl]methionine The desired compound was prepared in accordance with Example 407 except substituting N-benzyl-3-amino-5-fluoropyridine for N-benzyl-3-aminopyridine in Example 407A. $^{1}$H NMR (300 MHz, DMSO $d_6$) δ 8.14 (d, 1H), 7.91 (t, 1H), 7.76 (d, 1H), 7.48 (d, 1H), 7.34 (m, 3H), 7.27 (m, 3H), 7.19 (m, 2H), 7.09 (m, 3H), 6.90 (dt, 1H), 4.86 (s, 2H), 4.83 (s, 2H), 4.20 (ddd, 1H), 1.98–2.22 (m, 5H), 1.94 (s, 3H), 1.64–1.89 (m, 2H). MS (CI $NH_3$) m/e 558 $(M+H)^+$. Anal calcd for $C_{32}H_{32}FN_3O_3S$ (+0.46 $H_2O$): C, 67.91; H, 5.86; N, 7.42. Found: C, 67.92; H, 5.62; N, 7.31.

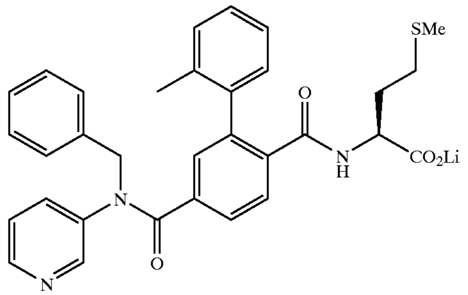

EXAMPLE 451

N-[4-(N-3-Pyridyl-N-benzyl)carbonyl-2-(2-methylphenyl)benzoyl]methionine

The product of Example 158B was coupled N-benzyl-3-aminopyridine using EDCI. The resultant amidoester was saponified, coupled with methionine methyl ester, and saponified to yield the desired compound. $^{1}$H NMR (300 MHz, $CD_3OD$) δ 8.28 (bd, 1H), 8.15 (m, 1H), 7.60 (dt, 1H), 7.54 (s, 1H), 7.36–6.96 (m, 12H), 5.20 (bd, 2H), 4.36–4.32 (m, 1H), 2.10–1.60 (m, 10H) CIMS, Calcd for $C_{32}H_{31}O_4N_3S$ MH+, 554.

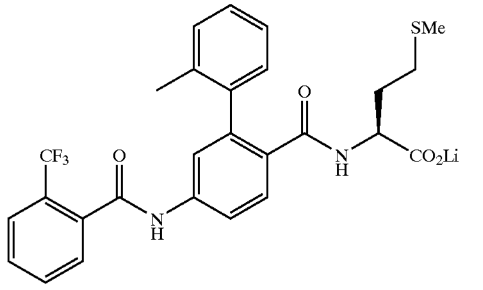

EXAMPLE 481

N-[4-N-(4-Trifluoromethylnicotinoyl)amino-2-(2-methylphenyl)benzoyl]methionine Lithium Salt The desired compound was prepared according to the method of Example 57. $^{1}$H nmr (300 MHz, DMSO-$d_6$): δ 11.04 (br s, 1H), 9.05 (s, 1H), 8.98 (d, 1H), 7.90 (d, 1H), 7.69 (br d, 1H), 7.57 (m, 2H), 7.23 (m, 4H), 6.97 (m, 1H), 3.70 (m, 1H), 2.20 (m, 1H), 2.03 (m, 1H), 1.91 (br s, 6H), 1.70 (m, 1H), 1.58 (m, 1H). MS (ESI−): m/e 530 $(M-H)^-$.

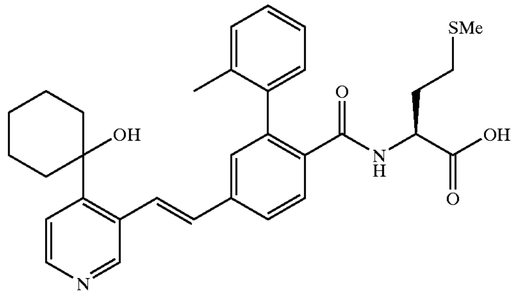

EXAMPLE 482

N-[4-(2-(4-Cyclohexan-1-ol-1-yl)-pyrid-3-ylethen-1-yl)-2-(2-methylphenyl)benzoyl]methionine Lithium Salt The desired compound was prepared according to the method of Examples 210 and 211. $^{1}$H nmr (300 MHz, DMSO-$d_6$): δ 8.72 (s, 1H), 8.48 (dd, 1H), 8.43 (d, 1H), 8.19 (d, 1H), 7.63 (br t, 1H), 7.60 (t, 1H), 7.43 (m, 2H), 7.35 (m, 1H), 7.24 (m, 3H), 7.06 (d 1H), 6.96 (m, 1H), 5.10 (s, 1H), 3.64 (m, 1H), 2.20 (m, 1H), 2.05 (m, 1H), 1.92 (br s, 6H), 1.90–1.40 (m, 12H). MS (ESI−): m/e 543 $(M-H)^-$.

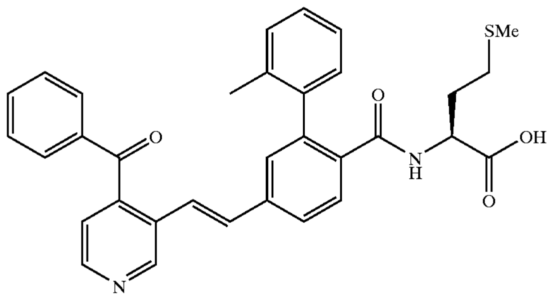

EXAMPLE 483

N-[4-(2-(4-Benzoyl)pyrid-3-ylethen-1-yl)-2-(2-methylphenyl)benzoyl]methionine Lithium Salt The desired compound was prepared according to the method of Examples 210 and 211 . $^{1}$H nmr (300 MHz, DMSO-$d_6$): δ 9.16 (s, 1H), 8.64 (d, 1H), 7.71 (m, 3H), 7.56–7.34 (m, 7H), 7.07–7.10 (m, 5H), 7.08 (d, 1H), 6.93 (m, 1H), 3.62 (m, 1H), 2.10 (m, 1H), 1.96 (m, 1H), 1.91 (br s, 6H), 1.82–1.50 (m, 2H). MS (ESI–): m/e 549 $(M-H)^-$.

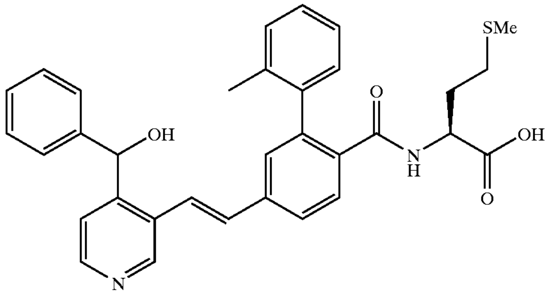

EXAMPLE 484

N-[4-(2-(4-α-Hydroxybenzyl)pyrid-3-ylethen-1-yl)-2-(2-methylphenyl)benzoyl]methionine Lithium Salt The desired compound was prepared according to the method of Examples 210 and 211. $^1$H nmr (300 MHz, DMSO-$d_6$): δ 8.81 (s, 1H), 8.48 (dd, 1H), 7.76 (m, 1H), 7.57 (m, 4H), 7.35 (m, 3H), 7.30–7.08 (m, 6H), 6.99 (m, 2H), 6.17 (d, 1H), 3.62 (m, 1H), 2.10 (m, 1H), 1.96 (m, 1H), 1.91 (br s, 6H), 1.82–1.50 (m, 2H). MS (ESI–): m/e 551 $(M-H)^-$.

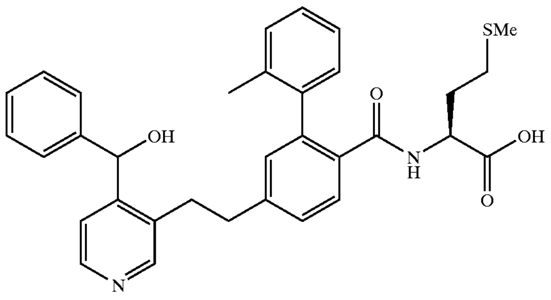

EXAMPLE 485

N-[4-(2-(4-α-Hydroxybenzyl)pyrid-3-ylethyl)-2-(2-methylphenyl)benzoyl]methionine Lithium Salt The desired compound was prepared according to the method of Examples 210–212. $^1$H nmr (300 MHz, DMSO-$d_6$): δ 8.39 (d, 1H), 8.31 (s, 1H), 7.59 (m, 2H), 7.46 (m, 2H), 7.38–7.10 (8H), 6.90 (m, 2H), 5.92 (s, 1H), 3.66 (m, 1H), 3.17 (br s, 2H), 2.69 (br s, 2H), 2.20–1.95 (m, 2H), 1.92 (br s, 6H), 1.75–1.50 (m, 2H). MS (ESI–): m/e 553 $(M-H)^-$.

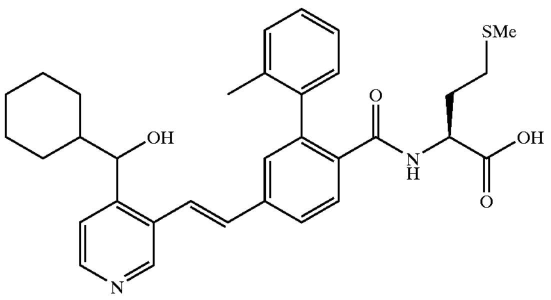

EXAMPLE 486

N-[4-(2-(4-(1-Cyclohexyl)hydroxmethyl)pyrid-3-ylethen-1-yl)-2-(2-methylphenyl)benzoyl]methionine Lithium Salt The desired compound was prepared according to the method of Examples 210–211 $^1$H nmr (300 MHz, DMSO-$d_6$): δ 8.81 (s, 1H), 8.43 (dd, 1H), 7.76 (m, 1H), 7.57 (m, 2), 7.42 (m, 1H), 7.39 (d, 1H), 7.29–7.21 (m, 4H), 6.99 (m, 2H), 5.34 (m, 1H), 3.65 (m, 1H), 2.20 (m, 1H), 2.05 (m, 1H), 2.93 (br s, 6H), 1.80–1.00 (m, 13H), MS (ESI–): m/e 557 $(M-H)^-$.

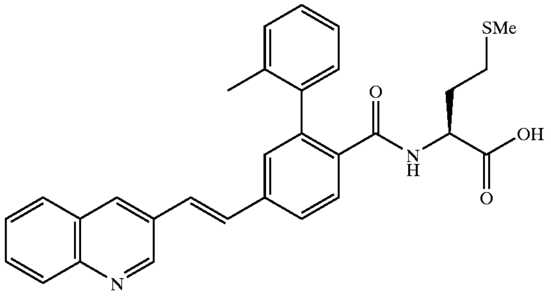

EXAMPLE 487

N-[4-(2-Quinolin-3-ylethen-1-yl)-2-(2-methylphenyl)benzoyl]methionine Lithium Salt The desired compound was prepared according to the method of Examples 210–211 $^1$H nmr (300 MHz, DMSO-$d_6$): δ 9.22 (d, 1H), 8.50 (d, 1H), 8.01 (d, 1H), 7.97 (dd, 1H), 7.72 (m, 2H), 7.62 (m, 4H), 7.50 (m, 1H), 7.34–7.00 (m, 4H), 7.10–6.95 (m, 2H), 3.65 (m, 1H), 2.22 (m, 1H), 2.05 (m, 1H), 1.93 (br s, 6H), 1.90–1.50 (m, 2H). MS (APCI–): m/e 495 $(M-H)^-$.

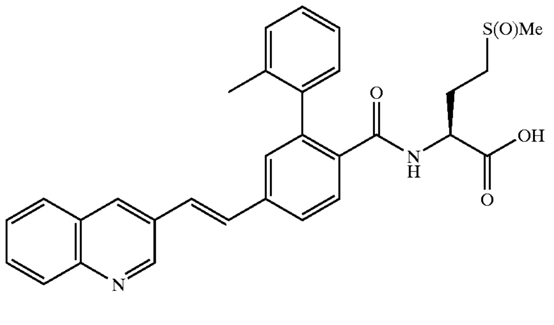

EXAMPLE 488

N-[4-(2-Quinolin-3-ylethen-1-yl)-2-(2-methylphenyl)benzoyl-2-amino-4-methylsulfinylbutanoic Acid Lithium Salt The desired compound was prepared according to the method of Examples 210–211 $^1$H nmr (300 MHz, DMSO-$d_6$): δ 9.22 (d, 1H), 8.50 (d, 1H), 8.01 (d, 1H), 7.98 (d, 1H), 7.75 (m, 2H), 7.68–7.58 (m, 4H), 7.52 (m, 1H), 7.30–7.14 (m, 4H), 7.08 (m, 1H), 3.80 (m, 1H), 2.50–2.48 (many s's, 6H), 2.30–1.50 (m, 4H). MS (ESI–): m/e 511 (M–H)$^{31}$ .

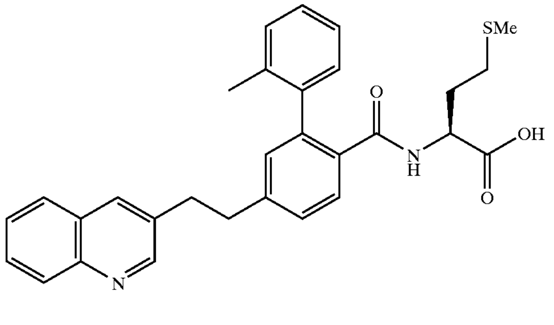

EXAMPLE 489

N-[4-(2-Quinolin-3-ylethen-1-yl)-2-(2-methylphenyl)benzoyl]methionine Lithium Salt The desired compound was prepared according to the method of Examples 210–212 $^1$H nmr (300 MHz, DMSO-$d_6$): δ 8.77 (d, 1H), 8.11 (d, 1H), 7.96 (d, 1H), 7.87 (dd, 1H), 7.69 (dt, 1H), 7.57 (dt, 1H), 7.46 (d, 1H), 7.32 (dd, 1H), 7.30–7.00 (m, 5H), 6.95 (m, 1H), 6.88 (br d, 1H), 3.66 (m, 1H), 3.15 (m, 2H), 3.05 (m, 2H), 2.00–1.80 (m, 2H), 1.91 (br s, 6H), 1.75–1.50(m, 2H). MS (APCI–): m/e 497 (M–H)$^-$.

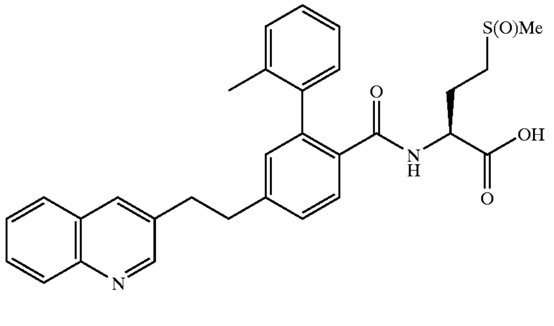

EXAMPLE 490

N-[4-(2-Quinolin-3-ylethyl)-2-(2-methylphenyl)benzoyl]-2-amino-4-methylsulfinylbutanoic Acid Lithium Salt The desired compound was prepared according to the method of Examples 210–212 $^1$H nmr (300 MHz, DMSO-$d_6$): δ 8.77 (d, 1H), 8.11 (d, 1H), 7.96 (d, 1H), 7.87 (dd, 1H), 7.69 (dt, 1H), 7.57 (dt, 1H), 7.46 (d, 1H), 7.32 (dd, 1H), 7.30–7.00 (m, 5H), 6.95 (m, 1H), 6.88 (br d, 1H), 3.80 (m, 1H), 3.15 (m, 2H), 3.05 (m, 2H), 2.45–2.35 (many s's, 6H), 2.13 (m, 1H), 2.00–1.50 (m, 3H). MS (ESI–): m/e 513 (M–H)$^-$.

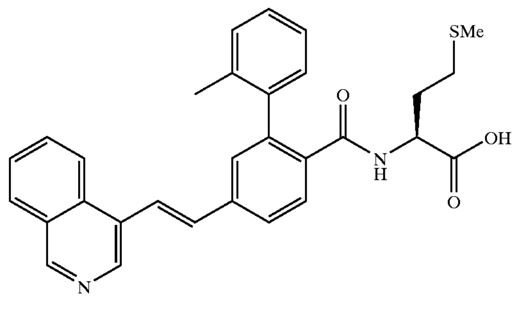

EXAMPLE 491

N-[4-(2-Isoquinolin-4-ylethen-1-yl)-2-(2-methylphenyl)benzoyl]methionine Lithium Salt The desired compound was prepared according to the method of Examples 210–211 $^1$H nmr (300 MHz, DMSO-$d_6$): δ 9.25 (s, 1H), 8.90 (s, 1H), 8.49 (d, 1H), 8.16 (d, 1H), 8.13 (d, 1H), 7.84 (m, 2H), 7.73 (t, 1H), 7.61 (m, 2H), 7.49 (d, 1H), 7.33–7.13 (m, 4H), 7.02 (m, 2H), 3.70 (m, 1H), 2.23 (m, 1H), 2.08 (m, 1H), 1.94 (br s, 6H), 1.70 (m, 1H), 1.60 (m, 1H). MS (APCI–): m/e 495 (M–H)$^-$.

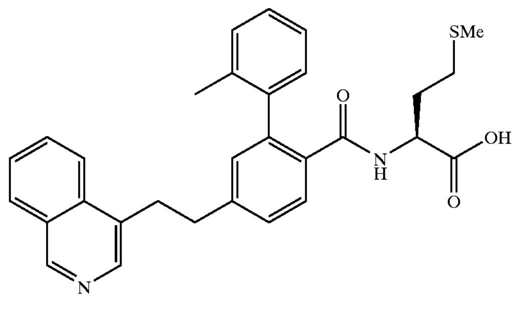

EXAMPLE 492

N-[4-(2-Isoquinolin-4-ylethyl)-2-(2-methylphenyl)benzoyl]methionine Lithium Salt The desired compound was prepared according to the method of Examples 210–212 $^1$H nmr (300 MHz, DMSO-$d_6$): δ 9.16 (s, 1H), 8.31 (s, 1H), 8.17 (d, 1H), 8.12 (d, 1H), 7.81 (dt, 1H), 7.68 (dt, 1H), 7.45 (d, 1H), 7.32 (dd, 1H), 7.17 (m, 2H), 6.92 (m, 2H), 3.64 (m, 1H), 3.05 (t, 4H), 2.06 (m, 1H), 1.94 (m, 1H), 1.91 (br s, 6H), 1.68 (m, 1H), 1.58 (m, 1H).

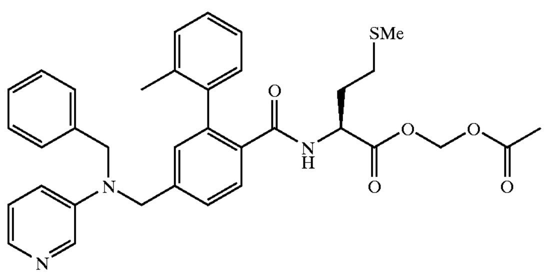

EXAMPLE 499

Acetoxymethyl N-[4-N-Benzyl-N-pyridin-3-ylaminomethyl-2-(2-methylphenyl)benzoyl] methionine N-[4-N-benzyl-N-pyridin-3-ylaminomethyl-2-(2-methylphenyl)benzoyl]methionine (150 mg, 0.28 mmol), bromomethyl acetate (42 mg, 0.28 mmol), and potassium iodide (15 mg, 0.09 mmol) were combined and dissolved in 2 mL DMF. Sodium hydride (60% dispersion in mineral oil, 11 mg, 0.28 mmol) was added, and the mixture was heated at 100° C. for 18 h. The reaction was evaporated to dryness under reduced pressure and chromatographed (50% EtOAc in hexanes to 100% EtOAc) to provide 96.7 mg of the title compound. MS m/e 612 $(M+H)^+$. $^1H$ NMR ($CDCl_3$, 300 MHz) δ 1.60 (m, 1H), 1.85 (m, 1H), 2.02 (m, 8H), 2.10 (m, 3H), 4.62 (m, 1H), 4.71 (m, 4H), 5.70 (m, 2H), 5.83 (d, 1H, J=8 Hz), 7.02–7.28 (m, 13H), 7.96 (m, 2H), 8.17 (m, 1H).

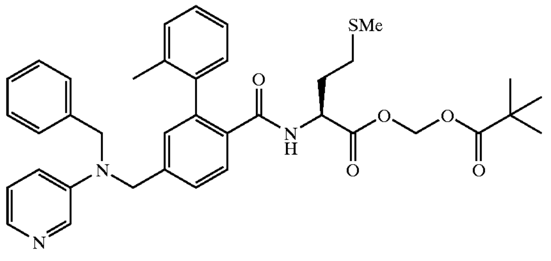

EXAMPLE 500

Pivaloyloxymethyl N-[4-N-Benzyl-N-pyridin-3-ylaminomethyl-2-(2-methylphenyl)benzoyl] methionine N-[4-N-benzy]-N-pyridin-3-ylaminomethyl-2-(2-methylphenyl)benzoyl]methionine (150 mg, 0.28 mmol), chloromethyl pivalate (42 mg, 0.28 mmol), and potassium iodide (15 mg, 0.09 mmol) were combined and dissolved in 2 mL DMF. Sodium hydride (60% dispersion in mineral oil, 11 mg, 0.28 mmol) was added, and the mixture was heated at 100° C. for 18 h. The reaction was evaporated to dryness under reduced pressure and chromatographed (50% EtOAc in hexanes to 100% EtOAc) to provide 66.7 mg of the title compound. MS m/e 654 $(M+H)^+$. $^1H$ NMR ($CDCl_3$, 300 MHz) δ 1.20 (s, 9H), 1.58 (m, 1H), 1.83 (m, 1H), 2.05 (m, 8H), 4.62 (m, 1H), 4.73 (m, 4H), 5.66 (m, 1H), 5.78 (m, 1H), 5.82 (d, 1H, J=8 Hz), 7.01–7.28 (m, 13H), 7.95 (m, 2H), 8.17 (m, 1H).

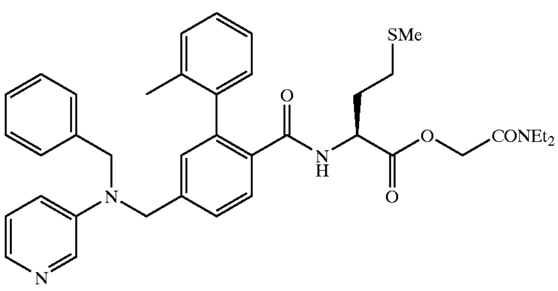

EXAMPLE 501

N,N-Diethylaminocarbonylmethyl N-[4-N-benzyl-N-pyridin-3-ylaminomethyl-2-(2-methylphenyl) benzoyl]methionine N-[4-N-benzyl-N-pyridin-3-ylaminomethyl-2-(2-methylphenyl)benzoyl]methionine (150 mg, 0.28 mmol), 2-chloro-N,N-diethylacetamide (42 mg, 0.28 mmol), and potassium iodide (15 mg, 0.09 mmol) were combined and dissolved in 2 mL DMF. Sodium hydride (60% dispersion in mineral oil, 11 mg, 0.28 mmol) was added, and the mixture was heated at 100° C. for 18 h, evaporated to dryness under reduced pressure and chromatographed (50% EtOAc in hexanes to 100% EtOAc) to provide 129.5 mg of the title compound. $^1H$ NMR ($CDCl_3$, 300 MHz) δ 1.10 (t, 3H, J=7 Hz), 1.21 (t, 3H, J=7 Hz), 1.64 (m, 2H), 2.03 (m, 7H), 2.21 (m, 1H), 3.21 (q, 2H, J=7 Hz), 3.37 (m, 2H), 4.69 (m, 7H), 5.89 (d, 1H, J=8 Hz), 6.97 (m, 1H), 7.06 (m, 2H), 7.15–7.28 (m, 10H), 7.92 (m, 2H), 8.18 (m, 1H). MS m/e 653 $(M+H)^+$.

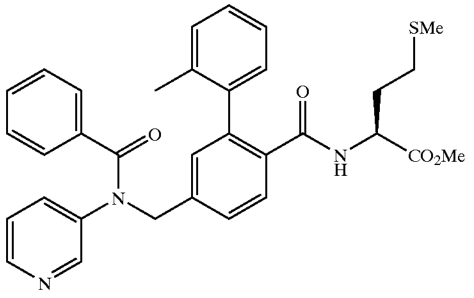

EXAMPLE 569

N-[4-N-Benzoyl-N-pyrid-3-ylaminomethyl-2-(2-methylphenyl)benzoyl]methionine

The desired compound was prepared according to the method of Example 157 $^1H$ nmr (300 MHz, DMSO $d_6$): δ 12.54, bs, 1H; 8.24, dd, 1H; 8.13, m, 2H; 7.61, m, 1H; 7.43, m, 2H; 7.29, m, 6H; 7.00–7.21, m, 5H; 5.21, s, 2H; 4.18, m, 1H; 1.97–2.22, m, 2H; 1.94, s, 6H; 1.63–1.88, m, 2H. MS (APCI(+)) 554 (MH+). Calc'd for $C_{32}H_{31}N_3O_4S.0.50H_2O$: C, 68.31, H, 5.73, N, 7.47: Found: C, 68.30, H, 5.82, N, 7.43.

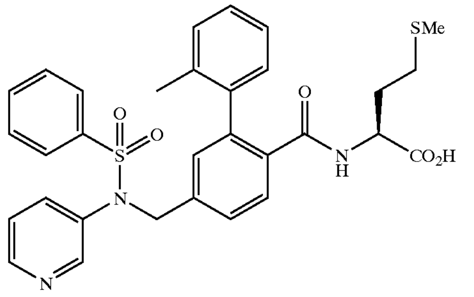

EXAMPLE 570

N-[4-N-Phenylsulfonyl-N-pyrid-3-ylaminomethyl-2-(2-methylphenyl)benzoyl]methionine The desired compound was prepared according to the method of Example 157 $^1$H nmr (300 MHz, $D_2O$): δ 8.42, d, 1H; 8.30, s, 1H; 8.12, d, 1H; 7.76, m, 1H; 7.60–7.73, m, 4H; 7.53, m, 1H; 7.38, m, 3H; 7.19, m, 2H; 6.90–7.15, m, 3H; 4.91, s, 2H; 4.17, m, 1H; 1.93–2.20, m, 3H; 1.92, s, 3H; 1.61–1.90, m, 6H. MS (ESI(+)) 590 (MH+). Calc'd for $C_{31}H_{31}N_3O_5S_2.0.31H_2O$: C, 62.55, H, 5.35, N, 7.06: Found: C, 62.54, H, 5.13, N, 6.90.

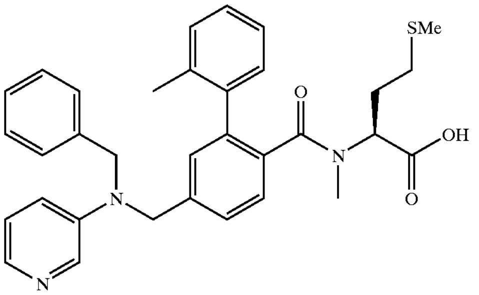

EXAMPLE 602

N-[4-(N-Benzyl-N-pyrid-3-ylaminomethyl)-2-(2-methylphenyl)benzoyl]-N-methylmethionine The desired compound was prepared according to the method of Example 157. (DMSO-$d_6$) δ 8.04 (d, 1H), 7.82 (m, 1H), 7.39 (m, 1H), 7.27 (m, 8H), 7.10 (m, 5H), 4.83 (s, 2H), 4.77 (s, 2H), 2.00, 1.95, 1.90, 1.65 (all m, total 10H). MS (APCI) 554 $(M+H)^+$. Anal calcd for $C_{33}H_{35}N_3O_3S.0.70H_2O$: C, 69.99; H, 6.48; N, 7.42. Found: C, 69.90; H, 5.68; N, 7.38.

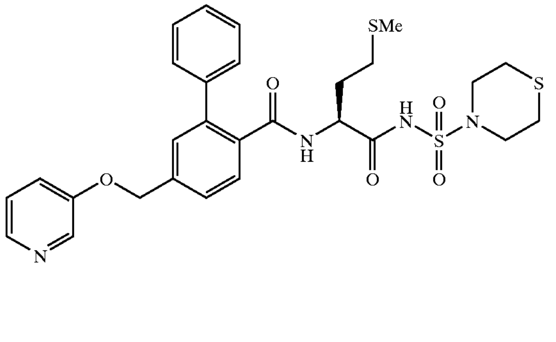

EXAMPLE 603

Thiomorpholinesulfonyl N-2-[4-(Pyrid-3-yloxymethyl)-2-phenylbenzoyl]amino-4-methylthiobutanamide The desired compound was prepared according to the method of Example 157. (DMSO-$d_6$) δ 8.59 (br d, 1H), 8.38 (d, 1H), 8.18 (d, 1H), 7.50 (m, 4H), 7.40,7.35 (both m, total 6H), 5.27 (s, 2H), 4.22 (m, 1H), 3.43 (m, 4H), 2.63 (m, 4H), 2.18 (m, 2H), 2.00 (s, 3H), 1.78 (m, 2H). MS (APCI) 601 $(M+H)^+$. Anal calcd for $C_{28}H_{32}N_4O_5S_3$: C, 55.98; H, 5.37; N, 9.33. Found: C, 55.85; H, 5.37; N, 9.47.

EXAMPLES 668 and 722

Compounds 626–727 were synthezised by reductive amination of the compound described in Example 625, by the procedure described in Example 158.

| | | |
|---|---|---|
| 668 | 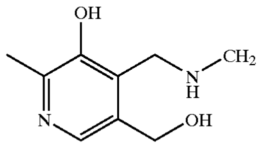 | 510 |
| 722 | 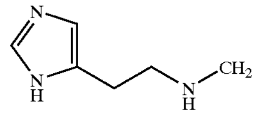 | 467 |

Example 728 were prepared by the procedure described in Example 157

$R_1$=2-$MeC_6H_4$—.

| | | |
|---|---|---|
| 728 | 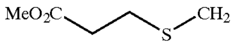 | 476 |

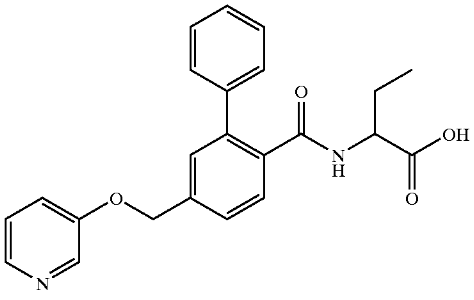

EXAMPLE 760

(2S)-2-N-[4-(3-Pyridyloxymethyl)-2-phenylbenzoyl]aminobutanoic Acid

The desired compound was prepared according to the method of Example 157, except the amino acid methionine was replaced with homoalanine methyl ester followed by saponification. $^1$H NMR (300 MHz, DMSO-$d_6$) δ 0.62 (t, J=7.3 Hz, 3H), 1.52 (m, 1H), 1.64 (m, 1H), 3.99 (m, 1H), 5.26 (s, 2H), 7.30–7.50 (m, 10H), 7.85 (bs, 1H), 8.17 (d, J=4.4 Hz, 1H), 8.37 (d, J=2.7 Hz, 1H); MS (CDI) m/z 391 (MH+); Anal calcd for $C_{23}H_{22}N_2O_4.0.65HCl$: C, 66.71. H, 5.51. N, 6.76. Found: C, 66.74; H, 5.63; N, 6.50.

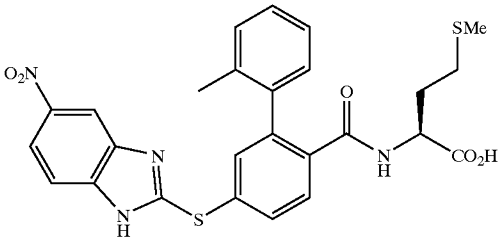

EXAMPLE 761

N-[4-(5-Nitro-]H-benzimidazol-2-thiyl)-2-(2-methylphenyl)benzoyl]methionine

This compound was prepared in a fashion analogous to Example 733, and was characterized by mass spectometry m/z 551 (MH+).

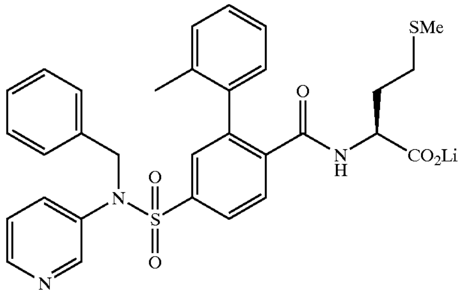

EXAMPLE 771

N-[4-(N-Benzyl-N-pyrid-3-ylaminosulfonyl)-2-phenylbenzoyl]methionine Lithium Salt The desired compound was prepared according to the method of Example 5E. $^1$H ($d_6$-DMSO): δ 8.38–8.39 (1H, d); 8.33–8.34 (1H, d); 7.78–7.81 (2H, m); 7.58–7.62 (1H, m); 7.1–7.4 (1H, m); 4.89 (2H, s); 3.5 (1H, m); 3.15 (3H, s); 1.91 (3H, s); 2.2–1.6 (4H, m). ESI(−)/MS: 588 (M-Li).

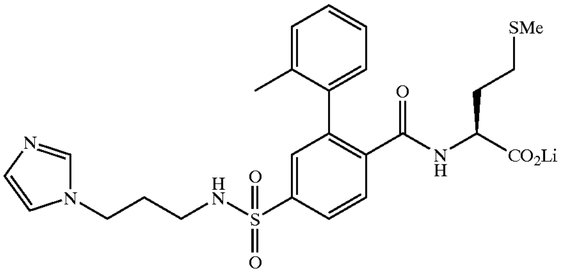

EXAMPLE 777

N-[4-(3-Imidazol-1-ylprolpylaminosulfonyl)-2-phenylbenzoyl]methionine Lithium Salt The desired compound was prepared according to the method of Example 5E. $^1$N (MeOH-$d_4$): δ 7.78–7.9 (2H, dd); 7.5–7.6 (2H, m); 7.1–7.3 (4H, m); 7.1 (1H, s); 6.92 (1H, s); 4.2–4.3 (1H, m); 4.05–4.18 (2H, t); 2.8–2.9 (2H, t); 1.6–2.3 (12H, m). ESI (−)/MS: 529 (M-Li); 281; 255.

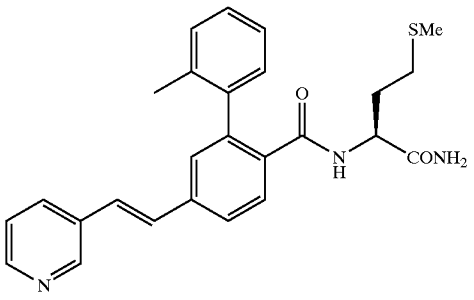

EXAMPLE 796

N-[4-(2-Pyrid-3-ylethen-1-yl)-2-(2-methylphenyl)benzoyl]methioninamide

The desired compound was prepared according to the method of Examples 210–211. $^1$H nmr (300 MHz, $CDCl_3$): δ 8.73 (dd, 1H), 8.52 (dd, 1H), 7.94 (dd, 1H), 7.84 (dt, 1H), 7.61 (dd, 1H), 7.40–7.22 (m, 6H), 7.17 (s, 2H), 6.0 (m, 2H), 5.25 (m, 1H), 4.55 (m, 1H), 2.10–1.96 (m, 2H), 2.18, 2.13 (2 s's, 3H), 2.05, 2.04 (2 s's, 3H), 1.83 (m, 1H), 1.57 (m, 1H). MS (Cl +) m/e 446 $(M+H)^+$.

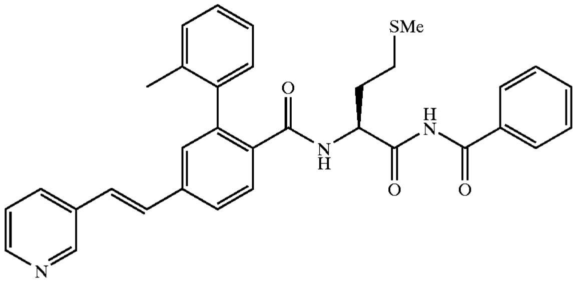

EXAMPLE 797

Benzoyl N-[4-(2-Pyrid-3-ylethen-1-yl)-2-(2-methylphenyl)benzoyl]methioninamide

The desired compound was prepared according to the method of Examples 210–211. $^1$H nmr (300 MHz, $CDCl_3$): δ 8.76 (m, 1H), 8.51 (m, 1H), 8.10 (m, 2H), 7.85 (m, 1H), 7.60 (m, 2H), 7.50–7.23 (m, 10H), 7.17 (m, 3H), 3.10 (m, 1H), 3.00 (m, 2H), 2.89, 2.81 (2 s's, 3H), 2.15, 2.01 (2 s's, 3H).

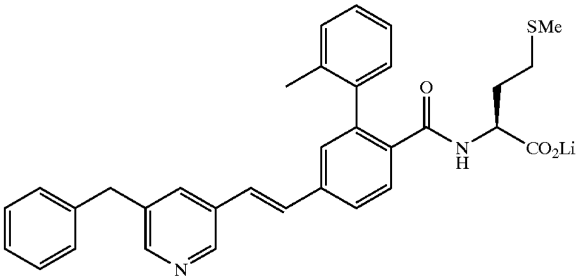

EXAMPLE 798

N-[4-(2-(5-Phenylpyrid-3-yl)ethen-1-yl)-2-(2-methylphenyl)benzoyl]methionine Lithium Salt The desired compound was prepared according to the method of Examples 210–211. $^1$H nmr (300 MHz, DMSO- $d_6$): δ 8.62 (d, 1H), 8.39 (d, 1H), 7.92 (t, 1H), 7.65 (dd, 1H), 7.56 (d, 1H), 7.40 (m, 3H), 7.29 (m, 4H), 7.25–7.10 (m, 6H), 6.95 (m, 1H), 3.99 (s, 2H), 3.65 (m, 1H), 2.18 (m, 2H), 2.02 (br s, 3H), 1.92 (br s, 3H), 1.70 (m, 1H), 1.58 (m, 1H). MS (ESI−): m/e 535 (M−H)$^-$.

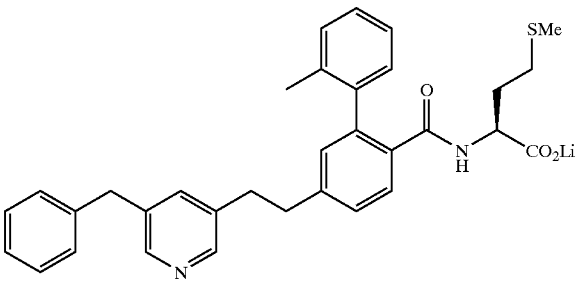

EXAMPLE 799

N-[4-(2-(5-Phenylpyrid-3-yl)ethyl)-2-(2-methylphenyl)benzoyl]methionine Lithium Salt The desired compound was prepared according to the method of Examples 210–212. $^1$H nmr (300 MHz, DMSO-$d_6$): δ 8.29 (d, 1H), 8.23 (d, 1H), 7.44 (m, 2H), 7.30–7.10 (m, 10H), 6.91 (m, 2H), 3.90 (s, 2H), 3.65 (m, 1H), 2.90 (br s, 4H), 2.07 (m, 2H), 1.97–1.89 (m, 7H), 1.70 (m, 1H), 1.58 (m, 1H). MS (ESI−): m/e 537 (M−H)$^-$.

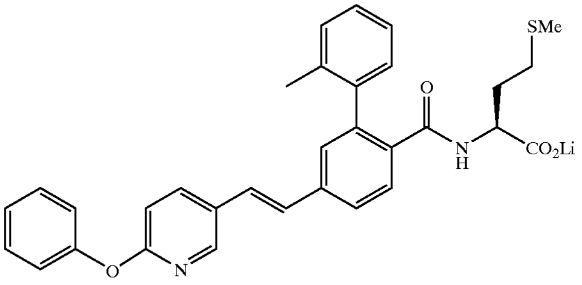

EXAMPLE 800

N-[4-(2-(6-Phenyloxypyrid-3-yl)ethen-1-yl)-2-(2-methylphenyl)benzoyl]methionine Lithium Salt The desired compound was prepared according to the method of Examples 210–211. $^1$H nmr (300 MHz, DMSO-$d_6$): δ 8.33 (d, 1H), 8.16 (dd, 1H), 7.65 (m, 1H), 7.56 (d, 1H), 7.46–7.30 (m, 6H), 7.27–7.10 (m, 7H), 7.05 (dd, 1H), 3.65 (m, 1H), 2.18 (m, 2H), 2.02–1.90 (3 br s's, 6H), 1.70 (m, 1H), 1.58 (m, 1H). MS (ESI−): m/e 537 (M−H)$^-$.

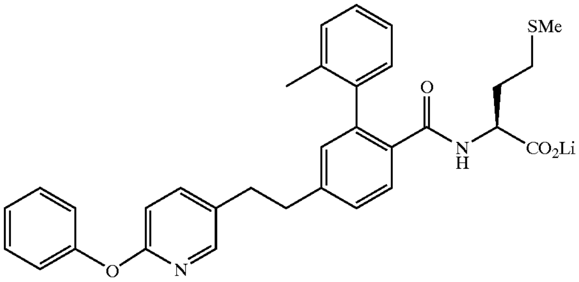

EXAMPLE 801

N-[4-(2-(6-Phenyloxypyrid-3-yl)ethyl)-2-(2-methylphenyl)benzoy]methionine Lithium Salt The desired compound was prepared according to the method of Examples 210–212. $^1$H nmr (300 MHz, DMSO-$d_6$): δ 8.25 (m, 1H), 7.95 (t, 1H), 7.71 (m, 1H), 7.50–7.36 (m, 3H), 7.30 (m, 1H), 7.25–7.10 (m, 5H), 7.05 (d, 2H), 7.95 (m, 1H), 7.93 (dd, 1H), 3.65 (m, 1H), 2.90 (br s, 4H), 2.18 (m, 1H), 2.02 (m, 1H), 1.96, 1.91 (2 br s's, 6H), 1.70 (m, 1H), 1.58 (m, 1H). MS (ESI−): m/e 539 (M−H)$^-$.

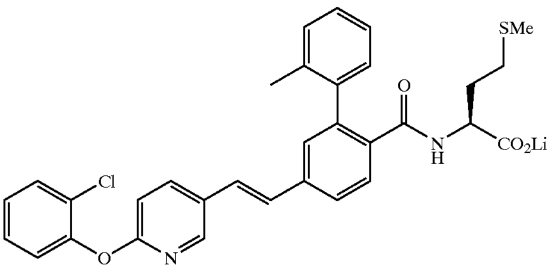

EXAMPLE 802

N-[4-(2-(6-(2-Chlorophenyloxy)pyrid-3-yl)ethyl)-2-(2-methylphenyl)benzoyl]methionine Lithium Salt The desired compound was prepared according to the method of Examples 210–211. $^1$H nmr (300 MHz, DMSO-$d_6$): δ 8.26 (d, 1H), 8.19 (dd, 1H), 7.57 (m, 2H), 7.46 (m, 2H), 7.37–7.20 (m, 9H), 7.15 (d, 1H), 7.00 (m, 1H), 3.65 (m, 1H), 2.18 (m, 2H), 2.02 (br s, 3H), 1.92 (br s, 3H), 1.70 (m, 1H), 1.58 (m, 1H). MS (ESI−): m/e 571 (M−H)$^-$.

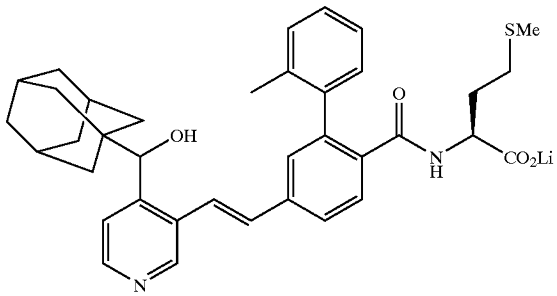

EXAMPLE 803

N-[4-(2-(4-(1-Adamantan-1-yl-1-hydroxymethyl)pyrid-3-yl)ethyl)-2-(2-methylphenyl)benzoyl]methionine Lithium Salt The desired compound was prepared according to the method of Examples 210–211. $^1$H nmr (300 MHz, DMSO- $d_6$): δ 8.84 (s, 1H), 8.46 (d, 1H), 8.42 (d, 1H), 7.75 (m, 1H), 7.63 (m, 1H), 7.57 (d, 1H), 7.38 (m, 2H), 7.29–7.17 (m, 4H), 6.98 (dd, 1H), 5.30 (m, 1H), 4.65 (m, 1H), 3.65 (m, 1H), 2.21 (m, 2H), 2.05 (br s, 3H), 1.92 (br s, 3H), 1.90–1.82 (m, 3H), 1.70–1.30 (m, 14H). MS (ESI−): m/e 609 $(M-H)^-$.

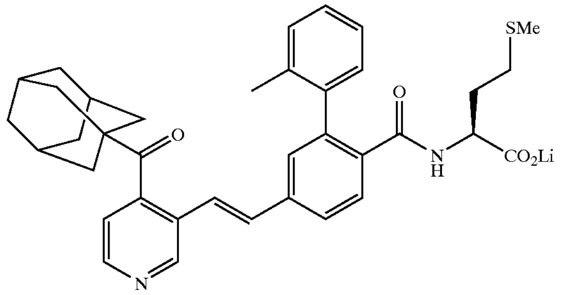

EXAMPLE 804

N-[4-(2-(4-Adamantan-1-oylpyrid-3-yl)ethyl)-2-(2-methylphenyl)benzoyl]methionine Lithium Salt The desired compound was prepared according to the method of Examples 210–211. $^1$H nmr (300 MHz, DMSO-$d_6$): δ 9.05 (s, 1H), 8.52 (d, 1H), 7.60 (m, 2H), 7.40 (d, 1H), 7.35–7.10 (m, 6H), 7.01 (d, 1H), 6.89 (d, 1H), 3.65 (m, 1H), 2.18 (m, 2H), 2.05–1.92 (m, 14H), 1.1.75–1.50 (m, 9H). MS (ESI−): m/e 607 $(M-H)^-$.

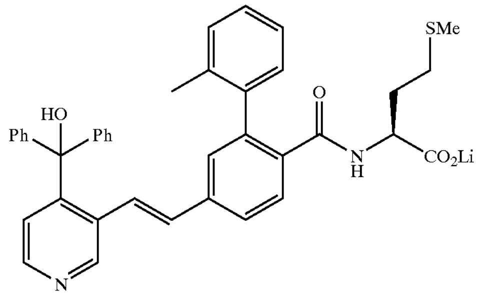

EXAMPLE 805

N-[4-(2-(4-(1,1-Diphenyl-1-hydroxymethyl)pyrid-3-yl)ethyl)-2-(2-methylphenyl)-benzoyl]methionine Lithium Salt The desired compound was prepared according to the method of Examples 210–211. $^1$H nmr (300 MHz, DMSO-$d_6$): δ 8.95 (s, 1H), 8.36 (d, 1H), 7.45 (d, 1H), 7.33 (d, 1H), 7.35–7.00 (m, 14H), 7.08 (d, 1H), 6.99–6.88 (m, 2H), 6.83 (s, 1H), 6.69 (d, 1H), 3.65 (m, 1H), 2.12 (m, 2H), 1.96 (br s, 3H), 1.92 (br s, 3H), 1.70 (m, 1H), 1.58 (m, 1H). MS (ESI−): m/e 627 $(M-H)^-$.

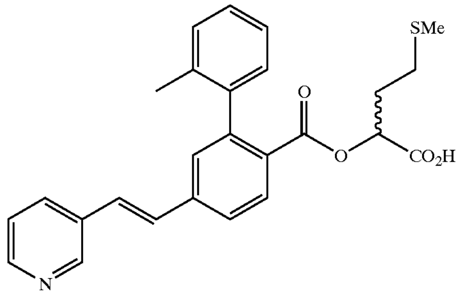

EXAMPLE 814

2-[4-(2-Pyrid-3-ylethen-1-yl)-2-(2-methylphenyl)benzoyl]oxy-4-methylthiobutanoic Acid The desired compound was prepared according to the method of Examples 210–211. $^1$H nmr (300 MHz, $CDCl_3$): δ 8.81 (s, 1H), 8.53 (dd, 1H), 8.13 (m, 1H), 7.95 (m, 1H), 7.58 (m, 1H), 7.40 (m, 2H), 7.30–7.15 (m, 5H), 7.10 (m, 1H), 5.15 (m, 1H), 2.20–2.00 (m, 10H). MS (ESI−): m/e 446 $(M-H)^-$.

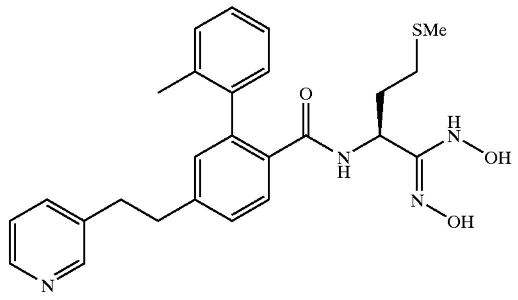

EXAMPLE 815

N-[4-(2-Pyrid-3-yleth-1-yl)-2-(2-methylphenyl)benzoyl]methionine N,N-Dihydroxyamidine The desired compound was prepared according to the method of Examples 210–212. This compound is in a mixture with the monohydroxyamidine, the ratio of dihydroxyamidine to monohydroxyamidine is about 2.5 to 1. $^1$H nmr (300 MHz, DMSO-$d_6$) of title dihydroxyamidine: δ 9.66 (br s, 1H), 8.45 (m, 2H), 8.10 (br s, 1H), 7.69 (dt, 1H), 7.55 (d, 1H), 7.35 (m, 2H), 7.30–7.10 (m, 5H), 7.05 (m, 1H), 5.64 (br pk, 1H), 4.80 (m, 1H), 3.01 (br s, 4H), 2.08–2.00 (m, 2H), 2.05–2.01 (3 s's, 6H), 1.84 (m, 1H), 1.58 (m, 1H). MS (ESI+): m/e 479 $(M+H)^+$.

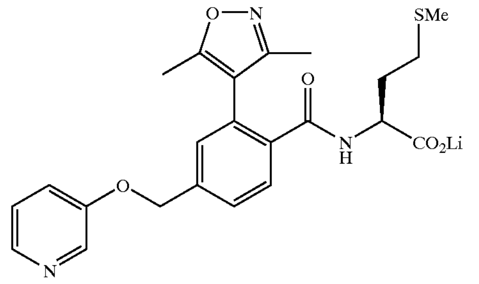

EXAMPLE 823

N-[4-3-Pyridyloxymethyl)-2-(3,5-dimethylisoxazol-4-yl)benzoyl]methionine Lithium Salt The desired compound was prepared according to the method of Example 157. $^1$H NMR (300 MHz, $d_6$DMSO) δ 8.38 (d, 1H), 8.34–8.31 (m, 1H), 8.20–8.17 (m, 1H), 7.59 (s, 1H), 7.46 (ddd, 1H), 7.37–7.32 (m, 2H), 5.28 (s, 2H), 4.25–4.15 (m, 1H), 2.36–2.22 (m, 2H), 2.20 (s, 3H), 2.01 (s, 6H), 1.94 (m, 2H). CIMS Calcd for the acid $C_{23}H_{25}O_5N_3S$ MH+ 456.

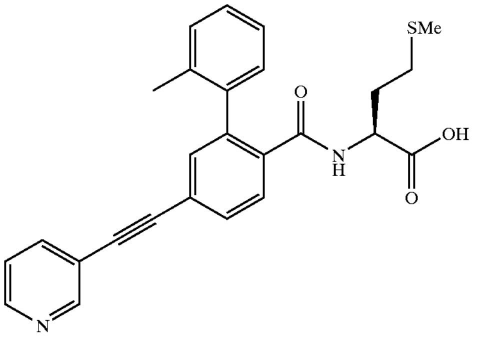

EXAMPLE 865

N-[4-(2-Pyrid-3-ylethyn-1-yl)-2-(2-methylphenyl)benzoyl]methionine

EXAMPLE 865A

Methyl N-4-(Dibromoethen-1-yl-2-(2-methylphenyl)benzoate 4-(Carboxymethyl)-3-(2-methylphenyl)benzaldehyde (7.7 g, 30.3 mmol) and carbon tetrabromide (30.1 g, 90.8 mmol) were combined in methylene chloride (100 mL) and cooled to −78° C. under dry nitrogen. Triphenylphosphine was added, and the reaction was warmed to ambient temperature over 1 h. The mixture was filtered, washed with sodium bisulfite, water, and brine, and chromatographed (20% methylene chloride, 5% ether, 75% hexane) to give 9.77 g (79%) of the title compound which was used directly in the next step.

EXAMPLE 865B

N-4-(Bromoethyn-1-yl)-2-(2-methylphenyl)benzoic Acid

Methyl N-4-(dibromoethen-1-yl)-2-(2-methylphenyl)benzoate (5.0 g, 12.2 mmol) and lithium hydroxide (sat., 6 mL) were refluxed in 50 mL methanol for 24 h. The reaction was evaporated to dryness and partitioned between ether and water. The aqueous layer was washed with ether, acidified, and extracted with ethyl acetate. The combined organic extract was washed with brine and dried over $Na_2SO_4$ to provide 1.73 of the acid which had lost HBr. MS m/e 332 $(M+NH_4)^+$. $^1$H NMR ($CDCl_3$, 300 MHz) δ 2.06 (s, 3H), 7.06 (m, 1H), 7.22 (m, 4H), 7.50 (m, 1H), 7.99 (m, 1H).

EXAMPLE 865C

Methyl N-[4-(Bromoethyn-1-yl)-2-(2-methylphenyl)benzoyl]methionine

N-4-(Bromoethen-1-yl)-2-(2-methylphenyl)benzoic acid (1.73 g, 5.5 mmol), Met-OMe.HCl (0.96 g, 4.80 mmol), EDAC (1.26 g, 6.55 mmol), HOBt (1.34 g, 8.74 mmol) were combined in DMF (25 mL). TEA was added to bring the pH of the mixture to approximately 7. Standard workup followed by chromatography (20% methylene chloride, 5% ethyl acetate, 75% hexane) provided 1.30 g (59%) of the title compound. MS m/e 460 $(M+H)^+$. $^1$H NMR ($CDCl_3$, 300 MHz) δ 1.60 (m, 1H), 1.85 (m, 1H), 2.08 (m, 8H), 3.68 (s, 3H), 4.61 (m, 1H), 5.92 (m, 1H), 7.30 (m, 5H), 7.53 (m, 1H), 7.92 (m, 1H).

EXAMPLE 865D

Methyl N-[4-(2-Pyrid-3-ylethyn-1-yl)-2-(2-methylphenyl)benzoyl]methionine

Methyl N-[4-(bromoethyn-1-yl)-2-(2-methylphenyl)benzoyl]methionine (200 mg, 0.43 mmol), trimethyl-3-pyridyltin (89 mg, 0.37 mmol), and [1,1'-bis(diphenylphosphino)ferrocene]dichloropalladium(II), complex with dichloromethane (1:1) (15 mg, 0.02 mmol) were heated at 80° C. for 18 h. The mixture was evaporated and chromatographed (50% ethyl acetate in hexane) to give 43 mg of the title compound. MS m/e 459 $(M+H)^+$. $^1$H NMR ($CDCl_3$, 300 MHz) δ 1.60 (m, 1H), 1.86 (m, 1H), 2.1 (m, 8H), 3.68 (s, 3H), 4.63 (m, 1H), 5.97 (m, 1H), 7.30 (m, 6H), 7.63 (m, 1H), 7.83 (m, 1H), 7.99 (m, 1H), 8.59 (m, 1H), 8.78 (m, 1H).

EXAMPLE 865E

N-[4-(2-Pyrid-3-ylethyn-1-yl)-2-(2-methylphenyl)benzoyl]methionine

Methyl N-[4-(2-pyrid-3-ylethyn-1-yl)-2-(2-methylphenyl)benzoyl]methionine (43 mg, 0.09 mmol) was dissolved in MeOH (2 mL) and treated with excess 1 M LiOH. After 18 h at room temperature, the reaction was evaporated, and partitioned between ether and water. The aqueous layer was acidified with 1 M HCl and extracted with EtOAc. The combined extracts were washed with water and brine, dried over $Na_2SO_4$, and evaporated to provide 35 mg of the title compound. MS m/e 445 $(M+H)^+$. $^1$H NMR ($CDCl_3$, 300 MHz) 1.62 (m, 1H), 1.96 (m, 1H), 2.1 (m, 8H), 4.62 (m, 1H), 6.02 (m, 1H), 7.37 (m, 6H), 7.63 (m, 1H), 7.88 (m, 1H), 7.99 (m, 1H), 8.59 (m, 1H), 8.79 (m, 1H).

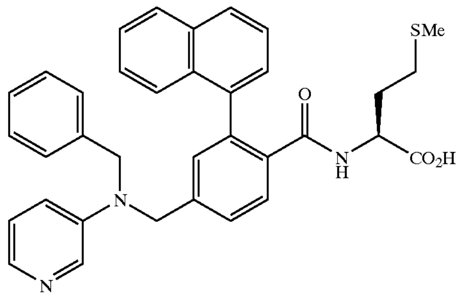

EXAMPLE 870

N-[4-(N-Benzyl-N-pyrid-3-ylaminomethyl)-2-naphth-2-ylbenzoyl]methionine

The desired compound was prepared according to the method of Example 157. $^1$H NMR ($CD_3OD$-$d_4$, 500 MHz) δ: 8.04 (m, 1H), 7.90–7.67 (m, 4H), 7.57–7.40 (m, 7H), 7.36–7.20 (m, 7H), 4.90 (s, 2H), 4.81 (s, 2H), 4.27–4.18 (m, 1H), 1.76 (s, 3H), 1.75–1.37 (m, 4H). MS: APCI (+) m/z: $(M+H)^+$ 576.

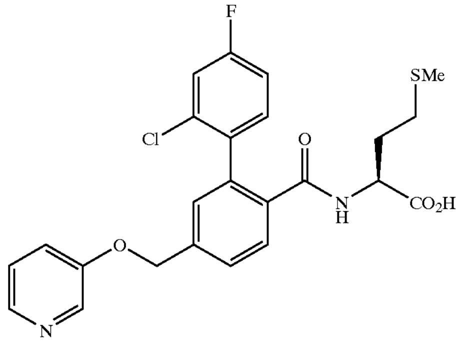

EXAMPLE 871

N-[4-(Pyrid-3-yloxymethyl)-2-(2-chloro-4-fluorophenyl)benzoyl]methionine

The desired compound was prepared according to the method of Example 157. $^1$H NMR ($CD_3OD$-$d_4$, 500 MHz) δ 8.32 (m, 1H), 8.15 (d, J=5 Hz, 1H), 7.68 (d, J=7.75 Hz, 1H), 7.60 (d, J=7.5 Hz, 1H), 7.57 (dd, $J_1$=2.5 Hz, $J_2$=7.5 Hz, 1H), 7.29 (m, 3H), 7.27 (dd, $J_1$=2.5 Hz, $J_2$=7.5 Hz, 1H), 7.11 (m, 1H), 5.29 (s, 2H), 4.57 (m, 1H), 2.46–2.24 (m, 2H), 2.04 (s, 3H), 1.96–1.84 (m, 1H). MS: ESI (+) m/z: $(M+H)^+$ 489.

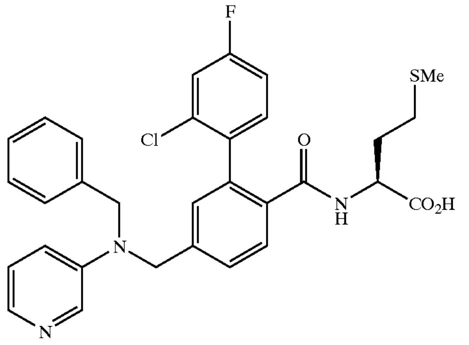

EXAMPLE 873

N-(4-(N-Benzyl-N-pyrid-3-ylaminomethyl)-2-(2-chloro-4-fluorophynel)beonzoyl)methionine The desired compound was prepared according to the method of Example 157. $^1$H NMR ($CD_3OD$-$d_4$, 500 MHZ) δ 8.02 (m, 1H), 7.84 (m, 1H), 7.63 (d, J=7.5 Hz, 1H), 7.42 (m, 1H), 7.35–7.21 (m, 10H), 7.07 (m, 1H), 4.85 (s, 2H), 4.5 (m, 1H), 2.43–2.12 (m, 3H), 2/03 (s, 3H), 2.87 (m, 1H). MS: ESI (+) m/z: $(M+H)^+$ 578.

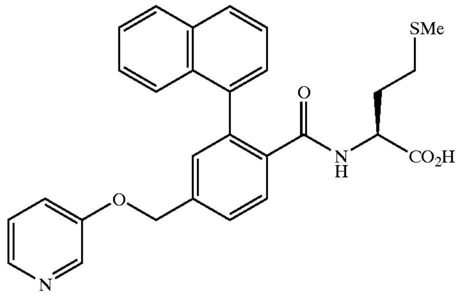

EXAMPLE 874

N-[4-(Pyrid-3-yloxymethyl)-2-naphth-2-ylbenzoyl]methionine

The desired compound was prepared according to the method of Example 157. $^1$H NMR ($CD_3OD$-$d_4$, 500 MHz) δ 8.31 (m, 1H), 8.12 (m, 1H), 7.89 (m, 2H), 7.78 (d, J=7.5 Hz, 1H), 7.70 (d, J=7.5 Hz, 1H), 7.63 (m, 2H), 7.57–7.32 (m, 8H), 5.27 (s, 2H), 4.28–4.18 (m, 1H), 1.77 (s, 3H), 1.47–1.2 (m, 4H). MS: APCI (+) m/z: $(M+H)^+$ 487.

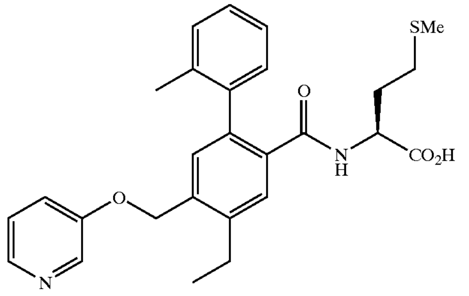

EXAMPLE 918

N-[5-Ethyl-4-(pyrid-3-yloxymethyl)-2-(2-methylphenyl)benzoyl]methionine

The desired compound was prepared according to the method of Example 343 using 9-ethyl-9-BBN as the coupling partner. $^1H$ (300 MHz, DMSO-$d_6$, δ) 8.38 (1H, d, J=3 Hz), 8.18 (1H, d, J=4 Hz), 7.93 (1H, m), 7.51 (1H, m), 7.40 (1H, s), 7.35 (1H, m), 7.28 (1H, bs), 7.20 (2H, m), 7.13 (2H, m), 5.27 (2H, s), 4.12 (1H, m), 2.78 (2H, q, J=8 Hz), 2.20–2.00 (5H, m), 1.96 (3H, s), 1.90–1.60 (2H, m), 1.26 (3H, t, J=8 Hz). m/z (DCI $NH_3$) 479 ($MH^+$) Anal. calc. for $C_{27}H_{30}N_2O_4S$.100$H_2O$ C, 65.30, H, 6.49, N, 5.64; Found C, 65.34, H, 6.41, N, 5.38.

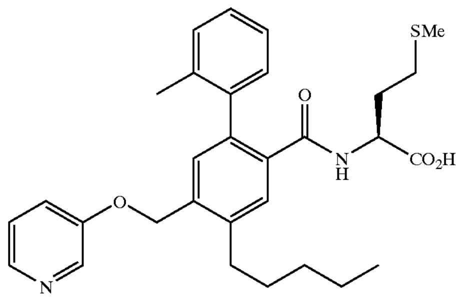

EXAMPLE 919

N-[5-Pentyl-4-(pyrid-3-yloxymethyl)-2-(2-methylphenyl)benzoyl]methionine

The desired compound was prepared according to the method of Example 343 using 9-pentyl-9-BBN as the coupling partner. 1H (300 MHz, DMSO-$d_6$, δ) 8.37 (1H, d, J=3 Hz), 8.18 (1H, dd, J=4&1 Hz), 8.09 (1H, bd, J=12 Hz), 7.48 (1H, m), 7.36 (1H, s), 7.34 (1H, m), 7.26 (1H, bs), 7.19 (2H, m), 7.13 (2H, m), 5.26 (2H, s), 4.21 (1H, m), 2.73 (2H, m), 2.20–2.00 (5H, m), 1.96 (3H, s), 1.90–1.60 (4H, m), 1.36 (4H, m), 0.86 (3H, t, J=8 Hz). m/z (DCI, $NH_3$) 521 ($MH^+$) Anal. calc. for $C_{30}H_{36}N_2O_4S$ C, 69.20, H, 6.97, N, 5.38; Found C, 69.13, H, 6.92, N, 5.40.

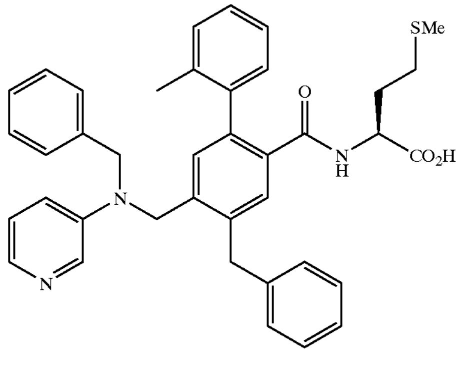

EXAMPLE 920

N-[5-Benzyl-4-(N-pyrid-3-yl-N-benzylaminomethyl)-2-(2-metbylphenyl)benzoyl]methionine The desired compound was prepared according to the method of Example 343 using 9-benzyl-9-BBN as the coupling partner. $^1H$ (300 MHz, DMSO-$d_6$, δ) 8.05 (1H, bd, J=12 Hz), 7.82 (1H, d, J=4 Hz), 7.78 (1H, bd, J=8 Hz), 7.40–7.00 (16H, m), 6.80 (2H, m), 4.75 (2H, m), 4.65 (2H, m), 4.18 (1H, m), 4.14 (2H, bs), 2.20–2.00 (2H, m), 1.93 (3H, s), 1.84 (3H, s), 1.90–1.60 (2H, m). m/z (ESI) 628 ($MH^-$).

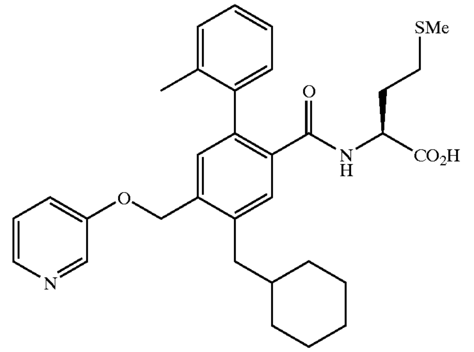

EXAMPLE 921

N-[5-Cyclohexylmethyl-4-(pyrid-3-yloxymethyl)-2-(2-methylphenyl)benzoyl]methionine The desired compound was prepared according to the method of Example 343 using 9-cyclohexylmethyl-9-BBN as the coupling partner. The desired compound was prepared according to the method of Example 157 $^1H$ (300 MHz, DMSO-$d_6$, δ) 12.60 (1H, bs), 8.40–8.20 (1H, m), 8.20–8.10 (2H, m), 7.52 (1H, m), 7.40–7.25 (4H, m), 7.20 (2H, m), 7.14 (2H, m), 5.23 (2H, s), 4.21 (1H, m), 2.62 (1H, m), 2.20–2.00 (5H, m), 1.96 (3H, s), 1.90–1.50 (8H, m), 1.30–0.90 (5H, m). m/z (ESI) 547 ($MH^+$) Anal. calc. for $C_{32}H_{38}N_2O_4S$ C, 70.30, H, 7.01, N, 5.12; Found C, 69.92, H, 6.84, N, 5.82.

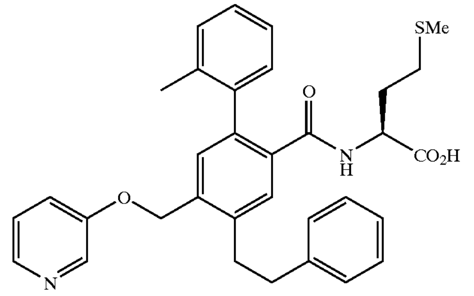

EXAMPLE 922

N-[5-(2-Phenylethyl)-4-(pyrid-3-yloxymethyl)-2-(2-methylphenyl)benzoyl]methionine The desired compound was prepared according to the method of Example 343 using 9-phenethyl-9-BBN as the coupling partner. $^1H$ (300 MHz, DMSO-$d_6$, δ) 8.47 (1H, m), 8.26 (1H, d, J=4 Hz), 8.13 (1H, bd, J=12 Hz), 7.65 (1H, dd, J=9&3 Hz), 7.50 (1H, s), 7.48 (1H, m), 7.40–7.25 (4H, m), 7.25–7.00 (6H, m), 5.30 (2H, s), 4.22 (1H, m), 2.99 (4H, m), 2.25–2.00 (5H, m), 1.97 (3H, s), 1.95–1.60 (2H, m). m/z (DCI, $NH_3$) 555 ($MH^+$) Anal. calc. for $C_{33}H_{34}N_2O_4S$.1.00 TFA C, 62.86, H, 5.28, N, 4.19; Found C, 62.98, H, 5.43, N, 4.17.

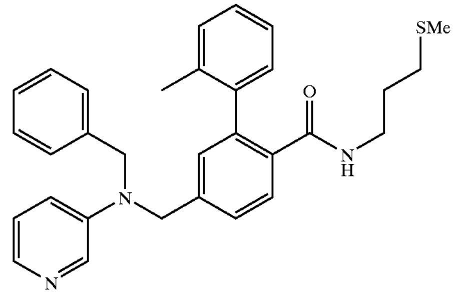

EXAMPLE 926

3-Methylthiopropyl N-4-(N-Pyrid-3-yl-N-benzylaminomethyl)-2-(2-methylphenyl)benzamide The desired compound was prepared according to the method of Example 157 $^1$H (300 MHz, DMSO-$d_6$, δ) 8.02 (2H, m), 7.95 (1H, d, J=9 Hz), 7.60–7.45 (3H, m), 7.45–7.20 (6H, m), 7.20–7.10 (3H, m), 7.00 (1H, d, J=3 Hz), 5.40 (1H, m), 4.83 (2H, s), 4.79 (2H, s), 3.22 (2H, m), 2.15 (2H, t, J=8 Hz), 2.07 (3H, s), 2.02 (3H, s), 1.43 (2H, m). m/z (APCI) 496 ($MH^+$) Anal. calc. for $C_{31}H_{33}N_3OS$.2.00 HCl C, 65.48, H, 6.20, N, 7.39; Found C, 65.15, H, 6.31, N, 7.13.

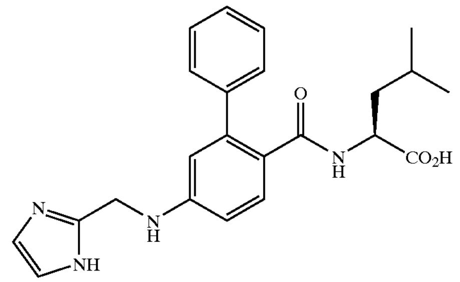

EXAMPLE 953

N-[4-(Imidazol-2-ylmethylamino)-2-phenylbenzoyl] leucine

EXAMPLE 953A

N-[4-(Imidazol-2-ylmethylamino)-2-phenylbenzoyl] leucine Methyl Ester

Reductive animation of N-[4-amino-2-phenylbenzoyl]-L-leucine methylester hydrochloride and imidazole-2-carboxaldehyde following similar procedures to those described for GGTI-2132 afforded after purification N-[4-(Imidazol-2-ylmethylamino)-2-phenylbenzoyl]leucine methyl ester as a white solid. 42%. mp=156–160° C. $^1$H NMR (DMSO-$d_6$) 8.19 (m, 1H, aryl), 7.58 (s, 2H), 7.34–7.22 (m, 6H), 6.67 (d, 1H, J=8.3 Hz), 6.60 (s, 1H), 4.72 (s, 2H, $CH_2$), 4.17 (m, 1H), 3.59 (s, 3H), 1.52–1.35 (m, 3H), 0.80 (d, 3H, J=5.3 Hz), 0.75 (d, 3H, J=5.04 Hz).

EXAMPLE 953B

N-[4-(Imidazol-2-ylmethylamino)-2-phenylbenzoyl] leucine

Saponification of the methyl ester using LiOH afforded, after lyophilization, a white solid.

84%. mp 113–117° C. $^1$H NMR (DMSO-$d_6$) 8.27 (m, 1H), 7.46–7.20 (m, 8H), 6.59 (d, 1H, J=7.9 Hz, H-5), 6.51 (s, 1H, H-3), 4.43 (s, 2H, $CH_2$), 4.08 (m, 1H), 1.48–1.27 (m, 3H), 0.96 (d, 6H).

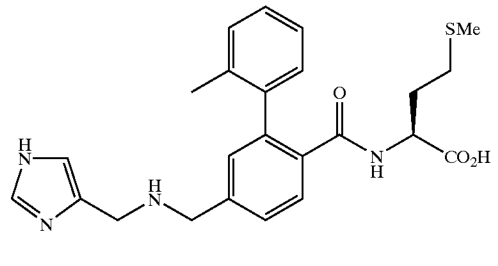

EXAMPLE 954

N-[4-(Imidazol-4-ylmethylaminomethyl)-2-(2-methylphenyl)benzoyl]methionine

EXAMPLE 954A

Methyl 4-Nitro-2-(2-methylphenyl)benzoate

Methyl 4-nitro-2-bromobenzoate (11.40 g, 43.85 mmol) was dissolved in 100 mL of DMF. Air was removed and the system was flushed with nitrogen. To this solution was added $Pd(PPh_3)_4$ (1.63 g, 3.1% eq). The pale yellow solution was stirred for 15 min until the color changed to deep brown. 2-Tolylboronic acid (6.6 g, 48.5 mmol) was added followed by anhydrous $K_2CO_3$ (18.2 g, 3.0 eq). The mixture was heated at 115° C. for 18 hr and then cooled down. This mixture was diluted with 100 mL of ether and 50 mL of water. The aqueous solution was extracted with ether. The ether solution was washed with 1N hydrochloric acid and then dried and evaporated. The residue was purified by flash column chromatography (10:1=hexane/ethyl acetate) to give a pale yellow oil which slowly solidifies (11.53 g, 97% yield). $^1$H NMR ($CDCl_3$) δ 8.28 (d, J=8.7 Hz, 1H), 8.06–8.13 (s and d, 2H), 7.22–7.34 (m, 3H), 7.07 (d, J=7.3 Hz, 1H), 3.66 (s, 3H), 2.10 (s, 3H), $^{13}$C NMR ($CDCl_3$) δ 165.7, 148.6, 143.5, 138.5, 135.9, 134.7, 130.5, 129.3, 127.9, 127.7, 125.1, 121.5, 51.8, 19.3; HRMS (EI) calcd for $Cl_5H_{13}O_4N$ 271.0844, obsd 271.0842.

EXAMPLE 954B

Methyl 4-Iodo-2-(2-methylphenyl)benzoate

The compound from Example 954A (5.23 g, 19.31 mmol) was dissolved in 80 mL of THF. Catalytic amount of Pd/C was added and the mixture was hydrogenated at 40 psi for 1 hr. After removal of the catalyst, the reduced product was obtained (4.24 g, 91%). This amine was dissolved in 7 mL of concentrated hydrochloric acid (12N), 1 mL of water and 3 mL of acetic acid. To this clear solution was added sodium nitrite (1.33 g, 19.31 mmol) in 4 mL of water at 0° C. The mixture was stirred at 0° C. for 25 min. Then a solution of KI (4.81 g, 28.97 mmol, 1.5 eq) in 4 mL of 2N HCl was added. The mixture was warmed up to 60° C. and then extracted with ethyl acetate. The ethyl acetate solution was washed with sodium bicarbonate. After evaporation of solvents, the residue was purified by flash column chromatography to give a pale yellow oil (3.40 g, 55% yield). $^1H$ NMR ($CDCl_3$) δ 7.79 (d, J=8.3 Hz, 1H), 7.64–7.70 (s and d, 2H), 7.21–7.27 (m, 3H), 7.05 (d, J=7.3 Hz, 3.62 (s, 3H), 2.07 (s, 3H); $^{13}C$ NMR ($CDCl_3$) δ 166.5, 144.2, 139.5, 139.3, 135.9, 134.7, 131.0, 129.3, 129.1, 127.9, 127.3, 125.0, 98.7, 51.6, 19.7.

EXAMPLE 954C Methyl 4-Cyano-2-(2-methylphenyl)benzoate

The compound from Example 954B (1.55 g, 4.41 mmol) was dissolved in 10 mL of THF. Then $Pd(PPh_3)_4$ (120 mg, 2.2% eq) and powdered KCN (430 mg, 6.61 mmol, 1.5 eq) was added. The mixture was refluxed for 12 hr. GC/MS showed all the starting material was converted to the product. The mixture was extracted with ethyl acetate and water. After evaporation of solvents, the residue was purified by flash column chromatography (10:1=hexane/ethyl acetate) to give an oily product (978 mg, 88% yield). $^1H$ NMR ($CDCl_3$) δ 8.02 (d, J=8.1 Hz, 1H), 7.72 (d, J=7.9 Hz, 1H), 7.56 (s, 1H), 7.20–7.33 (m, 3H), 7.03 (d, J=7.4 Hz, 1H), 3.63 (s, 3H), 2.06 (s, 3H); $^{13}C$ NMR ($CDCl_3$) δ 165.9, 143.0, 138.5, 134.6, 134.2, 133.9, 130.3, 130.0, 129.3, 127.9, 127.6, 125.0, 117.3, 114.6, 51.8, 19.4.

EXAMPLE 954

Methyl 4-(N-t-Butoxycarbonylaminomethyl)-2-(2-methylphenyl)benzoate

The compound from Example 954C (797 mg, 3.17 mmol) was dissolved in 40 mL of THF. To this solution was added catalytic amount of Pd/C and di-tert-butyldicarbonate (1.39 g, 2.0 eq). The mixture was hydrogenated at 40 psi for 12 hr. After removal of the catalyst, the residue was purified by flash column chromatography to give an oily product (1.0 g, 89% yield). $^1H$ NMR ($CDCl_3$) δ 7.97 (d, J=8.0 Hz, 1H), 7.37 (d, J=7.7 Hz, 1H), 7.19–7.28 (m, 3H), 7.17 (s, 1H), 7.08 (d, J=7.1 Hz, 1H), 5.10 (br, 1H), 4.40 (d, J=5.8 Hz, 2H), 3.63 (s, 3H), 2.08 (s, 3H), 1.48 (s, 9H); $^{13}C$ NMR ($CDCl_3$) δ 167.2, 155.7, 143.0, 141.1, 134.9, 130.1, 129.2, 129.1, 128.6, 128.1, 126.9, 125.5, 124.9, 79.2, 51.5, 43.8, 28.1, 19.7.

EXAMPLE 954E

Methyl N-[4-(N-t-Butoxycarbonylaminomethyl)-2-(2-methylphenyl)benzoyl]methionine Methyl Ester The compound from Example 954D (980 mg, 2.76 mmol) was dissolved in 6.0 mL of THF and 3 mL of methanol. To this solution was added 6.0 mL of 0.5N LiOH solution. The mixture was stirred at r.t for 4 hr and then refluxed for 1 hr until most of the starting material disappeared. This solution was acidified with 1N HCl and extracted with ethyl acetate. After the evaporation of solvents, a white solid (900 mg) was obtained. This white solid (900 mg, 2.64 mmol) was suspended in 40 mL of methylene chloride and then (L)-methionine methyl ester hydrochloride (632 mg, 3.16 mmol) and triethylamine (0.54 mL, 3.91 mmol) were added. To this solution was added EDCI (605 mg, 3.16 mmol) and HOBT (427 mg, 3.16 mmol) at 0° C. The mixture was stirred at r.t overnight. This reaction was extracted with 1N HCl and ethyl acetate. After evaporation of solvents, the residue was purified by flash column chromatography (1:1=ethyl acetate/hexane) to give a waxy product (1.10 g, 86% yield). $^1H$ NMR ($CDCl_3$) δ 7.93 (dd, J=8.0 Hz, 1H), 7.24–7.36 (m, 4.5H), 7.15 (d, J=7.3 Hz, 0.5H), 7.09 (s, 1H), 5.89 (d, J=7.7 Hz, 1H), 4.98 (br, 1H), 4.54–4.64 (m, 1H), 4.35 (d, J=5.6 Hz, 2H), 3.62 (s, 3H), 2.15 (s, 1.5H), 2.09 (s, 1.5H), 1.98–2.05 (m, 5H), 1.78–1.87 (m, 1H), 1.51–1.63 (m, 1H), 1.43 (s, 9H); $^{13}C$ NMR ($CDCl_3$) δ 171.5, 171.3, 167.3, 167.0, 155.6, 141.9, 139.9, 139.6, 139.2, 135.8, 135.6, 132.6, 132.2, 130.2, 130.1, 129.5, 129.2, 128.6, 128.0, 125.9, 125.8, 79.0, 51.9, 51.4, 51.3, 43.6, 31.1, 31.0, 28.9, 28.0, 19.6, 14.8.

EXAMPLE 954F

N-[4-(Imidazol-4-ylmethylaminomethyl)-2-(2-methylphenyl)benzoyl]methionine

The compound from Example 954E (1.06 g) was dissolved in 7 mL of methylene chloride. To this solution was added 4 mL of 4N HCl in ether. The mixture was stirred at r.t for 15 min. TLC showed all starting material disappeared. The solvents were evaporated and the amine hydrochloride salt was obtained (918 mg, yield 100%). $^1H$ NMR ($CDCl_3$) δ 8.30 (br s, 3H), 7.80 (m, 1H), 7.57 (d, J=8.0 Hz, 1H), 7.24 (m, 4.5H), 7.07 (d, J=7.4 Hz, 0.5H), 6.26 (d, J=6.9 Hz, 1H), 4.55 (m, 1H), 4.04 (br s, 2H), 3.60 (s, 3H), 2.13 (s, 1.5H), 2.00 (s, 1.5H), 1.99 (m, 5H), 1.80–1.88 (m, 1H), 1.57–1.64 (m, 1H).

The above hydrochloride salt (480 mg, 1.24 mmol) was extracted with ethyl acetate and 5% aqueous ammonium hydroxide. After evaporation of solvents, a corresponding amine was obtained. This amine was dissolved in 4 mL of THF. To this solution was added N-tritylimidazol-4-yl-aldehyde (525 mg, 1.55 mmol, 1.25 eq) and titanium isopropoxide (441 mg, 1.25 eq). The mixture was stirred at r.t for 1 hr. This reaction mixture was diluted with 6 mL of anhydrous methanol and then 2.0 mL of 0.43 N $NaBH_3CN$ (0.67 eq) in THF was added dropwise. The mixture was stirred at r.t for 4 hr and then solvents were evaporated. The residue was extracted with ethyl acetate and 5% ammonium hydroxide. The ethyl acetate layer was filtered to remove the white precipitate. The solvents were evaporated and the residue was dissolved in 3 mL of methylene chloride. To this solution was added TFA (2 mL) and then triethylsilane was added dropwise until the deep brown color disappeared. The mixture was stirred at r.t for 1 hr. The solvents were evaporated and the residue was dried on vacuum. The white residue was washed with ether. The white precipitate was filtered and dried (485 mg). This white solid (189 mg) was dissolved in 1 mL of methanol and then 2 mL of 1N NaOH was added. The mixture was stirred at r.t for 30 min. The solvents were evaporated and the residue was lyophilized. The crude mixture was purified by reverse phase HPLC to give the final product as a trifluoroacetate (90 mg, 32% yield for 3 steps). $^1H$ NMR ($CD_3OD$) δ 8.63 (s, 1H), 7.72 (d, J=7.9 Hz, 1H), 7.60 (s, 1H), 7.58 (d, J=7.9 Hz, 1H), 7.39 (br s, 1H), 7.22–7.25 (m, 4H), 4.42 (m, 3H), 4.36 (s, 2H), 2.04–2.18 (m, 4H), 1.98–2.05 (m, 5H), 1.70–1.75 (m, 1H).

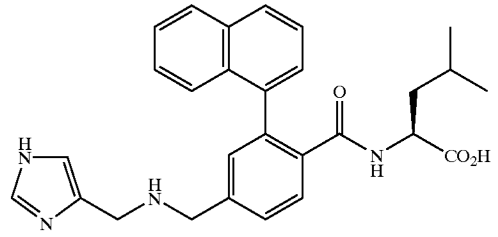

EXAMPLE 955

N-[4-(Imidazol-4-ylmethylaminomethyl)-2-naphth-1-ylbenzoyl]leucine

EXAMPLE 955A

Methyl 4-Nitro-2-(1-naphthyl)benzoate

Methyl 2-bromo-4-nitrobenzoate (3.86 g, 14.85 mmol) was coupled with 1-naphthylboronic acid (3.06 g, 17.79 mmol) in DMF in the presence of $K_2CO_3$ (3.0 eq) and $Pd(PPh_3)_4$ (0.03 eq) at 110° C. for 15 hrs. After flash column chromotography purification, the desired compound was obtained as a pale yellow oil (3.86 g, yield 85%). $^1$H NMR ($CDCl_3$) δ 8.34 (d, J=8.5 Hz, 1H), 8.28 (s, 1H), 8.14 (d, J=8.5 Hz, 1H), 7.92 (m, 2H), 7.47–7.56 (m, 2H), 7.41 (d, J=3.8 Hz, 2H), 7.34 (d, J=6.8 Hz, 1H), 3.40 (s, 3H); $^{13}$C NMR ($CDCl_3$) δ 166.4, 149.2, 142.7, 137.2, 136.8, 133.2, 131.3, 131.0, 128.6, 128.4, 126.6, 126.2, 126.0, 125.0, 124.7, 122.3, 52.3.

EXAMPLE 955B

Methyl 4-Iodo-2-(1-naphthyl)benzoate

This compound was prepared using the same method described in the preparation of the compound: in Example 955B (yield 54%). $^1$H NMR ($CDCl_3$) δ 7.85–7.90 (m, 3H), 7.73–7.80 (m, 2H), 7.31–7.53 (m, 4H), 7.28 (t, J=6.8 Hz, 1H), 3.37 (s, 3H); $^{13}$C NMR ($CDCl_3$) δ 166.7, 142.8, 140.3, 137.7, 136.5, 132.8, 131.4, 131.2, 130.5, 128.0, 127.7, 125.9, 125.6, 125.5, 124.9, 124.8, 98.8, 51.6.

EXAMPLE 955C

Methyl 4-Cyano-2-(1-naphthyl)benzoate

This compound was prepared with the same method described in the preparation of the compound described in Example 955C (yield 50%). $^1$H NMR ($CDCl_3$) δ 8.10 (d, J=8.1 Hz, 1H), 7.92 (d, J=8.2 Hz, 2H), 7.81 (d, J=8.1 Hz, 1H), 7.75 (s, 1H), 7.46–7.56 (m, 2H), 7.38 (d, J=3.7 Hz, 2H), 7.32 (d, J=7.0 Hz, 1H), 3.40 (s, 3H); $^{13}$C NMR ($CDCl_3$) δ 165.9, 141.5, 136.5, 135.2, 134.7, 132.7, 131.0, 130.7, 130.1, 128.0, 126.1, 125.8, 125.5, 124.7, 124.3, 117.3, 114.7, 51.7.

EXAMPLE 955D

N-[4-Cyano-2-(1-naphthyl)benzoyl]leucine Methyl Ester

The compound resulting from Example 955C (780 mg, 2.72 mmol) was dissolved in 8.0 mL of THF. To this solution was added 0.5 N LiOH (6.5 mL, 1.2 eq) and 4.0 mL of methanol. The mixture was refluxed for 2 hr. TLC showed the disappearance of the starting material. Solvents were evaporated and the residue was first acidified with 1N HCl and then extracted with ethyl acetate. After the evaporation of solvents, a white solid was obtained (752 mg, yield 100%). This acid (741 mg, 2.71 mmol) was coupled with (L)-leucine methyl ester hydrochloride (542 mg, 1.10 eq) by using coupling reagents EDCI and HOBT. After purification by flash column chromatography (2:1=hexane/ethyl acetate), there was obtained (775 mg, yield 72%). $^1$H NMR ($CDCl_3$) δ 8.10 (d, J=8.0 Hz, 0.6H), 7.89–7.97 (m, 2.4H), 7.80 (m, 1H), 7.67 (s, 1H), 7.36–7.59 (m, 5H), 5.68 (d, J=7.9 Hz, 0.5H), 5.60 (d, J=7.9 Hz, 0.5H), 4.25 (m, 1H), 3.55 (s, 1.5H), 3.50 (s, 1.5H), 1.02–1.05 (m, 0.5H), 0.87–0.95 (m, 0.5H), 0.73–0.76 (m, 0.5H), 0.40–0.58 (m, 6.5H), 0.18–0.25 (m, 1H); $^{13}$C NMR ($CDCl_3$) δ 172.2, 172.0, 166.3, 165.6, 140.0, 139.0, 138.7, 135.6, 135.0, 134.6, 134.5, 133.3, 131.3, 131.2, 131.1, 130.1, 129.5, 129.0, 128.8, 128.3, 128.2, 127.0, 126.9, 126.6, 126.4, 126.1, 125.1, 124.6, 124.4, 117.6, 117.5, 114.2, 113.4, 51.8, 50.4, 40.3, 23.6, 23.5, 22.2, 20.9, 20.8.

EXAMPLE 955E

N-[4-(N-t-Butoxycarbonylaminomethyl)-2-(1-naphthyl)benzoyl]leucine Methyl Ester

The compound resulting from Example 955D (700 mg, 1.75 mmol) was dissolved in 1 mL of THF and 12 mL of methanol. To this solution was added $CoCl_2.6H_2O$ (835 mg, 3.5 mmol). The mixture was vigorously stirred and then $NaBH_4$ (670 mg, 17.5 mmol) was added in several portions ($H_2$ gas evolved and color turned to black). The black mixture was stirred at r.t for 3 hr. The solvents were evaporated and the residue was extracted with ethyl acetate. After evaporation of solvents, the residue (550 mg) was dissolved in 10 mL of methylene chloride. To this solution was added di-tert-butyldicarbonate (445 mg, 1.5 eq) and the mixture was stirred for 10 hr. After evaporation of solvents, the residue was purified by flash column chromatography (1.3:1=hexane/ethyl acetate) to give a colorless oil (300 mg, yield 34% for 2 steps). $^1$H NMR ($CDCl_3$) δ 8.00 (d, J=8.0 Hz, 0.6H), 7.84–7.92 (m, 2.4H), 7.55 (d, J=8.0 Hz, 1H), 7.35–7.50 (m, 5H), 7.23 (s, 1H), 5.63 (d, J=7.9 Hz, 0.6H), 5.55 (d, J=7.9 Hz, 0.4H), 5.07 (br s, 1H), 4.38 (br s, 2H), 4.21–4.29 (m, 1H), 3.52 (s, 1.8H), 3.44 (s, 1.2H), 1.42 (s, 9H), 1.01–1.10 (m, 0.4H), 0.84–0.93 (m, 0.6H), 0.71–0.77 (m, 0.5H), 0.46–0.55 (m, 3.3H), 0.39–0.45 (m, 3.7H), 0.14–0.19 (m, 0.6H).

EXAMPLE 955F

N-[4-(Imidazol-4-ylmethylaminomethyl)-2-naphth-1-ylbenzoyl]leucine

By a procedure analogous to that described for Example 955F there was obtained the title compound. $^1$H NMR ($CD_3OD$) δ 8.66 (s, 1H), 7.88–7.93 (m, 2H), 7.80 (d, J=7.9 hz, 0.5H), 7.68–7.75 (m, 1.5H), 7.66 (s, 1H), 7.46–7.62 (m, 4.5H), 7.34–7.42 (m, 1.5H), 4.45 (s, 2H), 4.39 (s, 2H), 4.00–4.11 (m, 1H), 1.04–1.26 (m, 2H), 0.59 (d, J=6.3 hz, 1.5H), 0.51 (br s, 2H), 0.43–0.50 (m, 0.5H), 0.29–0.34 (m, 3H).

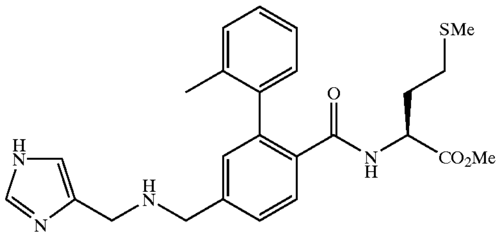

EXAMPLE 956

N-[4-(Imidazol-4-ylmethylaminomethyl)-2-(2-methylphenyl)benzoyl]methionine methyl Ester This compound was prepared by using the same method described in the preparation of FTI-2148 except that the methyl ester was not hydrolyzed. The crude product was purified by reverse phase preparative HPLC to give the title compound (36.5 mg, 35% yield for 2 steps). $^1$H NMR ($CD_3OD$) δ 8.76 (br m, 1H), 7.59–7.66 (m, 3H), 7.40 (br s, 1H), 7.22–7.25 (br m, 4H), 4.43–4.45 (m, 3H), 4.37 (s, 2H), 3.66 (s, 3H), 2.17 (br s, 2H), 2.09 (br s, 2H), 1.96–1.99 (m, 5H), 1.71–1.74 (m, 1H).

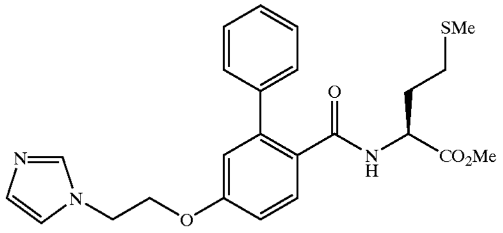

EXAMPLE 957

N-[4-(2-Imidazol-1-ylethoxy)-2-phenylbenzoyl] methionine Methyl Ester

EXAMPLE 957A

Methyl 4-Methoxy-2-phenylbenzoate

Methyl 2-hydroxy-4-methoxybenzoate (11.0 g, 60.4 mmol) was dissolved in 30 mL of pyridine. To this solution was slowly added trifluoromethanesulfonic anhydride (20 g, 70.8 mmol) at 0° C. The mixture was stirred at r.t for 20 hr. After evaporation of pyridine, the residue was extracted with ether and water. The ether solution was washed with 1N HCl. After evaporation of solvent, the residue was purified by flash column chromatography to give a desired triflate (16.5 g, 87% yield). GC/MS showed this compound was pure (M/z=314). $^1$H NMR ($CDCl_3$) δ 8.06 (d, J=8.8 Hz, 1H), 6.94 (d, J=8.8 Hz, 1H), 6.77 (s, 1H), 3.93 (s, 3H), 3.88 (s, 3H). This aryltriflate (5.02 g, 16.0 mmol) was reacted with phenylboronic acid in DMF in the presence of $Pd(PPh_3)_4$ (0.03 eq) and potassium carbonate (6.62 g, 3.0 eq). After stirring at 100° C. for 7 hr, the mixture was worked up and the mixture was purified by flash column chromatography to give compound 35 (3.53 g, 91% yield). GC/MS showed the compound was pure (M/Z=242). $^1$H NMR ($CDCl_3$) δ 7.90 (d, J=8.7 Hz, 1H), 7.30–7.43 (m, 5H), 6.92 (d, J=8.7 Hz, 1H), 6.86 (s, 1H), 3.86 (s, 3H), 3.63 (s, 3H); $^{13}$C NMR ($CDCl_3$) δ 167.4, 161.2, 144.7, 141.1, 131.8, 127.8, 127.3, 126.6, 122.0, 115.8, 111.8, 54.6, 50.8.

EXAMPLE 957B

Methyl 4-(2-Bromethoxy)-2-phenylbenzoate $AlCl_3$ (4.0 g, 30 mmol) was dissolved in 6 mL of methylene chloride and 9.5 mL of EtSH at 0° C. To this solution was added the compound prepared in Example 957A (2.42 g, 10 mmol) in 10 mL of methylene chloride. The mixture was stirred at 0° C. for 2 hr and r.t for 30 min. This mixture was poured into ice water and neutralized with 3 N aqueous HCl. The mixture was extracted with ethyl acetate. After evaporation of solvents, a pale pink oil was obtained (2.20 g). This material was pure as shown by TLC. The oily compound (2.20 g, 10 mmol) was dissolved in 60 mL of acetone. To this solution was added 1,2-dibromoethane (7.52 g, 40 mmol) and potassium carbonate (5.52 g, 40 mmol). The mixture was refluxed for 2 days. After the workup, the crude material was purified by flash column chromatography (12% ethyl acetate in hexane) to give the title compound as a pale yellow oil (1.69 g, 52% yield). $^1$H NMR ($CDCl_3$) δ 7.89 (d, J=8.7 Hz, 1H), 7.36–7.40 (m, 3H), 7.26–7.30 (m, 2H), 6.92 (d, J=8.7 Hz, 1H), 6.86 (s, 1H), 4.35 (t, J=6.2 Hz, 2H), 3.66 (t, J=6.2 Hz, 2H), 3.62 (s, 3H); $^{13}$C NMR ($CDCl_3$) δ 167.9, 160.1, 145.3, 141.3, 132.3, 128.1, 127.8, 127.2, 123.2, 116.8, 113.0, 67.8, 51.6, 28.6.

EXAMPLE 957C

Methyl 4-[2-(Imidazol-1-yl)ethoxyl-2-phenylbenzoate

The compound resulting from Example 957B (1.62 g, 4.83 mmol) was dissolved in 20 mL of THF. To this solution was added imidazole (656 mg, 9.64 mmol) and triethylamine (1.38 mL, 10 mmol). The mixture was refluxed overnight. After evaporation of solvents, the crude material was purified by flash column chromatography (7% methanol in methylene chloride) to give unreacted starting material (530 mg) and the desired product as a colorless oil (748 mg, yield 71%). $^1$H NMR ($CDCl_3$) δ 7.87 (d, J=8.6 Hz, 1H), 7.59 (s, 1H), 7.35–7.42 (m, 3H), 7.26–7.28 (m, 2H), 7.05 (d, J=12 Hz, 2H), 6.87 (d, J=8.6 Hz, 1H), 6.81 (s, 1H), 4.36 (t, J=5.0 Hz, 2H), 4.27 (t, J=4.9 Hz, 2H), 3.61 (s, 3H); $^{13}$C NMR ($CDCl_3$) δ 167.4, 159.6, 144.8, 140.7, 137.0, 131.9, 128.9, 127.7, 127.4, 126.8, 122.8, 118.9, 116.3, 112.4, 66.8, 51.2, 45.6.

EXAMPLE 957D

N-[4-(2-Imidazol-1-ylethoxy)-2-phenylbenzoyl] methionine Methyl Ester

The compound prepared in Example 957C (738 mg, 2.29 mmol) was dissolved in 5 mL of methanol. To this solution was added 4.5 mL of 1N NaOH solution and the mixture was refluxed for 5 hr. The solution was filtered and the filtrate was acidified with 1 N aqueous HCl to PH about 4.2. After cooling in ice bath, white crystals were collected (701 mg, 99% yield). m.p 242–244° C. This carboxylic acid (250 mg, 0.81 mmol) was coupled with (L)-methionine methyl ester in methylene chloride by using coupling reagent EDCI and HOBT. After the work up with sodium bicarbonate solution, the residue was purified by flash column chromatography (6% methanol in methylene chloride) to give the title compound as a white foam solid (340 mg, 93% yield). $^1$H NMR ($CDCl_3$) δ 7.66 (d, J 8.6 Hz, 1H), 7.54 (s, 1H), 7.34–7.42 (m, 5H), 7.01 (br s, 2H), 6.85 (d, J=8.6 Hz, 1H), 6.76 (s, 1H), 6.00 (d, J=7.7 Hz, 1H), 4.60 (ddd, J=5.3, 5.7 and 7.7 Hz, 1H), 4.30 (t, J=4.9 Hz, 2H), 4.21 (t, J=4.9 Hz, 2H), 3.62 (s, 3H), 2.05 (t, J=7.6 hz, 2H), 1.97 (s, 3H), 1.81–1.92 (m, 1H), 1.61–1.73 (m, 1H); $^{13}$C NMR ($CDCl_3$): δ 171.6, 168.3, 158.6, 141.5, 139.6, 137.0, 130.4, 128.8, 128.2, 127.9, 127.6, 119.0, 115.8, 112.8, 67.0, 51.9, 51.4, 45.8, 30.8, 19.1, 14.8.

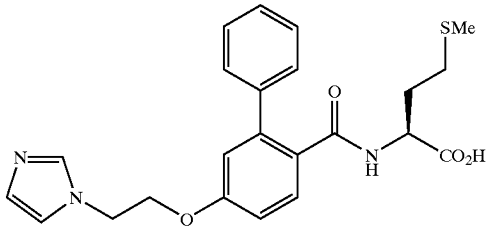

EXAMPLE 958

N-[4-(2-Imidazol-1-ylethoxy)-2-phenylbenzoyl] methionine

The compound resulting from Example 957D (184 mg, 0.37 mmol) was dissolved in 2 mL of methanol. To this solution was added 2.0 mL of 0.5 N LiOH solution. The mixture was stirred at 0° C. for 1 hr. Solvents were evaporated and the residue was dissolved in 4 mL of water and filtered. The aqueous solution was acidified with 1 N aqueous HCl. The resulting solution was lyophilized. The crude solid was purified by reverse phase preparative HPLC to give the desired compound (189 mg, 85% yield). $^1$H NMR ($CD_3OD$) δ 9.06 (s, 1H), 7.75 (s, 1H), 7.58 (s, 1H), 7.50 (d, J=8.5 hz, 1H), 7.33–7.42 (m, 5H), 6.99 (d, J=8.4 Hz, 1H), 6.95 (s, 1H), 4.69 (t, J=4.7 Hz, 2H), 4.47 (t and m, J=4.8 Hz, 3H), 2.10–2.19 (m, 1H), 2.03–2.07 (m, 1H), 2.01 (s, 3H), 1.94–1.99 (m, 1H), 1.75–1.81 (m, 1H).

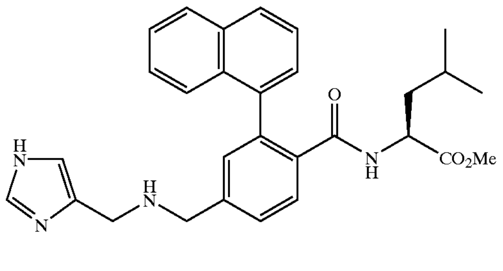

EXAMPLE 961

N-[4-(Imidazol-4-ylmethylaminomethyl)-2-naphth-1-ylbenzoyl]leucine Methyl Ester

This compound was prepared with the same method as described in the preparation of FTI-2153. The final product was purified by reverse phase preparative HPLC (20% yield, 3 steps). $^1$H NMR ($CD_3OD$) δ 8.54 (s, 1H), 7.91 (br d, J=5.2 Hz, 2H), 7.69–7.79 (m, 2H), 7.38–7.58 (m, 7H), 4.40 (br s, 4H), 4.03–4.14 (m, 1H), 3.59 (s, 1.3H), 3.54 (s, 1.7H), 1.11–1.21 (m, 2H), 0.60 (m, 1.7H), 0.52 (br s, 2.3H), 0.31–0.33 (m, 3H).

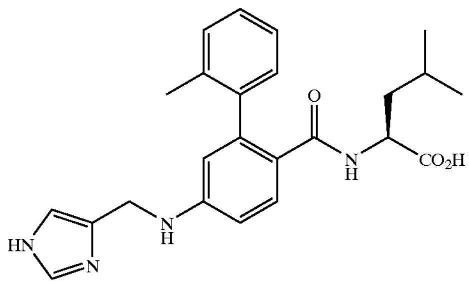

EXAMPLE 962

N-[4-(Imidazol-4-ylmethylamino)-2-(2-methylphenyl)benzoyl]leucine Hydrochloride

EXAMPLE 962A

N-[4-Nitro-2-(2-methylphenyl)benzoyl]leucine Methyl Ester 4-nitro-2-(2-tolyl)benzoic acid (1.72 g, 6.7 mmol) was coupled with (L)-leucine methyl ester in the presence of EDCI and HOBT to give the desired compound (2.55 g, 99% yield). $^1$H NMR ($CDCl_3$) δ 8.29 (d, J=8.7 Hz, 1H), 8.10–8.16 (m, 2H), 7.18–7.42 (m, 4H), 5.76 (d, J=7.6 Hz, 1H), 4.49 (br m, 1H), 3.66 (s, 3H), 2.19 (s, 1H), 2.08 (s, 2H), 1.30–1.39 (m, 1H), 1.02–1.09 (m, 2H), 0.75–0.80 (dd, J=6.7 and 7.1 Hz, 6H).

EXAMPLE 962B

N-[4-(1-Tritylimidazol-4-yl)methylamino)-2-(2-methylphenyl)benzoyl]leucine Methyl Ester The compound prepared in Example 962A (2.42 g, 6.29 mmol) was hydrogenated at 1 atm with catalytic amount of Pd/C for 12 hr. After removal of the catalyst and evaporation of the solvents, the amine was dissolved in chloroform and 4N gaseous HCl in ether. The solvents were evaporated and the residue was dried on vacuum to give a hydrochloride salt (2.36 g, 96% yield). This hydrochloride salt (2.26 g, 5.79 mmol) was dissolved in 40 mL of dry methanol. To this solution was added 1-N-tritylimidazol-4-yl-aldehyde (2.06 g, 6.01 mmol) and 2.5 mL of acetic acid. The mixture was stirred at r.t for 1 hr. Then $NaBCNH_3$ (365 mg, 5.79 mmol) in 10 mL of methanol was added dropwise. The mixture was stirred at r.t for 10 min. Another portions of 1-N-tritylimidazol-4-yl-aldehyde (750 mg, 1.9 mmol) was added until no starting material amine was observed from TLC. The reaction mixture was stirred for 4 hr and then worked up. After flash column chromatography purification (10:10:1:1=ethyl acetate/hexane/methanol/methylene chloride), the title compound was obtained as a white fluffy solid (2.98 g, 76% yield). $^1$H NMR ($CDCl_3$) δ 8.00 (d, J=8.7 Hz, 0.5H), 7.92 (d, J=8.7 Hz, 0.5H), 7.40 (s, 1H), 7.22–7.33 (m, 10H), 7.09–7.15 (m, 9H), 6.73 (s, 1H), 6.64 (d, J=8.6 Hz, 1H), 6.32 (s, 1H), 5.48 (t, J=7.7 Hz, 1H), 4.57 (br s, 1H), 4.40–4.50 (m, 1H), 4.25 (d, J=5.3 Hz, 2H), 3.62 (s, 3H), 2.14 (s, 1.5H), 2.04 (s, 1.5H), 1.02–1.20 (m, 2H), 0.88–0.97 (m, 1H), 0.76 (dd, J=5.4 and 6.5 Hz, 6H).

EXAMPLE 962C

N-[4-(Imidazol-4-ylmethylamino)-2-(2-methylphenyl)benzoyl]leucine Hydrochloride

The compound prepared in Example 962B (647 mg) was first hydrolyzed under basic conditions to deprotect the ester and then treated with TFA and triethylsilane. After evaporation of solvents, the residue was dried on vacuum. The crude mixture was washed with ether and the white solid was dissolved in 5 mL of methylene chloride. To this solution was added 5 mL of 4N gaseous HCl in ether. Solvents were evaporated to give the desired compound (350 mg, 74% yield) as a hydrochloride salt. Analytical HPLC showed the purity of this compound over 99%. $^1$H NMR ($CD_3OD$) δ 8.82 (s, 1H), 7.65 (dd, J=8.6 Hz, 1H), 7.45 (s, 1H), 7.21–7.26 (m, 3.5H), 7.10 (d, J=7.3 Hz, 0.5H), 6.72 (d, J=8.7 Hz, 6.41 (s, 1H), 4.49 (s, 2H), 4.27 (m, 1H), 2.12 (s, 1.5H), 2.02 (s, 1.5H), 1.30–1.39 (m, 1H), 1.04–1.19 (m, 2H), 0.75 (t, J=7.4 Hz, 6H).

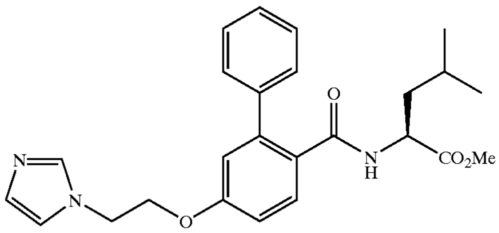

EXAMPLE 963

N-[4-(2-Imidazol-1-ylethoxy)-2-phenylbenzoyl]leucine Methyl Ester

This compound was prepared by using the same method as described for the preparation of FTI-2156 except methionine was replaced with leucine (93% yield). $^1$H NMR ($CDCl_3$) δ 7.72 (d, J=8.6 Hz, 1H), 7.57 (br s, 1H), 7.33–7.43 (m, 5H), 7.02 (br s, 2H), 6.86 (d, J=8.6 Hz, 1H), 6.75 (s, 1H), 5.64 (d, J=7.7 Hz, 1H), 4.47 (ddd, J=3.1, 5.1 and 7.7 Hz, 1H), 4.32 (t, J=4.9 Hz, 2H), 4.23 (t, J=4.8 Hz, 2H), 3.61 (s, 3H), 1.28–1.38 (m, 1H), 1.07–1.18 (m, 2H), 0.76 (t, J=6.4 Hz, 6H); $^{13}C$ NMR ($CDCl_3$) δ 1.72.7, 168.1, 158.6, 141.5, 139.7, 137.1, 130.5, 128.9, 128.2, 127.9, 127.5, 119.1, 115.8, 112.7, 67.0, 51.7, 50.7, 45.9, 40.5, 24.0, 22.4, 21.4.

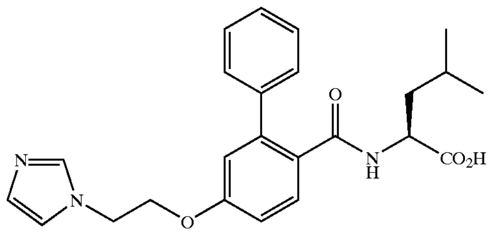

EXAMPLE 964

N-[4-(2-Imidazol-1-ylethoxy)-2-phenylbenzoyl] leucine

This compound was prepared from the hydrolysis of Example 963 the compound prepared in Example XXX. The final product was purified from preparative HPLC (85% yield). $^1H$ NMR ($CD_3OD$) δ 9.07 (s, 1H), 7.75 (s, 1H), 7.58 (s, 1H), 7.48 (d, J=8.4 Hz, 1H), 7.34–7.39 (m, 5H), 6.99 (d, J=8.5 Hz, 1H), 6.94 (s, 1H), 4.69 (t, J=4.6 Hz, 2H), 4.45 (t, J=4.6 Hz, 2H), 4.33 (t, J=7.4 Hz, 1H), 1.46 (t, J=7.1 Hz, 2H), 1.15–1.24 (m, 1H), 0.80 (dd, J=6.5 Hz, 6H).

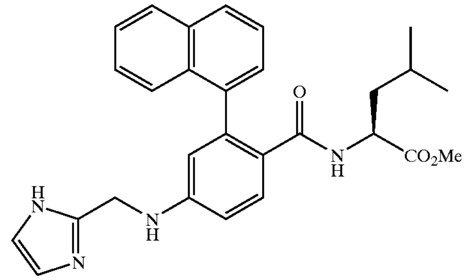

EXAMPLE 965

N-[4-(Imidazol-2-ylmethylamino)-2-naphth-1-ylbenzoyl]leucine Methyl Ester

This compound was prepared in a fashion analogous to Example 963 wherein the 2-phenyl substituent has been replaced with 2-naphth-1-yl $^1H$ NMR ($CDCl_3$) δ 9.10 (brs, 1H), 7.89–7.80 (m, 3H), 7.55–7.45 (m, 3H), 7.35–7.28 (m, 2H), 6.90 (s, 2H), 6.58 (m, 1H, J=8.7 Hz), 6.51 (d, 1H, J=2 Hz), 5.62 (m, 1H), 4.43 (d, 2H, $CH_2$), 4.14 (m, 1H), 3.50 (s, 2H), 3.36 (s, 1H), 1.25–1.18 (m, 1H), 1.03 (m, 2H), 0.56 (d, 2H), 0.40 (m, 4H).

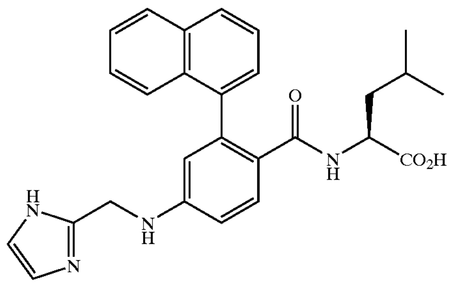

EXAMPLE 966???

N-[4-(Imidazol-2-ylmethylamino)-2-naphth-1-ylbenzoyl]leucine

Hydrolysis of the compound prepared in Example XXX afforded the corresponding acid. $^1H$ NMR (DMSO-$d_6$) δ 7.92–7.77 (m, 3H), 7.57–7.13 (m, 9H), 6.84 (m, 1H), 6.56 (s, 1H), 4.73 (d, 2H, $CH_2$), 3.86 (nm, 1H), 1.32–1.02 (m, 3H), 0.65 (d, J=6.2 Hz, 1.5H), 0.56 (d, J=6.2 Hz, 1.5H), 0.45 (d, J=6.09 Hz, 1.5H), 0.36 (d, J=6.2 Hz, 1.5H).

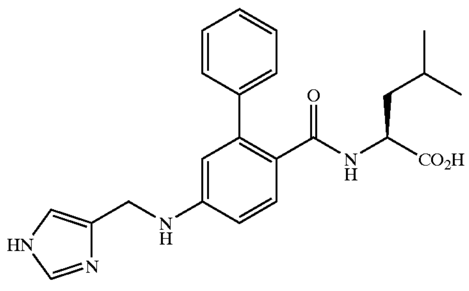

EXAMPLE 967

N-[4-(Imidazol-4-ylmethylamino)-2-phenylbenzoyl] leucine

EXAMPLE 967A

N-[4-(1-Tritylimidazol-4-ylmethylamino)-2-phenylbenzoyl]leucine Ester

Reductive amination of N-[4-amino-2-phenylbenzoyl] leucine methyl ester with tritylimidazole-4-carboxaldehyde afforded N-[4-(1-tritylimidazole-4-ylmethylamino)-2-phenylbenzoyl]leucine ester in 66% yield as a white solid, after purification. $^1H$ NMR: (DMSO-$d_6$) 8.84 (s, 1H), 8.38 (d, 1H, J=7.7 Hz), 7.43 (m, 9H, trityl), 7.32–7.20 (m, 6H, trityl), 7.13 (m, 7H, aryl), 6.74 (d, 1H, J=8.7 Hz), 6.70 (s, 1H), 4.39 (brs, 2H), 4.15 (m, 1H, leu α-CH), 1.53–1.14 (m, 3H), 0.87–0.74 (overlapping d, 6H, leu $CH_3$) $^{13}C$ NMR: 174.0, 169.6, 146.4, 140.3, 136.7, 132.7, 130.6, 129.3, 128.79, 128.23, 128.06, 126.12, 121.13, 113.30, 113.01, 77.55, 50.51, 37.70, 24.21, 23.14, 21.20.

EXAMPLE 967B

N-[4-(Imidazol-4-ylmethylamino)-2-phenylbenzoyl] leucine

Saponification of the methyl ester followed by detritylation afforded the desired compound in 56% yield (over 2 steps) as a white solid. mp 114–116° C. $^1$H NMR (DMSO-$d_6$) 8.69 (s, 1H), 8.36 (d, J=7.8 Hz, 1H), 7.39–7.12 (m, 7H), 6.76–6.47 (m, 3H), 4.34 (d, 2H), 4.12 (dd, 1H), 1.56–1.37 (m, 3H), 0.81–0.75 (dd, 6H). $^{13}$C NMR (DMSO-$d_6$) 173.49, 169.09, 147.57, 146.31, 139.97, 133.82, 132.34, 130.01, 127.58, 127.36, 126.97, 125.38, 115.97, 112.21, 111.96, 49.86, 37.43, 23.58, 22.51, 20.53.

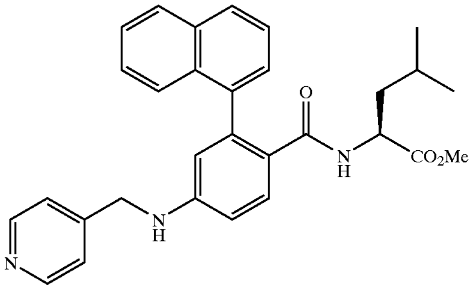

EXAMPLE 968

N-[4-(Pyrid-4-ylmethylamino)-2-naphth-1-ylbenzoyl]leucine Methyl Ester

This compound was synthesized via the reductive amination of N-[4-amino-2-naphth-1-ylbenzoyl]leucine methyl ester and pyridine-4-carboxaldehyde in methanol to afford, after purification, a white solid. $^1$H NMR (DMSO-$d_6$) δ 0.71 (d, J=5.45 Hz, 3H), 0.82 (d, J=5.13 Hz, 3H), 1.20–1.27 (m, 2H), 1.29–1.32 (m, 1H), 3.72 (s, 2H), 3.79 (s, 1H), 4.15 (m, 1H), 4.41 (d, 2H, $CH_2$), 5.52 (d, 1H, NH), 6.67–6.75 (dd, 1H), 6.89 (d, 1H), 7.23 (m, 2H), 7.25–7.35 (m, 8H), 8.55 (m, 2H).

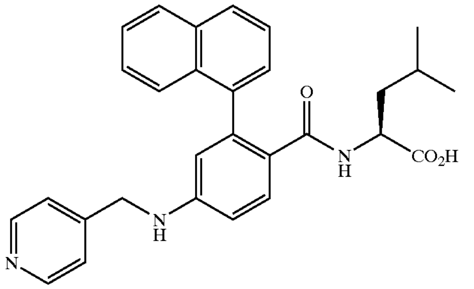

EXAMPLE 969

N-[4-(Pyrid-4-ylmethylamino)-2-naphth-1-ylbenzoyl]leucine

Saponification of the methyl ester prepared in Example 698 afforded the desired compound as a white solid. (82%) $^1$H NMR (DMSO-$d_6$) δ 8.46 (d, 2H), 7.55 (d, J=8.3 Hz, 1H), 7.31–7.21 (m, 7H), 7.01 (m, 1H), 6.83–6.79 (m, 2H), 6.72 (d, J=6.6 Hz, 1H), 4.22 (d, J=5.7 Hz, 2H), 4.01 (m, 1H), 1.47–1.32 (m, 3H), 0.77 (d, J=5.5 Hz, 6H).

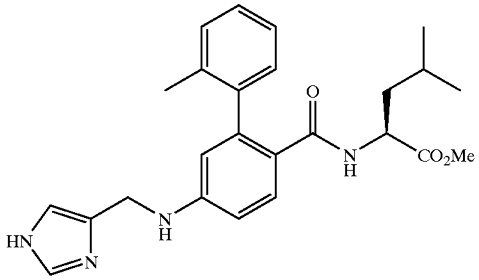

EXAMPLE 970

N-[4-(Imidazol-4-ylmethylamino)-2-(2-methylphenyl)benzoyl]leucine Methyl Ester

Detritylation of the compound prepared in Example 962 afforded the title compound. $^1$H NMR ($CD_3OD$) δ 8.82 (s, 1H), 7.21–7.26 (m, 3.5H), 7.12 (d, J=7.5 Hz, 0.5H), 6.72 (d, J=8.5 Hz, 1H), 6.42 (s, 1H), 4.49 (s, 2H), 4.28 (m, 1H), 3.62 (s, 3H), 2.12 (s, 1.5H), 2.03 (s, 1.5H), 1.27–1.36 (m, 1H), 1.12–1.21 (m, 1.4H), 0.98–1.10 (br m, 0.6H), 0.72–0.79 (m, 6H).

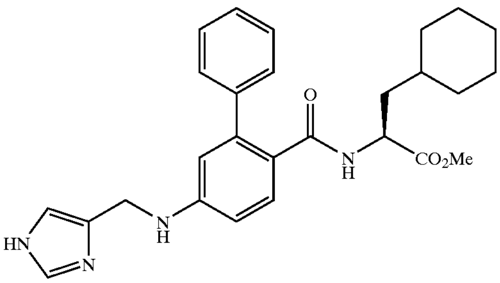

EXAMPLE 972

N-[4-(Imidazol-4-ylmethylamino)-2-phenylbenzoyl]cyclohexyalanine Methyl Ester

Reductive amination of N-[4-amino-2-phenylbenzoyl]cyclohexyalanine methyl ester with trityl-imidzole-4-carboxaldehyde to afforded the title compound in 62% yield. This compound was first sponified and the corresponding carboxylic acid was treated with TFA and triethylsilane to afford GGTI-2169. $^1$H NMR ($CDCl_3$) 9.00 (s, 1H, imidazole NH), 8.06 (d, 1H), 7.56 (s, 1H, imidazole NH), 7.14–7.30 (m, 6H), 6.65 (d, 1H), 6.60 (s, 1H), 4.40 (s, 2H, $CH_2$), 4.17 (m, 1H, α-H), 3.67 (s, 3H), 1.20–1.18 (m, 5H), 1.07–1.16 (m, 5H), 0.72–0.89 (m, 3H).

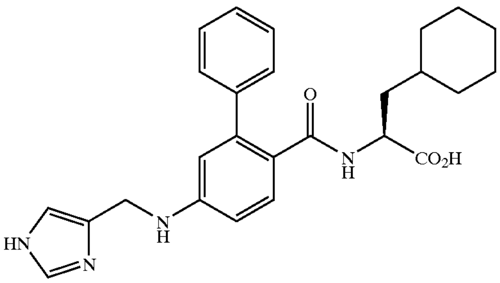

EXAMPLE 973

N-[4-(Imidazol-4-ylmethylamino)-2-phenylbenzoyl]cyclohexyalanine

Saponification of the compound prepared in Example XXX afforded the corresponding acid in 45% yield. mp 124–126° C. $^1$H NMR (DMSO-$d_6$) δ 9.02 (s, 1H), 8.04 (d, J=7.8 Hz, 1H, H-6), 7.55 (s, 1H), 7.30–7.24 (m, 6H), 6.66 (d, J=8.28 Hz, 1H, H-5), 6.60 (s, 1H, H-3), 4.43 (br s, 2H, $CH_2$), 4.18 (br m, 1H), 1.52.1.24 (m, 5H), 1.16–1.06 (m, 5H), 0.93–0.75 (m, 3H). $^{13}$C NMR (DMSO-$d_6$) δ 173.75, 168.51, 148.71, 140.55, 133.61, 131.24, 129.12, 127.72, 127.33, 126.37, 116.14, 113.58, 209.67, 49.21, 37.47, 36.47, 32.94, 32.70, 30.80, 25.52, 25.21, 25.01.

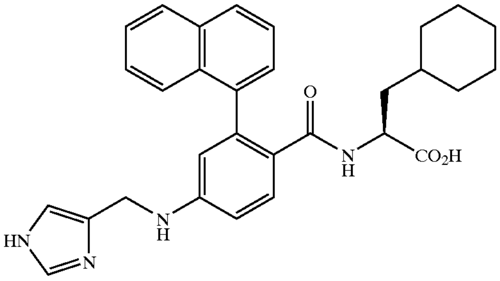

EXAMPLE 974

N-[4-(Imidazol-4-ylmethylamino)-2-naphth-1-ylbenzoyl]cyclohexyalanine

EXAMPLE 974A

N-[4-(1-Tritylimidazol-4-ylmethylamino)-2-naphth-1-ylbenzoyl]cyclohexyalanine Methyl Ester Reductive amination of N-[4-amino-2-naphth-1-ylbenzoyl]cyclohexyalanine Methyl ester with trityl-imidazole-4-carboxaldehyde afforded the title compound in 59% yield. $^1$H NMR (300 MHz, $CDCl_3$) 0.74–0.88 (m, 5H), 1.08–1.15 (m, 8H), 3.68 (s, 1H, $COOCH_3$), 3.77 (s, 2H, $COOCH_3$), 4.24 (m, 1H, α-CH), 5.29 (d, J=7.89 Hz, 0.4H, amide-NH), 5.36 (d, J=7.83 Hz, 0.6H, amide-NH), 6.39 (s, 1H, H-3), 7.01 (m, 2H, imidazole+aryl), 7.19–7.22 (m, 6H, trityl+imidazole), 7.40–7.42 (m, 10H, trityl), 7.51–7.59 (m, 5H, aryl), 7.89 (m, 2H), 8.28 (d, J=8.64 Hz, 1H, H-6).

EXAMPLE 974B

N-[4-(Imidazol-4-ylmethylamino)-2-naphth-1-ylbenzoyl]cyclohexyalanine

Saponification of the ester followed by de-tritylation afforded the title compound as a white solid in 39% yield. mp 106–108° C. (softens). $^1$H NMR (300 MHz, DMSO-$d_6$) δ 0.69–0.87 (m, 3H), 1.04–1.14 (m, 5H), 1.22–1.46 (m, 5H), 4.11 (m, 1H, α-CH), 4.49 (d, 2H, $CH_2$), 6.49 (s, 1H), 6.99 (m, 1H), 7.14 (m, 1H), 7.56–7.68 (m, 8H), 7.80–791 (m, 2H), 8.46 (s, 1H).

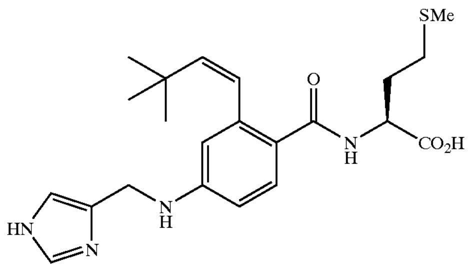

EXAMPLE 977

N-[4-(Imidazol-4-ylmethylamino)-2-(3,3-dimethyl-Z-butenyl)benzoyl]methionine

EXAMPLE 977A

Methyl 2-(3,3-Dimethylbutynyl)-4-nitrobenzoate

Methyl 2-bromo-4-nitrobenzoate (2.0 g, 7.7 mmol) and t-butylacetylene (0.70 g, 8.5 mmol) were dissolved into 50 mLs. of dry triethylamine to which 2 mole % of copper iodide (0.029 g, 0.15 mmol) and 5 mole. % of tetrakis (triphenylphosine)palladium(0) (0.45 g, 0.38 mmol) were added. The reaction was stirred at 400° C. for 16 hours before an additional ½ equivalent of t-butylacetylene was added. The reaction continued for an additional 24 hours at which time the reaction was completed as determined by TLC. The reaction mixture was taken up in ethyl acetate, washed with distilled water and the organic layer dried over magnesium sulfate. After concentrating, the residue was purified by chromatography (1:9 ethyl acetate/hexanes ) to give the title compound (1.7 g, 85%) as a white solid. m.p. 88–89° C.; $^1$H NMR (300 MHz, $CDCl_3$) δ 8.30 (d, J=2.2 Hz, 1H, Aromatic), 8.10 (dd, J=2.3, 8.6 Hz, 1H, Aromatic), 7.99 (d, J=8.7 Hz, 1H, Aromatic), 3.99 (s, 3H, $OCH_3$), 1.35 (s, 9H, t-Butyl); $^{13}$C NMR (75 MHz, $CDCl_3$) δ 165.9, 149.4, 137.7, 131.4, 128.7, 126.2, 121.8, 107.1, 76.5, 52.8, 30.8, 28.6; MS m/e calc'd 261.1001, found 261.1007.

EXAMPLE 977B 2-(3,3-Dimethylbutynyl)-4-nitrobenzoic Acid

Methyl 2-(3,3-dimethylbutynyl)-4-nitrobenzoate (0.8 g, 3.1 phenol) was dissolved in 50 mL of methanol containing 5% potassium hydroxide solution and the reaction was stirred at room temperature for 2 hours. The reaction mixture was concentrated and the residue was taken up in water and washed with diethyl ether. The aqueous fraction was carefully acidified with concentrated HCl to a pH of 2.0 and extracted with ethyl acetate (2×50 mLs). The organic fractions were combined, washed once with a saturated solution of sodium chloride, dried over magnesium sulfate and concentrated to give the title compound (0.7 g, 91%) an off-white solid: m.p. 170–173° (C.); $^1$H NMR (300 MHz, methanol-$d_4$) δ 8.16 (d, J=2.2 Hz, 1H, Aromatic), 8.12 (dd, J=8.7, 2.3 Hz, 1H, Aromatic), 7.96 (d, J=8.5 Hz, 1H, Aromatic), 1.35 (s, 9H, t-Butyl); $^{13}$C NMR (75 MHz, methanol-$d_4$) δ 168.5, 150.7, 140.4, 132.4, 129.0, 126.6, 123.1, 107.4, 77.7, 31.2, 29.6; MS m/e calc'd for: 247.0845, found 247.0821.

EXAMPLE 977C

N-[2-(3,3-Dimethylbutynyl)-4-nitrobenzoyl] methonine Methyl Ester

The compound resulting from Example 977B (0.7 g, 2.8 mmol) and L-Methonine Methyl Ester (0.6 g, 2.8 mmol) were dissolved in 50 mL of dry methylene chloride and cooled to 0° C. 1-hydroxybenzotriazole (0.4 g, 2.8 mmol), EDCI (0.6 g, 3.1 mmol) and triethylamine (0.3 g, 2.8 mmol) were added to the cooled solution. The reaction was stirred under nitrogen overnight as the reaction warmed to room temperature. Additional methylene chloride was added and the reaction mixture was washed with 1N HCl followed by a saturated solution of sodium bicarbonate and a saturated solution of sodium chloride. The organic layer was dried over magnesium sulfate, concentrated to a slight yellowish oil which was purified by flash chromatography (1:1 ethyl acetate/hexanes) to give the title compound (0.8 g, 73%). $^1$H NMR (300 MHz, $CDCl_3$) δ 8.24 (d, J=1.9 Hz, 1H, Aromatic), 8.18 (dd, J=9.6, 1 Hz, 1H, Aromatic), 7.98–8.11 (m, 2H), 4.86 (dd, J=7.4, 5.8 Hz, 1H, α-Methionine), 3.72 (s, 3H, $OCH_3$), 2.45–2.55 (m, 2H), 2.16–2.28 (m, 1H), 2.02 (s, 3H), 1.98–2.10 (m, 1H), 1.31 (s, 9H, t-Butyl); $^{13}$C NMR (75 MHz, $CDCl_3$) δ 171.7, 164.1, 148.6, 139.1, 131.3, 128.8, 122.4, 122.2, 108.6, 76.0, 52.6, 52.4, 32.0, 30.4, 30.0, 28.5, 15.4; MS m/e calc'd for: 392.1406, found 392.1399.

EXAMPLE 977D

N-[4-Amino-2-(3 .3-dimethyl-Z-butenyl)benzoyl] methionine Methyl Ester

Hydrazine hydrate (5 equivalents, 0.18 g, 5.74 mmol) and raney nickel (0.75 g, mmol) were dissolved in 25 mL of methanol and heated to reflux. The compound resulting from Example 977C (0.45 g, 1.1 mmol) dissolved in 5 mL of methanol was slowly added to the refluxing mixture. The reaction was complete after 15 minutes as determine by TLC (1:1 ethyl acetate/hexanes) and the reaction mixture was concentrated. The residue which was taken up in ethyl acetate was washed once with a saturated solution of sodium bicarbonate and dried over magnesium sulfate. The organics were concentrated and the product converted to the hydrochloride and dried under vacuum to yield the desired compound (0.33 g, 79%): $^1$H NMR (300 MHz, methanol-$d_4$) δ 7.64 (d, J=8.2 Hz, 1H), 7.38 (dd, J=8.2 Hz, 1.3H, a), 7.26 (d, J=1.1 Hz, 1H), 6.51 (d, J=12.7 Hz, 1H, cis-Alkene), 5.68 (d, J=12.7 Hz, 1H, cis-Alkene), 4.75 (dd, J=9.4, 4.6 Hz, 1H), 3.75 (s, 3H, $OCH_3$), 2.51–2.69 (m, 2H), 2.14–2.40 (m, 1H), 2.09 (s, 3H), 0.92 (s, 9H, t-Butyl); $^{13}$C NMR (75 MHz, methanol-$d_4$) δ 173.5, 170.6, 145.0, 141.0, 137.3, 133.0, 130.4, 126.1, 124.5, 122.5, 52.9, 52.7, 35.4, 31.7, 31.3, 15.1; MS m/e calc'd for: 364.1821, found 364.1835.

EXAMPLE 977E

N-[4-(1-Triphenylimidazol-4-ylmethylamino)-2-(3, 3-dimethyl-Z-butenyl)benzoyl]methionine Methyl Ester 1-Triphenylmethylimidazole-4-carboxaldehyde (0.38 g, 1.1 mmol) and the compound resulting from Example 977D (0.3 g, 0.7 5 mmol) were dissolve in 10 mLs of 95% methanol and 5% acetic acid and stirred for 10 minutes before 1.1 equivalents of sodium cyanoborohydride (0.056 g, 0.83 mmol) was added. The reaction was stirred for 1 hour while additional aldehyde was added until all of the amine hydrochloride had disappeared. The reaction mixture was concentrated and the residue taken up in ethyl acetate and was washed with a saturated solution of sodium bicarbonate. The organic phase was dried over magnesium sulfate, concentrated and the residue purified by flash chromatography (1:1 ethyl acetate/hexanes) to give the desired compound (0.28 g, 54%) as a white foam: $^1$H NMR.(300 MHz, $CDCl_3$) δ 7.89 (d, J=8.7 Hz, 1H), 7.40–7.42 (m, 2H), 7.27–7.35 (m, 9H, Trityl), 7.10–7.15 (m, 6H, Trityl), 6.74 (s, 1H), 6.53–6.59 (m, 2H), 6.37 (d, J=2.0 Hz, 1H), 5.79 (d, J=12.5 Hz, 1H, cis-Alkene), 4.90 (dd, J=7.0 Hz, 1H), 4.60 (t, J=5.2 Hz, 1H), 4.25 (d, J=5.2 Hz, 2H), 3.76 (s, 3H), 2.51–2.60 (m, 2H), 2.21–2.26 (m, 1H), 2.02–2.12 (m, 1H), 0.98 (s, 9H, t-Butyl); $^{13}$C NMR (75 MHz, $CDCl_3$) δ 172.8, 167.2, 149.8, 144.3, 142.4, 139.1, 138.8, 138.2, 131.8, 129.9, 129.7, 128.4, 128.2, 127.1, 120.7, 119.3, 114.4, 111.6, 75.5, 52.5, 52.3, 41.9, 34.8, 31.7, 30.8, 30.1, 15.6; MS m/e calc'd for: 686.3250, found 686.3260.

EXAMPLE 977F

N-[4-(Imidazol-4-ylmethylamino)-2-(3,3-dimethyl-Z-butenyl)benzoyl]methionine

The compound prepared in Example 977E (0.15 g, 0.22 mmol) was dissolved into 4 mLs of tetrahydrofuran and cooled to 0° C. Sodium hydroxide (2 equivalents, 0.18 g, 0.44 mmol) was dissolved in 4 mLs of distilled water and slowly added to the stirred solution. The reaction was complete after 2 hours as determined by TLC. The reaction was acidified with 0.5 N hydrochloric acid and concentrated. The residue was extracted with ethyl acetate, dried over magnesium sulfate and concentrated. The residue was taken up in 4 mLs of methylene chloride to which 4 mLs of trifluororacetic acid was added followed by the immediate addition of triethylsilane. The reaction was stirred for an additional 2 hours. The mixture was concentrated and the residue taken up in diethyl ether to which 3N HCl dissolved in diethyl ether was added. The solid which precipitated was washed with additional diethyl ether and dried by vacuum to give the desired compound (0.09 g 86%) as a white solid: $^1$H NMR (300 MHz, methanol-$d_4$) δ 8.50 (s, 1H), 7.36 (d, J=8.6 Hz, 1H), 7.27 (s, 1H), 6.64 (dd, J=8.6, 2.2 Hz, 1H), 6.33–6.37 (m, 2H), 5.53 (d, J=12.7 Hz, 1H), 4.53 (dd, J=9.1, 4.6 Hz, 1H), 4.42 (s, 2H), 2.42–2.60 (m, 2H), 1.89–2.16 (m, 5H), 0.63 (s, 9H, t-Butyl); $^{13}$C NMR (75 MHz, methanol-$d_4$) δ 176.3, 171.7, 149.2, 145.2, 140.9, 135.2, 132.4, 131.8, 126.9, 124.3, 118.3, 116.4, 114.4, 53.6, 39.2, 35.4, 31.9, 31.5, 31.2, 16.0.

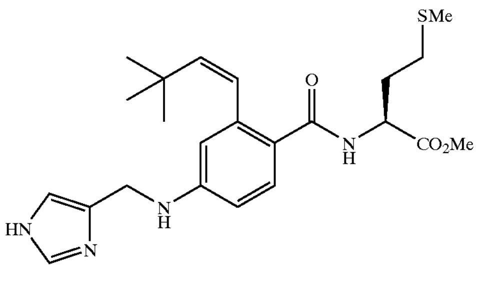

EXAMPLE 978

N-[4-(Imidazol-4-ylmethylamino)-2-(3,3-dimethyl-Z-butenyl)benzoyl]methionine Methyl Ester The compound prepared in Example 977E (0.15 g, 0.22 mmol) was dissolved into 4 mLs of methylene chloride. To the reaction was added 4 mLs of trifluoroacetic acid followed by the immediate addition of triethylsilane. The reaction was stirred at room temperature for an additional 2 hours. The reaction was concentrated and the residue taken up into methylene chloride to which a 3N HCl in diethylether was added. The hydrochloride was washed with additional diethyl ether and dried under vacuum to give the title compound (0.04 g, 60%): $^1$H NMR (300 MHz, methanol-$d_4$) δ 8.86 (s, 1H), 7.53 (d, J=8.5 Hz, 1H), 7.28 (s, 1H), 6.65 (dd, J=8.5, 2.6 Hz, 1H), 6.54 (d, J=12.5 Hz, 1H), 6.44 (s, 1H), 5.61 (d, J=12.5 Hz, 1H), 4.71 (dd, J=8.6, 5.0 Hz, 1H), 4.49 (s, 2H), 3.73 (s, 3H), 2.49–2.71 (m, 2H), 1.9602.22 (m, 5H), 0.88 (s, 9H); $^{13}$C NMR (75 MHz, methanol-$d_4$) δ 173.8, 171.1, 147.2, 144.1, 140.9, 135.6, 131.8, 131.2, 127.1, 126.7, 119.0, 117.8, 114.7, 53.2, 52.9, 40.1, 35.3, 32.0, 31.2, 15.2.

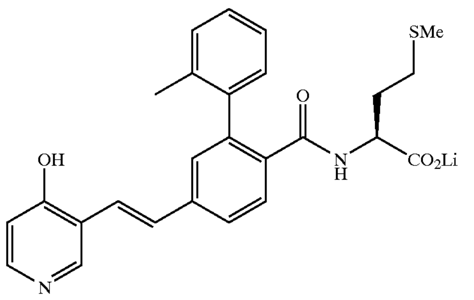

EXAMPLE 1039

N-[4-(2-(4-Hydroxypyridin-3-yl)ethenyl)-2-(2-methylphenyl)benzoyl]methionine Lithium Salt The compound was prepared as in Example 1040 by saponification with 2 equivalents of LiOH. MS m/e 461 $(M-H)^-$. $^1$H NMR ($d_6$-DMSO, 300 MHz) δ 1.7 (m, 4H), 2.05 (m, 7H), 3.80 (bs, 1H), 7.1 (bs, 1H), 7.3 (m, 3H), 7.6 (m, 6H), 7.83 (m, 1H), 8.6 (m, 1H), 9.11 (s, 1H).

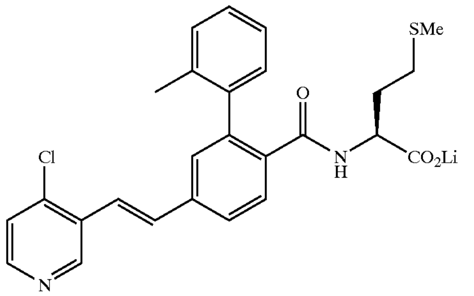

EXAMPLE 1040

N-[4-(2-(4-Chloropyridin-3-yl)ethenyl)-2-(2-methylphenyl)benzoyl]methionine Lithium Salt The title compound was prepared by standard LiOH saponification. MS m/e 479 $(M-H)^-$. $^1$H NMR ($d_6$-DMSO, 300 MHz) δ 1.6 (m, 3H), 2.0 (m, 7H), 3.68 (bs, 1H), 7.0 (bs, 1H), 7.5 (m, 9H), 7.74 (m, 1H), 8.42 (m, 1H), 9.02 (s, 1H).

N-[4-(2-(4-Chloropyridin-3-yl)ethenyl)-2-(2-methylphenyl)benzoyl]methionine Methyl Ester N-[4-iodo-2-(2-methylphenyl)benzoyl]methionine methyl ester (2.1 g, 4.34 mmol), 4-chloro-3-vinylpyridine (1.4 g, 10 mmol), and 1,1'-[bis(diphenylphosphino)ferrocene]dichloropalladium(II) (complex with methylene chloride 1:1, 177 mg, 0.22 mmol) were combined in NMP (9 mL) and TEA (3 mL) and heated at 100° C. for 5 hours. The mixture was concentrated and purified by flash chromatography (50% EtOAc in hexanes) to give 1.0 g of the title compound. MS m/e 495 $(M+H)^+$. $^1$H NMR ($CDCl_3$, 300 MHz) δ 1.61 (m, 2H), 1.90 (m, 2H), 2.15 (m, 6H), 3.69 (s, 3H), 4.65 (m, 1H), 5.95 (m, 1H), 7.3–7.5 (m, 9H), 7.69 (m, 1H), 8.05 (m, 1H), 8.45 (s, 1H).

4-Choro-3-vinylpyridine

Methyltriphenylphosphonium bromide (4.45 g, 12.5 mmol) was suspended in THF (25 mL) under dry nitrogen and treated with butyllithium (2.5 M in hexanes, 5 mL). After stirring the suspension for 30 minutes, 4-chloropyridine-3-carboxaldehyde (1.47 g, 10.4 mmol) was added. After 2 hours at ambient temperature, the reaction was diluted with hexanes, filtered, and evaporated. The material thus obtained was used directly without further purification or characterization.

4-Chloropyridine-3-carboxaldehyde

4-Chloropyridine (3.1 g, 27.3 mmol, after drying over $Na_2SO_4$) was extracted from a mixture of 4-chloropyridine hydrochloride in 5% $NaHCO_3$ with methylene chloride, dissolved in THF (50 mL), and cooled to −78° C. under dry nitrogen, followed by addition of LDA (1.5 M in cylclohexane, 18.2 mL). After 4 hours at −78° C., excess ethyl formate was added quickly. After 3 hours at −78° C., the reaction was allowed to warm to ambient temperature overnight. The reaction was diluted with water and extracted with EtOAc. The combined organic extracts were washed with brine, dried over $Na_2SO_4$, chromatographed (20% EtOAc in hexanes), and dried under high vacuum to give 1.47 g of the aldehyde. MS m/e 142 $(M+H)^+$. $^1$H NMR ($CDCl_3$, 300 MHz) δ 7.44 (d, 1H, J=6 Hz), 8.69 (d, 1H, J=6 Hz), 9.06 (s, 1H), 10.51 (s, 1H).

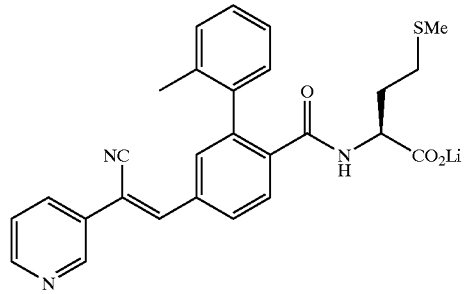

EXAMPLE 1075

N-[4-(E-2-Cyano-2-pyrid-3-ylethenyl)-2-(2-methylphenyl)benzoyl]methionine, Lithium Salt

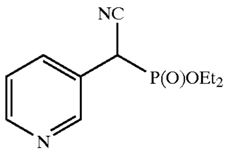

EXAMPLE 1075A

Diethyl 3-Pyridylcyanomethyl Phosphonate

Palladium acetate (45 mg) and triphenylphosphine (157 mg) were dissolved in DME (20 mL), followed by addition of diethyl cyanomethylphosphonate (0.97 mL), and NaH (420 mg of a 60% dispersion in mineral oil). After 15 min, 3-bromopyridine (0.48 mL) was added, and the reaction was refluxed for 3 h. The reaction was cooled, concentrated, neutralized with 1M HCl, and extracted into dichloromethane (50 mL). The organic extracts were washed with brine (20 mL), dried ($MgSO_4$), filtered and concentrated. The residue was purified by silica gel chromatography eluting with 100% EtOAc to afford a yellow liquid (695 mg, 55%). MS ($CI/NH_3$) 255 $(M+H)^+$, 272 $(M+NH_4)^+$.

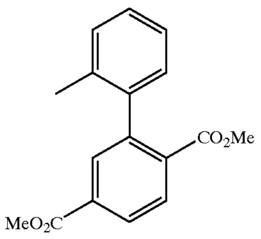

EXAMPLE 1075B

Dimethyl-(2-methylphenyl)terephthalate

A mixture of dimethyliodoterephthalate (278 g, 0.87 mol), 2-methylphenylboronic acid (141 g, 1.04 mol), palladium (II) acetate (1.95 g, 0.0087 mol) and triphenylphosphine (9.1 g, 0.035 mol) in 2.2 L of toluene and 2.2 L of 2M sodium carbonate was degassed with nitrogen and heated to 80° C. for 1.5 hours and cooled to ambient temperature. The layers were separated and the organic layer filtered through a plug of silica gel (600 g) prewetted with methyl t-butylether (MTBE, 1.2 L). The frit was washed with 5 L of MTBE and the filtrate was then concentrated to provide 237 g (96%) of the title compound. $^1H$ NMR ($CDCl_3$) δ 8.09, dd, 1H; 8.02, d, 1H; 7.95, d, 1H; 7.20–7.34, m, 3H; 7.10, bd, 1H; 3.96, s, 3H; 3.64, s, 3H; 2.08, s, 3H. MS ($DCI/NH_3$) 302 $(M+NH_4)^+$.

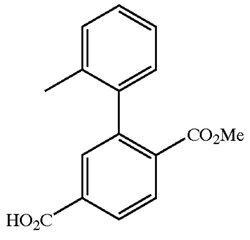

EXAMPLE 1075C 2-(2-Methylphenyl)-4-carboxybenzoic Acid, Methyl Ester

A solution of example 1075B (194 g, 0.68 mol) in 2:1 THF/methanol (~0.3M) was cooled to 0° C. and lithium hydroxide (0.38 L of a 2.2 M aqueous solution, 0.82 mol) was added such that the reaction temperature remained below 10° C. The cooling bath was removed and the mixture allowed to warm to 11° C. overnight and then warmed to ~20° C. over 4 hours. The mixture was concentrated to a volume of 1.2 L and then diluted to a volume of 5.6 L with water. The mixture was extracted with hexanes and the aqueous layer filtered through celite (200 g) and the celite pad washed with water. The mixture was diluted with ethyl acetate (6 L) and the pH of the aqueous phase adjusted to 5.5 by the addition of 3M aqueous HCl (250 mL). The organic phase was removed and concentrated to provide 171 g (93%) of the title compound. The material was 87% pure. An analytical sample was obtained by recrystallization from aqueous ethanol. $^1H$ NMR ($CDCl_3$) δ 8.14, dd, 1H; 8.03, d, 1H; 8.01, d, 1H; 7.28–7.42, m, 3H; 7.09, bd, 1H; 3.64, s, 3H; 2.08, s, 3H. MS ($DCI/NH_3$): 271 $(MH)^+$; 288 $(M+NH_4)^+$.

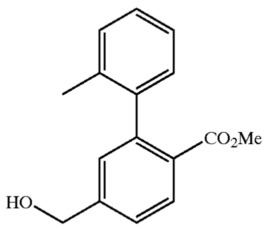

EXAMPLE 1075D

4-Hydroxymethyl-2-(2-methylphenyl)benzoic, Methyl Ester

A solution of example 1075C (4.67 g, 17.3 mmol) in 35 mL of THF was cooled in an ice bath and treated with borane (0.88M in THF, 39 mL, 34.6 mmol) such that the internal temperature remained below 10° C. The cooling bath was removed and the solution stirred for 3 hours and then cooled in an ice bath. The reaction was quenched by the careful addition of 8 mL of water (vigorous evolution of hydrogen gas) keeping the temperature below 10° C. An additional 8 mL of water was added and the mixture partitioned between ethyl acetate and 2N sodium hydroxide. The layers were separated and the organic layer was extracted with water, dried, filtered and concentrated. The residue was purified by column chromatography on silica gel to provide 3.90 g (88%) of the title compound. $^1H$ NMR ($CDCl_3$) δ 7.98, d, 1H; 743, dd, 1H; 7.16–7.28, m, 4H; 7.07, bd, 1H; 4.77, s, 2H; 3.62, s, 3H; 2.05, s, 3H; 1.78, bs, 1H. MS ($DCI/NH_3$): 257 $(MH)^+$; 274 $(M+NH_4)^+$.

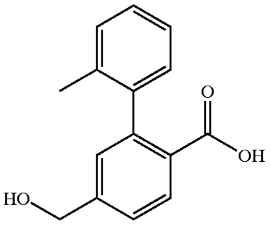

EXAMPLE 1075E

4-Hydroxymethyl-2-(2-methylphenyl)benzoic Acid

To a solution of 4-hydroxymethyl-2-(2-methylphenyl) benzoic acid methyl ester (73 g, 285 mmol), prepared as in example 1075D, in EtOH (300 mL) was added an aqueous 4N NaOH solution (350 mL, 1.4 mol), and mixture heated at 80° C. overnight. Reaction concentrated in vacuo, and residue mixed with water (300 mL). Aqueous mixture acidified to pH 6 using aqueous 3N HCl, and acid product extracted out with $CHCl_3$ (3×200 mL). Organic extracts dried with $Na_2SO_4$, filtered, and concentrated in vacuo to produce a white solid (69 g, 100% crude yield). m/e (DCI) 243 $(MH^+)$.

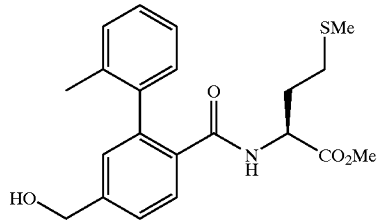

EXAMPLE 1075F

N-[4-Hydroxymethyl-2-(2-methylphenyl)benzoyl] methionine Methyl Ester

4-Hydroxymethyl-2-(2-methylphenyl)benzoic acid (69 g, 285 mmol), prepared as in example 1075E, L-methionine methyl ester.HCl (68.3 g, 342 mmol), 1-hydroxybenzotriazole (46.2 g, 342 mmol), and 1-ethyl-3-(3-dimethylaminopropyl)-carbodiimide (65.6 g, 342 mmol) were dissolved at ambient temperature in DMF (700 mL). To this solution was added triethylamine (47.7 mL, 342 mmol) and the resulting thick slurry was stirred overnight at ambient temperature. The reaction was diluted with EtOAc (700 mL) and washed with water (2×1L), saturated $NaHCO_3$ (2×500 mL), 1N $H_3PO_4$ (2×500 mL), and brine. Organic layer dried with $Na_2SO_4$, filtered, and concentrated in vacuo to produce a pale yellow solid (110 g, 100% crude yield). $^1$H(300 MHz, $CDCl_3$) δ 7.93 (1H, m), 7.44 (1H, dd, J=8, 2 Hz), 7.40–7.20 (4H, m), 7.19 (1H, bs), 5.92 (1H, m), 4.78 (2H, s), 4.63 (1H, m), 3.66 (3H, s), 2.20–2.00 (8H, m), 1.87 (1H, m), 1.75 (1H, m), 1.60 (1H, m). m/e (ESI) 386 ($MH^-$).

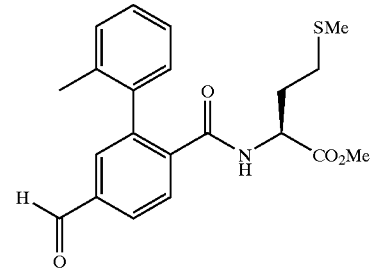

EXAMPLE 1075G

N-[4-Formyl-2-(2-methylphenyl)benzoyl]methionine Methyl Ester

To a mechanically stirred solution at −78° C. under $N_2$ of anhydrous DMSO (16.9 mL, 1.08 mol) in $CH_2Cl_2$ (750 mL) was added dropwise via addition funnel oxalyl chloride (44.8 mL, 513 mmol) such that temperature was maintained below −65° C. The reaction was stirred 15 minutes, and a solution of N-[4-Hydroxymethyl-2-(2-methylphenyl) benzoyl]methionine methyl ester (110 g, 285 mmol), prepared as in example 1075F, in $CH_2Cl_2$ (100 mL) was added dropwise via addition funnel such that temperature was again maintained below −65° C. After one hour, triethylamine (159 mL, 1.14 mol) was added, and the reaction was warmed to ambient temperature over one hour. The reaction was poured into ether (1.5 L) and washed with brine (2×1.5 L). The organic layer was dried with $Na_2SO_4$, filtered, and concentrated in vacuo. The residue was purified by flash chromatography on silica gel (30% EtOAC/Hexanes) to give the desired product as a pale yellow solid (66 g, 60%). $^1$H(300 MHz, $CDCl_3$) δ 11.00 (1H, s), 8.07 (1H, m), 7.97 (1H, dd, J=8, 2 Hz), 7.75 (1H, bs), 7.40–7.20 (4H, bs), 6.01 (1H, m), 4.63 (1H, m), 3.68 (3H, s), 2.20–2.00 (8H, m), 1.87 (1H, m), 1.63 (1H, m). m/e (ESI) 384 ($MH^-$).

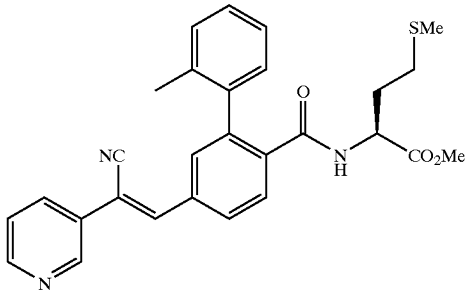

EXAMPLE 1075H

N-[4-(E-2-Cyano-2-pyrid-3-ylethenyl)-2-(2-methylphenyl)benzoyl]methionine, Methyl Ester To a solution of diethyl 3-pyridylcyanomethyl phosphonate (269 mg) in DME (3 mL) was added NaH (39 mg@60%). To the red solution was added N-[4-formyl-2-(2-methylphenyl)benzoyl] methionine methyl ester (example 10756, 340 mg). After 30 min, the reaction was warmed to reflux for 2.5 h. The reaction was cooled, quenched with water (5 mL), and extracted into EtOAc (20 mL). The organic extracts were washed with brine (5 mL), dried ($MgSO_4$), filtered and concentrated. The residue was purified by silica gel chromatography eluting with 50%–100% EtOAc/hexane to afford two products as colorless oils. The more mobile isomer (68 mg, 13%) was assigned the Z configuration based on a ROESY experiment. MS (APCI(+)) m/e 486 $(M+H)^+$. MS (APCI(−)) m/e 485 $M^-$. The less mobile isomer (246 mg, 48%) was assigned the E configuration based on a ROESY experiment. MS (APCI (+)) m/e 486 $(M+H)^+$. MS (APCI(−)) m/e 485 $M^-$.

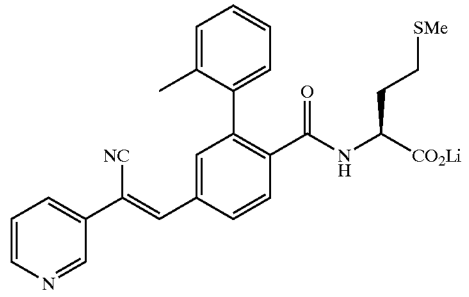

EXAMPLE 10751

N-[4-(E-2-Cyano-2-pyrid-3-ylethenyl)-2-(2-methylpbenyl)benzoyl]methionine, Lithium Salt To a solution of N-[4-(E-2-cyano-2-pyrid-3-ylethenyl)-2-(2-methylphenyl)benzoyl]methionine methyl ester (230 mg) in MeOH (1.5 mL) was added 5M LiOH (0.123 mL). After stirring at ambient temperature for 5 h, the reaction was concentrated, the residue was dissolved in water (23 mL), frozen (−78° C.) and lyophylized. The title compound was isolated as a light red powder. $^1$H NMR (300 MHz, DMSO)

δ 1.51–1.88 (m, 4H), 1.91 (s, 3H), 2.02–2.26 (m, 3H), 3.63–3.74 (m, 1H), 7.12–7.30 (m, 5H), 7.56 (dd, J=8.4, 5.1 Hz, 1H), 7.71 (d, J=8.1 Hz, 1H), 7.77 (brs, 1H), 8.01 (brd, J=7.8 Hz, 1H), 8.16 (ddd, J=8.1, 2.7, 1.8 Hz 1H), 8.24 (s, 1H), 8.64 (dd, J=4.8, 1.5 Hz, 1H), 8.98 (d, J=2.1 Hz, 1H). MS (APCI(−)) m/e 470 (M−H); Analysis calcd for $C_{27}H_{24}LiN_3O_3S.4.0H_2O$: C, 58.82; H, 5.89; N, 7.62; found: C, 58.81; H, 5.12; N, 7.33.

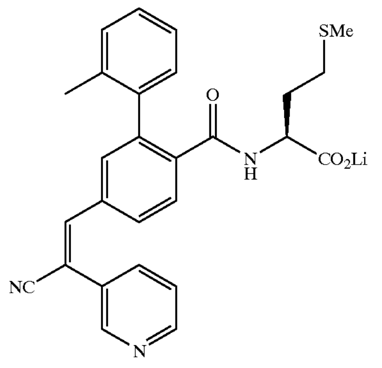

EXAMPLE 1076

N-[4-(Z-2-Cyano-2-pyrid-3-ylethenyl)-2-(2-methylphenyl)benzoyl]methionine, Lithium Salt The title compound was prepared from N-[4-(Z-2-Cyano-2-pyrid-3-ylethenyl)-2-(2-methylphenyl)benzoyl]methionine methyl ester (example 1075H) according to the procedure in example 1075I, and was isolated as a light red powder. $^1$H NMR (300 MHz, DMSO) δ 1.50–1.89 (m, 4H), 1.91 (s, 3H), 2.02–2.25 (m, 3H), 3.64–3.75 (m, 1H), 7.00–7.28 (m, 5H), 7.55 (dd, J=8.1, 4.8 Hz, 1H), 7.71 (d, J=7.8 Hz, 1H), 7.77 (brs, 1H), 8.00 (brd, J=7.8 Hz, 1H), 8.15 (ddd, J=8.1, 2.4, 1.8 Hz, 1H), 8.23 (s, 1H), 8.64 (dd, J=4.8, 1.5 Hz, 1H), 8.97 (d, J=2.4 Hz, 1H). MS (APCI(−)) m/e 470 (M−H); Analysis calc'd for $C_{27}H_{24}LiN_3O_3S.1.00H_2O$: C, 65.45; H, 5.29; N, 8.48; found: C, 65.40; H, 5.27; N, 8.35.

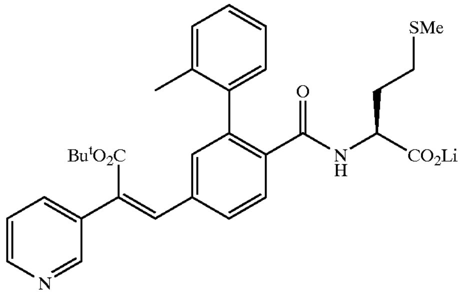

EXAMPLE 1077

N-[4-(E-2-t-Butoxycarbonyl-2-pyrid-3-ylethenyl)-2-(2-methylphenyl)benzoyl]methionine, Lithium Salt

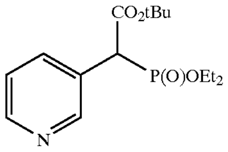

EXAMPLE 1077A

Diethyl-3-pyridyl-t-butylphosphonoacetate

The title compound was prepared in 15% yield according to the procedure in example 1075A substituting tert-butyl diethylphosphonoacetate for diethyl cyanomethylphosphonate. MS ($CI/NH_3$) 330 $(M+H)^+$.

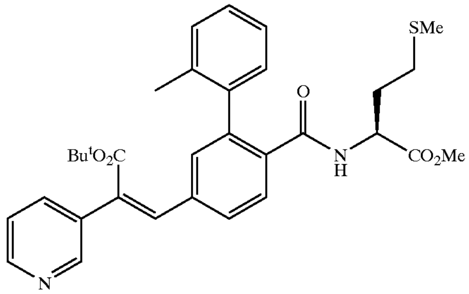

EXAMPLE 1077B

N-[4-(E-2-t-Butoxycarbonyl-2-pyrid-3-ylethenyl)-2-(2-methylphenyl)benzoyl]methionine, Methyl Ester The title compound was prepared according to the procedure described in example 1075H, substituting diethyl-3-pyridyl-t-butylphosphonoacetate for diethyl-3-pyridylcyanoacetate. The crude product was purified by silica gel chromatography eluting with 50%–60% EtOAc/hexane to give two products. The more mobile product (140 mg, 25%) was assigned the Z configuration based on a ROESY experiment. MS (ESI(+)) m/e 561 $(M+H)^+$. MS (ESI(−)) m/e 559 $M^-$. The less mobile isomer (60 mg, 14%) was assigned the E configuration (the title compound) based on a ROESY experiment. MS (ESI(+)) m/e 561 $(M+H)^+$. MS (ESI(−)) m/e 559 $M^-$.

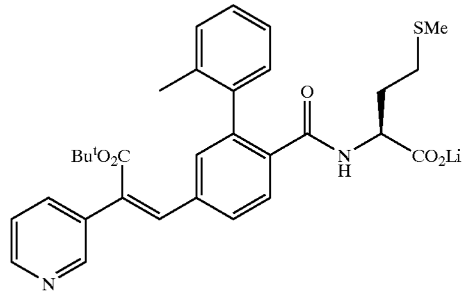

EXAMPLE 1077C

N-[4-(E-2-t-Butoxycarbonyl-2-pyrid-3-ylethenyl)-2-(2-methylphenyl)benzoyl]methionine, Lithium Salt The title compound was prepared from N-[4-(E-2-t-butoxycarbonyl-2-pyrid-3-ylethenyl)-2-(2-methylphenyl) benzoyl]methionine methyl ester according to the procedure in example 10751, and was isolated as a white powder. $^1H$ NMR (300 MHz, DMSO) δ 1.37 (s, 9H), 1.45–1.75 (m, 4H), 1.91 (s, 3H), 1.98–2.19 (m, 3H), 3.60–3.73 (m, 1H), 6.97–7.34 (m, 6H), 7.32 (s, 1H), 7.47 (dd, J=8.1, 4.8 Hz, 1H), 7.52 (brd, J=8.4 Hz, 1H), 7.60 (d, J=8.1 Hz, 1H), 7.81 (ddd, J=7.8, 1.8, 1.8 Hz, 1H), 8.57 (55, J=4.8, 1.5 Hz, 1H), 8.71 (d, J=2.1 Hz, 1H). MS (APCI(−)) m/e 545 (M−H); Analysis calc'd for $C_{31}H_{33}LiN_2O_5S.2.7H_2O$: C, 61.8.6; H, 6.45; N, 4.65; found: C, 61.72; H, 5.89; N, 4.44.

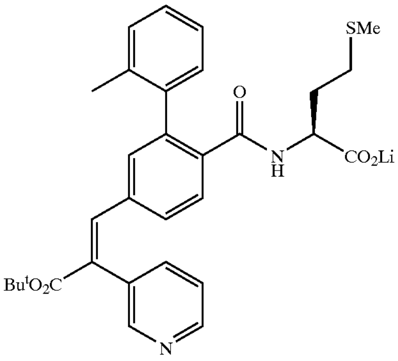

EXAMPLE 1078

N-[4-(Z-2-t-Butoxycarbonyl-2-pyrid-3-ylethenyl)-2-(2-methylphenyl)benzoyl]methionine, Lithium Salt The title compound was prepared from N-[4-(Z-2-t-butoxycarbonyl-2-pyrid-3-ylethenyl)-2-(2-methylphenyl) benzoyl]methionine methyl ester (example 1077B) according to the procedure in example 10751, and was isolated as a white powder. $^1H$ NMR (300 MHz, DMSO) 8,1.46 (s, 9H), 1.50–1.70 (m, 4H), 1.83–1.92 (m, 6H), 3.56–3.67 (m, 1H), 7.00–7.20 (m, 5H), 7.35–7.43 (m, 1H), 7.65 (ddd, J=8.1, 2.1, 2.1 Hz, 1H), 7.88 (s, 1H), 8.33 (dd, J=2.4, 0.9 Hz, 1H), 8.51 (dd, J=4.8, 1.5 Hz, 1H). MS (APCI(−)) m/e 545 (M−H); Analysis calc'd for $C_{31}H_{33}LiN_2O_5S.2.00H_2O$: C, 63.25; H, 6.34; N, 4.76; found: C, 63.24; H, 6.20; N, 4.57.

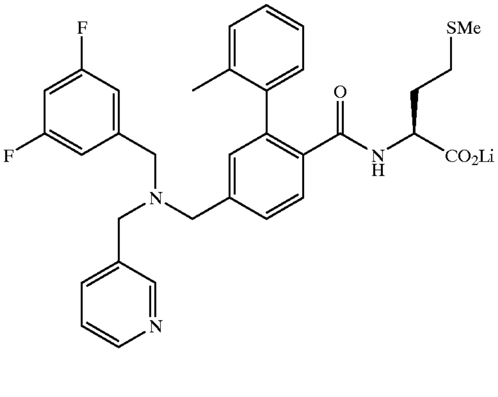

EXAMPLE 1286

N-[4-N-(N-(3-Pyridylmethyl)-N-(3,5-difluorobenzyl)aminomethyl)-2-(2-methylphenyl) benzoyl]methionine Lithium Salt

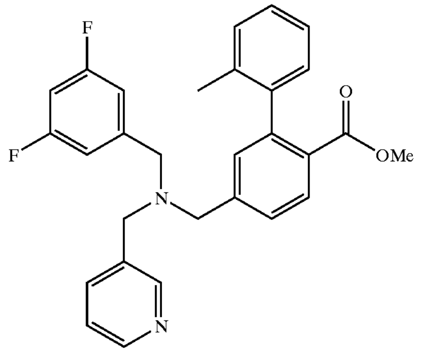

EXAMPLE 1286A

Prepared according to the procedure of example 1258A from reaction between 1258A and 3-pyridinecarboxaldehyde. NMR ($CDCl_3$) 8.50–8.60 (m, 2H); 7.92–8.00 (m, 1H); 7.71–7.79 (m, 1H); 7.45–7.50 (m, 1H); 7.19–7.35 (m, 5H); 7.05–7.10 (m, 1H); 6.90–6.95 (m, 2H); 6.68–6.75 (m, 1H); 3.69 (m, 5H); 3.58 (s, 2H); 2.05 (s, 3H). (DSI/NH3)/MS: 473 $(M+H)^+$.

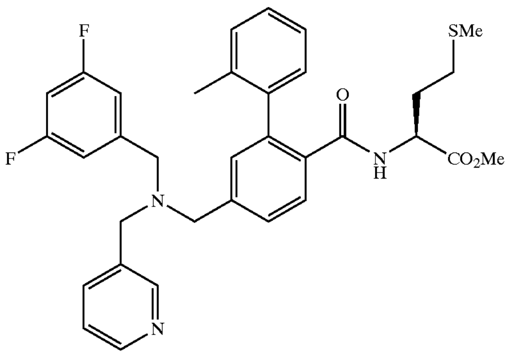

EXAMPLE 1286B

N-[4-N-(N-(3-Pyridylmethyl)-N-(3,5-difluorobenzyl)aminomethyl)-2-(2-methylphenyl) benzoyl]methionine, Methyl Ester A mixture of 1286A (0.304 g, 0.62 mmol) and lithium hydroxide (0.076 g, 3.15 mmol) in 30 ml of 1:1 water/methanol was refluxed for 12 hours. After cooling to room temperature, the reaction mixture was neutralized to PH=5–6 carefully by 1.0 M $NaHSO_4$. The precipitate front neutralization was extracted into 40 ml of EtOAc. The organic solution was then washed by brine, and dried over anhydrous $MgSO_4$. Evaporation of the solvent afforded pure corresponding acid which was used directly for methionine coupling reaction.

A mixture of the acid (0.30 g, 0.62 mmol) from previous step, L-methionine methyl ester hydrochloride (0.252 g, 1.26 mmol), 1-hydroxybenzotriazole hydrate (0.43 g, 3.15 mmol), 1-ethyl-3-(3-dimethyl-aminopropyl)carbodiimide (0.61 g, 3.15 mmol), and triethylamine hydrochloride (0.43 g, 3.15 mmol) in 15 ml of anhydrous DMF was heated under $N_2$ at 75° C. for 20 hours. After cooling to room temperature, the solution was diluted with 50 ml of EtOAc, then was put to 200 ml of water. The aqueous solution was extracted. with another portion of 50 ml of EtOAC. Combined organic solution was washed with 30 ml of saturated $NaHCO_3$ twice, then with 50 ml of brine, finally dried over anhydrous $MgSO_4$. Flash chromatography of the residue from evaporation of the EtOAc solution eluting with 70:30 EtOAc/Hexane afforded 0.235 g of the title compound. (61%). NMR ($CDCl_3$) 8.50–8.60 (m, 2H); 7.92–8.00 (m, 1H); 7.71–8.00 (m, 1H); 7.50–7.55 (m, 1H); 7.19–7.37 (m, 5H); 7.18 (s, 1H); 6.85–6.95 (m, 2H); 6.68–6.75 (m, 1H); 5.85–5.91 (m, 1H); 4.55–4.70 (m, 1H); 3.69 (m, 5H); 3.58 (s, 2H); 2.0–2.15 (m, 8H); 1.7–2.0 (m, 1H); 1.5–1.7 (m, 1H). ($DSI/NH_3$)/MS: 604 $(M+H)^+$.

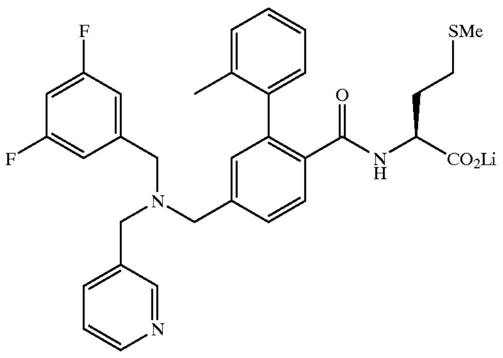

EXAMPLE 1286C

N-[4-N-(N-(3-Pyridylmethyl)-N-(3,5-difluorobenzyl)aminomethyl)-2-(2-methylphenyl)benzoyl]methionine Lithium Salt 1286B (0.301 g, 0.5 mmol) in a mixture of 10 ml of water and 10 ml of methanol was treated 1.0N LiOH solution (0.5 ml, 0.5 mmol). The solution was stirred for 24 hours. Then methanol was removed under reduced pressure. Concentrated solution was then extracted with ethyl ether, and lyophilized. NMR 1N ($MeOH-d_4$): 8.5 (1H, m); 8.4 (1H, m); 7.8–7.9 (1H, m); 7.6–7.7 (1H, m); 7.4–7.5 (1H, m); 7.35–7.4 (1H, m); 7.0–7.38 (5H, m); 6.9–7.0 (2H, m); 6.7–6.8 (1H, m); 4.1–4.22 (1H, m); 3.68 (4H, s); 3.6 (2H, s); 1.76–2.2 (10H, m). ESI(−)/MS: 588 (M-Li). Anal. Calcd for $C_{33}H_{32}F_2N_3O_3SLi.3.40H_2O$: C, 60.54; H, 5.94; N, 6.42. Found: C, 60.26; H, 5.55; N, 6.45.

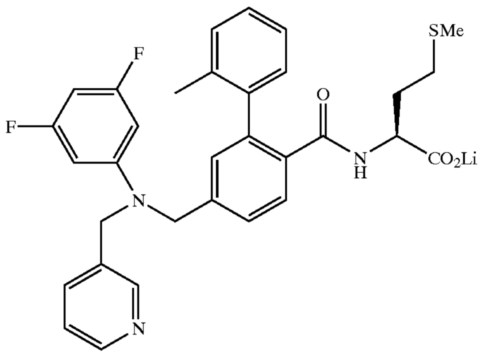

EXAMPLE 1287

N-[4-N-(N-3,5-Difluorophenyl-N-(3-pyridylmethyl)aminomethyl)-2-(2-methylphenyl)benzoyl]methionine Lithium Salt

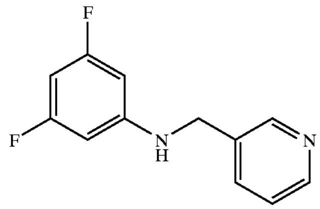

EXAMPLE 1287A

Prepared according to the procedure of example 1258A from reaction between 3,5-difluoroaniline and 3-pyridinecarboxaldehyde. NMR ($CDCl_3$) 8.50–8.70 (m, 4H); 7.64–7.74 (m, 1H); 7.23–7.35 (m, 1H); 6.05–6.21 (m, 3H); 4.25 (m, 3H). $DSI/NH_3$)/MS: 221 $(M+H)^+$; 238 $(M+NH_4)^+$.

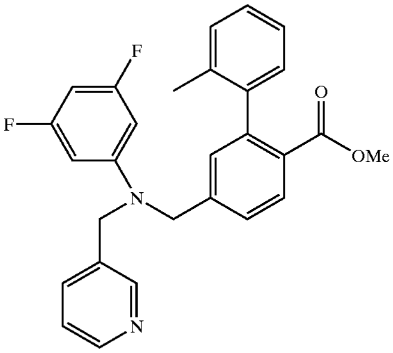

EXAMPLE 1287B

A mixture of 1287A (0.26 g, 1.12 mmol) and 4-bromomethyl-2-(2-methylphenyl)benzoic acid methyl ester (0.452 g, 1.4 mmol) in 10 ml of anhydrous THF was treated with 1.0 M sodium bis(trimethylsilyl) amide (1.6 ml, 1.6 mmol) at −78° C. The solution was stirred at that temperature for 1 hour, and the stirred at room temperature for another 24 hours. The solution was diluted with 30 ml of EtOAc, washed with water, brine, and dried over anhydrous $MgSO_4$. Flash chromatography of the residue eluting with EtOAc afforded 0.45 g of the title compound (87%). NMR ($CDCl_3$) 8.45–8.60 (m, 2H); 7.92–8.00 (m, 1H); 7.33–7.40 (m, 1H); 7.18–7.30 (m, 5H); 7.00–7.10 (m, 2H); 6.15–6.25 (m, 3H); 4.65 (s, 4H); 3.60 (s, 3H); 2.05 (s, 3H). $DSI/NH_3$)/MS: 459 $(M+H)^+$.

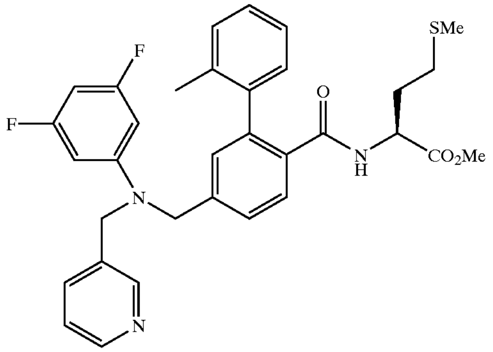

EXAMPLE 1287C

N-[4-N-(N-3,5-Difluorophenyl-N-(3-pyridylmethyl) aminomethyl)-2-(2-methylphenyl)benzoyl] methionine, Methyl Ester Prepared according to the procedure of example 1286B from 1287B. NMR ($CDCl_3$) 8.55–8.75 (m, 2H); 7.95–8.08 (m, 1H); 7.80–7.88 (m, 1H); 7.30–7.43 (m, 1H); 7.20–7.43 (m, 5H); 7.12 (s, 1H); 6.22–6.38 (m, 3H); 6.00–6.08 (m, 1H); 4.81 (s, 2H); 4.75 (s, 2H); 4.65–4.75 (m, 1H); 3.78 (s, 3H); 2.1–2.3 (m, 8H); 1.85–2.10 (m, 1H); 1.60–1.80 (m, 1H). DSI/$NH_3$)/MS: 590 $(M+H)^+$.

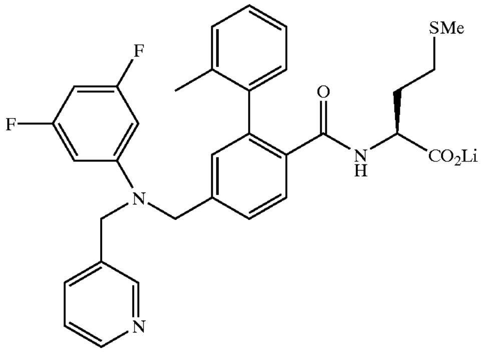

EXAMPLE 1287D

N-[4-N-(N-3,5-Difluorophenyl-N-(3-pyridylmethyl) aminomethyl)-2-(2-methylphenyl)benzoyl] methionine Lithium Salt Prepared according to the procedure of example 1286 from 1287° C. NMR $^1N$ (MeOH-$d_4$): 8.4–8.5 (2H, m); 7.7–7.8 (1H, m); 7.6–7.7 (1H, m); 7.3–7.4 (2H, m); 7.1–7.3 (5H, m); 7.05 (1H, s); 6.2–6.38 (2H, m); 6.1–6.2 (1H, m); 4.8 (4H, s); 4.1–4.22 (1H, m); 1.76–2.1 (8H, m); 1.6–1.76 (2H, m). ESI(−)/MS: 574 (M-Li). Anal. Calcd for $C_{32}H_{30}F_2N_3O_3SLi.1.86H_2O$: C, 62.49; H, 5.53; N, 6.83. Found: C, 62.49; H, 5.38; N, 6.62.

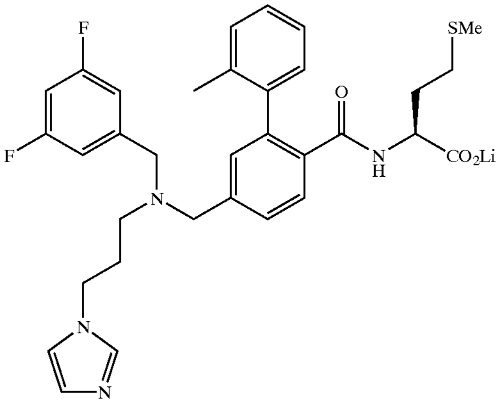

EXAMPLE 1298

N-[4-N-(N-(3-(1-Imidazole)-propyl)-N-(3,5-difluorobenzyl)aminomethyl)-2-(2-methylphenyl) benzoyl]methionine Lithium Salt

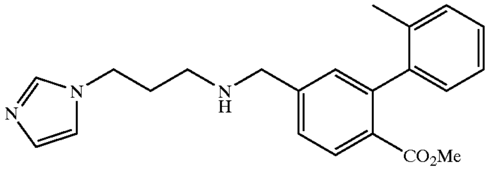

EXAMPLE 1298A

Prepared according to the procedure of example 1258A from reaction between 4-formyl-2-2-(methylphenyl)benzoic acid methyl ester and 1-(3-aminopropyl)imidazole. NMR ($CDCl_3$) 7.84–7.98 (m, 1H); 7.50 (s, 1H); 7.35–7.40 (m, 1H); 7.16–7.30 (m, 4H); 7.0–7.1 (m, 2H); 6.90 (s, 1H); 4.00–4.10 (t, 2H); 3.82 (s, 2H); 3.60 (s, 3H); 2.60–2.68 (t, 2H); 2.07 (s, 3H); 1.90–2.00 (m, 2H); (DSI/$NH_3$)/MS: 364 $(M+H)^+$.

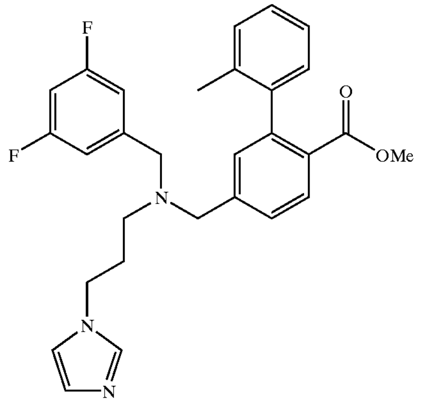

EXAMPLE 1298B

Prepared according to the procedure of example 1258A from reaction between 1298A and 3,5-difluorobenzaldehyde. NMR ($CDCl_3$) 7.84–7.98 (m, 1H); 7.56 (s, 1H); 7.35–7.40 (m, 1H); 7.16–7.30 (m, 4H); 7.02–7.11 (m, 2H); 6.80–6.90 (s, 2H); 6.70–6.78 (m, 2H);

3.82–4.00 (t, 2H); 3.60 (s, 5H); 3.55 (s, 2H); 2.60–2.68 (t, 2H); 2.07 (s, 3H); 1.90–2.00 (m, 2H); (DSI/$NH_3$)/MS: 490 $(M+H)^+$.

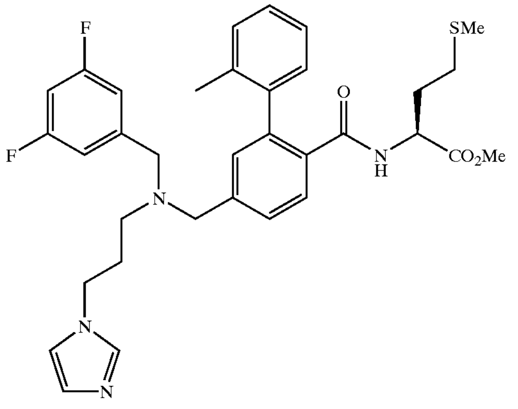

EXAMPLE 1298C

N-[4-N-(N-(3-(1-Imidazole)-propyl)-N-(3,5-difluorobenzyl)aminomethyl)-2-(2-methylphenyl) benzoyl]methionine, Methyl Ester Prepared according to the procedure of example 1258C from 1298B. NMR ($CDCl_3$) 7.84–7.98 (m, 1H); 7.16–7.30 (m, 6H); 7.10 (s, 1H); 7.05 (s, 1H); 6.80–6.90 (s, 2H); 6.70–6.80 (m, 2H); 6.45–6.70 (m, 1H); 4.55–4.70 (m, 1H); 3.82–4.00 (t, 2H); 3.60 (s, 5H); 3.55 (s, 2H); 2.45–2.58 (t, 2H); 2.0–2.15 (m, 10H); 1.7–2.0 (m, 1H); 1.5–1.7 (m, 1H). (DSI/$NH_3$)/MS: 621 $(M+H)^+$.

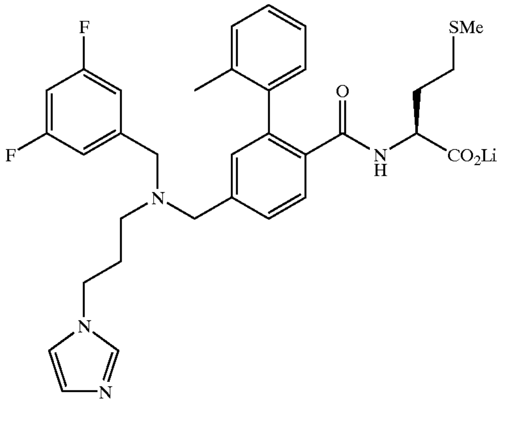

EXAMPLE 1298D

N-[4-N-(N-(3-(1-Imidazole)-propyl)-N-(3,5-difluorobenzyl)aminomethyl)-2-(2-methylphenyl) benzoyl]methionine Lithium Salt Prepared according to the procedure of example 1178J from 1298° C. NMR $^1N$ ($CDCl_3$): 7.6–7.7 (1H, m); 6.8–7.3 (1H, m); 6.65–6.85 (1H, m); 6.6–6.65 (1H, m); 4.1–4.22 (1H, m); 3.8–4.0 (2H, m); 3.4–3.7 (4H, m); 2.3–2.4 (2H, m); 1.3–2.1 (12H, m). ESI(−)/MS: 505 (M-Li).

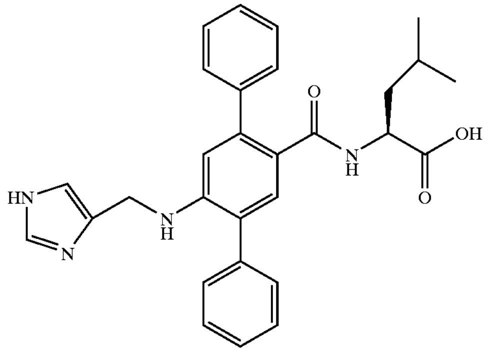

EXAMPLE 1322

4-[N-(1-H-Imidazole-4-yl)methyleneamino-2,5-diphenyl-benzoyl Methionine Hydrochloride 2,6-Diphenyl-4-nitro Toluene (42)

10 g (65.30 mmol) of 3-hydroxy-4-nitro toluene were dissolved in 125 ml of $CCl_4$. The solution was cooled to 0° C. in an ice bath and after that 10.4 g (65.30 mmol) of $Br_2$ and 3.65 g (65.30 mmol) of iron powder were added to the solution. The reaction was stirred overnight (10 h) at room temperature, filtered and evaporated under vacuum. Flash chromatography gave two products, the one with the Br in position 2 (13%, yield) and the one with Br in position 6 (87% yield). $^1H$ ($Cl_3CD$) δ: 2.44 (s, 3H), 7.06 (1H, s), 8.26 (s, 1H), 10.44 (s, 1H). $^{13}C$ ($Cl_3CD$) δ: 23.67, 114.74, 121.31, 127.91, 132.18, 149.31, 153.95.

7.48 g (35.44 mmol) of 6-bromo-3-hydroxy-4-nitro toluene were dissolved in 75 ml of pyridine under $N_2$. To this solution 10 g (35.44 mmol) of triflic anhidride were added slowly and the reaction was stirred for 1 h. Evaporation of the pyridine under pressure and extraction of the residue dilute hydrochloric acid medium gave the triflate in 98% yield. $^1H$ ($Cl_3CD$) δ: 2.49 (s, 3H), 7.27 (s, 1H), 8.30 (s, 1H). $^{13}C$ ($Cl_3CD$) δ: 23.50, 116.43, 120.69, 124.45, 124.94, 125.71, 130.20, 139.42, 140.20, 147.61.

The foregoing bromo triflate. (12.41 mmol), $(Ph_3P)_2PdCl_2$ (435 mg, 0.62 mmol) and CuI (236 mg, 1.24 mmol) were dissolved in anhydrous toluene (10 ml) and LiCl (2.63 g, 62.04 mmol) and 2-trimethylstannylbenzene in anhydrous toluene (5 ml) were added. The mixture was refluxed for 13 h. and then cooled and filtered. Evaporation under vacuum and flash chromatography (from hexane:ether 7:3 to ether); afforded 66% yield of 2,6-diphenyl-4-nitro toluene. $^1H$ ($Cl_3CD$) δ: 2.34 (s, 3H), 7.28–7.44 (m, 11H), 7.76 (s, 1H). 4-[N-(1-H-imidazole-4-yl)methylene]amino-2,5-diphenyl-benzoyl methionine hydrochloride.FTI-2194.

The oxidation of tolyl group was quantitatively carried out using $KMnO_4$ (10 equivalents) in pyridine/$H_2O$ (3/1). After the filtration through celite and evaporation of the solvent to the half of the initial volume, the solution was acidified with HCl to pH<1 and extracted three times with ethyl acetate. Evaporation of the ethyl acetate under reduced pressure gave 2,6-diphenyl-4-nitro benzoic acid in 96%yield. $^1H$ ($Cl_3CD$) δ: 7.32–7.40 (m, 10H), 7.78 (s, 1H), 7.96 (s, 1H). $^{13}C$ ($Cl_3CD$) δ: 126.26, 127.92, 128.36, 128.49, 128.76, 128.91, 133.12, 134.00, 134.73, 135.86, 138.39, 143.24, 150.46, 171.65.

The coupling between methionine methyl ester and 2,6-diphenyl-4-nitro benzoic acid was carried out using ($NEt_3$, EDCI, HOBT). When the reaction was completed the solvent was evaporated and the residue was purified, without extraction, through flash column chromatography (from hexane:ethyl ether 1:1 to ethyl ether, silica) to give the desired amide in 92%yield. $^1H$ ($Cl_3CD$) δ: 1.82 (m, 1H), 1.97 (s, 3H), 2.05 (m, 2H), 3.65 (s, 3H), 4.67 (m, 1H), 6.18 (d, J=7.71, 1H), 7.33–77.46 (m, 10H), 7.74 (s, 1H), 7.83 (s, 1H).

The foregoing nitroamide (0.95 mmol) and Raney Ni(1 mg, catalyst) were dissolved in MeOH (15 ml). The mixture was heated to reflux and then hydrazine (92 mg, 2.87 mmol) was added. The reaction was refluxed for 10 minutes following which it was filtered to remove the Raney Ni. After evaporation of the solvent and flash chromatography the desired aminoamide was obtained in 99%yield. $^1H$ ($Cl_3CD$) δ: 1.66 (m, 1H), 1.96 (s, 3H), 2.06 (m, 1H), 3.59 (s, 3H), 4.15 (br s, 2H), 4.59 (m, 1H), 5.81 (d, J=7.56 Hz, 1H), 6.59 (s, 1H), 7.32–7.43 (m, 10H), 7.59 (s, 1H). $^{13}C$ ($Cl_3CD$) δ: 15.13, 29.35, 31.41, 51.69, 52.22, 116.62, 123.87, 125.99, 127.45, 127.69, 128.50, 128.59, 128.82, 131.90, 137.99, 140.47, 140.58, 145.62, 168.45, 171.91.

Reductve amination was carried out by treating the foregoing amine (1 equiv.) with 1-trityl-4-formylimidazole (1 equiv.) and sodium cyanoborohydride (2 equiv.) in 5% acetic acid. The mixture was stirred at room temperature overnight. Evaporation of the methanol and flash chromatography (hexane:AcOEt 7:3) gave the desired product protected imidazole derivative in 83%yield). $^1H$ ($Cl_3CD$) δ: 0.80 (m, 6H), 1.10–1.37 (m, 4H), 3.63 (s, 3H), 4.82 (m, 1H), 5.53 (d, J=7.77 Hz, 1H), 6.59 (s, 1H), 7.06 (s, 1H), 7.08 (s, 1H), 7.25–7.45 (m, 25H), 7.63 (s, 1H).

The methionine methyl ester was hydrolyzed with 2.0 eq of lithium hydroxide 0.5N and MeOH (same volume) at room temperature for 2 h. When the reaction was complete concentrated HCl (2.0 eq) was added and the solvents were evaporated under vacuum. The product was used in the next reaction without further purification (98%yield). $^1H$ ($Cl_3CD$) δ: 0.77 (m, 6H), 1.25 (m, 4H), 4.45 (m, 1H), 5.58 (d, J=7.53 Hz, 1H), 6.46 (s, 1H), 6.66 (s, 1H) 6.96 (s, 1H), 6.97 (s, 1H), 7.27–7.34 (m, 23H), 7.52 (s, 1H). $^{13}C$ ($Cl_3CD$) δ: 21.71, 22.70, 24.27, 39.01, 40.83, 51.24, 112.10, 119.96, 123.44, 127.23, 127.67, 128.54, 129.96, 129.08, 129.26, 131.90, 134.25, 136.30, 137.28, 139.94, 140.50, 140.77, 145.36, 168.82, 175.40.

The detritylation was carried out quantitatively using trifluoroacetic acid in methylene choride. After the evaporation of the solvent, the residue was washed with ethyl ether saturated with HCl. The solid product was purified using HPLC (C18 5 m, from $H_2O$ to $CNCH_3$ in 30 minutes) to give 4-[N-(1-H-imidazole-4-yl)methylene]amino-2,5-diphenylbenzoyl methionine hydrochloride in 98%yield. $^1H$ ($CD3CN/H_2O$) δ: 0.77 (m, 6H), 1.38 (m, 1H), 1.41 (m, 2H), 4.23 (m, 1H), 6.60 (s, 1H), 7.23–7.49 (m, 12H), 8.48 (s, 1H). $^{13}C$ ($CD3CN/H_2O$) δ: 21.60, 23.22, 25.22, 38.28, 40.68, 52.09, 113.03, 117.28, 125.34, 127.56, 128.50, 129.39, 129.57, 129.77, 130.16, 130.22, 131.78, 132.92, 134.76, 138.70, 141.51, 142.21, 146.36, 171.17, 175.49.

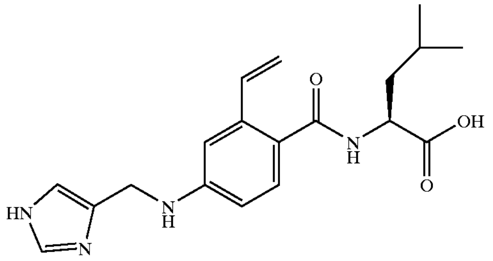

EXAMPLE 1323

Hydrazine hydrate (5 equivalents, 0.026 g, 0.8 mmol) and Raney nickel (0.15 g) were dissolved into 25 mL. of methanol and heated to reflux temperatures. Compound 6 (0.10 g, 0.16 mmol) was dissolved in 5 mL. of methanol and slowly added to the refluxing mixture. The reaction was complete after 30 minutes and the reaction mixture concentrated. The residue was taken up in ethyl acetate, was washed once with a saturated solution of sodium bicarbonate and dried over magnesium sulfate. The organics were concentrated and the residue taken up into 5 mL. of tetrahydrofuran and cooled to 0° C. Lithium hydroxide (0.013 g, 0.32 mmol) was dissolved in 5 mL. of distilled water and slowly added to the stirred solution. The reaction was complete after 4 hours as determined by TLC. The reaction was acidified with 1.0 N hydrochloric acid to a pH of 2 and concentrated. The residue was extracted twice with ethyl acetate, dried over magnesium sulfate and concentrated. The residue was taken up in 5 mL. of methylene chloride to which 5 mL. of trifluoroacetic acid was added followed by the immediate addition of triethylsilane. The reaction was stirred for 2 hr. at room temperature. The mixture was concentrated and the residue taken up in diethyl ether to which 3N HCl dissolved in diethyl ether was added. The solid precipate was collected to give 8 (0.03 g, 42%) as a white solid. The HPLC assay was determined to be 99%. $^1H$ NMR (300 MHz, $CD_3OD$) δ 8.83 (d, 1.1H, imidazole), 7.45 (s, 1H, imidazole), 7.42 (d, J=8.8 Hz 1H, aromatic), 6.57–6.62 (m, 2H), 6.52 (d, J=2.3 Hz 1H, aromatic), 5.79 (m, 1H, cis alkene), 4.55 (m, 1H, α Leu-H), 4.48 (s, 2H, $CH_2NH$), 1.64–1.79 (m, 6H), 0.97 (d, J=3.2 Hz, 3H, $CH(CH_3)_2$), 0.95 (d, J=3.2 Hz, 3H, $CH(CH_3)_2$).

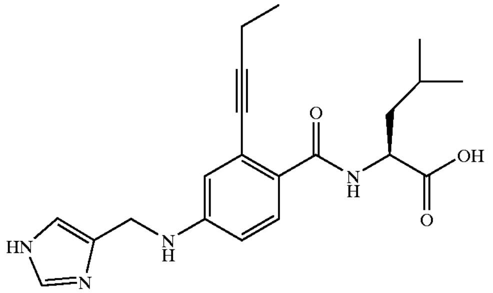

EXAMPLE 1324

4-[N-(1-H-Imidazole-4-yl)methyleneramino-2-(1-propynyl)benzoyl]]-leucine Hydrochloride Methyl 2-(3-Trimethylsilyl-1-propynyl)-4-nitrobenzoate. (1)

Methyl 2-bromo-4-nitrobenzoate (1.0 g, 3.8 mmol) and 1-(trimethysilyl)-1-propyne (0.43 g, 3.8 mmol) were dissolved into 50 mL. of dry diethylamine to which 2 mole % of copper iodide (0.014 g, 0.076 mmol) and 5 mole % of tetrakis(triphenylphosine) palladium(0) (0.45 g, 0.38 mmol) were added. The reaction was stirred at r.t. for 24 hours before additional 1-(trimethysilyl)-1-propyne (0.6 g, 5.3 mmol) was added. The reaction continued for an additional 72 hours. The reaction mixture was concentrated, taken up in ethyl acetate, washed with distilled water followed by a saturated solution of sodium chloride and the organic layer dried over magnesium sulfate. After concentrating, the residue was purified by column chromatography (1:9 ethyl acetate/hexanes) to give 1 (1.7 g, 85%) as a white solid. $^1$H NMR (300 MHz, $CDCl_3$) δ 8.22 (d, J=2.3 Hz, 1H, aromatic), 8.02 (dd, J=8.6, 2.3 Hz, 1H, aromatic), 7.91 (d, J=8.6 Hz, 1H, aromatic), 3.91 (s, 3H, $OCH_3$), 1.79 (s, 2H, $CH_2Si(CH_3)_3$), 0.16 (s, 9H, $Si(CH_3)_3$); $^{13}$C NMR (75 MHz, $CDCl_3$) δ 165.7, 149.3, 137.1, 131.1, 128.6, 126.9, 121.0, 98.5, 76.7, 52.8, 8.9, −1.8; HRMS calc'd for: m/e 291.0927, found 291.0932.

Methyl 2-(1-Propynyl)-4-nitrobenzoate. (2)

Compound 1 was dissolved into 50 mL. of THF and tetrabutylammonium fluoride (8 mL. of a 1.0M solution in water) was added slowly to the reaction mixture. After 20 min. the reaction mixture was concentrated and the residue taken up into water and extracted with ethyl acetate. The organics were combined, dried over magnesium sulfate and concentrated to yield a dark oil which was purified by column chromatography (1:9 ethyl acetate/hexanes on silica) to give 2 (0.6 g, 40%) as a colorless oil. $^1$H NMR (300 MHz, $CDCl_3$) δ 8.32 (d, J=2.2 Hz, 1H, aromatic), 8.11 (dd, J=8.7, 2.2 Hz, 1H, aromatic), 8.01 (d, J=8.6 Hz, 1H, aromatic), 3.96 (s, 3H, $OCH_3$), 2.15 (s, 3H,$CH_3$); $^{13}$C NMR (75 MHz, $CDCl_3$) δ 165.5, 149.4, 137.2, 131.3, 128.9, 126.4, 121.7, 95.2, 52.9, 4.93; HRMS calc'd for: m/e 219.0532, found 219.0529.

2-(1-Propynyl)-4-nitrobenzoic Acid. (3)

Compound 2 above (0.6 g, 2.7 mmol) was dissolved into 50 mL. of methanol containing 5% KOH and was stirred for 3 Hr. The reaction mixture was concentrated and the residue taken up into distilled water and washed once with ethyl acetate. The aqueous layer was carefully acidified to a pH of 2 with concentrated HCl. and was extracted with ethyl acetate, dried over magnesium sulfate and concentrated to give 3 (0.5 g, 91%) an off white solid.

N-[2-(1-Propynyl)-4-nitrobenzoyl]-leucine Methyl Ester. (4)

Compound 3 above (0.5 g, 2.4 mmol) and L-leucine methyl ester (0.44 g, 2.4 mmol) were dissolved into 50 mL. of dry methylene chloride and cooled to 0° C. 1-hydroxybenzotriazole (0.32 g, 2.4 mmol), EDCI (0.51 g, 2.6 mmol) and triethylamine (0.24 g, 2.4 mmol) were added to the cooled solution. The reaction was stirred under nitrogen for 11/2 Hr. before the ice bath was removed. The reaction continued for 6 Hr. as the reaction warmed to room temperature. Additional methylene chloride was added and the reaction mixture was washed with 1N HCl followed by a saturated solution of sodium bicarbonate and a saturated solution of sodium chloride. The organic layer was dried over magnesium sulfate, concentrated to a slight yellowish oil which was crystallized from hexane to give 4 (0.7 g, 88%): $^1$H NMR (300 MHz, $CDCl_3$) δ 8.32 (d, J=2.1 Hz, 1H, aromatic), 8.22 (d, J=8.6 Hz, 1H; aromatic), 8.16 (dd, J=8.7, 2.2 Hz, 1H, aromatic), 8.11 (d, J=7.7 Hz, 1H, C(O)NH), 4.89 (dd, J=7.8, 5.2 Hz, 1H, α Leu-H), 3.79 (s, 3H, $OCH_3$), 2.20 (s, 3H,$CH_3$), 1.66–1.83 (m, 3H, $CH_2CH(CH_3)_2$), 1.0 (d, J=3.9 Hz, 3H, $CH_2CH(CH_3)_2$), 0.99 (d, J=4.0 Hz, 3H, $CH_2CH(CH_3)_2$); $^{13}$C NMR (75 MHz, $CD_3OD$) δ 174.3, 169.6, 150.0, 149.9, 130.3, 128.6, 124.7, 123.6, 94.8, 76.8, 53.0, 52.8, 41.6, 26.2, 23.6, 21.9, 4.4; HRMS calc'd for: m/e 332.1372, found 332.1375.

N-[4-Amino-2-(12-propynyl)benzoyl]-leucine Methyl Ester Hydrochloride. (5)

Compound 4 (0.7 g, 2.1 mmol) above was dissolved in 30 mL. of a 3:1 solution containing acetic acid and 5% aqueous HCl. Zinc dust (0.55 g, 8.4 mmol) was added at once and the reaction vigorously stirred for ½ hour. The reaction mixture was concentrated and the residue taken up in a saturated solution of sodium bicarbonate and extracted 3×50 mL. with ethyl acetate. The extracts were combined, dried over magnesium sulfate and concentrated. The residue taken up in methylene chloride and several mL. of 3N HCl dissolved in diethyl ether added. The solvents were evaporated leaving the hydrochloride 5 (0.65 g, 92%). $^1$H NMR (300 MHz, $CD_3OD$) δ 7.68 (d, J=8.2 Hz, 1H, aromatic), 7.44 (s, 1H, aromatic), 7.37 (d, J=8.3 Hz, 1H, aromatic), 4.68 (dd, J=8.8, 6.0 Hz, 1H, α Leu-H), 3.75 (s, 3H, $OCH_3$), 2.08 (s, 3H, $CH_3$), 1.68–1.86 (m, 3H, $CH_2CH(CH_3)_2$), 0.99 (d, J=6.4 Hz, 6H, $CH(CH_3)_2$); $^{13}$C NMR (75 MHz, $CD_3OD$) δ 174.2, 169.6, 139.4, 138.0, 133.7, 130.8, 128.4, 124.7, 123.6, 94.5, 77.0, 52.9, 52.7, 41.4, 26.0, 23.4, 21.8, 4.3; HRMS calc'd for: m/e 302.1630, found 302.1627.

4-[N-(1-Triphenylmethylimidazole-4-yl)methylene[amino-2-(1-propynyl!benzoyl)-leucine Methyl Ester. (6)

Compound 5 (0.56 g, 1.7 mmol) and 1-Triphenylmethylcarboxaldehyde (0.62 g, 1.8 mmol) were dissolved in 10 mL. of methanol and stirred for 15 min. before adding dropwise 1 mL. of a methanol solution containing sodium cyanoborohydride (0.10 g, 1.7 mmol). The reaction was stirred at room temperature for 4 Hr. and then concentrated. The residue was taken up in ethyl acetate, washed with a saturated solution of sodium bicarbonate followed by a saturated solution of sodium chloride. The organic phase was dried over magnesium sulfate and concentrated. The residue was purified by column chromatography using 1:1 ethyl acetate/hexanes as the eluants. The product was collected and dried to give 6 (0.8 g, 80%) as a white foam. $^1$H NMR (300 MHz, $CDCl_3$) δ 8.31 (d, J=7.7 Hz, 1H, C(O)NH), 7.97 (d, 8.7H, aromatic), 7.41 (d, J=0.84 Hz, 1H, imidazole), 7.27–7.41 (m, 9H, trityl-H), 7.09–7.16 (m, 6H, trityl-H), 6.71 (s, 1H, imidazole), 6.65 (d, J=2.3 Hz, 1H, aromatic), 6.57 (dd, J=8.7, 2.4 Hz, 1H, aromatic), 4.84 (ddd, J=7.8, 6.8 Hz, 2.6H, α Leu-H), 4.70 (t, 5.4H, $CH_2NH$), 4.24 (d, 5.4H, $CH_2NH$), 3.75 (s, 3H, $OCH_3$), 2.13 (s, 3H, $CH_3$), 1.65–1.81 (m, 3H, $CH_2CH(CH_3)_2$), 0.98 (d, J=5.9 Hz, 6H, $CH(CH_3)_2$); $^{13}$C NMR (75 MHz, $CDCl_3$) δ 173.9, 165.8, 149.9, 142.4, 139.1, 138.7, 138.1, 132.2, 129.8, 128.2, 122.6, 121.7, 120.0, 119.4, 116.7, 113.1, 100.2, 92.6, 79.7, 75.5, 52.9, 52.3, 51.5, 42.1, 41.8, 31.7, 25.4, 25.1, 23.1, 22.8, 22.3, 14.3, 4.7.

4-[N-(1-H-Imidazole-4-yl)methylenefamino-2-(1-propynyl) benzoyl]]-leucine Hydrochloride. (7)

Compound 6 (0.2 g, 0.3 mmol) was dissolved into 5 mL. of tetrahydrofuran and cooled to 0° C. lithium hydroxide (2 equivalents, 0.027 g, 0.64 mmol) was dissolved in 5 mL. of distilled water and slowly added to the stirred solution. The reaction was complete after 2 hours as determined by TLC. The reaction was acidified with 1.0 N hydrochloric acid to a pH of 2 and concentrated. The residue was extracted twice with ethyl acetate (50 mL). The extracts were combined, dried over magnesium sulfate and concentrated. The residue was taken up in 5 mL. of methylene chloride to which 5 mL. of trifluoroacetic acid was added followed by the immediate addition of triethylsilane. The reaction was stirred for an additional 2 Hr. at room temperature. The mixture was concentrated and the residue taken up in diethyl ether to which 3N HCl dissolved in diethyl ether was added. The solid which precipitated was washed with additional diethyl ether and purified by reverse phase HPLC to give 7 (0.06 g 41%) as a TFA salt. The HPLC assay was determined to be 99%. $^1$H NMR (300 MHz, $CDCl_3$) δ 8.84 (d, J=1.0 Hz, 1H, imidazole), 7.68 (d, J=8.7 Hz, 1H, aromatic), 7.46 (s, 1H, imidazole), 6.73 (d, J=2.2 Hz, 1H, aromatic), 6.67 (dd, J=8.7, 2.3 Hz, 1H, aromatic), 4.66 (m, 1H, α Leu-H), 4.48 (s, 2H, $CH_2N$), 2.09 (s, 3H, $CH_3$), 1.67–1.84 (m, 3H, $CH_2CH(CH_3)_2$), 0.98 (app t, 6H, $CH(CH_3)_2$); $^{13}$C NMR (75 MHz, $CDCl_3$) δ 176.0, 169.0, 151.3, 135.5, 133.8, 132.4, 132.1, 124.9, 123.9, 118.0, 117.8, 113.3, 93.4, 79.6, 53.0, 42.6, 38.5, 26.3, 23.5, 22.4, 4.4.

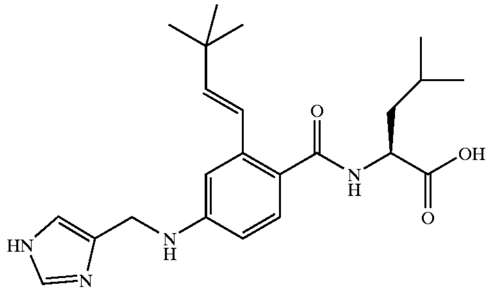

EXAMPLE 1325

4-[N-(1-H-Imidazole-4-yl)methylene[amino-2-(3,3-dimethyl-(Z)-1-butenyl)benzoyl Leucine Hydrochloride N-[4-Amino-2-(3,3-dimethyl-(Z)-1-butenyl)benzoyl]-leucine Methyl Ester. (15)

Hydrazine hydrate (5 equivalents, 0.21 g, 6.7 mmol) and raney nickel (0.15 g) were dissolved into 25 mL. of methanol and heated to reflux temperatures. Compound 11 (0.5 g, 1.3 mmol) was dissolved in 5 mL. of methanol and slowly added to the refluxing mixture. The reaction was complete after 30 minutes and the reaction mixture concentrated. The residue was taken up in ethyl acetate, was washed once with a saturated solution of sodium bicarbonate and dried over magnesium sulfate. The organics were concentrated and the residue taken up into methylene chloride to which 3N HCl dissolved in diethyl ether added to give 15 (0.45 g, 88%) after drying as the hydrochloride.

4-[N-(1-Triphenylmethylimidazole-4-yl)methylene[amino-2-(3,3-dimethyl-(Z)-1-butenyl)benzoyl Leucine Methyl Ester. (16)

1-Triphenylmethylimidazole-4-carboxaldehyde (0.53 g, 1.6 mmol) and compound 15 (0.4 g, 1.0 mmol) were dissolve in 10 mL. of 95% methanol and 5% acetic acid and stirred for 10 minutes before 1.1 equivalents of sodium cyanoborohydride (0.056 g, 0.83 mmol) was added. The reaction was stirred for 1 hour while additional aldehyde was added until all of the amine hydrochloride had disappeared. The reaction mixture was concentrated and the residue taken up in ethyl acetate and was washed with a saturated solution of sodium bicarbonate. The organic phase was dried over magnesium sulfate, concentrated and the residue purified by flash chromatography (1:1 ethyl acetate/hexanes) to give 16 (0.28 g, 54%) as a white foam.

4-[N-(1-H-Imidazole-4-yl)methylene[amino-2-(3,3-dimethyl-(Z)-1-butenyl)benzoyl Leucine Hydrochloride. (17)

The fully protected compound 16 (0.20 g, 0.30 mmol) was dissolved into 4 mL. of tetrahydrofuran and cooled to 0° C. Sodium hydroxide (2 equivalents, 0.025 g, 0.60 mmol) was dissolved in 4 mL. of distilled water and slowly added to the stirred solution. The reaction was complete after 2 hours as determined by TLC. The reaction was acidified with 1 N hydrochloric acid and concentrated. The residue was extracted with ethyl acetate, dried over magnesium sulfate and concentrated. The residue was taken up in 4 mL. of methylene chloride to which 4 mL. of trifluoroacetic acid was added followed by the immediate addition of triethylsilane. The reaction was stirred for an additional 2 hours. The mixture was concentrated and the residue taken up in diethyl ether to which 3N HCl dissolved in diethyl ether was added. The solid which precipitated was washed with additional ether and purified by reverse phase HPLC to give 17 (0.08 g 50%). The HPLC asay was determined to be 99%. $^1$H NMR (300 MHz, $CD_3OD$) δ 8.80 (d, 1.1H, imidazole), 7.55 (d, J=8.6 Hz, 1H, aromatic), 7.42 (s, 1H, imidazole), 6.63 (dd, J=8.6, 2.1 Hz, 1H, aromatic), 6.54 (d, J=12.6 Hz, 1H, cis alkene), 6.40 (d, J=1.5 Hz, 1H, aromatic), 5.61 (d, J=12.5 Hz, 1H, cis alkene), 4.57 (t, J=7.5 Hz, 1H, α leu-H), 4.47 (s, 2H, $CH_2NH$), 1.65–1.79 (m, 3H, $CH_2CH(CH_3)_2$), 0.97 (d, J=3.8 Hz, 3H, $CH(CH_3)_2$), 0.95 (d, J=3.9 Hz, 3H, $CH(CH_3)_2$), 0.88 (s, 9H, t-butyl); $^{13}$C NMR (75 MHz, $CD_3OD$) δ 176.2, 171.1, 150.6, 143.9, 140.8, 135.4, 134.3, 131.5, 127.8, 124.0, 117.9, 115.3, 112.3, 52.8, 42.2, 38.7, 35.4, 31.3, 26.3, 23.5, 22.1.

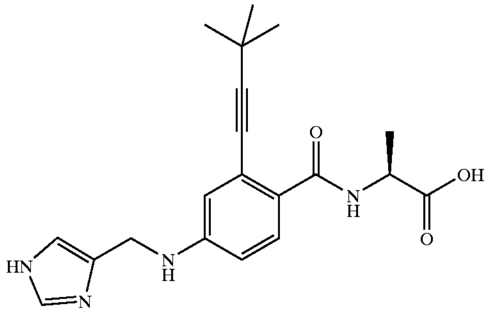

EXAMPLE 1326

4-[N-(1-H-Imidazole-4-yl)methylene[amino-2-(3,3-dimethyl-1-butynyl)benzoyl Alanine Hydrochloride N-[2-(3,3-Dimethyl-1-butynyl)-4-nitrobenzoyl]-alanine Methyl Ester. (30)

Compound 10 above (0.78 g, 3.2 mmol) and L-alanine methyl ester (0.45 g, 3.2 mmol) were dissolved into 100 mL. of dry methylene chloride and cooled to 0° C. 1-hydroxybenzotriazole (0.34 g, 3.4 mmol), EDCI (0.67 g, 3.5 mmol) and triethylamine (0.34 g, 3.4 mmol) were added to the cooled solution. The reaction was stirred under nitrogen overnight as the reaction warmed to room temperature. Additional methylene chloride was added and the reaction mixture was washed with 1N HCl followed by a saturated solution of sodium bicarbonate and a saturated solution of sodium chloride. The organic layer was dried over magnesium sulfate, concentrated, and purified by column chromatography (3:2 ethyl acetate/hexanes) to give 30 (0.9 g, 85%). $^1$H NMR (300 MHz, $CDCl_3$) δ 8.30 (d, J=2.2 Hz, 1H, aromatic), 8.07 (d, J=6.7 Hz, 1H, C(O)NH), 4.84 (m, a Ala H), 3.79 (s, 3H, $OCH_3$), 1.57 (d, 7.1H, $CHCH_3$), 1.38 (s, 9H, t-butyl); MS calc'd for: m/e 332.1372, found 332.1364.

N-[4-Amino-2-(3,3-dimethyl-1-butynyl)benzoyl]-alanine Methyl Ester hydrochloride. (31)

Compound 30 (0.6 g, 1.8 mmol) above was dissolved in 30 mL. of a 3:1 solution containing acetic acid and 5% aqueous HCl. Zinc dust (0.47 g, 7.2 mmol) was added at once and the reaction vigorously stirred for ½ hour. The reaction mixture was concentrated and the residue taken up in a saturated solution of sodium bicarbonate and extracted with ethyl acetate. The extracts were combined, dried over magnesium sulfate and concentrated. The residue taken up in methylene chloride and several mL. of 3N HCl dissolved in diethyl ether added. The solvents were evaporated leaving the hydrochloride salt and washed with additional diethyl ether to give 31 (0.47 g, 61%). $^1H$ NMR (300 MHz, $CD_3OD$) δ 7.68 (d, J=8.2 Hz, 1H, aromatic), 7.44 (d, J=2.0 Hz, 1H, aromatic), 7.40 (dd, J=8.3, 2.2 Hz, 1H, aromatic), 4.59 (q, J=7.4 Hz, 1H, a Ala H), 3.76 (s, 3H, $OCH_3$), 1.52 (d, J=7.1 Hz, 3H, $CHCH_3$), 1.32 (s, 9H, t-butyl); $^{13}C$ NMR (75 MHz, $CD_3OD$) δ 174.2, 169.3, 139.1, 134.0, 130.9, 128.0, 124.8, 123.3, 106.3, 76.8, 52.9, 50.1, 30.9, 29.3, 17.5; MS calc'd for: m/e 302.1630, found 302.1643.

4-[N-(1-Triphenylmethylimidazole-4-yl)methylene[amino-2-(3,3-dimethyl-1-butynyl)benzoyl Alanine Methyl Ester. (32)

Compound 31 (0.4 g, 1.2 mmol) and 1-Triphenylmethylimidazole carboxaldehyde (0.4 g, 1.4 mmol) were dissolved in 10 mL. of methanol and stirred for 10 mins. before adding dropwise 1 mL. of a methanol solution containing sodium cyanoborohydride (0.10 g, 1.7 mmol). The reaction was stirred at room temperature for 3 Hr. and then concentrated. The residue was taken up in ethyl acetate, washed with a saturated solution of sodium bicarbonate followed by a saturated solution of sodium chloride. The organic phase was dried over magnesium sulfate and concentrated. The residue was purified by flash column chromatography using 1:1 ethyl acetate/hexanes as the eluants. The product was collected and dried to give 32 (0.42 g, 56%) as a white foam. $^1H$ NMR (300 MHz, $CDCl_3$) δ 8.26 (d, J=7.3 Hz, 1H, C(O)NH), 7.97 (d, J=8.7 Hz, 1H, aromatic), 7.41 (s, 1H, imidazole), 7.32–7.34 (m 9, trityl), 7.09–7.12 (m, 6H, trityl), 6.70 (s, 1H, imidazole), 6.64 (d, J=2.3 Hz, 1H, aromatic), 6.58 (dd, J=8.8, 2.4 Hz, 1H, aromatic), 4.88 (m, 1H, a Ala H), 4.56 (t, J=5.2 Hz, 1H, $CH_2NH$), 4.26 (d, J=5.3 Hz, 2H, $CH_2NH$), 3.76 (s, 3H, $OCH_3$), 1.53 (d, 7.2H, $CHCH_3$), 1.34 (s, 9H, t-butyl).

4-[N-(-H-Imidazole-4-yl)methylene[amino-2-(3,3-dimethyl-1-butynyl)benzoyl Alanine Hydrochloride. (33)

Compound 32 (0.2 g, 0.3 mmol) was dissolved into 5 mL. of tetrahydrofuran and cooled to 0° C. lithium hydroxide (2 equivalents, 0.027 g, 0.64 mmol) was dissolved in 5 mL. of distilled water and slowly added to the stirred solution. The reaction was complete after 3 hours as determined by TLC. The reaction was acidified with 1.0 N hydrochloric acid to a pH of 2 and concentrated. The residue was extracted twice with ethyl acetate (50 mL). The extracts were combined, dried over magnesium sulfate and concentrated. The residue was taken up in 5 mL. of methylene chloride to which 5 mL. of trifluoroacetic acid was added followed by the immediate addition of triethylsilane. The reaction was stirred for an additional 2 Hr. at room temperature. The mixture was concentrated and the residue taken up in diethyl ether to which 3N HCl dissolved in diethyl ether was added. The solid which precipitated was washed with additional diethyl ether to give 33 (0.1 g %) as a TFA salt a white solid. An assay showed the product to be 99% pure. $^1H$ NMR (300 MHz, $CD_3OD$) δ 8.85 (s, 1H, imidazole), 7.69 (d, J=8.6 Hz, 1H, aromatic), 7.47 (s, 1H, imidazole), 6.72 (d, J=2.1 Hz, 1H, aromatic), 6.67 (dd, J=9.9, 2.4 Hz, 1H, aromatic), 4.61 (m, 1H, a Ala H), 1.51 (d, J=7.2 Hz, 3H, $CHCH_3$), 1.33 (s, 9H, t-butyl).

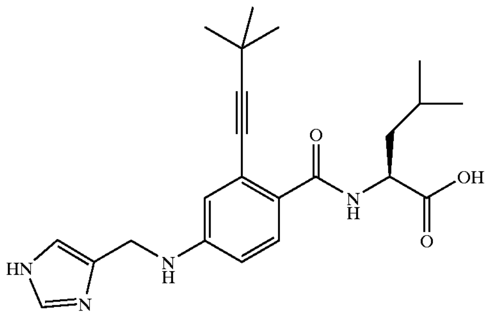

EXAMPLE 1329

4-[N-(1-H-Imidazole-4-yl)methylene[amino-2-(3,3-dimethyl-1-butynyl)benzoyl Leucine Hydrochloride Methyl 2-(3,3-Dimethyl-1-butynyl)-4-nitrobenzoate. (9)

Methyl 2-bromo-4-nitrobenzoate (2.0 g, 7.7 mmol) and 3,3-dimethyl-1-butyne (0.70 g, 8.5 mmol) were dissolved into 50 mL. of dry triethylamine to which 2 mole % of copper iodide (0.029 g, 0.15 mmol) and 5 mole % of tetrakis(triphenylphosine)palladium(0) (0.45 g, 0.38 mmol) were added. The reaction was stirred at 400° C. for 16 hours before an additional ½ equivalent of t-butylacetylene was added. The reaction continued for an additional 24 hours at which time the reaction was completed as determined by TLC. The reaction mixture was taken up in ethyl acetate, washed with distilled water and the organic layer dried over magnesium sulfate. After concentrating, the residue was purified by chromatography (1:9 ethyl acetate/hexanes) to give 9 (1.7 g, 85%) as a white solid: m.p. 88–89° (C.); $^1H$ NMR (300 MHz, $CDCl_3$) δ 8.30 (d, J=2.2 Hz, 1H, Aromatic), 8.10 (dd, J=2.3, 8.6 Hz, 1H, Aromatic), 7.99 (d, J=8.7 Hz, 1H, Aromatic), 3.99 (s, 3H, $OCH_3$), 1.35 (s, 9H, t-Butyl); $^{13}C$ NMR (75 MHz, $CDCl_3$) δ 165.9, 149.4, 137.7, 131.4, 128.7, 126.2, 121.8, 107.1, 76.5, 52.8, 30.8, 28.6; HRMS m/e calc'd for: 261.1001, found 261.1107.

2-(3,3-Dimethyl-1-butynyl)-4-nitrobenzoic Acid. (10)

Compound 9 (0.8 g, 3.1 mmole) was dissolved into 50 mL. of methanol containing 5% potassium hydroxide solution and the reaction was stirred at room temperature for 2 hours. The reaction mixture was concentrated and the residue was taken up in water and washed with diethyl ether. The aqueous fraction was carefully acidified with concentrated HCl to a pH of 2.0 and extracted with ethyl acetate (2×50 mL). The organic fractions were combined, washed once with a saturated solution of sodium chloride, dried over magnesium sulfate and concentrated to give 10 (0.7 g, 91%) an off-white solid: m.p. 170–173° (C.); $^1H$ NMR (300 MHz, $CD_3OD$) 8.16 (d, J=2.2 Hz, 1H, Aromatic), 8.12 (dd, J=8.7, 2.3 Hz, 1H, Aromatic), 7.96 (d, J=8.5 Hz, 1H, Aromatic), 1.35 (s, 9H, t-Butyl); $^{13}C$ NMR (75 MHz, $CD_3OD$) δ 168.5, 150.7, 140.4, 132.4, 129.0, 126.6, 123.1, 107.4, 77.7, 31.2, 29.6; HRMS m/e calc'd for: 247.0845, found 247.0821.

N-[2-(3,3-Dimethyl-1-butynyl)-4-nitrobenzoyl]-leucine Methyl Ester. (11)

Compound 10 (0.8 g, 3.2 mmol) and L-leucine methyl ester (0.62 g, 3.4 mmol) were dissolved into 50 mL. of dry methylene chloride and cooled to 0° C. 1-hydroxybenzotriazole (0.43 g, 3.2 mmol), EDCI (0.67 g, 3.5 mmol) and triethylamine (0.34 g, 3.4 mmol) were added to the cooled solution. The reaction was stirred under nitrogen overnight as the reaction warmed to room temperature. After 48 hours the reaction was worked up. Additional methylene chloride was added and the reaction mixture was washed with 1N HCl followed by a saturated solution of sodium bicarbonate and a saturated solution of sodium chloride. The organic layer was dried over magnesium sulfate, concentrated to a slight yellowish oil which was purified by flash chromatography (1:5 ethyl acetate/hexanes) to give 11 (0.6 g, 50%). m.p. 60–62° (C.); $^1H$ NMR (300 MHz, $CDCl_3$) δ 8.32 (d, J=2.0 Hz, 1H, aromatic), 8.26 (d, J=8.7 Hz, 1H, aromatic), 8.16 (dd, J=8.7, 2.2 Hz, 1H, aromatic), 8.08 (d, J=7.8 Hz, 1H, C(O)NH), 4.91 (m, 1H, α Leu-H), 3.78 (s, 3H, $OCH_3$), 1.67–1.82 (m, 3H, $CH_2CH(CH_3)_2$), 1.40 (s, 9H, t-butyl), 1.00 (d, J=5.1 Hz, 6H, $CH(CH_3)_2$); $^{13}C$ NMR (75 MHz, $CDCl_3$) δ 173.1, 164.0, 148.8, 139.0, 131.7, 129.1, 122.4, 108.8, 76.4, 52.5, 51.6, 42.0, 30.5, 28.7, 25.1, 22.9, 22.2; HRMS calc'd for: m/e 374.1842, found 374.1828.

N-[4-Amino-2-(3,3-dimethyl-1-butynyl)benzoyl]-leucine Methyl Ester Hydrochloride. (12)

Compound 11 (0.4 g, 1.1 mmol) above was dissolved in 16 mL. of a 3:1 solution containing acetic acid and 5% aqueous HCl. Zinc dust (0.25 g, 3.8 mmol) was added at once and the reaction vigorously stirred for 50 min. The reaction mixture was concentrated and the residue taken up in a saturated solution of sodium bicarbonate and extracted twice with ethyl acetate. The extracts were combined, dried over magnesium sulfate and concentrated. The residue taken up in methylene chloride and several mL. of 3N HCl dissolved in diethyl ether added. The solvents were evaporated leaving the hydrochloride 12 (0.38 g, 92%). $^1H$ NMR (300 MHz, $CD_3OD$) δ 7.65 (d, J=8.3 Hz, 1H, aromatic), 7.37 (d, J=2.2 Hz, 1H, aromatic), 7.32 (dd, J=8.3, 2.2 Hz, 1H, aromatic), 4.67 (t, J=7.4 Hz, 1H, α Leu-H), 3.75 (s, 3H, $OCH_3$), 1.69–1.82 (m, 3H, $CH_2CH(CH_3)_2$), 1.32 (s, 9H, t-butyl), 0.99 (d, 6.0H, $CH(CH_3)_2$); $^{13}C$ NMR (75 MHz, $CD_3OD$) δ 174.3, 169.6, 137.6, 135.8, 130.9, 127.3, 124.7, 122.4, 106.0, 77.2, 52.8, 41.7, 31.0, 29.3, 26.1, 23.3, 22.2.

4-[N-(1-Triphenylmethylimidazole-4-yl)methylene[amino-2-(3,3-dimethyl-1-butynyl)]-leucine Methyl Ester. (13)

The above compound 12 (0.25 g, 0.66 mmol) and 1-triphenylmethyimidazole carboxaldehyde (0.27 g, 0.79 mmol) were dissolve in 10 mL. of 95% methanol and 5% acetic acid. Triacetoxyborohydride (0.15 g, 0.73 mmol) was added at once and the reaction stirred for 16 hr. The reaction was concentrated and the residue column chromatography (1:4 ethyl acetate/hexanes on silica) to give 13 (0.20 g, 46%) as a white foam. $^1H$ NMR (300 MHz, $CDCl_3$) δ 8.27 (d, J=8.3 Hz, 1H, C(O)NH), 8.02 (d, J=8.8 Hz, 1H, aromatic), 7.42 (s, 1H, imidazole), 7.27–7.37 (m, 9H, trityl), 7.09–7.15 (m, 6H, trityl), 6.70 (s, 1H, imidazole), 6.65 (d, J=2.2 Hz, 1H, aromatic), 6.58 (dd, J=8.8, 2.2 Hz, 1H, aromatic), 4.96 (m, 1H, α Leu H), 4.66 (t, J=5.3 Hz, 1H, $CH_2NH$), 4.26 (d, J=5.3 Hz, 2H, $CH_2NH$), 3.74 (s, 3H, $OCH_3$), 1.71–1.84 (m, 3H, $CH_2CH(CH_3)_2$), 1.35 (s, 9H, t-butyl), 0.98 (d, J=5.6 Hz, 6H, $CH(CH_3)_2$).

4-[N-(1-H-Imidazole-4-yl)methylenelamino-2-(3,3-dimethyl-1-butynyl)benzoyl Leucine Hydrochloride. (14)

Compound 13 (0.15 g, 0.23 mmol) was dissolved into 5 mL. of tetrahydrofuran and cooled to 0° C. Lithium hydroxide (2 equivalents, 0.019 g, 0.46 mmol) was dissolved in 5 mL. of distilled water and slowly added to the stirred solution. The reaction was complete after 3 hours as determined by TLC. The reaction was acidified with 1.0 N hydrochloric acid to a pH of 2 and concentrated. The residue was extracted twice with ethyl acetate, dried over magnesium sulfate and concentrated. The residue was taken up in 5 mL. of methylene chloride to which 5 mL. of trifluoroacetic acid was added followed by the immediate addition of triethylsilane. The reaction was stirred for an additional 2 Hr. at room temperature. The mixture was concentrated and the residue taken up in diethyl ether to which 3N HCl dissolved in diethyl ether was added. The solid was purified by reverse phase HPLC to give 14 (0.04 g 36%) as a TFA salt. The HPLC assay was determined to be 98% $^1H$ NMR (300 MHz, $CD_3OD$) δ 8.79 (s, 1H, imidazole), 7.70 (d, J=8.7 Hz, 1H, aromatic), 7.45 (s, 1H, imidazole), 6.72 (d, J=2.3 Hz, 1H, aromatic), 6.66 (dd, J=8.7, 2.2 Hz, 1H, aromatic), 4.72 (m, 1H, α Leu-H), 4.48 (s, 2H, $CH_2NH$), 1.69–1.77 (m, 3H, $CH_2CH(CH_3)_2$), 1.33 (s, 9H, t-butyl), 0.99 (m, 6H, $CH_2CH(CH_3)_2$); $^{13}C$ NMR (75 MHz, $CD_3OD$) δ 176.0, 169.0, 151.3, 135.6, 134.1, 132.4, 124.4, 123.7, 118.4, 118.0, 113.1, 105.3, 79.5, 52.8, 42.9, 38.7, 31.2, 29.5, 26.3, 23.5, 22.4.

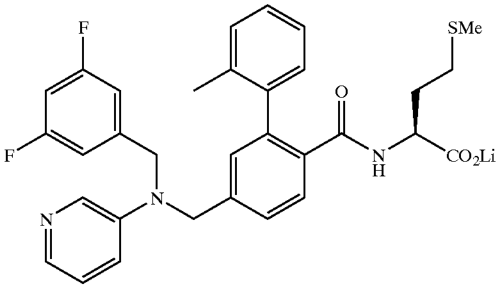

EXAMPLE 1360

N-[4-N-3,5-Difluorobenzyl-N-(3-pyridyl)aminomethyl-2-(2-methylphenyl)benzoyl]methionine Lithium Salt

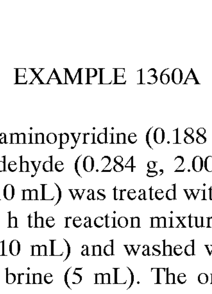

EXAMPLE 1360A

A solution of 3-aminopyridine (0.188 g, 2.00 mmol) and 3,5-difluorobenzaldehyde (0.284 g, 2.00 mmol) in dichloroethane solvent (10 mL) was treated with $NaBH_4$ (0.844 g, 4 mmol). After 24 h the reaction mixture was diluted with dichloromethane (10 mL) and washed with 4 N NaOH (5 mL), followed by brine (5 mL). The organic portion was dried over $MgSO_4$ and then concentrated under reduced pressure. Flash column chromatography eluting with ethyl acetate afforded 0.220 g of XXXA as a colorless oil (50% yield). $^1H$ NMR ($CDCl_3$): δ 4.28 (s, 1H), 4.38 (s, 2H), 6.72 (m, 1H), 6.80–6.90 (comp, 3H), 7.08 (m, 1H), 8.01 (dd, J=1.3, 4.7 Hz, 1H), 8.05 (d, J=2.7 Hz, 1H). LRMS (ESI+): $(M+H)^+$ calc for $C_{12}H_{11}N_2F_2$: 221; found: 221.

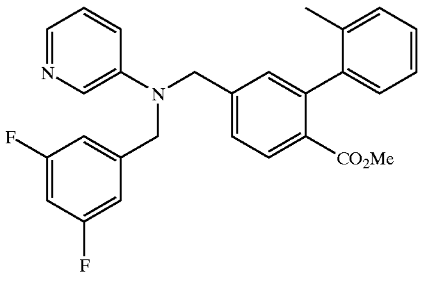

EXAMPLE 1360B

A solution of 4-bromomethyl-2-(2-methylphenyl)benzoic acid, methyl ester (example 1178D) (0.308 g, 1.40 mmol) and XXXA (0.447 g, 1.40 mmol) in tetrahydrofuran solution (7 mL) at −78° C. was treated with sodium bis (trimethylsilyl)amide (1.54 mL of a 1 M tetrahydrofuran solution, 1.54 mmol), and the reaction mixture was allowed to very gradually warm to room temperature. After 20 h the reaction mixture was filtered through silica gel with ethyl acetate rinses and concentrated under reduced pressure. Radial chromatography eluting with hexane and ethyl acetate using an elution gradient of 80:20 to 60:40 afforded 0.175 g of XXXB asa colorless oil (27% yield). $^{1}$H NMR ($CDCl_3$): δ 2.01 (s, 3H), 3.60 (s, 3H), 4.64 (s, 2H), 4.72 (s, 2H), 6.66–6.72 (m, 1H), 6.75 (d, J=7.0 Hz, 2H), 6.91–6.96 (m, 1H), 7.03 (d, J=7.7 Hz, 1H), 7.06–7.11 (comp, 2H), 7.16–7.31 (comp, 4H), 7.95 (d, J=8.1 Hz, 1H), 8.02 (dd, J=1.1, 4.8 Hz, 1H), 8.12 (d, J=3.3 Hz, 1H). LRMS (ESI+): $(M+H)^+$ calc for $C_{28}H_{25}F_2N_2O_2$: 459; found: 459.

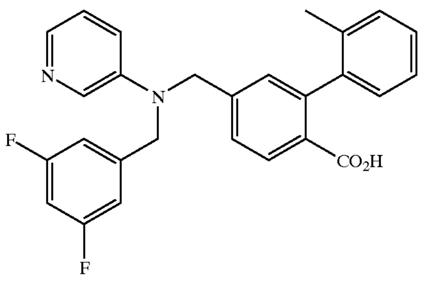

EXAMPLE 1360C

Compound 1360C was prepared in the same fashion as 1014B (95% yield). $^{1}$H NMR ($CDCl_3$): δ 1.99 (s, 3H), 4.63 (s, 2H), 4.71 (s, 3H), 6.67–6.75 (comp, 3H), 7.00–7.26 (comp, 8H), 7.88–7.94 (br, 1H), 7.98 (d, J=8.2 Hz, 1H), 8.09 (br, 1H). LRMS (ESI+): $(M+H)^+$ calc for $C_{27}H_{23}F_2N_2O_2$: 445; found: 445. LRMS (ESI−): $(M-H)^-$ calc for $C_{27}H_{21}F_2N_2O_2$: 443; found: 443.

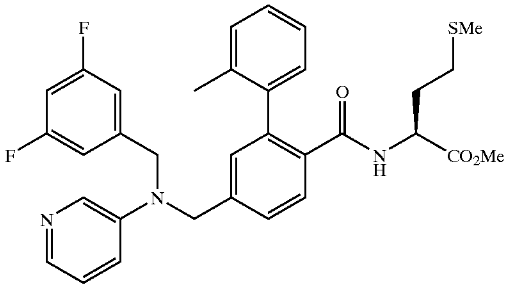

EXAMPLE 1360D

Compound 1360D was prepared in the same fashion as 1014C (46% yield). $^{1}$H NMR ($CDCl_3$): δ 1.53–1.66 (m, 1H), 1.80–1.91 (m, 1H), 2.00–2.12 (comp, 8H), 3.65 (s, 3H), 4.56–4.64 (m, 1H), 4.64 (s, 2H), 4.71 (s, 2H), 5.87–5.92 (m, 1H), 6.66–6.71 (comp, 3H), 6.92–6.97 (m, 1H), 7.04–7.11 (comp, 2H), 7.13–7.34 (comp, 5H), 7.93 (dd, J=8.1, 13.9 Hz, 1H), 8.02 (dd, J=1.4, 4.8 Hz, 1H), 8.14 (d, J=3.0 Hz, 1H). LRMS (ESI+): $(M+H)^+$ calc for $C_{33}H_{34}F_2N_3O_3S$: 590; found: 590. LRMS (ESI−): $(M-H)^-$ calc for $C_{33}H_{32}F_2N_3O_3S$: 598; found: 598.

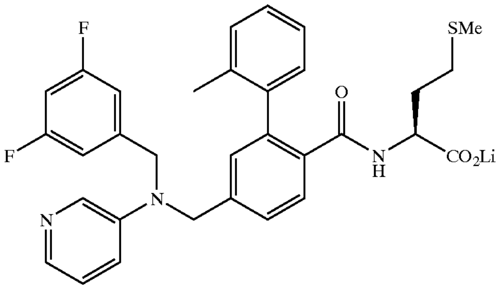

EXAMPLE 1360E

N-[4-N-3,5-Difluorobenzyl-N-(3-pyridyl)aminomethyl-2-(2-methylphenyl)benzoyl]methionine Lithium Salt Compound 1360E was prepared by hydolysis of the methyl ester using lithium hydroxiode (86% yield). $^{1}$H NMR ($d_6$-DMSO): δ 1.48–1.76 (comp, 2H), 1.85–2.05 (comp, 8H), 3.62–3.74 (br, 1H), 4.80 (s, 2H), 4.86 (s, 2H), 6.92–7.23 (comp, 11H), 7.33 (dd, J=1.1, 7.7 Hz, 1H), 7.52 (d, J=8.1 Hz, 1H), 7.84 (dd, J=0.9, 4.6 Hz, 1H), 8.03 (d, J=3.0 Hz, 1H). LRMS (ESI+): $(M+2H-Li)^+$ calc for $C_{32}H_{32}F_2N_3O_3S$: 576; found: 576. LRMS (ESI−): $(M-Li)^-$ calc for $C_{32}H_3oF_2N_3O_3S$: 574; found: 574.

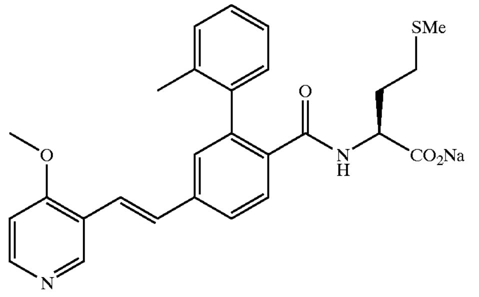

EXAMPLE 1361

N-[4-(2-(4-Methoxypyridin-3-yl)ethenyl)-2-(2-methylphenyl)benzoyl]methionine Sodium Salt N-[4-(2-(4-chloropyridin-3-yl)ethenyl)-2-(2-methylphenyl)benzoyl]methionine methyl ester, prepared as in Example 1040, (62 mg, 0.12 mmol) was dissolved in DMF (1 mL) and treated with NaOMe (0.5 M in MeOH, 1.25 mL, 0.63 mmol). After stirring 18 hours at ambient temperature, the reaction was evaporated and lyophilized from water to provide 68 mg of the title compound. MS m/e 477 $(M+H)^+$.

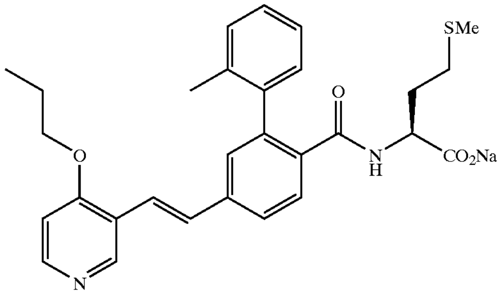

EXAMPLE 1362

N-[4-(2-(4-Propyloxypyridin-3-yl)ethenyl)-2-(2-methylphenyl)benzoyl]methionine Sodium Salt N-[4-(2-(4-chloropyridin-3-yl)ethenyl)-2-(2-methylphenyl)benzoyl]methionine methyl ester, prepared as in Example 1040, (28 mg, 0.06 mmol) was dissolved in DMF (1 mL) with n-propanol (0.1 mL) and treated with NaH (60% in mineral oil, 6.8 mg, 0.17 mmol). After stirring 18 hours at ambient temperature, the reaction was evaporated and lyophilized from water to provide 29 mg of the title compound. MS m/e 505 $(M+H)^+$. $^1$H NMR ($d_6$-DMSO, 300 MHz) δ 1.03 (m, 3H), 1.24 (m, 2H), 1.6 (m, 3H), 2.0 (m, 7H), 3.71 (m, 2H), 6.94 (m, 1H), 7.3 (m, 9H), 7.74 (m, 1H), 8.33 (m, 1H), 8.52 (m, 1H), 8.67 (s, 1H).

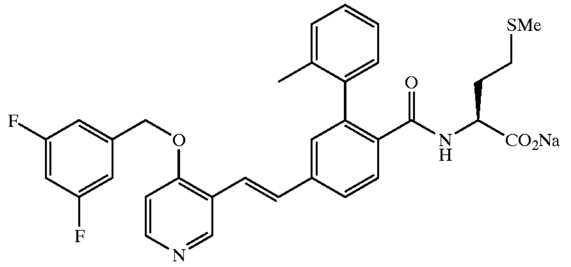

EXAMPLE 1363

N-[4-(2-(4-(3,5-Difluorobenzyl)oxypyridin-3-yl)ethenyl)-2-(2-methylphenyl)benzoyl]methionine Sodium Salt N-[4-(2-(4-chloropyridin-3-yl)ethenyl)-2-(2-methylphenyl)benzoyl]methionine methyl ester, prepared as in Example 1040, (27 mg, 0.05 mmol) was dissolved in DMF (1 mL) with 3,5-difluorobenzyl alcohol (0.1 mL) and treated with NaH (60% in mineral oil, 6.5 mg, 0.16 mmol). After stirring 18 hours at ambient temperature, the reaction was evaporated and lyophilized from water to provide 29 mg of the title compound. MS m/e 589 $(M+H)^+$.

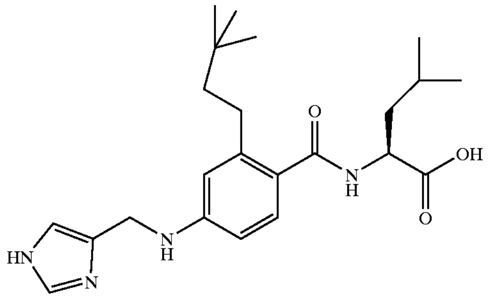

EXAMPLE 1365

4-[N-(1-H-Imidazole-4-yl)methylene[amino-2-(3,3-dimethylbutane)benzoyl Leucine Hydrochloride N-[4-Amino-2-(3,3-dimethylbutane)benzoyl]-leucine Methyl Ester. (27)

Compound 11 (0.75 g, 2.0 mmol) was dissolved in ethyl acetate (20 mL) and hydrogenated at room temperature using 10% Palladium on carbon (0.1 g) under a hydrogen atmosphere (45 psi) for 16 Hr. The solvent was filtered through a celite plug and concentrated. The residue was taken up into methylene chloride to which several mL. of 3N HCl in diethyl ether was added. The off-white solid was collected and dried to give 27 (0.64 g, 80%). $^1$H NMR (300 MHz, $CD_3OD$) δ 7.49 (d, J=7.8 Hz, 1H, aromatic), 7.30–7.34 (m, 2H, aromatic), 4.65 (m, 1H, α Leu-H), 3.75 (s, 3H, $OCH_3$), 2.73–2.85 (m, 2H), 1.67–1.79 (m, 3H), 1.50 (m, 2H), 0.99 (d, J=6.1 Hz, 6.0H, $CH(CH_3)_2$), 0.96 (s, 9H, t-butyl); $^{13}$C NMR (75 MHz, $CD_3OD$) δ 174.6, 172.0, 145.6, 138.4, 133.4, 130.5, 125.7, 121.7, 53.1, 52.7, 47.3, 41.3, 31.7, 29.9, 29.8, 26.4, 23.7, 22.1; HRMS calc'd for: m/e 348.2413, found 348.2418.

4-[N-(1-Triphenlmethylimidazole-4-yl)methylene[amino-2-(3,3-dimethylbutane)benzoyl Leucine Methyl Ester. (28)

Compound 27 (0.5 g, 1.3 mmol) and 1-triphenylmethylimidazole carboxaldehyde (0.5 g, 1.4 mmol) were dissolved in 10 mL. of methanol and stirred for 10 min. before. adding dropwise 1 mL. of a methanol solution containing sodium cyanoborohydride (0.09 g, 1.4 mmol). The reaction was stirred at room temperature for ½ Hr. and then concentrated. The residue was taken up in ethyl acetate, washed with a saturated solution of sodium bicarbonate followed by a saturated solution of sodium chloride. The organic phase was dried over magnesium sulfate and concentrated. The residue was purified by flash column chromatography using 3:2 ethyl acetate/hexanes as the eluants. The product was collected and dried to give 28 (0.6 g, 70%) as a white foam. $^1$H NMR (300 MHz, $CDCl_3$) δ 7.41 (s, 1H, imidazole), 7.33 (m, 9H, trityl), 7.25 (d, J=8.4 Hz, 1H, aromatic), 7.12 (m, 6H, trityl), 6.72 (s, 1H, imidazole), 6.45 (s, 1H, aromatic), 6.42 (d, J=8.4 Hz, 1H, aromatic), 6.02 (d, J=8.6 Hz, 1H), 4.82 (m, 1H, α leu-H), 4.40 (br s, 1H, $CH_2NH$), 4.24 (s, 2H, $CH_2NH$), 3.75 (s, 3H, $OCH_3$), 2.72 (m, 2H), 1.58–1.75 (m, 3H), 1.41 (m, 2H), 1.00 (d, J=5.8 Hz, 3H, $CH(CH_3)_2$), 0.97 (d, J=5.9 Hz, 3H, $CH(CH_3)_2$), 0.91 (s, 9H, t-butyl); $^{13}$C NMR (75 MHz, $CDCl_3$) δ 174.0, 170.0, 149.8, 144.4, 142.4, 138.9, 138.5, 129.8, 128.8, 128.2, 124.4, 119.2, 114.7, 109.7, 75.4, 52.3, 50.9, 46.5, 42.0, 11435 41.8, 30.7, 29.4, 29.1, 25.1, 23.1, 22.1.

4-[N-(1-H-Imidazole-4-yl)methylene[amino-2-(3,3-dimethylbutane)benzoyl Leucine Hydrochloride. (29)

Compound 28 (0.2 g, 0.3 mmol) was dissolved into 5 mL. of tetrahydrofuran and cooled to 0° C. lithium hydroxide (2 equivalents, 0.025 g, 0.6 mmol) was dissolved in 5 mL. of distilled water and slowly added to the stirred solution. The reaction was complete after 2 hours as determined by TLC. The reaction wasacidified with 1.0 N hydrochloric acid to a pH of 2 and concentrated. The residue was extracted twice with ethyl acetate (50 mL). The extracts were combined, dried over magnesium sulfate and concentrated. The residue was taken up in 5 mL. of methylene chloride to which 5 mL. of trifluoroacetic acid was added followed by the immediate addition of triethylsilane. The reaction was stirred for an additional 2 Hr. at room temperature. The mixture was concentrated and the residue taken up in diethyl ether to which 3N HCl dissolved in diethyl ether was added. The solid which precipitated was washed with additional diethyl ether and purified by reverse phase HPLC to give 29 (0.11 g 81%) as a TFA salt a white solid. An assay showed the product tobe 99% pure. $^1$H NMR (300 MHz, $CD_3OD$) 88.87 (s 1, imidazole), 7.50 (s, 1H, imidazole), 7.27 (d, J=8.1 Hz, 1H, aromatic), 6.64–6.70 (m, 2H, aromatic), 4.60 (m, 1H, α leu-H), 4.53 (s, 2H, $CH_2NH$), 2.71 (m, 2H), 1.63–1.74 (m, 3H, $CH_2CH(CH_3)_2$), 1.40 (m, 2H), 0.97 (d, J=6.2 Hz, 6H, $CH(CH_3)_2$), 0.92 (s, 9H, t-butyl).

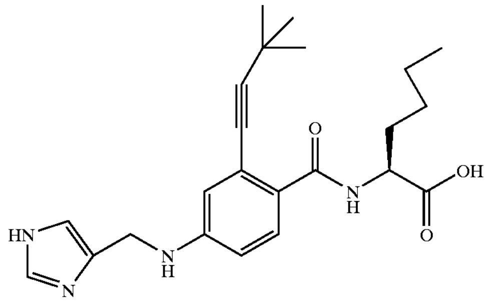

EXAMPLE 1407

4-N-(1-H-Imidazole-4-yl)methylene[amino-2-(3,3-dimethyl-1-butynyl)benzoyl Norleucine Hydrochloride N-[2-(3,3-Dimethyl-1-butynyl)-4-nitrobenzoyl]-norleucine Methyl Ester. (34)

Compound 10 (0.50 g, 2.0 mmol) was coupled with L-norleucine (0.36 g, 2.0 mmol) in a similar manner described for compound 11 to give 34 (0.65 g, 87%) as a white solid. $^1$H NMR (300 MHz, $CDCl_3$) δ 8.32 (d, J=2.3 Hz, 1H, aromatic), 8.25 (d, J=8.7 Hz, 1H, aromatic), 8.15 (dd, J=8.8, 2.3 Hz, 1H, aromatic), 8.12 (br s, 1H, C(O)NH), 4.87 (ddd, J=7.4, 6.1, 1.3 Hz, 1H, α norleu-H), 3.79 (s, 3H, $OCH_3$), 1.96–2.05 (m, 1H), 1.81–1.87 (m, 1H), 1.61 (m, 1H), 1.31–1.39 (m, 12H), 0.91 (t, J=6.9 Hz, 3H); $^{13}$C NMR (75 MHz, $CDCl_3$) δ 172.6, 164.0, 148.6, 139.1, 131.6, 129.0, 122.4, 122.3, 108.7, 76.2, 53.3, 52.5, 32.3, 30.4, 28.6, 27.7, 22.4, 13.9.

N-[4-Amino-2-(3,3-dimethyl-1-butynyl)benzoyl]-norleucine Methyl Ester Hydrochloride (35)

Compound 34 (0.6 g, 1.6 mmol) was reduced using a similar procedure for the reduction of compound 12 with zinc in acetic acid to give 35 (0.60 g, 98%) as the hydrochloride. $^1$H NMR (300 MHz, DMSO-$d_6$) δ 8.80 (d, J=7.4 Hz, 1H, C(O)NH), 7.90 (d, J=8.3 Hz, 1H, aromatic), 7.36 (s, 1H, aromatic), 7.33 (d, J=8.5 Hz, 1H, aromatic), 4.85 (m, 1H, α norleu-H), 4.06 (s, 3H, $OCH_3$), 2.07–2.23 (m, 2H), 1.72 (m, 4H), 1.69 (s, 9H, t-butyl), 1.27 (t, J=6.9 Hz, 3H); $^{13}$C NMR (75 MHz, $CD_3OD$) δ 173.8, 169.6, 139.6, 133.5, 130.8, 128.4, 124.8, 123.6, 106.3, 76.8, 54.5, 52.8, 32.3, 31.0, 29.2, 23.3, 14.23; MS calc'd for: m/e 344.2100, found 344.2088.

4-[N-(1-Triphenylmethylimidazole-4-yl)methylene[amino-2-(3,3-dimethyl-1-butynyl)benzoyl Norleucine Methyl Ester. (36)

Compound 35 (0.21 g, 0.54 mmol) was coupled with 1-triphenylmethylimidazole carboxaldehyde (0.20 g, 0.60 mmol) in a similar manner as described for the preparation of 22 to give 36 (0.15 g, 42%) as a white foam.

4-[N-(1-H-Imidazole-4-yl)methylene[amino-2-(3,3-dimethyl-1-butynyl)benzoyl Norleucine Hydrochloride. (37)

Compound 36 (0.15 g, 0.23 mmol) was deprotected in a similar manner as described for the deprotection of 17 to give 37 (0.06 g, 64%) as the TFA salt after purification by reverse phase HPLC. $^{13}$C NMR (75 MHz, $CD_3OD$) δ 175.5, 168.8, 151.4, 135.6, 134.0, 132.6, 124.2, 123.7, 118.5, 118.0, 113.2, 105.6, 79.4, 54.4, 38.6, 33.3, 31.2, 29.6, 29.2, 23.6, 14.4.

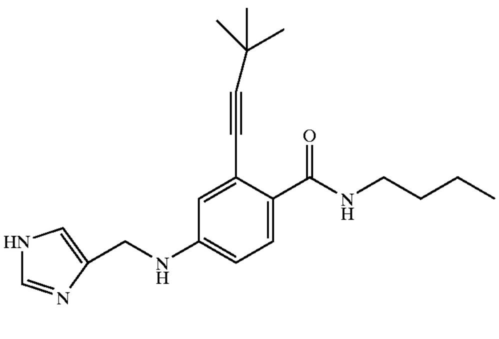

EXAMPLE 1408

4-[N-(1-H-Imidazole-4-yl)methylene[amino-2-(3,3-dimethyl-1-butynyl)-N-butylbenzamide 2-(3,3-Dimethyl-1-butynyl)-4-nitro-N-butylbenzamide. (38)

2-t-Butylacetylene-4-nitrobenzoic acid (0.7 g, 2.8 mmol) and n-butyl amine (0.31 g, 4.3 mmol) were dissolved into 25 mL. of dry methylene chloride and cooled to 0° C. EDCI (0.6 g, 3.1 mmol) was added to the cooled solution and the reaction was stirred under a nitrogen atmosphere for 1 hour. The ice bath was removed and the reaction warmed to room temperature overnight. Additional methylene chloride was added and the reaction, mixture was washed with 1N HCl followed by a saturated solution of sodium bicarbonate and a saturated solution of sodium chloride. The organic layer was dried over magnesium sulfate, concentrated to a slight yellowish oil and purified by flash column chromatography (4:1 ethyl acetate/hexanes) to give 38 (0.36 g, 60%). $^{1}H$ NMR (300 MHz, $CDCl_3$) δ 8.25 (s, 1H, aromatic), 8.14 (s, 2H, aromatic), 7.56 (br s, 1H, C(O)NH), 3.50 (dd, J=13.1, 7.0 Hz, 2H), 1.65 (m, 2H), 1.43 (m, 2H), 1.39 (s, 9H, t-butyl), 0.98 (t, J=7.4 Hz, 3H); $^{13}C$ NMR (75 MHz, $CDCl_3$) δ 165.0, 148.9, 141.0, 131.8, 128.9, 122.9, 122.4, 108.2, 78.1, 40.6, 32.1, 31.0, 29.0, 20.8, 14.3; MS calc'd for: m/e 302.1630, found 302.1628.

N-[4-Amino-2-(3,3-dimethyl-1-butynyl)-N-butylbenzamidel Hydrochloride. (39)

Compound 38 (0.36 g, 1.2 mmol) was dissolved in 30 mL. of a 3:1 solution containing acetic acid and 5% aqueous HCl. Zinc dust (0.31 g, 4.8 mmol) was added at once and the reaction vigorously stirred for ½ hour. The reaction mixture was concentrated and the residue taken up in a saturated solution of sodium bicarbonate and extracted 3×50 mL. with ethyl acetate. The extracts were combined, dried over magnesium sulfate and concentrated. The residue taken up in methylene chloride and several mL. of 3N HCl dissolved in diethyl ether added. The solvents were evaporated leaving 39 as the hydrochloride. (0.35 g, 95%). $^{1}H$ NMR (300 MHz, $CD_3OD$) δ 7.57 (d, J=8.2 Hz, 1H, aromatic), 7.44 (d, J=2 Hz, 1H, aromatic), 7.40 (dd, J=8.2, 2.0 Hz, 1H, aromatic), 3.38 (t, J=7.0 Hz, 2H), 1.62 (m, 2H), 1.44 (m, 2H), 1.32 (s, 9H, t-butyl), 0.97 (t, J=7.4 Hz, 3H); $^{13}C$ NMR (75 MHz, $CD_3OD$) δ 169.9, 140.5, 133.2, 130.3, 128.0, 124.5, 123.6, 105.7, 76.8, 40.8, 32.5, 31.0, 29.2, 21.2, 14.2; MS calc'd for: m/e 272.1889, found 272.1885.

4-[N-(1-Triphenylmethylimidazole-4-yl)methylene [amino-2-(3,3-dimethyl-1-butynyl)-N-butylbenzamide. (40)

Compound 39 (0.34 g, 1.1 mmol) and 1-Triphenylmethylimidazole carboxaldehyde (0.45 g, 1.3 mmol) were dissolved in 10 mL. of methanol and stirred for 15 min. before adding dropwise 1 mL. of a methanol solution containing sodium cyanoborohydride (0.076 g, 1.2 mmol). The reaction was stirred at room temperature for 2 Hr. and then concentrated. The residue was taken up in ethyl acetate, washed with a saturated solution of sodium bicarbonate followed by a saturated solution of sodium chloride. The organic phase was dried over magnesium sulfate and concentrated. The residue was purified by column chromatography using 1:1 ethyl acetatethexanes as the eluants. The product was collected and dried to give 40 (0.44 g, 67%) as a white foam. $^{1}H$ NMR (300 MHz, $CDCl_3$) δ 7.99 (d, J=8.7 Hz, 1H, aromatic), 7.85 (t, J=5.6 Hz, 1H), 7.43 (s, 1H, imidazole), 7.30 (m, 9H, trityl), 7.01–7.12 (m, 6H, trityl), 6.71 (s, 1H, imidazole), 6.64 (d, J=2.3 Hz, 1H, aromatic), 6.57 (dd, J=8.7, 2.4 Hz, 1H, aromatic), 4.73 (br s, 1H), 4.25 (s, 2H, $CH_2NH$), 3.47 (dd, J=13.0, 6.8 Hz, 2H), 1.61 (m, 2H), 1.44 (m, 2H), 1.33 (s, 9H, t-butyl), 0.95 (m, 3H); $^{13}C$ NMR (75 MHz, $CDCl_3$) δ 166.2, 149.5, 142.2, 138.8, 137.9, 132.0, 129.8, 128.2, 123.3, 121.0, 119.4, 117.2, 113.0, 104.1, 79.3, 41.6, 39.7, 32.1, 11550 30.9, 28.4, 20.4, 14.0; MS calc'd for: nie 594.3359, found 594.3351.

4-[N-(1-H-Imidazole-4-yl)methylene[amino-2-(3,3-dimethyl-1-butynyl)-N-butylbenzamide. (41)

The above protected compound 40 (0.20 g, 0.34 mmol) was dissolved into 5 mL. of methylene chloride. To the reaction was added 5 mL. of trifluoroacetic acid followed by the immediate addition of triethylsilane. The reaction was stirred at room temperature for an additional 2 hours. The reaction was concentrated and the residue taken up into methylene chloride to which 3N HCl in diethyl ether was added. The precipitated hydrochloride was washed with additional diethyl ether, dried under vacuum and purified by reverse phase HPLC to give 41 (0.06 g, 50%).

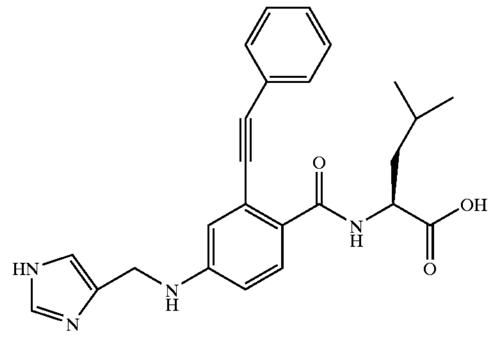

EXAMPLE 1409

4-[N-(1-H-Imidazole-4-yl)methylene[amino-2-(1-phenylethynl)benzoyl Leucine Hydrochloride Methyl 2-(1-Phenylethynl)-4-nitrobenzoate. (18)

Methyl 2-bromo-4-nitrobenzoate (3.9 mmol) was dissolved into 10 mL. of dry TEA containing phenylacetylene (0.83 g, 8.1 mmol) followed by the immediate addition of copper iodide (0.033 g, 0.17 mmol) and The reaction mixture was refluxed for 3 hr. and concentrated. The residue was taken up into water and extracted with ethyl acetate. The Iorganics were dried with magnesium sulfate, concentrated and purified by column chromatography twice (1:4 ethyl acetate/hexanes and 100% chloroform). The:solid was recrystallized from hexanes to give 18 (0.64 g, 64%) as yellow needles. m.p. 95–96° (C.); $^{1}H$ NMR (300 MHz, $CDCl_3$) δ 8.47 (d, J=2.2 Hz, 1H), 8.18 (dd, J=8.7, 2.3 Hz, 1H, aromatic), 8.12 (d, J=8.6 Hz, 1H, aromatic), 7.60 (m, 2H, aromatic), 7.38–7.42 (m, 3H, aromatic), 4.02 (s, 3H, $OCH_3$); $^{13}C$ NMR (75 MHz, $CDCl_3$) δ 165.2, 149.5, 137.0, 132.1, 131.7, 129.5, 128.7, 125.6, 122.4, 122.3, 97.3, 86.3, 52.9; HRMS calc'd for: m/e 281.0688, found 281.0690.

2-(1-Phenylethynl)-4-nitrobenzoic Acid. (19)

Compound 18 (0.60 g, 2.3 mmol) was hydrolyzed using methanoic KOH in a similar manner described for compound 10 to give 19 (0.6 g, 98%) as a white solid. $^{1}H$ NMR (300 MHz, $CD_3OD$) δ 8.43 (d, J=2.3 Hz, 1H, aromatic), 8.24 (dd, J=8.7, 2.2 Hz, 1H, aromatic), 8.14 (d, J=8.6 Hz, 1H, aromatic), 7.58–7.61 (m, 2H, aromatic), 7.40–7.42 (m, 3H, aromatic); $^{13}C$ NMR (75 MHz, $CD_3OD$) δ 150.6,132.9, 132.7, 130.3, 129.6, 129.0, 126.1, 123.8, 123.4, 97.5, 87.2; (Expected 13 carbons observed 11) HRMS calc'd for: m/e 267.0532, found 267.0529.

N-[2-(1-Phenylethynl)-4-nitrobenzoyl]-leucine Methyl Ester. (20)

Compound 19 (0.60 g, 2.2 mmol) was coupled with L-leucine (0.41 g, 2.2 mmol) in a similar manner described for compound 11 to give 20 (0.63 g, 72%) as a white solid. $^{1}H$ NMR (300 MHz, $CDCl_3$) δ 8.47 (d, J=1.3 Hz, 1H, aromatic), 8.23 (d, J=1.0 Hz, 2H, aromatic), 7.77 (d, J=7.8 Hz, 1H, C(O)NH), 7.57–7.62 (m, 2H, aromatic), 7.39–7.48 (m, 3H, aromatic), 4.88 (m, 1H, α leu-H), 3.73 (s, 3H, $OCH_3$), 1.67–1.75 (m, 3H, $CH_2CH(CH_3)_2$), 0.94 (d, J=6.5 Hz, 3H, $CH(CH_3)_2$), 0.84 (d, J=6.6 Hz, 3H, $CH(CH_3)_2$); $^{13}C$ NMR (75 MHz, $CDCl_3$) δ 173.1, 164.4, 148.9, 140.1, 132.0, 131.6, 130.0, 128.8, 128.6, 123.2, 121.8, 121.3, 98.3, 85.3, 52.6, 51.9, 41.8, 25.0, 22.7, 22.1; HRMS calc'd for: m/e 394.1529, found 394.1528.

N-[4-Amino-2-(1-phenylethynl)benzoyl]-leucine Methyl Ester. (21)

Compound 20 was reduced using a similar procedure for the reduction of compound 12 with zinc in acetic acid to give 21(0.25 g, 82%) as the hydrochloride. $^1$H NMR (300 MHz, $CD_3OD$) δ 7.70 (d, J=8.3 Hz, 1H, aromatic), 7.53–7.56 (m, 3H, aromatic), 7.37–7.43 (m, 4H, aromatic), 4.68 (dd, J=6.0, 2.9 Hz, 1H, α leu-H), 3.70 (s, 3H, $OCH_3$), 1.63–1.78 (m, 3H, $CH_2CH(CH_3)_2$), 0.86 (d, J=6.2 Hz, 3H, $CH(CH_3)_2$), 0.83 (d, J=6.5 Hz, 3H, $CH(CH_3)_2$); $^{13}$C NMR (75 MHz, $CD_3OD$) δ 174.3, 169.8, 139.3, 134.8, 132.8, 130.9, 130.4, 129.7, 127.6, 124.1, 123.7, 123.5, 96.2, 86.4, 52.8, 41.4, 26.0, 23.2, 21.8; HRMS calc'd for: m/e 364.1787, found 364.1790.

4-[N-(1-Triphenylmethylimidazole-4-yl)methylene[amino-2-(1-phenylethynl)l-leucine Methyl Ester. (22)

Compound 21 (0.25 g, 0.62 mmol) was coupled with 1-triphenylmethylimidazole carboxaldehyde (0.23 g, 0.69 mmol) in a similar manner as described for the preparation of 13 instead however, without the addition of 5% acetic acid to give 22 (0.3 g, 67%) as a white foam.

4-[N-(1-H-Imidazole-4-yl)methylene[amino-2-(1-phenylethynl)benzoyl Leucine Hydrochloride. (23)

Compound 22 was deprotected in a similar manner as described for the deprotection of 14 to give 23 (0.12 g, ) as the TFA salt after purification by reverse phase HPLC. $^1$H NMR.(300 MHz, DMSO-$d_6$) δ 12.00 (br s, 1H), 10.21 (br s, 1H), 8.98 (s, 1H, imidazole), 8.18 (d, J=7.8 Hz, 1H), 7.56 (s, 1H, imidazole), 7.48–7.53 (m, 3H, aromatic), 7.41–7.43 (m, 3H, aromatic), 6.83 (d, J=2.4 Hz, 1H, aromatic), 6.72 (dd, J=8.7, 2.1 Hz, 1H, aromatic), 4.41 (m, 3H), 1.51–1.64 (m, 3H, $CH_2CH(CH_3)_2$), 0.79 (d, 3H, $CH(CH_3)_2$), 0.75 (d, 3H, $CH(CH_3)_2$); $^{13}$C NMR (75 MHz, $CD_3OD$) δ 176.2, 169.7, 151.2, 135.5,;133.8, 132.9, 132.1, 130.2, 129.8, 125.9, 124.0, 123.1, 118.0, 117.6, 113.9, 95.1, 88.8, 52.9, 42.2, 38.5, 26.2, 23.4, 22.1.

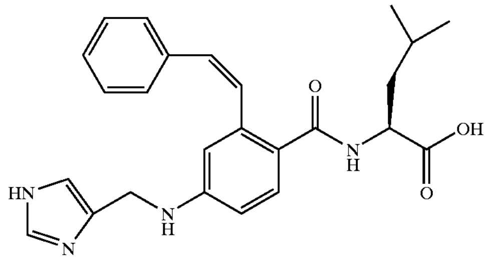

EXAMPLE 1410

4-[N-(1-H-Imidazole-4-yl)methylene[amino-2-(2-phenyl-(Z)-1-ethenyl)benzoyl Leucine Hydrochloride N-[4-Amino-2-(2-phenyl-(Z)-1-ethenyl)benzoyl]-leucine Methyl Ester. (24)

Compound 24 was reduced using a similar procedure for the reduction of compound 15 with raney nickel and hydrazine hydrate in methanol to give 24 (0.18 g, 64%) as the hydrochloride.

4-[N-(1-Triphenylmethylimidazole-4-yl)methylene[amino-2-(2-phenyl-(Z)-1-ethenyl)benzoyl Leucine Methyl Ester. (25)

Compound 24 (0.19 g, 0.52 mmol) was coupled with 1-triphenylmethylimidazole carboxaldehyde (0.19 g, 0.69 mmol) in a similar manner as described for the preparation of 22 to give 25 (0.19 g, 53%) as a white foam. $^1$H NMR (300 MHz, $CDCl_3$) δ 7.75 (d, J=8.6 Hz, 1H, aromatic), 7.44 (s, 1H, imidazole), 7.30–7.36 (m, 9H, trityl), 7.07–7.10 (m, 10H), 6.87 (d, J=12.2 Hz, 1H, cis alkene); $^{13}$C NMR (75 MHz, $CDCl_3$) δ 173.9, 167.8, 150.2, 142.4, 139.0, 138.1, 137.9, 136.2, 131.5, 131.3, 130.2, 129.9, 129.3, 128.3, 128.2, 127.5, 121.9, 119.3, 113.7, 111.9, 75.5, 52.3, 51.5, 41.7, 25.1, 22.9, 22.2.

4-[N-(1-H-Imidazole-4-yl)methylene[amino-2-(2-phenyl-(Z)-1-ethenyl)benzoyl Leucine Hydrochloride. (26)

Compound 25 was deprotected in a similar manner as described for the deprotection of 17 to give 26 (0.028 g, 33%) as the TFA salt after purification by reverse phase HPLC. $^1$H NMR (300 MHz, DMSO-$d_6$) δ 12.00 (br s, 1H), 10.30 (br s, 1H), 8.92 (s, 1H, imidazole), 8.06 (d, J=7.9 Hz, 1H), 7.43 (d, J=8.6 Hz, 1H, aromatic), 7.05–7.14 (m, 4H, aromatic), 6.80 (d, J=12.2 Hz, 1H, cis alkene), 6.58 (dd, J=8.5, 2.1 Hz, 1H, aromatic), 6.46 (d, J=12.3 Hz, 1H, cis alkene), 6.32 (d, J=2.0 Hz, 1H), 4.30 (dd, J=7.8, 4.8 Hz, 1H, α leu-H), 4.16 (s, 3H, $CH_2NH$), 1.61–1.68 (m, 2H, $CH_2CH(CH_3)_2$), 1.48–1.52 (m, 1H, $CH_2CH(CH_3)_2$), 0.86 (d, J=6.1 Hz, 3H, $CH(CH_3)_2$), 0.82 (d, J=6.2 Hz, $CH(CH_3)_2$); $^{13}$C NMR (75 MHz, $CD_3OD$) δ 176.4, 171.7, 151.1, 139.8, 138.3, 135.3, 134.2, 131.8, 131.2, 131.1, 130.4, 129.2, 128.3, 125.1, 117.4, 114.0, 113.2, 52.7, 41.8, 38.7, 26.3, 23.5, 22.0.

TABLE 6

Amines of the Type A(B)N-$L_1$

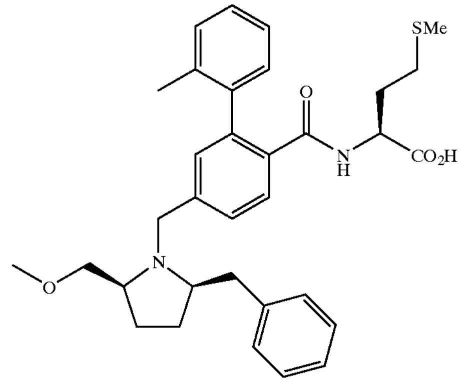

1

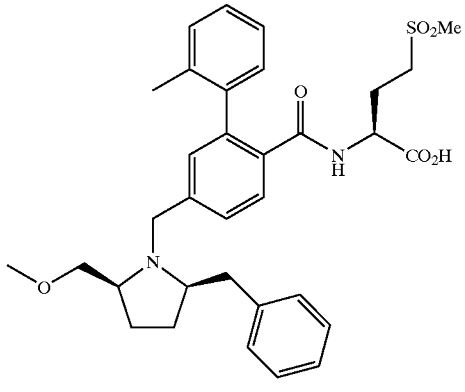

2

TABLE 6-continued
Amines of the Type A(B)N-$L_1$
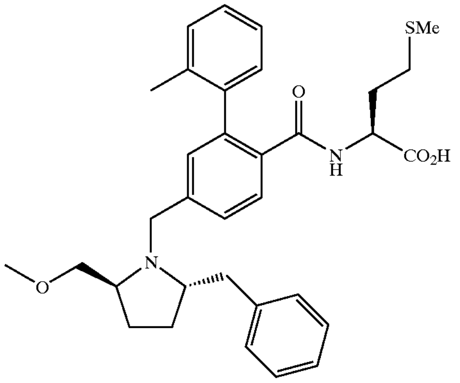
3
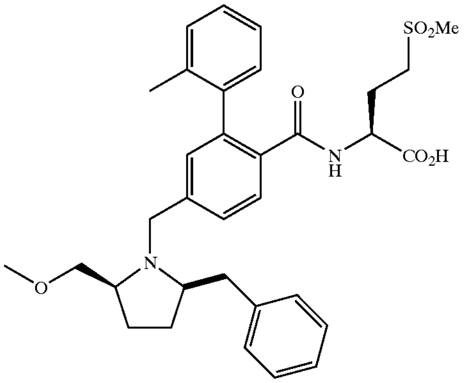
4
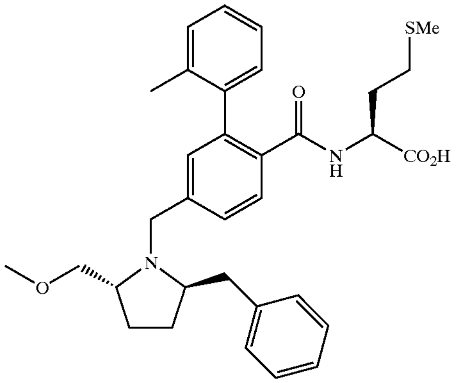
5
TABLE 6-continued
Amines of the Type A(B)N-$L_1$
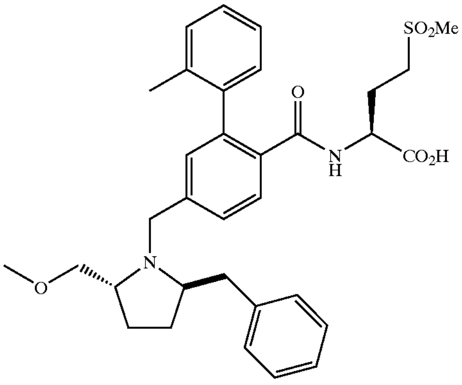
6
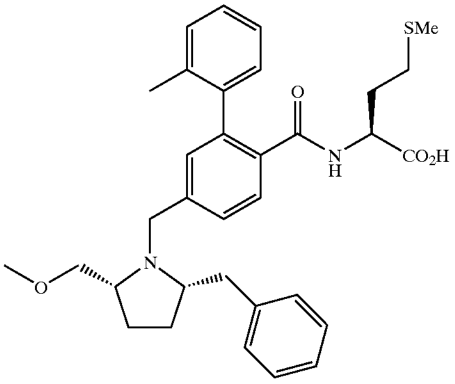
7
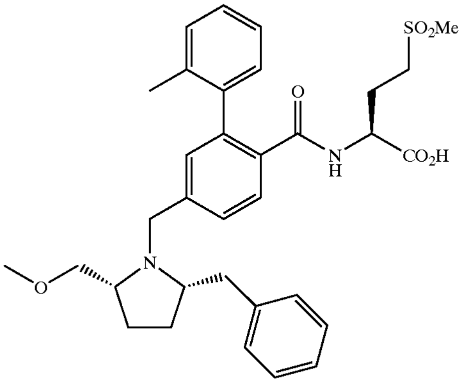
8

TABLE 6-continued
| Amines of the Type A(B)N-$L_1$ |
| --- |
| 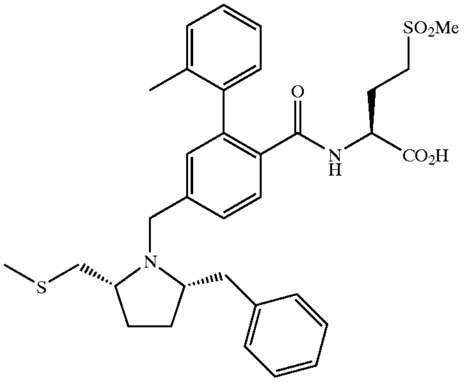 |
| 9 |
| 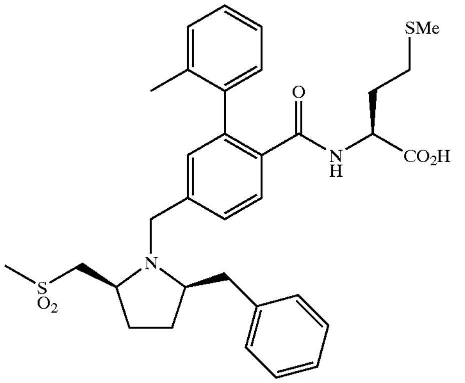 |
| 10 |
| 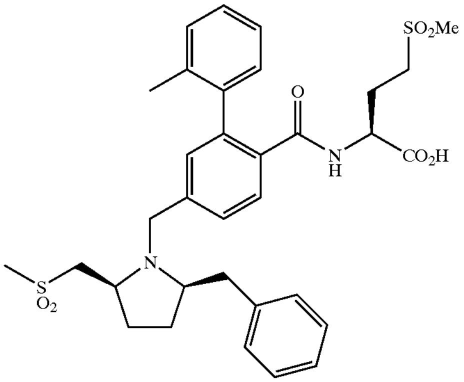 |
| 11 |
TABLE 6-continued
| Amines of the Type A(B)N-$L_1$ |
| --- |
| 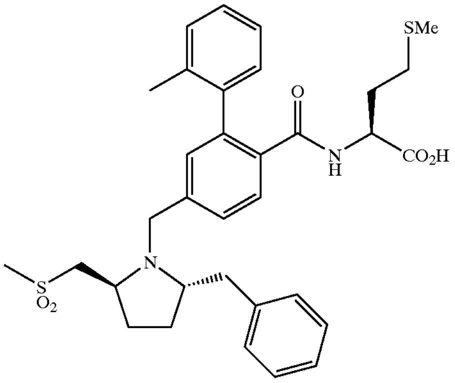 |
| 12 |
| 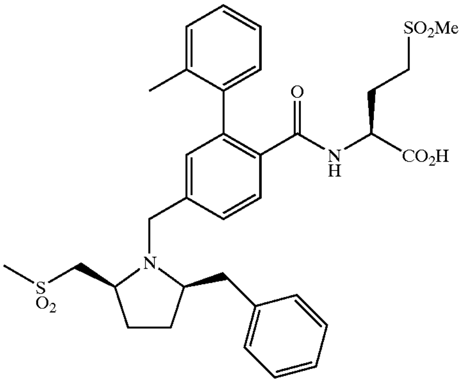 |
| 13 |
| 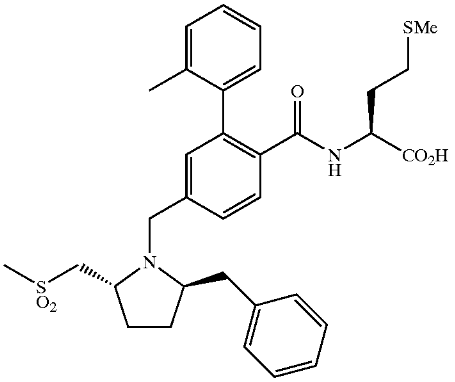 |
| 14 |

TABLE 6-continued
| Amines of the Type A(B)N-$L_1$ |
|---|
| 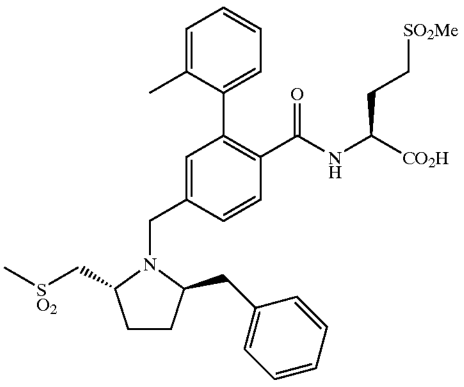 |
| 15 |
| 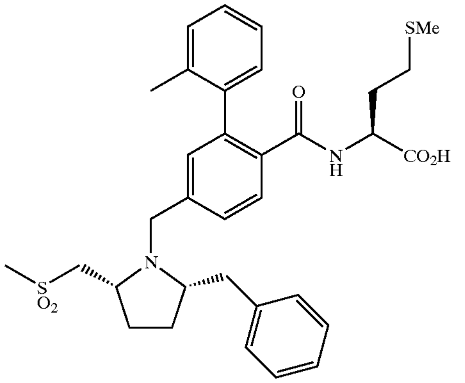 |
| 16 |
| 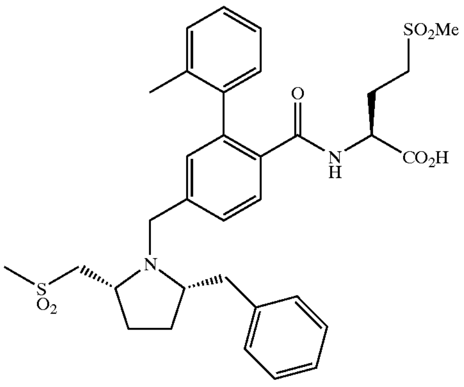 |
| 17 |
TABLE 6-continued
| Amines of the Type A(B)N-$L_1$ |
|---|
| 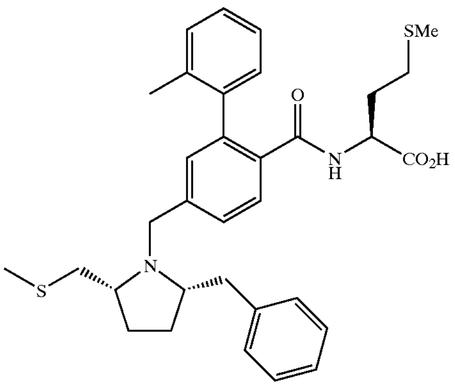 |
| 18 |
| 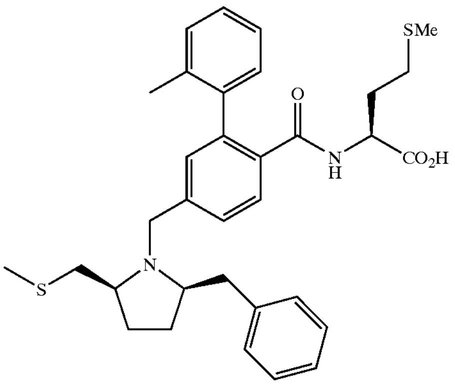 |
| 19 |
| 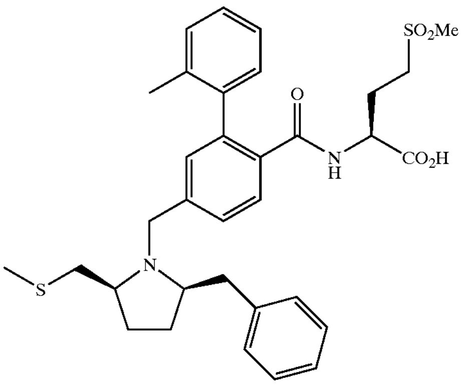 |
| 20 |

TABLE 6-continued
| Amines of the Type A(B)N-$L_1$ |
|---|
| 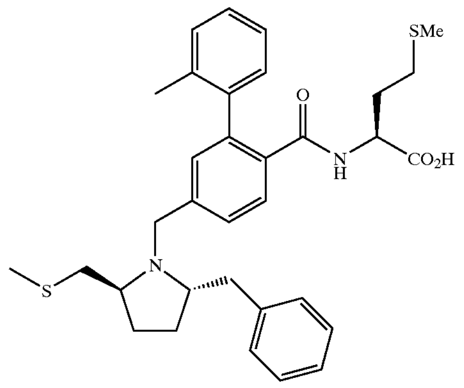 |
| 21 |
| 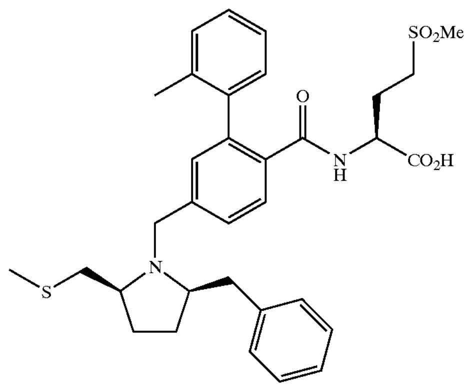 |
| 22 |
| 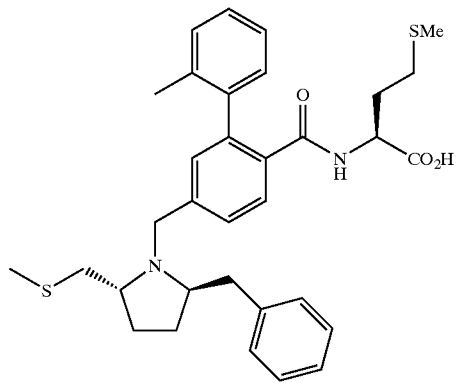 |
| 23 |
TABLE 6-continued
| Amines of the Type A(B)N-$L_1$ |
|---|
| 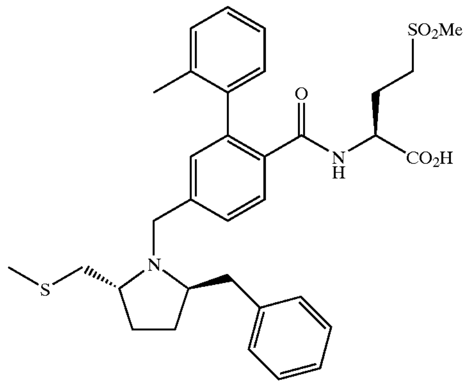 |
| 24 |
| 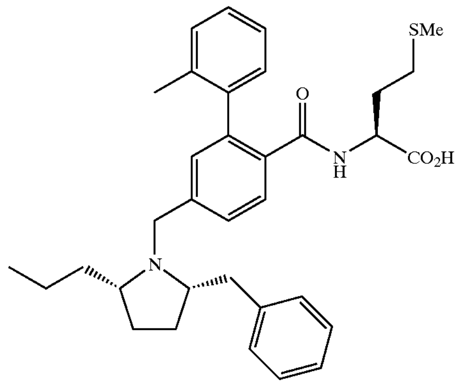 |
| 25 |
| 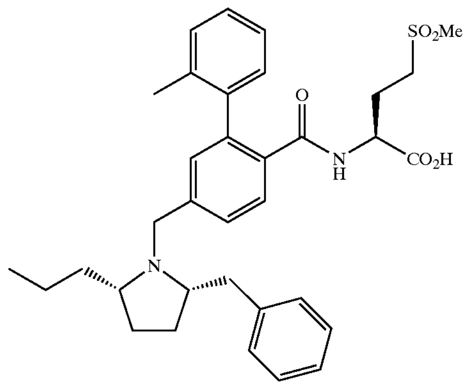 |
| 26 |

TABLE 6-continued
| Amines of the Type A(B)N-$L_1$ |
| --- |
| 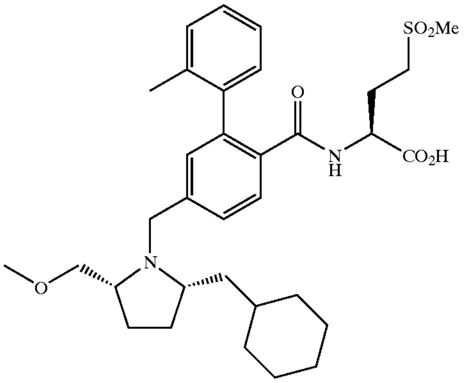 |
| 27 |
| 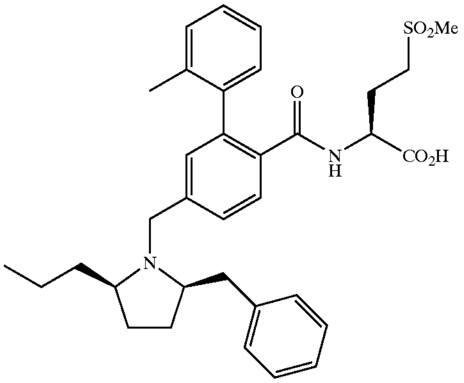 |
| 28 |
| 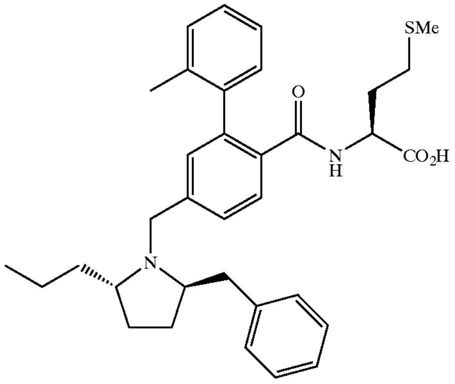 |
| 29 |
TABLE 6-continued
| Amines of the Type A(B)N-$L_1$ |
| --- |
| 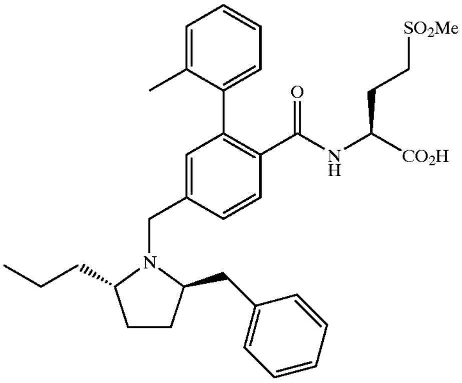 |
| 30 |
| 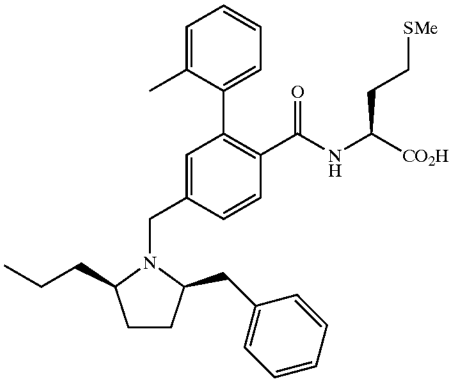 |
| 31 |
| 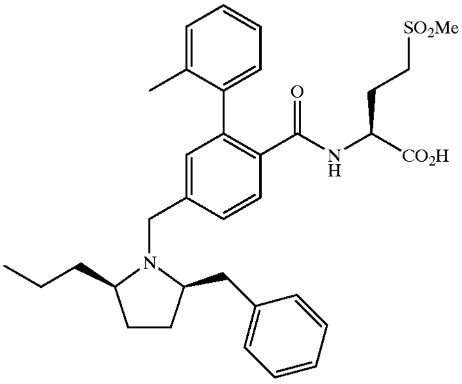 |
| 32 |

TABLE 6-continued
Amines of the Type A(B)N-$L_1$
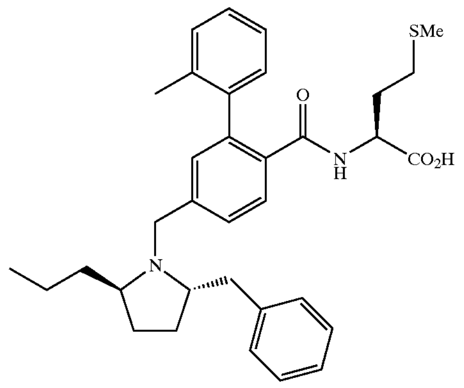
33
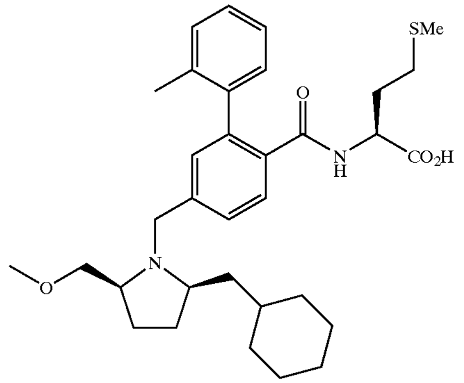
34
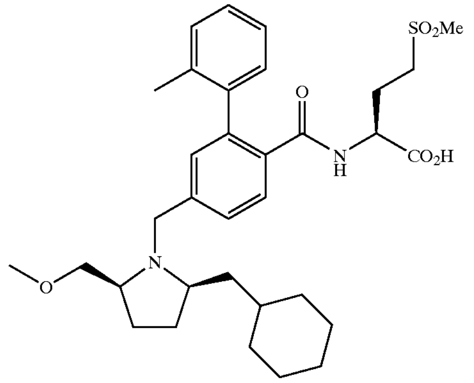
35
TABLE 6-continued
Amines of the Type A(B)N-$L_1$
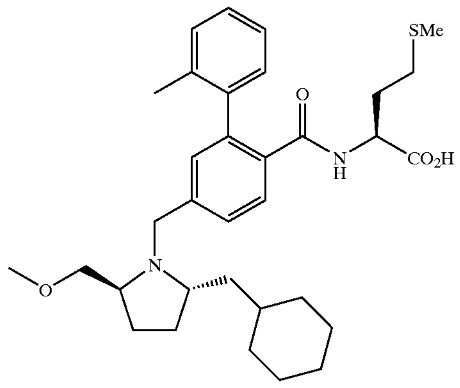
36
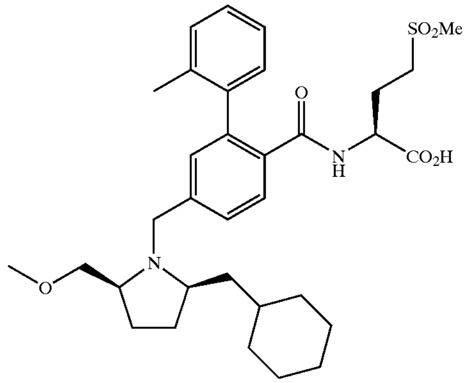
37
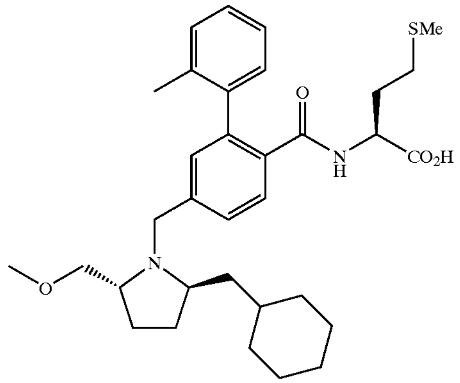
38

TABLE 6-continued
Amines of the Type A(B)N-$L_1$
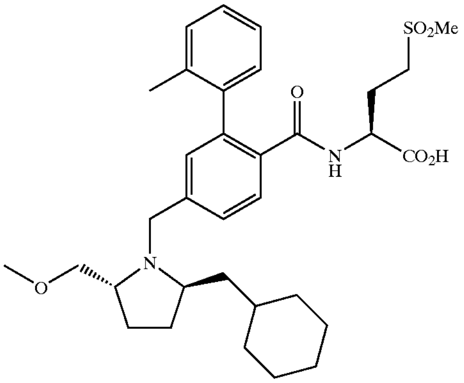
39
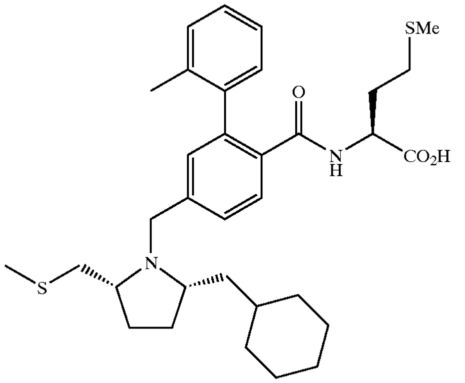
40
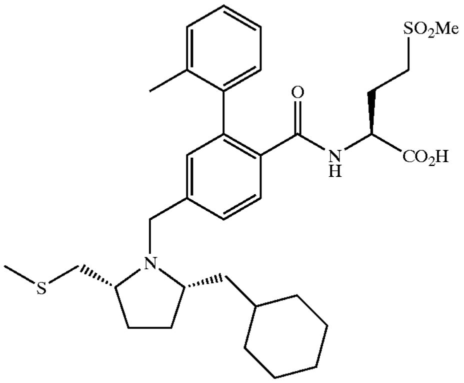
41
TABLE 6-continued
Amines of the Type A(B)N-$L_1$
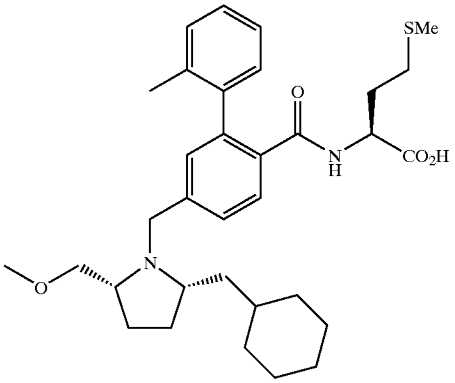
42
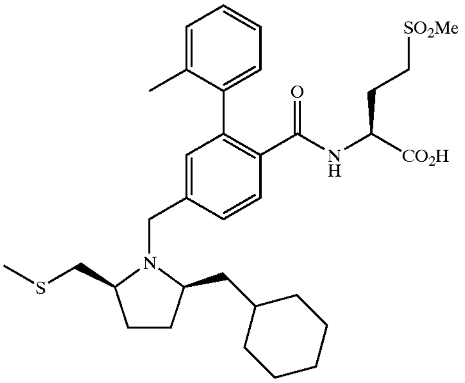
43
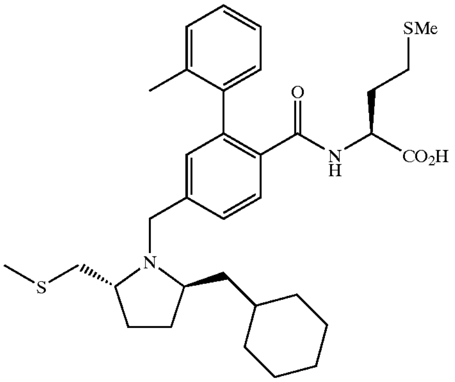
44

TABLE 6-continued
| Amines of the Type A(B)N-$L_1$ |
|---|
| 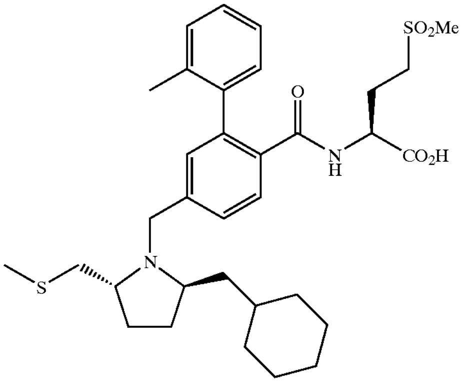 |
| 45 |
| 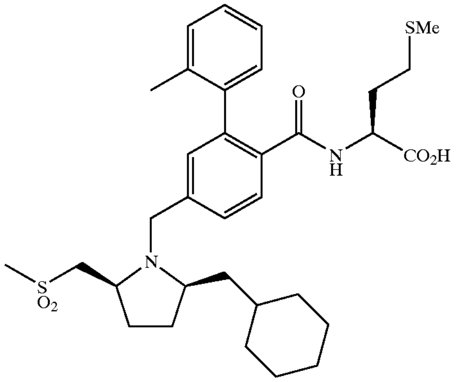 |
| 46 |
| 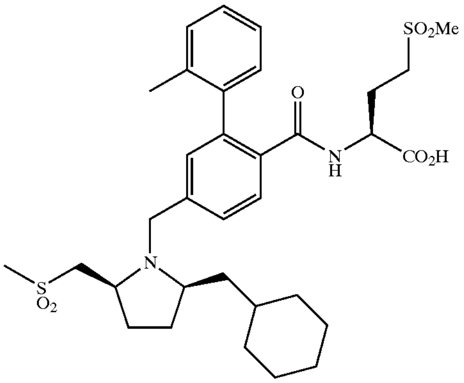 |
| 47 |
TABLE 6-continued
| Amines of the Type A(B)N-$L_1$ |
|---|
| 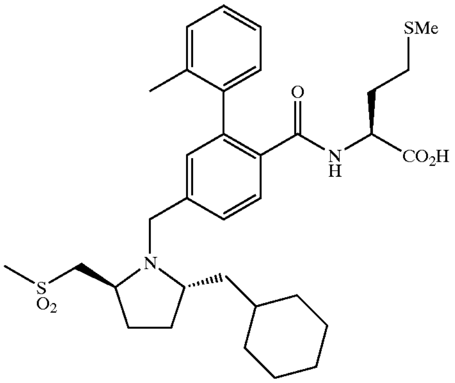 |
| 48 |
| 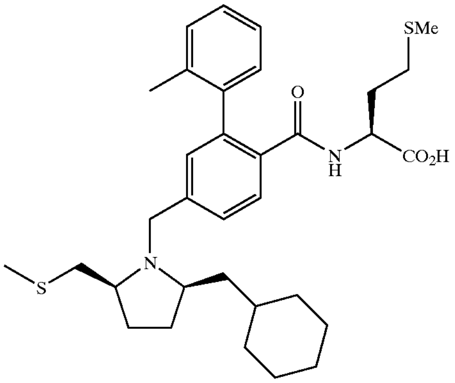 |
| 49 |
| 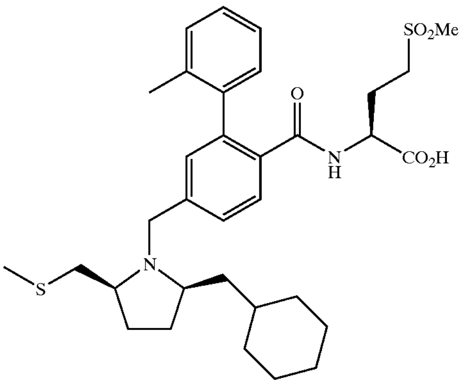 |
| 50 |

TABLE 6-continued
Amines of the Type A(B)N-$L_1$
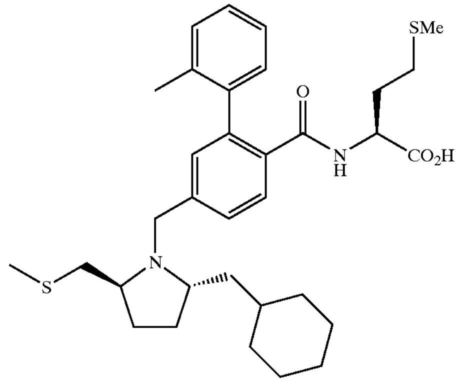
51
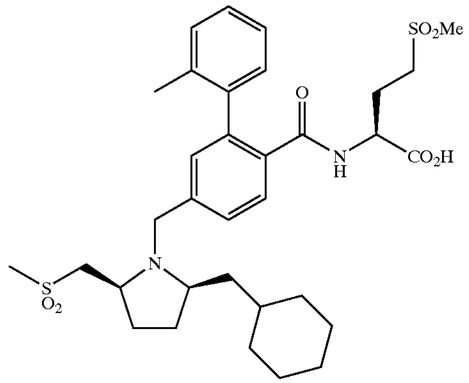
52
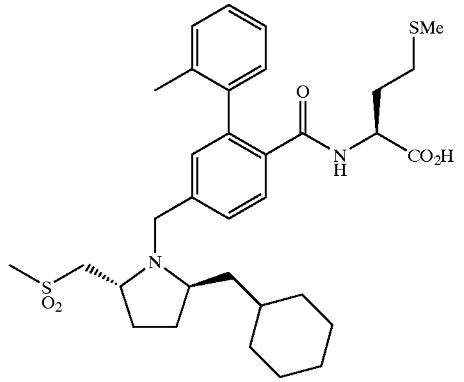
53
TABLE 6-continued
Amines of the Type A(B)N-$L_1$
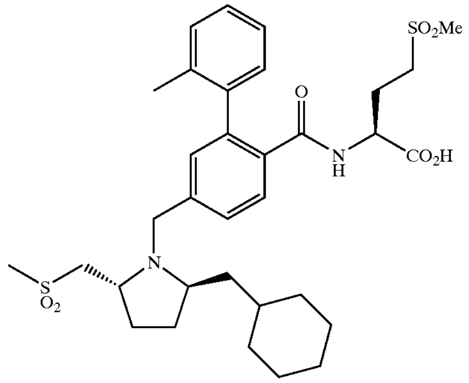
54
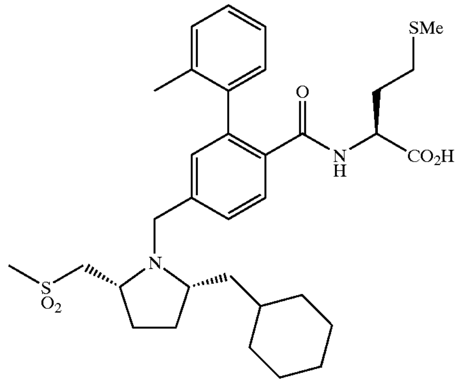
55
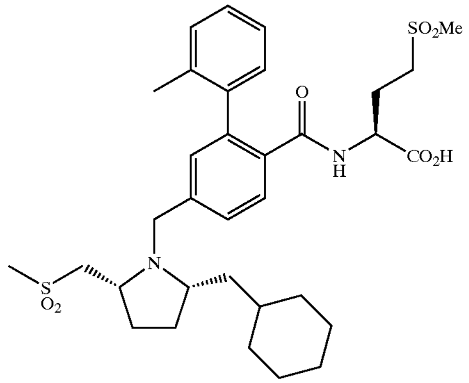
56

TABLE 6-continued
| Amines of the Type A(B)N-$L_1$ |
|---|
| 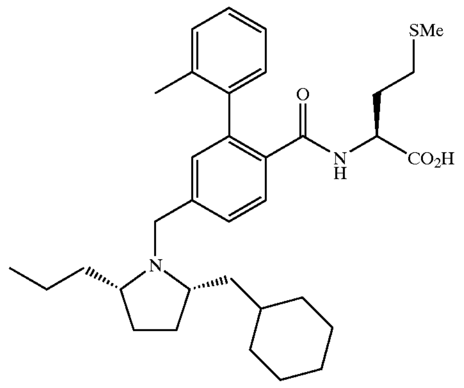 |
| 57 |
| 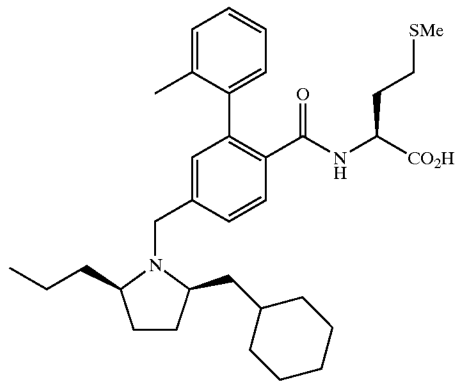 |
| 58 |
| 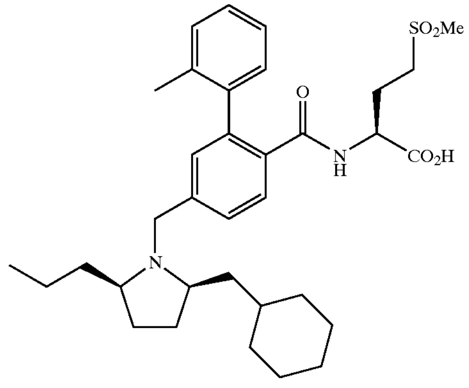 |
| 59 |
TABLE 6-continued
| Amines of the Type A(B)N-$L_1$ |
|---|
| 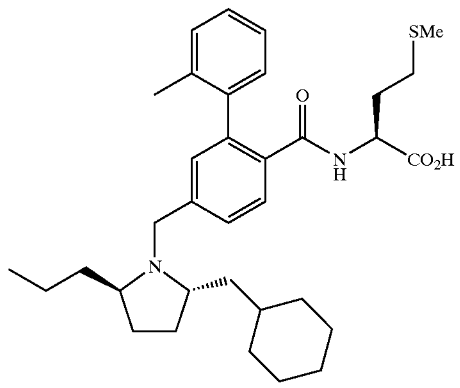 |
| 60 |
| 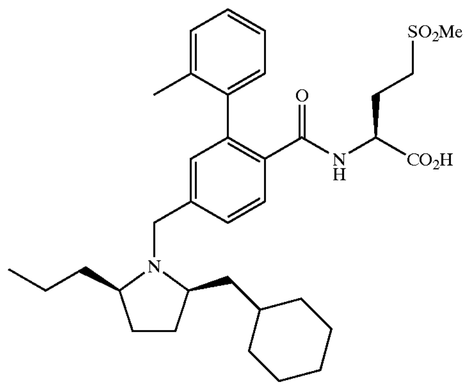 |
| 61 |
| 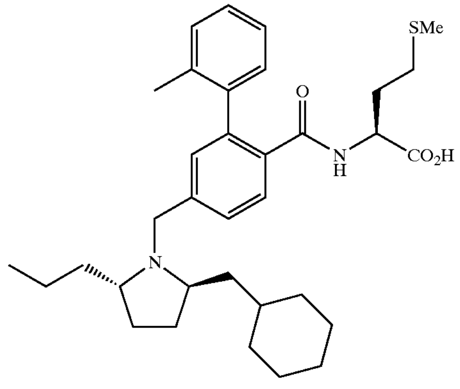 |
| 62 |

TABLE 6-continued
| Amines of the Type A(B)N-$L_1$ |
|---|
| 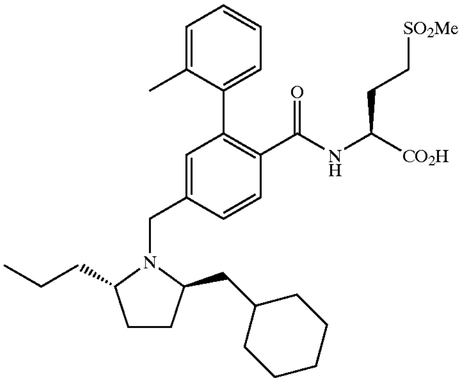 |
| 63 |
| 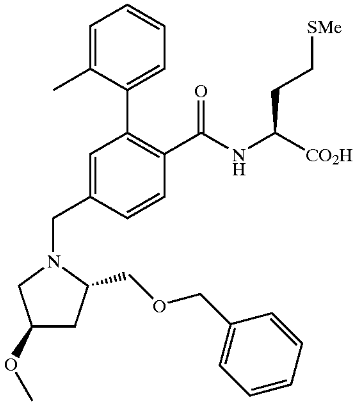 |
| 64 |
| 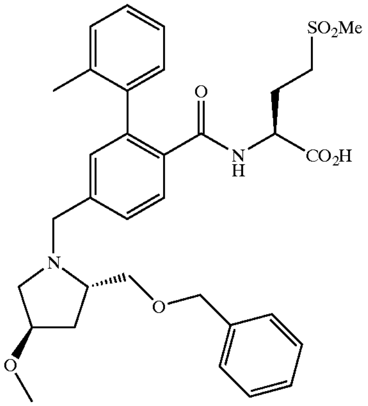 |
| 65 |
TABLE 6-continued
| Amines of the Type A(B)N-$L_1$ |
|---|
| 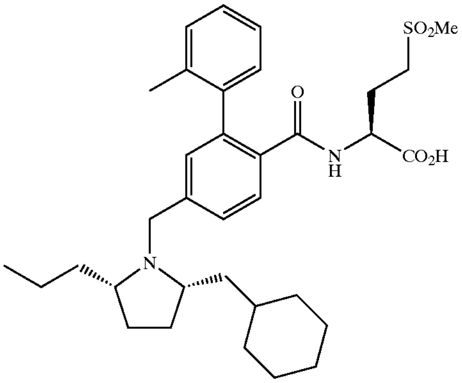 |
| 66 |
| 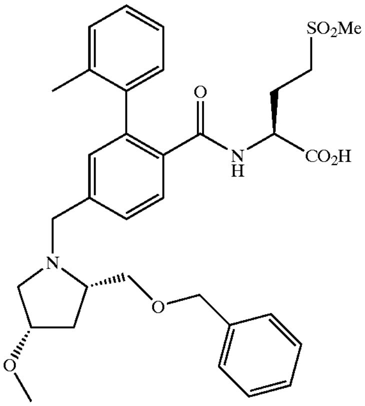 |
| 67 |
| 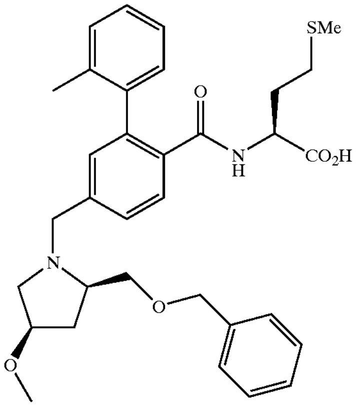 |
| 68 |

TABLE 6-continued
Amines of the Type A(B)N-$L_1$
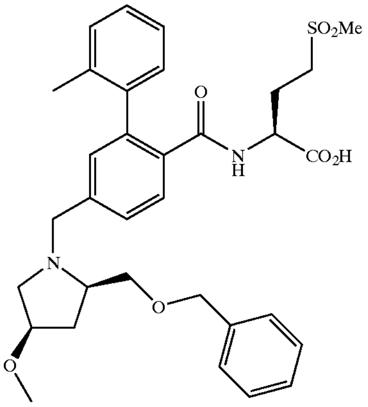
69
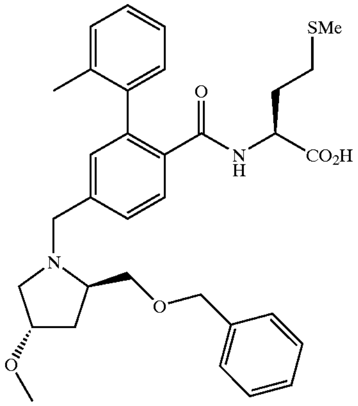
70
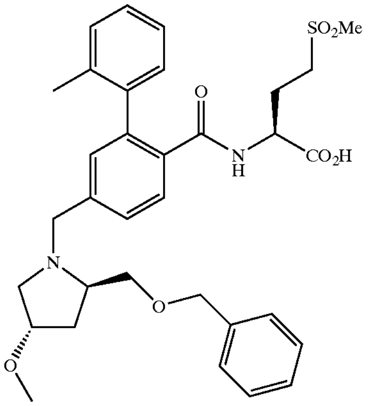
71
TABLE 6-continued
Amines of the Type A(B)N-$L_1$
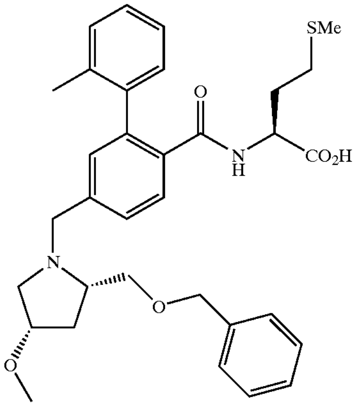
72
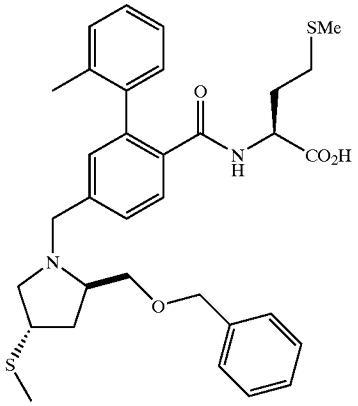
73
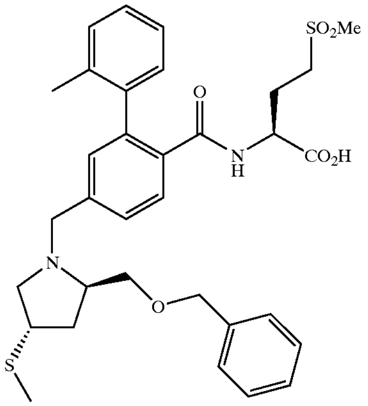
74

TABLE 6-continued
Amines of the Type A(B)N-$L_1$
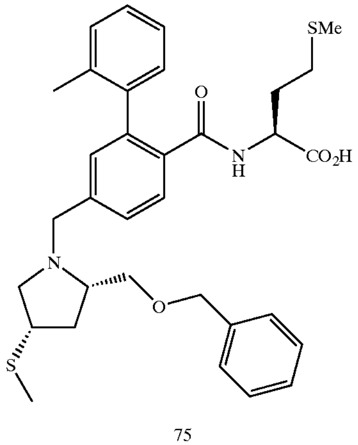
75
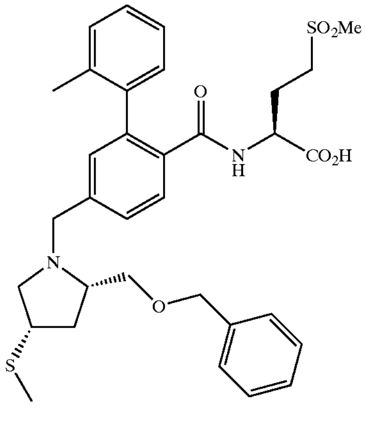
76
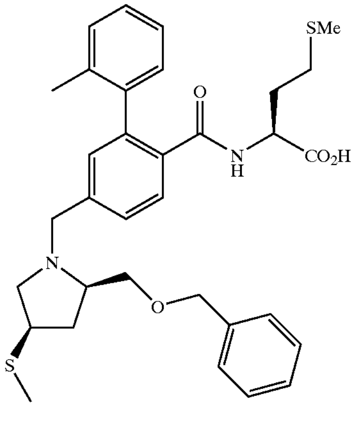
77
TABLE 6-continued
Amines of the Type A(B)N-$L_1$
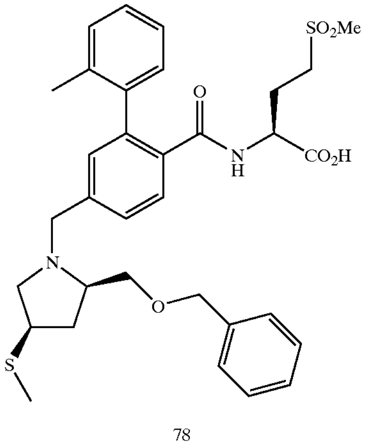
78
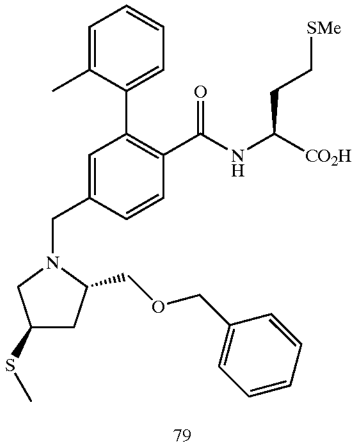
79
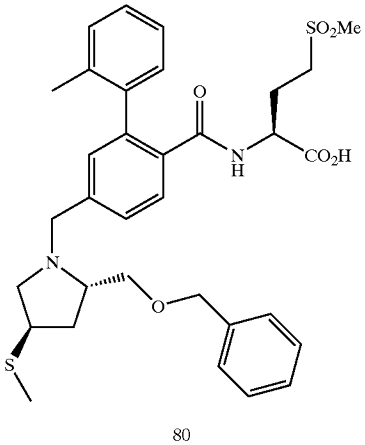
80

TABLE 6-continued
| Amines of the Type A(B)N-$L_1$ |
|---|
| 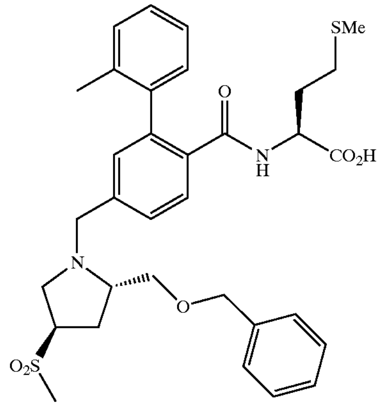 |
| 81 |
| 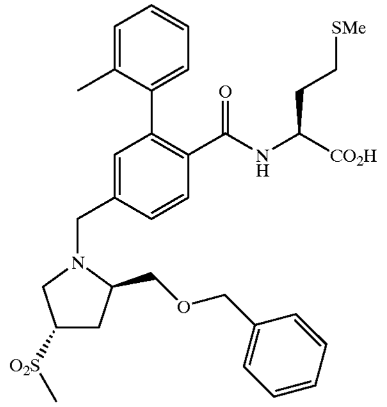 |
| 82 |
| 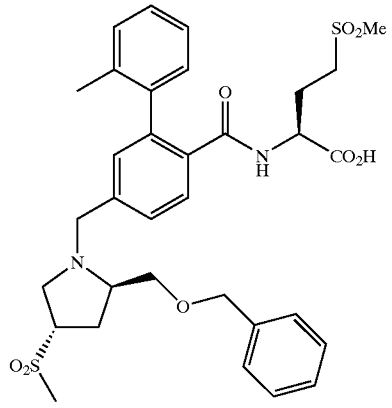 |
| 83 |
TABLE 6-continued
| Amines of the Type A(B)N-$L_1$ |
|---|
| 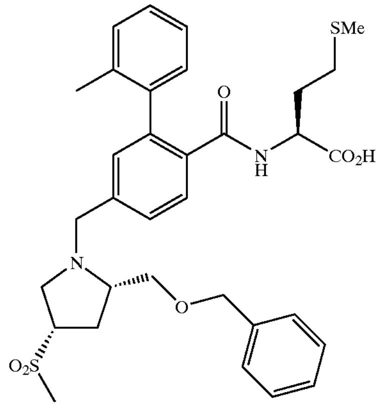 |
| 84 |
| 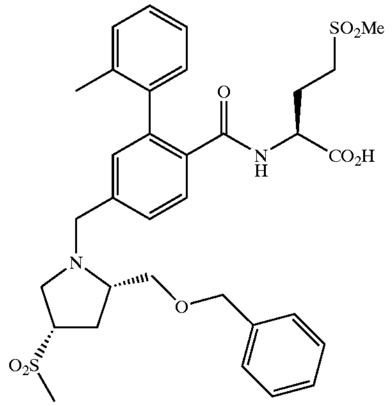 |
| 85 |
| 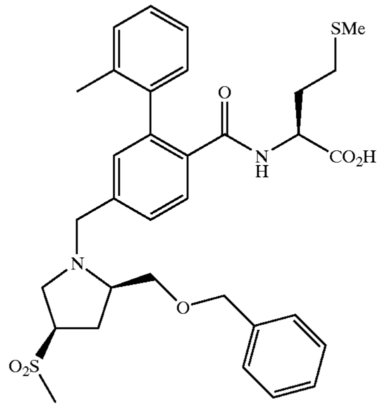 |
| 86 |

TABLE 6-continued
Amines of the Type A(B)N-$L_1$
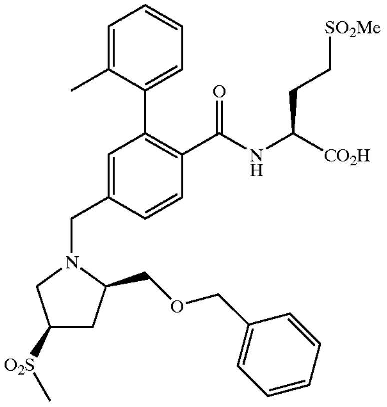
87
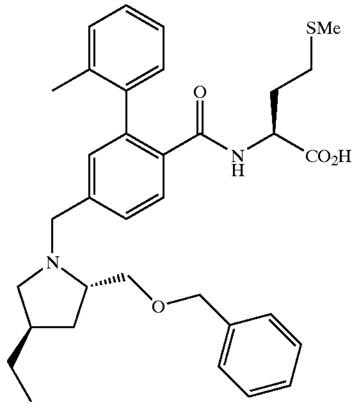
88
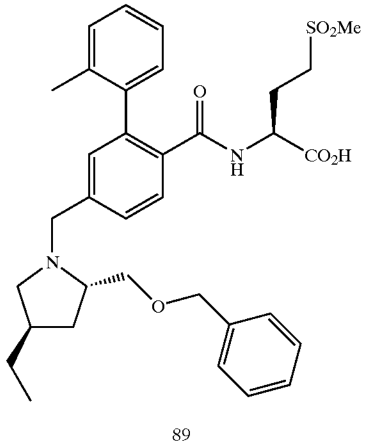
89
TABLE 6-continued
Amines of the Type A(B)N-$L_1$
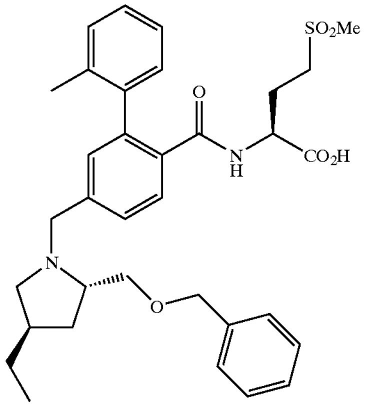
90
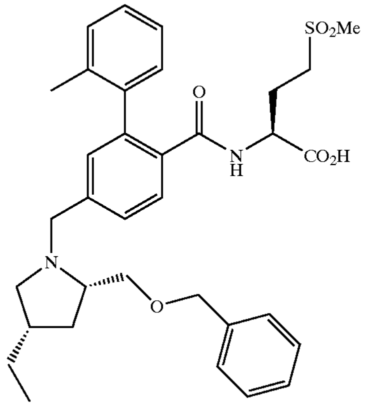
91
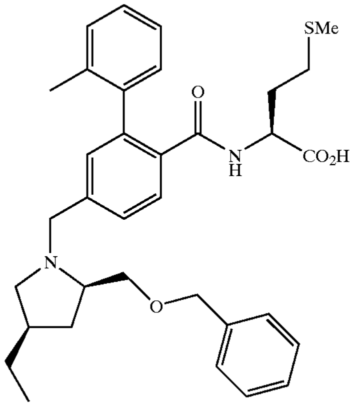
92

TABLE 6-continued
| Amines of the Type A(B)N-$L_1$ |
| --- |
| 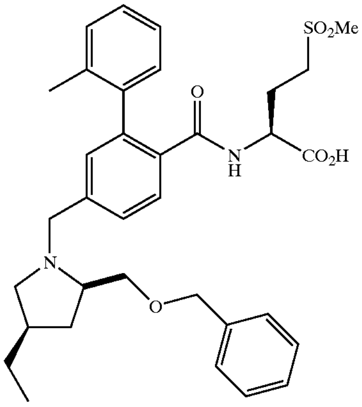 93 |
| 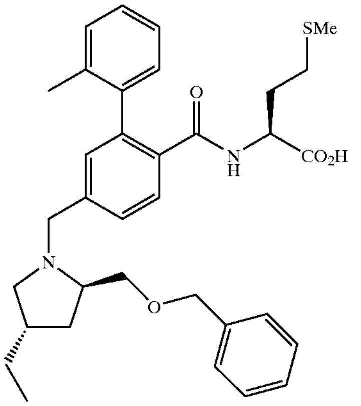 94 |
| 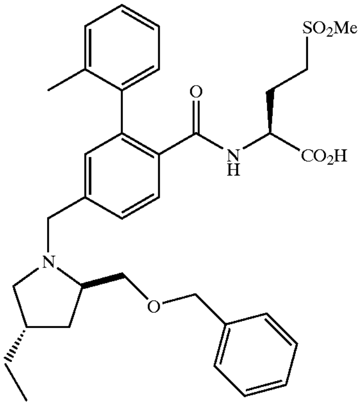 95 |
TABLE 6-continued
| Amines of the Type A(B)N-$L_1$ |
| --- |
| 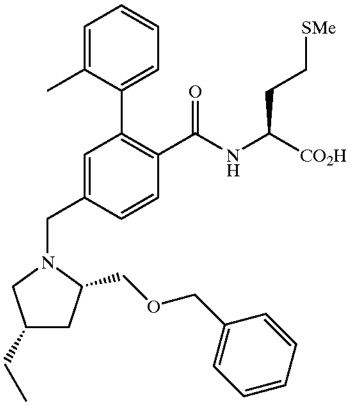 96 |
| 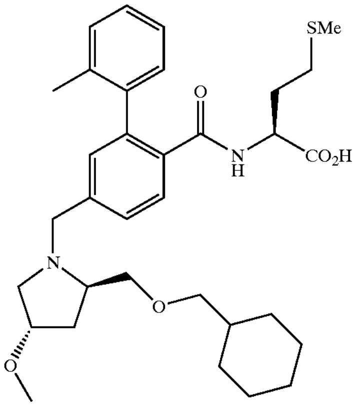 97 |
| 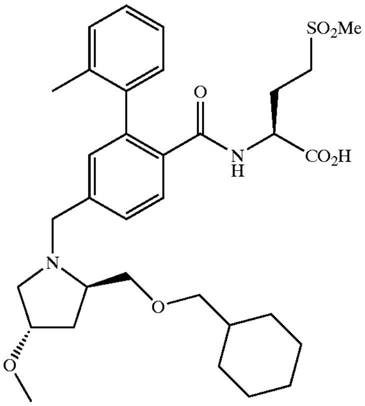 98 |

TABLE 6-continued
| Amines of the Type A(B)N-$L_1$ |
|---|
| 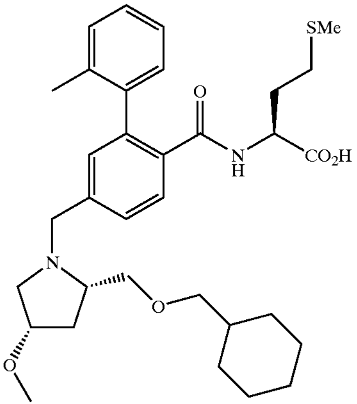 |
| 99 |
| 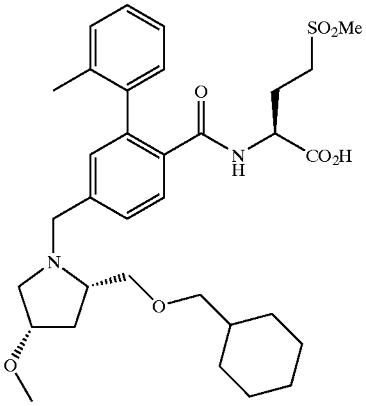 |
| 100 |
| 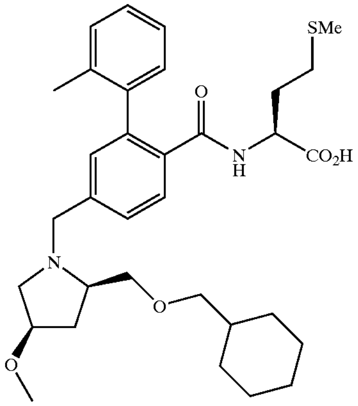 |
| 101 |
TABLE 6-continued
| Amines of the Type A(B)N-$L_1$ |
|---|
| 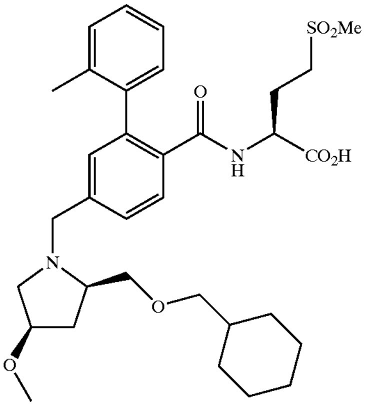 |
| 102 |
| 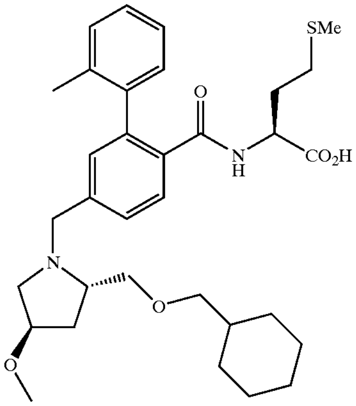 |
| 103 |
| 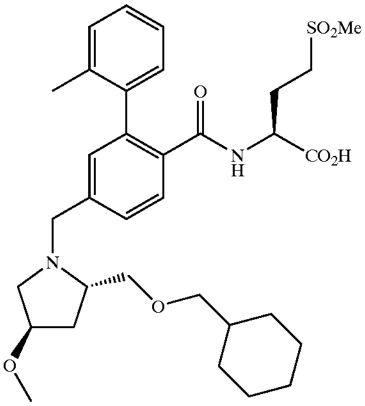 |
| 104 |

TABLE 6-continued
Amines of the Type A(B)N-$L_1$
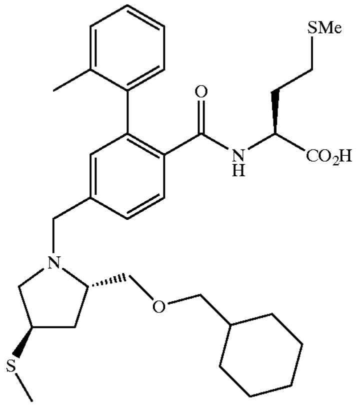
105
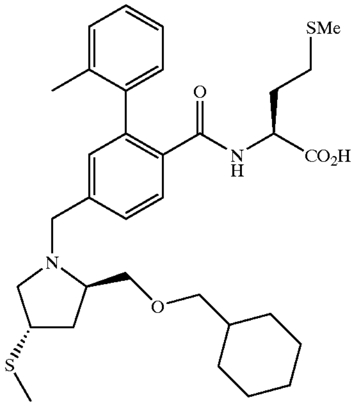
106
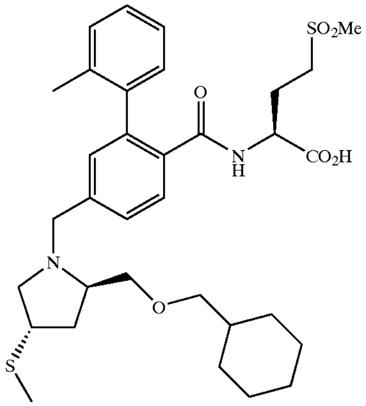
107
TABLE 6-continued
Amines of the Type A(B)N-$L_1$
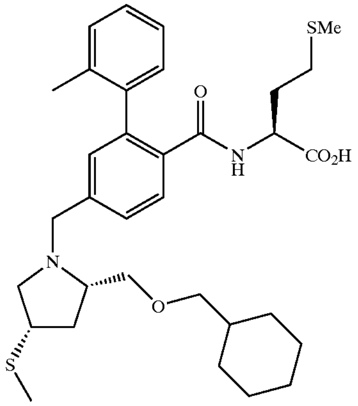
108
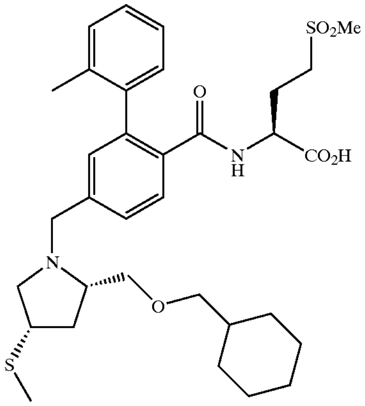
109
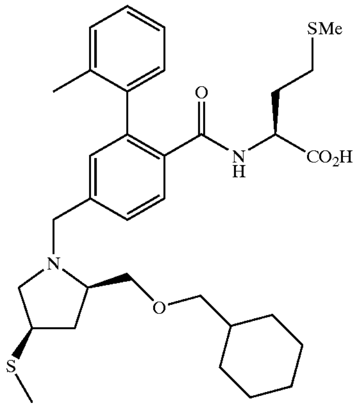
110

TABLE 6-continued
Amines of the Type A(B)N-$L_1$
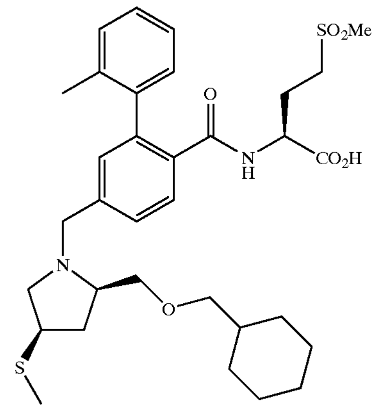
111
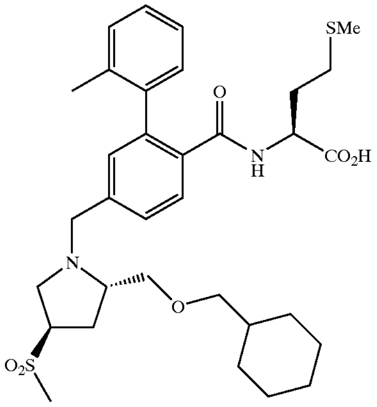
112
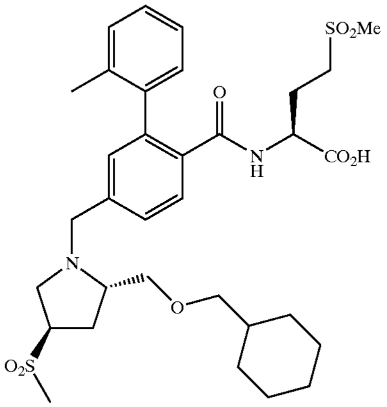
113
TABLE 6-continued
Amines of the Type A(B)N-$L_1$
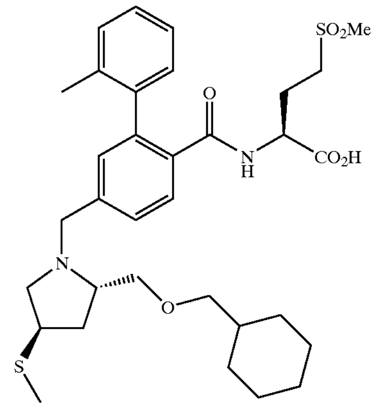
114
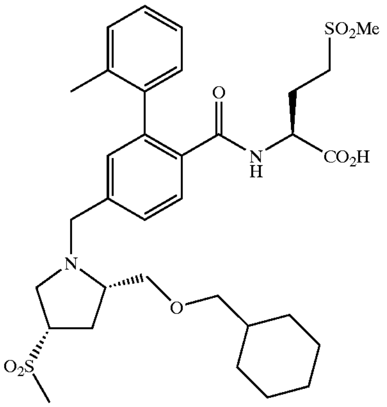
115
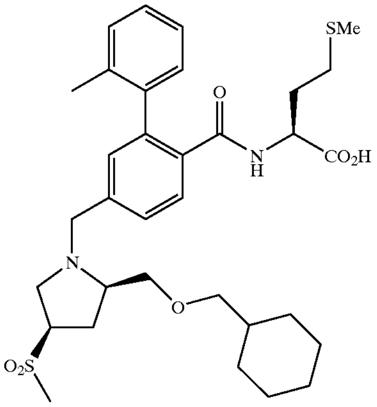
116

TABLE 6-continued
Amines of the Type A(B)N-$L_1$
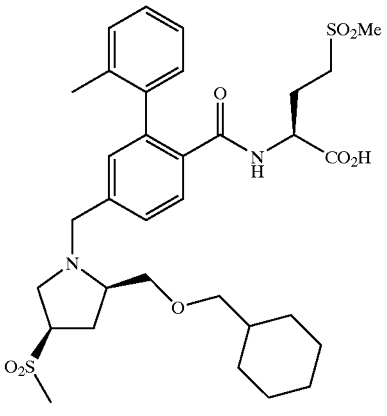
117
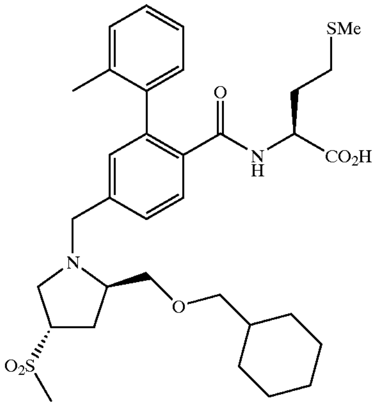
118
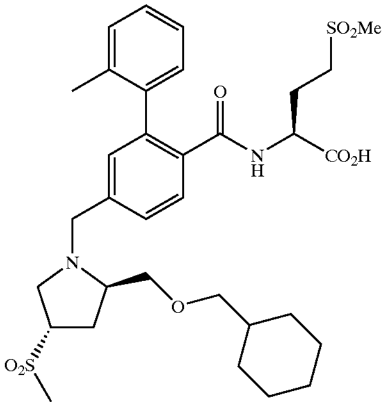
119
TABLE 6-continued
Amines of the Type A(B)N-$L_1$
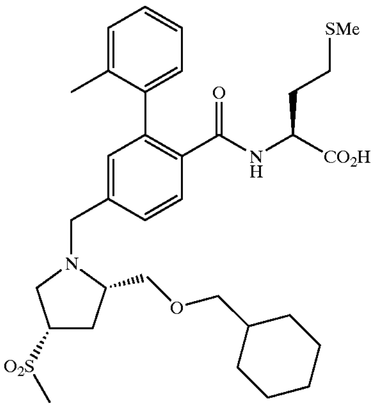
120
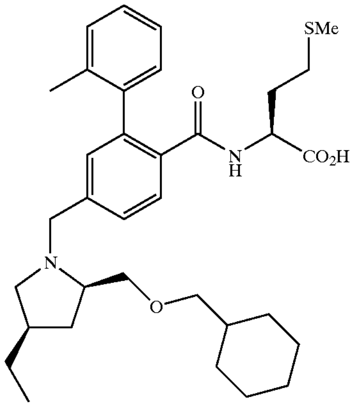
121
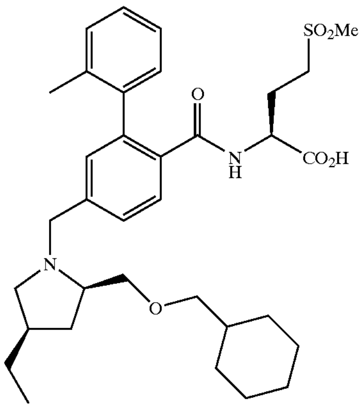
122

TABLE 6-continued
Amines of the Type A(B)N-$L_1$
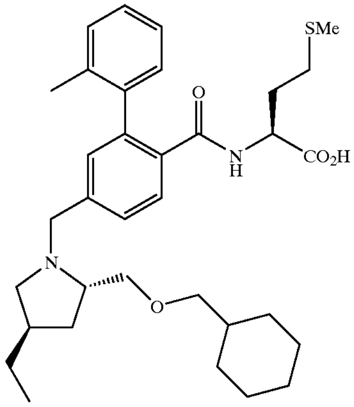
123
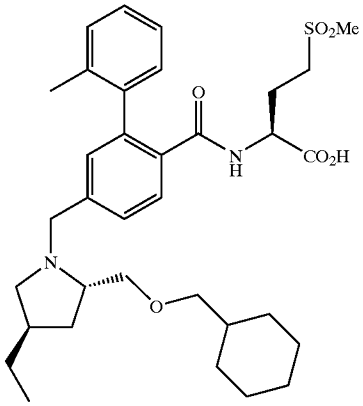
124
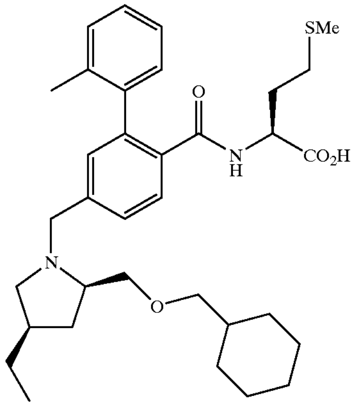
125
TABLE 6-continued
Amines of the Type A(B)N-$L_1$
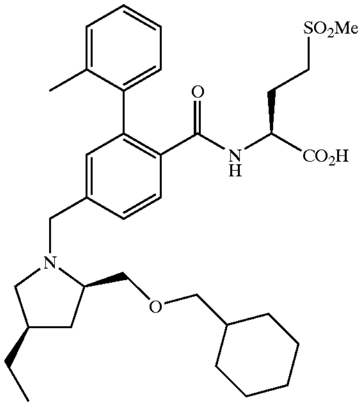
126
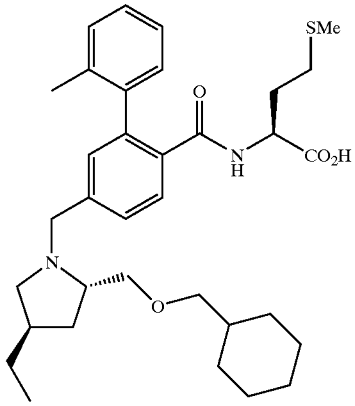
127
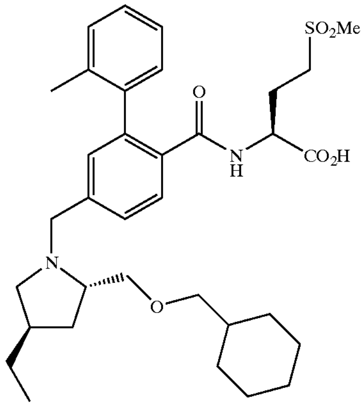
128

TABLE 6-continued
Amines of the Type A(B)N-$L_1$
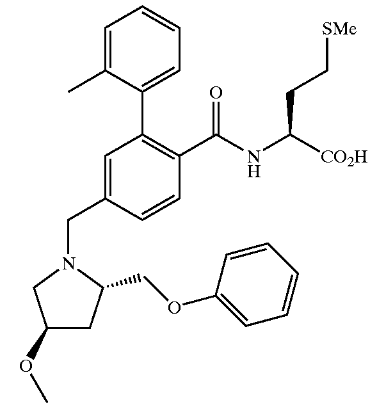
129
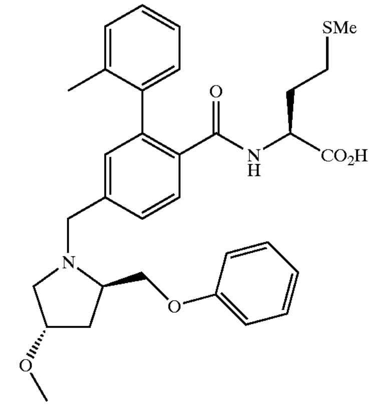
130
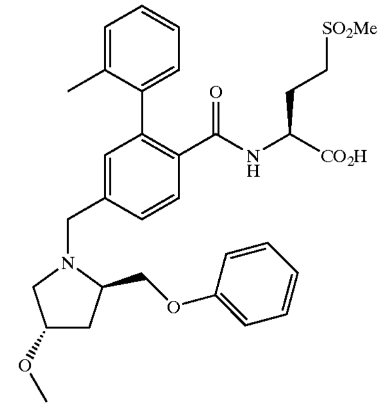
131
TABLE 6-continued
Amines of the Type A(B)N-$L_1$
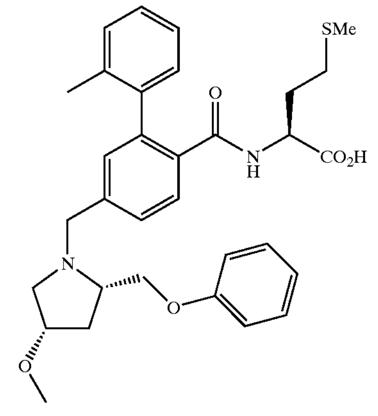
132
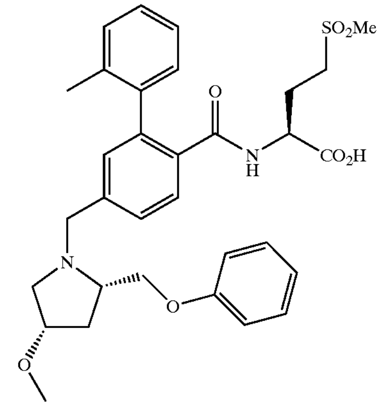
133
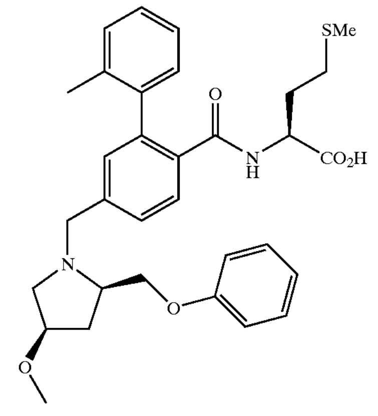
134

TABLE 6-continued
| Amines of the Type A(B)N-$L_1$ |
| --- |
| 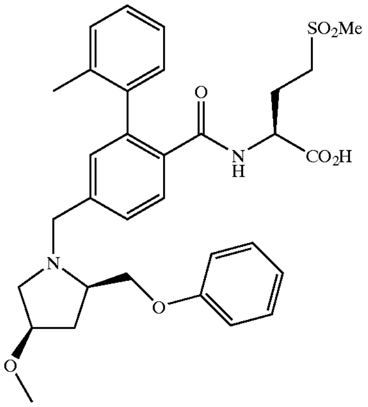 |
| 135 |
| 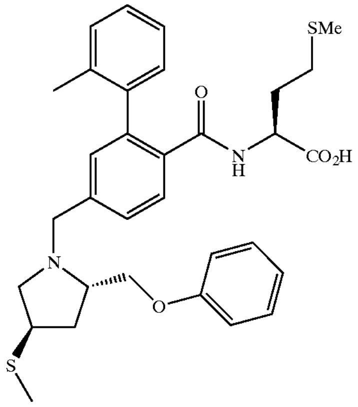 |
| 136 |
| 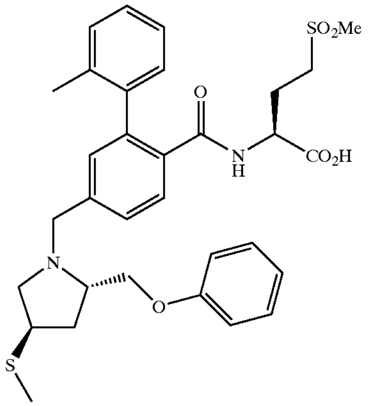 |
| 137 |
TABLE 6-continued
| Amines of the Type A(B)N-$L_1$ |
| --- |
| 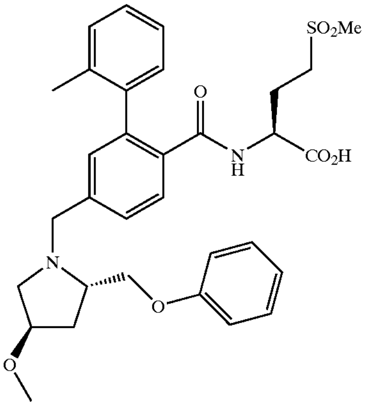 |
| 138 |
| 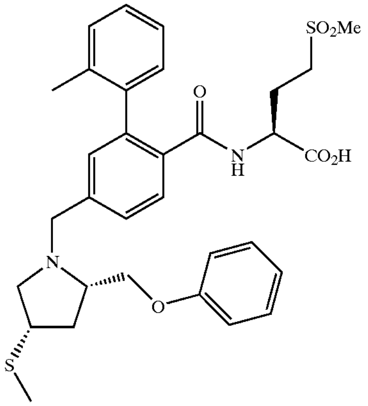 |
| 139 |
| 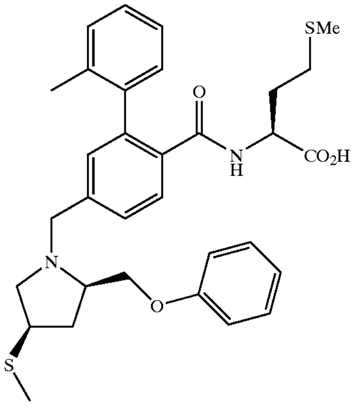 |
| 140 |

TABLE 6-continued
Amines of the Type A(B)N-$L_1$
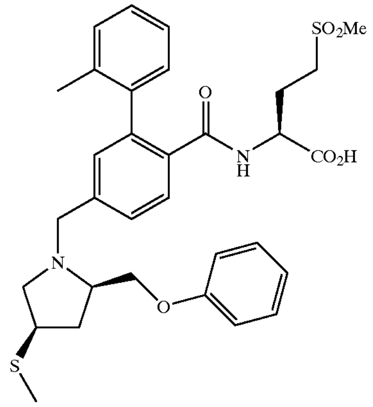
141
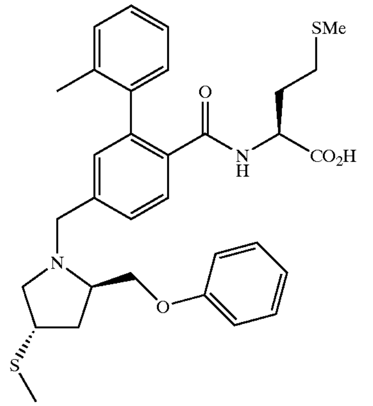
142
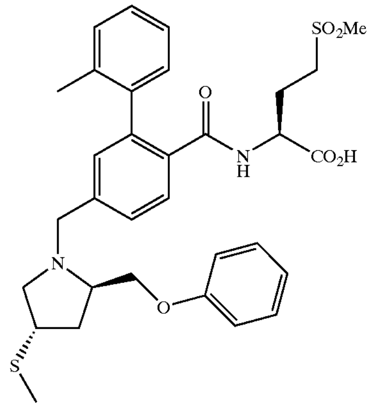
143
TABLE 6-continued
Amines of the Type A(B)N-$L_1$
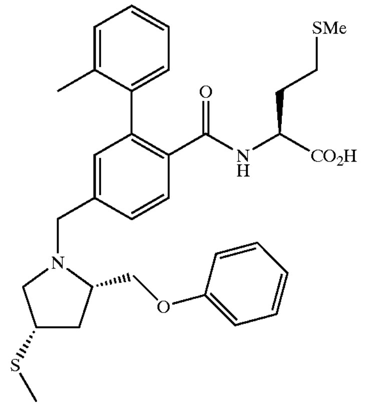
144
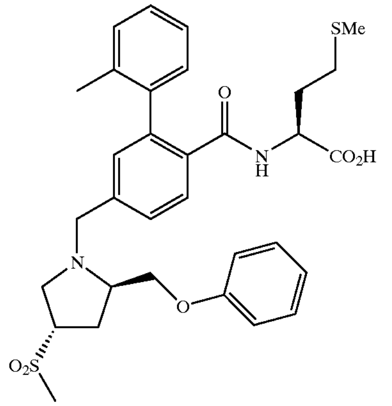
145
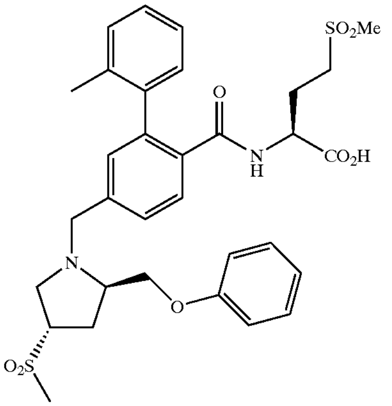
146

TABLE 6-continued
Amines of the Type A(B)N-$L_1$
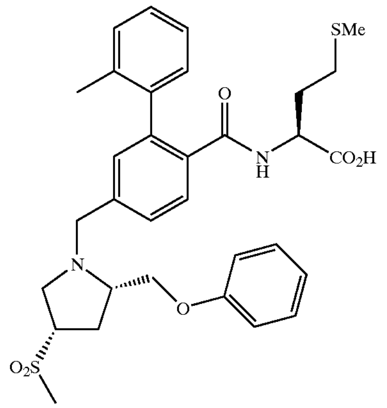
147
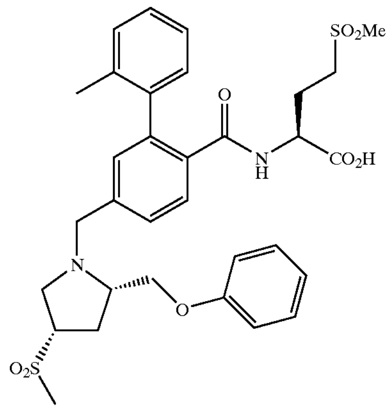
148
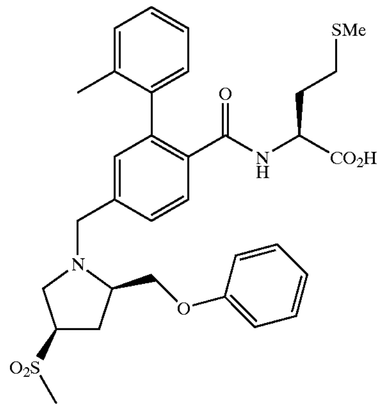
149
TABLE 6-continued
Amines of the Type A(B)N-$L_1$
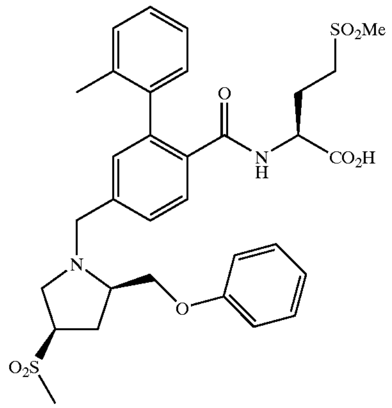
150
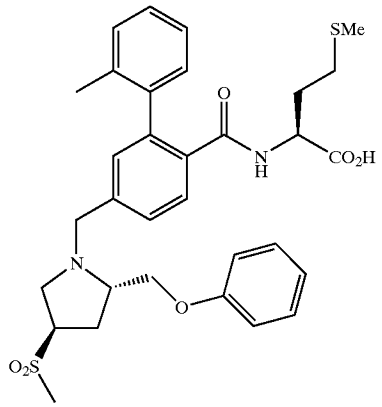
151
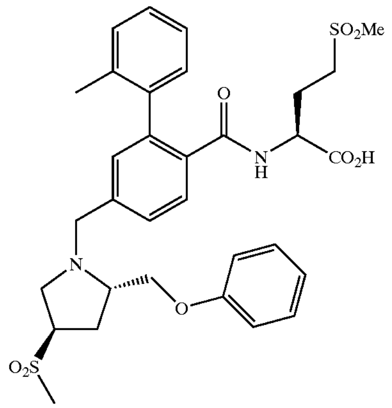
152

TABLE 6-continued
Amines of the Type A(B)N-$L_1$
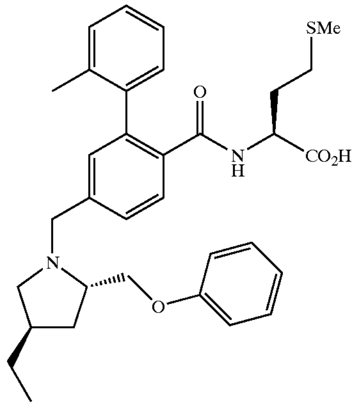
153
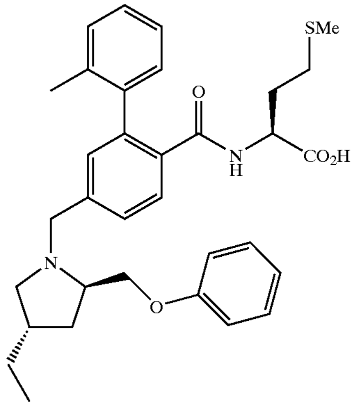
154
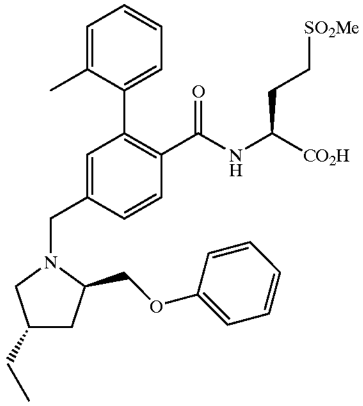
155
TABLE 6-continued
Amines of the Type A(B)N-$L_1$
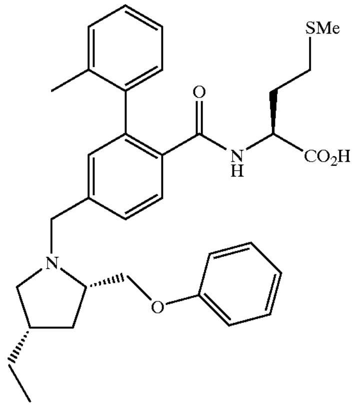
156
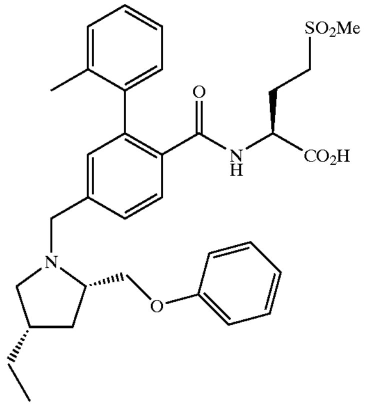
157
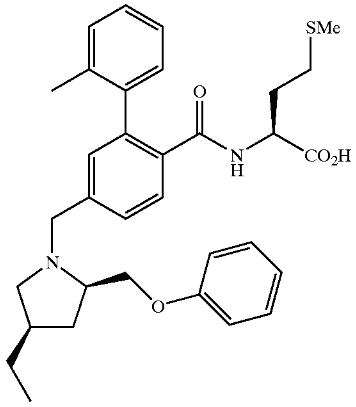
158

TABLE 6-continued
Amines of the Type A(B)N-$L_1$
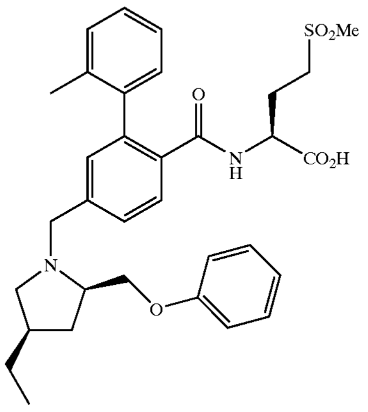
159
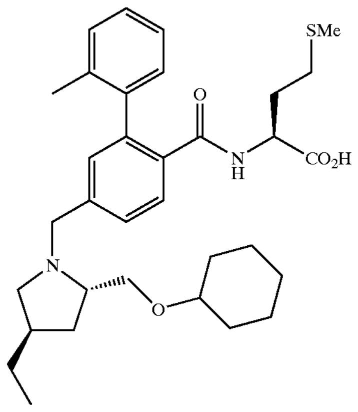
160
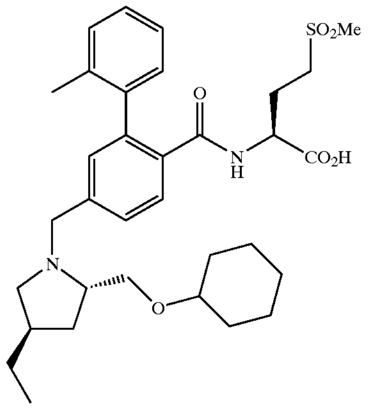
161
TABLE 6-continued
Amines of the Type A(B)N-$L_1$
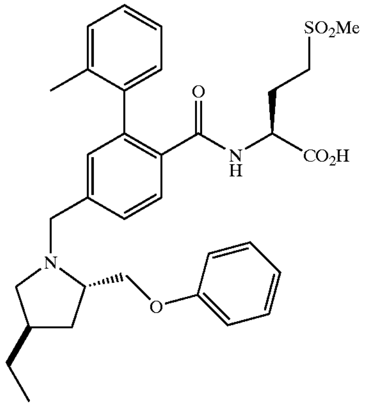
162
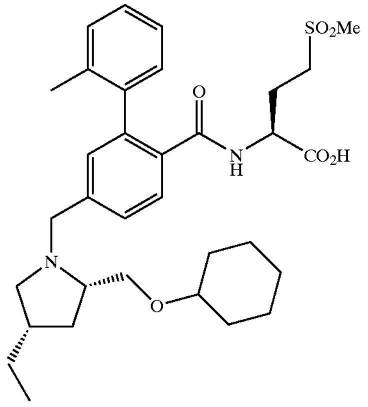
163
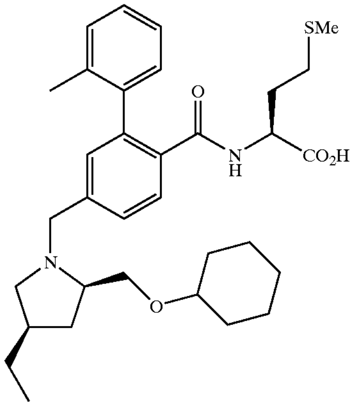
164

TABLE 6-continued
Amines of the Type A(B)N-$L_1$
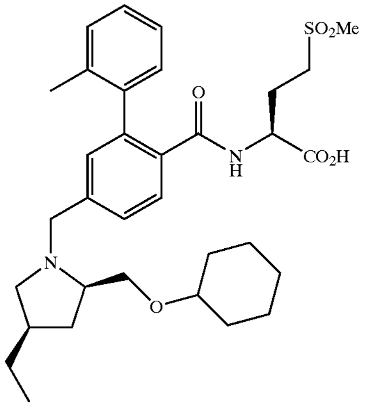
165
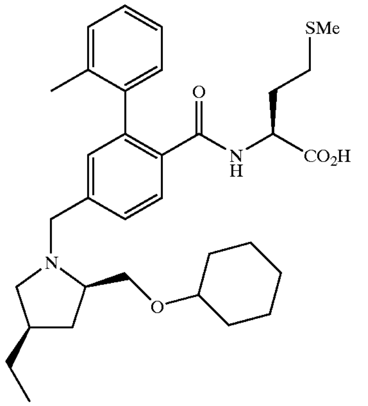
166
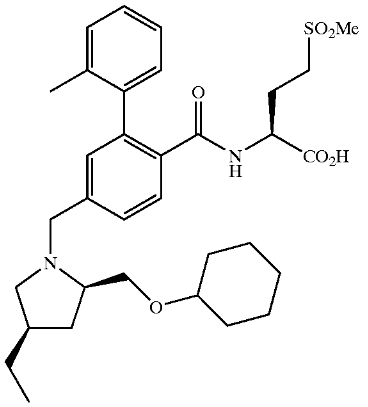
167
TABLE 6-continued
Amines of the Type A(B)N-$L_1$
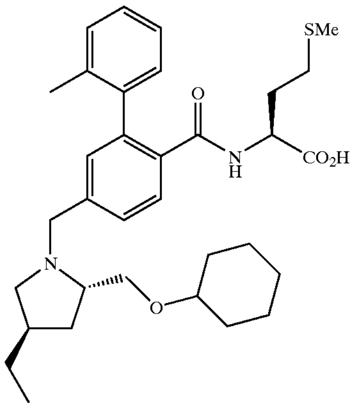
168
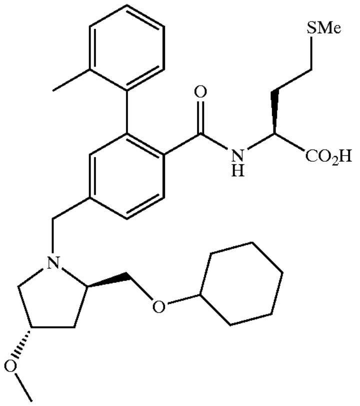
169
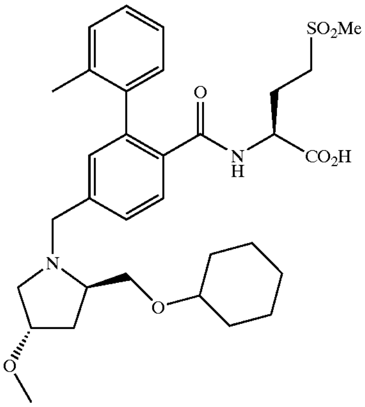
170

TABLE 6-continued
Amines of the Type A(B)N-$L_1$
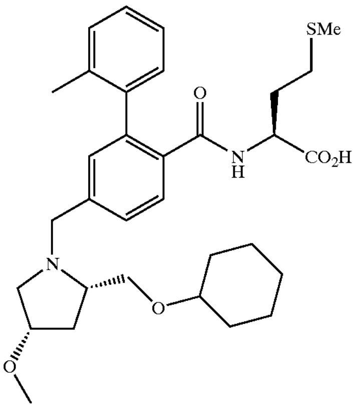
171
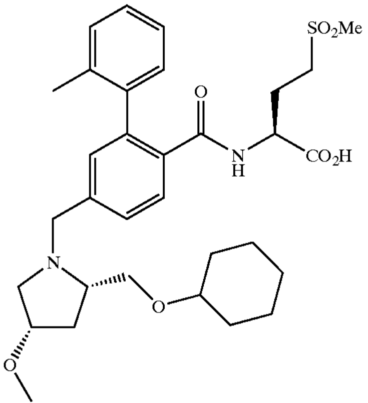
172
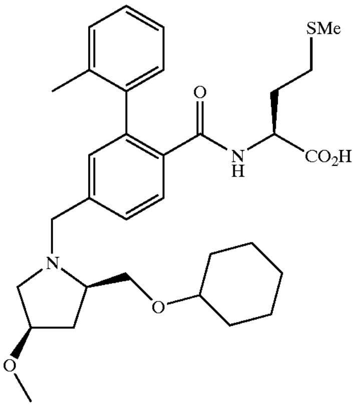
173
TABLE 6-continued
Amines of the Type A(B)N-$L_1$
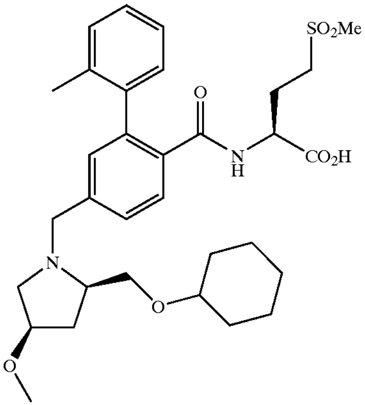
174
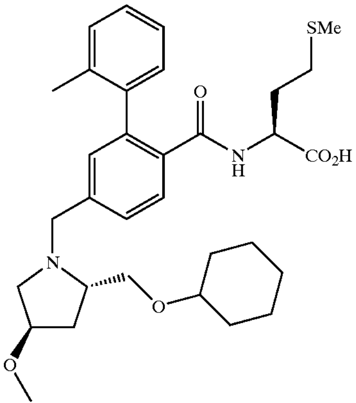
175
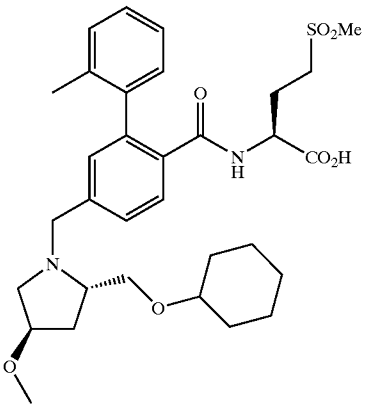
176

TABLE 6-continued
Amines of the Type A(B)N-$L_1$
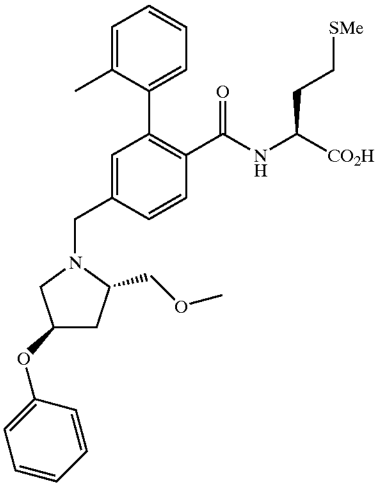
177
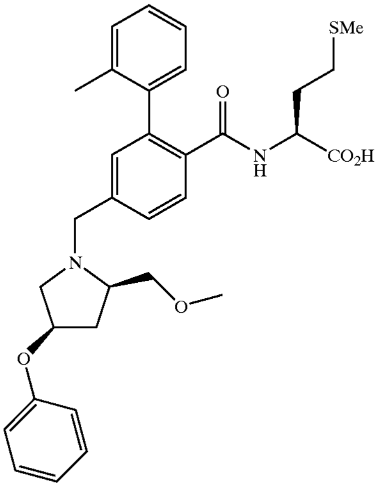
178
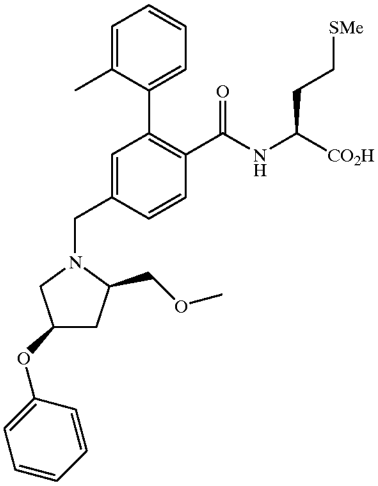
179
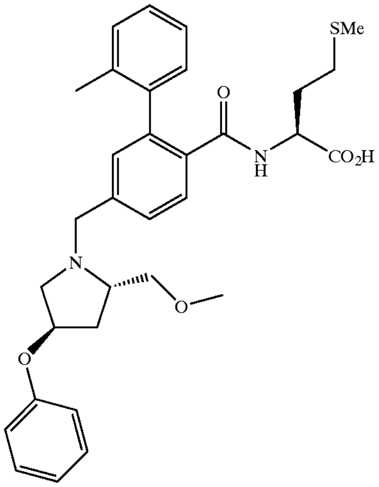
180
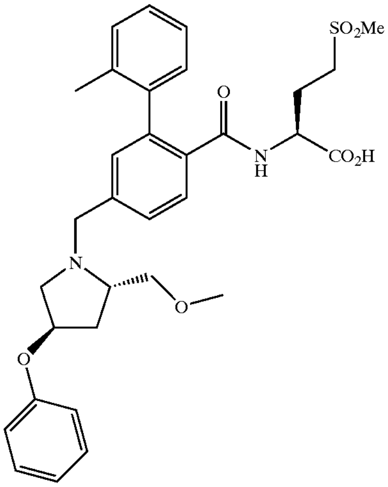
181
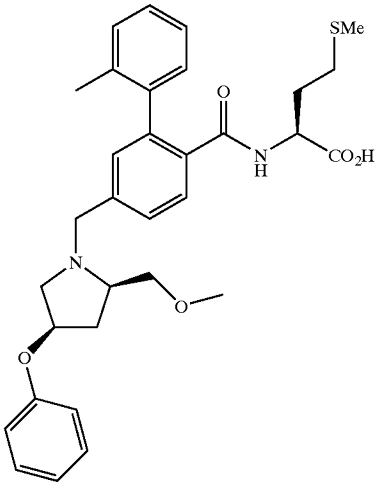
182

TABLE 6-continued
Amines of the Type A(B)N-$L_1$
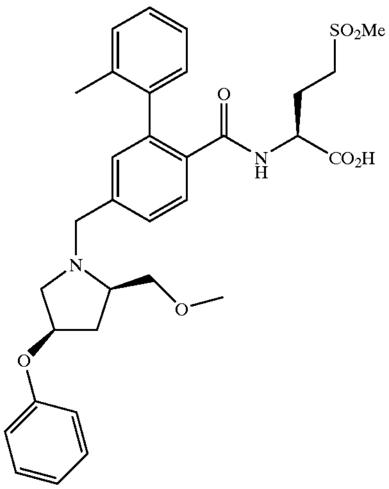
183
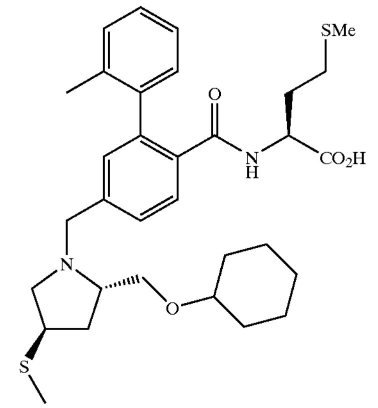
184
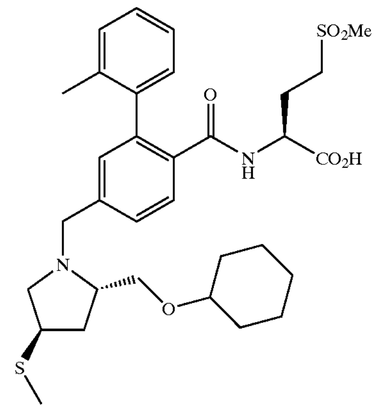
185
TABLE 6-continued
Amines of the Type A(B)N-$L_1$
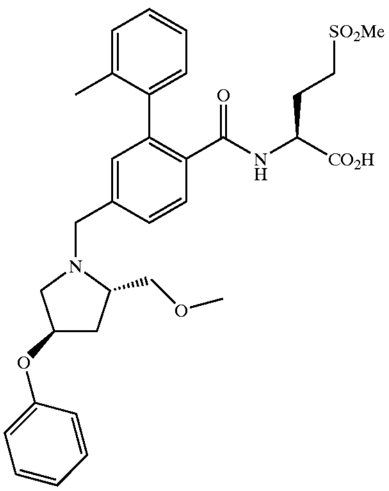
186
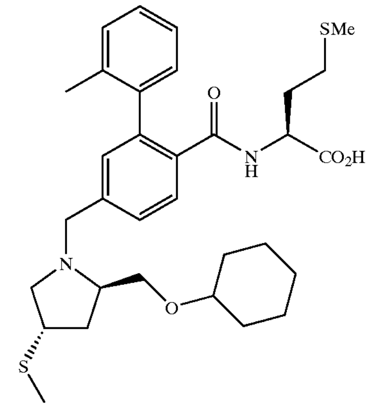
187
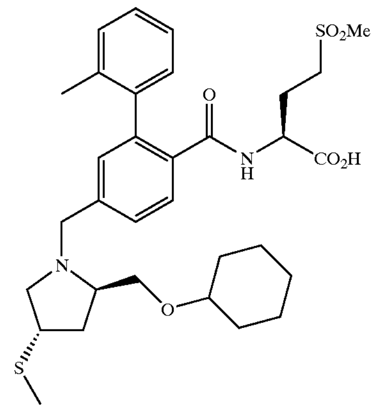
188

TABLE 6-continued
Amines of the Type A(B)N-$L_1$
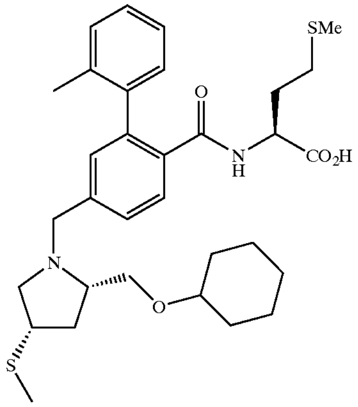
189
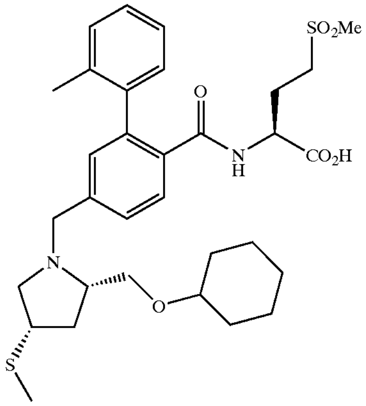
190
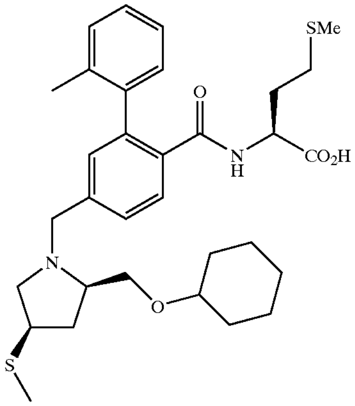
191
TABLE 6-continued
Amines of the Type A(B)N-$L_1$
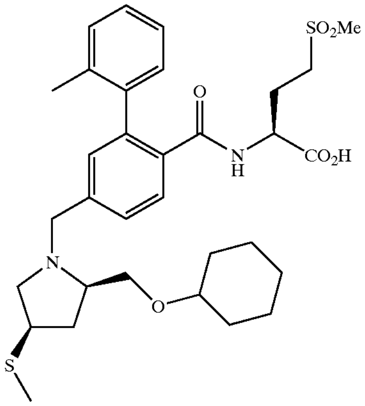
192
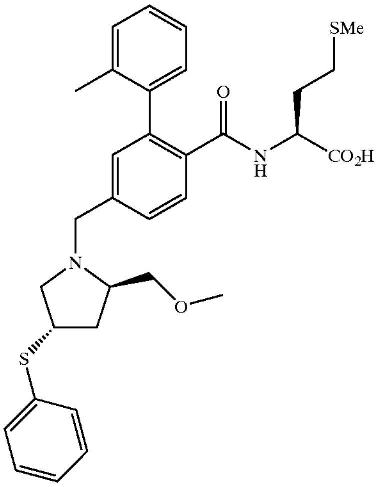
193
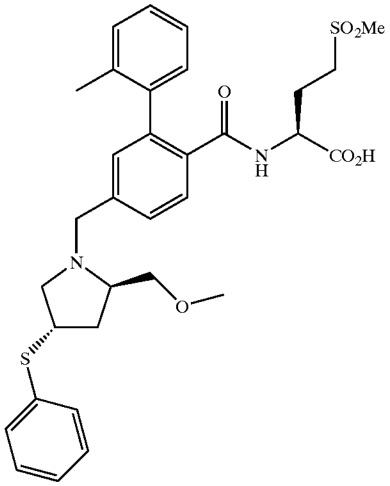
194

TABLE 6-continued
Amines of the Type A(B)N-$L_1$
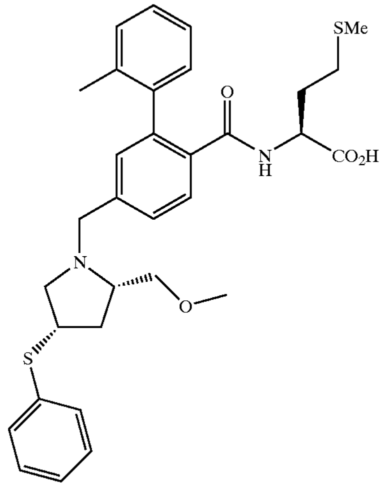
195
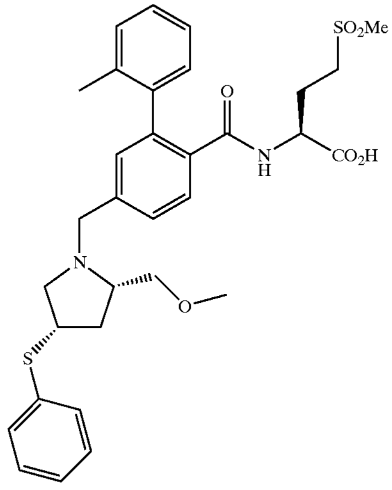
196
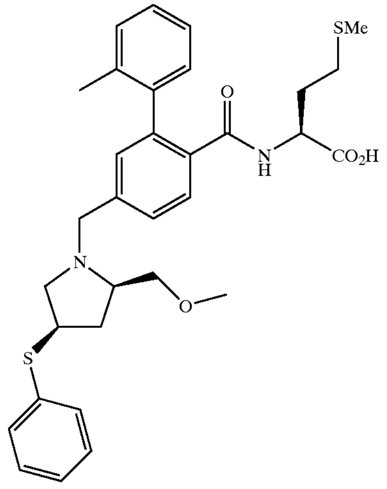
197
TABLE 6-continued
Amines of the Type A(B)N-$L_1$
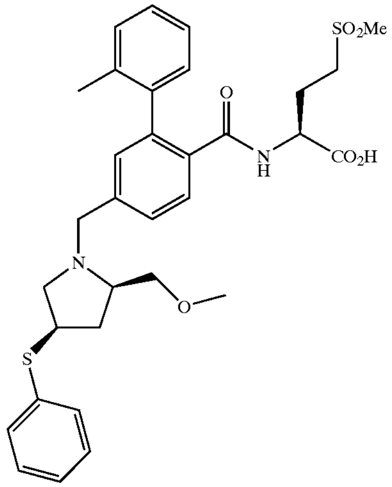
198
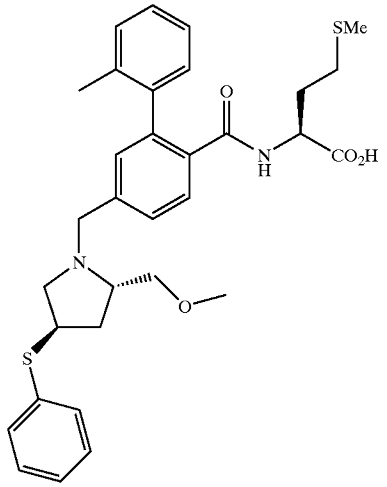
199
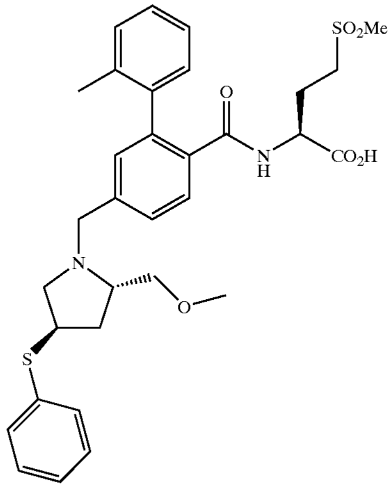
200

TABLE 6-continued
Amines of the Type A(B)N-$L_1$
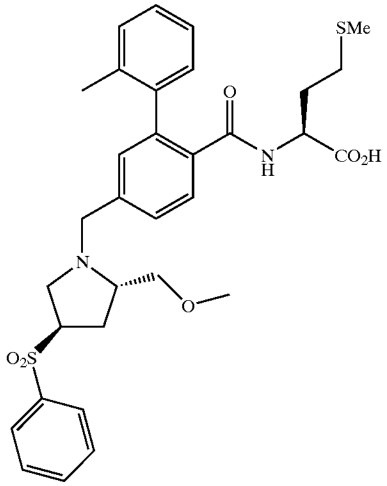
201
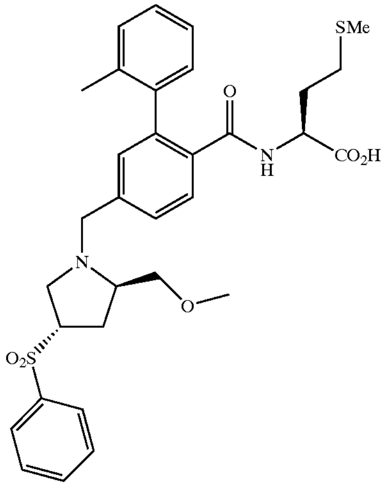
202
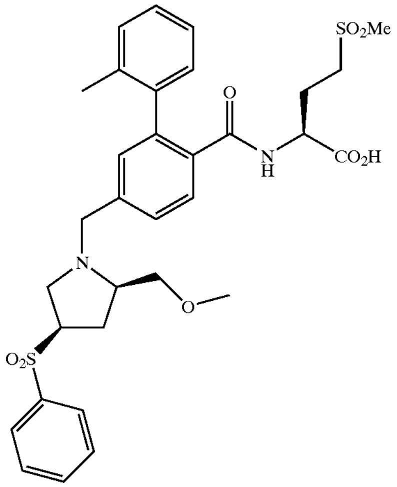
203
TABLE 6-continued
Amines of the Type A(B)N-$L_1$
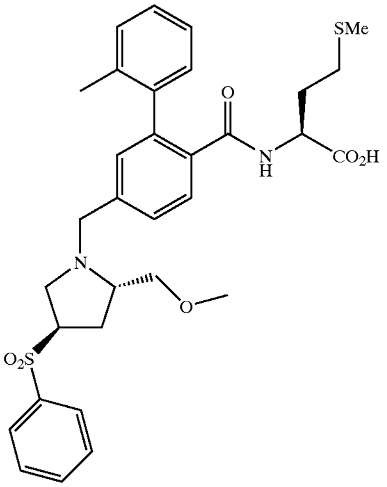
204
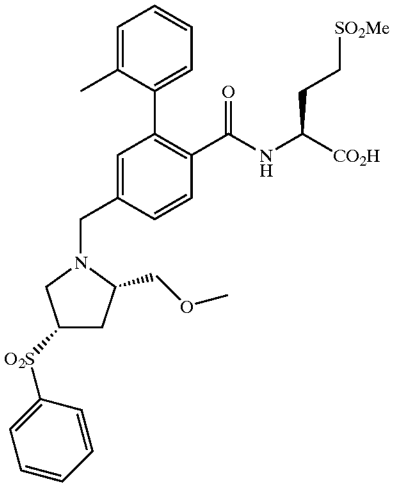
205
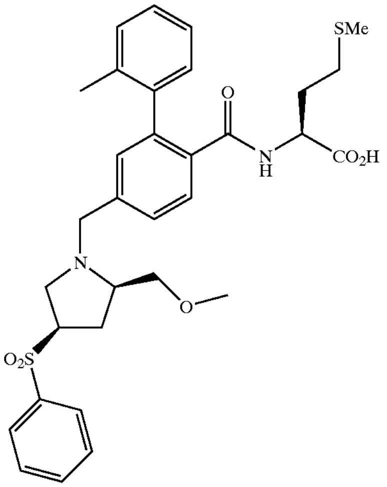
206

TABLE 6-continued
Amines of the Type A(B)N-$L_1$
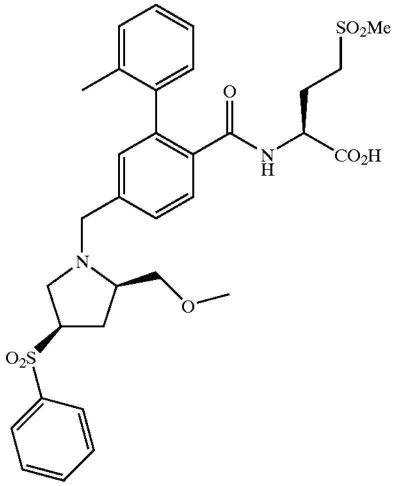
207
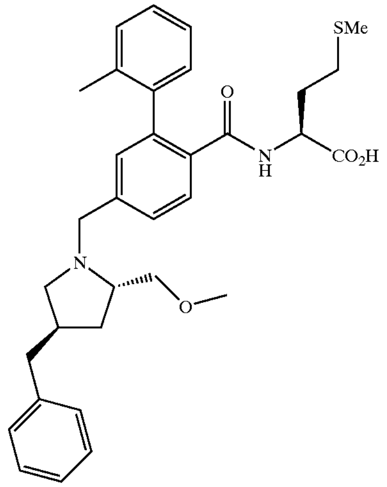
208
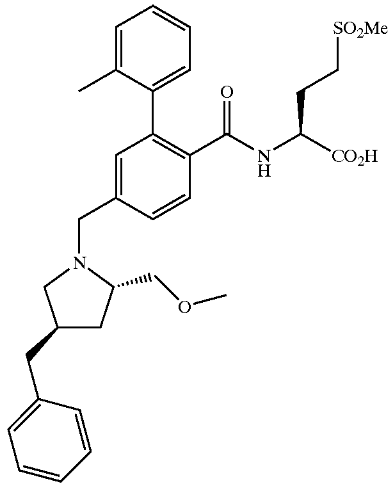
209
TABLE 6-continued
Amines of the Type A(B)N-$L_1$
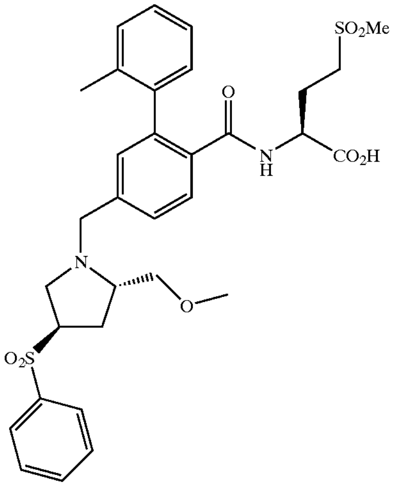
210
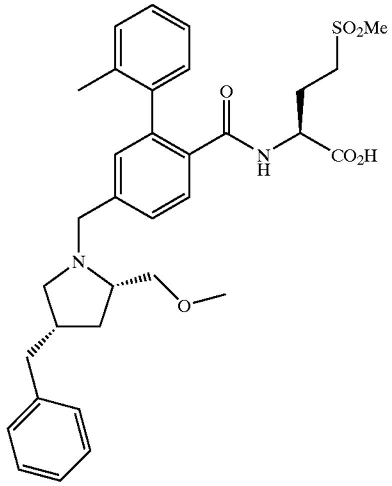
211
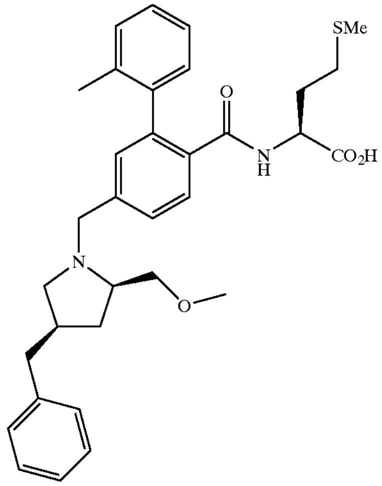
212

TABLE 6-continued
| Amines of the Type A(B)N-$L_1$ |
|---|
| 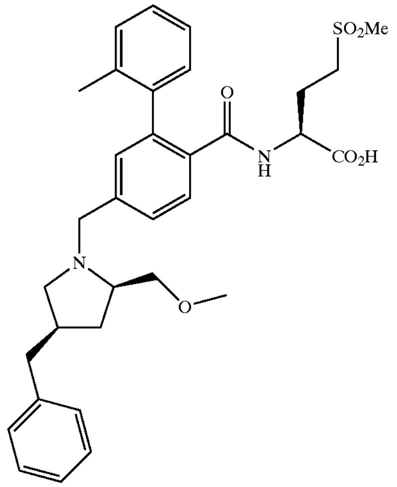 |
| 213 |
| 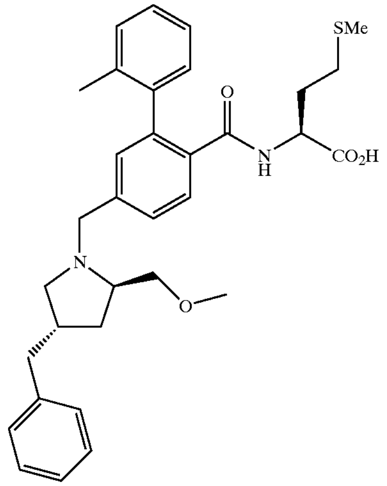 |
| 214 |
| 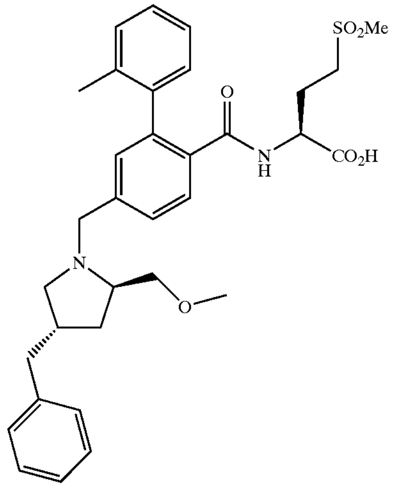 |
| 215 |
TABLE 6-continued
| Amines of the Type A(B)N-$L_1$ |
|---|
| 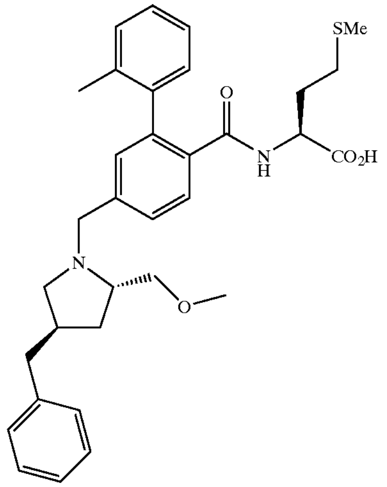 |
| 216 |
| 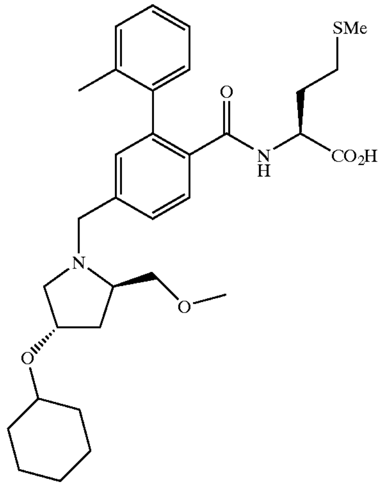 |
| 217 |
| 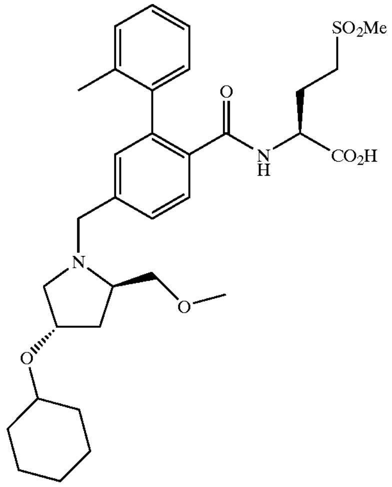 |
| 218 |

TABLE 6-continued
Amines of the Type A(B)N-$L_1$
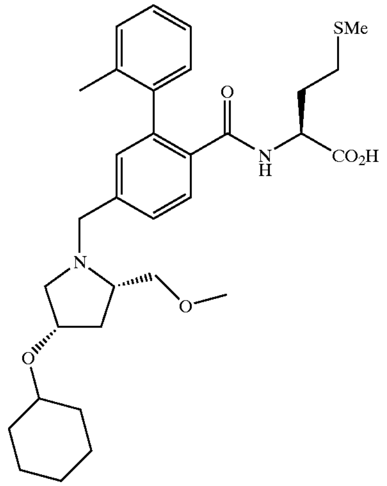
219
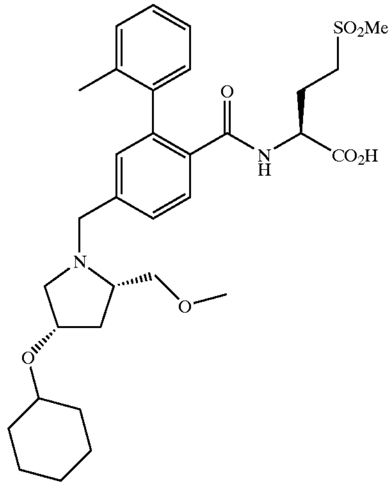
220
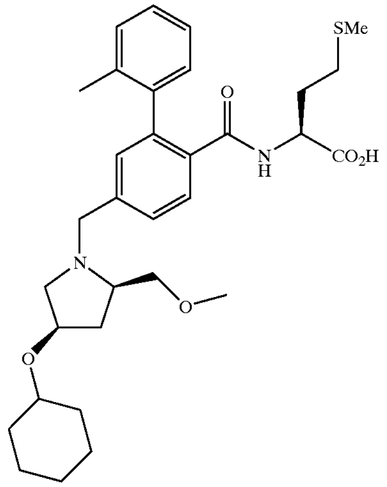
221
TABLE 6-continued
Amines of the Type A(B)N-$L_1$
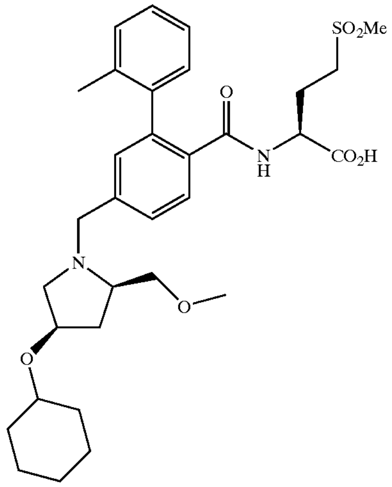
222
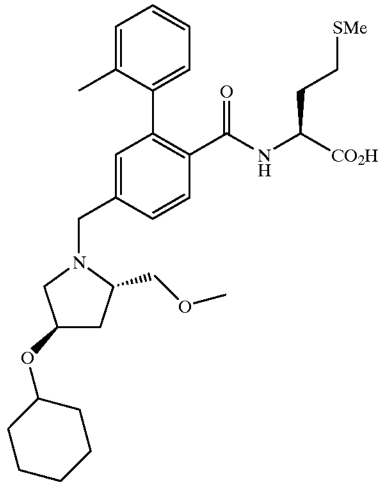
223
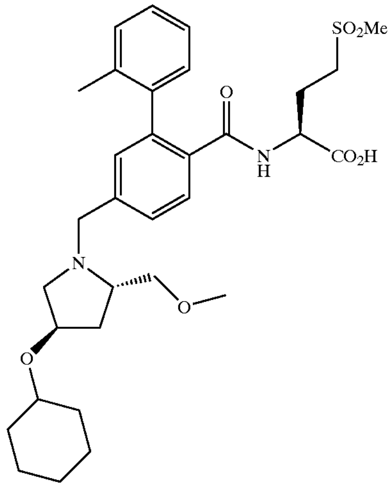
224

TABLE 6-continued
Amines of the Type A(B)N-$L_1$
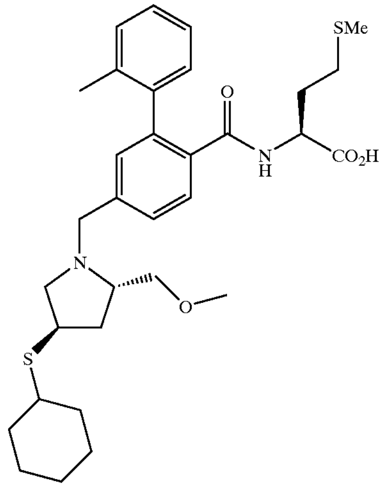
225
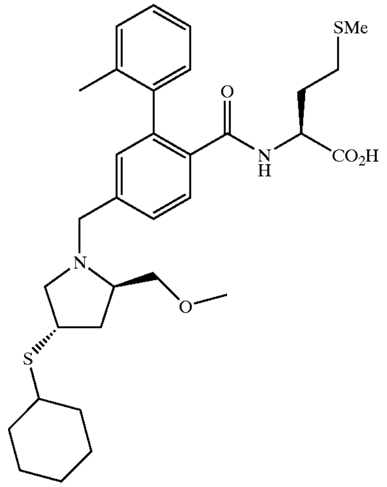
226
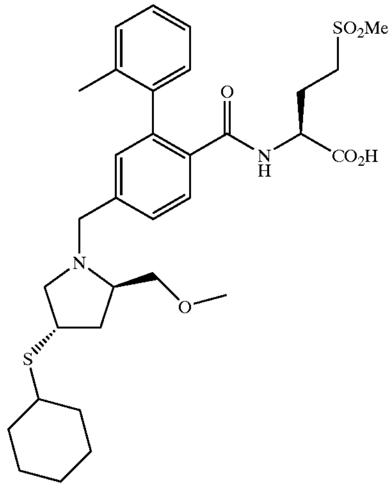
227
TABLE 6-continued
Amines of the Type A(B)N-$L_1$
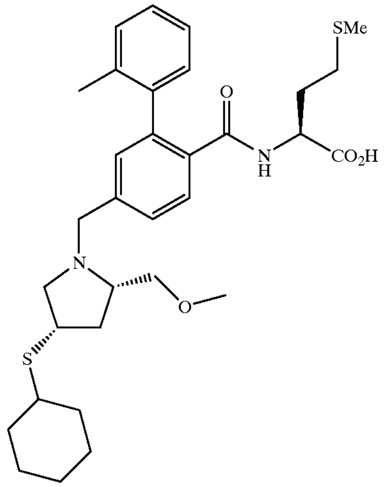
228
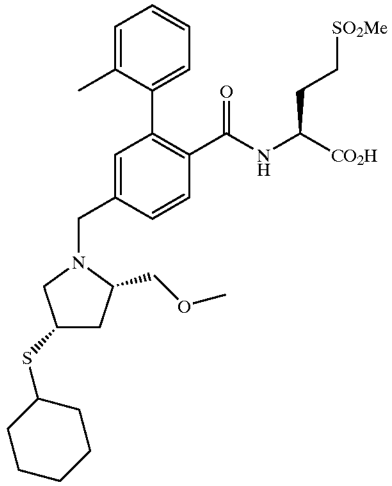
229

TABLE 6-continued
Amines of the Type A(B)N-$L_1$
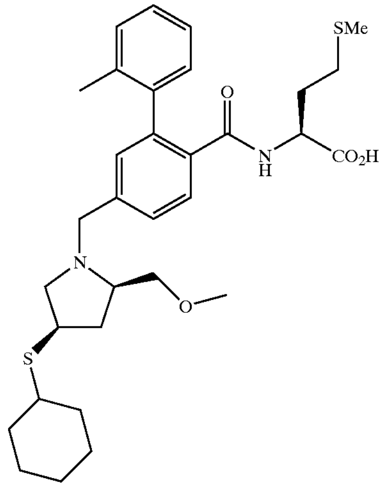
230
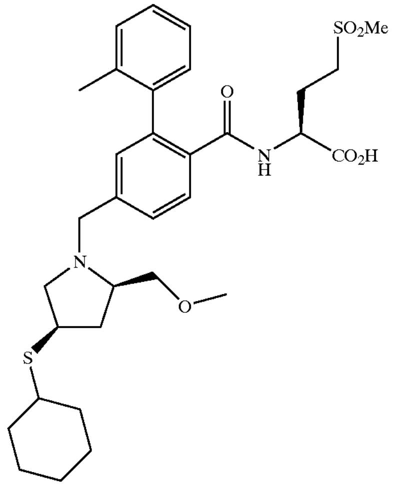
231
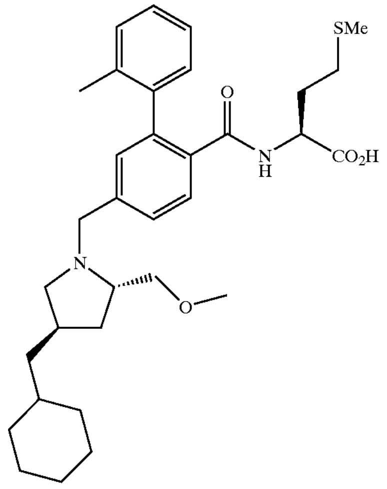
232
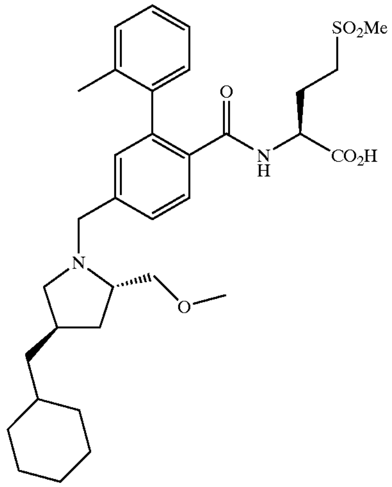
233
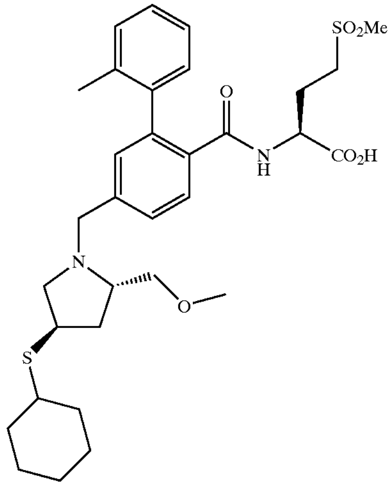
234

TABLE 6-continued
Amines of the Type A(B)N-$L_1$
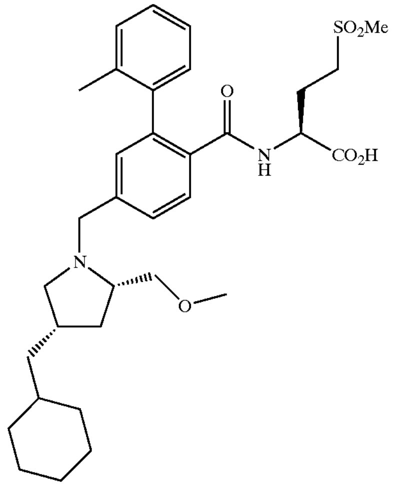
235
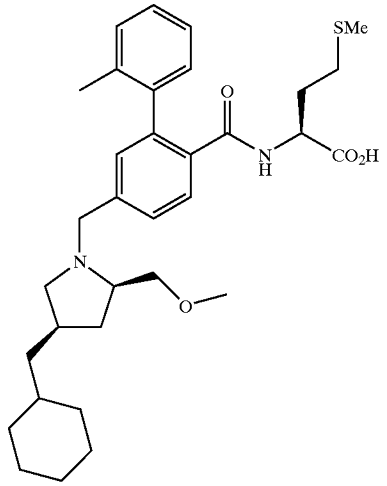
236
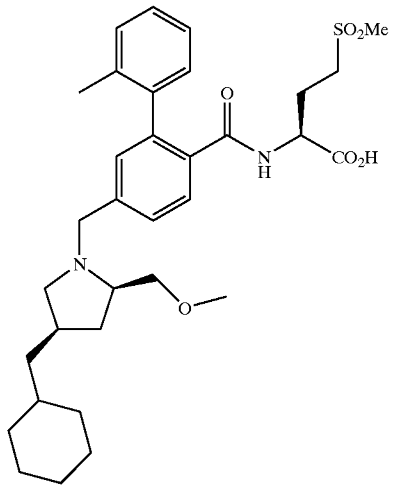
237
TABLE 6-continued
Amines of the Type A(B)N-$L_1$
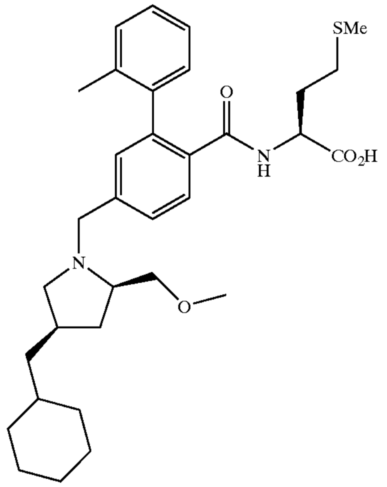
238
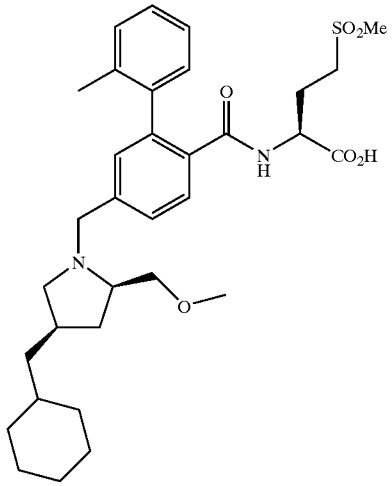
239
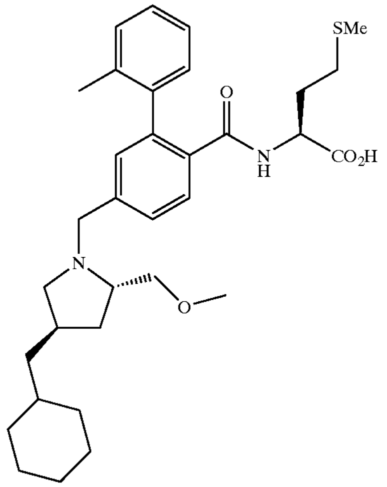
240

TABLE 6-continued
| Amines of the Type A(B)N-$L_1$ |
| --- |
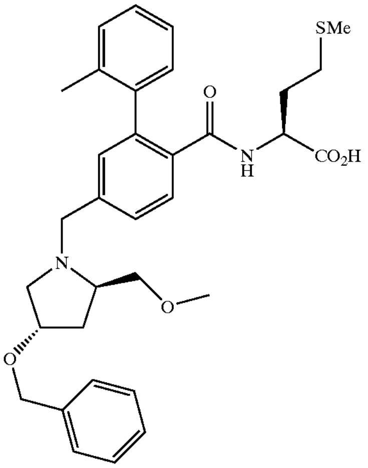
241
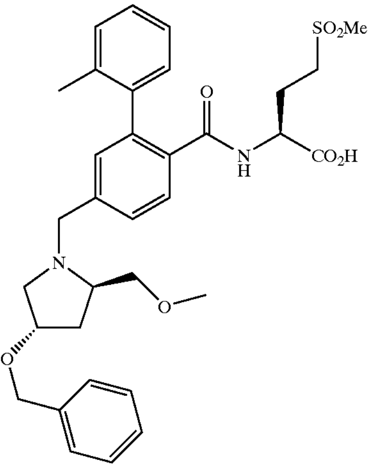
242
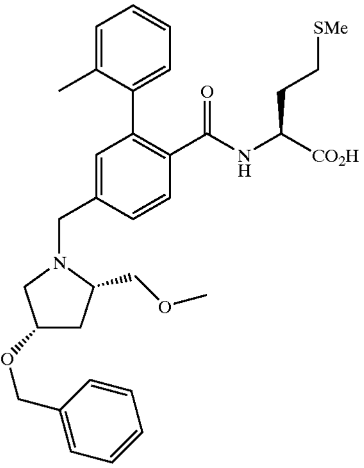
243
TABLE 6-continued
| Amines of the Type A(B)N-$L_1$ |
| --- |
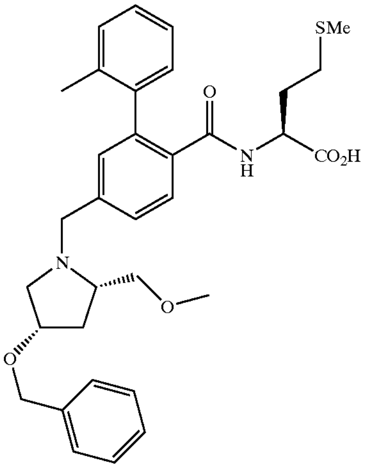
244
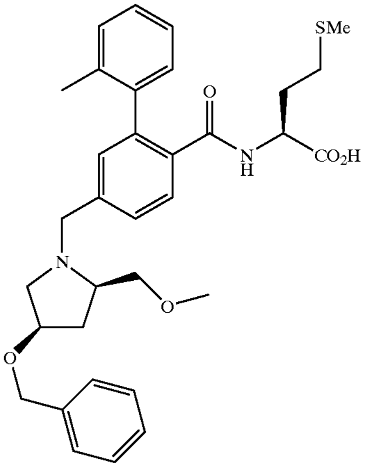
245

TABLE 6-continued
| Amines of the Type A(B)N-$L_1$ |
| --- |
| 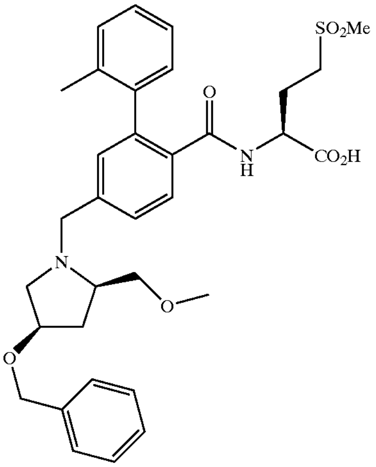 |
| 246 |
| 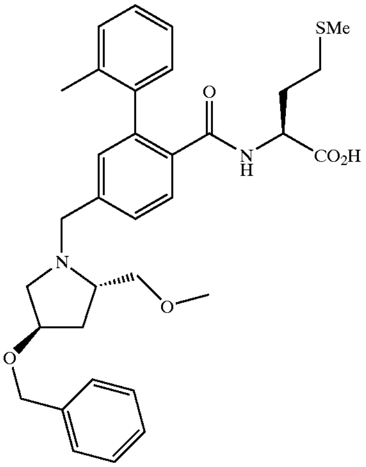 |
| 247 |
| 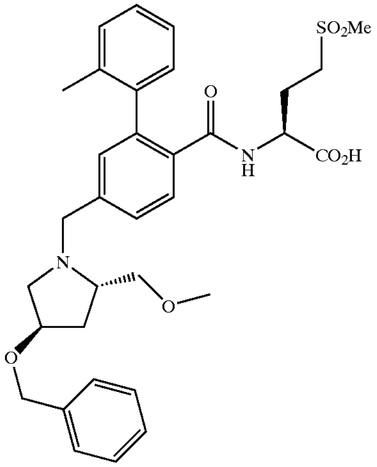 |
| 248 |
TABLE 6-continued
| Amines of the Type A(B)N-$L_1$ |
| --- |
| 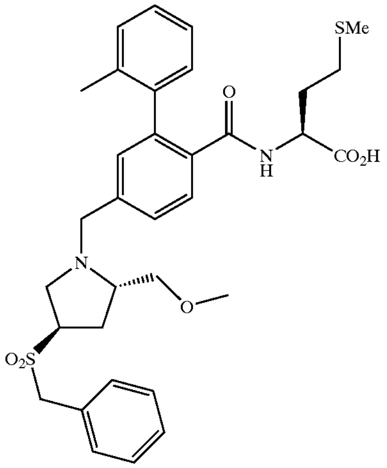 |
| 249 |
| 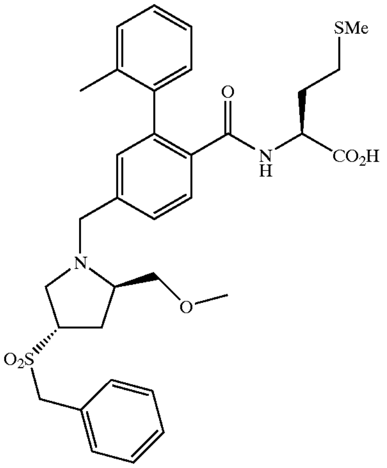 |
| 250 |
| 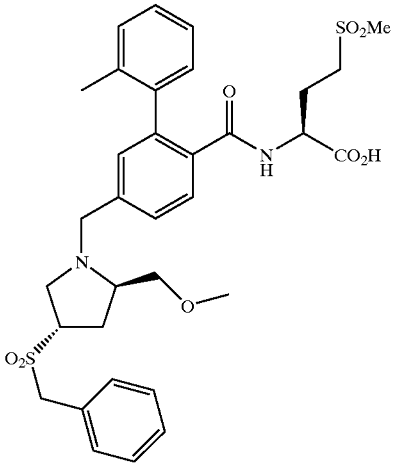 |
| 251 |

TABLE 6-continued
Amines of the Type A(B)N-$L_1$
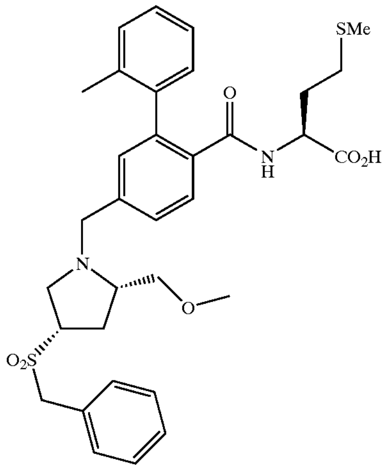
252
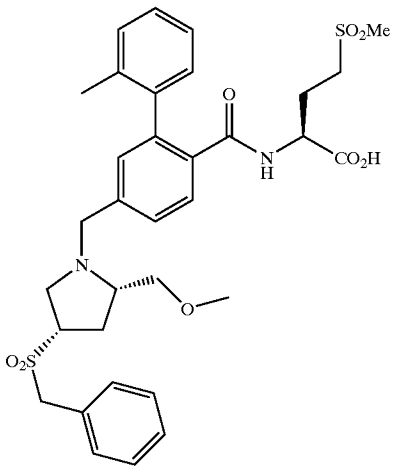
253
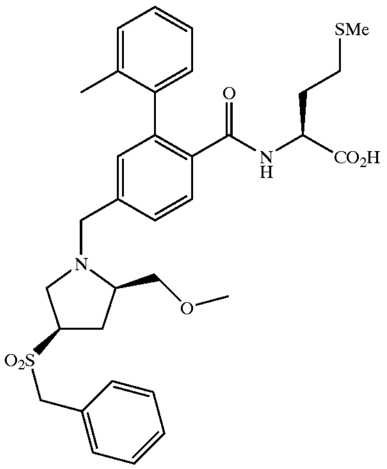
254
TABLE 6-continued
Amines of the Type A(B)N-$L_1$
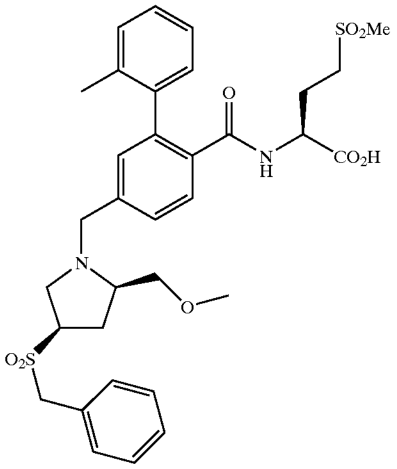
255
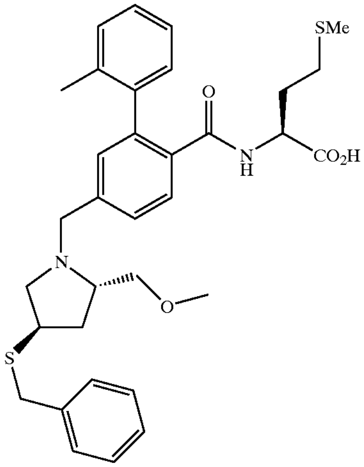
256

TABLE 6-continued
Amines of the Type A(B)N-$L_1$
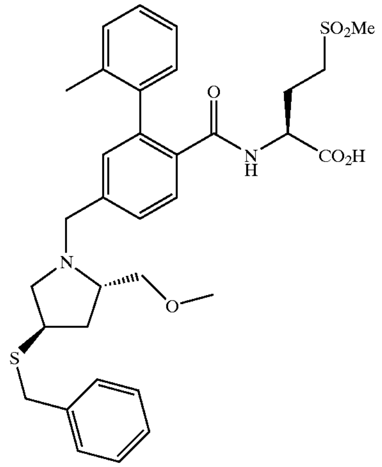
257
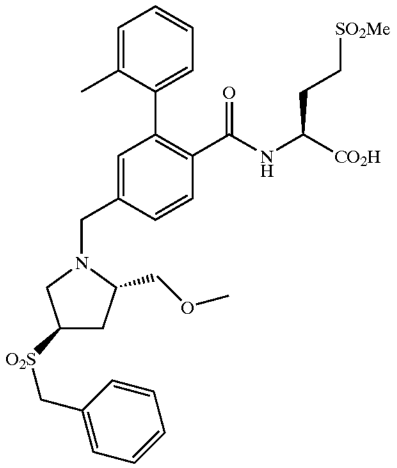
258
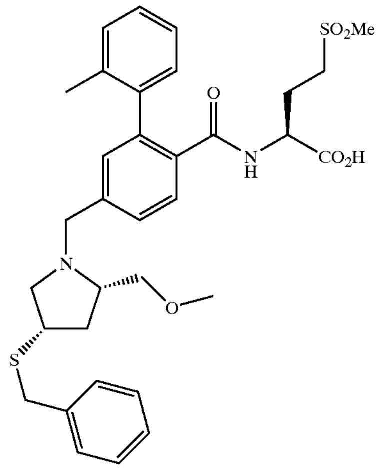
259
TABLE 6-continued
Amines of the Type A(B)N-$L_1$
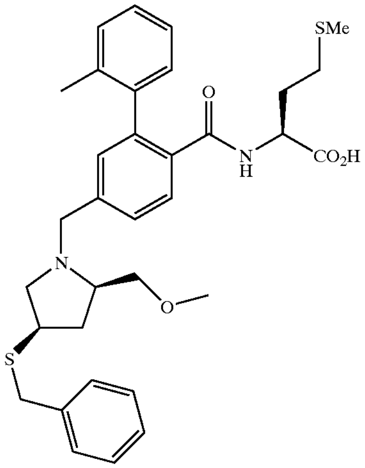
260
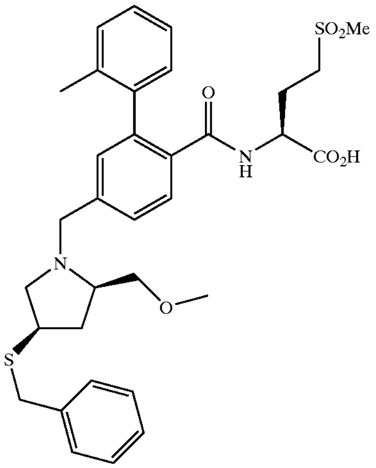
261
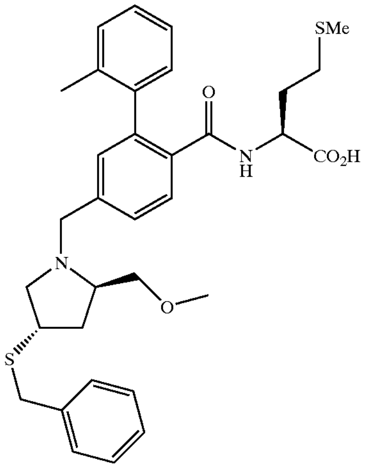
262

TABLE 6-continued
Amines of the Type A(B)N-$L_1$
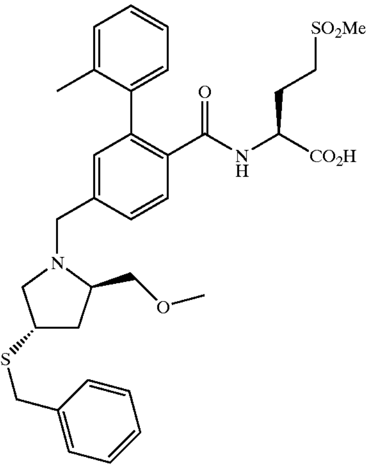
263
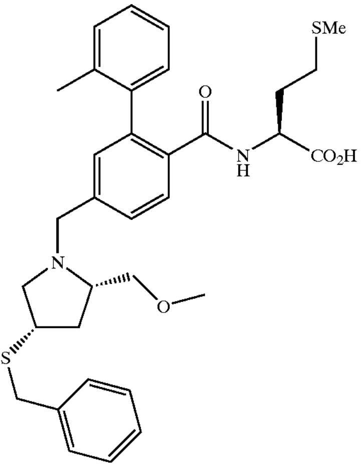
264
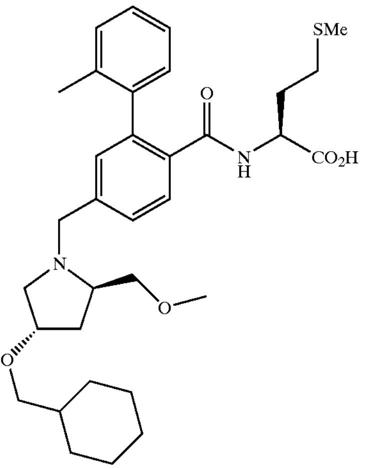
265
TABLE 6-continued
Amines of the Type A(B)N-$L_1$
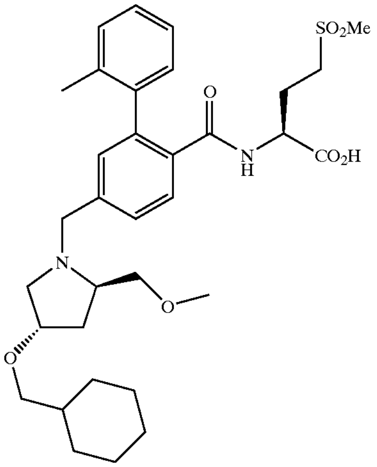
266
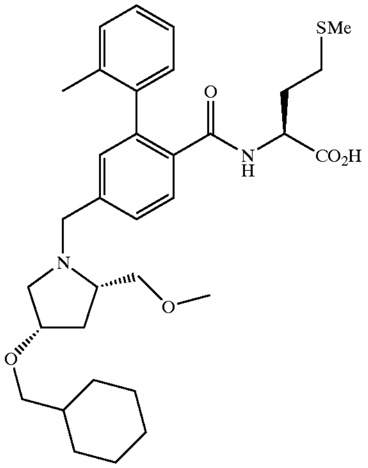
267

TABLE 6-continued
| Amines of the Type A(B)N-$L_1$ |
|---|
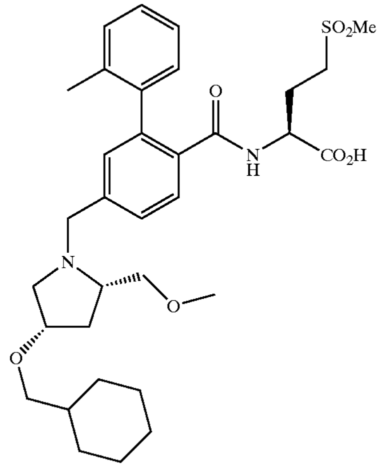
268
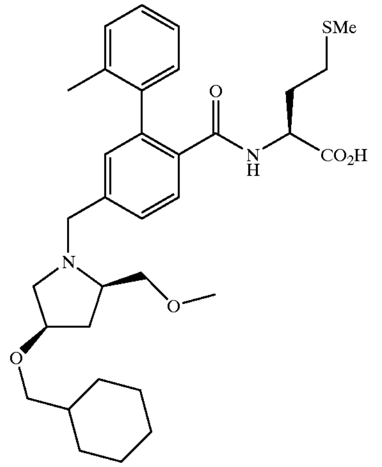
269
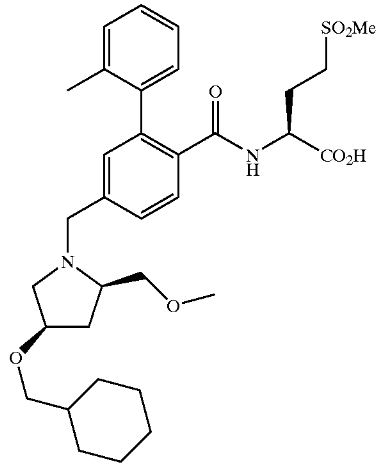
270
TABLE 6-continued
| Amines of the Type A(B)N-$L_1$ |
|---|
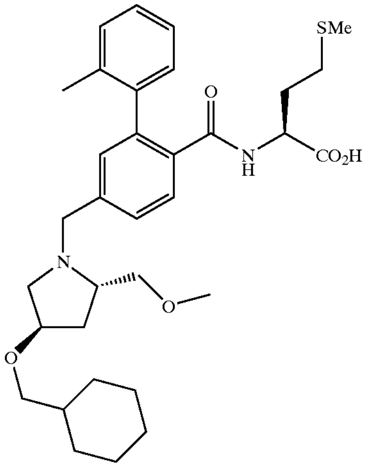
271
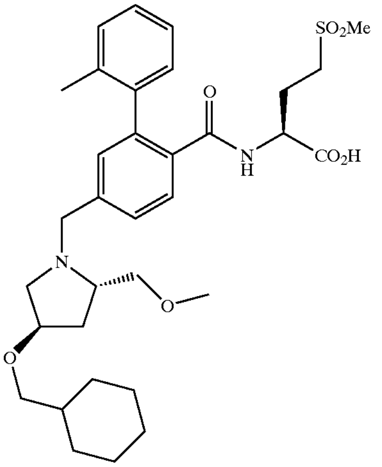
272
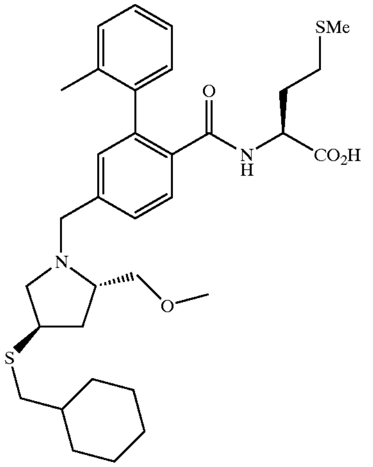
273

TABLE 6-continued
Amines of the Type A(B)N-$L_1$
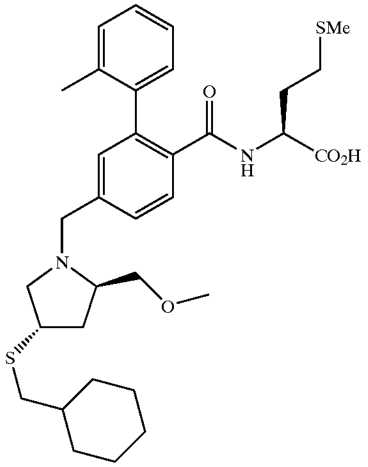
274
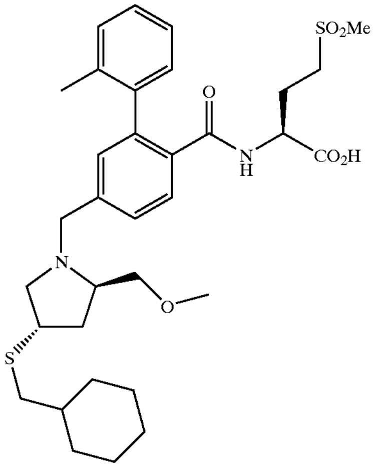
275
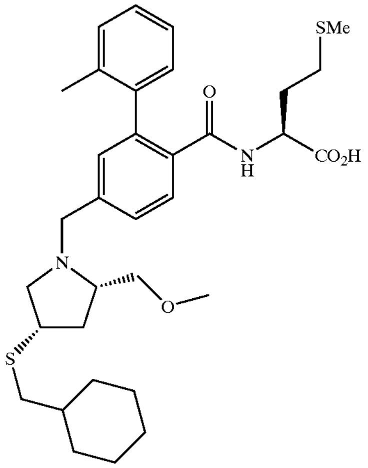
276
TABLE 6-continued
Amines of the Type A(B)N-$L_1$
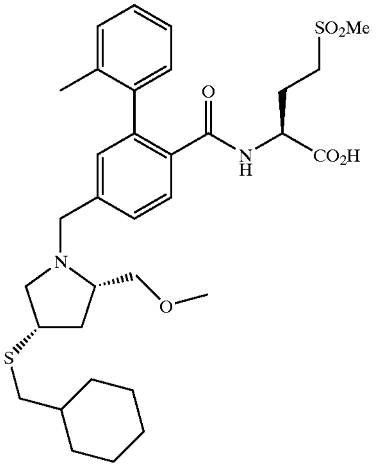
277
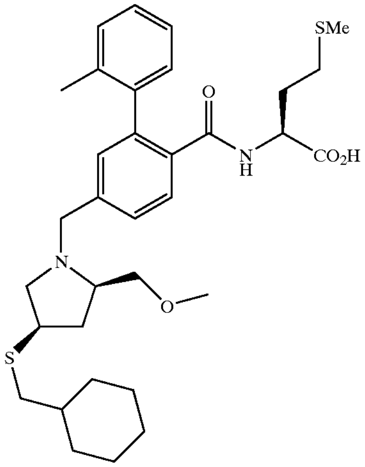
278
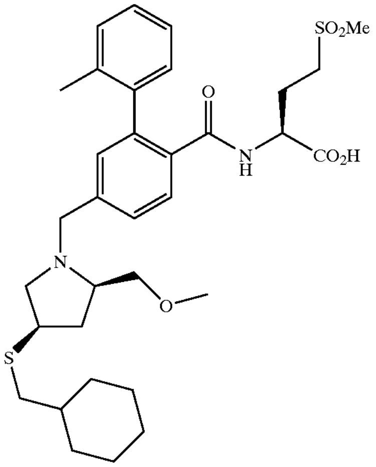
279

TABLE 6-continued
Amines of the Type A(B)N-$L_1$
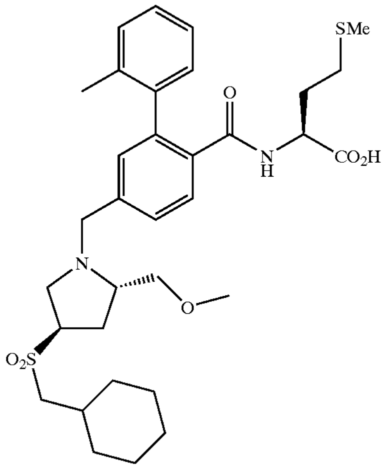
280
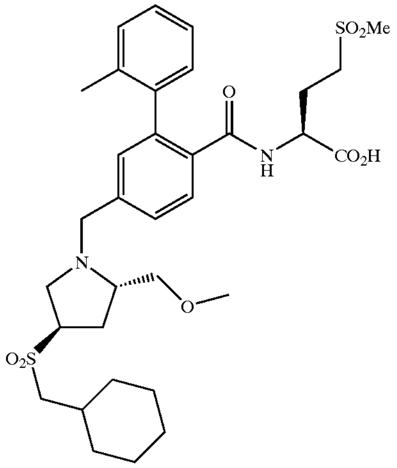
281
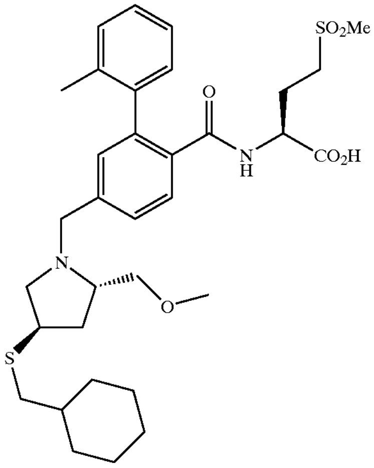
282
TABLE 6-continued
Amines of the Type A(B)N-$L_1$
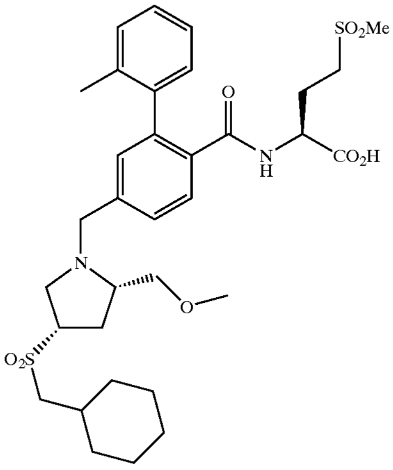
283
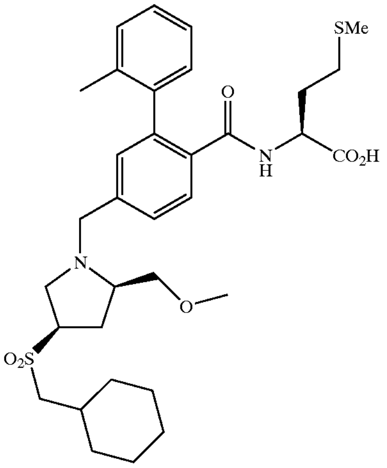
284
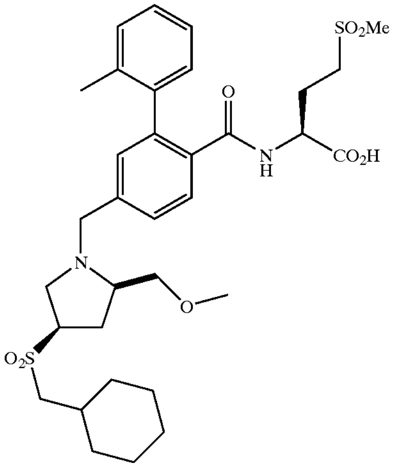
285

TABLE 6-continued
Amines of the Type A(B)N-$L_1$
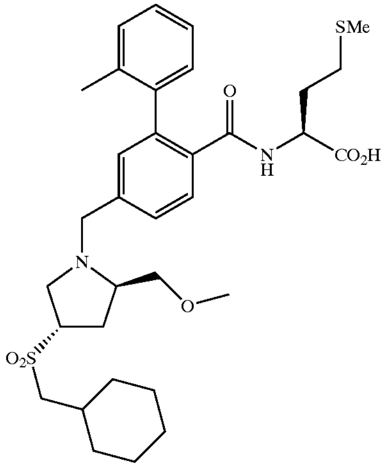
286
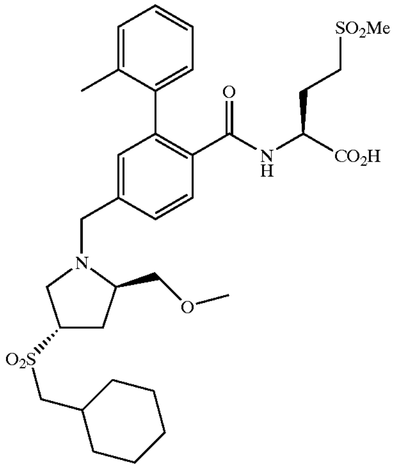
287
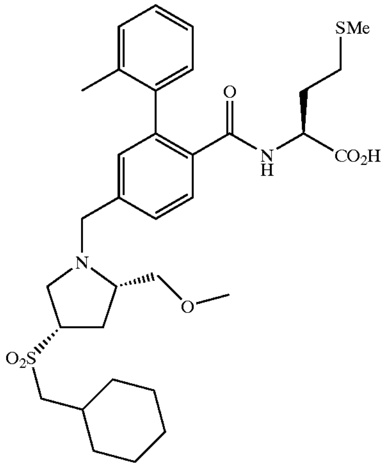
288
TABLE 6-continued
Amines of the Type A(B)N-$L_1$
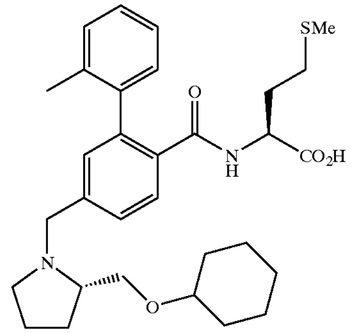
289
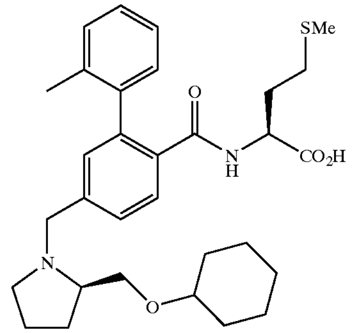
290
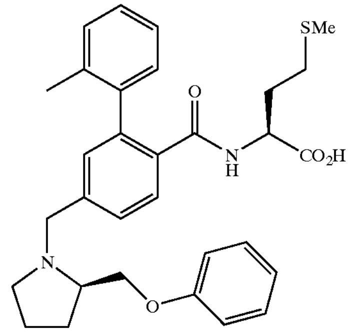
291
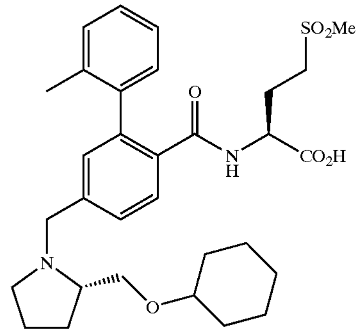
292

TABLE 6-continued
| Amines of the Type A(B)N-$L_1$ |
|---|
| 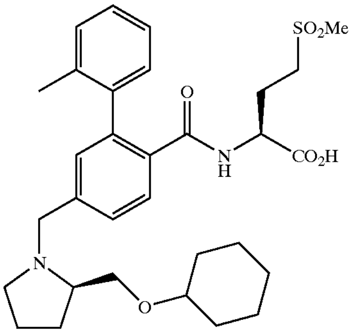 293 |
| 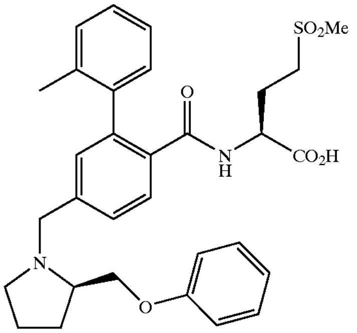 294 |
| 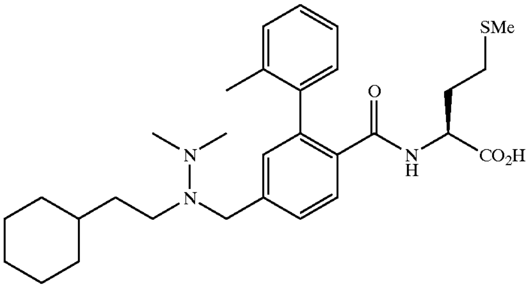 295 |
| 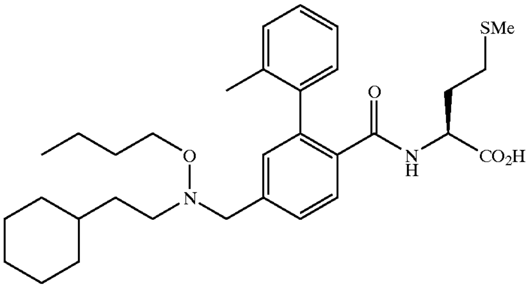 296 |
TABLE 6-continued
| Amines of the Type A(B)N-$L_1$ |
|---|
| 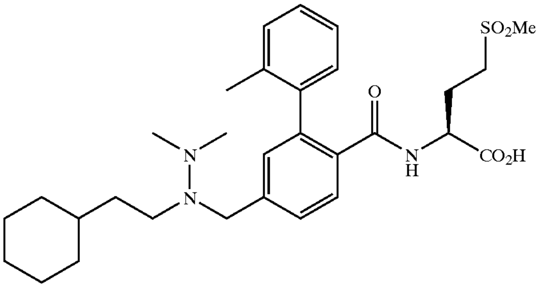 297 |
| 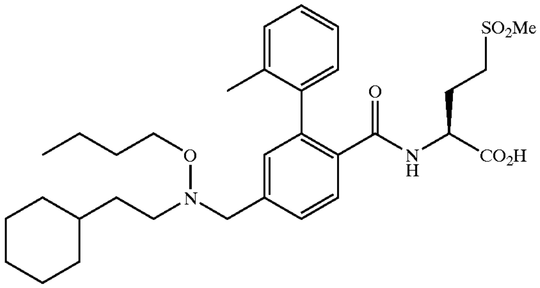 298 |
| 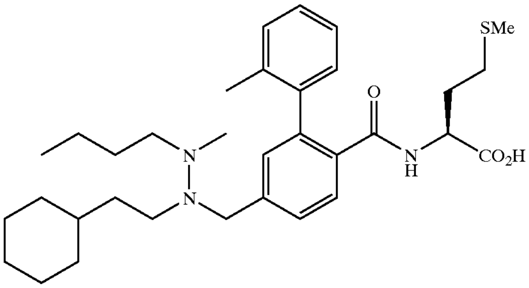 299 |
| 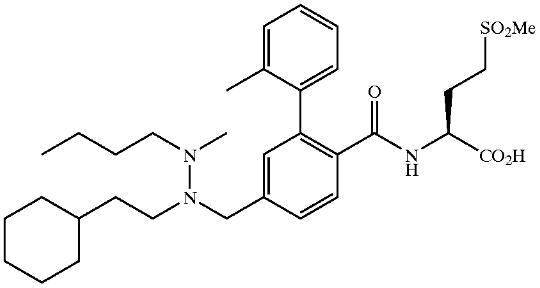 300 |

TABLE 6-continued
Amines of the Type A(B)N-$L_1$
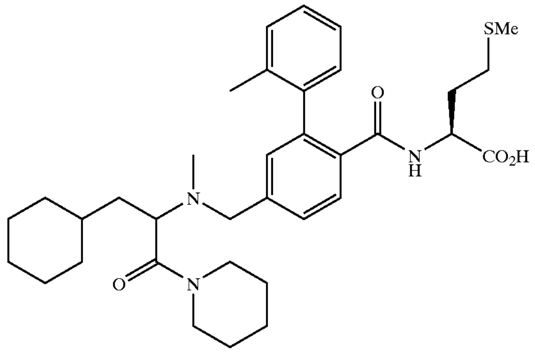
301
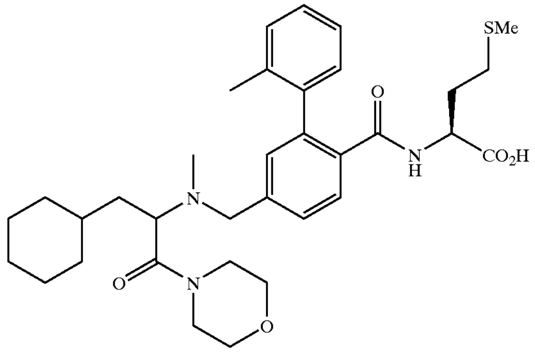
302
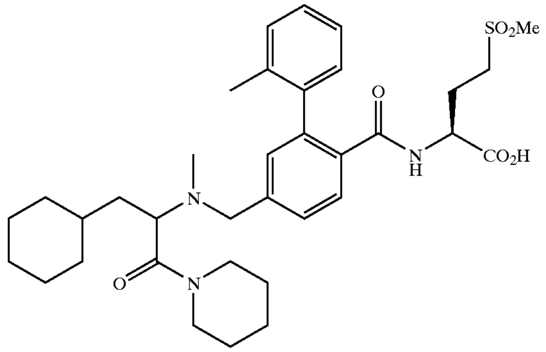
303
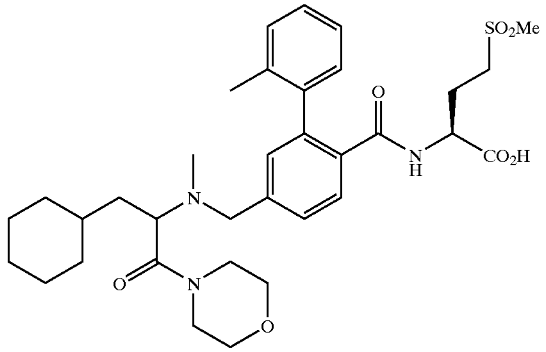
304
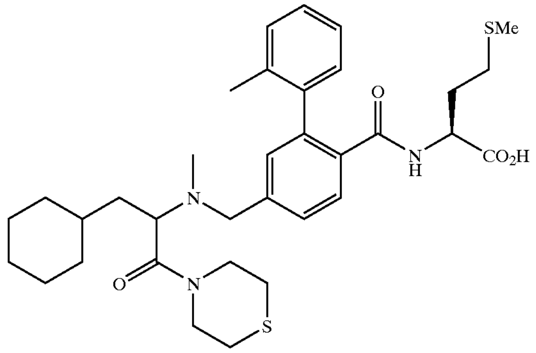
305
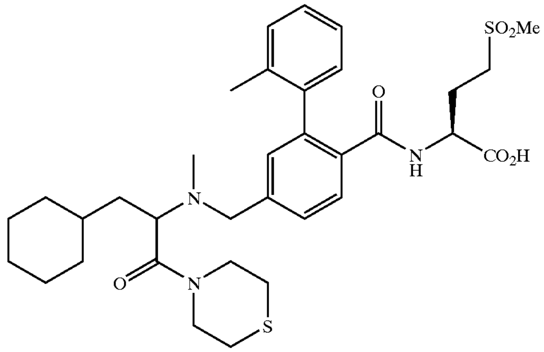
306
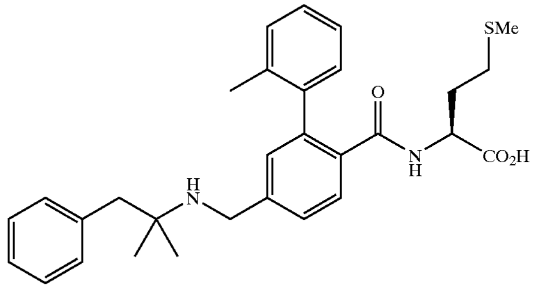
307
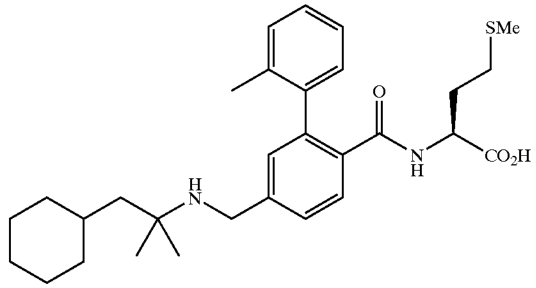
308

TABLE 6-continued
Amines of the Type A(B)N-$L_1$
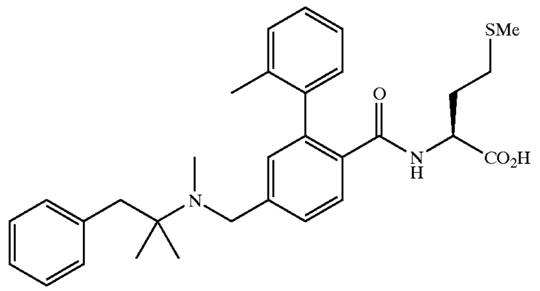
309
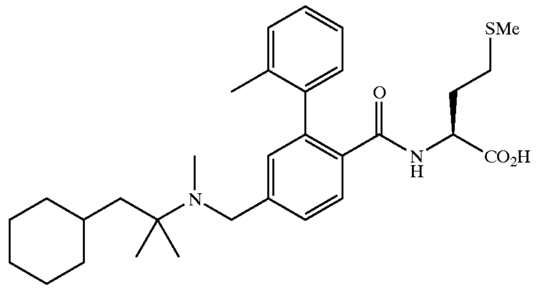
310
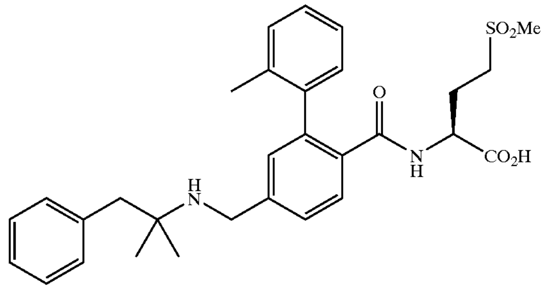
311
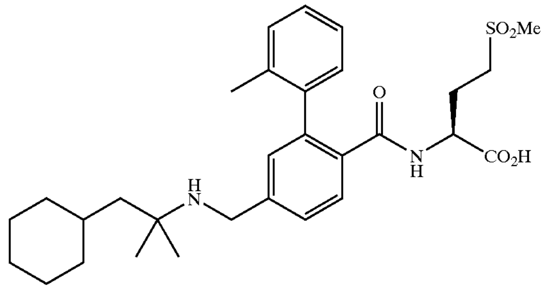
312
TABLE 6-continued
Amines of the Type A(B)N-$L_1$
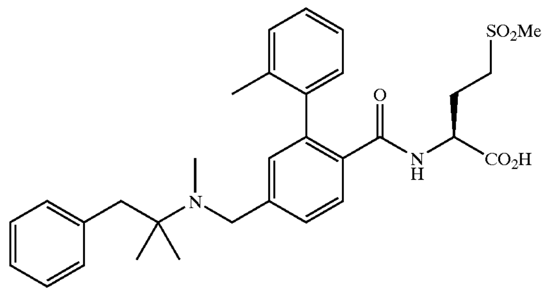
313
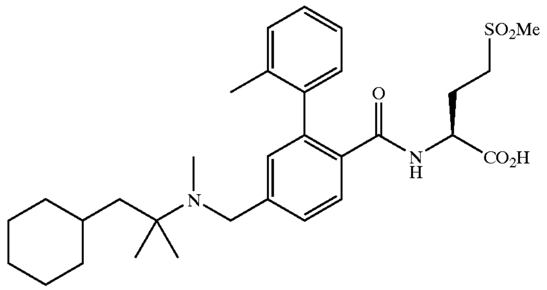
314
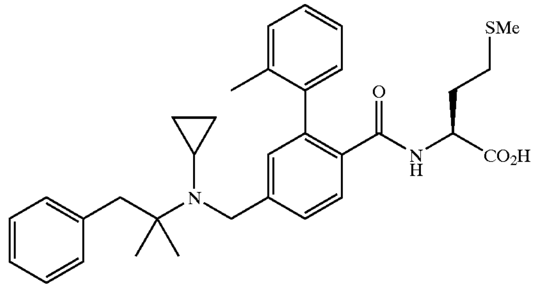
315
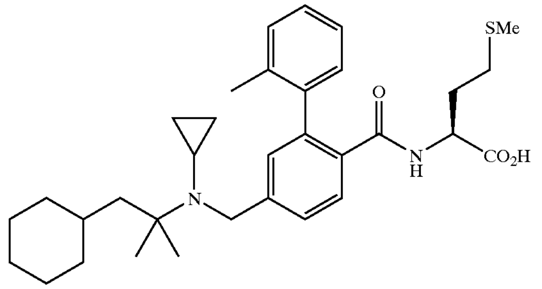
316

TABLE 6-continued
| Amines of the Type A(B)N-$L_1$ |
| --- |
| 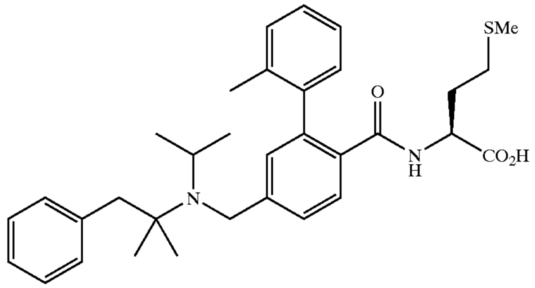 |
| 317 |
| 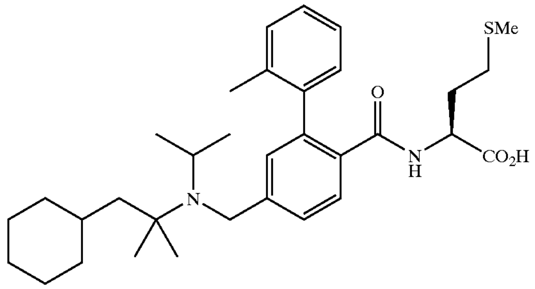 |
| 318 |
| 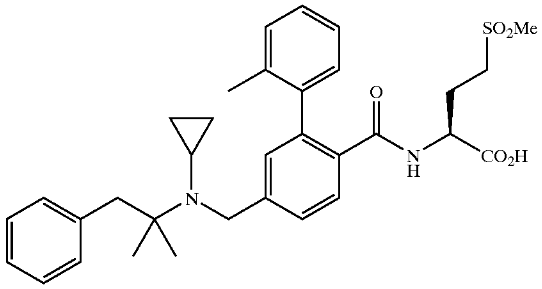 |
| 319 |
| 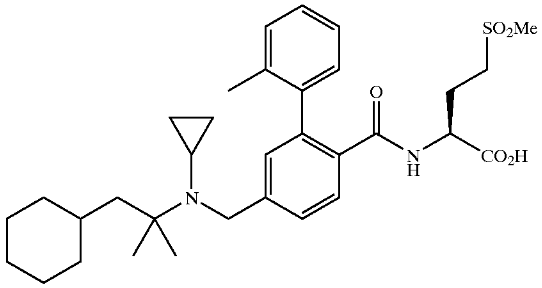 |
| 320 |
TABLE 6-continued
| Amines of the Type A(B)N-$L_1$ |
| --- |
| 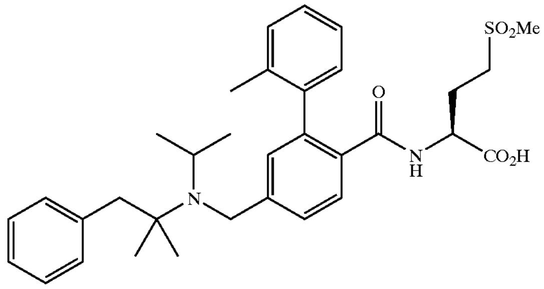 |
| 321 |
| 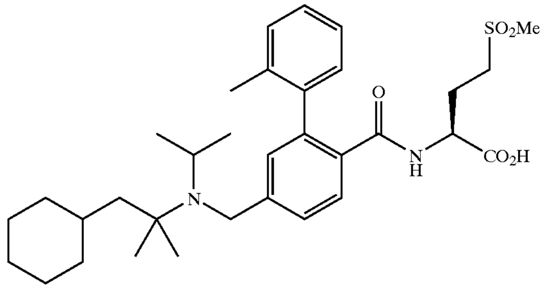 |
| 322 |
| 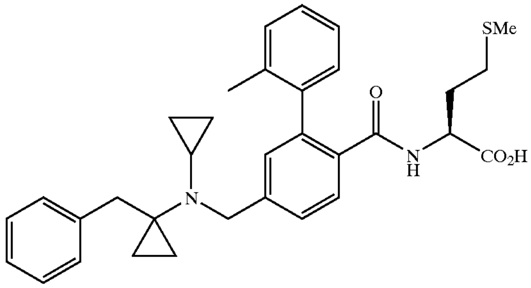 |
| 323 |
| 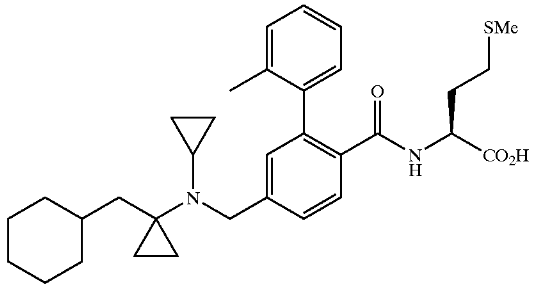 |
| 324 |

TABLE 6-continued
Amines of the Type A(B)N-$L_1$
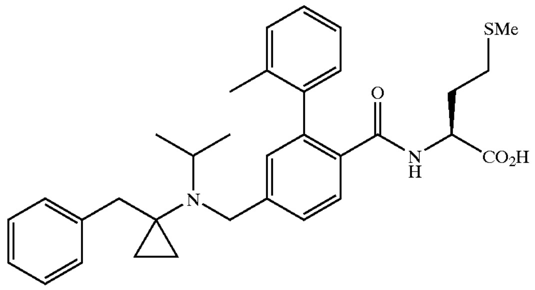
325
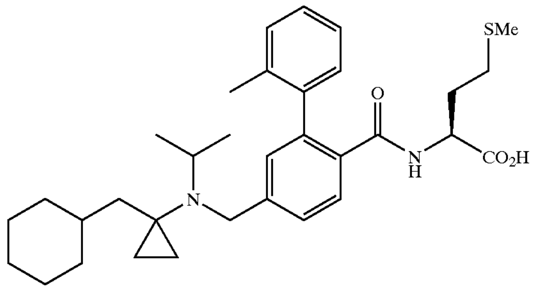
326
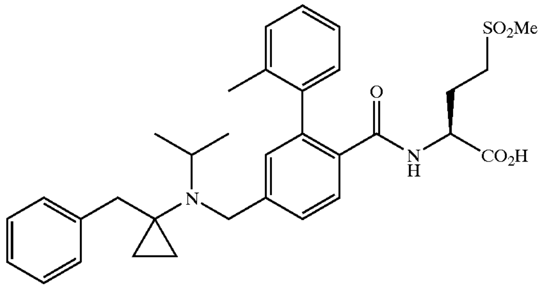
327
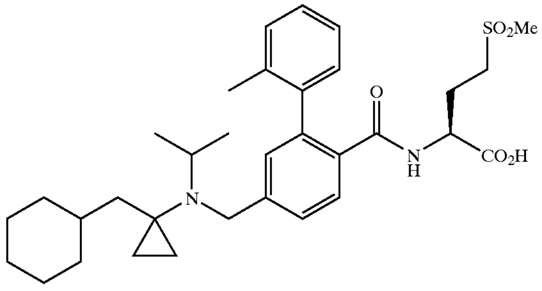
328
TABLE 6-continued
Amines of the Type A(B)N-$L_1$
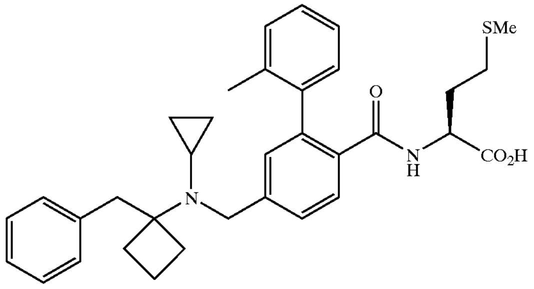
329
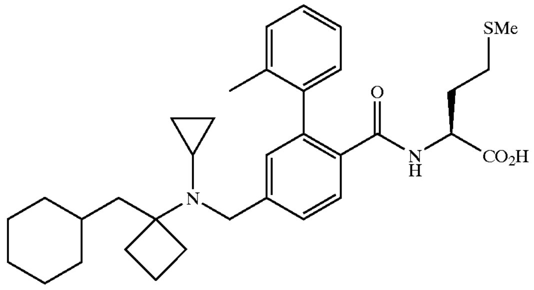
330
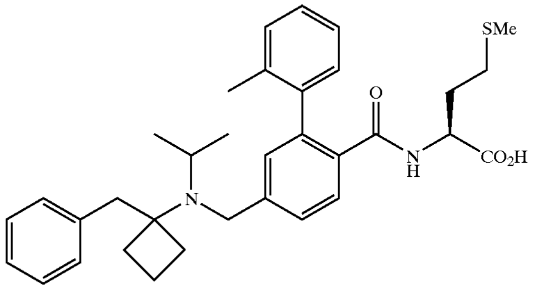
331
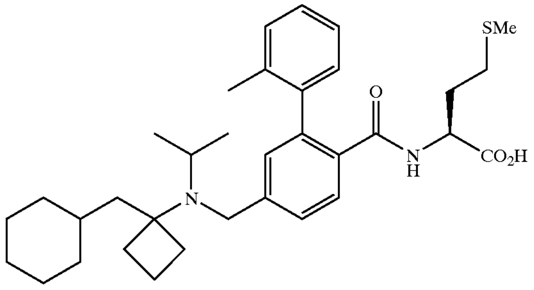
332

TABLE 6-continued
Amines of the Type A(B)N-$L_1$
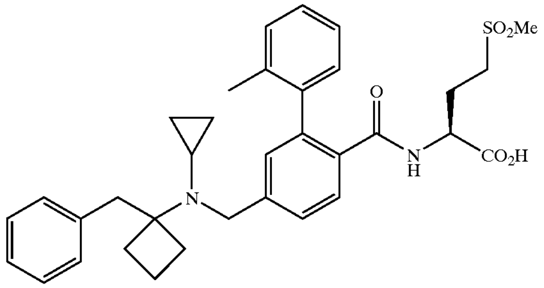
333
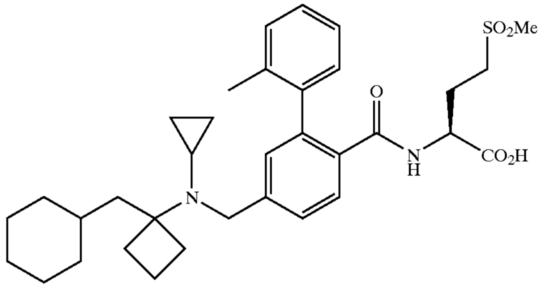
334
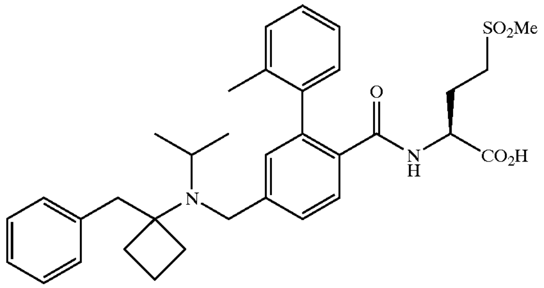
335
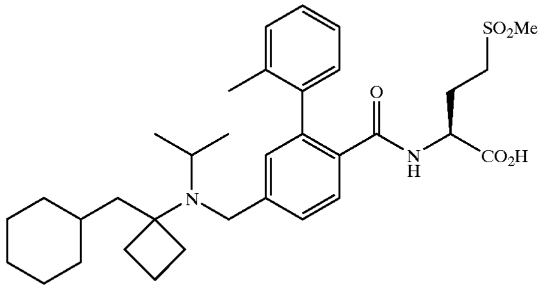
336
TABLE 6-continued
Amines of the Type A(B)N-$L_1$
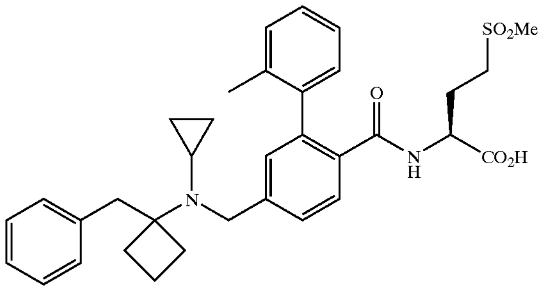
337
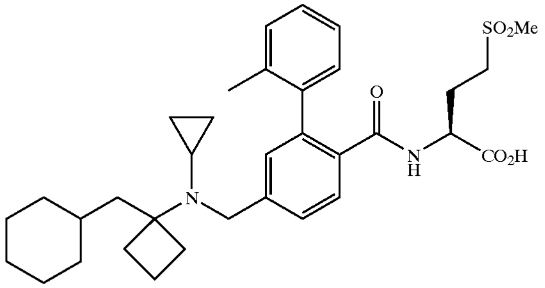
338
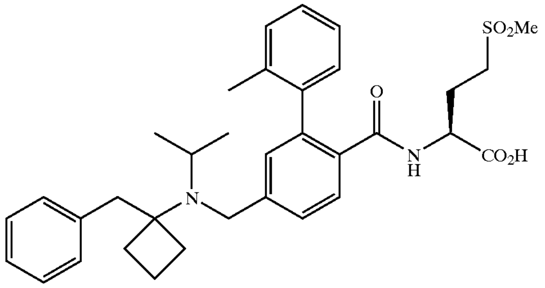
339
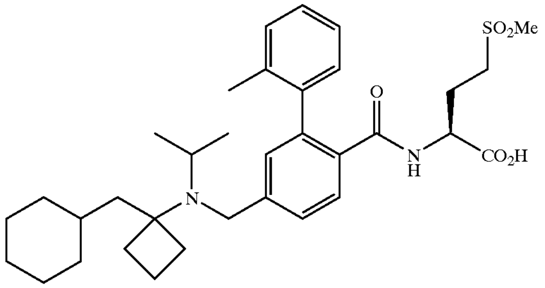
340

TABLE 6-continued
Amines of the Type A(B)N-$L_1$
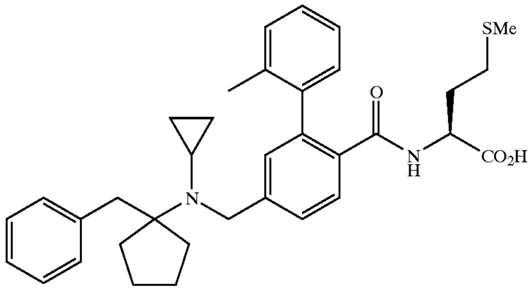
341
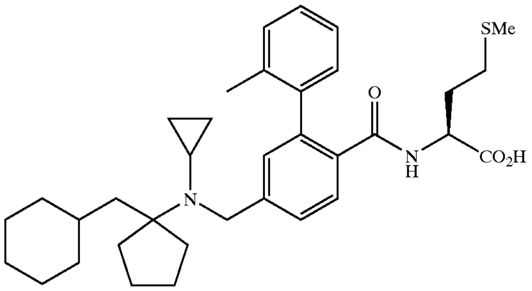
342
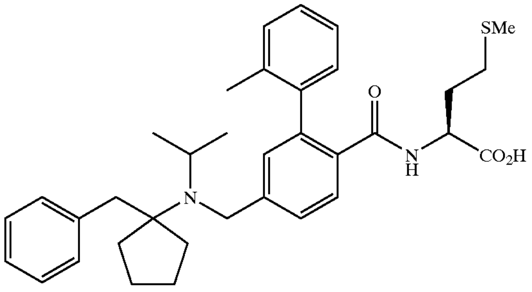
343
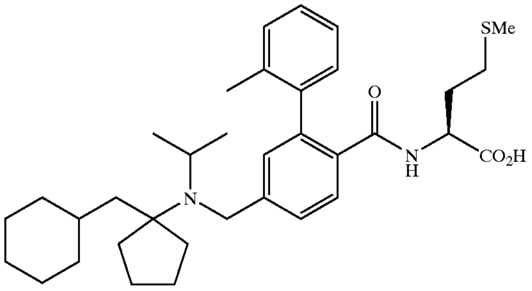
344
TABLE 6-continued
Amines of the Type A(B)N-$L_1$
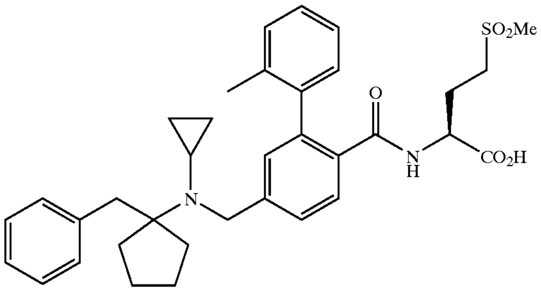
345
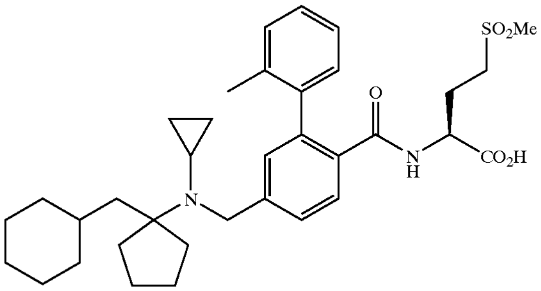
346
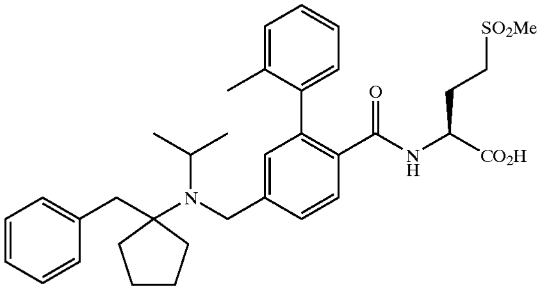
347
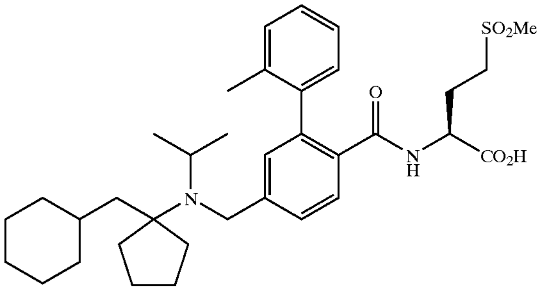
348

TABLE 6-continued
Amines of the Type A(B)N-$L_1$
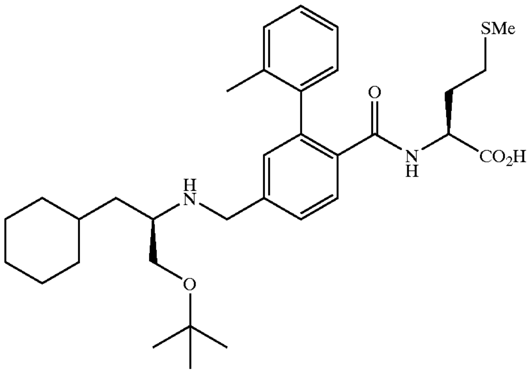
349
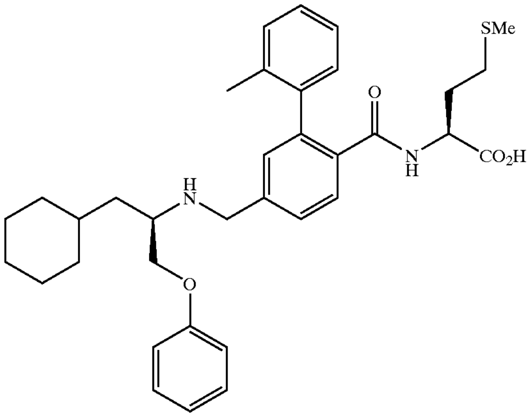
350
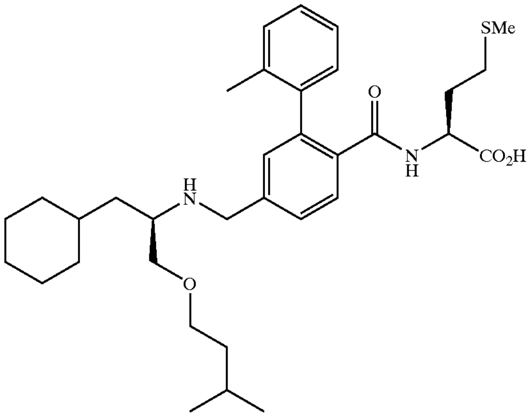
351
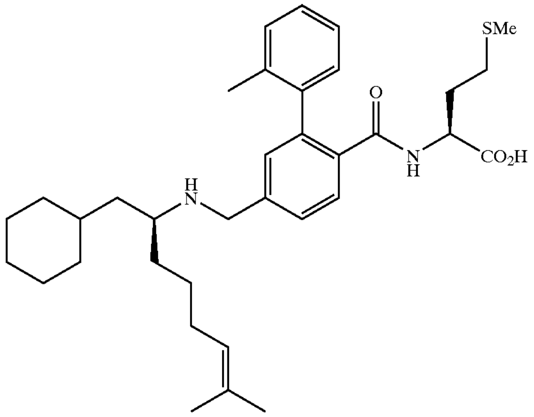
352
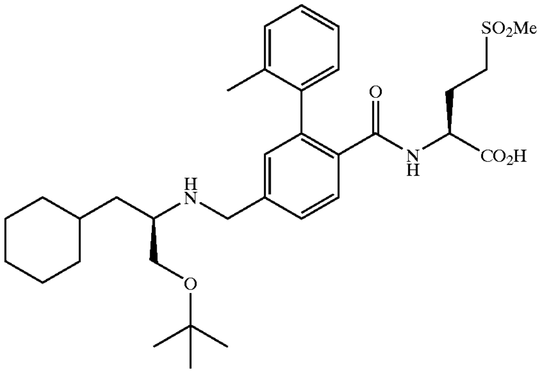
353
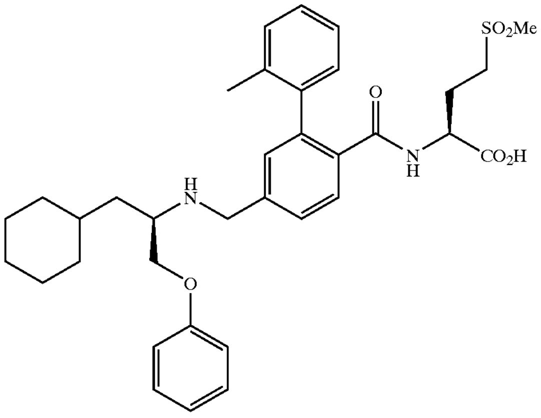
354

TABLE 6-continued
| Amines of the Type A(B)N-$L_1$ |
| --- |
| 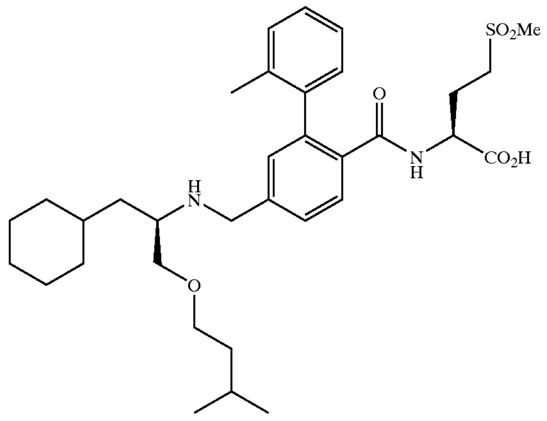 |
| 355 |
| 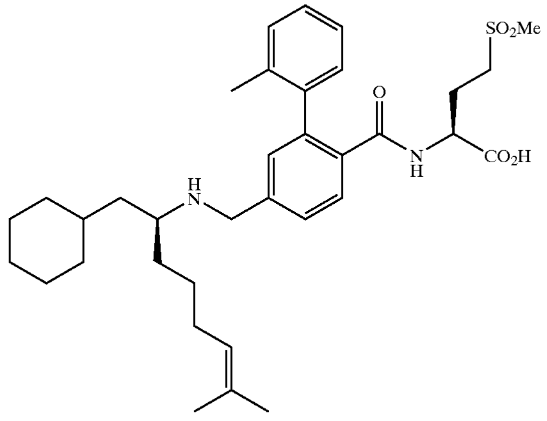 |
| 356 |
| 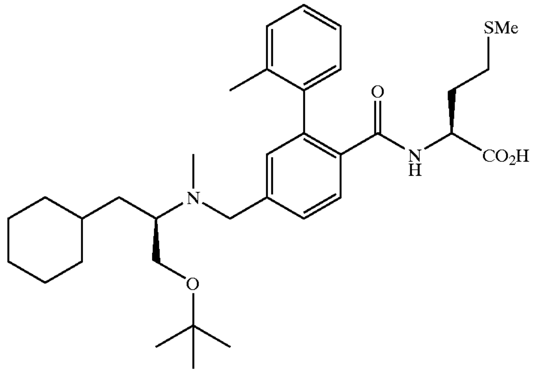 |
| 357 |
TABLE 6-continued
| Amines of the Type A(B)N-$L_1$ |
| --- |
| 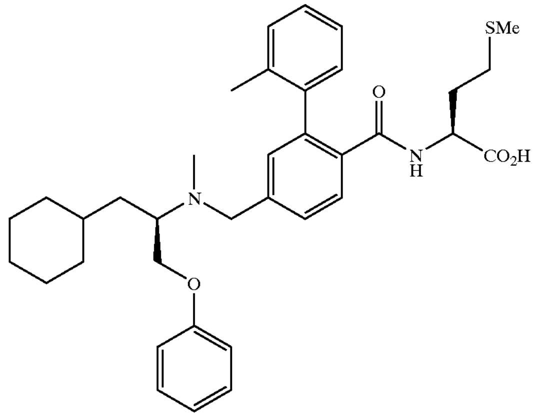 |
| 358 |
| 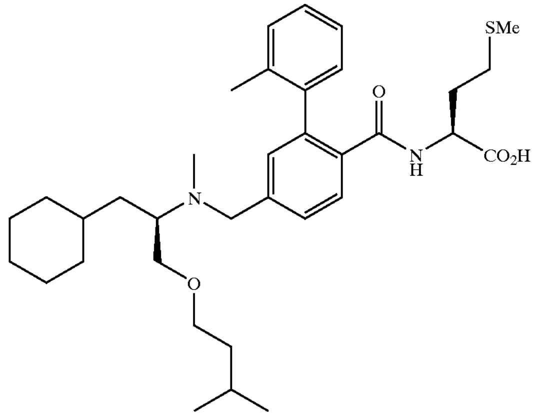 |
| 359 |
| 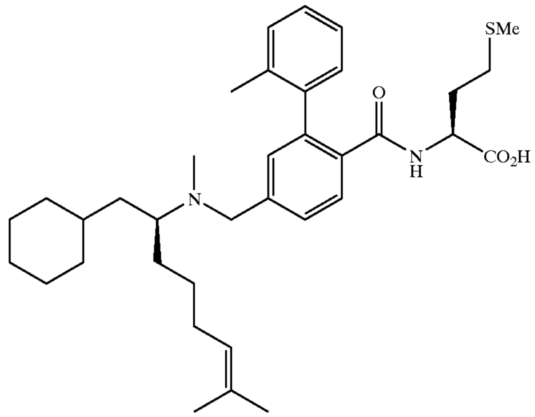 |
| 360 |

TABLE 6-continued
| Amines of the Type A(B)N-$L_1$ |
|---|
| 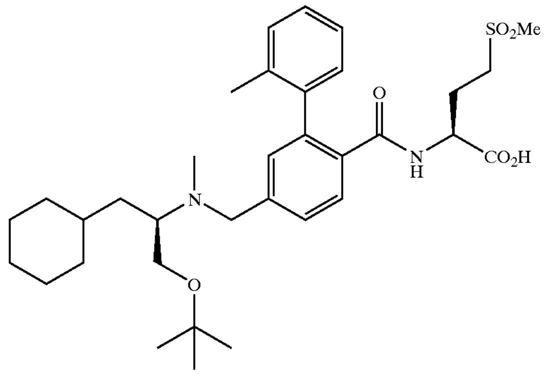 |
| 361 |
| 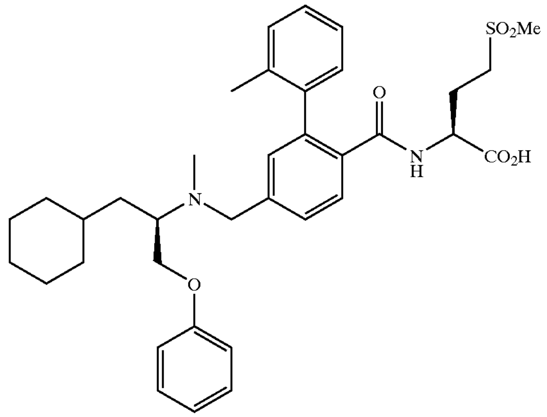 |
| 362 |
| 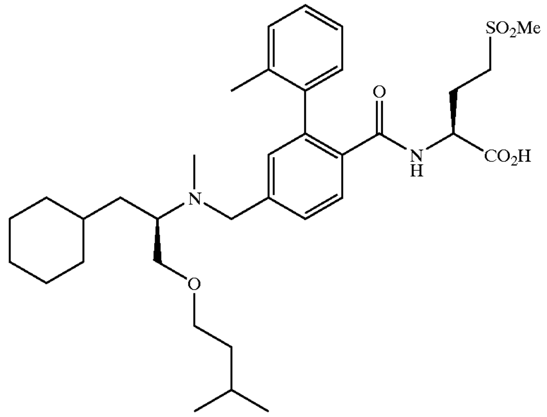 |
| 363 |
TABLE 6-continued
| Amines of the Type A(B)N-$L_1$ |
|---|
| 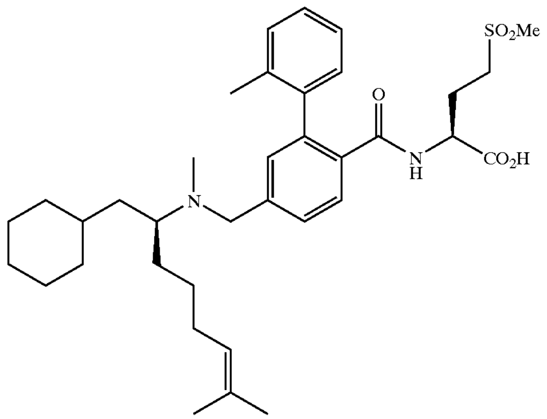 |
| 364 |
| 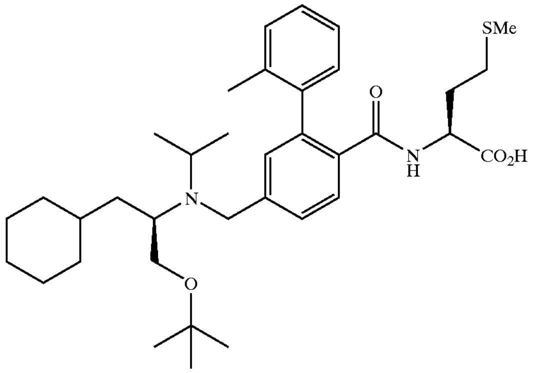 |
| 365 |
| 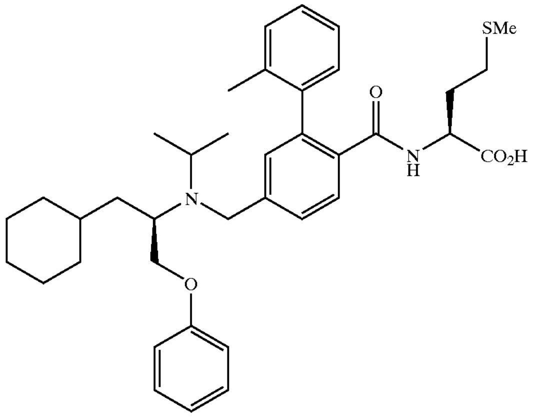 |
| 366 |

TABLE 6-continued
| Amines of the Type A(B)N-$L_1$ |
|---|
| 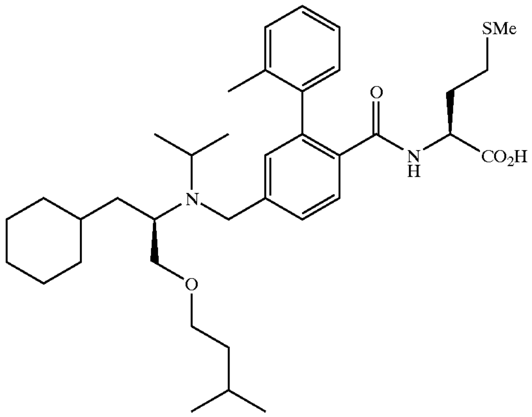 |
| 367 |
| 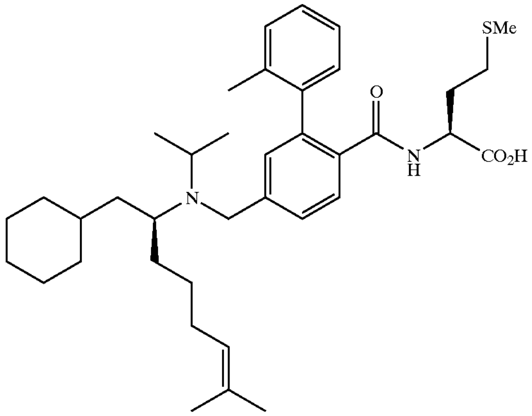 |
| 368 |
| 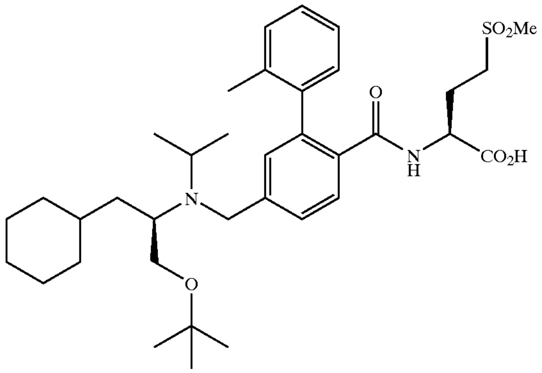 |
| 369 |
TABLE 6-continued
| Amines of the Type A(B)N-$L_1$ |
|---|
| 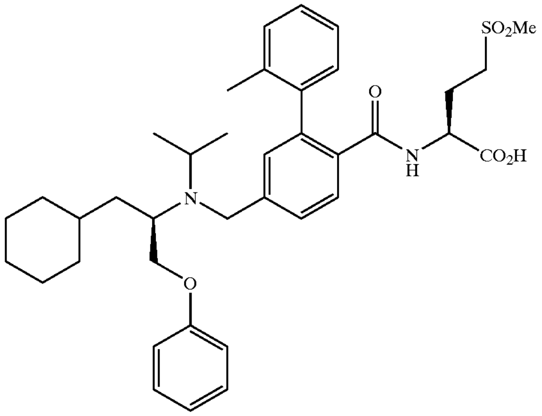 |
| 370 |
| 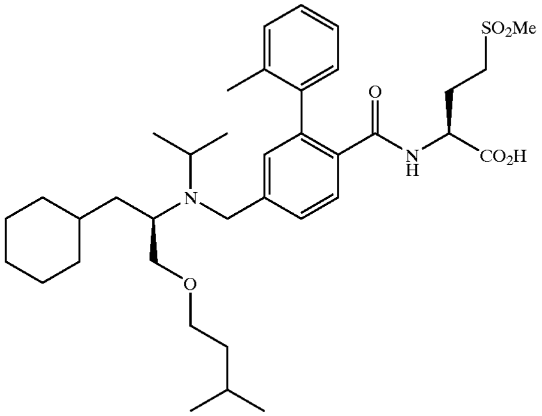 |
| 371 |
| 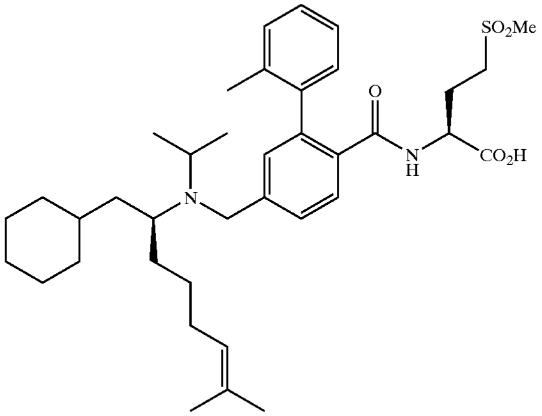 |
| 372 |

TABLE 6-continued
| Amines of the Type A(B)N-$L_1$ |
|---|
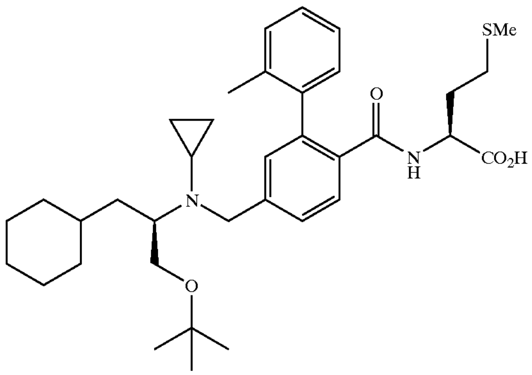
373
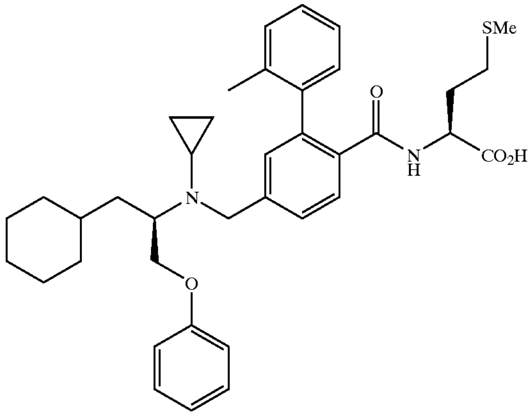
374
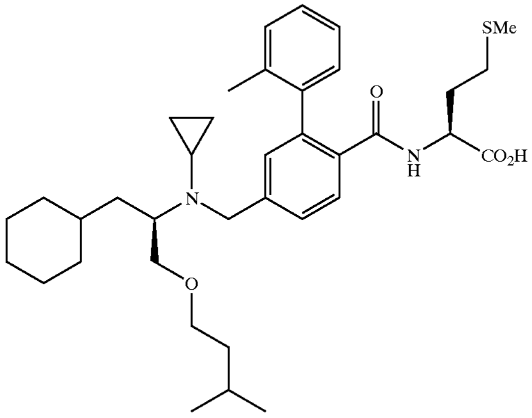
375
TABLE 6-continued
| Amines of the Type A(B)N-$L_1$ |
|---|
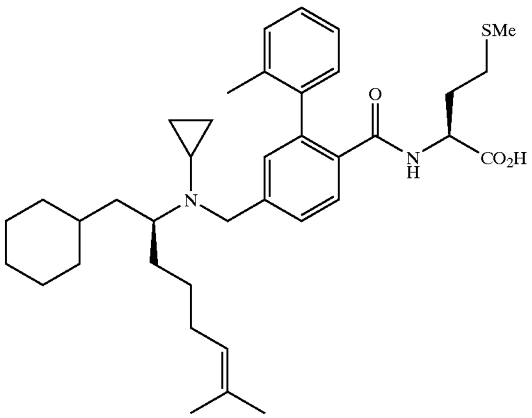
376
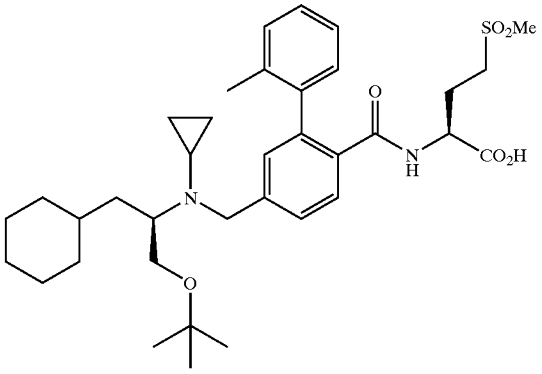
377
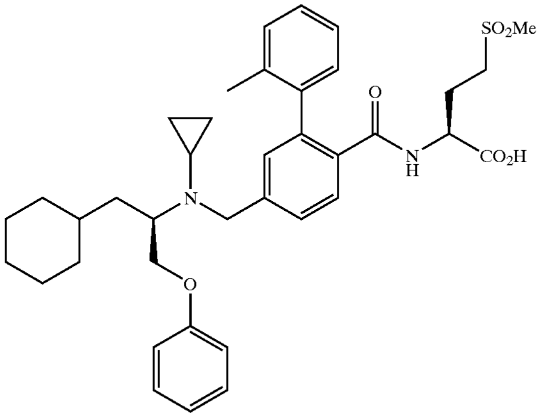
378

TABLE 6-continued
| Amines of the Type A(B)N-$L_1$ |
| --- |
| 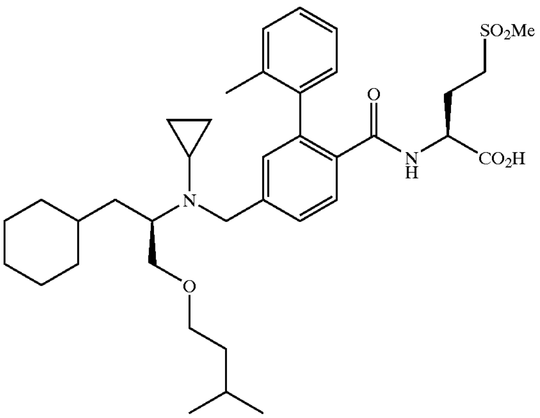 |
| 379 |
TABLE 6-continued
| Amines of the Type A(B)N-$L_1$ |
| --- |
| 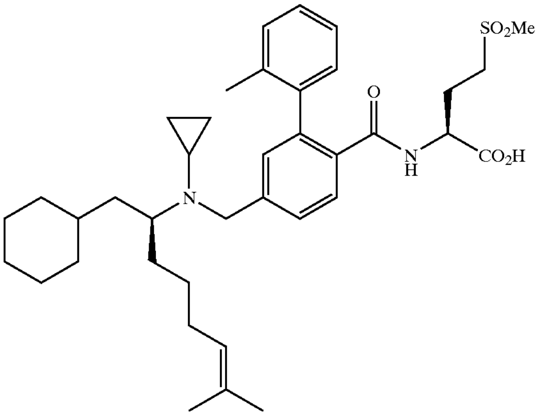 |
| 380 |
TABLE 7
| Ethers of the Type A-$OL_1$ |
| --- |
| 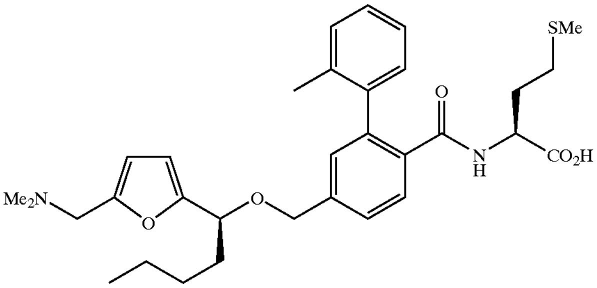 |
| 1 |
| 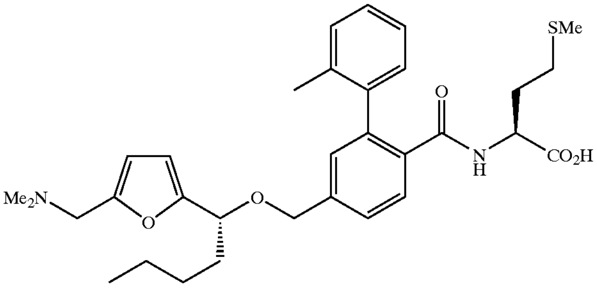 |
| 2 |

TABLE 7-continued
| Ethers of the Type A-$OL_1$ |
| --- |
| 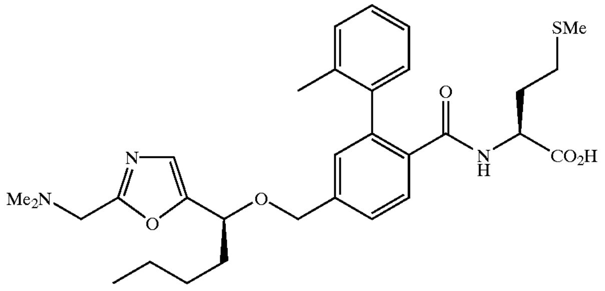 |
| 3 |
| 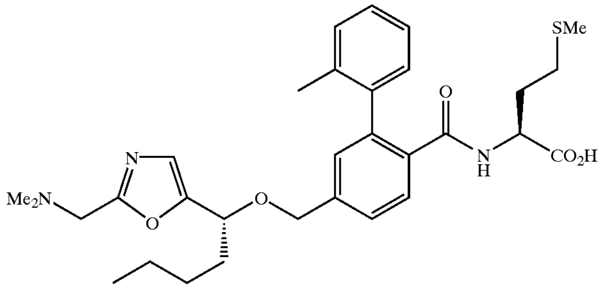 |
| 4 |
| 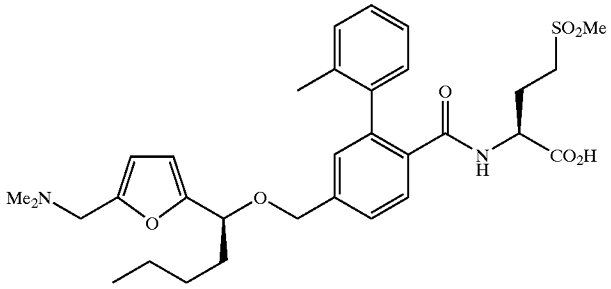 |
| 5 |
| 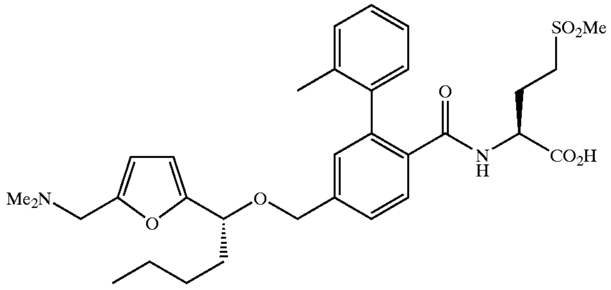 |
| 6 |

TABLE 7-continued
| Ethers of the Type A-$OL_1$ |
| --- |
| 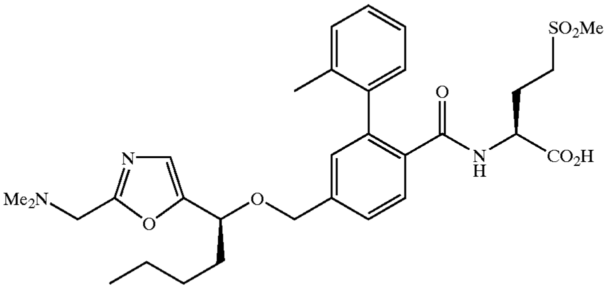 7 |
| 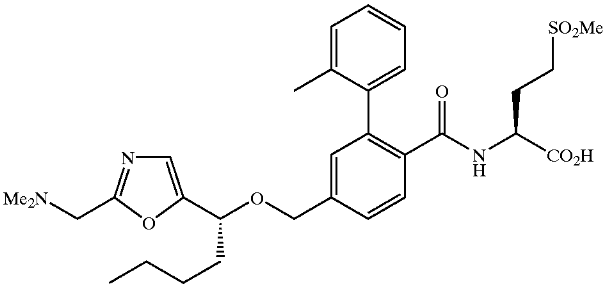 8 |
| 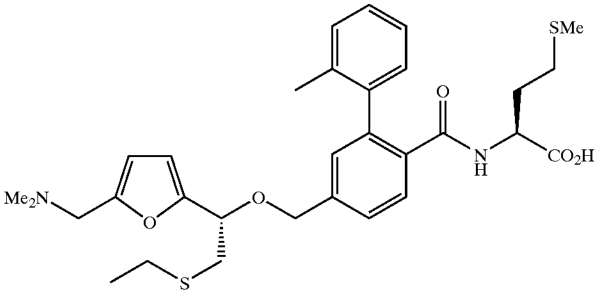 9 |
| 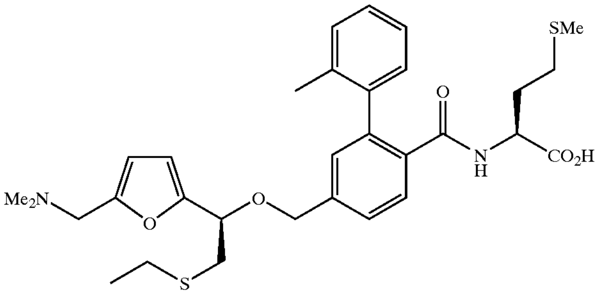 10 |

TABLE 7-continued
Ethers of the Type A-$OL_1$
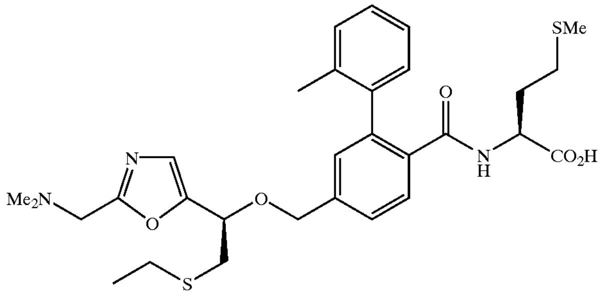
11
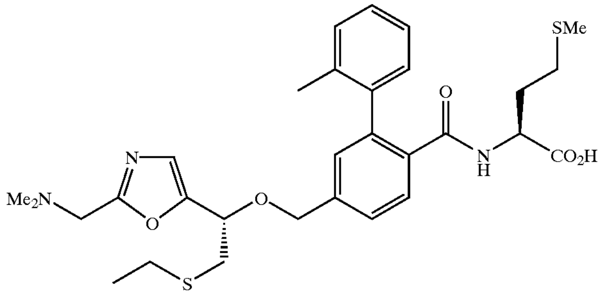
12
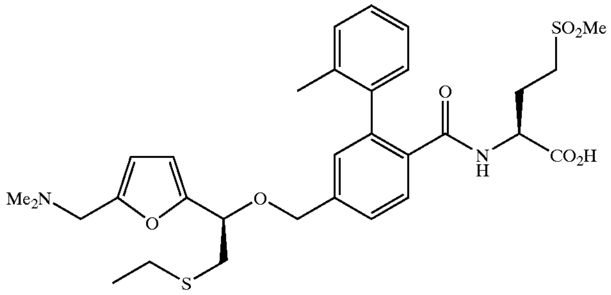
13
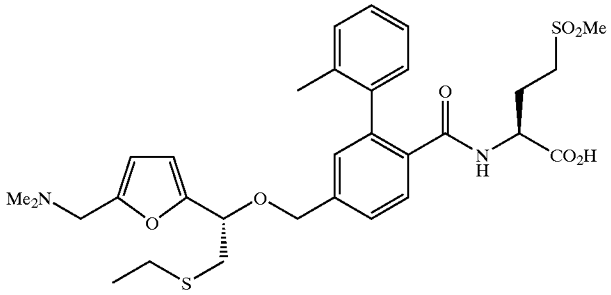
14

TABLE 7-continued
| Ethers of the Type A-$OL_1$ |
| --- |
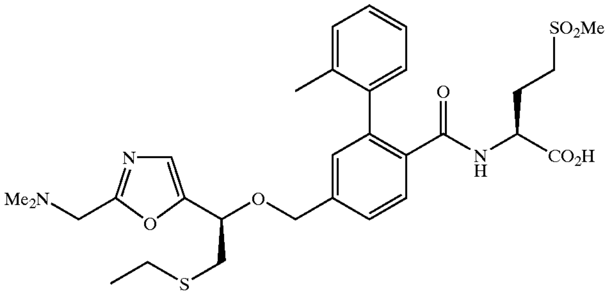
15
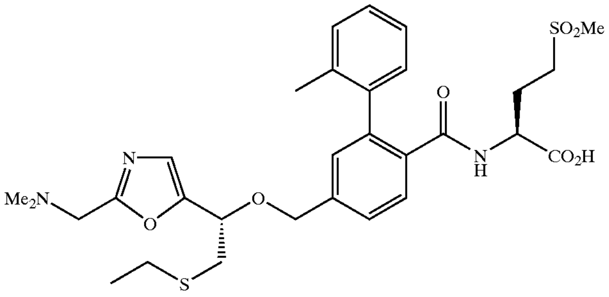
16
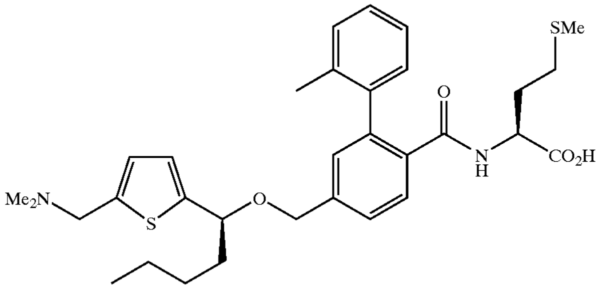
17
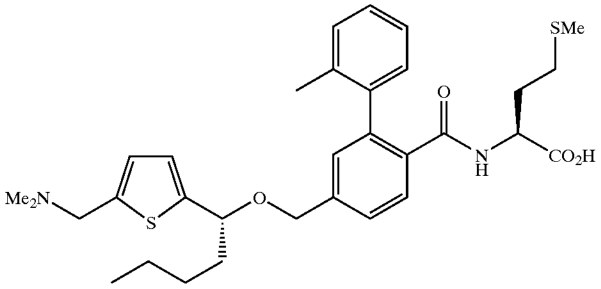
18

TABLE 7-continued
| Ethers of the Type A-$OL_1$ |
| --- |
| 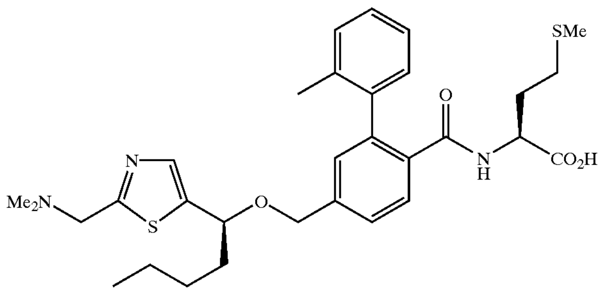 19 |
| 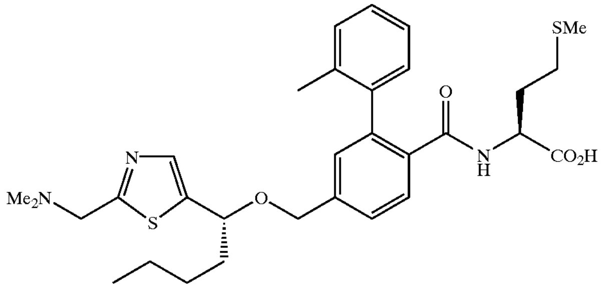 20 |
| 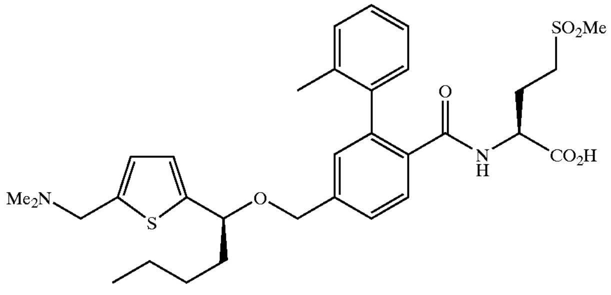 21 |
| 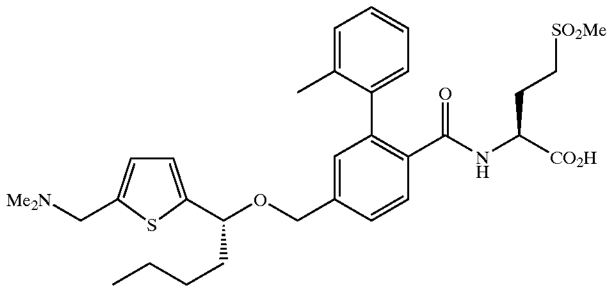 22 |

TABLE 7-continued
Ethers of the Type A-$OL_1$
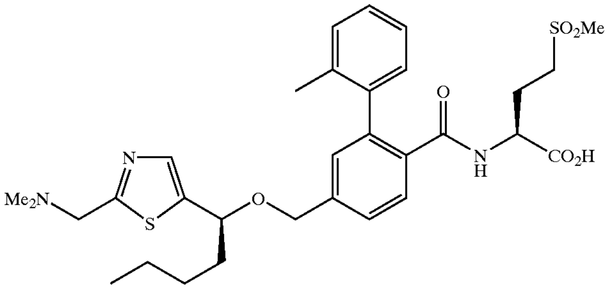
23
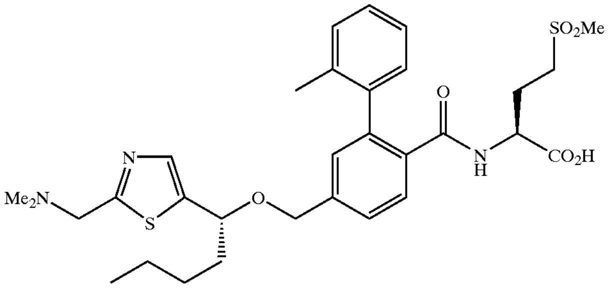
24
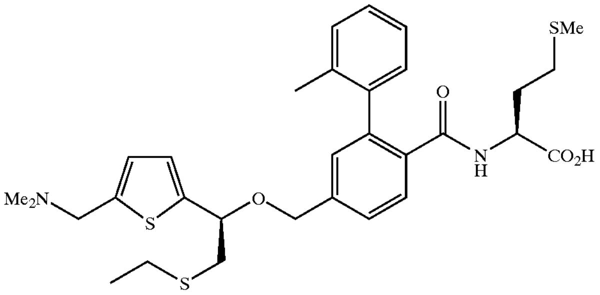
25
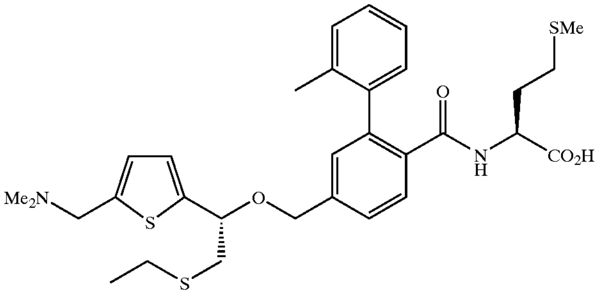
26

TABLE 7-continued
Ethers of the Type A-$OL_1$
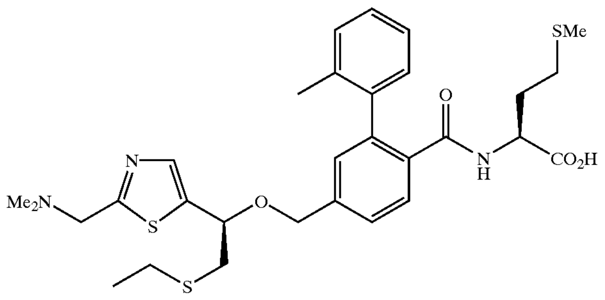
27
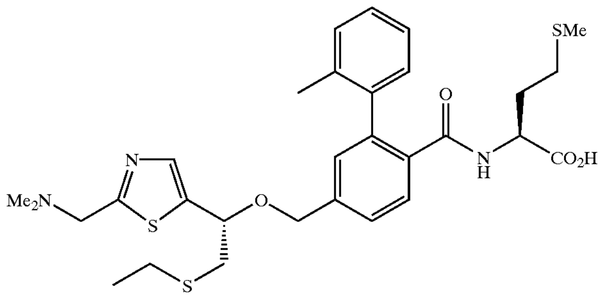
28
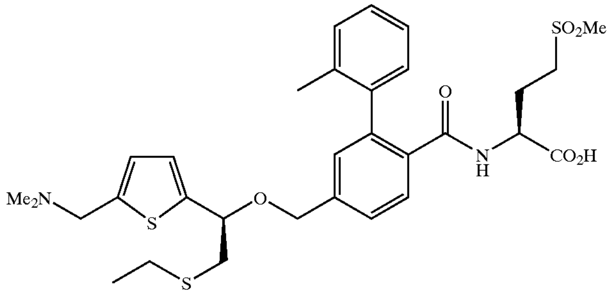
29
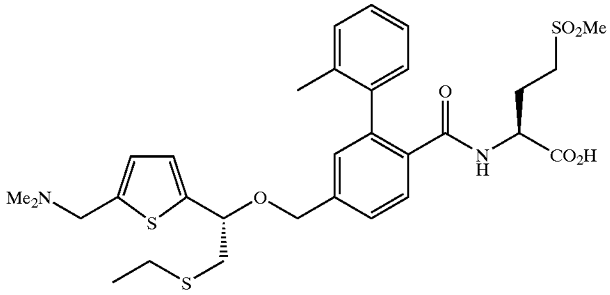
30

TABLE 7-continued
Ethers of the Type A-$OL_1$
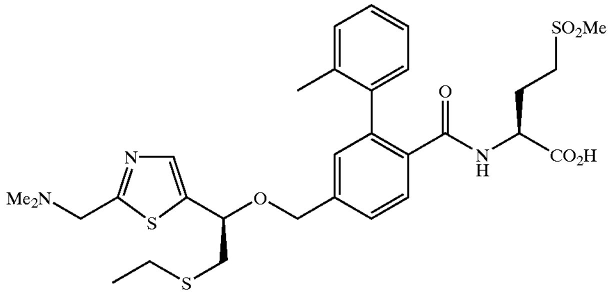
31
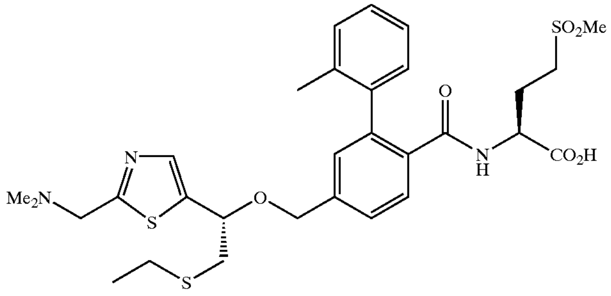
32
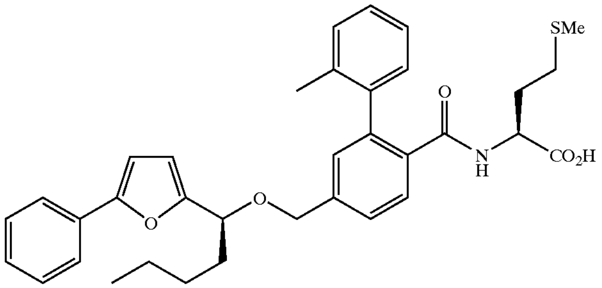
33
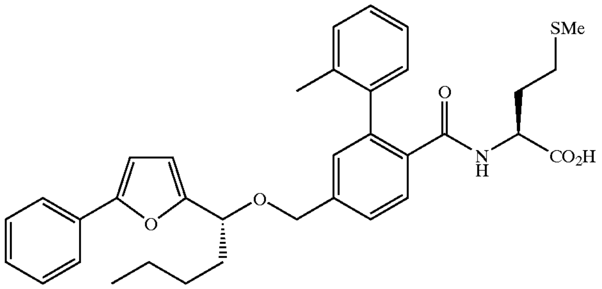
34

TABLE 7-continued
Ethers of the Type A-$OL_1$
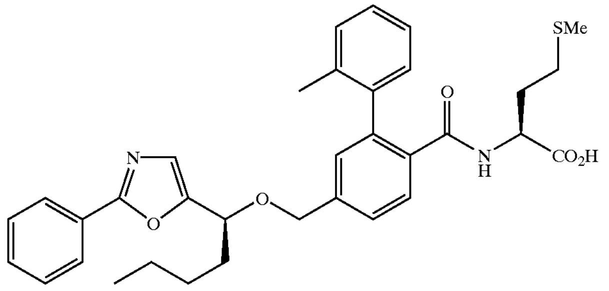
35
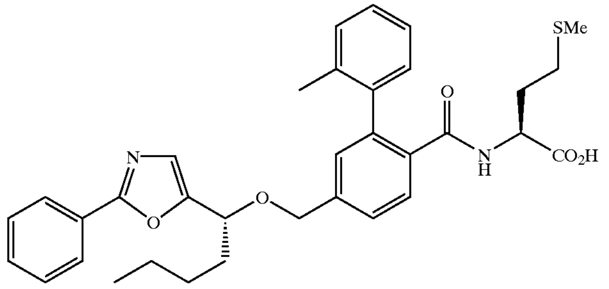
36
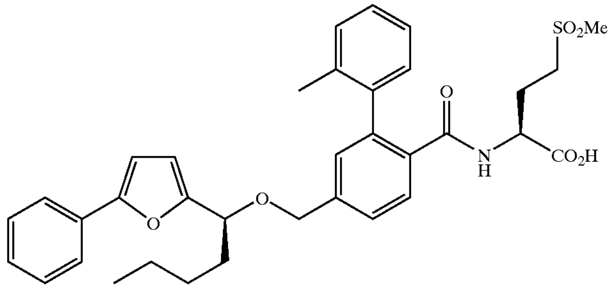
37
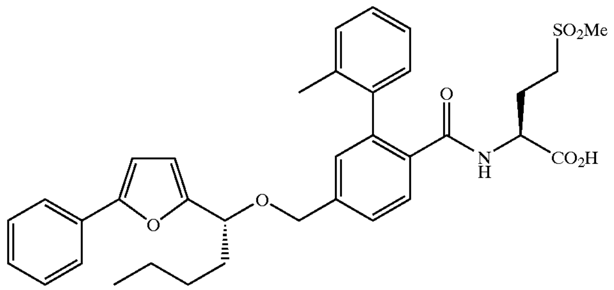
38

TABLE 7-continued
Ethers of the Type A-$OL_1$
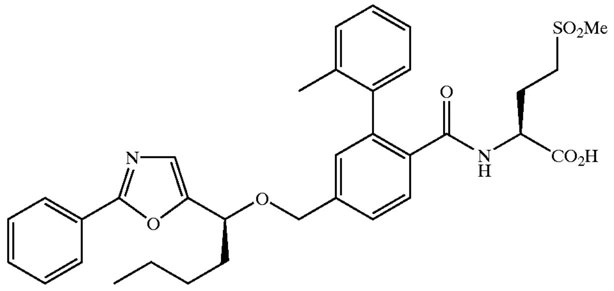
39
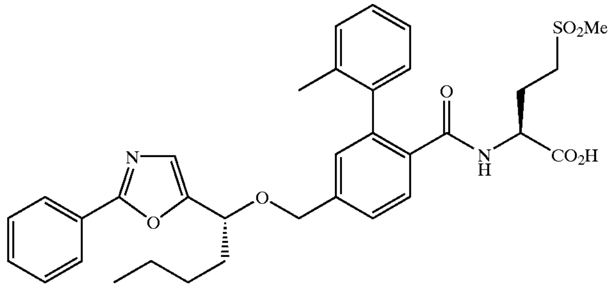
40
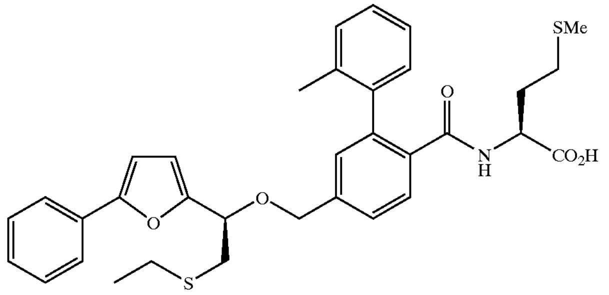
41
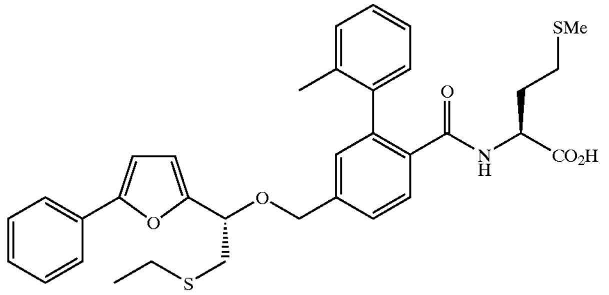
42

TABLE 7-continued
| Ethers of the Type A-$OL_1$ |
| --- |
| 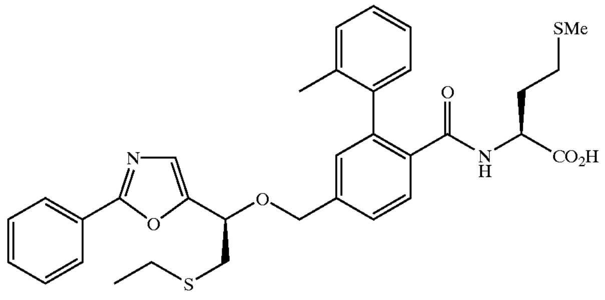 |
| 43 |
| 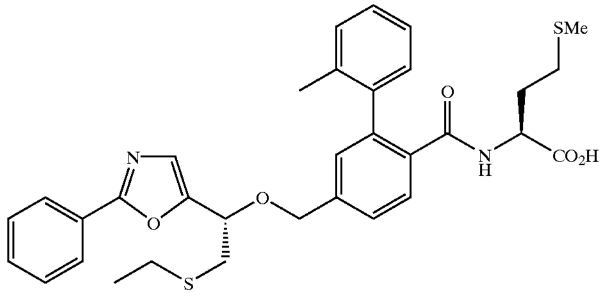 |
| 44 |
| 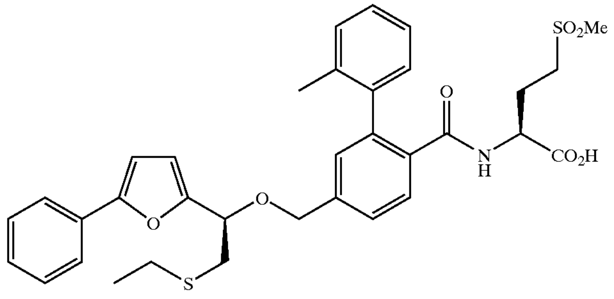 |
| 45 |
| 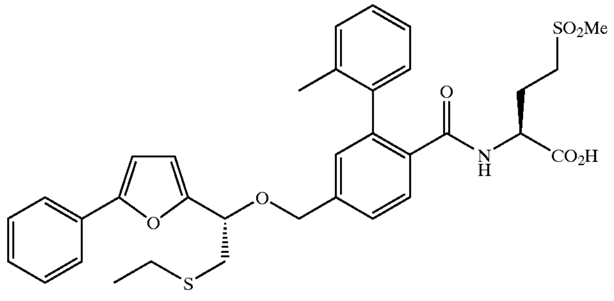 |
| 46 |

TABLE 7-continued
| Ethers of the Type A-$OL_1$ |
| --- |
| 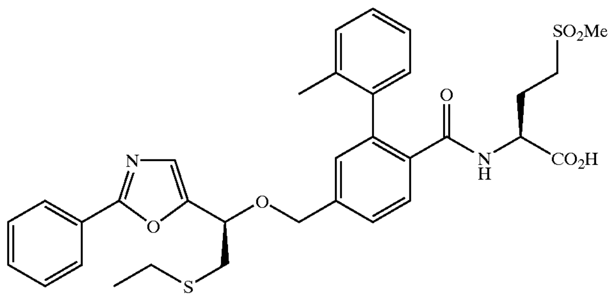 |
| 47 |
| 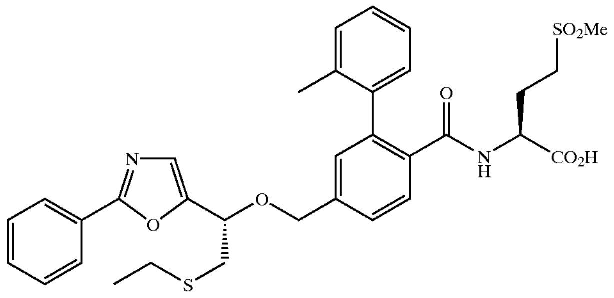 |
| 48 |
| 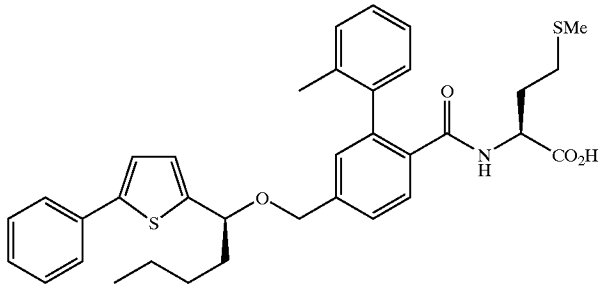 |
| 49 |
| 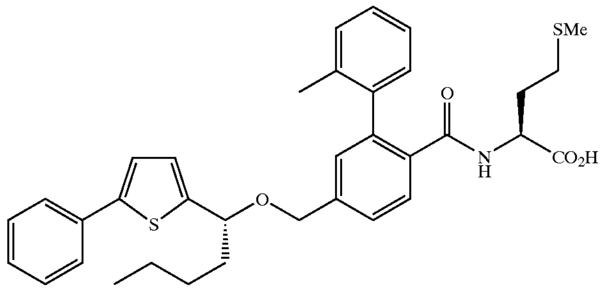 |
| 50 |

TABLE 7-continued
Ethers of the Type A-$OL_1$
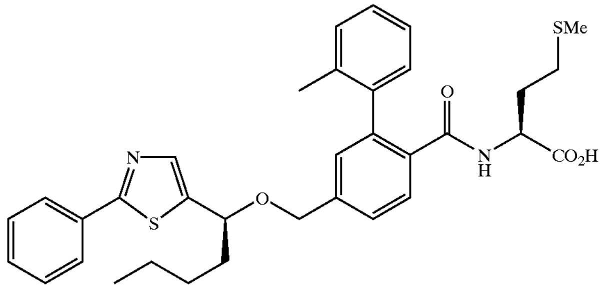
51
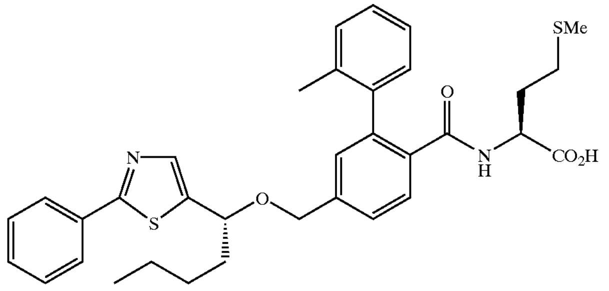
52
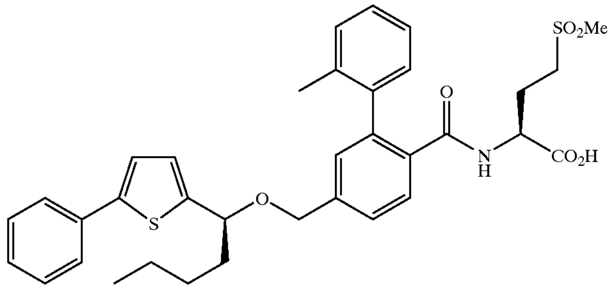
53
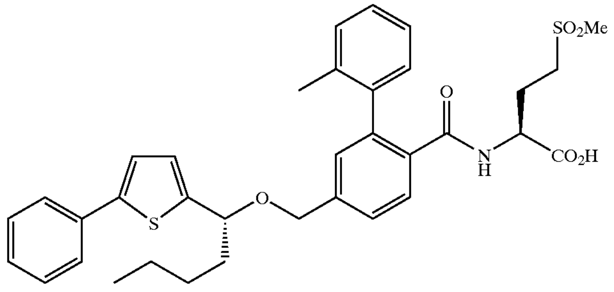
54

TABLE 7-continued
| Ethers of the Type A-$OL_1$ |
|---|
| 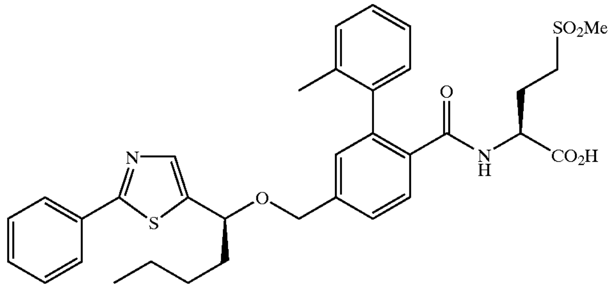 |
| 55 |
| 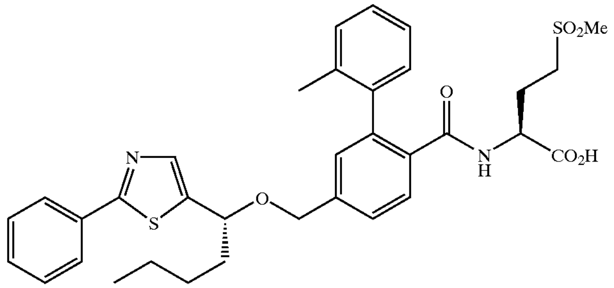 |
| 56 |
| 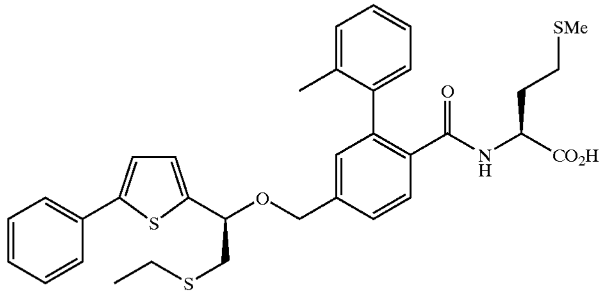 |
| 57 |
| 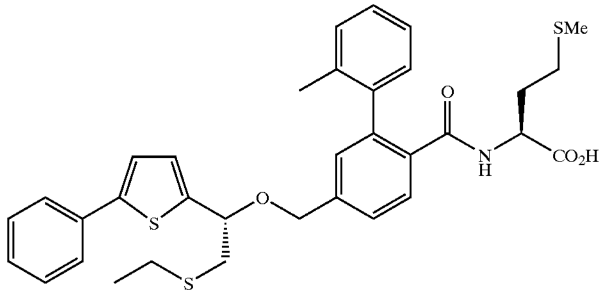 |
| 58 |

TABLE 7-continued
Ethers of the Type A-$OL_1$
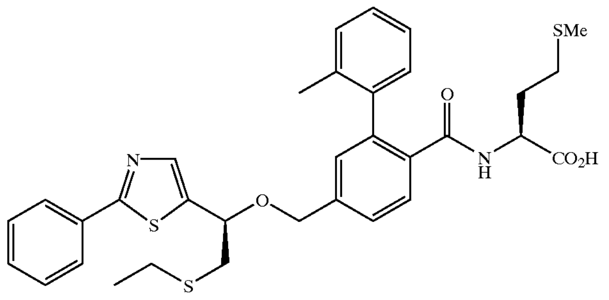
59
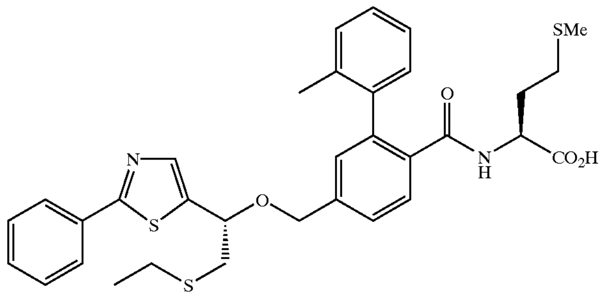
60
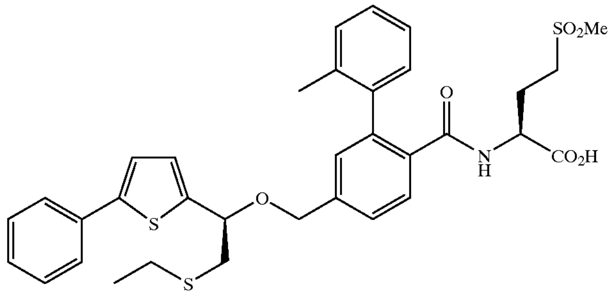
61
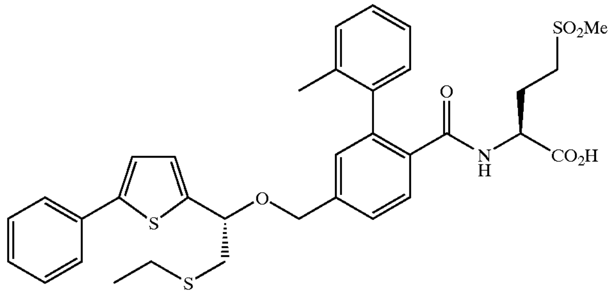
62

TABLE 7-continued
| Ethers of the Type A-$OL_1$ |
|---|
| 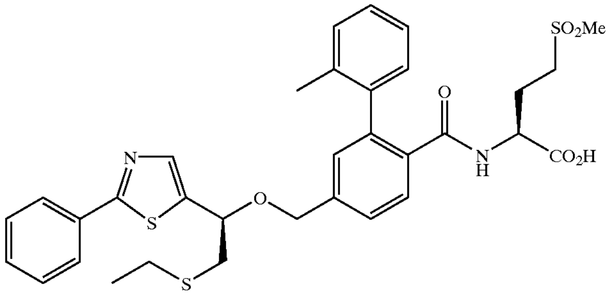 |
| 63 |
| 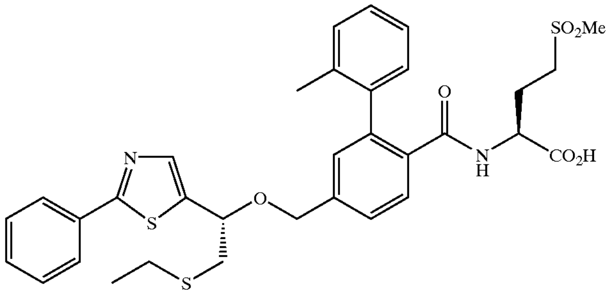 |
| 64 |
| 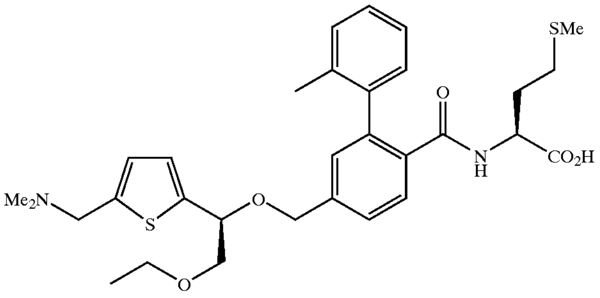 |
| 65 |
| 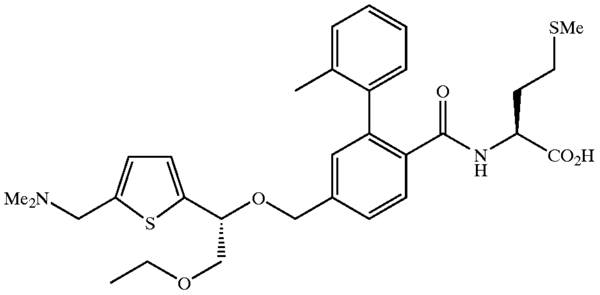 |
| 66 |

TABLE 7-continued
| Ethers of the Type A-$OL_1$ |
|---|
| 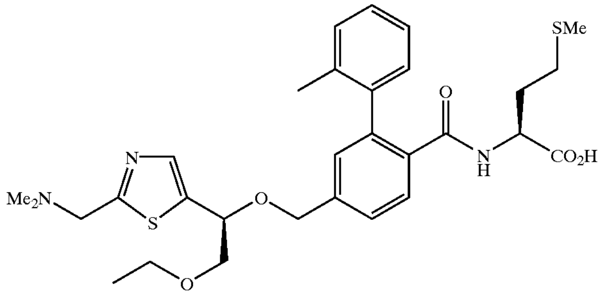 |
| 67 |
| 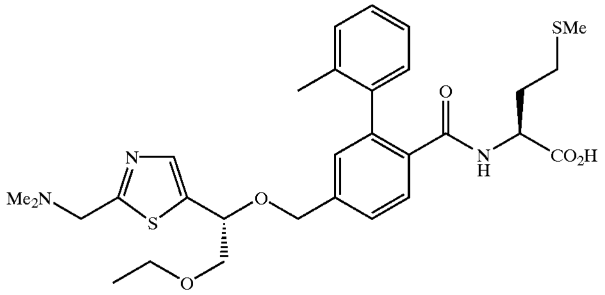 |
| 68 |
| 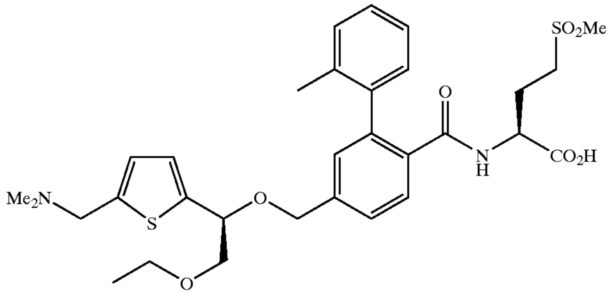 |
| 69 |
| 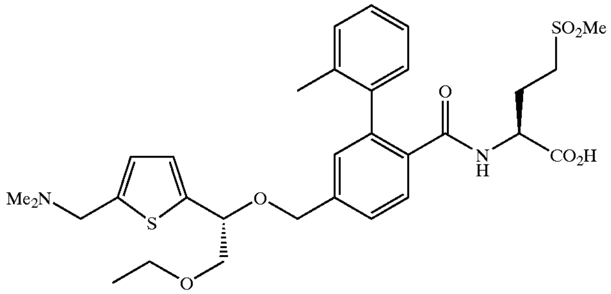 |
| 70 |

TABLE 7-continued
| Ethers of the Type A-$OL_1$ |
|---|
| 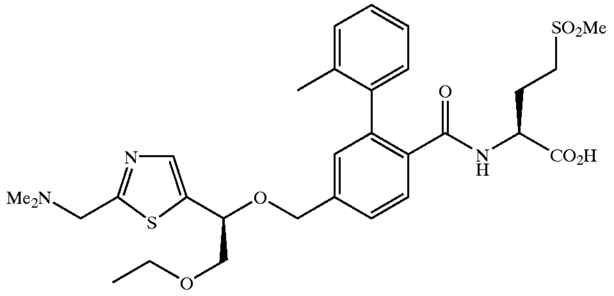 |
| 71 |
| 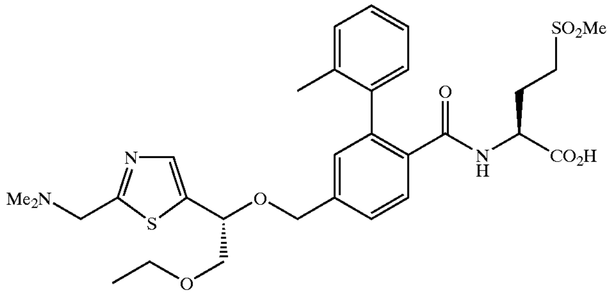 |
| 72 |
| 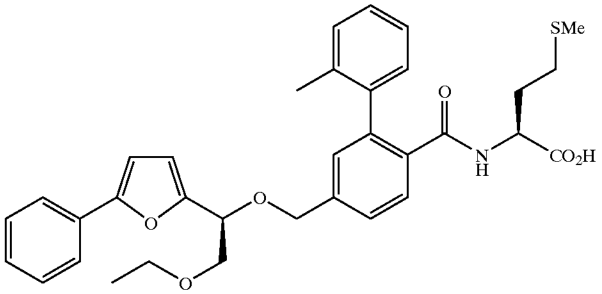 |
| 73 |
| 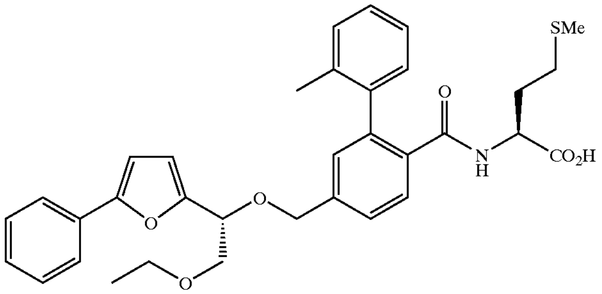 |
| 74 |

TABLE 7-continued
Ethers of the Type A-$OL_1$
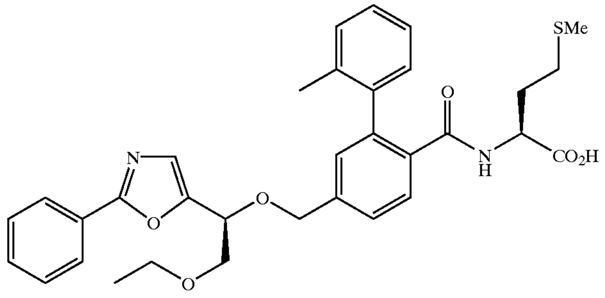
75
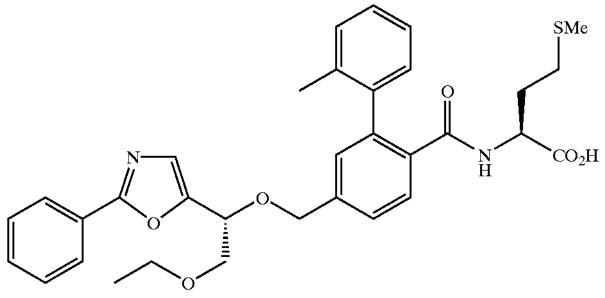
76
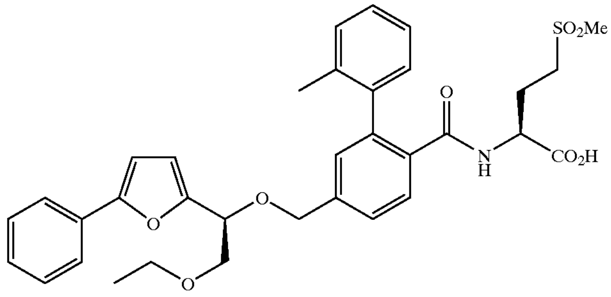
77
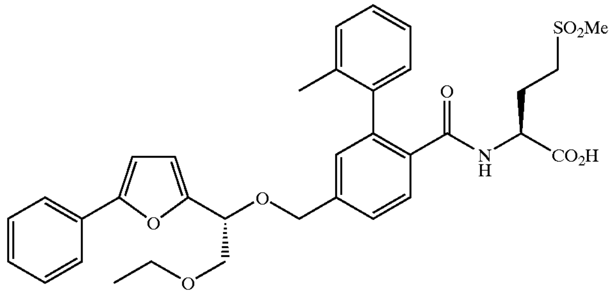
78

TABLE 7-continued
Ethers of the Type A-$OL_1$
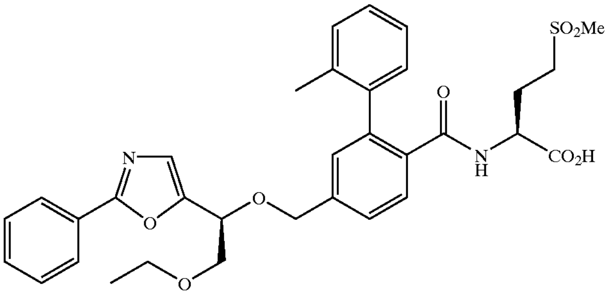
79
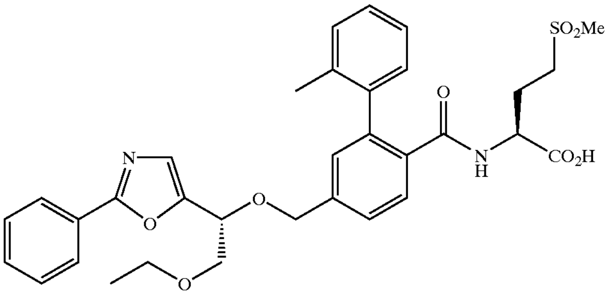
80
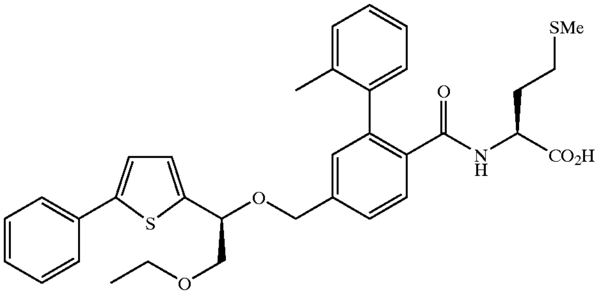
81
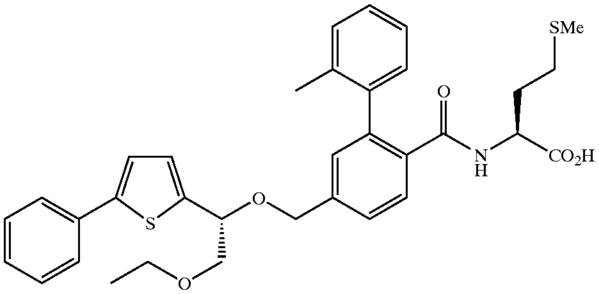
82

TABLE 7-continued
| Ethers of the Type A-$OL_1$ |
| --- |
| 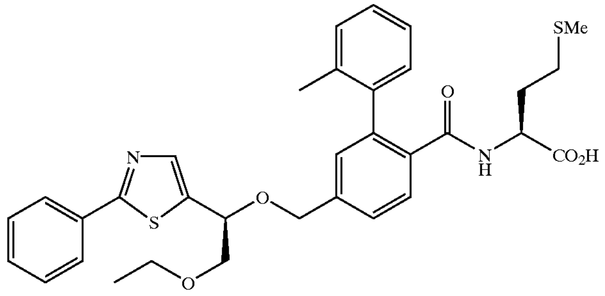 83 |
| 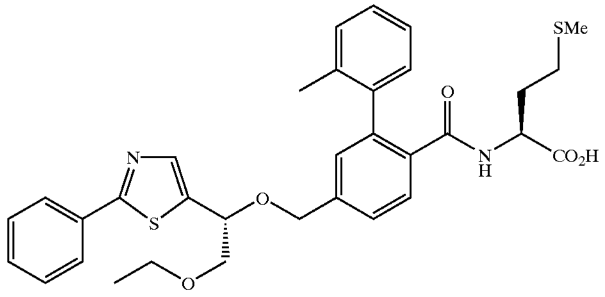 84 |
| 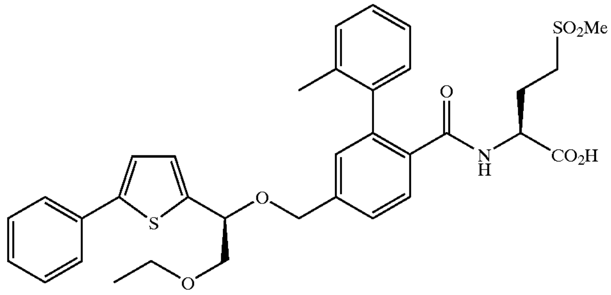 85 |
| 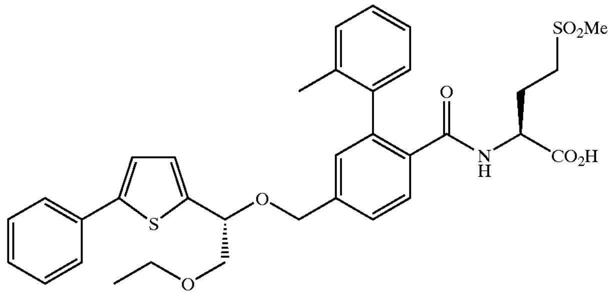 86 |

TABLE 7-continued
| Ethers of the Type A-$OL_1$ |
|---|
| 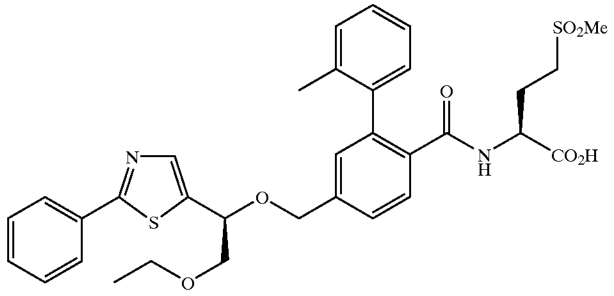 |
| 87 |
| 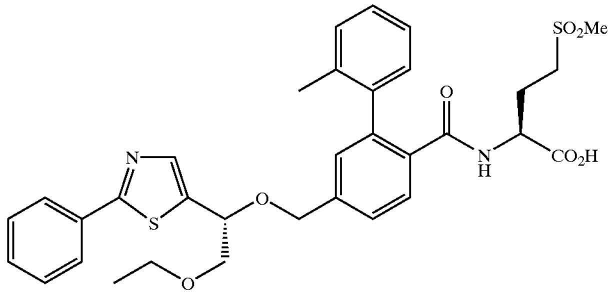 |
| 88 |
| 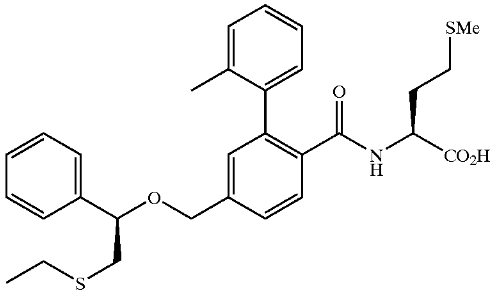 |
| 89 |
| 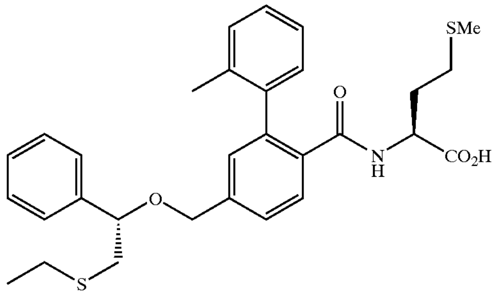 |
| 90 |

TABLE 7-continued
| Ethers of the Type A-$OL_1$ |
|---|
| 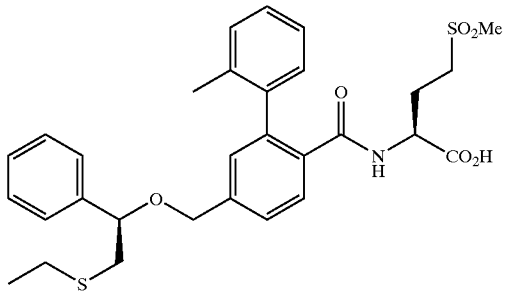 |
| 91 |
| 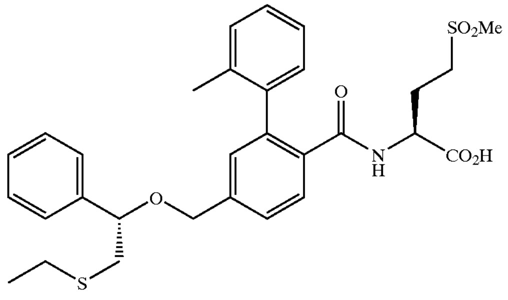 |
| 92 |
| 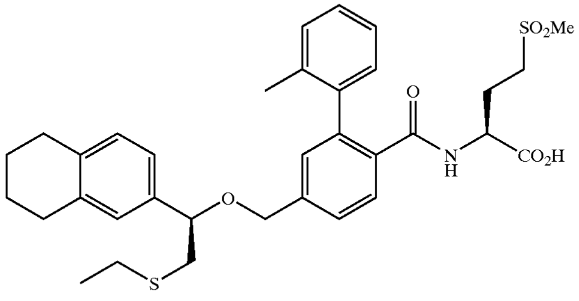 |
| 93 |
| 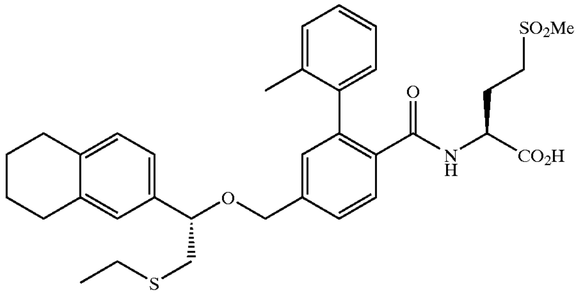 |
| 94 |

TABLE 7-continued
| Ethers of the Type A-$OL_1$ |
|---|
| 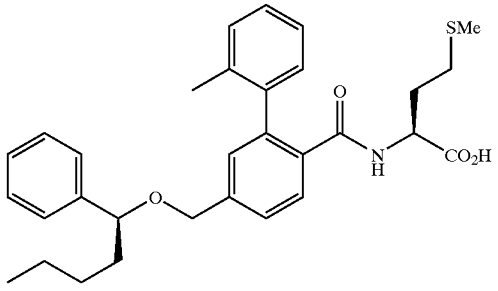 |
| 95 |
| 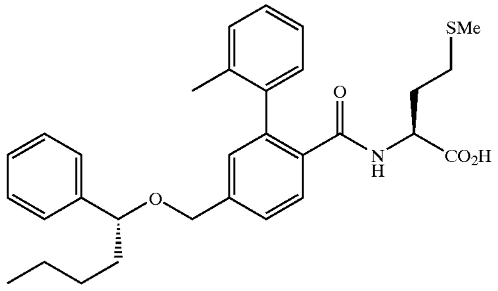 |
| 96 |
| 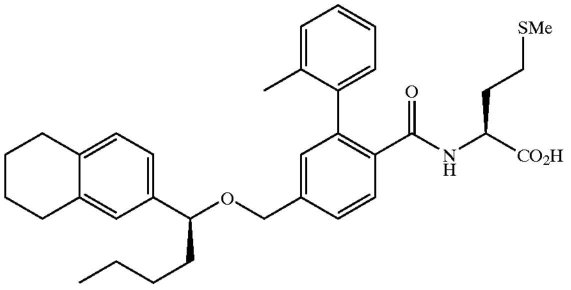 |
| 97 |
| 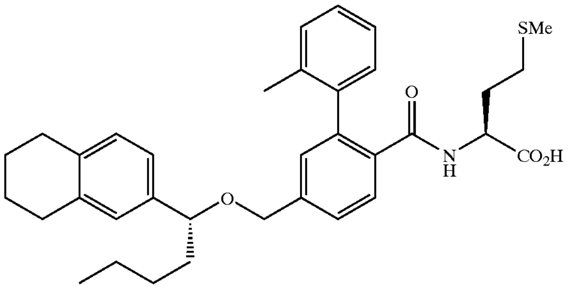 |
| 98 |

TABLE 7-continued
| Ethers of the Type A-$OL_1$ |
|---|
| 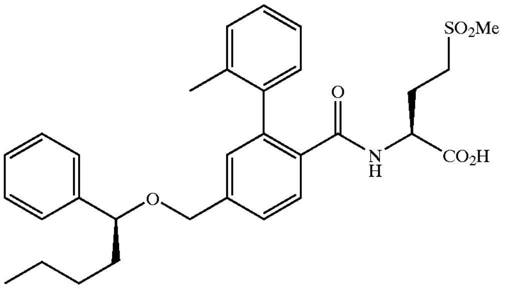 |
| 99 |
| 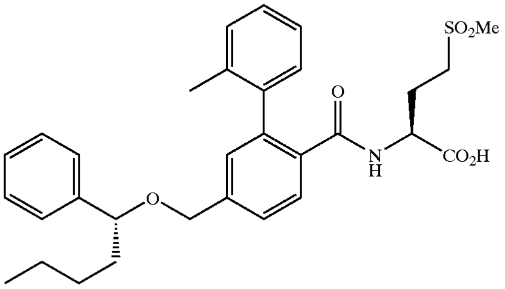 |
| 100 |
| 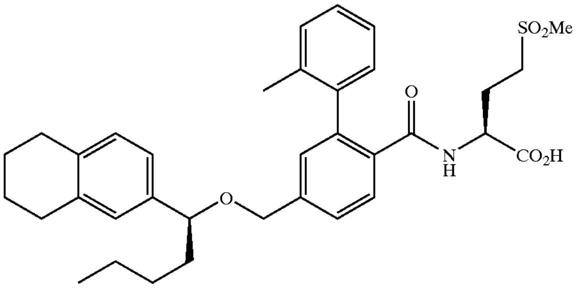 |
| 101 |
| 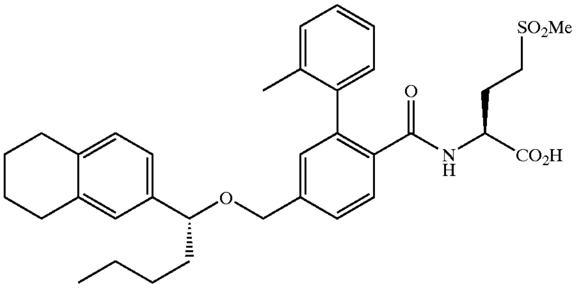 |
| 102 |

TABLE 7-continued
| Ethers of the Type A-$OL_1$ |
|---|
| 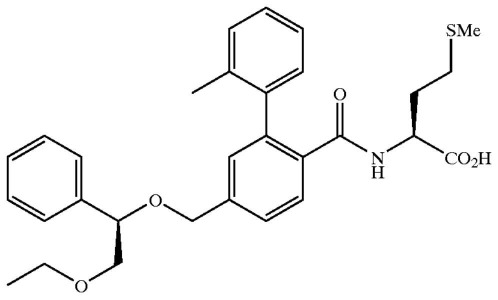 |
| 103 |
| 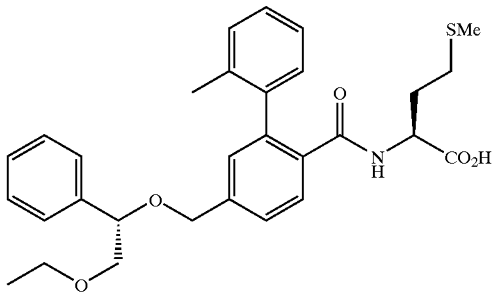 |
| 104 |
| 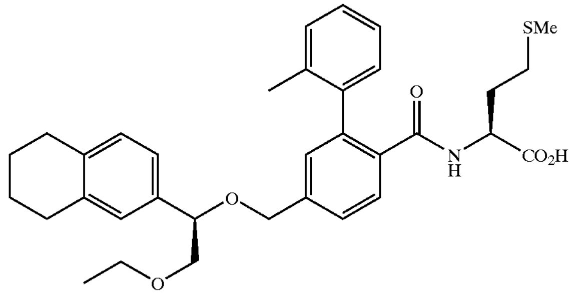 |
| 105 |
| 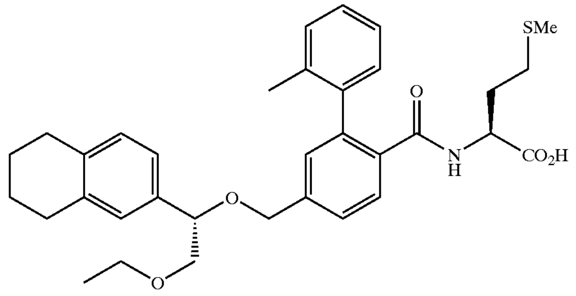 |
| 106 |

TABLE 7-continued
| Ethers of the Type A-$OL_1$ |
|---|
| 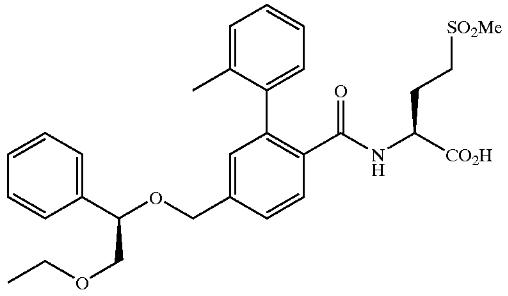 |
| 107 |
| 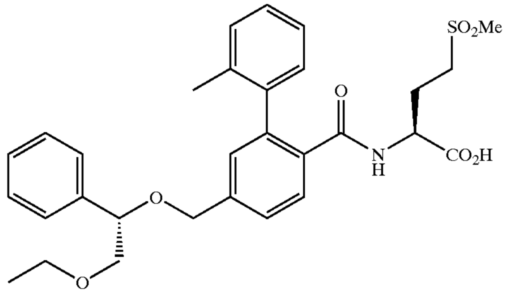 |
| 108 |
| 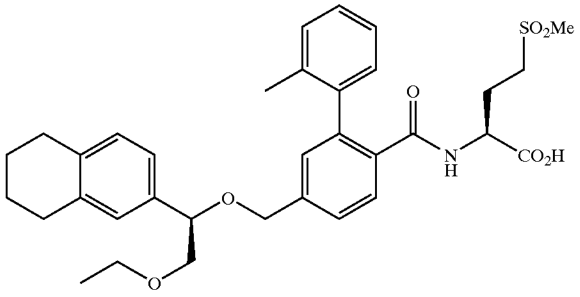 |
| 109 |
| 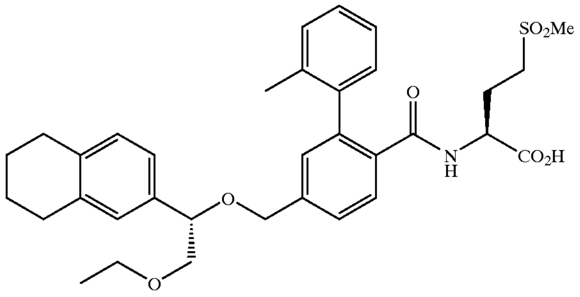 |
| 110 |

TABLE 7-continued
| Ethers of the Type A-$OL_1$ |
|---|
| 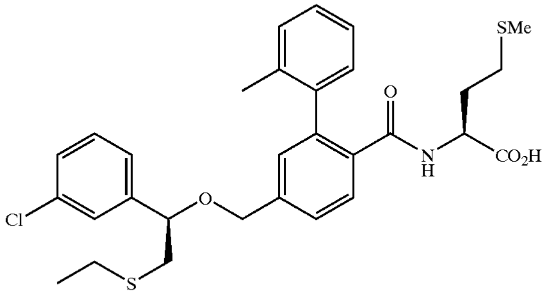 |
| 111 |
| 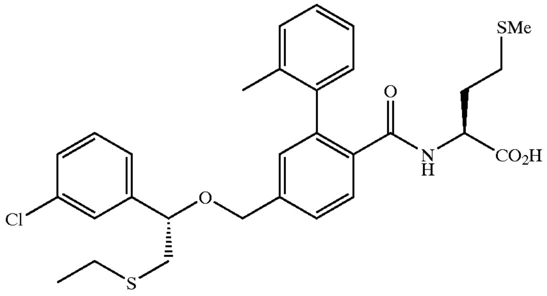 |
| 112 |
| 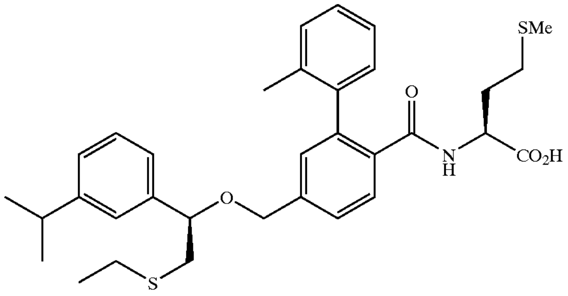 |
| 113 |
| 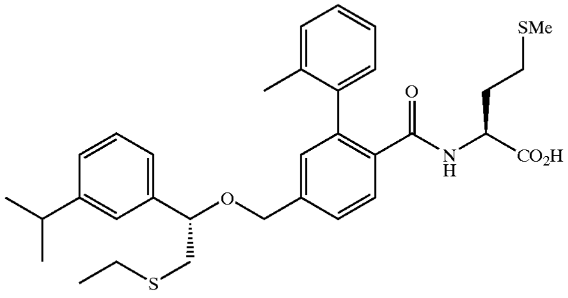 |
| 114 |

TABLE 7-continued
| Ethers of the Type A-$OL_1$ |
| --- |
| 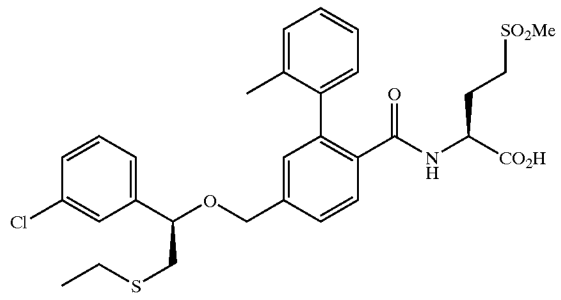 |
| 115 |
| 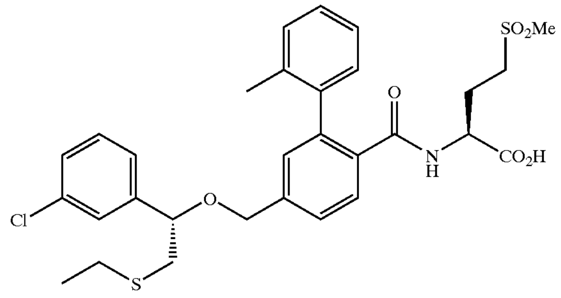 |
| 116 |
| 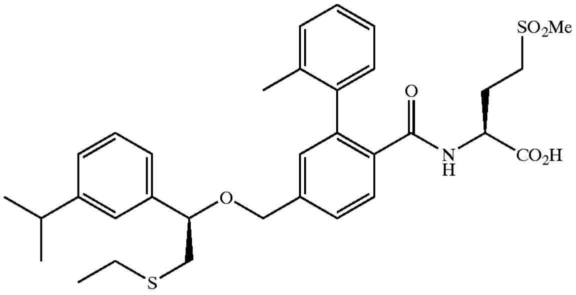 |
| 117 |
| 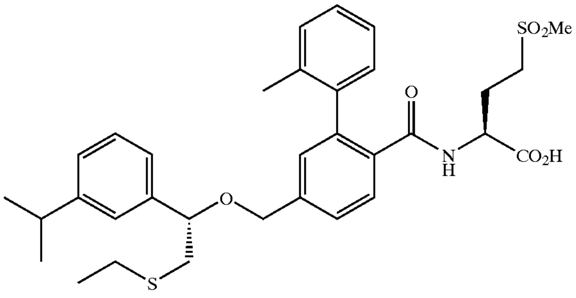 |
| 118 |

TABLE 7-continued
Ethers of the Type A-$OL_1$
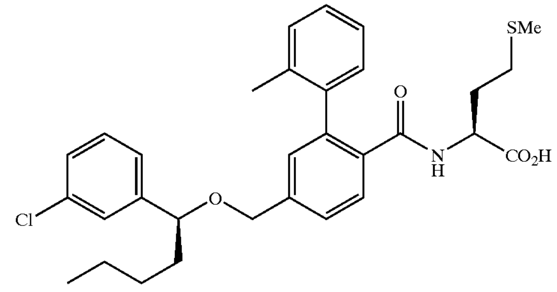
119
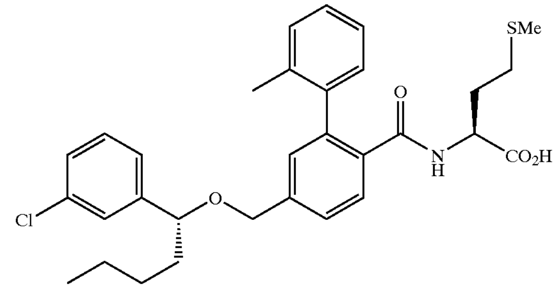
120
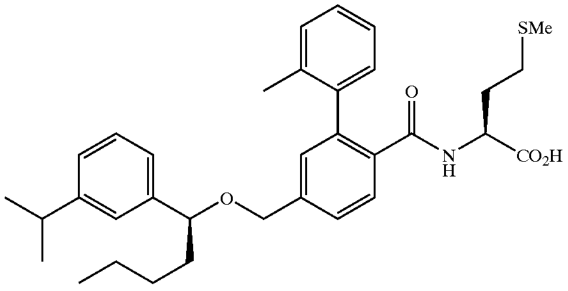
121
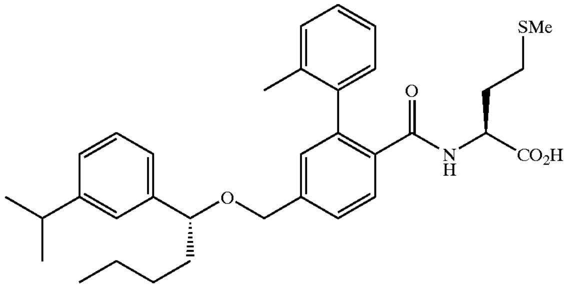
122

TABLE 7-continued
| Ethers of the Type A-$OL_1$ |
|---|
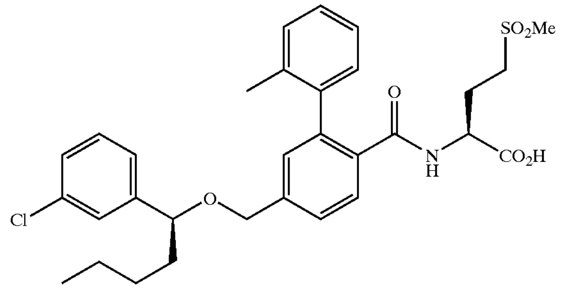
123
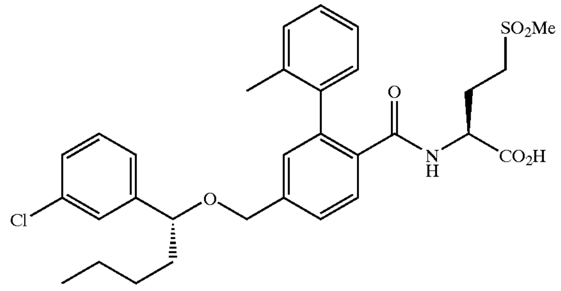
124
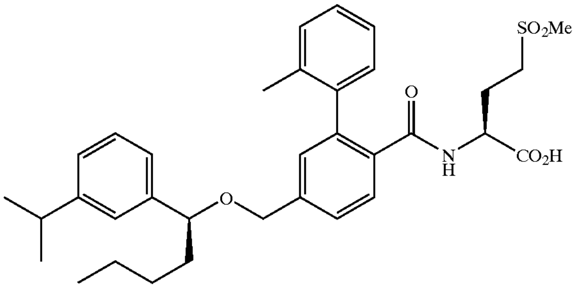
125
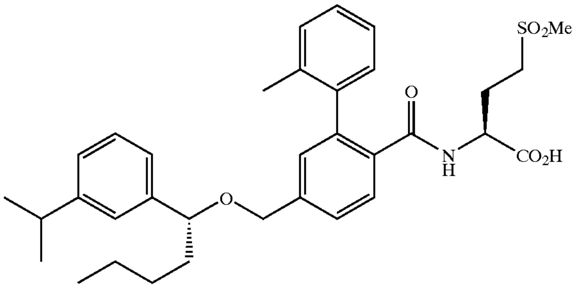
126

TABLE 7-continued
| Ethers of the Type A-$OL_1$ |
|---|
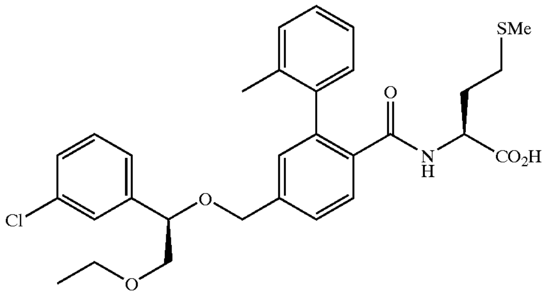
127
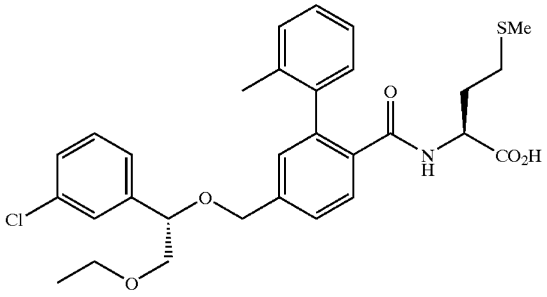
128
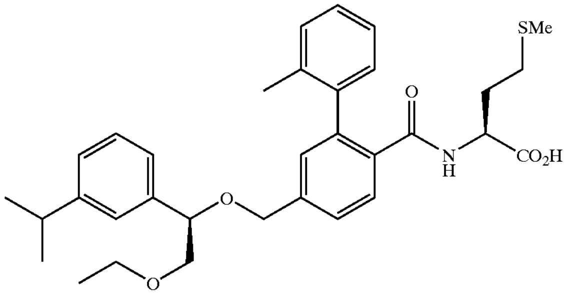
129
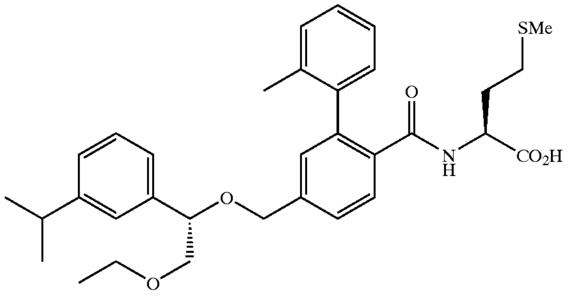
130

TABLE 7-continued
Ethers of the Type A-$OL_1$
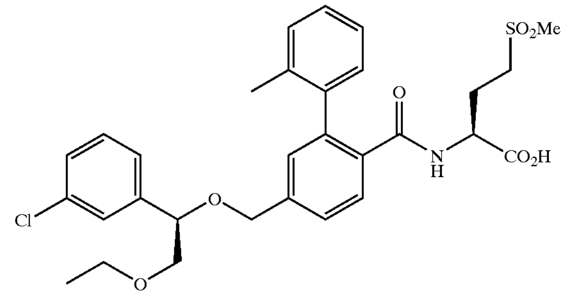
131
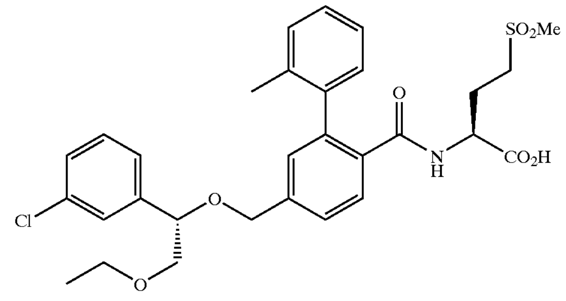
132
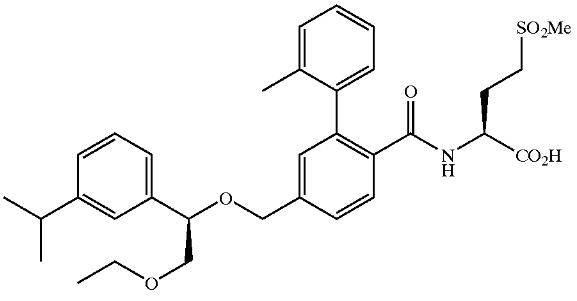
133
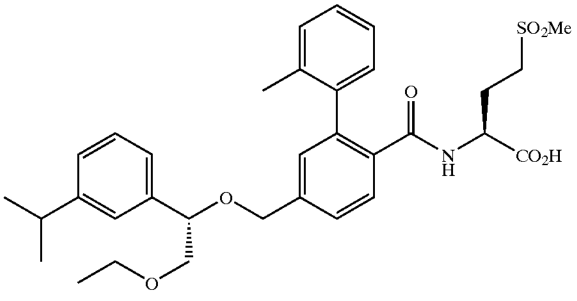
134

TABLE 7-continued
Ethers of the Type A-$OL_1$
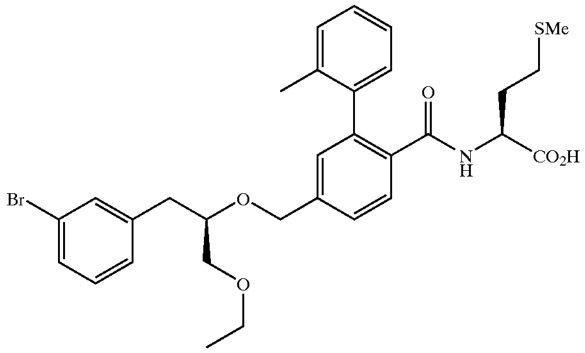
135
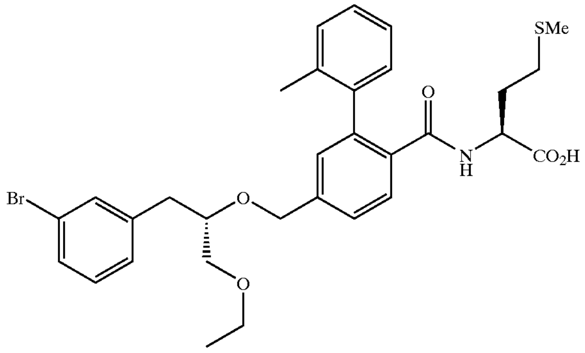
136
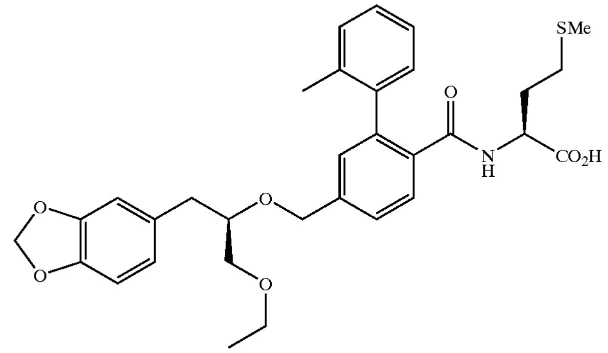
137
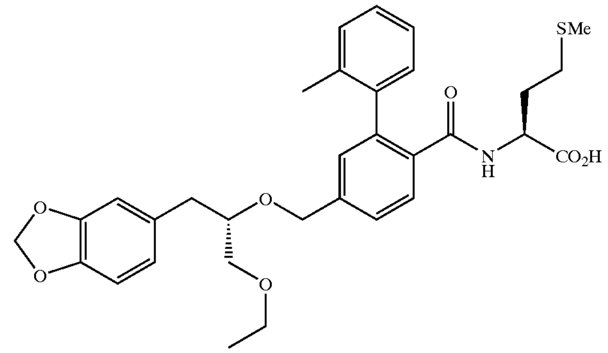

TABLE 7-continued
| Ethers of the Type A-$OL_1$ |
|---|
| 138 |
| 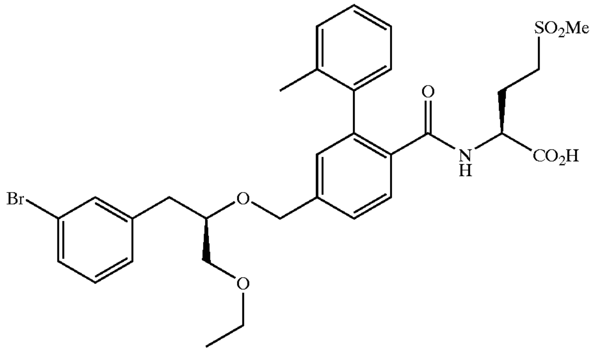 |
| 139 |
| 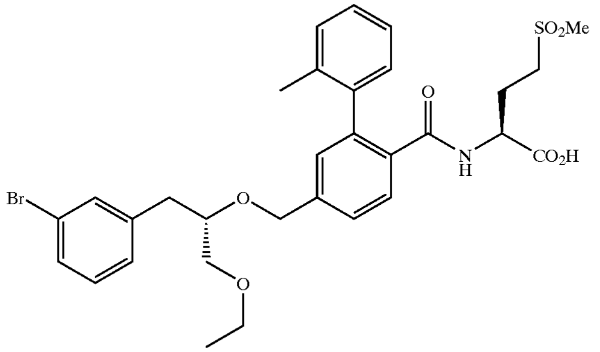 |
| 140 |
| 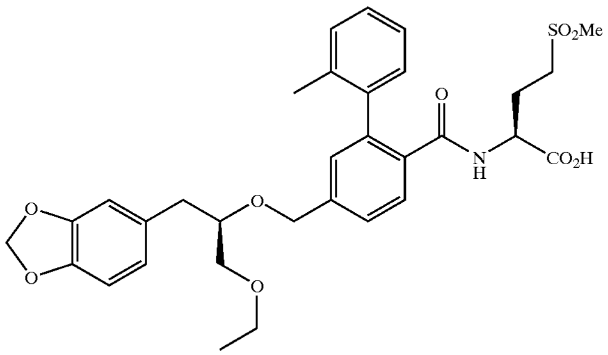 |
| 141 |

TABLE 7-continued
| Ethers of the Type A-$OL_1$ |
| --- |
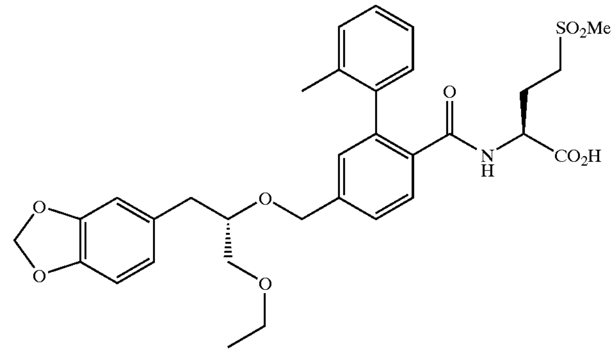
142
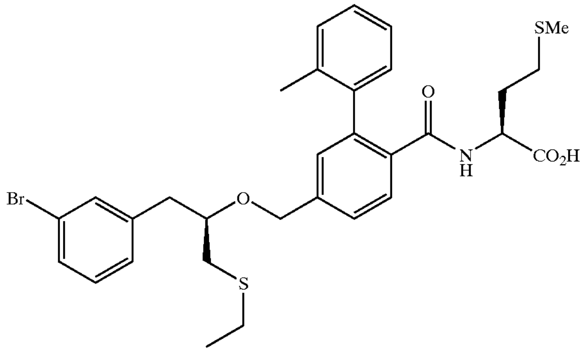
143
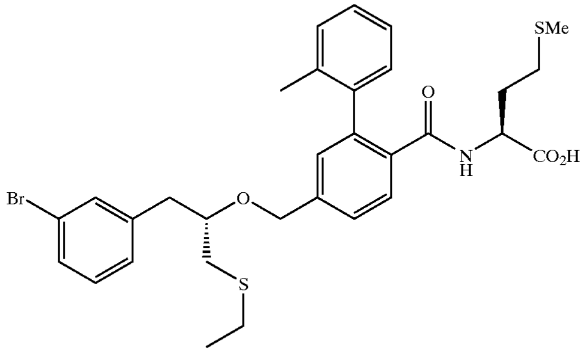
144
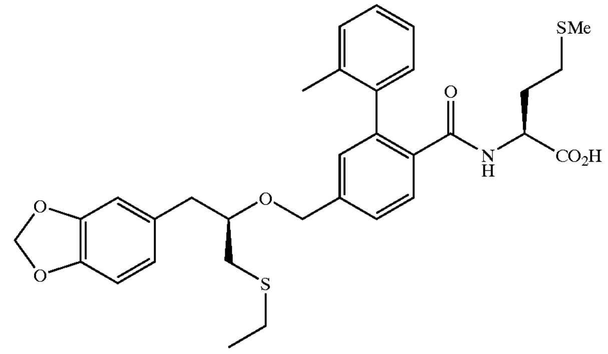

TABLE 7-continued
| Ethers of the Type A-$OL_1$ |
| --- |
145
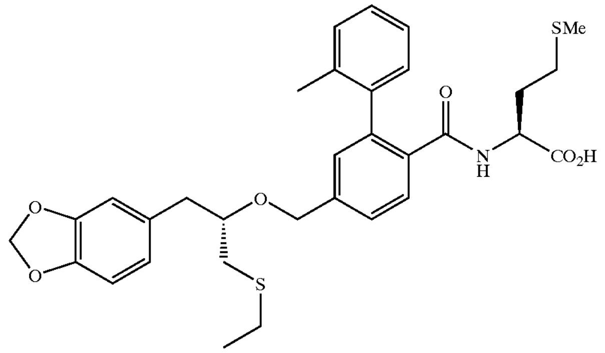
146
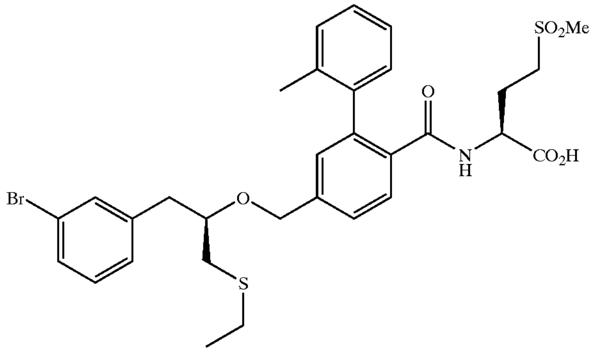
147
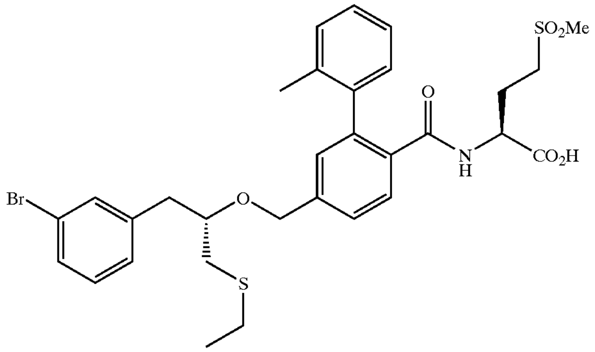
148

TABLE 7-continued
Ethers of the Type A-$OL_1$
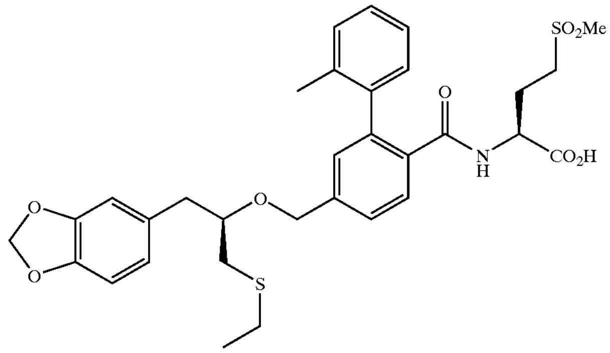
149
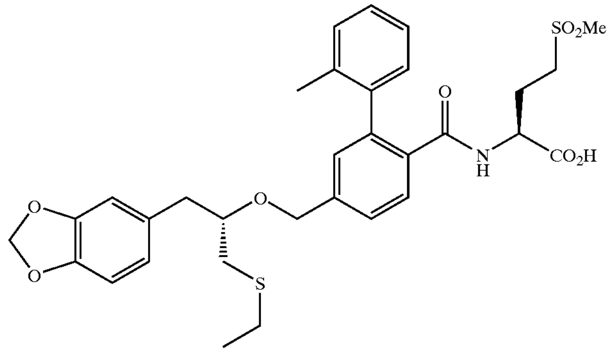
150
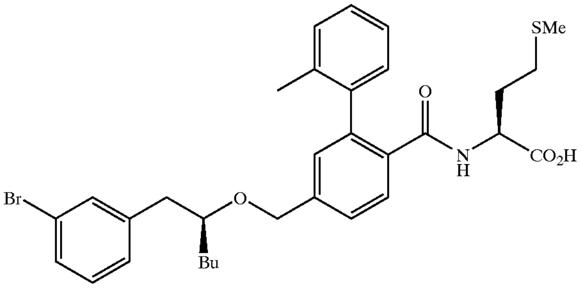
151
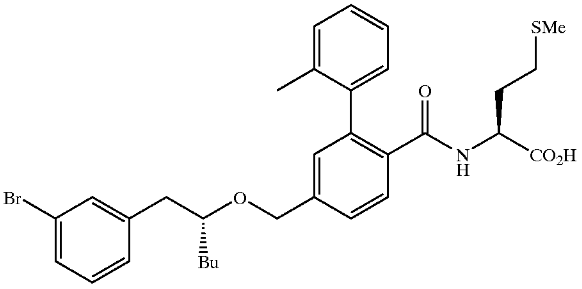
152

TABLE 7-continued
| Ethers of the Type A-$OL_1$ |
|---|
| 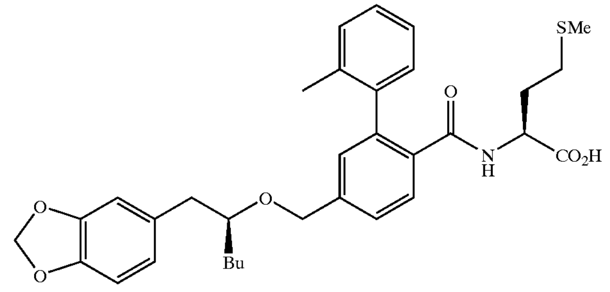 |
| 153 |
| 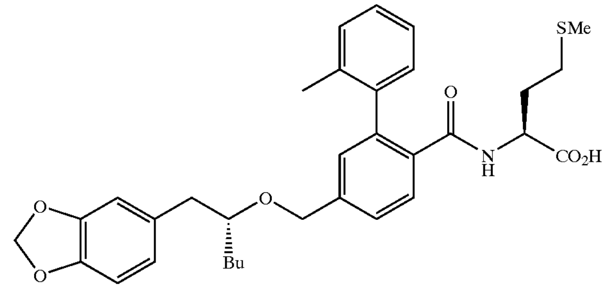 |
| 154 |
| 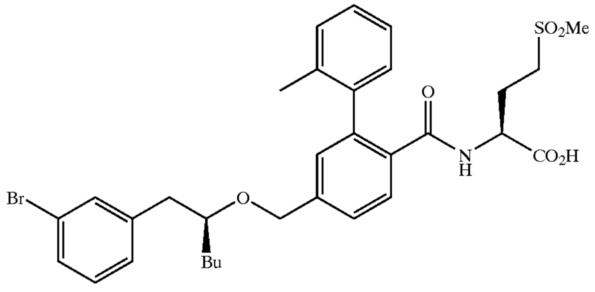 |
| 155 |
| 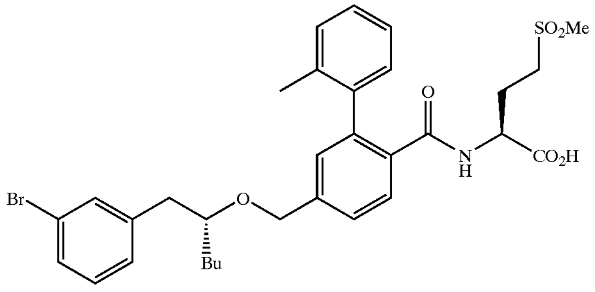 |
| 156 |

TABLE 7-continued
| Ethers of the Type A-$OL_1$ |
| --- |
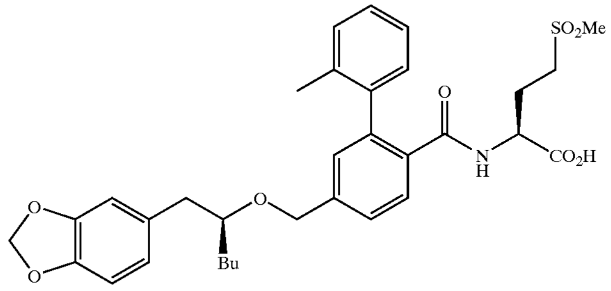
157
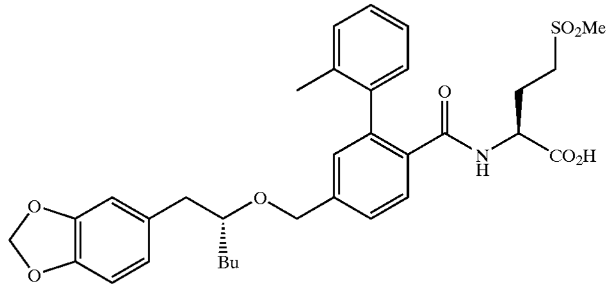
158
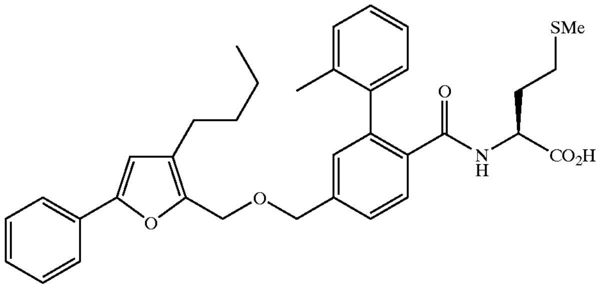
159
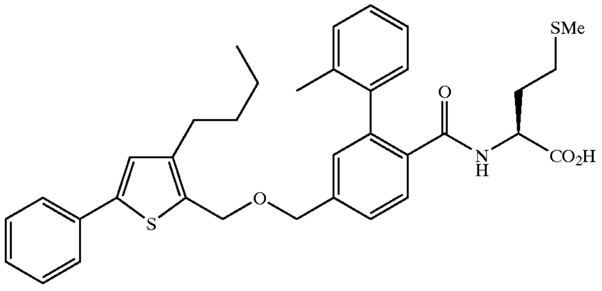
160

TABLE 7-continued
| Ethers of the Type A-$OL_1$ |
|---|
| 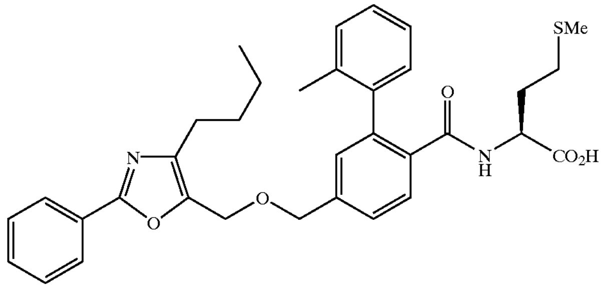 |
| 161 |
| 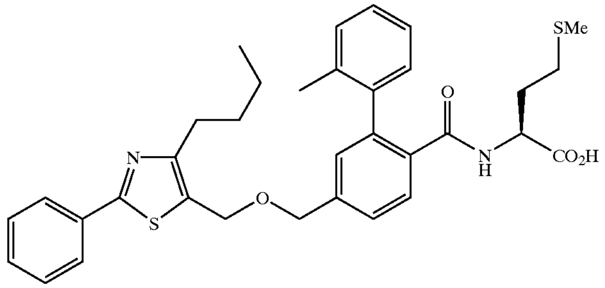 |
| 162 |
| 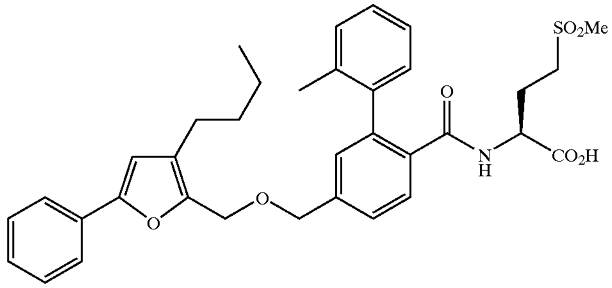 |
| 163 |
| 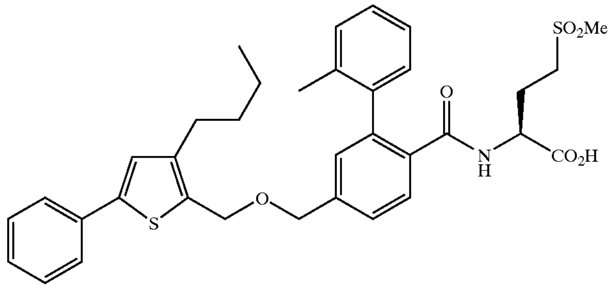 |
| 164 |

TABLE 7-continued
Ethers of the Type A-$OL_1$
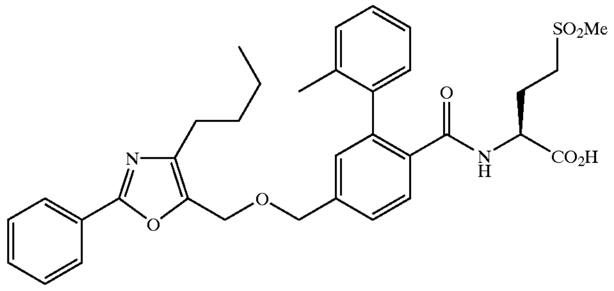
165
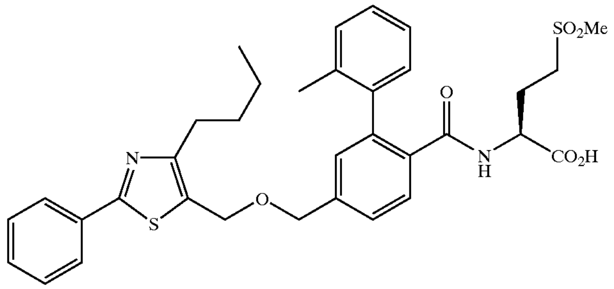
166
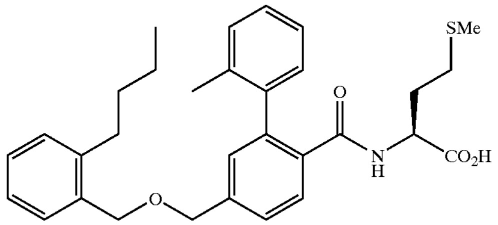
167
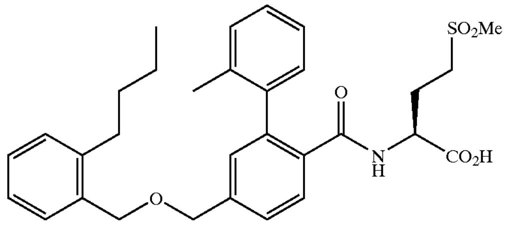
168
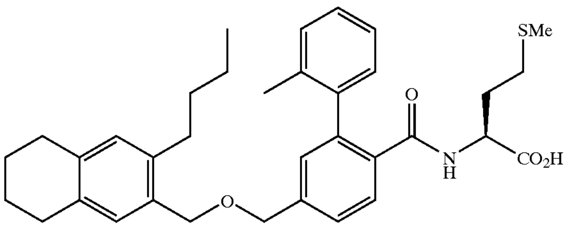
169

TABLE 7-continued
| Ethers of the Type A-$OL_1$ |
|---|
| 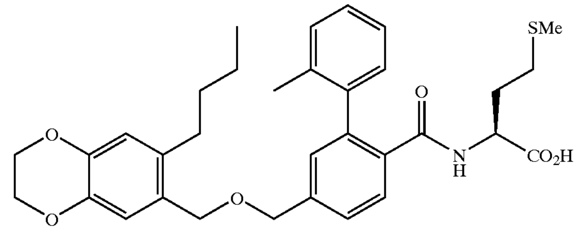 |
| 170 |
| 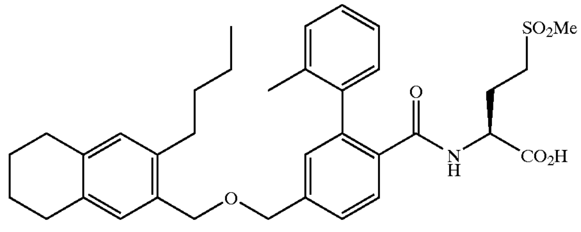 |
| 171 |
| 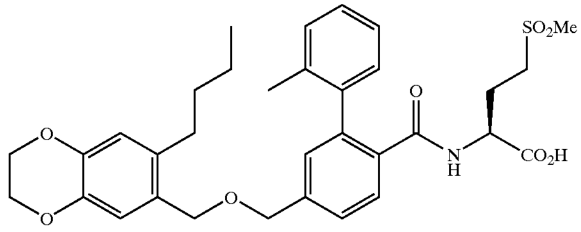 |
| 172 |
| 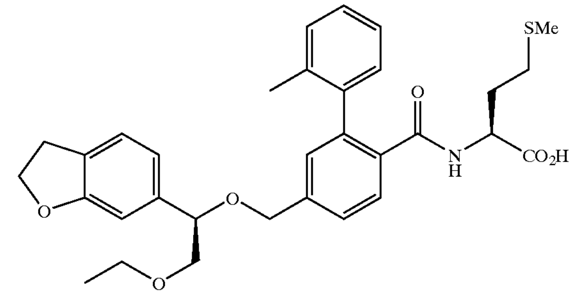 |
| 173 |
| 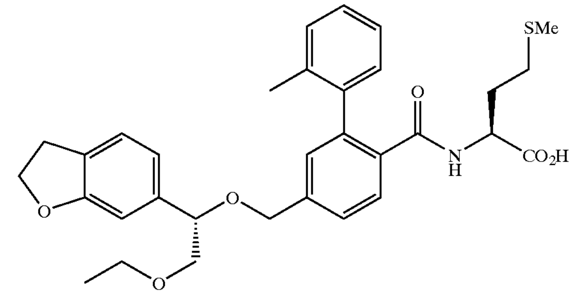 |
| 174 |

TABLE 7-continued
| Ethers of the Type A-$OL_1$ |
|---|
| 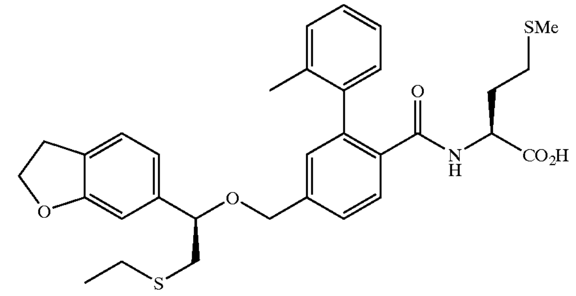 |
| 175 |
| 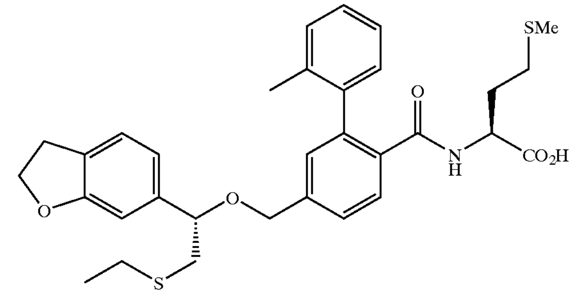 |
| 176 |
| 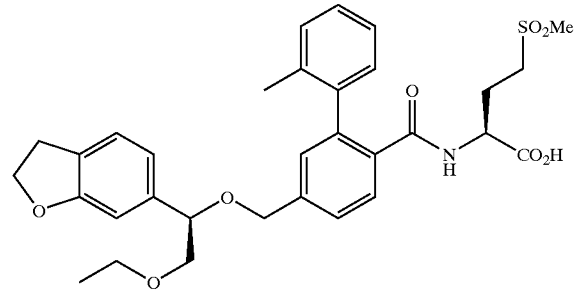 |
| 177 |
| 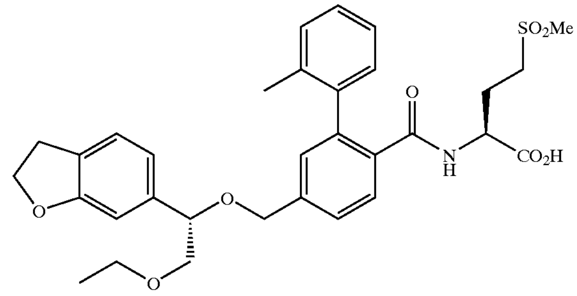 |
| 178 |

TABLE 7-continued
Ethers of the Type A-$OL_1$
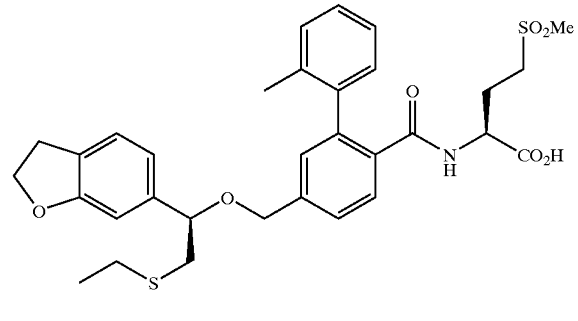
179
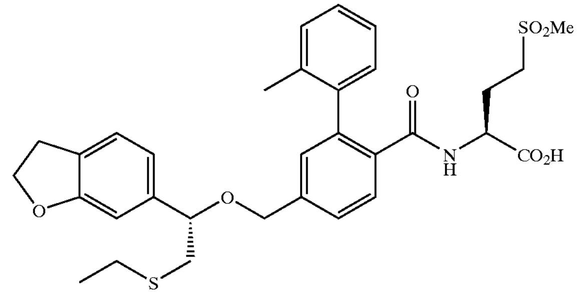
180
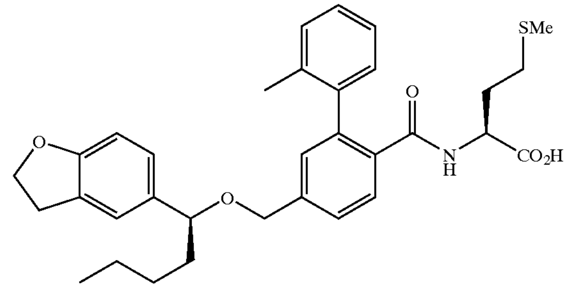
181
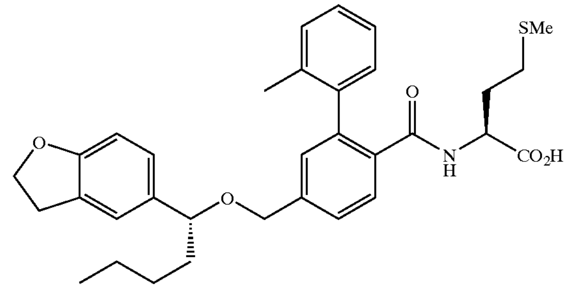
182

TABLE 7-continued
Ethers of the Type A-$OL_1$
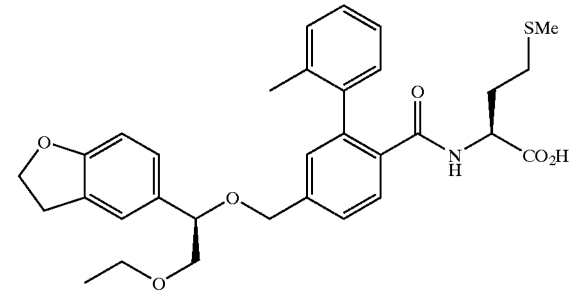
183
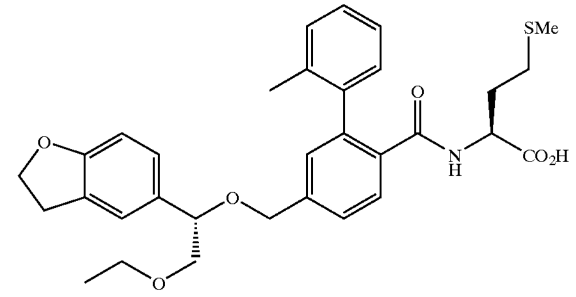
184
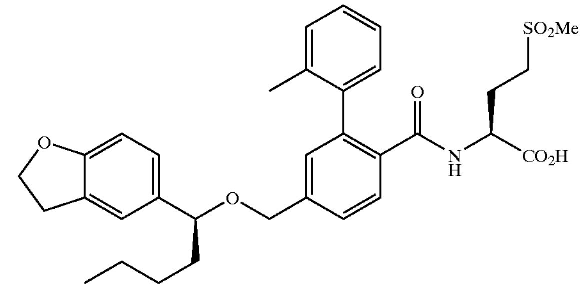
185
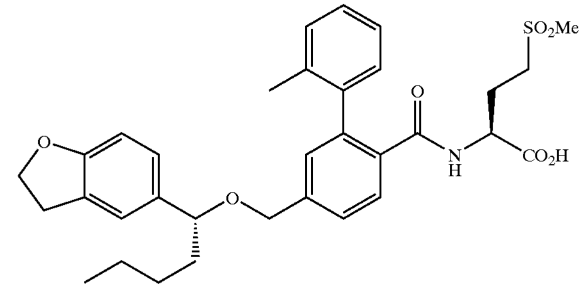
186

TABLE 7-continued
Ethers of the Type A-$OL_1$
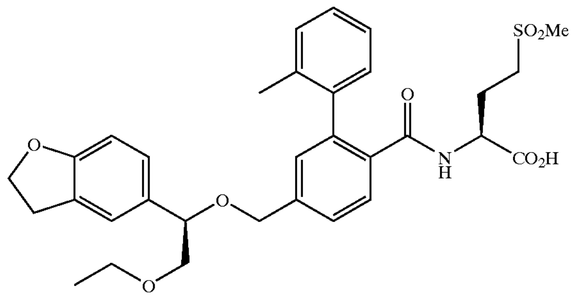
187
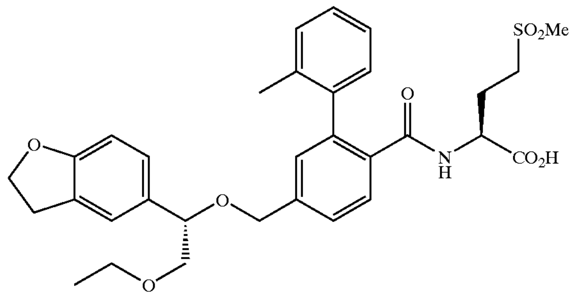
188
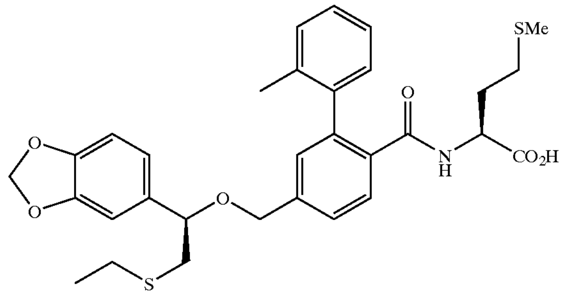
189
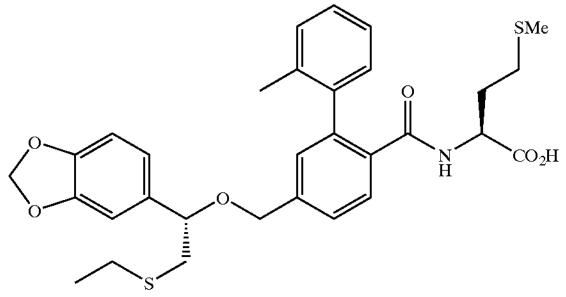
190

TABLE 7-continued
Ethers of the Type A-$OL_1$
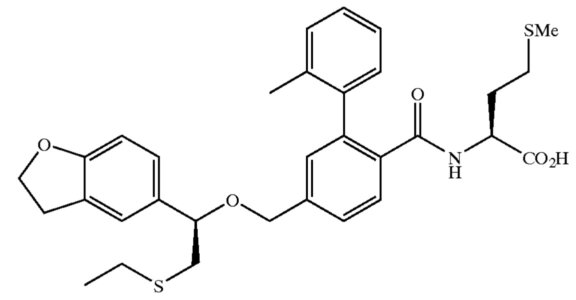
191
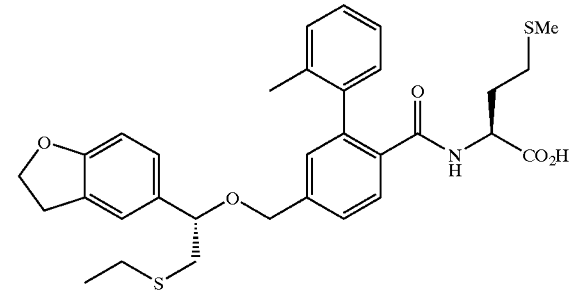
192
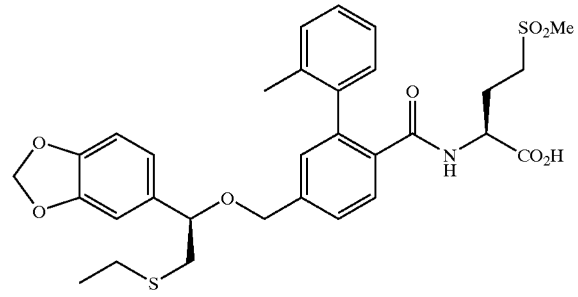
193
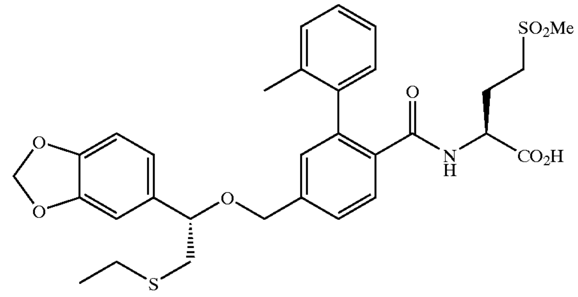
194

TABLE 7-continued
| Ethers of the Type A-$OL_1$ |
|---|
| 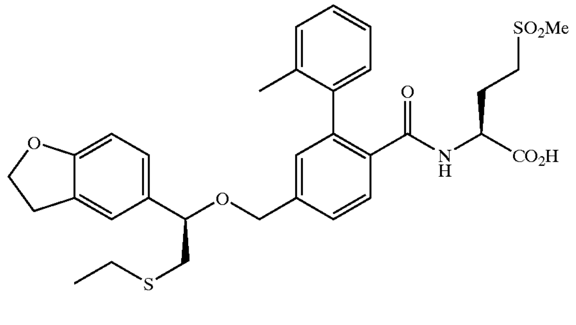 |
| 195 |
| 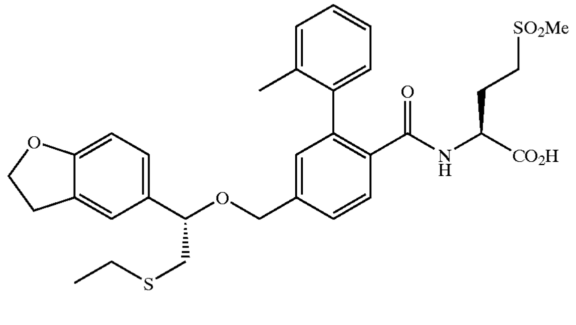 |
| 196 |
| 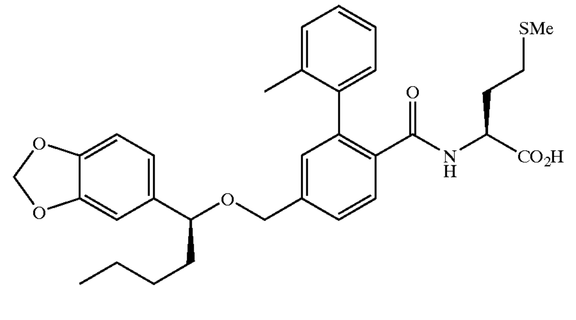 |
| 197 |
| 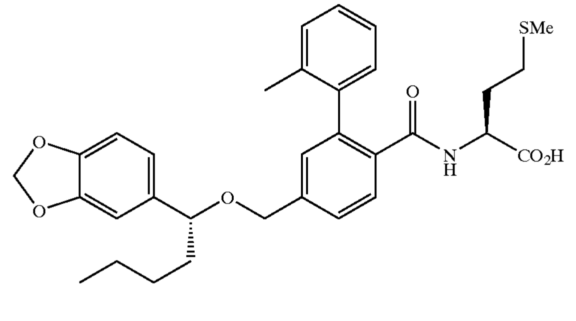 |
| 198 |

TABLE 7-continued
| Ethers of the Type A-$OL_1$ |
|---|
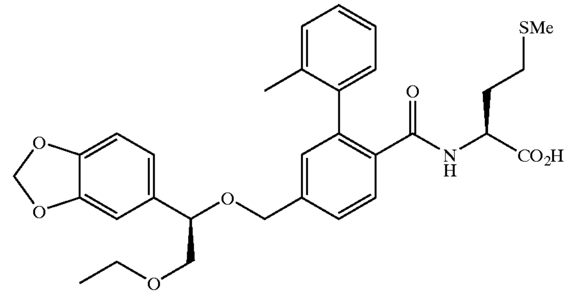
199
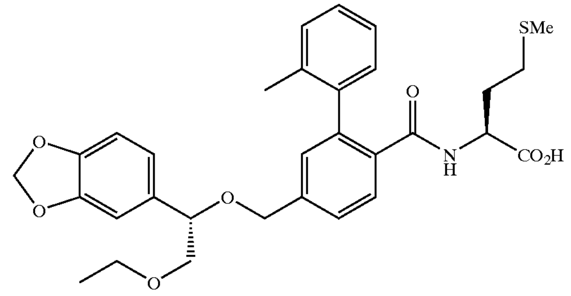
200
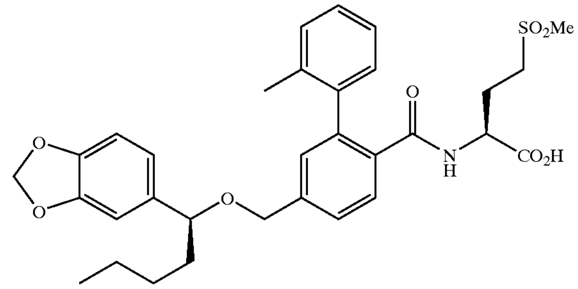
201
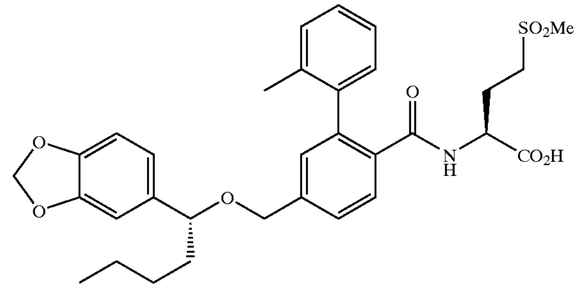
202

TABLE 7-continued
| Ethers of the Type A-$OL_1$ |
|---|
| 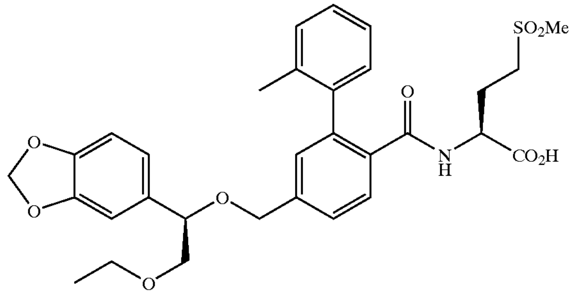 |
| 203 |
| 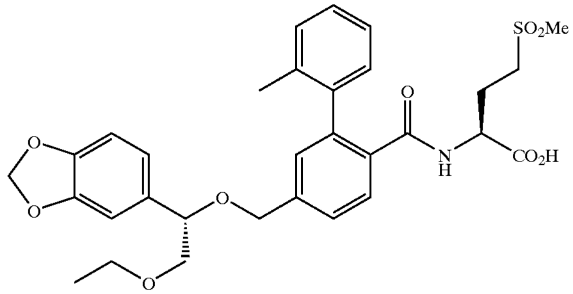 |
| 204 |
| 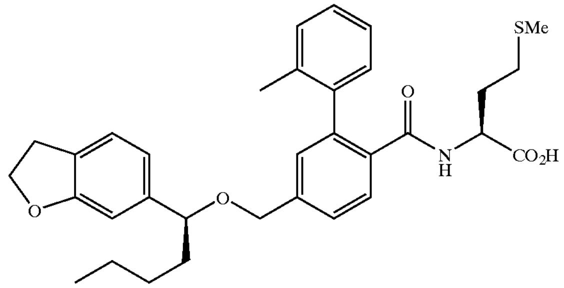 |
| 205 |
| 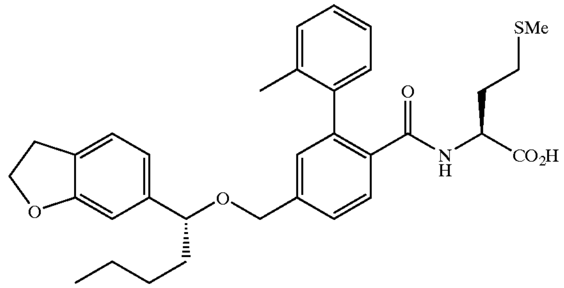 |
| 206 |

TABLE 7-continued
Ethers of the Type A-$OL_1$
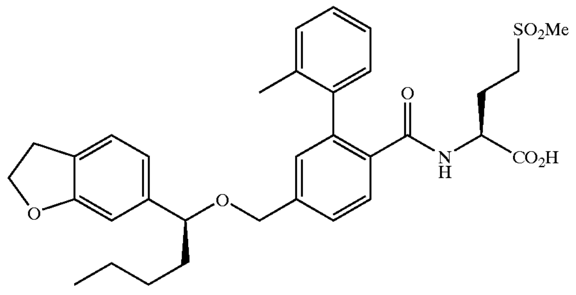
206
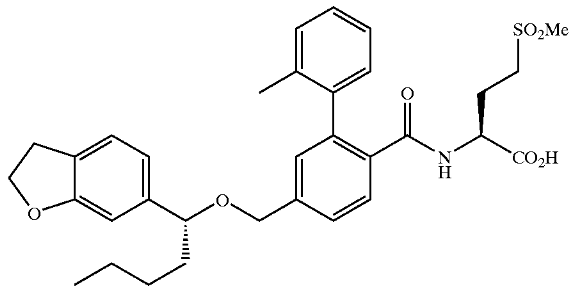
208
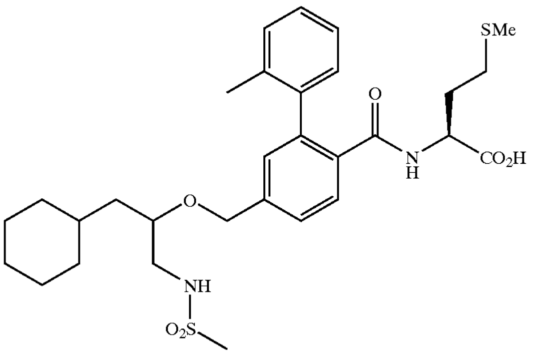
209
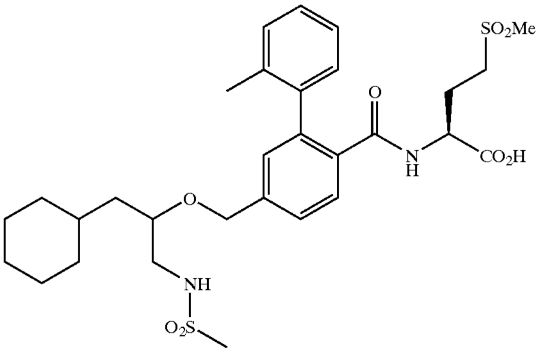
210

TABLE 7-continued
| Ethers of the Type A-OL$_1$ |
|---|
| 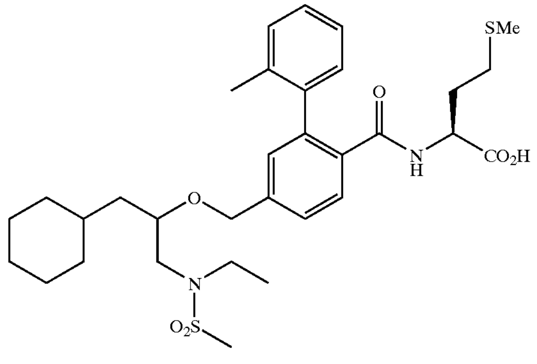 |
| 211 |
| 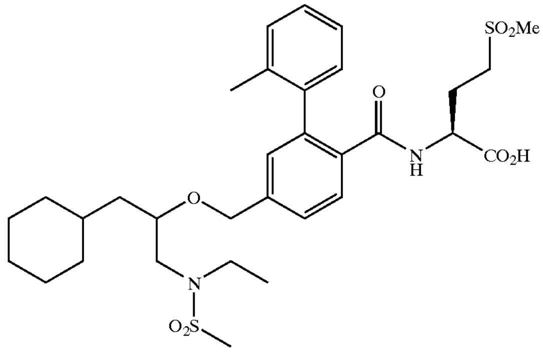 |
| 212 |
| 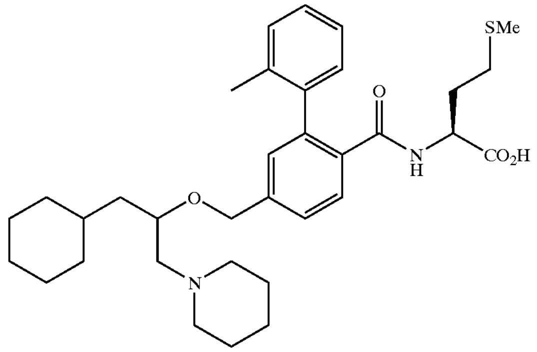 |
| 213 |
| 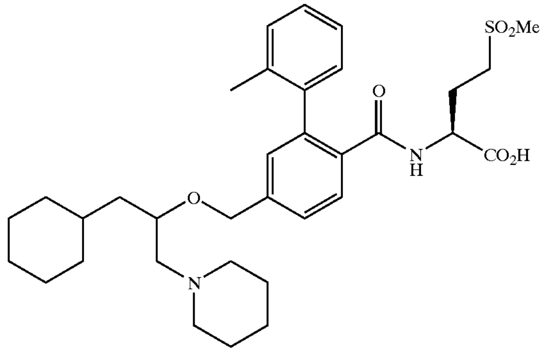 |

TABLE 7-continued
| Ethers of the Type A-$OL_1$ |
|---|
| 214 |
| 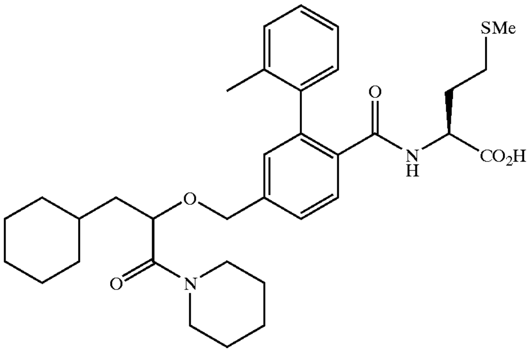 |
| 215 |
| 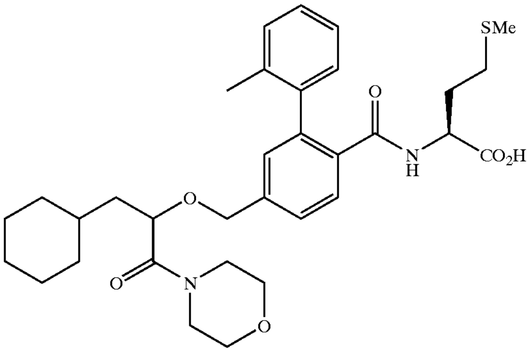 |
| 216 |
| 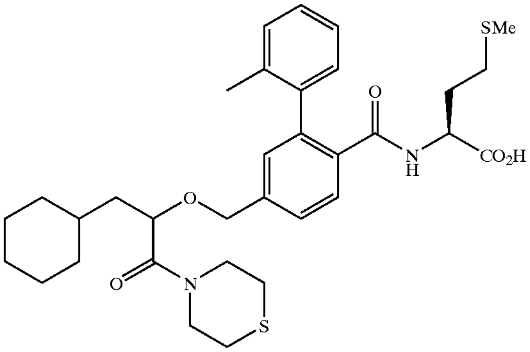 |
| 217 |

TABLE 7-continued
| Ethers of the Type A-$OL_1$ |
| --- |
| 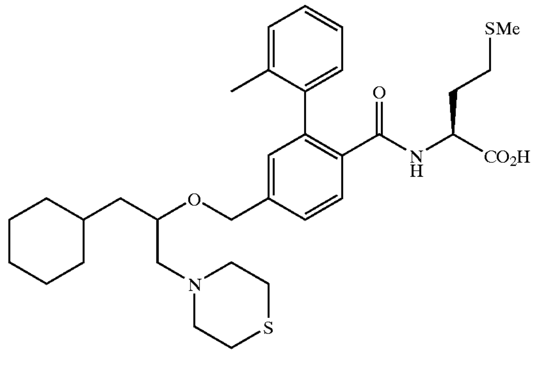 |
| 218 |
| 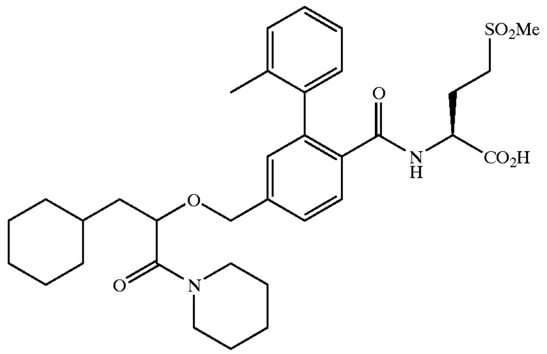 |
| 219 |
| 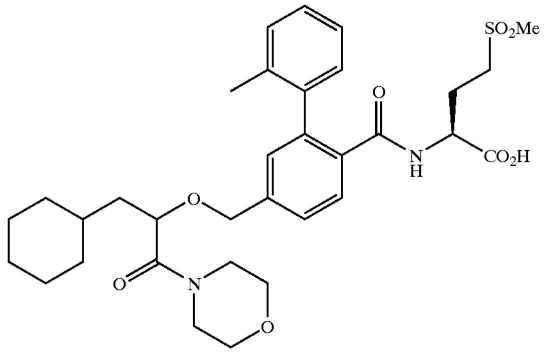 |
| 220 |
| 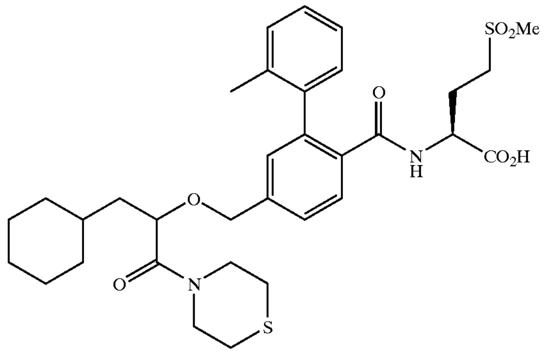 |

TABLE 7-continued
| Ethers of the Type A-$OL_1$ |
|---|
221
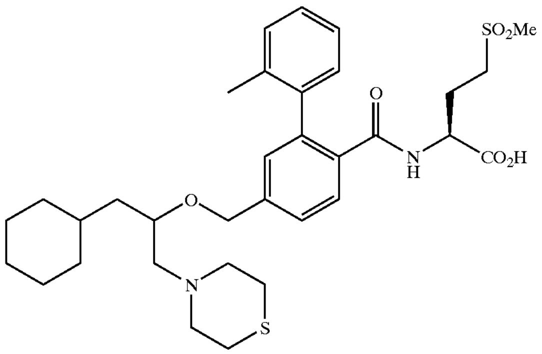
222
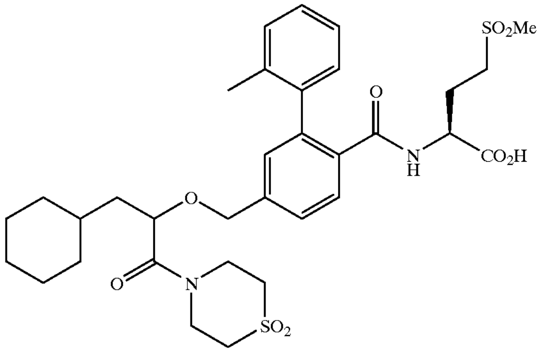
223
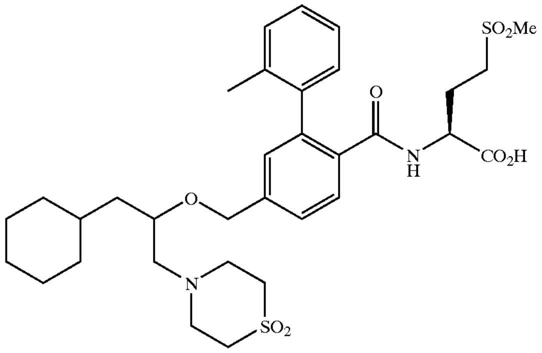
224

TABLE 7-continued
| Ethers of the Type A-$OL_1$ |
|---|
| 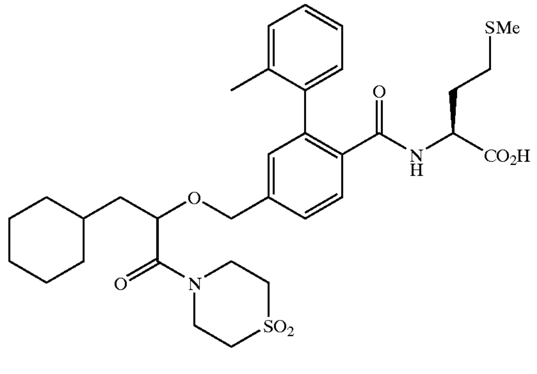 |
| 225 |
| 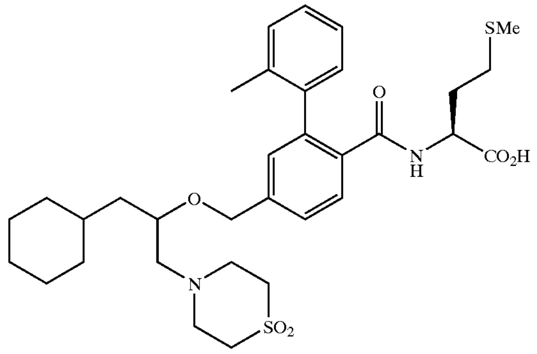 |
| 226 |
| 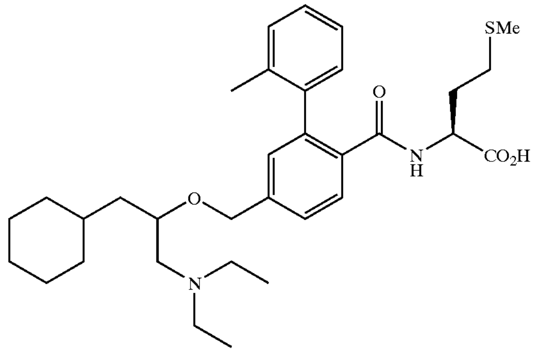 |
| 227 |
| 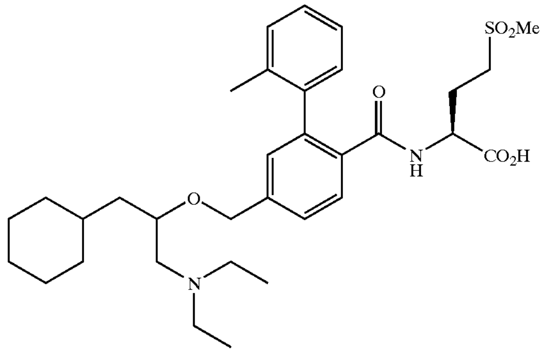 |

TABLE 7-continued
| Ethers of the Type A-$OL_1$ |
|---|
| 228 |
TABLE 8
| Sulfonamides of the Type $ASO_2(B)N$-$L_1$ |
|---|
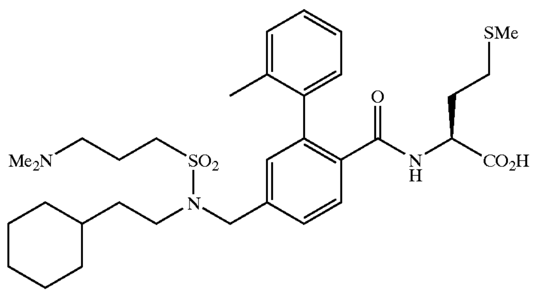
1
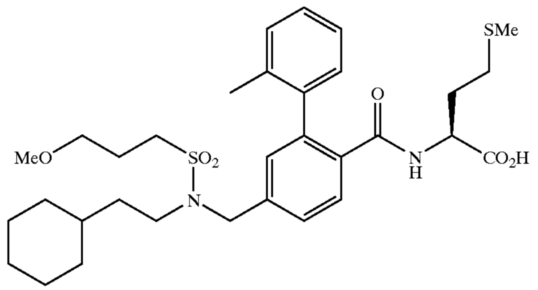
2
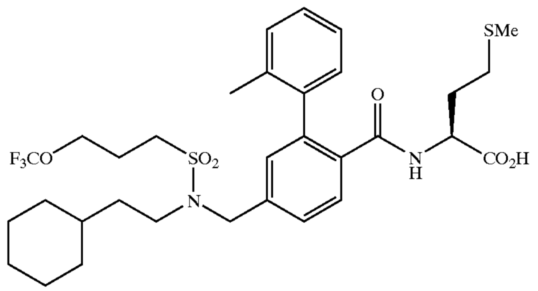
3
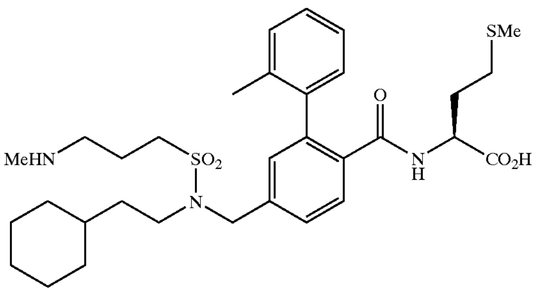
4
TABLE 8-continued
| Sulfonamides of the Type $ASO_2(B)N$-$L_1$ |
|---|
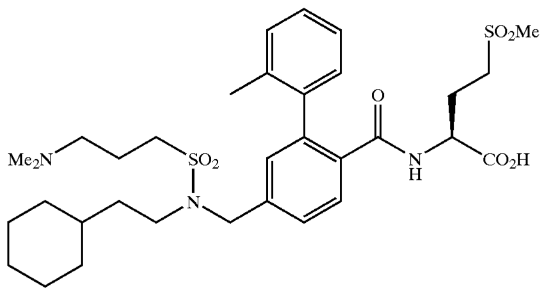
5
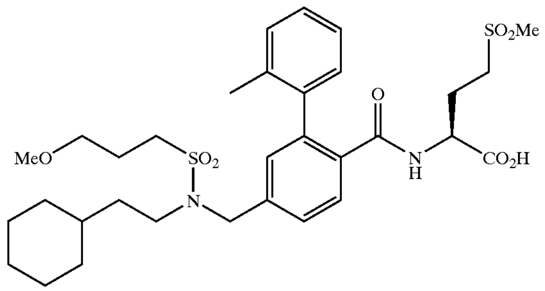
6
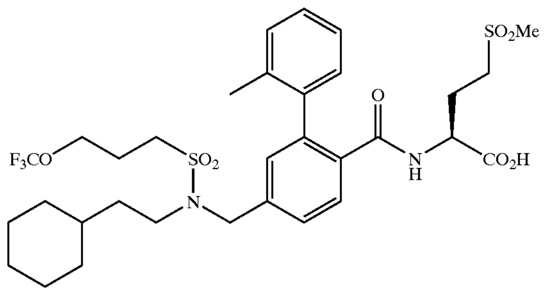
7
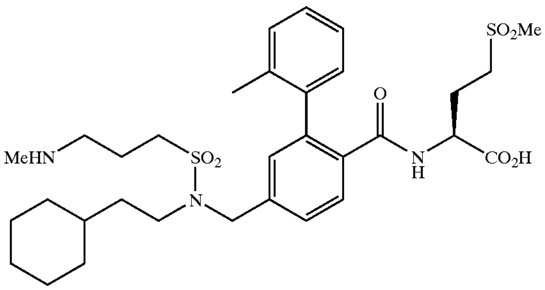
8

TABLE 8-continued
Sulfonamides of the Type $ASO_2(B)N-L_1$
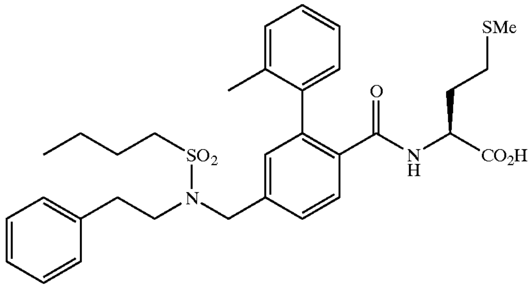
9
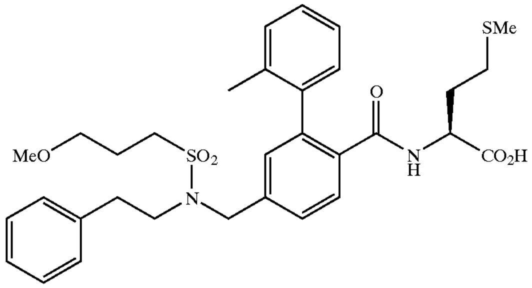
10
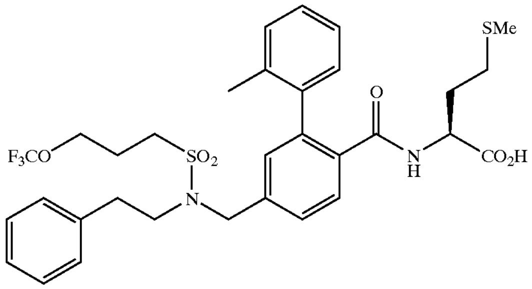
11
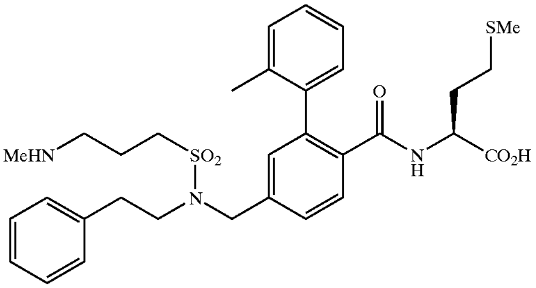
12
TABLE 8-continued
Sulfonamides of the Type $ASO_2(B)N-L_1$
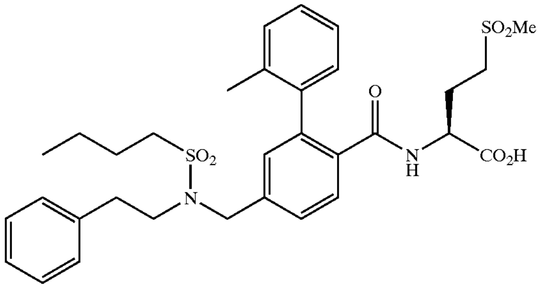
13
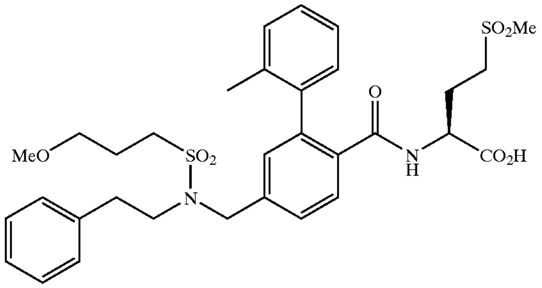
14
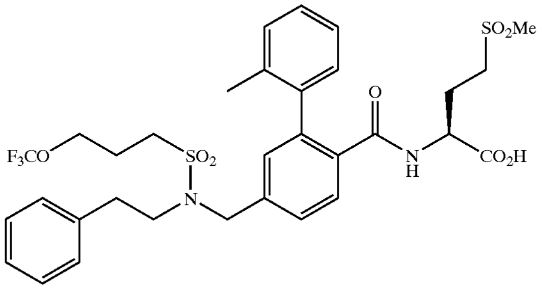
15
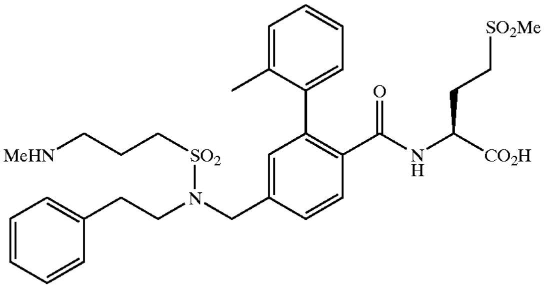
16

TABLE 8-continued
| Sulfonamides of the Type $ASO_2(B)N-L_1$ |
|---|
| 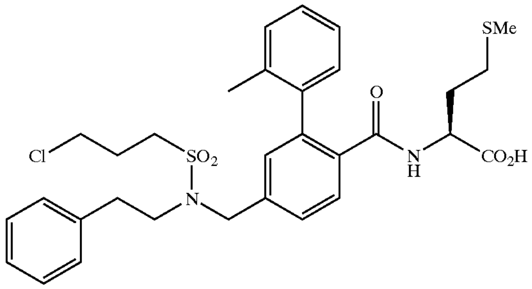 |
| 17 |
| 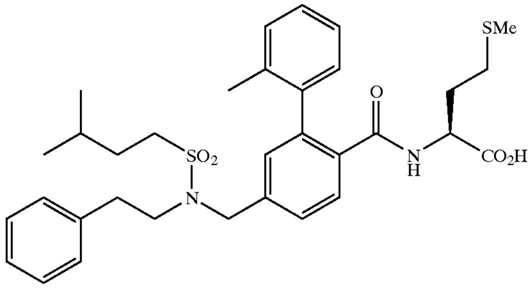 |
| 18 |
| 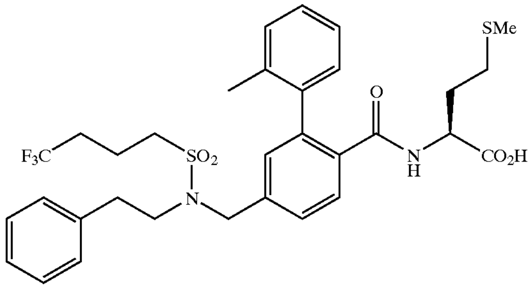 |
| 19 |
| 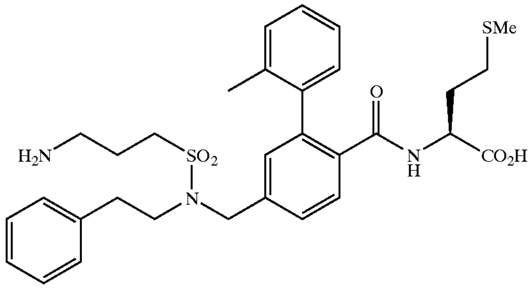 |
| 20 |
TABLE 8-continued
| Sulfonamides of the Type $ASO_2(B)N-L_1$ |
|---|
| 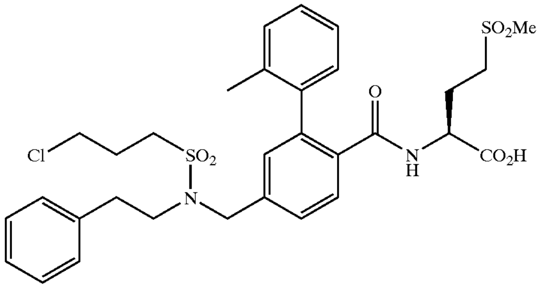 |
| 21 |
| 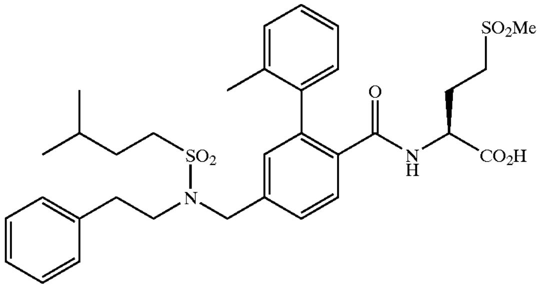 |
| 22 |
| 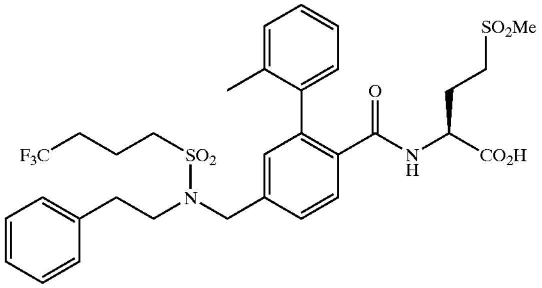 |
| 23 |
| 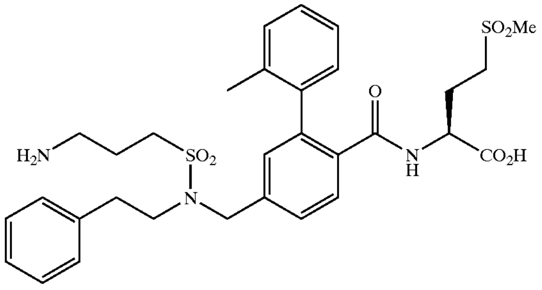 |
| 24 |

TABLE 8-continued
| Sulfonamides of the Type $ASO_2(B)N-L_1$ |
| --- |
| 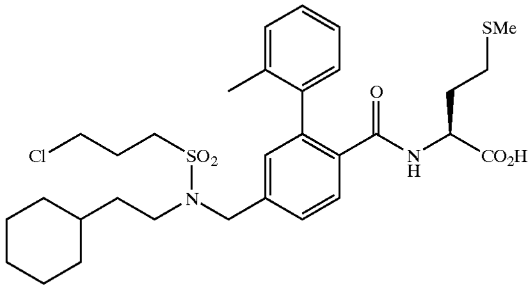 |
| 25 |
| 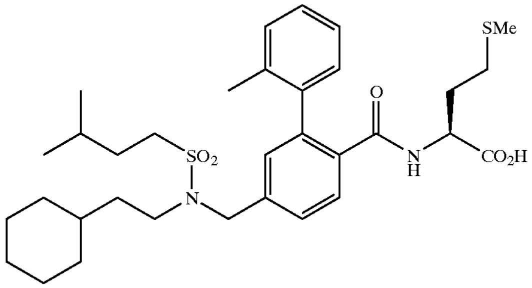 |
| 26 |
| 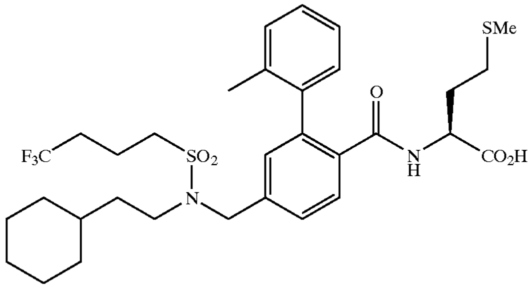 |
| 27 |
| 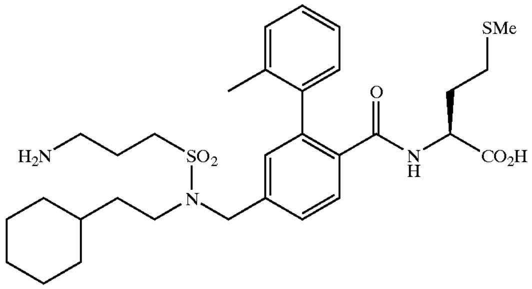 |
| 28 |
TABLE 8-continued
| Sulfonamides of the Type $ASO_2(B)N-L_1$ |
| --- |
| 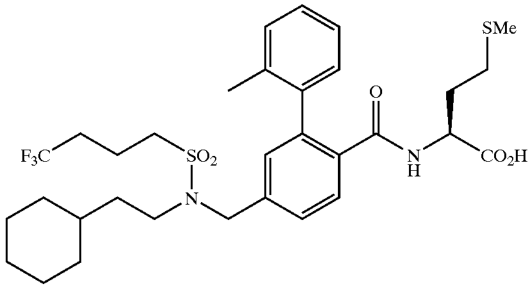 |
| 29 |
| 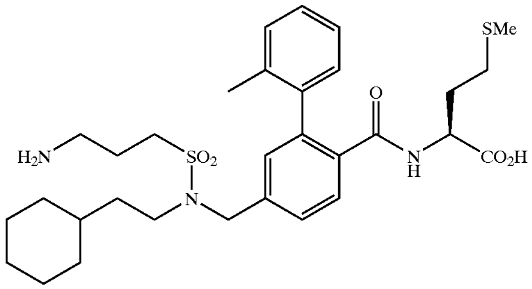 |
| 30 |
| 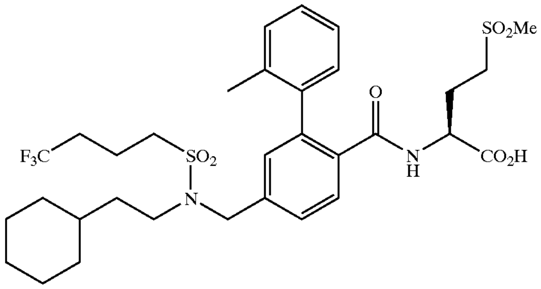 |
| 31 |
| 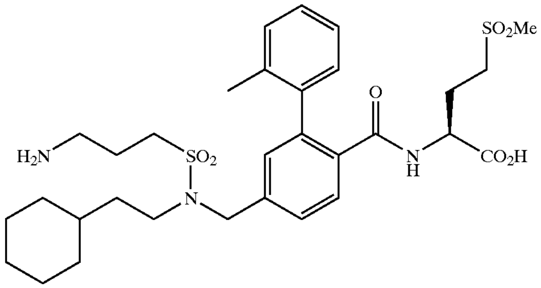 |
| 32 |

TABLE 9
| Hydrocarbons of the Type A(B)$CH_2$—$L_1$ |
|---|
| 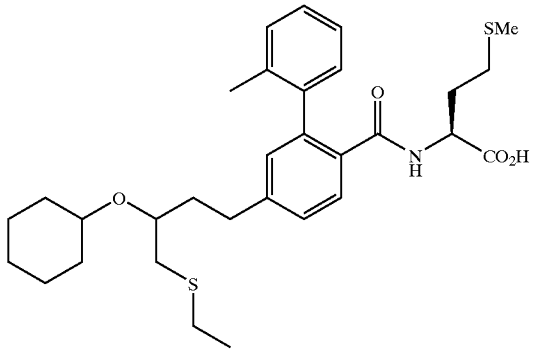 |
| 1 |
| 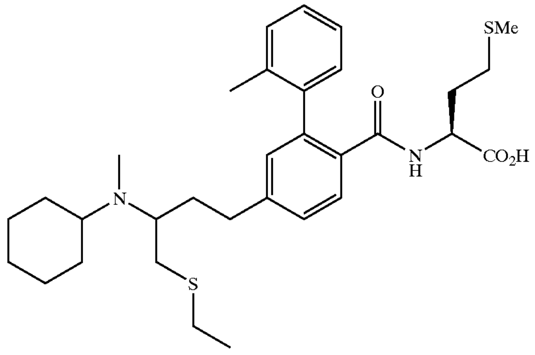 |
| 2 |
| 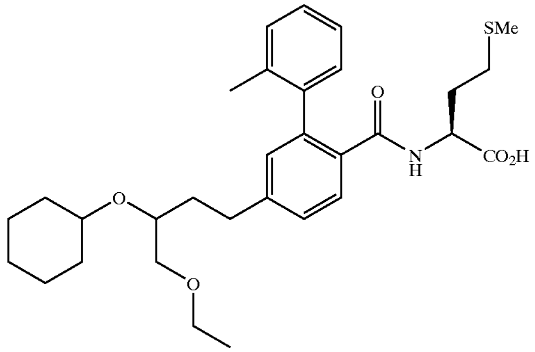 |
| 3 |
| 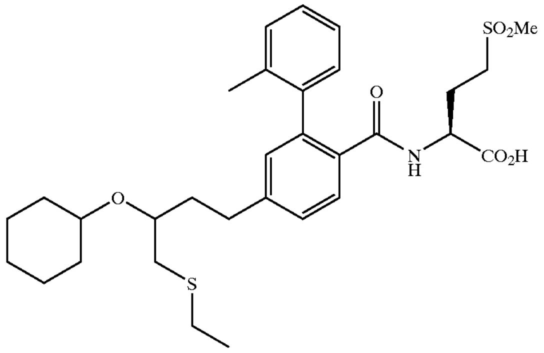 |
| 4 |
TABLE 9-continued
| Hydrocarbons of the Type A(B)$CH_2$—$L_1$ |
|---|
| 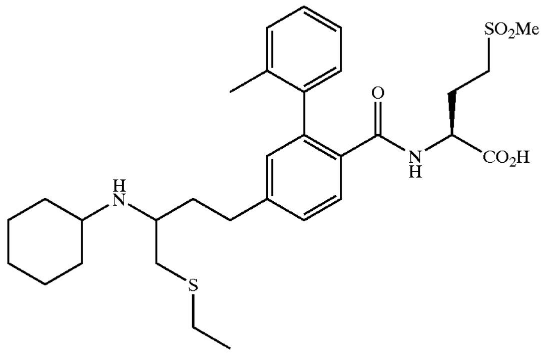 |
| 5 |
| 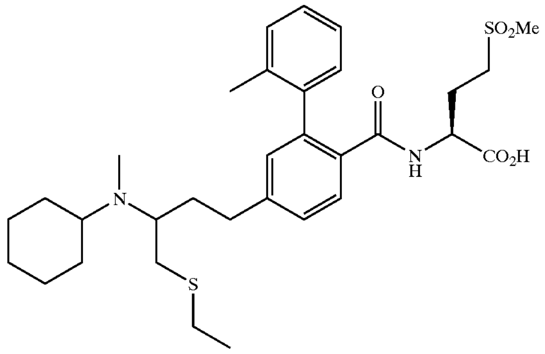 |
| 6 |
| 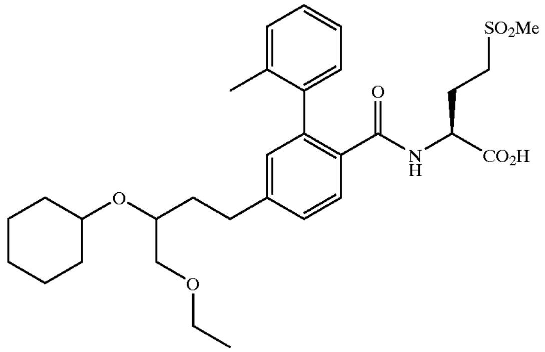 |
| 7 |
| 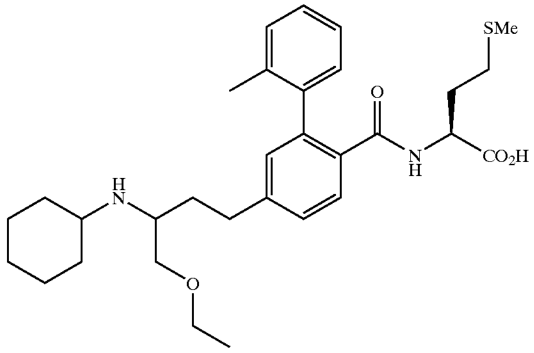 |
| 8 |

TABLE 9-continued
| Hydrocarbons of the Type A(B)$CH_2$—$L_1$ |
|---|
| 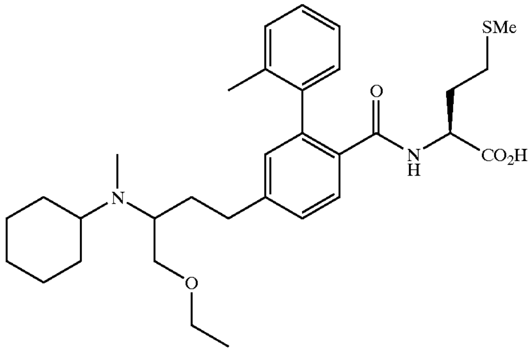 |
| 9 |
| 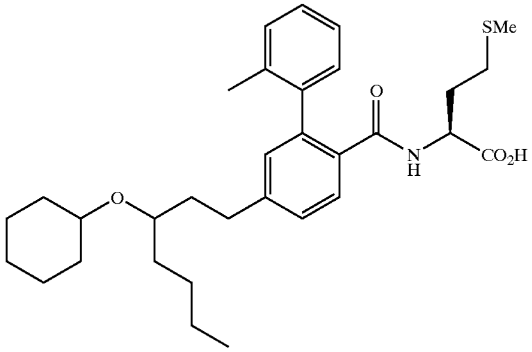 |
| 10 |
| 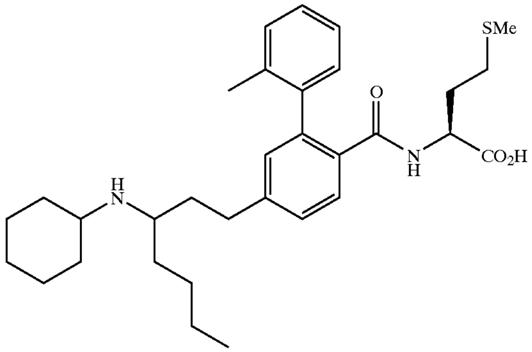 |
| 11 |
| 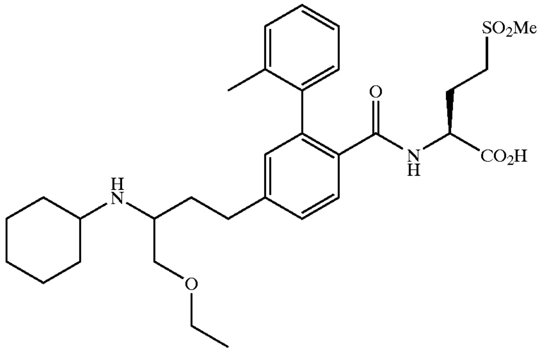 |
| 12 |
TABLE 9-continued
| Hydrocarbons of the Type A(B)$CH_2$—$L_1$ |
|---|
| 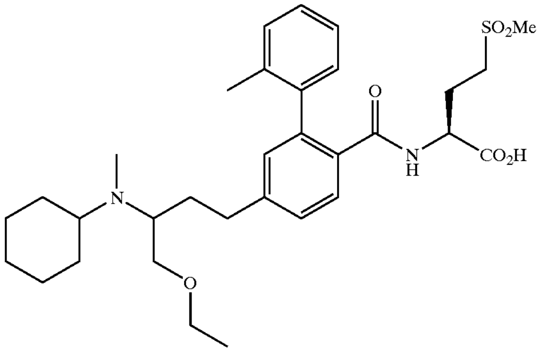 |
| 13 |
| 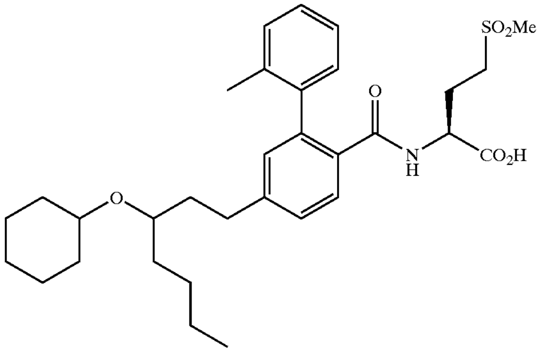 |
| 14 |
| 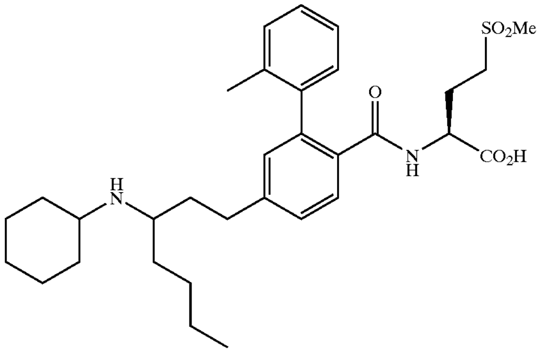 |
| 15 |
| 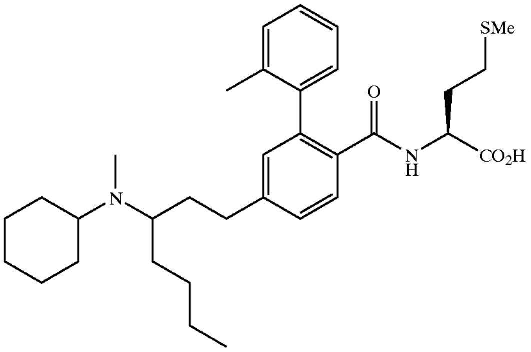 |
| 16 |

TABLE 9-continued
Hydrocarbons of the Type $A(B)CH_2—L_1$
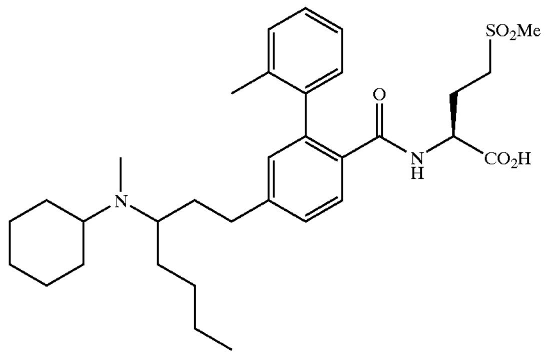
17
TABLE 10
Amines of the type $B—NH_2$
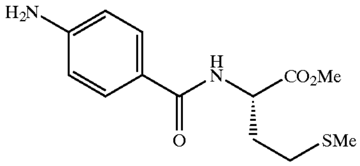
1
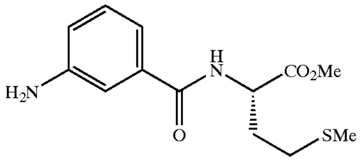
2
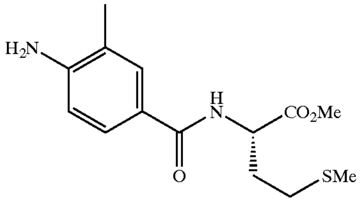
3
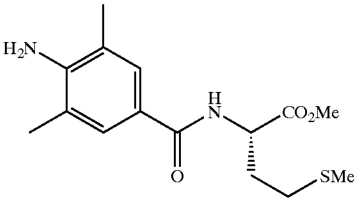
4
TABLE 10-continued
Amines of the type $B—NH_2$
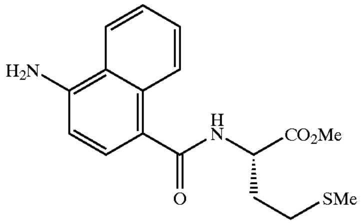
5
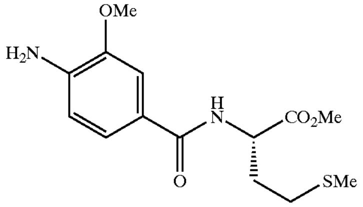
6
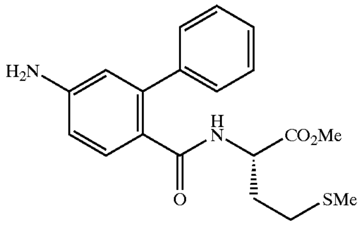
7
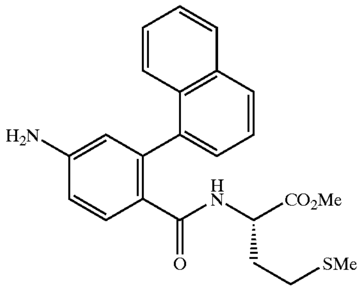
8
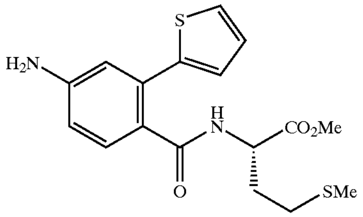
9
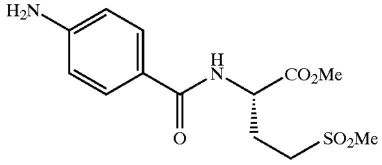
10

TABLE 10-continued
| Amines of the type B—$NH_2$ |
|---|
| 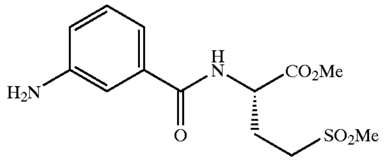 |
| 11 |
| 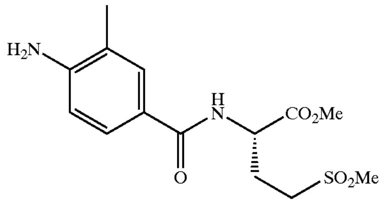 |
| 12 |
| 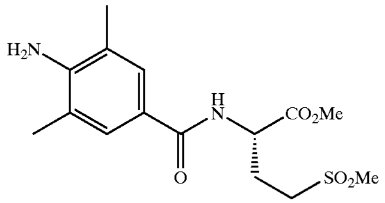 |
| 13 |
| 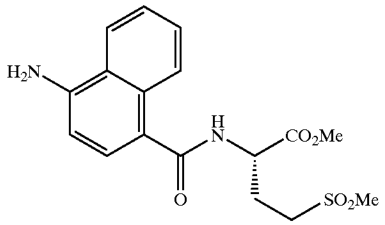 |
| 14 |
| 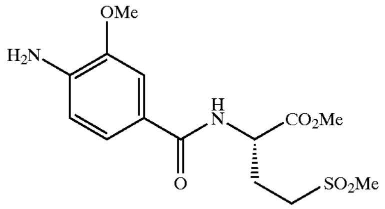 |
| 15 |
| 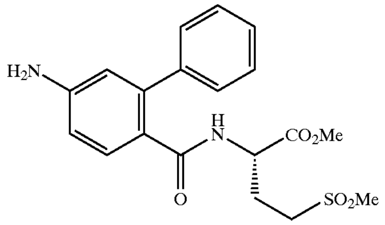 |
| 16 |
TABLE 10-continued
| Amines of the type B—$NH_2$ |
|---|
| 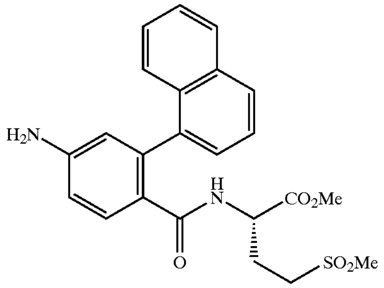 |
| 17 |
| 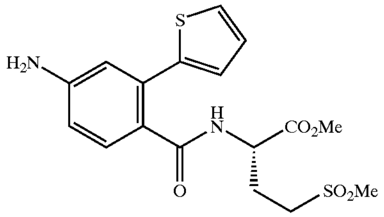 |
| 18 |
| 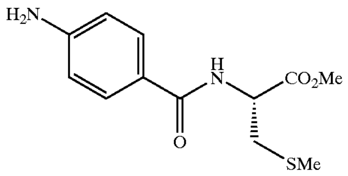 |
| 19 |
| 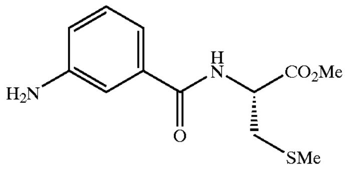 |
| 20 |
| 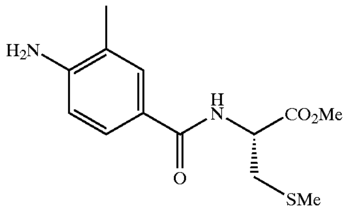 |
| 21 |
| 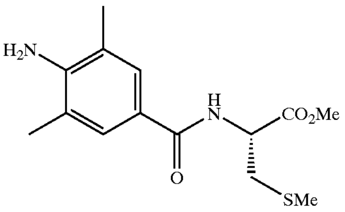 |
| 22 |

TABLE 10-continued
Amines of the type B—$NH_2$
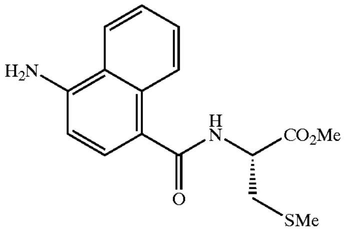
23
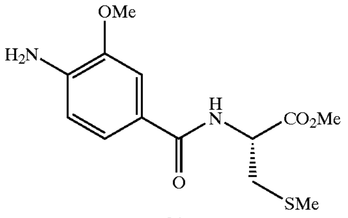
24
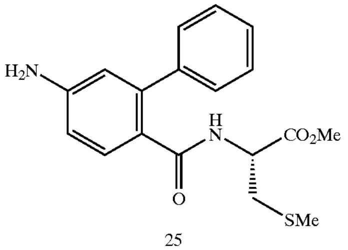
25
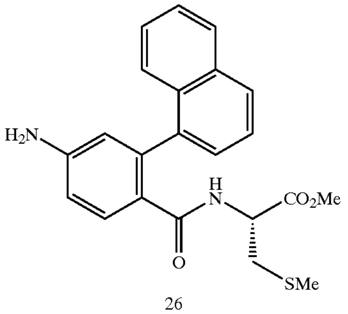
26
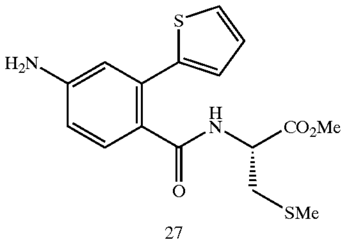
27
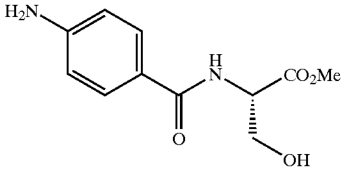
28
TABLE 10-continued
Amines of the type B—$NH_2$
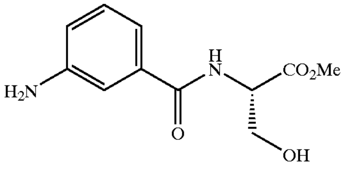
29
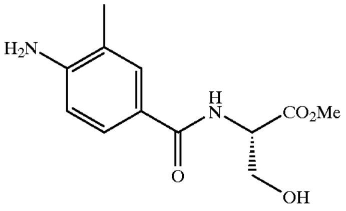
30
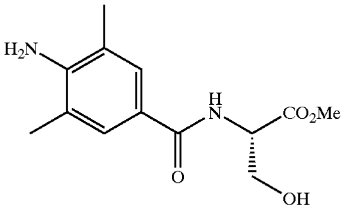
31
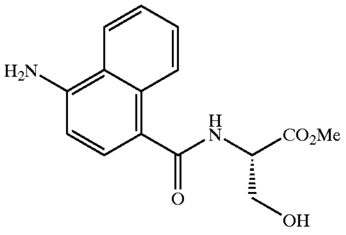
32
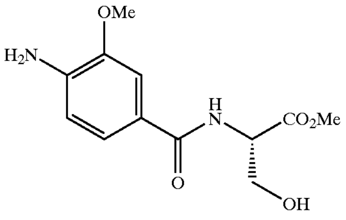
33
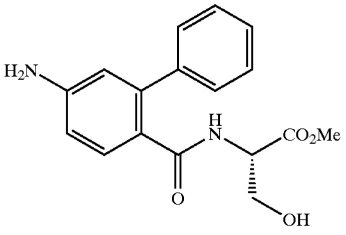
34

TABLE 10-continued
Amines of the type B—$NH_2$
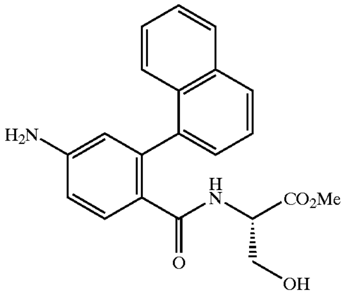
35
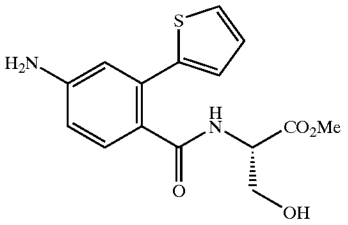
36
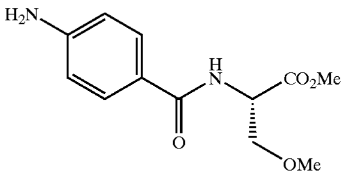
37
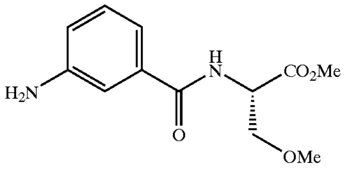
38
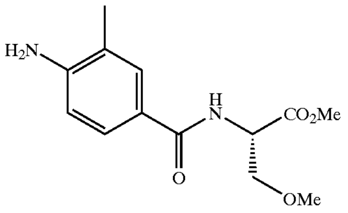
39
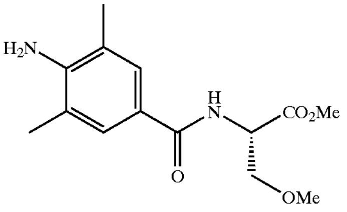
40
TABLE 10-continued
Amines of the type B—$NH_2$
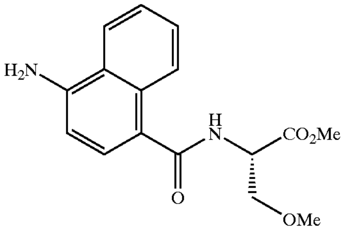
41
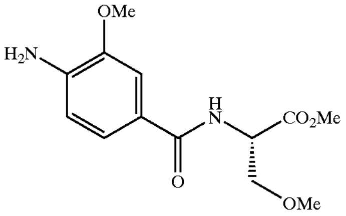
42
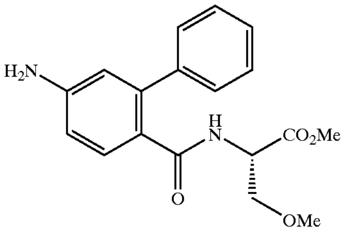
43
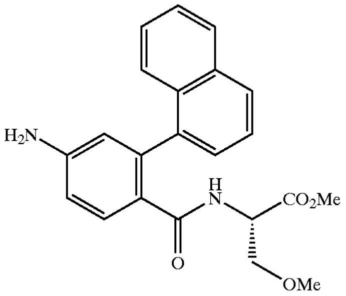
44
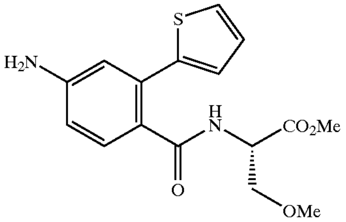
45
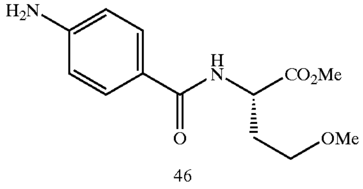
46

TABLE 10-continued
| Amines of the type B—$NH_2$ |
|---|
| 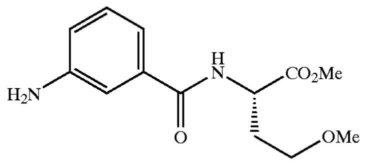 |
| 47 |
| 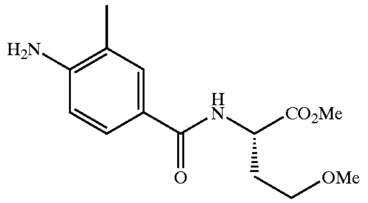 |
| 48 |
| 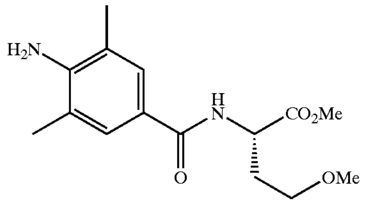 |
| 49 |
| 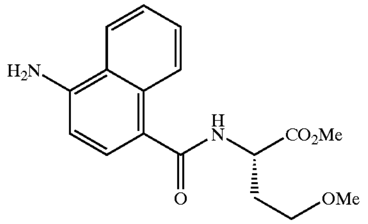 |
| 50 |
| 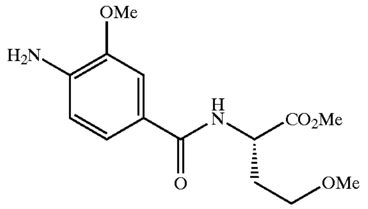 |
| 51 |
| 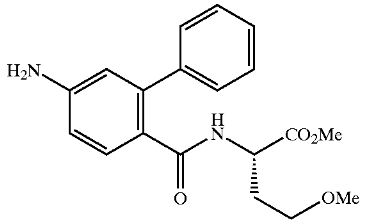 |
| 52 |
TABLE 10-continued
| Amines of the type B—$NH_2$ |
|---|
| 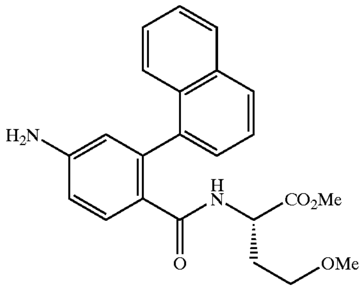 |
| 53 |
| 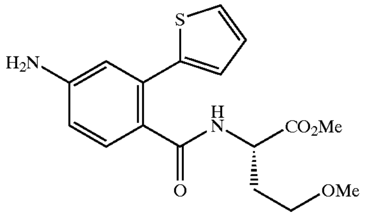 |
| 54 |
| 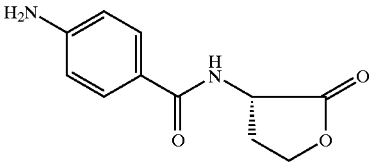 |
| 55 |
| 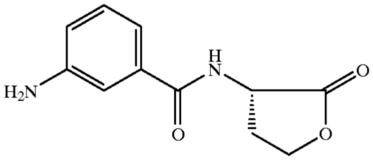 |
| 56 |
| 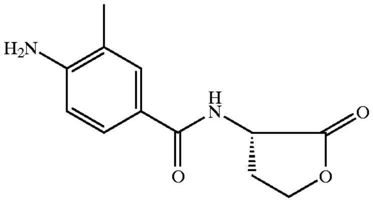 |
| 57 |
| 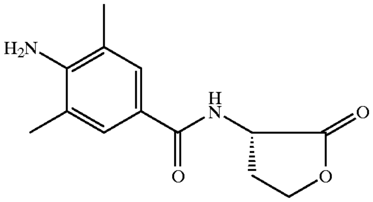 |
| 58 |

TABLE 10-continued
| Amines of the type B—$NH_2$ |
|---|
| 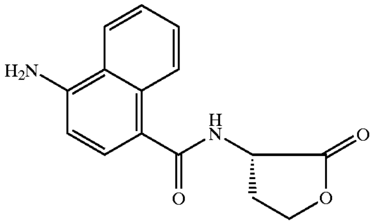 |
| 59 |
| 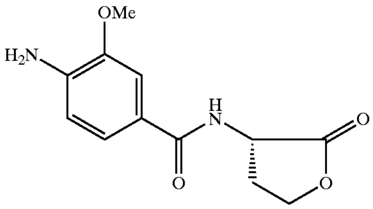 |
| 60 |
| 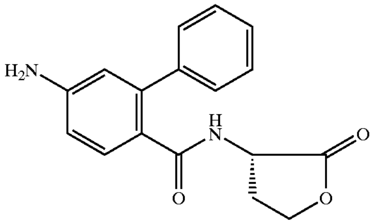 |
| 61 |
| 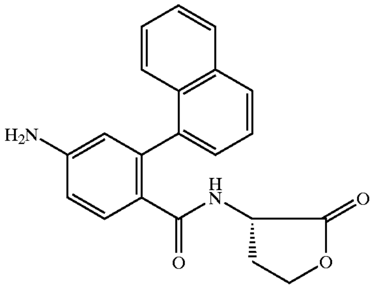 |
| 62 |
| 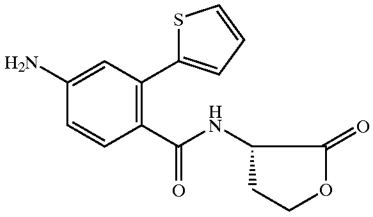 |
| 63 |
| 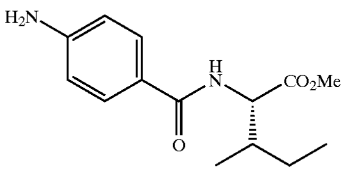 |
| 64 |
TABLE 10-continued
| Amines of the type B—$NH_2$ |
|---|
| 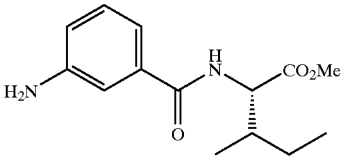 |
| 65 |
| 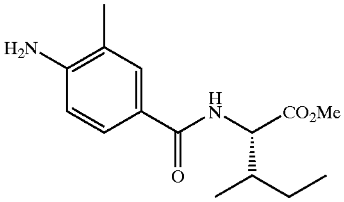 |
| 66 |
| 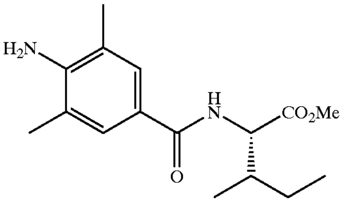 |
| 67 |
| 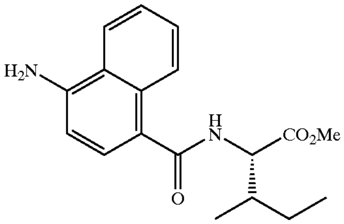 |
| 68 |
| 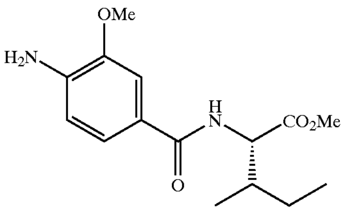 |
| 69 |
| 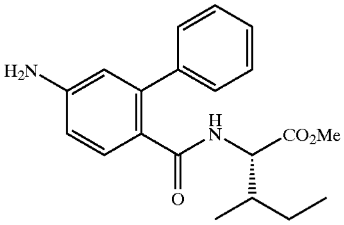 |
| 70 |

TABLE 10-continued
| Amines of the type B—$NH_2$ |
|---|
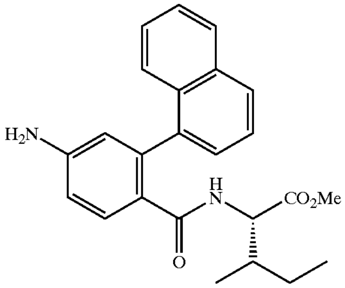
71
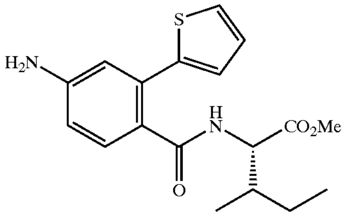
72
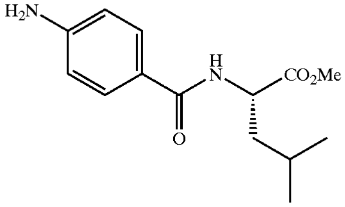
73
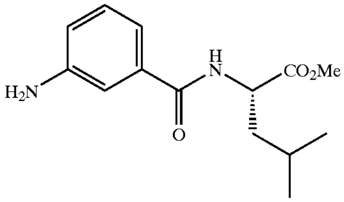
74
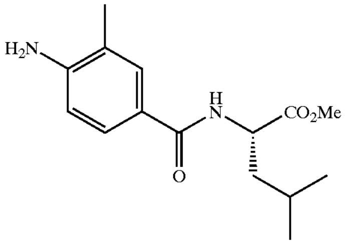
75
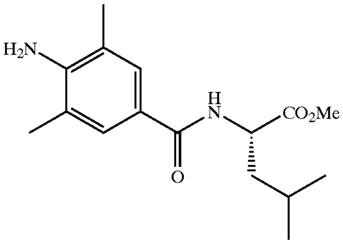
TABLE 10-continued
| Amines of the type B—$NH_2$ |
|---|
76
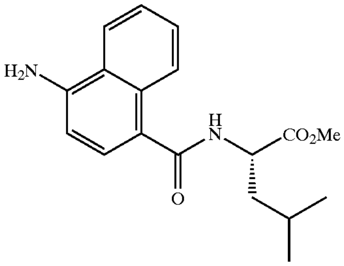
77
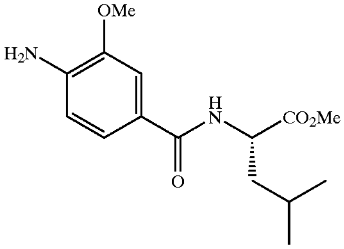
78
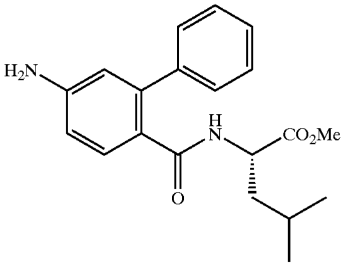
79
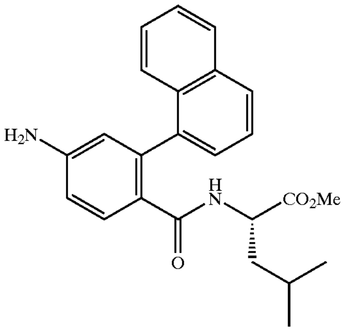
80
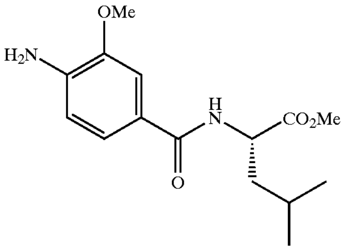
81

TABLE 10-continued
Amines of the type B—$NH_2$
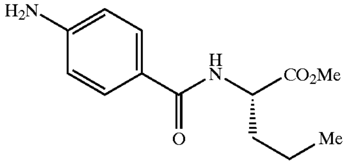
82
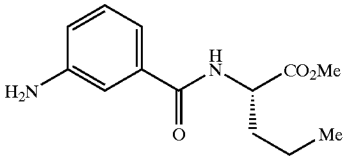
83
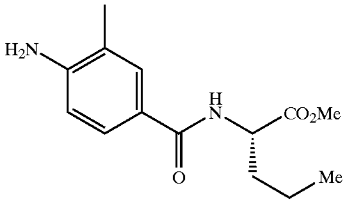
84
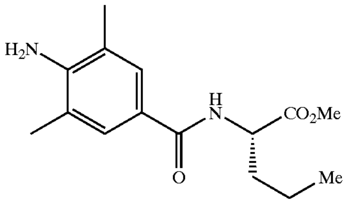
85
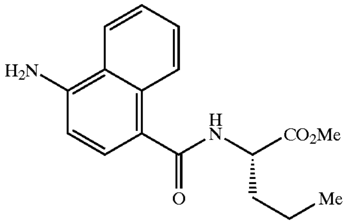
86
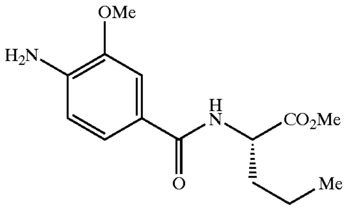
87
TABLE 10-continued
Amines of the type B—$NH_2$
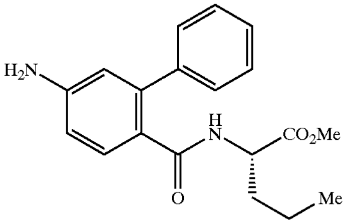
88
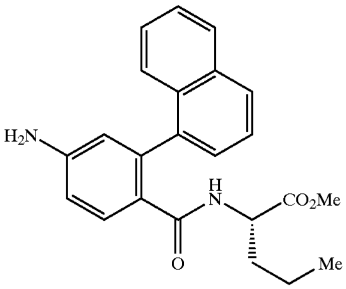
89
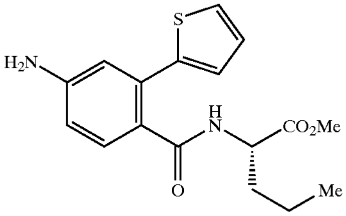
90
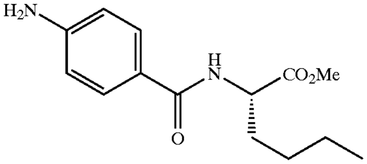
91
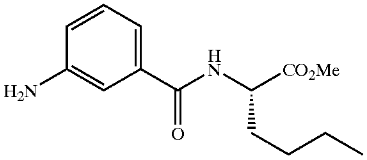
92
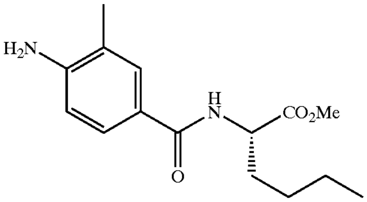
93

TABLE 10-continued
Amines of the type B—$NH_2$
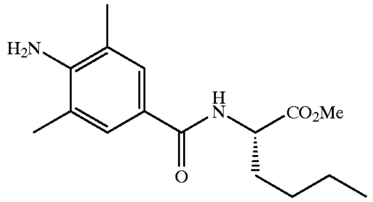
94
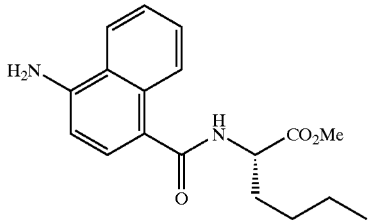
95
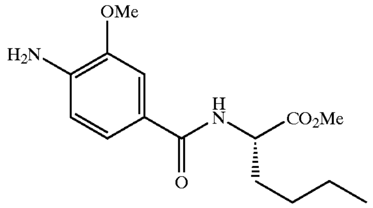
96
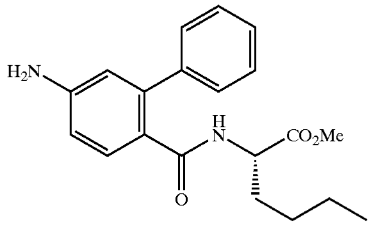
97
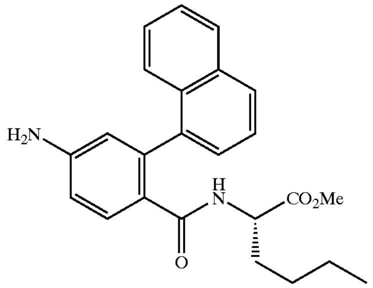
98
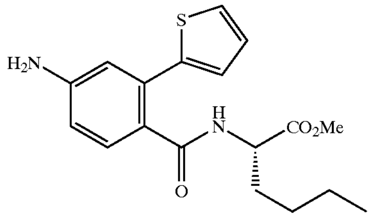
99
TABLE 10-continued
Amines of the type B—$NH_2$
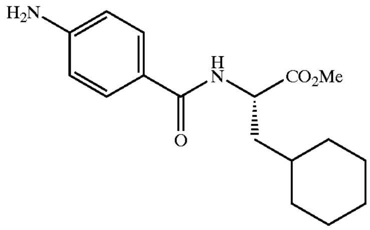
100
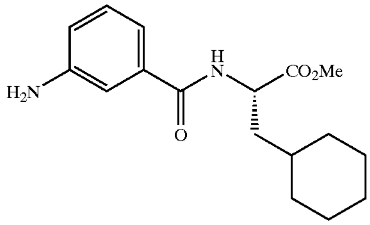
101
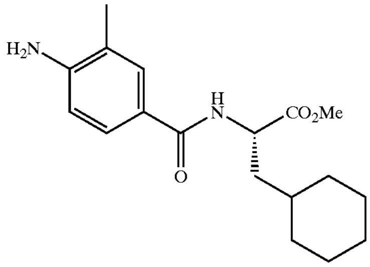
102
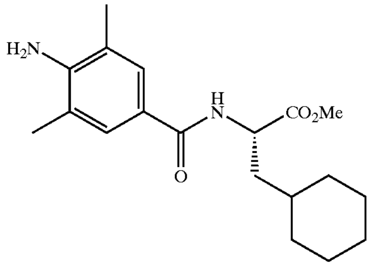
103
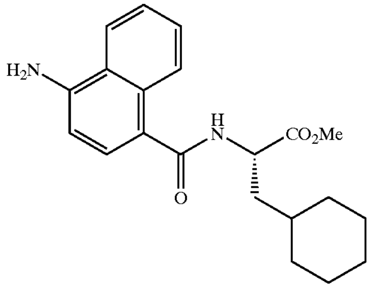
104

TABLE 10-continued
Amines of the type B—$NH_2$
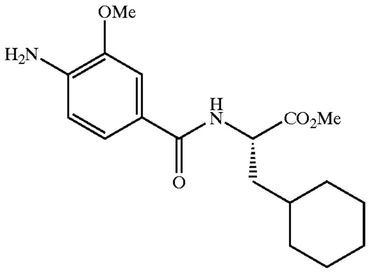
105
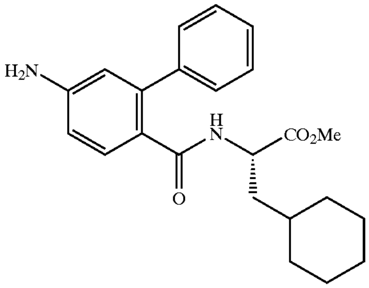
106
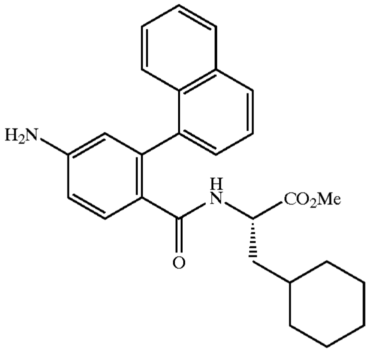
107
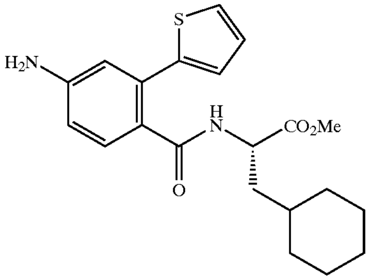
108
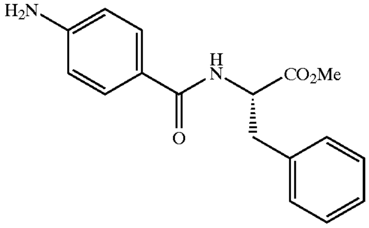
109
TABLE 10-continued
Amines of the type B—$NH_2$
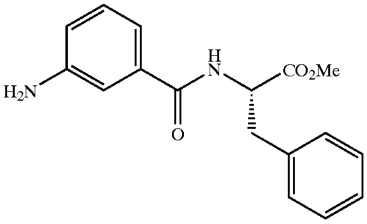
110
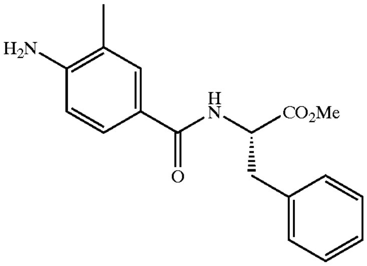
111
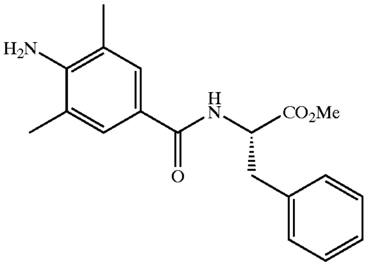
112
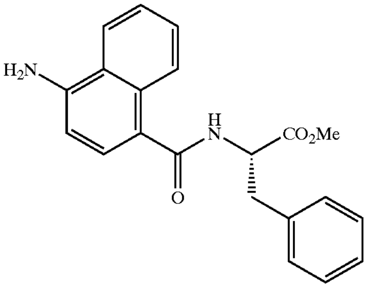
113
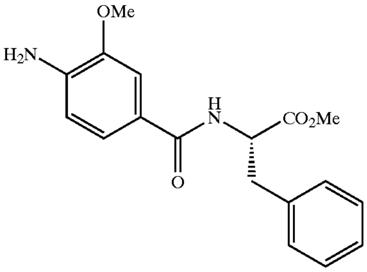
114

TABLE 10-continued
| Amines of the type B—$NH_2$ |
|---|
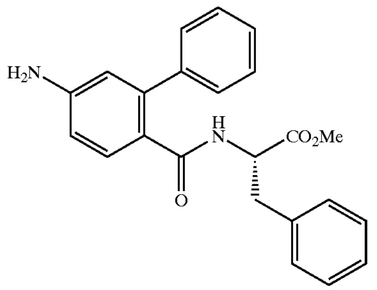
115
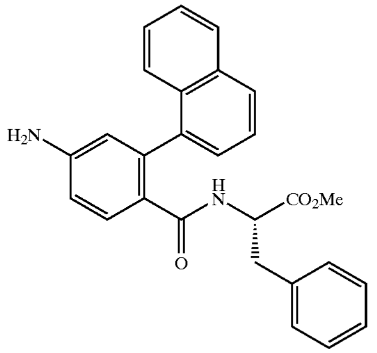
116
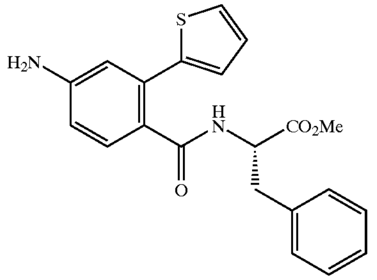
117
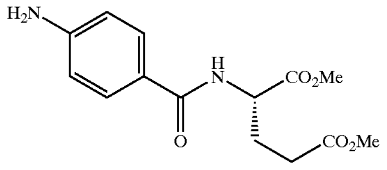
118
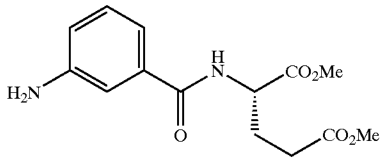
119
TABLE 10-continued
| Amines of the type B—$NH_2$ |
|---|
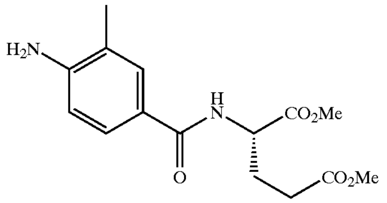
120
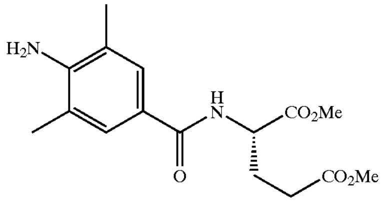
121
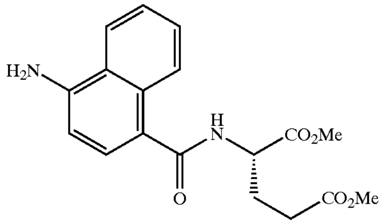
122
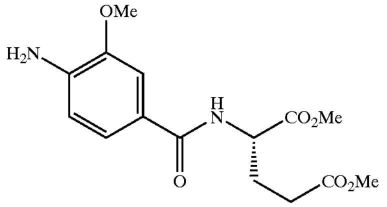
123
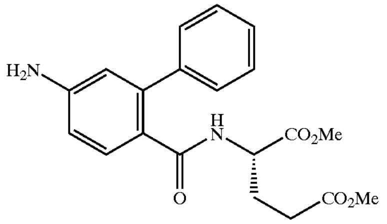
124
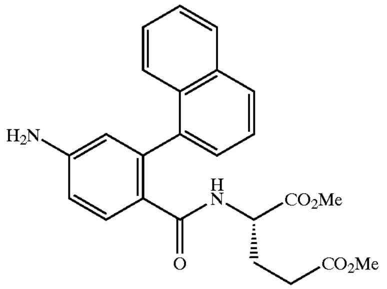
125

TABLE 10-continued
Amines of the type B—$NH_2$
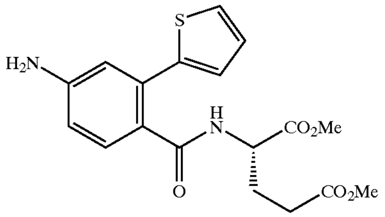
126
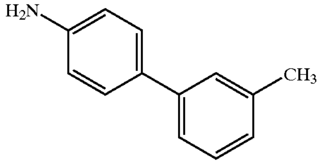
127
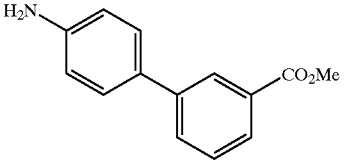
128
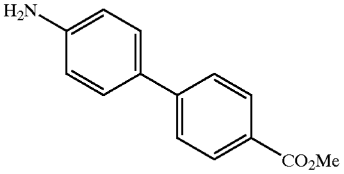
129
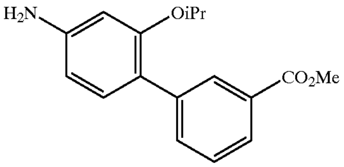
130
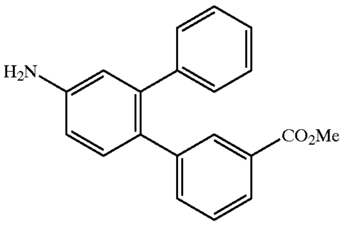
131
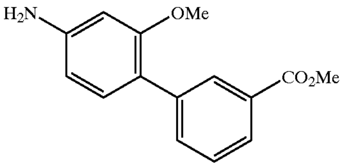
132
TABLE 11
Bromides of the type B—Br
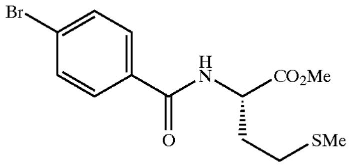
1
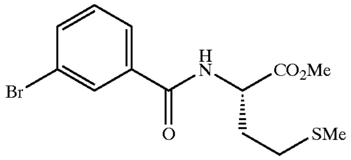
2
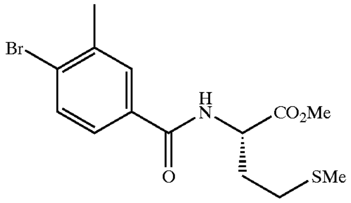
3
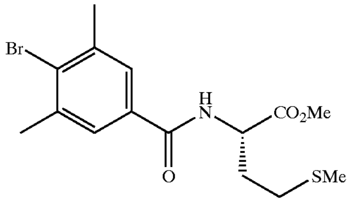
4
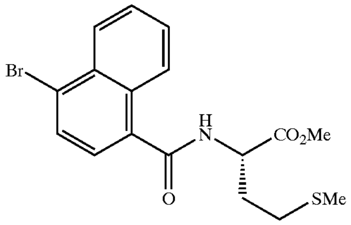
5
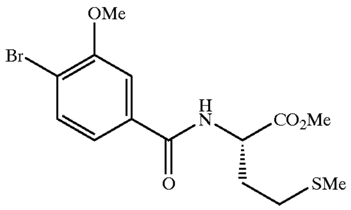
6

TABLE 11-continued
| Bromides of the type B—Br |
|---|
| 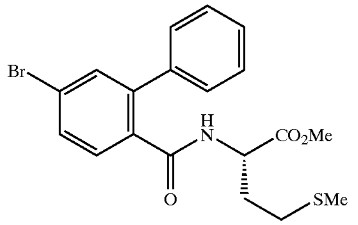 |
| 7 |
| 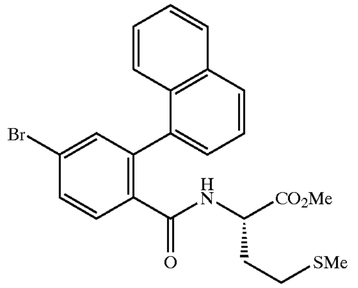 |
| 8 |
| 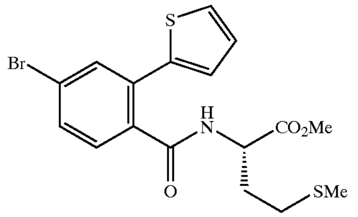 |
| 9 |
| 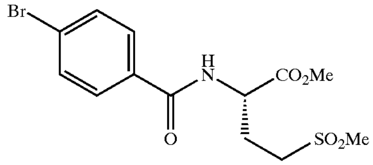 |
| 10 |
| 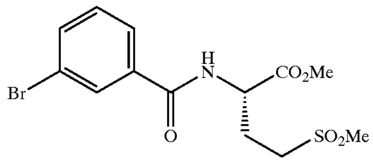 |
| 11 |
| 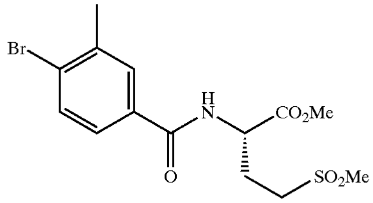 |
| 12 |
TABLE 11-continued
| Bromides of the type B—Br |
|---|
| 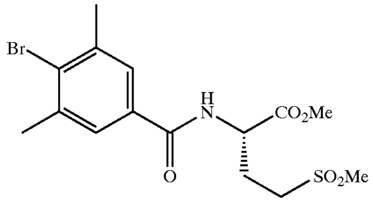 |
| 13 |
| 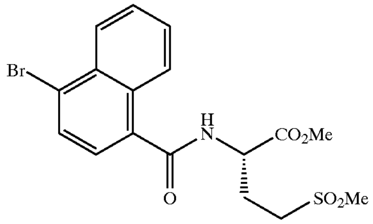 |
| 14 |
| 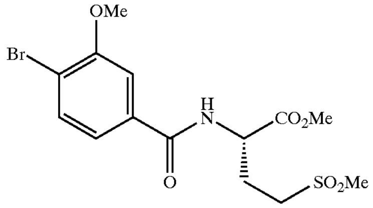 |
| 15 |
| 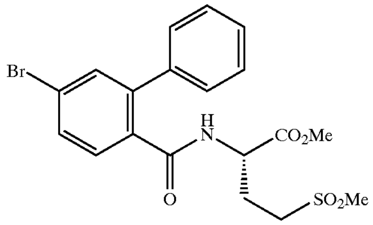 |
| 16 |
| 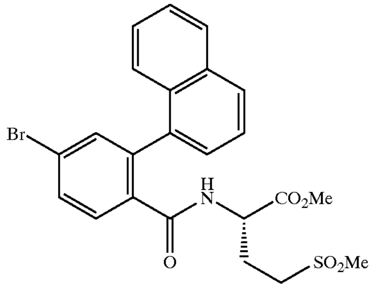 |
| 17 |
| 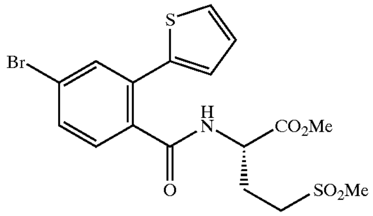 |
| 18 |

TABLE 11-continued
Bromides of the type B—Br
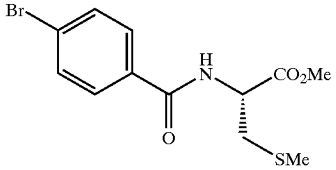
19
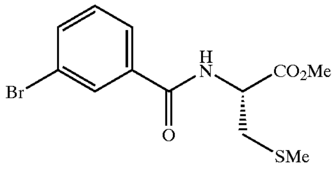
20
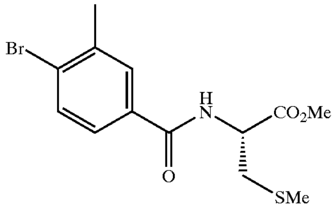
21
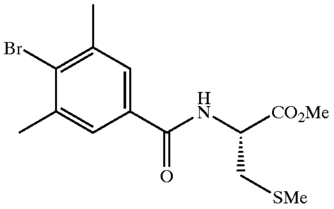
22
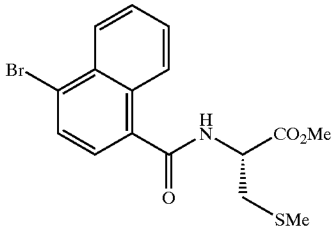
23
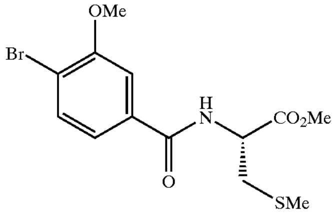
24
TABLE 11-continued
Bromides of the type B—Br
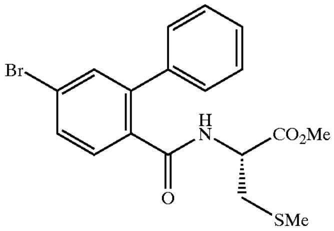
25
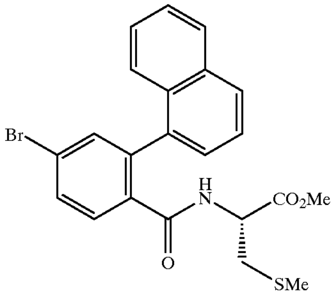
26
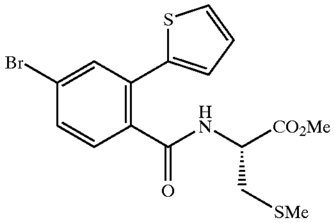
27
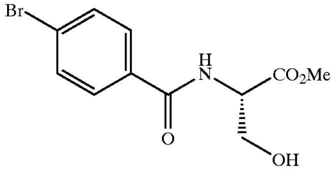
28
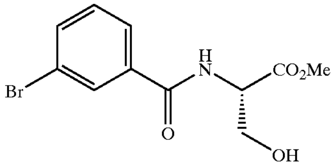
29
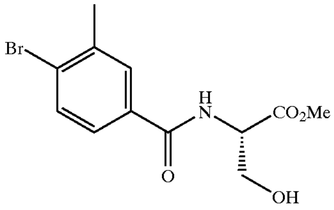
30

TABLE 11-continued
Bromides of the type B—Br
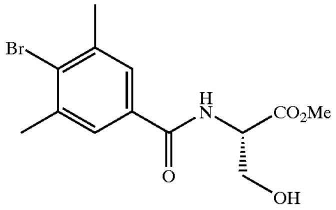
31
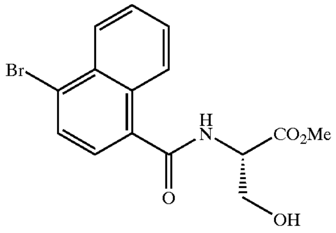
32
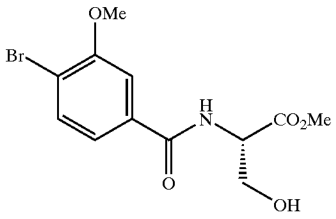
33
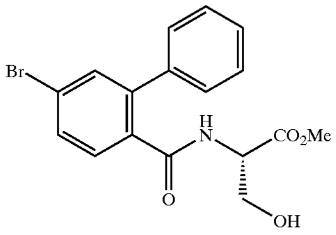
34
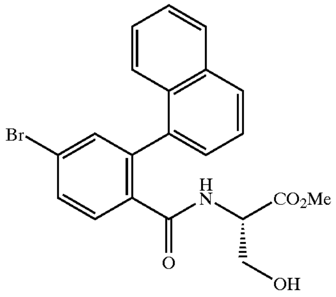
35
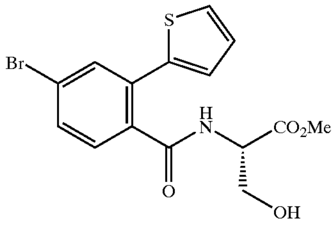
TABLE 11-continued
Bromides of the type B—Br
36
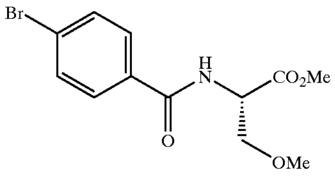
37
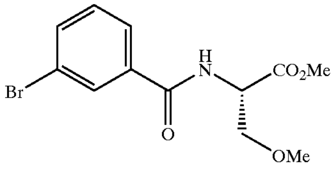
38
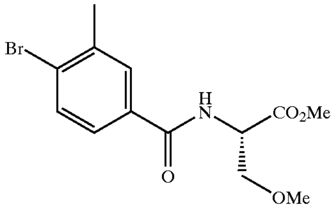
39
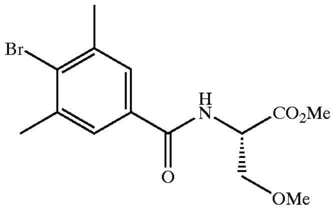
40
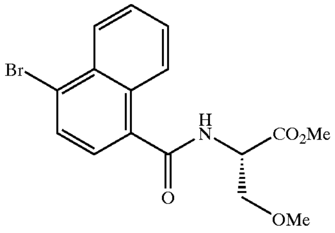
41
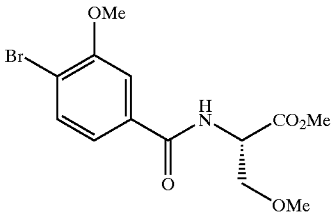
42

TABLE 11-continued
| Bromides of the type B—Br |
|---|
| 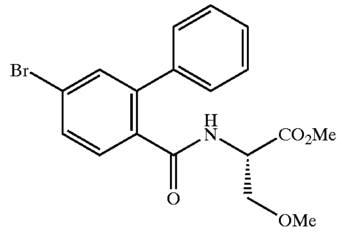 |
| 43 |
| 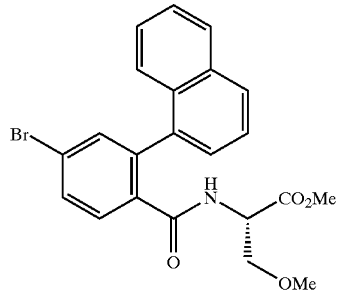 |
| 44 |
| 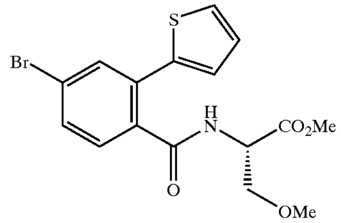 |
| 45 |
| 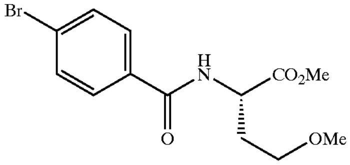 |
| 46 |
| 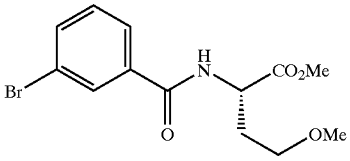 |
| 47 |
| 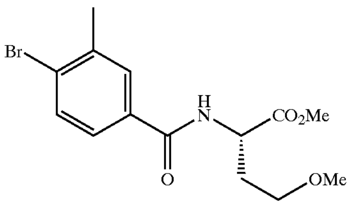 |
| 48 |
TABLE 11-continued
| Bromides of the type B—Br |
|---|
| 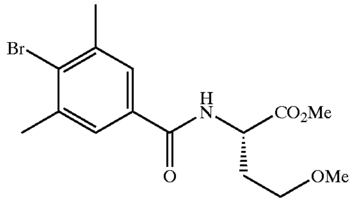 |
| 49 |
| 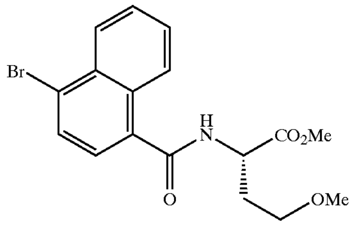 |
| 50 |
| 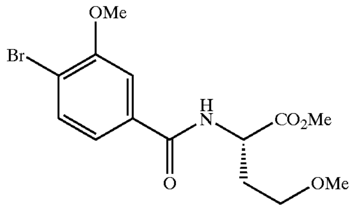 |
| 51 |
| 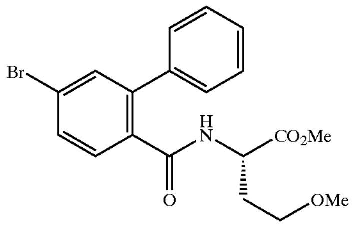 |
| 52 |
| 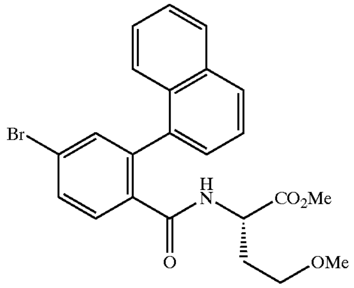 |
| 53 |
| 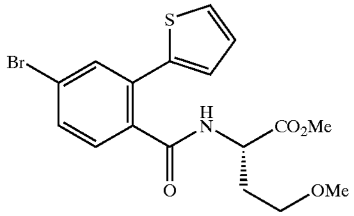 |
| 54 |

TABLE 11-continued
Bromides of the type B—Br
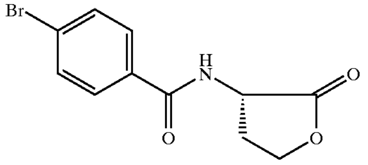
55
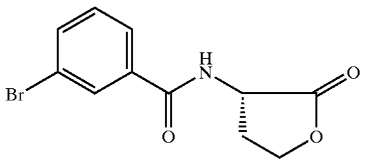
56
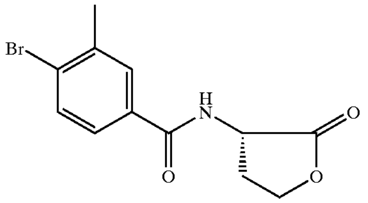
57
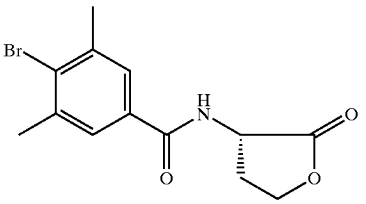
58
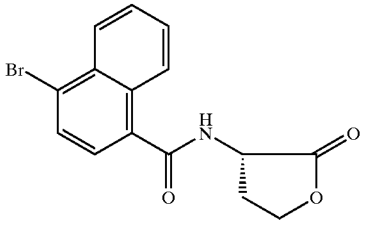
59
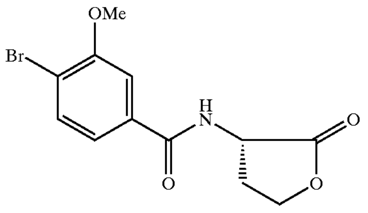
60
TABLE 11-continued
Bromides of the type B—Br
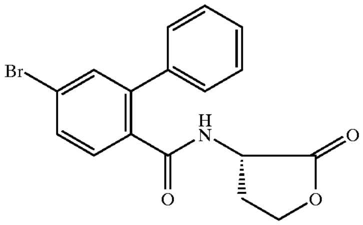
61
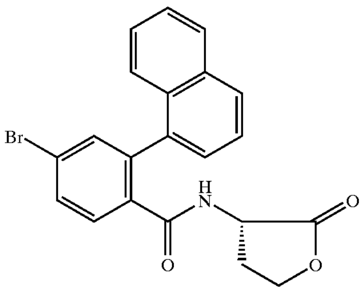
62
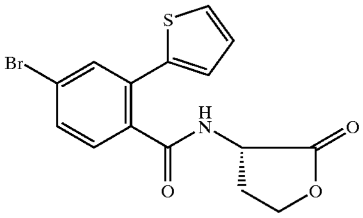
63
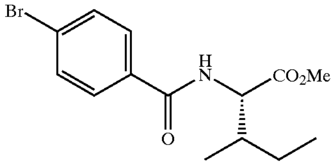
64
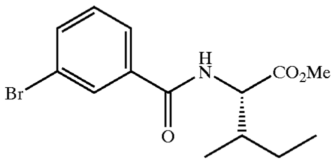
65
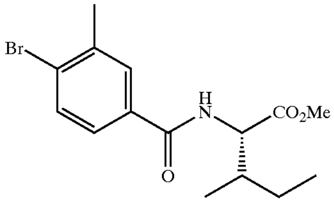
66

TABLE 11-continued
| Bromides of the type B—Br |
|---|
| 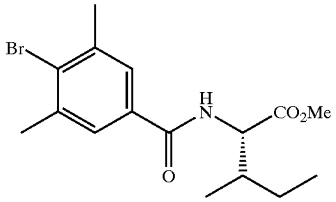 |
| 67 |
| 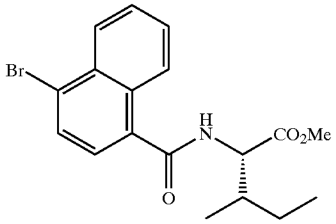 |
| 68 |
| 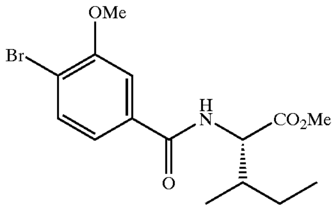 |
| 69 |
| 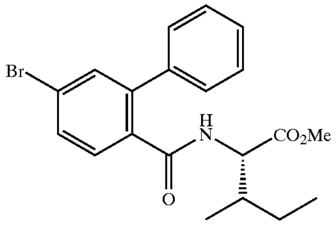 |
| 70 |
| 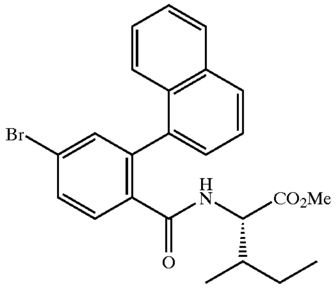 |
| 71 |
| 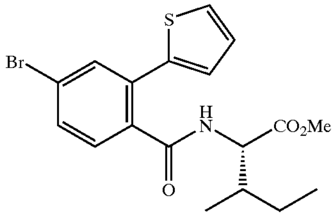 |
| 72 |
TABLE 11-continued
| Bromides of the type B—Br |
|---|
| 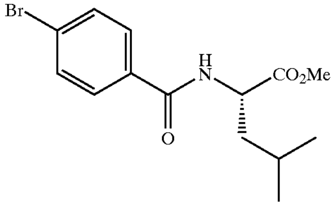 |
| 73 |
| 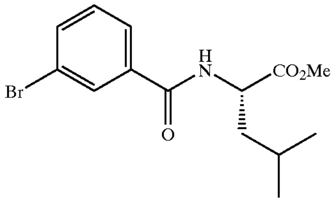 |
| 74 |
| 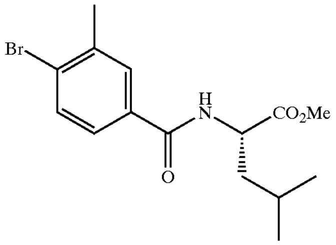 |
| 75 |
| 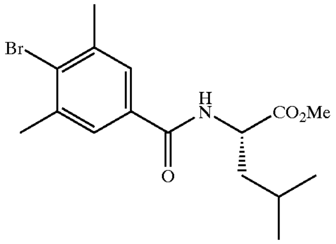 |
| 76 |
| 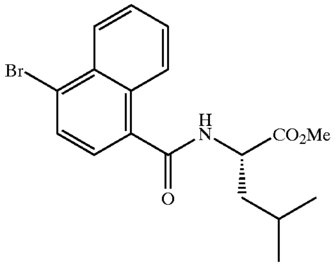 |
| 77 |
| 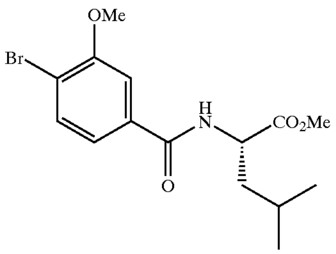 |

TABLE 11-continued
Bromides of the type B—Br
78
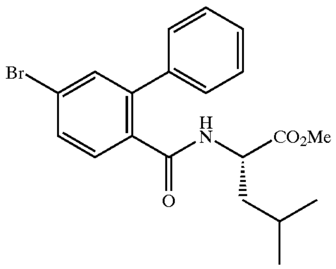
79
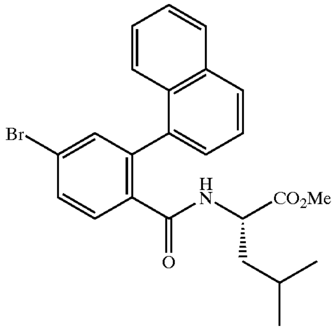
80
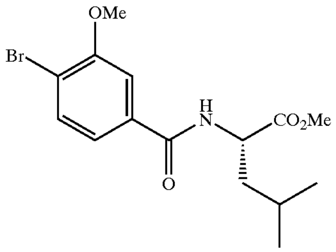
81
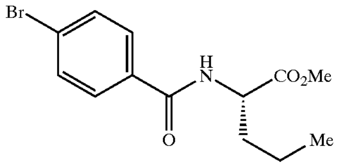
82
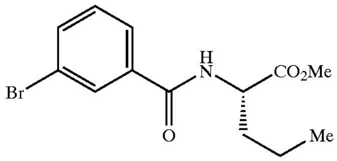
83
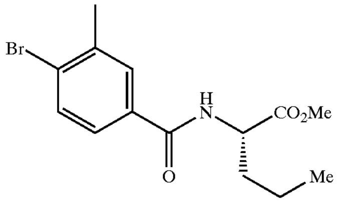
TABLE 11-continued
Bromides of the type B—Br
84
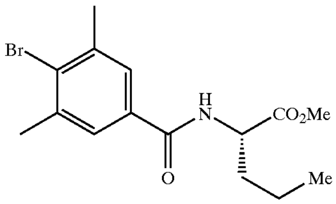
85
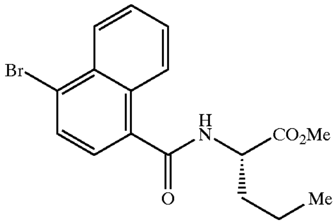
86
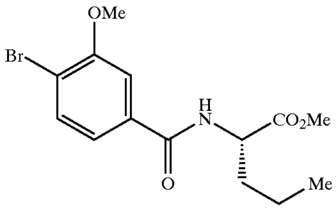
87
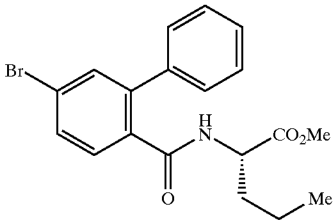
88
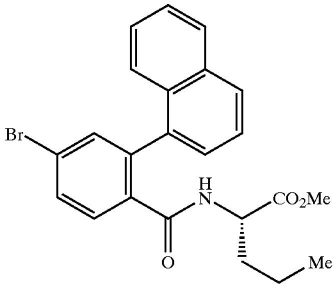
89
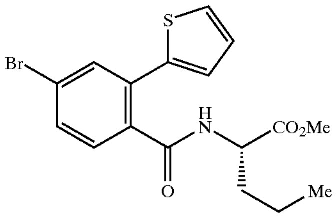

TABLE 11-continued
Bromides of the type B—Br
90
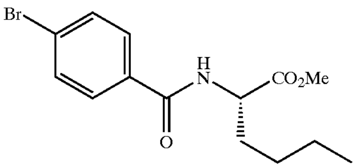
91
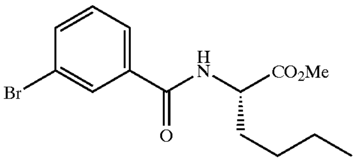
92
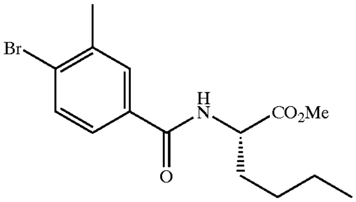
93
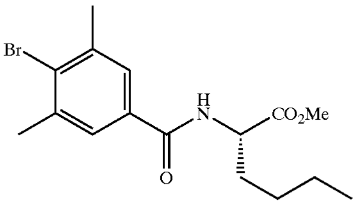
94
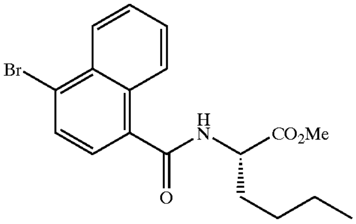
95
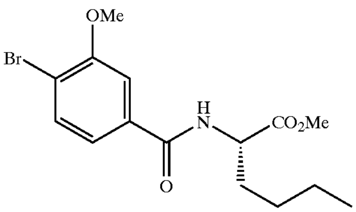
96
TABLE 11-continued
Bromides of the type B—Br
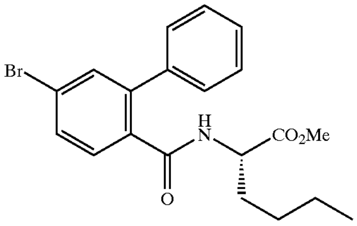
97
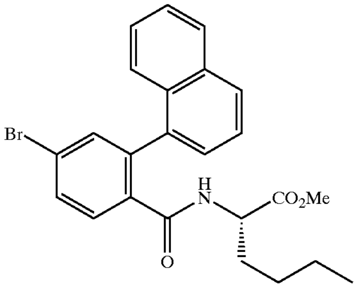
98
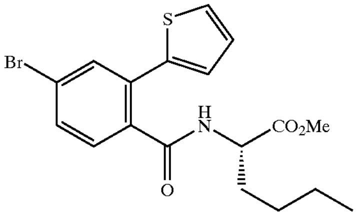
99
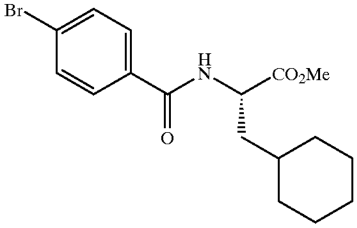
100
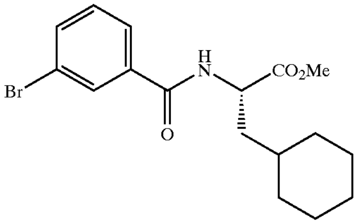
101

TABLE 11-continued
| Bromides of the type B—Br |
|---|
| 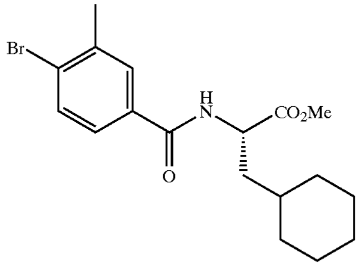 |
| 102 |
| 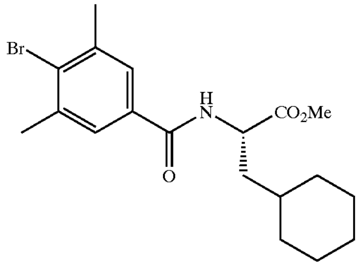 |
| 103 |
| 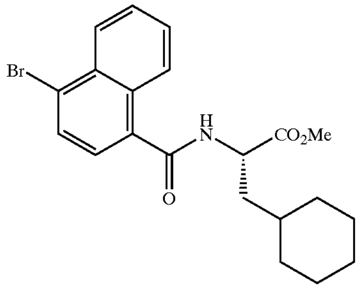 |
| 104 |
| 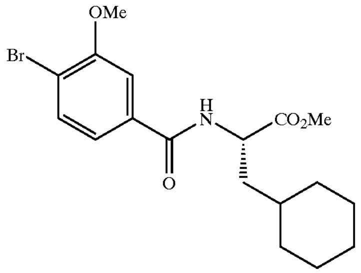 |
| 105 |
| 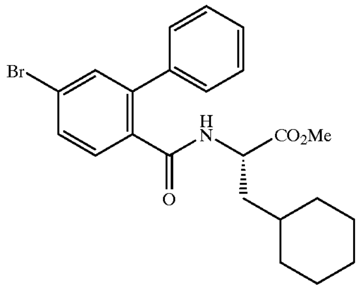 |
| 106 |
TABLE 11-continued
| Bromides of the type B—Br |
|---|
| 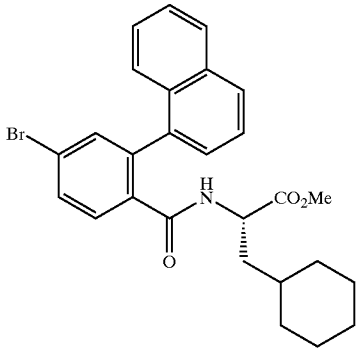 |
| 107 |
| 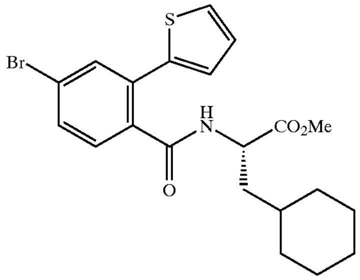 |
| 108 |
| 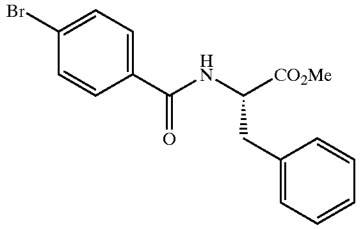 |
| 109 |
| 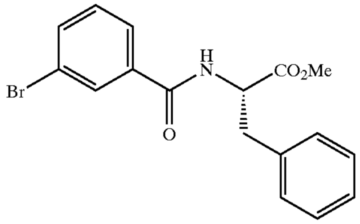 |
| 110 |
| 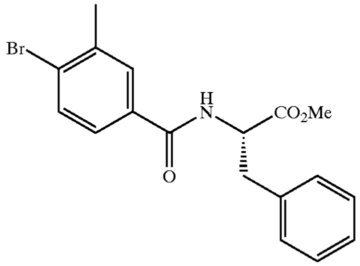 |
| 111 |

TABLE 11-continued
Bromides of the type B—Br
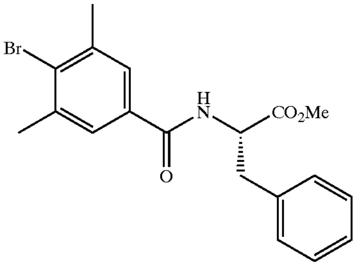
112
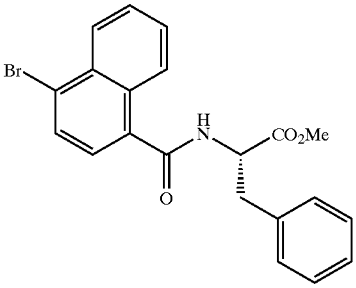
113
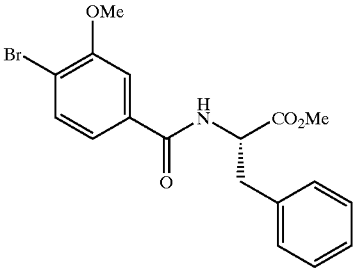
114
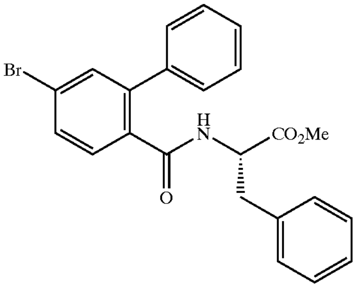
115
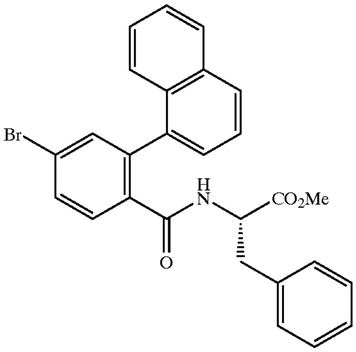
TABLE 11-continued
Bromides of the type B—Br
116
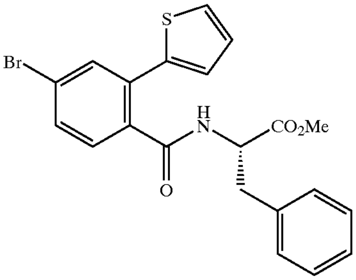
117
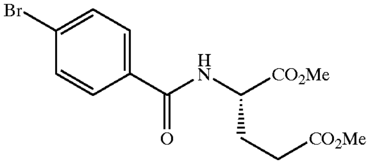
118
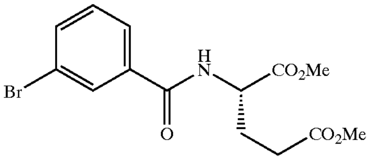
119
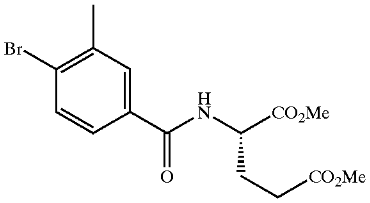
120
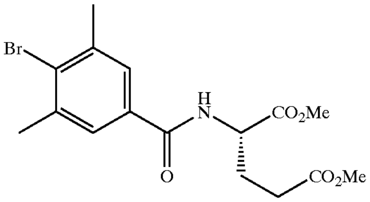
121
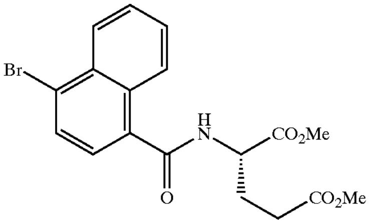
122

TABLE 11-continued
| Bromides of the type B—Br |
|---|
| 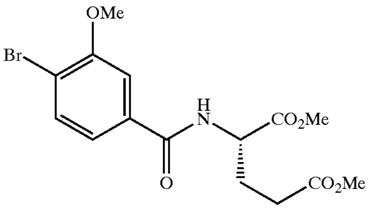 |
| 123 |
| 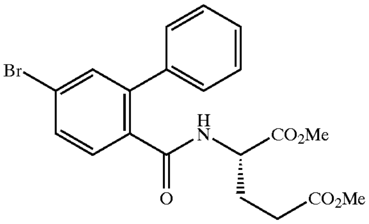 |
| 124 |
| 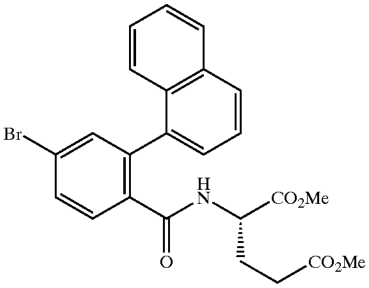 |
| 125 |
| 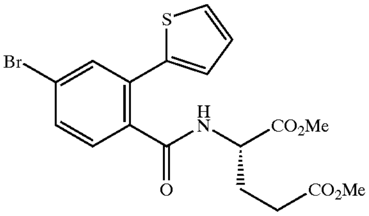 |
| 126 |
| 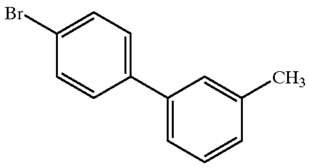 |
| 127 |
| 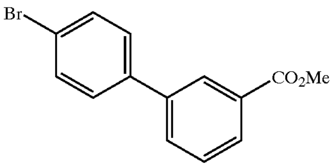 |
| 128 |
TABLE 11-continued
| Bromides of the type B—Br |
|---|
| 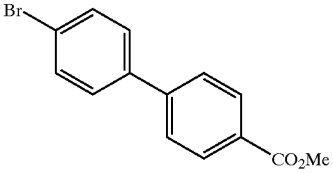 |
| 129 |
| 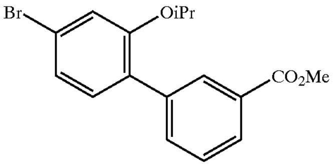 |
| 130 |
| 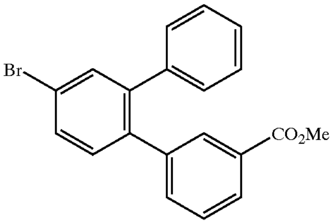 |
| 131 |
| 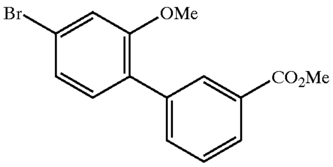 |
| 132 |
TABLE 12
| Amines of the type A—$NH_2$ |
|---|
| 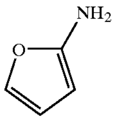 |
| 1 |
| 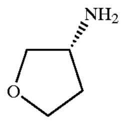 |
| 2 |
| 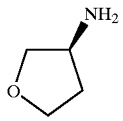 |
| 3 |
| 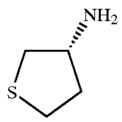 |

TABLE 12-continued
Amines of the type A—$NH_2$
4
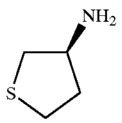
5
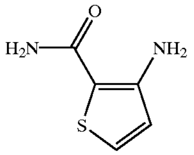
6
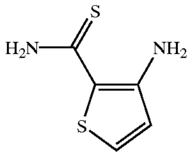
7
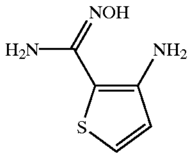
8
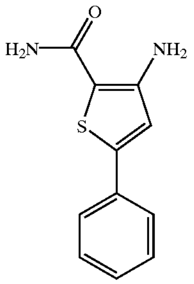
9
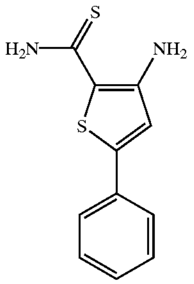
10
TABLE 12-continued
Amines of the type A—$NH_2$
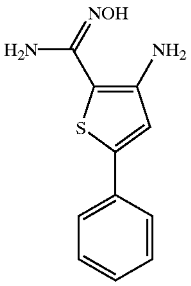
11
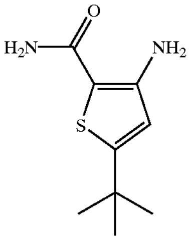
12
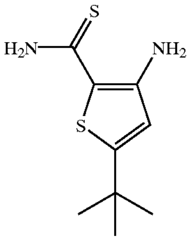
13
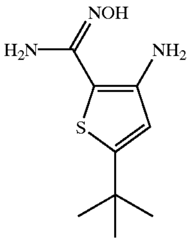
14
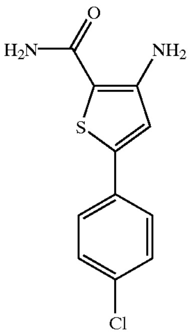
15

TABLE 12-continued
| Amines of the type A—$NH_2$ |
|---|
| 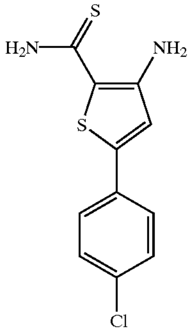 16 |
| 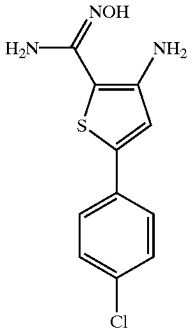 17 |
| 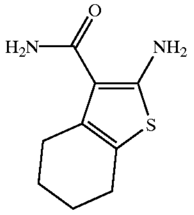 18 |
| 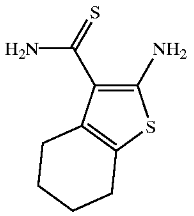 19 |
| 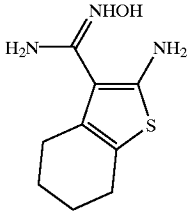 20 |
TABLE 12-continued
| Amines of the type A—$NH_2$ |
|---|
| 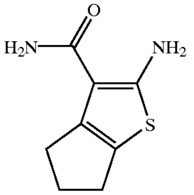 21 |
| 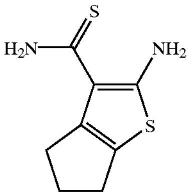 22 |
| 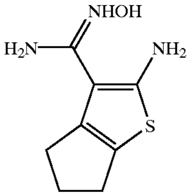 23 |
| 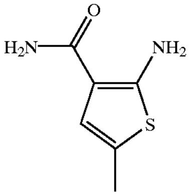 24 |
| 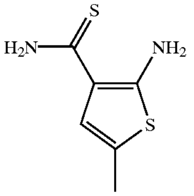 25 |
| 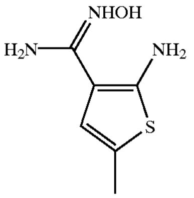 26 |
| 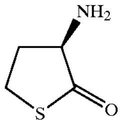 27 |

TABLE 12-continued
Amines of the type A—$NH_2$
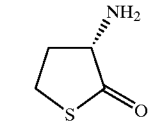
28
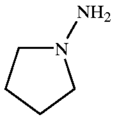
29
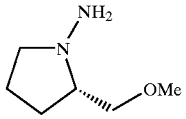
30
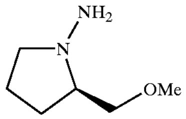
31
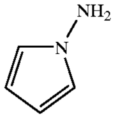
32
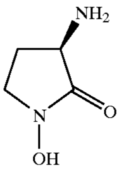
33
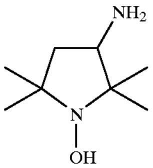
34
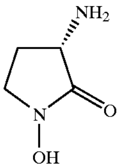
35
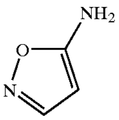
36
TABLE 12-continued
Amines of the type A—$NH_2$
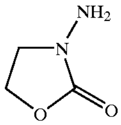
37
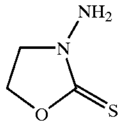
38
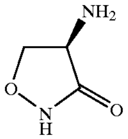
39
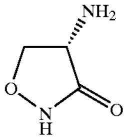
40
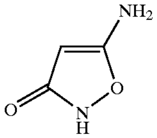
41
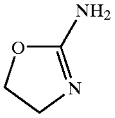
42
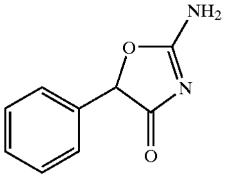
43
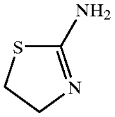
44
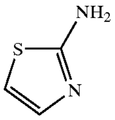
45

TABLE 12-continued
Amines of the type A—$NH_2$
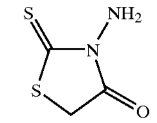
46
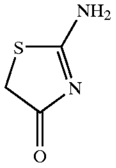
47
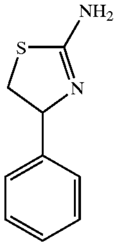
48
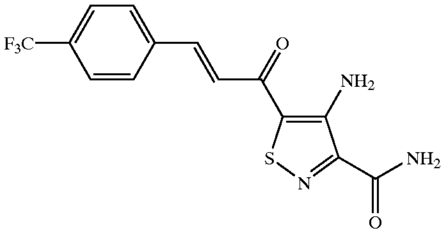
49
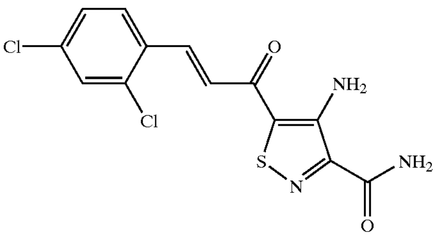
50
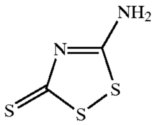
51
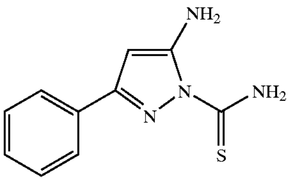
52
TABLE 12-continued
Amines of the type A—$NH_2$
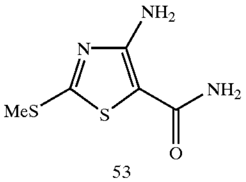
53
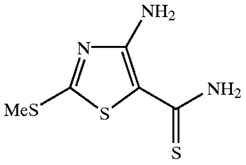
54
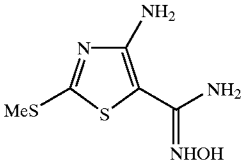
55
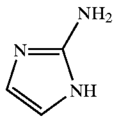
56
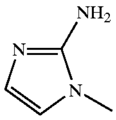
57
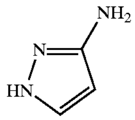
58
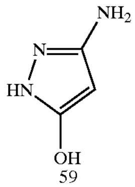
59
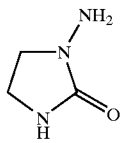
60
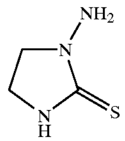

TABLE 12-continued
Amines of the type A—$NH_2$
61
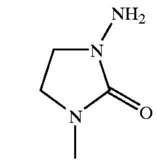
62
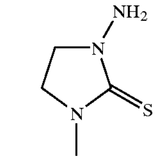
63
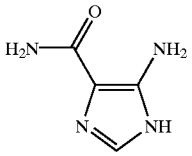
64
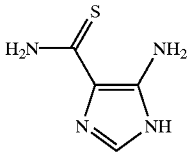
65
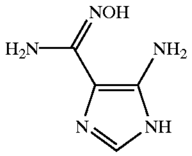
66
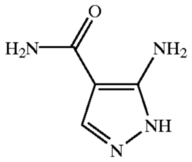
67
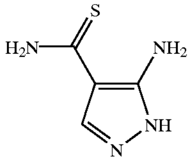
68
TABLE 12-continued
Amines of the type A—$NH_2$
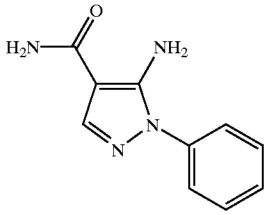
69
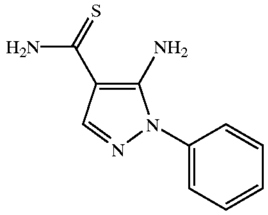
70
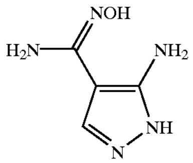
71
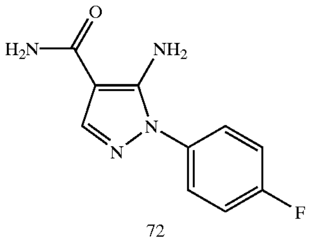
72
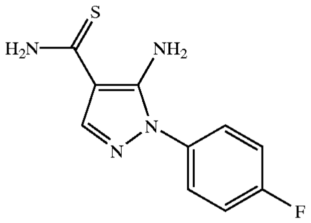
73
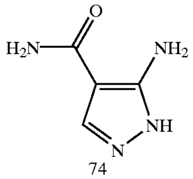
74
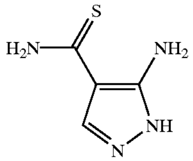
75

TABLE 12-continued
| Amines of the type A—$NH_2$ |
|---|
| 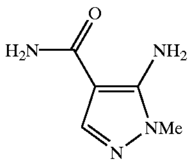 76 |
| 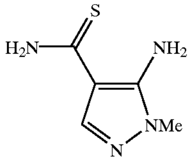 77 |
| 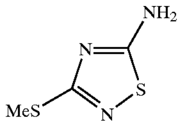 78 |
| 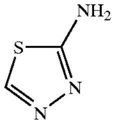 79 |
| 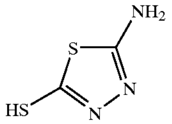 80 |
| 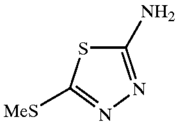 81 |
| 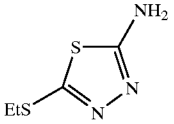 82 |
| 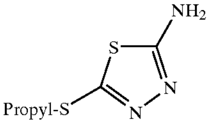 83 |
| 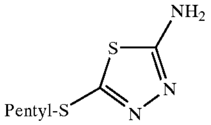 84 |
TABLE 12-continued
| Amines of the type A—$NH_2$ |
|---|
| 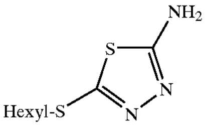 85 |
| 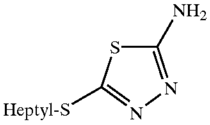 86 |
| 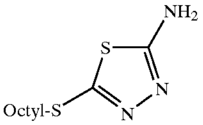 87 |
| 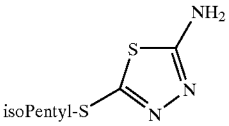 88 |
| 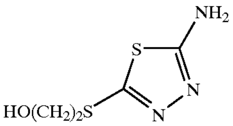 89 |
| 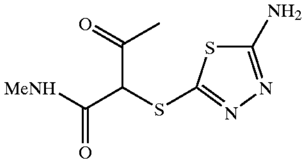 90 |
| 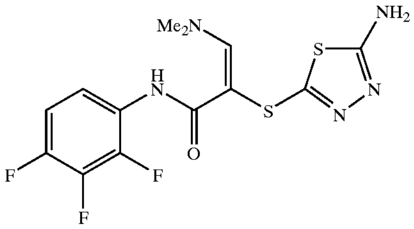 91 |
| 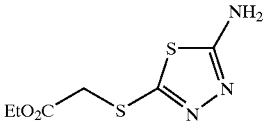 92 |

TABLE 12-continued
| Amines of the type A—$NH_2$ |
| --- |
| 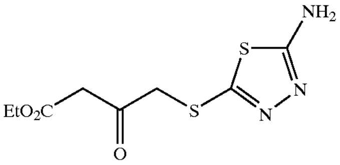 93 |
| 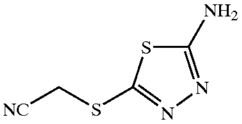 94 |
| 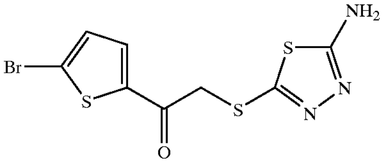 95 |
| 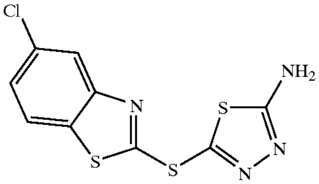 96 |
| 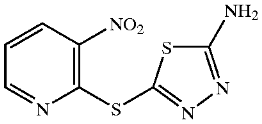 97 |
| 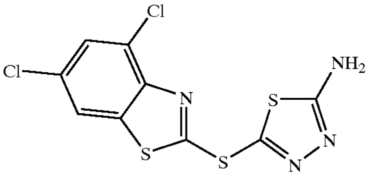 98 |
| 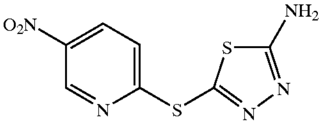 99 |
| 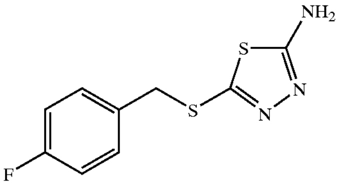 100 |
TABLE 12-continued
| Amines of the type A—$NH_2$ |
| --- |
| 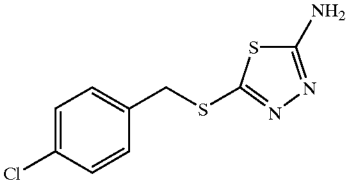 101 |
| 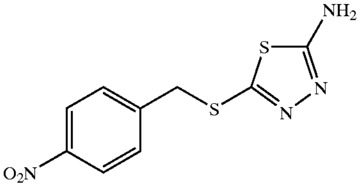 102 |
| 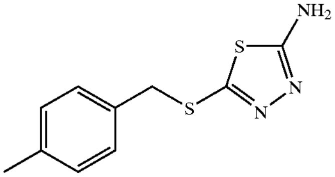 103 |
| 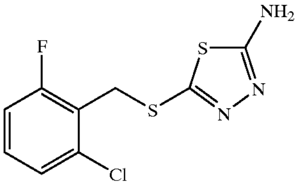 104 |
| 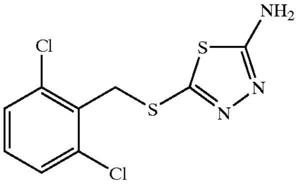 105 |
| 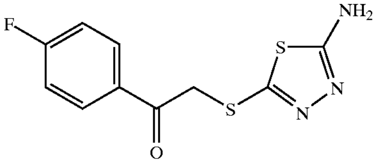 107 |
| 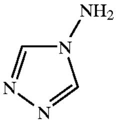 108 |
| 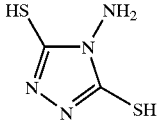 |

TABLE 12-continued
| Amines of the type A—$NH_2$ |
|---|
109
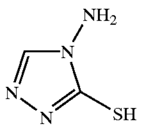
110
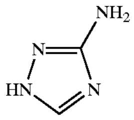
111
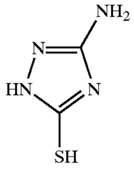
112
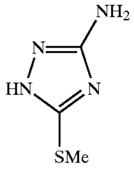
113
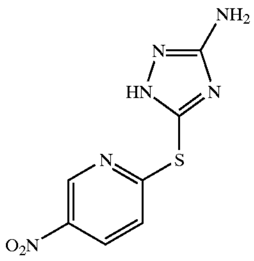
114
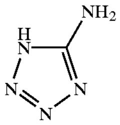
115
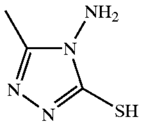
116
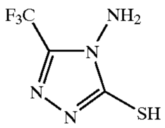
117
TABLE 12-continued
| Amines of the type A—$NH_2$ |
|---|
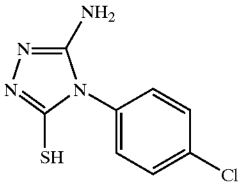
118
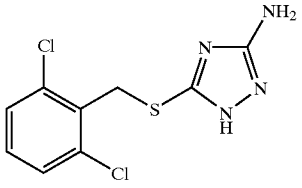
119
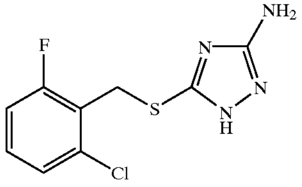
120
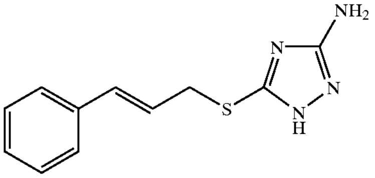
121
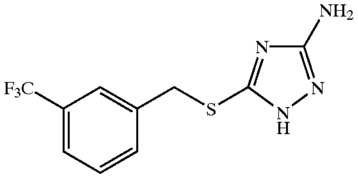
122
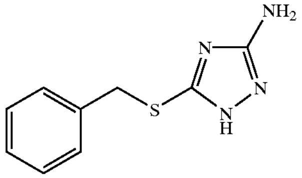
123
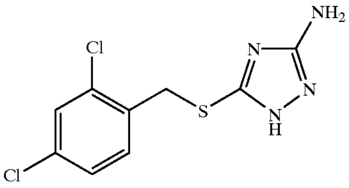
124

TABLE 12-continued
Amines of the type A—$NH_2$
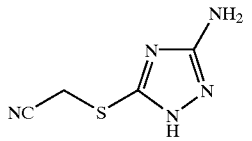
125
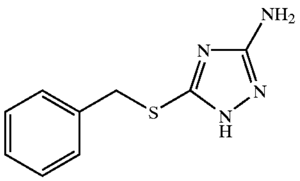
126
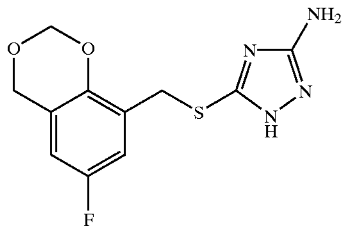
127
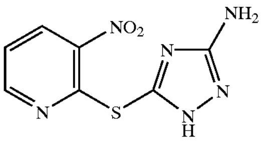
128
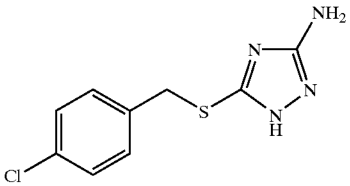
129
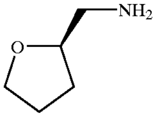
130
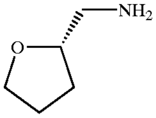
131
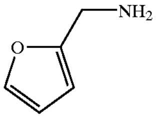
132
TABLE 12-continued
Amines of the type A—$NH_2$
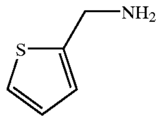
133
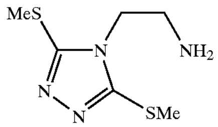
134
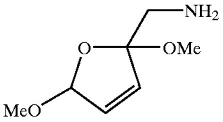
135
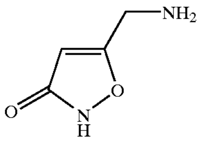
136
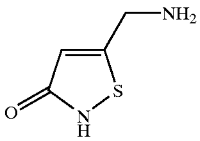
137
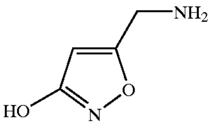
138
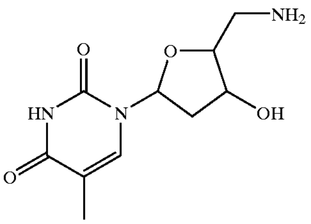
139
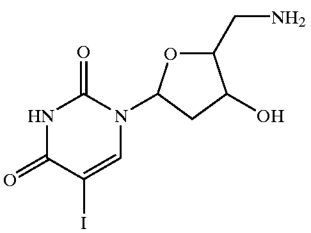
140

TABLE 12-continued
Amines of the type A—$NH_2$
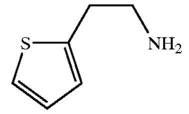
141
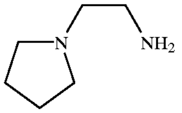
142
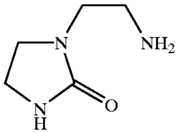
143
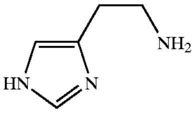
144
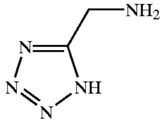
145
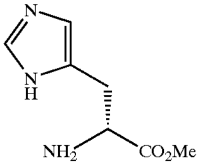
146
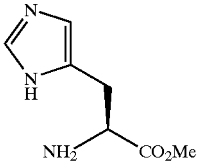
147
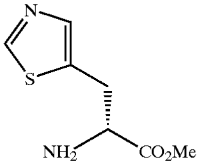
148
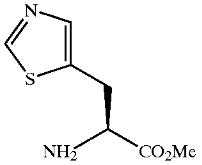
149
TABLE 12-continued
Amines of the type A—$NH_2$
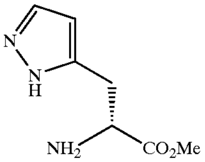
150
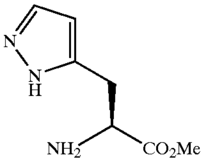
151
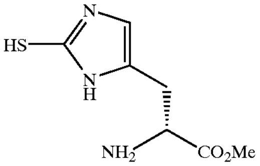
152
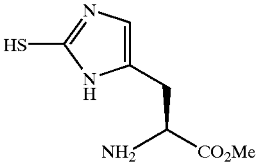
153
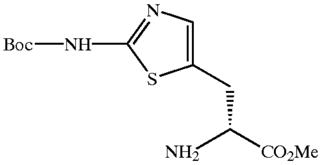
154
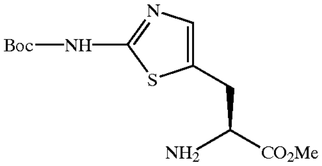
155
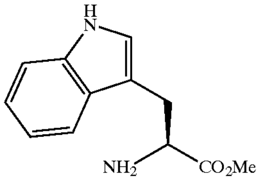
156

TABLE 12-continued
| Amines of the type A—$NH_2$ |
| --- |
| 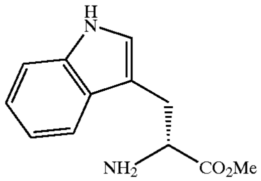 157 |
| 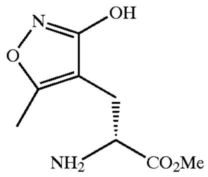 158 |
| 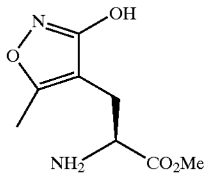 159 |
| 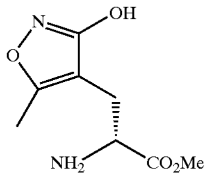 160 |
| 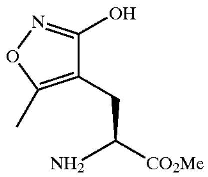 161 |
| 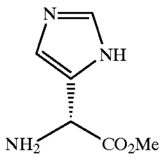 162 |
| 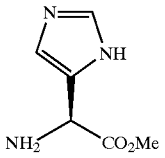 163 |
TABLE 12-continued
| Amines of the type A—$NH_2$ |
| --- |
| 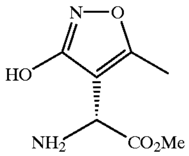 164 |
| 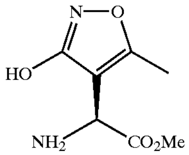 165 |
| 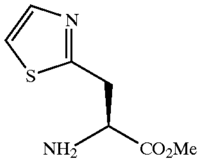 166 |
| 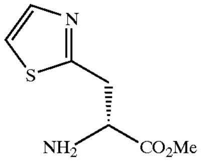 167 |
| 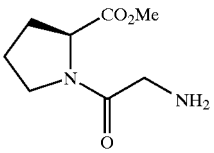 168 |
| 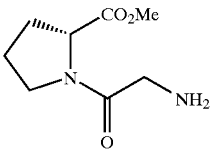 169 |
| 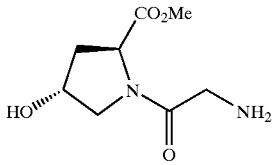 170 |
| 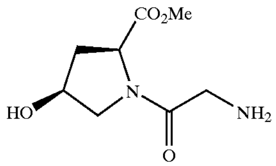 171 |

TABLE 12-continued
Amines of the type A—$NH_2$
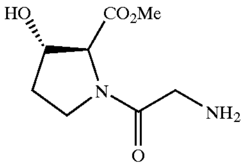
172
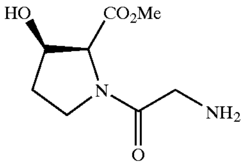
173
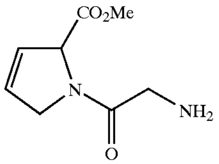
174
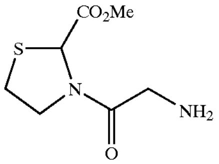
175
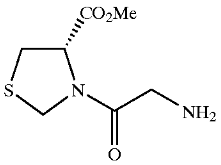
176
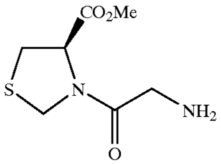
177
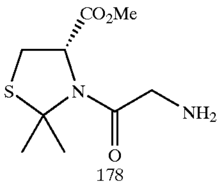
178
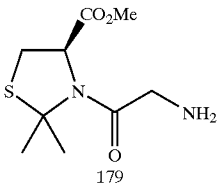
179
TABLE 12-continued
Amines of the type A—$NH_2$
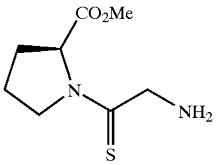
180
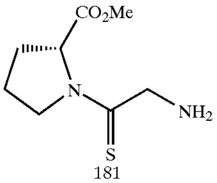
181
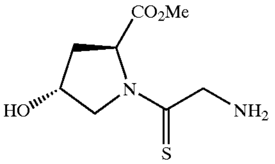
182
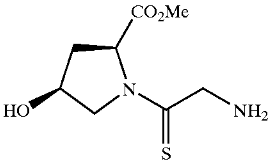
183
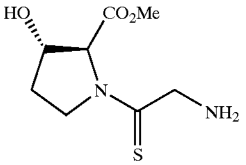
184
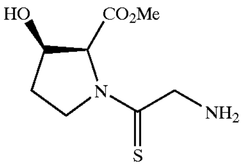
185
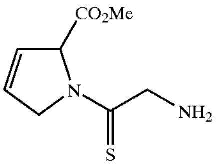
186
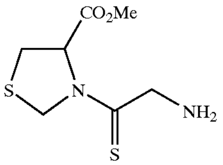

TABLE 12-continued
| Amines of the type A—$NH_2$ |
|---|
| 187 |
| 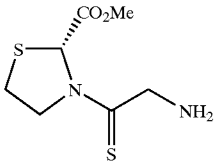 |
| 188 |
| 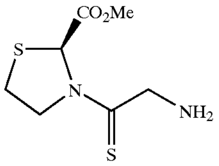 |
| 189 |
| 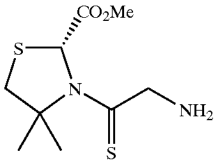 |
| 190 |
| 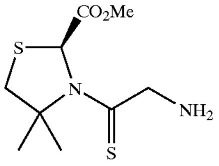 |
| 191 |
| 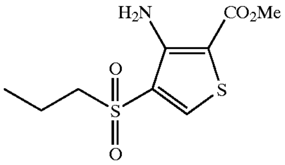 |
| 192 |
| 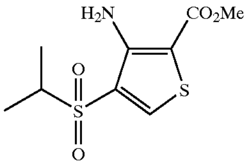 |
| 193 |
| 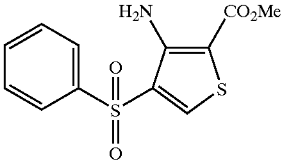 |
| 194 |
TABLE 12-continued
| Amines of the type A—$NH_2$ |
|---|
| 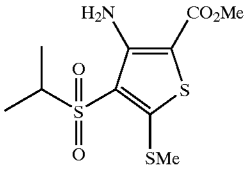 |
| 195 |
| 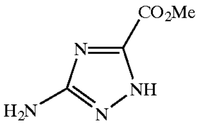 |
| 196 |
| 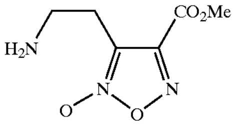 |
| 197 |
| 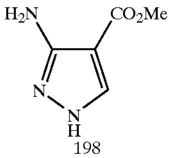 |
| 198 |
| 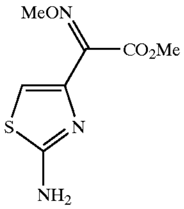 |
| 199 |
| 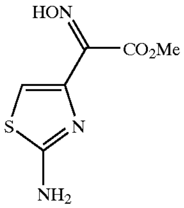 |
| 200 |
| 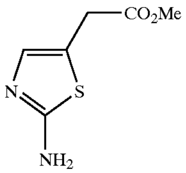 |
| 201 |
| 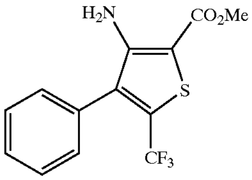 |

TABLE 12-continued
| Amines of the type A—$NH_2$ |
|---|
| 202 |
| 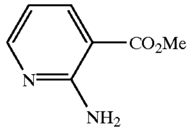 |
| 203 |
| 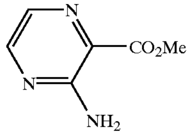 |
| 204 |
| 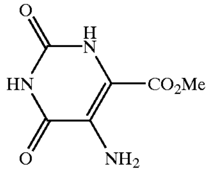 |
| 205 |
| 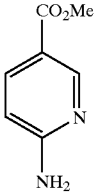 |
| 206 |
| 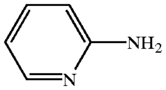 |
| 207 |
| 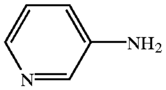 |
| 208 |
| 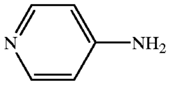 |
| 209 |
| 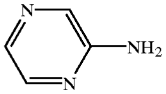 |
| 210 |
| 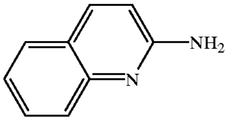 |
| 211 |
TABLE 12-continued
| Amines of the type A—$NH_2$ |
|---|
| 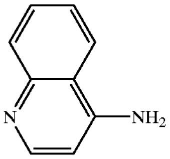 |
| 212 |
| 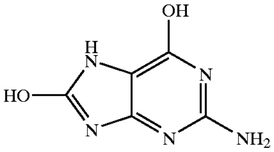 |
| 213 |
| 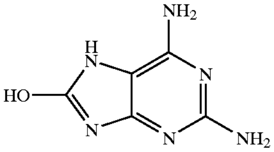 |
| 214 |
| 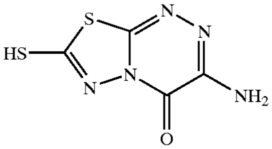 |
| 215 |
| 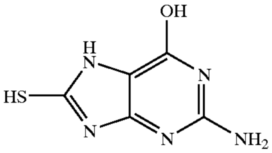 |
| 216 |
| 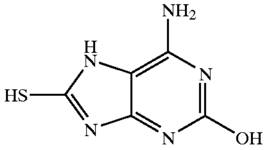 |
| 217 |
| 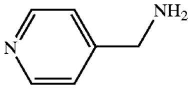 |
| 218 |
| 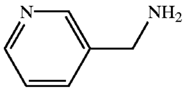 |
| 219 |
| 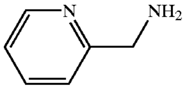 |
| 220 |

TABLE 12-continued
Amines of the type A—$NH_2$
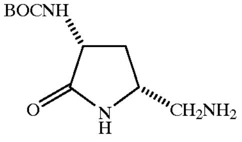
221
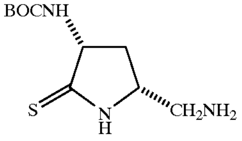
222
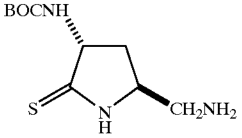
223
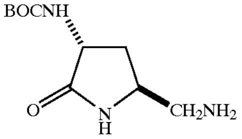
224
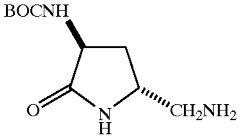
225
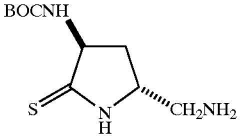
226
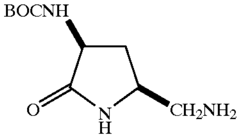
227
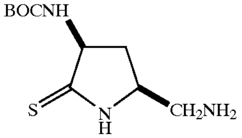
228
TABLE 12-continued
Amines of the type A—$NH_2$
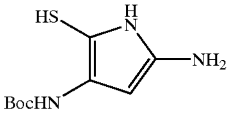
229
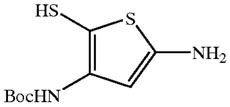
230
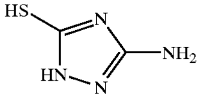
231
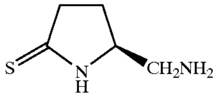
232
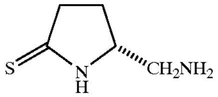
233
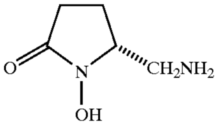
234
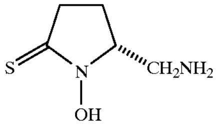
235
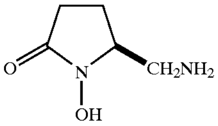
236
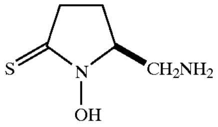
237

TABLE 13
Acids of the type A—$CO_{22}H$
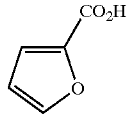
1
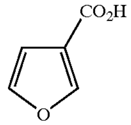
2
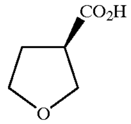
3
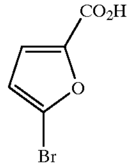
4
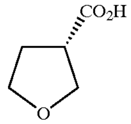
5
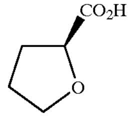
6
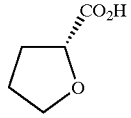
7
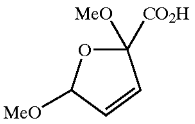
8
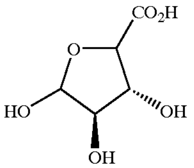
9
TABLE 13-continued
Acids of the type A—$CO_{22}H$
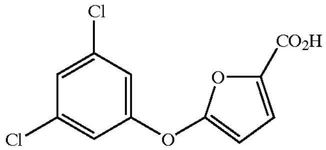
10
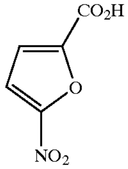
11
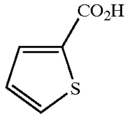
12
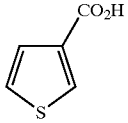
13
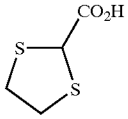
14
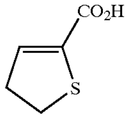
15
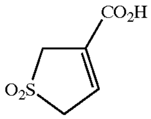
16
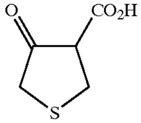
17
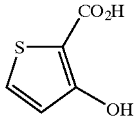
18

TABLE 13-continued
| Acids of the type A—$CO_{22}H$ |
|---|
| 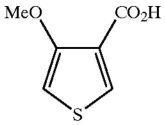 |
| 19 |
| 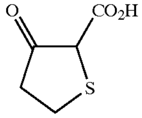 |
| 20 |
| 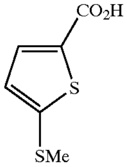 |
| 21 |
| 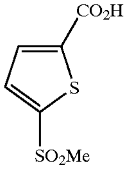 |
| 22 |
| 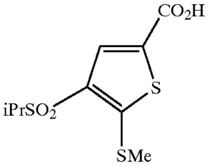 |
| 23 |
| 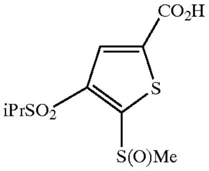 |
| 24 |
| 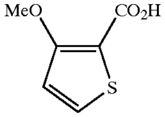 |
| 25 |
| 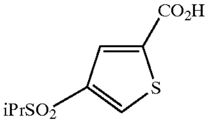 |
| 26 |
| 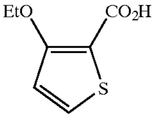 |
TABLE 13-continued
| Acids of the type A—$CO_{22}H$ |
|---|
| 27 |
| 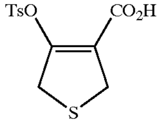 |
| 28 |
| 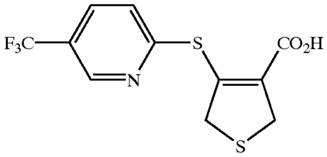 |
| 29 |
| 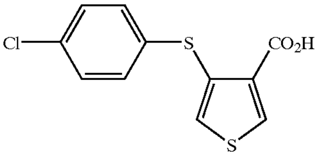 |
| 30 |
| 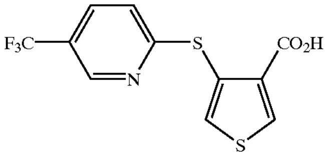 |
| 31 |
| 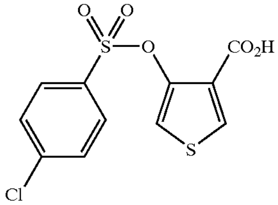 |
| 32 |
| 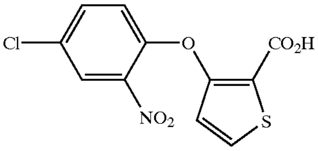 |
| 33 |
| 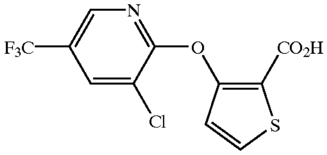 |
| 34 |
| 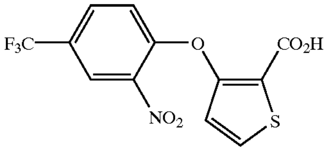 |
| 35 |

TABLE 13-continued
| Acids of the type A—$CO_{22}$H |
|---|
| 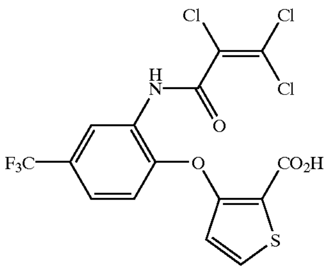 |
| 36 |
| 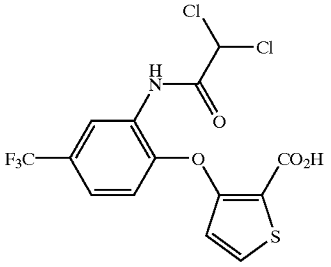 |
| 37 |
| 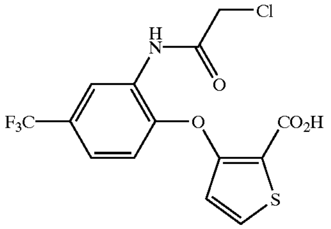 |
| 38 |
| 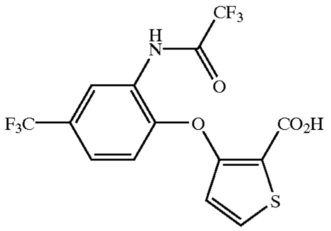 |
| 39 |
| 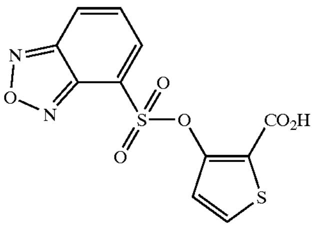 |
| 40 |
TABLE 13-continued
| Acids of the type A—$CO_{22}$H |
|---|
| 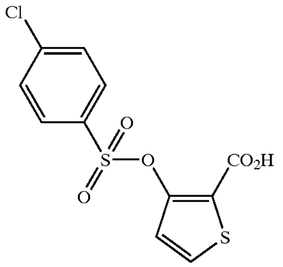 |
| 41 |
| 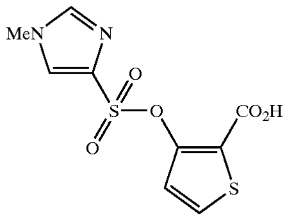 |
| 42 |
| 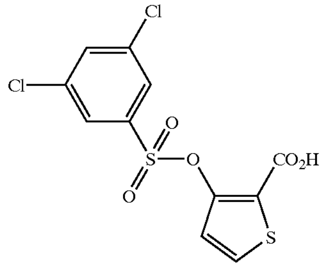 |
| 43 |
| 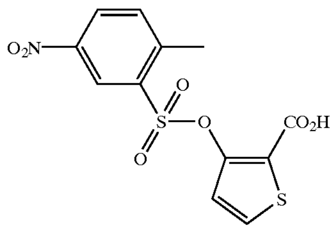 |
| 44 |
| 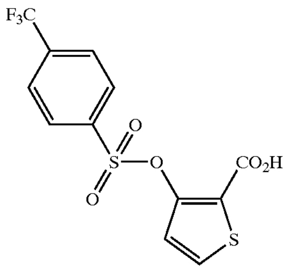 |
| 45 |
| 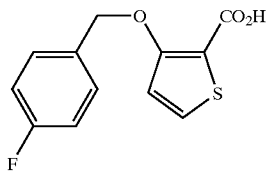 |

TABLE 13-continued
| Acids of the type A—$CO_{22}H$ |
| --- |
| 46 |
| 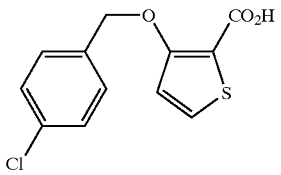 |
| 47 |
| 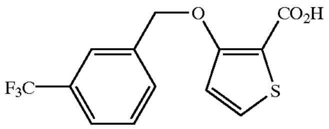 |
| 48 |
| 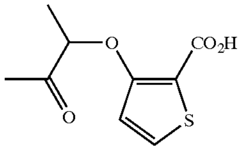 |
| 49 |
| 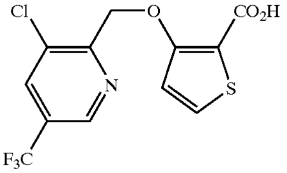 |
| 50 |
| 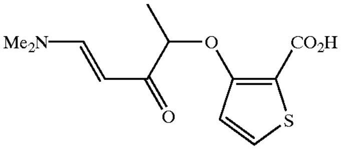 |
| 51 |
| 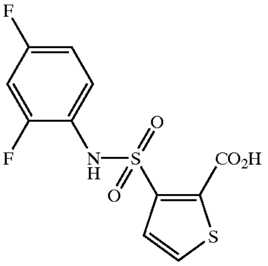 |
| 52 |
| 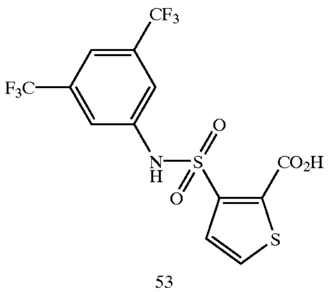 |
| 53 |
TABLE 13-continued
| Acids of the type A—$CO_{22}H$ |
| --- |
| 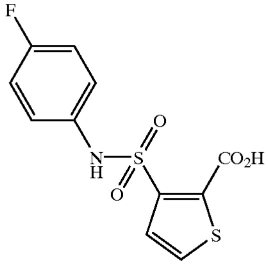 |
| 54 |
| 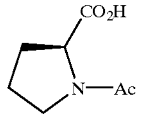 |
| 55 |
| 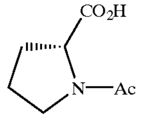 |
| 56 |
| 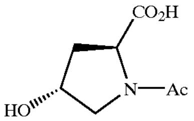 |
| 57 |
| 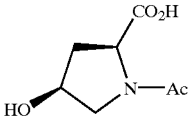 |
| 58 |
| 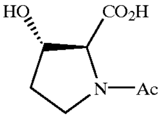 |
| 59 |
| 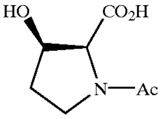 |
| 60 |
| 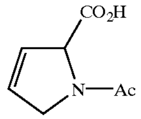 |
| 61 |
| 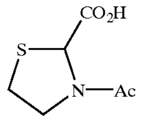 |
| 62 |

TABLE 13-continued
| Acids of the type A—$CO_{22}H$ |
| --- |
| 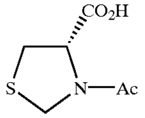 63 |
| 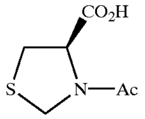 64 |
| 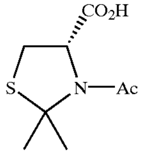 65 |
| 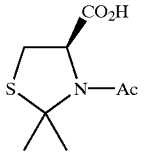 66 |
| 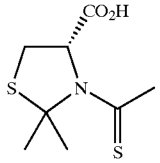 67 |
| 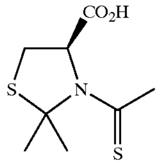 68 |
| 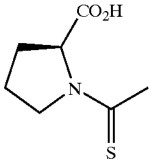 69 |
| 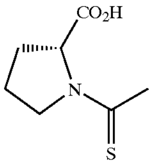 70 |
| 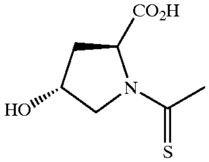 71 |
| 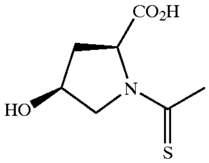 72 |
| 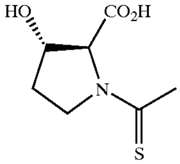 73 |
| 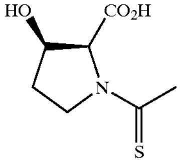 74 |
| 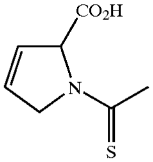 75 |
| 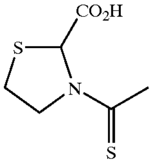 76 |
| 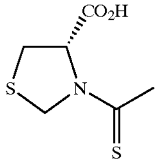 77 |
| 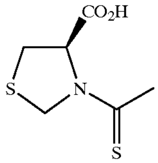 78 |

TABLE 13-continued
Acids of the type A—$CO_{22}$H
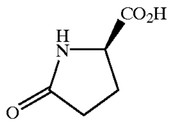
79
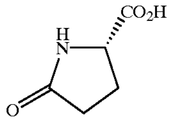
80
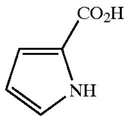
81
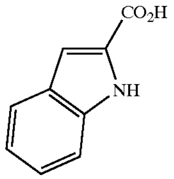
82
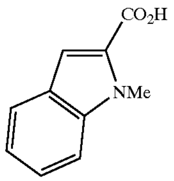
83
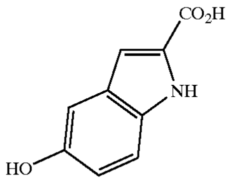
84
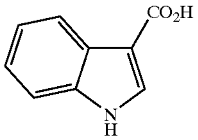
85
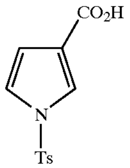
86
TABLE 13-continued
Acids of the type A—$CO_{22}$H
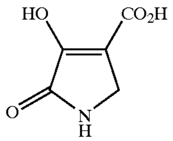
87
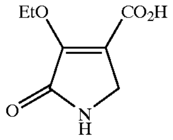
88
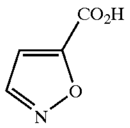
89
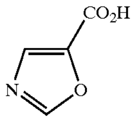
90
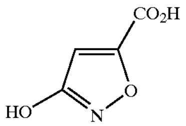
91
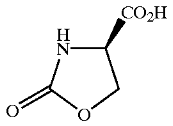
92
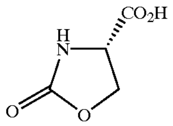
93
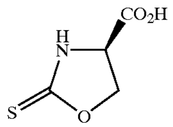
94
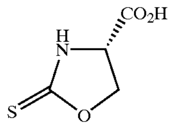
95

TABLE 13-continued
| Acids of the type A—$CO_{22}H$ |
|---|
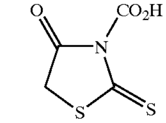
96
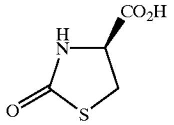
97
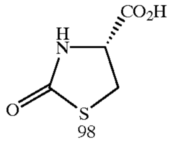
98
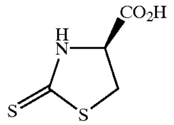
99
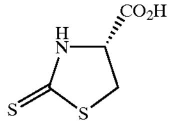
100
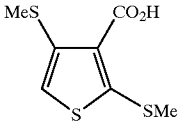
101
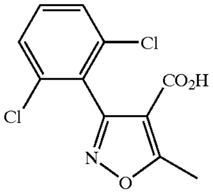
102
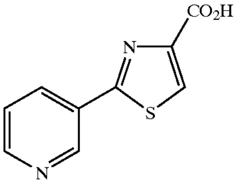
103
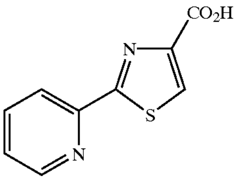
104
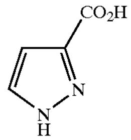
105
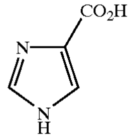
106
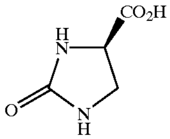
107
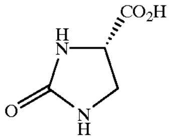
108
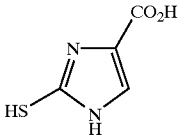
109
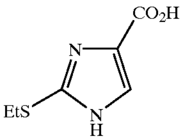
110
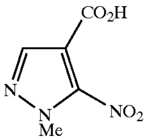
111
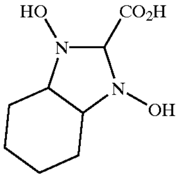
112

TABLE 13-continued
| Acids of the type A—$CO_{22}H$ |
|---|
| 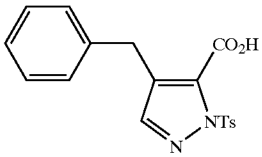 113 |
| 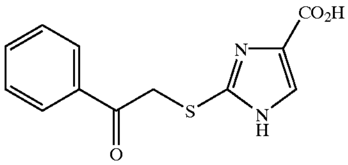 114 |
| 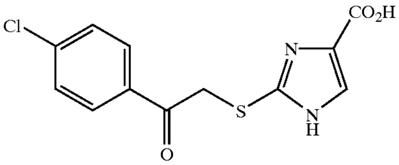 115 |
| 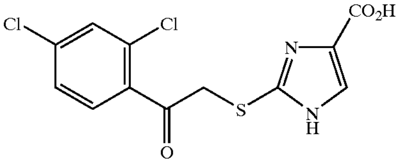 116 |
| 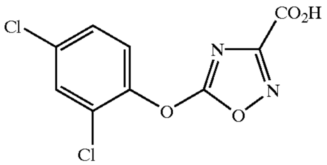 117 |
| 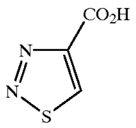 118 |
| 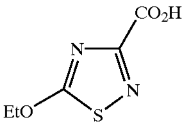 119 |
| 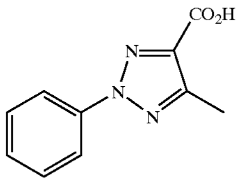 120 |
TABLE 13-continued
| Acids of the type A—$CO_{22}H$ |
|---|
| 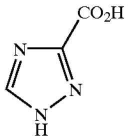 121 |
| 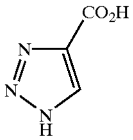 122 |
| 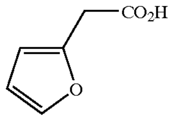 123 |
| 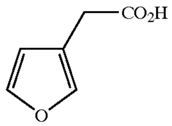 124 |
| 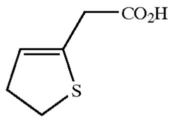 125 |
| 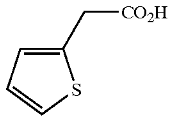 126 |
| 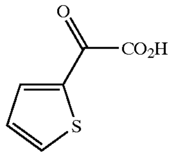 127 |
| 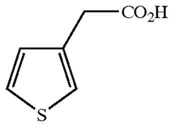 128 |
| 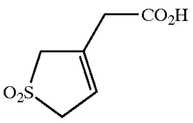 129 |

TABLE 13-continued
| Acids of the type A—$CO_{22}H$ |
|---|
| 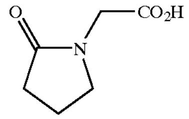 130 |
| 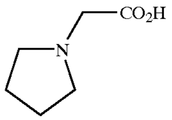 131 |
| 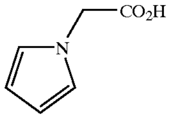 132 |
| 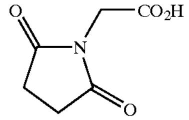 133 |
| 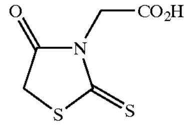 134 |
| 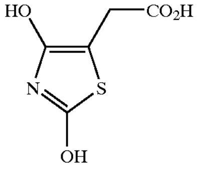 135 |
| 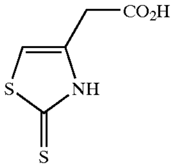 136 |
| 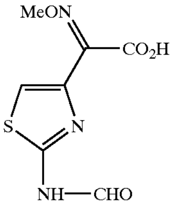 137 |
TABLE 13-continued
| Acids of the type A—$CO_{22}H$ |
|---|
| 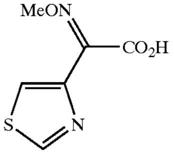 138 |
| 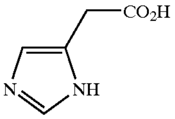 139 |
| 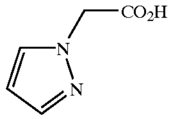 140 |
| 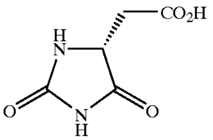 141 |
| 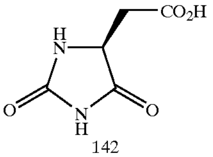 142 |
| 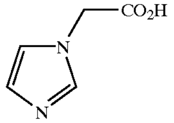 143 |
| 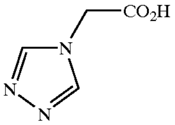 144 |
| 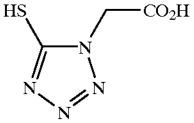 145 |
| 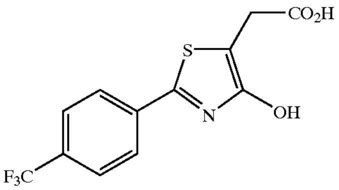 146 |

TABLE 13-continued
| Acids of the type A—$CO_{22}H$ |
|---|
| 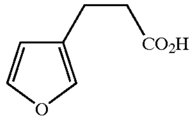 147 |
| 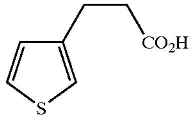 148 |
| 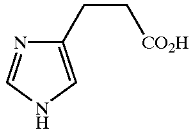 149 |
| 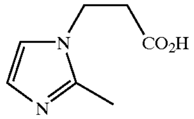 150 |
| 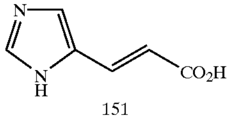 151 |
| 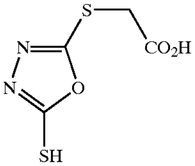 152 |
| 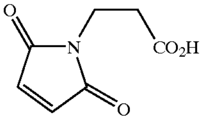 153 |
| 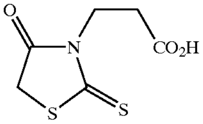 154 |
| 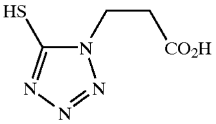 155 |
| 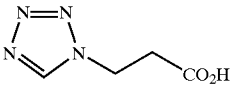 156 |
TABLE 13-continued
| Acids of the type A—$CO_{22}H$ |
|---|
| 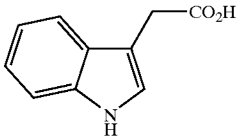 157 |
| 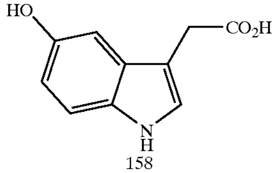 158 |
| 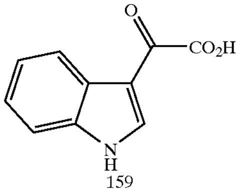 159 |
| 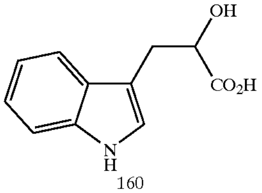 160 |
| 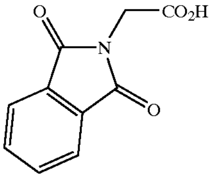 161 |
| 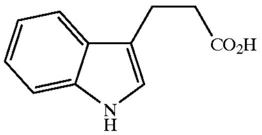 162 |
| 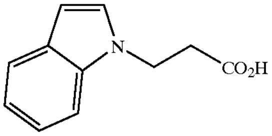 163 |
| 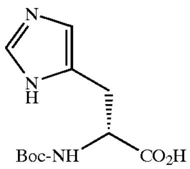 164 |

TABLE 13-continued
| Acids of the type A—$CO_{22}H$ |
| --- |
| 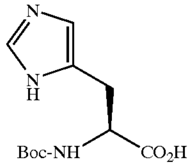 |
| 165 |
| 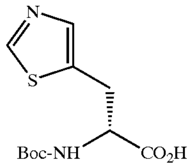 |
| 166 |
| 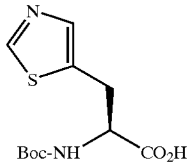 |
| 167 |
| 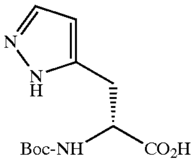 |
| 168 |
| 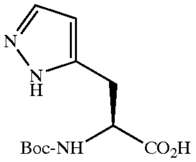 |
| 169 |
| 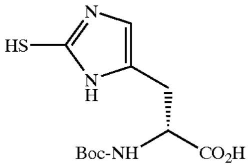 |
| 170 |
| 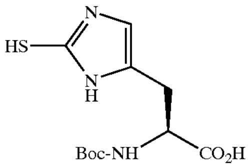 |
| 171 |
| 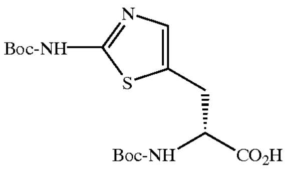 |
TABLE 13-continued
| Acids of the type A—$CO_{22}H$ |
| --- |
| 172 |
| 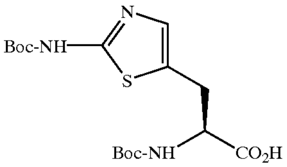 |
| 173 |
| 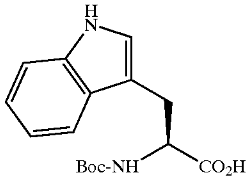 |
| 174 |
| 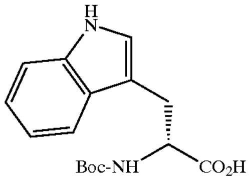 |
| 175 |
| 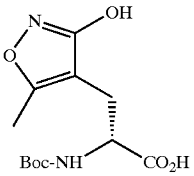 |
| 176 |
| 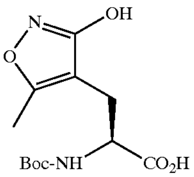 |
| 177 |
| 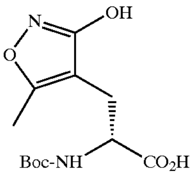 |
| 178 |
| 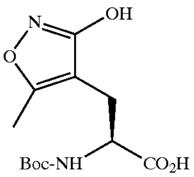 |
| 179 |

TABLE 13-continued
| Acids of the type A—$CO_{22}H$ |
|---|
| 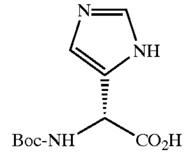 180 |
| 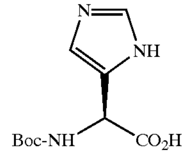 181 |
| 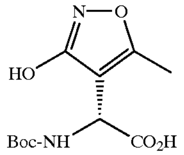 182 |
| 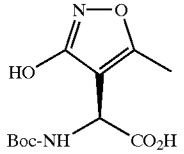 183 |
| 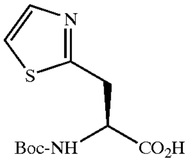 184 |
| 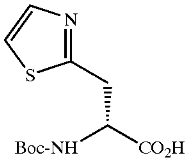 185 |
| 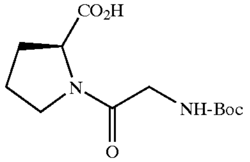 186 |
| 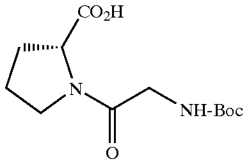 187 |
TABLE 13-continued
| Acids of the type A—$CO_{22}H$ |
|---|
| 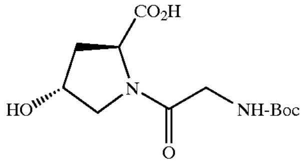 188 |
| 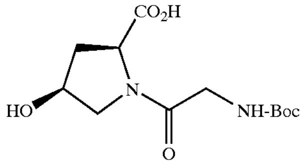 189 |
| 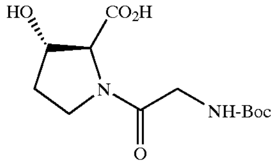 190 |
| 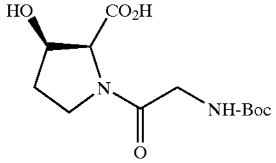 191 |
| 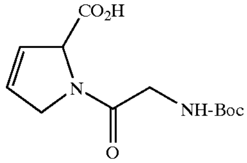 192 |
| 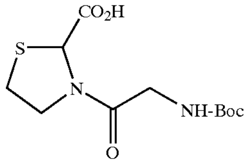 193 |
| 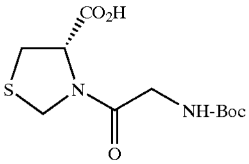 194 |
| 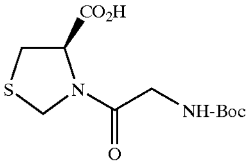 195 |

TABLE 13-continued
| Acids of the type A—$CO_{22}H$ |
|---|
| 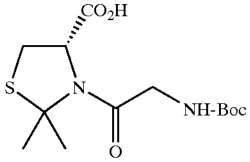 |
| 196 |
| 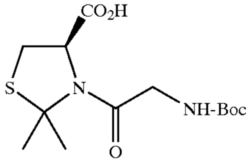 |
| 197 |
| 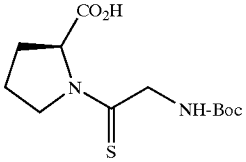 |
| 198 |
| 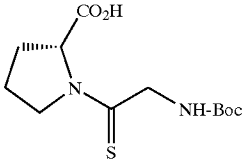 |
| 199 |
| 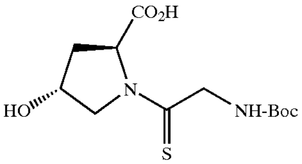 |
| 200 |
| 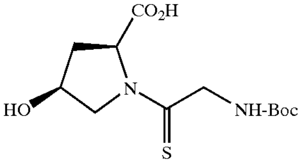 |
| 201 |
| 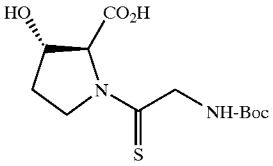 |
| 202 |
| 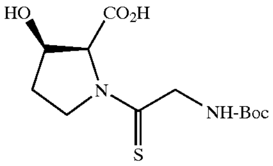 |
TABLE 13-continued
| Acids of the type A—$CO_{22}H$ |
|---|
| 203 |
| 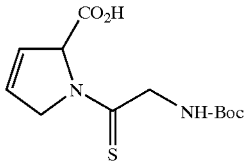 |
| 204 |
| 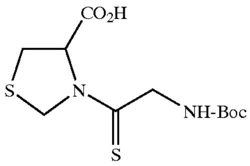 |
| 205 |
| 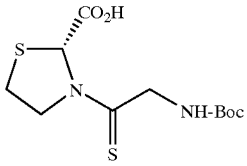 |
| 206 |
| 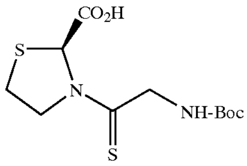 |
| 207 |
| 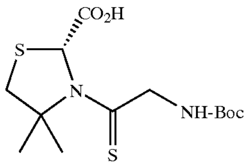 |
| 208 |
| 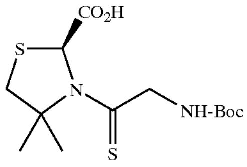 |
| 209 |
| 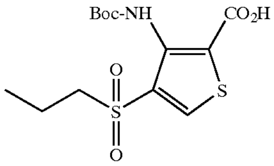 |
| 210 |

TABLE 13-continued
| Acids of the type A—$CO_{22}H$ |
|---|
| 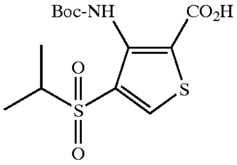 211 |
| 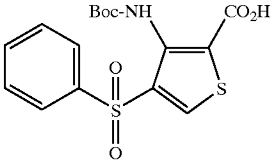 212 |
| 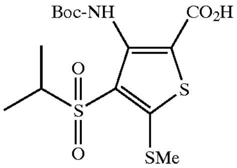 213 |
| 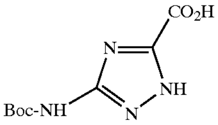 214 |
| 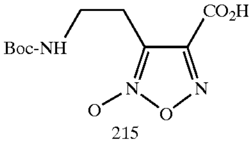 215 |
| 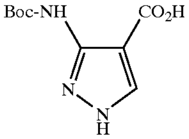 216 |
| 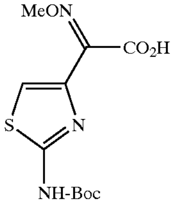 217 |
| 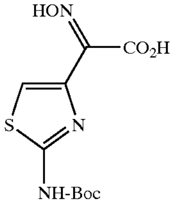 218 |
TABLE 13-continued
| Acids of the type A—$CO_{22}H$ |
|---|
| 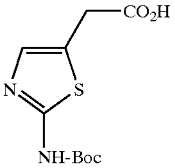 219 |
| 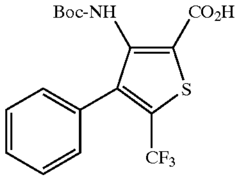 220 |
| 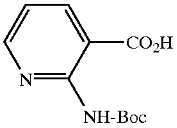 221 |
| 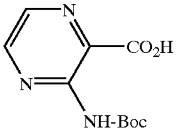 222 |
| 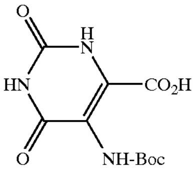 223 |
| 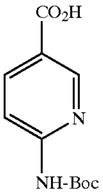 224 |
| 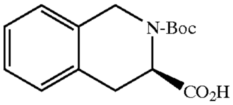 225 |
| 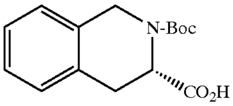 226 |

TABLE 13-continued
Acids of the type A—$CO_{22}$H
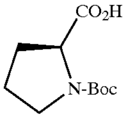
227
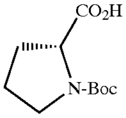
228
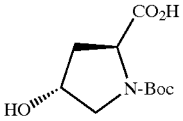
229
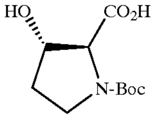
230
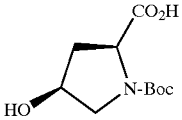
231
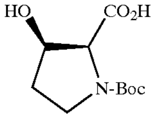
232
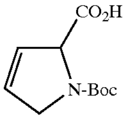
233
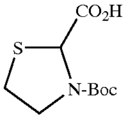
234
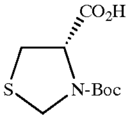
235
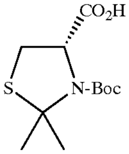
236
TABLE 13-continued
Acids of the type A—$CO_{22}$H
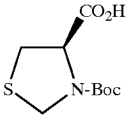
237
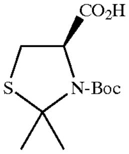
238
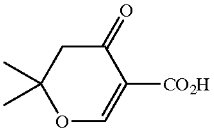
239
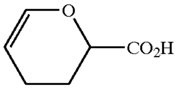
240
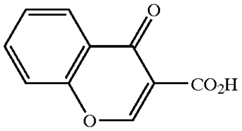
241
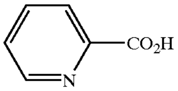
242
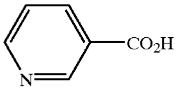
243
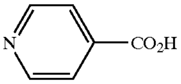
244
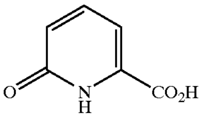
245
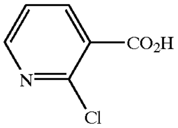
246

TABLE 13-continued
Acids of the type A—$CO_{22}H$
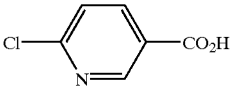
247
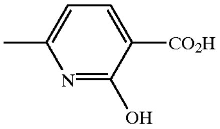
248
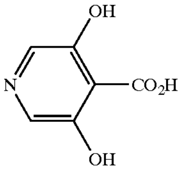
249
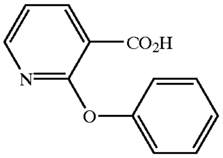
250
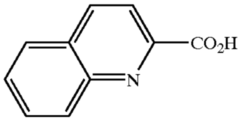
251
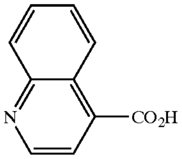
252
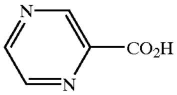
253
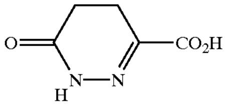
254
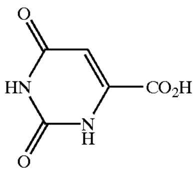
255
TABLE 13-continued
Acids of the type A—$CO_{22}H$
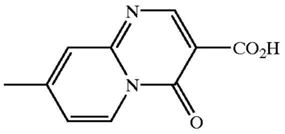
256
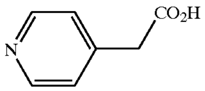
257
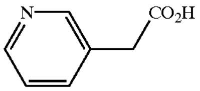
258
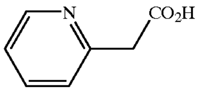
259
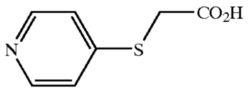
260
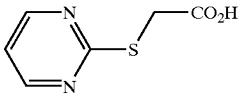
261
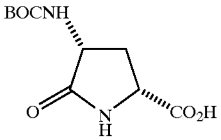
262
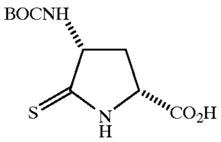
263
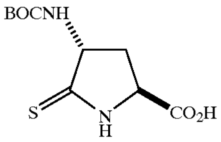
264
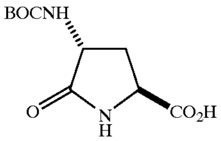
265

TABLE 13-continued
| Acids of the type A—$CO_{22}H$ |
|---|
| 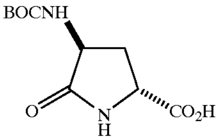 266 |
| 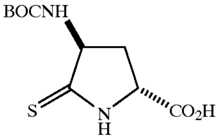 267 |
| 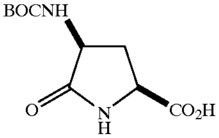 268 |
| 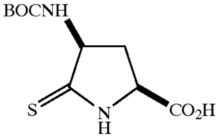 269 |
| 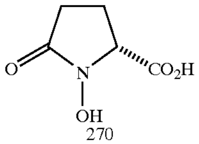 270 |
| 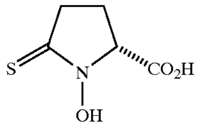 271 |
| 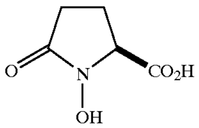 272 |
| 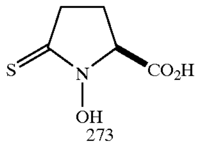 273 |
| 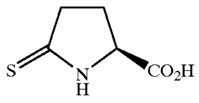 274 |
| 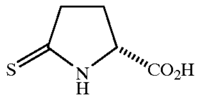 275 |
TABLE 14
| Aldehydes of the type A—CHO |
|---|
| 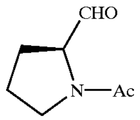 1 |
| 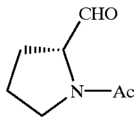 2 |
| 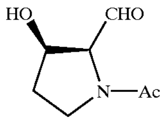 3 |
| 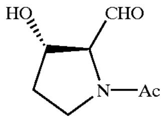 4 |
| 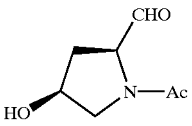 5 |
| 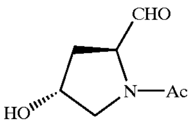 6 |
| 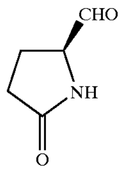 7 |
| 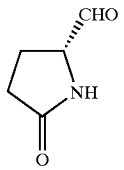 8 |

TABLE 14-continued
| Aldehydes of the type A—CHO |
| --- |
| 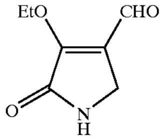<br>9 |
| 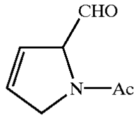<br>10 |
| 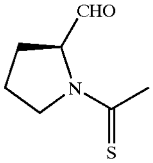<br>11 |
| 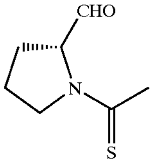<br>12 |
| 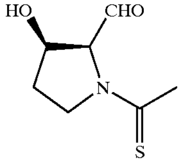<br>13 |
| 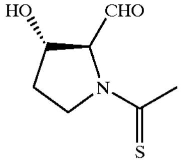<br>14 |
| 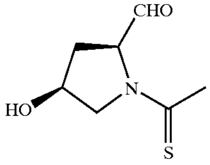<br>15 |
| 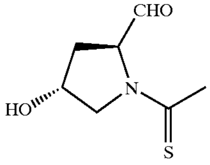<br>16 |
TABLE 14-continued
| Aldehydes of the type A—CHO |
| --- |
| 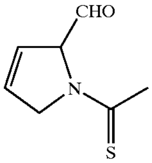<br>17 |
| 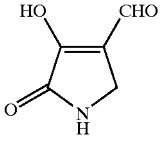<br>18 |
| 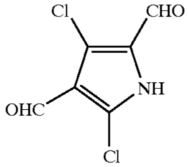<br>19 |
| 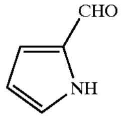<br>20 |
| 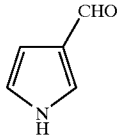<br>21 |
| 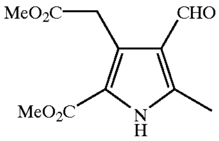<br>22 |
| 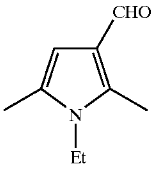<br>23 |
| 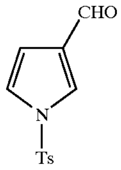<br>24 |

TABLE 14-continued
Aldehydes of the type A—CHO
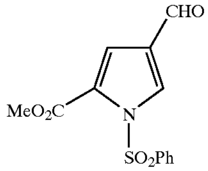
25
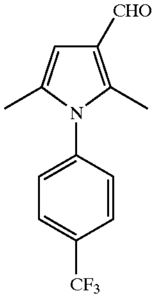
26
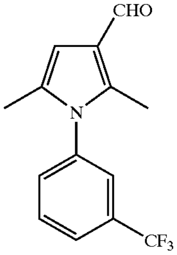
27
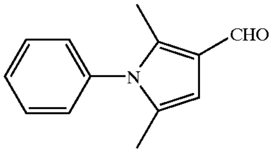
28
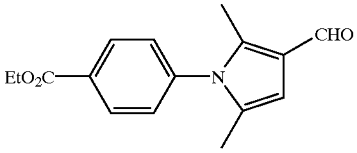
29
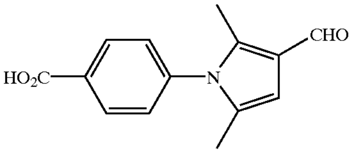
30
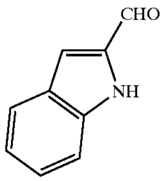
TABLE 14-continued
Aldehydes of the type A—CHO
31
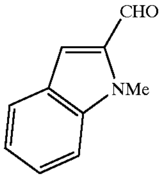
32
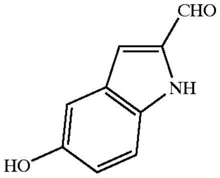
33
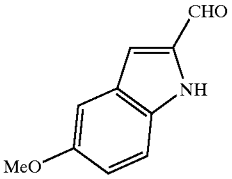
34
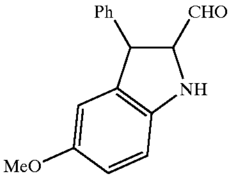
35
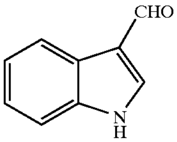
36
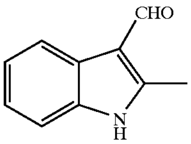
37
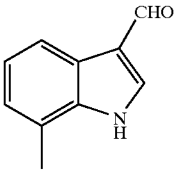
38

TABLE 14-continued
| Aldehydes of the type A—CHO |
| --- |
| 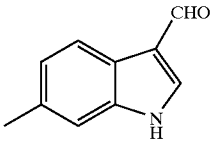 39 |
| 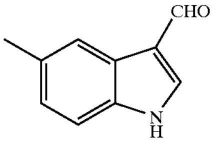 40 |
| 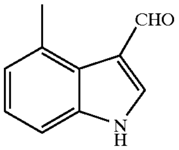 41 |
| 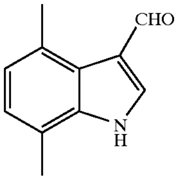 42 |
| 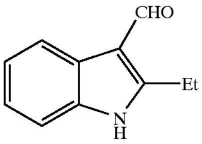 43 |
| 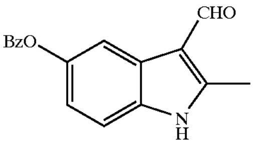 44 |
| 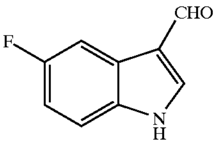 45 |
| 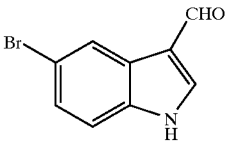 46 |
TABLE 14-continued
| Aldehydes of the type A—CHO |
| --- |
| 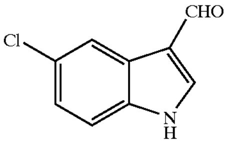 47 |
| 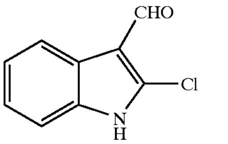 48 |
| 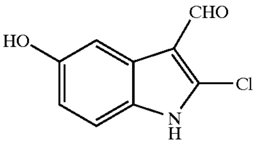 49 |
| 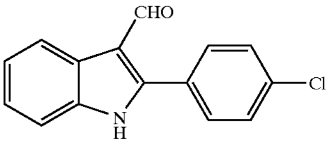 50 |
| 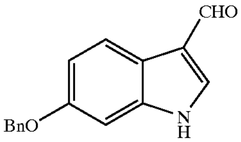 51 |
| 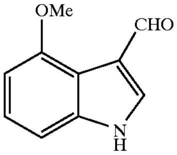 52 |
| 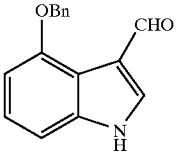 53 |
| 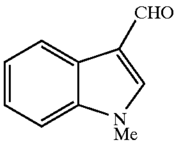 54 |

TABLE 14-continued
| Aldehydes of the type A—CHO |
|---|
| 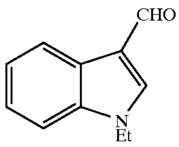 55 |
| 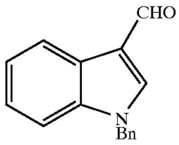 56 |
| 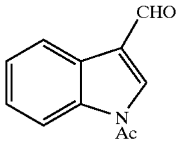 57 |
| 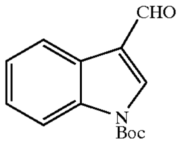 58 |
| 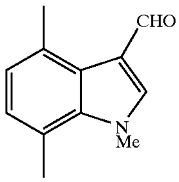 59 |
| 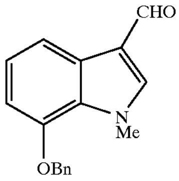 60 |
| 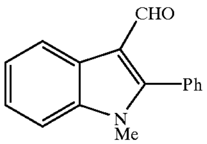 61 |
| 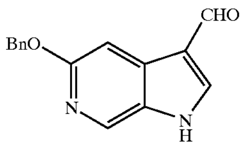 62 |
TABLE 14-continued
| Aldehydes of the type A—CHO |
|---|
| 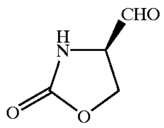 63 |
| 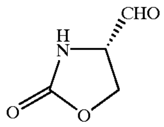 64 |
| 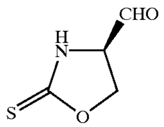 65 |
| 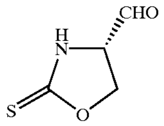 66 |
| 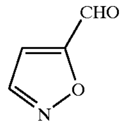 67 |
| 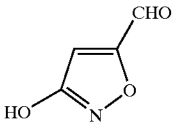 68 |
| 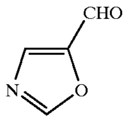 69 |
| 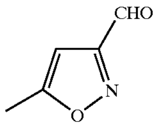 70 |
| 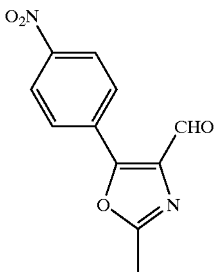 71 |

TABLE 14-continued
| Aldehydes of the type A—CHO |
| --- |
| 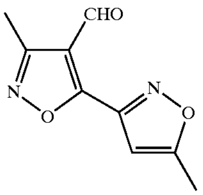 |
| 72 |
| 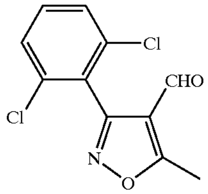 |
| 73 |
| 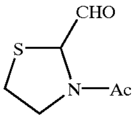 |
| 74 |
| 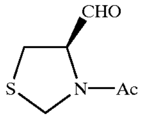 |
| 75 |
| 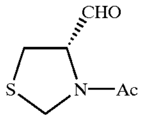 |
| 76 |
| 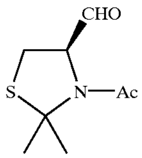 |
| 77 |
| 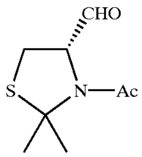 |
| 78 |
| 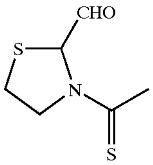 |
| 79 |
TABLE 14-continued
| Aldehydes of the type A—CHO |
| --- |
| 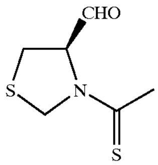 |
| 80 |
| 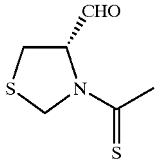 |
| 81 |
| 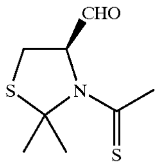 |
| 82 |
| 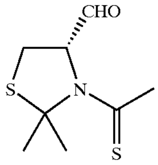 |
| 83 |
| 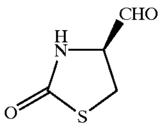 |
| 84 |
| 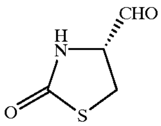 |
| 85 |
| 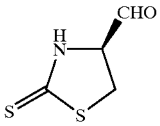 |
| 86 |
| 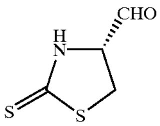 |
| 87 |
| 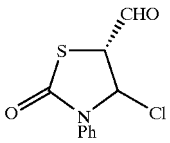 |

TABLE 14-continued
| Aldehydes of the type A—CHO |
|---|
| 88 |
| 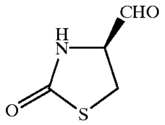 |
| 89 |
| 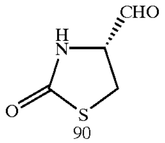 |
| 90 |
| 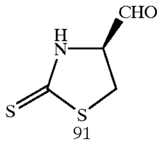 |
| 91 |
| 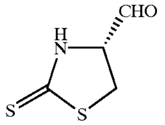 |
| 92 |
| 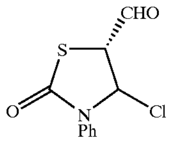 |
| 93 |
| 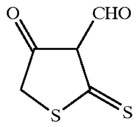 |
| 94 |
| 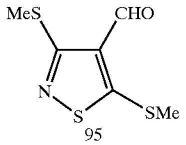 |
| 95 |
| 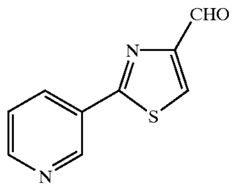 |
| 96 |
| 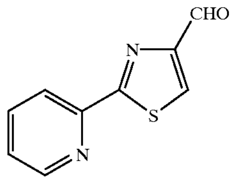 |
TABLE 14-continued
| Aldehydes of the type A—CHO |
|---|
| 97 |
| 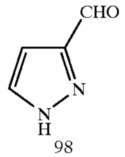 |
| 98 |
| 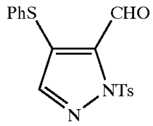 |
| 99 |
| 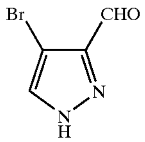 |
| 100 |
| 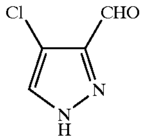 |
| 101 |
| 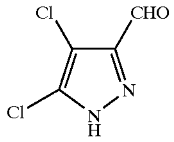 |
| 102 |
| 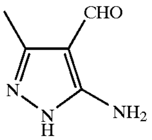 |
| 103 |
| 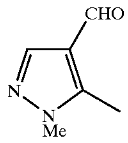 |
| 104 |
| 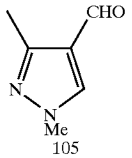 |
| 105 |
| 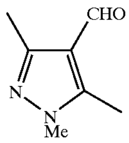 |
| 106 |

TABLE 14-continued
| Aldehydes of the type A—CHO |
|---|
| 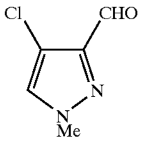 107 |
| 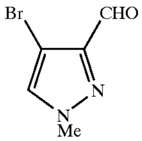 108 |
| 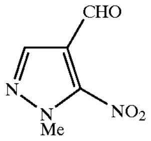 109 |
| 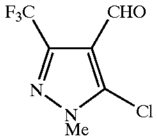 110 |
| 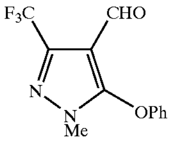 111 |
| 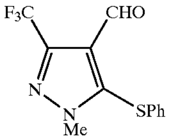 112 |
| 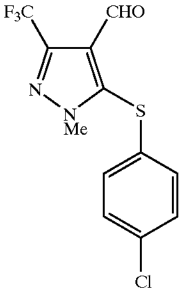 113 |
TABLE 14-continued
| Aldehydes of the type A—CHO |
|---|
| 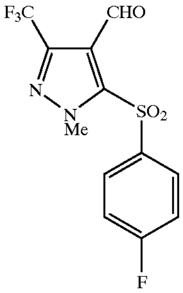 114 |
| 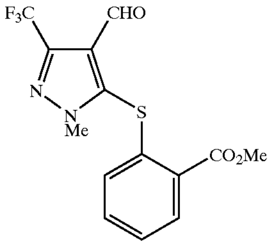 115 |
| 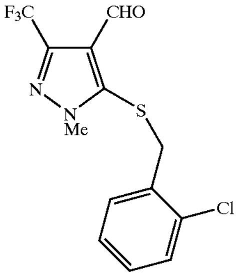 116 |
| 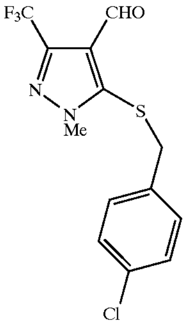 117 |

TABLE 14-continued
Aldehydes of the type A—CHO
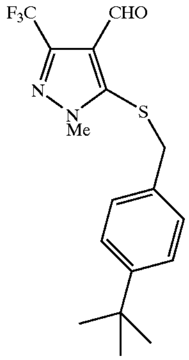
118
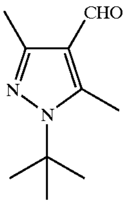
119
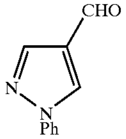
120
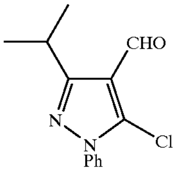
121
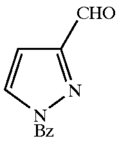
122
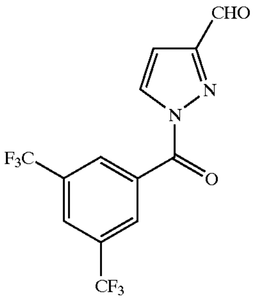
123
TABLE 14-continued
Aldehydes of the type A—CHO
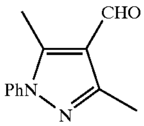
124
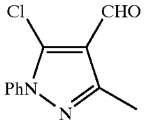
125
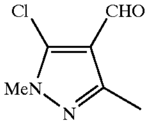
126
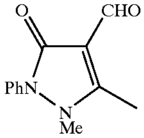
127
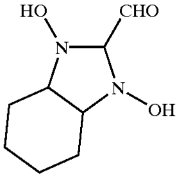
128
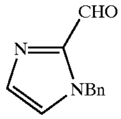
129
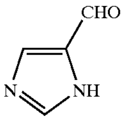
130
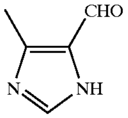
131
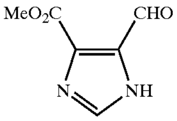
132

TABLE 14-continued
Aldehydes of the type A—CHO
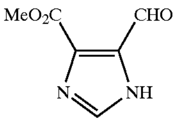
133
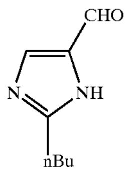
134
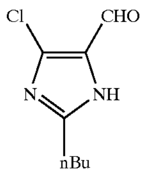
135
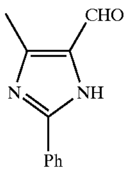
136
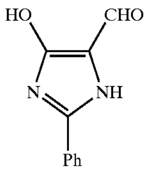
137
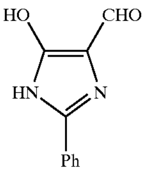
138
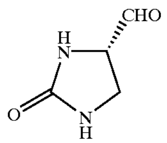
139
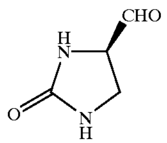
140
TABLE 14-continued
Aldehydes of the type A—CHO
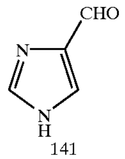
141
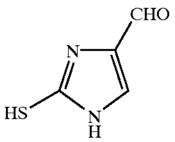
142
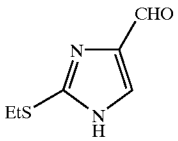
143
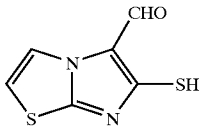
144
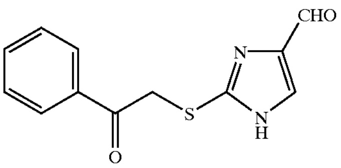
145
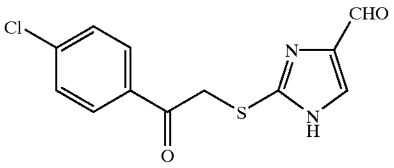
146
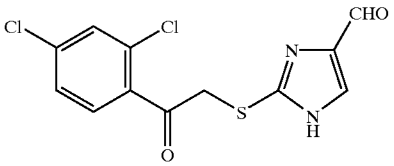
147
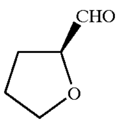
148
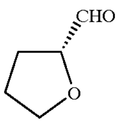
149

TABLE 14-continued
| Aldehydes of the type A—CHO |
|---|
| 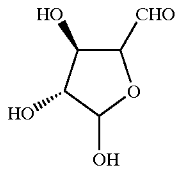 150 |
| 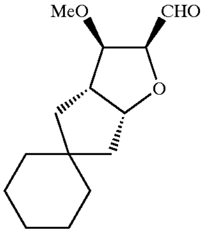 151 |
| 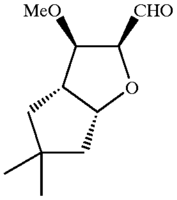 152 |
| 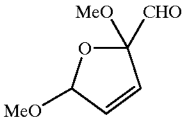 153 |
| 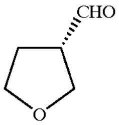 154 |
| 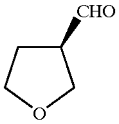 155 |
| 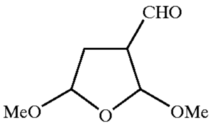 156 |
| 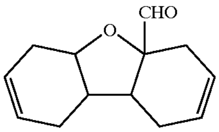 157 |
TABLE 14-continued
| Aldehydes of the type A—CHO |
|---|
| 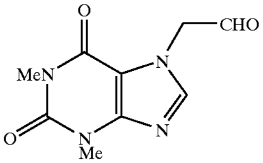 158 |
| 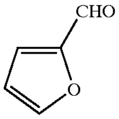 159 |
| 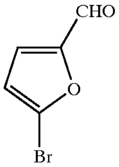 160 |
| 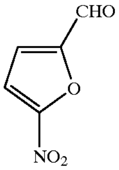 161 |
| 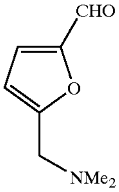 162 |
| 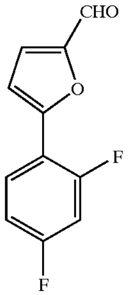 163 |
| 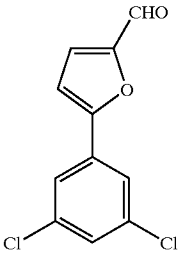 |

TABLE 14-continued
| Aldehydes of the type A—CHO |
|---|
| 164 |
| 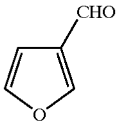 |
| 165 |
| 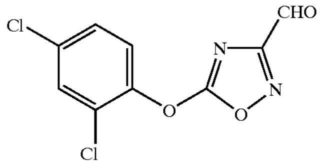 |
| 166 |
| 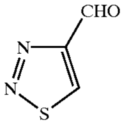 |
| 167 |
| 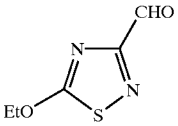 |
| 168 |
| 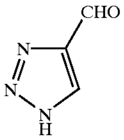 |
| 169 |
| 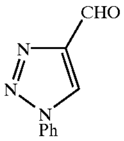 |
| 170 |
| 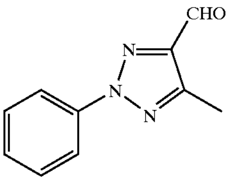 |
| 171 |
| 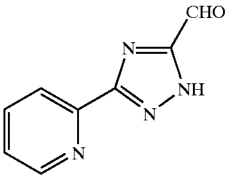 |
| 172 |
TABLE 14-continued
| Aldehydes of the type A—CHO |
|---|
| 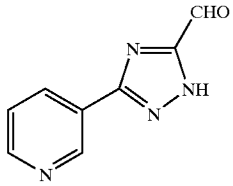 |
| 173 |
| 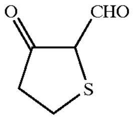 |
| 174 |
| 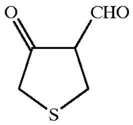 |
| 175 |
| 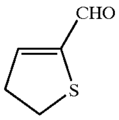 |
| 176 |
| 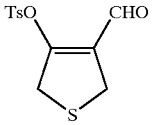 |
| 177 |
| 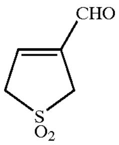 |
| 178 |
| 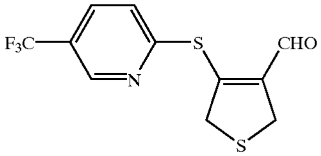 |
| 179 |
| 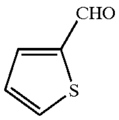 |
| 180 |
| 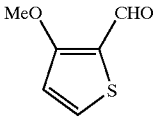 |
| 181 |

TABLE 14-continued
Aldehydes of the type A—CHO
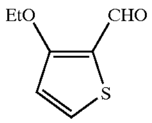
182
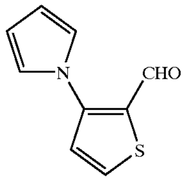
183
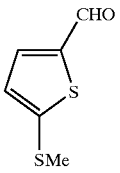
184
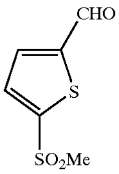
185
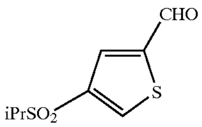
186
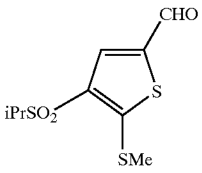
187
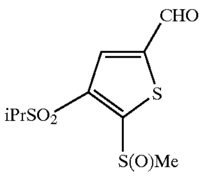
188
TABLE 14-continued
Aldehydes of the type A—CHO
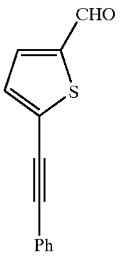
189
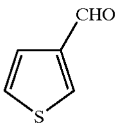
190
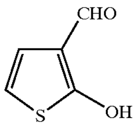
191
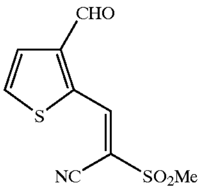
192
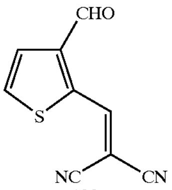
193
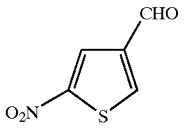
194
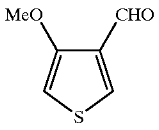
195
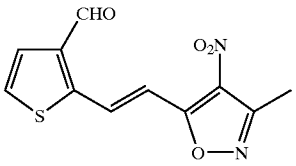
196

TABLE 14-continued
| Aldehydes of the type A—CHO |
|---|
| 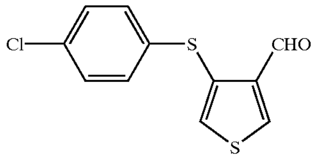 197 |
| 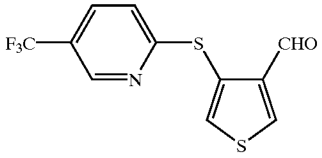 198 |
| 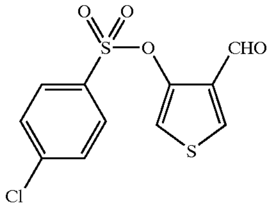 199 |
| 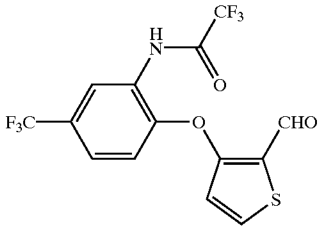 200 |
| 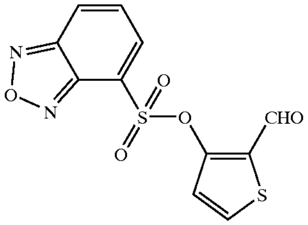 201 |
| 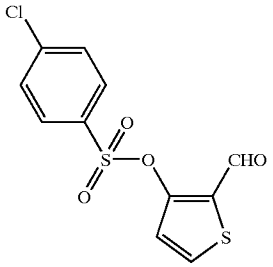 202 |
TABLE 14-continued
| Aldehydes of the type A—CHO |
|---|
| 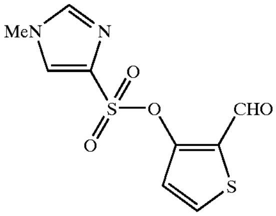 203 |
| 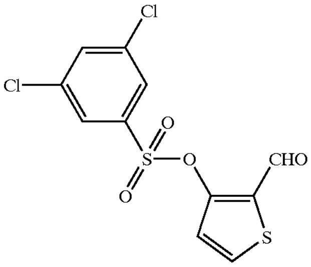 204 |
| 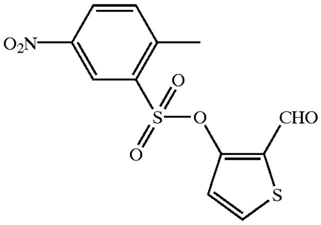 205 |
| 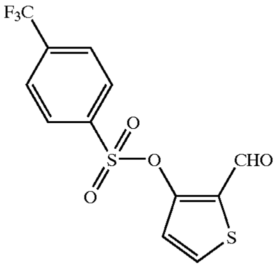 206 |
| 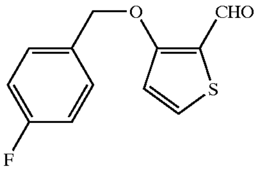 207 |
| 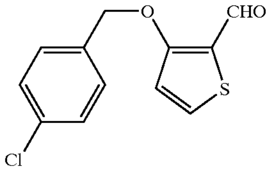 208 |

TABLE 14-continued
| Aldehydes of the type A—CHO |
|---|
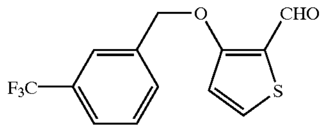
209
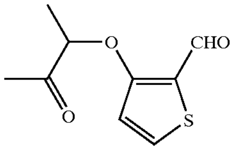
210
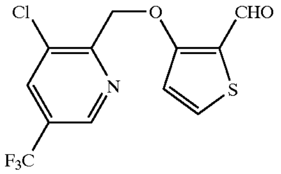
211
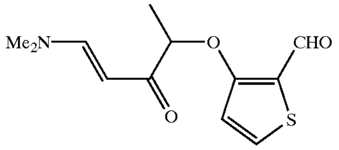
212
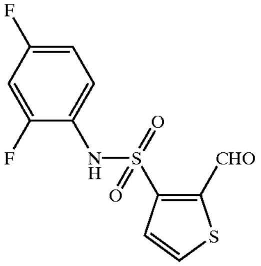
213
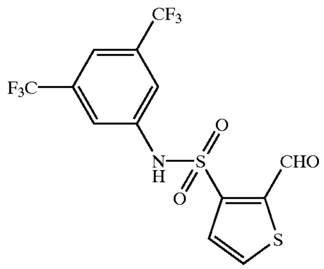
214
TABLE 14-continued
| Aldehydes of the type A—CHO |
|---|
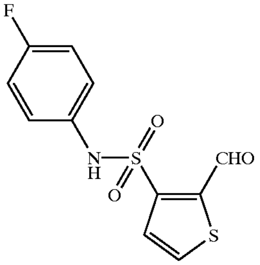
215
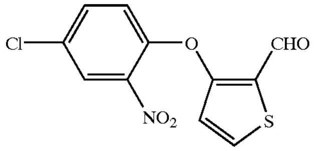
216
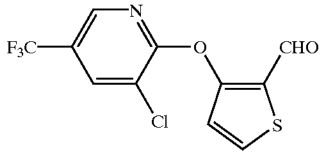
217
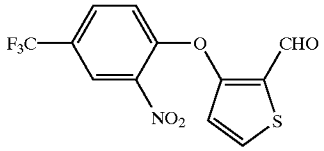
218
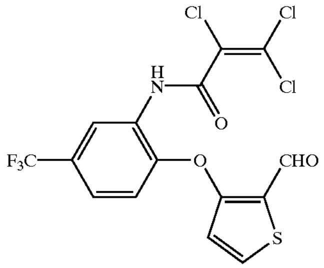
219
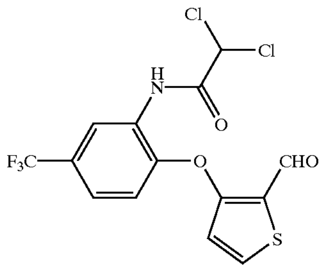
220

TABLE 14-continued
Aldehydes of the type A—CHO
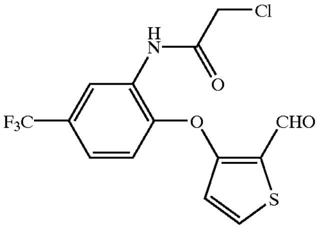
221
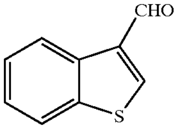
222
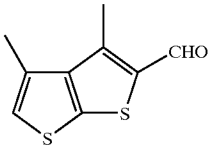
223
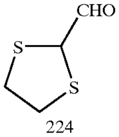
224
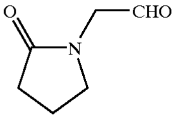
225
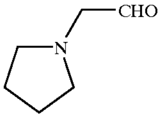
226
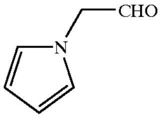
227
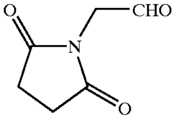
228
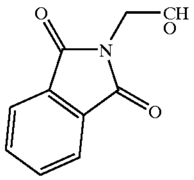
TABLE 14-continued
Aldehydes of the type A—CHO
229
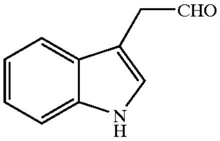
230
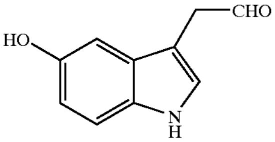
231
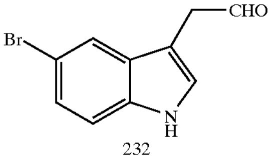
232
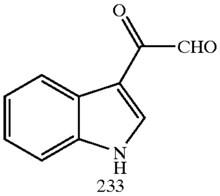
233
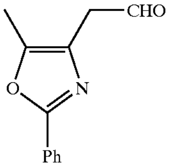
234
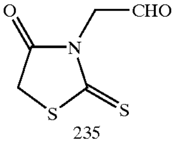
235
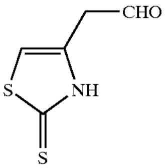
236
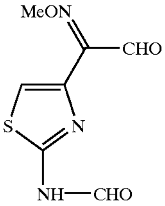
237

TABLE 14-continued
| Aldehydes of the type A—CHO |
|---|
| 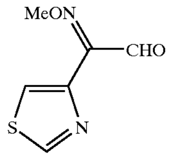 |
| 238 |
| 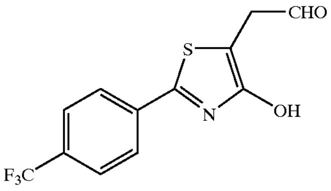 |
| 239 |
| 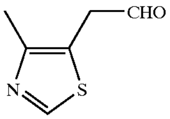 |
| 240 |
| 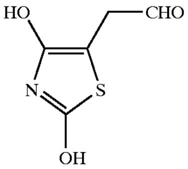 |
| 241 |
| 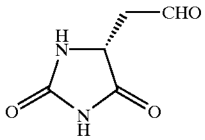 |
| 242 |
| 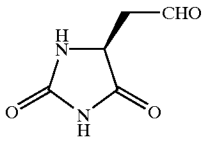 |
| 243 |
| 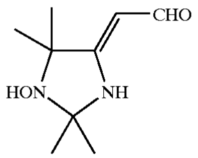 |
| 244 |
| 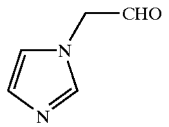 |
| 245 |
TABLE 14-continued
| Aldehydes of the type A—CHO |
|---|
| 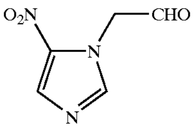 |
| 246 |
| 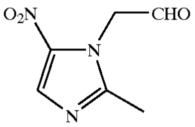 |
| 247 |
| 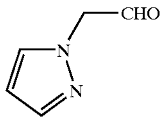 |
| 248 |
| 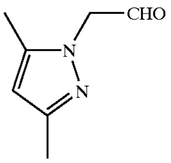 |
| 249 |
| 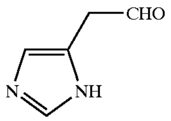 |
| 250 |
| 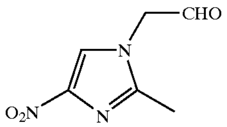 |
| 251 |
| 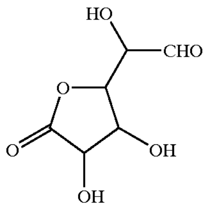 |
| 252 |
| 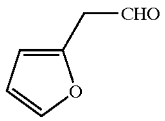 |
| 253 |
| 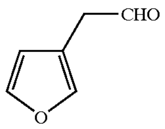 |
| 254 |

TABLE 14-continued
Aldehydes of the type A—CHO
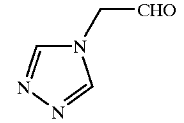
255
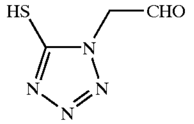
256
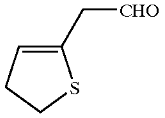
257
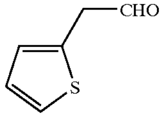
258
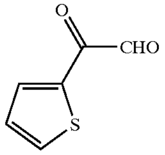
259
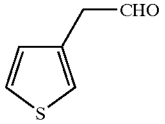
260
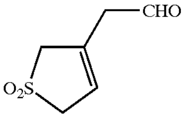
261
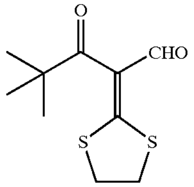
262
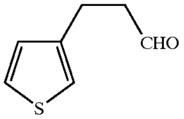
263
TABLE 14-continued
Aldehydes of the type A—CHO
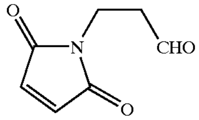
264
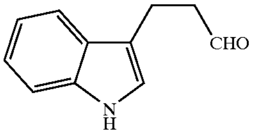
265
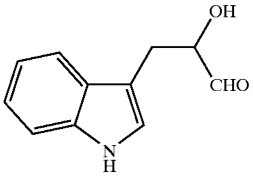
266
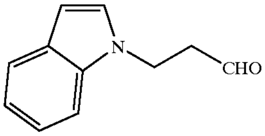
267
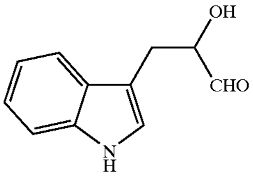
268
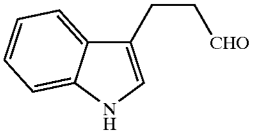
269
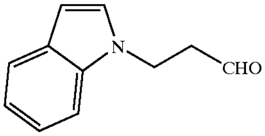
270
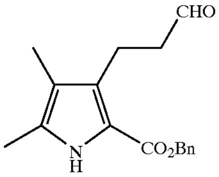
271

TABLE 14-continued
| Aldehydes of the type A—CHO |
|---|
| 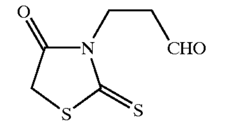 272 |
| 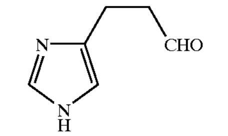 273 |
| 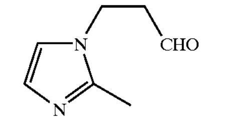 274 |
| 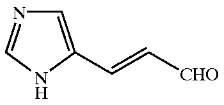 275 |
| 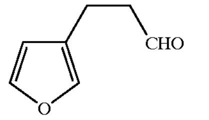 276 |
| 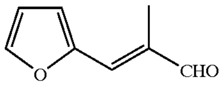 277 |
| 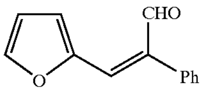 278 |
| 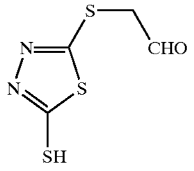 279 |
| 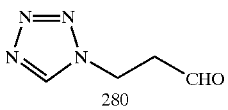 280 |
| 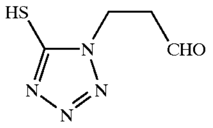 281 |
TABLE 14-continued
| Aldehydes of the type A—CHO |
|---|
| 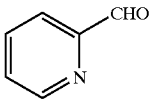 282 |
| 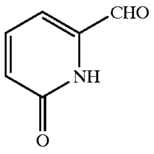 283 |
| 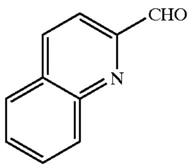 284 |
| 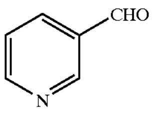 285 |
| 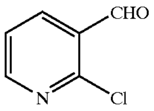 286 |
| 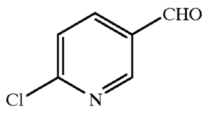 287 |
| 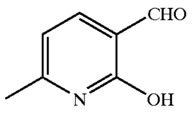 288 |
| 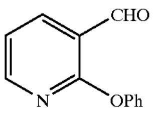 289 |
| 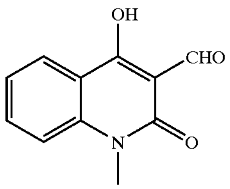 290 |

TABLE 14-continued
Aldehydes of the type A—CHO
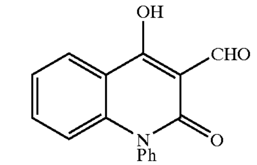
291
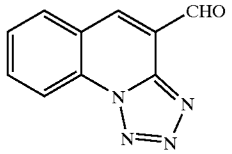
292
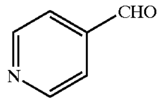
293
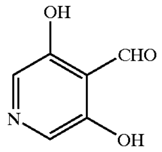
294
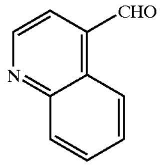
295
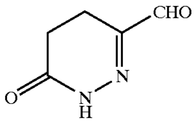
296
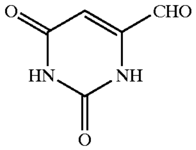
297
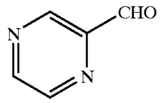
298
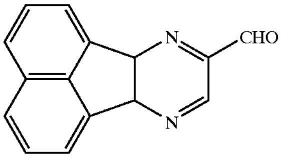
299
TABLE 14-continued
Aldehydes of the type A—CHO
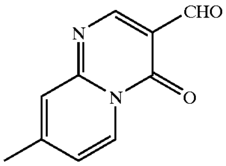
300
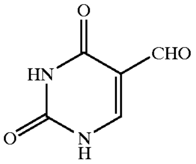
301
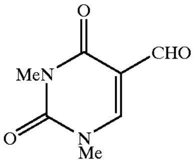
302
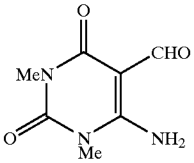
303
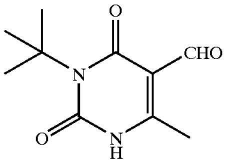
304
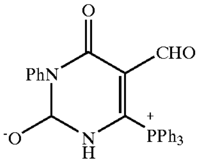
305
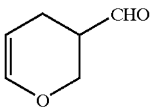
306
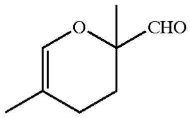
307

TABLE 14-continued
Aldehydes of the type A—CHO
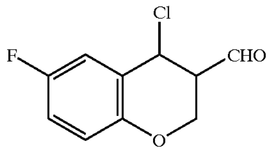
308
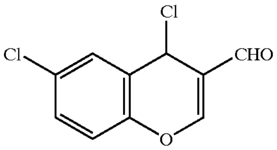
309
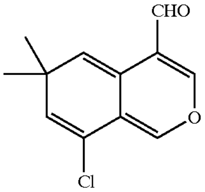
310
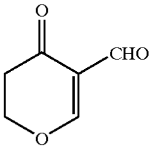
311
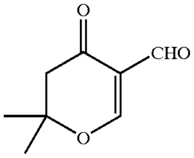
312
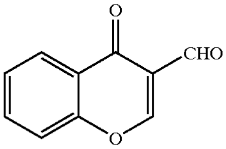
313
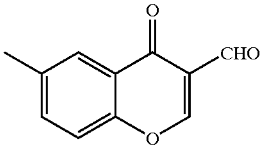
314
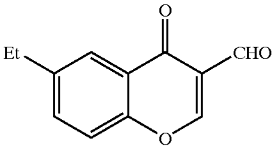
315
TABLE 14-continued
Aldehydes of the type A—CHO
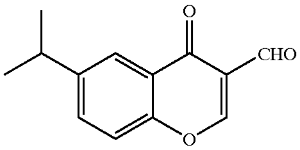
316
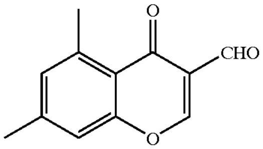
317
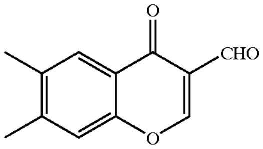
318
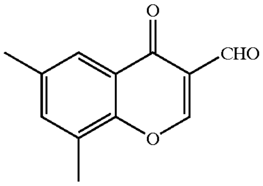
319
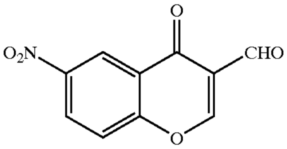
320
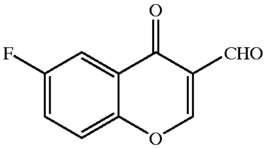
321
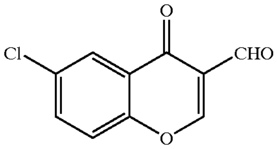
322
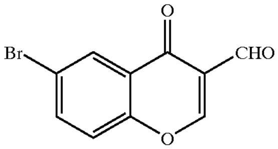
323

TABLE 14-continued
| Aldehydes of the type A—CHO |
|---|
| 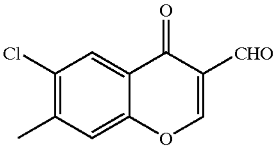 324 |
| 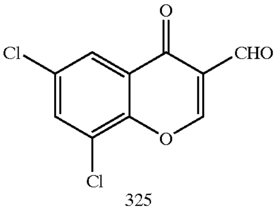 325 |
| 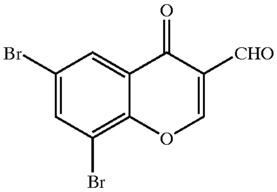 326 |
| 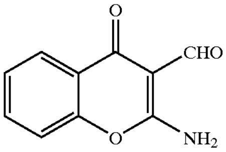 327 |
| 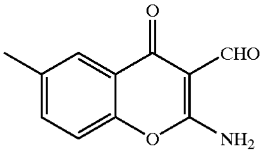 328 |
| 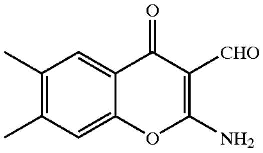 329 |
| 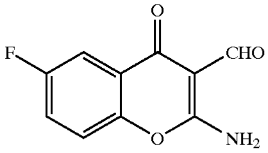 330 |
| 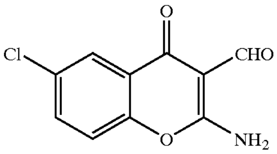 331 |
TABLE 14-continued
| Aldehydes of the type A—CHO |
|---|
| 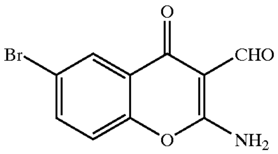 332 |
| 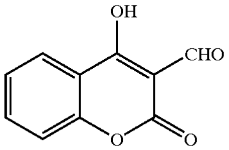 333 |
| 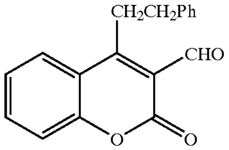 334 |
| 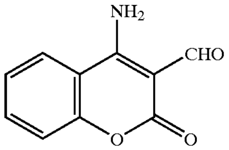 335 |
| 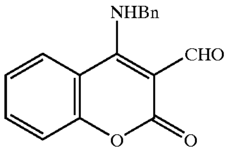 336 |
| 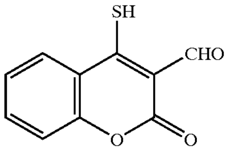 337 |
| 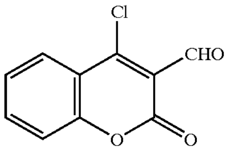 338 |
| 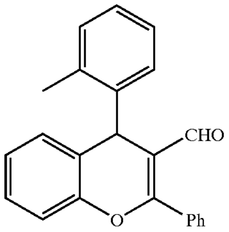 339 |

TABLE 14-continued
Aldehydes of the type A—CHO
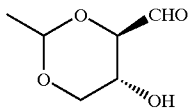
340
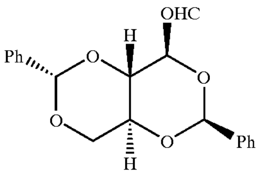
341
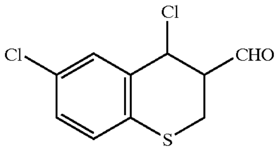
342
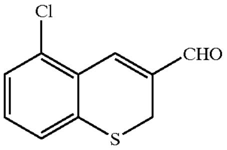
343
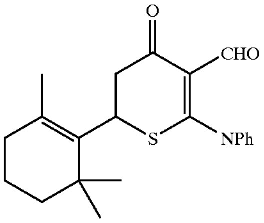
344
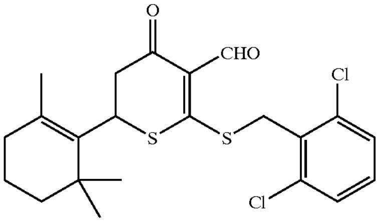
345
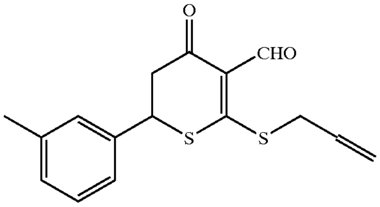
346
TABLE 14-continued
Aldehydes of the type A—CHO
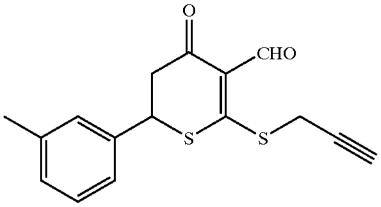
347
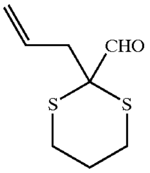
348
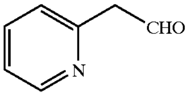
349
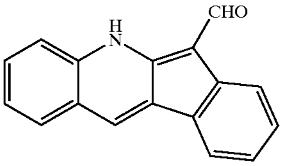
350
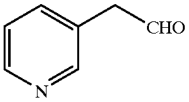
351
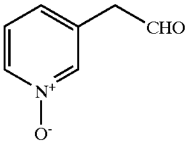
352
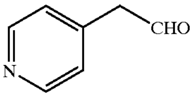
353
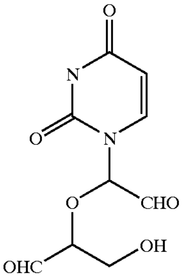
354

TABLE 14-continued
Aldehydes of the type A—CHO
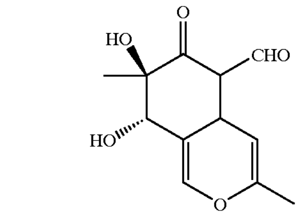
355
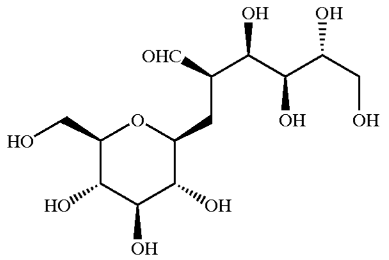
356
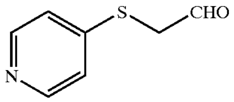
357
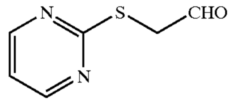
358
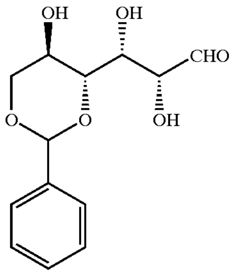
359
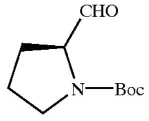
360
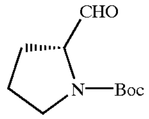
361
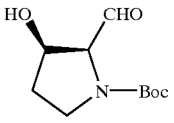
362
TABLE 14-continued
Aldehydes of the type A—CHO
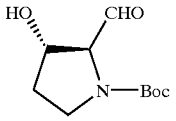
363
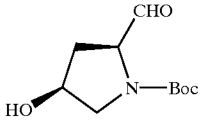
364
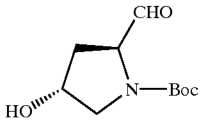
365
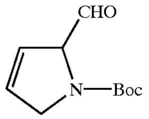
366
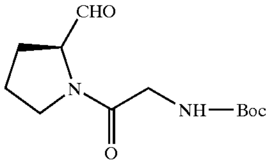
367
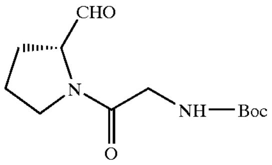
368
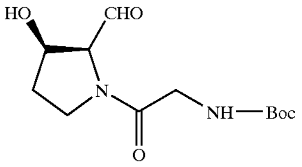
369
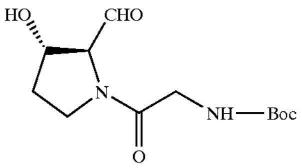
370

TABLE 14-continued
Aldehydes of the type A—CHO
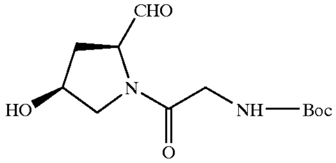
371
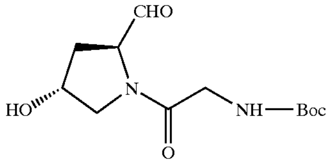
372
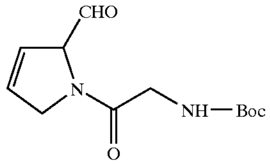
373
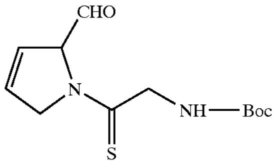
374
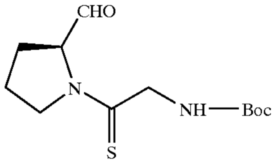
375
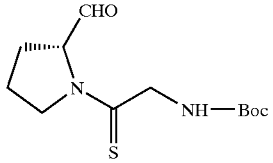
376
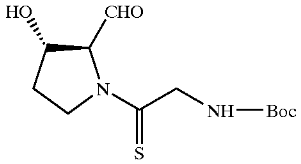
377
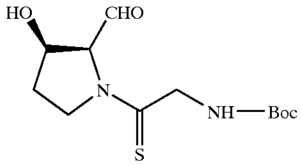
378
TABLE 14-continued
Aldehydes of the type A—CHO
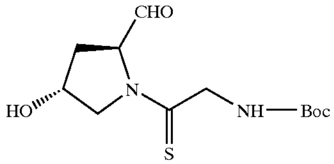
379
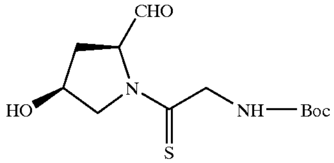
380
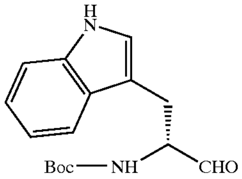
381
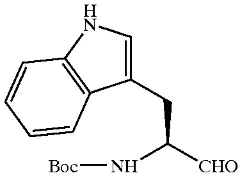
382
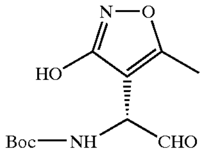
383
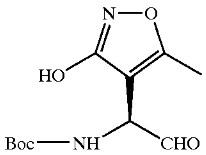
384
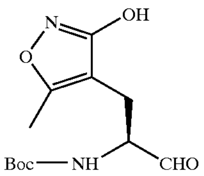
385

TABLE 14-continued
Aldehydes of the type A—CHO
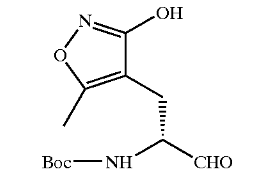
386
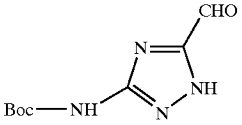
387
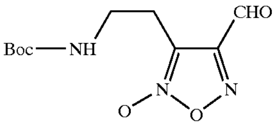
388
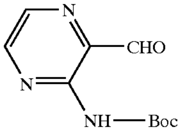
389
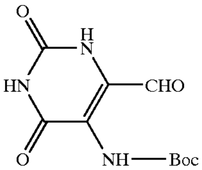
390
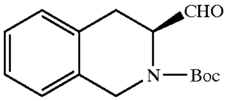
391
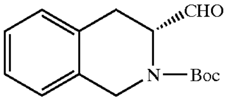
392
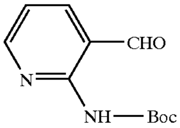
393
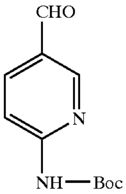
394
TABLE 14-continued
Aldehydes of the type A—CHO
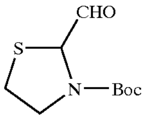
395
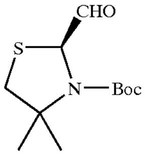
396
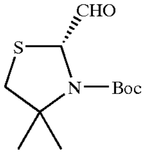
397
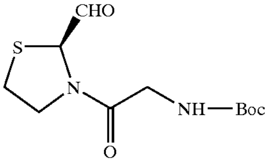
398
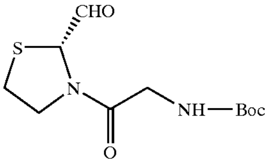
399
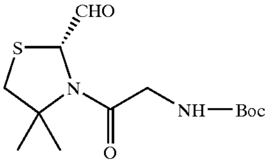
400
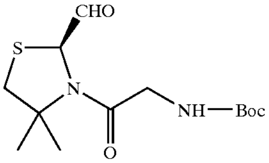
401
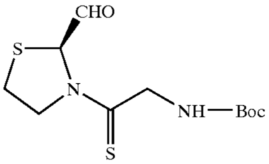
402

TABLE 14-continued
Aldehydes of the type A—CHO
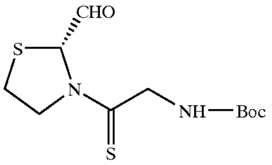
403
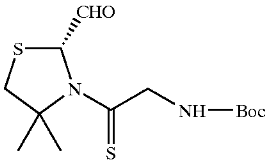
404
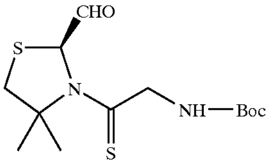
405
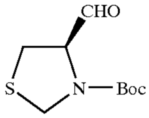
406
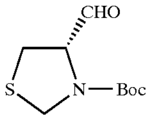
407
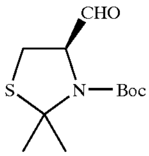
408
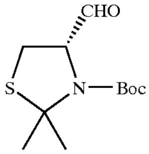
409
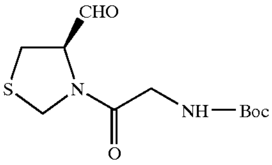
410
TABLE 14-continued
Aldehydes of the type A—CHO
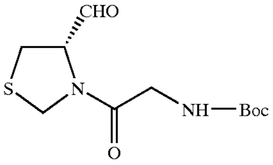
411
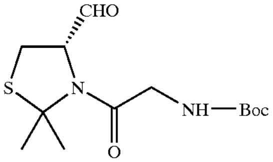
412
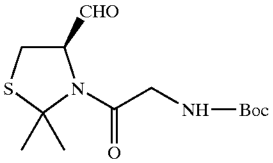
413
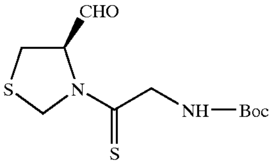
414
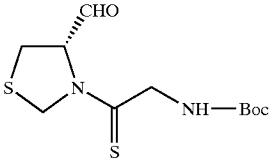
415
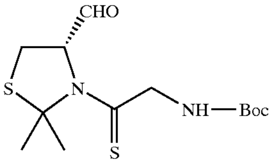
416
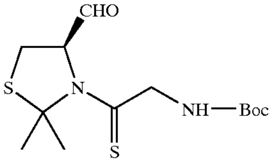
417
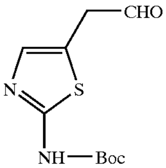
418

TABLE 14-continued
| Aldehydes of the type A—CHO |
|---|
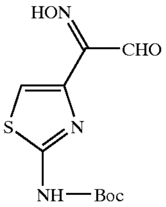
419
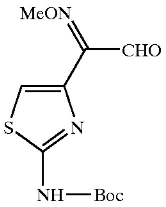
420
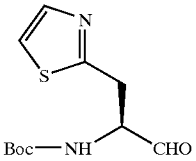
421
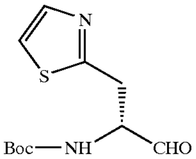
422
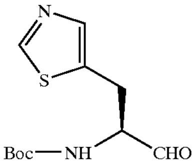
423
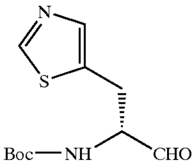
424
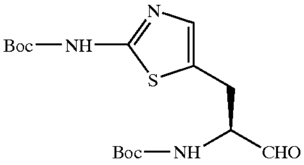
425
TABLE 14-continued
| Aldehydes of the type A—CHO |
|---|
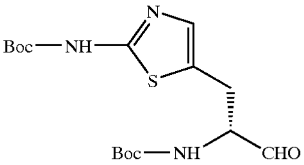
426
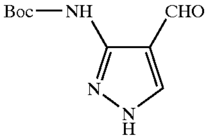
427
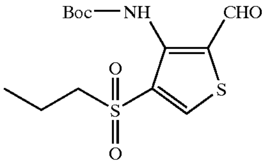
428
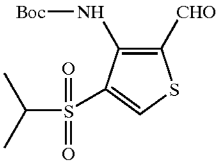
429
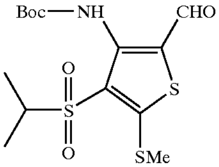
430
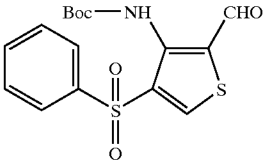
431
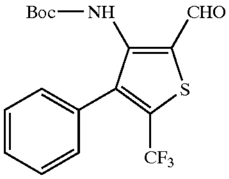
432
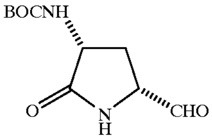
433

TABLE 14-continued
| Aldehydes of the type A—CHO |
|---|
| 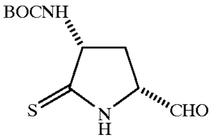 434 |
| 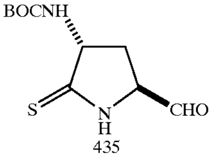 435 |
| 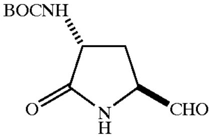 436 |
| 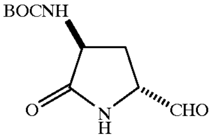 437 |
| 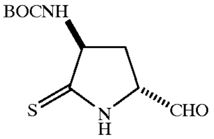 438 |
| 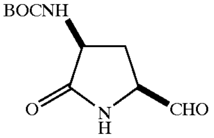 439 |
| 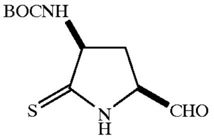 440 |
| 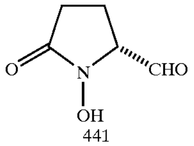 441 |
| 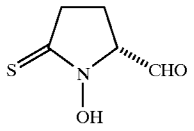 442 |
| 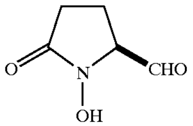 443 |
| 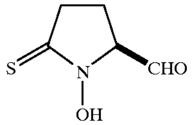 444 |
| 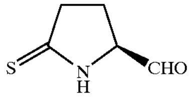 445 |
| 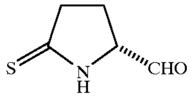 446 |
TABLE 15
| Alcohols of the type A—OH |
|---|
| 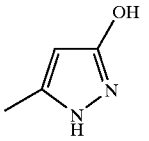 1 |
| 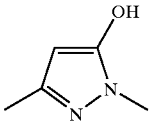 2 |
| 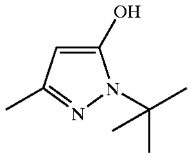 3 |
| 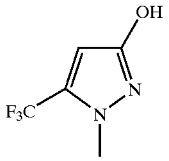 4 |
| 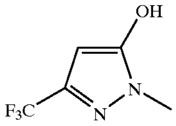 |

TABLE 15-continued
| Alcohols of the type A—OH |
|---|
| 5 |
| 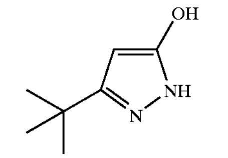 |
| 6 |
| 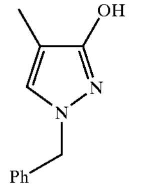 |
| 7 |
| 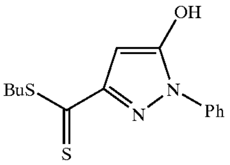 |
| 8 |
| 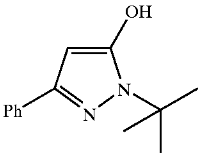 |
| 9 |
| 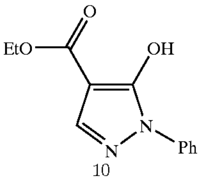 |
| 10 |
| 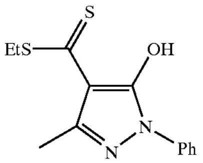 |
| 11 |
| 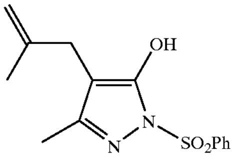 |
| 12 |
| 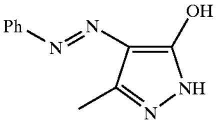 |
| 13 |
TABLE 15-continued
| Alcohols of the type A—OH |
|---|
| 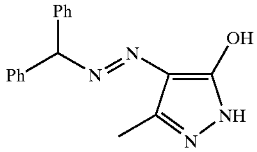 |
| 14 |
| 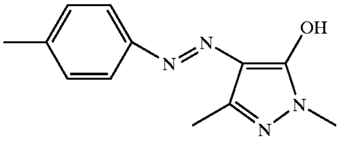 |
| 15 |
| 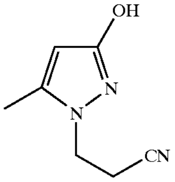 |
| 16 |
| 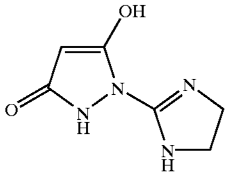 |
| 17 |
| 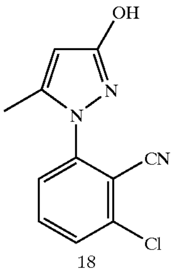 |
| 18 |
| 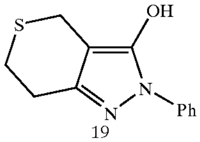 |
| 19 |
| 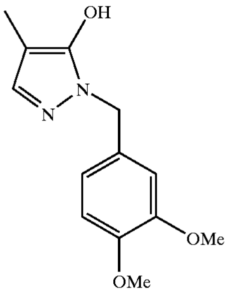 |
| 20 |

TABLE 15-continued
Alcohols of the type A—OH
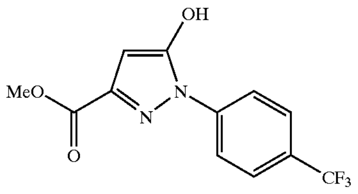
21
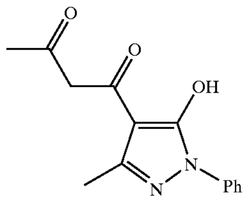
22
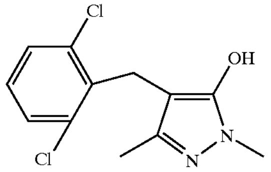
23
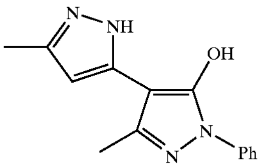
24
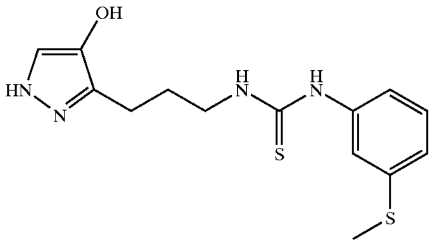
25
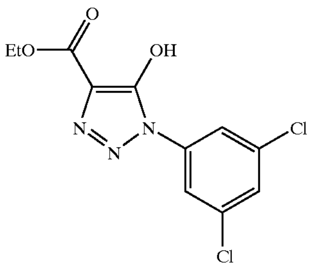
26
TABLE 15-continued
Alcohols of the type A—OH
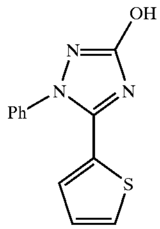
27
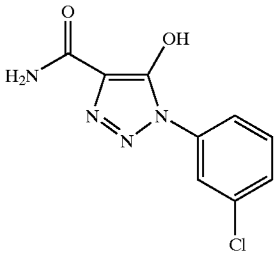
28
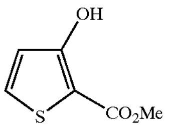
29
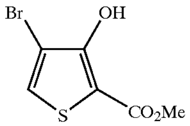
30
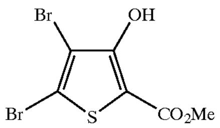
31
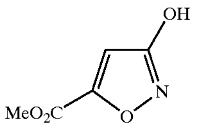
32
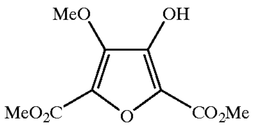
33
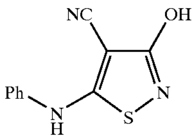
34

TABLE 15-continued
Alcohols of the type A—OH
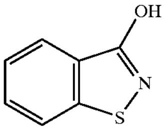
35
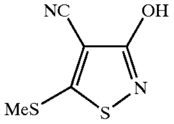
36
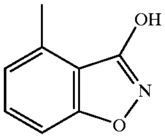
37
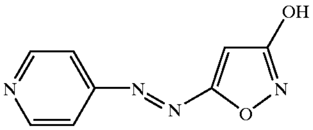
38
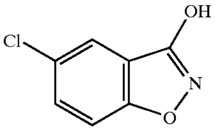
39
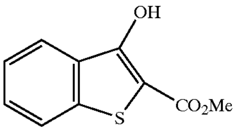
40
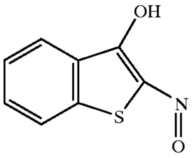
41
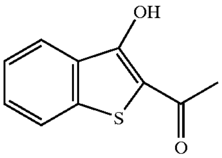
42
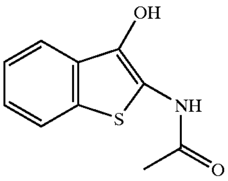
TABLE 15-continued
Alcohols of the type A—OH
43
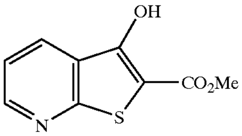
44
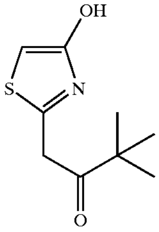
45
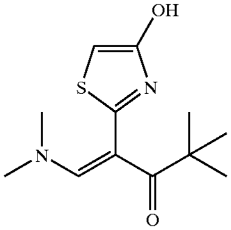
46
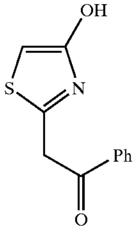
47
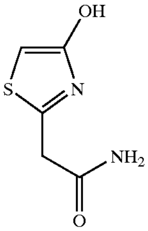
48
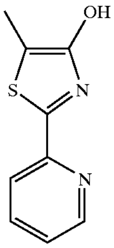
49

TABLE 15-continued
| Alcohols of the type A—OH |
| --- |
| 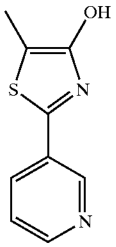 |
| 50 |
| 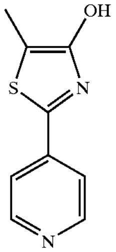 |
| 51 |
| 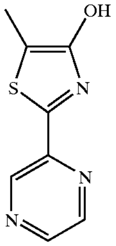 |
| 52 |
| 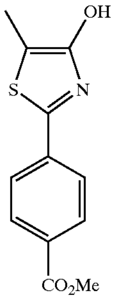 |
| 53 |
| 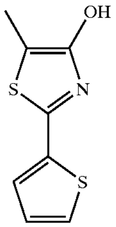 |
| 54 |
TABLE 15-continued
| Alcohols of the type A—OH |
| --- |
| 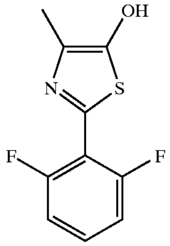 |
| 55 |
| 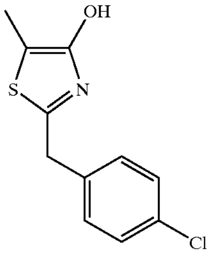 |
| 56 |
| 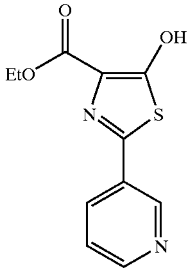 |
| 57 |
| 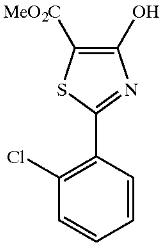 |
| 58 |
| 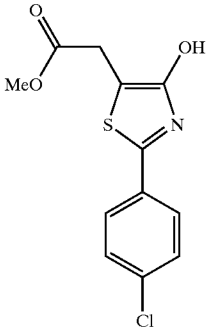 |
| 59 |

TABLE 15-continued
| Alcohols of the type A—OH |
|---|
| 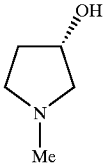 60 |
| 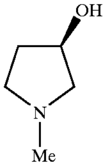 61 |
| 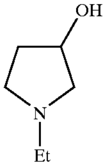 62 |
| 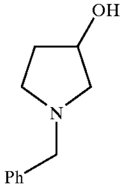 63 |
| 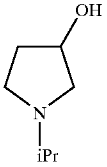 64 |
| 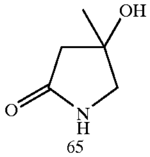 65 |
| 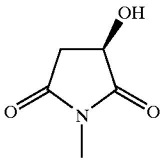 66 |
| 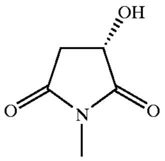 67 |
TABLE 15-continued
| Alcohols of the type A—OH |
|---|
| 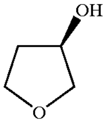 68 |
| 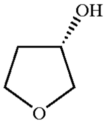 69 |
| 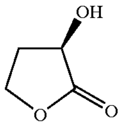 70 |
| 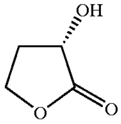 71 |
| 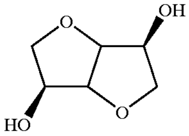 72 |
| 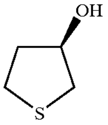 73 |
| 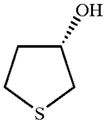 74 |
| 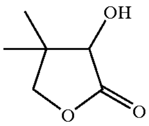 75 |
| 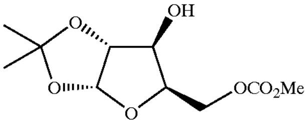 76 |

TABLE 15-continued
Alcohols of the type A—OH
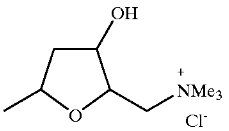
77
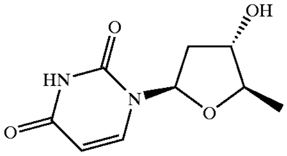
78
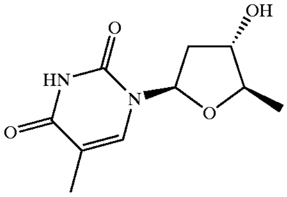
79
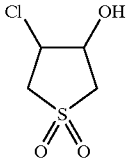
80
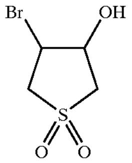
81
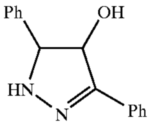
82
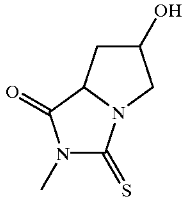
83
TABLE 15-continued
Alcohols of the type A—OH
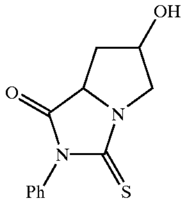
84
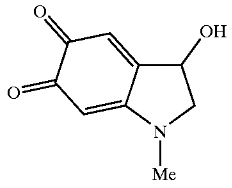
85
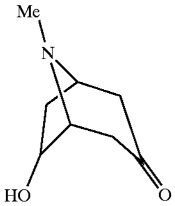
86
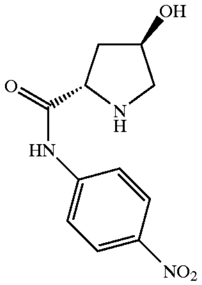
87
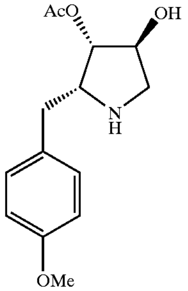
88
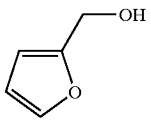
89

TABLE 15-continued
Alcohols of the type A—OH
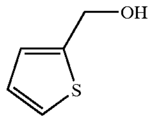
90
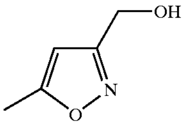
91
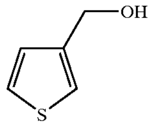
92
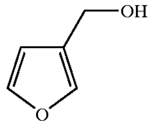
93
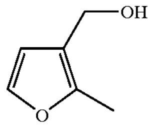
94
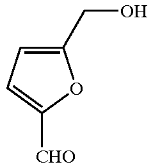
95
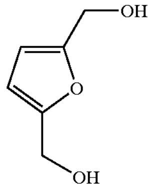
96
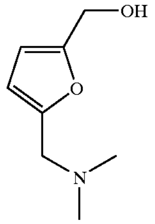
97
TABLE 15-continued
Alcohols of the type A—OH
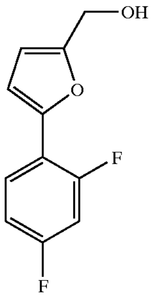
98
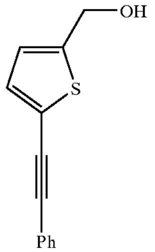
99
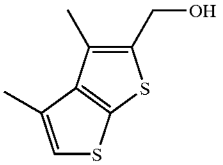
100
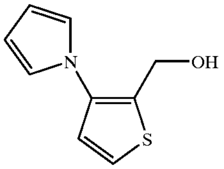
101
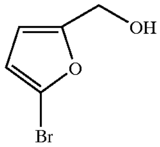
102
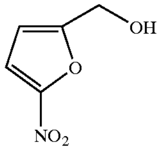
103
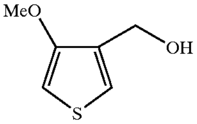
104

TABLE 15-continued
| Alcohols of the type A—OH |
|---|
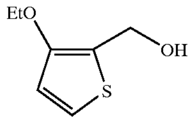
105
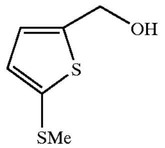
106
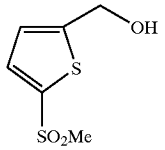
107
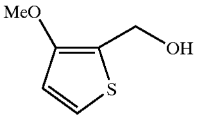
108
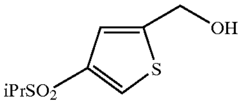
109
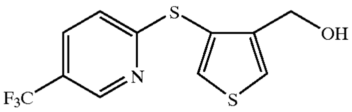
110
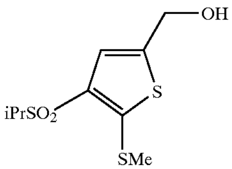
111
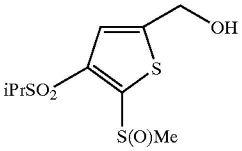
112
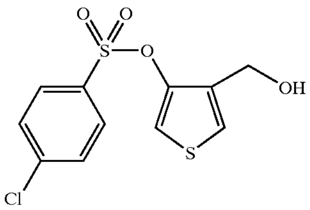
TABLE 15-continued
| Alcohols of the type A—OH |
|---|
113
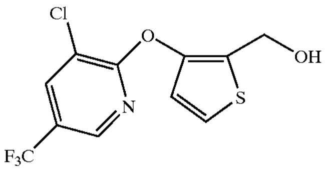
114
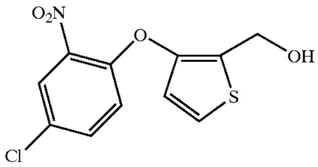
115
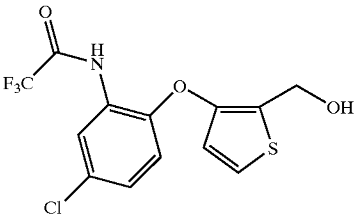
116
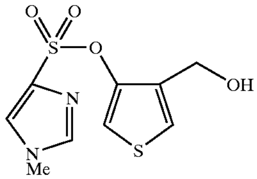
117
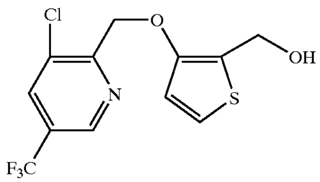
118
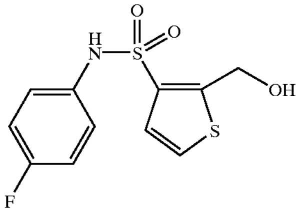
119

TABLE 15-continued
Alcohols of the type A—OH
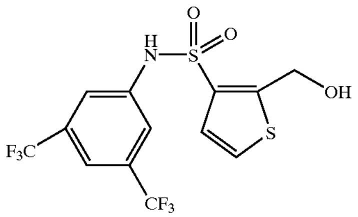
120
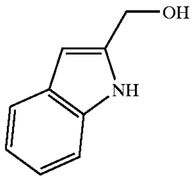
121
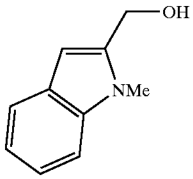
122
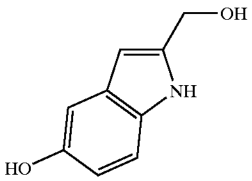
123
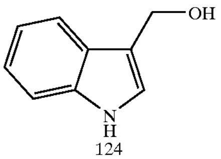
124
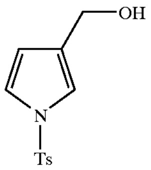
125
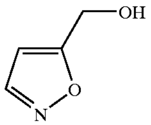
126
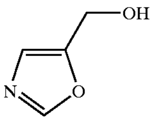
127
TABLE 15-continued
Alcohols of the type A—OH
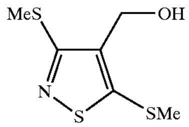
128
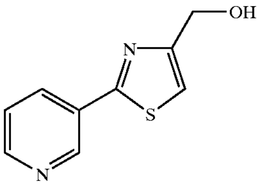
129
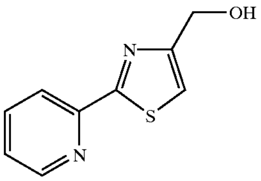
130
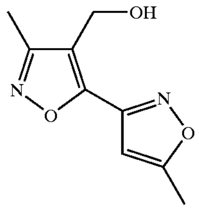
131
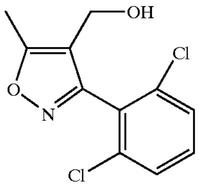
132
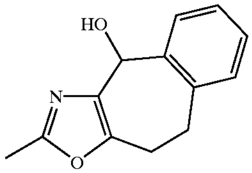
133
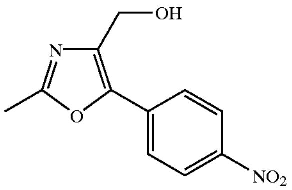
134

TABLE 15-continued
Alcohols of the type A—OH
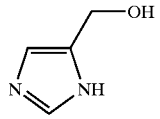
135
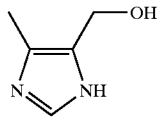
136
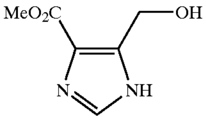
137
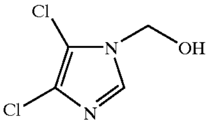
138
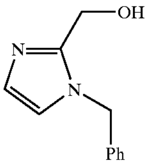
139
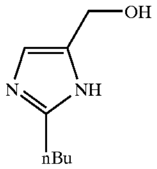
140
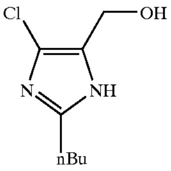
141
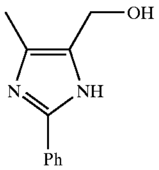
142
TABLE 15-continued
Alcohols of the type A—OH
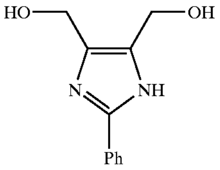
143
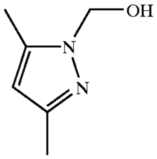
144
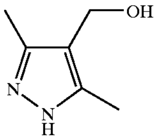
145
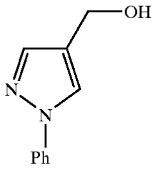
146
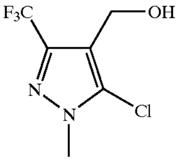
147
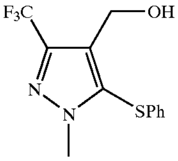
148
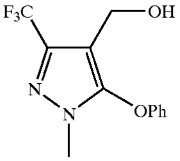
149

TABLE 15-continued
| Alcohols of the type A—OH |
|---|
| 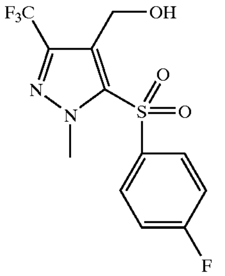 150 |
| 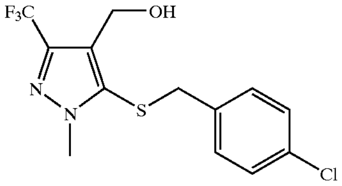 151 |
| 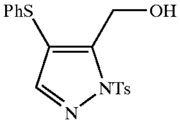 152 |
| 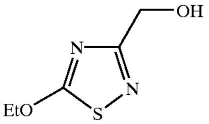 153 |
| 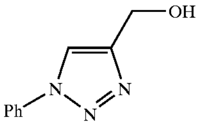 154 |
| 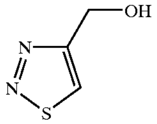 155 |
| 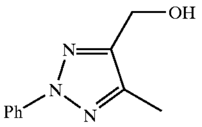 156 |
| 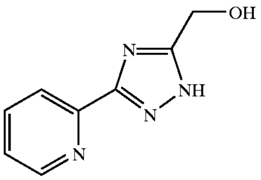 157 |
TABLE 15-continued
| Alcohols of the type A—OH |
|---|
| 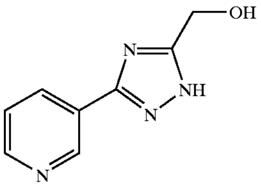 158 |
| 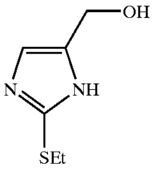 159 |
| 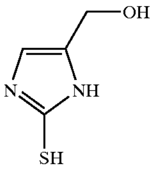 160 |
| 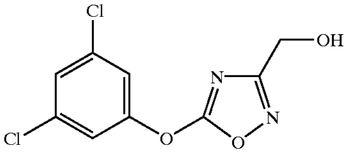 161 |
| 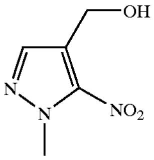 162 |
| 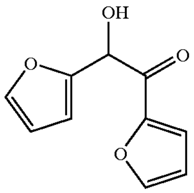 163 |
| 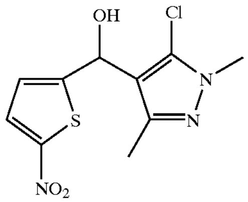 164 |

TABLE 15-continued
Alcohols of the type A—OH
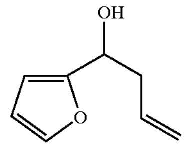
165
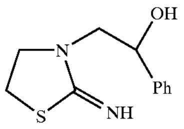
166
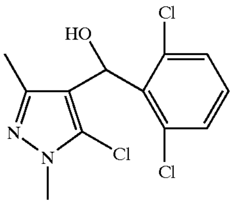
167
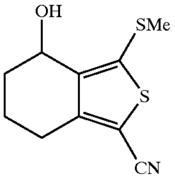
168
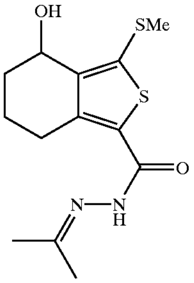
169
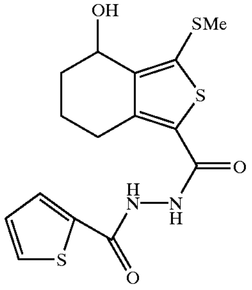
170
TABLE 15-continued
Alcohols of the type A—OH
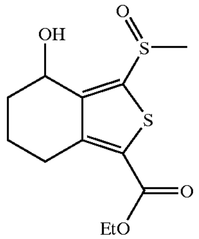
171
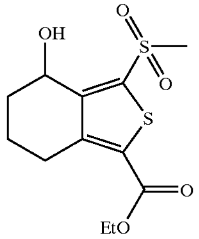
172
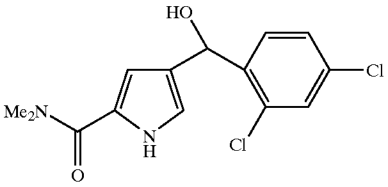
173
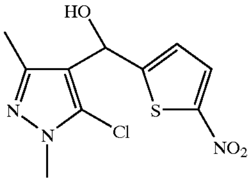
174
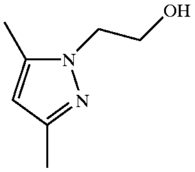
175
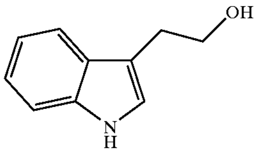
176
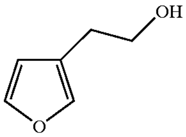
177

TABLE 15-continued
Alcohols of the type A—OH
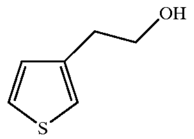
178
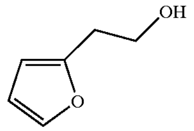
179
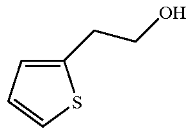
180
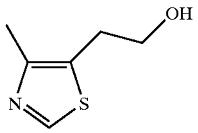
181
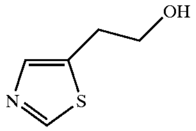
182
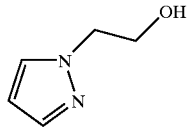
183
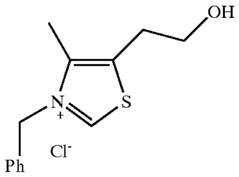
184
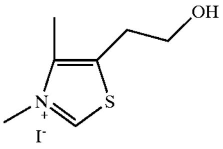
185
TABLE 15-continued
Alcohols of the type A—OH
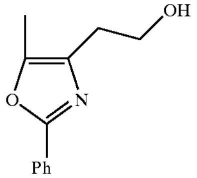
186
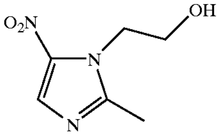
187
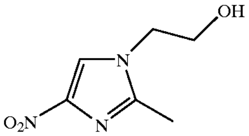
188
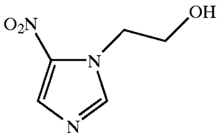
189
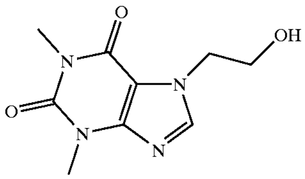
190
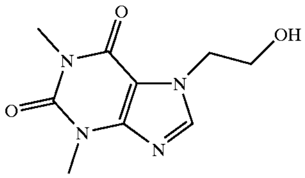
191
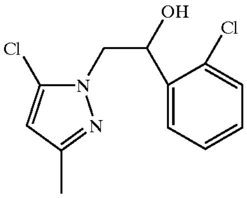
192
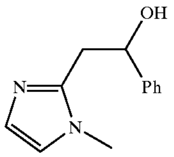
193

TABLE 15-continued
Alcohols of the type A—OH
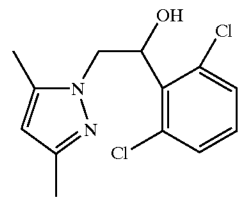
194
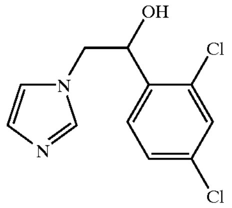
195
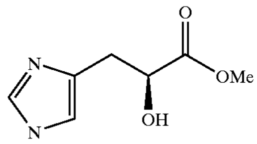
196
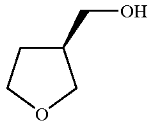
197
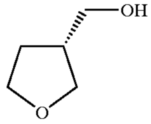
198
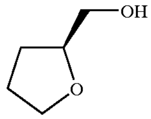
199
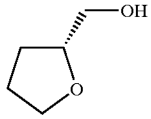
200
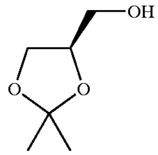
201
TABLE 15-continued
Alcohols of the type A—OH
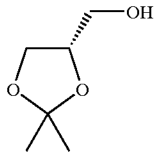
202
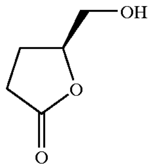
203
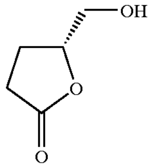
204
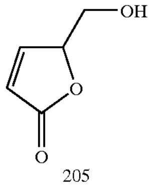
205
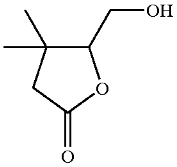
206
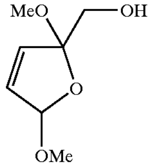
207
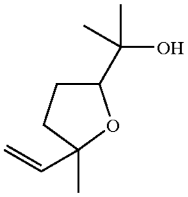
208
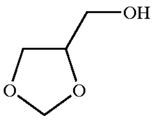
209

TABLE 15-continued
Alcohols of the type A—OH
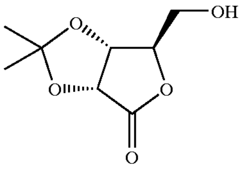
210
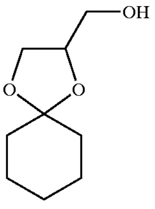
211
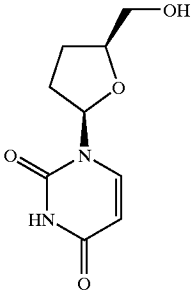
212
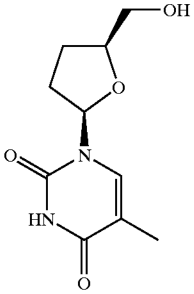
213
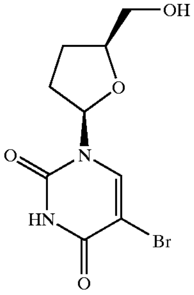
214
TABLE 15-continued
Alcohols of the type A—OH
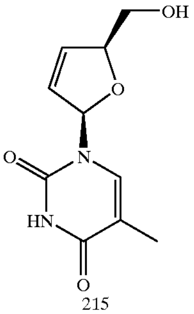
215
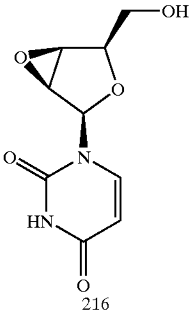
216
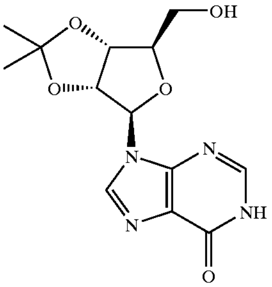
217
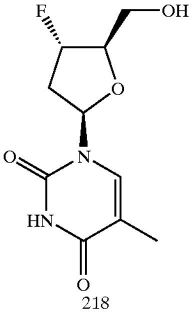
218
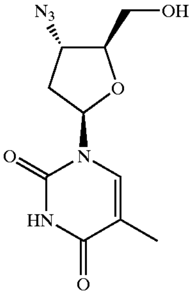

TABLE 15-continued
| Alcohols of the type A—OH |
| --- |
| 219 |
| 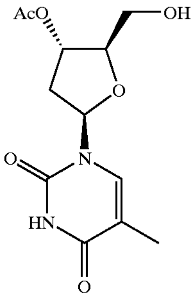 |
| 220 |
| 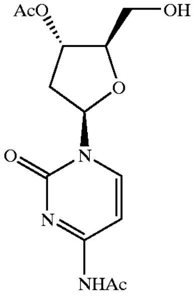 |
| 221 |
| 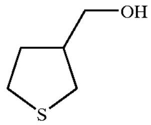 |
| 222 |
| 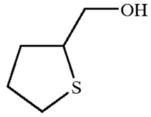 |
| 223 |
| 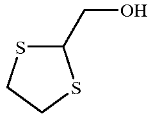 |
| 224 |
| 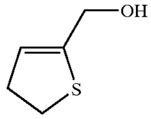 |
| 225 |
| 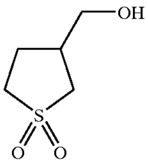 |
| 226 |
| 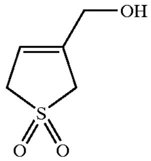 |
| 227 |
| 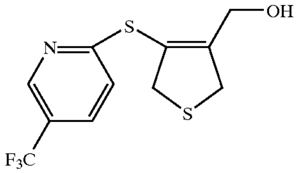 |
| 228 |
| 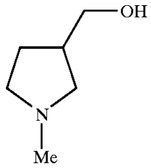 |
| 229 |
| 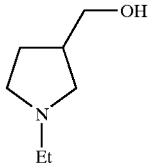 |
| 230 |
| 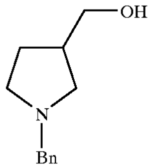 |
| 231 |
| 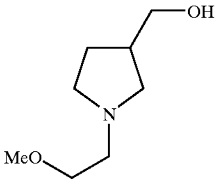 |
| 232 |
| 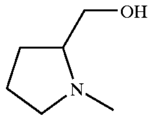 |
| 233 |
| 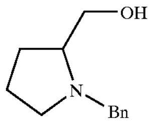 |
| 234 |

TABLE 15-continued
Alcohols of the type A—OH
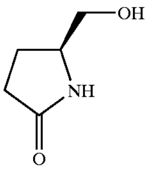
235
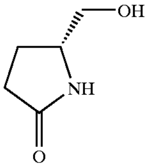
236
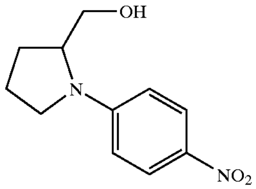
237
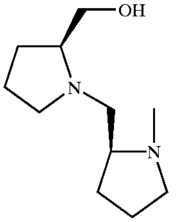
238
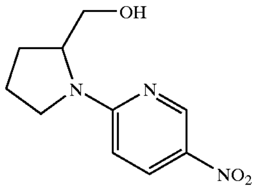
239
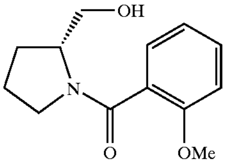
240
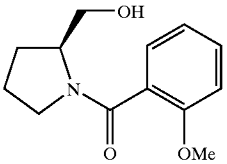
241
TABLE 15-continued
Alcohols of the type A—OH
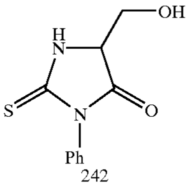
242
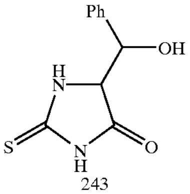
243
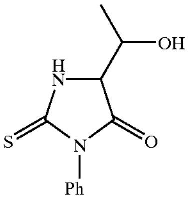
244
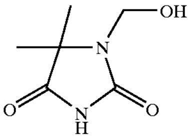
245
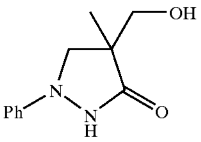
246
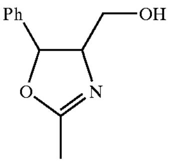
247
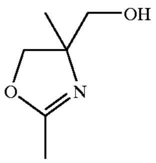
248
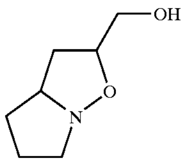
249

TABLE 15-continued
| Alcohols of the type A—OH |
| --- |
| 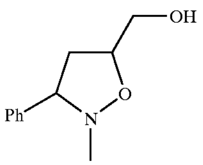 |
| 250 |
| 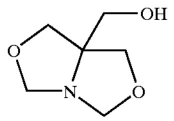 |
| 251 |
| 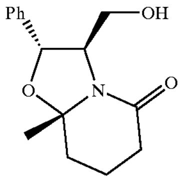 |
| 252 |
| 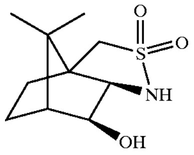 |
| 253 |
| 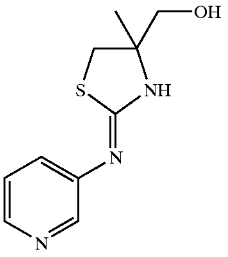 |
| 254 |
| 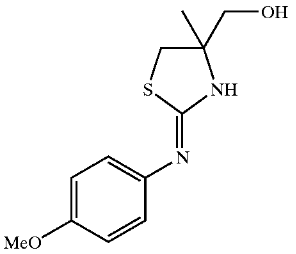 |
| 255 |
TABLE 15-continued
| Alcohols of the type A—OH |
| --- |
| 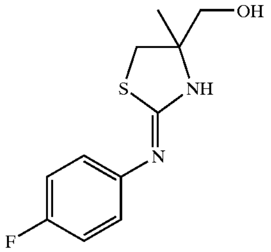 |
| 256 |
| 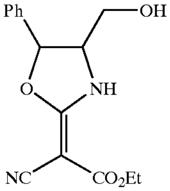 |
| 257 |
| 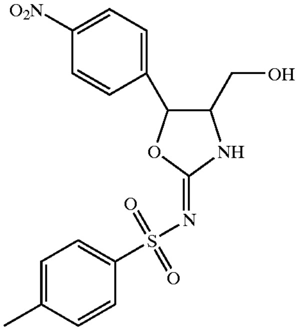 |
| 258 |
| 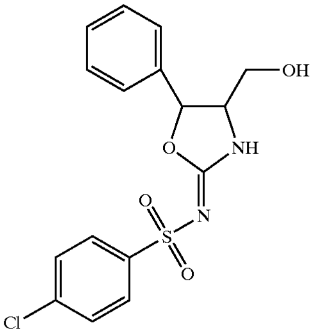 |
| 259 |
| 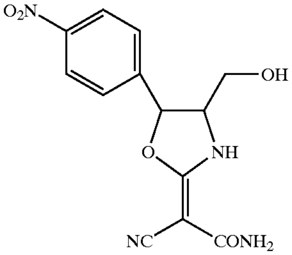 |
| 260 |

TABLE 15-continued
| Alcohols of the type A—OH |
|---|
| 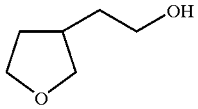 261 |
| 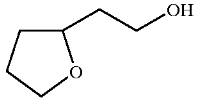 262 |
| 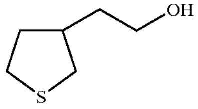 263 |
| 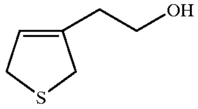 264 |
| 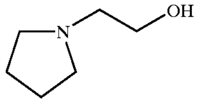 265 |
| 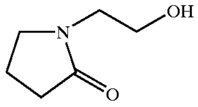 266 |
| 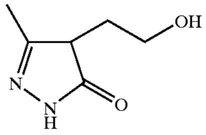 267 |
| 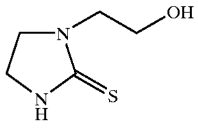 268 |
| 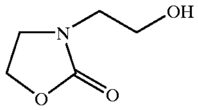 269 |
| 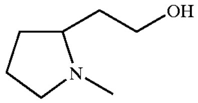 270 |
TABLE 15-continued
| Alcohols of the type A—OH |
|---|
| 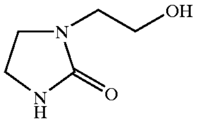 271 |
| 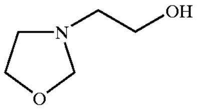 272 |
| 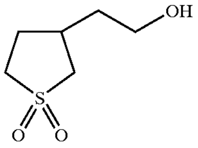 273 |
| 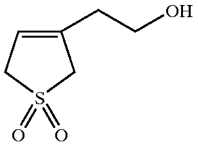 274 |
| 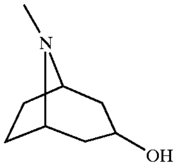 275 |
| 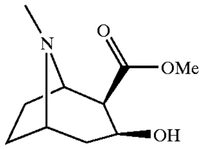 276 |
| 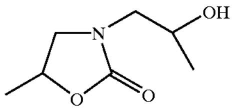 277 |
| 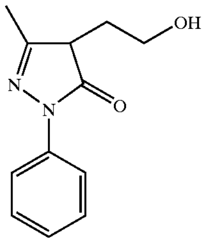 278 |

TABLE 15-continued
| Alcohols of the type A—OH |
|---|
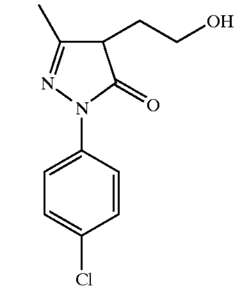
279
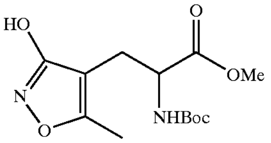
280
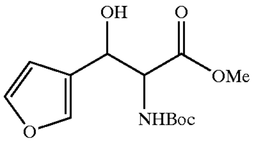
281
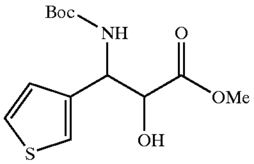
282
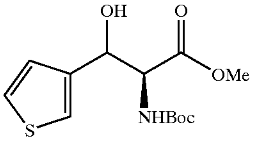
283
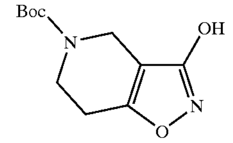
284
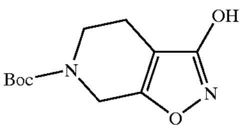
285
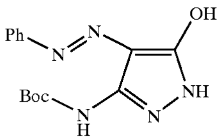
286
TABLE 15-continued
| Alcohols of the type A—OH |
|---|
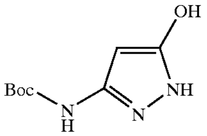
287
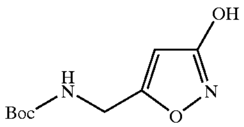
288
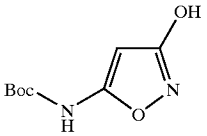
289
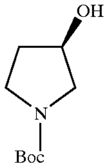
290
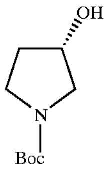
291
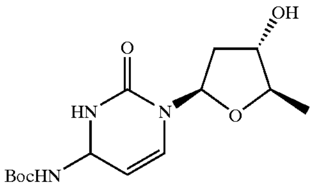
292
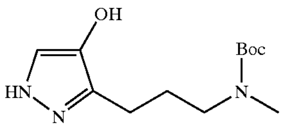
293
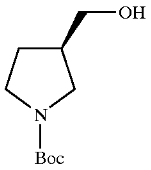
294

TABLE 15-continued
Alcohols of the type A—OH
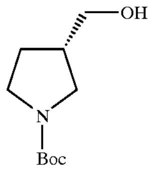
295
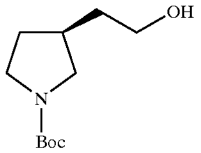
296
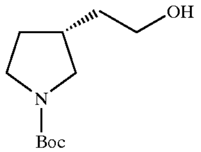
297
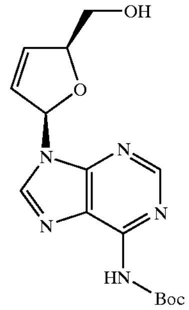
298
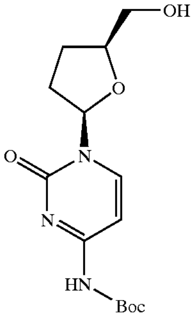
299
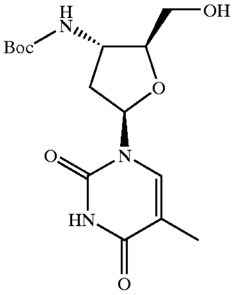
300
TABLE 15-continued
Alcohols of the type A—OH
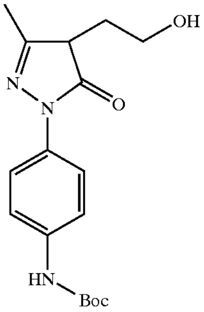
301
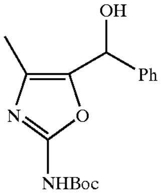
302
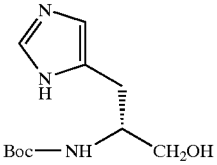
303
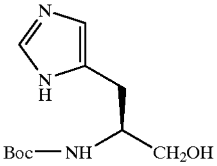
304
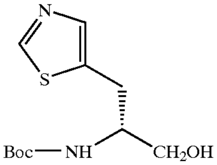
305
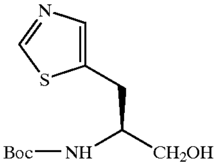
306
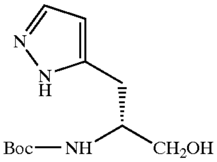
307

TABLE 15-continued
| Alcohols of the type A—OH |
|---|
| 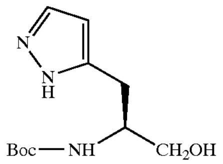 308 |
| 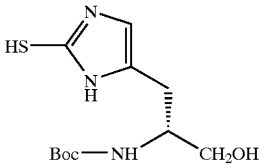 309 |
| 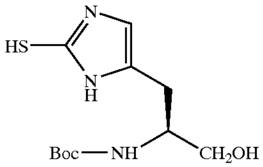 310 |
| 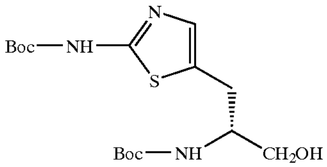 311 |
| 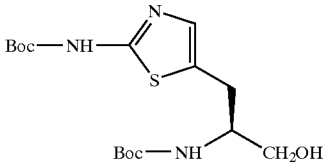 312 |
| 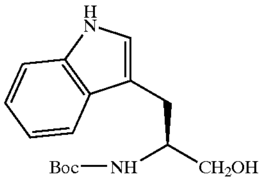 313 |
| 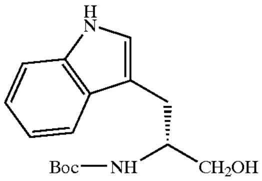 314 |
TABLE 15-continued
| Alcohols of the type A—OH |
|---|
| 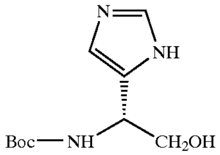 315 |
| 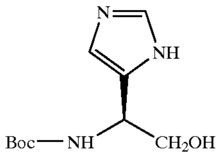 316 |
| 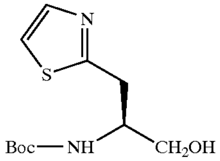 317 |
| 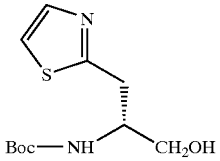 318 |
| 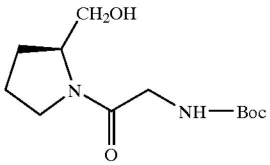 319 |
| 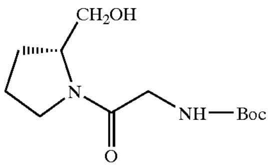 320 |
| 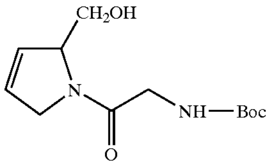 321 |
| 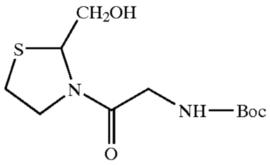 322 |

TABLE 15-continued
Alcohols of the type A—OH
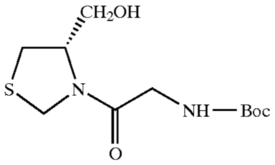
323
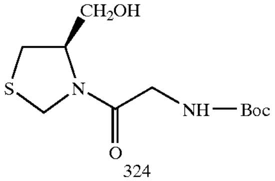
324
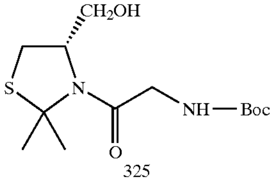
325
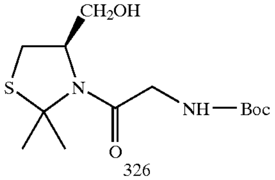
326
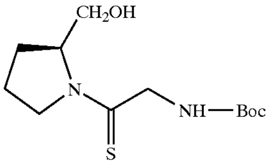
327
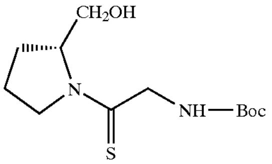
328
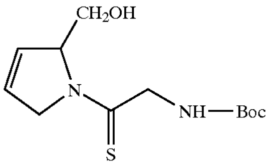
329
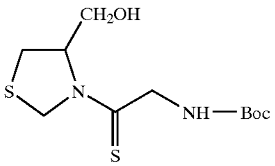
330
TABLE 15-continued
Alcohols of the type A—OH
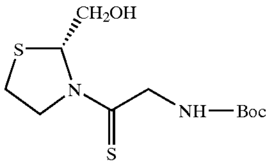
331
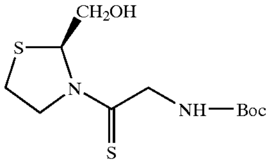
332
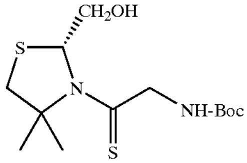
333
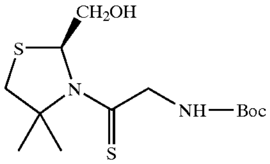
334
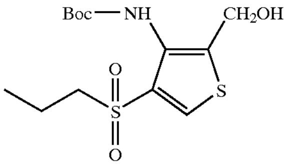
335
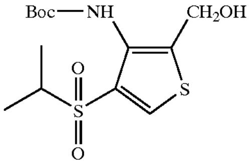
336
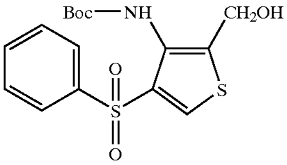
337
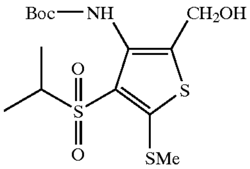

TABLE 15-continued
Alcohols of the type A—OH
338
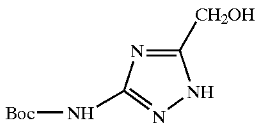
339
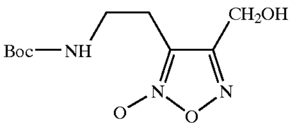
340
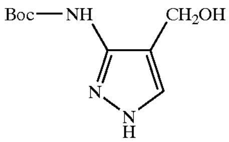
341
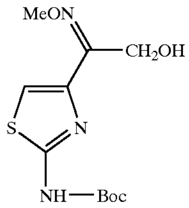
342
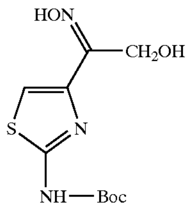
343
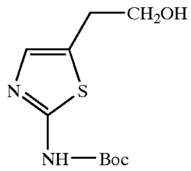
344
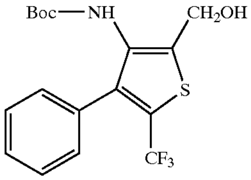
345
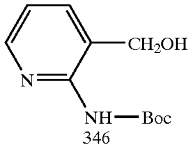
346
TABLE 15-continued
Alcohols of the type A—OH
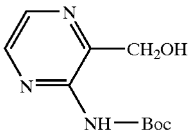
347
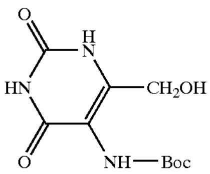
348
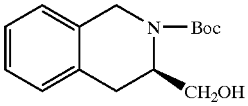
349
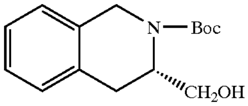
350
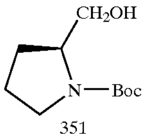
351
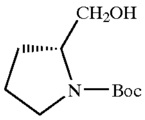
352
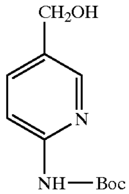
353
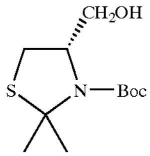
354
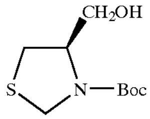
355

TABLE 15-continued
Alcohols of the type A—OH
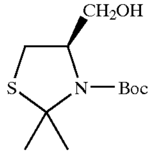
356
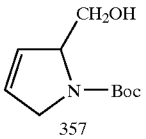
357
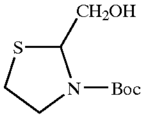
358
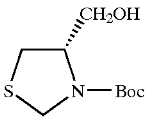
359
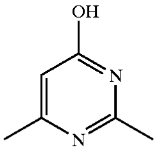
360
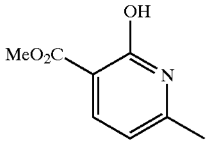
361
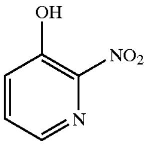
362
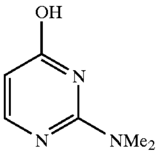
363
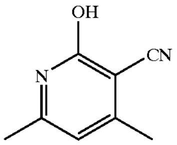
364
TABLE 15-continued
Alcohols of the type A—OH
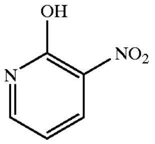
365
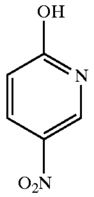
366
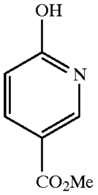
367
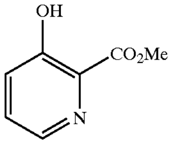
368
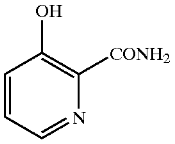
369
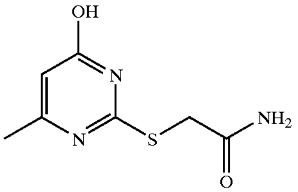
370
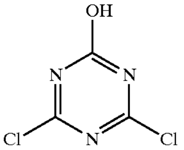
371
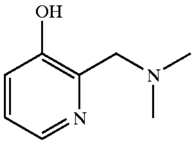

TABLE 15-continued
Alcohols of the type A—OH
372
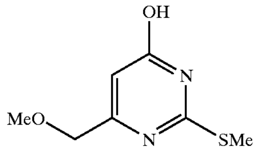
373
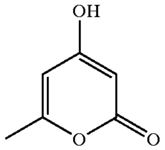
374
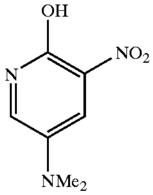
375
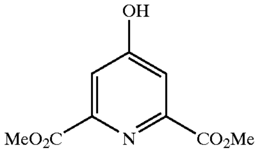
376
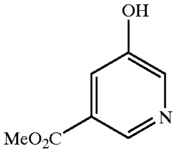
377
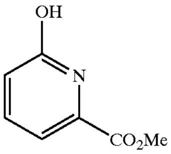
378
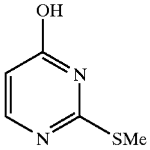
379
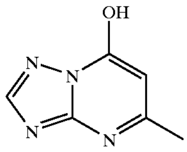
380
TABLE 15-continued
Alcohols of the type A—OH
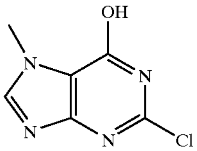
381
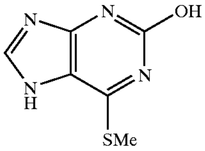
382
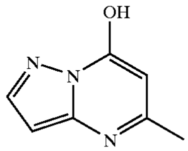
383
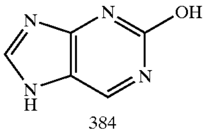
384
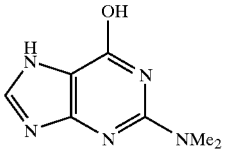
385
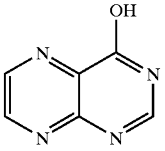
386
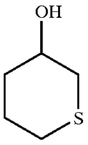
387
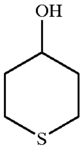
388
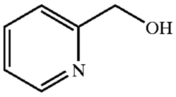
389

TABLE 15-continued
Alcohols of the type A—OH
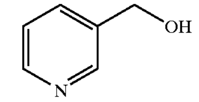
390
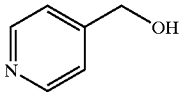
391
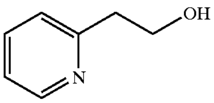
392
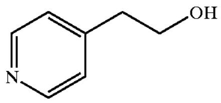
393
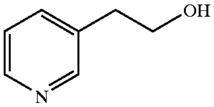
394
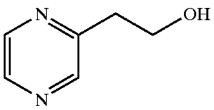
395
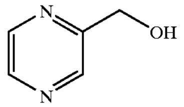
396
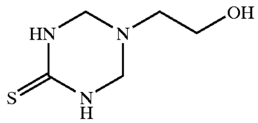
397
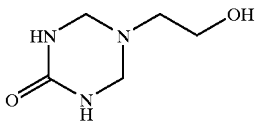
398
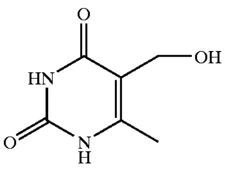
399
TABLE 15-continued
Alcohols of the type A—OH
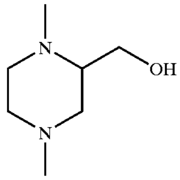
400
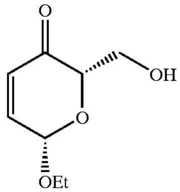
401
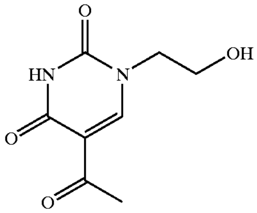
402
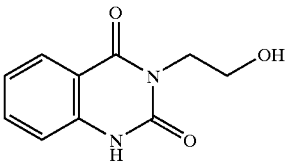
403
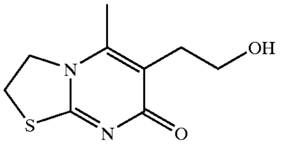
404
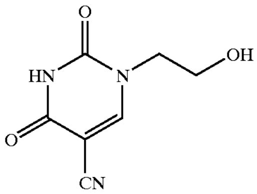
405
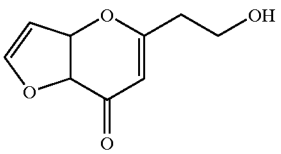
406

TABLE 15-continued
| Alcohols of the type A—OH |
|---|
| 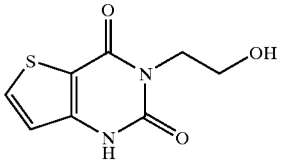 407 |
| 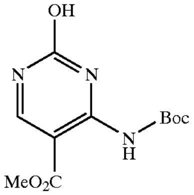 408 |
| 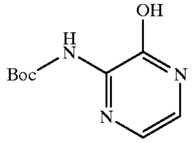 409 |
| 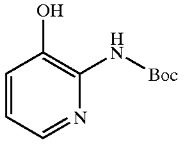 410 |
| 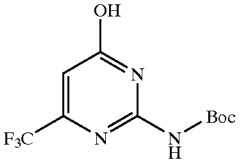 411 |
| 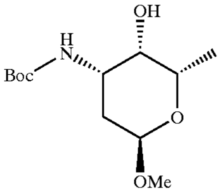 412 |
| 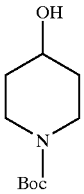 413 |
TABLE 15-continued
| Alcohols of the type A—OH |
|---|
| 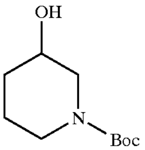 414 |
| 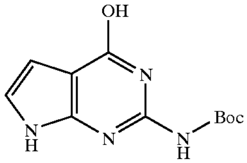 415 |
| 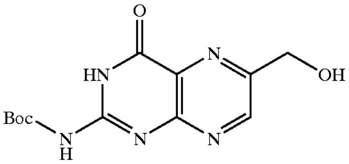 416 |
| 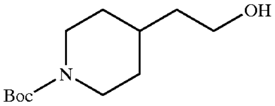 417 |
| 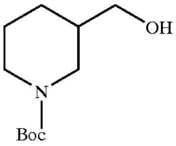 418 |
| 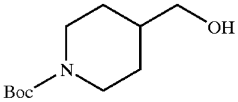 419 |
| 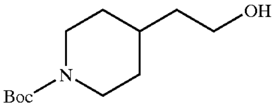 420 |
| 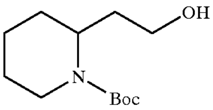 421 |
| 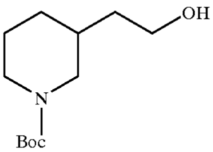 422 |

TABLE 15-continued
| Alcohols of the type A—OH |
|---|
| 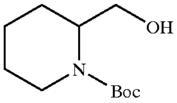 423 |
| 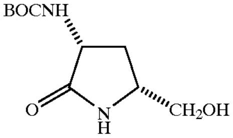 424 |
| 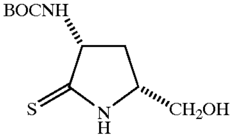 425 |
| 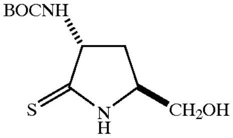 426 |
| 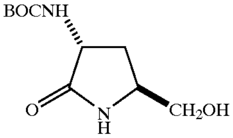 427 |
| 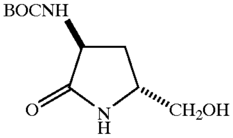 428 |
| 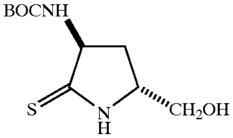 429 |
| 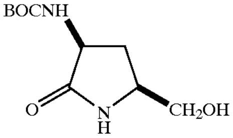 430 |
| 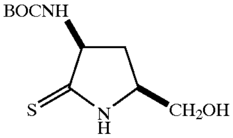 431 |
TABLE 15-continued
| Alcohols of the type A—OH |
|---|
| 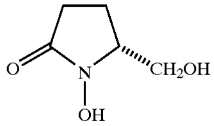 432 |
| 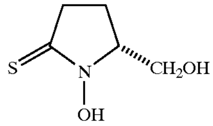 433 |
| 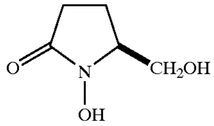 434 |
| 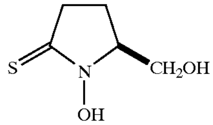 435 |
| 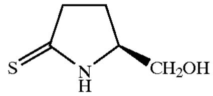 436 |
| 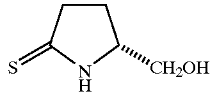 437 |
TABLE 16
| Mercaptans of the type A—SH |
|---|
| 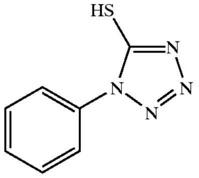 1 |
| 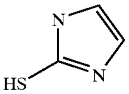 2 |
| 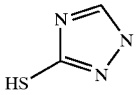 3 |

TABLE 16-continued
Mercaptans of the type A—SH
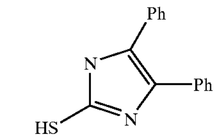
4
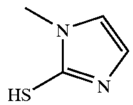
5
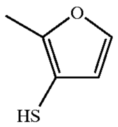
6
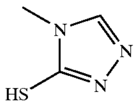
7
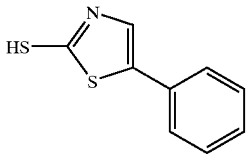
8
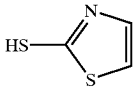
9
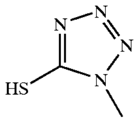
10
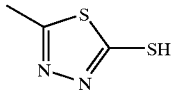
11
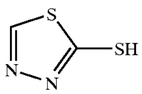
12
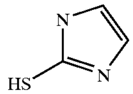
13
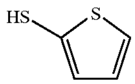
TABLE 16-continued
Mercaptans of the type A—SH
14
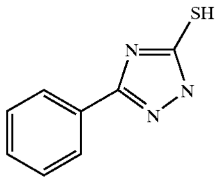
15
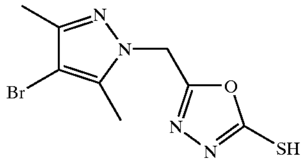
16
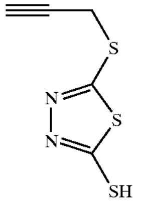
17
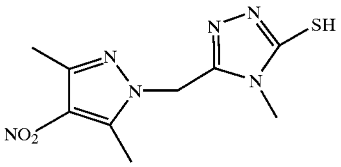
18
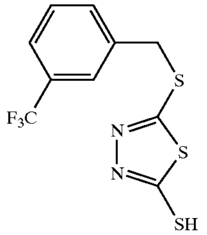
19
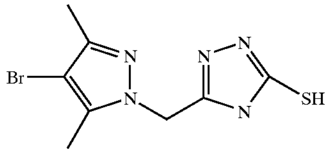
20
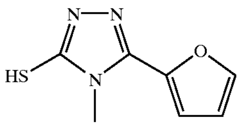
21

TABLE 16-continued
| Mercaptans of the type A—SH |
| --- |
| 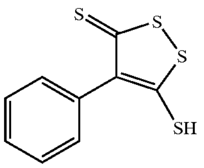 22 |
| 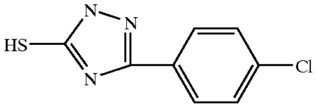 23 |
| 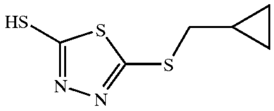 24 |
| 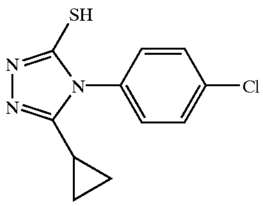 25 |
| 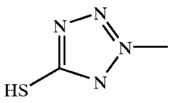 26 |
| 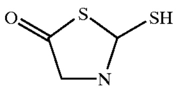 27 |
| 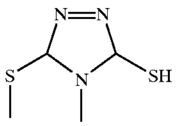 28 |
| 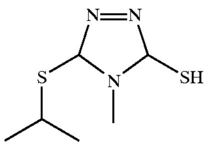 29 |
| 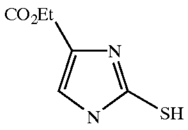 30 |
TABLE 16-continued
| Mercaptans of the type A—SH |
| --- |
| 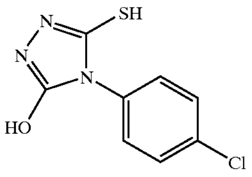 31 |
| 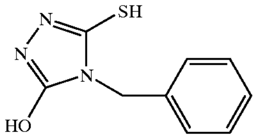 32 |
| 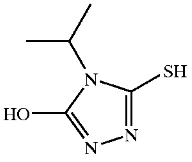 33 |
| 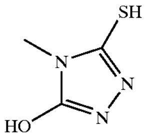 34 |
| 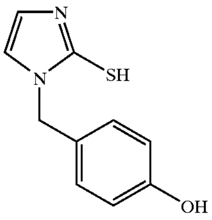 35 |
| 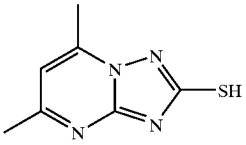 36 |
| 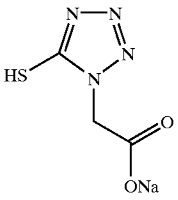 37 |

TABLE 16-continued
Mercaptans of the type A—SH
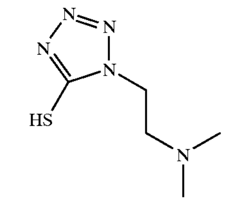
38
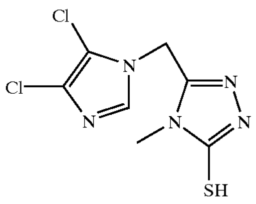
39
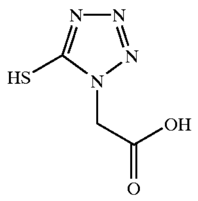
40
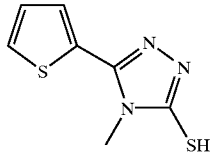
41
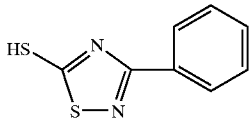
42
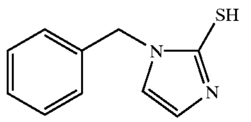
43
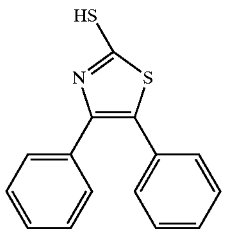
44
TABLE 16-continued
Mercaptans of the type A—SH
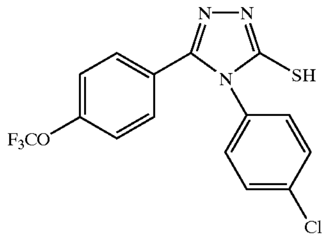
45
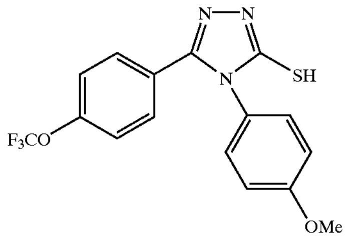
46
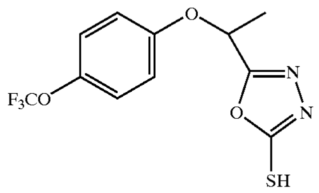
47
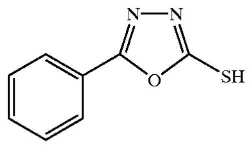
48
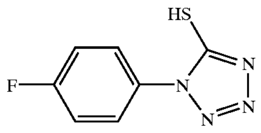
49
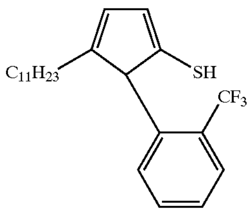
50
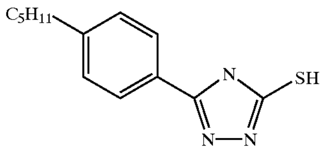
51

TABLE 16-continued
| Mercaptans of the type A—SH |
|---|
| 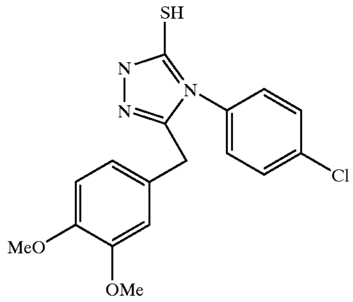 |
| 52 |
| 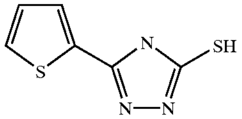 |
| 53 |
| 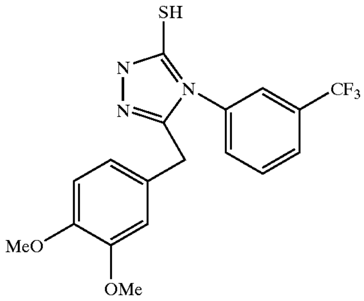 |
| 54 |
| 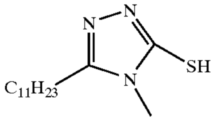 |
| 55 |
| 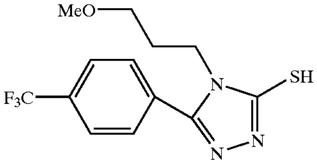 |
| 56 |
| 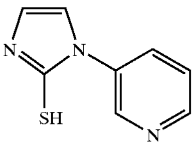 |
| 57 |
| 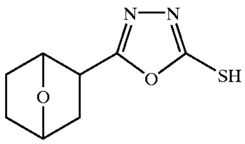 |
| 58 |
TABLE 16-continued
| Mercaptans of the type A—SH |
|---|
| 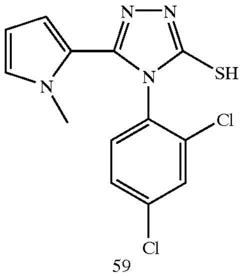 |
| 59 |
| 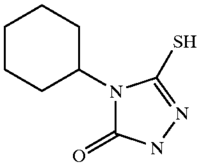 |
| 60 |
| 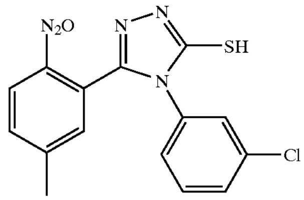 |
| 61 |
| 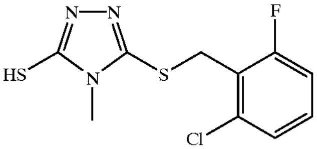 |
| 62 |
| 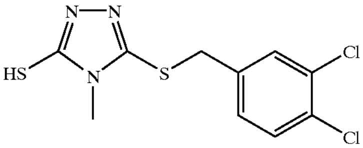 |
| 63 |
| 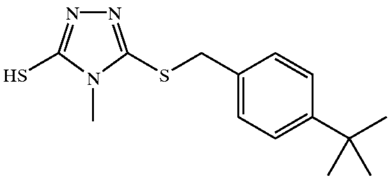 |
| 64 |
| 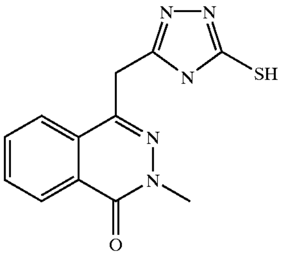 |
| 65 |

TABLE 16-continued
Mercaptans of the type A—SH
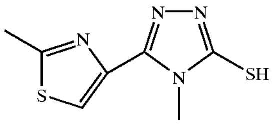
66
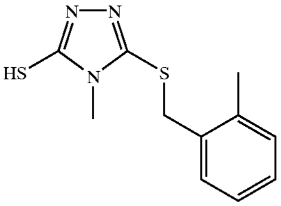
67
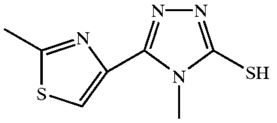
68
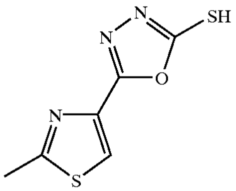
69
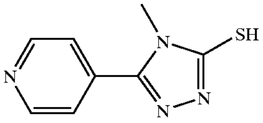
70
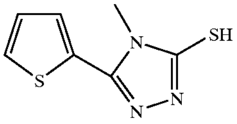
71
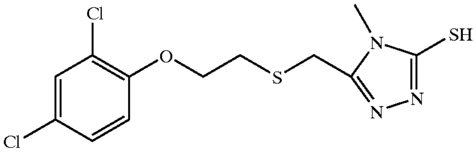
72
TABLE 16-continued
Mercaptans of the type A—SH
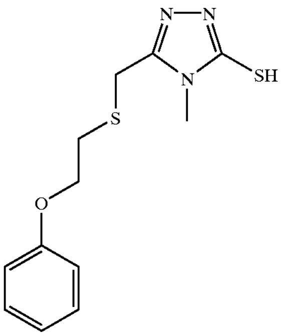
73
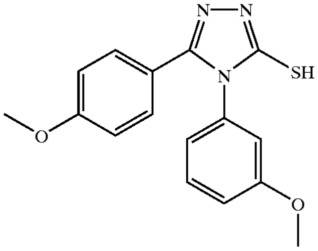
74
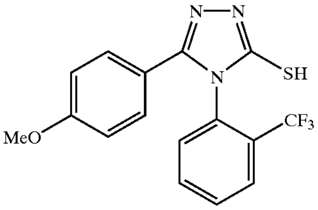
75
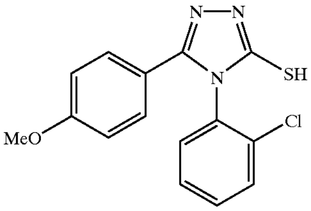
76
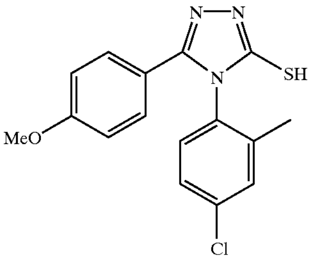
77

TABLE 16-continued
Mercaptans of the type A—SH
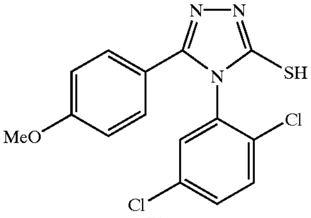
78
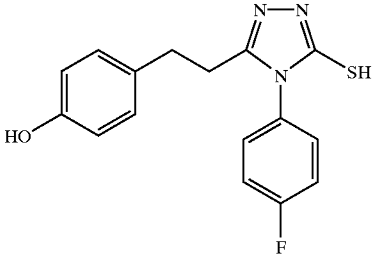
79
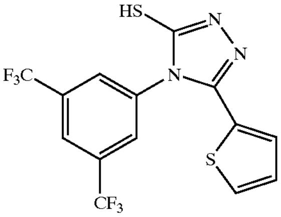
80
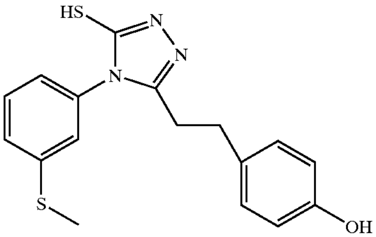
81
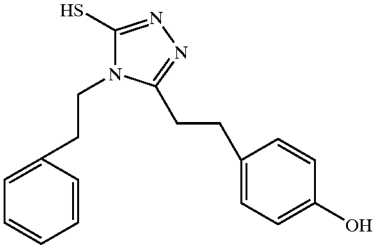
82
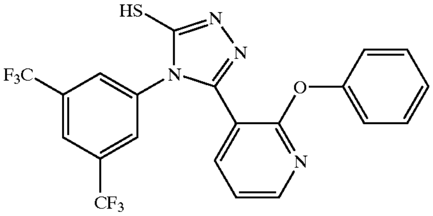
83
TABLE 16-continued
Mercaptans of the type A—SH
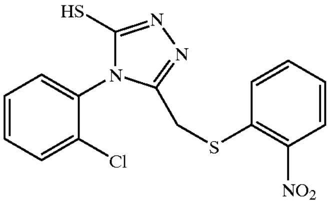
84
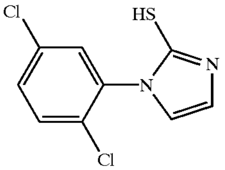
85
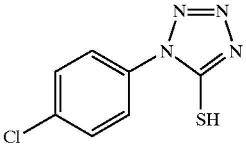
86
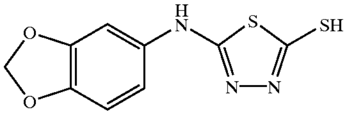
87
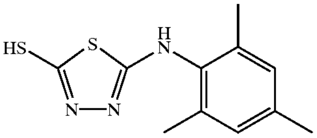
88
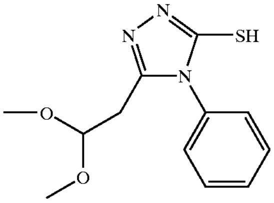
89
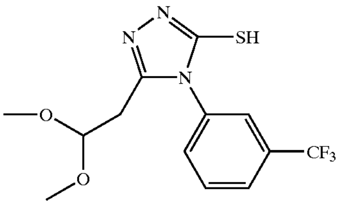
90
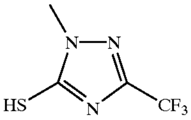

TABLE 16-continued
| Mercaptans of the type A—SH |
|---|
91
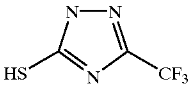
92
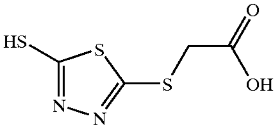
93
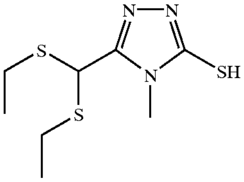
94
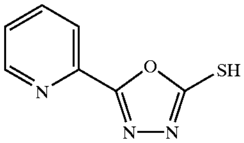
95
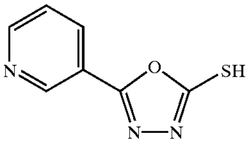
96
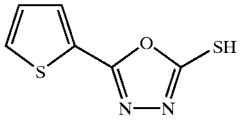
97
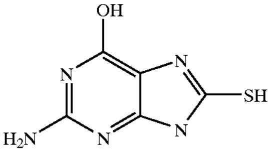
98
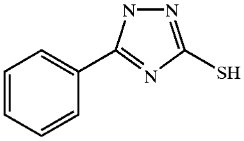
99
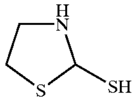
100
TABLE 16-continued
| Mercaptans of the type A—SH |
|---|
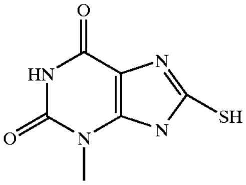
101
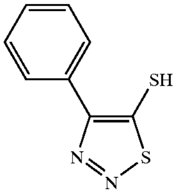
102
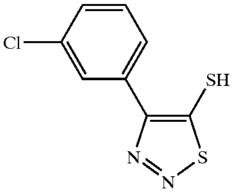
103
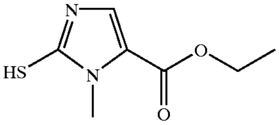
104
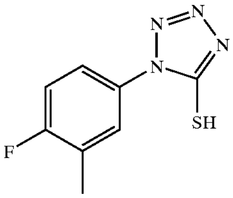
105
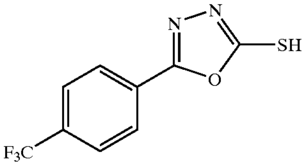
106
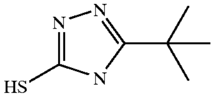
107
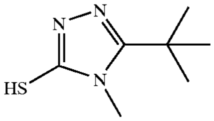
108

TABLE 16-continued
| Mercaptans of the type A—SH |
| --- |
| 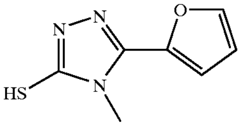 |
| 109 |
| 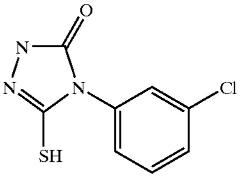 |
| 110 |
| 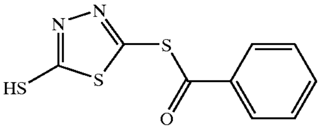 |
| 111 |
| 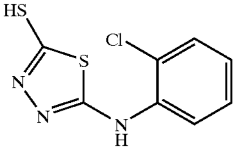 |
| 112 |
| 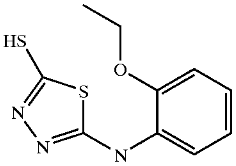 |
| 113 |
| 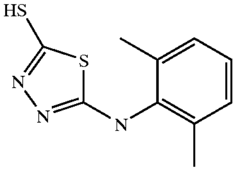 |
| 114 |
| 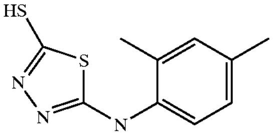 |
| 115 |
| 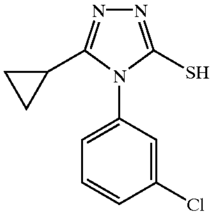 |
| 116 |
TABLE 16-continued
| Mercaptans of the type A—SH |
| --- |
| 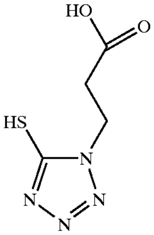 |
| 117 |
| 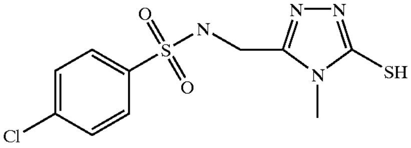 |
| 118 |
| 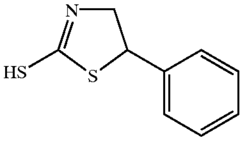 |
| 119 |
| 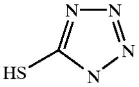 |
| 120 |
| 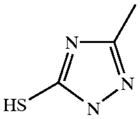 |
| 121 |
| 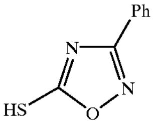 |
| 121 |
| 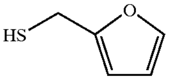 |
| 122 |
| 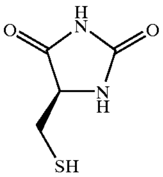 |
| 123 |
| 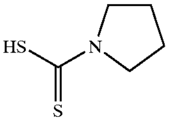 |
| 124 |

TABLE 16-continued
Mercaptans of the type A—SH
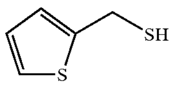
125
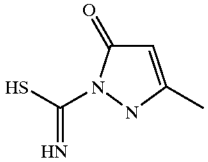
126
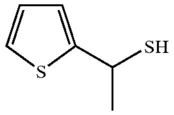
127
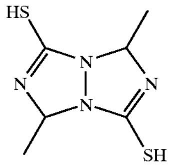
128
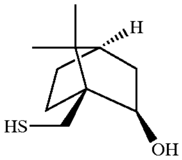
129
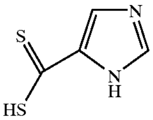
130
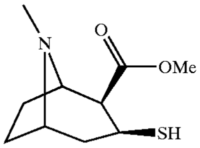
131
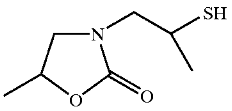
132
TABLE 16-continued
Mercaptans of the type A—SH
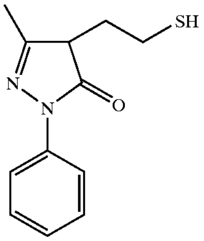
133
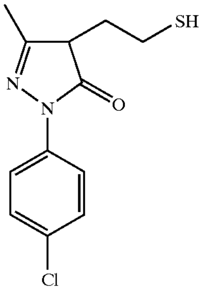
134
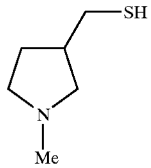
135
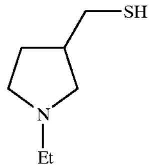
136
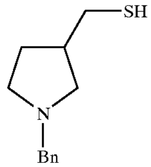
137
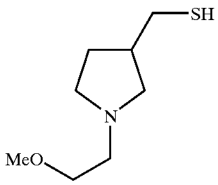
138
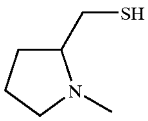
139

TABLE 16-continued
Mercaptans of the type A—SH
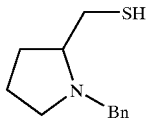
140
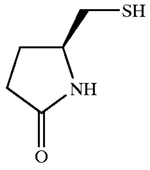
141
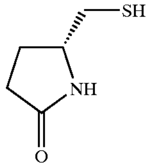
142
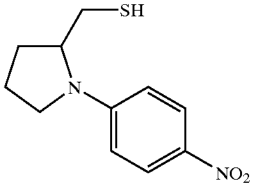
143
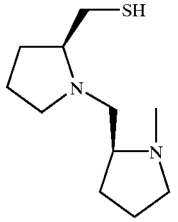
144
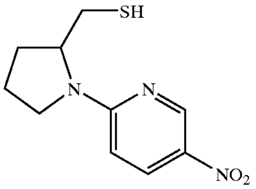
145
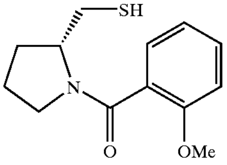
146
TABLE 16-continued
Mercaptans of the type A—SH
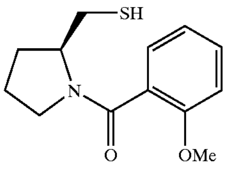
147
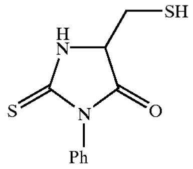
148
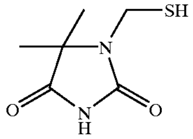
149
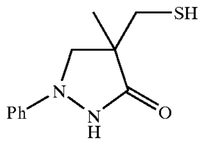
150
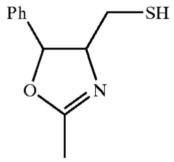
151
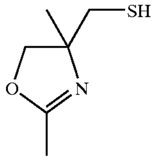
152
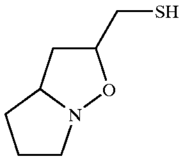
153
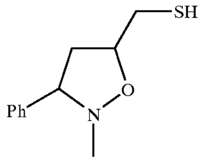
154

TABLE 16-continued
| Mercaptans of the type A—SH |
| --- |
| 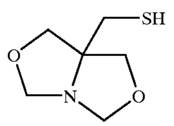 155 |
| 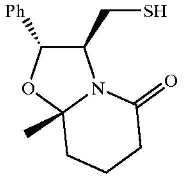 156 |
| 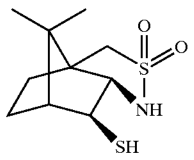 157 |
| 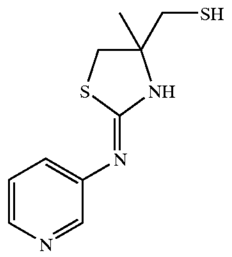 158 |
| 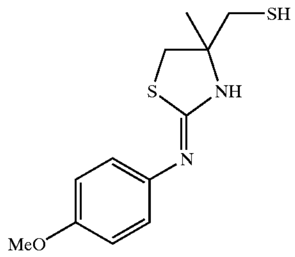 159 |
| 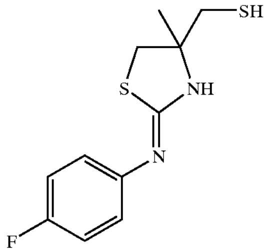 160 |
TABLE 16-continued
| Mercaptans of the type A—SH |
| --- |
| 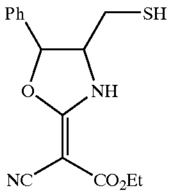 161 |
| 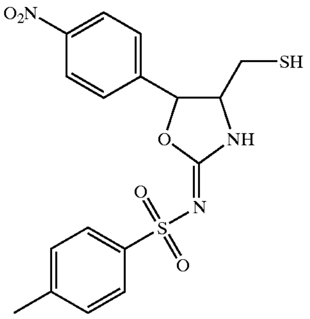 162 |
| 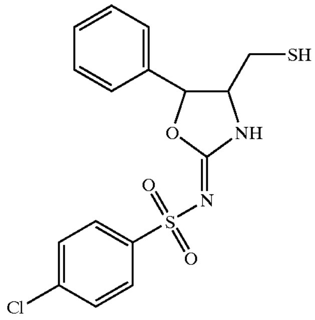 163 |
| 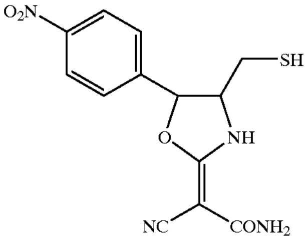 164 |
| 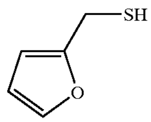 165 |
| 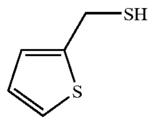 166 |

TABLE 16-continued
Mercaptans of the type A—SH
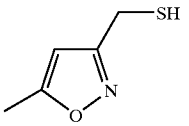
167
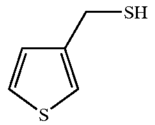
168
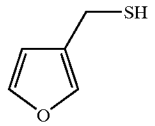
169
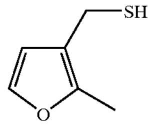
170
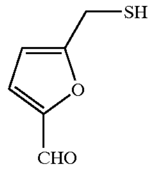
171
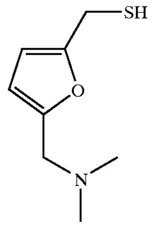
172
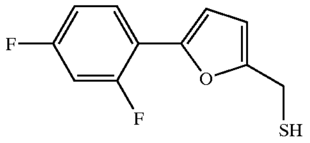
173
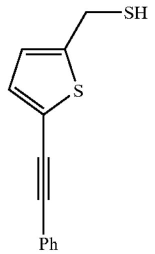
174
TABLE 16-continued
Mercaptans of the type A—SH
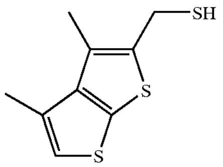
175
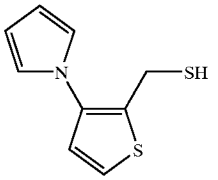
176
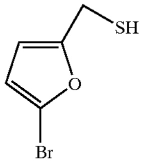
177
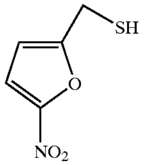
178
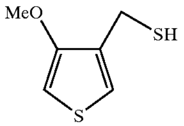
179
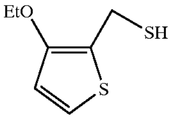
180
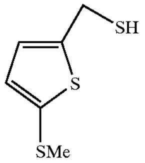
181
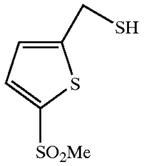
182

TABLE 16-continued
Mercaptans of the type A—SH
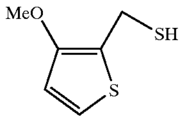
183
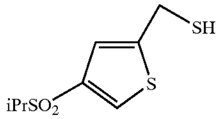
184
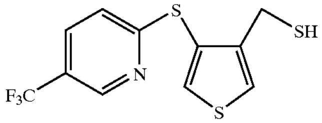
185
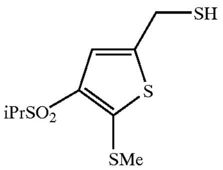
186
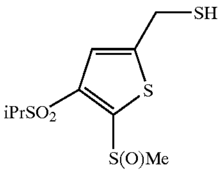
187
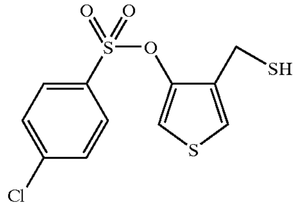
188
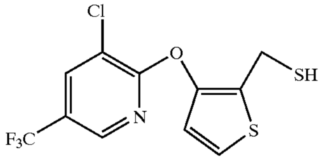
189
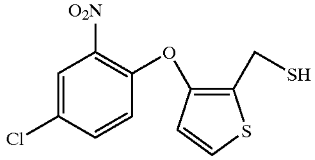
190
TABLE 16-continued
Mercaptans of the type A—SH
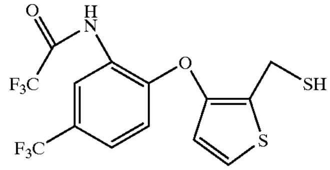
191
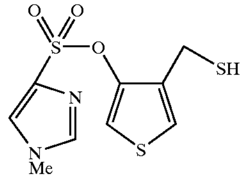
192
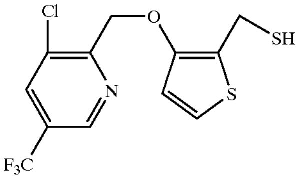
193
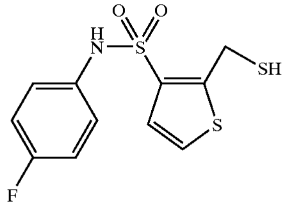
194
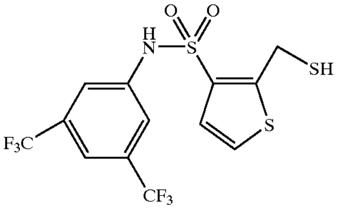
195
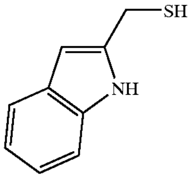
196
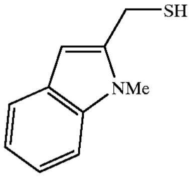
197

TABLE 16-continued
Mercaptans of the type A—SH
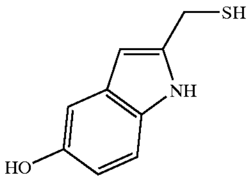
198
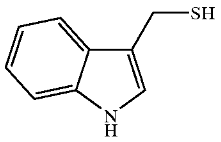
199
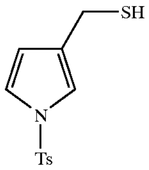
200
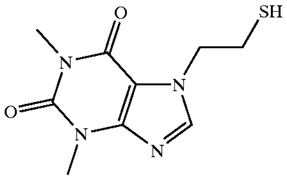
201
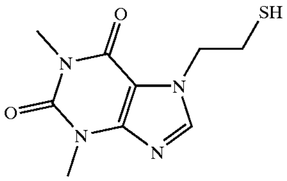
202
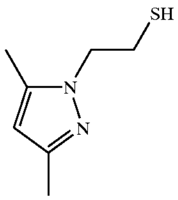
203
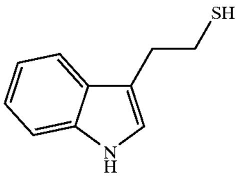
204
TABLE 16-continued
Mercaptans of the type A—SH
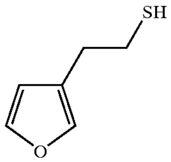
205
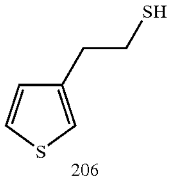
206
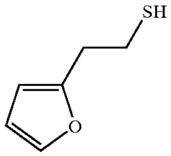
207
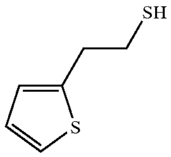
208
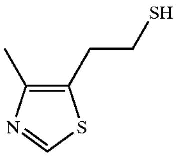
209
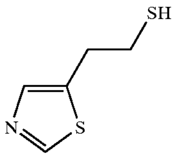
210
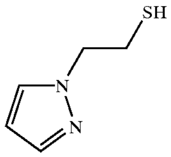
211
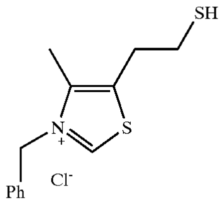
212

TABLE 16-continued
Mercaptans of the type A—SH
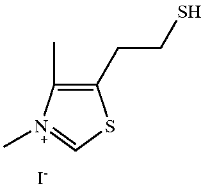
213
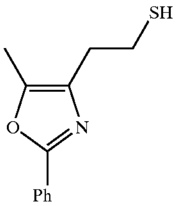
214
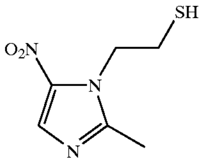
215
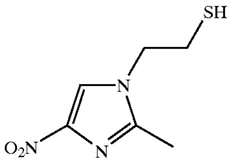
216
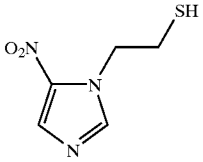
217
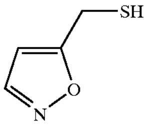
218
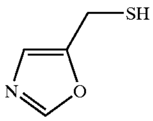
219
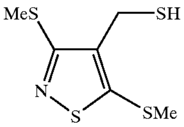
220
TABLE 16-continued
Mercaptans of the type A—SH
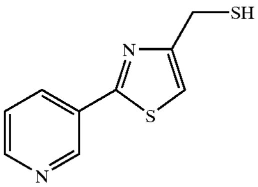
221
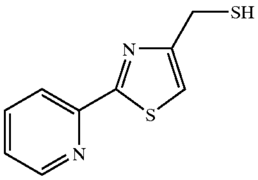
222
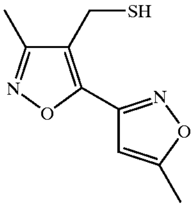
223
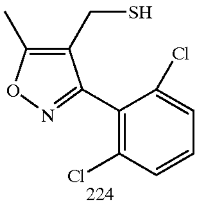
224
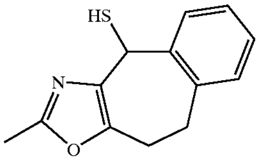
225
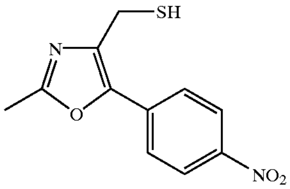
226
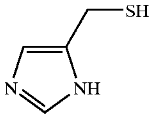
227
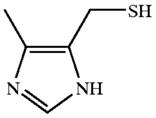

TABLE 16-continued
| Mercaptans of the type A—SH |
|---|
228
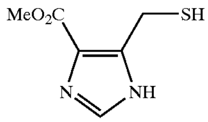
229
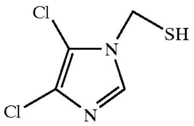
230
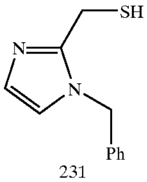
231
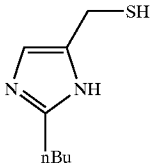
232
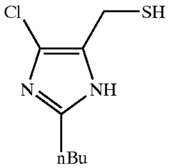
233
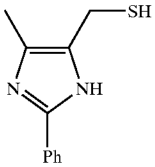
234
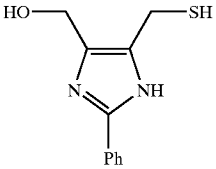
235
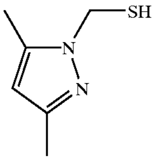
236
TABLE 16-continued
| Mercaptans of the type A—SH |
|---|
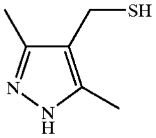
237
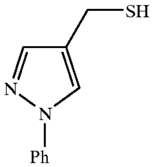
238
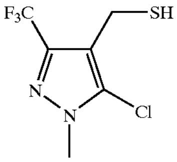
239
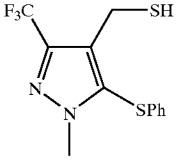
240
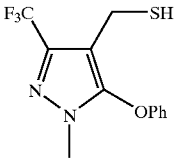
241
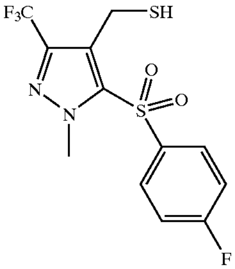
242
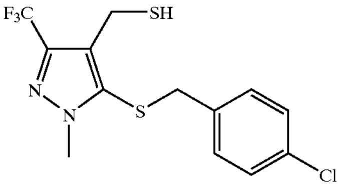
243

TABLE 16-continued
Mercaptans of the type A—SH
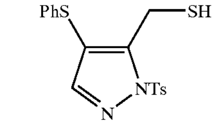
244
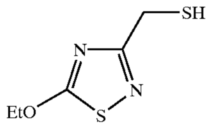
245
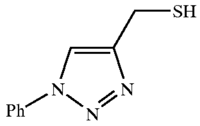
246
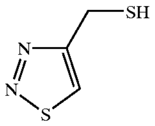
247
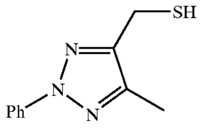
248
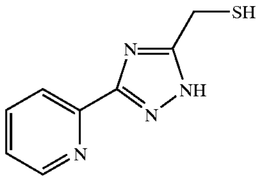
249
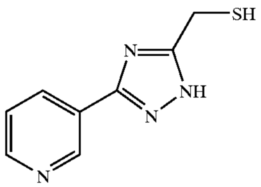
250
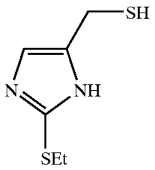
251
TABLE 16-continued
Mercaptans of the type A—SH
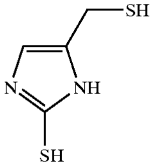
252
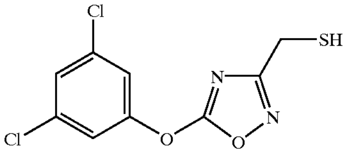
253
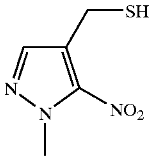
254
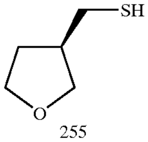
255
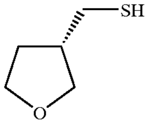
256
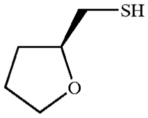
257
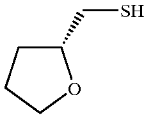
258
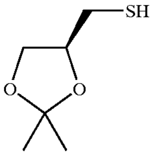
259
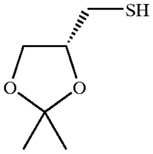

TABLE 16-continued
Mercaptans of the type A—SH
260
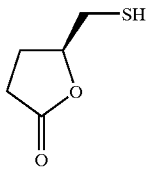
261
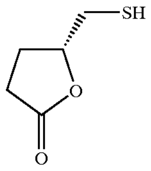
262
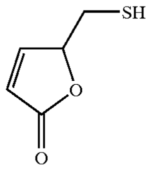
263
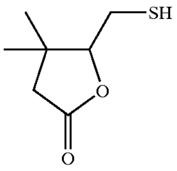
264
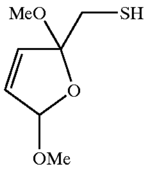
265
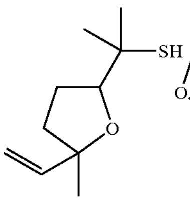
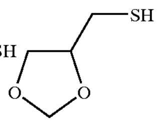
266
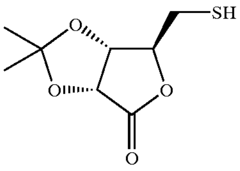
267
TABLE 16-continued
Mercaptans of the type A—SH
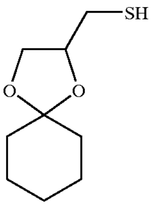
268
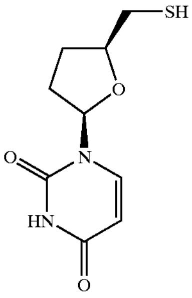
269
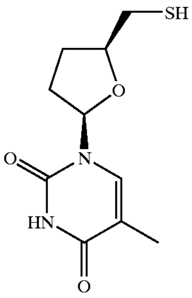
270
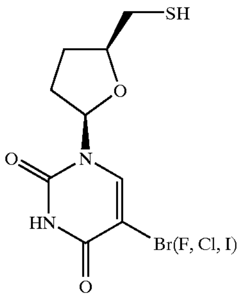
271
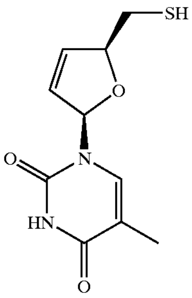
272

TABLE 16-continued
| Mercaptans of the type A—SH |
|---|
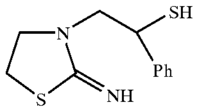
273
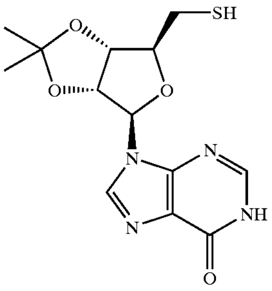
274
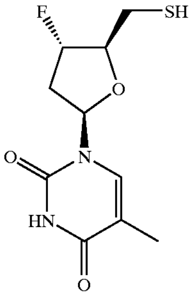
275
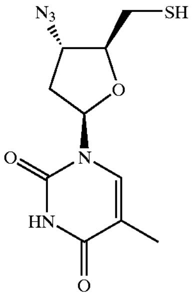
276
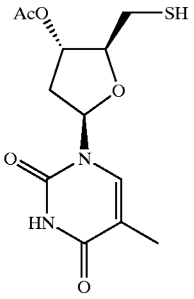
277
TABLE 16-continued
| Mercaptans of the type A—SH |
|---|
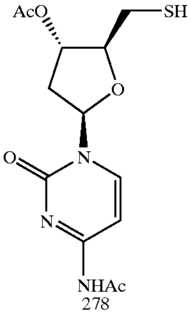
278
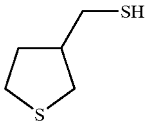
279
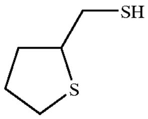
280
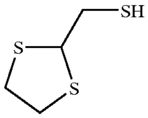
281
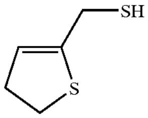
282
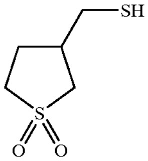
283
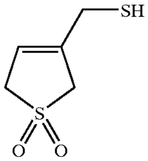
284
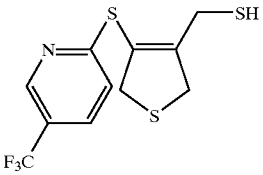
285

TABLE 16-continued
| Mercaptans of the type A—SH |
|---|
| 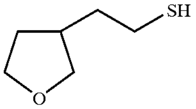 286 |
| 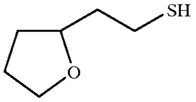 287 |
| 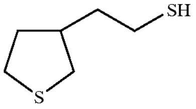 288 |
| 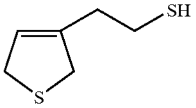 289 |
| 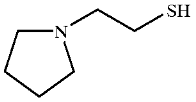 290 |
| 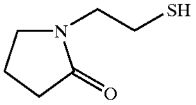 291 |
| 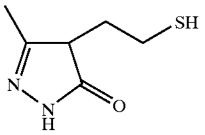 292 |
| 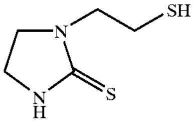 293 |
| 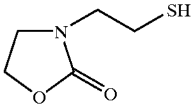 294 |
| 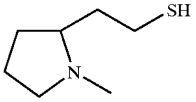 295 |
TABLE 16-continued
| Mercaptans of the type A—SH |
|---|
| 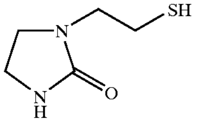 296 |
| 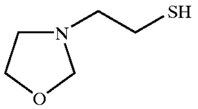 297 |
| 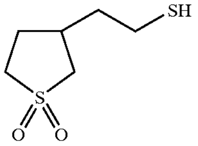 298 |
| 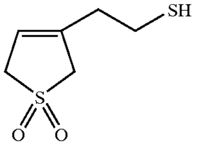 299 |
| 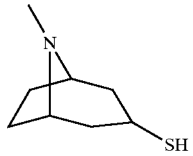 300 |
| 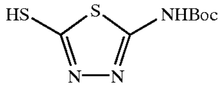 301 |
| 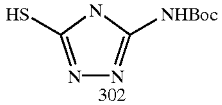 302 |
| 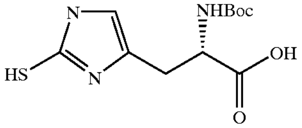 303 |
| 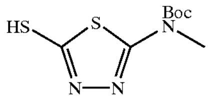 304 |
| 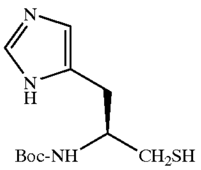 |

TABLE 16-continued
Mercaptans of the type A—SH
305
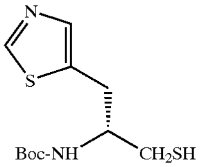
306
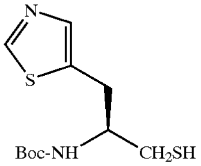
307
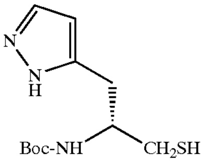
308
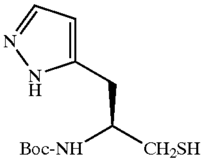
309
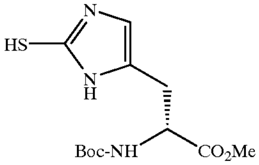
310
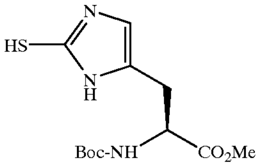
311
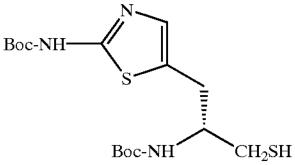
312
TABLE 16-continued
Mercaptans of the type A—SH
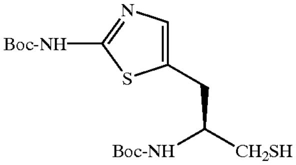
313
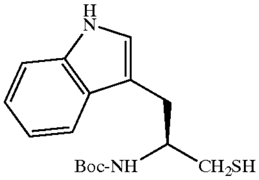
314
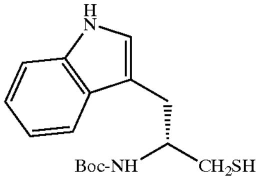
315
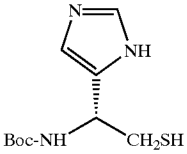
316
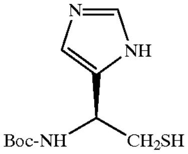
317
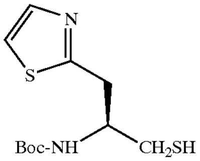
318
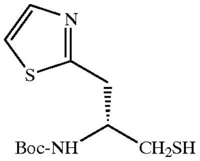
319

TABLE 16-continued
| Mercaptans of the type A—SH |
|---|
| 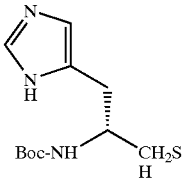 320 |
| 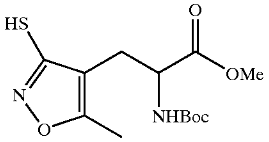 321 |
| 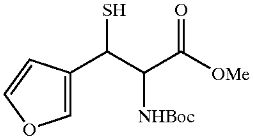 322 |
| 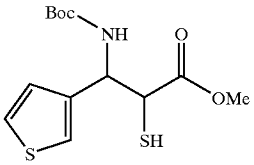 323 |
| 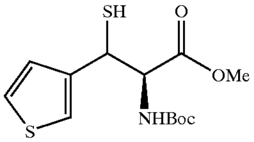 324 |
| 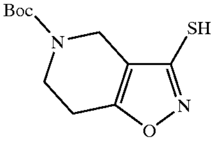 325 |
| 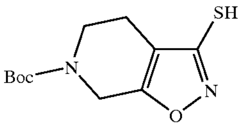 326 |
| 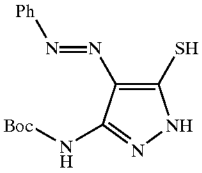 327 |
TABLE 16-continued
| Mercaptans of the type A—SH |
|---|
| 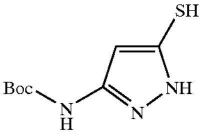 328 |
| 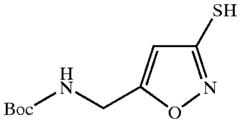 329 |
| 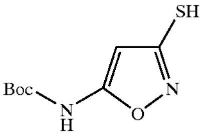 330 |
| 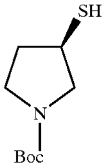 331 |
| 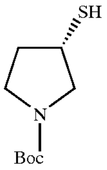 332 |
| 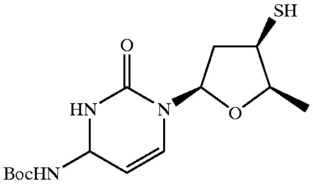 333 |
| 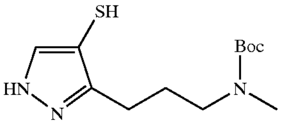 334 |
| 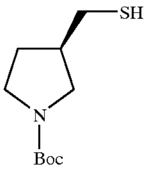 335 |

TABLE 16-continued
Mercaptans of the type A—SH
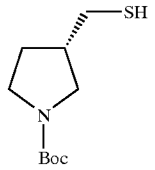
336
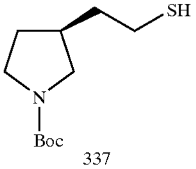
337
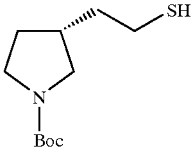
338
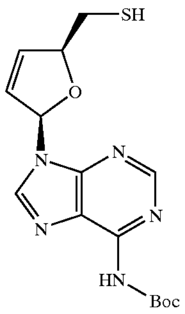
339
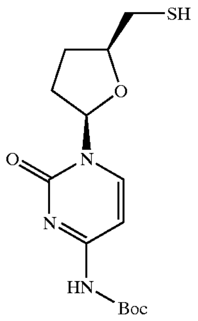
340
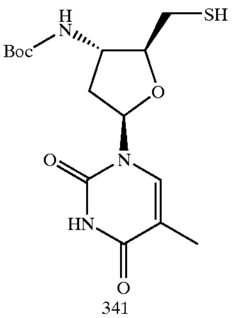
341
TABLE 16-continued
Mercaptans of the type A—SH
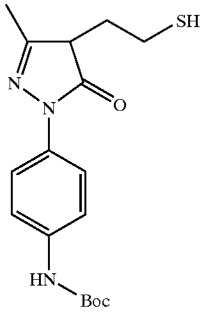
342
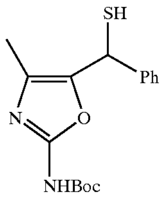
343
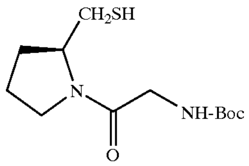
344
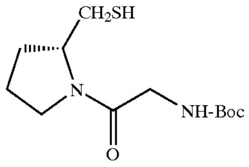
345
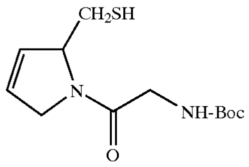
346
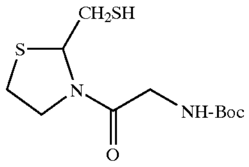
347
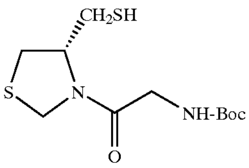
348

TABLE 16-continued
Mercaptans of the type A—SH
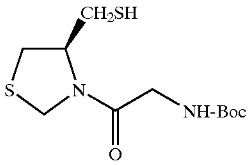
349
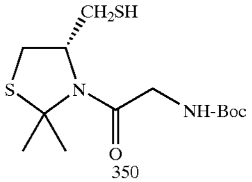
350
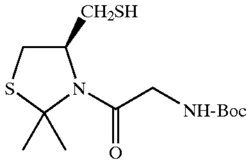
351
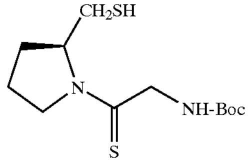
352
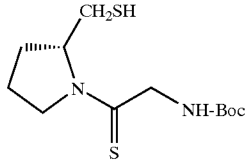
353
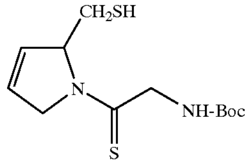
354
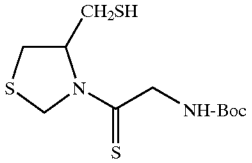
355
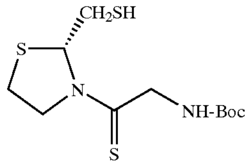
TABLE 16-continued
Mercaptans of the type A—SH
356
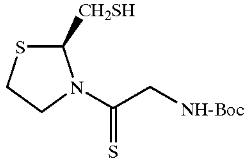
357
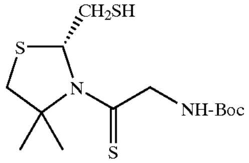
358
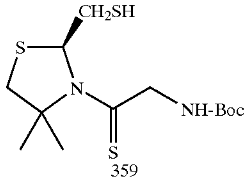
359
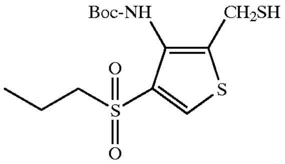
360
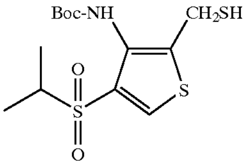
361
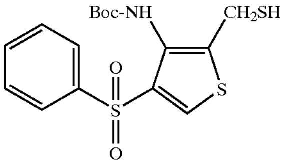
362
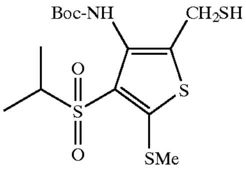
363
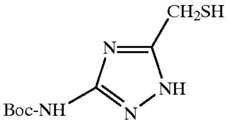

TABLE 16-continued
| Mercaptans of the type A—SH |
|---|
| 364 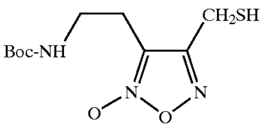 |
| 365 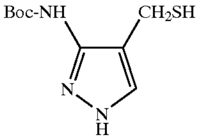 |
| 366 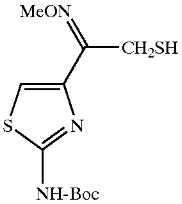 |
| 367 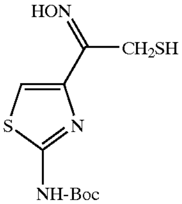 |
| 368 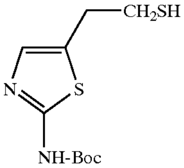 |
| 369 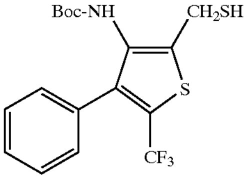 |
| 370 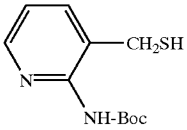 |
| 371 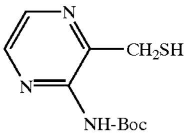 |
TABLE 16-continued
| Mercaptans of the type A—SH |
|---|
| 372 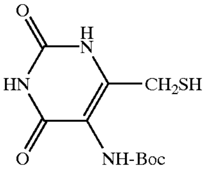 |
| 373 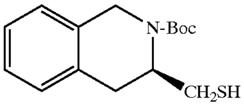 |
| 374 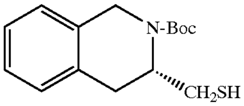 |
| 375 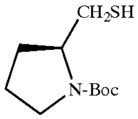 |
| 376 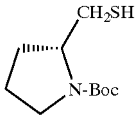 |
| 377 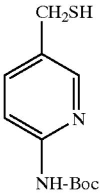 |
| 378 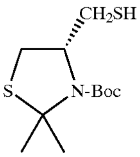 |
| 379 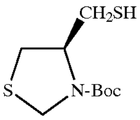 |
| 380 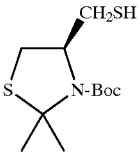 |

TABLE 16-continued
| Mercaptans of the type A—SH |
| --- |
| 381 |
| 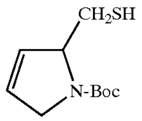 |
| 382 |
| 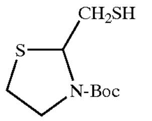 |
| 383 |
| 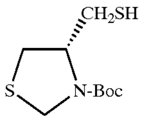 |
| 384 |
| 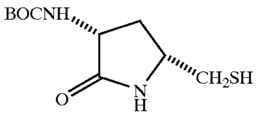 |
| 385 |
| 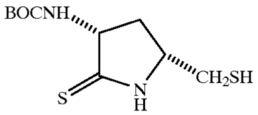 |
| 386 |
| 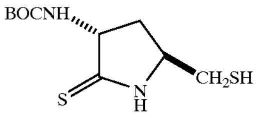 |
| 387 |
| 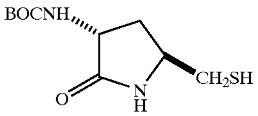 |
| 388 |
| 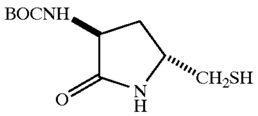 |
| 389 |
| 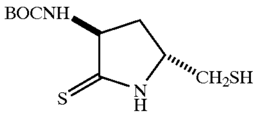 |
| 390 |
| 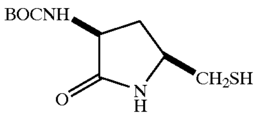 |
| 391 |
TABLE 16-continued
| Mercaptans of the type A—SH |
| --- |
| 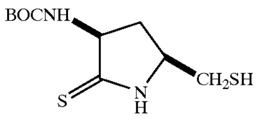 |
| 392 |
| 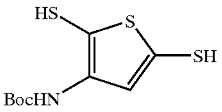 |
| 393 |
| 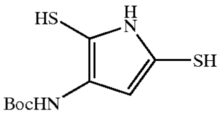 |
| 394 |
| 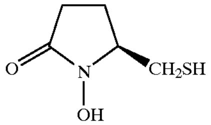 |
| 395 |
| 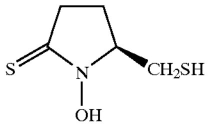 |
| 396 |
| 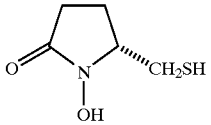 |
| 397 |
| 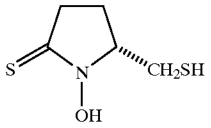 |
| 398 |
| 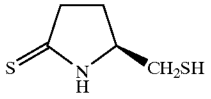 |
| 399 |
| 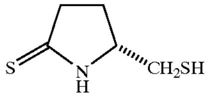 |
| 400 |

TABLE 17
Halides of the type A—Cl, A—Br, and A—I
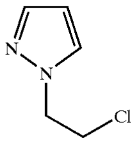
1
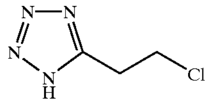
2
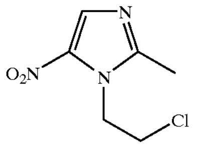
3
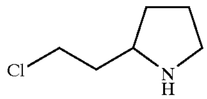
4
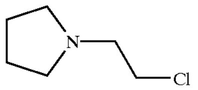
5
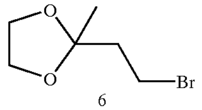
6
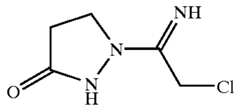
7
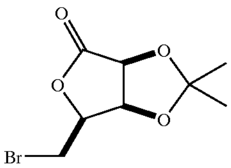
8
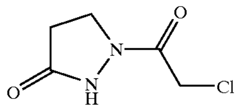
9
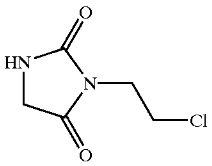
10
TABLE 17-continued
Halides of the type A—Cl, A—Br, and A—I
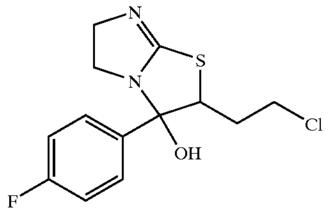
11
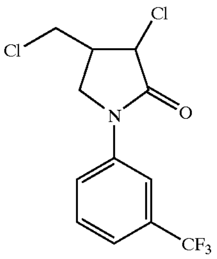
12
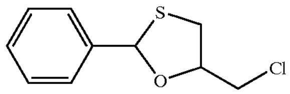
13
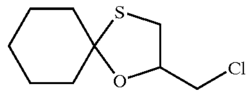
14
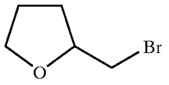
15
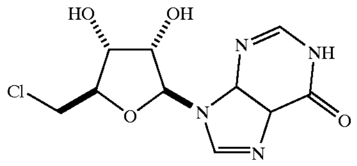
16
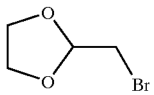
17
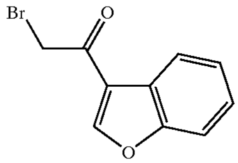
18

TABLE 17-continued
| Halides of the type A—Cl, A—Br, and A—I |
| --- |
| 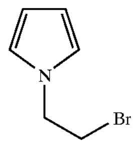 |
| 19 |
| 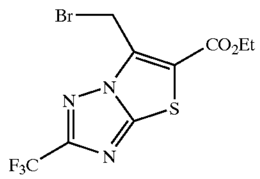 |
| 20 |
| 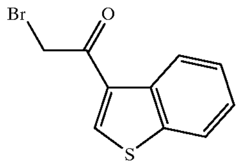 |
| 21 |
| 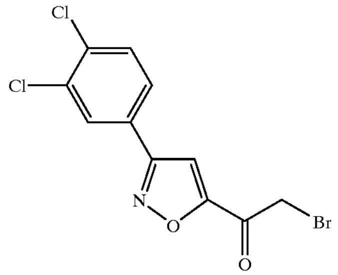 |
| 22 |
| 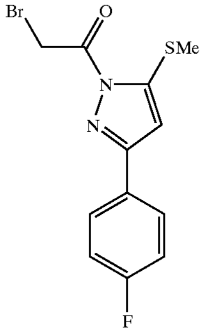 |
| 23 |
| 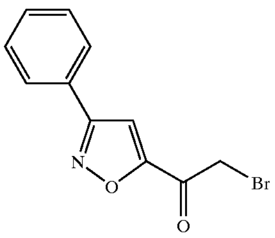 |
| 24 |
TABLE 17-continued
| Halides of the type A—Cl, A—Br, and A—I |
| --- |
| 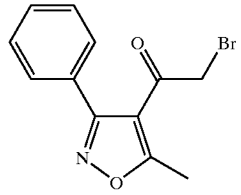 |
| 25 |
| 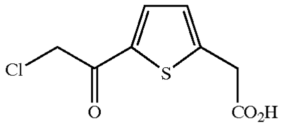 |
| 26 |
| 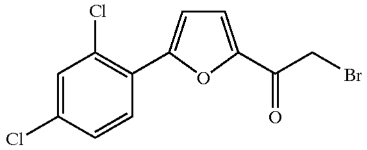 |
| 27 |
| 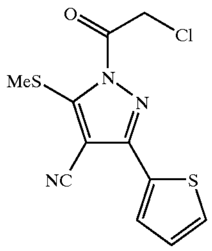 |
| 28 |
| 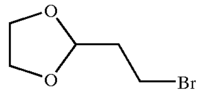 |
| 29 |
| 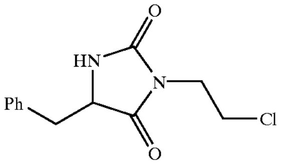 |
| 30 |
| 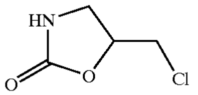 |
| 31 |
| 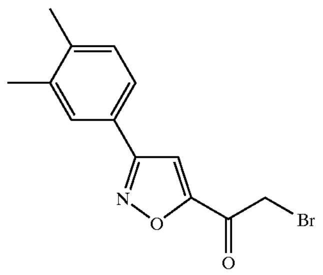 |

TABLE 17-continued
Halides of the type A—Cl, A—Br, and A—I
32
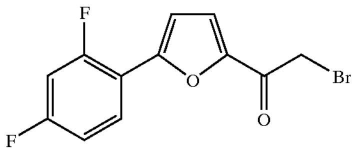
33
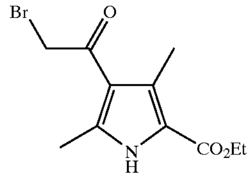
34
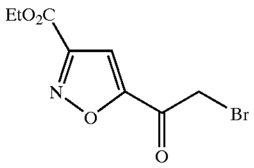
35
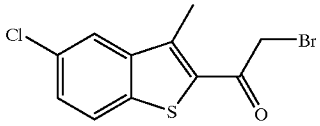
36
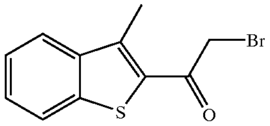
37
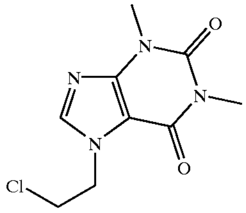
38
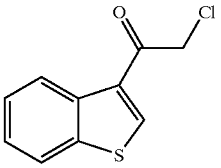
39
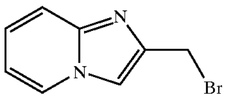
40
TABLE 17-continued
Halides of the type A—Cl, A—Br, and A—I
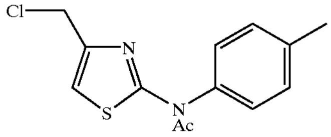
41
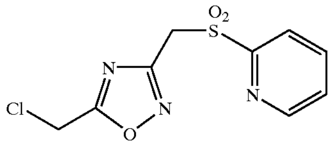
42
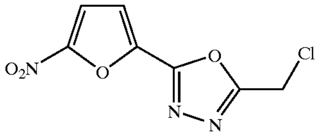
43
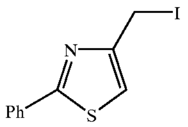
44
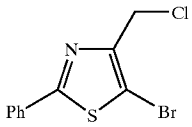
45
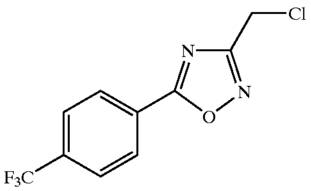
46
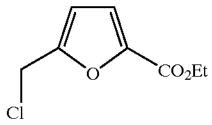
47
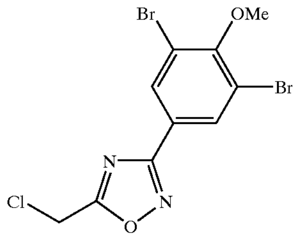
48

TABLE 17-continued
Halides of the type A—Cl, A—Br, and A—I
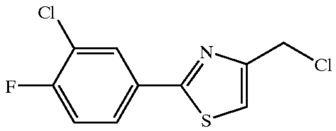
49
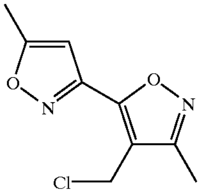
50
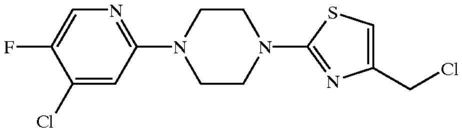
51
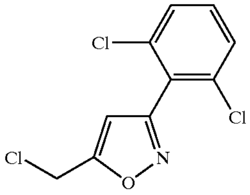
52
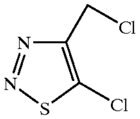
53
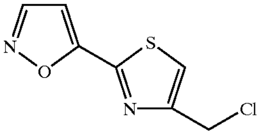
54
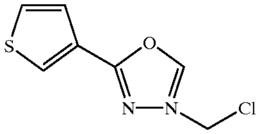
55
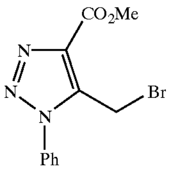
56
TABLE 17-continued
Halides of the type A—Cl, A—Br, and A—I
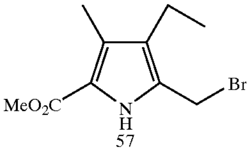
57
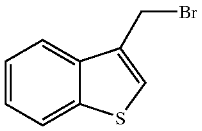
58
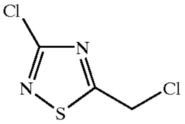
59
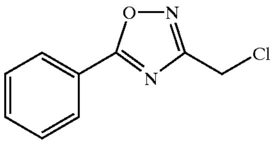
60
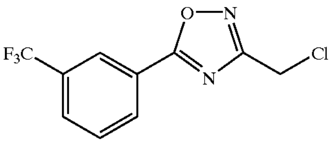
61
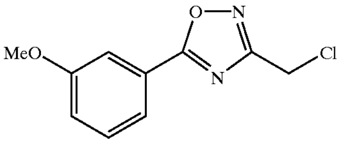
62
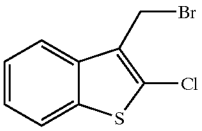
63
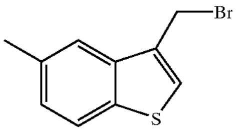
64
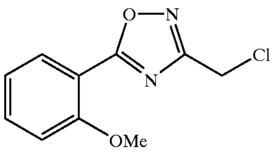
65

TABLE 17-continued
Halides of the type A—Cl, A—Br, and A—I
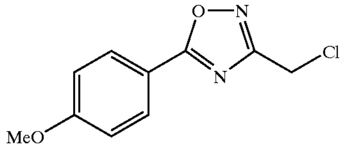
66
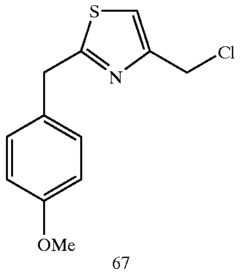
67
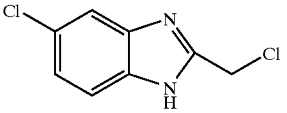
68
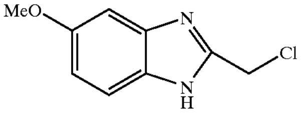
69
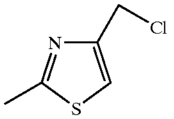
70
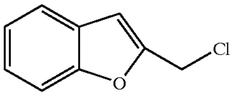
71
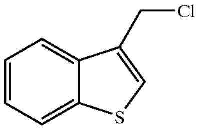
72
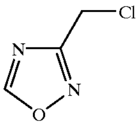
73
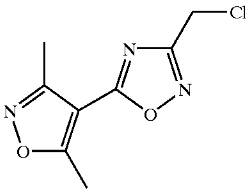
TABLE 17-continued
Halides of the type A—Cl, A—Br, and A—I
74
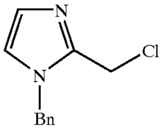
75
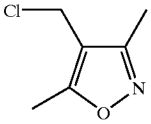
76
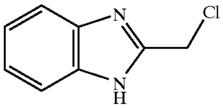
77
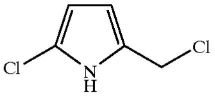
78
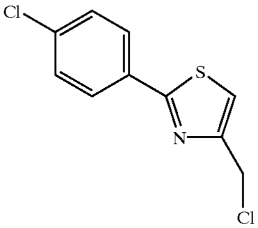
79
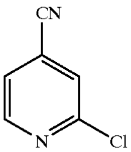
80
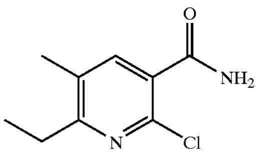
81
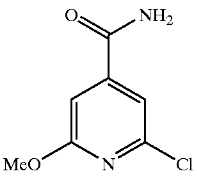
82

TABLE 17-continued
Halides of the type A—Cl, A—Br, and A—I
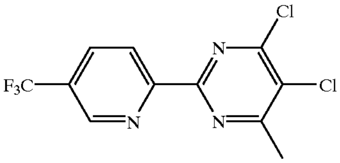
83
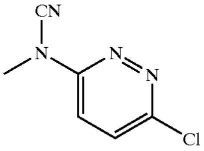
84
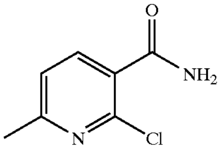
85
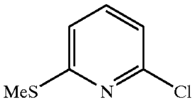
86
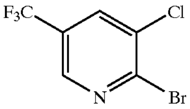
87
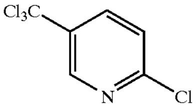
88
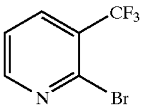
89
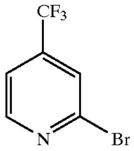
90
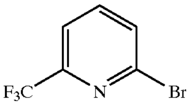
91
TABLE 17-continued
Halides of the type A—Cl, A—Br, and A—I
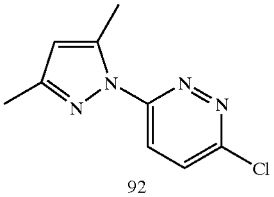
92
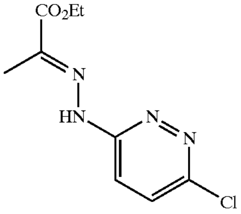
93
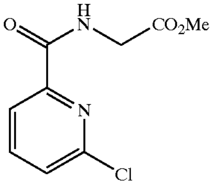
94
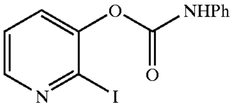
95
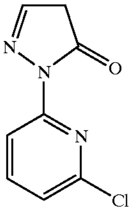
96
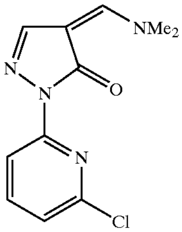
97
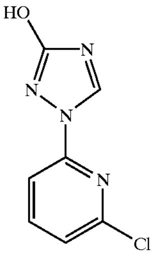

TABLE 17-continued
| Halides of the type A—Cl, A—Br, and A—I |
| --- |
| 98 |
| 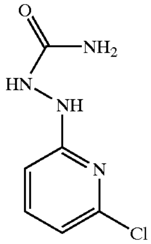 |
| 99 |
| 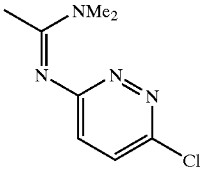 |
| 100 |
| 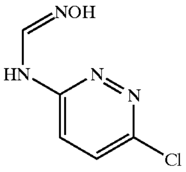 |
| 101 |
| 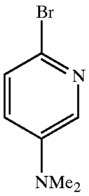 |
| 102 |
| 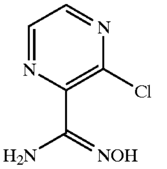 |
| 103 |
| 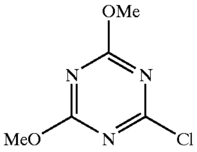 |
| 104 |
TABLE 17-continued
| Halides of the type A—Cl, A—Br, and A—I |
| --- |
| 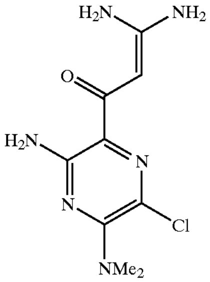 |
| 105 |
| 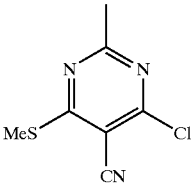 |
| 106 |
| 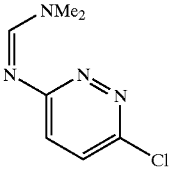 |
| 107 |
| 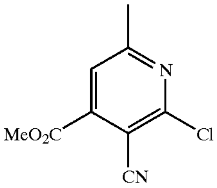 |
| 108 |
| 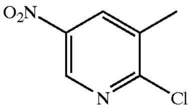 |
| 109 |
| 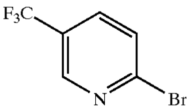 |
| 110 |
| 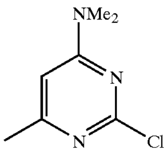 |
| 111 |

TABLE 17-continued
| Halides of the type A—Cl, A—Br, and A—I |
|---|
| 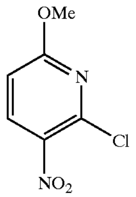 |
| 112 |
| 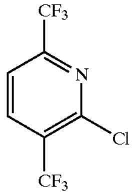 |
| 113 |
| 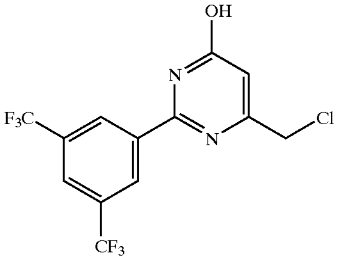 |
| 114 |
| 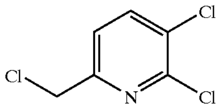 |
| 115 |
| 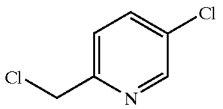 |
| 116 |
| 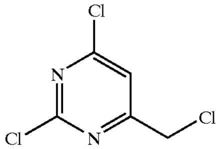 |
| 117 |
| 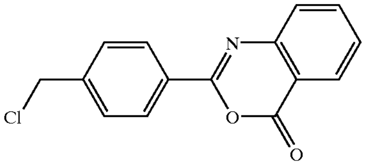 |
| 118 |
TABLE 17-continued
| Halides of the type A—Cl, A—Br, and A—I |
|---|
| 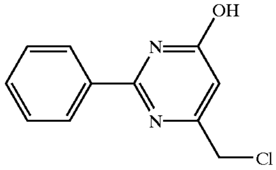 |
| 119 |
| 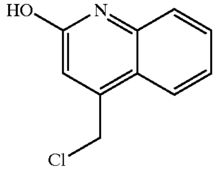 |
| 120 |
| 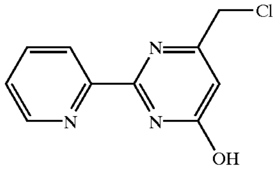 |
| 121 |
| 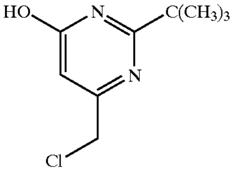 |
| 122 |
| 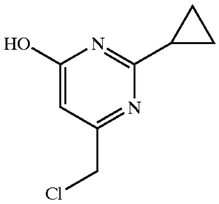 |
| 123 |
| 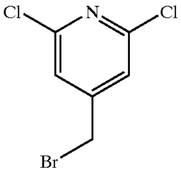 |
| 124 |
| 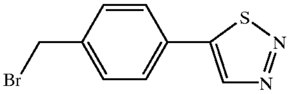 |
| 125 |
| 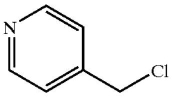 |
| 126 |

TABLE 17-continued
| Halides of the type A—Cl, A—Br, and A—I |
|---|
| 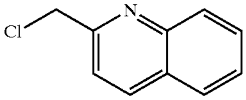 127 |
| 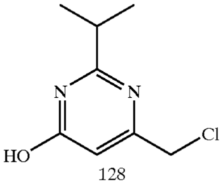 128 |
| 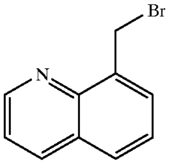 129 |
| 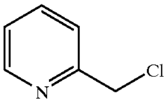 130 |
| 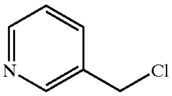 131 |
| 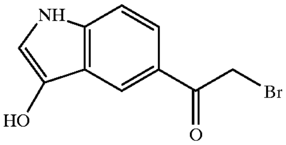 132 |
| 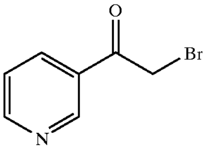 133 |
| 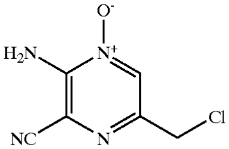 134 |
| 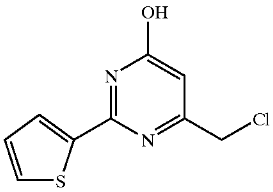 135 |
TABLE 17-continued
| Halides of the type A—Cl, A—Br, and A—I |
|---|
| 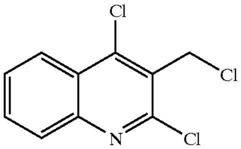 136 |
| 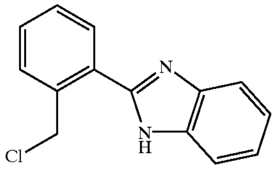 137 |
| 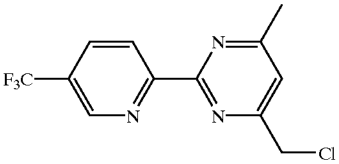 138 |
| 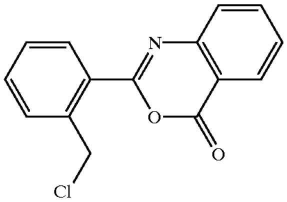 139 |
| 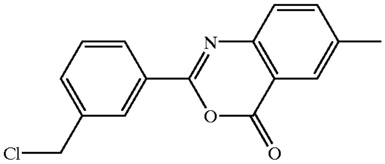 140 |
| 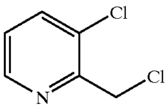 141 |
| 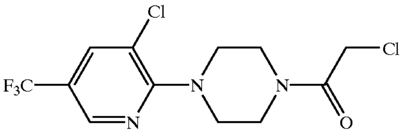 142 |
| 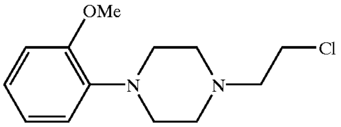 143 |

TABLE 17-continued
| Halides of the type A—Cl, A—Br, and A—I |
| --- |
| 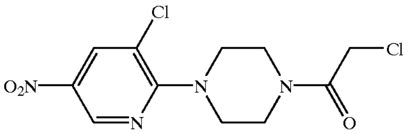 |
| 144 |
| 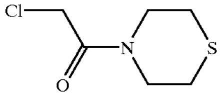 |
| 145 |
| 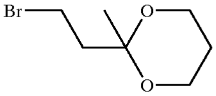 |
| 146 |
| 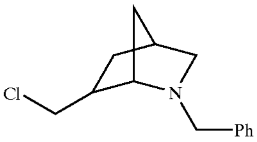 |
| 147 |
| 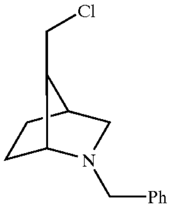 |
| 148 |
| 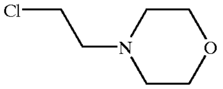 |
| 149 |
| 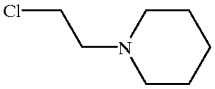 |
| 150 |
| 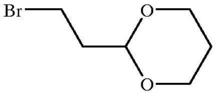 |
| 151 |
| 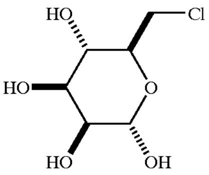 |
| 152 |
TABLE 17-continued
| Halides of the type A—Cl, A—Br, and A—I |
| --- |
| 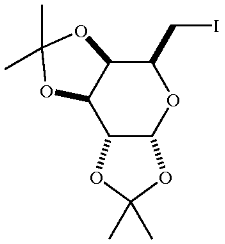 |
| 153 |
| 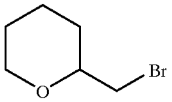 |
| 154 |
| 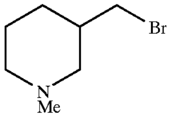 |
| 155 |
| 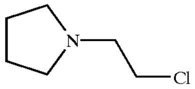 |
| 156 |
| 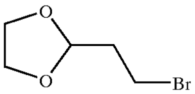 |
| 157 |
| 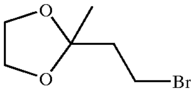 |
| 158 |
| 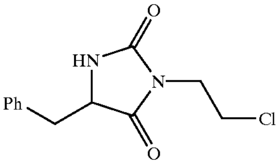 |
| 159 |
| 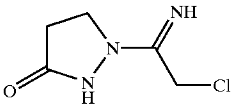 |
| 160 |
| 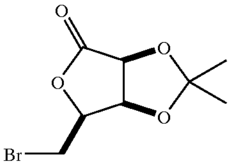 |
| 161 |

TABLE 17-continued
Halides of the type A—Cl, A—Br, and A—I
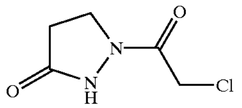
162
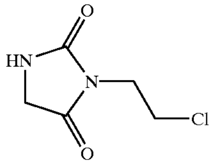
163
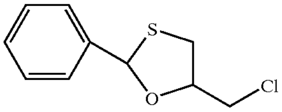
164
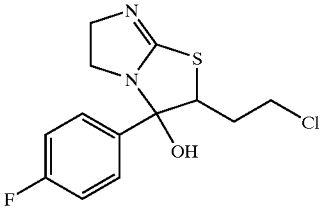
165
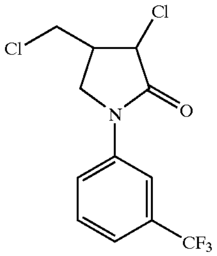
166
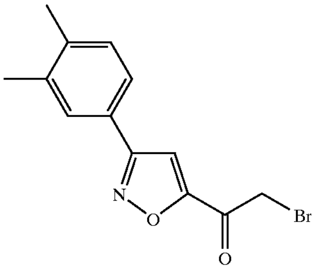
167
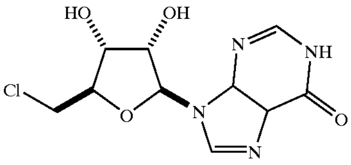
168
TABLE 17-continued
Halides of the type A—Cl, A—Br, and A—I
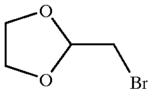
169
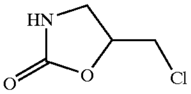
170
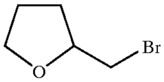
171
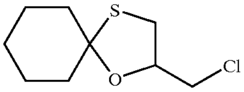
172
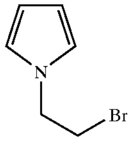
173
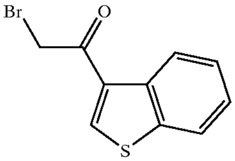
174
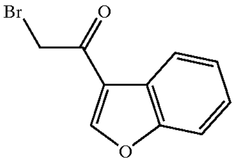
175
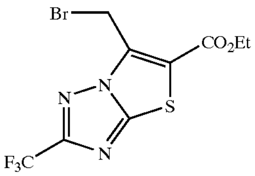
176
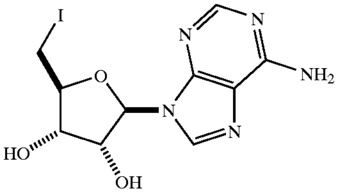
177

TABLE 17-continued
Halides of the type A—Cl, A—Br, and A—I
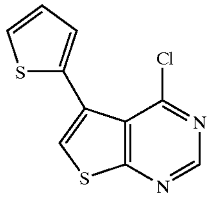
178
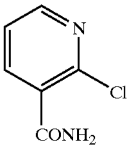
179
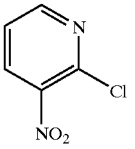
180
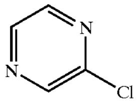
181
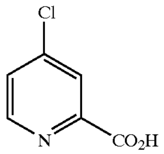
182
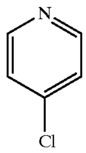
183
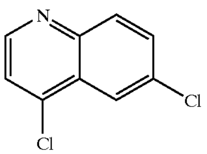
184
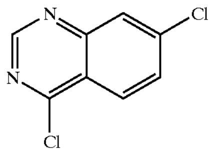
185
TABLE 17-continued
Halides of the type A—Cl, A—Br, and A—I
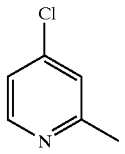
186
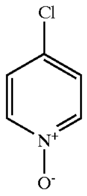
187
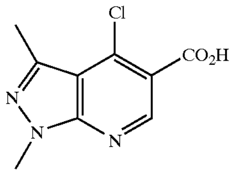
188
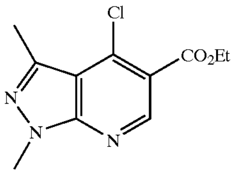
189
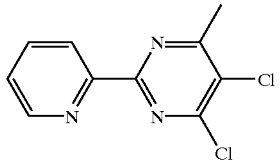
190
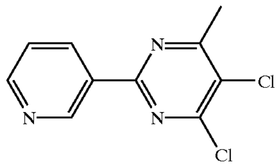
191
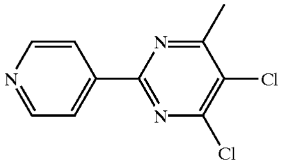
192

TABLE 17-continued
| Halides of the type A—Cl, A—Br, and A—I |
|---|
| 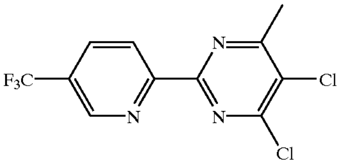 193 |
| 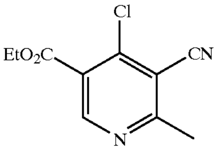 194 |
| 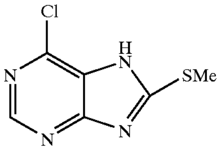 195 |
| 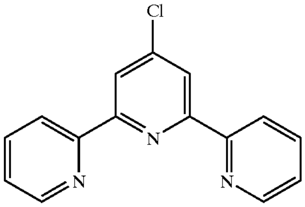 196 |
| 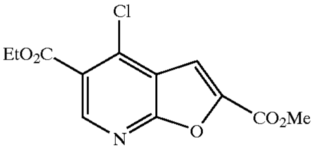 197 |
| 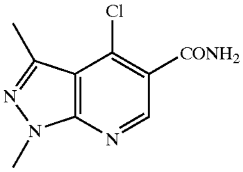 198 |
| 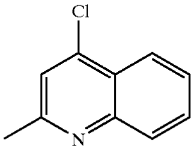 199 |
| 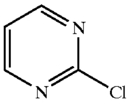 200 |
TABLE 17-continued
| Halides of the type A—Cl, A—Br, and A—I |
|---|
| 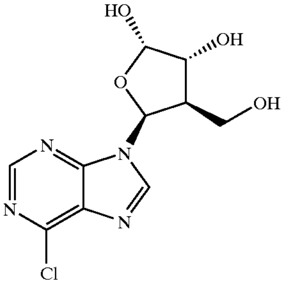 201 |
| 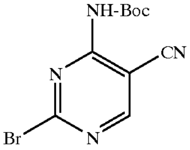 202 |
| 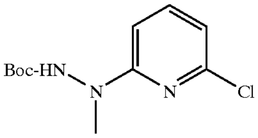 203 |
| 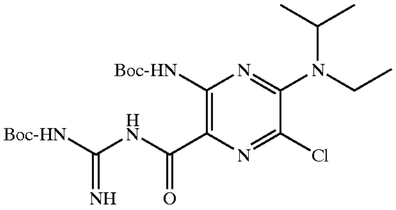 204 |
| 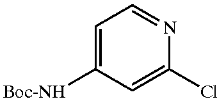 205 |
| 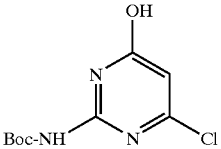 206 |
| 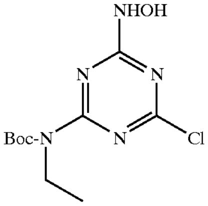 207 |

TABLE 17-continued
| Halides of the type A—Cl, A—Br, and A—I |
|---|
| 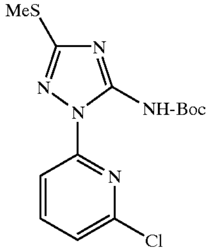 208 |
| 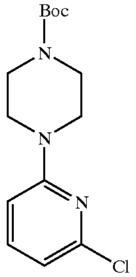 209 |
| 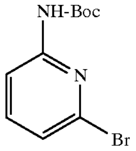 210 |
| 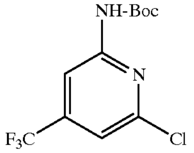 211 |
| 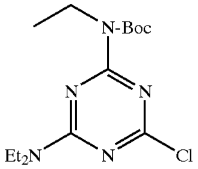 212 |
| 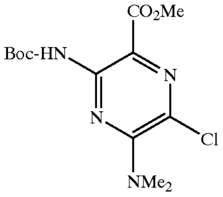 213 |
TABLE 17-continued
| Halides of the type A—Cl, A—Br, and A—I |
|---|
| 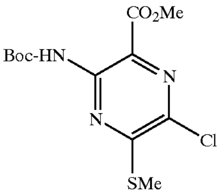 214 |
| 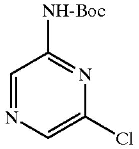 215 |
| 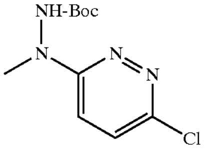 216 |
| 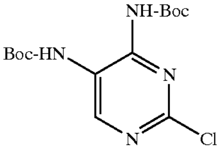 217 |
| 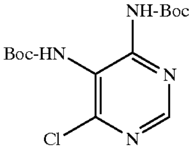 218 |
| 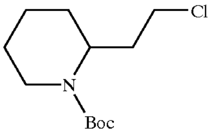 219 |
| 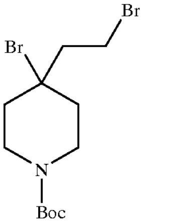 220 |
| 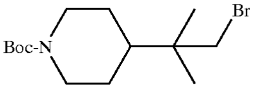 221 |

TABLE 17-continued
| Halides of the type A—Cl, A—Br, and A—I |
|---|
| 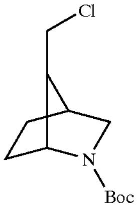 222 |
| 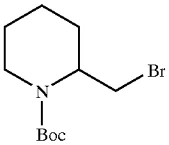 223 |
| 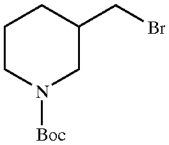 224 |
| 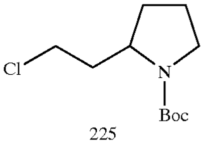 225 |
| 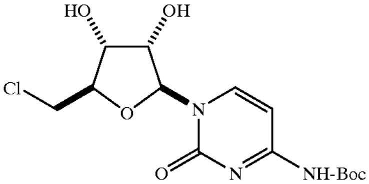 226 |
| 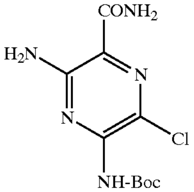 227 |
| 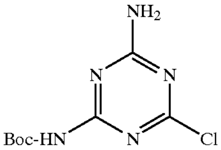 228 |
| 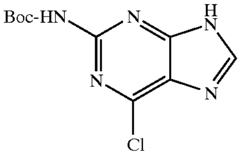 229 |
| 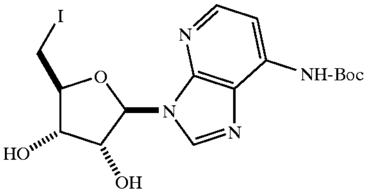 230 |
| 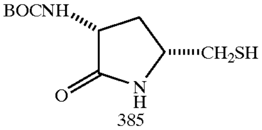 385 |
| 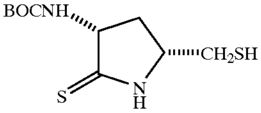 386 |
| 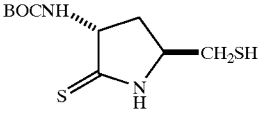 387 |
| 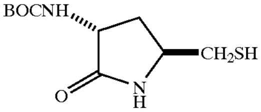 388 |
| 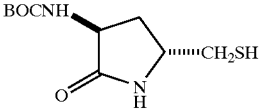 389 |
| 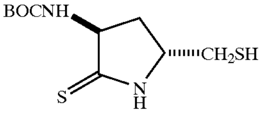 390 |
| 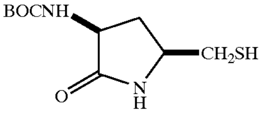 391 |
| 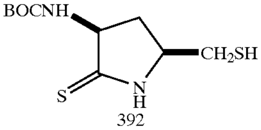 392 |
| 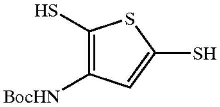 393 |

TABLE 17-continued
| Halides of the type A—Cl, A—Br, and A—I |
|---|
| 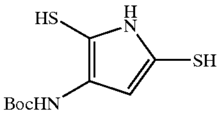 394 |
| 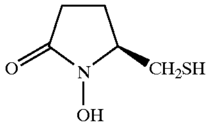 395 |
| 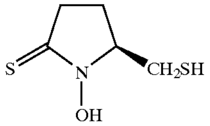 396 |
| 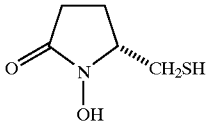 397 |
| 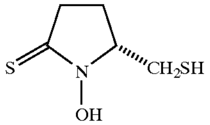 398 |
| 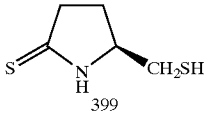 399 |
| 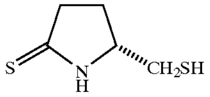 400 |
TABLE 18
| Sulfonyl chlorides of the type A—$SO_2Cl$ |
|---|
| 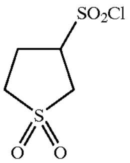 1 |
| 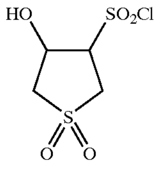 |
TABLE 18-continued
| Sulfonyl chlorides of the type A—$SO_2Cl$ |
|---|
| 2 |
| 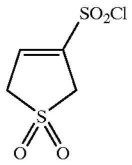 3 |
| 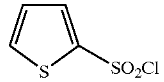 4 |
| 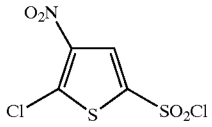 5 |
| 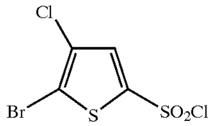 6 |
| 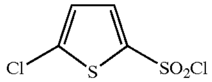 7 |
| 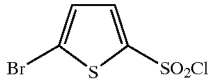 8 |
| 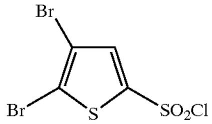 9 |
| 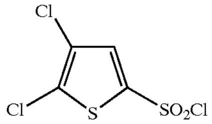 10 |
| 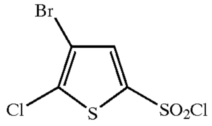 11 |
| 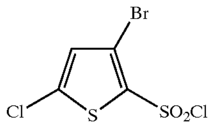 12 |

TABLE 18-continued
Sulfonyl chlorides of the type A—$SO_2Cl$
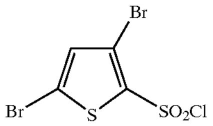
13
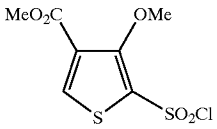
14
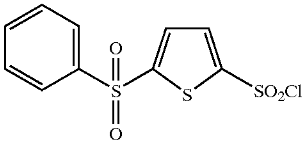
15
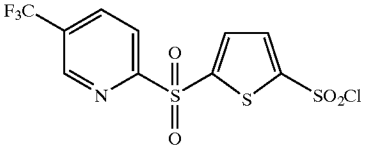
16
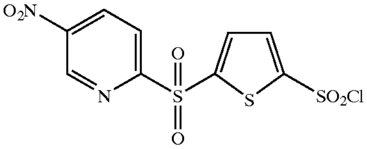
17
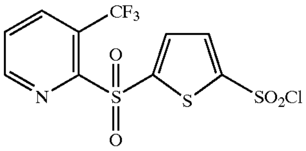
18
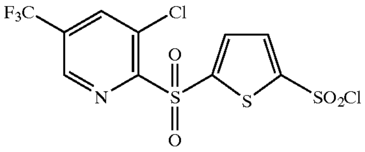
19
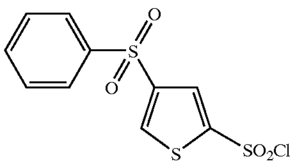
20
TABLE 18-continued
Sulfonyl chlorides of the type A—$SO_2Cl$
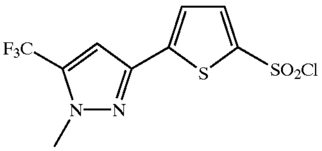
21
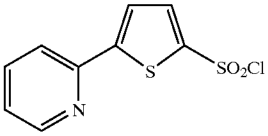
22
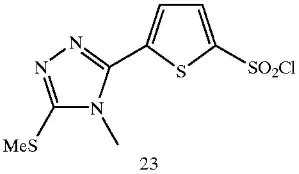
23
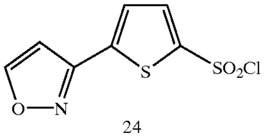
24
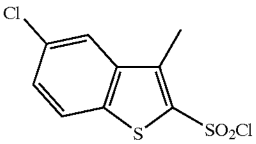
25
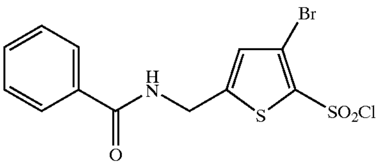
26
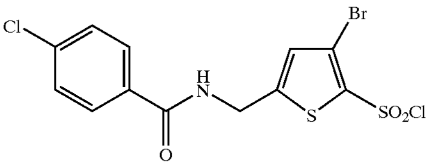
27
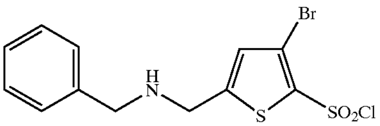
28
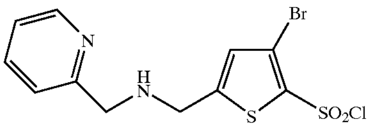

TABLE 18-continued
Sulfonyl chlorides of the type A—$SO_2Cl$
29
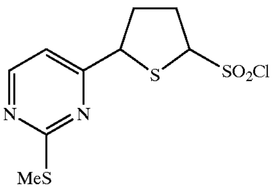
30
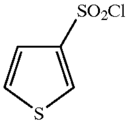
31
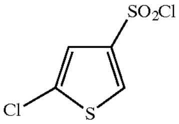
32
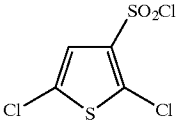
33
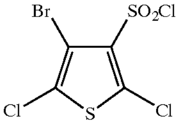
34
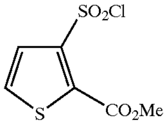
35
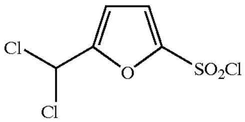
36
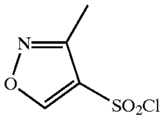
37
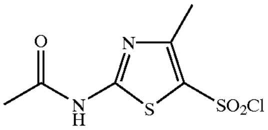
38
TABLE 18-continued
Sulfonyl chlorides of the type A—$SO_2Cl$
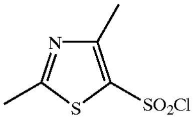
39
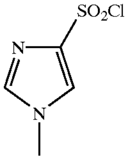
40
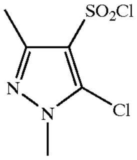
41
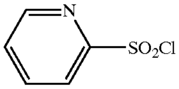
42
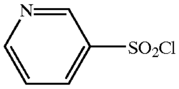
43
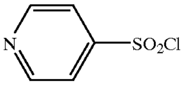
44
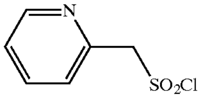
45
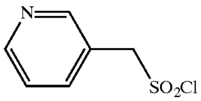
46
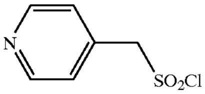
47
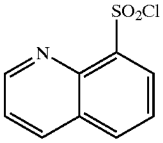
48

TABLE 18-continued

| Sulfonyl chlorides of the type A—$SO_2Cl$ |
| --- |
| 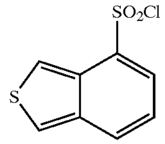 |
| 49 |
| 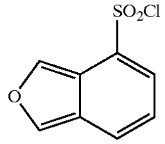 |
| 50 |
| 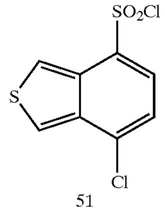 |
| 51 |
| 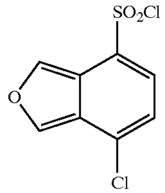 |
| 52 |
| 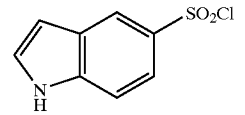 |
| 53 |
| 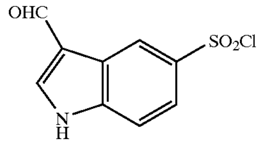 |
| 54 |
| 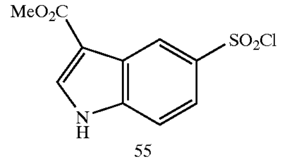 |
| 55 |

What is claimed is:

1. A compound of formula

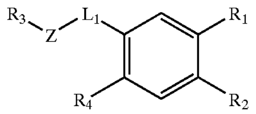

or a pharmaceutically acceptable salt thereof, wherein $L_1$ is —$L_4$—N($R_5$)—$L_5$— wherein $L_4$ and $L_5$ are absent or alkylene and $R_5$ is selected from the group consisting of hydrogen, cycloalkylalkyl, 3,5-difluorobenzyl, and arylalkyl;

$R_1$ is aryl-$L_2$— wherein $L_2$ is absent and the aryl is phenyl which can be optionally substituted;

$R_2$ is —C(O)—NH—CH—($R_{14}$)—COO$R_{15}$ wherein $R_{14}$ is thioalkoxyalkyl and $R_{15}$ is selected from the group consisting of hydrogen, alkanoyloxyalkyl, lower alkyl, and a carboxy protecting group;

$R_3$ is pyrid-3-yl;

$R_4$ is hydrogen; and

Z is absent.

2. A method of inhibiting farnesyltransferases or geranylgeranyltransferases in a mammal in need of such inhibition comprising administering to the mammal a therapeutically effective amount of a compound of claim 1.

3. A method for inhibiting post-translational modification of the oncogenic Ras protein by protein farnesyltransferase, protein geranylgeranyltransferase, or both, in a mammal comprising administering to the mammal a therapeutically effective amount of a compound of claim 1.

4. A compound according to claim 1 wherein the aryl is selected from the group consisting of unsubstituted phenyl, 2-trifluoromethylphenyl, 2-methylphenyl and 2-chloro-4-fluorophenyl.

5. A compound according to claim 1 wherein $R_{14}$ is 2-thiomethoxyethyl.

6. A compound according to claim 1 wherein $R_5$ is selected from the group consisting of hydrogen, cyclohexylmethyl, benzyl, and 3,5-difluorobenzyl.

7. A compound selected from the group consisting of (4-(3-pyridylaminomethyl)-2-phenylbenzoyl)methionine, lithium 4-(3-pyridylmethylamino)-2-phenylbenzoyl-L-homoserinate, (4-(3-pyridylmethylamino)-2-phenylbenzoyl)methionine, (4-(3-pyridylmethylamino)-2-phenylbenzoyl)methionine, isoamyl ester, (4-(3-pyridylmethylamino)-2-phenylbenzoyl)methionine, 1-adamantylethyl ester, (4-(3-pyridylmethylamino)-2-phenylbenzoyl)methionine, octyl ester, (4-(3-pyridylmethylamino)-2-phenylbenzoyl)methionine, methyl ester, (4-(pyrid-3-ylaminomethyl)-2-phenylbenzoyl) methionine, methyl ester, hydrochloride, (4-(pyrid-3-ylaminomethyl)-2-phenylbenzoyl) methionine, (4-(3-pyrdylaminomethyl)-2-phenylbenzoyl)methionine, isopropyl ester, N-(4-(3-pyridylaminomethyl)-2-phenylbenzoyl)-2-amino-4-(methylsulfonyl)butanoic acid methyl ester, N-(4-(3-pyridylaminomethyl)-2-phenylbenzoyl)-2-amino-4-(methylsulfonyl)butanoic acid, (4-(4-methylpyrid-3-ylaminomethyl)-2-phenylbenzoyl) methionine, sodium salt, (4-(4-methoxypyrid-3-ylaminomethyl)-2-phenylbenzoyl) methionine, sodium salt, (4-(3-pyridylmethylamino)-2-(2-methylphenyl)benzoyl) methionine, methyl ester, (4-(3-pyridylaminomethyl)-2-(2-methylphenyl)benzoyl) methionine, methylphenyl)benzoyl)methionine, (4-(N-cyclohexylmethyl-N-3-pyridylaminomethyl)-2-(2-(4-(N-benzyl-N-3-pyridylaminomethyl)-2-(2-trifluoromethylphenyl)benzoyl)methionine, (4-(N-benzyl-N-3-(5-fluoropyridyl)aminomethyl)-2-(2-methylphenyl)benzoyl)methionine, acetoxymethyl N-(4-N-benzyl-N-pyridin-3-ylaminomethyl-2-(2-methylphenyl)benzoyl)methionine, pivaloyloxymethyl N-(4-N-benzyl-N-pyridin-3-ylaminomethyl-2-(2-methylphenyl)benzoyl)methionine, N,N-diethylaminocarbonylmethyl N-(4-N-benzyl-N-pyridin-3-ylaminomethyl-2-(2-methylphenyl)benzoyl)methionine, N-(4-(N-benzyl-N-pyrid-3-ylaminomethyl)-2-(2-chloro-4-fluorophenyl)-benzoyl)methionine, N-(4-N-(N-(3-pyridylmethyl)-N-(3,5-difluorobenzyl)aminomethyl)-2-(2-methylphenyl)benzoyl)methionine, lithium salt, N-(4-N-(N-3,5-difluorophenyl-N-(3-pyridylmethyl)aminomethyl)-2-(2-methylphenyl)benzoyl)methionine lithium salt, and N-(4-N-3,5-difluorobenzyl-N-(3-pyridyl)aninomethyl-2-(2-methylphenyl)-benzoyl)methionine, lithium salt.

* * * * *

UNITED STATES PATENT AND TRADEMARK OFFICE

CERTIFICATE OF CORRECTION

PATENT NO. : 6,693,123 B2
DATED : February 17, 2004
INVENTOR(S) : Sebti et al.

It is certified that error appears in the above-identified patent and that said Letters Patent is hereby corrected as shown below:

Title page,
Item [75], should read as follows:

-- [75] Inventors: Said M. Sebti, Tampa, FL (US); Andrew D. Hamilton, Guilford, CT (US); David J. Augeri, Kenosha, WI (US); Kenneth J. Barr, Chicago, IL (US); Stephen A. Fakhoury, Mendelein, IL (US); Stephen J. O'Connor, Wilmette, IL (US); Saul H. Rosenberg, Grayslake, IL (US); Wang Shen, Gurnee, IL (US); Bruce G. Szczepankiewicz, Lindenhurst, IL (US); Indrani W. Gunawardana, Libertyville, IL (US) --

Signed and Sealed this

Twenty-ninth Day of June, 2004

JON W. DUDAS
*Acting Director of the United States Patent and Trademark Office*